(12) United States Patent
Okuyama et al.

(10) Patent No.: US 10,065,972 B2
(45) Date of Patent: Sep. 4, 2018

(54) BICYCLIC OR TRICYCLIC HETEROCYCLIC COMPOUND

(71) Applicant: MITSUBISHI TANABE PHARMA CORPORATION, Osaka-shi, Osaka (JP)

(72) Inventors: Masahiro Okuyama, Osaka (JP); Kenji Fukunaga, Osaka (JP); Kenji Usui, Osaka (JP); Norimitsu Hayashi, Osaka (JP); Daisuke Iijima, Osaka (JP); Hideki Horiuchi, Osaka (JP); Noriaki Itagaki, Osaka (JP)

(73) Assignee: MITSUBISHI TANABE PHARMA CORPORATION, Osaka-Shi (JP)

(*) Notice: Subject to any disclaimer, the term of this patent is extended or adjusted under 35 U.S.C. 154(b) by 0 days.

(21) Appl. No.: 14/891,845

(22) PCT Filed: Apr. 22, 2015

(86) PCT No.: PCT/JP2015/062165
§ 371 (c)(1),
(2) Date: Nov. 17, 2015

(87) PCT Pub. No.: WO2015/163339
PCT Pub. Date: Oct. 29, 2015

(65) Prior Publication Data
US 2016/0376289 A1 Dec. 29, 2016

(30) Foreign Application Priority Data
Apr. 23, 2014 (JP) ................. 2014-089185

(51) Int. Cl.
| | | |
|---|---|---|
| *C07D 513/04* | (2006.01) | |
| *C07D 471/04* | (2006.01) | |
| *C07D 487/04* | (2006.01) | |
| *C07D 513/14* | (2006.01) | |
| *C07D 519/00* | (2006.01) | |
| *C07B 59/00* | (2006.01) | |

(52) U.S. Cl.
CPC .......... *C07D 513/04* (2013.01); *C07B 59/002* (2013.01); *C07D 471/04* (2013.01); *C07D 487/04* (2013.01); *C07D 513/14* (2013.01); *C07D 519/00* (2013.01); *C07B 2200/05* (2013.01)

(58) Field of Classification Search
CPC . C07B 2200/05; C07B 59/002; C07D 471/04; C07D 487/04; C07D 513/04; C07D 513/14; C07D 519/00
See application file for complete search history.

(56) References Cited

FOREIGN PATENT DOCUMENTS

| WO | WO 95/04714 A1 | 2/1995 |
|---|---|---|
| WO | WO 99/06375 A1 | 2/1999 |
| WO | WO 2010/146488 A1 | 12/2010 |
| WO | WO 2012/073143 A1 | 6/2012 |
| WO | WO 2013/186666 A1 | 12/2013 |

OTHER PUBLICATIONS

RN 1098125-34-8, entered into STN on Jan. 30, 2009 cited by the International Searching Authority.*
Albuquerque et al., "Mammalian Nicotinic Acetylcholine Receptors: From Structure to Function," Physiological Reviews, vol. 89, pp. 73-120, 2009.
Alkondon et al., "Targeted Deletion of the Kynurenine Aminotransferase II Gene Reveals a Critical Role of Endogenous Kynurenic Acid in . . . Synaptic Transmission via α7 Nicotinic Receptors in the Hippocampus," The Journal of Neuroscience, vol. 24, No. 19, pp. 4635-4648, May 12, 2004.
Baran et al., "Kynurenic Acid Metabolism in Various Types of Brain Pathology in HIV-1 Infected Patients," International Journal of Tryptophan Research, vol. 5, pp. 49-64, 2012.
Baran et al., "Kynurenine Metabolism in Alzheimer's Disease," Journal of Neural Transmission, vol. 106, pp. 165-181, 1999.
Campbell et al., "Advancing Drug Discovery for Schizophrenia," The New York Academy of Sciences, Mar. 9-11, 2011, pp. 1-28 (Final program, pp. 17-18).
Chemcats Database, Reg No. 1034775-63-7, Jul. 18, 2008 (retrieved online Jul. 1, 2015), 1 page.
Chemcats Database, Reg No. 1096092-07-7, Jan. 26, 2009 (retrieved online Jul. 1, 2015), 1 page.
Chemcats Database, Reg No. 1098125-34-8, Jan. 30, 2009 (retrieved online Jul. 1, 2015), 1 page.
Chemcats Database, Reg No. 1101851-30-2, Feb. 6, 2009 (retrieved online Jul. 1, 2015), 1 page.
(Continued)

*Primary Examiner* — Erich A Leeser
(74) *Attorney, Agent, or Firm* — Birch, Stewart, Kolasch & Birch, LLP

(57) ABSTRACT

The present invention provides a novel bicyclic or tricyclic heterocyclic compound represented by the formula (I)

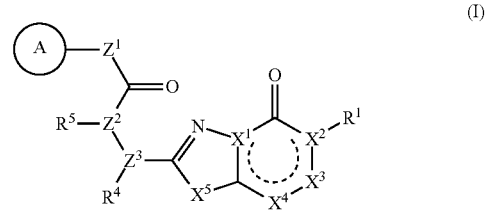

(I)

wherein ring A is an optionally substituted aromatic group, one of $X^1$ and $X^2$ is a carbon atom, and the other is a nitrogen atom,
$X^3$ is a nitrogen atom, or $CR^2$,
$X^4$ is a nitrogen atom, or $CR^3$,
$X^5$ is a sulfur atom, or —CH=CH—,
$Z^1$ is an oxygen atom, —C($R^6$)($R^7$)—, —NH—, —C($R^6$)($R^7$)—NH—, —NH—C($R^6$)($R^7$)—, —C($R^6$)($R^7$)—O—, —O—C($R^6$)($R^7$)—, or a single bond,
one of $Z^2$ and $Z^3$ is CH and the other is a nitrogen atom, or both are nitrogen atoms,
and other symbols are as defined in the DESCRIPTION, or a pharmacologically acceptable salt thereof.

31 Claims, No Drawings

(56) References Cited

OTHER PUBLICATIONS

Chemcats Database, Reg No. 1103987-19-4, Feb. 10, 2009 (retrieved online Jul. 1, 2015), 1 page.
Chemcats Database, Reg No. 1104251-15-1, Feb. 11, 2009 (retrieved online Jul. 1, 2015), 1 page.
Chemcats Database, Reg No. 950429-18-2, Oct. 12, 2007 (retrieved online Jul. 1, 2015), 1 page.
Chemcats Database, Reg Nos. 1037016-93-5, 1037016-88-8, Jul. 30, 2008 (retrieved online Jul. 1, 2015), 1 page.
Chemcats Database, Reg Nos. 1061746-32-4, 1061544-32-8, 1061540-74-6, Oct. 15 2008 (retrieved online Jul. 1, 2015), 1 page.
Chemcats Database, Reg Nos. 1086713-13-4, 1086691-70-4, Dec. 18, 2008 (retrieved online Jul. 1, 2015), 1 page.
Chemcats Database, Reg Nos. 1096536-96-7, 1096536-85-4, 1096536-73-0, 1096373-35-1, 1096373-32-8, Jan. 27, 2009 (retrieved online Jul. 1, 2015), 2 pages.
Chemcats Database, Reg Nos. 1097192-74-9, 1097192-72-7, 1097192-70-5, Jan. 28, 2009 (retrieved online Jul. 1, 2015), 2 pages.
Chemcats Database, Reg Nos. 1097704-19-4, 1097704-64-7, 1097704-19-2, 1097704-04-5, 1097703-82-6, 1097703-74-6, 1097703-69-9 . . . 1097702-84-5, 1097702-79-8, 1097702-53-8, 1097702-31-2, 1097702-12-9, 1097701-66-0, Jan. 29, 2009 (retrieved online Jul. 1, 2015), 7 pages.
Chemcats Database, Reg Nos. 1101193-85-5, 1101193-83-2, Feb. 5, 2009 (retrieved online Jul. 1, 2015), 1 page.
Chemcats Database, Reg Nos. 1103320-60-0, 1103231-76-0, Feb. 9, 2009 (retrieved online Jul. 1, 2015), 1 page.
Chemcats Database, Reg Nos. 1105688-11-6, 1105682-43-6, Feb. 13, 2009 (retrieved online Jul. 1, 2015), 1 page.
Chemcats Database, Reg Nos. 1219359-05-3, 1219351-95-7, 1219336-23-8, 1219267-77-2, 1219180-33-2, Apr. 15, 2010 (retrieved online Jul. 1, 2015), 3 pages.
Chemcats Database, Reg Nos. 1219429-01-2, 1219419-63-2, 1219381-85-7, Apr. 16, 2010 (retrieved online Jul. 1, 2015), 3 pages.
Chemcats Database, Reg Nos. 890791-05-6, 890790-98-4, 890790-91-7, 890790-84-8, 890790-47-3, 890790-39-3 . . . 890789-75-0, 890789-67-0, 890789-59-0, 890789-51-2, 890789-27-2, 890788-87-1, 890788-55-3, 890788-47-3, 890788-31-5, Jul. 6, 2006 (retrieved online Jul. 1, 2015), 6 pages.
Chemcats Database, Reg Nos. 931327-86-5, 931327-83-2, 931327-71-8, Apr. 20, 2007 (retrieved online Jul. 1, 2015), 1 page.
Chemcats Database, Reg Nos. 931736-15-1, 931736-12-8, 931736-06-0, 931736-00-4, 931735-97-6, 931735-94-3, 931678-99-8, 931678-93-2, Apr. 22, 2007 (retrieved online Jul. 1, 2015), 3 pages.
Chemcats Database, Reg Nos. 931957-29-8, 931957-26-5, 931957-20-9, 931957-17-4, 931957-11-8, Apr. 23, 2007 (retrieved online Jul. 1, 2015), 2 pages.
Chemcats Database, Reg Nos. 950407-51-9, 950407-29-1, 950407-15-5, 950406-87-8, 950406-64-1, 950406-48-1, 950406-25-4, 950406-17-4, 950406-09-4 . . . 950314-15-5, 950314-12-2, 950314-04-2, 950314-00-8, 950313-96-9, 950292-67-8, Oct. 11, 2007 (retrieved online Jul. 1, 2015), 15 pages.
Chess et al., "Elevations of Endogenous Kynurenic Acid Produce Spatial Working Memory Deficits," Schizophrenia Bulletin, vol. 33, No. 3, pp. 797-804, 2007.
Chess et al., "Increased Concentration of Cerebral Kynurenic Acid Alters Stimulus Processing and Conditioned Responding," Behavioural Brain Research, vol. 170, pp. 326-332, 2006.
Chess et al., "L-Kynurenine Treatment Alters Contextual Fear Conditioning and Context Discrimination but Not Cue-Specific Fear Conditioning," Behavioural Brain Research, vol. 201, pp. 325-331, 2009.
Gold et al., "The Relationship Between Indoleamine 2,3-Dioxygenase Activity and Post-Stroke Cognitive Impairment," Journal of Neuroinflammation, vol. 8, No. 17, pp. 1-8, 2011.
Henderson et al., "Competitive Antagonists and Partial Agonists at the Glycine Modulatory Site of the Mouse N-methyl-D-aspartate Receptor," Journal of Physiology, vol. 430, pp. 189-212, 1990.
International Search Report (Form PCT/ISA/210), dated Jul. 14, 2015, for International Application No. PCT/JP2015/062165.
Linderholm et al., "Increased Levels of Kynurenine and Kynurenic Acid in the CSF of Patients with Schizophrenia," Schizophrenia Bulletin, vol. 38, No. 3, pp. 426-432, 2012.
McGehee, "Nicotinic Receptors and Hippocampal Synaptic Plasticity . . . It's All in the Timing," Trends in Neurosciences, vol. 25, No. 4, pp. 171-172, Apr. 2002.
McTighe et al., "The BTBR Mouse Model of Autism Spectrum Disorders Has Learning and Attentional Impairments and Alterations in Acetylcholine and Kynurenic Acid in Prefrontal Cortex," PLoS One, vol. 8, Issue 4, pp. 1-11, Apr. 2013.
Morris et al., "Hippocampal Synaptic Plasticity and NMDA Receptors: A Role in Information Storage?" Philosophical Transactions of the Royal Society of London, vol. 329, pp. 187-204, 1990.
Olsson et al., "Cerebrospinal Fluid Kynurenic Acid is Associated with Manic and Psychotic Features in Patients with Bipolar I Disorder," Bipolar Disorders, vol. 14, pp. 719-726, 2012.
Potter et al., "Reduction of Endogenous Kynurenic Acid Formation Enhances Extracellular Glutamate, Hippocampal Plasticity, and Cognitive Behavior," Neuropsychopharmacology, vol. 35, pp. 1734-1742, 2010.
Rassoulpour et al., "Nanomolar Concentrations of Kynurenic Acid Reduce Extracellular Dopamine Levels in the Striatum," Journal of Neurochemistry, vol. 93, pp. 762-765, 2005.
Schwarcz et al., "Kynurenines in the Mammalian Brain: When Physiology Meets Pathology," Nature Reviews Neuroscience, vol. 13, pp. 465-477, Jul. 2012.
Wu et al., "The Astrocyte-Derived α7 Nicotinic Receptor Antagonist Kynurenic Acid Controls Extracellular Glutamate Levels in the Prefrontal Cortex," Journal of Molecular Neuroscience, vol. 40, pp. 204-210, 2010.
Zmarowski et al., "Astrocyte-Derived Kynurenic Acid Modulates Basal and Evoked Cortical Acetylcholine Release," European Journal of Neuroscience, vol. 29, pp. 529-538, 2009.
Database Registry [Online], "Chemical Abstracts Service", Columbus, Ohio, US, Sep. 18, 2014, Chemical Library; Supplier: Ukrorgsyntez Ltd., XP-002774536, Database accession No. 1623339-89-8, pp. 1-2.
Database Registry [Online], "Chemical Abstracts Service", Columbus, Ohio, US, Sep. 23, 2014, Chemical Library; Supplier: Ukrorgsyntez Ltd., XP-002774535, Database accession No. 1624866-34-7, pp. 1.
Database Registry [Online], "Chemical Abstracts Service", Columbus, Ohio, US, Sep. 25, 2014, Chemical Library; Supplier: Ukrorgsyntez Ltd., XP-002774534, Database accession No. 1626195-37-6, pp. 1.
Extended European Search Report, dated Nov. 17, 2017, for European Application No. 15782852.6.

\* cited by examiner

BICYCLIC OR TRICYCLIC HETEROCYCLIC COMPOUND

TECHNICAL FIELD

The present invention relates to a bicyclic or tricyclic heterocyclic compound. More particularly, the present invention relates to a novel bicyclic or tricyclic heterocyclic compound having a Kynurenine Aminotransferase-II (hereinafter sometimes to be also indicated as KAT-II) inhibitory action, and useful as a medicament for cognitive impairment, neurodegenerative disease, or schizophrenia, and use thereof.

BACKGROUND ART

N-methyl-D-aspartic acid receptor (hereinafter sometimes to be also indicated as NMDAR) and nicotinic acetylcholine receptor (hereinafter sometimes to be also indicated as nAChR) are known to be involved in some cognitive function processes. It is shown from animal studies that activation of NMDAR or nAChR improves some mental diseases including schizophrenia, dementia, depression, and stress vulnerability (see non-patent document 1 for NMDAR, non-patent documents 2 and 3 for nAChR).

Kynurenic acid (hereinafter sometimes to be also indicated as KYNA) is an endogenous tryptophan metabolite produced in the brain by kynurenine pathway. Tryptophan is metabolized by indoleamine 2,3-dioxygenase (IDO) and the like to produce kynurenine, and kynurenine is metabolized to produce KYNA. There are 4 kinds of known enzymes that catalyze the reaction to produce KYNA from kynurenine. That is, kynurenine-aminotransferases 1, 2, 3, and 4. Of these, KAT-II plays a key role in the production of KYNA in the brain, and it is known that KYNA concentration significantly decreases in hippocampus in KAT-II knockout mouse, as compared to that in wild-type mouse (see non-patent document 4).

KYNA is known to be an antagonist of NMDAR and nicotinic acetylcholine α7 receptor (hereinafter sometimes to be also indicated as α7nAChR). Therefore, KYNA is considered to be mainly involved in the control of presynaptic activity of GABA neuron, glutamic acid neuron via α7nAChR in the brain, and control of postsynaptic activity of glutamic acid neuron via NMDAR (see non-patent documents 5, 6 and 7).

Therefore, KAT-II inhibitor is expected to be useful for the treatment of central diseases such as schizophrenia, attention deficit/hyperactivity disorder, Alzheimer's disease, major depression and the like through activation of NMDAR and/or nAChR based on a decrease in the KYNA concentration in the brain. As documents describing the relationship between KAT-II and/or KYNA and dementia, depression, or stress vulnerability, the following are reported.

In the studies of mammals, it was confirmed that an increase in the KYNA concentration in the brain causes disorders of cognitive functions such as context learning, working memory and the like, and that an increase in the KYNA concentration may be involved in the cognitive dysfunction such as schizophrenia and the like (see non-patent documents 8-10).

R. Schwarcz et al. show that topical injection of KYNA into the brain of rodents suppresses release of dopamine, acetylcholine or glutamic acid in the site, and a possibility is proposed that attenuation of KYNA production in the brain improves cognitive function of schizophrenia (see non-patent document 11 for dopamine, non-patent document 12 for acetylcholine, non-patent document 13 for glutamic acid).

It has been reported that KYNA concentration in the cerebrospinal fluid of schizophrenia patients and bipolar disorder patients is significantly higher than that of normal volunteers and patients free of mental diseases, and the results support involvement of KYNA in the pathophysiology of schizophrenia and bipolar disorder (see non-patent document 14 for schizophrenia, and non-patent document 15 for bipolar disorder).

It has been reported that administration of a KAT-II inhibitor decreases the KYNA concentration in the brain to dialysates in a dose-dependent manner, and KAT-II inhibitors show activity in anhedonia model [chronic mild stress], which is one kind of depression models, and it has been reported that KAT-II inhibitors may be suitable for cognitive function and negative symptoms of schizophrenia (see non-patent document 16).

BTBR mouse, which is one kind of autism spectrum disorder mice, is reported to show high KYNA concentration in the medial prefrontal cortex, as compared to C57 Bl/6J mouse (see non-patent document 17).

It is known that KYNA concentration is significantly high in the putamen and caudate nucleus of postmortem brain of Alzheimer's disease patients, as compared to the control group free of dementia. It has been reported that inhibition of NMDAR by KYNA possibly causes memory disorder, learning and cognition function of Alzheimer's disease patients (see non-patent document 18).

It has been reported that patients with ischemic cerebrovascular diseases (cerebral infarction) and showing a greater kynurenine/tryptophan ratio show degraded cognitive function, and correlation between inflammatory reactions characterized by an increased IDO activity and cerebrovascular dementia is suggested (see non-patent document 19).

It has been reported that the concentration of kynurenic acid in the frontal cortex of postmortem brain of a subgroup such as HIV encephalopathy (HIV in brain) and the like in the HIV-1 (human immunodeficiency virus 1) infected patients is significantly higher than that of the control group. In addition, it is suggested that a decrease in the kynurenic acid production can be useful for an antidementia drug (see non-patent document 20).

As a compound having a KAT-II inhibitory activity, for example, the following compound has been reported.

R. Schwarcz et al. disclosed that a novel kynurenine derivative having a KAT-II inhibitory activity is effective for the treatment of cognitive impairment related to the aging of the brain and perinatal brain damage (see patent document 1).

M. M. Claffey et al. and A. B. Dounay et al. disclose that the compounds represented by the following formulas are KAT-II inhibitory compounds, and useful for the treatment of schizophrenia and cognitive deficit relating to other neurodegeneration and/or neurological disorder (see patent documents 2-4).

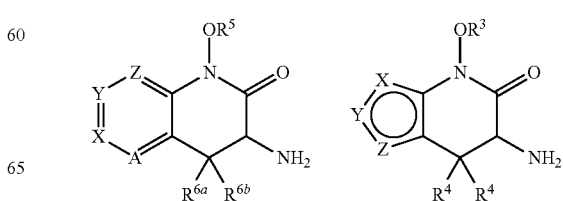

-continued

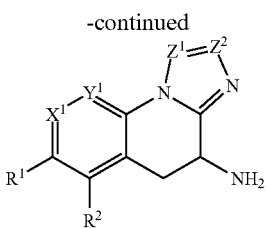

However, a KAT-II inhibitory action of a bicyclic or tricyclic heterocyclic compound like that of the compound of the present invention has not been reported.

Thiadiazolopyrimidone derivatives represented by the following structural formulas and the like have been sold by plural companies (e.g., AKos Consulting & Solutions GmbH, Ambinter, Aurora Fine Chemicals, ChemDiv, Inc.). However, a KAT-II inhibitory action and other pharmacological activities of these compounds have not been disclosed at all.

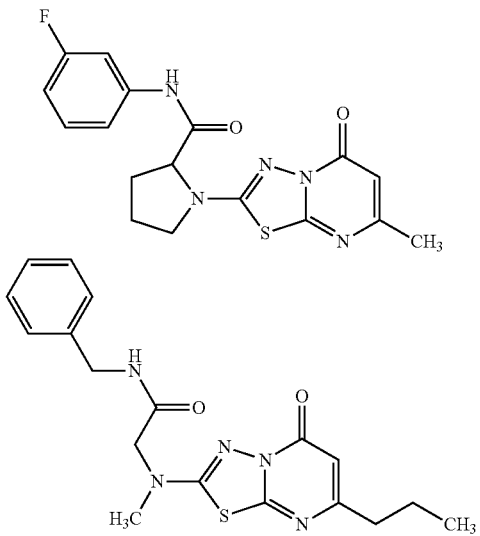

DOCUMENT LIST

Patent Documents patent document 1: WO 1995/004714
patent document 2: WO 2010/146488
patent document 3: WO 2012/073143
patent document 4: WO 2013/186666

Non-Patent Documents non-patent document 1: R. G. M. Morris et al., "Philosophical transactions of the Royal Society of London" vol. 329, pages 187-204, 1990
non-patent document 2: E. X. Albuquerque et al., "Physiological Reviews" vol. 89, pages 73-120, 2009
non-patent document 3: D. S. McGehee, "Trends in Neurosciences" vol. 25, pages 171-172, 2002
non-patent document 4: M. C. Potter et al., "Neuropsychopharmacology" vol. 35, pages 1734-1742, 2010
non-patent document 5: R. Schwarcz et al., "Nature Reviews Neuroscience" vol. 13, pages 465-477, 2012
non-patent document 6: M. Alkondon et al., "The Journal of Neuroscience" vol. 24, pages 4635-4648, 2004
non-patent document 7: G. Henderson et al., "Journal of Physiology" vol. 430, pages 189-212, 1990
non-patent document 8: A. C. Chess et al., "Behavioural Brain Research" vol. 170, pages 326-332, 2006
non-patent document 9: A. C. Chess et al., "Schizophrenia Bulletin" vol. 33, pages 797-804, 2007
non-patent document 10: A. C. Chess et al., "Behavioural Brain Research" vol. 201, pages 325-331, 2009
non-patent document 11: A. Rassoulpour et al., "Journal of Neurochemistry" vol. 93, pages 762-765, 2005
non-patent document 12: A. Zmarowski et al., "European Journal of Neuroscience" vol. 29, pages 529-538, 2009
non-patent document 13: H.-Q. Wu et al., "Journal of Molecular Neuroscience" vol. 40, pages 204-210, 2010
non-patent document 14: K. R. Linderholm et al., "Schizophrenia Bulletin" vol. 38, pages 426-432, 2012
non-patent document 15: S. K. Olssona et al., "Bipolar Disorders" vol. 14, pages 719-726, 2012
non-patent document 16: B. Campbell et al., "Advancing Drug Discovery for Schizophrenia" The New York Academy of Sciences Mar. 9-11, 2011 (Final program, pages 17-18)
non-patent document 17: S. M. McTighe et al., "PLoS ONE" vol. 8, e62189, 2013
non-patent document 18: H. Baran et al., "Journal of Neural Transmission" vol. 106, pages 165-181, 1999
non-patent document 19: A. B. Gold et al., "Journal of Neuroinflammation" vol. 8, 17, 2011
non-patent document 20: H. Baran et al., "International Journal of Tryptophan Research" vol. 5, pages 49-64, 2012

SUMMARY OF THE INVENTION

Problems to be Solved by the Invention

An object to be solved by the present invention is provision of a novel compound having a superior inhibitory action on KAT-II, a production method thereof, use thereof, and a pharmaceutical composition containing the aforementioned compound and the like.

Means of Solving the Problems

The present inventors have conducted intensive studies in an attempt to solve the above-mentioned problems and found a novel bicyclic or tricyclic heterocyclic compound having a superior KAT-II inhibitory action and completed the present invention.

That is, the present invention relates to a compound represented by the formula (I):

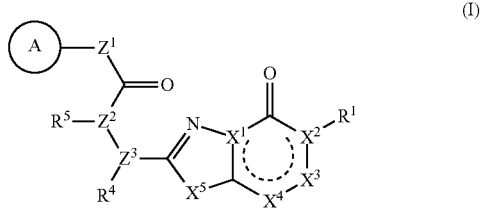

wherein ring A is an optionally substituted aromatic group,
one of $X^1$ and $X^2$ is a carbon atom, and the other is a nitrogen atom,
$X^3$ is a nitrogen atom, or $CR^2$,
$X^4$ is a nitrogen atom, or $CR^3$,
$X^5$ is a sulfur atom, or —CH=CH—,
$Z^1$ is an oxygen atom, —C($R^6$)($R^7$)—, —NH—, —C($R^6$)($R^7$)—NH—, —NH—C($R^6$)($R^7$)—, —C($R^6$)($R^7$)—O—, —O—C($R^6$)($R^7$)—, or a single bond (where the left end shows a bond to ring A, and the right end shows a bond to the adjacent carbonyl),
one of $Z^2$ and $Z^3$ is CH and the other is a nitrogen atom, or both are nitrogen atoms,
$R^1$ is a hydrogen atom, optionally substituted alkyl, optionally substituted cycloalkyl, optionally substituted aryl, an optionally substituted nonaromatic heterocyclic group, or a halogen atom,
$R^2$ is a hydrogen atom, optionally substituted alkyl, optionally substituted cycloalkyl, optionally substituted amino, optionally substituted aryl, an optionally substituted nonaromatic heterocyclic group, optionally substituted heteroaryl, optionally substituted alkoxy, or optionally substituted cycloalkoxy,
or, $R^1$ and $R^2$ are bonded to each other to form, together with the adjacent $X^2$ and carbon atom, an optionally substituted ring,
$R^3$ is a hydrogen atom, optionally substituted alkyl, optionally substituted cycloalkyl, or a halogen atom,
$R^4$ and $R^5$ are each independently a hydrogen atom, or optionally substituted alkyl,
or, $R^4$ and $R^5$ are bonded to each other to form, together with the adjacent $Z^2$ and $Z^3$, an optionally substituted nitrogen-containing non-aromatic heterocycle,
$R^6$ and $R^7$ are each independently a hydrogen atom, optionally substituted alkyl, or optionally substituted cycloalkyl,
or, $R^6$ and $R^7$ are bonded to each other to form, together with the adjacent carbon atom, an optionally substituted cycloalkane,
a part represented by the following formula in the aforementioned formula (I):

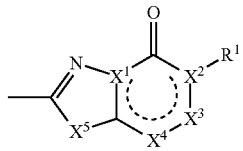

is
(A) when $X^1$ is a carbon atom and $X^2$ is a nitrogen atom, a group represented by the following formula (i-a):

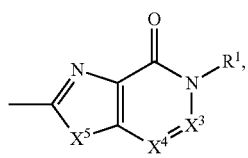

(i-a)

and
(B) when $X^1$ is a nitrogen atom and $X^2$ is a carbon atom, a group represented by the following formula (i-b):

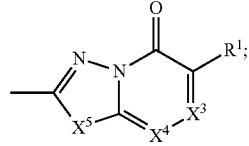

(i-b)

provided (a) when a part represented by the following formula in the aforementioned formula (I):

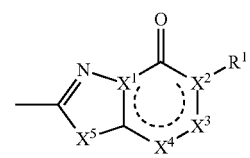

is a group represented by the formula (ii-a):

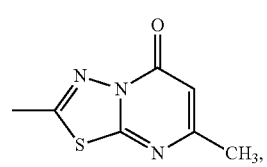

(ii-a)

(a-1) $Z^2$ is a nitrogen atom, and $Z^3$ is CH or a nitrogen atom;
(a-2) $Z^2$ is CH, and $Z^3$ is a nitrogen atom, and a part represented by the following formula in the formula (I):

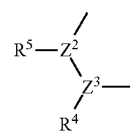

is a group represented by the formula (v-x):

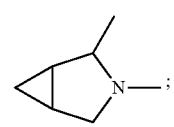

(v-x)

or
(a-3) $Z^2$ is CH, and $Z^3$ is a nitrogen atom, and a part represented by the following formula in the formula (I):

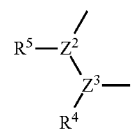

is a group represented by the formula (v-y):

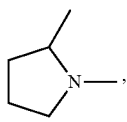

and a part represented by the following formula in the formula (I):

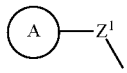

is a group represented by the formula (iii-a), (iii-b), or (iii-c):

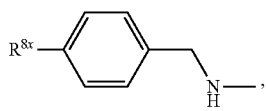

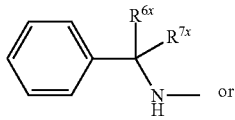

or

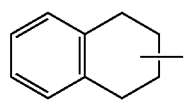

wherein $R^{6x}$ and $R^{7x}$ are each optionally substituted alkyl or $R^{6x}$ and $R^{7x}$ are bonded to each other to form, together with the adjacent carbon atom, an optionally substituted cycloalkane, $R^{8x}$ is halogenoalkyl, or a fluorine atom, and
(b) when a part represented by the following formula in the aforementioned formula (I):

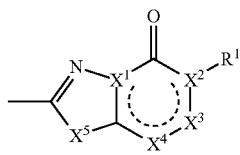

is a group represented by the formula (ii-b):

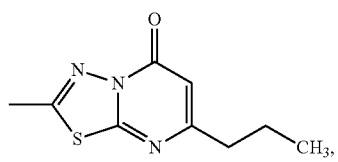

(b-1) $Z^2$ is a nitrogen atom, and $Z^3$ is CH or a nitrogen atom; or
(b-2) $Z^2$ is CH, and $Z^3$ is a nitrogen atom,
$R^4$ and $R^5$ are bonded to each other to form, together with the adjacent $Z^2$ and $Z^3$, an optionally substituted nitrogen-containing non-aromatic heterocycle, and a part represented by the following formula in the formula (I):

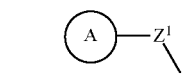

is a group represented by the formula (iii-d):

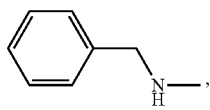

or a pharmacologically acceptable salt thereof.

The present invention also relates to a method for the treatment or prophylaxis of various diseases (e.g., schizophrenia) involving KAT-II, which comprises administering an effective amount of a compound represented by the aforementioned formula (I) (hereinafter to be also indicated as compound (I)), or a pharmacologically acceptable salt to a patient.

The present invention also relates to a pharmaceutical composition comprising the aforementioned compound (I) or a pharmacologically acceptable salt thereof as an active ingredient, and use of the aforementioned compound (I) or a pharmacologically acceptable salt thereof for the production of the pharmaceutical composition.

Effect of the Invention

Since a compound represented by the formula (I) or a pharmacologically acceptable salt thereof affords a superior KAT-II inhibitory action, a pharmaceutical composition containing same as an active ingredient is useful for the prophylaxis or treatment of various diseases (e.g., schizophrenia) involving KAT-II.

DESCRIPTION OF EMBODIMENTS

The definition of each term used in the present specification is as follows.

The term "alkyl" means a linear or branched chain saturated hydrocarbon group having 1 to 6 carbon atoms ($C_1$-$C_6$), and specific examples include methyl, ethyl, propyl, isopropyl, butyl, tert-butyl, isobutyl, pentyl, hexyl, and various branched chain isomers thereof.

The term "alkenyl" means a linear or branched chain unsaturated hydrocarbon group having 1 or 2 carbon-carbon double bonds and 2 to 6 carbon atoms ($C_2$-$C_6$), and specific examples include, vinyl, propenyl, isopropenyl, butenyl, pentenyl, hexenyl, and various branched chain isomers thereof.

The term "alkylidene" means a linear or branched chain divalent hydrocarbon group having 1 to 6 carbon atoms ($C_1$-$C_6$), and specific examples include, methylidene, ethylidene, propylidene, butylidene, pentylidene, hexylidene, and various branched chain isomers thereof.

The term "cycloalkyl" means a 3-8-membered ($C_3$-$C_8$) monocyclic alicyclic saturated hydrocarbon group, and specific examples include cyclopropyl, cyclobutyl, cyclopentyl, cyclohexyl, cycloheptyl, and cyclooctyl.

The term "cycloalkane" means a 3-8-membered ($C_3$-$C_8$) monocyclic alicyclic saturated hydrocarbon, and specific examples include cyclopropane, cyclobutane, cyclopentane, cyclohexane, cycloheptane, and cyclooctane.

The term "cycloalkenyl" means a 3-8-membered ($C_3$-$C_8$) monocyclic alicyclic hydrocarbon group having 1 or 2 carbon-carbon double bonds, and specific examples include cyclopropenyl, cyclobutenyl, cyclopentenyl, cyclohexenyl, cycloheptenyl, and cyclooctenyl.

The term "cycloalkene" means 3-8-membered ($C_3$-$C_8$) monocyclic alicyclic hydrocarbon having 1 or 2 carbon-carbon double bonds, and specific examples include cyclopropene, cyclobutene, cyclopentene, cyclohexene, cycloheptene, and cyclooctene.

The term "aryl" means a monocyclic or bicyclic aromatic hydrocarbon group having 6-11 ring-constituting carbon atoms ($C_6$-$C_{11}$), and specific examples include monocyclic aryl such as phenyl and the like; and optionally partly saturated bicyclic aryl having 9-11 ring-constituting carbon atoms ($C_9$-$C_{11}$) such as naphthyl, tetrahydronaphthyl, indenyl, indanyl and the like.

The term "arene" means monocyclic or bicyclic aromatic hydrocarbon having 6-11 ring-constituting carbon atoms ($C_6$-$C_{11}$), and specific examples include monocyclic arene such as benzene and the like; and optionally partly saturated bicyclic arene having 9-11 ring-constituting carbon atoms ($C_9$-$C_{11}$) such as naphthalene, tetrahydronaphthalene, indene, indane and the like.

The term "nonaromatic heterocyclic group" means a 4- to 12-membered monocyclic or bicyclic nonaromatic heterocyclic group containing, besides carbon atom, 1-4 hetero atoms selected from the group consisting of oxygen atom, sulfur atom and nitrogen atom, and specific examples include a 4- to 7-membered monocyclic nonaromatic heterocyclic group containing, besides carbon atom, 1 or 2 hetero atoms selected from the group consisting of oxygen atom, sulfur atom and nitrogen atom such as azetidinyl, pyrrolidyl, pyrazolidinyl, piperidyl, oxetanyl, tetrahydrofuryl, dihydropyranyl, tetrahydropyranyl, tetrahydrothienyl, dihydroimidazolyl, imidazolidinyl, tetrahydropyrazinyl, piperazinyl, morpholinyl and the like; and a 6- to 12-membered bicyclic nonaromatic heterocyclic group containing, besides carbon atom, 1-4 hetero atoms selected from the group consisting of oxygen atom, sulfur atom and nitrogen atom such as azabicyclo[3.1.0]hexyl and the like.

The term "nitrogen-containing nonaromatic heterocyclic group" means the aforementioned nonaromatic heterocyclic group containing at least one nitrogen atom, and specific examples include azetidinyl, pyrrolidyl, pyrazolidinyl, piperidyl, dihydroimidazolyl, imidazolidinyl, tetrahydropyrazinyl, piperazinyl, morpholinyl, and azabicyclo[3.1.0]hexyl.

The term "non-aromatic heterocycle" means a 4- to 12-membered monocyclic or bicyclic non-aromatic heterocycle containing, besides carbon atom, 1-4 hetero atoms selected from the group consisting of oxygen atom, sulfur atom and nitrogen atom, and specific examples include a 4- to 7-membered monocyclic non-aromatic heterocycle containing, besides carbon atom, 1 or 2 hetero atoms selected from the group consisting of oxygen atom, sulfur atom and nitrogen atom such as azetidine, pyrrolidine, pyrazolidine, piperidine, oxetane, tetrahydrofuran, tetrahydropyran, tetrahydrothiophene, dihydroimidazole, imidazolidine, tetrahydropyrazine, piperazine, morpholine and the like; and a 6-12-membered bicyclic non-aromatic heterocycle containing, besides carbon atom, 1-4 hetero atoms selected from the group consisting of oxygen atom, sulfur atom and nitrogen atom such as azabicyclo[3.1.0]hexane and the like.

The term "nitrogen-containing non-aromatic heterocycle" means the aforementioned non-aromatic heterocycle containing at least one nitrogen atom, and specific examples include azetidine, pyrrolidine, pyrazolidine, piperidine, dihydroimidazole, imidazolidine, tetrahydropyrazine, piperazine, morpholine, and azabicyclo[3.1.0]hexane.

The term "heteroaryl" means a 5- to 11-membered monocyclic or bicyclic aromatic heterocyclic group containing, besides carbon atom, 1-4 hetero atoms selected from the group consisting of oxygen atom, sulfur atom and nitrogen atom, and specific examples include 5- to 6-membered monocyclic heteroaryl containing, besides carbon atom, 1-4 hetero atoms selected from the group consisting of oxygen atom, sulfur atom and nitrogen atom such as pyrrolyl, furyl, thienyl, pyrazolyl, imidazolyl, oxazolyl, isoxazolyl, oxadiazolyl, thiazolyl, isothiazolyl, thiadiazolyl, pyridyl, pyrazyl, pyrimidinyl, pyridazinyl and the like; and optionally partly saturated 8- to 11-membered bicyclic heteroaryl containing, besides carbon atom, 1-4 hetero atoms selected from the group consisting of oxygen atom, sulfur atom and nitrogen atom such as indolinyl, isoindolinyl, dihydrobenzofuranyl, dihydroisobenzofuranyl, benzodioxolanyl, thienopyridyl, thiazolopyridyl, thiazolopyrimidinyl, thiazolopyridazyl, thiadiazolopyridyl, thiadiazolopyrimidinyl, quinolyl, tetrahydroquinolyl, isoquinolyl, tetrahydroisoquinolyl, pyridopyrimidinyl, pyrimidopyridazyl, triazolopyridyl and the like.

The term "nitrogen-containing heteroaryl" means the aforementioned heteroaryl containing at least one nitrogen atom, and specific examples include 5- to 6-membered monocyclic nitrogen-containing heteroaryl such as pyrrolyl, pyrazolyl, imidazolyl, oxazolyl, isoxazolyl, oxadiazolyl, thiazolyl, isothiazolyl, thiadiazolyl, pyridyl, pyrazyl, pyrimidinyl, pyridazinyl and the like; and optionally partly saturated 8- to 11-membered bicyclic nitrogen-containing heteroaryl such as indolinyl, isoindolinyl, thienopyridyl, thiazolopyridyl, thiazolopyrimidinyl, thiazolopyridazyl, thiadiazolopyridyl, thiadiazolopyrimidinyl, quinolyl, tetrahydroquinolyl, isoquinolyl, tetrahydroisoquinolyl, pyridopyrimidinyl, pyrimidopyridazyl, triazolopyridyl and the like.

The term "heteroarene" means a 5- to 11-membered monocyclic or bicyclic aromatic heterocycle containing, besides carbon atom, 1-4 hetero atoms selected from the group consisting of oxygen atom, sulfur atom and nitrogen atom, and specific examples include a 5- to 6-membered monocyclic heteroarene containing, besides carbon atom, 1-4 hetero atoms selected from the group consisting of oxygen atom, sulfur atom and nitrogen atom such as pyrrole, furan, thiophene, pyrazole, imidazole, oxazole, isoxazole, oxadiazole, thiazole, isothiazole, thiadiazole, pyridine, pyrazine, pyrimidine, pyridazine and the like; and an optionally partly saturated 8- to 11-membered bicyclic heteroarene containing, besides carbon atom, 1-4 hetero atoms selected from the group consisting of oxygen atom, sulfur atom and nitrogen atom such as indoline, isoindoline, dihydrobenzofuran, dihydroisobenzofuran, benzodioxolane, thienopyridine, thiazolopyridine, thiazolopyrimidine, thiazolopyridazine, thiadiazolopyridine, thiadiazolopyrimidine, quinoline, tetrahydroquinoline, isoquinoline, tetrahydroisoquinoline, pyridopyrimidine, pyrimidopyridazine, triazolopyridine and the like.

The term "nitrogen-containing heteroarene" means the aforementioned heteroarene containing at least one nitrogen atom, and specific examples include 5- to 6-membered monocyclic nitrogen-containing heteroarene such as pyrrole, pyrazole, imidazole, oxazole, isoxazole, oxadiazole, thiazole, isothiazole, thiadiazole, pyridine, pyrazine, pyrimidine, pyridazine and the like; and 8- to 11-membered bicyclic nitrogen-containing heteroarene such as indoline, isoindoline, thienopyridine, thiazolopyridine, thiazolopyrimidine, thiazolopyridazine, thiadiazolopyridine, thiadiazolopyrimidine, quinoline, tetrahydroquinoline, isoquinoline, tetrahydroisoquinoline, pyridopyrimidine, pyrimidopyridazine, triazolopyridine and the like.

The term "aromatic group" means a 5- to 11-membered monocyclic or bicyclic aromatic group optionally containing, besides carbon atom, 1-4 hetero atoms selected from the group consisting of oxygen atom, sulfur atom and nitrogen atom, and specific examples include the aforementioned aryl, heteroaryl, more specifically, monocyclic aryl such as phenyl and the like; optionally partly saturated bicyclic aryl having 9-11 ring-constituting carbon atoms ($C_9$-$C_{11}$) such as naphthyl, tetrahydronaphthyl, indenyl, indanyl and the like; 5- to 6-membered monocyclic heteroaryl containing, besides carbon atom, 1-4 hetero atoms selected from the group consisting of oxygen atom, sulfur atom and nitrogen atom such as pyrrolyl, furyl, thienyl, pyrazolyl, imidazolyl, oxazolyl, isoxazolyl, oxadiazolyl, thiazolyl, isothiazolyl, thiadiazolyl, pyridyl, pyrazyl, pyrimidinyl, pyridazinyl and the like; and optionally partly saturated 8- to 11-membered bicyclic heteroaryl containing, besides carbon atom, 1-4 hetero atoms selected from the group consisting of oxygen atom, sulfur atom and nitrogen atom such as indolinyl, isoindolinyl, dihydrobenzofuranyl, dihydroisobenzofuranyl, benzodioxolanyl, thienopyridyl, triazolopyridyl, thiazolopyrimidinyl, thiazolopyridazyl, thiadiazolopyridyl, thiadiazolopyrimidinyl, quinolyl, tetrahydroquinolyl, isoquinolyl, tetrahydroisoquinolyl, pyridopyrimidinyl, pyrimidopyridazyl, triazolopyridyl and the like.

The term "aromatic ring" means a 5- to 11-membered monocyclic or bicyclic aromatic ring optionally containing, besides carbon atom, 1-4 hetero atoms selected from the group consisting of oxygen atom, sulfur atom and nitrogen atom, and specific examples include the aforementioned arene, heteroarene, more specifically, monocyclic arene such as benzene and the like; optionally partly saturated bicyclic arene having 9-11 ring-constituting carbon atoms ($C_9$-$C_{11}$) such as naphthalene, tetrahydronaphthalene, indene, indane and the like; a 5- to 6-membered monocyclic heteroarene containing, besides carbon atom, 1-4 hetero atoms selected from the group consisting of oxygen atom, sulfur atom and nitrogen atom such as pyrrole, furan, thiophene, pyrazole, imidazole, oxazole, isoxazole, oxadiazole, thiazole, isothiazole, thiadiazole, pyridine, pyrazine, pyrimidine, pyridazine and the like; and optionally partly saturated 8- to 11-membered bicyclic heteroarene containing, besides carbon atom, 1-4 hetero atoms selected from the group consisting of oxygen atom, sulfur atom and nitrogen atom such as indoline, isoindoline, dihydrobenzofuran, dihydroisobenzofuran, benzodioxolane, thienopyridine, triazolopyridine, thiazolopyrimidine, thiazolopyridazine, thiadiazolopyridine, thiadiazolopyrimidine, quinoline, tetrahydroquinoline, isoquinoline, tetrahydroisoquinoline, pyridopyrimidine, pyrimidopyridazine, triazolopyridine and the like.

The term "ring" means a 5- to 11-membered monocyclic or bicyclic ring optionally containing, besides carbon atom, 1-4 hetero atoms selected from the group consisting of oxygen atom, sulfur atom and nitrogen atom, and specific examples include the aforementioned cycloalkane, arene, non-aromatic heterocycle, and heteroarene.

The term "halogen atom" or "halogeno" means fluorine atom, chlorine atom, bromine atom or iodine atom.

The term "alkoxy" means a group wherein an oxygen atom is bonded to the aforementioned linear or branched chain alkyl having 1 to 6 carbon atoms ($C_1$-$C_6$), and specific examples include methoxy, ethoxy, propoxy, isopropoxy, butoxy, tert-butoxy, isobutoxy, pentyloxy, hexyloxy, and various branched chain isomers thereof.

The term "alkoxyphenyl" means phenyl substituted by 1, 2 or 3 alkoxys mentioned above, and specific examples include methoxyphenyl, and dimethoxyphenyl.

The term "cycloalkoxy" means a group wherein an oxygen atom is bonded to the aforementioned 3-8-membered ($C_3$-$C_8$) monocyclic alicyclic saturated hydrocarbon group, and specific examples include cyclopropoxy, cyclobutoxy, cyclopentyloxy, cyclohexyloxy, cycloheptyloxy, and cyclooctyloxy.

The term "halogenoalkyl", "halogenocycloalkyl" and "halogenoalkoxy" mean the aforementioned alkyl, cycloalkyl and alkoxy, each substituted by 1-7 halogen atoms, respectively, and specific examples include trifluoromethyl, chlorocyclopropyl, and trifluoromethoxy, respectively.

The term "alkanoyl" means a group having 2-7 carbon atoms ($C_2$-$C_7$) wherein carbonyl is bonded to the aforementioned linear or branched chain alkyl having 1 to 6 carbon atoms ($C_1$-$C_6$), and specific examples include acetyl, propanoyl, butyryl, and various branched chain isomers thereof.

The term "aralkyl" means a group wherein the aforementioned linear or branched chain alkyl having 1 to 6 carbon atoms ($C_1$-$C_6$) is bonded to the aforementioned monocyclic or bicyclic aromatic hydrocarbon group having 6-11 ring-constituting carbon atoms ($C_6$-$C_{11}$), and specific examples include phenylmethyl.

Each abbreviation used in the present specification means the following unless particularly defined.
Boc: tert-butoxycarbonyl
D: deuterium ($^2$H)
DBU: 1,8-diazabicyclo[5.4.0]undec-7-ene
DME: 1,2-dimethoxyethane
DMF: N,N-dimethylformamide
EDC hydrochloride: 1-(3-dimethylaminopropyl)-3-ethylcarbodiimide hydrochloride
HATU: O-(7-azabenzotriazol-1-yl)-N,N,N',N'-tetramethyluronium hexafluorophosphate
HOBt monohydrate: 1-hydroxybenzotriazole monohydrate
HPLC: high performance liquid chromatography
mCPBA: methachloroperbenzoic acid
THF: tetrahydrofuran
TLC: thin layer chromatography
Lawesson's reagent: 2,4-bis(4-methoxyphenyl)-1,3,2,4-dithiadiphosphetane-2,4-disulfide In the following, each symbol in the formula (I) represented by the aforementioned compound is explained by showing specific examples.

The aromatic group of the "optionally substituted aromatic group" for ring A is as defined above, and specific examples thereof include aryl and heteroaryl. Preferable aryl or heteroaryl includes phenyl, tetrahydronaphthyl, furyl, thienyl, pyrazolyl, isoxazolyl, thiazolyl, pyridyl, pyrimidinyl, pyrazyl, indolinyl, tetrahydroquinolyl, thienopyridyl, dihydrobenzofuranyl, benzodioxolanyl, and triazolopyridyl. Of these, phenyl, thienyl, and benzodioxolanyl are more preferable, and phenyl is particularly preferable.

$Z^1$ is as defined above, from which an oxygen atom, —C($R^6$)($R^7$)—, —C($R^6$)($R^7$)—NH—, —NH—C($R^6$)($R^7$)—, or —O—C($R^6$)($R^7$)— is preferable.

$Z^2$ and $Z^3$ are as defined above. Preferably, one is CH and the other is a nitrogen atom.

When $R^1$ is "optionally substituted alkyl", the alkyl moiety of the group is as defined above, and is preferably $C_1$-$C_6$ alkyl, more preferably $C_1$-$C_4$ alkyl.

When $R^1$ is "optionally substituted cycloalkyl", the cycloalkyl moiety of the group is as defined above, and is preferably $C_3$-$C_8$ cycloalkyl, more preferably $C_3$-$C_6$ cycloalkyl.

When $R^1$ is "optionally substituted aryl", the aryl moiety of the group is as defined above, preferably phenyl.

When $R^1$ is "optionally substituted nonaromatic heterocyclic group", the nonaromatic heterocyclic group moiety of the group is as defined above, and is preferably a 4- to 7-membered monocyclic nonaromatic heterocyclic group containing, besides carbon atom, 1 or 2 hetero atoms selected from the group consisting of oxygen atom and nitrogen atom. Of these, pyrrolidyl, piperidyl, oxetanyl, tetrahydrofuryl, dihydropyranyl, tetrahydropyranyl, or morpholinyl is more preferable, and pyrrolidyl, oxetanyl, or tetrahydropyranyl is particularly preferable.

When $R^1$ is "halogen atom", the halogen atom is as defined above, and is preferably a fluorine atom, a chlorine atom, a bromine atom, or an iodine atom, more preferably a fluorine atom, a chlorine atom, or a bromine atom.

Preferable examples of $R^1$ include a hydrogen atom, optionally substituted alkyl, optionally substituted cycloalkyl, an optionally substituted nonaromatic heterocyclic group, and a halogen atom. Of these, a hydrogen atom, optionally substituted $C_1$-$C_4$ alkyl, optionally substituted $C_3$-$C_6$ cycloalkyl, an optionally substituted nonaromatic heterocyclic group which is selected from the group consisting of pyrrolidyl, oxetanyl, and tetrahydropyranyl, a fluorine atom, and a chlorine atom are more preferable.

When $R^2$ is "optionally substituted alkyl", the alkyl moiety of the group is as defined above, and is preferably $C_1$-$C_6$ alkyl, more preferably $C_1$-$C_4$ alkyl.

When $R^2$ is "optionally substituted cycloalkyl", the cycloalkyl moiety of the group is as defined above, and is preferably $C_3$-$C_8$ cycloalkyl, more preferably $C_3$-$C_6$ cycloalkyl.

When $R^2$ is "optionally substituted aryl", the aryl moiety of the group is as defined above, preferably phenyl.

When $R^2$ is "optionally substituted nonaromatic heterocyclic group", the nonaromatic heterocyclic group moiety of the group is as defined above, and is preferably, a 4- to 7-membered monocyclic nonaromatic heterocyclic group containing, besides carbon atom, 1 or 2 hetero atoms selected from the group consisting of oxygen atom and nitrogen atom. Of these, azetidinyl, pyrrolidyl, piperidyl, oxetanyl, tetrahydrofuryl, tetrahydropyranyl, piperazinyl, and morpholinyl are more preferable, and azetidinyl, pyrrolidyl, piperidyl, oxetanyl, tetrahydrofuryl, tetrahydropyranyl, and morpholinyl are particularly preferable.

When $R^2$ is "optionally substituted heteroaryl", the heteroaryl moiety of the group is as defined above, and is preferably a 5- to 6-membered monocyclic aromatic heterocyclic group containing, besides carbon atom, 1, 2 or 3 hetero atoms selected from the group consisting of oxygen atom, sulfur atom and nitrogen atom. Of these, thienyl, pyrazolyl, oxadiazolyl, pyridyl, and pyrimidinyl are more preferable, and thienyl, oxadiazolyl, pyridyl, and pyrimidinyl are particularly preferable.

When $R^2$ is "optionally substituted alkoxy", the alkoxy moiety of the group is as defined above, and is preferably $C_1$-$C_6$ alkoxy, more preferably $C_1$-$C_4$ alkoxy.

When $R^2$ is "optionally substituted cycloalkoxy", the cycloalkoxy moiety of the group is as defined above, and is preferably $C_3$-$C_8$ cycloalkoxy, more preferably $C_3$-$C_6$ cycloalkoxy.

Preferable examples of $R^2$ include a hydrogen atom, optionally substituted $C_1$-$C_6$ alkyl, optionally substituted $C_3$-$C_8$ cycloalkyl, optionally substituted amino, optionally substituted phenyl, an optionally substituted nonaromatic heterocyclic group which is selected from the group consisting of azetidinyl, pyrrolidyl, piperidyl, oxetanyl, tetrahydrofuryl, tetrahydropyranyl, piperazinyl, and morpholinyl, optionally substituted heteroaryl, which is selected from the group consisting of thienyl, pyrazolyl, oxadiazolyl, pyridyl, and pyrimidinyl, optionally substituted $C_1$-$C_6$ alkoxy, and optionally substituted $C_3$-$C_8$ cycloalkoxy. Of these, a hydrogen atom, optionally substituted $C_1$-$C_4$ alkyl, optionally substituted $C_3$-$C_6$ cycloalkyl, optionally substituted amino, optionally substituted phenyl, an optionally substituted nonaromatic heterocyclic group which is selected from the group consisting of azetidinyl, pyrrolidyl, piperidyl, tetrahydrofuryl, tetrahydropyranyl, and morpholinyl, optionally substituted heteroaryl which is selected from the group consisting of thienyl, oxadiazolyl, pyridyl, and pyrimidinyl, and optionally substituted $C_1$-$C_4$ alkoxy are more preferable.

When $R^1$ and $R^2$ are bonded to each other to form, together with the adjacent $X^2$ and carbon atom, an "optionally substituted ring", the ring moiety of the group is as defined above, and is preferably cycloalkene, arene, non-aromatic heterocycle, or heteroarene. Said cycloalkene is as defined above, and monocyclic alicyclic unsaturated hydrocarbon having 1 or 2 carbon-carbon double bonds and 5-8 carbon atoms ($C_5$-$C_8$) is preferable, and cyclohexene is more preferable. Said arene is as defined above, and benzene is preferable. Said non-aromatic heterocycle is as defined above, and a 4- to 7-membered non-aromatic heterocycle containing 1 or 2 nitrogen atoms besides carbon atom is preferable, which is more preferably pyrrolidine, piperidine, dihydroimidazole, imidazolidine, tetrahydropyrazine, or piperazine, particularly preferably piperidine, dihydroimidazole, or imidazolidine. Said heteroarene is as defined above, and 5- to 6-membered monocyclic heteroarene containing, besides carbon atom, 1 or 2 hetero atoms selected from the group consisting of sulfur atom and nitrogen atom is preferable, more preferably thiophene or pyridine.

Preferable examples the "optionally substituted ring" formed by $R^1$ and $R^2$ bonded to each other and together with the adjacent $X^2$ and carbon atom include optionally substituted cyclohexene, optionally substituted benzene, an optionally substituted nonaromatic heterocyclic group, which is selected from the group consisting of pyrrolidine, piperidine, dihydroimidazole, imidazolidine, tetrahydropyrazine, and piperazine, optionally substituted heteroaryl selected from the group consisting of thiophene and pyridine, more preferably, optionally substituted benzene, or optionally substituted nonaromatic heterocyclic group which is selected from the group consisting of piperidine, dihydroimidazole, and imidazolidine.

When $R^3$ is "optionally substituted alkyl", the alkyl moiety of the group is as defined above, and is preferably $C_1$-$C_6$ alkyl, more preferably $C_1$-$C_4$ alkyl.

When $R^3$ is "optionally substituted cycloalkyl", the cycloalkyl moiety of the group is as defined above, and is preferably $C_3$-$C_8$ cycloalkyl, more preferably $C_3$-$C_6$ cycloalkyl.

When $R^3$ is "halogen atom", the halogen atom is as defined above, and is preferably a fluorine atom, a chlorine atom, a bromine atom, or an iodine atom, more preferably a fluorine atom, a chlorine atom, or a bromine atom.

When $R^4$ or $R^5$ is "optionally substituted alkyl", the alkyl moiety of the group is as defined above, and is preferably $C_1$-$C_6$ alkyl, more preferably $C_1$-$C_4$ alkyl.

When $R^4$ and $R^5$ are bonded to each other to form, together with the adjacent $Z^2$ and $Z^3$, "optionally substituted nitrogen-containing non-aromatic heterocycle", the nitrogen-containing non-aromatic heterocycle moiety of the group is as defined above, of which a 4- to 8-membered monocyclic or bicyclic nonaromatic heterocyclic group containing, besides carbon atom, at least one nitrogen atom, and containing 1 or 2 hetero atoms selected from the group consisting of oxygen atom and nitrogen atom is preferable, azetidine, pyrrolidine, pyrazolidine, piperidine, morpholine or azabicyclo[3.1.0]hexane is more preferable, pyrrolidine or piperidine is particularly preferable, and pyrrolidine is most preferable.

When $R^6$ or $R^7$ is "optionally substituted alkyl", the alkyl moiety of the group is as defined above, and is preferably $C_1$-$C_6$ alkyl, more preferably $C_1$-$C_4$ alkyl.

When $R^6$ or $R^7$ is "optionally substituted cycloalkyl", the cycloalkyl moiety of the group is as defined above, and is preferably $C_3$-$C_8$ cycloalkyl, more preferably $C_3$-$C_6$ cycloalkyl.

Preferable examples of $R^6$ and $R^7$ include a hydrogen atom, optionally substituted $C_1$-$C_4$ alkyl, and optionally substituted $C_3$-$C_6$ cycloalkyl, more preferably, a hydrogen atom, and optionally substituted $C_1$-$C_4$ alkyl.

When $R^6$ and $R^7$ are bonded to each other to form, together with the adjacent carbon atom, "optionally substituted cycloalkane", the cycloalkane moiety of the group is as defined above, of which $C_3$-$C_8$ cycloalkane is preferable, $C_3$-$C_6$ cycloalkane is more preferable.

When the "ring" or "group" defined by each symbol in the aforementioned formula (I) or a combination of each symbol is "optionally substituted aromatic group", "optionally substituted alkyl", "optionally substituted cycloalkyl", "optionally substituted aryl", "optionally substituted nonaromatic heterocyclic group", "optionally substituted amino", "optionally substituted heteroaryl", "optionally substituted alkoxy", "optionally substituted cycloalkoxy", "optionally substituted ring", "optionally substituted nitrogen-containing non-aromatic heterocycle" or "optionally substituted cycloalkane", these "ring" and "group" may be unsubstituted, or have one or more, the same or different substituent(s) at substitutable position(s) of each "ring" or "group". The aforementioned "ring" or "group" has substituent(s), the number thereof is preferably 1-7, more preferably 1, 2, or 3.

Examples of the aforementioned substituent of the "ring" or "group" include
(1) alkyl optionally substituted by the same or different 1-7 groups selected from the group consisting of phenyl optionally substituted by 1, 2 or 3 alkoxys, a halogen atom, hydroxy, amino optionally substituted by 1 or 2 alkyls, and alkoxy (preferably, alkyl optionally substituted by the same or different 1, 2 or 3 groups selected from the group consisting of phenyl optionally substituted by 1, 2 or 3 alkoxys, a halogen atom, hydroxy, amino optionally substituted by 1 or 2 alkyls, and alkoxy);
(2) aryl optionally substituted by 1, 2 or 3 alkoxys (preferably, phenyl optionally substituted by 1, 2 or 3 alkoxys);
(3) a nonaromatic heterocyclic group optionally substituted by the same or different 1, 2 or 3 groups selected from the group consisting of alkyl, alkoxy and alkoxycarbonyl (preferably, nonaromatic heterocyclic group which is selected from the group consisting of azetidinyl, pyrrolidyl, piperidyl, oxetanyl, tetrahydrofuryl, tetrahydropyranyl, and morpholinyl and optionally substituted by the same or different 1, 2 or 3 groups selected from the group consisting of alkyl, alkoxy and alkoxycarbonyl);
(4) heteroaryl optionally substituted by 1 or 2 oxos (preferably, pyridine, or isoindolinyl optionally substituted by 1 or 2 oxos);
(5) cyano;
(6) a halogen atom;
(7) hydroxy;
(8) oxo;
(9) amino optionally substituted by 1 or 2 groups selected from the group consisting of alkyl, halogenoalkyl, alkoxyalkyl, alkoxycarbonyl and phenylalkoxycarbonyl;
(10) alkylsulfonyl;
(11) phenylsulfonyl;
(12) alkoxy optionally substituted by 1-7 halogen atoms (preferably, alkoxy optionally substituted by 1, 2 or 3 halogen atoms);
(13) alkanoyloxy;
(14) alkoxycarbonyl; and
(15) alkylidene.

The substituent of the aforementioned "ring" or "group" defined by each symbol or a combination of each symbol is more specifically explained below.

Examples of preferable substituent of ring A (optionally substituted aromatic group) include
(1) alkyl optionally substituted by the same or different 1-7 groups selected from the group consisting of a halogen atom, amino optionally substituted by 1 or 2 alkyls, and alkoxy (preferably alkyl optionally substituted by the same or different 1, 2 or 3 groups selected from the group consisting of a halogen atom, amino optionally substituted by 1 or 2 alkyls, and alkoxy);
(2) cyano;
(3) a halogen atom;
(4) amino optionally substituted by 1 or 2 alkyls; and
(5) alkoxy optionally substituted by 1-7 halogen atoms (preferably alkoxy optionally substituted by 1, 2 or 3 halogen atoms).

Of those mentioned above, more preferable substituent is
(1) alkyl, or (2) a halogen atom.

When $R^1$ is "optionally substituted alkyl", examples of the preferable substituent of the group include
(1) aryl optionally substituted by 1, 2 or 3 alkoxys (preferably, phenyl optionally substituted by 1, 2 or 3 alkoxys);
(2) nonaromatic heterocyclic group optionally substituted by the same or different 1, 2 or 3 groups selected from the group consisting of alkyl and alkoxycarbonyl (preferably, nonaromatic heterocyclic group which is selected from the group consisting of pyrrolidyl, piperidyl, oxetanyl, tetrahydrofuryl, and tetrahydropyranyl and optionally substituted by the same or different 1, 2 or 3 groups selected from the group consisting of alkyl and alkoxycarbonyl);
(3) a halogen atom;
(4) hydroxy;
(5) amino optionally substituted by 1 or 2 groups selected from the group consisting of alkyl, halogenoalkyl, and alkoxycarbonyl; and
(6) alkoxy.

When $R^1$ is "optionally substituted cycloalkyl", "optionally substituted aryl", or "optionally substituted nonaromatic heterocyclic group", examples of the preferable substituent of the group include
(1) alkyl optionally substituted by 1, 2 or 3 alkoxys;
(2) aryl optionally substituted by 1, 2 or 3 alkoxys (preferably, phenyl optionally substituted by 1, 2 or 3 alkoxys);
(3) a nonaromatic heterocyclic group optionally substituted by the same or different 1, 2 or 3 groups selected from the group consisting of alkyl and alkoxycarbonyl (preferably, a nonaromatic heterocyclic group which is selected from the group consisting of pyrrolidyl, piperidyl, oxetanyl, tetrahydrofuryl, and tetrahydropyranyl and optionally substituted by the same or different 1, 2 or 3 groups selected from the group consisting of alkyl and alkoxycarbonyl);

(4) a halogen atom;
(5) hydroxy;
(6) amino optionally substituted by 1 or 2 groups selected from the group consisting of alkyl, halogenoalkyl, and alkoxycarbonyl; and
(7) alkoxy.

Of the above-mentioned substituents for $R^1$, more preferable substituents include (1) a nonaromatic heterocyclic group selected from the group consisting of oxetanyl, and tetrahydropyranyl;
(2) a halogen atom;
(3) amino optionally substituted by the same or different 1 or 2 groups selected from the group consisting of alkyl, and halogenoalkyl; and
(4) alkoxy.

When $R^2$ is "optionally substituted alkyl" or "optionally substituted alkoxy", preferable substituents of the group include (1) aryl optionally substituted by 1, 2 or 3 alkoxys (preferably, phenyl optionally substituted by 1, 2 or 3 alkoxys);
(2) nonaromatic heterocyclic group optionally substituted by 1, 2 or 3 alkoxys (preferably, nonaromatic heterocyclic group which is selected from the group consisting of azetidinyl, pyrrolidyl, piperidyl, and morpholinyl and optionally substituted by 1, 2 or 3 alkoxys, and a nonaromatic heterocyclic group);
(3) heteroaryl optionally substituted by 1 or 2 oxos (preferably, pyridine, or isoindolinyl optionally substituted 1 or 2 oxos);
(4) cyano;
(5) a halogen atom;
(6) hydroxy;
(7) oxo;
(8) amino optionally substituted by the same or different 1 or 2 groups selected from the group consisting of alkyl, halogenoalkyl, alkoxyalkyl and alkoxycarbonyl;
(9) alkylsulfonyl;
(10) phenylsulfonyl;
(11) alkoxy optionally substituted by 1-7 halogen atoms (preferably, alkoxy optionally substituted by 1, 2 or 3 halogen atoms);
(12) alkanoyloxy; and
(13) alkylidene.

Of these, more preferable substituents include
(1) phenyl;
(2) a nonaromatic heterocyclic group selected from the group consisting of piperidyl, and morpholinyl;
(3) heteroaryl selected from the group consisting of pyridine, and isoindolinyl;
(4) cyano;
(5) a halogen atom;
(6) hydroxy;
(7) oxo;
(8) amino optionally substituted by the same or different 1 or 2 groups selected from the group consisting of alkyl, and alkoxyalkyl;
(9) phenylsulfonyl; and
(10) alkoxy.

When $R^2$ is "optionally substituted cycloalkyl", "optionally substituted amino", "optionally substituted aryl", "optionally substituted nonaromatic heterocyclic group", "optionally substituted heteroaryl", or "optionally substituted cycloalkoxy", examples of the preferable substituent of the group include (1) alkyl optionally substituted by the same or different 1-7 groups selected from the group consisting of phenyl optionally substituted by 1, 2 or 3 alkoxys, a halogen atom, hydroxy, amino optionally substituted by 1 or 2 alkyls, and alkoxy (preferably, alkyl phenyl optionally substituted by the same or different 1, 2 or 3 groups selected from the group consisting of phenyl optionally substituted by 1, 2 or 3 alkoxys, a halogen atom, hydroxy, amino optionally substituted by 1 or 2 alkyls, and alkoxy);
(2) aryl optionally substituted by 1, 2 or 3 alkoxys (preferably, phenyl optionally substituted by 1, 2 or 3 alkoxys);
(3) nonaromatic heterocyclic group optionally substituted by 1, 2 or 3 alkoxys (preferably, nonaromatic heterocyclic group which is selected from the group consisting of azetidinyl, pyrrolidyl, piperidyl, and morpholinyl and optionally substituted by 1, 2 or 3 alkoxys);
(4) heteroaryl optionally substituted by 1 or 2 oxos (preferably, pyridine, or isoindolinyl optionally substituted by 1 or 2 oxos);
(5) cyano;
(6) a halogen atom;
(7) hydroxy;
(8) oxo;
(9) amino optionally substituted by the same or different 1 or 2 groups selected from the group consisting of alkyl, halogenoalkyl, alkoxyalkyl and alkoxycarbonyl;
(10) alkylsulfonyl;
(11) phenylsulfonyl;
(12) alkoxy optionally substituted by 1-7 halogen atoms (preferably, alkoxy optionally substituted by 1, 2 or 3 halogen atoms);
(13) alkanoyloxy; and
(14) alkylidene.

Of these, more preferable substituents when $R^2$ is "optionally substituted alkyl" or "optionally substituted alkoxy" include (1) phenyl;
(2) a nonaromatic heterocyclic group selected from the group consisting of piperidyl, and morpholinyl;
(3) heteroaryl selected from the group consisting of pyridine, and isoindolinyl;
(4) cyano;
(5) a halogen atom;
(6) hydroxy;
(7) oxo;
(8) amino optionally substituted by the same or different 1 or 2 groups selected from the group consisting of alkyl, and alkoxyalkyl;
(9) phenylsulfonyl; and
(10) alkoxy.

When $R^2$ is "optionally substituted cycloalkyl", "optionally substituted amino", "optionally substituted aryl", "optionally substituted nonaromatic heterocyclic group", "optionally substituted heteroaryl", or "optionally substituted cycloalkoxy", more preferable substituents include (1) alkyl optionally substituted by the same or different 1-7 groups selected from the group consisting of a halogen atom, and alkoxy (preferably, alkyl optionally substituted by the same or different 1, 2 or 3 groups selected from the group consisting of a halogen atom, and alkoxy);
(2) phenyl;
(3) a nonaromatic heterocyclic group selected from the group consisting of piperidyl, and morpholinyl;

19

(4) heteroaryl selected from the group consisting of pyridine, and isoindolinyl;
(5) cyano;
(6) a halogen atom;
(7) hydroxy;
(8) oxo;
(9) amino optionally substituted by the same or different 1 or 2 groups selected from the group consisting of alkyl, and alkoxyalkyl;
(10) phenylsulfonyl; and
(11) alkoxy.

When $R^1$ and $R^2$ are bonded to each other to form, together with the adjacent $X^2$ and carbon atom, "optionally substituted ring", preferable substituent on the ring includes
(1) alkyl optionally substituted by 1-7 halogen atoms (preferably, alkyl optionally substituted by 1, 2 or 3 halogen atoms); and
(2) a halogen atom.

When $R^3$ is "optionally substituted alkyl", or "optionally substituted cycloalkyl", preferable substituent of the group includes a halogen atom.

When $R^4$ and $R^5$ are each "optionally substituted alkyl", and when $R^4$ and $R^5$ are bonded to each other to form, together with the adjacent $Z^2$ and $Z^3$, "optionally substituted nitrogen-containing non-aromatic heterocycle", preferable substituent of the group or on the ring includes, respectively,
(1) a halogen atom; and
(2) amino optionally substituted by the same or different 1 or 2 groups selected from the group consisting of alkoxycarbonyl and phenylalkoxycarbonyl.

Of these, a halogen atom is more preferable.

When $R^6$ and $R^7$ are each "optionally substituted alkyl", or "optionally substituted cycloalkyl", and when $R^6$ and $R^7$ are bonded to each other to form, together with the adjacent carbon atom, "optionally substituted cycloalkane", preferable substituent of the group or on the ring includes, respectively, a halogen atom, and alkoxy.

One embodiment of the present invention (hereinafter sometimes to be abbreviated as embodiment A) is a compound wherein a part represented by the following formula in the aforementioned formula (I):

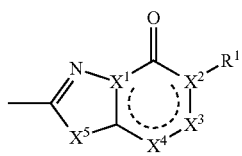

(hereinafter sometimes to be abbreviated as partial structure A) is a group represented by the following formula (iv-a), (iv-b), (iv-c), (iv-d), (iv-e), (iv-f), or (iv-g):

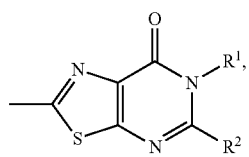

(iv-a)

20

-continued

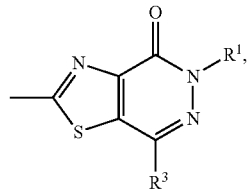

(iv-b)

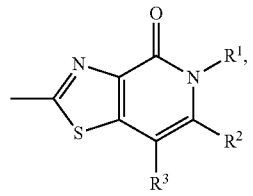

(iv-c)

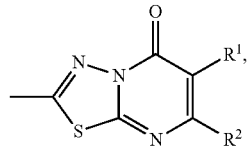

(iv-d)

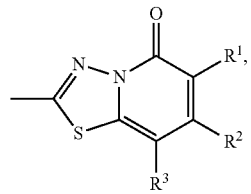

(iv-e)

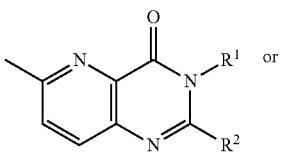

(iv-f)

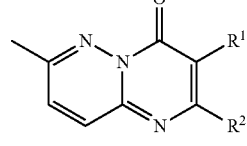

(iv-g)

wherein the symbols are as defined above, or a pharmacologically acceptable salt thereof.

Of the compounds of the aforementioned embodiment A, a compound wherein the partial structure A is a group represented by the above-mentioned formula (iv-a), (iv-c), or (iv-d), or a pharmacologically acceptable salt thereof is more preferable, a compound wherein the partial structure A is a group represented by the above-mentioned formula (iv-a), or a pharmacologically acceptable salt thereof is particularly preferable.

When the compound (I) of the present invention including the aforementioned embodiment A is more specifically explained, a compound of the formula (I), wherein
ring A is a 5- to 11-membered monocyclic or bicyclic aromatic group optionally containing, besides carbon atom, 1-4 hetero atoms selected from the group consisting of oxygen atom, sulfur atom and nitrogen atom (said aromatic group is optionally substituted by the same or different 1, 2 or 3 groups selected from the group consisting of (1) alkyl optionally substituted by the same or different 1-7 groups selected from the group consisting of amino optionally substituted by 1 or 2 alkyls, alkoxy, and a halogen atom; (2) cyano; (3) amino optionally substituted by 1 or 2 alkyls; (4) alkoxy optionally substituted by 1-7 halogen atoms; and (5) a halogen atom), $R^1$ is (a) a hydrogen atom; (b) alkyl optionally substituted by the same or different 1-7 groups selected from the group consisting of amino (said amino is optionally substituted by the same or different 1 or 2 groups selected from the group consisting of alkyl, halogenoalkyl, and alkoxycarbonyl), hydroxy, alkoxy, a halogen atom, phenyl, alkoxyphenyl, and a 4- to 7-membered monocyclic nonaromatic heterocyclic group containing, besides carbon atom, 1 or 2 hetero atoms selected from the group consisting of oxygen atom, sulfur atom and nitrogen atom (said nonaromatic heterocyclic group is optionally substituted by the same or different 1, 2 or 3 groups selected from the group consisting of alkyl, and alkoxycarbonyl); (c) cycloalkyl optionally substituted by 1, 2 or 3 alkoxyalkyls; (d) a halogen atom; (e) phenyl; or (f) a 4- to 7-membered monocyclic nonaromatic heterocyclic group containing, besides carbon atom, 1 or 2 hetero atoms selected from the group consisting of oxygen atom, sulfur atom and nitrogen atom (said nonaromatic heterocyclic group is optionally substituted by the same or different 1, 2 or 3 groups selected from the group consisting of alkyl, and alkoxycarbonyl), $R^2$ is (a) a hydrogen atom; (b) alkyl optionally substituted by the same or different 1-7 groups selected from the group consisting of alkylidene, cyano, amino (said amino is optionally substituted by the same or different 1 or 2 groups selected from the group consisting of alkyl, alkoxyalkyl, halogenoalkyl, and alkoxycarbonyl), hydroxy, alkoxy, alkylsulfonyloxy, oxo, phenylsulfonyl, a halogen atom, phenyl, 5- to 11-membered monocyclic or bicyclic heteroaryl containing, besides carbon atom, 1-4 hetero atoms selected from the group consisting of oxygen atom, sulfur atom and nitrogen atom (said heteroaryl is optionally substituted by 1 or 2 oxos), and a 4- to 7-membered monocyclic nonaromatic heterocyclic group containing, besides carbon atom, 1 or 2 hetero atoms selected from the group consisting of oxygen atom, sulfur atom and nitrogen atom (said nonaromatic heterocyclic group is optionally substituted by alkoxy); (c) cycloalkyl optionally substituted by the same or different 1, 2 or 3 groups selected from the group consisting of alkyl, alkoxyalkyl, halogenoalkyl, cyano, hydroxy, alkoxy, alkanoyloxy, and a halogen atom; (d) amino optionally substituted by the same or different 1 or 2 groups selected from the group consisting of alkyl and alkoxyphenylalkyl; (e) alkoxy optionally substituted by the same or different 1, 2 or 3 groups selected from the group consisting of amino (said amino is optionally substituted by the same or different 1 or 2 groups selected from the group consisting of alkyl, and alkoxycarbonyl), and a halogen atom; (f) cycloalkoxy optionally substituted by alkyl; (g) phenyl optionally substituted by the same or different 1, 2 or 3 groups selected from the group consisting of alkyl (said alkyl is optionally substituted by the same or different 1, 2 or 3 groups selected from the group consisting of alkylamino, dialkylamino, hydroxy, and a halogen atom), alkoxy optionally substituted by 1, 2 or 3 halogen atoms, alkylsulfonyl, and a halogen atom; (h) 5- to 6-membered monocyclic heteroaryl containing, besides carbon atom, 1-4 hetero atoms selected from the group consisting of oxygen atom, sulfur atom and nitrogen atom (said heteroaryl is optionally substituted by the same or different 1, 2 or 3 groups selected from the group consisting of alkyl, alkoxy, and a halogen atom); or (i) a 4- to 7-membered monocyclic nonaromatic heterocyclic group containing, besides carbon atom, 1 or 2 hetero atoms selected from the group consisting of oxygen atom, sulfur atom and nitrogen atom (said nonaromatic heterocyclic group is optionally substituted by the same or different 1, 2 or 3 groups selected from the group consisting of alkyl, halogenoalkyl, and alkoxy), or, $R^1$ and $R^2$ are bonded to each other to form, together with the adjacent $X^2$ and carbon atom, a ring selected from the group consisting of 4- to 7-membered ($C_4$-$C_7$) cycloalkene, benzene, a 4- to 7-membered monocyclic non-aromatic heterocycle containing, besides carbon atom, 1 or 2 hetero atoms selected from the group consisting of oxygen atom, sulfur atom and nitrogen atom, and 5- to 6-membered monocyclic heteroarene containing, besides carbon atom, 1-4 hetero atoms selected from the group consisting of oxygen atom, sulfur atom and nitrogen atom (said ring is optionally substituted by the same or different 1, 2 or 3 groups selected from the group consisting of alkyl, halogenoalkyl, alkoxycarbonyl, and a halogen atom), $R^3$ is (a) a hydrogen atom; (b) alkyl optionally substituted by 1, 2 or 3 halogen atoms; (c) cycloalkyl; or (d) a halogen atom, $R^4$ and $R^5$ are each independently a hydrogen atom, or alkyl, or, $R^4$ and $R^5$ are bonded to each other to form, together with the adjacent $Z^2$ and $Z^3$, 4- to 12-membered monocyclic or bicyclic nitrogen-containing non-aromatic heterocycle containing, besides carbon atom, at least one nitrogen atom and 1-4 hetero atoms selected from the group consisting of oxygen atom, sulfur atom and nitrogen atom (said nitrogen-containing non-aromatic heterocycle is optionally substituted by the same or different 1, 2 or 3 groups selected from the group consisting of amino optionally substituted by a group selected from the group consisting of alkoxycarbonyl and phenylalkoxycarbonyl, and a halogen atom), and $R^6$ and $R^7$ are each independently (a) a hydrogen atom; (b) alkyl optionally substituted by the same or different 1, 2 or 3 groups selected from the group consisting of alkoxy, and a halogen atom; or (c) cycloalkyl, or, $R^6$ and $R^7$ are bonded to each other to form, together with the adjacent carbon atom, cycloalkane, or a pharmacologically acceptable salt thereof can be mentioned.

Of the embodiments, a more preferable embodiment is a compound wherein ring A is an aromatic group selected from the group consisting of phenyl, tetrahydronaphthyl, indanyl, furyl, thienyl, pyrazolyl, isoxazolyl, thiazolyl, pyridyl, pyrimidinyl, pyrazyl, indolinyl, tetrahydroquinolyl, thienopyridyl, dihydrobenzofuranyl, benzodioxolanyl, and triazolopyridine (said aromatic group is optionally substituted by the same or different 1, 2 or 3 groups selected from the group consisting of (1) alkyl optionally substituted by a group selected from the group consisting of amino optionally substituted by 1 or 2 alkyls, and alkoxy; (2) halogenoalkyl; (3) cyano; (4) amino optionally substituted by 1 or 2 alkyls; (5) alkoxy; (6) halogenoalkoxy, and (7) a halogen atom), $R^1$ is (a) a hydrogen atom; (b) alkyl optionally substituted by a group selected from the group consisting of amino (said amino is optionally substituted by the same or different 1 or 2 groups selected from the group consisting of alkyl, halogenoalkyl, and alkoxycarbonyl), hydroxy, alkoxy, alkoxyphenyl, and a nonaromatic heterocyclic group selected from the group consisting of pyrrolidyl, piperidyl, oxetanyl, tetrahydrofuryl, and tetrahydropyranyl (said nonaromatic heterocyclic group is optionally substituted by a group selected from the group consisting of alkyl, and alkoxycarbonyl); (c) halogenoalkyl; (d) cycloalkyl optionally substituted by alkoxyalkyl; (e) a halogen atom; (f) phenyl; or (g) a nonaromatic heterocyclic group selected from the group consisting of pyrrolidyl, piperidyl, oxetanyl, tetrahydrofuryl, dihydropyranyl, tetrahydropyranyl, and morpholinyl (said nonaromatic heterocyclic group is optionally substituted by a group selected from the group consisting of alkyl, and alkoxycarbonyl), $R^2$ is (a) a hydrogen atom; (b) alkyl optionally substituted by the same or different 1 or 2 groups selected from the group consisting of alkylidene, cyano, amino (said amino is optionally substituted by the same or different 1 or 2 groups selected from the group consisting of alkyl, alkoxyalkyl, halogenoalkyl, and alkoxycarbonyl), hydroxy, alkoxy, alkylsulfonyloxy, oxo, isoindolinyl optionally substituted by 1 or 2 oxos, and a nonaromatic heterocyclic group selected from the group consisting of azetidinyl, pyrrolidyl, piperidyl, and morpholinyl (said nonaromatic heterocyclic group is optionally substituted by alkoxy); (c) halogenoalkyl optionally substituted by a group selected from the group consisting of amino (said amino is optionally substituted by the same or different 1 or 2 groups selected from the group consisting of alkyl, and alkoxycarbonyl), alkoxy, phenylsulfonyl, phenyl, and pyridyl; (d) cycloalkyl optionally substituted by a group selected from the group consisting of alkyl, alkoxyalkyl, halogenoalkyl, cyano, hydroxy, alkoxy, and alkanoyloxy; (e) halogenocycloalkyl; (f) amino optionally substituted by the same or different 1 or 2 groups selected from the group consisting of alkyl and alkoxyphenylalkyl; (g) alkoxy optionally substituted by amino (said amino is optionally substituted by the same or different 1 or 2 groups selected from the group consisting of alkyl, and alkoxycarbonyl); (h) halogenoalkoxy; (i) cycloalkoxy optionally substituted by alkyl; (j) phenyl optionally substituted by the same or different 1, 2 or 3 groups selected from the group consisting of alkyl (said alkyl is optionally substituted by the same or different 1, 2 or 3 groups selected from the group consisting of dialkylamino, hydroxy, and a halogen atom), alkoxy optionally substituted by 1, 2 or 3 halogen atoms, alkylsulfonyl, and a halogen atom; (k) heteroaryl selected from the group consisting of thienyl, pyrazolyl, oxadiazolyl, pyridyl, and pyrimidinyl (said heteroaryl is optionally substituted by the same or different 1 or 2 groups selected from the group consisting of alkyl, alkoxy, and a halogen atom); or (l) a nonaromatic heterocyclic group selected from the group consisting of azetidinyl, pyrrolidyl, piperidyl, oxetanyl, tetrahydrofuryl, tetrahydropyranyl, piperazinyl, and morpholinyl (said nonaromatic heterocyclic group is optionally substituted by a group selected from the group consisting of alkyl, halogenoalkyl, and alkoxy), or, $R^1$ and $R^2$ are bonded to each other to form, together with the adjacent $X^2$ and carbon atom, a ring selected from the group consisting of (1) 4- to 7-membered ($C_4$-$C_7$) cycloalkene, (2) benzene, (3) non-aromatic heterocycle selected from the group consisting of pyrrolidine, piperidine, dihydroimidazole, imidazolidine, and piperazine, and (4) heteroarene selected from the group consisting of thiophene, and pyridine (said ring is optionally substituted by the same or different 1 or 2 groups selected from the group consisting of alkyl, halogenoalkyl, alkoxycarbonyl, and a halogen atom), $R^3$ is (a) a hydrogen atom; (b) alkyl optionally substituted by 1, 2 or 3 halogen atoms; (c) cycloalkyl; or (d) a halogen atom, $R^4$ is a hydrogen atom, or alkyl, $R^5$ is alkyl, or, $R^4$ and $R^5$ are bonded to each other to form, together with the adjacent $Z^2$ and $Z^3$, nitrogen-containing non-aromatic heterocycle selected from the group consisting of azetidine, pyrrolidine, pyrazolidine, piperidine, morpholine, and azabicyclo[3.1.0]hexane (said nitrogen-containing non-aromatic heterocycle is optionally substituted by the same or different 1 or 2 groups selected from the group consisting of amino optionally substituted by a group selected from the group consisting of alkoxycarbonyl and phenylalkoxycarbonyl, and a halogen atom), $R^6$ and $R^7$ are each independently (a) a hydrogen atom; (b) alkyl optionally substituted by the same or different 1, 2 or 3 groups selected from the group consisting of alkoxy, and a halogen atom; or (c) cycloalkyl, or, $R^6$ and $R^7$ are bonded to each other to form, together with the adjacent carbon atom, cycloalkane, or a pharmacologically acceptable salt thereof can be mentioned.

A specifically preferable embodiment of the present invention including the above-mentioned embodiment A (hereinafter sometimes to be abbreviated as embodiment B) is a compound wherein a part represented by the following formula in the aforementioned formula (I):

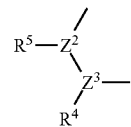

(hereinafter sometimes to be referred to as partial structure B) is the following formula (v):

(v)

wherein the symbols are as defined above, or a pharmacologically acceptable salt thereof.

When the compound (I) of the present invention including the aforementioned embodiment B is more specifically explained, a compound of the formula (I), wherein ring A is a 5- to 11-membered monocyclic or bicyclic aromatic group optionally containing, besides carbon atom, 1-4 hetero atoms selected from the group consisting of oxygen atom, sulfur atom and nitrogen atom (said aromatic group is optionally substituted by the same or different 1, 2 or 3 groups selected from the group consisting of (1) alkyl optionally substituted by the same or different 1-7 groups selected from the group consisting of amino optionally substituted by 1 or 2 alkyls, alkoxy, and a halogen atom; (2) cyano; (3) amino optionally substituted by 1 or 2 alkyls; (4) alkoxy; and (5) a halogen atom), $R^1$ is (a) a hydrogen atom; (b) alkyl optionally substituted by the same or different 1-7 groups selected from the group consisting of amino (said amino is optionally substituted by the same or different 1 or 2 groups selected from the group consisting of alkyl, halogenoalkyl, and alkoxycarbonyl), hydroxy, alkoxy, a halogen atom, phenyl, alkoxyphenyl, and a 4- to 7-membered monocyclic nonaromatic heterocyclic group containing, besides carbon atom, 1 or 2 hetero atoms selected from the group consisting of oxygen atom, sulfur atom and nitrogen atom (said nonaromatic heterocyclic group is optionally substituted by the same or different 1, 2 or 3 groups selected from the group consisting of alkyl, and alkoxycarbonyl); (c) cycloalkyl optionally substituted by 1, 2 or 3 alkoxyalkyls; (d) a halogen atom; (e) phenyl; or (f) a 4- to 7-membered monocyclic nonaromatic heterocyclic group containing, besides carbon atom, 1 or 2 hetero atoms selected from the group consisting of oxygen atom, sulfur atom and nitrogen atom (said nonaromatic heterocyclic group is optionally substituted by the same or different 1, 2 or 3 groups selected from the group consisting of alkyl, and alkoxycarbonyl), $R^2$ is (a) a hydrogen atom; (b) alkyl optionally substituted by the same or different 1-7 groups selected from the group consisting of alkylidene, amino (said amino is optionally substituted by the same or different 1 or 2 groups selected from the group consisting of alkyl, alkoxyalkyl, halogenoalkyl, and alkoxycarbonyl), hydroxy, alkoxy, alkylsulfonyloxy, oxo, phenylsulfonyl, a halogen atom, phenyl, 5- to 11-membered monocyclic or bicyclic heteroaryl containing, besides carbon atom, 1-4 hetero atoms selected from the group consisting of oxygen atom, sulfur atom and nitrogen atom (said heteroaryl is optionally substituted by 1 or 2 oxos), and a 4- to 7-membered monocyclic nonaromatic heterocyclic group containing, besides carbon atom, 1 or 2 hetero atoms selected from the group consisting of oxygen atom, sulfur atom and nitrogen atom (said nonaromatic heterocyclic group is optionally substituted by alkoxy); (c) cycloalkyl optionally substituted by the same or different 1, 2 or 3 groups selected from the group consisting of alkoxyalkyl, halogenoalkyl, cyano, hydroxy, alkoxy, and a halogen atom; (d) amino optionally substituted by the same or different 1 or 2 groups selected from the group consisting of alkyl and alkoxyphenylalkyl; (e) alkoxy optionally substituted by the same or different 1, 2 or 3 groups selected from the group consisting of amino (said amino is optionally substituted by the same or different 1 or 2 groups selected from the group consisting of alkyl, and alkoxycarbonyl), and a halogen atom; (f) phenyl optionally substituted by the same or different 1, 2 or 3 groups selected from the group consisting of alkyl (said alkyl is optionally substituted by the same or different 1, 2 or 3 groups selected from the group consisting of alkylamino, dialkylamino, hydroxy, and a halogen atom), alkoxy optionally substituted by 1, 2 or 3 halogen atoms, alkylsulfonyl, and a halogen atom (g) 5- to 6-membered monocyclic heteroaryl containing, besides carbon atom, 1-4 hetero atoms selected from the group consisting of oxygen atom, sulfur atom and nitrogen atom (said heteroaryl is optionally substituted by the same or different 1, 2 or 3 groups selected from the group consisting of alkyl, alkoxy, and a halogen atom); or (h) a 4- to 7-membered monocyclic nonaromatic heterocyclic group containing, besides carbon atom, 1 or 2 hetero atoms selected from the group consisting of oxygen atom, sulfur atom and nitrogen atom (said nonaromatic heterocyclic group is optionally substituted by the same or different 1, 2 or 3 groups selected from the group consisting of alkyl, halogenoalkyl, and alkoxy), or, $R^1$ and $R^2$ are bonded to each other to form, together with the adjacent $X^2$ and carbon atom, a ring selected from the group consisting of 4- to 7-membered ($C_4$-$C_7$) cycloalkene, benzene, a 4- to 7-membered monocyclic non-aromatic heterocycle containing, besides carbon atom, 1 or 2 hetero atoms selected from the group consisting of oxygen atom, sulfur atom and nitrogen atom, and 5- to 6-membered monocyclic heteroarene containing, besides carbon atom, 1-4 hetero atoms selected from the group consisting of oxygen atom, sulfur atom and nitrogen atom (said ring is optionally substituted by the same or different 1, 2 or 3 groups selected from the group consisting of alkyl, halogenoalkyl, alkoxycarbonyl, and a halogen atom), $R^3$ is (a) a hydrogen atom; (b) alkyl optionally substituted by 1, 2 or 3 halogen atoms; (c) cycloalkyl; or (d) a halogen atom, $R^4$ and $R^5$ are each independently a hydrogen atom, or alkyl, or, $R^4$ and $R^5$ are bonded to each other to form, together with the adjacent $Z^2$ and $Z^3$, 4- to 12-membered monocyclic or bicyclic nitrogen-containing non-aromatic heterocycle containing, besides carbon atom, at least one nitrogen atom and 1-4 hetero atoms selected from the group consisting of oxygen atom, sulfur atom and nitrogen atom (said nitrogen-containing non-aromatic heterocycle is optionally substituted by the same or different 1, 2 or 3 groups selected from the group consisting of amino optionally substituted by a group selected from the group consisting of alkoxycarbonyl and phenylalkoxycarbonyl, and a halogen atom), and $R^6$ and $R^7$ are each independently (a) a hydrogen atom; (b) alkyl optionally substituted by the same or different 1, 2 or 3 groups selected from the group consisting of alkoxy, and a halogen atom; or (c) cycloalkyl, or, $R^6$ and $R^7$ are bonded to each other to form, together with the adjacent carbon atom, cycloalkane, or a pharmacologically acceptable salt thereof can be mentioned.

Of the embodiments, a more preferable embodiment is a compound wherein ring A is an aromatic group selected from the group consisting of phenyl, tetrahydronaphthyl, furyl, thienyl, pyrazolyl, isoxazolyl, thiazolyl, pyridyl, pyrimidinyl, pyrazyl, dihydrobenzofuranyl, benzodioxolanyl, and triazolopyridine (said aromatic group is optionally substituted by the same or different 1, 2 or 3 groups selected from the group consisting of (1) alkyl optionally substituted by a group selected from the group consisting of amino optionally substituted by 1 or 2 alkyls, and alkoxy; (2) halogenoalkyl; (3) cyano; (4) amino optionally substituted by 1 or 2 alkyls; (5) alkoxy; and (6) a halogen atom), $R^1$ is (a) a hydrogen atom; (b) alkyl optionally substituted by a group selected from the group consisting of amino (said amino is optionally substituted by the same or different 1 or 2 groups selected from the group consisting of alkyl, halogenoalkyl, and alkoxycarbonyl), hydroxy, alkoxy, alkoxyphenyl, and a nonaromatic heterocyclic group selected from the group consisting of pyrrolidyl, piperidyl, oxetanyl, tetrahydrofuryl, and tetrahydropyranyl (said nonaromatic heterocyclic group is optionally substituted by a group selected from the group consisting of alkyl, and alkoxycarbonyl); (c) halogenoalkyl; (d) cycloalkyl optionally substituted by alkoxyalkyl; (e) a halogen atom; (f) phenyl; or (g) a nonaromatic heterocyclic group selected from the group consisting of pyrrolidyl, piperidyl, oxetanyl, tetrahydrofuryl, dihydropyranyl, tetrahydropyranyl, and morpholinyl (said nonaromatic heterocyclic group is optionally substituted by a group selected from the group consisting of alkyl, and alkoxycarbonyl), $R^2$ is (a) a hydrogen atom; (b) alkyl optionally substituted by the same or different 1 or 2 groups selected from the group consisting of alkylidene, amino (said amino is optionally substituted by the same or different 1 or 2 groups selected from the group consisting of alkyl, alkoxyalkyl, halogenoalkyl, and alkoxycarbonyl), hydroxy, alkoxy, alkylsulfonyloxy, oxo, isoindolinyl optionally substituted by 1 or 2 oxos, and a nonaromatic heterocyclic group selected from the group consisting of azetidinyl, pyrrolidyl, piperidyl, and morpholinyl (said nonaromatic heterocyclic group is optionally substituted by alkoxy); (c) halogenoalkyl optionally substituted by a group selected from the group consisting of amino (said amino is optionally substituted by the same or different 1 or 2 groups selected from the group consisting of alkyl, and alkoxycarbonyl), alkoxy, phenylsulfonyl, phenyl, and pyridyl; (d) cycloalkyl optionally substituted by a group selected from the group consisting of alkoxyalkyl, halogenoalkyl, cyano, hydroxy, and alkoxy; (e) halogenocycloalkyl; (f) amino optionally substituted by the same or different 1 or 2 groups selected from the group consisting of alkyl and alkoxyphenylalkyl; (g) alkoxy optionally substituted by amino (said amino is optionally substituted by the same or different 1 or 2 groups selected from the group consisting of alkyl, and alkoxycarbonyl); (h) halogenoalkoxy; (i) phenyl optionally substituted by the same or different 1, 2 or 3 groups selected from the group consisting of alkyl (said alkyl is optionally substituted by the same or different 1, 2 or 3 groups selected from the group consisting of dialkylamino, hydroxy, and a halogen atom), alkoxy optionally substituted by 1, 2 or 3 halogen atoms, alkylsulfonyl, and a halogen atom; (j) heteroaryl selected from the group consisting of thienyl, pyrazolyl, oxadiazolyl, pyridyl, and pyrimidinyl (said heteroaryl is optionally substituted by the same or different 1 or 2 groups selected from the group consisting of alkyl, alkoxy, and a halogen atom); or (k) a nonaromatic heterocyclic group selected from the group consisting of azetidinyl, pyrrolidyl, piperidyl, tetrahydrofuryl, tetrahydropyranyl, piperazinyl, and morpholinyl (said nonaromatic heterocyclic group is optionally substituted by a group selected from the group consisting of alkyl, halogenoalkyl, and alkoxy), or, $R^1$ and $R^2$ are bonded to each other to form, together with the adjacent $X^2$ and carbon atom, a ring selected from the group consisting of (1) 4- to 7-membered ($C_4$-$C_7$) cycloalkene, (2) benzene, (3) non-aromatic heterocycle selected from the group consisting of pyrrolidine, piperidine, dihydroimidazole, imidazolidine, and piperazine, and (4) heteroarene selected from the group consisting of thiophene, and pyridine (said ring is optionally substituted by the same or different 1 or 2 groups selected from the group consisting of alkyl, halogenoalkyl, alkoxycarbonyl, and a halogen atom), $R^3$ is (a) a hydrogen atom; (b) alkyl optionally substituted by 1, 2 or 3 halogen atoms; (c) cycloalkyl; or (d) a halogen atom, $R^4$ is a hydrogen atom, or alkyl, $R^5$ is alkyl, or, $R^4$ and $R^5$ are bonded to each other to form, together with the adjacent $Z^2$ and $Z^3$, nitrogen-containing non-aromatic heterocycle selected from the group consisting of azetidine, pyrrolidine, piperidine, morpholine, and
azabicyclo[3.1.0]hexane (said nitrogen-containing non-aromatic heterocycle is optionally substituted by the same or different 1 or 2 groups selected from the group consisting of amino optionally substituted by a group selected from the group consisting of alkoxycarbonyl and phenylalkoxycarbonyl, and a halogen atom), $R^6$ and $R^7$ are each independently (a) a hydrogen atom; (b) alkyl optionally substituted by the same or different 1, 2 or 3 groups selected from the group consisting of alkoxy, and a halogen atom; or (c) cycloalkyl, or, $R^6$ and $R^7$ are bonded to each other to form, together with the adjacent carbon atom, cycloalkane, or a pharmacologically acceptable salt thereof can be mentioned.

In the compound of the above-mentioned embodiment B, a compound wherein $Z^1$ is a group represented by —C($R^6$)($R^7$)—NH— is more preferable.

In the embodiment of the present invention including the above-mentioned embodiment A, other preferable embodiment (hereinafter sometimes to be abbreviated as embodiment C) is specifically a compound wherein a part represented by the following formula:

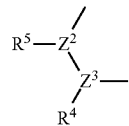

(partial structure B) is shown by the formula (vi):

(vi)

wherein the symbols are as defined above, or a pharmacologically acceptable salt thereof.

When the compound (I) of the present invention including the aforementioned embodiment C is more specifically explained, a compound of the formula (I), wherein ring A is a 5- to 11-membered monocyclic or bicyclic aromatic group optionally containing, besides carbon atom, 1-4 hetero atoms selected from the group consisting of oxygen atom, sulfur atom and nitrogen atom (said aromatic group is optionally substituted by the same or different 1, 2 or 3 groups selected from the group consisting of (1) alkyl optionally substituted by 1-7 halogen atoms; (2) alkoxy optionally substituted by 1-7 halogen atoms; and (3) a halogen atom), $R^1$ is (a) a hydrogen atom; (b) alkyl optionally substituted by 1, 2 or 3 alkoxyphenyls; (c) a halogen atom; or (d) a 4- to 7-membered monocyclic nonaromatic heterocyclic group containing, besides carbon atom, 1 or 2 hetero atoms selected from the group consisting of oxygen atom, sulfur atom and nitrogen atom, $R^2$ is (a) alkyl optionally substituted by the same or different 1-7 groups selected from the group consisting of cyano, a halogen atom, and a 4- to 7-membered monocyclic nonaromatic heterocyclic group containing, besides carbon atom, 1 or 2 hetero atoms selected from the group consisting of oxygen atom, sulfur atom and nitrogen atom; (b) cycloalkyl optionally substituted by the same or different 1, 2 or 3 groups selected from the group consisting of alkyl, alkoxyalkyl, halogenoalkyl, cyano, hydroxy, alkoxy, alkanoyloxy, and a halogen atom; (c) amino optionally substituted by 1 or 2 alkyls; (d) alkoxy optionally substituted by 1, 2 or 3 halogen atoms; (e) cycloalkoxy optionally substituted by alkyl; (f) phenyl optionally substituted by the same or different 1, 2 or 3 groups selected from the group consisting of alkyl, alkoxy optionally substituted by 1, 2 or 3 halogen atoms, and a halogen atom; (g) 5- to 6-membered monocyclic heteroaryl containing, besides carbon atom, 1-4 hetero atoms selected from the group consisting of oxygen atom, sulfur atom and nitrogen atom (said heteroaryl is optionally substituted by 1, 2 or 3 alkyls); or (h) a 4- to 7-membered monocyclic nonaromatic heterocyclic group containing, besides carbon atom, 1 or 2 hetero atoms selected from the group consisting of oxygen atom, sulfur atom and nitrogen atom (said nonaromatic heterocyclic group is optionally substituted by 1, 2 or 3 alkyls), or, $R^1$ and $R^2$ are bonded to each other to form, together with the adjacent $X^2$ and carbon atom, a ring selected from the group consisting of 4- to 7-membered ($C_4$-$C_7$) cycloalkene, and benzene (said ring is optionally substituted by 1, 2 or 3 halogen atoms), $R^3$ is a hydrogen atom, $R^4$ and $R^5$ are each independently a hydrogen atom, or alkyl, or, $R^4$ and $R^5$ are bonded to each other to form, together with the adjacent $Z^2$ and $Z^3$, a 4- to 7-membered monocyclic nitrogen-containing non-aromatic heterocycle containing, besides carbon atom, at least one nitrogen atom and 1 or 2 hetero atoms selected from the group consisting of oxygen atom, sulfur atom and nitrogen atom, $R^6$ and $R^7$ are each independently a hydrogen atom, or alkyl, or, $R^6$ and $R^7$ are bonded to each other to form, together with the adjacent carbon atom, cycloalkane, or a pharmacologically acceptable salt thereof can be mentioned.

Of the embodiments, a more preferable embodiment is a compound wherein ring A is an aromatic group selected from the group consisting of phenyl, tetrahydronaphthyl, indanyl, indolinyl, tetrahydroquinolyl, and thienopyridyl (said aromatic group is optionally substituted by the same or different 1, 2 or 3 groups selected from the group consisting of alkyl, halogenoalkyl, alkoxy, halogenoalkoxy, and a halogen atom), $R^1$ is a hydrogen atom, alkyl optionally substituted by alkoxyphenyl, a halogen atom, or tetrahydropyranyl, $R^2$ is (a) alkyl optionally substituted by a group selected from the group consisting of cyano, and morpholinyl; (b) halogenoalkyl; (c) cycloalkyl optionally substituted by a group selected from the group consisting of alkyl, alkoxyalkyl, halogenoalkyl, cyano, hydroxy, alkoxy, and alkanoyloxy; (d) halogenocycloalkyl; (e) amino optionally substituted by 1 or 2 alkyls; (f) halogenoalkoxy; (g) cycloalkoxy optionally substituted by alkyl; (h) phenyl optionally substituted by the same or different 1, 2 or 3 groups selected from the group consisting of alkyl, alkoxy optionally substituted by 1, 2 or 3 halogen atoms, and a halogen atom; (i) oxadiazolyl optionally substituted by alkyl; or (j) a nonaromatic heterocyclic group selected from the group consisting of piperidyl, oxetanyl, and tetrahydropyranyl (said nonaromatic heterocyclic group is optionally substituted by alkyl), or, $R^1$ and $R^2$ are bonded to each other to form, together with the adjacent $X^2$ and carbon atom, a ring selected from the group consisting of 4- to 7-membered ($C_4$-$C_7$) cycloalkene, and benzene (said ring is optionally substituted by a halogen atom), $R^3$ is a hydrogen atom, $R^4$ and $R^5$ are each alkyl, or, $R^4$ and $R^5$ are bonded to each other to form, together with the adjacent $Z^2$ and $Z^3$, a nitrogen-containing non-aromatic heterocycle selected from the group consisting of pyrrolidine, and piperidine, $R^6$ and $R^7$ are each independently a hydrogen atom, or alkyl, or, $R^6$ and $R^7$ are bonded to each other to form, together with the adjacent carbon atom, cycloalkane, or a pharmacologically acceptable salt thereof.

In the compound of the above-mentioned embodiment C, a compound wherein $R^4$ and $R^5$ are bonded to each other to form, together with the adjacent nitrogen atom and carbon atom, pyrrolidine is more preferable.

In the compound (I) of the present invention including the above-mentioned each embodiment, preferable examples of a part represented by the following formula:

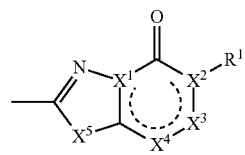

(partial structure A) include a group represented by the following formula (iv-a), (iv-b), (iv-c), (iv-d), or (iv-e):

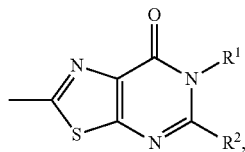
(iv-a)

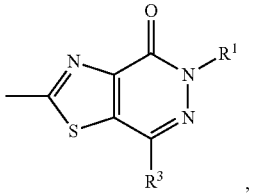
(iv-b)

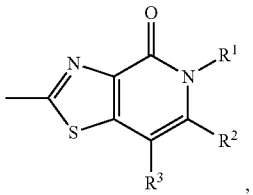
(iv-c)

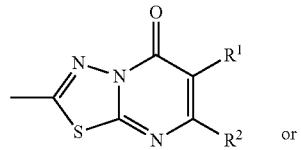
(iv-d) or

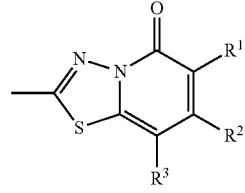
(iv-e)

wherein the symbols are as defined above. Of these, a group represented by the formula (iv-a), (iv-c), or (iv-d) is more preferable, and a group represented by the formula (iv-a) is particularly preferable.

Examples of embodiment in the present invention other than the above (hereinafter sometimes to be abbreviated as embodiment D) include a compound of the aforementioned formula (I) wherein a part represented by the following formula:

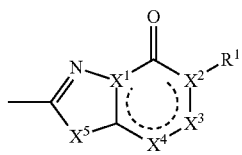

(partial structure A) is a cyclic group shown by the following formula:

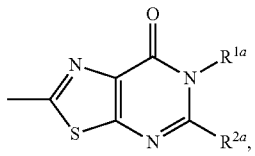

a part represented by the following formula:

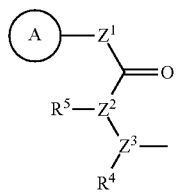

is a group represented by the following formula:

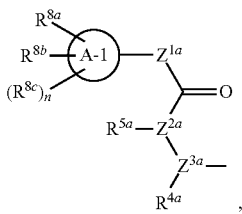

namely, a compound represented by the following formula (I-I):

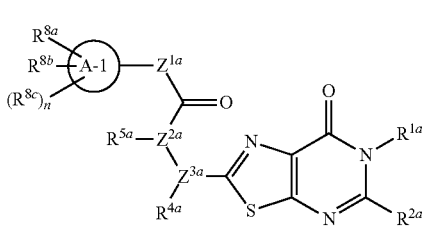

wherein ring A-1 is $C_6$-$C_{11}$ monocyclic or bicyclic aryl, or 5- to 11-membered monocyclic or bicyclic heteroaryl containing, besides carbon atom, 1, 2 or 3 hetero atoms selected from the group consisting of oxygen atom, sulfur atom and nitrogen atom, $Z^{1a}$ is an oxygen atom, —$C(R^{6a})(R^{7a})$—, —NH—, —$C(R^{6a})(R^{7a})$—NH—, —NH—$C(R^{6a})(R^{7a})$—, —$C(R^{6a})(R^{7a})$—O—, —O—$C(R^{6a})(R^{7a})$—, or a single bond (wherein the left end shows a bond to ring A-i, and the right end shows a bond to the adjacent carbonyl), (a) one of $Z^{2a}$ and $Z^{3a}$ is CH and the other is a nitrogen atom, or (b) both of them are nitrogen atoms, $R^{1a}$ is (a) a hydrogen atom; (b) alkyl optionally substituted by 1-7 groups selected from the group consisting of amino (said amino is optionally substituted by 1 or 2 groups selected from the group consisting of alkyl, halogenoalkyl, and alkoxycarbonyl), hydroxy, alkoxy, a halogen atom, phenyl, alkoxyphenyl, and a 4- to 7-membered monocyclic nonaromatic heterocyclic group containing, besides carbon atom, 1 or 2 hetero atoms selected from the group consisting of oxygen atom and nitrogen atom (said nonaromatic heterocyclic group is optionally substituted by 1, 2 or 3 groups selected from the group consisting of alkyl, and alkoxycarbonyl); (c) cycloalkyl; (d) phenyl; or (e) a 4- to 7-membered monocyclic nonaromatic heterocyclic group containing, besides carbon atom, 1 or 2 hetero atoms selected from the group consisting of oxygen atom and nitrogen atom (said nonaromatic heterocyclic group is optionally substituted by 1, 2 or 3 groups selected from the group consisting of alkyl, and alkoxycarbonyl), $R^{2a}$ is (a) a hydrogen atom; (b) alkyl optionally substituted by 1-7 groups selected from the group consisting of cyano, amino (said amino is optionally substituted by 1 or 2 groups selected from the group consisting of alkyl, alkoxyalkyl, halogenoalkyl, and alkoxycarbonyl), hydroxy, alkoxy, alkylsulfonyloxy, oxo, phenylsulfonyl, a halogen atom, phenyl, pyridyl, isoindolyl optionally substituted by 1 or 2 oxos, and a 4- to 7-membered monocyclic nonaromatic heterocyclic group containing, besides carbon atom, 1 or 2 hetero atoms selected from the group consisting of oxygen atom, and nitrogen atom (said nonaromatic heterocyclic group is optionally substituted by alkoxy); (c) cycloalkyl optionally substituted by 1, 2 or 3 groups selected from the group consisting of alkyl, alkoxyalkyl, halogenoalkyl, cyano, hydroxy, alkoxy, alkanoyloxy, and a halogen atom; (d) amino optionally substituted by 1 or 2 groups selected from the group consisting of alkyl and alkoxyphenyl; (e) alkoxy optionally substituted by 1, 2 or 3 groups selected from the group consisting of amino (said amino is optionally substituted by 1 or 2 groups selected from the group consisting of alkyl, and alkoxycarbonyl), and a halogen atom; (f) cycloalkoxy optionally substituted by alkyl; (g) phenyl optionally substituted by 1, 2 or 3 groups selected from the group consisting of alkyl (said alkyl is optionally substituted by 1, 2 or 3 groups selected from the group consisting of alkylamino, dialkylamino, hydroxy, and a halogen atom), alkoxy optionally substituted by 1, 2 or 3 halogen atoms, alkylsulfonyl, and a halogen atom; (h) 5- to 6-membered monocyclic heteroaryl containing, besides carbon atom, 1, 2 or 3 hetero atoms selected from the group consisting of oxygen atom, sulfur atom and nitrogen atom (said heteroaryl is optionally substituted by 1, 2 or 3 groups selected from the group consisting of alkyl, alkoxy, and a halogen atom); or (i) a 4- to 7-membered monocyclic nonaromatic heterocyclic group containing, besides carbon atom, 1 or 2 hetero atoms selected from the group consisting of oxygen atom, and nitrogen atom (said nonaromatic heterocyclic group is optionally substituted by 1, 2 or 3 groups selected from the group consisting of alkyl, halogenoalkyl, and alkoxy), or $R^{1a}$ and $R^{2a}$ are bonded to each other to form, together with the adjacent nitrogen atom and carbon atom, (a) a 4- to 7-membered monocyclic nitrogen-containing non-aromatic heterocycle containing 1 or 2 nitrogen atoms besides carbon atom (said nitrogen-containing non-aromatic heterocycle is optionally substituted by 1, 2 or 3 groups selected from the group consisting of alkyl, halogenoalkyl, alkoxycarbonyl, and a halogen atom); or (b) 5- to 6-membered monocyclic nitrogen-containing heteroarene containing, besides carbon atom, at least one nitrogen atom and 1 or 2 hetero atoms selected from the group consisting of sulfur atom and nitrogen atom (said nitrogen-containing heteroarene is optionally substituted by 1, 2 or 3 groups selected from the group consisting of alkyl, halogenoalkyl, alkoxycarbonyl, and a halogen atom), $R^{4a}$ and $R^{5a}$ are each independently a hydrogen atom, or alkyl, or, $R^{4a}$ and $R^{5a}$ are bonded to each other to form, together with the adjacent $Z^{2a}$ and $Z^{3a}$, 4- to 7-membered monocyclic nitrogen-containing non-aromatic heterocycle containing, besides carbon atom, at least one nitrogen atom and 1 or 2 hetero atoms selected from the group consisting of oxygen atom, and nitrogen atom (said nitrogen-containing non-aromatic heterocycle is optionally substituted by 1, 2 or 3 groups selected from the group consisting of amino optionally substituted by a group selected from the group consisting of alkoxycarbonyl and phenylalkoxycarbonyl, and a halogen atom), and $R^{6a}$ and $R^{7a}$ are each independently (a) a hydrogen atom; (b) alkyl optionally substituted by 1, 2 or 3 groups selected from the group consisting of alkoxy, and a halogen atom; or (c) cycloalkyl, or $R^{6a}$ and $R^{7a}$ are bonded to each other to form, together with the adjacent carbon atom, cycloalkane, $R^{8a}$, $R^{8b}$ and $R^{8c}$ are each independently (a) a hydrogen atom; (b) alkyl optionally substituted by 1, 2 or 3 groups selected from the group consisting of alkylamino, dialkylamino, alkoxy, and a halogen atom; (c) cyano; (d) amino optionally substituted by 1 or 2 alkyls; (e) alkoxy optionally substituted by 1-7 halogen atoms; or (f) a halogen atom, and n is 0 or 1, or a pharmacologically acceptable salt thereof can be mentioned.

$Z^{2a}$ and $Z^{3a}$ in the above-mentioned formula (I-I) are as defined above, and (a) $Z^{2a}$ is CH, and $Z^{3a}$ is a nitrogen atom, or (b) $Z^{2a}$ is a nitrogen atom, and $Z^{3a}$ is CH is preferable.

When ring A-1 in the above-mentioned formula (I-I) is "$C_6$-$C_{11}$ monocyclic or bicyclic aryl", preferable examples of the aryl include phenyl, indanyl, and tetrahydronaphthyl, of which phenyl is more preferable. In the above-mentioned formula (I-I), specific examples of "$C_6$-$C_{11}$ monocyclic or bicyclic aryl, or 5- to 11-membered monocyclic or bicyclic heteroaryl containing, besides carbon atom, 1, 2 or 3 hetero atoms selected from the group consisting of oxygen atom, sulfur atom and nitrogen atom" for ring A-1 include phenyl, indanyl, tetrahydronaphthyl, furyl, thienyl, pyrazolyl, isoxazolyl, thiazolyl, dihydrobenzofuranyl, benzodioxolanyl, and tetrahydroquinolyl. Of these, phenyl, thienyl, or benzodioxolanyl is preferable, and phenyl is particularly preferable.

Preferable examples of $Z^{1a}$ in the above-mentioned formula (I-I) include an oxygen atom, —C($R^{6a}$)($R^{7a}$)—, —NH—, —C($R^{6a}$)($R^{7a}$)—NH—, —NH—C($R^{6a}$)($R^{7a}$)—, —C($R^{6a}$)($R^{7a}$)—O—, and —O—C($R^{6a}$)($R^{7a}$)—, of which an oxygen atom, —C($R^{6a}$)($R^{7a}$)—, —C($R^{6a}$)($R^{7a}$)—NH—, —NH—C($R^{6a}$)($R^{7a}$)—, or —O—C($R^{6a}$)($R^{7a}$)— is more preferable.

Preferable examples of $R^{1a}$ in the above-mentioned formula (I-I) include (a) a hydrogen atom; (b) alkyl optionally substituted by 1-7 groups selected from the group consisting of amino (said amino is optionally substituted by 1 or 2 groups selected from the group consisting of alkyl, halogenoalkyl, and alkoxycarbonyl), hydroxy, alkoxy, a halogen atom, phenyl, alkoxyphenyl, and a nonaromatic heterocyclic group selected from the group consisting of pyrrolidyl, piperidyl, oxetanyl, and tetrahydropyranyl (said nonaromatic heterocyclic group is optionally substituted by 1, 2 or 3 groups selected from the group consisting of alkyl, and alkoxycarbonyl); (c) cycloalkyl; (d) phenyl; or (e) a nonaromatic heterocyclic group selected from the group consisting of pyrrolidyl, piperidyl, morpholinyl, oxetanyl, tetrahydrofuranyl, and tetrahydropyranyl (said nonaromatic heterocyclic group is optionally substituted by 1, 2 or 3 groups selected from the group consisting of alkyl, and alkoxycarbonyl). Of these $R^{1a}$, (a) a hydrogen atom; (b) alkyl optionally substituted by 1-7 groups selected from the group consisting of amino (said amino is optionally substituted by 1 or 2 groups selected from the group consisting of alkyl, and halogenoalkyl), alkoxy, a halogen atom, and a nonaromatic heterocyclic group selected from the group consisting of oxetanyl, and tetrahydropyranyl; (c) cycloalkyl; or (d) a nonaromatic heterocyclic group selected from the group consisting of pyrrolidyl, oxetanyl, and tetrahydropyranyl is more preferable, (a) a hydrogen atom; (b) alkyl optionally substituted by 1, 2 or 3 groups selected from the group consisting of alkoxy, and oxetanyl; (c) cycloalkyl; or (d) tetrahydropyranyl is particularly preferable.

Preferable examples of $R^{2a}$ in the above-mentioned formula (I-I) include (a) a hydrogen atom; (b) alkyl optionally substituted by 1-7 groups selected from the group consisting of cyano, amino (said amino is optionally substituted by 1 or 2 groups selected from the group consisting of alkyl, alkoxyalkyl, halogenoalkyl, and alkoxycarbonyl), hydroxy, alkoxy, alkylsulfonyloxy, oxo, phenylsulfonyl, a halogen atom, phenyl, pyridyl, isoindolyl optionally substituted by 1 or 2 oxos, and a monocyclic nonaromatic heterocyclic group selected from the group consisting of azetidinyl, pyrrolidyl, piperidyl, and morpholinyl (said nonaromatic heterocyclic group is optionally substituted by alkoxy); (c) cycloalkyl optionally substituted by 1, 2 or 3 groups selected from the group consisting of alkyl, alkoxyalkyl, halogenoalkyl, cyano, hydroxy, alkoxy, and a halogen atom; (d) amino optionally substituted by 1 or 2 groups selected from the group consisting of alkyl and alkoxyphenyl; (e) alkoxy optionally substituted by 1, 2 or 3 groups selected from the group consisting of amino (said amino is optionally substituted by 1 or 2 groups selected from the group consisting of alkyl, and alkoxycarbonyl), and a halogen atom; (f) cycloalkoxy optionally substituted by alkyl; (g) phenyl optionally substituted by 1, 2 or 3 groups selected from the group consisting of alkyl (said alkyl is optionally substituted by 1-7 groups selected from the group consisting of alkylamino, dialkylamino, hydroxy, and a halogen atom), alkoxy optionally substituted by 1, 2 or 3 halogen atoms, alkylsulfonyl, and a halogen atom; (h) heteroaryl selected from the group consisting of thienyl, pyrazolyl, oxadiazolyl, pyridyl, and pyrimidinyl (said heteroaryl is optionally substituted by 1, 2 or 3 groups selected from the group consisting of alkyl, alkoxy, and a halogen atom); and (i) a nonaromatic heterocyclic group selected from the group consisting of azetidinyl, pyrrolidyl, piperidyl, tetrahydrofuryl, tetrahydropyranyl, piperazinyl, and morpholinyl (said nonaromatic heterocyclic group is optionally substituted by 1, 2 or 3 groups selected from the group consisting of alkyl, halogenoalkyl, and alkoxy). Of these $R^{2a}$, (a) a hydrogen atom; (b) alkyl optionally substituted by 1-7 groups selected from the group consisting of cyano, amino (said amino is optionally substituted by 1 or 2 groups selected from the group consisting of alkyl, and alkoxyalkyl), hydroxy, alkoxy, oxo, phenylsulfonyl, a halogen atom, phenyl, pyridyl, isoindolyl optionally substituted by 1 or 2 oxos, piperidyl, and morpholinyl; (c) cycloalkyl optionally substituted by 1, 2 or 3 groups selected from the group consisting of alkoxyalkyl, halogenoalkyl, cyano, hydroxy, alkoxy, and a halogen atom;

(d) amino optionally substituted by 1 or 2 alkyls; (e) alkoxy; (f) phenyl optionally substituted by 1, 2 or 3 groups selected from the group consisting of alkyl optionally substituted by 1, 2 or 3 halogen atoms, alkoxy, and a halogen atom; (g) heteroaryl selected from the group consisting of thienyl, oxadiazolyl, pyridyl, and pyrimidinyl (said heteroaryl is optionally substituted by 1, 2 or 3 groups selected from the group consisting of alkyl, and a halogen atom); or (h) a nonaromatic heterocyclic group selected from the group consisting of azetidinyl, pyrrolidyl, piperidyl, tetrahydrofuryl, tetrahydropyranyl, piperazinyl, and morpholinyl (said nonaromatic heterocyclic group is optionally substituted by one group selected from the group consisting of alkyl, halogenoalkyl, and alkoxy) is more preferable, and (a) a hydrogen atom; (b) alkyl optionally substituted by 1-7 groups selected from the group consisting of hydroxy, oxo, phenylsulfonyl, a halogen atom, phenyl, and piperidyl; (c) cycloalkyl optionally substituted by 1, 2 or 3 halogen atoms; (d) phenyl optionally substituted by 1, 2 or 3 halogen atoms; (e) oxadiazolyl optionally substituted by alkyl; or (f) a nonaromatic heterocyclic group selected from the group consisting of azetidinyl, and piperidyl (said nonaromatic heterocyclic group is optionally substituted by alkoxy) is particularly preferable.

When $R^{1a}$ and $R^{2a}$ in the above-mentioned formula (I-I) are bonded to each other to form, together with the adjacent nitrogen atom and carbon atom, a ring, preferable examples of the ring include a non-aromatic heterocycle selected from the group consisting of pyrrolidine, piperidine, dihydroimidazole, imidazolidine, and piperazine (said non-aromatic heterocycle is optionally substituted by 1, 2 or 3 groups selected from the group consisting of alkyl, halogenoalkyl, alkoxycarbonyl, and a halogen atom). Of these, a non-aromatic heterocycle selected from the group consisting of piperidine, dihydroimidazole, imidazolidine, and piperazine (said non-aromatic heterocycle is optionally substituted by 1, 2 or 3 groups selected from the group consisting of alkyl, and a halogen atom) is more preferable, and a non-aromatic heterocycle selected from the group consisting of piperidine, and piperazine (said non-aromatic heterocycle is optionally substituted by 1, 2 or 3 groups selected from the group consisting of alkyl, and a halogen atom) is particularly preferable.

Preferable examples of $R^{4a}$ and $R^{5a}$ in the above-mentioned formula (I-I) include alkyl. Other preferable examples of $R^{4a}$ and $R^{5a}$ include ring formed by them, bonded to each other, together with the adjacent $Z^{2a}$ and $Z^{3a}$. Examples of such ring include a nitrogen-containing non-aromatic heterocycle selected from the group consisting of azetidine, pyrrolidine, and piperidine (said nitrogen-containing non-aromatic heterocycle is optionally substituted by 1, 2 or 3 groups selected from the group consisting of amino optionally substituted by one group selected from the group consisting of alkoxycarbonyl and phenylalkoxycarbonyl, and a halogen atom). Of these, a nitrogen-containing non-aromatic heterocycle selected from the group consisting of pyrrolidine, and piperidine (said nitrogen-containing non-aromatic heterocycle is optionally substituted by 1, 2 or 3 halogen atoms) is more preferable.

Preferable examples of $R^{6a}$ and $R^{7a}$ in the above-mentioned formula (I-I) include, each independently, a hydrogen atom and alkyl.

Preferable examples of $R^{8a}$, $R^{8b}$ and $R^{8c}$ in the above-mentioned formula (I-I) include, each independently, (a) a hydrogen atom; (b) alkyl optionally substituted by one group selected from the group consisting of dialkylamino, and alkoxy; (c) cyano; (d) amino optionally substituted by 1 or 2 alkyls; (e) alkoxy; and (f) a halogen atom. Of these, a hydrogen atom, alkyl, and a halogen atom are more preferable, and a hydrogen atom and a halogen atom is particularly preferable.

In the above-mentioned formula (I-I), n is preferably 1.

Of the above-mentioned embodiment D, preferable examples include a compound wherein a part represented by the following formula in the formula (I-I) of said embodiment D:

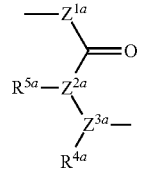

is a group represented by the following formula:

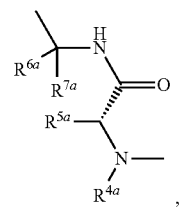

namely, a compound represented by the following formula (I-II):

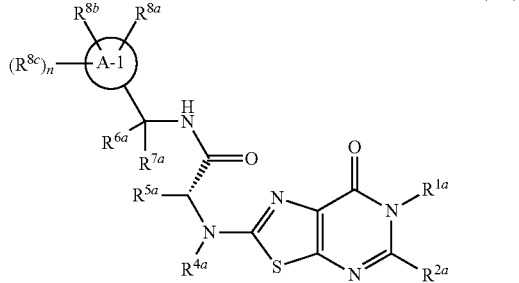

wherein the symbols are as defined above, or a pharmacologically acceptable salt thereof.

In the above-mentioned formula (I-II), specific examples of "$C_6$-$C_{11}$ monocyclic or bicyclic aryl, or 5- to 11-membered monocyclic or bicyclic heteroaryl containing, besides carbon atom, 1, 2 or 3 hetero atoms selected from the group consisting of oxygen atom, sulfur atom and nitrogen atom" for ring A-1 include phenyl, furyl, thienyl, pyrazolyl, isoxazolyl, thiazolyl, dihydrobenzofuranyl, and benzodioxolanyl. Of these, phenyl, thienyl and benzodioxolanyl are preferable, and phenyl is particularly preferable.

Preferable examples of $R^{1a}$ in the above-mentioned formula (I-II) include (a) a hydrogen atom; (b) alkyl optionally substituted by 1-7 groups selected from the group consisting of amino (said amino is optionally substituted by 1 or 2 groups selected from the group consisting of alkyl, halogenoalkyl, and alkoxycarbonyl), hydroxy, alkoxy, a halogen atom, phenyl, alkoxyphenyl, and a nonaromatic heterocyclic group selected from the group consisting of pyrrolidyl, piperidyl, oxetanyl, and tetrahydropyranyl (said nonaromatic heterocyclic group is optionally substituted by 1, 2 or 3 groups selected from the group consisting of alkyl, and alkoxycarbonyl); (c) cycloalkyl; (d) phenyl; or (e) a nonaromatic heterocyclic group selected from the group consisting of pyrrolidyl, piperidyl, morpholinyl, oxetanyl, tetrahydrofuranyl, and tetrahydropyranyl (said nonaromatic heterocyclic group is optionally substituted by 1, 2 or 3 groups selected from the group consisting of alkyl, and alkoxycarbonyl). Of these $R^{1a}$, (a) a hydrogen atom; (b) alkyl optionally substituted by 1-7 groups selected from the group consisting of amino (said amino is optionally substituted by 1 or 2 groups selected from the group consisting of alkyl, and halogenoalkyl), alkoxy, a halogen atom, and a nonaromatic heterocyclic group selected from the group consisting of oxetanyl, and tetrahydropyranyl; (c) cycloalkyl; or (d) a nonaromatic heterocyclic group selected from the group consisting of pyrrolidyl, oxetanyl, and tetrahydropyranyl is more preferable, (a) a hydrogen atom; (b) alkyl optionally substituted by 1, 2 or 3 groups selected from the group consisting of alkoxy, and oxetanyl; (c) cycloalkyl; or (d) tetrahydropyranyl is particularly preferable.

Preferable examples of $R^{2a}$ in the above-mentioned formula (I-II) include (a) a hydrogen atom; (b) alkyl optionally substituted by 1-7 groups selected from the group consisting of cyano, amino (said amino is optionally substituted by 1 or 2 groups selected from the group consisting of alkyl, alkoxyalkyl, halogenoalkyl, and alkoxycarbonyl), hydroxy, alkoxy, alkylsulfonyloxy, oxo, phenylsulfonyl, a halogen atom, phenyl, pyridyl, isoindolyl optionally substituted by 1 or 2 oxos, and a monocyclic nonaromatic heterocyclic group selected from the group consisting of azetidinyl, pyrrolidyl, piperidyl, and morpholinyl (said nonaromatic heterocyclic group is optionally substituted by alkoxy); (c) cycloalkyl optionally substituted by 1, 2 or 3 groups selected from the group consisting of alkyl, alkoxyalkyl, halogenoalkyl, cyano, hydroxy, alkoxy, and a halogen atom; (d) amino optionally substituted by 1 or 2 groups selected from the group consisting of alkyl and alkoxyphenyl; (e) alkoxy optionally substituted by 1, 2 or 3 groups selected from the group consisting of amino (said amino is optionally substituted by 1 or 2 groups selected from the group consisting of alkyl, and alkoxycarbonyl), and a halogen atom; (f) cycloalkoxy optionally substituted by alkyl; (g) phenyl optionally substituted by 1, 2 or 3 groups selected from the group consisting of alkyl (said alkyl is optionally substituted by 1, 2 or 3 groups selected from the group consisting of alkylamino, dialkylamino, hydroxy, and a halogen atom), alkoxy optionally substituted by 1, 2 or 3 halogen atoms, alkylsulfonyl, and a halogen atom; (h) heteroaryl selected from the group consisting of thienyl, pyrazolyl, oxadiazolyl, pyridyl, and pyrimidinyl (said heteroaryl is optionally substituted by 1, 2 or 3 groups selected from the group consisting of alkyl, alkoxy, and a halogen atom); and (i) a nonaromatic heterocyclic group selected from the group consisting of azetidinyl, pyrrolidyl, piperidyl, tetrahydrofuryl, tetrahydropyranyl, piperazinyl, and morpholinyl (said nonaromatic heterocyclic group is optionally substituted by 1, 2 or 3 groups selected from the group consisting of alkyl, halogenoalkyl, and alkoxy). Of these $R^{2a}$, (a) a hydrogen atom; (b) alkyl optionally substituted by 1, 2 or 3 groups selected from the group consisting of cyano, amino (said amino is optionally substituted by 1 or 2 groups selected from the group consisting of alkyl, and alkoxyalkyl), hydroxy, alkoxy, oxo, phenylsulfonyl, a halogen atom, phenyl, pyridyl, isoindolyl optionally substituted by 1 or 2 oxos, piperidyl, and morpholinyl; (c) cycloalkyl optionally substituted by 1, 2 or 3 groups selected from the group consisting of alkoxyalkyl, halogenoalkyl, cyano, hydroxy, alkoxy, and a halogen atom; (d) amino optionally substituted by 1 or 2 alkyls; (e) alkoxy; (f) phenyl optionally substituted by 1, 2 or 3 groups selected from the group consisting of alkyl optionally substituted by 1, 2 or 3 halogen atoms, alkoxy, and a halogen atom; (g) heteroaryl selected from the group consisting of thienyl, oxadiazolyl, pyridyl, and pyrimidinyl (said heteroaryl is optionally substituted by 1, 2 or 3 groups selected from the group consisting of alkyl, and a halogen atom); or (h) a nonaromatic heterocyclic group selected from the group consisting of azetidinyl, pyrrolidyl, piperidyl, tetrahydrofuryl, tetrahydropyranyl, piperazinyl, and morpholinyl (said nonaromatic heterocyclic group is optionally substituted by 1, 2 or 3 groups selected from the group consisting of alkyl, halogenoalkyl, and alkoxy) is more preferable, and (a) a hydrogen atom; (b) alkyl optionally substituted by 1-7 groups selected from the group consisting of hydroxy, oxo, phenylsulfonyl, a halogen atom, phenyl, and piperidyl; (c) cycloalkyl optionally substituted by 1, 2 or 3 halogen atoms; (d) phenyl optionally substituted by 1, 2 or 3 halogen atoms; (e) oxadiazolyl optionally substituted by alkyl; or (f) a nonaromatic heterocyclic group selected from the group consisting of azetidinyl, and piperidyl (said nonaromatic heterocyclic group is optionally substituted by alkoxy) is particularly preferable.

When $R^{1a}$ and $R^{2a}$ in the above-mentioned formula (I-II) are bonded to each other to form, together with the adjacent nitrogen atom and carbon atom, a ring, preferable examples of the ring include a non-aromatic heterocycle selected from the group consisting of pyrrolidine, piperidine, dihydroimidazole, imidazolidine, and piperazine (said non-aromatic heterocycle is optionally substituted by 1, 2 or 3 groups selected from the group consisting of alkyl, halogenoalkyl, alkoxycarbonyl, and a halogen atom). Of these, a non-aromatic heterocycle selected from the group consisting of piperidine, dihydroimidazole, imidazolidine, and piperazine (said non-aromatic heterocycle is optionally substituted by 1, 2 or 3 groups selected from the group consisting of alkyl, and a halogen atom) is more preferable, and a non-aromatic heterocycle selected from the group consisting of piperidine, and piperazine (said non-aromatic heterocycle is optionally substituted by 1, 2 or 3 groups selected from the group consisting of alkyl, and a halogen atom) is particularly preferable.

Preferable examples of $R^{4a}$ and $R^{5a}$ in the above-mentioned formula (I-II) include alkyl. Other preferable examples of $R^{4a}$ and $R^{5a}$ include ring formed by them, bonded to each other, together with the adjacent nitrogen atom and carbon atom. Examples of such ring include a nitrogen-containing non-aromatic heterocycle selected from the group consisting of azetidine, pyrrolidine, and piperidine (said nitrogen-containing non-aromatic heterocycle is optionally substituted by 1, 2 or 3 groups selected from the group consisting of amino optionally substituted by one group selected from the group consisting of alkoxycarbonyl and phenylalkoxycarbonyl, and a halogen atom). Of these, a nitrogen-containing non-aromatic heterocycle selected from the group consisting of pyrrolidine, and piperidine (said nitrogen-containing non-aromatic heterocycle is optionally substituted by 1, 2 or 3 halogen atoms) is more preferable.

Preferable examples of $R^{6a}$ and $R^{7a}$ in the above-mentioned formula (I-II) include, each independently, a hydrogen atom and alkyl.

Preferable examples of $R^{8a}$, $R^{8b}$ and $R^{8c}$ in the above-mentioned formula (I-II) include, each independently, (a) a hydrogen atom; (b) alkyl optionally substituted by one group selected from the group consisting of dialkylamino, and alkoxy; (c) cyano; (d) amino optionally substituted by 1 or 2 alkyls; (e) alkoxy; and (f) a halogen atom. Of these, a hydrogen atom, alkyl, and a halogen atom are more preferable, and a hydrogen atom or a halogen atom is particularly preferable.

In the above-mentioned formula (I-II), n is preferably 1.

In the embodiments of the present invention, examples of the preferable embodiment include compound (I-I) and compound (I-II) defined above, wherein $R^{4a}$ and $R^{5a}$ are bonded to each other to form, together with the adjacent $Z^{2a}$ and $Z^{3a}$, or a nitrogen atom and carbon atom, pyrrolidine, and $R^{6a}$ and $R^{7a}$ are both hydrogen atoms, or a pharmacologically acceptable salt thereof.

In the embodiments of the present invention, examples of other preferable embodiment include a compound wherein $R^{4a}$ is $C_1$-$C_6$ alkyl, $R^{5a}$ is $C_1$-$C_6$ alkyl, and $R^{6a}$ and $R^{7a}$ are both hydrogen atoms, or a pharmacologically acceptable salt thereof.

Of the above-mentioned embodiment D, other preferable examples include a compound wherein a part represented by the following formula in the formula (I-I) of said embodiment D:

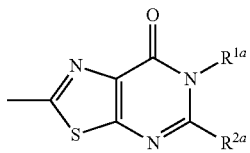

is a cyclic group shown by the following formula:

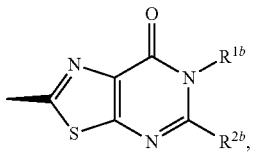

and a part represented by the following formula:

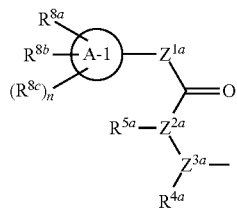

is a group represented by the following formula:

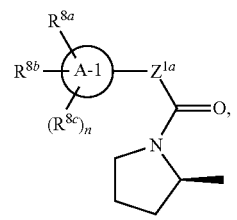

namely, a compound represented by the following formula (I-III):

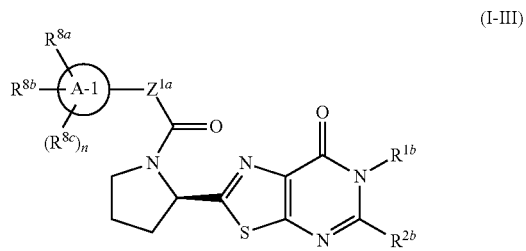

(I-III)

wherein $R^{1b}$ is (a) a hydrogen atom; (b) alkyl optionally substituted by 1-7 groups selected from the group consisting of amino (said amino is optionally substituted by 1 or 2 groups selected from the group consisting of alkyl, halogenoalkyl, and alkoxycarbonyl), hydroxy, alkoxy, a halogen atom, phenyl, alkoxyphenyl, and a 4- to 7-membered monocyclic nonaromatic heterocyclic group containing, besides carbon atom, 1 or 2 hetero atoms selected from the group consisting of oxygen atom and nitrogen atom (said nonaromatic heterocyclic group is optionally substituted by 1, 2 or 3 groups selected from the group consisting of alkyl, and alkoxycarbonyl); (c) cycloalkyl; (d) phenyl; or (e) a 4- to 7-membered monocyclic nonaromatic heterocyclic group containing, besides carbon atom, 1 or 2 hetero atoms selected from the group consisting of oxygen atom and nitrogen atom (said nonaromatic heterocyclic group is optionally substituted by 1, 2 or 3 groups selected from the group consisting of alkyl, and alkoxycarbonyl), $R^{2b}$ is (a) a hydrogen atom; (b) alkyl optionally substituted by 1-7 groups selected from the group consisting of cyano, amino (said amino is optionally substituted by the same or different 1 or 2 groups selected from the group consisting of alkyl, alkoxyalkyl, halogenoalkyl, and alkoxycarbonyl), hydroxy, alkoxy, alkylsulfonyloxy, oxo, phenylsulfonyl, a halogen atom, phenyl, pyridyl, isoindolyl optionally substituted by 1 or 2 oxos, and a 4- to 7-membered monocyclic nonaromatic heterocyclic group containing, besides carbon atom, 1 or 2 hetero atoms selected from the group consisting of oxygen atom, and nitrogen atom (said nonaromatic heterocyclic group is optionally substituted by alkoxy); (c) cycloalkyl optionally substituted by 1, 2 or 3 groups selected from the group consisting of alkyl, alkoxyalkyl, halogenoalkyl, cyano, hydroxy, alkoxy, alkanoyloxy, and a halogen atom; (d) amino optionally substituted by 1 or 2 groups selected from the group consisting of alkyl and alkoxyphenyl; (e) alkoxy optionally substituted by 1, 2 or 3 groups selected from the group consisting of amino (said amino is optionally substituted by 1 or 2 groups selected from the group consisting of alkyl, and alkoxycarbonyl), and a halogen atom; (f) cycloalkoxy optionally substituted by alkyl; (g) phenyl optionally substituted by 1, 2 or 3 groups selected from the group consisting of alkyl (said alkyl is optionally substituted by 1, 2 or 3 groups selected from the group consisting of alkylamino, dialkylamino, hydroxy, and a halogen atom), alkoxy optionally substituted by 1, 2 or 3 halogen atoms, alkylsulfonyl, and a halogen atom; (h) 5- to 6-membered monocyclic heteroaryl containing, besides carbon atom, 1, 2 or 3 hetero atoms selected from the group consisting of oxygen atom, sulfur atom and nitrogen atom (said heteroaryl is optionally substituted by 1, 2 or 3 groups selected from the group consisting of alkyl, alkoxy, and a halogen atom); or (i) a 4- to 7-membered monocyclic nonaromatic heterocyclic group containing, besides carbon atom, 1 or 2 hetero atoms selected from the group consisting of oxygen atom, and nitrogen atom (said nonaromatic heterocyclic group is optionally substituted by 1, 2 or 3 groups selected from the group consisting of alkyl, halogenoalkyl, and alkoxy),
and other symbols are as defined above, or a pharmacologically acceptable salt thereof can be mentioned.

In the above-mentioned formula (I-III), specific examples of "$C_6$-$C_{11}$ monocyclic or bicyclic aryl, or 5- to 11-membered monocyclic or bicyclic heteroaryl containing, besides carbon atom, 1, 2 or 3 hetero atoms selected from the group consisting of oxygen atom, sulfur atom and nitrogen atom" for ring A-1 include phenyl, indanyl, tetrahydronaphthyl, and tetrahydroquinolyl. Of these, phenyl is particularly preferable.

Preferable examples of $Z^{1a}$ in the above-mentioned formula (I-III) include an oxygen atom, —C($R^{6a}$)($R^{7a}$)—, —NH—, —C($R^{6a}$)($R^{7a}$)—NH—, and —C($R^{6a}$)($R^{7a}$)—O—. Of these, an oxygen atom, and —C($R^{6a}$)($R^{7a}$)— are more preferable.

Preferable examples of $R^{1b}$ in the above-mentioned formula (I-III) include (a) a hydrogen atom; (b) alkyl optionally substituted by 1-7 groups selected from the group consisting of amino (said amino is optionally substituted by 1 or 2 groups selected from the group consisting of alkyl, halogenoalkyl, and alkoxycarbonyl), hydroxy, alkoxy, a halogen atom, phenyl, alkoxyphenyl, and a nonaromatic heterocyclic group selected from the group consisting of pyrrolidyl, piperidyl, oxetanyl, and tetrahydropyranyl (said nonaromatic heterocyclic group is optionally substituted by 1, 2 or 3 groups selected from the group consisting of alkyl, and alkoxycarbonyl); (c) a nonaromatic heterocyclic group selected from the group consisting of pyrrolidyl, piperidyl, morpholinyl, oxetanyl, tetrahydrofuranyl, and tetrahydropyranyl (said nonaromatic heterocyclic group is optionally substituted by 1, 2 or 3 groups selected from the group consisting of alkyl, and alkoxycarbonyl). Of these $R^{1b}$, (a) a hydrogen atom; (b) alkyl optionally substituted by 1, 2 or 3 alkoxyphenyls; or (c) tetrahydropyranyl is more preferable, and (a) a hydrogen atom; or (b) alkyl is particularly preferable.

Preferable examples of $R^{2b}$ in the above-mentioned formula (I-III) include (a) alkyl optionally substituted by 1-7 groups selected from the group consisting of cyano, amino (said amino is optionally substituted by 1 or 2 groups selected from the group consisting of alkyl, alkoxyalkyl, halogenoalkyl, and alkoxycarbonyl), hydroxy, alkoxy, alkylsulfonyloxy, oxo, phenylsulfonyl, a halogen atom, phenyl, pyridyl, isoindolyl optionally substituted by 1 or 2 oxos, and a monocyclic nonaromatic heterocyclic group selected from the group consisting of azetidinyl, pyrrolidyl, piperidyl, and morpholinyl (said nonaromatic heterocyclic group is optionally substituted by alkoxy); (b) cycloalkyl optionally substituted by 1, 2 or 3 groups selected from the group consisting of alkyl, alkoxyalkyl, halogenoalkyl, cyano, hydroxy, alkoxy, and a halogen atom; (c) amino optionally substituted by 1 or 2 groups selected from the group consisting of alkyl and alkoxyphenyl; (d) alkoxy optionally substituted by 1, 2 or 3 groups selected from the group consisting of amino (said amino is optionally substituted by 1 or 2 groups selected from the group consisting of alkyl, and alkoxycarbonyl), and a halogen atom; (e) cycloalkoxy optionally substituted by alkyl; (f) phenyl optionally substituted by 1, 2 or 3 groups selected from the group consisting of alkyl (said alkyl is optionally substituted by 1, 2 or 3 groups selected from the group consisting of alkylamino, dialkylamino, hydroxy, and a halogen atom), alkoxy optionally substituted by 1, 2 or 3 halogen atoms, alkylsulfonyl, and a halogen atom; (g) heteroaryl selected from the group consisting of thienyl, pyrazolyl, oxadiazolyl, pyridyl, and pyrimidinyl (said heteroaryl is optionally substituted by 1, 2 or 3 groups selected from the group consisting of alkyl, alkoxy, and a halogen atom); and (h) a nonaromatic heterocyclic group selected from the group consisting of azetidinyl, pyrrolidyl, piperidyl, tetrahydrofuryl, tetrahydropyranyl, piperazinyl, and morpholinyl (said nonaromatic heterocyclic group is optionally substituted by 1, 2 or 3 groups selected from the group consisting of alkyl, halogenoalkyl, and alkoxy). Of these $R^{2b}$, (a) alkyl optionally substituted by 1, 2 or 3 groups selected from the group consisting of cyano, a halogen atom, and morpholinyl; (b) cycloalkyl optionally substituted by 1, 2 or 3 groups selected from the group consisting of alkyl, alkoxyalkyl, halogenoalkyl, cyano, alkoxy, and a halogen atom; (c) amino optionally substituted by 1 or 2 alkyls; (d) alkoxy optionally substituted by 1, 2 or 3 halogen atoms; (e) phenyl optionally substituted by 1, 2 or 3 groups selected from the group consisting of alkyl, alkoxy optionally substituted by 1, 2 or 3 halogen atoms, and a halogen atom; (f) oxadiazolyl optionally substituted by alkyl; or (g) a nonaromatic heterocyclic group selected from the group consisting of piperidyl, oxetanyl, and tetrahydropyranyl (said nonaromatic heterocyclic group is optionally substituted by alkyl) is more preferable, and (a) alkyl optionally substituted by 1, 2 or 3 groups selected from the group consisting of cyano, and a halogen atom; (b) cycloalkyl optionally substituted by 1, 2 or 3 groups selected from the group consisting of alkyl, alkoxyalkyl, halogenoalkyl, cyano, alkoxy, and a halogen atom; (c) phenyl optionally substituted by 1, 2 or 3 groups selected from the group consisting of alkyl, and a halogen atom; (d) oxadiazolyl optionally substituted by alkyl; or (e) a nonaromatic heterocyclic group selected from the group consisting of oxetanyl, and tetrahydropyranyl (said nonaromatic heterocyclic group is optionally substituted by alkyl) is particularly preferable.

Preferable examples of $R^{6a}$ and $R^{7a}$ in the above-mentioned formula (I-III) include, each independently, a hydrogen atom and alkyl.

Preferable examples of $R^{8a}$, $R^{8b}$ and $R^{8c}$ in the above-mentioned formula (I-III) include, each independently, (a) a hydrogen atom; (b) alkyl optionally substituted by 1, 2 or 3 groups selected from the group consisting of alkylamino, dialkylamino, alkoxy, and a halogen atom; (c) alkoxy optionally substituted by 1, 2 or 3 halogen atoms; or (d) a halogen atom. Of these, (a) a hydrogen atom; (b) alkyl optionally substituted by 1, 2 or 3 halogen atoms; (c) alkoxy optionally substituted by 1, 2 or 3 halogen atoms; or (d) a halogen atom is more preferable, and a hydrogen atom, alkyl, or a halogen atom is particularly preferable.

In the above-mentioned formula (I-III), n is preferably 1.

Of the compound (I-III) defined as above, examples of preferable compound include a compound wherein ring A-1 is phenyl, $Z^{1a}$ is an oxygen atom, $R^{1b}$ is (a) a hydrogen atom; (b) alkyl optionally substituted by phenyl (said phenyl is optionally substituted by 1, 2 or 3 alkoxys); or (c) tetrahydropyranyl, $R^{2b}$ is (a) alkyl optionally substituted by 1, 2 or 3 groups selected from the group consisting of cyano, a halogen atom, and morpholinyl; (b) cycloalkyl optionally substituted by 1, 2 or 3 groups selected from the group consisting of alkyl, alkoxyalkyl, halogenoalkyl, cyano, alkoxy, and a halogen atom; (c) amino optionally substituted by 1 or 2 alkyls; (d)

alkoxy optionally substituted by 1, 2 or 3 halogen atoms; (e) cycloalkoxy optionally substituted by alkyl; (f) phenyl optionally substituted by 1, 2 or 3 groups selected from the group consisting of alkyl, alkoxy optionally substituted by 1, 2 or 3 halogen atoms, and a halogen atom; (g) oxadiazolyl optionally substituted by alkyl; or (h) a nonaromatic heterocyclic group selected from the group consisting of piperidyl, oxetanyl, and tetrahydropyranyl (said nonaromatic heterocyclic group is optionally substituted by 1, 2 or 3 alkyls), $R^{8a}$, $R^{8b}$ and $R^{8c}$ are each independently (a) a hydrogen atom, (b) alkyl optionally substituted by 1, 2 or 3 halogen atoms, (c) alkoxy optionally substituted by 1, 2 or 3 halogen atoms, or (d) a halogen atom, and n is 1.

Specific examples of the compound (I) or a pharmacologically acceptable salt thereof of the present invention non-limitatively include the compounds described in the following Examples, and a pharmacologically acceptable salt thereof. Of these, examples of preferable compound or a pharmacologically acceptable salt thereof include compounds selected from the group consisting of (R)-2-[6-methyl-5-(3-methyl-[1,2,4]oxadiazol-5-yl)-7-oxo-6,7-dihydro[1,3]thiazolo[5,4-d]pyrimidin-2-yl]pyrrolidine-1-carboxylic acid phenyl ester;

(R)-2-(5-ethyl-6-methyl-7-oxo-6,7-dihydro[1,3]thiazolo[5,4-d]pyrimidin-2-yl)pyrrolidine-1-carboxylic acid phenyl ester;

(R)-2-[7-oxo-5-(propan-2-yl)-6,7-dihydro[1,3]thiazolo[5,4-d]pyrimidin-2-yl]pyrrolidine-1-carboxylic acid phenyl ester;

(R)-2-(5-ethyl-7-oxo-6,7-dihydro[1,3]thiazolo[5,4-d]pyrimidin-2-yl)pyrrolidine-1-carboxylic acid phenyl ester;

(R)-2-[5-(3-methyl-[1,2,4]oxadiazol-5-yl)-7-oxo-6,7-dihydro[1,3]thiazolo[5,4-d]pyrimidin-2-yl]pyrrolidine-1-carboxylic acid phenyl ester; and (R)-2-[6-methyl-7-oxo-5-(propan-2-yl)-6,7-dihydro[1,3]thiazolo[5,4-d]pyrimidin-2-yl]pyrrolidine-1-carboxylic acid phenyl ester; or a pharmacologically acceptable salt thereof, or compounds selected from the group consisting of (R)-N-benzyl-1-(6-methyl-7-oxo-5-phenyl-6,7-dihydro[1,3]thiazolo[5,4-d]pyrimidin-2-yl)pyrrolidine-2-carboxamide;

(R)-N-benzyl-1-(6-methyl-7-oxo-5-trifluoromethyl-6,7-dihydro-[1,3]thiazolo[5,4-d]pyrimidin-2-yl)pyrrolidine-2-carboxamide;

(R)-N-benzyl-1-[5-(2,6-difluorophenyl)-6-methyl-7-oxo-6,7-dihydro[1,3]thiazolo[5,4-d]pyrimidin-2-yl]pyrrolidine-2-carboxamide;

(R)-N-benzyl-1-[6-methyl-5-(3-methyl-1,2,4-oxadiazol-5-yl)-7-oxo-6,7-dihydro[1,3]thiazolo[5,4-d]pyrimidin-2-yl]pyrrolidine-2-carboxamide;

(R)-N-benzyl-1-[7-oxo-6-(tetrahydro-2H-pyran-4-yl)-5-trifluoromethyl-6,7-dihydro-[1,3]thiazolo[5,4-d]pyrimidin-2-yl]pyrrolidine-2-carboxamide;

(R)-N-benzyl-1-[5-(1-fluorocyclopropyl)-6-methyl-7-oxo-6,7-dihydro[1,3]thiazolo[5,4-d]pyrimidin-2-yl]pyrrolidine-2-carboxamide;

(R)-N-benzyl-1-(5-difluoromethyl-6-methyl-7-oxo-6,7-dihydro-[1,3]thiazolo[5,4-d]pyrimidin-2-yl)pyrrolidine-2-carboxamide;

(R)-N-benzyl-1-[6-methyl-7-oxo-5-(piperidin-1-yl)-6,7-dihydro[1,3]thiazolo[5,4-d]pyrimidin-2-yl]pyrrolidine-2-carboxamide;

(R)-N-benzyl-1-[5-(2-fluorophenyl)-6-methyl-7-oxo-6,7-dihydro[1,3]thiazolo[5,4-d]pyrimidin-2-yl]pyrrolidine-2-carboxamide;

(R)-N-benzyl-1-[5-(2-fluoropropan-2-yl)-7-oxo-6,7-dihydro[1,3]thiazolo[5,4-d]pyrimidin-2-yl]pyrrolidine-2-carboxamide;

(R)-N-benzyl-1-[5-(2-fluorophenyl)-7-oxo-6,7-dihydro[1,3]thiazolo[5,4-d]pyrimidin-2-yl]pyrrolidine-2-carboxamide;

(R)-N-benzyl-1-(7-oxo-5-trifluoromethyl-6,7-dihydro[1,3]thiazolo[5,4-d]pyrimidin-2-yl)pyrrolidine-2-carboxamide;

(R)-N-benzyl-1-(5-difluoromethyl-7-oxo-6,7-dihydro[1,3]thiazolo[5,4-d]pyrimidin-2-yl)pyrrolidine-2-carboxamide;

(R)-N-benzyl-1-[5-(2,6-difluorophenyl)-7-oxo-6,7-dihydro[1,3]thiazolo[5,4-d]pyrimidin-2-yl]pyrrolidine-2-carboxamide;

(R)-N-benzyl-1-[5-(3-methyl-[1,2,4]oxadiazol-5-yl)-7-oxo-6,7-dihydro[1,3]thiazolo[5,4-d]pyrimidin-2-yl]pyrrolidine-2-carboxamide;

(R)-N-benzyl-1-[5-(2-hydroxypropan-2-yl)-7-oxo-6,7-dihydro[1,3]thiazolo[5,4-d]pyrimidin-2-yl]pyrrolidine-2-carboxamide; and (R)-N-benzyl-1-[7-oxo-5-(piperidin-1-yl)-6,7-dihydro[1,3]thiazolo[5,4-d]pyrimidin-2-yl]pyrrolidine-2-carboxamide; or a pharmacologically acceptable salt thereof.

The compound (I) of the present invention can be present in the form of tautomer or a mixture thereof. The compound (I) of the present invention can be present in the form of a stereoisomer such as enantiomer, diastereomer and the like or a mixture thereof. The compound (I) of the present invention encompasses a mixture of tautomer or stereoisomer and a pure or substantially pure isomer thereof.

When compound (I) is obtained in the form of a diastereomer or enantiomer, it can be resolved by a method conventionally used in the pertinent field, for example, chromatography, and a fractional crystallization method.

The present invention encompasses compound (I) wherein one or more atoms are substituted by one or more isotopes. Examples of the isotope include $^2$H(D), $^3$H, $^{13}$C, and $^{14}$C.

Examples of the pharmacologically acceptable salt of compound (I) include alkali metal salts such as lithium, sodium, potassium and the like; group 2 metal salts such as magnesium, calcium and the like; salts with aluminum or zinc; salts with amine such as ammonia, choline, diethanolamine, lysine, ethylenediamine, tert-butylamine, tert-octylamine, tris(hydroxymethyl)aminomethane, N-methylglucosamine, triethanolamine, dehydroabiethylamine and the like; salts with inorganic acids such as hydrogen chloride, hydrogen bromide, hydrogen iodide, sulfuric acid, nitric acid, phosphoric acid and the like; salts with organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, benzenesulfonic acid and the like; and salts with acidic amino acid such as aspartic acid, glutamic acid and the like.

Moreover, the pharmacologically acceptable salt of compound (I) encompasses intramolecular salt, hydrate, solvate of compound (I).

The compound (I) or a pharmacologically acceptable salt thereof of the present invention can be administered orally or parenterally. In addition, it can be used as a conventionally-used drug preparation such as tablet, granule, capsule, powder, injection, inhalant and the like.

While the dose of the compound (I) or a pharmacologically acceptable salt thereof of the present invention varies depending on the administration method, age, body weight and condition of the patient, generally, it is preferably set to 0.001-500 mg/kg, particularly 0.01-10 mg/kg.

The compound (I) or a pharmacologically acceptable salt thereof of the present invention has a superior KAT-II inhibitory activity. A pharmaceutical composition containing compound (I) or a pharmacologically acceptable salt thereof of the present invention is useful for the treatment or prophylaxis of a disease or symptom (e.g., dementia, depression, stress vulnerability) in which inhibition of KAT-II activity is expected to improve the pathology. More specific examples of such disease and symptom include, for example, schizophrenia, bipolar disorder, attention deficit/hyperactivity disorder, Alzheimer's disease, major depression, autism, cerebrovascular dementia, HIV encephalopathy, and age-related cognitive dysfunction. Preferably, a pharmaceutical composition containing the compound (I) or a pharmacologically acceptable salt thereof of the present invention is useful for the treatment or prophylaxis of schizophrenia, attention deficit/hyperactivity disorder, Alzheimer's disease, or major depression, particularly for the treatment or prophylaxis of schizophrenia.

A therapeutic or prophylactic method including administering an effective amount of compound (I) or a pharmacologically acceptable salt thereof of the present invention to a patient (individual to be the target of treatment or prophylaxis) is also applied to the aforementioned object and encompassed in the present invention.

Also, use of compound (I) or a pharmacologically acceptable salt thereof of the present invention for the production of a medicament having a KAT-II inhibitory action is also applied to the aforementioned object and encompassed in the present invention.

According to the present invention, compound (I) or a pharmacologically acceptable salt thereof can be produced by the following method, but the method is not limited thereto.

In each production step of compound (I) to be described below, when protection of functional group contained in the compound is necessary, the functional group can be appropriately protected by a conventional method. The protecting group and general description of the use thereof are contained in T. W. Greene et al., "Protective Groups in Organic Synthesis", John Wiley & Sons, New York, 2006. The protecting group is removed by a conventional method in a subsequent step.

[Production of Compound (I)]

Of compound (I), a compound represented by the formula (I-a):

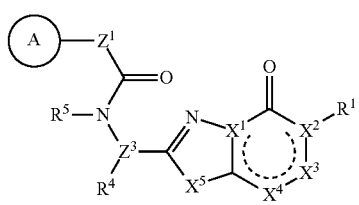

wherein the symbols are as defined above, can be produced by reacting a compound represented by the formula (II):

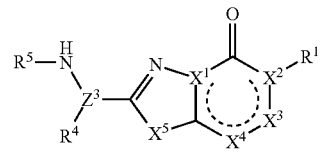

wherein the symbols are as defined above, with a compound represented by the formula (III-a):

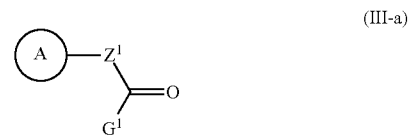

wherein $G^1$ is a leaving group, and other symbols are as defined above, in a solvent in the presence of a base.

$G^1$ represented by Examples of the leaving group include halogen atom (particularly, chlorine atom), optionally substituted aryloxy (particularly, methoxyphenyloxy) can be mentioned.

Examples of the base include amine such as triethylamine, N,N-diisopropylethylamine, pyridine, 1,8-diazabicyclo[5.4.0]-undec-7-ene (DBU) and the like.

The solvent may be any as long as it does not influence the reaction, and examples thereof include halogenohydrocarbon such as methylene chloride, chloroform, 1,2-dichloroethane and the like; ether such as tetrahydrofuran, 1,4-dioxane, 1,2-dimethoxyethane and the like; alkylnitrile such as acetonitrile, propionitrile and the like; or a mixed solvent thereof.

The amount of compound (III-a) to be used in this reaction is 0.5-20 mol, preferably 1.0-7.0 mol, per 1 mol of compound (II). The amount of the base to be used is 0.5-30 mol, preferably 0.9-7.0 mol, per 1 mol of compound (II). This reaction can be performed at 0-150° C., preferably 20-90° C.

Of compound (I), a compound represented by the formula (I-b):

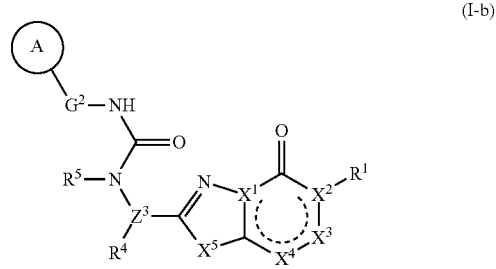

wherein $G^2$ is —C($R^6$)($R^7$)— or a single bond, and other symbols are as defined above, can be produced by reacting the aforementioned compound (II) with a compound represented by the formula (III-b):

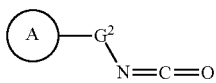

(III-b)

wherein the symbols are as defined above, in a solvent in the presence of a base.

Examples of the base include amine such as triethylamine, N,N-diisopropylethylamine, pyridine, 1,8-diazabicyclo[5.4.0]-undec-7-ene (DBU) and the like.

The solvent may be any as long as it does not influence the reaction, and examples thereof include halogenohydrocarbon such as methylene chloride, chloroform, 1,2-dichloroethane and the like.

The amount of compound (III-b) to be used in this reaction is 0.5-10 mol, preferably 1.0-1.5 mol, per 1 mol of compound (II). The amount of the base to be used is 0.5-15 mol, preferably 0.8-2.0 mol, per 1 mol of compound (II). This reaction can be performed at 0-50° C., preferably 10-30° C.

Alternatively, compound (I-b) can be produced from the aforementioned compound (II) according to a method describe below. Compound (II) is reacted with a carbonylating agent to give a reactive intermediate. Furthermore, the reactive intermediate is reacted with a compound represented by the formula (III-c):

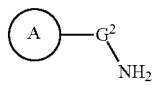

(III-c)

wherein the symbols are as defined above, whereby compound (I-b) can be produced.

The reaction of compound (II) and a carbonylating agent can be performed in a solvent in the presence of a base.

Examples of the carbonylating agent include triphosgene, phosgene, and carbonyldiimidazole. Examples of the base include amine such as triethylamine, N,N-diisopropylethylamine, pyridine and the like. The solvent may be any as long as it does not influence the reaction, and examples thereof include halogenohydrocarbon such as methylene chloride, chloroform, 1,2-dichloroethane and the like; aromatic hydrocarbon such as benzene, toluene, xylene and the like. The amount per carbonyl of the carbonylating agent to be used in this reaction is 0.5-10 mol, preferably 1.5-2.5 mol, per 1 mol of compound (II). The amount of the base to be used is 0.5-15 mol, preferably 1.8-3.0 mol, per 1 mol of compound (II). This reaction can be performed at −20 to 50° C., preferably 0-30° C.

The reaction of the obtained reactive intermediate and compound (III-c) can be performed in a solvent in the presence of a base.

Examples of the base include amine such as triethylamine, N,N-diisopropylethylamine, N,N-dimethyl-4-aminopyridine and the like. The solvent may be any as long as it does not influence the reaction, and examples thereof include halogenohydrocarbon such as methylene chloride, chloroform, 1,2-dichloroethane and the like. The amount of compound (III-c) to be used in this reaction is 1.0-10 mol, preferably 3.0-7.0 mol, per 1 mol of compound (II). The amount of the base to be used is 1.0-15 mol, preferably 3.0-8.0 mol, per 1 mol of compound (II). This reaction can be performed at 0-50° C., preferably 10-30° C.

Of compound (I), a compound represented by the formula (I-c):

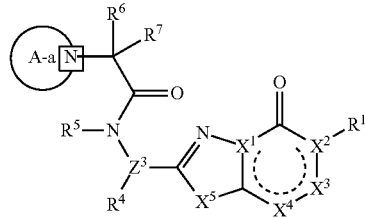

(I-c)

wherein ring A-a is optionally substituted nitrogen-containing heteroaryl wherein a bond of the ring is a nitrogen atom, can be produced from the aforementioned compound (II) according to a method describe below. Compound (II) is reacted with a compound represented by the formula (IV):

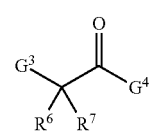

(IV)

wherein $G^3$ and $G^4$ are each independently a leaving group, and other symbols are as defined above, to give a reactive intermediate. Furthermore, the reactive intermediate is reacted with a compound represented by the formula (V):

(V)

wherein the symbols are as defined above, whereby compound (I-c) can be produced.

The leaving groups for $G^3$ and $G^4$ are each independently, for example, a halogen atom (particularly, chlorine atom).

The reaction of compound (II) and compound (IV) can be performed in a solvent in the presence of a base.

Examples of the base include amine such as triethylamine, N,N-diisopropylethylamine, pyridine and the like. The solvent may be any as long as it does not influence the reaction, and examples thereof include halogenohydrocarbon such as methylene chloride, chloroform, 1,2-dichloroethane and the like. The amount of compound (IV) to be used in this reaction is 0.5-10 mol, preferably 1.0-1.2 mol, per 1 mol of compound (II). The amount of the base to be used is 0.5-15 mol, preferably 1.0-1.3 mol, per 1 mol of compound (II). This reaction can be performed at 0-50° C., preferably 10-30° C.

The reaction of the obtained reactive intermediate and compound (V) can be performed in a solvent with or without additive in the presence of a base.

Examples of the base include alkali metal carbonate such as potassium carbonate, cesium carbonate, sodium carbonate and the like; alkali metal hydride such as sodium hydride and the like. As the additive, alkali metal iodide such as potassium iodide, sodium iodide and the like can be mentioned. The solvent may be any as long as it does not influence the reaction, and examples thereof include ether such as tetrahydrofuran, 1,4-dioxane, 1,2-dimethoxyethane and the like; alkylnitrile such as acetonitrile, propionitrile and the like; or a mixed solvent thereof can be mentioned. The amount of compound (V) to be used in this reaction is 1.0-3.0 mol, preferably 1.1-1.8 mol, per 1 mol of compound (II). The amount of the base to be used is 1.0-15 mol, preferably 1.2-2.0 mol, per 1 mol of compound (II). The amount of the additive to be used is 1.0-10 mol, preferably 1.1-2.5 mol, per 1 mol of compound (II). This reaction can be performed at 20-120° C., preferably 60-100° C.

Of compound (I), a compound represented by the formula (I-d):

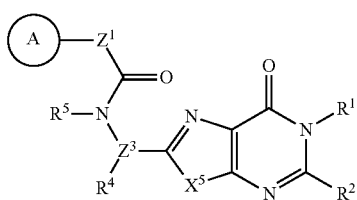

(I-d)

wherein the symbols are as defined above, can be produced by reacting a compound represented by the formula (VI):

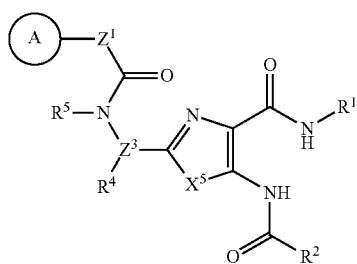

(VI)

wherein the symbols are as defined above, in a solvent in the presence of a condensation agent in the presence of a base.

Examples of the condensation agent include chlorotrialkylsilane such as chlorotrimethylsilane and the like, N,O-bis(trialkylsilyl)acetamide such as N,O-bis(trimethylsilyl)acetamide and the like. Examples of the base include amine such as triethylamine, N,N-diisopropylethylamine, pyridine and the like. The solvent may be any as long as it does not influence the reaction, and examples thereof include halogenohydrocarbon such as methylene chloride, chloroform, 1,2-dichloroethane and the like; amide such as N,N-dimethylformamide, N,N-dimethylacetamide, 1,3-dimethyl-2-imidazolidinone, N-methylpyrrolidone and the like. The amount of the condensation agent to be used in this reaction is 1.0-500 mol, preferably 5.0-100 mol, per 1 mol of compound (VI). The amount of the base to be used is 3.0-1500 mol, preferably 15-300 mol, per 1 mol of compound (VI). This reaction can be performed at 0-50° C., preferably 10-30° C.

Alternatively, compound (I-d) can be produced by reacting compound (VI) in a solvent (e.g., acetic acid) in the presence of an acid (e.g., concentrated sulfuric acid).

Alternatively, compound (I-d) can be produced by reacting a compound represented by the formula (VII):

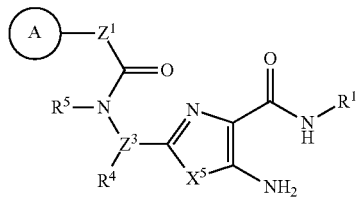

(VII)

wherein the symbols are as defined above, with a compound represented by the formula (VIII-a):

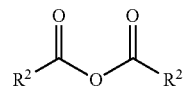

(VIII-a)

wherein the symbols are as defined above, in a solvent in the presence of a base.

Examples of the base include amine such as triethylamine, N,N-diisopropylethylamine, pyridine and the like. The solvent may be any as long as it does not influence the reaction, and examples thereof include halogenohydrocarbon such as methylene chloride, chloroform, 1,2-dichloroethane and the like.

The amount of compound (VIII-a) to be used in this reaction is 3.0-100 mol, preferably 5.0-30 mol, per 1 mol of compound (VII). The amount of the base to be used is 3.0-100 mol, preferably 5.0-30 mol, per 1 mol of compound (VII) This reaction can be performed at 0-150° C., preferably 20-100° C.

Alternatively, compound (I-d) can be produced by reacting the aforementioned compound (VII) with a compound represented by the formula (VIII-b):

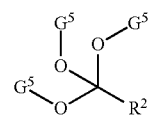

(VIII-b)

wherein $G^5$ is alkyl, and other symbols are as defined above, without solvent in the presence of acid anhydride (e.g., acetic anhydride).

The amount of compound (VIII-b) to be used in this reaction is 1.0-30 mol, preferably 5.0-20 mol, per 1 mol of compound (VII). The amount of acid anhydride to be used is 1.0-30 mol, preferably 5.0-20 mol, per 1 mol of compound (VII). This reaction can be performed at 60-180° C., preferably 100-150° C.

Of compound (I), a compound represented by the formula (I-e):

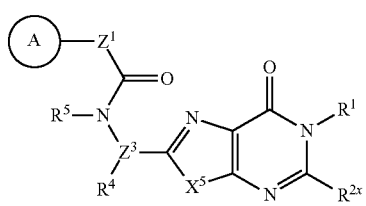

(I-e)

wherein $R^{2x}$ is an optionally substituted nitrogen-containing nonaromatic heterocyclic group wherein a bond of the group is a nitrogen atom, optionally substituted amino, optionally substituted alkoxy, or optionally substituted cycloalkoxy, and other symbols are as defined above, can be produced by reacting a compound represented by the formula (IX):

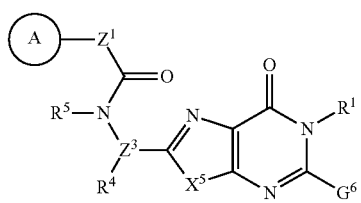

(IX)

wherein $G^6$ is a leaving group, and other symbols are as defined above, with a compound represented by the formula (X):

HR$^{2x}$ (X)

wherein the symbols are as defined above.

Examples of the leaving group for $G^6$ include alkylsulfinyl (particularly, methylsulfinyl), and alkylsulfonyl (particularly, methylsulfonyl).

When $R^{2x}$ is an optionally substituted nitrogen-containing nonaromatic heterocyclic group wherein a bond of the group is a nitrogen atom or optionally substituted amino, this reaction can be performed in a solvent.

The solvent may be any as long as it does not influence the reaction, and examples thereof include ether such as tetrahydrofuran, 1,4-dioxane, 1,2-dimethoxyethane and the like.

The amount of compound (X) to be used in this reaction is 1.0-20 mol, preferably 3.0-8.0 mol, per 1 mol of compound (IX). This reaction can be performed at 0-60° C., preferably 10-30° C.

When $R^{2x}$ is optionally substituted alkoxy or optionally substituted cycloalkoxy, this reaction can be performed in a solvent in the presence of a base.

Examples of the base include alkali metal tert-butoxide such as potassium tert-butoxide, sodium tert-butoxide and the like; and alkali metal hydride such as sodium hydride and the like.

The solvent may be any as long as it does not influence the reaction, and examples thereof include amide such as N,N-dimethylformamide, N,N-dimethylacetamide, 1,3-dimethyl-2-imidazolidinone, N-methylpyrrolidone and the like.

The amount of compound (X) to be used in this reaction is 1.0-3.0 mol, preferably 1.2-1.8 mol, per 1 mol of compound (IX). The amount of the base to be used is 0.9-2.7 mol, preferably 1.1-1.7 mol, per 1 mol of compound (IX). This reaction can be performed at 20-100° C., preferably 40-80° C.

Of compound (I), a compound represented by the formula (I-f):

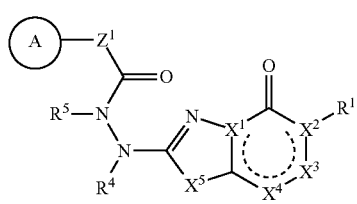

(I-f)

wherein the symbols are as defined above, can be produced by reacting a compound represented by the formula (XI):

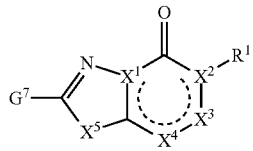

(XI)

wherein $G^7$ is a leaving group, and other symbols are as defined above, with a compound represented by the formula (XII):

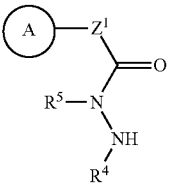

(XII)

wherein the symbols are as defined above, or a salt thereof.

Examples of the leaving group for $G^7$ include halogen atom (particularly, bromine atom), alkylsulfinyl (particularly, methylsulfinyl), and alkylsulfonyl (particularly, methylsulfonyl).

This reaction can be performed in a solvent in the presence of a base, in the presence of a copper salt in the presence of a ligand.

Examples of the base include trialkali metal phosphate such as trisodium phosphate, tripotassium phosphate and the like. Examples of the copper salt include copper (I) halide such as copper (I) iodide and the like. Examples of the ligand include diamine such as trans-N,N'-dimethylcyclohexane-1,2-diamine, trans-cyclohexane-1,2-diamine and the like. The solvent may be any as long as it does not influence the reaction, and examples thereof include ether such as tetrahydrofuran, 1,4-dioxane, 1,2-dimethoxyethane and the like.

The amount of compound (XII) to be used in this reaction is 0.5-10 mol, preferably 1.0-6.0 mol, per 1 mol of compound (XI). The amount of the base to be used is 1.0-10 mol, preferably 1.2-3.0 mol, per 1 mol of compound (XI). The amount of the copper salt to be used is 0.05-1.0 mol, preferably 0.1-0.3 mol, per 1 mol of compound (XI). The amount of the ligand to be used is 0.05-1.0 mol, preferably 0.1-0.3 mol, per 1 mol of compound (XI). This reaction can be performed at 50-150° C., preferably 80-120° C.

Alternatively, this reaction can be performed in a solvent or without solvent, in the presence of a base.

Examples of the base include amine such as triethylamine, N,N-diisopropylethylamine, pyridine and the like. The solvent may be any as long as it does not influence the reaction, and examples thereof include ether such as tetrahydrofuran, 1,4-dioxane, 1,2-dimethoxyethane and the like.

The amount of compound (XII) to be used in this reaction is 0.5-10 mol, preferably 1.0-6.0 mol, per 1 mol of compound (XI). The amount of the base to be used is 0.9-10 mol, preferably 1.0-5.0 mol, per 1 mol of compound (XI). This reaction can be performed at 80-200° C., preferably 120-180° C.

Of compound (I), a compound represented by the formula (I-g)

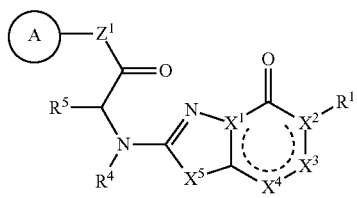

wherein the symbols are as defined above, can be produced by reacting a compound represented by the formula (XIII):

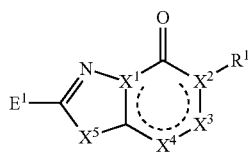

wherein $E^1$ is a leaving group, and other symbols are as defined above, with a compound represented by the formula (XIV):

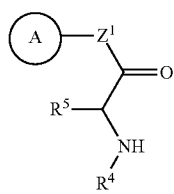

wherein the symbols are as defined above, in a solvent or without solvent, in the presence of a base.

Examples of the leaving group for $E^1$ include halogen atom (particularly, bromine atom), optionally substituted alkylsulfinyl (particularly, methylsulfinyl, benzylsulfinyl), and optionally substituted alkylsulfonyl (particularly, methylsulfonyl, benzylsulfonyl).

Examples of the base include amine such as triethylamine, N,N-diisopropylethylamine, pyridine and the like; and alkali metal carbonate such as sodium carbonate, potassium carbonate, cesium carbonate and the like. The solvent may be any as long as it does not influence the reaction, and examples thereof include ether such as tetrahydrofuran, 1,4-dioxane, 1,2-dimethoxyethane and the like; amide such as N,N-dimethylformamide, N,N-dimethylacetamide, 1,3-dimethyl-2-imidazolidinone and N-methylpyrrolidone and the like; amine such as pyridine and the like; or a mixed solvent thereof.

The amount of compound (XIV) to be used in this reaction is 0.9-30 mol, preferably 1.2-5.0 mol, per 1 mol of compound (XIII). The amount of the base to be used is 1.0-100 mol, preferably 1.2-10 mol, per 1 mol of compound (XIII). This reaction can be performed at 60° C.-180° C., preferably 100° C. 150° C.

Of compound (I), a compound represented by the formula (I-h):

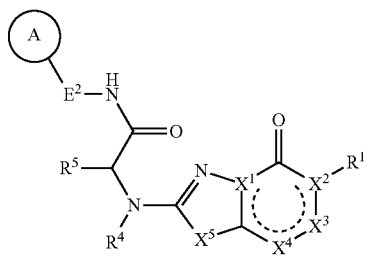

wherein $E^2$ is —C($R^6$)($R^7$)—, or a single bond, and other symbols are as defined above, can be produced from the aforementioned compound (XIII) according to a method describe below.

Compound (XIII) and a compound represented by the formula (XV-a):

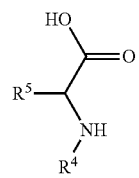

wherein the symbols are as defined above, are reacted to give a compound represented by the formula (XVI-a):

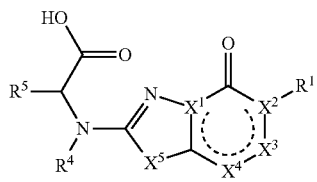

wherein the symbols are as defined above. The compound (XVI-a) is reacted with a compound represented by the formula (XVII):

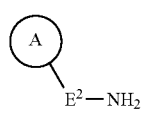

wherein the symbols are as defined above, whereby compound (I-h) can be produced.

Compound (XVI-a) can be produced by reacting compound (XIII) and compound (XV-a), which is similar to the method of producing the aforementioned compound (I-g) from compound (XIII) and compound (XIV).

Compound (I-h) can be produced by reacting compound (XVI-a) and compound (XVII) in a solvent with or without an activator, in the presence of a condensation agent, in the presence of a base.

Examples of the condensation agent include 1-(3-dimethylaminopropyl)-3-ethylcarbodiimide hydrochloride (EDC hydrochloride), and O-(7-azabenzotriazol-1-yl)-N,N,N',N'-tetramethyluronium hexafluorophosphate (HATU).

Examples of the activator include 1-hydroxybenzotriazole monohydrate (HOBt monohydrate), 1-hydroxy-7-azabenzotriazole (HOAt). Examples of the base include amine such as triethylamine, N,N-diisopropylethylamine, pyridine and the like. The solvent may be any as long as it does not influence the reaction, and examples thereof include ether such as tetrahydrofuran, 1,4-dioxane, 1,2-dimethoxyethane and the like; amide such as N,N-dimethylformamide, N,N-dimethylacetamide, 1,3-dimethyl-2-imidazolidinone and N-methylpyrrolidone and the like; or a mixed solvent thereof.

The amount of compound (XVII) to be used in this reaction is 0.9-5.0 mol, preferably 1.2-3.0 mol, per 1 mol of compound (XVI-a). The amount of the condensation agent to be used is 0.9-5.0 mol, preferably 1.2-3.0 mol, per 1 mol of compound (XVI-a). The amount of the base to be used is 0.9-5.0 mol, preferably 1.2-3.0 mol, per 1 mol of compound (XVI-a). The amount of the activator to be used is 0.9-5.0 mol, preferably 1.2-3.0 mol, per 1 mol of compound (XVI-a). This reaction can be performed at 0° C.-80° C., preferably 10-40° C.

Alternatively, compound (I-h) can be produced the aforementioned compound (XIII) according to a method describe below.

Compound (XIII) and a compound represented by the formula (XV-b):

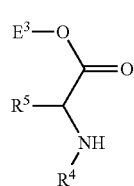

(XV-b)

wherein $E^3$ is a carboxylic acid-protecting group, and other symbols are as defined above, are reacted to give a compound represented by the formula (XVI-b):

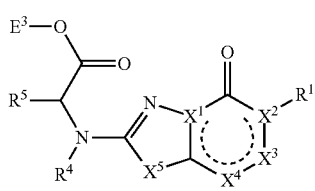

(XVI-b)

wherein the symbols are as defined above. $E^3$ of the compound (XVI-b) is removed to give compound (XVI-a). This is reacted with the aforementioned compound (XVII) to give compound (I-h).

Examples of the protecting group for $E^3$ include optionally substituted alkyl (tert-butyl etc.).

Compound (XVI-b) can be produced by reacting the aforementioned compound (XIII) and compound (XV-b), which is similar to the method of producing compound (I-g) from compound (XIII) and compound (XIV).

Compound (XVI-a) can be produced by a conventional method such as acid treatment, base treatment and the like according to the kind of $E^3$ of compound (XVI-b).

For example, compound (XVI-b) wherein $E^3$ is tert-butyl can be deprotected in a solvent in the presence of an acid.

Examples of the acid include trifluoroacetic acid, formic acid, hydrogen chloride. The solvent may be any as long as it does not influence the reaction, and examples thereof include halogenohydrocarbon such as methylene chloride, chloroform and 1,2-dichloroethane and the like. This reaction can be performed at 0° C.-100° C.

Compound (I-h) can be produced by reacting compound (XVI-a) and compound (XVII) in a solvent with or without an activator, in the presence of a condensation agent, in the presence of a base, as mentioned above.

Of compound (I), a compound represented by the formula (I-i):

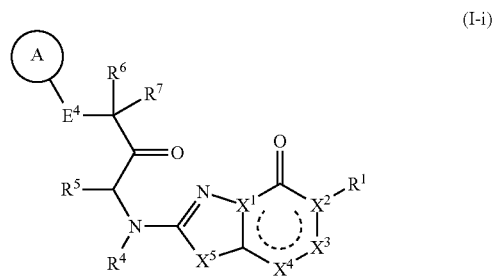

(I-i)

wherein $E^4$ is an oxygen atom, or NH, and other symbols are as defined above, can be produced from the aforementioned compound (XIII) according to a method describe below.

Compound (XIII) and a compound represented by the formula (XVIII):

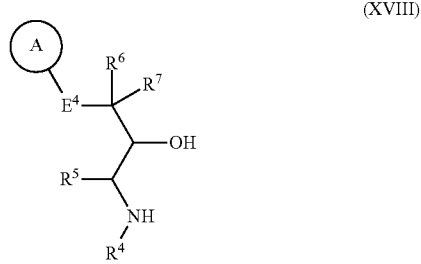

(XVIII)

wherein the symbols are as defined above, are reacted to give a compound represented by the formula (XIX):

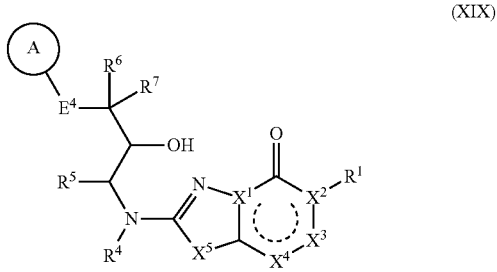

(XIX)

wherein the symbols are as defined above. The compound (XIX) is oxidized by a conventional method, whereby compound (I-i) can be produced.

Compound (XIX) can be produced by reacting compound (XIII) and compound (XVIII), which is similar to the method of producing the aforementioned compound (I-g) from compound (XIII) and compound (XIV)

Compound (I-i) can be produced by reacting, for example, compound (XIX) in a solvent (e.g., methylene chloride), in the presence of dimethyl sulfoxide, in the presence of oxalyl chloride, in the presence of a base (e.g., triethylamine).

Of compound (I), a compound represented by the formula (I-j):

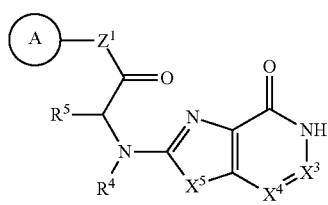

(I-j)

wherein the symbols are as defined above, can be produced by removing $E^5$ of a compound represented by the formula (XX):

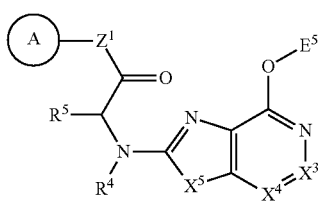

(XX)

wherein $E^5$ is a hydroxy-protecting group, and other symbols are as defined above, by a conventional method such as acid treatment, base treatment and the like according to the kind thereof.

Examples of the protecting group for $E^5$ include optionally substituted alkyl (p-methoxybenzyl etc.).

For example, compound (XX) wherein $E^5$ is p-methoxybenzyl can be deprotected in a solvent (e.g., methylene chloride) or without solvent, with or without water and with or without trialkylsilane (e.g., triethylsilane), in the presence of an acid (e.g., trifluoroacetic acid). This reaction can be performed at 0° C.-100° C.

Of compound (I), a compound represented by the formula (I-k)

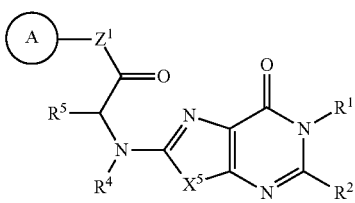

(I-k)

wherein the symbols are as defined above, can be produced by reacting a compound represented by the formula (XXI):

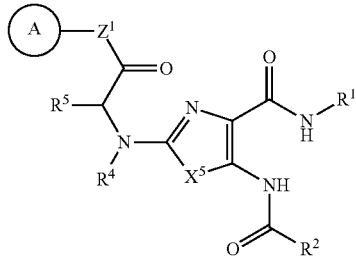

(XXI)

wherein the symbols are as defined above, in a solvent in the presence of trimethylsilyl trifluoromethanesulfonate, and a base.

Examples of the base include amine such as triethylamine, N,N-diisopropylethylamine, pyridine and the like. The solvent may be any as long as it does not influence the reaction, and examples thereof include halogenohydrocarbon such as methylene chloride, chloroform and 1,2-dichloroethane and the like. This reaction can be performed at 0° C.-50° C.

Of compound (I), a compound represented by the formula (I-m):

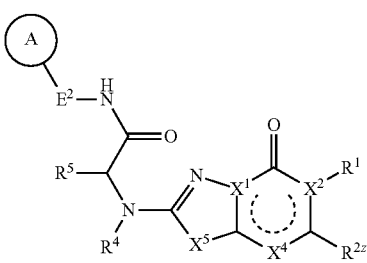

(I-m)

wherein $R^{2z}$ is optionally substituted alkenyl, or optionally substituted cycloalkyl, and other symbols are as defined above, can be produced by reacting a compound represented by the formula (XXII):

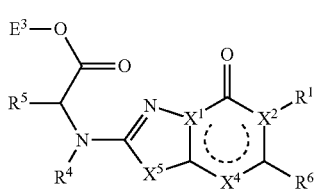

(XXII)

wherein $E^6$ is a halogen atom, and other symbols are as defined above, with a compound represented by the formula (XXIII): $R^{2z}$-$E^7$ (XXIII)

wherein $E^7$ is trialkylstannyl or dihydroxyboryl, and other symbols are as defined above, to give a compound represented by the formula (XXIV):

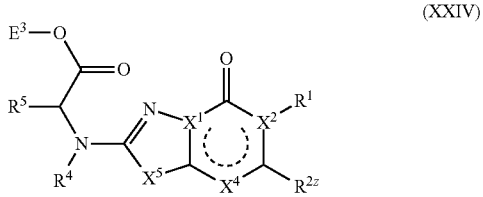

(XXIV)

wherein the symbols are as defined above, and $E^3$ of compound (XXIV) is removed to give a compound represented by the formula (XXV):

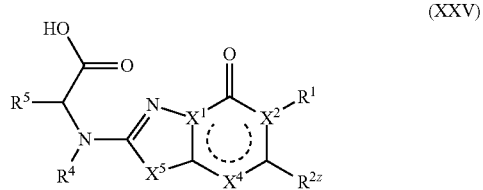

(XXV)

wherein the symbols are as defined above. This is reacted with the aforementioned compound (XVII), whereby compound (I-m) can be produced.

Compound (XXIV) can be produced by reacting compound (XXII) and compound (XXIII) in a solvent in the presence of palladiums, in the presence or absence of a ligand, in the presence or absence of a base.

Examples of the palladiums include tris(dibenzylideneacetone)dipalladium (0), tetrakis(triphenylphosphine)palladium (0), palladium (II) acetate, palladium (II) chloride, bis(triphenylphosphine)dichloropalladium (II), [1,1'-bis(diphenylphosphino)ferrocene]dichloropalladium (II), bis(di-tert-butyl(4-dimethylaminophenyl)phosphine)dichloropalladium (II), dichlorobis(tricyclohexylphosphine)palladium (II). Examples of the ligand include phosphine ligand such as triphenylphosphine, 2-di-tert-butylphosphino-2',4',6'-triisopropylbiphenyl, 2-dicyclohexyl-phosphino-2',6'-dimethoxybiphenyl, 2-di-tert-butylphosphino-3,4,5,6-tetramethyl-2',4',6'-triisopropyl-1,1'-biphenyl and the like. Examples of the base include alkali metal carbonate such as sodium carbonate, potassium carbonate, cesium carbonate and the like; alkali metal phosphate such as trisodium phosphate, disodium hydrogen phosphate and tripotassium phosphate and the like; alkali metal fluoride such as potassium fluoride, cesium fluoride and the like. The solvent may be any as long as it does not influence the reaction, and examples thereof include ether such as tetrahydrofuran, 1,2-dimethoxyethane, 1,4-dioxane and the like; alcohol such as tert-butanol and the like; aromatic hydrocarbon such as toluene, xylene and the like; amide such as N,N-dimethylformamide, N,N-dimethylacetamide, 1,3-dimethyl-2-imidazolidinone, N-methylpyrrolidone and the like; water, or a mixed solvent thereof.

The amount of compound (XXIII) to be used in this reaction is 0.9-10 mol, preferably 1.2-3.0 mol, per 1 mol of compound (XXII). The amount of the palladiums to be used is 0.001-1.0 mol, preferably 0.01-0.3 mol, per 1 mol of compound (XXII). The amount of the ligand to be used is 0.001-3.0 mol, preferably 0.01-1.0 mol, per 1 mol of compound (XXII). The amount of the base to be used is 0.9-10 mol, preferably 1.0-3.0 mol, per 1 mol of compound (XXII). This reaction can be performed at 50-180° C., preferably 60-150° C.

Compound (XXV) can be produced by treating compound (XXIV) by a conventional method, which is similar to the removal of $E^3$ from the aforementioned compound (XVI-b).

Compound (I-m) can be produced by reacting compound (XXV) and compound (XVII) in a solvent in the presence of a condensation agent, in the presence of a base, in the presence or absence of an activator, which is similar to the reaction of the aforementioned compound (XVI-a) and compound (XVII).

Compound (I) produced by the above-mentioned production method may be subjected to interconversion of substituents by a conventional method. As a method of interconversion of substituents, the following methods 1-28 can be specifically mentioned.

These methods can also be applied to an intermediate compound obtained during production of compound (I).

Method 1:

Compound (I) having optionally substituted amino as a substituent, an optionally substituted nitrogen-containing nonaromatic heterocyclic group wherein a bond of the group is a nitrogen atom, or optionally substituted nitrogen-containing heteroaryl wherein a bond of the group is a nitrogen atom can be produced by, for example, reacting corresponding compound (I) having a halogen atom (particularly, chlorine atom) as a substituent, in a solvent (e.g., alkylnitrile such as acetonitrile and the like), in the presence of a base (e.g., alkali metal carbonate such as potassium carbonate and the like), with corresponding optionally substituted amine, optionally substituted nitrogen-containing nonaromatic heterocyclic group, or optionally substituted nitrogen-containing heteroarene to perform amination.

Method 2:

Compound (I) wherein $X^2$ is a nitrogen atom and $R^1$ is optionally substituted alkyl can be produced by reacting, for example, corresponding compound (I) wherein $X^2$ is a nitrogen atom and $R^1$ is a hydrogen atom with corresponding alkyl iodide in a solvent (e.g., alkylnitrile such as acetonitrile and the like), in the presence of a base (e.g., alkali metal carbonate such as potassium carbonate and the like).

Method 3:

Compound (I) wherein $X^2$ is a nitrogen atom and $R^1$ is optionally substituted alkyl can be produced by reacting compound (I) wherein $X^2$ is a nitrogen atom and $R^1$ is a hydrogen atom in a solvent in the presence of corresponding optionally substituted alkyl halide, in the presence of a base.

Examples of the base include alkali metal carbonate such as potassium carbonate and the like. The solvent may be any as long as it does not influence the reaction, and examples thereof include amide such as N,N-dimethylformamide, N,N-dimethylacetamide, 1,3-dimethyl-2-imidazolidinone, N-methylpyrrolidone and the like.

The amount of alkyl halide to be used in this reaction is 0.9-5.0 mol, preferably 1.0-2.0 mol, per 1 mol of compound (I). The amount of the base to be used is 0.9-3.0 mol, preferably 1.0-2.0 mol, per 1 mol of compound (I). This reaction can be performed at 0-120° C., preferably 15-80° C.

Method 4:

Compound (I) wherein $X^2$ is a nitrogen atom and $R^1$ is a hydrogen atom can be produced by reacting compound (I) wherein $X^2$ is a nitrogen atom and $R^1$ is alkoxyphenylmethyl in a solvent in the presence of an acid, in the presence or absence of a hydrogenating agent.

Examples of the acid include trifluoroacetic acid. Examples of the hydrogenating agent include trialkylsilane such as triethylsilane and the like. The solvent may be any as long as it does not influence the reaction, and examples thereof include a solvent amount of the above-mentioned acid, a solvent amount of the above-mentioned trialkylsilane, water, or a mixed solvent thereof.

Method 5:

Compound (I) wherein $R^1$ is a hydrogen atom can be produced by reacting, for example, corresponding compound (I) wherein $R^1$ is 2,4-dimethoxybenzyl in a solvent in the presence or absence of trialkylsilane, in the presence or absence of iodotrialkylsilane.

Examples of trialkylsilane include triethylsilane. Examples of iodotrialkylsilane include trimethylsilyl iodide. The solvent may be any as long as it does not influence the reaction, and examples thereof include alkylnitrile such as acetonitrile, propionitrile and the like; halogenohydrocarbon to such as methylene chloride, chloroform, 1,2-dichloroethane and the like; trifluoroacetic acid; water; and a mixed solvent thereof.

Method 6:

Compound (I) wherein $R^1$ or $R^3$ is a halogen atom can be produced by reacting compound (I) wherein $R^1$ or $R^3$ is a hydrogen atom in a solvent in the presence of a halogenating agent.

Examples of the halogenating agent include corresponding N-halogenosuccinimide. The solvent may be any as long as it does not influence the reaction, and examples thereof include ether such as tetrahydrofuran, 1,2-dimethoxyethane and the like, amide such as N,N-dimethylformamide, N-methylpyrrolidone and the like.

Method 7:

Compound (I) wherein $R^2$ is pyrazolyl can be produced by reacting compound (I) wherein $R^2$ is hydrazino in a solvent (e.g., alkyl alcohol such as ethanol and the like, water, or a mixed solvent thereof) in the presence of 1,1,3,3-tetramethoxypropane, in the presence of an acid (e.g., inorganic acid such as hydrogen chloride and the like).

Method 8:

Compound (I) wherein $R^2$ is optionally substituted cyclopropane can be produced by reacting compound (I) wherein $R^2$ is corresponding optionally substituted alkenyl in a solvent (e.g., aromatic hydrocarbon such as toluene and the like), in the presence of methylene iodide, in the presence of diethyl zinc.

Method 9:

Compound (I) wherein $R^1$ and $R^2$ are bonded to each other to form, together with the adjacent $X^2$ and carbon atom, an optionally substituted nitrogen-containing non-aromatic heterocycle can be produced by reacting compound (I) wherein $R^1$ is aminoalkyl further optionally having substituent(s) and $R^2$ is halogenoalkyl further optionally having substituent(s) in a solvent (e.g., ether such as tetrahydrofuran and the like, is water, or a mixed solvent thereof), in the presence of a base (e.g., alkali metal carbonate such as sodium hydrogen carbonate and the like).

Method 10:

Compound (I) wherein $R^1$ and $R^2$ are bonded to each other to form, together with the adjacent $X^2$ and carbon atom, an optionally substituted nitrogen-containing non-aromatic heterocycle can be produced from compound (I) wherein $R^1$ is (tert-butoxycarbonylamino)alkyl further optionally having substituent(s) and $R^2$ is hydroxyalkyl further optionally having substituent(s), according to a method describe below. Compound (I) wherein $R^1$ is (tert-butoxycarbonylamino) alkyl further optionally having substituent(s) and $R^2$ is hydroxyalkyl further optionally having substituent(s) is reacted in a solvent (e.g., halogenohydrocarbon such as methylene chloride and the like), in the presence of methanesulfonyl chloride in the presence of a base (e.g., trialkylamine such as triethylamine and the like) to give a compound wherein corresponding $R^2$ is methanesulfonyloxyalkyl further optionally having substituent(s). This is reacted in a solvent (e.g., halogenohydrocarbon such as methylene chloride and the like, an acid in a solvent amount or less, or a mixed solvent thereof) in the presence of an acid (e.g., trifluoroacetic acid), whereby compound (I) wherein $R^1$ and $R^2$ are bonded to each other to form, together with the adjacent $X^2$ and carbon atom, an optionally substituted nitrogen-containing non-aromatic heterocycle can be produced.

Method 11:

Compound (I) wherein $R^1$ and $R^2$ are bonded to each other to form, together with the adjacent nitrogen atom and carbon atom, an optionally substituted nitrogen-containing non-aromatic heterocycle can be produced by reacting compound (I) wherein $X^2$ is a nitrogen atom and $R^1$ is a hydrogen atom and $R^2$ is (hydroxyalkyl)amino further optionally having substituent(s) in the presence of a solvent amount of concentrated sulfuric acid.

Method 12:

Compound (I) wherein $R^1$ and $R^2$ are bonded to each other to form, together with the adjacent nitrogen atom and carbon atom, an optionally substituted nitrogen-containing non-aromatic heterocycle can be produced by reacting compound (I) wherein $X^2$ is a nitrogen atom and $R^1$ is a hydrogen atom and $R^2$ is (gem-dialkoxyalkyl)amino further optionally having substituent(s) in the presence of a solvent amount of concentrated sulfuric acid.

Method 13:

Compound (I) wherein $R^1$ and $R^2$ are bonded to each other to form, together with the adjacent nitrogen atom and carbon atom, an optionally substituted nitrogen-containing non-aromatic heterocycle can be produced by reacting compound (I) wherein $X^2$ is a nitrogen atom and $R^1$ is a hydrogen atom and $R^2$ is hydroxyalkyl further optionally having substituent(s) in a solvent (e.g., amide such as N,N-dimethylformamide and the like) in the presence of methyl triphenoxyphosphonium iodide in the presence of a base (e.g., trialkylamine such as triethylamine and the like).

Method 14:

Compound (I) having hydroxy as a substituent can be produced by hydrolysis of compound (I) having alkanoyloxy as a substituent by a conventional method.

The hydrolysis can be performed by reacting compound (I) having alkanoyloxy as a substituent in a solvent (e.g., tetrahydrofuran, 1,4-dioxane, methanol, ethanol, water, or these used in combination), in the presence of a base (e.g., alkali metal hydroxide such as sodium hydroxide, potassium hydroxide, lithium hydroxide and the like; alkali metal alkoxide such as sodium methoxide, sodium ethoxide and the like).

Method 15:

Compound (I) having hydroxy as a substituent can be produced by reacting compound (I) having alkoxycarbonyl as a substituent in a solvent (e.g., ether such as tetrahydrofuran and the like) in the presence of a reducing agent (e.g., lithium aluminum hydride).

Method 16:

Compound (I) having hydroxy as a substituent can be produced by reacting compound (I) having methoxy as a substituent in a solvent (e.g., halogenohydrocarbon such as methylene chloride and the like) in the presence of boron tribromide.

Method 17:

Compound (I) having hydroxy as a substituent can be produced by reacting compound (I) having halogen (e.g., fluorine atom) as a substituent in a solvent (e.g., alkylnitrile such as acetonitrile and the like), water, or a mixed solvent thereof), in the presence of a base (e.g., alkali metal carbonate such as sodium hydrogen carbonate and the like)

Method 18:

Compound (I) having oxo as a substituent can be produced by reacting compound (I) having hydroxy as a substituent in a solvent (e.g., halogenohydrocarbon such as chloroform and the like), in the presence of an oxidant (e.g., manganese dioxide).

Method 19:

Compound (I) having optionally substituted alkoxy as a substituent can be produced by reacting compound (I) having hydroxy as a substituent in a solvent (e.g., amide such as N,N-dimethylformamide and the like), in the presence of the corresponding optionally substituted alkyl halide (e.g., alkyl iodide), in the presence of a base (e.g., alkali metal hydride such as sodium hydride and the like).

Method 20:

Compound (I) having optionally substituted alkoxy as a substituent can be produced by reacting compound (I) having halogen atom (e.g., fluorine atom) as a substituent in the presence of a solvent amount of the corresponding optionally substituted alkylalcohol, in the presence of a base (e.g., alkali metal carbonate such as potassium carbonate and the like).

Method 21:

Compound (I) having optionally substituted amino as a substituent can be produced by reacting compound (I) having halogen atom (e.g., chlorine atom) as a substituent in a solvent (e.g., alkylnitrile such as acetonitrile and the like) in the presence of the corresponding optionally substituted amine, in the presence of a base (e.g., alkali metal carbonate such as potassium carbonate and the like) in the presence of an additive (e.g., alkali metal iodide such as potassium iodide and the like).

Method 22:

Compound (I) having optionally substituted amino as a substituent can be produced from compound (I) having hydroxy as a substituent according to a method describe below. Compound (I) having hydroxy as a substituent is reacted in a solvent (e.g., halogenohydrocarbon such as methylene chloride and the like), in the presence of methanesulfonyl chloride, in the presence of a base (e.g., trialkylamine such as triethylamine and the like) to give a compound having methanesulfonyloxy as the corresponding substituent. This is reacted in a solvent (e.g., alkylnitrile such as acetonitrile and the like), in the presence of an excess amount of the corresponding optionally substituted amine in the presence or absence of an additive (e.g., alkali metal iodide such as sodium iodide and the like), whereby compound (I) having optionally substituted amino as a substituent can be produced.

Method 23:

Compound (I) having carbobenzoxyamino as a substituent can be produced from compound (I) having hydroxy as a substituent, according to a method describe below. Compound (I) having hydroxy as a substituent is reacted in a solvent (e.g., ether such as tetrahydrofuran and the like, aromatic hydrocarbon such as toluene and the like, or a mixed solvent thereof) in the presence of diphenylphosphoryl azide, in the presence of triarylphosphine such as triphenylphosphine and the like, in the presence of dialkyl azodicarboxylate such as diethyl azodicarboxylate and the like to give a compound having an azide group as the corresponding substituent. This is reacted in a solvent (e.g., alkylalcohol such as methanol and the like), in the presence of tin(II) chloride to give a compound having amino as a substituent. This is reacted in a solvent (e.g., dialkylketone such as acetone and the like, water, or a mixed solvent thereof) in the presence of N-(carbobenzoxy)succinimide in the presence of a base (e.g., alkali metal carbonate such as sodium hydrogen carbonate and the like), whereby compound (I) having carbobenzoxyamino as a substituent can be produced.

Method 24:

Compound (I) having optionally substituted alkylamino can be produced by reacting compound (I) having NH in a solvent (e.g., halogenohydrocarbon such as methylene chloride and the like) in the presence of the corresponding compound having is carbonyl in the presence of a reducing agent (e.g., boron hydride compound such as sodium triacetoxyborohydride and the like).

Method 25:

Compound (I) having NH can be produced by reacting compound (I) having tert-butoxycarbonylamino in a solvent (e.g., halogenohydrocarbon such as methylene chloride and the like, acid in a solvent amount or less, or a mixed solvent thereof), in the presence of an acid (e.g., trifluoroacetic acid).

Method 26:

Compound (I) having NH can be produced by reacting compound (I) having carbobenzoxyamino in a solvent (e.g., halogenohydrocarbon such as methylene chloride and the like), in the presence of iodotrialkylsilane such as trimethylsilyl iodide and the like.

Method 27:

Compound (I) having an optionally substituted nitrogen-containing nonaromatic heterocyclic group as a substituent can be produced by reacting compound (I) having a halogen atom (e.g., chlorine atom) as a substituent in a solvent (e.g., alkylnitrile such as acetonitrile and the like), in the presence of the corresponding optionally substituted nitrogen-containing non-aromatic heterocyclic compound, in the presence of a base (e.g., alkali metal carbonate such as potassium carbonate and the like) in the presence or absence of an additive (e.g., alkali metal iodide such as potassium iodide and the like).

Method 28:

Compound (I) having phthalimidoyl as a substituent can be produced by reacting compound (I) having hydroxy as a substituent in a solvent (e.g., ether such as tetrahydrofuran and the like, aromatic hydrocarbon such as toluene and the like, or a mixed solvent thereof) in the presence of phthalimide, in the presence of triarylphosphine such as triphenylphosphine and the like, in the presence of dialkyl azodicarboxylate such as diisopropyl azodicarboxylate and the like.

[Production of Intermediate Compound]

Of the aforementioned compound (VII) of the present invention, a compound represented by the formula (VII-a):

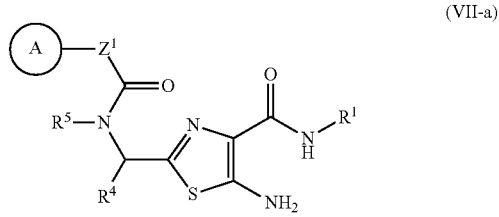

wherein the symbols are as defined above, can be produced, for example, by the method shown in the following scheme 1.

Scheme 1:

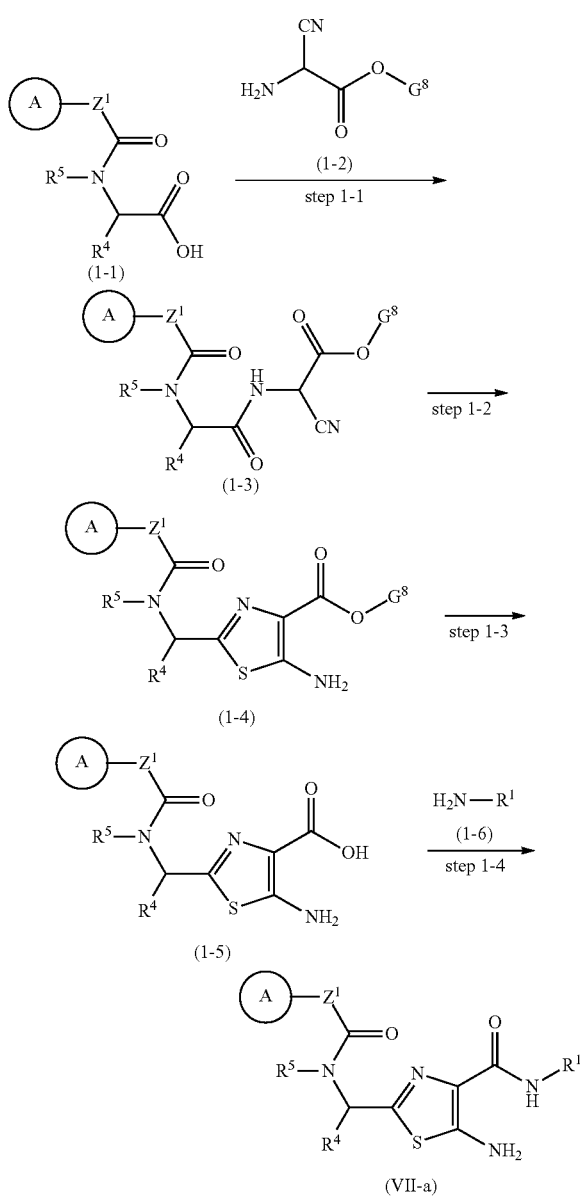

in the scheme, $G^8$ is alkyl, and other symbols are as defined above.

Compound (1-1) and compound (1-2) are reacted to give compound (1-3). This is cyclized to give compound (1-4) or a salt thereof. This is converted to give compound (1-5). This is reacted with compound (1-6) to give compound (VII-a).

Step 1-1:

Compound (1-3) can be produced by reacting compound (1-1) and compound (1-2) in a solvent in the presence of a condensation agent, in the presence of a base.

Examples of the condensation agent include chloroformic acid alkyl ester such as methyl chloroformate, ethyl chloroformate, propyl chloroformate, isopropyl chloroformate, butyl chloroformate, isobutyl chloroformate and the like. Examples of the base include amine such as triethylamine, N,N-diisopropylethylamine, pyridine and the like. The solvent may be any as long as it does not influence the reaction, and examples thereof include ether such as tetrahydrofuran, 1,4-dioxane, 1,2-dimethoxyethane and the like.

The amount of compound (1-2) to be used in this reaction is 0.5-2.0 mol, preferably 0.9-1.0 mol, per 1 mol of compound (1-1). The amount of the condensation agent to be used is 0.8-3.0 mol, preferably 1.0-1.1 mol, per 1 mol of compound (1-1). The amount of the base to be used is 1.5-5.0 mol, preferably 2.0-2.5 mol, per 1 mol of compound (1-1). This reaction can be performed at −20-60° C., preferably 0-30° C.

Step 1-2:

Compound (1-4) or a salt thereof can be produced by reacting compound (1-3), in a solvent in the presence of a sulfating agent, in the presence of a base and, when desired, converting the resultant product to a salt thereof.

Examples of the sulfating agent include Lawesson's reagent (2,4-bis(4-methoxyphenyl)-1,3,2,4-dithiadiphosphetane-2,4-disulfide). Examples of the base include amine such as triethylamine, N,N-diisopropylethylamine, pyridine and the like. The solvent may be any as long as it does not influence the reaction, and examples thereof include aromatic hydrocarbon such as toluene, xylene and the like; ether such as tetrahydrofuran, 1,4-dioxane, 1,2-dimethoxyethane and the like.

The amount of the sulfating agent to be used in this reaction is 0.4-2.0 mol, preferably 0.5-0.7 mol, per 1 mol of compound (1-3). The amount of the base to be used is 1.0-20 mol, preferably 2.0-7.0 mol, per 1 mol of compound (1-3). This reaction can be performed at 50-180° C., preferably 80-130° C.

Step 1-3:

Compound (1-5) can be produced by hydrolysis of compound (1-4) by a conventional method.

The hydrolysis can be performed by, for example, treating compound (1-4) with a base in a solvent.

Examples of the base include alkali metal hydroxide such as sodium hydroxide, potassium hydroxide and the like. The solvent may be any as long as it does not influence the reaction, and examples thereof include alkylalcohol such as methanol, ethanol, isopropylalcohol and the like; water; or a mixed solvent thereof.

The amount of the base to be used in this reaction is 1.0-10 mol, preferably 2.0-5.0 mol, per 1 mol of compound (1-4). This reaction can be performed at 20-100° C., preferably 60-90° C.

Step 1-4:

Compound (VII-a) can be produced by reacting compound (1-5) and compound (1-6) or a salt thereof in a solvent in the presence of a condensation agent, in the presence or absence of an activator, in the presence or absence of a base.

Examples of the condensation agent include carbodiimide such as 1-(3-dimethylaminopropyl)-3-ethylcarbodiimide hydrochloride (EDC hydrochloride) and the like, uronium salt such as O-(7-azabenzotriazol-1-yl)-N,N,N',N'-tetramethyluronium hexafluorophosphate (HATU) and the like. Examples of the activator include 1-hydroxybenzotriazole monohydrate (HOBt monohydrate). The solvent may be any as long as it does not influence the reaction, and examples thereof include amide such as N,N-dimethylformamide, N,N-dimethylacetamide, 1,3-dimethyl-2-imidazolidinone, N-methylpyrrolidone and the like.

The amount of compound (1-6) to be used in this reaction is 0.5-10 mol, preferably 1.0-5.0 mol, per 1 mol of compound (1-5). The amount of the condensation agent to be used is 1.0-10 mol, preferably 1.2-5.0 mol, per 1 mol of compound (1-5). The amount of the activator to be used is 1.0-10 mol, preferably 1.2-5.0 mol, per 1 mol of compound (XVII). The amount of the base to be used is 1.0-20 mol, preferably 1.2-10 mol, per 1 mol of compound (1-5). This reaction can be performed at 0-50° C., preferably 10-300° C.

Of the aforementioned compound (VI) of the present invention, a compound represented by the formula (VI-a):

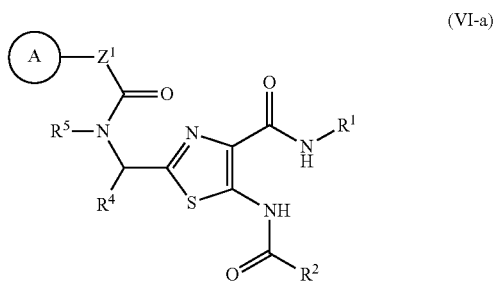

wherein the symbols are as defined above, can be produced, for example, by the method shown in the following scheme 2.

Scheme 2:

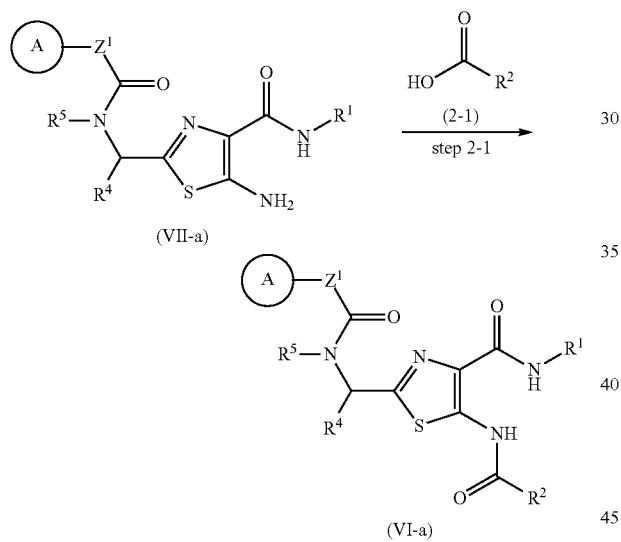

[in the scheme, the symbols are as defined above.]

Compound (VI-a) can be produced by reacting compound (VII-a) and compound (2-1) or a reactive derivative thereof.

Step 2-1:

Compound (VI-a) can be produced by treating compound (VII-a) and compound (2-1) as in the aforementioned Scheme 1, step 1-4.

Alternatively, compound (VI-a) can be produced by reacting compound (VII-a) and a reactive derivative of the above-mentioned compound (2-1) in a solvent in the presence of a base.

Examples of the base include amine such as triethylamine, N,N-diisopropylethylamine, pyridine and the like. The solvent may be any as long as it does not influence the reaction, and examples thereof include halogenohydrocarbon such as methylene chloride, chloroform, 1,2-dichloroethane and the like; alkylnitrile such as acetonitrile, propionitrile and the like; or a mixed solvent thereof.

The amount of the reactive derivative of compound (2-1) to be used in this reaction is 1.0-5.0 mol, preferably 1.1-3.0 mol, per 1 mol of compound (VII-a). The amount of the base to be used is 1.0-10 mol, preferably 1.1-5.0 mol, per 1 mol of compound (VII-a). This reaction can be performed at 0-50° C., preferably 10-30° C.

The reactive derivative of compound (2-1) to be used can be a commercially available reactive derivative.

Alternatively, the reactive derivative of compound (2-1) can be produced by reacting compound (2-1) or a salt thereof, in a solvent or without solvent, in the presence of a halogenating agent, in the presence or absence of an activator.

Examples of the halogenating agent include oxalyl chloride, thionyl chloride. Examples of the activator include N,N-dimethylformamide. The solvent may be any as long as it does not influence the reaction, and examples thereof include halogenohydrocarbon such as methylene chloride, chloroform, 1,2-dichloroethane and the like; alkylnitrile such as acetonitrile, propionitrile and the like.

The amount of the halogenating agent to be used in this reaction is 0.5-2.0 mol, preferably 0.8-1.2 mol, per 1 mol of compound (2-1) or a salt thereof. The amount of the activator to be used is a catalytic amount of 1 mol of compound (2-1) or a salt thereof. This reaction can be performed at 0-100° C., preferably 10-30° C.

Of the aforementioned compound (IX) of the present invention, a compound represented by the formula (IX-a):

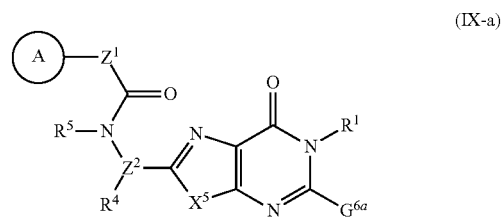

wherein $G^{6a}$ is alkylsulfinyl or alkylsulfonyl, and other symbols are as defined above, can be produced, for example, by the method shown in the following Scheme 3.

Scheme 3:

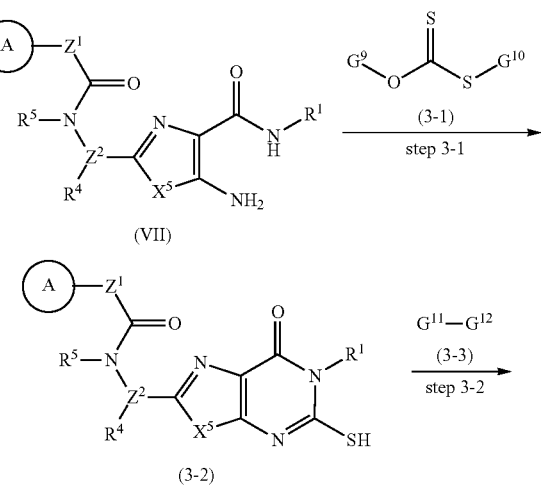

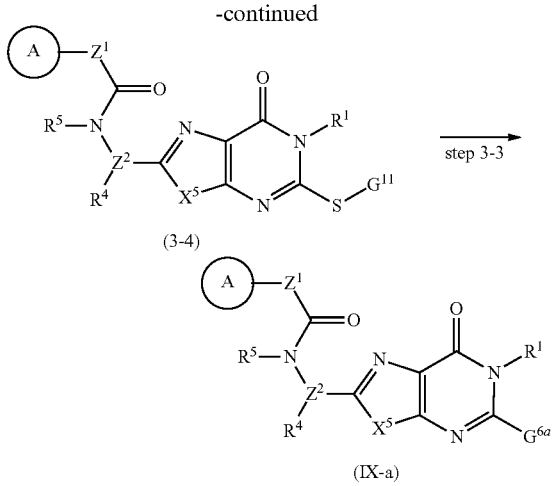

(3-4)

(IX-a)

[in the scheme, $G^{6a}$ is alkylsulfinyl or alkylsulfonyl, $G^9$ is alkyl, $G^{10}$ is alkali metal, $G^{11}$ is alkyl, $G^{12}$ is a leaving group, and other symbols are as defined above.]

Compound (VII) and compound (3-1) are reacted to give compound (3-2). This is reacted with compound (3-3) to give compound (3-4). The compound (3-4) is oxidized, whereby compound (IX-a) can be produced.

Step 3-1:

Compound (3-2) can be produced by reacting compound (VII) and compound (3-1) in a solvent.

The alkali metal for $G^{10}$ is preferably sodium or potassium, and potassium is particularly preferable. The solvent may be any as long as it does not influence the reaction, and examples thereof include alkylalcohol such as methanol, ethanol, isopropylalcohol and the like. The amount of compound (3-1) to be used in this reaction is 1.0-10 mol, preferably 2.0-5.0 mol, per 1 mol of compound (VII). This reaction can be performed at 40-150° C., preferably 60-100° C.

Step 3-2:

Compound (3-4) can be produced by reacting compound (3-2) and compound (3-3) in a solvent in the presence of a base.

The alkyl for $G^{11}$ is preferably $C_1$-$C_6$ alkyl, and particularly preferably methyl. Examples of the leaving group for $G^{12}$ include halogen atom (particularly, iodine atom). Examples of the base include alkali metal carbonate such as potassium carbonate, cesium carbonate, sodium carbonate and the like. The solvent may be any as long as it does not influence the reaction, and examples thereof include amide such as N,N-dimethylformamide, N,N-dimethylacetamide, 1,3-dimethyl-2-imidazolidinone, N-methylpyrrolidone and the like.

The amount of compound (3-3) to be used in this reaction is 1.0-5.0 mol, preferably 1.2-1.8 mol, per 1 mol of compound (3-2). The amount of the base to be used is 1.0-5.0 mol, preferably 1.2-1.8 mol, per 1 mol of compound (3-2). This reaction can be performed at 0-50° C., preferably 10-40° C.

Step 3-3:

Compound (IX-a) can be produced by treating compound (3-4) with an oxidant in a solvent.

Examples of the oxidant include methachloroperbenzoic acid (mCPBA). The solvent may be any as long as it does not influence the reaction, and examples thereof include halogenohydrocarbon such as methylene chloride, chloroform, 1,2-dichloroethane and the like.

When compound (IX-a) wherein $G^{6a}$ is alkylsulfinyl is produced in this reaction, the amount of the oxidant to be used is 0.9-1.5 mol, preferably 1.0-1.2 mol, per 1 mol of compound (3-4). When compound (IX-a) wherein $G^{6a}$ is alkylsulfonyl is produced in this reaction, the amount of the oxidant to be used is 2.0-5.0 mol, preferably 2.4-3.5 mol, per 1 mol of compound (3-4). This reaction can be performed at −20 to 30° C., preferably −10 to 10° C.

The aforementioned compound (II) of the present invention can be produced from compound (I-z) having carbobenzoxy by, for example, a method shown in the following Scheme 4.

Scheme 4:

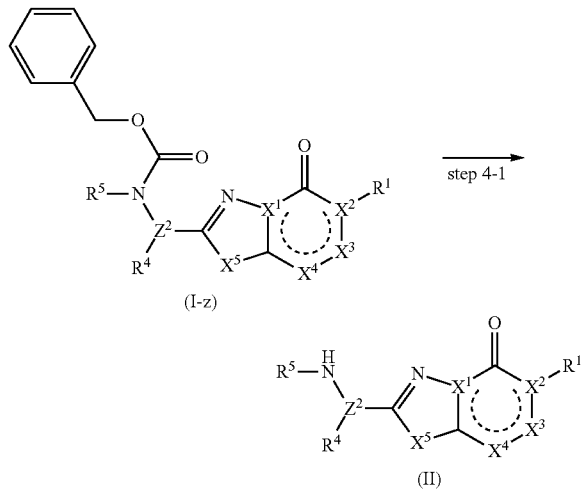

(I-z)

(II)

[in the scheme, the symbols are as defined above.]

Compound (II) can be produced by de-carbobenzoxylation of compound (I-z) by a conventional method.

Compound (II) can be produced by, for example, treating compound (I-z) with iodosilane in a solvent in the presence or absence of a silane compound.

Examples of iodosilane include iodotrialkylsilane such as trimethylsilyl iodide and the like. Examples of the silane compound include trialkylsilane such as triethylsilane and the like. The solvent may be any as long as it does not influence the reaction, and examples thereof include alkylnitrile such as acetonitrile, propionitrile and the like.

The amount of iodosilane to be used in this reaction is 1.0-10 mol, preferably 1.5-5.0 mol, per 1 mol of compound (I-z). The amount of the silane compound to be used is 1.0-20 mol, preferably 3.0-10 mol, per 1 mol of compound (I-z). This reaction can be performed at 0-50° C., preferably 10-30° C.

Compound (II) can be produced by treating compound (I-z) with palladium hydroxide carbon under a hydrogen atmosphere, in a solvent (e.g., methanol).

Alternatively, compound (II) can be produced by treating compound (I-z) with an acid (e.g., hydrogen bromide-acetic acid solution, sulfuric acid-acetic acid solution) in a solvent (e.g., methylene chloride, acetic acid, or a mixed solvent thereof).

Of the aforementioned compound (II) of the present invention, a compound represented by the formula (II-a):

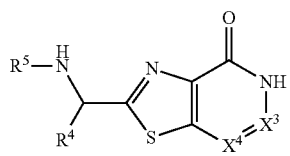

(II-a)

wherein the symbols are as defined above, can be produced by, for example, a method shown in the following Scheme 5-1 or 5-2.

Scheme 5-1:

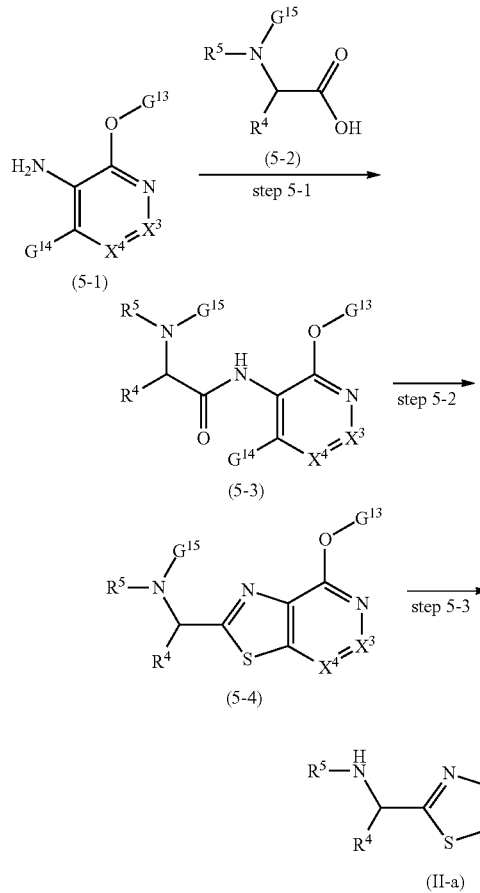

[In the Scheme, $G^{13}$ is a hydroxy-protecting group, $G^{14}$ is a leaving group, $G^{15}$ is amino-protecting group, and other symbols are as defined above.]

Compound (5-1) and compound (5-2) are reacted to give compound (5-3). The compound (5-3) is subjected to cyclization reaction to give compound (5-4). This is deprotected to give compound (II-a).

As the hydroxy-protecting group for $G^{13}$, conventionally-used hydroxy-protecting groups can be used and, for example, methyl, methoxybenzyl, dimethoxybenzyl can be mentioned. As the leaving group for $G^{14}$, conventionally-used leaving groups can be used and, for example, a halogen atom (particularly, chlorine atom, bromine atom) can be mentioned. As the amino-protecting group for $G^{15}$, conventionally-used amino-protecting groups can be used and, for example, carbobenzoxy, tert-butoxycarbonyl, nitrophenylsulfonyl can be mentioned.

Step 5-1:
In the same manner as in the aforementioned Scheme 2, step 2-1, compound (5-3) can be produced by converting compound (5-2) to a reactive derivative of compound (5-2), and reacting the reactive derivative with compound (5-1).

Step 5-2:
Compound (5-4) can be produced in the same manner as in the aforementioned Scheme 1, step 1-2 by reacting compound (5-3) in a solvent in the presence of a sulfating agent, in the presence of a base.

Step 5-3:
Compound (II-a) can be produced by removing the protecting groups $G^{13}$ and $G^{15}$ of compound (5-4) by a is conventional method, each according to the kind of the protecting group used.

When methyl, methoxybenzyl, or dimethoxybenzyl is used as the protecting group $G^{13}$, for example, the protecting group can be removed by treating compound (5-4) with trialkylsilane (e.g., triethylsilane) and iodotrialkylsilane (e.g., trimethylsilyl iodide) in a solvent (e.g., alkylnitrile such as acetonitrile and the like).

When carbobenzoxy is used as the protecting group $G^{15}$, for example, the protecting group can be removed by treating compound (5-4) with trialkylsilane (e.g., triethylsilane) and iodotrialkylsilane (e.g., trimethylsilyl iodide) in a solvent (e.g., alkylnitrile such as acetonitrile and the like).

When tert-butoxycarbonyl is used as the protecting group $G^{15}$, for example, the protecting group can be removed by treating compound (5-4) with an acid (e.g., trifluoroacetic acid) in a solvent (e.g., halogenohydrocarbon such as methylene chloride and the like), or without solvent.

When nitrophenylsulfonyl is used as the protecting group $G^{15}$, for example, the protecting group can be removed by treating compound (5-4) with arylthiol (e.g., methylbenzenethiol) in a solvent (e.g., alkylnitrile such as acetonitrile and the like), in the presence of a base (e.g., alkali metal carbonate such as cesium carbonate and the like)

Scheme 5-2:

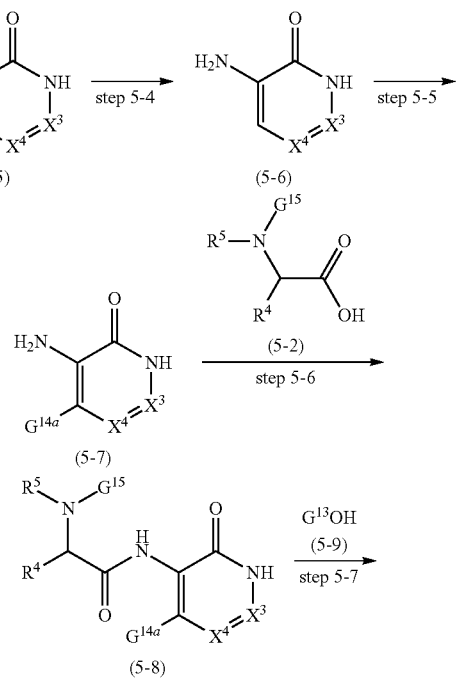

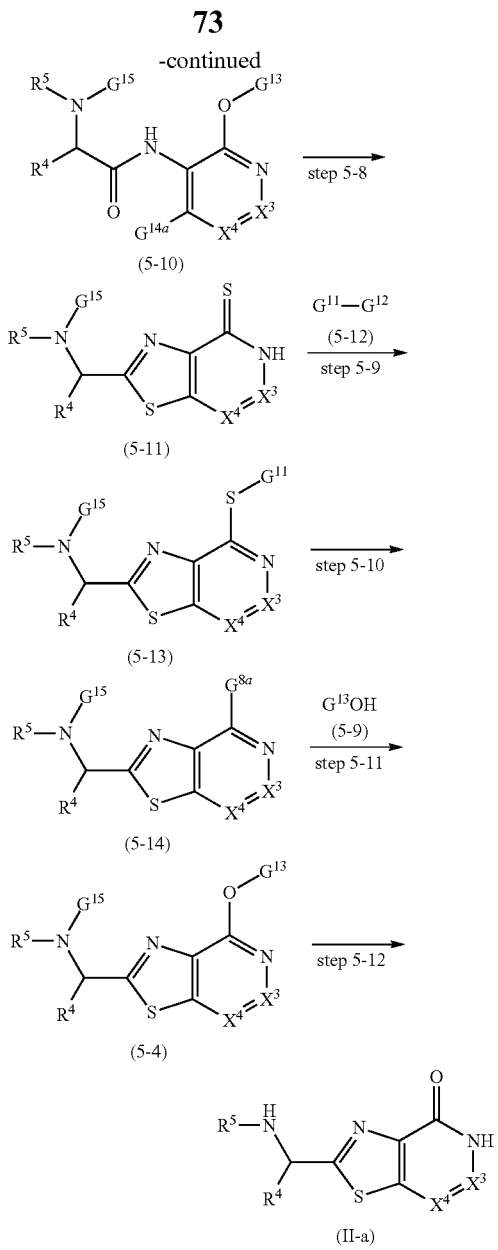

[In the Scheme, $G^{14a}$ is a halogen atom, and other symbols are as defined above.]

Compound (5-5) is reduced to give compound (5-6). This is converted to give compound (5-7). This is reacted with compound (5-2) to give compound (5-8). This is reacted with compound (5-9) to give compound (5-10). This is converted to give compound (5-11). This is reacted with compound (5-12) to give compound (5-13). The compound (5-13) is oxidized to give compound (5-14). This is reacted with compound (5-9) to give compound (5-4). This is deprotected to give compound (II-a)

Step 5-4:
Compound (5-6) can be produced by reacting compound (5-5) in a solvent (e.g., mixed solvent of alkylalcohol such as methanol and the like and halogenohydrocarbon chloroform and the like), in the presence of palladium carbon, under a hydrogen atmosphere.

The amount of palladium carbon to be used in this reaction is 0.001-1.0 mol, preferably 0.01-0.5 mol, per 1 mol of compound (5-5). This reaction can be performed at 0-80° C., preferably 20-60° C.

Step 5-5:
Compound (5-7) can be produced by treating compound (5-6) with a halogenating agent (e.g., N-halogenosuccinimide) corresponding to $G^{14a}$ in a solvent (e.g., amide such as N,N-dimethylformamide and the like).

The amount of the halogenating agent to be used in this reaction is 0.9-3.0 mol, preferably 1.0-2.0 mol, per 1 mol of compound (5-6). This reaction can be performed at −20-100° C., preferably 0-60° C.

Step 5-6:
In the same manner as in the aforementioned Scheme 2, step 2-1, compound (5-8) can be produced by converting compound (5-2) to a reactive derivative of compound (5-2), and reacting the reactive derivative with compound (5-7).

Step 5-7:
Compound (5-10) can be produced by reacting compound (5-8) and compound (5-9) in a solvent (e.g., ether such as tetrahydrofuran and the like) in the presence of azodicarboxylic acid ester (e.g., diisopropyl azodicarboxylate), in the presence of triarylphosphine (e.g., triphenylphosphine).

The amount of compound (5-9) to be used in this reaction is 0.9-5.0 mol, preferably 1.0-2.0 mol, per 1 mol of compound (5-8). The amount of azodicarboxylic acid ester to be used is 0.9-5.0 mol, preferably 1.0-2.0 mol, per 1 mol of compound (5-8). The amount of triarylphosphine to be used is 0.9-5.0 mol, preferably 1.0-2.0 mol, per 1 mol of compound (5-8). This reaction can be performed at 0-120° C., preferably 15-80° C.

Step 5-8:
Compound (5-11) can be produced in the same manner as in Scheme 1, step 1-2, by reacting compound (5-10) in a solvent in the presence of a sulfating agent, in the presence of a base.

Step 5-9:
Compound (5-13) can be produced in the same manner as in Scheme 3, step 3-2, by reacting compound (5-11) and compound (5-12) in a solvent in the presence of a base.

Step 5-10:
Compound (5-14) can be produced in the same manner as in Scheme 3, step 3-3, by treating compound (5-13) with an oxidant in a solvent.

Step 5-11:
Compound (5-4) can be produced by reacting compound (5-14) and compound (5-9) in a solvent (e.g., amide such as N,N-dimethylformamide and the like), in the presence of a base (e.g., alkali metal hydride such as sodium hydride and the like).

The amount of compound (5-9) to be used in this reaction is 0.9-5.0 mol, preferably 1.0-2.0 mol, per 1 mol of compound (5-14). The amount of the base to be used is 0.9-5.0 mol, preferably 1.0-2.0 mol, per 1 mol of compound (5-14). This reaction can be performed at −40-80° C., preferably −20-40° C.

Step 5-12:
Compound (II-a) can be produced in the same manner as in Scheme 5-1, step 5-3, by removing the protecting group of compound (5-4) by a conventional method.

Of the aforementioned compound (II) of the present invention, a compound represented by the formula (II-b):

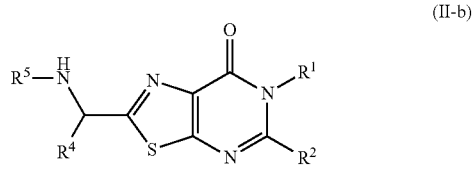

wherein the symbols are as defined above, can be produced, for example, by a method shown in the following Schemes 6-1, 6-2.
Scheme 6-1:
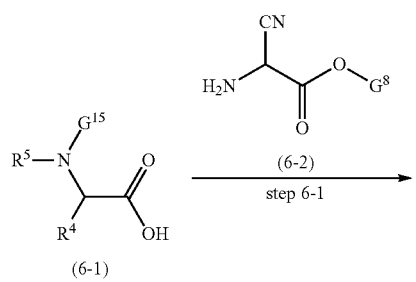
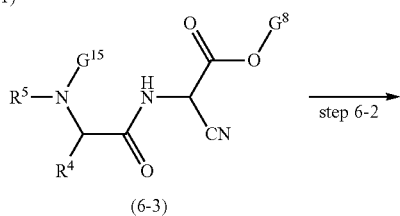
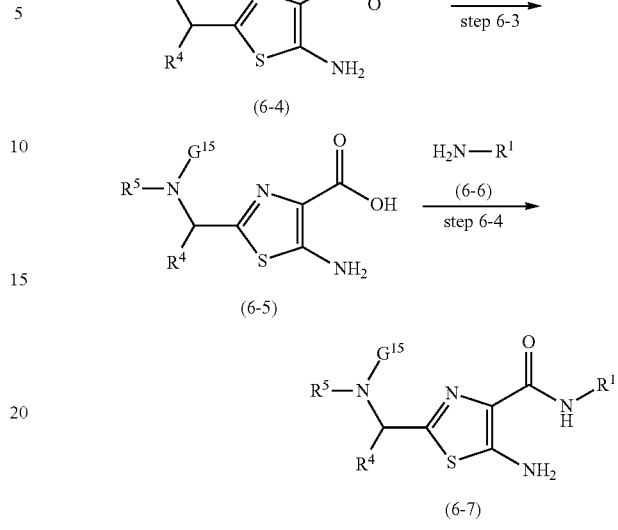
Scheme 6-2:
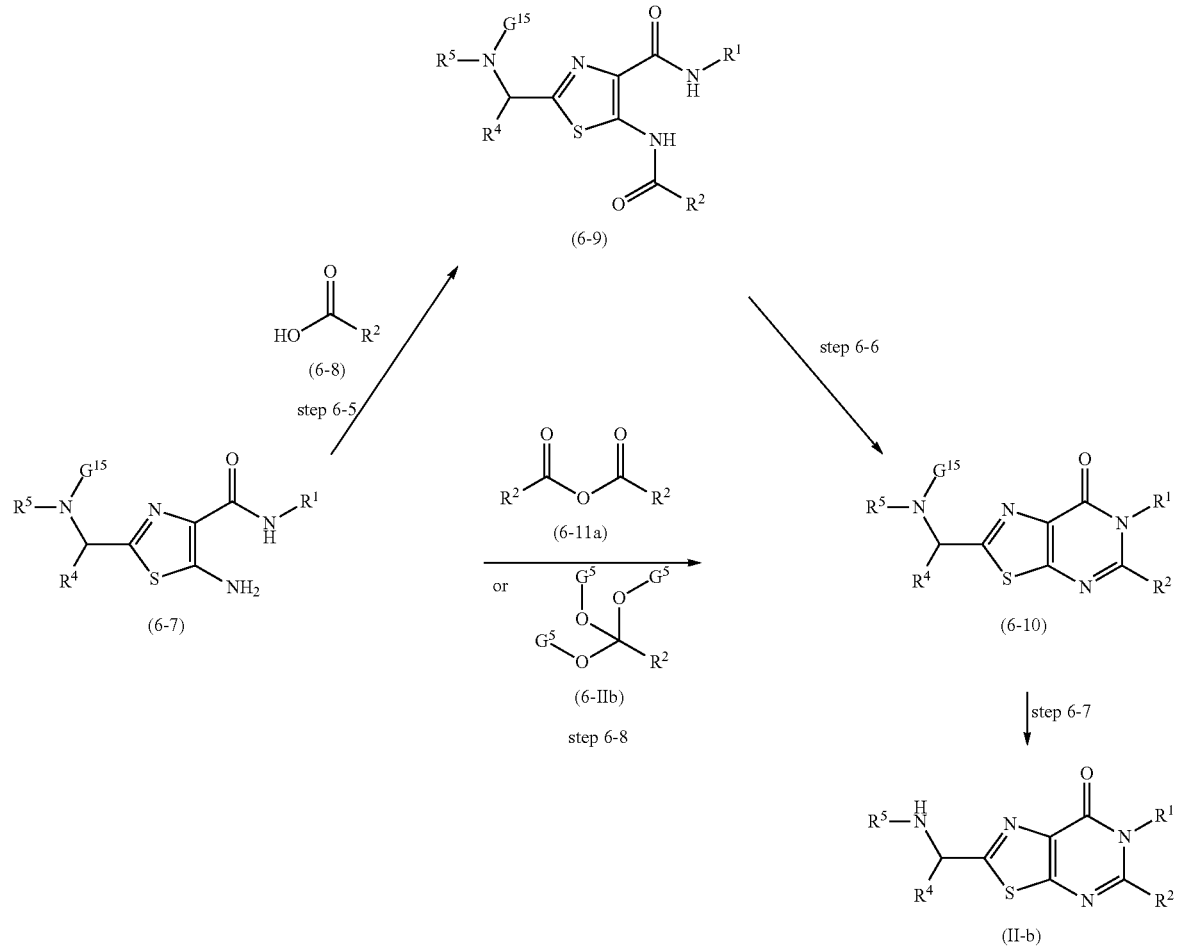

[In the Scheme, the symbols are as defined above.]

Compound (6-1) and compound (6-2) are reacted to give compound (6-3). This is cyclized to give compound (6-4) or a salt thereof. This is converted to give compound (6-5). This is reacted with compound (6-6) to give compound (6-7). This is reacted with compound (6-8) or a reactive derivative thereof to give compound (6-9). This is cyclized to give compound (6-10). This is converted to give compound (II-b).

Alternatively, compound (6-7) and compound (6-11a) or compound (6-11b) are reacted to give compound (6-10). This is converted to give compound (II-b).

Step 6-1:
Compound (6-3) can be produced in the same manner as in Scheme 1, step 1-1, by reacting compound (6-1) and compound (6-2) in a solvent in the presence of a condensation agent, in the presence of a base.

Step 6-2:
Compound (6-4) or a salt thereof can be produced in the same manner as in Scheme 1, step 1-2, by reacting compound (6-3) in a solvent in the presence of a sulfating agent, in the presence of a base and, when desired, converting the resultant product to a salt thereof.

Step 6-3:
Compound (6-5) can be produced in the same manner as in Scheme 1, step 1-3, by hydrolysis of compound (6-4) or a salt thereof by a conventional method.

Step 6-4:
Compound (6-7) can be produced in the same manner as in Scheme 1, step 1-4, by reacting compound (6-5) and compound (6-6) or a salt thereof in a solvent in the presence of a condensation agent, in the presence or absence of an activator, in the presence or absence of a base.

Step 6-5:
Compound (6-9) can be produced in the same manner as in Scheme 2, step 2-1, by reacting compound (6-7) and compound (6-8) or a reactive derivative thereof.

Step 6-6:
Compound (6-10) can be produced by reacting compound (6-9) in a solvent in the presence of a condensation agent, in the presence of a base, in the same manner as in the method of producing compound (I-d) from compound (VI).

Step 6-7:
Compound (II-b) can be produced in the same manner as in Scheme 5, step 5-3, by removing the protecting group $G^{15}$ of compound (6-10), by a conventional method according to the kind of the protecting group used.

Step 6-8:
Compound (6-10) can be produced by reacting compound (6-7) with compound (6-11a) or compound (6-11b), in the same manner as in the method of producing compound (I-d) from compound (VII) and compound (VIII-a) or compound (VIII-b).

Of the aforementioned compound (II) of the present invention, a compound represented by the formula (II-c):

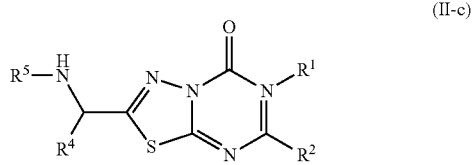

(II-c)

wherein the symbols are as defined above, can be produced, for example, by a method shown in the following Scheme 7.

Scheme 7:

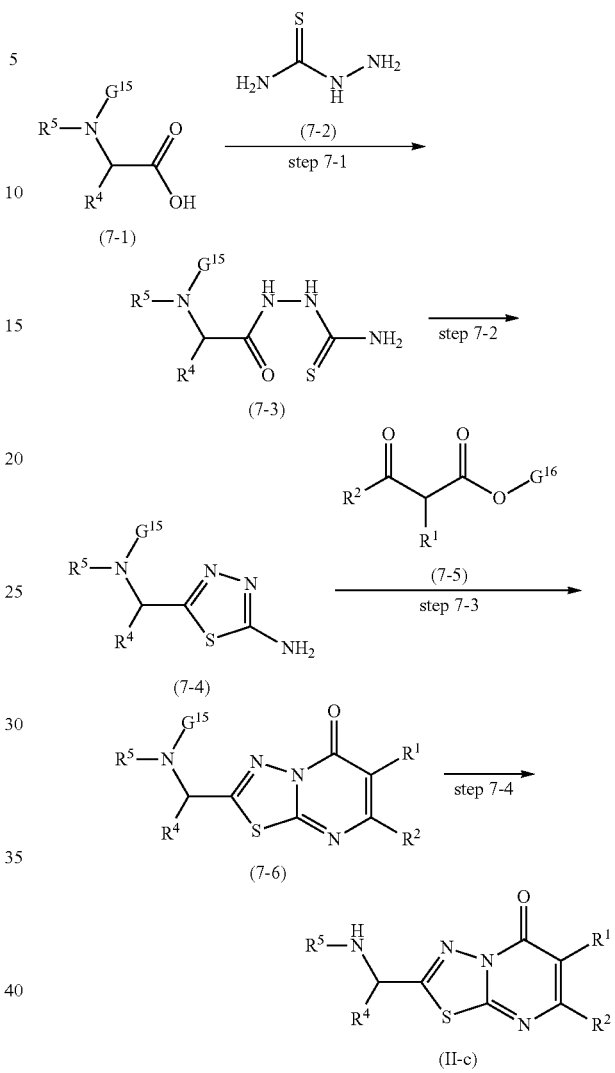

[In the Scheme, $G^{16}$ is alkyl, and other symbols are as defined above.]

Compound (7-1) and compound (7-2) are reacted to give compound (7-3). This is cyclized to give compound (7-4). This is reacted with compound (7-5) to give compound (7-6). This is converted to give compound (II-c).

Step 7-1:
Compound (7-3) can be produced by reacting compound (7-1) and compound (7-2) in a solvent in the presence of a condensation agent, in the presence or absence of an activator, in the presence or absence of a base.

Examples of the condensation agent include carbodiimide such as 1-(3-dimethylaminopropyl)-3-ethylcarbodiimide hydrochloride (EDC hydrochloride) and the like. Examples of the activator include 1-hydroxybenzotriazole monohydrate (HOBt monohydrate). The solvent may be any as long as it does not influence the reaction, and examples thereof include amide such as N,N-dimethylformamide, N,N-dimethylacetamide, 1,3-dimethyl-2-imidazolidinone, N-methylpyrrolidone and the like.

The amount of compound (7-2) to be used in this reaction is 0.5-2.0 mol, preferably 0.8-1.5 mol, per 1 mol of compound (7-1). The amount of the condensation agent to be used is 1.0-2.0 mol, preferably 1.1-1.5 mol, per 1 mol of compound (7-1). The amount of the activator to be used is 1.0-2.0 mol, preferably 1.1-1.5 mol, per 1 mol of compound (7-1). The amount of the base to be used is 1.0-2.0 mol, preferably 1.1-1.5 mol, per 1 mol of compound (7-1). This reaction can be performed at 0-50° C., preferably 10-30° C.

Step 7-2:

Compound (7-4) can be produced by reacting compound (7-3) in a solvent in the presence of an acid.

Examples of the acid include alkylsulfonic acid such as methanesulfonic acid and the like. The solvent may be any as long as it does not influence the reaction, and examples thereof include aromatic hydrocarbon such as toluene, xylene and the like.

The amount of the acid to be used in this reaction is 1.0-5.0 mol, preferably 1.2-1.8 mol, per 1 mol of compound (7-3). This reaction can be performed at 50-180° C., preferably 80-150° C.

Step 7-3:

Compound (7-6) can be produced by reacting compound (7-4) and compound (7-5) without solvent in the presence of an acid.

Examples of the acid include sulfuric acid.

The amount of compound (7-5) to be used in this reaction is 0.9-5.0 mol, preferably 1.2-2.0 mol, per 1 mol of compound (7-4). The amount of the acid to be used is 10-200 mol, preferably 40-80 mol, per 1 mol of compound (7-4). This reaction can be performed at 30-120° C., preferably 60-1000° C.

Step 7-4:

Compound (II-c) can be produced in the same manner as in Scheme 5, step 5-3 by removing the protecting group $G^{15}$ of compound (7-6) by a conventional method according to the kind of the protecting group used.

Of the aforementioned compound (XI) of the present invention, a compound represented by the formula (XI-a):

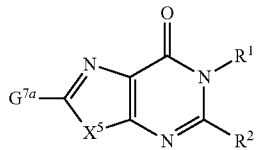

(XI-a)

wherein $G^{7a}$ is a halogen atom, and other symbols are as defined above, can be produced, for example, by a method shown in the following Scheme 8.

Scheme 8:

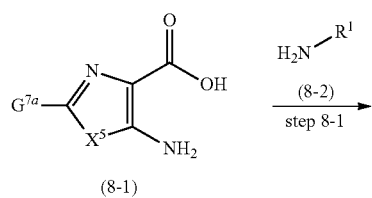

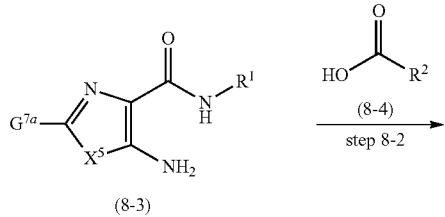

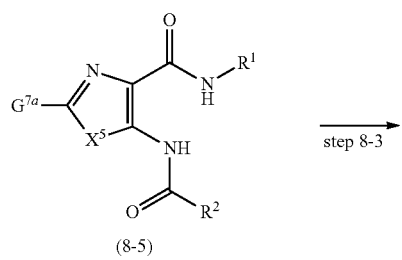

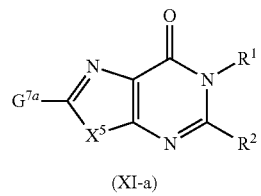

(XI-a)

[In the Scheme, the symbols are as defined above.]

Compound (8-1) and compound (8-2) are reacted to give compound (8-3). This is reacted with compound (8-4) or a reactive derivative thereof to give compound (8-5). This is cyclized to give compound (XI-a).

Step 8-1:

Compound (8-3) can be produced in the same manner as in Scheme 1, step 1-4, by reacting compound (8-1) and compound (8-2) or a salt thereof in a solvent in the presence of a condensation agent, in the presence or absence of an activator, in the presence or absence of a base.

Step 8-2:

Compound (8-5) can be produced in the same manner as in Scheme 2, step 2-1, by reacting compound (8-3) and compound (8-4) or a reactive derivative thereof.

Step 8-3:

Compound (XI-a) can be produced by reacting compound (8-5) in a solvent in the presence of a condensation agent, in the presence of a base, in the same manner as in the method of producing compound (I-d) from compound (VI).

The aforementioned compound (XII) in the present invention can be produced, for example, by a method shown in the following Scheme 9.

Scheme 9:

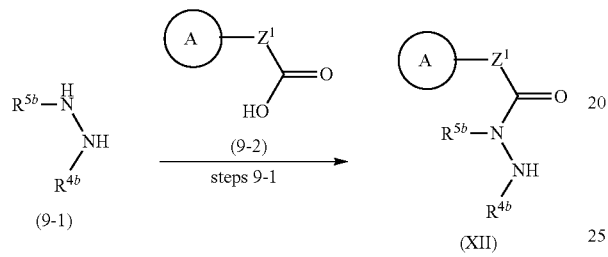

[In the Scheme, the symbols are as defined above.]

Compound (XII) can be produced by reacting compound (9-1) or a salt thereof with compound (9-2) or a reactive derivative thereof.

Step 9-1:

Compound (XII) can be produced in the same manner as in Scheme 2, step 2-1, by reacting compound (9-1) or a salt thereof with compound (9-2) or a reactive derivative thereof.

Of the aforementioned compound (XII) of the present invention, a compound represented by the formula (XII-a):

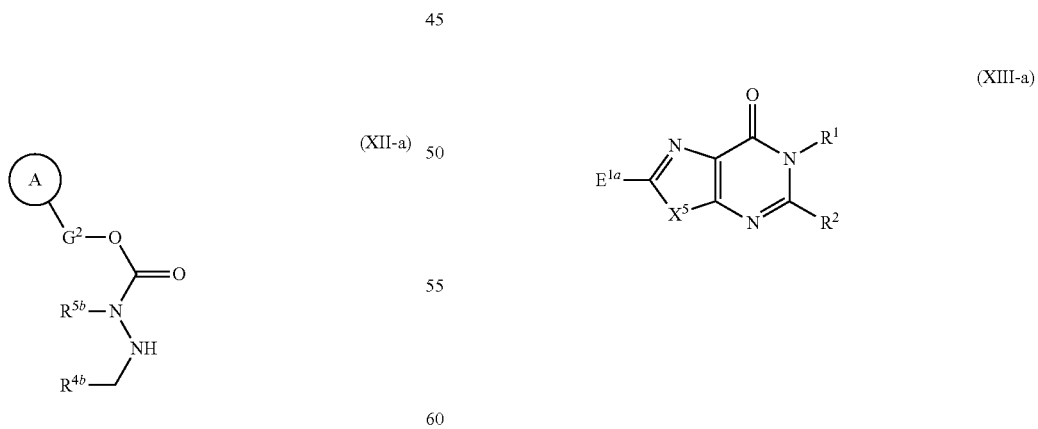

wherein the symbols are as defined above, can be produced, for example, by a method shown in the following Scheme 10.

Scheme 10:

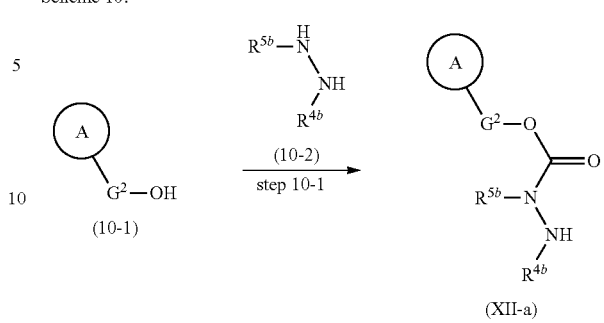

[In the Scheme, the symbols are as defined above.]

Step 10-1:

Compound (XII-a) can be produced by reacting compound (10-1) with a carbonylating agent (e.g., triphosgene) in a solvent (e.g., toluene), in the presence of a base (e.g., pyridine) to give a reactive intermediate, and further reacting the reactive intermediate with compound (10-2) or a salt thereof in a solvent (e.g., methylene chloride), in the presence of a base (e.g., triethylamine).

Of the aforementioned compound (XIII) of the present invention, a compound represented by the formula (XIII-a):

wherein $E^{1a}$ is alkylsulfinyl, alkoxyphenylalkylsulfinyl, alkylsulfonyl, or alkoxyphenylalkylsulfonyl, and other symbols are as defined above, can be produced, for example, by a method shown in the following Scheme 11.

Scheme 11:

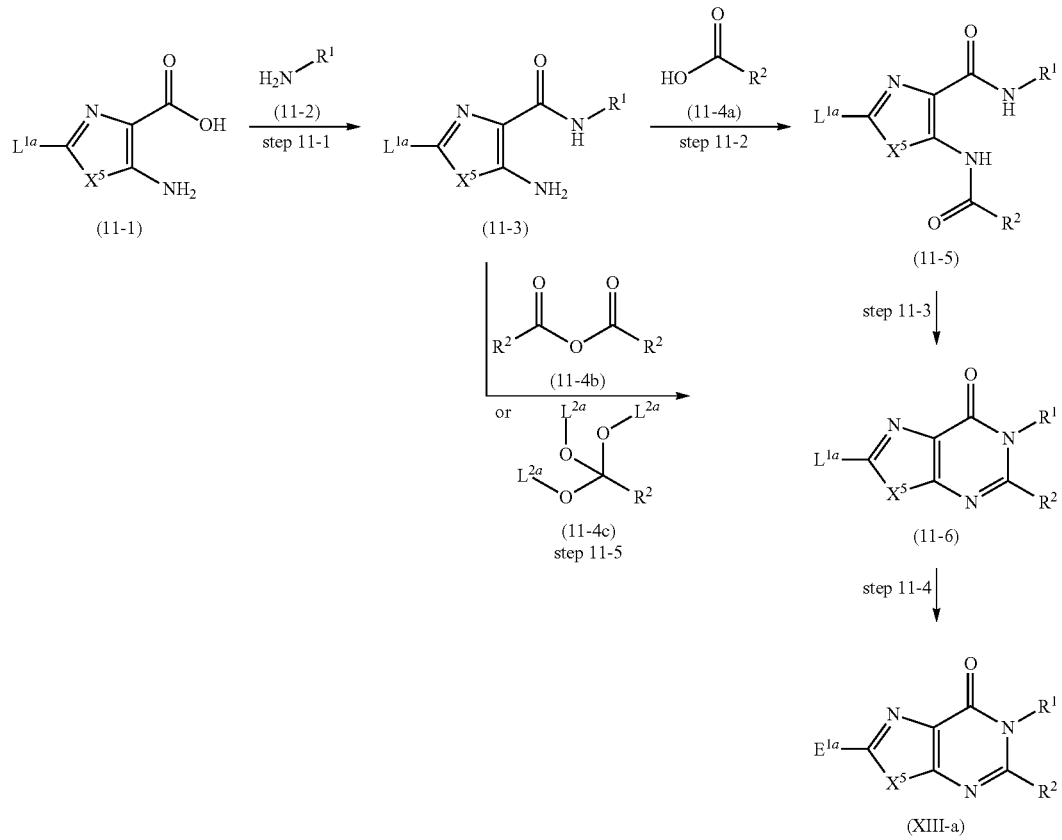

[In the Scheme, $L^{1a}$ is alkylsulfanyl, or alkoxyphenylalkylsulfanyl, $L^{2a}$ is alkyl, and other symbols are as defined above.]

Compound (11-1) and compound (11-2) or a salt thereof are reacted to give compound (11-3). This is reacted with compound (11-4a) or a reactive derivative thereof to give compound (11-5). This is cyclized to give compound (11-6). This is oxidized to give compound (XIII-a).

Alternatively, compound (11-6) can be obtained by reacting compound (11-3) and compound (11-4b) or compound (11-4c).

Step 11-1:
Compound (11-3) can be produced in the same manner as in Scheme 1, step 1-4, by reacting compound (11-1) and compound (11-2) or a salt thereof in a solvent in the presence of a condensation agent, in the presence or absence of an activator, in the presence or absence of a base.

Step 11-2:
Compound (11-5) can be produced in the same manner as in Scheme 2, step 2-1, by reacting compound (11-3) and compound Jo (11-4a) or a reactive derivative thereof.

Step 11-3:
Compound (11-6) can be produced by reacting compound (11-5) in a solvent in the presence of a condensation agent, in the presence of a base, in the same manner as in the method of producing compound (I-d) from compound (VI).

Step 11-4:
Compound (XIII-a) can be produced by treating compound (11-6) with an oxidant in a solvent.

Examples of the oxidant include methachloroperbenzoic acid (mCPBA). The solvent may be any as long as it does not influence the reaction, and examples thereof include halogenohydrocarbon such as methylene chloride, chloroform, 1,2-dichloroethane and the like.

When compound (XIII-a) wherein $E^{1a}$ is alkylsulfinyl or alkoxyphenylalkylsulfinyl is produced by this reaction, the amount of the oxidant to be used is 0.9-1.5 mol, preferably 1.0-1.2 mol, per 1 mol of compound (11-6). When compound (XIII-a) wherein $E^{1a}$ is alkylsulfonyl or alkoxyphenylalkylsulfonyl is produced by this reaction, the amount of the oxidant to be used is 2.0-5.0 mol, preferably 2.4-3.5 mol, per 1 mol of compound (11-6). This reaction can be performed at −20-30° C., preferably −10-30° C.

Step 11-5:
Compound (11-6) can be produced by reacting compound (11-3) with compound (11-4b) or compound (11-4c), in the same manner as in the method of producing compound (I-d) from compound (VII) and compound (VIII-a) or compound (VIII-b).

Of the aforementioned compound (XIII) of the present invention, a compound represented by the formula (XIII-b):

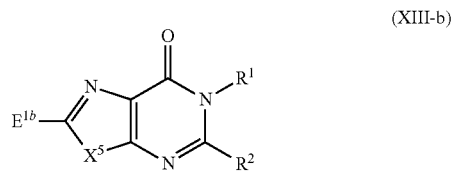

wherein $E^{1b}$ is a halogen atom, and other symbols are as defined above, can be produced, for example, by a method shown in the following Scheme 12.

Scheme 12:

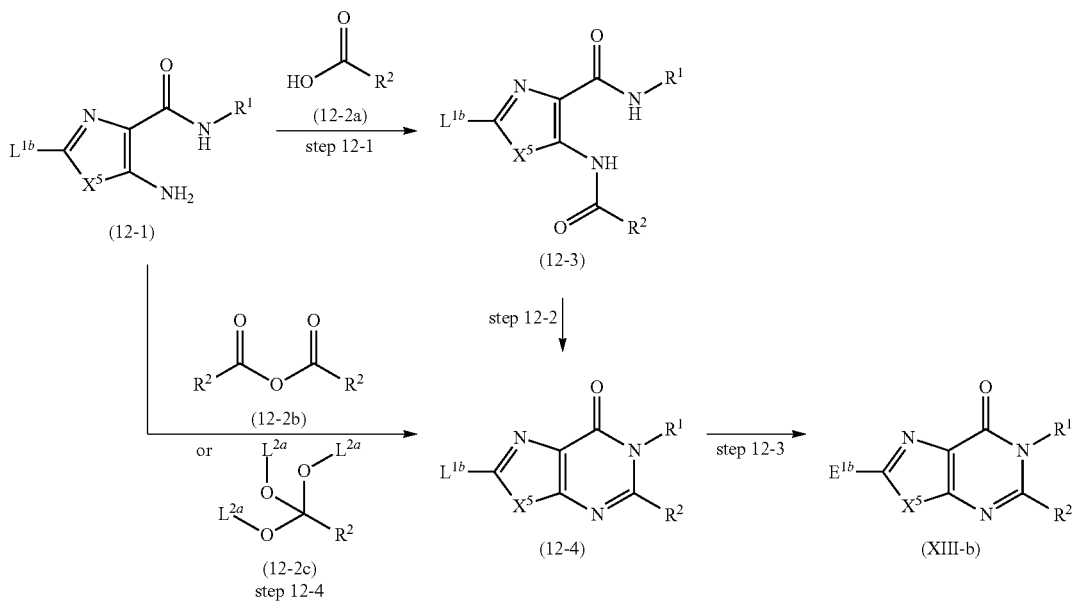

[In the Scheme, $L^{1b}$ is a hydrogen atom or $NH_2$, and other symbols are as defined above.]

Compound (12-1) and compound (12-2a) or a reactive derivative thereof are reacted to give compound (12-3). This is cyclized to give compound (12-4). Said $L^{1b}$ is halogenated to give compound (XIII-b).

Alternatively, compound (12-4) can be obtained by reacting compound (12-1) and compound (12-2b) or compound (12-2c).

Step 12-1:

Compound (12-3) can be produced in the same manner as in Scheme 2, step 2-1, by reacting compound (12-1) and compound (12-2a) or a reactive derivative thereof.

Step 12-2:

Compound (12-4) can be produced by reacting compound (12-3) in a solvent in the presence of a condensation agent, in the presence of a base, in the same manner as in the method of producing compound (I-d) from compound (VI).

Step 12-3:

Compound (XIII-b) can be produced by treating compound (12-4) wherein $L^{1b}$ is a hydrogen atom with a halogenating agent in a solvent.

Examples of the halogenating agent include N-halogenosuccinimide corresponding to $E^{1b}$. The solvent may be any as long as it does not influence the reaction, and examples thereof include alkylnitrile such as acetonitrile, propionitrile and the like.

The amount of the halogenating agent to be used in this reaction is 0.9-3.0 mol, preferably 1.0-2.0 mol, per 1 mol of compound (12-4). This reaction can be performed at 0-100° C., preferably 20-80° C.

Alternatively, compound (XIII-b) can be produced by reacting compound (12-4) wherein $L^{1b}$ is $NH_2$ in a solvent (alkylnitrile such as acetonitrile and the like), in the presence of copper(I) halide corresponding to $E^{1b}$ and nitrous acid alkyl ester (tert-butyl nitrite etc.).

The amount of copper(I) halide to be used in this reaction is 0.9-5.0 mol, preferably 1.0-2.0 mol, per 1 mol of compound (12-4). The amount of nitrous acid alkyl ester to be used is 0.9-5.0 mol, preferably 1.0-2.0 mol, per 1 mol of compound (12-4). This reaction can be performed at 0-120° C., preferably 20-80° C.

Step 12-4:

Compound (12-4) can be produced by reacting compound (12-1) with compound (12-2b) or compound (12-2c), in the same manner as in the method of producing compound (I-d) from compound (VII) and compound (VIII-a) or compound (VIII-b).

Alternatively, compound (XIII-b) can be produced, for example, by a method shown in the following Scheme 13.

Scheme 13:

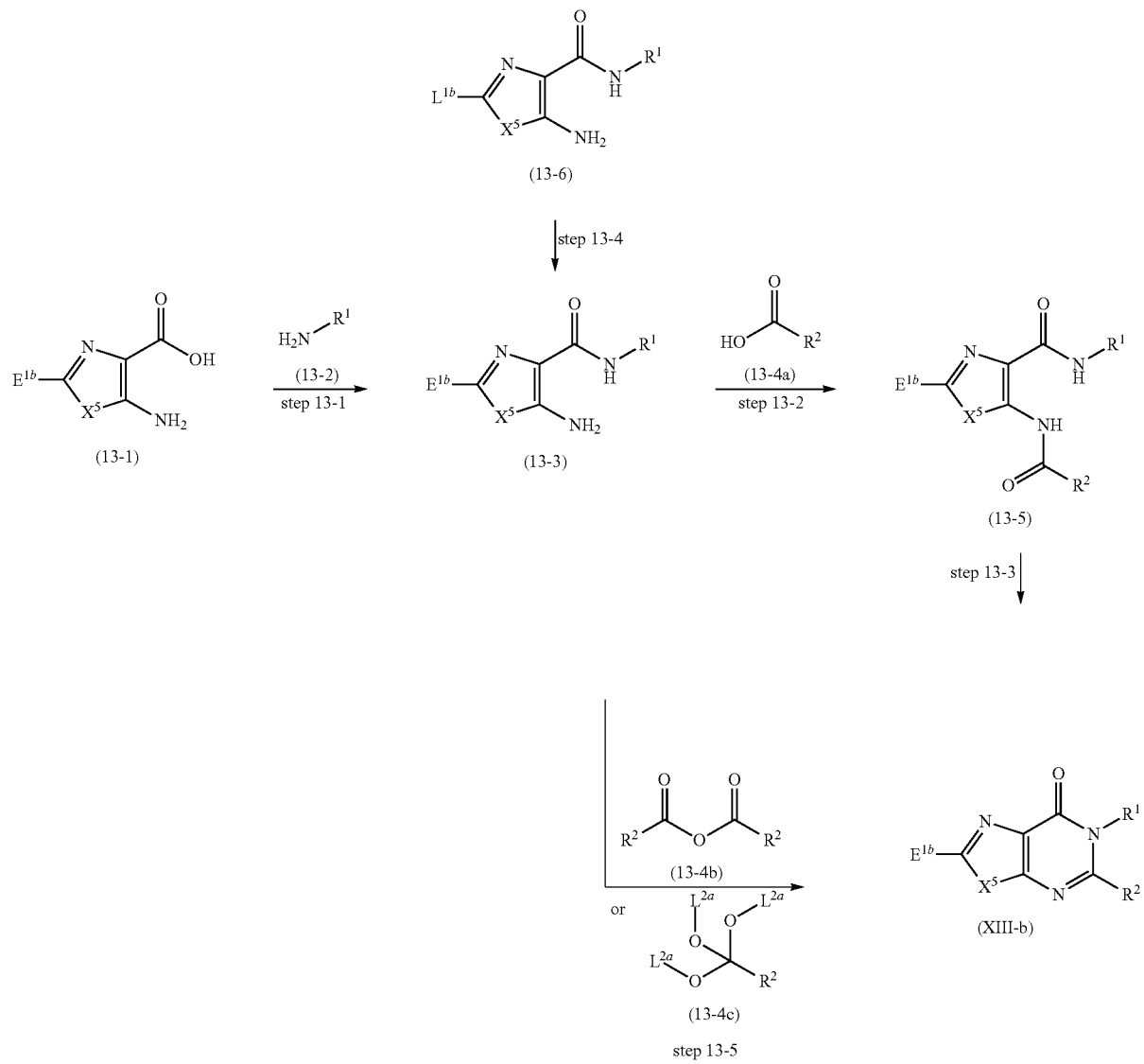

[In the Scheme, the symbols are as defined above.]

Compound (13-1) and compound (13-2) or a salt thereof are reacted to give compound (13-3). This is reacted with compound (13-4a) or a reactive derivative thereof to give compound (13-5). This is cyclized to give compound (XIII-b).

Alternatively, compound (13-3) can be obtained by halogenating $L^{1b}$ of compound (13-6).

Compound (XIII-b) can be produced by reacting compound (13-3) and compound (13-4b) or compound (13-4c).

Step 13-1:

Compound (13-3) can be produced in the same manner as in Scheme 1, step 1-4, by reacting compound (13-1) and compound (13-2) or a salt thereof in a solvent in the presence of a condensation agent, in the presence or absence of an activator, in the presence or absence of a base.

Step 13-2:

Compound (13-5) can be produced in the same manner as in Scheme 2, step 2-1, by reacting compound (13-3) and compound (13-4a) or a reactive derivative thereof.

Step 13-3:

Compound (XIII-b) can be produced by reacting compound (13-5) in a solvent in the presence of a condensation agent, in the presence of a base, in the same manner as in the method of producing compound (I-d) from compound (VI).

Step 13-4:

Compound (13-3) can be produced in the same manner as in Scheme 12, step 12-3, by halogenation corresponding to $E^{1b}$ of compound (13-3) and $L^{1b}$ of compound (13-6).

Step 13-5:

Compound (XIII-b) can be produced by reacting compound (13-3) with compound (13-4b) or compound (13-4c), in the same manner as in the method of producing compound (I-d) from compound (VII) and compound (VIII-a) or compound (VIII-b).

Of the aforementioned compound (XIII) of the present invention, a compound represented by the formula (XIII-c):

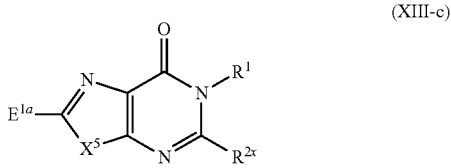

(XIII-c)

wherein $R^{2x}$ is optionally substituted amino, optionally substituted alkoxy, or an optionally substituted nitrogen-containing nonaromatic heterocyclic group wherein a bond of the ring is a nitrogen atom, and other symbols are as defined above, can be produced, for example, by a method shown in the following Scheme 14.

Scheme 14:

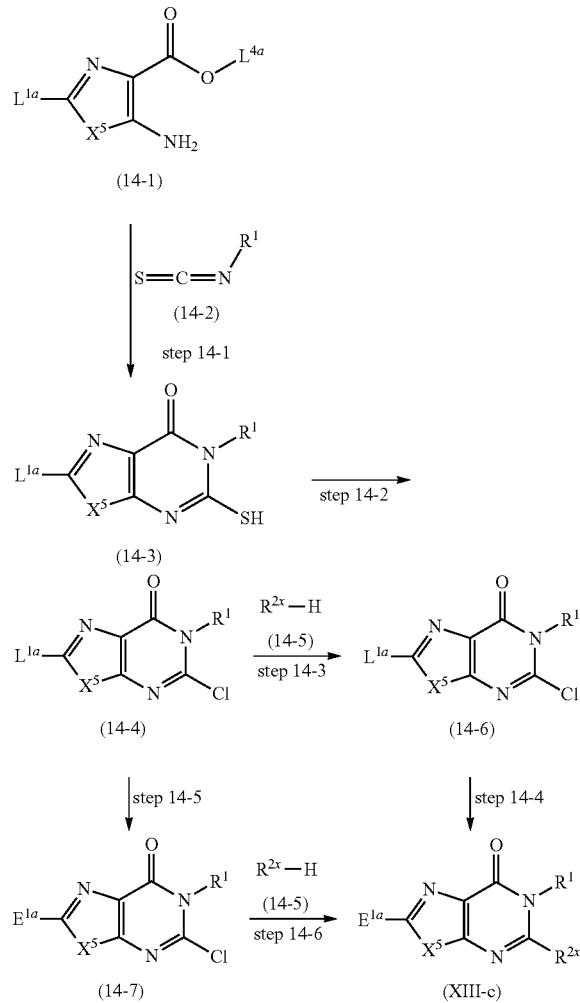

[In the Scheme, $L^{4a}$ is alkyl, and other symbols are as defined above.]

Compound (14-1) and compound (14-2) are reacted to give compound (14-3). This is converted to give compound (14-4) This is reacted with compound (14-5) to give compound (14-6). This is oxidized to give compound (XIII-c).

Alternatively, compound (14-4) is oxidized to give compound (14-7). This is reacted with compound (14-5) to give compound (XIII-c).

Step 14-1:

Compound (14-3) can be produced by reacting compound (14-1) and compound (14-2) in a solvent (e.g., alkylalcohol such as ethanol and the like), in the presence of a base (e.g., amine such as DBU and the like).

The amount of compound (14-2) to be used in this reaction is 0.9-3.0 mol, preferably 1.0-2.0 mol, per 1 mol of compound (14-1). The amount of the base to be used is 1.0-5.0 mol, preferably 1.0-3.0 mol, per 1 mol of compound (14-1). This reaction can be performed at 0-100° C., preferably 20-80° C.

Step 14-2:

Compound (14-4) can be produced by reacting compound (14-3) in a solvent (e.g., a mixed solvent of halogenohydrocarbon such as 1,2-dichloroethane and the like and amide such as N,N-dimethylformamide and the like), in the presence of a chlorinating agent (e.g., oxalyl chloride, phosphorus oxychloride).

The amount of the chlorinating agent to be used in this reaction is 0.9-3.0 mol, preferably 1.0-2.0 mol, per 1 mol of compound (14-3). This reaction can be performed at 0-100° C., preferably 20-80° C.

Step 14-3:

Compound (14-6) wherein $R^{2x}$ is optionally substituted amino, or optionally substituted nitrogen-containing nonaromatic heterocyclic group wherein a bond of the ring is a nitrogen atom can be produced by reacting compound (14-4) with the corresponding compound (14-5), in a solvent (e.g., ether such as tetrahydrofuran and the like), in the presence of a base (e.g., trialkylamine such as N,N-diisopropylethylamine and the like).

The amount of compound (14-5) to be used in this reaction is 1.0-10 mol, preferably 1.2-3.0 mol, per 1 mol of compound (14-4). The amount of the base to be used is 1.2-10 mol, preferably 1.2-3.0 mol, per 1 mol of compound (14-4). This reaction can be performed at 0-100° C., preferably 20-60° C.

Compound (14-6) wherein $R^{2x}$ is optionally substituted is alkoxy can be produced by reacting compound (14-4) with the corresponding compound (14-5), in a solvent (e.g., amide such as N,N-dimethylformamide and the like), in the presence of a base (e.g., alkali metal hydride such as sodium hydride and the like).

The amount of compound (14-5) to be used in this reaction is 0.9-5.0 mol, preferably 1.2-2.0 mol, per 1 mol of compound (14-4). The amount of the base to be used is 0.9-5.0 mol, preferably 1.2-2.0 mol, per 1 mol of compound (14-4). This reaction can be performed at 0-100° C., preferably 2-60° C.

Step 14-4:

Compound (XIII-c) can be produced in the same manner as in Scheme 11, step 11-4, by treating compound (14-6) with an oxidant.

Step 14-5:

Compound (14-7) can be produced in the same manner as in Scheme 11, step 11-4, by treating compound (14-4) with an oxidant.

Step 14-6:

Compound (XIII-c) can be produced by reacting compound (14-7) and compound (14-5) in the same manner as in step 14-3.

Of the aforementioned compound (XIII) of the present invention, a compound represented by the formula (XIII-d):

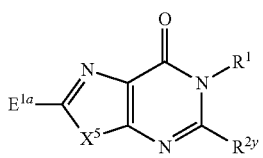

(XIII-d)

wherein $R^{2y}$ is optionally substituted aryl, and other symbols are as defined above, can be produced, for example, by a method shown in the following Scheme 15.

Scheme 15:

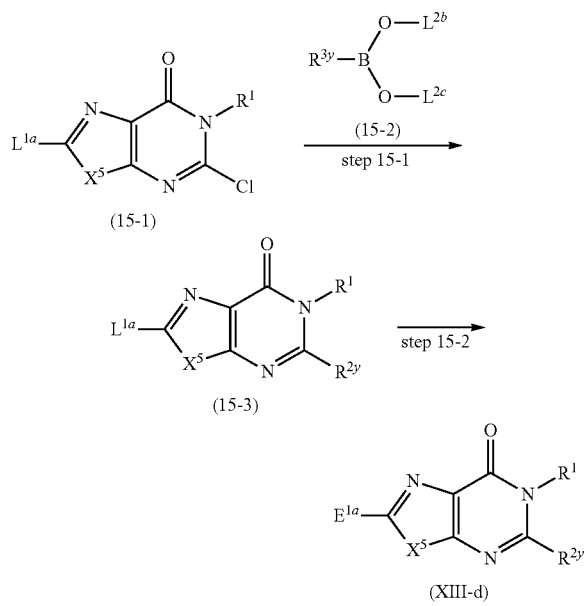

[In the Scheme, $L^{2b}$ and $L^{2c}$ are each a hydrogen atom, or $L^{2b}$ and $L^{2c}$ are bonded to each other to form alkylene, and other symbols are as defined above.]

Compound (15-1) and compound (15-2) are reacted to give compound (15-3). This is oxidized to give compound (XIII-d).

Step 15-1:

Compound (15-3) can be produced by reacting compound (15-1) and compound (15-2) in a solvent in the presence of palladiums and a base, in the presence or absence of a ligand.

Examples of the palladiums include tris(dibenzylideneacetone)dipalladium (0), tetrakis(triphenylphosphine)palladium (0), palladium (II) acetate, palladium (II) chloride, bis(triphenylphosphine)dichloropalladium (II), [1,1'-bis(diphenylphosphino)ferrocene]dichloropalladium (II), bis(di-tert-butyl(4-dimethylaminophenyl)phosphine)dichloropalladium (II), dichlorobis(tricyclohexylphosphine)palladium (II). Examples of the base include alkali metal carbonate such as sodium carbonate, potassium carbonate, cesium carbonate and the like; alkali metal phosphate such as trisodium phosphate, disodium hydrogen phosphate, tripotassium phosphate and the like; alkali metal fluoride such as potassium fluoride, cesium fluoride and the like. Examples of the ligand include phosphine ligand such as triphenylphosphine, 2-di-tert-butylphosphino-2',4',6'-triisopropylbiphenyl, 2-dicyclohexyl-phosphino-2',6'-dimethoxybiphenyl, 2-di-tert-butylphosphino-3,4,5,6-tetramethyl-2',4',6'-triisopropyl-1,1'-biphenyl and the like. The solvent may be any as long as it does not influence the reaction, and examples thereof include ether such as tetrahydrofuran, 1,2-dimethoxyethane, 1,4-dioxane and the like; alcohol such as tert-butanol and the like; aromatic hydrocarbon such as toluene, xylene and the like; water, or a mixed solvent thereof.

The amount of compound (15-2) to be used in this reaction is 0.9-5.0 mol, preferably 1.2-2.0 mol, per 1 mol of compound (15-1). The amount of the palladiums to be used is 0.001-1.0 mol, preferably 0.01-0.1 mol, per 1 mol of compound (15-1). The amount of the base to be used is 0.9-5.0 mol, preferably 1.0-3.0 mol, per 1 mol of compound (15-1). The amount of the ligand to be used is 0.001-1.0 mol, preferably 0.01-0.1 mol, per 1 mol of compound (15-1). This reaction can be performed at 20-150° C., preferably 50-100° C.

Step 15-2:

Compound (XIII-d) can be produced in the same manner as in Scheme 11, step 11-4, by treating compound (15-3) with an oxidant.

Of the aforementioned compound (XIII) of the present invention, a compound represented by the formula (XIII-e):

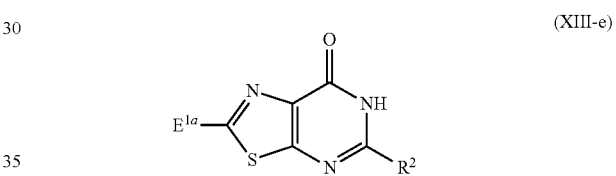

(XIII-e)

wherein the symbols are as defined above, can be produced, for example, by a method shown in the following Scheme 16.

Scheme 16:

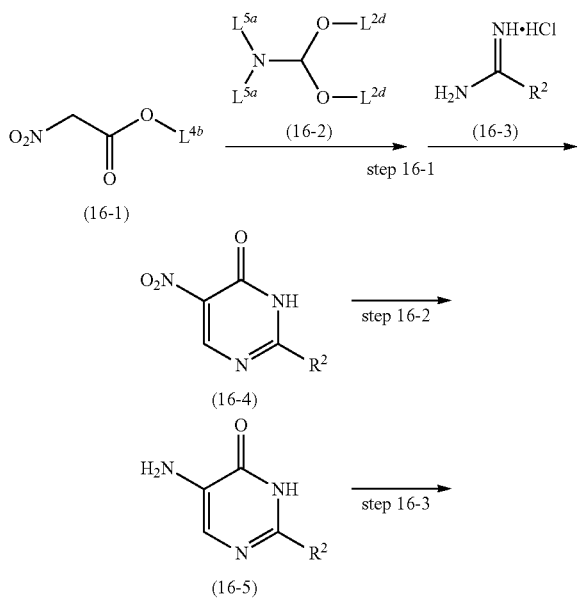

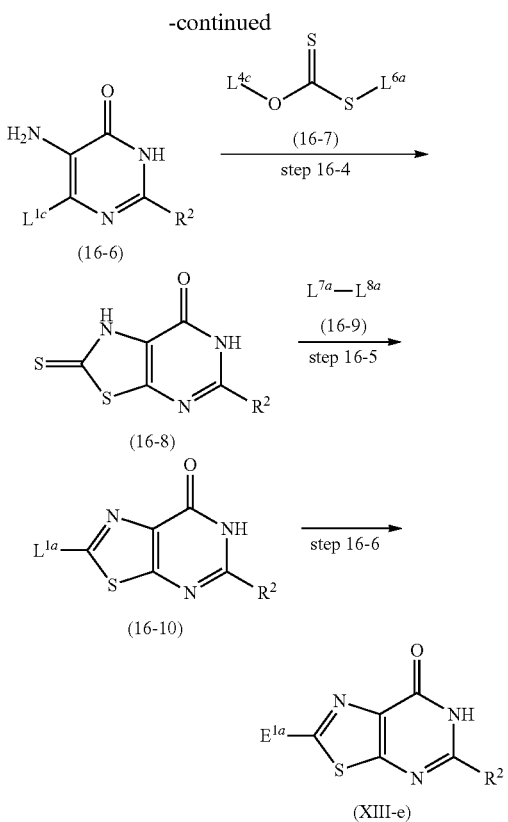

[In the Scheme, $L^{1c}$ is a halogen atom, $L^{2d}$ is alkyl, $L^{4b}$ is alkyl, $L^{4c}$ is alkyl, $L^{5a}$ is alkyl, $L^{6a}$ is alkali metal, $L^{7a}$ is alkyl or alkoxyphenylalkyl, $L^{8a}$ is a leaving group, and other symbols are as defined above.]

Compound (16-1) and compound (16-2) are reacted, and then, compound (16-3) is reacted to give compound (16-4). This is reduced to give compound (16-5). This is halogenated to give compound (16-6). This is reacted with compound (16-7) to give compound (16-8). This is reacted with compound (16-9) to give compound (16-10). This is oxidized to give compound (XIII-e)

Step 16-1:

Compound (16-4) can be produced by reacting compound (16-1) and compound (16-2) without solvent and then reacting the resulting compound with compound (16-3) in a solvent (e.g., alkylalcohol such as ethanol and the like), in the presence of a base (e.g., trialkylamine such as triethylamine and the like).

The amount of compound (16-2) to be used in this reaction is 1.0-5.0 mol, preferably 1.2-3.0 mol, per 1 mol of compound (16-1). The amount of compound (16-3) to be used is 1.0-3.0 mol, preferably 1.2-2.0 mol, per 1 mol of compound (16-1). The amount of the base to be used is 1.0-5.0 mol, preferably 1.2-3.0 mol, per 1 mol of compound (16-1). This reaction can be performed at 20-150° C., preferably 40-100° C.

Step 16-2:

Compound (16-5) can be produced by reacting compound (16-4) in a solvent (e.g., a mixed solvent of alkylalcohol such as methanol and the like, and halogenohydrocarbon such as chloroform and the like), in the presence of palladium carbon, under a hydrogen atmosphere.

The amount of palladium carbon to be used in this reaction is 0.001-1.0 mol, preferably 0.01-0.5 mol, per 1 mol of compound (16-4). This reaction can be performed at 0-80° C., preferably 20-60° C.

Step 16-3:

Compound (16-6) can be produced by treating compound (16-5) with a halogenating agent (e.g., N-halogenosuccinimide) corresponding to $L^{1c}$ in a solvent (e.g., amide such as N,N-dimethylformamide and the like).

The amount of the halogenating agent to be used in this reaction is 0.9-3.0 mol, preferably 1.0-2.0 mol, per 1 mol of compound (16-5). This reaction can be performed at −20-100° C., preferably 0-60° C.

Step 16-4:

Compound (16-8) can be produced by reacting compound (16-6) and compound (16-7) in a solvent (e.g., amide such as N,N-dimethylformamide and the like).

The amount of compound (16-7) to be used in this reaction is 1.0-3.0 mol, preferably 1.2-2.0 mol, per 1 mol of compound (16-6). This reaction can be performed at 80-200° C., preferably 100-150° C.

Step 16-5:

Compound (16-10) can be produced by reacting compound (16-8) with compound (16-9) having $L^{7a}$ corresponding to $L^{1a}$ in a solvent in the presence of a base.

Examples of the leaving group for $L^{8a}$ include halogen atom. Examples of the base include alkali metal carbonate such as sodium hydrogen carbonate, sodium carbonate and the like. The solvent may be any as long as it does not influence the reaction, and examples thereof include amide such as N,N-dimethylformamide and the like.

The amount of alkylating agent or alkoxyphenylalkylating agent to be used in this reaction is 0.9-3.0 mol, preferably 1.0-2.0 mol, per 1 mol of compound (16-8). The amount of the base to be used is 0.9-3.0 mol, preferably 1.0-2.0 mol, per 1 mol of compound (16-8). This reaction can be performed at −20-60° C., preferably 0-30° C.

Step 16-6:

Compound (XIII-e) can be produced in the same manner as in Scheme 11, step 11-4, by treating compound (16-9) with an oxidant.

Of the aforementioned compound (XIII) of the present invention, a compound represented by the formula (XIII-f):

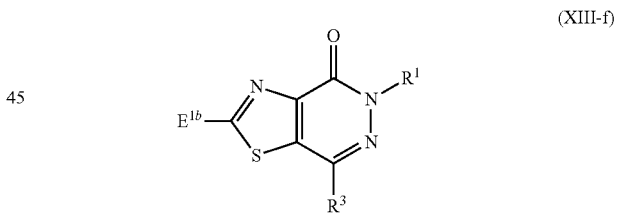

wherein the symbols are as defined above, can be produced, for example, by a method shown in the following Scheme 17.

Scheme 17:

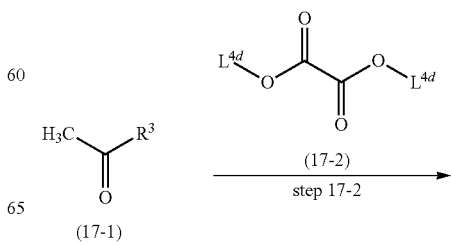

-continued

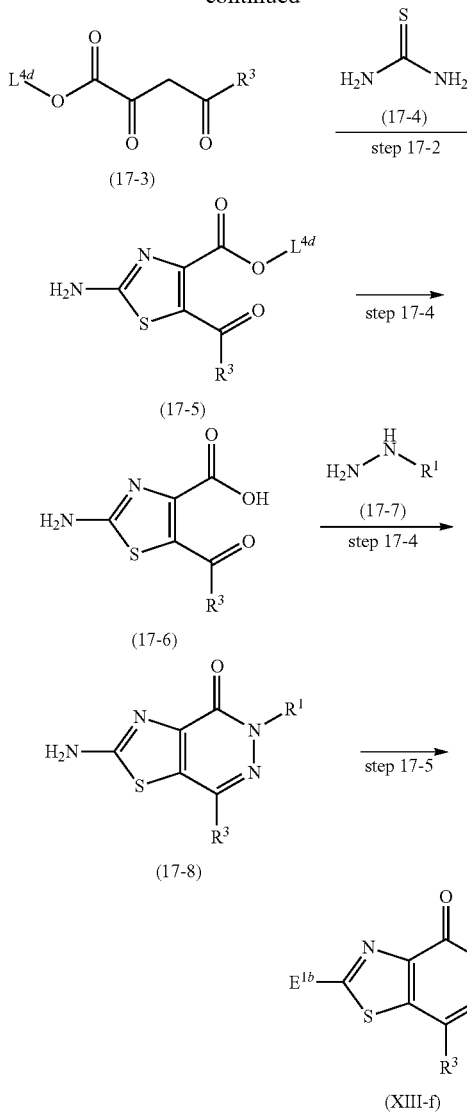

[In the Scheme, $L^{4d}$ is alkyl, and other symbols are as defined above.]

Compound (17-1) and compound (17-2) are reacted to give compound (17-3). This is reacted with compound (17-4) to give compound (17-5). This is hydrolyzed to give compound (17-6). This is reacted with compound (17-7) to give compound (17-8). This is halogenated to give compound (XIII-f).

Step 17-1:
Compound (17-3) can be produced by reacting compound (17-1) and compound (17-2) in a solvent in the presence of a base.

Examples of the base include alkali metal alkoxide corresponding to $L^{4d}$ such as sodium alkoxide and the like. The solvent may be any as long as it does not influence the reaction, and examples thereof include alkylalcohol corresponding to $L^{4d}$.

The amount of compound (17-2) to be used in this reaction is 0.9-2.0 mol, preferably 1.1-1.6 mol, per 1 mol of compound (17-1). The amount of the base to be used is 0.9-2.0 mol, preferably 1.1-1.6 mol, per 1 mol of compound (17-1). This reaction can be performed at 0-120° C., preferably 20-80° C.

Step 17-2:
Compound (17-5) can be produced by reacting compound (17-3) and compound (17-4) in a solvent (e.g., halogenohydrocarbon such as carbon tetrachloride and the like, alkylalcohol corresponding to $L^{4d}$), in the presence of sulfuryl chloride.

The amount of compound (17-4) to be used in this reaction is 0.9-2.0 mol, preferably 1.0-1.5 mol, per 1 mol of compound (17-3). The amount of sulfuryl chloride to be used is 0.9-2.0 mol, preferably 1.0-1.5 mol, per 1 mol of compound (17-3). This reaction can be performed at 0-80° C., preferably 20-60° C.

Step 17-3:
Compound (17-6) can be produced in the same manner as in Scheme 1, step 1-3, by hydrolysis by a conventional method.

Step 17-4:
Compound (17-8) can be produced by reacting compound (17-6) and compound (17-7) in a solvent (e.g., a mixed solvent of aromatic hydrocarbon such as toluene and the like and amide such as N-methylpyrrolidone and the like).

The amount of compound (17-7) to be used in this reaction is 0.9-3.0 mol, preferably 1.0-2.0 mol, per 1 mol of compound (17-6). This reaction can be performed at 80-200° C., preferably 100-150° C.

Step 17-5:
Compound (XIII-f) can be produced in the same manner as in Scheme 12, step 12-3, by reacting compound (17-8) in a solvent in the presence of copper(I) halide corresponding to $E^{1b}$ and nitrous acid alkyl ester.

Of the aforementioned compound (XIII) of the present invention, a compound represented by the formula (XIII-g):

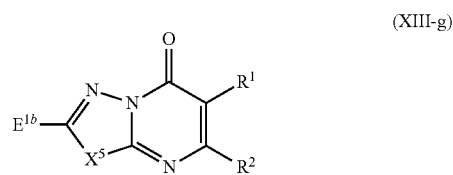

wherein the symbols are as defined above, can be produced, for example, by a method shown in the following Scheme 18.

Scheme 18:

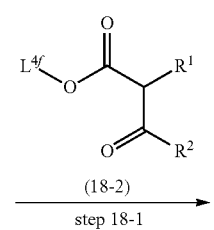

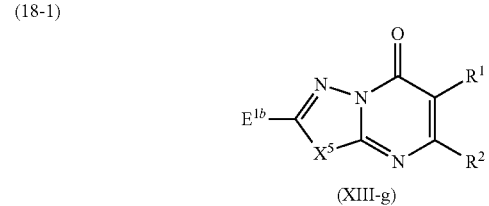

[In the Scheme, $L^{4f}$ is alkyl, and other symbols are as defined above.]

Compound (18-1) and compound (18-2) are reacted to give compound (XIII-g).

Step 18-1:

Compound (XIII-g) can be produced by reacting compound (18-1) and compound (18-2) in the presence of polyphosphoric acid.

The amount of compound (18-2) to be used in this reaction is 0.9-3.0 mol, preferably 1.0-2.0 mol, per 1 mol of compound (18-1). This reaction can be performed at 60-200° C., preferably 80-120° C.

Of the aforementioned compound (XIII) of the present invention, a compound represented by the formula (XIII-h):

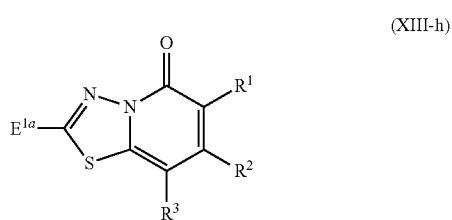

(XIII-h)

wherein the symbols are as defined above, can be produced, for example, by a method shown in the following Scheme 19.

Scheme 19:

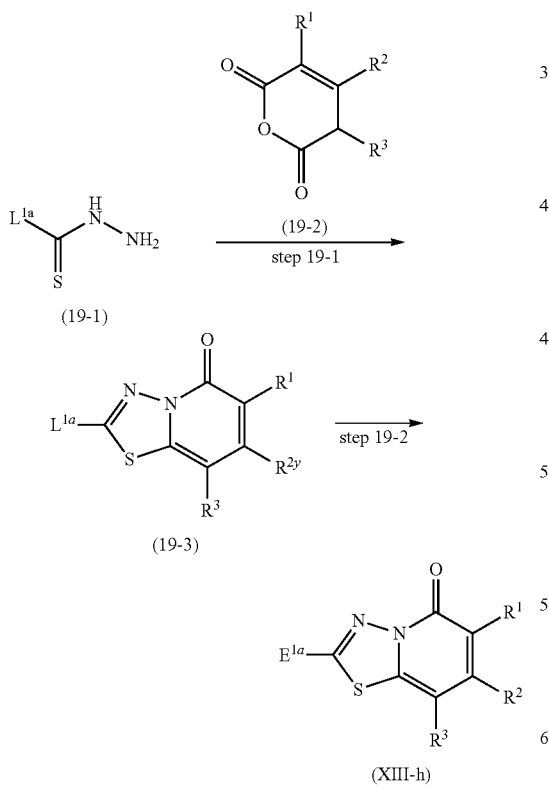

[In the Scheme, the symbols are as defined above.]

Compound (19-1) and compound (19-2) are reacted to give compound (19-3). This is oxidized to give compound (XIII-h).

Step 19-1:

Compound (19-3) can be produced by reacting compound (19-1) and compound (19-2) in a solvent (e.g., ether such as tetrahydrofuran and the like) and then reacting the resulting compound in the presence of phosphoric acid.

The amount of compound (19-2) to be used in this reaction is 0.9-2.0 mol, preferably 1.0-1.5 mol, per 1 mol of compound (19-1). This reaction can be performed at 0-200° C., preferably 20-120° C.

Step 19-2:

Compound (XIII-h) can be produced in the same manner as in Scheme 11, step 11-4, by treating compound (19-3) with an oxidant.

Of the aforementioned compound (XIV) of the present invention, a compound represented by the formula (XIV-a):

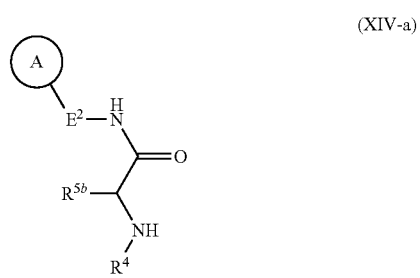

(XIV-a)

wherein the symbols are as defined above, can be produced, for example, by a method shown in the following Scheme 20.

Scheme 20:

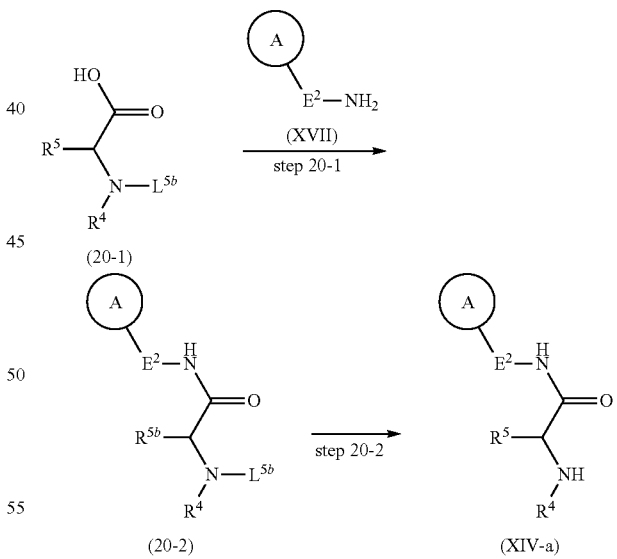

[In the Scheme, $L^{5b}$ is alkyloxycarbonyl or aralkyloxycarbonyl, and other symbols are as defined above.]

Compound (20-1) and compound (XVII) are reacted to give compound (20-2). $L^{5b}$ therein is removed to give compound (XIV-a).

Step 20-1:

Compound (20-2) can be produced in the same manner as in Scheme 1, step 1-4, by reacting compound (20-1) and compound (XVII)

Step 20-2:

Compound (XIV-a) can be produced by removing $L^{5b}$ of compound (20-2) by a conventional method such as acid treatment, hydrogenation and the like according to the kind of $L^{5b}$.

The aforementioned compound (XVIII) in the present invention can be produced, for example, by a method shown in the following Scheme 21.

Scheme 21:

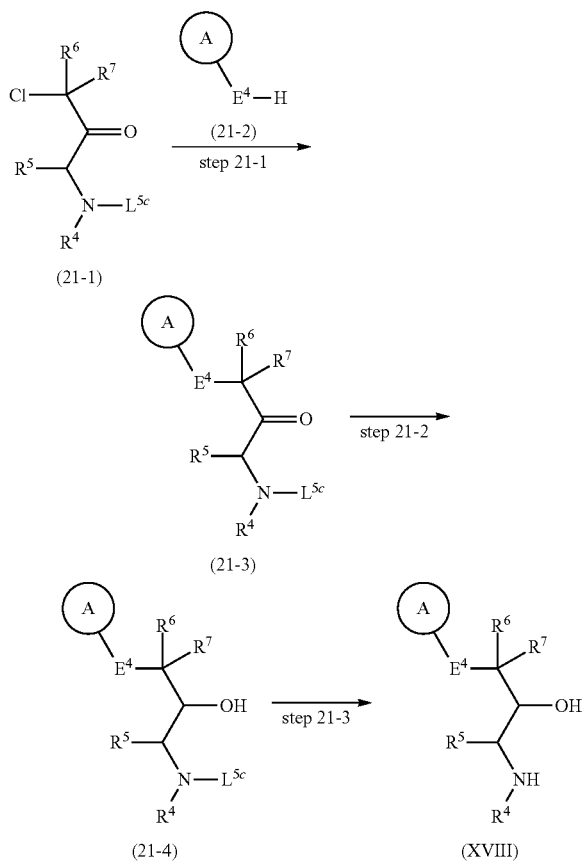

[In the Scheme, $L^{5c}$ is alkyloxycarbonyl or aralkyloxycarbonyl, and other symbols are as defined above.]

Compound (21-1) and compound (21-2) are reacted to give compound (21-3). This is reduced to give compound (21-4). $L^{5c}$ therein is removed to give compound (XVIII).

Step 21-1:

Compound (21-3) can be produced by reacting compound (21-1) and compound (21-2) in a solvent (e.g., amide such as N,N-dimethylformamide and the like), in the presence of a base (e.g., alkali metal carbonate such as potassium carbonate and the like) in the presence of potassium iodide.

The amount of compound (21-2) to be used in this reaction is 0.9-2.0 mol, preferably 1.0-1.5 mol, per 1 mol of compound (21-1). The amount of the base to be used is 0.9-2.0 mol, preferably 1.0-1.5 mol, per 1 mol of compound (21-1). The amount of potassium iodide to be used is 0.9-2.0 mol, preferably 1.0-1.5 mol, per 1 mol of compound (21-1). This reaction can be performed at 0-80° C., preferably 20-60° C.

Step 21-2:

Compound (21-4) can be produced by reacting compound (21-3) in a solvent (e.g., alkylalcohol such as methanol and the like), in the presence of a hydrogenating agent (e.g., boron hydride compound such as sodium borohydride and the like).

The amount of the hydrogenating agent to be used in this reaction is 0.9-2.0 mol, preferably 1.0-1.5 mol, per 1 mol of compound (21-3). This reaction can be performed at 20-150° C., preferably 50-100° C.

Step 21-3:

Compound (XVIII) can be produced by removing $L^{5C}$ of compound (21-4) by a conventional method such as acid treatment, hydrogenation and the like according to the kind of $L^{5C}$.

Of the aforementioned compound (XX) of the present invention, a compound represented by the formula (XX-a):

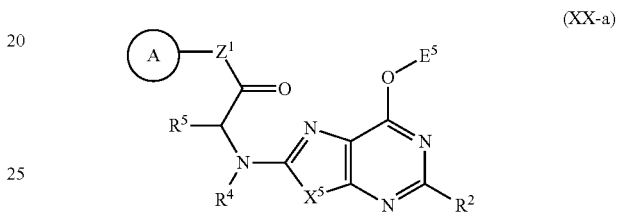

(XX-a)

wherein the symbols are as defined above, can be produced, for example, by a method shown in the following Scheme 22.

Scheme 22:

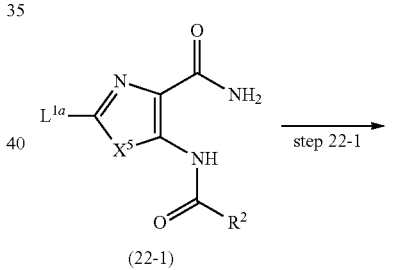

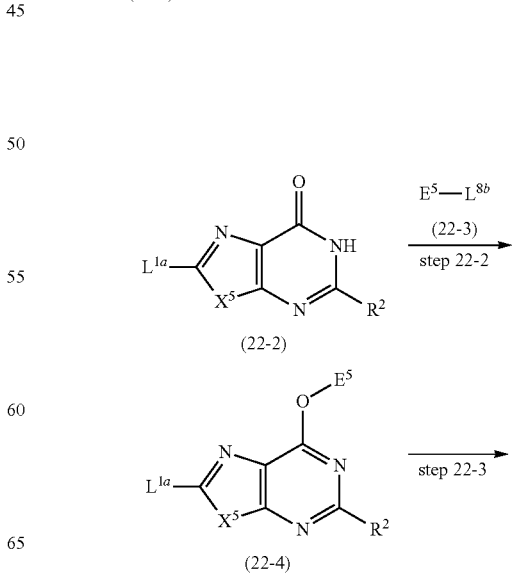

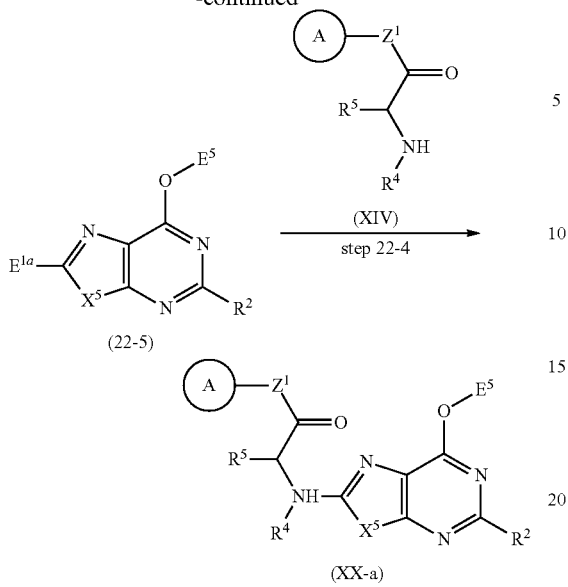

[In the Scheme, $L^{8b}$ is a leaving group, and other symbols are as defined above.]

Compound (22-1) is cyclized to give compound (22-2). This is reacted with compound (22-3) to give compound (22-4). This is oxidized to give compound (22-5). This is reacted with compound (XIV) to give compound (XX-a).

Step 22-1:

Compound (22-2) can be produced by reacting compound (22-1) in a solvent in the presence of a condensation agent, in the presence of a base, in the same manner as' in the method of producing compound (I-d) from compound (VI).

Step 22-2:

Compound (22-4) can be produced by reacting compound (22-2) and compound (22-3) by a conventional method according to the kind of $E^5$.

Examples of the leaving group for $L^{8b}$ include a halogen atom.

Step 22-3:

Compound (22-5) can be produced in the same manner as in Scheme 11, step 11-4, by treating compound (22-4) with an oxidant.

Step 22-4:

Compound (XX-a) can be produced by reacting compound (22-5) and compound (XIV) in the same manner as in the method of producing compound (I-g) from compound (XIII) and compound (XIV).

Of the aforementioned compound (XX) of the present invention, a compound represented by the formula (XX-b):

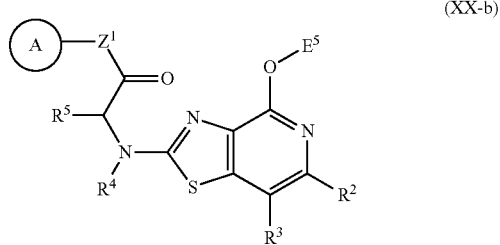

wherein the symbols are as defined above, can be produced, for example, by a method shown in the following Scheme 23.

Scheme 23:

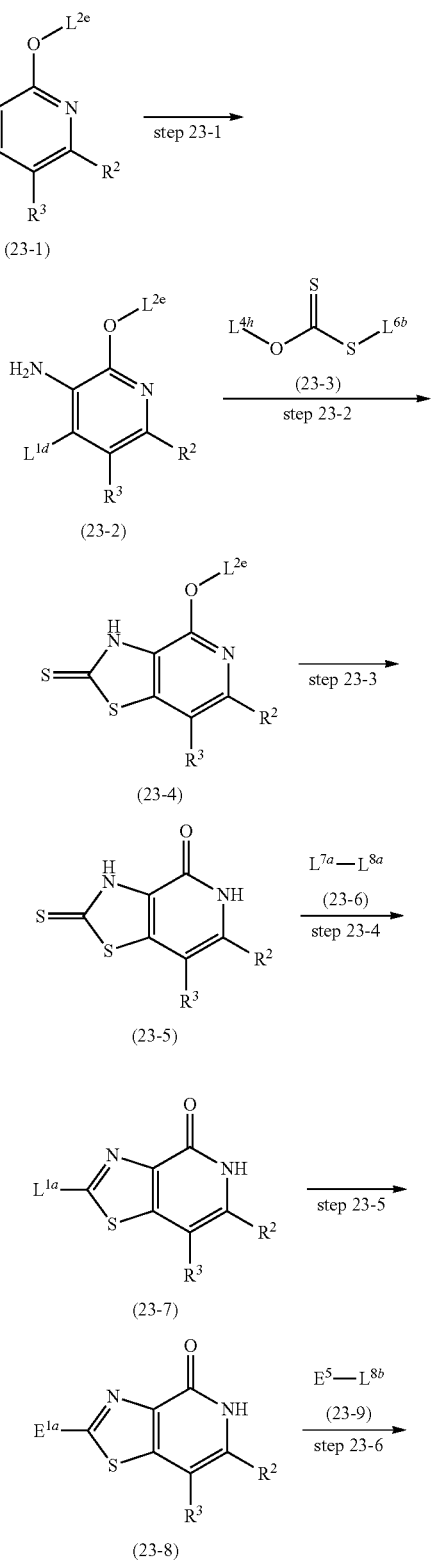

The aforementioned compound (XXI) in the present invention can be produced, for example, by a method shown in the following Scheme 24.

Scheme 24:

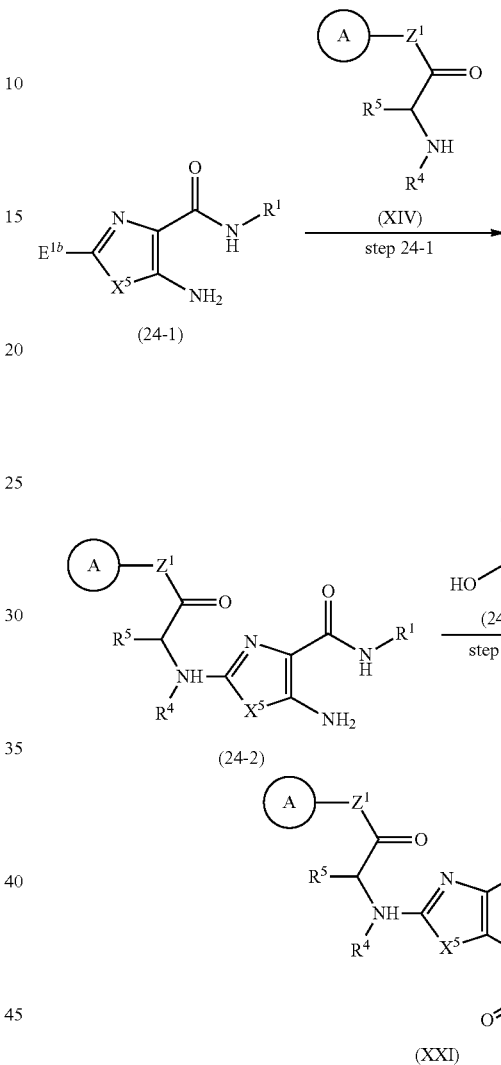

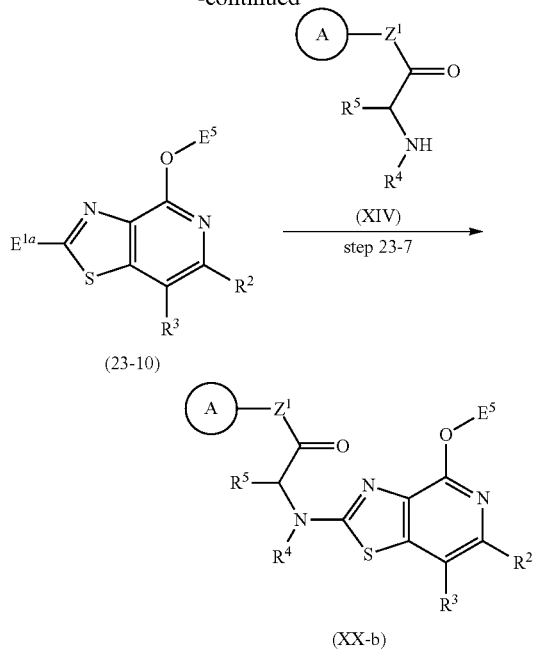

[In the Scheme, $L^{1d}$ is a halogen atom, $L^{2e}$ is alkyl, $L^{4h}$ is alkyl, $L^{6b}$ is alkali metal, and other symbols are as defined above.]

Compound (23-1) is halogenated to give compound (23-2) This is reacted with compound (23-3) to give compound (23-4). $L^{2e}$ therein is removed to give compound (23-5). This is reacted with compound (23-6) to give compound (23-7). This is oxidized to give compound (23-8). This is reacted with compound (23-9) to give compound (23-10). This is reacted with compound (XIV) to give compound (XX-b).

Step 23-1:
Compound (23-2) can be produced in the same manner as in Scheme 12, step 12-3, by treating compound (23-1) with a halogenating agent in a solvent.

Step 23-2:
Compound (23-4) can be produced in the same manner as in Scheme 16, step 16-4, by reacting compound (23-2) and compound (23-3) in a solvent.

Step 23-3:
Compound (23-5) can be produced by deprotecting compound (23-4) by a conventional method according to the kind of $L^{2e}$.

Step 23-4:
Compound (23-7) can be produced in the same manner as in Scheme 16, step 16-5, by reacting compound (23-5) and compound (23-6).

Step 23-5:
Compound (23-8) can be produced in the same manner as in Scheme 11, step 11-4, by treating compound (23-7) with an oxidant.

Step 23-6:
Compound (23-10) can be produced by reacting compound (23-8) and compound (23-9) by a conventional method according to the kind of $E^5$.

Step 23-7:
Compound (XX-b) can be produced by reacting compound (23-10) and compound (XIV) in the same manner as in the method of producing compound (I-g) from compound (XIII) and compound (XIV).

[In the Scheme, the symbols are as defined above.]

Compound (24-1) and compound (XIV) are reacted to give compound (24-2). This is reacted with compound (24-3) or a reactive derivative thereof to give compound (XXI).

Step 24-1:
Compound (24-2) can be produced by reacting compound (24-1) and compound (XIV) in the same manner as in the method of producing compound (I-g) from compound (XIII) and compound (XIV).

Step 24-2:
Compound (XXI) can be produced in the same manner as in Scheme 2, step 2-1, by reacting compound (24-2) and compound (24-3) or a reactive derivative thereof.

Of the aforementioned compound (XXII) of the present invention, a compound represented by the formula (XXII-a):

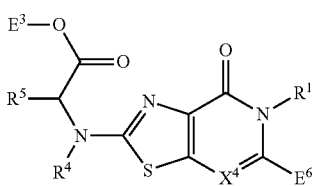

wherein the symbols are as defined above, can be produced, for example, by a method shown in the following Scheme 25.

Scheme 15:

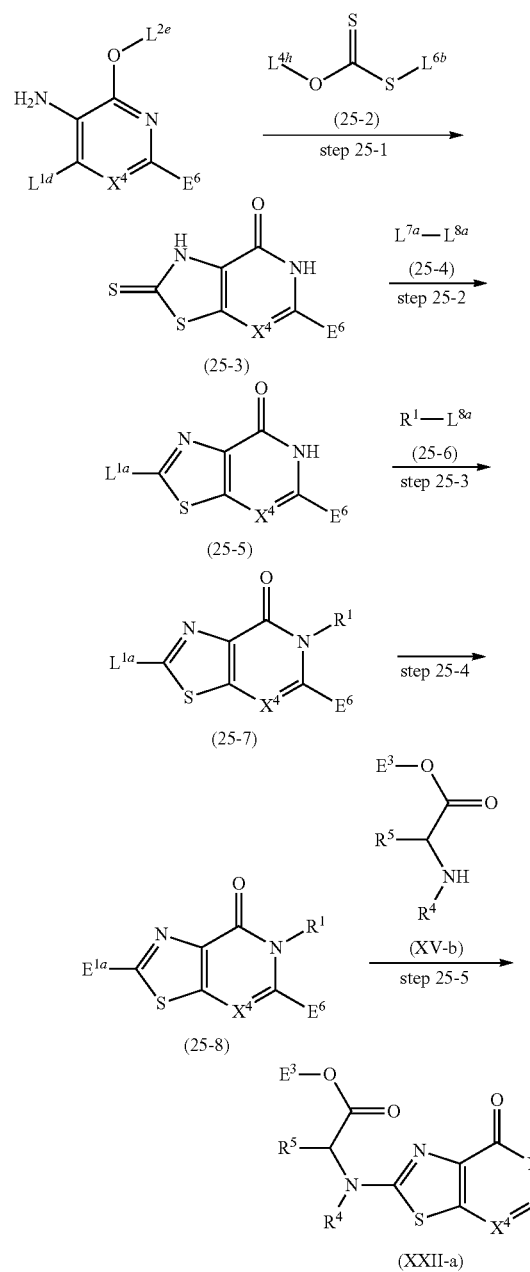

[In the Scheme, $L^{8c}$ is a leaving group, and other symbols are as defined above.]

Compound (25-1) and compound (25-2) are reacted to give compound (25-3). This is reacted with compound (25-4) to give compound (25-5). This is reacted with compound (25-6) to give compound (25-7). This is oxidized to give compound (25-8). This is reacted with compound (XV-b) to give compound (XXII-a).

Step 25-1:
Compound (25-3) can be produced in the same manner as in Scheme 16, step 16-4, by reacting compound (25-1) and compound (25-2) in a solvent.

Step 25-2:
Compound (25-5) can be produced in the same manner as in Scheme 16, step 16-5, by reacting compound (25-3) and compound (25-4).

Step 25-3:
Compound (25-7) can be produced by reacting compound (25-5) and compound (25-6) by a conventional method according to the kind of $R^1$.
Examples of the leaving group for $L^{8c}$ include a halogen atom.

Step 25-4:
Compound (25-8) can be produced in the same manner as in Scheme 11, step 11-4, by treating compound (25-7) with an oxidant.

Step 25-5:
Compound (XXII-a) can be produced by reacting compound (25-8) and compound (XV-b) in the same manner as in the method of producing compound (I-g) from compound (XIII) and compound (XIV).

Other starting compounds of the aforementioned production methods ([Production of compound (I)], and [Production of intermediate compound]) are commercially available, or can be easily produced by a method well known to those of ordinary skill in the art.

EXAMPLES

The present invention is explained in more detail in the following by referring to Examples and the like, which are not to be construed as limitative. Note that % described in the following Examples and the like means wt % unless specifically indicated, and the solvent ratio in column chromatography means volume ratio.

Example 1

(R)-2-[6-methyl-5-(3-methyl-[1,2,4]oxadiazol-5-yl)-7-oxo-6,7-dihydro[1,3]thiazolo[5,4-d]pyrimidin-2-yl]pyrrolidine-1-carboxylic acid benzyl ester

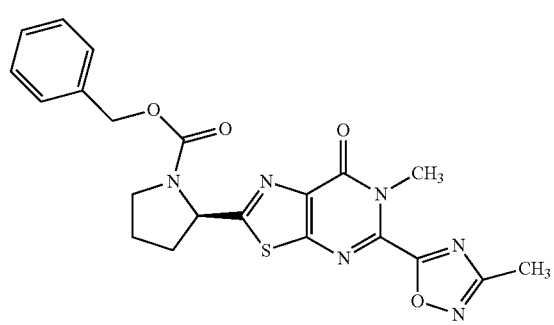 [SMILES: Cc1noc(-c2nc3sc([C@H]4CCCN4C(=O)OCc4ccccc4)nc3c(=O)n2C)n1]

To a solution (50.0 mL) of the compound (1.68 g) obtained in Reference Example 10 in 1,2-dichloroethane were added chlorotrimethylsilane (2.30 mL) and triethylamine (7.50 mL), and the reaction mixture was stirred at room temperature for 3 hr. Water and 1.0 mol/L hydrochloric acid were added to the reaction mixture, and the mixture was extracted twice with chloroform. The organic layer was dried over anhydrous magnesium sulfate, filtered and concentrated. The residue was purified by silica gel column chromatography (solvent; hexane/ethyl acetate=50/50-0/100) to give the title compound (1.45 g).

MS (ESI) m/z; 453 [M+H]$^+$

Example 2

(R)-2-[6-methyl-5-(5-methyl-[1,2,4]oxadiazol-3-yl)-7-oxo-6,7-dihydro[1,3]thiazolo[5,4-d]pyrimidin-2-yl]pyrrolidine-1-carboxylic acid benzyl ester

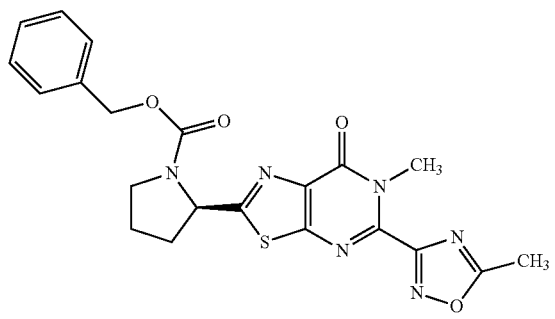 [SMILES: Cc1nc(-c2nc3sc([C@H]4CCCN4C(=O)OCc4ccccc4)nc3c(=O)n2C)no1]

The compound (760 mg) obtained in Reference Example 11 was treated by a method similar to that in Example 1 to give the title compound (700 mg).

MS (ESI) m/z; 453 [M+H]$^+$

Example 3

(R)-2-[6-methyl-5-(5-methyl-[1,3,4]oxadiazol-2-yl)-7-oxo-6,7-dihydro[1,3]thiazolo[5,4-d]pyrimidin-2-yl]pyrrolidine-1-carboxylic acid benzyl ester

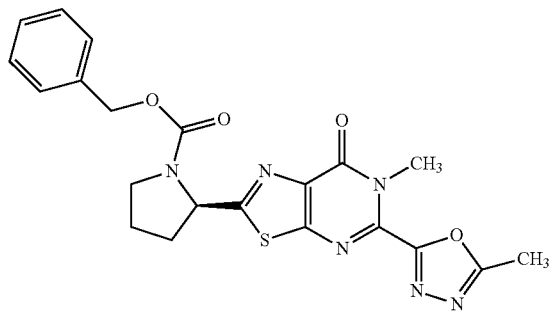 [SMILES: Cc1nnc(-c2nc3sc([C@H]4CCCN4C(=O)OCc4ccccc4)nc3c(=O)n2C)o1]

The compound (1800 mg) obtained in Reference Example 12 was treated by a method similar to that in Example 1 to give the title compound (1300 mg).

MS (ESI) m/z; 453 [M+H]$^+$

Example 4

(R)-2-(5-chloromethyl-6-methyl-7-oxo-6,7-dihydro[1,3]thiazolo[5,4-d]pyrimidin-2-yl)pyrrolidine-1-carboxylic acid benzyl ester

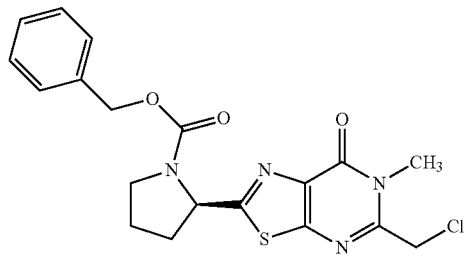 [SMILES: Cn1c(CCl)nc2sc([C@H]3CCCN3C(=O)OCc3ccccc3)nc2c1=O]

The compound (775 mg) obtained in Reference Example 13 was treated by a method similar to that in Example 1 to give the title compound (626 mg).

MS (ESI) m/z; 419 [M+H]$^+$

Example 5

(R)-2-[6-methyl-7-oxo-5-(tetrahydro-2H-pyran-4-yl)-6,7-dihydro[1,3]thiazolo[5,4-d]pyrimidin-2-yl]pyrrolidine-1-carboxylic acid benzyl ester

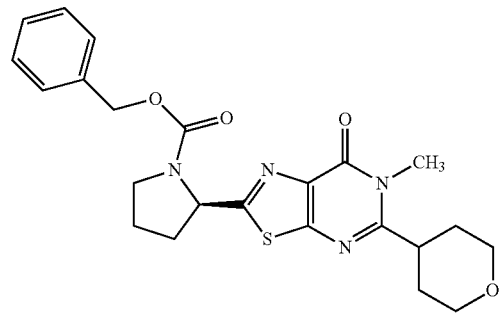 [SMILES: Cn1c(C2CCOCC2)nc2sc([C@H]3CCCN3C(=O)OCc3ccccc3)nc2c1=O]

The compound (1960 mg) obtained in Reference Example 15 was treated by a method similar to that in Example 1 to give the title compound (1600 mg).

MS (ESI) m/z; 455 [M+H]$^+$

Example 6

(R)-2-[7-oxo-6-(propan-2-yl)-5-trifluoromethyl-6,7-dihydro[1,3]thiazolo[5,4-d]pyrimidin-2-yl]pyrrolidine-1-carboxylic acid benzyl ester

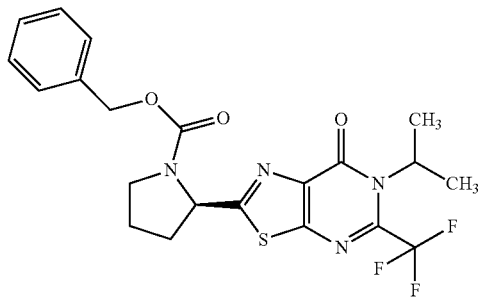 [SMILES: CC(C)n1c(C(F)(F)F)nc2sc([C@H]3CCCN3C(=O)OCc3ccccc3)nc2c1=O]

To a solution (60 mL) of the compound (2.45 g) obtained in Reference Example 8 in methylene chloride was added dropwise trifluoroacetic anhydride (6.7 g), and the reaction mixture was stirred at room temperature for 1 hr. Pyridine (2.50 g) was added dropwise, and the reaction mixture was stirred at room temperature overnight. Furthermore, 1,2-dichloroethane (10 mL), trifluoroacetic anhydride (13.4 g) and pyridine (5.00 g) were added dropwise, and the reaction mixture was heated under reflux for 4 hr. The reaction mixture was concentrated under reduced pressure, the residue was dissolved in ethyl acetate, and the solution was washed with 1.0 mol/L hydrochloric acid, dried over anhydrous magnesium sulfate, filtered and concentrated. The residue was purified by silica gel column chromatography (solvent; hexane/ethyl acetate=80/20-60/40) to give the title compound (2.46 g).

MS (ESI) m/z; 467 [M+H]+

Example 7

(R)-2-(5-ethyl-6-methyl-7-oxo-6,7-dihydro[1,3]thiazolo[5,4-d]pyrimidin-2-yl)pyrrolidine-1-carboxylic acid benzyl ester

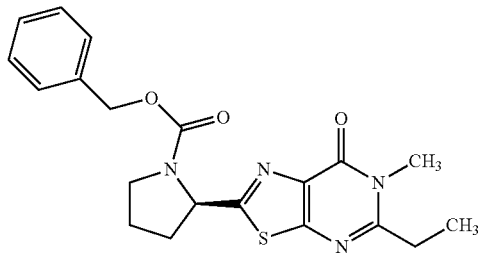 [SMILES: CCc1nc2sc([C@H]3CCCN3C(=O)OCc3ccccc3)nc2c(=O)n1C]

A mixture of the compound (3.00 g) obtained in Reference Example 7, acetic anhydride (8.5 g) and trimethyl orthopropionate (11.2 g) was stirred with heating at 120° C. for 2 hr. The reaction mixture was concentrated under reduced pressure, and the residue was purified by silica gel column chromatography (solvent; hexane/ethyl acetate=100/0-60/40) to give the title compound (0.47 g).

MS (ESI) m/z; 399 [M+H]+

Example 8

(R)-2-{6-methyl-5-[(morpholin-4-yl)methyl]-7-oxo-6,7-dihydro[1,3]thiazolo[5,4-d]pyrimidin-2-yl}pyrrolidine-1-carboxylic acid benzyl ester

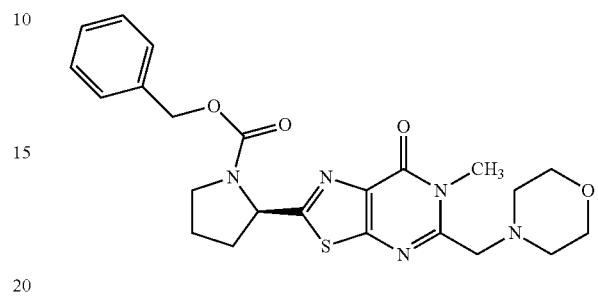

To a solution (3.0 mL) of the compound (259 mg) obtained in Example 4 in acetonitrile were added potassium carbonate (171 mg) and morpholine (80.6 mg), and the reaction mixture was stirred at room temperature for 3 hr. Water was added to the reaction mixture, and the mixture was extracted twice with ethyl acetate. The organic layer was dried over anhydrous magnesium sulfate, filtered and concentrated. The residue was purified by silica gel column chromatography (solvent; ethyl acetate/methanol=100/0-95/5) to give the title compound (285 mg).

MS (ESI) m/z; 470 [M+H]+

Example 9

(R)-N-benzyl-2-(5-ethyl-6-methyl-7-oxo-6,7-dihydro[1,3]thiazolo[5,4-d]pyrimidin-2-yl)pyrrolidine-1-carboxamide

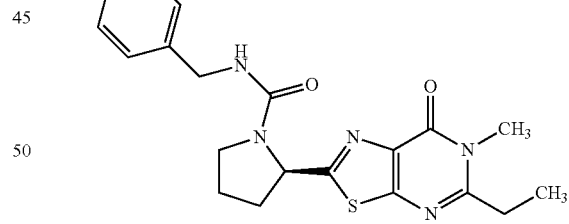

To a solution (9 mL) of the compound (300 mg) obtained in Reference Example 21, and N,N-diisopropylethylamine (0.24 mL) in methylene chloride was added dropwise benzyl isocyanate (0.15 mL) under ice-cooling. The reaction mixture was stirred at room temperature for 1 hr. 0.5 mol/L Hydrochloric acid was added to the reaction mixture, and the mixture was extracted twice with chloroform. The organic layer was dried over anhydrous magnesium sulfate, filtered and concentrated. The residue was purified by silica gel column chromatography (solvent; hexane/ethyl acetate=90/10-20/80) to give the title compound (483 mg).

MS (ESI) m/z; 398 [M+H]+

Example 10

(R)-N-(2-chlorobenzyl)-2-(5-ethyl-6-methyl-7-oxo-6,7-dihydro[1,3]thiazolo[5,4-d]pyrimidin-2-yl)pyrrolidine-1-carboxamide

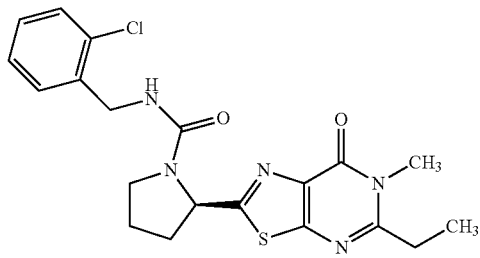 [SMILES: CCc1nc2sc([C@H]3CCCN3C(=O)NCc3ccccc3Cl)nc2c(=O)n1C]

The compound (150 mg) obtained in Reference Example 21 was treated by a method similar to that in Example 9 to give the title compound (210 mg).

MS (ESI) m/z; 432 [M+H]$^+$

Example 11

(R)-N-(2-chlorobenzyl)-2-[7-oxo-6-(propan-2-yl)-5-trifluoromethyl-6,7-dihydro[1,3]thiazolo[5,4-d]pyrimidin-2-yl]pyrrolidine-1-carboxamide

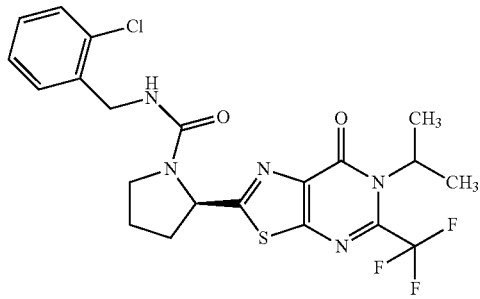 [SMILES: CC(C)n1c(C(F)(F)F)nc2sc([C@H]3CCCN3C(=O)NCc3ccccc3Cl)nc2c1=O]

The compound (150 mg) obtained in Reference Example 20 was treated by a method similar to that in Example 9 to give the title compound (120 mg).

MS (ESI) m/z; 500 [M+H]$^+$

Example 12

(R)-2-(5-ethyl-6-methyl-7-oxo-6,7-dihydro[1,3]thiazolo[5,4-d]pyrimidin-2-yl)-N-(1-phenylcyclopropyl)pyrrolidine-1-carboxamide

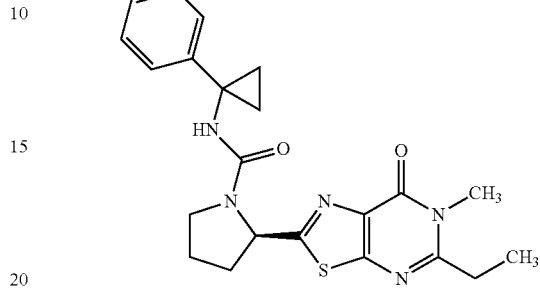

To a solution (60 mL) of 1-phenylcyclopropylamine (2.00 g) in chloroform were added triethylamine (4.11 mL) and 4-methoxyphenyl chloroformate (1.92 mL), and the reaction mixture was stirred at room temperature for 3 hr. Water was added to the reaction mixture, and the mixture was extracted twice with chloroform. The organic layer was dried over anhydrous magnesium sulfate, filtered and concentrated. The residue was washed with diethyl ether, filtered and dried to give (1-phenylcyclopropyl)-carbamic acid-4-methoxyphenyl ester (2.59 g) To a solution (6.0 mL) of the compound (80 mg) obtained in Reference Example 21 and DBU (0.32 mL) in acetonitrile was added (1-phenylcyclopropyl)-carbamic acid-4-methoxyphenyl ester (595 mg), and the reaction mixture was stirred with heating at 85° C. for 4 hr. 0.5 mol/L Hydrochloric acid was added to the reaction mixture, and the mixture was extracted twice with chloroform. The organic layer was dried over anhydrous magnesium sulfate, filtered and concentrated. The residue was purified by silica gel column chromatography (solvent; chloroform/methanol=100/0-95/5) to give the title compound (65 mg).

MS (ESI) m/z; 424 [M+H]$^+$

Example 13

(R)-5-ethyl-2-{1-[((R)-indan-1-yl)aminocarbonyl]pyrrolidin-2-yl}-6-methyl-6,7-dihydro[1,3]thiazolo[5,4-d]pyrimidin-7-one

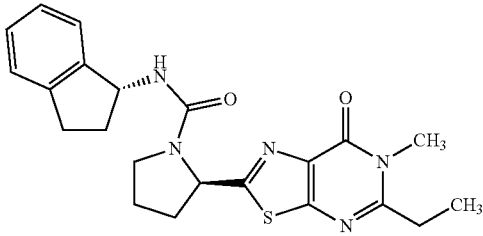 [SMILES: CCc1nc2sc([C@H]3CCCN3C(=O)N[C@@H]3CCc4ccccc43)nc2c(=O)n1C]

The compound (80 mg) obtained in Reference Example 21 was treated by a method similar to that in Example 12 to give the title compound (100 mg).

MS (ESI) m/z; 424 [M+H]$^+$

Example 14

(R)-2-{1-[2-(3,4-dihydro-2H-quinolin-1-yl)acetyl]pyrrolidin-2-yl}-5-ethyl-6-methyl-6H-[1,3]thiazolo[5,4-d]pyrimidin-7-one

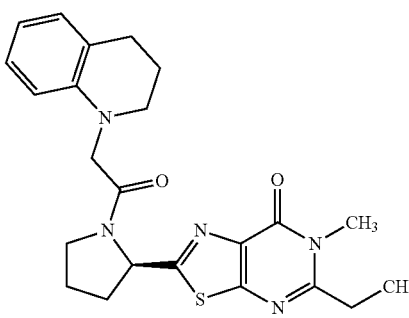

To a solution (7.5 mL) of the compound (200 mg) obtained in Reference Example 21 and N,N-diisopropylethylamine (0.16 mL) in methylene chloride was added dropwise chloroacetyl chloride (65 µL) under ice-cooling. The reaction mixture was stirred at room temperature for 1 hr. 0.5 mol/L Hydrochloric acid was added to the reaction mixture, and the mixture was extracted is twice with chloroform. The organic layer was dried over anhydrous magnesium sulfate, filtered and concentrated. To a solution (7.5 mL) of the residue in acetonitrile were added potassium iodide (150 mg), potassium carbonate (205 mg) and 1,2,3,4-tetrahydroquinoline (145 µL), and the reaction mixture was stirred with heating at 80° C. for 4 hr. Water was added to the reaction mixture, and the mixture was extracted twice with chloroform. The organic layer was dried over anhydrous magnesium sulfate, filtered and concentrated. The residue was purified by silica gel column chromatography (solvent; hexane/ethyl acetate=90/10-20/80) to give the title compound (330 mg).

MS (ESI) m/z; 438 [M+H]$^+$

Example 15

(R)-2-(5-ethyl-6-methyl-7-oxo-6,7-dihydro[1,3]thiazolo[5,4-d]pyrimidin-2-yl)-N-(1-methyl-1-phenylethyl)pyrrolidine-1-carboxamide

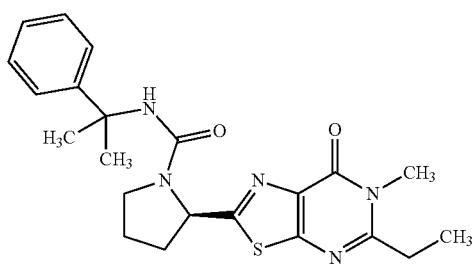 [SMILES: CCc1nc2sc([C@H]3CCCN3C(=O)NC(C)(C)c3ccccc3)nc2c(=O)n1C]

To a solution (15 mL) of triphosgene (110 mg) in methylene chloride was added pyridine (0.1 mL) under ice-cooling, and the reaction mixture was stirred at the same temperature for 30 min. The compound (150 mg) obtained in Reference Example 21 was added, and the reaction mixture was stirred at room temperature for 30 min. The solvent was evaporated under reduced pressure, methylene chloride (10 mL), 4-dimethylaminopyridine (370 mg) and 2-phenylpropane-2-amine (390 mg) were added at room temperature, and the reaction mixture was stirred overnight. 0.5 mol/L Hydrochloric acid was added to the reaction mixture, and the mixture was extracted twice with chloroform. The organic layer was dried over anhydrous magnesium sulfate, filtered and concentrated. The residue was purified by silica gel column chromatography (solvent; hexane/ethyl acetate=60/40-0/100) to give the title compound (30 mg).

MS (ESI) m/z; 426 [M+H]$^+$

Example 16

(R)-5-ethyl-2-{1-[((R)-1,2,3,4-tetrahydronaphthalen-1-yl)aminocarbonyl]pyrrolidin-2-yl}-6-methyl-6,7-dihydro[1,3]thiazolo[5,4-d]pyrimidin-7-one

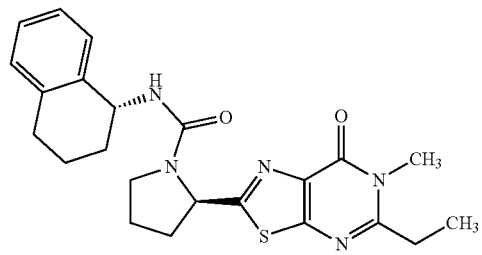 [SMILES: CCc1nc2sc([C@H]3CCCN3C(=O)N[C@@H]3CCCc4ccccc43)nc2c(=O)n1C]

The compound (150 mg) obtained in Reference Example 21 was treated by a method similar to that in Example 15 to give the title compound (67 mg).

MS (ESI) m/z; 438 [M+H]$^+$

Example 17

(R)-2-(5-ethyl-6-methyl-7-oxo-6,7-dihydro[1,3]thiazolo[5,4-d]pyrimidin-2-yl)-N-((R)-1-phenylethyl)pyrrolidine-1-carboxamide

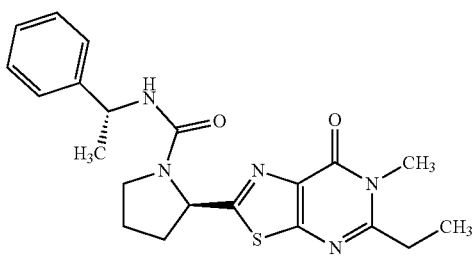 [SMILES: CCc1nc2sc([C@H]3CCCN3C(=O)N[C@H](C)c3ccccc3)nc2c(=O)n1C]

The compound (150 mg) obtained in Reference Example 21 was treated by a method similar to that in Example 15 to give the title compound (120 mg).

MS (ESI) m/z; 412 [M+H]$^+$

Example 18

(R)-2-(7-oxo-6-(propan-2-yl)-5-trifluoromethyl-6,7-dihydro[1,3]thiazolo[5,4-d]pyrimidin-2-yl)-N-(1-phenylcyclopropyl)pyrrolidine-1-carboxamide

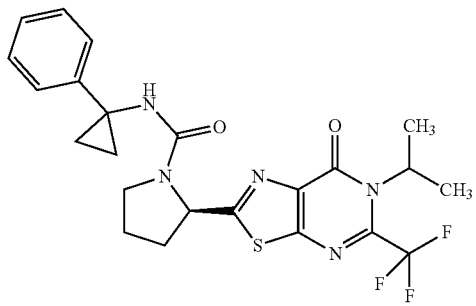 [SMILES: CC(C)n1c(C(F)(F)F)nc2sc([C@H]3CCCN3C(=O)NC3(c4ccccc4)CC3)nc2c1=O]

The compound (150 mg) obtained in Reference Example 20 was treated by a method similar to that in Example 15 to give the title compound (41 mg).
MS (ESI) m/z; 492 [M+H]$^+$

Example 19

(R)-2-[6-methyl-5-(3-methyl-[1,2,4]oxadiazol-5-yl)-7-oxo-6,7-dihydro[1,3]thiazolo[5,4-d]pyrimidin-2-yl]pyrrolidine-1-carboxylic acid phenyl ester

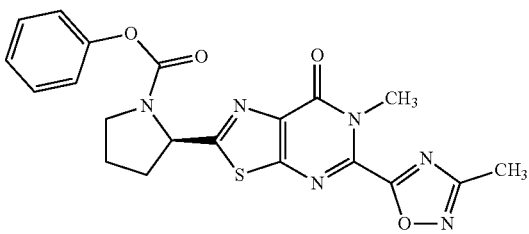 [SMILES: Cc1noc(-c2nc3sc([C@H]4CCCN4C(=O)Oc4ccccc4)nc3c(=O)n2C)n1]

To a solution (5.0 mL) of the compound (80 mg) obtained in Reference Example 16 in methylene chloride were added N,N-diisopropylethylamine (55 μL) and phenyl chloroformate (40 mg), and the reaction mixture was stirred at room temperature for 30 min. Water was added to the reaction mixture, and the mixture was extracted twice with chloroform. The organic layer was dried over anhydrous magnesium sulfate, filtered and concentrated. The residue was purified by silica gel column chromatography (solvent; hexane/ethyl acetate=70/30-20/80) to give the title compound (50 mg).
MS (ESI) m/z; 439 [M+H]$^+$

Example 20

(R)-2-[6-methyl-5-(3-methyl-[1,2,4]oxadiazol-5-yl)-7-oxo-6,7-dihydro[1,3]thiazolo[5,4-d]pyrimidin-2-yl]pyrrolidine-1-carboxylic acid 4-methylphenyl ester

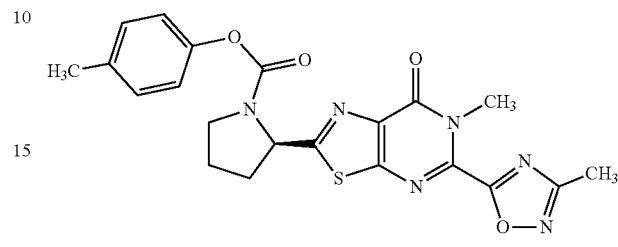

The compound (50 mg) obtained in Reference Example 16 was treated by a method similar to that in Example 19 to give the title compound (68 mg).
MS (ESI) m/z; 453 [M+H]$^+$

Example 21

(R)-2-[6-methyl-5-(3-methyl-[1,2,4]oxadiazol-5-yl)-7-oxo-6,7-dihydro[1,3]thiazolo[5,4-d]pyrimidin-2-yl]pyrrolidine-1-carboxylic acid 4-methoxyphenyl ester

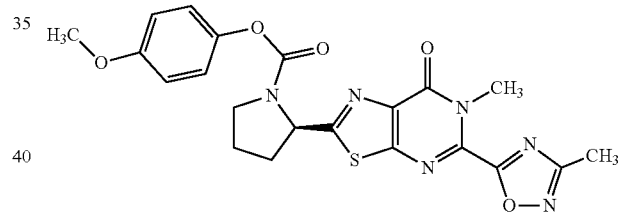

The compound (30 mg) obtained in Reference Example 16 was treated by a method similar to that in Example 19 to give the title compound (27 mg).
MS (ESI) m/z; 469 [M+H]$^+$

Example 22

6-methyl-5-(3-methyl-[1,2,4]oxadiazol-5-yl)-2-[(R)-1-(phenylacetyl)pyrrolidin-2-yl]-6H-[1,3]thiazolo[5,4-d]pyrimidin-7-one

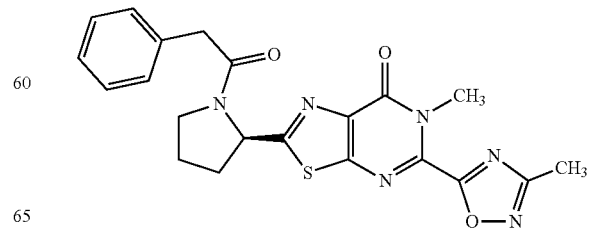

The compound (70 mg) obtained in Reference Example 16 was treated by a method similar to that in Example 19 to give the title compound (90 mg).
MS (ESI) m/z; 437 [M+H]+

Example 23

6-methyl-5-(3-methyl-[1,2,4]oxadiazol-5-yl)-2-[(R)-1-(3-methylphenylacetyl)pyrrolidin-2-yl]-6H-[1,3]thiazolo[5,4-d]pyrimidin-7-one

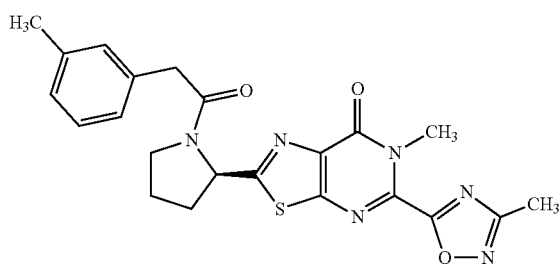

The compound (70 mg) obtained in Reference Example 16 was treated by a method similar to that in Example 19 to give the title compound (90 mg).
MS (ESI) m/z; 451 [M+H]+

Example 24

(R)-2-[6-methyl-5-(5-methyl-[1,2,4]oxadiazol-3-yl)-7-oxo-6,7-dihydro[1,3]thiazolo[5,4-d]pyrimidin-2-yl]pyrrolidine-1-carboxylic acid phenyl ester

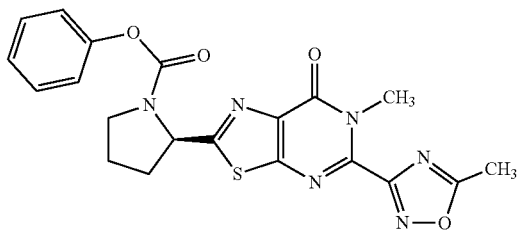 [SMILES: Cc1nc(-c2nc3sc([C@H]4CCCN4C(=O)Oc4ccccc4)nc3c(=O)n2C)no1]

The compound (330 mg) obtained in Reference Example 17 was treated by a method similar to that in Example 19 to give the title compound (440 mg).
MS (ESI) m/z; 439 [M+H]+

Example 25

(R)-2-[6-methyl-5-(5-methyl-[1,3,4]oxadiazol-2-yl)-7-oxo-6,7-dihydro[1,3]thiazolo[5,4-d]pyrimidin-2-yl]pyrrolidine-1-carboxylic acid phenyl ester

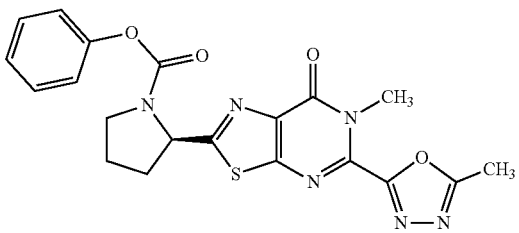 [SMILES: Cc1nnc(-c2nc3sc([C@H]4CCCN4C(=O)Oc4ccccc4)nc3c(=O)n2C)o1]

The compound (100 mg) obtained in Reference Example 18 was treated by a method similar to that in Example 19 to give the title compound (130 mg).
MS (ESI) m/z; 439 [M+H]+

Example 26

6-methyl-5-(5-methyl-[1,3,4]oxadiazol-2-yl)-2-[(R)-1-(phenylacetyl)pyrrolidin-2-yl]-6H-[1,3]thiazolo[5,4-d]pyrimidin-7-one

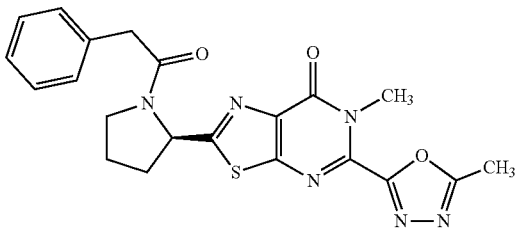

The compound (100 mg) obtained in Reference Example 18 was treated by a method similar to that in Example 19 to give the title compound (130 mg).
MS (ESI) m/z; 437 [M+H]+

Example 27

(R)-2-[6-methyl-7-oxo-5-(tetrahydro-2H-pyran-4-yl)-6,7-dihydro[1,3]thiazolo[5,4-d]pyrimidin-2-yl]pyrrolidine-1-carboxylic acid phenyl ester

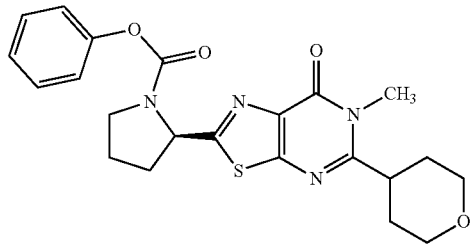 [SMILES: Cn1c(C2CCOCC2)nc2sc([C@H]3CCCN3C(=O)Oc3ccccc3)nc2c1=O]

The compound (200 mg) obtained in Reference Example 19 was treated by a method similar to that in Example 19 to give the title compound (270 mg).
MS (ESI) m/z; 441 [M+H]+

Example 28

(R)-2-(5-ethyl-6-methyl-7-oxo-6,7-dihydro[1,3]thi-azolo[5,4-d]pyrimidin-2-yl)pyrrolidine-1-carboxylic acid phenyl ester

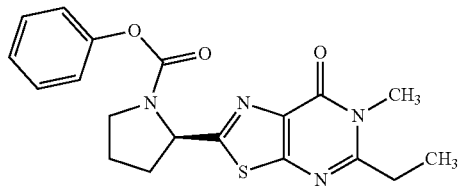 [SMILES: CCc1nc2sc([C@H]3CCCN3C(=O)Oc3ccccc3)nc2c(=O)n1C]

The compound (64 mg) obtained in Reference Example 21 was treated by a method similar to that in Example 19 to give the title compound (69 mg).
MS (ESI) m/z; 385 [M+H]$^+$

Example 29

5-ethyl-6-methyl-2-[(R)-1-(phenylacetyl)pyrrolidin-2-yl]-6H-[1,3]thiazolo[5,4-d]pyrimidin-7-one

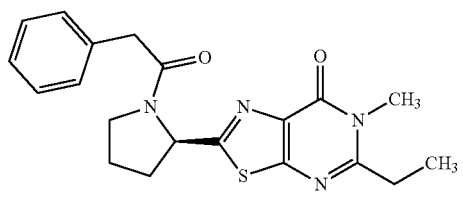

The compound (100 mg) obtained in Reference Example 21was treated by a method similar to that in Example 19 to give the title compound (53 mg).
MS (ESI) m/z; 383 [M+H]$^+$

Example 30

2-[(R)-1-(phenylacetyl)pyrrolidin-2-yl]-6-(propan-2-yl)-5-trifluoromethyl-6H-[1,3]thiazolo[5,4-d]pyrimidin-7-one

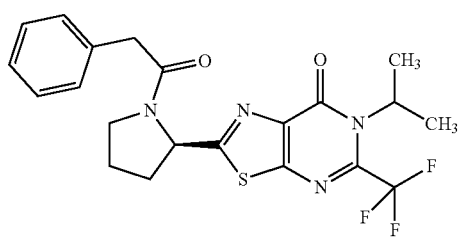 [SMILES: CC(C)n1c(C(F)(F)F)nc2sc([C@H]3CCCN3C(=O)Cc3ccccc3)nc2c1=O]

The compound (210 mg) obtained in Reference Example 20 was treated by a method similar to that in Example 19 to give the title compound (85 mg).
MS (ESI) m/z; 451 [M+H]$^+$

Example 31

(R)-2-{6-methyl-5-[(morpholin-4-yl)methyl]-7-oxo-6,7-dihydro[1,3]thiazolo[5,4-d]pyrimidin-2-yl}pyrrolidine-1-carboxylic acid phenyl ester

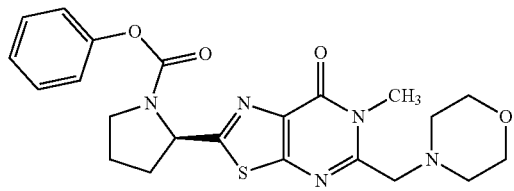 [SMILES: Cn1c(CN2CCOCC2)nc2sc([C@H]3CCCN3C(=O)Oc3ccccc3)nc2c1=O]

The compound (43 mg) obtained in Reference Example 22 was treated by a method similar to that in Example 19 to give the title compound (28 mg).
MS (ESI) m/z; 456 [M+H]$^+$

Example 32

(R)-2-[5-methyl-7-oxo-6-(tetrahydro-2H-pyran-4-yl)-6,7-dihydro[1,3]thiazolo[5,4-d]pyrimidin-2-yl]pyrrolidine-1-carboxylic acid phenyl ester

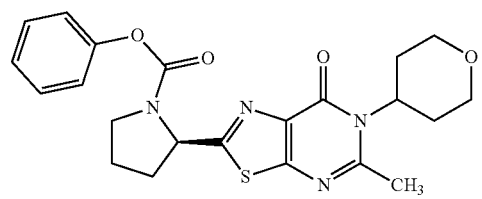 [SMILES: Cc1nc2sc([C@H]3CCCN3C(=O)Oc3ccccc3)nc2c(=O)n1C1CCOCC1]

The compound (60 mg) obtained in Reference Example 23 was treated by a method similar to that in Example 19 to give the title compound (14 mg).
MS (ESI) m/z; 441 [M+H]$^+$

Example 33

(R)-2-[6-methyl-5-(3-methyl-[1,2,4]oxadiazol-5-yl)-7-oxo-6,7-dihydro[1,3]thiazolo[5,4-d]pyrimidin-2-yl]pyrrolidine-1-carboxylic acid 3-methylphenyl ester

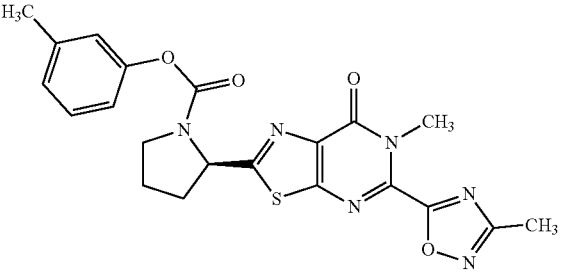

To a solution (2.0 mL) of triphosgene (38 mg) in toluene were added 3-cresol (35 mg) and pyridine (33 μL) under ice-cooling, and the reaction mixture was stirred at room temperature for 30 min. The solvent was evaporated under reduced pressure, methylene chloride (5.0 mL), triethylamine (100 μL) and the compound (50 mg) obtained in Reference Example 16 were added, and the reaction mixture was stirred at room temperature for 1 hr. Water was added to the reaction mixture, and the mixture was extracted twice with chloroform. The organic layer was dried over anhydrous magnesium sulfate, filtered and concentrated. The residue was purified by silica gel column chromatography (solvent; hexane/ethyl acetate=70/30-0/100) to give the title compound (50 mg).

MS (ESI) m/z; 453 [M+H]$^+$

Example 34

(R)-2-[6-methyl-5-(3-methyl-[1,2,4]oxadiazol-5-yl)-7-oxo-6,7-dihydro[1,3]thiazolo[5,4-d]pyrimidin-2-yl]pyrrolidine-1-carboxylic acid 2-methylphenyl ester

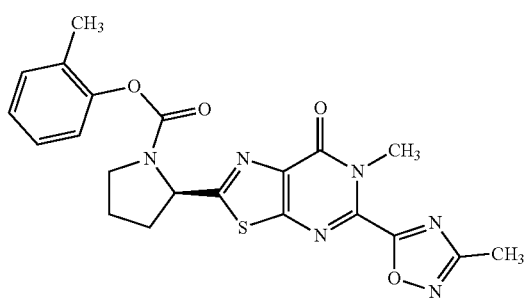 [SMILES: Cc1noc(-c2nc3sc([C@H]4CCCN4C(=O)Oc4ccccc4C)nc3c(=O)n2C)n1]

The compound (70 mg) obtained in Reference Example 16 was treated by a method similar to that in Example 33 to give the title compound (66 mg).

MS (ESI) m/z; 453 [M+H]$^+$

Example 35

(R)-2-[6-methyl-5-(3-methyl-[1,2,4]oxadiazol-5-yl)-7-oxo-6,7-dihydro[1,3]thiazolo[5,4-d]pyrimidin-2-yl]pyrrolidine-1-carboxylic acid 3-methoxyphenyl ester

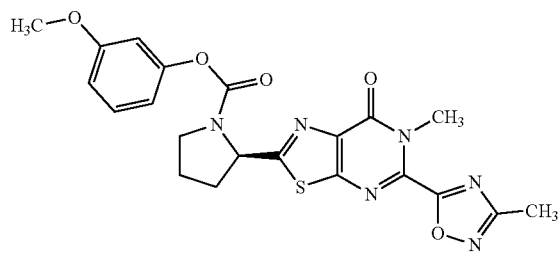

The compound (50 mg) obtained in Reference Example 16 was treated by a method similar to that in Example 33 to give the title compound (50 mg).

MS (ESI) m/z; 469 [M+H]$^+$

Example 36

(R)-2-[6-methyl-7-oxo-5-(tetrahydro-2H-pyran-4-yl)-6,7-dihydro[1,3]thiazolo[5,4-d]pyrimidin-2-yl]pyrrolidine-1-carboxylic acid 3-methylphenyl ester

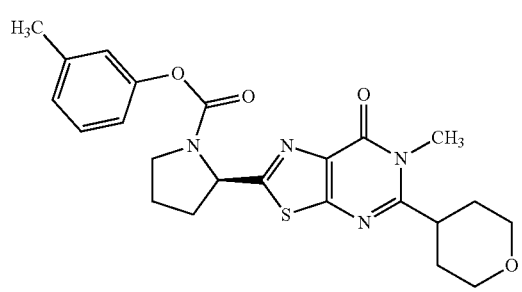 [SMILES: Cc1cccc(OC(=O)N2CCC[C@@H]2c2nc3c(=O)n(C)c(C4CCOCC4)nc3s2)c1]

The compound (100 mg) obtained in Reference Example 19 was treated by a method similar to that in Example 33 to give the title compound (130 mg).

MS (ESI) m/z; 455 [M+H]$^+$

Example 37

(R)-2-[6-methyl-7-oxo-5-(tetrahydro-2H-pyran-4-yl)-6,7-dihydro[1,3]thiazolo[5,4-d]pyrimidin-2-yl]pyrrolidine-1-carboxylic acid 3-methoxyphenyl ester

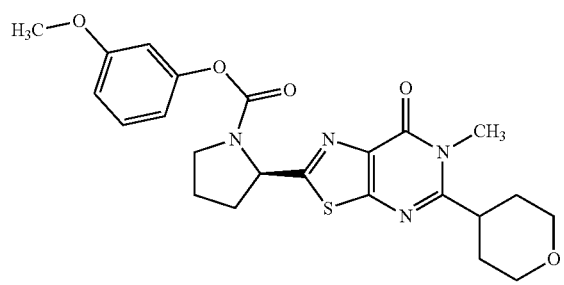 [SMILES: COc1cccc(OC(=O)N2CCC[C@@H]2c2nc3c(=O)n(C)c(C4CCOCC4)nc3s2)c1]

The compound (80 mg) obtained in Reference Example 19 was treated by a method similar to that in Example 33 to give the title compound (115 mg).

MS (ESI) m/z; 471 [M+H]$^+$

Example 38

(R)-2-[6-methyl-7-oxo-5-(tetrahydro-2H-pyran-4-yl)-6,7-dihydro[1,3]thiazolo[5,4-d]pyrimidin-2-yl]pyrrolidine-1-carboxylic acid 3-(trifluoromethoxy)phenyl ester

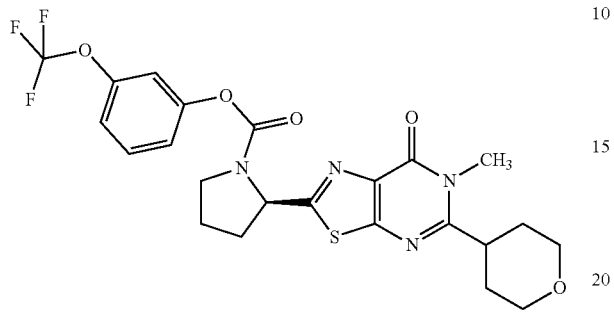

The compound (50 mg) obtained in Reference Example 19 was treated by a method similar to that in Example 33 to give the title compound (57 mg).
MS (ESI) m/z; 525 [M+H]$^+$

Example 39

(R)-2-[6-methyl-7-oxo-5-(tetrahydro-2H-pyran-4-yl)-6,7-dihydro[1,3]thiazolo[5,4-d]pyrimidin-2-yl]pyrrolidine-1-carboxylic acid 3-fluorophenyl ester

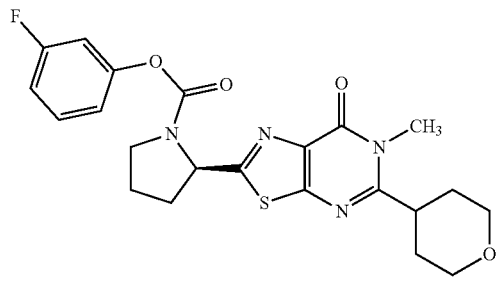 [SMILES: Cn1c(C2CCOCC2)nc2sc([C@H]3CCCN3C(=O)Oc3cccc(F)c3)nc2c1=O]

The compound (50 mg) obtained in Reference Example 19 was treated by a method similar to that in Example 33 to give the title compound (44 mg).
MS (ESI) m/z; 459 [M+H]$^+$

Example 40

(R)-2-[6-methyl-7-oxo-5-(tetrahydro-2H-pyran-4-yl)-6,7-dihydro[1,3]thiazolo[5,4-d]pyrimidin-2-yl]pyrrolidine-1-carboxylic acid 3-chlorophenyl ester

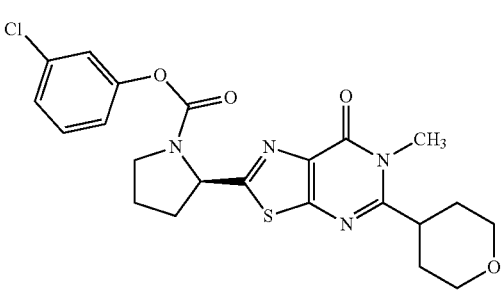 [SMILES: Cn1c(C2CCOCC2)nc2sc([C@H]3CCCN3C(=O)Oc3cccc(Cl)c3)nc2c1=O]

The compound (50 mg) obtained in Reference Example 19 was treated by a method similar to that in Example 33 to give the title compound (60 mg).
MS (ESI) m/z; 475 [M+H]$^+$

Example 41

(R)-2-[6-methyl-7-oxo-5-(tetrahydro-2H-pyran-4-yl)-6,7-dihydro[1,3]thiazolo[5,4-d]pyrimidin-2-yl]pyrrolidine-1-carboxylic acid 3-(trifluoromethyl)phenyl ester

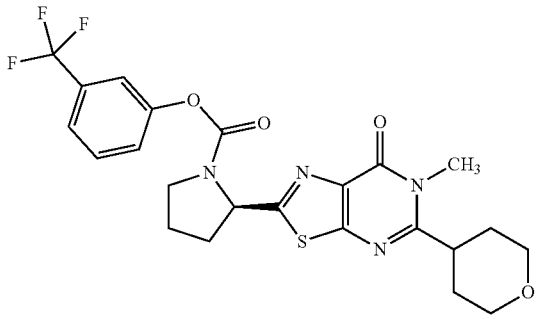 [SMILES: Cn1c(C2CCOCC2)nc2sc([C@H]3CCCN3C(=O)Oc3cccc(C(F)(F)F)c3)nc2c1=O]

The compound (50 mg) obtained in Reference Example 19 was treated by a method similar to that in Example 33 to give the title compound (60 mg).
MS (ESI) m/z; 509 [M+H]$^+$

Example 42

(R)-2-[6-(2,4-dimethoxybenzyl)-7-oxo-5-(propan-2-yl)-6,7-dihydro[1,3]thiazolo[5,4-d]pyrimidin-2-yl]pyrrolidine-1-carboxylic acid benzyl ester

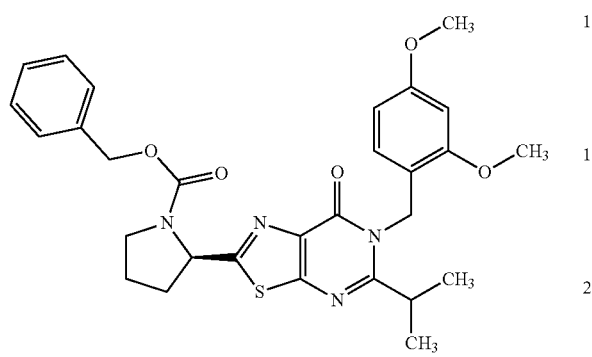

To a solution (15 mL) of the compound (1.80 g) obtained in Reference Example 26 in methylene chloride were added chlorotrimethylsilane (3.8 mL) and triethylamine (13.2 mL), and the reaction mixture was stirred at room temperature overnight. Water and 1.0 mol/L hydrochloric acid were added to the reaction mixture, and the mixture was extracted twice with chloroform. The organic layer was dried over anhydrous magnesium sulfate, filtered and concentrated. The residue was purified by silica gel column chromatography (solvent; hexane/ethyl acetate=70/30-50/50) to give the title compound (1.46 g).

MS (ESI) m/z; 549 [M+H]$^+$

Example 43

(R)-2-[5-cyclopropyl-6-(2,4-dimethoxybenzyl)-7-oxo-6,7-dihydro[1,3]thiazolo[5,4-d]pyrimidin-2-yl]pyrrolidine-1-carboxylic acid benzyl ester

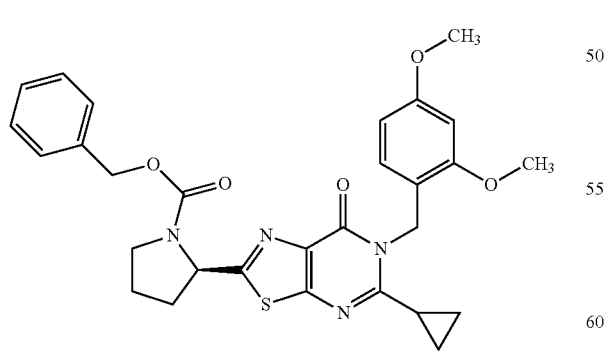

The compound (1.27 g) obtained in Reference Example 27 was treated by a method similar to that in Example 42 to give the title compound (1.05 g).

MS (ESI) m/z; 547 [M+H]$^+$

Example 44

(R)-2-[6-(2,4-dimethoxybenzyl)-7-oxo-5-phenyl-6,7-dihydro[1,3]thiazolo[5,4-d]pyrimidin-2-yl]pyrrolidine-1-carboxylic acid benzyl ester

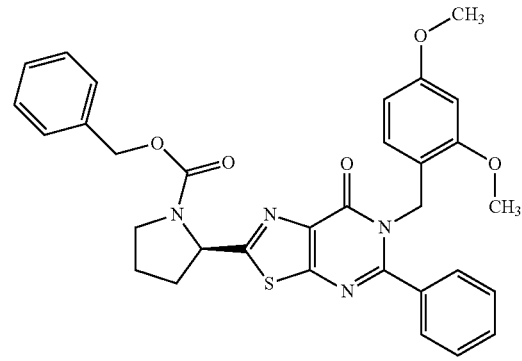 [SMILES: COc1ccc(Cn2c(-c3ccccc3)nc3sc([C@H]4CCCN4C(=O)OCc4ccccc4)nc3c2=O)c(OC)c1]

The compound (1.74 g) obtained in Reference Example 28 was treated by a method similar to that in Example 42 to give the title compound (1.80 g).

MS (ESI) m/z; 583 [M+H]$^+$

Example 45

(R)-2-[6-(2,4-dimethoxybenzyl)-5-(2-fluorophenyl)-7-oxo-6,7-dihydro[1,3]thiazolo[5,4-d]pyrimidin-2-yl]pyrrolidine-1-carboxylic acid benzyl ester

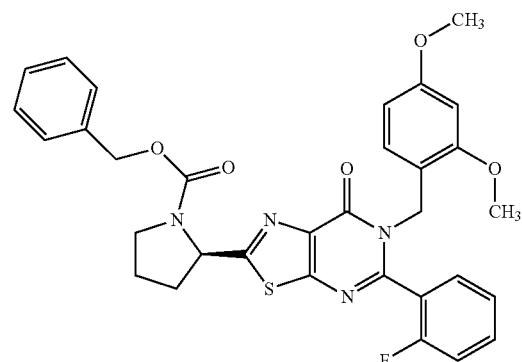

The compound (1.90 g) obtained in Reference Example 29 was treated by a method similar to that in Example 42 to give the title compound (1.90 g).

MS (ESI) m/z; 601 [M+H]$^+$

Example 46

(R)-2-[5-(2,4-difluorophenyl)-6-(2,4-dimethoxybenzyl)-7-oxo-6,7-dihydro[1,3]thiazolo[5,4-d]pyrimidin-2-yl]pyrrolidine-1-carboxylic acid benzyl ester

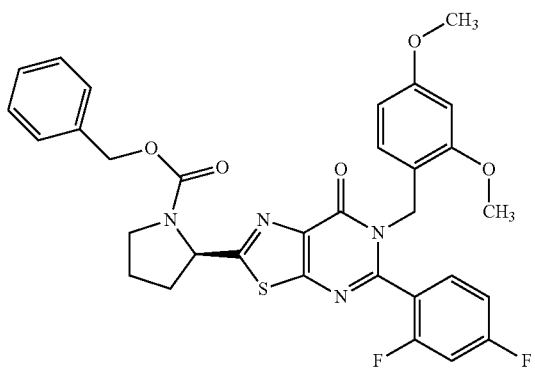 [SMILES: COc1ccc(Cn2c(-c3ccc(F)cc3F)nc3sc([C@H]4CCCN4C(=O)OCc4ccccc4)nc3c2=O)c(OC)c1]

The compound (1.47 g) obtained in Reference Example 30 was treated by a method similar to that in Example 42 to give the title compound (1.22 g).

MS (ESI) m/z; 619 [M+H]$^+$

Example 47

(R)-2-{6-(2,4-dimethoxybenzyl)-7-oxo-5-[2-(trifluoromethoxy)phenyl]-6,7-dihydro[1,3]thiazolo[5,4-d]pyrimidin-2-yl}pyrrolidine-1-carboxylic acid benzyl ester

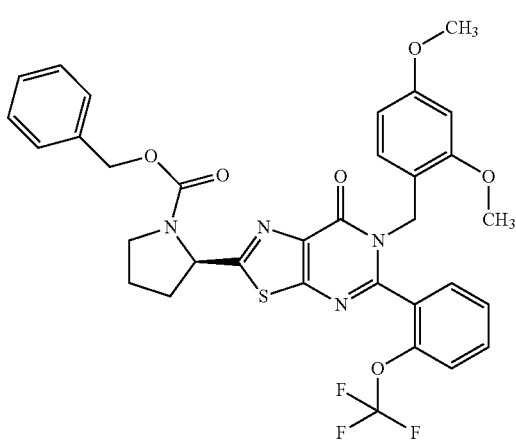 [SMILES: COc1ccc(Cn2c(-c3ccccc3OC(F)(F)F)nc3sc([C@H]4CCCN4C(=O)OCc4ccccc4)nc3c2=O)c(OC)c1]

The compound (1.90 g) obtained in Reference Example 31 was treated by a method similar to that in Example 42 to give the title compound (1.46 g).

MS (ESI) m/z; 667 [M+H]$^+$

Example 48

(R)-2-[6-(2,4-dimethoxybenzyl)-5-(2-methylphenyl)-7-oxo-6,7-dihydro[1,3]thiazolo[5,4-d]pyrimidin-2-yl]pyrrolidine-1-carboxylic acid benzyl ester

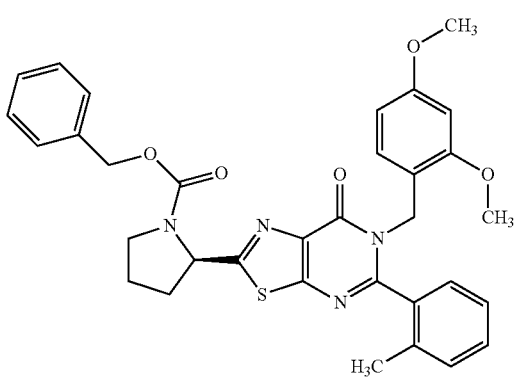 [SMILES: COc1ccc(Cn2c(-c3ccccc3C)nc3sc([C@H]4CCCN4C(=O)OCc4ccccc4)nc3c2=O)c(OC)c1]

The compound (1.45 g) obtained in Reference Example 32 was treated by a method similar to that in Example 42 to give the title compound (1.40 g).

MS (ESI) m/z; 597 [M+H]$^+$

Example 49

(R)-2-[6-(2,4-dimethoxybenzyl)-5-(2-methoxyphenyl)-7-oxo-6,7-dihydro[1,3]thiazolo[5,4-d]pyrimidin-2-yl]pyrrolidine-1-carboxylic acid benzyl ester

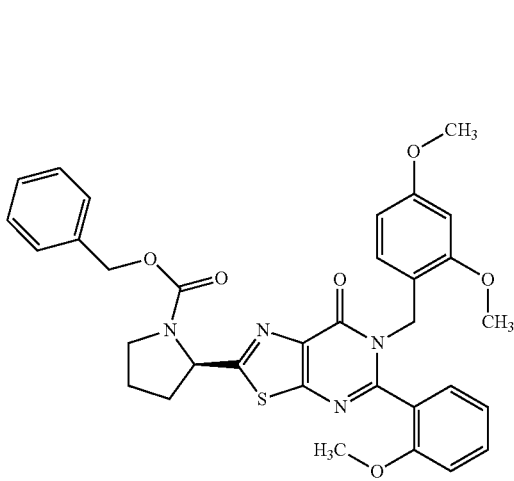 [SMILES: COc1ccc(Cn2c(-c3ccccc3OC)nc3sc([C@H]4CCCN4C(=O)OCc4ccccc4)nc3c2=O)c(OC)c1]

The compound (1.90 g) obtained in Reference Example 33 was treated by a method similar to that in Example 42 to give the title compound (1.65 g).

MS (ESI) m/z; 613 [M+H]$^+$

Example 50

(R)-2-[6-(2,4-dimethoxybenzyl)-5-(1-fluorocyclopropyl)-7-oxo-6,7-dihydro[1,3]thiazolo[5,4-d]pyrimidin-2-yl]pyrrolidine-1-carboxylic acid benzyl ester

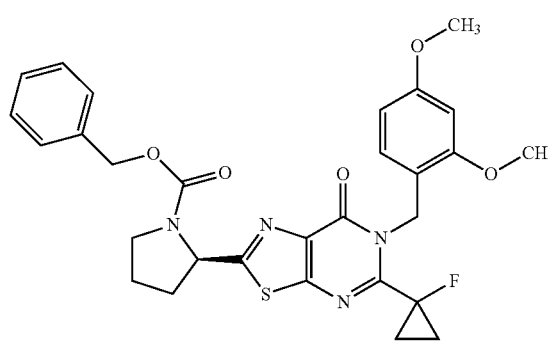

The compound (1.80 g) obtained in Reference Example 35 was treated by a method similar to that in Example 42 to give the title compound (1.75 g).

MS (ESI) m/z; 565 [M+H]$^+$

Example 51

(R)-2-[5-(1-chlorocyclopropyl)-6-(2,4-dimethoxybenzyl)-7-oxo-6,7-dihydro[1,3]thiazolo[5,4-d]pyrimidin-2-yl]pyrrolidine-1-carboxylic acid benzyl ester

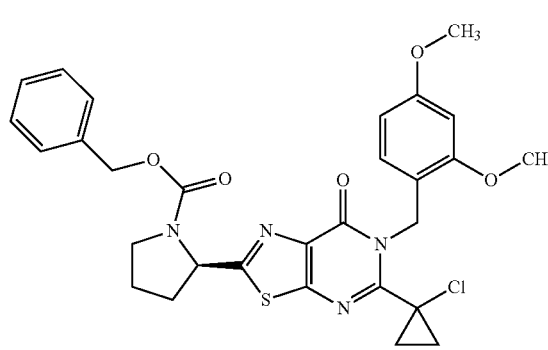

The compound (180 mg) obtained in Reference Example 36 was treated by a method similar to that in Example 42 to give the title compound (175 mg).

MS (ESI) m/z; 581 [M+H]$^+$

Example 52

(R)-2-[5-(1,1-di fluoroethyl)-6-(2,4-dimethoxybenzyl)-7-oxo-6,7-dihydro[1,3]thiazolo[5,4-d]pyrimidin-2-yl]pyrrolidine-1-carboxylic acid benzyl ester

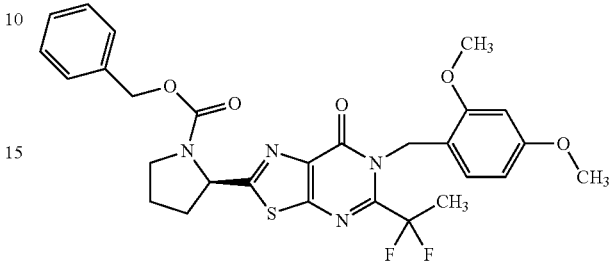

The compound (335 mg) obtained in Reference Example 37 was treated by a method similar to that in Example 42 to give the title compound (348 mg).

MS (ESI) m/z; 571 [M+H]$^+$

Example 53

(R)-2-[5-(4,4-difluorocyclohexyl)-6-(2,4-dimethoxybenzyl)-7-oxo-6,7-dihydro[1,3]thiazolo[5,4-d]pyrimidin-2-yl]pyrrolidine-1-carboxylic acid benzyl ester

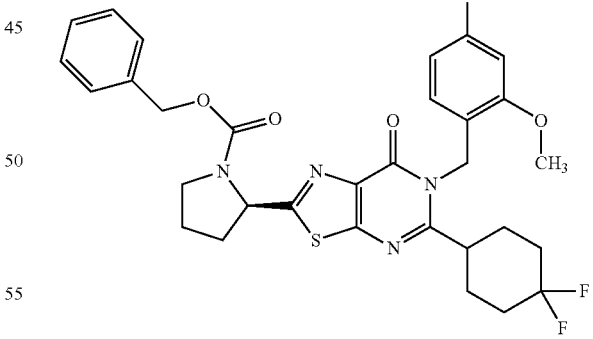

The compound (1.90 g) obtained in Reference Example 38 was treated by a method similar to that in Example 42 to give the title compound (1.54 g).

MS (ESI) m/z; 625 [M+H]$^+$

Example 54

(R)-2-[6-(2,4-dimethoxybenzyl)-5-(1-fluorocyclohexyl)-7-oxo-6,7-dihydro[1,3]thiazolo[5,4-d]pyrimidin-2-yl]pyrrolidine-1-carboxylic acid benzyl ester

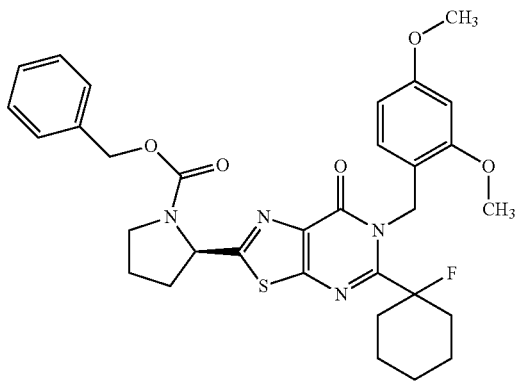 [SMILES: COc1ccc(Cn2c(C3(F)CCCCC3)nc3sc([C@H]4CCCN4C(=O)OCc4ccccc4)nc3c2=O)c(OC)c1]

The compound (1.34 g) obtained in Reference Example 39 was treated by a method similar to that in Example 42 to give the title compound (0.80 g).

MS (ESI) m/z; 607 [M+H]$^+$

Example 55

(R)-2-[5-(3,3-difluorocyclobutyl)-6-(2,4-dimethoxybenzyl)-7-oxo-6,7-dihydro[1,3]thiazolo[5,4-d]pyrimidin-2-yl]pyrrolidine-1-carboxylic acid benzyl ester

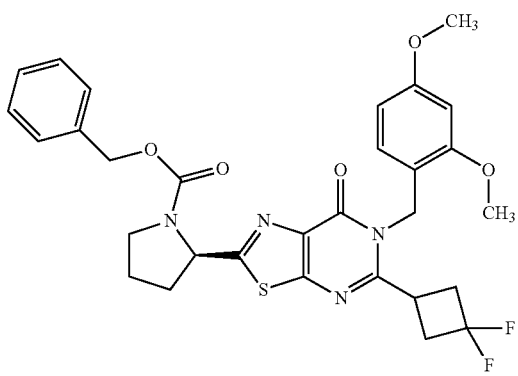 [SMILES: COc1ccc(Cn2c(C3CC(F)(F)C3)nc3sc([C@H]4CCCN4C(=O)OCc4ccccc4)nc3c2=O)c(OC)c1]

The compound (1.68 g) obtained in Reference Example 40 was treated by a method similar to that in Example 42 to give the title compound (1.30 g).

MS (ESI) m/z; 597 [M+H]$^+$

Example 56

(R)-2-[6-(2,4-dimethoxybenzyl)-5-(1-ethoxycyclopropyl)-7-oxo-6,7-dihydro[1,3]thiazolo[5,4-d]pyrimidin-2-yl]pyrrolidine-1-carboxylic acid benzyl ester

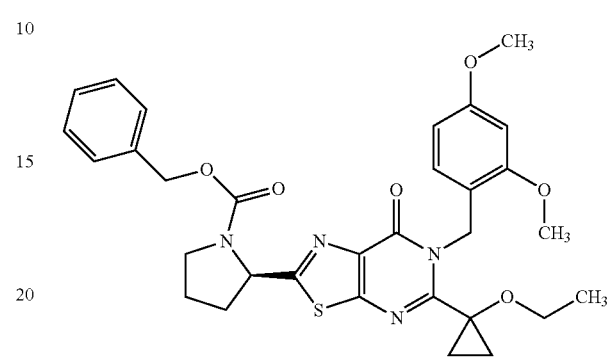

The compound (1.40 g) obtained in Reference Example 41 was treated by a method similar to that in Example 42 to give the title compound (0.69 g).

MS (ESI) m/z; 591 [M+H]$^+$

Example 57

(R)-2-[5-(1-cyanocyclopropyl)-6-(2,4-dimethoxybenzyl)-7-oxo-6,7-dihydro[1,3]thiazolo[5,4-d]pyrimidin-2-yl]pyrrolidine-1-carboxylic acid benzyl ester

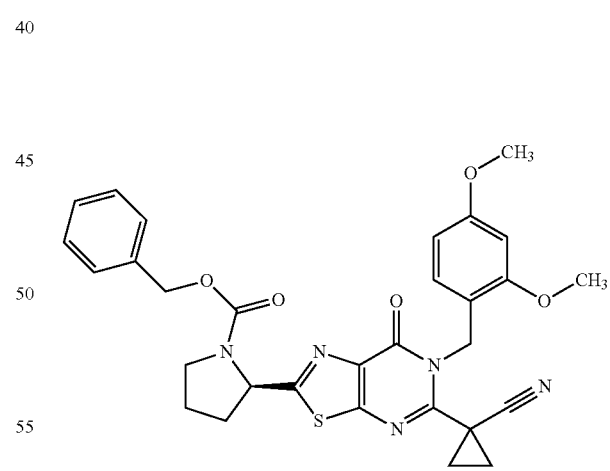

The compound (4.10 g) obtained in Reference Example 42 was treated by a method similar to that in Example 42 to give the title compound (1.85 g).

MS (ESI) m/z; 572 [M+H]$^+$

Example 58

(R)-2-[5-(2-cyanopropan-2-yl)-6-(2,4-dimethoxybenzyl)-7-oxo-6,7-dihydro[1,3]thiazolo[5,4-d]pyrimidin-2-yl]pyrrolidine-1-carboxylic acid benzyl ester

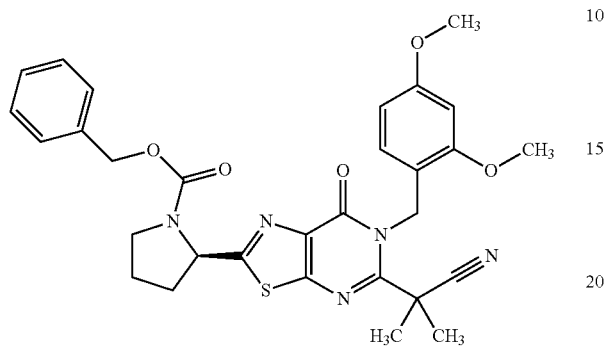

The compound (581 mg) obtained in Reference Example 43 was treated by a method similar to that in Example 42 to give the title compound (438 mg).

MS (ESI) m/z; 574 [M+H]$^+$

Example 59

(R)-2-[6-(2,4-dimethoxybenzyl)-5-[1-(fluoromethyl)cyclopropyl]-7-oxo-6,7-dihydro[1,3]thiazolo[5,4-d]pyrimidin-2-yl]pyrrolidine-1-carboxylic acid benzyl ester

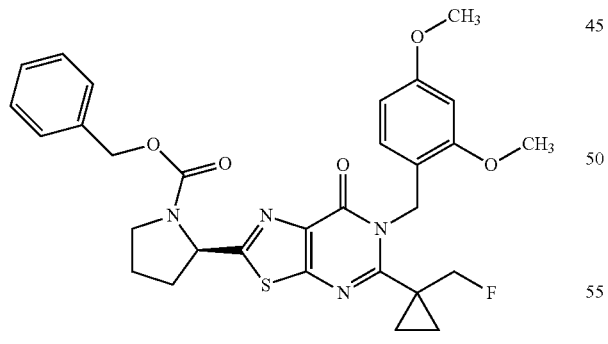

The compound (379 mg) obtained in Reference Example 44 was treated by a method similar to that in Example 42 to give the title compound (370 mg).

MS (ESI) m/z; 579 [M+H]$^+$

Example 60

(R)-2-[6-(2,4-dimethoxybenzyl)-7-oxo-5-[1-(trifluoromethyl)cyclopropyl]-6,7-dihydro[1,3]thiazolo[5,4-d]pyrimidin-2-yl]pyrrolidine-1-carboxylic acid benzyl ester

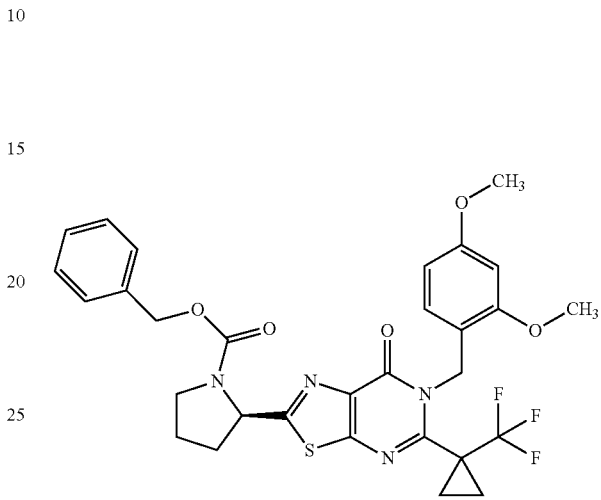

The compound (1.46 g) obtained in Reference Example 45 was treated by a method similar to that in Example 42 to give the title compound (1.15 g).

MS (ESI) m/z; 615 [M+H]$^+$

Example 61

(R)-2-[6-(2,4-dimethoxybenzyl)-7-oxo-5-trifluoromethyl-6,7-dihydro[1,3]thiazolo[5,4-d]pyrimidin-2-yl]pyrrolidine-1-carboxylic acid benzyl ester

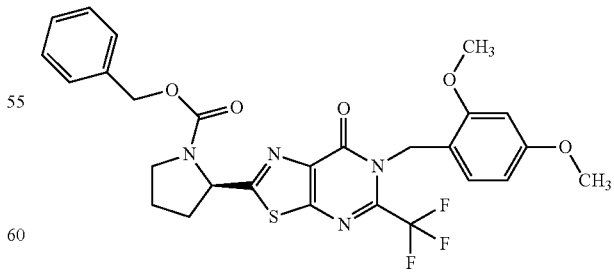

The compound (580 mg) obtained in Reference Example 47 was treated by a method similar to that in Example 42 to give the title compound (498 mg).

MS (ESI) m/z; 575 [M+H]$^+$

Example 62

(R)-2-[5-difluoromethyl-6-(2,4-dimethoxybenzyl)-7-oxo-6,7-dihydro[1,3]thiazolo[5,4-d]pyrimidin-2-yl]pyrrolidine-1-carboxylic acid benzyl ester

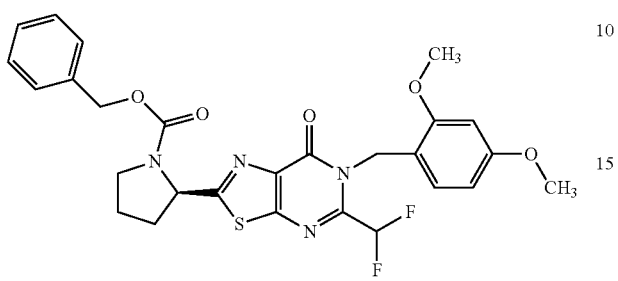

The compound (560 mg) obtained in Reference Example 48 was treated by a method similar to that in Example 42 to give the title compound (499 mg).

MS (ESI) m/z; 557 [M+H]$^+$

Example 63

(R)-2-[7-oxo-5-(propan-2-yl)-6,7-dihydro[1,3]thiazolo[5,4-d]pyrimidin-2-yl]pyrrolidine-1-carboxylic acid phenyl ester

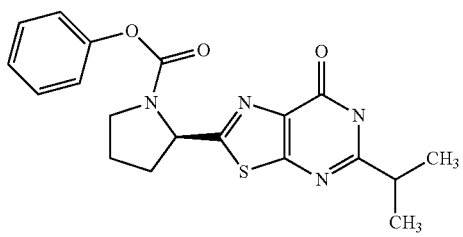 [SMILES: CC(C)c1nc2sc([C@H]3CCCN3C(=O)Oc3ccccc3)nc2c(=O)[nH]1]

To a solution (19 mL) of the compound (960 mg) obtained in Example 42 in acetonitrile were added triethylsilane (1.67 mL) and trimethylsilyl iodide (1.20 mL), and the reaction mixture was stirred at room temperature overnight. Triethylamine (1.95 mL) and phenyl chloroformate (663 μL) were added to the reaction mixture, and the reaction mixture was stirred at room temperature overnight. 1.0 mol/L Aqueous sodium hydroxide solution (4.0 mL) was added to the reaction mixture, and the mixture was stirred at room temperature for 15 min. The mixture was acidified with 1.0 mol/L hydrochloric acid and extracted twice with chloroform. The organic layer was dried over anhydrous magnesium sulfate, filtered and concentrated. The residue was purified by silica gel column chromatography (solvent; hexane/ethyl acetate=70/30-0/100) to give the title compound (379 mg).

MS (ESI) m/z; 385 [M+H]$^+$

Example 64

(R)-2-(5-cyclopropyl-7-oxo-6,7-dihydro[1,3]thiazolo[5,4-d]pyrimidin-2-yl)pyrrolidine-1-carboxylic acid phenyl ester

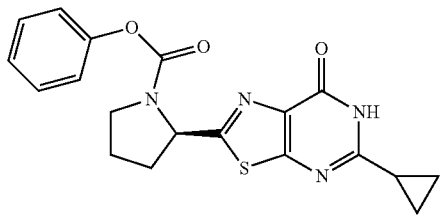 [SMILES: O=C(Oc1ccccc1)N1CCC[C@@H]1c1nc2c(=O)[nH]c(C3CC3)nc2s1]

The compound (1050 mg) obtained in Example 43 was treated by a method similar to that in Example 63 to give the title compound (275 mg).

MS (ESI) m/z; 383 [M+H]$^+$

Example 65

(R)-2-(7-oxo-5-phenyl-6,7-dihydro[1,3]thiazolo[5,4-d]pyrimidin-2-yl)pyrrolidine-1-carboxylic acid phenyl ester

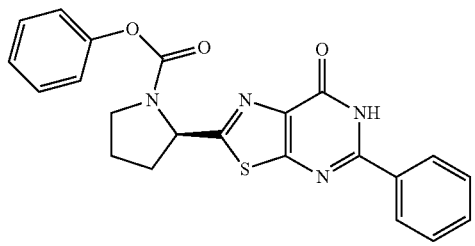 [SMILES: O=C(Oc1ccccc1)N1CCC[C@@H]1c1nc2c(=O)[nH]c(-c3ccccc3)nc2s1]

The compound (700 mg) obtained in Example 44 was treated by a method similar to that in Example 63 to give the title compound (280 mg).

MS (ESI) m/z; 419 [M+H]$^+$

Example 66

(R)-2-[5-(2-fluorophenyl)-7-oxo-6,7-dihydro[1,3]thiazolo[5,4-d]pyrimidin-2-yl]pyrrolidine-1-carboxylic acid phenyl ester

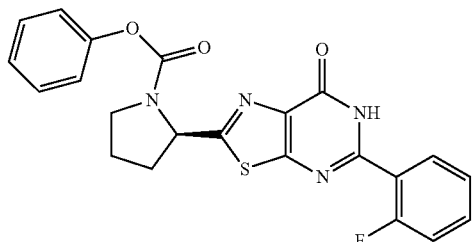

The compound (1000 mg) obtained in Example 45 was treated by a method similar to that in Example 63 to give the title compound (310 mg).

MS (ESI) m/z; 437 [M+H]$^+$

Example 67

(R)-2-[5-(2,4-difluorophenyl)-7-oxo-6,7-dihydro[1,3]thiazolo[5,4-d]pyrimidin-2-yl]pyrrolidine-1-carboxylic acid phenyl ester

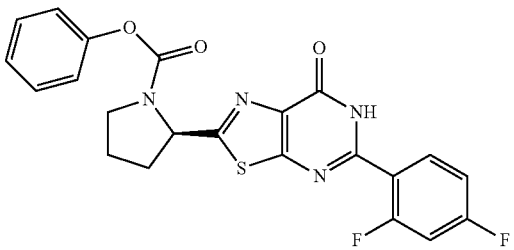 [SMILES: O=C(Oc1ccccc1)N1CCC[C@@H]1c1nc2c(=O)[nH]c(-c3ccc(F)cc3F)nc2s1]

The compound (600 mg) obtained in Example 46 was treated by a method similar to that in Example 63 to give the title compound (168 mg).
MS (ESI) m/z; 455 [M+H]$^+$

Example 68

(R)-2-{7-oxo-5-[2-(trifluoromethoxy)phenyl]-6,7-dihydro[1,3]thiazolo[5,4-d]pyrimidin-2-yl}pyrrolidine-1-carboxylic acid phenyl ester

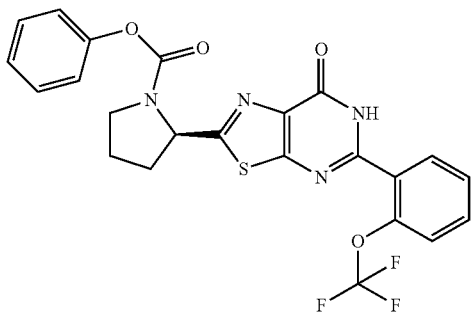 [SMILES: O=C(Oc1ccccc1)N1CCC[C@@H]1c1nc2c(=O)[nH]c(-c3ccccc3OC(F)(F)F)nc2s1]

The compound (700 mg) obtained in Example 47 was treated by a method similar to that in Example 63 to give the title compound (410 mg).
MS (ESI) m/z; 503 [M+H]$^+$

Example 69

(R)-2-[5-(2-methylphenyl)-7-oxo-6,7-dihydro[1,3]thiazolo[5,4-d]pyrimidin-2-yl]pyrrolidine-1-carboxylic acid phenyl ester

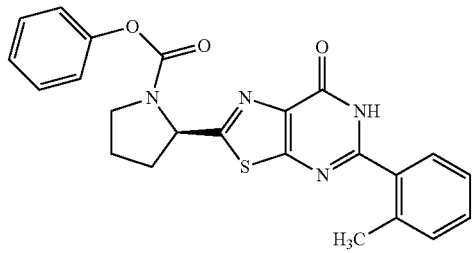 [SMILES: Cc1ccccc1-c1nc2sc([C@H]3CCCN3C(=O)Oc3ccccc3)nc2c(=O)[nH]1]

The compound (700 mg) obtained in Example 48 was treated by a method similar to that in Example 63 to give the title compound (170 mg).
MS (ESI) m/z; 433 [M+H]$^+$

Example 70

(R)-2-[5-(2-methoxyphenyl)-7-oxo-6,7-dihydro[1,3]thiazolo[5,4-d]pyrimidin-2-yl]pyrrolidine-1-carboxylic acid phenyl ester

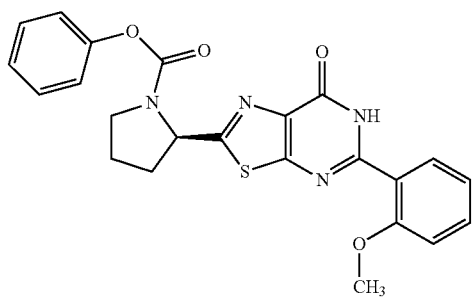 [SMILES: COc1ccccc1-c1nc2sc([C@H]3CCCN3C(=O)Oc3ccccc3)nc2c(=O)[nH]1]

The compound (800 mg) obtained in Example 49 was treated by a method similar to that in Example 63 to give the title compound (360 mg).
MS (ESI) m/z; 449 [M+H]$^+$

Example 71

(R)-2-[5-(1-fluorocyclopropyl)-7-oxo-6,7-dihydro[1,3]thiazolo[5,4-d]pyrimidin-2-yl]pyrrolidine-1-carboxylic acid phenyl ester

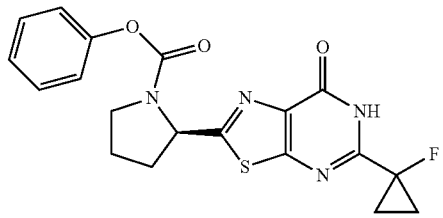 [SMILES: O=C(Oc1ccccc1)N1CCC[C@@H]1c1nc2c(=O)[nH]c(C3(F)CC3)nc2s1]

The compound (1.75 g) obtained in Example 50 was treated by a method similar to that in Example 63 to give the title compound (1.00 g).
MS (ESI) m/z; 401 [M+H]$^+$ Example 72

(R)-2-[5-(1-chlorocyclopropyl)-7-oxo-6,7-dihydro[1,3]thiazolo[5,4-d]pyrimidin-2-yl]pyrrolidine-1-carboxylic acid phenyl ester

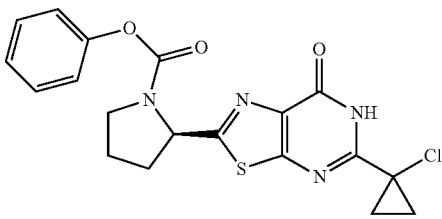 [SMILES: O=C(Oc1ccccc1)N1CCC[C@@H]1c1nc2c(=O)[nH]c(C3(Cl)CC3)nc2s1]

The compound (230 mg) obtained in Example 51 was treated by a method similar to that in Example 63 to give the title compound (33 mg).
MS (ESI) m/z; 417, 419 [M+H]$^+$ Example 73

(R)-2-[5-(1,1-difluoroethyl)-7-oxo-6,7-dihydro[1,3]thiazolo[5,4-d]pyrimidin-2-yl]pyrrolidine-1-carboxylic acid phenyl ester

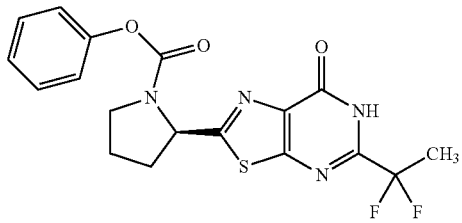 [SMILES: CC(F)(F)c1nc2sc([C@H]3CCCN3C(=O)Oc3ccccc3)nc2c(=O)[nH]1]

The compound (336 mg) obtained in Example 52 was treated by a method similar to that in Example 63 to give the title compound (86.0 mg).
MS (ESI) m/z; 407 [M+H]$^+$ Example 74

(R)-2-[5-(4,4-difluorocyclohexyl)-7-oxo-6,7-dihydro[1,3]thiazolo[5,4-d]pyrimidin-2-yl]pyrrolidine-1-carboxylic acid phenyl ester

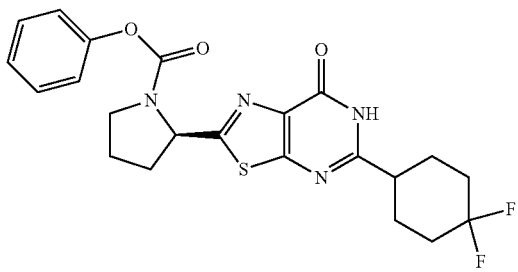 [SMILES: O=C(Oc1ccccc1)N1CCC[C@@H]1c1nc2c(=O)[nH]c(C3CCC(F)(F)CC3)nc2s1]

The compound (750 mg) obtained in Example 53 was treated by a method similar to that in Example 63 to give the title compound (190 mg).
MS (ESI) m/z; 461 [M+H]$^+$ Example 75

(R)-2-[5-(1-fluorocyclohexyl)-7-oxo-6,7-dihydro[1,3]thiazolo[5,4-d]pyrimidin-2-yl]pyrrolidine-1-carboxylic acid phenyl ester

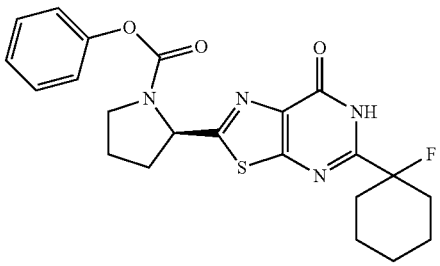 [SMILES: O=C(Oc1ccccc1)N1CCC[C@@H]1c1nc2c(=O)[nH]c(C3(F)CCCCC3)nc2s1]

The compound (800 mg) obtained in Example 54 was treated by a method similar to that in Example 63 to give the title compound (40.0 mg).
MS (ESI) m/z; 443 [M+H]$^+$ Example 76

(R)-2-[5-(3,3-difluorocyclobutyl)-7-oxo-6,7-dihydro[1,3]thiazolo[5,4-d]pyrimidin-2-yl]pyrrolidine-1-carboxylic acid phenyl ester

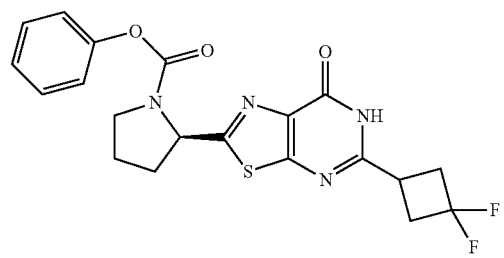 [SMILES: O=C(Oc1ccccc1)N1CCC[C@@H]1c1nc2c(=O)[nH]c(C3CC(F)(F)C3)nc2s1]

The compound (1300 mg) obtained in Example 55 was treated by a method similar to that in Example 63 to give the title compound (100 mg).
MS (ESI) m/z; 433 [M+H]$^+$

Example 77

(R)-2-[5-(1-ethoxycyclopropyl)-7-oxo-6,7-dihydro[1,3]thiazolo[5,4-d]pyrimidin-2-yl]pyrrolidine-1-carboxylic acid phenyl ester

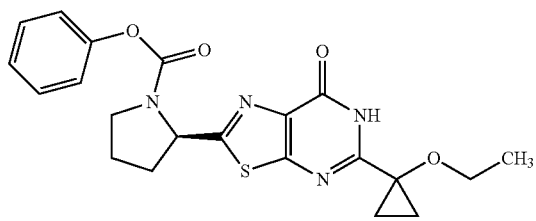 [SMILES: CCOC1(c2nc3sc([C@H]4CCCN4C(=O)Oc4ccccc4)nc3c(=O)[nH]2)CC1]

The compound (690 mg) obtained in Example 56 was treated by a method similar to that in Example 63 to give the title compound (37.0 mg).
MS (ESI) m/z; 427 [M+H]$^+$

Example 78

(R)-2-[5-(1-cyanocyclopropyl)-7-oxo-6,7-dihydro[1,3]thiazolo[5,4-d]pyrimidin-2-yl]pyrrolidine-1-carboxylic acid phenyl ester

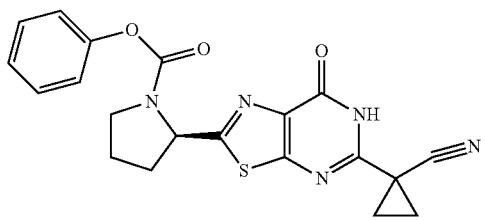 [SMILES: N#CC1(c2nc3sc([C@H]4CCCN4C(=O)Oc4ccccc4)nc3c(=O)[nH]2)CC1]

The compound (1850 mg) obtained in Example 57 was treated by a method similar to that in Example 63 to give the title compound (711 mg).
MS (ESI) m/z; 408 [M+H]$^+$

Example 79

(R)-2-[5-(2-cyanopropan-2-yl)-7-oxo-6,7-dihydro[1,3]thiazolo[5,4-d]pyrimidin-2-yl]pyrrolidine-1-carboxylic acid phenyl ester

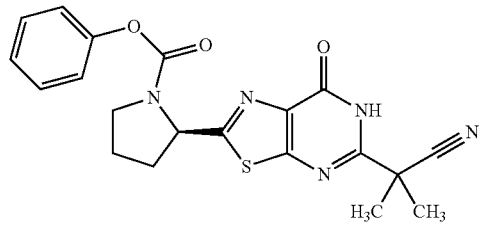 [SMILES: CC(C)(C#N)c1nc2sc([C@H]3CCCN3C(=O)Oc3ccccc3)nc2c(=O)[nH]1]

The compound (300 mg) obtained in Example 58 was treated by a method similar to that in Example 63 to give the title compound (129 mg).
MS (ESI) m/z; 410 [M+H]$^+$

Example 80

(R)-2-{5-[1-(fluoromethyl)cyclopropyl]-7-oxo-6,7-dihydro[1,3]thiazolo[5,4-d]pyrimidin-2-yl}pyrrolidine-1-carboxylic acid phenyl ester

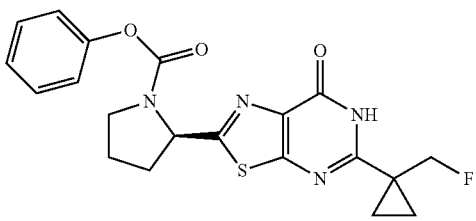 [SMILES: O=C(Oc1ccccc1)N1CCC[C@@H]1c1nc2c(=O)[nH]c(C3(CF)CC3)nc2s1]

The compound (370 mg) obtained in Example 59 was treated by a method similar to that in Example 63 to give the title compound (70.0 mg).
MS (ESI) m/z; 415 [M+H]$^+$

Example 81

(R)-2-{7-oxo-5-[1-(trifluoromethyl)cyclopropyl]-6,7-dihydro[1,3]thiazolo[5,4-d]pyrimidin-2-yl}pyrrolidine-1-carboxylic acid phenyl ester

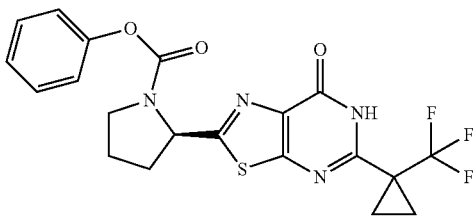

The compound (575 mg) obtained in Example 60 was treated by a method similar to that in Example 63 to give the title compound (279 mg).
MS (ESI) m/z; 451 [M+H]$^+$

Example 82

(R)-2-(7-oxo-5-trifluoromethyl-6,7-dihydro[1,3]thiazolo[5,4-d]pyrimidin-2-yl)pyrrolidine-1-carboxylic acid phenyl ester

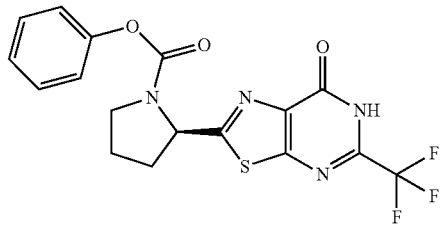 [SMILES: O=C(Oc1ccccc1)N1CCC[C@@H]1c1nc2c(=O)[nH]c(C(F)(F)F)nc2s1]

The compound (478 mg) obtained in Example 61 was treated is by a method similar to that in Example 63 to give the title compound (116 mg).
MS (ESI) m/z; 411 [M+H]$^+$

Example 83

(R)-2-(5-difluoromethyl-7-oxo-6,7-dihydro[1,3]thi-
azolo[5,4-d]pyrimidin-2-yl)pyrrolidine-1-carboxylic
acid phenyl ester

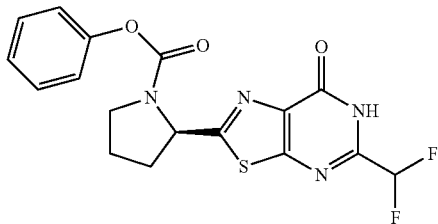 [SMILES: O=C(Oc1ccccc1)N1CCC[C@@H]1c1nc2c(=O)[nH]c(C(F)F)nc2s1]

The compound (267 mg) obtained in Example 62 was treated by a method similar to that in Example 63 to give the title compound (122 mg).
MS (ESI) m/z; 393 [M+H]$^+$

Example 84

N-methyl-N-{(R)-1-[7-oxo-5-(propan-2-yl)-6,7-di-
hydro[1,3]thiazolo[5,4-d]pyrimidin-2-yl]
ethyl}carbamic acid phenyl ester

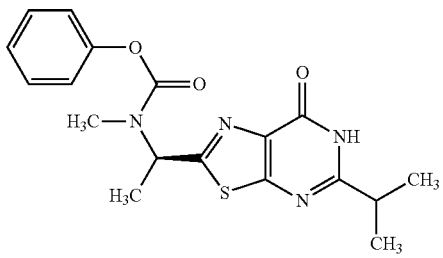 [SMILES: CC(C)c1nc2sc([C@@H](C)N(C)C(=O)Oc3ccccc3)nc2c(=O)[nH]1]

To a reaction mixture of trifluoroacetic acid (6.50 mL), triethylsilane (360 μL) and water (360 μL) was added the compound (800 mg) obtained in Reference Example 49 at 0° C., and the reaction mixture was stirred at room temperature for 2 hr. The solvent was evaporated under reduced pressure, 1.0 mol/L hydrochloric acid (10.0 mL) was added, and the mixture was washed with hexane. The aqueous layer was neutralized with 1.0 mol/L aqueous sodium hydroxide solution, sodium hydrogen carbonate (160 mg) and phenyl chloroformate (220 μL) were added at 0° C., and the reaction mixture was stirred at room temperature for 2 hr. The reaction mixture was acidified with 1.0 mol/L hydrochloric acid and extracted once with chloroform. The organic layer was dried over anhydrous magnesium sulfate, filtered and concentrated. To the residue was added diisopropyl ether, and the solid was collected by filtration and dried to give the title compound (420 mg).
MS (ESI) m/z; 373 [M+H]$^+$

Example 85

N-{(R)-1-[5-(1-chlorocyclopropyl)-7-oxo-6,7-di-
hydro[1,3]thiazolo[5,4-d]pyrimidin-2-yl]ethyl}-N-
methylcarbamic acid phenyl ester

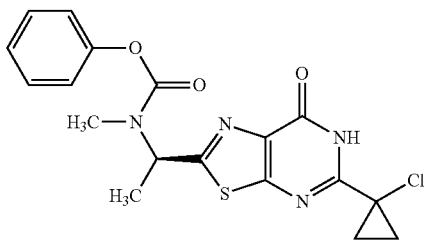 [SMILES: C[C@H](c1nc2c(=O)[nH]c(C3(Cl)CC3)nc2s1)N(C)C(=O)Oc1ccccc1]

The compound (765 mg) obtained in Reference Example 50 was treated by a method similar to that in Example 84 to give the title compound (310 mg).
MS (ESI) m/z; 405, 407 [M+H]$^+$

Example 86

(R)-2-(7-oxo-5-phenyl-6,7-dihydro[1,3]thiazolo[5,4-
d]pyrimidin-2-yl)pyrrolidine-1-carboxylic acid
3-methylphenyl ester

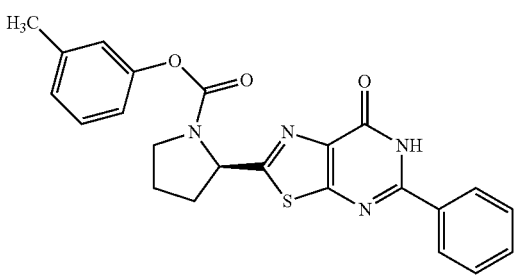 [SMILES: Cc1cccc(OC(=O)N2CCC[C@@H]2c2nc3c(=O)[nH]c(-c4ccccc4)nc3s2)c1]

To a solution (20 mL) of the compound (700 mg) obtained in Example 44 in acetonitrile were added triethylsilane (1.20 mL) and trimethylsilyl iodide (0.35 mL), and the reaction mixture was stirred at room temperature overnight (reaction mixture 1). To a solution (10.0 mL) of triphosgene (290 mg) in toluene were added m-cresol (260 mg) and pyridine (0.25 mL) under ice-cooling, and the reaction mixture was stirred at room temperature for 30 min (reaction mixture 2). The solvent of the above-mentioned reaction mixture 2 was evaporated under reduced pressure, and the obtained residue was dissolved in methylene chloride (5.0 mL), and added to the above-mentioned reaction mixture 1 at room temperature. Furthermore, triethylamine (1.0 mL) was added, and the reaction mixture was stirred at room temperature for 2 hr. The reaction mixture was acidified with 1.0 mol/L hydrochloric acid and extracted twice with ethyl acetate. The organic layer was dried over anhydrous magnesium sulfate, filtered and concentrated. The residue was purified by silica gel column chromatography (solvent; hexane/ethyl acetate=70/30-0/100) to give the title compound (310 mg).
MS (ESI) m/z; 433 [M+H]$^+$

Example 87

(R)-2-[5-(2-fluorophenyl)-7-oxo-6,7-dihydro[1,3]thiazolo[5,4-d]pyrimidin-2-yl]pyrrolidine-1-carboxylic acid 3-methylphenyl ester

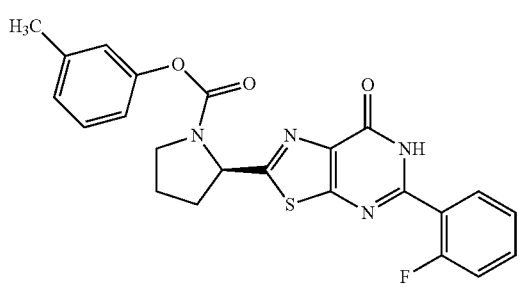 [SMILES: Cc1cccc(OC(=O)N2CCC[C@@H]2c2nc3c(=O)[nH]c(-c4ccccc4F)nc3s2)c1]

The compound (900 mg) obtained in Example 45 was treated by a method similar to that in Example 86 to give the title compound (250 mg).
MS (ESI) m/z; 451 [M+H]$^+$

Example 88

(R)-2-[5-(2,4-difluorophenyl)-7-oxo-6,7-dihydro[1,3]thiazolo[5,4-d]pyrimidin-2-yl]pyrrolidine-1-carboxylic acid 3-methylphenyl ester

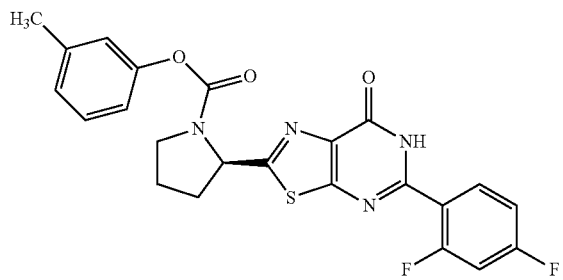 [SMILES: Cc1cccc(OC(=O)N2CCC[C@@H]2c2nc3c(=O)[nH]c(-c4ccc(F)cc4F)nc3s2)c1]

The compound (600 mg) obtained in Example 46 was treated by a method similar to that in Example 86 to give the title compound (225 mg).
MS (ESI) m/z; 469 [M+H]$^+$

Example 89

(R)-2-{7-oxo-5-[2-(trifluoromethoxy)phenyl]-6,7-dihydro[1,3]thiazolo[5,4-d]pyrimidin-2-yl}pyrrolidine-1-carboxylic acid 3-methylphenyl ester

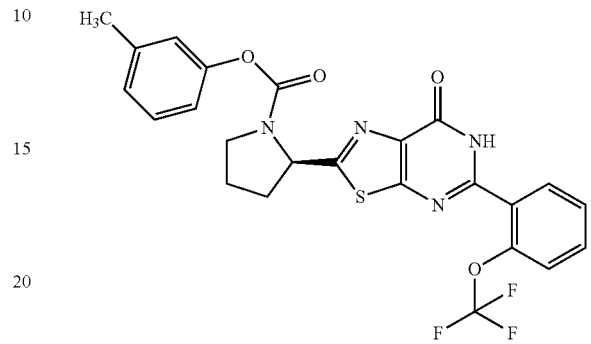

The compound (700 mg) obtained in Example 47 was treated by a method similar to that in Example 86 to give the title compound (450 mg).
MS (ESI) m/z; 517 [M+H]$^+$

Example 90

(R)-2-[5-(3-methylphenyl)-7-oxo-6,7-dihydro[1,3]thiazolo[5,4-d]pyrimidin-2-yl]pyrrolidine-1-carboxylic acid 3-methylphenyl ester

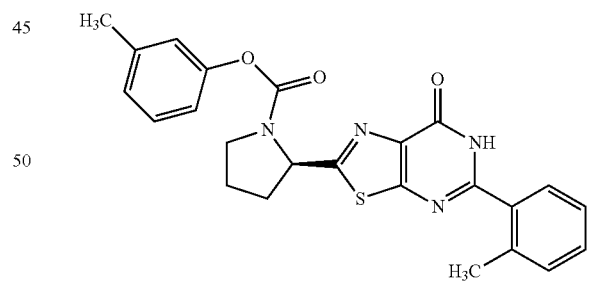

The compound (700 mg) obtained in Example 48 was treated by a method similar to that in Example 86 to give the title compound (150 mg).
MS (ESI) m/z; 447 [M+H]$^+$

Example 91

(R)-2-[5-(2-methoxyphenyl)-7-oxo-6,7-dihydro[1,3]thiazolo[5,4-d]pyrimidin-2-yl]pyrrolidine-1-carboxylic acid 3-methylphenyl ester

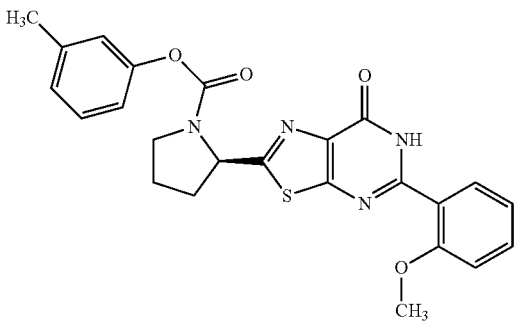 [SMILES: COc1ccccc1-c1nc2sc([C@H]3CCCN3C(=O)Oc3cccc(C)c3)nc2c(=O)[nH]1]

The compound (800 mg) obtained in Example 49 was treated by a method similar to that in Example 86 to give the title compound (430 mg).
MS (ESI) m/z; 463 [M+H]+

Example 92

(R)-2-[5-(1-fluorocyclopropyl)-7-oxo-6,7-dihydro[1,3]thiazolo[5,4-d]pyrimidin-2-yl]pyrrolidine-1-carboxylic acid 3-methylphenyl ester


The compound (490 mg) obtained in Example 50 was treated by a method similar to that in Example 86 to give the title compound (245 mg).
MS (ESI) m/z; 415 [M+H]+

Example 93

(R)-2-[5-(1-chlorocyclopropyl)-7-oxo-6,7-dihydro[1,3]thiazolo[5,4-d]pyrimidin-2-yl]pyrrolidine-1-carboxylic acid 3-methylphenyl ester


The compound (50 mg) obtained in Example 51 was treated by a method similar to that in Example 86 to give the title compound (27 mg).
MS (ESI) m/z; 431, 433 [M+H]+

Example 94

(R)-2-[5-(1-cyanocyclopropyl)-7-oxo-6,7-dihydro[1,3]thiazolo[5,4-d]pyrimidin-2-yl]pyrrolidine-1-carboxylic acid 3-methylphenyl ester

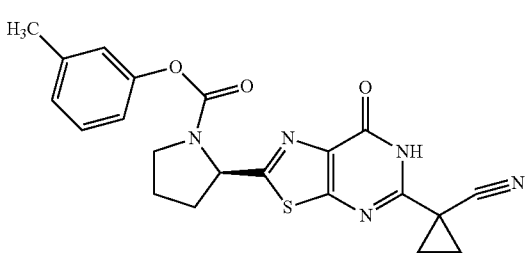 [SMILES: Cc1cccc(OC(=O)N2CCC[C@@H]2c2nc3c(=O)[nH]c(C4(C#N)CC4)nc3s2)c1]

The compound (350 mg) obtained in Example 57 was treated by a method similar to that in Example 86 to give the title compound (31.0 mg).
MS (ESI) m/z; 422 [M+H]+

Example 95

(R)-2-{6-(2,4-dimethoxybenzyl)-5-[1-(methoxymethyl)cyclopropyl]-7-oxo-6,7-dihydro[1,3]thiazolo[5,4-d]pyrimidin-2-yl}pyrrolidine-1-carboxylic acid benzyl ester

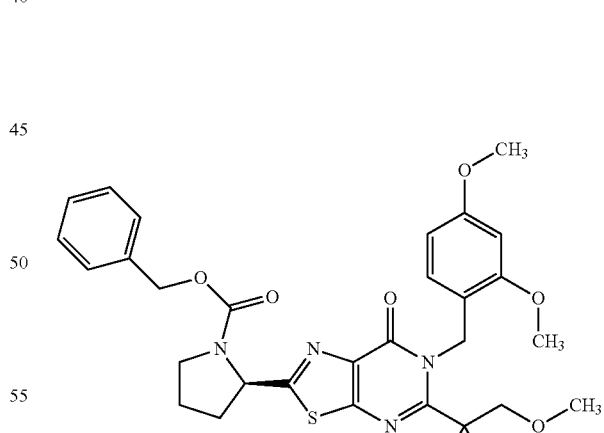

The compound (2.50 g) obtained in Reference Example 51 was treated by a method similar to that in Example 42 to give the title compound (2.30 g).
MS (ESI) m/z; 591 [M+H]+

Example 96

(R)-2-{5-[1-(methoxymethyl)cyclopropyl]-7-oxo-6,7-dihydro[1,3]thiazolo[5,4-d]pyrimidin-2-yl}pyrrolidine-1-carboxylic acid phenyl ester

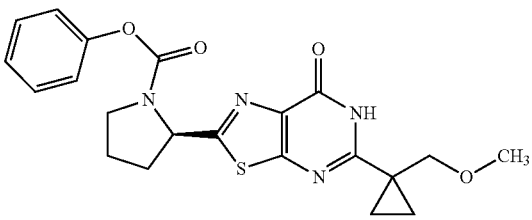 [SMILES: COCC1(c2nc3sc([C@H]4CCCN4C(=O)Oc4ccccc4)nc3c(=O)[nH]2)CC1]

To a solution (10 mL) of the compound (500 mg) obtained in Reference Example 52 in methylene chloride were added triethylamine (0.28 mL) and phenyl chloroformate (0.26 g), and the reaction mixture was stirred at room temperature for 1 hr. 1.0 mol/L Aqueous sodium hydroxide solution (8.0 mL) was added to the reaction mixture, and the reaction mixture was stirred at room temperature for 15 min. The reaction mixture was acidified with 1.0 mol/L hydrochloric acid and extracted twice with chloroform. The organic layer was dried over anhydrous magnesium sulfate, filtered and concentrated. The residue was is purified by silica gel column chromatography (solvent; hexane/ethyl acetate=70/30-0/100) to give the title compound (130 mg).

MS (ESI) m/z; 427 [M+H]$^+$

Example 97

2-[(R)-1-(phenylacetyl)pyrrolidin-2-yl]-5-[1-(trifluoromethyl)cyclopropyl]-6H-[1,3]thiazolo[5,4-d]pyrimidin-7-one

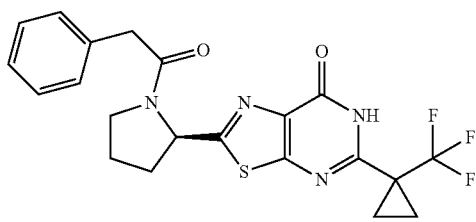 [SMILES: O=C(Cc1ccccc1)N1CCC[C@@H]1c1nc2c(=O)[nH]c(C3(C(F)(F)F)CC3)nc2s1]

The compound (45.0 mg) obtained in Reference Example 53 was treated by a method similar to that in Example 96 to give the title compound (45.0 mg).

MS (ESI) m/z; 449 [M+H]$^+$

Example 98

2-{(R)-1-[2-(3-methylphenyl)acetyl]pyrrolidin-2-yl}-5-[1-(trifluoromethyl)cyclopropyl]-6H-[1,3]thiazolo[5,4-d]pyrimidin-7-one

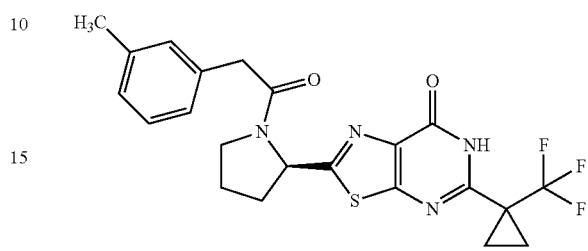

The compound (60.0 mg) obtained in Reference Example 53 was treated by a method similar to that in Example 96 to give the title compound (40.0 mg).

MS (ESI) m/z; 463 [M+H]$^+$

Example 99

(R)-2-{5-[1-(methoxymethyl)cyclopropyl]-7-oxo-6,7-dihydro[1,3]thiazolo[5,4-d]pyrimidin-2-yl}pyrrolidine-1-carboxylic acid 3-methylphenyl ester

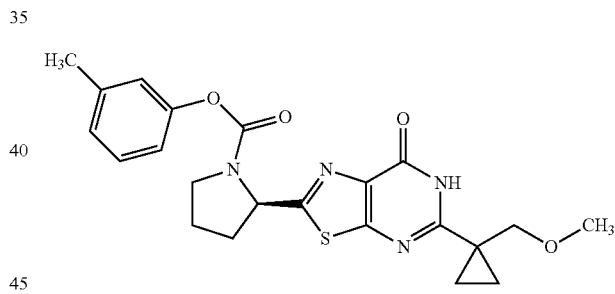

To a solution (15 mL) of triphosgene (0.39 g) in toluene were added m-cresol (0.36 g) and pyridine (0.33 mL) under ice-cooling, and the reaction mixture was stirred at room temperature for 30 min. The solvent was evaporated under reduced pressure, methylene chloride (10 mL), triethylamine (1.4 mL) and the compound (0.50 g) obtained in Reference Example 52 were added, and the reaction mixture was stirred at room temperature for 1 hr. 1.0 mol/L Aqueous sodium hydroxide solution (8.0 mL) was added to the reaction mixture, and the reaction mixture was stirred at room temperature for 15 min. The reaction mixture was acidified with 1.0 mol/L hydrochloric acid and extracted twice with chloroform. The organic layer was dried over anhydrous magnesium sulfate, filtered and concentrated. The residue was purified by silica gel column chromatography (solvent; hexane/ethyl acetate=70/30-0/100) to give the title compound (190 mg).

MS (ESI) m/z; 441 [M+H]$^+$

Example 100

(R)-2-[6-(2,4-dimethoxybenzyl)-5-(1-methylcyclopropoxy)-7-oxo-6,7-dihydro[1,3]thiazolo[5,4-d]pyrimidin-2-yl]pyrrolidine-1-carboxylic acid benzyl ester

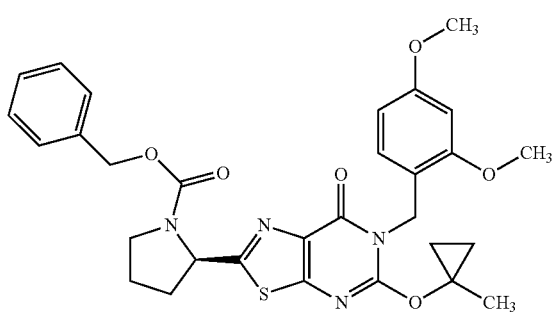 [SMILES: COc1ccc(Cn2c(OC3(C)CC3)nc3sc([C@H]4CCCN4C(=O)OCc4ccccc4)nc3c2=O)c(OC)c1]

To a solution (5.0 mL) of the compound (567 mg) obtained in Reference Example 56 in DMF were added 1-methylcyclopropanol (104 mg) and sodium hydride (60% oil dispersion, 48 mg) under ice-cooling. The reaction mixture was stirred at 60° C. for 2 hr. Water was added to the reaction mixture, and the mixture was extracted twice with ethyl acetate. The combined organic layer was washed with saturated brine, dried over anhydrous magnesium sulfate, filtered and concentrated. The residue was purified by silica gel column chromatography (solvent; hexane/ethyl acetate=70/30-50/50) and NH silica gel column chromatography (solvent; hexane/ethyl acetate=60/40-0/100) to give the title compound (239 mg).

MS (ESI) m/z; 577 [M+H]+

Example 101

(R)-2-[6-(2,4-dimethoxybenzyl)-7-oxo-5-(2,2,2-trifluoroethoxy)-6,7-dihydro[1,3]thiazolo[5,4-d]pyrimidin-2-yl]pyrrolidine-1-carboxylic acid benzyl ester

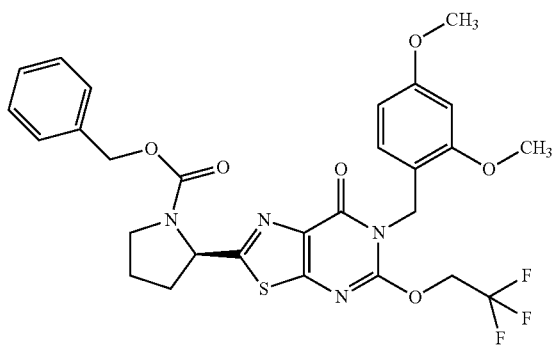 [SMILES: COc1ccc(Cn2c(OCC(F)(F)F)nc3sc([C@H]4CCCN4C(=O)OCc4ccccc4)nc3c2=O)c(OC)c1]

To a solution (4.0 mL) of the compound (250 mg) obtained in Reference Example 56 in DMF were added 2,2,2-trifluoroethanol (40 µL) and potassium tert-butoxide (59 mg) under ice-cooling. The reaction mixture was stirred at 60° C. for 1 hr. Water was added to the reaction mixture, and the mixture was extracted twice with ethyl acetate. The combined organic layer was washed with saturated brine, dried over anhydrous magnesium sulfate, filtered and concentrated. The residue was purified by silica gel column chromatography (solvent; hexane/ethyl acetate=70/30-30/70) to give the title compound (87 mg).

MS (ESI) m/z; 605 [M+H]+

Example 102

(R)-2-[6-(2,4-dimethoxybenzyl)-5-(N,N-dimethylamino)-7-oxo-6,7-dihydro[1,3]thiazolo[5,4-d]pyrimidin-2-yl]pyrrolidine-1-carboxylic acid benzyl ester

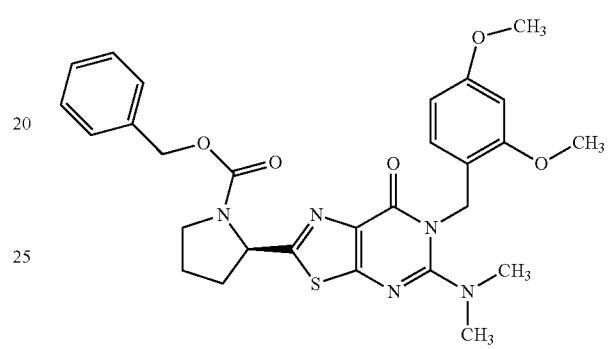

To a solution (3.0 mL) of the compound (190 mg) obtained in Reference Example 56 in THF was added 2.0 mol/L dimethylamine THF solution (0.85 mL) under ice-cooling. The reaction mixture was stirred at room temperature for 2 hr. The reaction mixture was concentrated, and the residue was purified by NH silica gel column chromatography (solvent; hexane/ethyl acetate=60/40-40/60) to give the title compound (129 mg).

MS (ESI) m/z; 550 [M+H]+

Example 103

(R)-2-[6-(2,4-dimethoxybenzyl)-7-oxo-5-(piperidin-1-yl)-6,7-dihydro[1,3]thiazolo[5,4-d]pyrimidin-2-yl]pyrrolidine-1-carboxylic acid benzyl ester

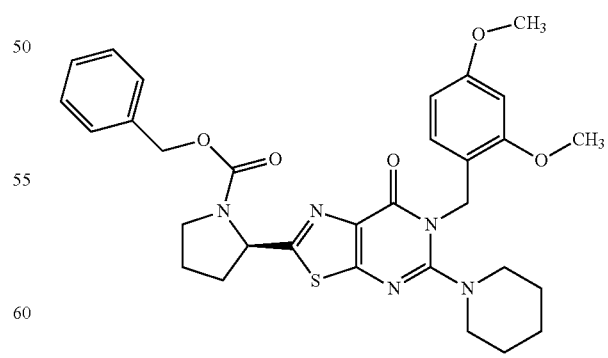

The compound (216 mg) obtained in Reference Example 56 was treated by a method similar to that in Example 102 to give the title compound (150 mg).

MS (ESI) m/z; 590 [M+H]+

Example 104

(R)-2-[5-(1-methylcyclopropoxy)-7-oxo-6,7-dihydro[1,3]thiazolo[5,4-d]pyrimidin-2-yl]pyrrolidine-1-carboxylic acid phenyl ester

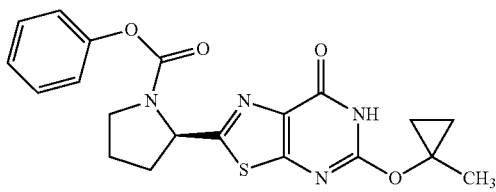 [SMILES: CC1(Oc2nc3sc([C@H]4CCCN4C(=O)Oc4ccccc4)nc3c(=O)[nH]2)CC1]

The compound (180 mg) obtained in Example 100 was treated by a method similar to that in Example 63 to give the title compound (62 mg).
MS (ESI) m/z; 413 [M+H]$^+$

Example 105

(R)-2-[7-oxo-5-(2,2,2-trifluoroethoxy)-6,7-dihydro[1,3]thiazolo[5,4-d]pyrimidin-2-yl]pyrrolidine-1-carboxylic acid phenyl ester

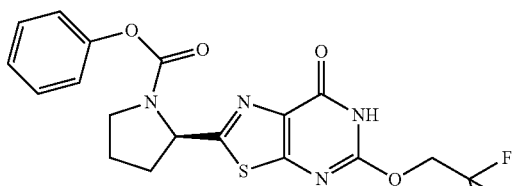

The compound (168 mg) obtained in Example 101 was treated by a method similar to that in Example 63 to give the title compound (59 mg).
MS (ESI) m/z; 441 [M+H]$^+$

Example 106

(R)-2-[5-(N,N-dimethylamino)-7-oxo-6,7-dihydro[1,3]thiazolo[5,4-d]pyrimidin-2-yl]pyrrolidine-1-carboxylic acid phenyl ester

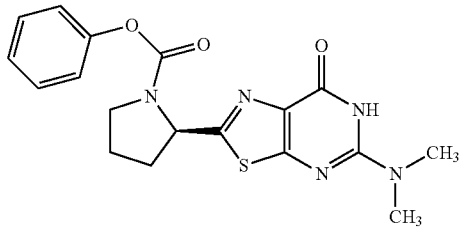

The compound (126 mg) obtained in Example 102 was treated by a method similar to that in Example 63 to give the title compound (68 mg).
MS (ESI) m/z; 386 [M+H]$^+$

Example 107

(R)-2-[7-oxo-5-(piperidin-1-yl)-6,7-dihydro[1,3]thiazolo[5,4-d]pyrimidin-2-yl]pyrrolidine-1-carboxylic acid phenyl ester

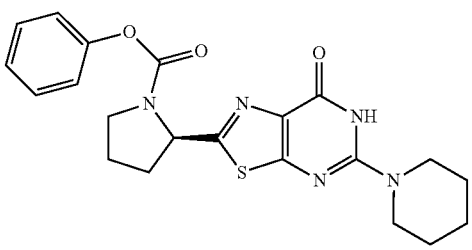 [SMILES: O=C(Oc1ccccc1)N1CCC[C@@H]1c1nc2c(=O)[nH]c(N3CCCCC3)nc2s1]

The compound (139 mg) obtained in Example 103 was treated by a method similar to that in Example 63 to give the title compound (61 mg).
MS (ESI) m/z; 426 [M+H]$^+$

Example 108

(R)-2-[6-(2,4-dimethoxybenzyl)-5-ethyl-7-oxo-6,7-dihydro[1,3]thiazolo[5,4-d]pyrimidin-2-yl]pyrrolidine-1-carboxylic acid benzyl ester

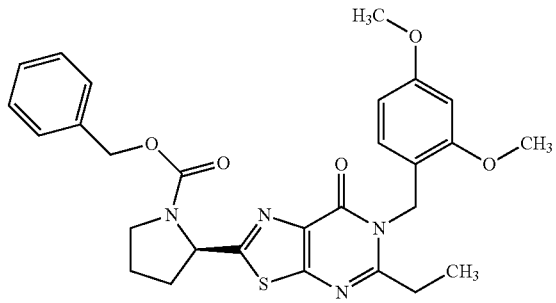 [SMILES: CCc1nc2sc([C@H]3CCCN3C(=O)OCc3ccccc3)nc2c(=O)n1Cc1ccc(OC)cc1OC]

The compound (0.92 g) obtained in Reference Example 57 was treated by a method similar to that in Example 42 to give the title compound (0.89 g).
MS (ESI) m/z; 535 [M+H]$^+$

Example 109

(R)-2-[6-(2,4-dimethoxybenzyl)-5-(1-methylcyclopropyl)-7-oxo-6,7-dihydro[1,3]thiazolo[5,4-d]pyrimidin-2-yl]pyrrolidine-1-carboxylic acid benzyl ester

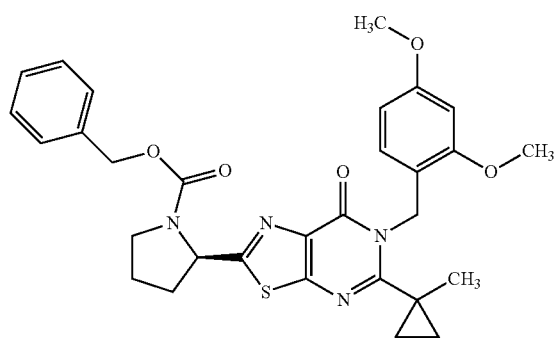

The compound (1.27 g) obtained in Reference Example 58 was treated by a method similar to that in Example 42 to give the title compound (1.08 g).

MS (ESI) m/z; 561 [M+H]$^+$

Example 110

(R)-2-[6-(2,4-dimethoxybenzyl)-5-(3-methyloxetan-3-yl)-7-oxo-6,7-dihydro[1,3]thiazolo[5,4-d]pyrimidin-2-yl]pyrrolidine-1-carboxylic acid benzyl ester

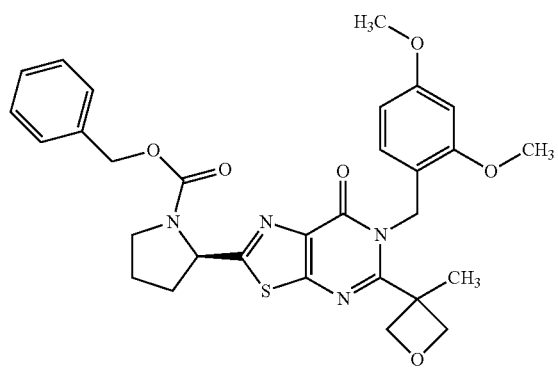 [SMILES: COc1ccc(Cn2c(C3(C)COC3)nc3sc([C@H]4CCCN4C(=O)OCc4ccccc4)nc3c2=O)c(OC)c1]

The compound (2.1 g) obtained in Reference Example 59 was treated by a method similar to that in Example 42 to give the title compound (1.29 g).

MS (ESI) m/z; 577 [M+H]$^+$

Example 111

(R)-2-[6-(2,4-dimethoxybenzyl)-5-ethyl-7-oxo-6,7-dihydro[1,3]thiazolo[5,4-d]pyrimidin-2-yl]pyrrolidine-1-carboxylic acid phenyl ester

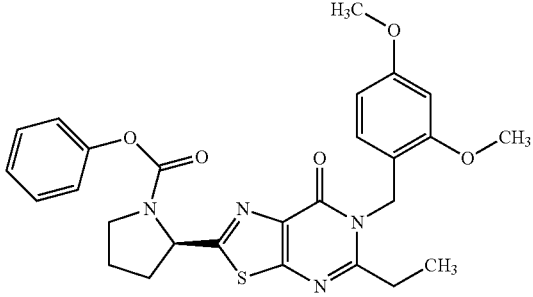 [SMILES: CCc1nc2sc([C@H]3CCCN3C(=O)Oc3ccccc3)nc2c(=O)n1Cc1ccc(OC)cc1OC]

To a solution (10 mL) of the compound (200 mg) obtained in Reference Example 60 in methylene chloride were added triethylamine (90 μL) and phenyl chloroformate (90.0 mg), and the reaction mixture was stirred at room temperature for 1 hr. Water was added to the reaction mixture, and the mixture was acidified with 1.0 mol/L hydrochloric acid and extracted twice with chloroform. The organic layer was dried over anhydrous magnesium sulfate, filtered and concentrated. The residue was purified by silica gel column chromatography (solvent; hexane/ethyl acetate=70/30-0/100) to give the title compound (200 mg).

MS (ESI) m/z; 521 [M+H]$^+$

Example 112

(R)-2-[6-(2,4-dimethoxybenzyl)-5-(1-methylcyclopropyl)-7-oxo-6,7-dihydro[1,3]thiazolo[5,4-d]pyrimidin-2-yl]pyrrolidine-1-carboxylic acid phenyl ester

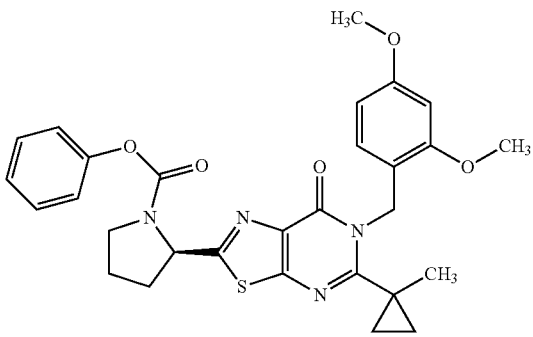 [SMILES: COc1ccc(Cn2c(C3(C)CC3)nc3sc([C@H]4CCCN4C(=O)Oc4ccccc4)nc3c2=O)c(OC)c1]

The compound (320 mg) obtained in Reference Example 61 was treated by a method similar to that in Example 111 to give the title compound (142 mg).

MS (ESI) m/z; 547 [M+H]$^+$

Example 113

(R)-2-[6-(2,4-dimethoxybenzyl)-5-(3-methyloxetan-3-yl)-7-oxo-6,7-dihydro[1,3]thiazolo[5,4-d]pyrimidin-2-yl]pyrrolidine-1-carboxylic acid phenyl ester

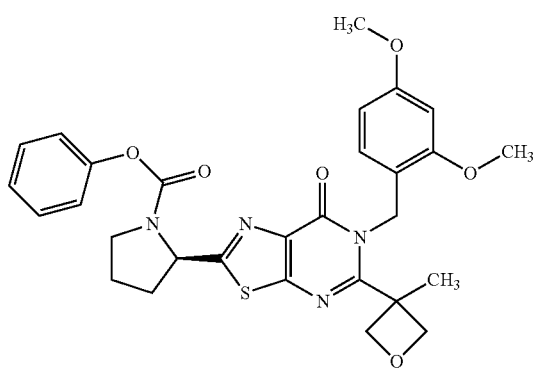 [SMILES: COc1ccc(Cn2c(C3(C)COC3)nc3sc([C@H]4CCCN4C(=O)Oc4ccccc4)nc3c2=O)c(OC)c1]

The compound (70.0 mg) obtained in Reference Example 62 was treated by a method similar to that in Example 111 to give the title compound (49 mg).
MS (ESI) m/z; 563 [M+H]+

Example 114

(R)-2-(5-ethyl-7-oxo-6,7-dihydro[1,3]thiazolo[5,4-d]pyrimidin-2-yl)pyrrolidine-1-carboxylic acid phenyl ester

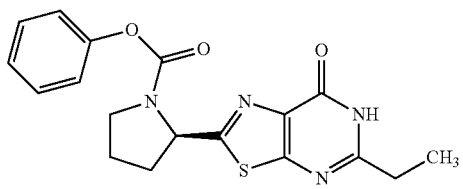 [SMILES: CCc1nc2sc([C@H]3CCCN3C(=O)Oc3ccccc3)nc2c(=O)[nH]1]

To the compound (180 mg) obtained in Example 111 was added a mixed solvent of triethylsilane (0.35 mL), water (0.35 mL) and trifluoroacetic acid (6.3 mL), and the reaction mixture was stirred at room temperature for 2 hr. The solvent was evaporated under reduced pressure, and the residue was purified by silica gel column chromatography (solvent; ethyl acetate/methanol=100/0-95/5) to give the title compound (118 mg).
MS (ESI) m/z; 371 [M+H]+

Example 115

(R)-2-[5-(1-methylcyclopropyl)-7-oxo-6,7-dihydro[1,3]thiazolo[5,4-d]pyrimidin-2-yl]pyrrolidine-1-carboxylic acid phenyl ester

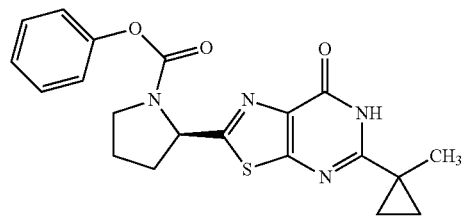 [SMILES: CC1(c2nc3sc([C@H]4CCCN4C(=O)Oc4ccccc4)nc3c(=O)[nH]2)CC1]

The compound (142 mg) obtained in Example 112 was treated by a method similar to that in Example 114 to give the title compound (80.0 mg).
MS (ESI) m/z; 397 [M+H]+

Example 116

(R)-2-[5-(3-methyloxetan-3-yl)-7-oxo-6,7-dihydro[1,3]thiazolo[5,4-d]pyrimidin-2-yl]pyrrolidine-1-carboxylic acid phenyl ester

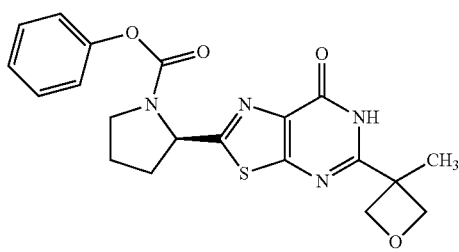 [SMILES: CC1(c2nc3sc([C@H]4CCCN4C(=O)Oc4ccccc4)nc3c(=O)[nH]2)COC1]

The compound (49.0 mg) obtained in Example 113 was treated by a method similar to that in Example 114 to give the title compound (28.0 mg).
MS (ESI) m/z; 413 [M+H]+

Example 117

(R)-2-[5-(2-fluoropropan-2-yl)-7-oxo-6,7-dihydro[1,3]thiazolo[5,4-d]pyrimidin-2-yl]pyrrolidine-1-carboxylic acid benzyl ester

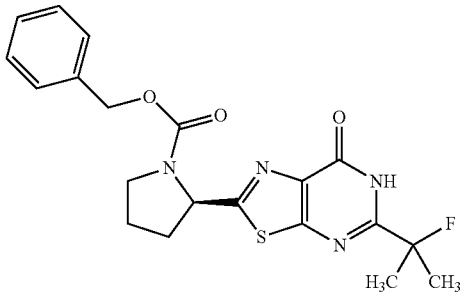 [SMILES: CC(C)(F)c1nc2sc([C@H]3CCCN3C(=O)OCc3ccccc3)nc2c(=O)[nH]1]

To a solution (30 mL) of the compound (1.30 g) obtained in Reference Example 64 in methylene chloride were added chlorotrimethylsilane (22.8 mL) and triethylamine (75.2 mL), and the reaction mixture was stirred at room temperature for 10 days. Water was added to the reaction mixture, and the mixture was extracted twice with chloroform. The organic layer was dried over anhydrous magnesium sulfate, filtered and concentrated. The residue was purified by silica gel column chromatography (solvent; chloroform/methanol=100/0-95/5) to give the title compound (0.40 g).
MS (ESI) m/z; 417 [M+H]+

Example 118

(R)-2-[5-(2-fluoropropan-2-yl)-7-oxo-6,7-dihydro[1,3]thiazolo[5,4-d]pyrimidin-2-yl]pyrrolidine-1-carboxylic acid phenyl ester

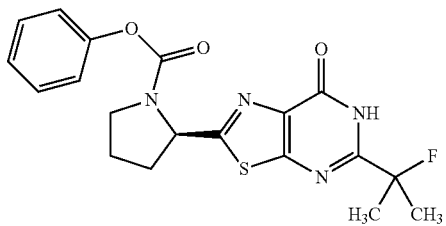 [SMILES: CC(C)(F)c1nc2sc([C@H]3CCCN3C(=O)Oc3ccccc3)nc2c(=O)[nH]1]

To a solution (15 mL) of the compound (300 mg) obtained in Example 117 in acetonitrile were added triethylsilane (0.69 mL) and trimethylsilyl iodide (0.21 mL), and the mixture was stirred at room temperature overnight. Triethylamine (0.60 mL) and phenyl chloroformate (0.23 g) were added to the reaction mixture, and the reaction mixture was stirred at room temperature for 4 hr. 1.0 mol/L Aqueous sodium hydroxide solution (0.8 mL) was added to the reaction mixture, and the mixture was stirred at room temperature for 15 min. The mixture was acidified with 1.0 mol/L hydrochloric acid and extracted twice with chloroform. The organic layer was dried over anhydrous magnesium sulfate, filtered and concentrated. The residue was purified by silica gel column chromatography (solvent; hexane/ethyl acetate=70/30-0/100) to give the title compound (97 mg).
MS (ESI) m/z; 403 [M+H]+

Example 119

(R)-2-[5-(2-fluoropropan-2-yl)-7-oxo-6,7-dihydro[1,3]thiazolo[5,4-d]pyrimidin-2-yl]pyrrolidine-1-carboxylic acid 3-methylphenyl ester

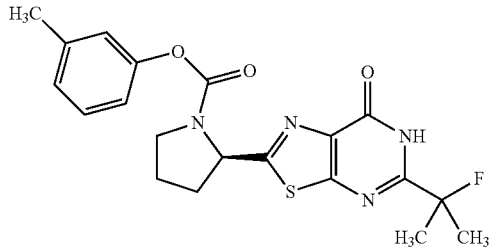 [SMILES: Cc1cccc(OC(=O)N2CCC[C@@H]2c2nc3c(=O)[nH]c(C(C)(C)F)nc3s2)c1]

(1) To a solution (5.0 mL) of the compound (100 mg) obtained in Example 117 in acetonitrile were added triethylsilane (0.23 mL) and trimethylsilyl iodide (70 μL), and the reaction mixture was stirred at room temperature overnight.
(2) To a solution (5.0 mL) of triphosgene (57 mg) in toluene were added m-cresol (52 mg) and pyridine (50 μL) under ice-cooling, and the reaction mixture was stirred at room temperature for 30 min. The solvent was evaporated under reduced pressure, the residue was dissolved in methylene chloride (5.0 mL), and added to the reaction mixture described in (1) at room temperature. Furthermore, triethylamine (0.20 mL) was added, and the reaction mixture was stirred at room temperature for 4 hr. The reaction mixture was acidified with 1.0 mol/L hydrochloric acid and extracted twice with chloroform. The organic layer was dried over anhydrous magnesium sulfate, filtered and concentrated. The residue was purified by silica gel column chromatography (solvent; hexane/ethyl acetate=70/30-0/100) to give the title compound (34 mg).
MS (ESI) m/z; 417 [M+H]+

Example 120

(R)-2-[5-(3-methyl-[1,2,4]oxadiazol-5-yl)-7-oxo-6,7-dihydro[1,3]thiazolo[5,4-d]pyrimidin-2-yl]pyrrolidine-1-carboxylic acid phenyl ester

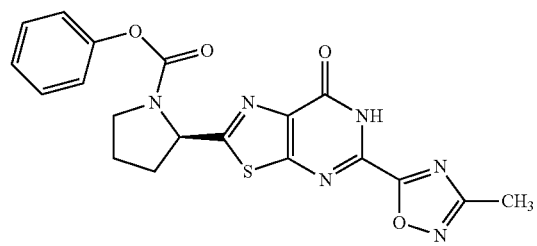 [SMILES: Cc1noc(-c2nc3sc([C@H]4CCCN4C(=O)Oc4ccccc4)nc3c(=O)[nH]2)n1]

To a solution (24.0 mL) of the compound (2.40 g) obtained in Example 584 in methylene chloride solution (24.0 mL) were added triethylsilane (1.75 mL) and trimethylsilyl iodide (1.56 mL) at 0° C., and the mixture was stirred at room temperature for 15 hr. The solvent was evaporated under reduced pressure, and to the residue were added 1.0 mol/L hydrochloric acid (28.8 mL) and hexane (24.0 mL) to partition the mixture. The aqueous layer was adjusted to pH about 4 with 4.0 mol/L aqueous sodium hydroxide solution (7.20 mL). To the obtained aqueous layer were successively added THF (12.0 mL), sodium hydrogen carbonate (2.30 g) and phenyl chloroformate (0.868 mL) under ice-cooling, and the reaction mixture was stirred at room temperature for 3 hr. 5% Aqueous citric acid solution (60.0 mL) was added to the reaction mixture, and the mixture was extracted three times with chloroform. The organic layer was dried over anhydrous magnesium sulfate, filtered and concentrated. The residue was purified by reversed-phase chromatography (Capcellpak C18 UG80 φ30 mm×250 mm, 5 μm, A: 0.05% trifluoroacetic acid-water, B: 0.05% trifluoroacetic acid-acetonitrile, 35 mL/min, B: 35-50%), and the solvent was evaporated by freeze-drying. The obtained residue was separated by chiral column (CHIRALPAK ID φ30 mm×250 mm, solvent:methanol-THF-acetic acid 85:15:0.5), and the solvent was evaporated to give the title compound (729 mg).
MS (ESI) m/z; 425 [M+H]+

Example 121

(R)-2-[5-(1-acetoxycyclopropyl)-6-(2,4-dimethoxybenzyl)-7-oxo-6,7-dihydro[1,3]thiazolo[5,4-d]pyrimidin-2-yl]pyrrolidine-1-carboxylic acid benzyl ester

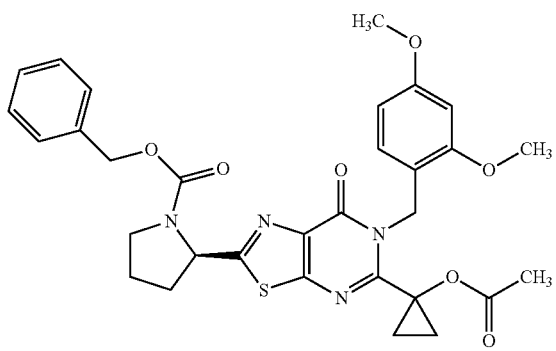 [SMILES: COc1ccc(Cn2c(C3(OC(C)=O)CC3)nc3sc([C@H]4CCCN4C(=O)OCc4ccccc4)nc3c2=O)c(OC)c1]

The compound (6.38 g) obtained in Reference Example 67 was treated by a method similar to that in Example 42 to give the title compound (6.20 g).

MS (ESI) m/z; 605 [M+H]$^+$

Example 122

(R)-2-[6-(2,4-dimethoxybenzyl)-5-(1-hydroxycyclopropyl)-7-oxo-6,7-dihydro[1,3]thiazolo[5,4-d]pyrimidin-2-yl]pyrrolidine-1-carboxylic acid benzyl ester

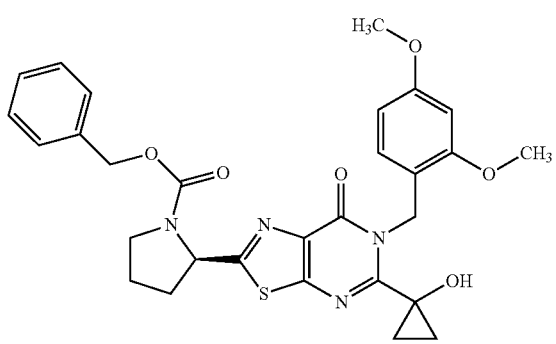 [SMILES: COc1ccc(Cn2c(C3(O)CC3)nc3sc([C@H]4CCCN4C(=O)OCc4ccccc4)nc3c2=O)c(OC)c1]

To a solution (60.0 mL) of the compound (6.20 g) obtained in Example 121 in THF was added 1.0 mol/L aqueous sodium hydroxide solution (12.2 mL), and the reaction mixture was stirred at room temperature overnight. The reaction mixture was neutralized with 1.0 mol/L hydrochloric acid, and extracted twice with chloroform. The organic layer was dried over anhydrous magnesium sulfate, filtered and concentrated. The residue was purified by NH silica gel column chromatography (solvent; hexane/ethyl acetate=70/30-0/100) to give the title compound (4.25 g).

MS (ESI) m/z; 563 [M+H]$^+$

Example 123

(R)-2-[6-(2,4-dimethoxybenzyl)-5-(1 1-methoxycyclopropyl)-7-oxo-6,7-dihydro[1,3]thiazolo[5,4-d]pyrimidin-2-yl]pyrrolidine-1-carboxylic acid benzyl ester

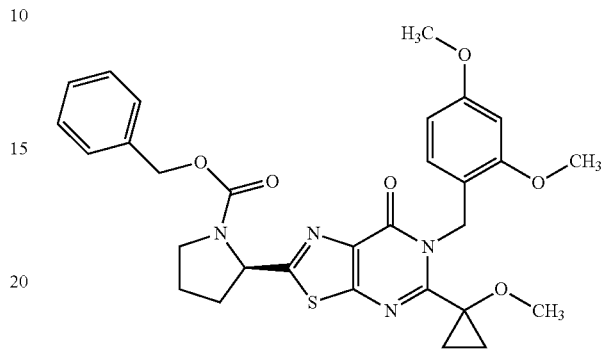

To a solution (50.0 mL) of the compound (4.25 g) obtained in Example 122 in DMF were added methyl iodide (1.30 g) and sodium hydride (60% oil dispersion, 0.31 g) at 0° C., and the reaction mixture was stirred at room temperature for 1 hr. Water was added to the reaction mixture, and the mixture was extracted twice with ethyl acetate. The organic layer was dried over anhydrous magnesium sulfate, filtered and concentrated. The residue was purified by NH silica gel column chromatography (solvent; hexane/ethyl acetate=70/30-0/100) to give the title compound (2.20 g).

MS (ESI) m/z; 577 [M+H]$^+$

Example 124

(R)-2-[5-(1-methoxycyclopropyl)-7-oxo-6,7-dihydro[1,3]thiazolo[5,4-d]pyrimidin-2-yl]pyrrolidine-1-carboxylic acid phenyl ester

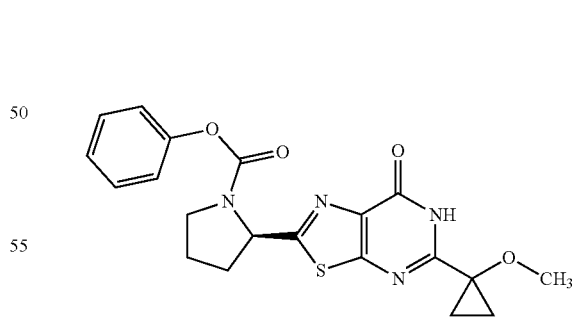

The compound (730 mg) obtained in Reference Example 68 was treated by a method similar to that in Example 96 to give the title compound (400 mg)

MS (ESI) m/z; 413 [M+H]$^+$

Example 125

(R)-2-[5-(1-methoxycyclopropyl)-7-oxo-6,7-dihydro[1,3]thiazolo[5,4-d]pyrimidin-2-yl]pyrrolidine-1-carboxylic acid 3-methylphenyl ester

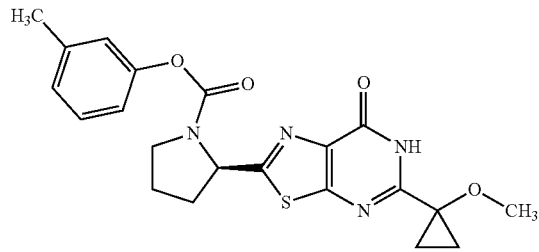

The compound (150 mg) obtained in Reference Example 68 was treated by a method similar to that in Example 99 to give the title compound (33.0 mg).

MS (ESI) m/z; 427 [M+H]$^+$

Example 126

(R)-2-(5-tert-butyl-7-oxo-6,7-dihydro[1,3]thiazolo[5,4-d]pyrimidin-2-yl)pyrrolidine-1-carboxylic acid phenyl ester

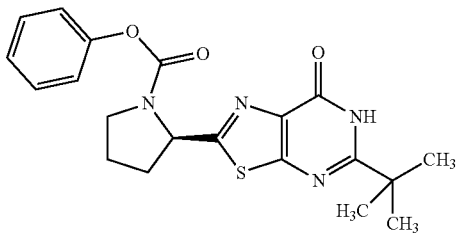 [SMILES: CC(C)(C)c1nc2sc([C@H]3CCCN3C(=O)Oc3ccccc3)nc2c(=O)[nH]1]

To a solution (5.0 mL) of the compound (120 mg) obtained in Reference Example 78 in methylene chloride were added triethylamine (80 μL) and phenyl chloroformate (68 mg), and the reaction mixture was stirred at room temperature for 1 hr. Furthermore, phenyl chloroformate (68 mg) was added, and the reaction mixture was stirred at room temperature for 1 hr. Water was added to the reaction mixture, and the mixture was acidified with 1.0 mol/L hydrochloric acid and extracted twice with chloroform. The organic layer was dried over anhydrous magnesium sulfate, filtered and concentrated. The residue was purified by silica gel column chromatography (solvent; hexane/ethyl acetate=70/30-0/100) to give the title compound (128 mg).

MS (ESI) m/z; 399 [M+H]$^+$

Example 127

2-[6-(2,4-dimethoxybenzyl)-5-(2-fluorophenyl)-7-oxo-6,7-dihydro[1,3]thiazolo[5,4-d]pyrimidin-2-yl]pyrazolidine-1-carboxylic acid phenyl ester

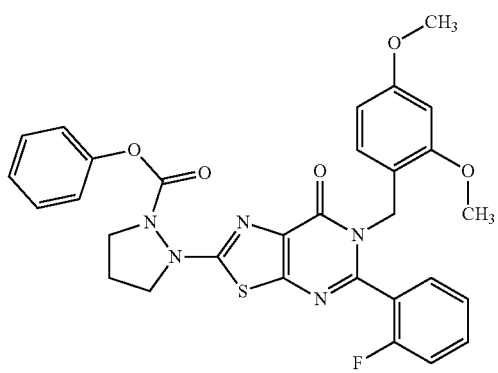 [SMILES: COc1ccc(Cn2c(-c3ccccc3F)nc3sc(N4CCCN4C(=O)Oc4ccccc4)nc3c2=O)c(OC)c1]

A solution (30 mL) of the compound (0.97 g) obtained in Reference Example 87, the compound (0.59 g) obtained in Reference Example 79, copper(I) iodide (80 mg), trans-N,N'-dimethylcyclohexane-1,2-diamine (60 mg) and tripotassium phosphate (0.91 g) in 1,4-dioxane was heated under reflux for 2 hr. The reaction mixture was cooled to room temperature, water was added thereto, and the mixture was extracted twice with chloroform. The organic layer was dried over anhydrous magnesium sulfate, filtered and concentrated. The residue was purified by silica gel column chromatography (solvent; hexane/ethyl acetate=70/30-50/50) to give the title compound (0.35 g).

MS (ESI) m/z; 588 [M+H]$^+$

Example 128

2-[6-(2,4-dimethoxybenzyl)-5-(1-methoxycyclopropyl)-7-oxo-6,7-dihydro[1,3]thiazolo[5,4-d]pyrimidin-2-yl]pyrazolidine-1-carboxylic acid phenyl ester

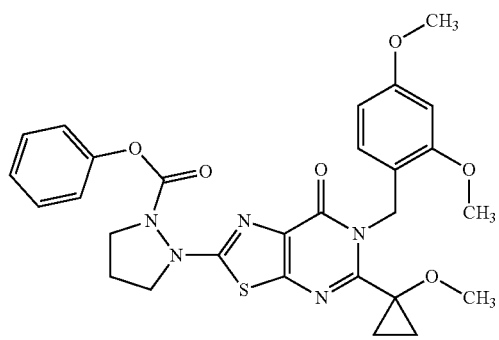 [SMILES: COc1ccc(Cn2c(C3(OC)CC3)nc3sc(N4CCCN4C(=O)Oc4ccccc4)nc3c2=O)c(OC)c1]

The compound (0.68 g) obtained in Reference Example 88 was treated by a method similar to that in Example 127 to give the title compound (0.26 g).

MS (ESI) m/z; 564 [M+H]$^+$

Example 129

2-[5-(2-fluorophenyl)-7-oxo-6,7-dihydro[1,3]thiazolo[5,4-d]pyrimidin-2-yl]pyrazolidine-1-carboxylic acid phenyl ester

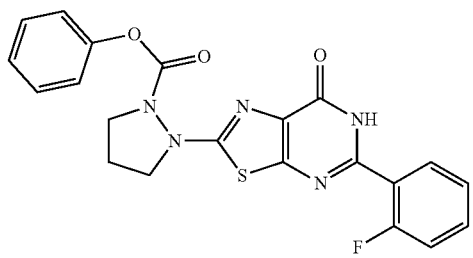 [SMILES: O=C(Oc1ccccc1)N1CCCN1c1nc2c(=O)[nH]c(-c3ccccc3F)nc2s1]

To a solution (6.0 mL) of the compound (350 mg) obtained in Example 127 in methylene chloride was added a mixture of triethylsilane (0.58 mL), water (0.38 mL) and trifluoroacetic acid (6.0 mL), and the reaction mixture was stirred at room temperature for 2 hr. The reaction mixture was neutralized with saturated aqueous sodium hydrogen carbonate solution, and extracted twice with chloroform. The organic layer was dried over anhydrous magnesium sulfate, filtered and concentrated. The residue was purified by silica gel column chromatography (solvent; chloroform/methanol=100/0-95/5) to give the title compound (170 mg).

MS (ESI) m/z; 438 [M+H]$^+$

Example 130

2-[5-(1-methoxycyclopropyl)-7-oxo-6,7-dihydro[1,3]thiazolo[5,4-d]pyrimidin-2-yl]pyrazolidine-1-carboxylic acid phenyl ester

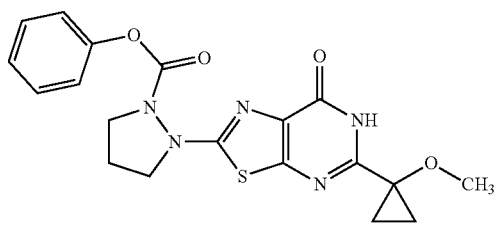 [SMILES: COC1(c2nc3sc(N4CCCN4C(=O)Oc4ccccc4)nc3c(=O)[nH]2)CC1]

The compound (260 mg) obtained in Example 128 was treated by a method similar to that in Example 129 to give the title compound (60.0 mg).

MS (ESI) m/z; 414 [M+H]$^+$

Example 131

2-[5-(2-fluoropropan-2-yl)-7-oxo-6,7-dihydro[1,3]thiazolo[5,4-d]pyrimidin-2-yl]pyrazolidine-1-carboxylic acid phenyl ester

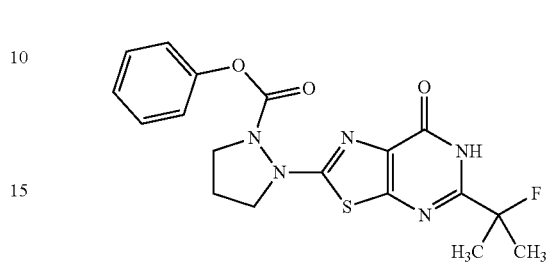

A solution (25 mL) of the compound (250 mg) obtained in Reference Example 91, the compound (930 mg) obtained in Reference Example 79, copper(I) iodide (33 mg), trans-N,N'-dimethylcyclohexane-1,2-diamine (25 mg) and tripotassium phosphate (386 mg) in 1,4-dioxane was heated under reflux for 1 hr. The reaction mixture was cooled to room temperature, water was added thereto, and the mixture was extracted twice with chloroform. The organic layer was dried over anhydrous magnesium sulfate, filtered and concentrated. The residue was purified by silica gel column chromatography (solvent; chloroform/methanol=100/0-95/5) to give the title compound (78.0 mg).

MS (ESI) m/z; 404 [M+H]$^+$

Example 132

2-[5-(2-fluoropropan-2-yl)-7-oxo-6,7-dihydro[1,3]thiazolo[5,4-d]pyrimidin-2-yl]pyrazolidine-1-carboxylic acid 3-methylphenyl ester

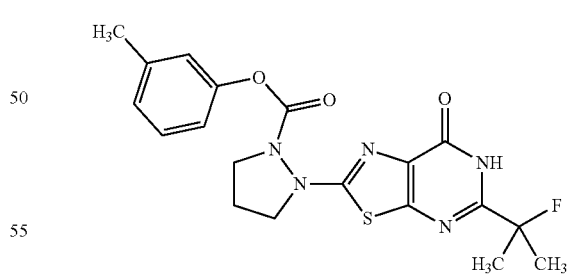

The compound (300 mg) obtained in Reference Example 91 and the compound (420 mg) obtained in Reference Example 82 were treated by a method similar to that in Example 131 to give the title compound (49.0 mg).

MS (ESI) m/z; 418 [M+H]$^+$

Example 133

5-(2-fluoropropan-2-yl)-2-[2-(phenylacetyl)pyrazolidin-1-yl]-6H-[1,3]thiazolo[5,4-d]pyrimidin-7-one

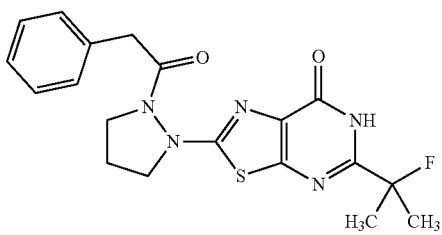 [SMILES: CC(C)(F)c1nc2sc(N3CCCN3C(=O)Cc3ccccc3)nc2c(=O)[nH]1]

A mixture of the compound (200 mg) obtained in Reference Example 91, the compound (400 mg) obtained in Reference Example 80 and N,N-diisopropylethylamine (1.20 mL) was heated at 150° C. for 12 hr. The reaction mixture was cooled to room temperature, neutralized with 1.0 mol/L hydrochloric acid, and extracted twice with chloroform. The organic layer was dried over anhydrous magnesium sulfate, filtered and concentrated. The residue was purified by silica gel column chromatography (solvent; ethyl acetate/methanol=100/0-95/5) to give the title compound (78.0 mg).

MS (ESI) m/z; 402 [M+H]$^+$

Example 134

5-(2-fluoropropan-2-yl)-2-{2-[2-(3-methylphenyl)acetyl]pyrazolidin-1-yl}-6H-[1,3]thiazolo[5,4-d]pyrimidin-7-one

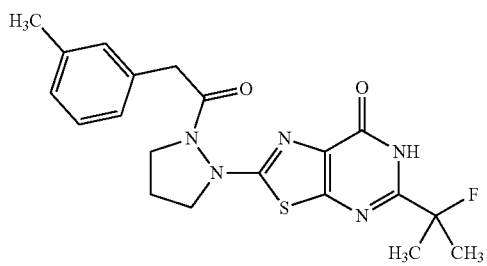 [SMILES: Cc1cccc(CC(=O)N2CCCN2c2nc3c(=O)[nH]c(C(C)(C)F)nc3s2)c1]

The compound (200 mg) obtained in Reference Example 91 and the compound (560 mg) obtained in Reference Example 81 were treated by a method similar to that in Example 133 to give the title compound (100 mg).

MS (ESI) m/z; 416 [M+H]$^+$

Example 135

(R)-2-[6-methyl-7-oxo-5-(propan-2-yl)-6,7-dihydro[1,3]thiazolo[5,4-d]pyrimidin-2-yl]pyrrolidine-1-carboxylic acid phenyl ester

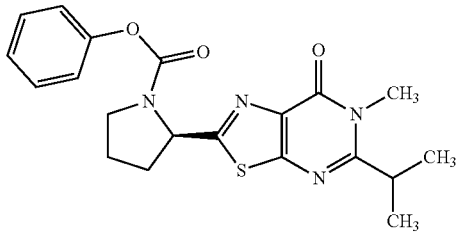 [SMILES: CC(C)c1nc2sc([C@H]3CCCN3C(=O)Oc3ccccc3)nc2c(=O)n1C]

To a solution (5.0 mL) of the compound (379 mg) obtained in Example 63 in acetonitrile were added potassium carbonate (205 mg) and methyl iodide (307 µL), and the reaction mixture was stirred with heating at 60° C. for 1 hr. The reaction mixture was allowed to cool to room temperature, water was added thereto, and the mixture was extracted twice with ethyl acetate. The organic layer was dried over anhydrous sodium sulfate, filtered and concentrated. The residue was purified by silica gel column chromatography (solvent; hexane/ethyl acetate=70/20-0/100) to give the title compound (303 mg).

MS (ESI) m/z; 399 [M+H]$^+$

Example 136

(R)-2-[5-(1-fluorocyclopropyl)-6-methyl-7-oxo-6,7-dihydro[1,3]thiazolo[5,4-d]pyrimidin-2-yl]pyrrolidine-1-carboxylic acid phenyl ester

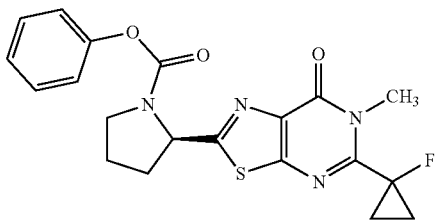 [SMILES: Cn1c(C2(F)CC2)nc2sc([C@H]3CCCN3C(=O)Oc3ccccc3)nc2c1=O]

The compound (100 mg) obtained in Example 71 was treated by a method similar to that in Example 135 to give the title compound (71 mg).

MS (ESI) m/z; 415 [M+H]$^+$

Example 137

(R)-2-[6-(2-fluorophenyl)-4-oxo-4,5-dihydro[1,3]
thiazolo[4,5-c]pyridin-2-yl]pyrrolidine-1-carboxylic
acid phenyl ester

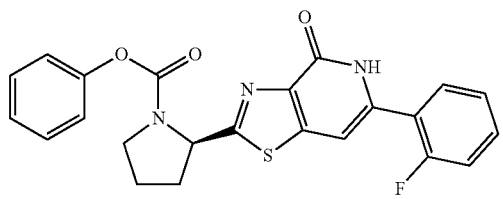 [SMILES: O=C(Oc1ccccc1)N1CCC[C@@H]1c1nc2c(=O)[nH]c(-c3ccccc3F)cc2s1]

To a solution (9.5 mL) of the compound (300 mg) obtained in Reference Example 97 in acetonitrile were added triethylsilane (619 μL) and trimethylsilyl iodide (355 μL), and the reaction mixture was stirred at room temperature for 1.5 hr. Triethylamine (541 μL) and phenyl chloroformate (162 μL) were added to the reaction mixture, and the reaction mixture was stirred at room temperature for 2 days. Triethylamine (90 μL) and phenyl chloroformate (81 μL) were added, and the reaction mixture was further stirred at room temperature for 5 hr. Water (475 μL) was added to the reaction mixture under ice-cooling, and the reaction mixture was stirred at room temperature for 15 hr. Furthermore, 1.0 mol/L aqueous sodium hydroxide solution (6.5 mL) was added, and the reaction mixture was stirred at room temperature for 4 hr. The reaction mixture was ice-cooled, acidified with 1.0 mol/L hydrochloric acid and extracted twice with ethyl acetate. The combined organic layer was dried over anhydrous sodium sulfate, filtered and concentrated. The residue was purified by silica gel column chromatography (solvent; ethyl acetate/MeOH=100/0-95/5), to the obtained product was added hexane/diethyl ether/ethyl acetate=2/2/1, and the solid was collected by filtration to give the title compound (106 mg).

MS (ESI) m/z; 436 [M+H]$^+$

Example 138

(R)-2-(4-oxo-6-trifluoromethyl-4,5-dihydro[1,3]
thiazolo[4,5-c]pyridin-2-yl)pyrrolidine-1-carboxylic
acid phenyl ester

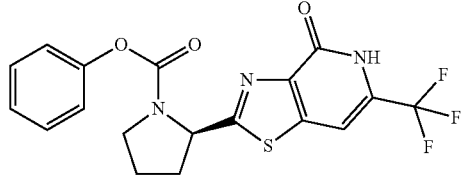 [SMILES: O=C(Oc1ccccc1)N1CCC[C@@H]1c1nc2c(=O)[nH]c(C(F)(F)F)cc2s1]

The compound (71 mg) obtained in Reference Example 98 was treated by a method similar to that in Example 137 to give the title compound (36 mg).

MS (ESI) m/z; 410 [M+H]$^+$

Example 139

(R)-2-[5-oxo-7-(propan-2-yl)-5H-[1,3,4]thiadiazolo
[3,2-a]pyrimidin-2-yl]pyrrolidine-1-carboxylic acid
phenyl ester

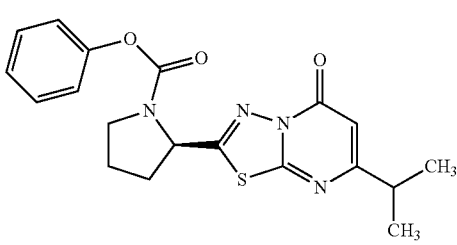 [SMILES: CC(C)c1cc(=O)n2nc([C@H]3CCCN3C(=O)Oc3ccccc3)sc2n1]

To a solution (10.0 mL) of the compound (200 mg) obtained in Reference Example 114 in methylene chloride were added N,N-diisopropylethylamine (120 μL) and phenyl chloroformate (120 mg), and the reaction mixture was stirred at room temperature for 1 hr. Water was added to the reaction mixture, and the mixture was extracted twice with chloroform. The organic layer was dried over anhydrous magnesium sulfate, filtered and concentrated. The residue was purified by silica gel column chromatography (solvent; hexane/ethyl acetate=70/30-0/100) to give the title compound (280 mg).

MS (ESI) m/z; 385 [M+H]$^+$

Example 140

(R)-2-[5-oxo-7-(propan-2-yl)-5H-[1,3,4]thiadiazolo
[3,2-a]pyrimidin-2-yl]pyrrolidine-1-carboxylic acid
4-fluorophenyl ester

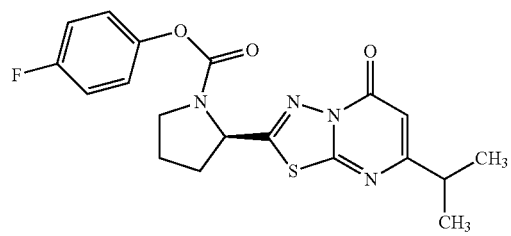 [SMILES: CC(C)c1cc(=O)n2nc([C@H]3CCCN3C(=O)Oc3ccc(F)cc3)sc2n1]

The compound (200 mg) obtained in Reference Example 114 was treated by a method similar to that in Example 139 to give the title compound (300 mg).

MS (ESI) m/z; 403 [M+H]$^+$

Example 141

(R)-2-[5-oxo-7-(propan-2-yl)-5H-[1,3,4]thiadiazolo[3,2-a]pyrimidin-2-yl]pyrrolidine-1-carboxylic acid 2-chlorophenyl ester

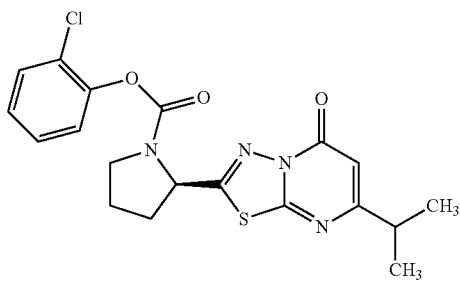 [SMILES: CC(C)c1cc(=O)n2nc([C@H]3CCCN3C(=O)Oc3ccccc3Cl)sc2n1]

The compound (200 mg) obtained in Reference Example 114 was treated by a method similar to that in Example 139 to give the title compound (310 mg).
MS (ESI) m/z; 419 [M+H]$^+$

Example 142

2-[(R)-1-(phenylacetyl)pyrrolidin-2-yl]-7-(propan-2-yl)-5H-[1,3,4]thiadiazolo[3,2-a]pyrimidin-5-one

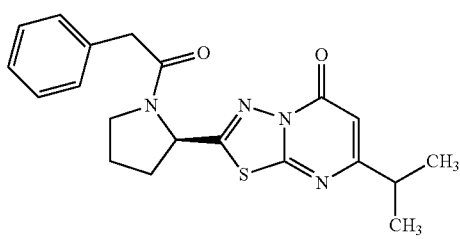 [SMILES: CC(C)c1cc(=O)n2nc([C@H]3CCCN3C(=O)Cc3ccccc3)sc2n1]

The compound (258 mg) obtained in Reference Example 114 was treated by a method similar to that in Example 139 to give the title compound (360 mg).
MS (ESI) m/z; 383 [M+H]$^+$

Example 143

2-{(R)-1-[2-(4-fluorophenyl)acetyl]pyrrolidin-2-yl}-7-(propan-2-yl)-5H-[1,3,4]thiadiazolo[3,2-a]pyrimidin-5-one

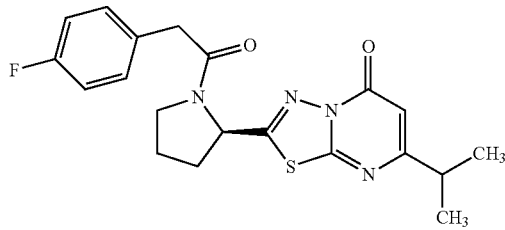 [SMILES: CC(C)c1cc(=O)n2nc([C@H]3CCCN3C(=O)Cc3ccc(F)cc3)sc2n1]

The compound (200 mg) obtained in Reference Example 114 was treated by a method similar to that in Example 139 to give the title compound (210 mg).
MS (ESI) m/z; 401 [M+H]$^+$

Example 144

(R)-2-[5-oxo-7-(propan-2-yl)-5H-[1,3,4]thiadiazolo[3,2-a]pyrimidin-2-yl]pyrrolidine-1-carboxylic acid benzyl ester

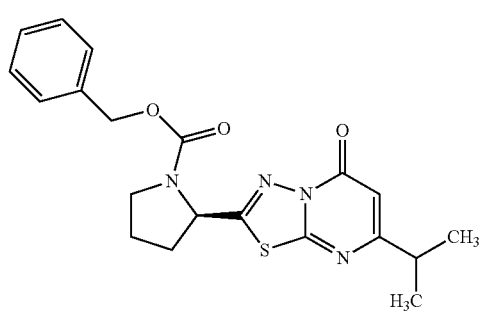 [SMILES: CC(C)c1cc(=O)n2nc([C@H]3CCCN3C(=O)OCc3ccccc3)sc2n1]

The compound (100 mg) obtained in Reference Example 114 was treated by a method similar to that in Example 139 to give the title compound (150 mg).
MS (ESI) m/z; 399 [M+H]$^+$

Example 145

2-[(R)-1-(2-phenoxyacetyl)pyrrolidin-2-yl]-7-(propan-2-yl)-5H-[1,3,4]thiadiazolo[3,2-a]pyrimidin-5-one

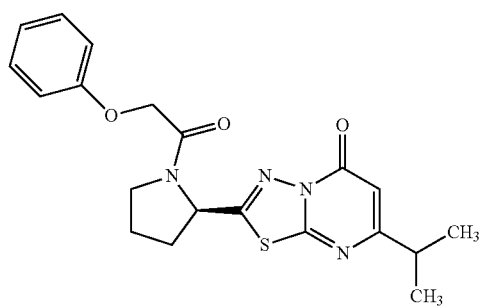 [SMILES: CC(C)c1cc(=O)n2nc([C@H]3CCCN3C(=O)COc3ccccc3)sc2n1]

The compound (200 mg) obtained in Reference Example 114 was treated by a method similar to that in Example 139 to give the title compound (218 mg).
MS (ESI) m/z; 399 [M+H]$^+$

Example 146

(R)-2-(7-ethyl-5-oxo-5H-[1,3,4]thiadiazolo[3,2-a]pyrimidin-2-yl)pyrrolidine-1-carboxylic acid phenyl ester

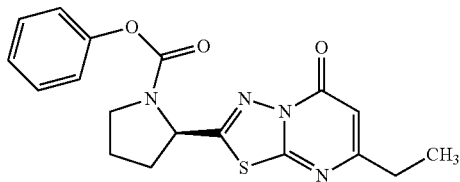 [SMILES: CCc1cc(=O)n2nc([C@H]3CCCN3C(=O)Oc3ccccc3)sc2n1]

The compound (100 mg) obtained in Reference Example 115 was treated by a method similar to that in Example 139 to give the title compound (143 mg).

MS (ESI) m/z; 371 [M+H]$^+$

Example 147

(R)-2-(6,7-dimethyl-5-oxo-5H-[1,3,4]thiadiazolo[3,2-a]pyrimidin-2-yl)pyrrolidine-1-carboxylic acid phenyl ester

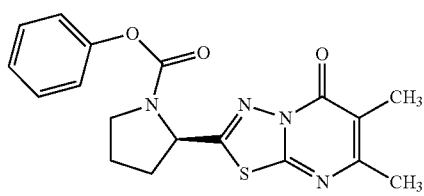 [SMILES: Cc1nc2sc([C@H]3CCCN3C(=O)Oc3ccccc3)nn2c(=O)c1C]

The compound (100 mg) obtained in Reference Example 116 was treated by a method similar to that in Example 139 to give the title compound (135 mg).

MS (ESI) m/z; 371 [M+H]$^+$

Example 148

(R)-2-(6-ethyl-7-methyl-5-oxo-5H-[1,3,4]thiadiazolo[3,2-a]pyrimidin-2-yl)pyrrolidine-1-carboxylic acid phenyl ester

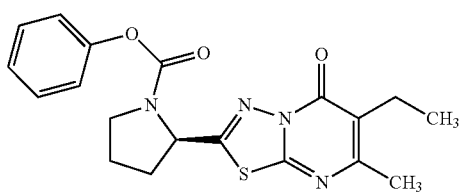 [SMILES: CCc1c(C)nc2sc([C@H]3CCCN3C(=O)Oc3ccccc3)nn2c1=O]

The compound (100 mg) obtained in Reference Example 117 was treated by a method similar to that in Example 139 to give the title compound (138 mg).

MS (ESI) m/z; 385 [M+H]$^+$

Example 149

(R)-2-(5-oxo-6,7,8,9-tetrahydro-5H-[1,3,4]thiadiazolo[2,3-b]quinazolin-2-yl)pyrrolidine-1-carboxylic acid phenyl ester

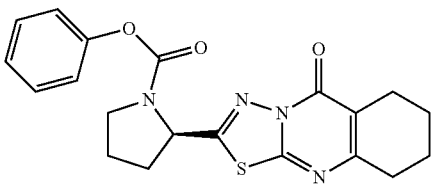 [SMILES: O=C(Oc1ccccc1)N1CCC[C@@H]1c1nn2c(=O)c3c(nc2s1)CCCC3]

The compound (200 mg) obtained in Reference Example 118 was treated by a method similar to that in Example 139 to give the title compound (280 mg).

MS (ESI) m/z; 397 [M+H]$^+$

Example 150

(R)-2-(5-oxo-6,7,8,9-tetrahydro-5H-[1,3,4]thiadiazolo[2,3-b]quinazolin-2-yl)pyrrolidine-1-carboxylic acid 4-fluorophenyl ester

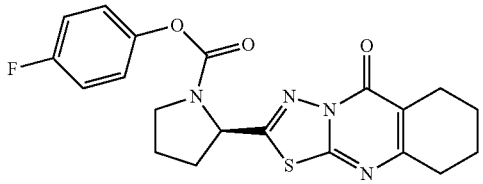 [SMILES: O=C(Oc1ccc(F)cc1)N1CCC[C@@H]1c1nn2c(=O)c3c(nc2s1)CCCC3]

The compound (230 mg) obtained in Reference Example 118 was treated by a method similar to that in Example 139 to give the title compound (320 mg).

MS (ESI) m/z; 415 [M+H]$^+$

Example 151

2-[(R)-1-(phenylacetyl)pyrrolidin-2-yl]-6,7,8,9-tetrahydro-5H-[1,3,4]thiadiazolo[2,3-b]quinazolin-5-one

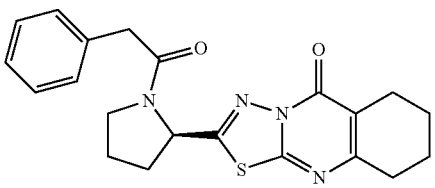 [SMILES: O=C(Cc1ccccc1)N1CCC[C@@H]1c1nn2c(=O)c3c(nc2s1)CCCC3]

The compound (200 mg) obtained in Reference Example 118 was treated by a method similar to that in Example 139 to give the title compound (280 mg).

MS (ESI) m/z; 395 [M+H]$^+$

Example 152

(R)-2-[5-oxo-7-(propan-2-yl)-5H-[1,3,4]thiadiazolo[3,2-a]pyrimidin-2-yl]piperidine-1-carboxylic acid phenyl ester

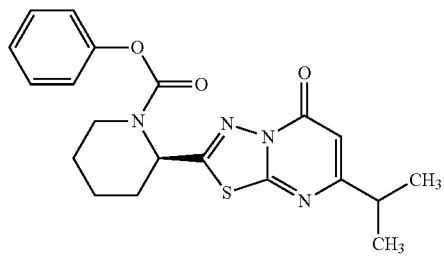 [SMILES: CC(C)c1cc(=O)n2nc([C@H]3CCCCN3C(=O)Oc3ccccc3)sc2n1]

The compound (130 mg) obtained in Reference Example 119 was treated by a method similar to that in Example 139 to give the title compound (187 mg).
MS (ESI) m/z; 399 [M+H]$^+$

Example 153

(R)-2-[6-chloro-5-oxo-7-(propan-2-yl)-5H-[1,3,4]thiadiazolo[3,2-a]pyrimidin-2-yl]pyrrolidine-1-carboxylic acid phenyl ester

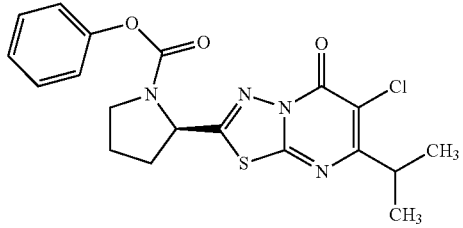 [SMILES: CC(C)c1nc2sc([C@H]3CCCN3C(=O)Oc3ccccc3)nn2c(=O)c1Cl]

The compound (150 mg) obtained in Reference Example 120 was treated by a method similar to that in Example 139 to give the title compound (210 mg).
MS (ESI) m/z; 419, 421 [M+H]$^+$

Example 154

6-chloro-2-[(R)-1-(phenylacetyl)pyrrolidin-2-yl]-7-(propan-2-yl)-5H-[1,3,4]thiadiazolo[3,2-a]pyrimidin-5-one

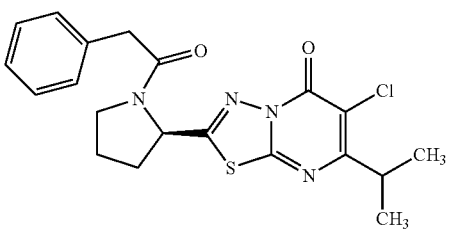 [SMILES: CC(C)c1nc2sc([C@H]3CCCN3C(=O)Cc3ccccc3)nn2c(=O)c1Cl]

The compound (150 mg) obtained in Reference Example 120 was treated by a method similar to that in Example 139 to give the title compound (160 mg).
MS (ESI) m/z; 417, 419 [M+H]$^+$

Example 155

(R)-2-(7-fluoro-5-oxo-5H-[1,3,4]thiadiazolo[2,3-b]quinazolin-2-yl)pyrrolidine-1-carboxylic acid phenyl ester

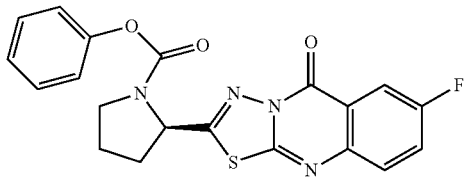 [SMILES: O=C(Cc1ccccc1)N1CCC[C@@H]1c1nn2c(=O)c3cc(F)ccc3nc2s1]

The compound (250 mg) obtained in Reference Example 121 was treated by a method similar to that in Example 139 to give the title compound (230 mg).
MS (ESI) m/z; 411 [M+H]$^+$

Example 156

7-fluoro-2-[(R)-1-(phenylacetyl)pyrrolidin-2-yl]-5H-[1,3,4]thiadiazolo[2,3-b]quinazolin-5-one

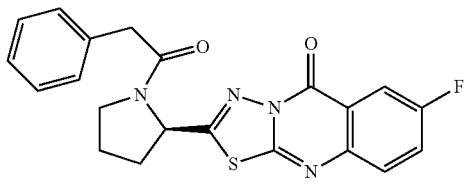

The compound (300 mg) obtained in Reference Example 121 was treated by a method similar to that in Example 139 to give the title compound (226 mg).
MS (ESI) m/z; 409 [M+H]$^+$

Example 157

(R)-N-benzyl-2-[5-oxo-7-(propan-2-yl)-5H-[1,3,4]thiadiazolo[3,2-a]pyrimidin-2-yl]pyrrolidine-1-carboxamide

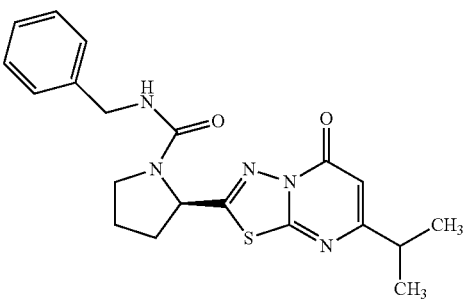 [SMILES: CC(C)c1cc(=O)n2nc([C@H]3CCCN3C(=O)NCc3ccccc3)sc2n1]

To a solution (10.0 mL) of the compound (300 mg) obtained in Reference Example 114 and N,N-diisopropylethylamine (180 μL) in methylene chloride was added dropwise benzyl isocyanate (150 mg) under ice-cooling. The reaction mixture was stirred at room temperature for 1 hr. 0.5 mol/L Hydrochloric acid was added to the reaction mixture, and the mixture was extracted twice with chloroform. The organic layer was dried over anhydrous magnesium sulfate, filtered and concentrated. The residue was purified by silica gel column chromatography (solvent; hexane/ethyl acetate=50/50-20/80) to give the title compound (430 mg).

MS (ESI) m/z; 398 [M+H]$^+$

Example 158

(R)-N-(2-chlorobenzyl)-2-[5-oxo-7-(propan-2-yl)-5H-[1,3,4]thiadiazolo[3,2-a]pyrimidin-2-yl]pyrrolidine-1-carboxamide

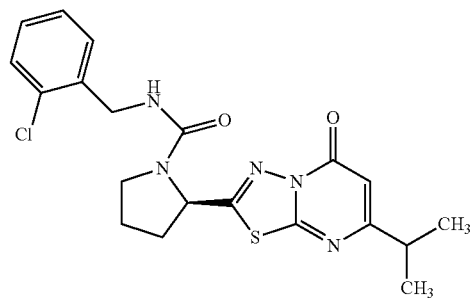 [SMILES: CC(C)c1cc(=O)n2nc([C@H]3CCCN3C(=O)NCc3ccccc3Cl)sc2n1]

The compound (100 mg) obtained in Reference Example 114 was treated by a method similar to that in Example 157 to give the title compound (180 mg).

MS (ESI) m/z; 432, 434 [M+H]$^+$

Example 159

(R)-N-(4-chlorobenzyl)-2-[5-oxo-7-(propan-2-yl)-5H-[1,3,4]thiadiazolo[3,2-a]pyrimidin-2-yl]pyrrolidine-1-carboxamide

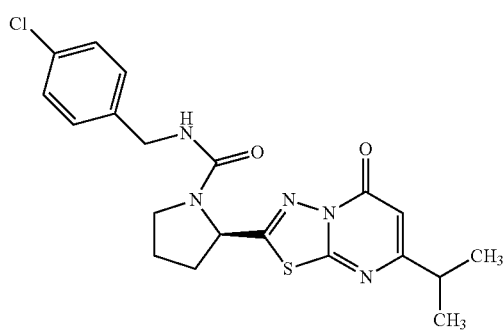 [SMILES: CC(C)c1cc(=O)n2nc([C@H]3CCCN3C(=O)NCc3ccc(Cl)cc3)sc2n1]

The compound (100 mg) obtained in Reference Example 114 was treated by a method similar to that in Example 157 to give the title compound (100 mg).

MS (ESI) m/z; 432, 434 [M+H]$^+$

Example 160

(R)-2-[5-oxo-7-(propan-2-yl)-5H-[1,3,4]thiadiazolo[3,2-a]pyrimidin-2-yl]-N-phenylpyrrolidine-1-carboxamide

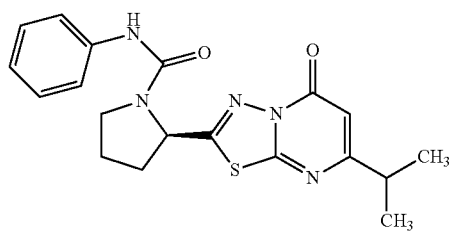 [SMILES: CC(C)c1cc(=O)n2nc([C@H]3CCCN3C(=O)Nc3ccccc3)sc2n1]

The compound (200 mg) obtained in Reference Example 114 was treated by a method similar to that in Example 157 to give is the title compound (290 mg).

MS (ESI) m/z; 384 [M+H]$^+$

Example 161

(R)-N-benzyl-2-(7-ethyl-5-oxo-5H-[1,3,4]thiadiazolo[3,2-a]pyrimidin-2-yl)pyrrolidine-1-carboxamide

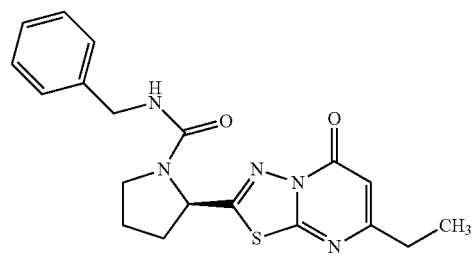 [SMILES: CCc1cc(=O)n2nc([C@H]3CCCN3C(=O)NCc3ccccc3)sc2n1]

The compound (150 mg) obtained in Reference Example 115 was treated by a method similar to that in Example 157 to give the title compound (183 mg).

MS (ESI) m/z; 384 [M+H]$^+$

Example 162

(R)-N-benzyl-2-(6,7-dimethyl-5-oxo-5H-[1,3,4]thiadiazolo[3,2-a]pyrimidin-2-yl)pyrrolidine-1-carboxamide

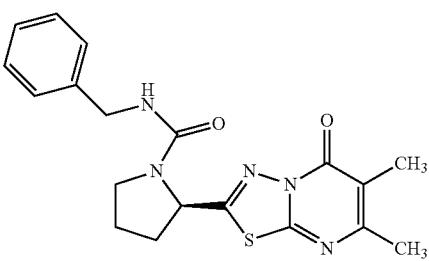 [SMILES: Cc1nc2sc([C@H]3CCCN3C(=O)NCc3ccccc3)nn2c(=O)c1C]

The compound (150 mg) obtained in Reference Example 116 was treated by a method similar to that in Example 157 to give the title compound (174 mg).

MS (ESI) m/z; 384 [M+H]+

Example 163

(R)-N-(2-chlorophenyl)-2-(6,7-dimethyl-5-oxo-5H-[1,3,4]thiadiazolo[3,2-a]pyrimidin-2-yl)pyrrolidine-1-carboxamide

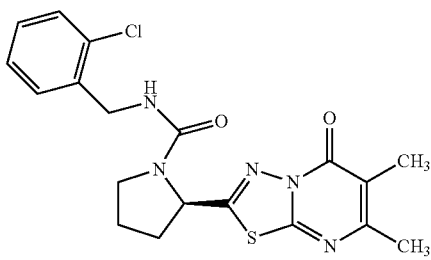 [SMILES: Cc1nc2sc([C@H]3CCCN3C(=O)NCc3ccccc3Cl)nn2c(=O)c1C]

The compound (150 mg) obtained in Reference Example 116 was treated by a method similar to that in Example 157 to give the title compound (230 mg).

MS (ESI) m/z; 418, 420 [M+H]+

Example 164

(R)-N-benzyl-2-(6-ethyl-7-methyl-5-oxo-5H-[1,3,4]thiadiazolo[3,2-a]pyrimidin-2-yl)pyrrolidine-1-carboxamide

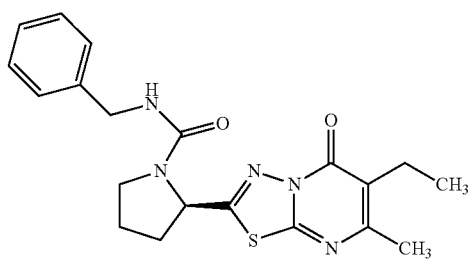 [SMILES: CCc1c(C)nc2sc([C@H]3CCCN3C(=O)NCc3ccccc3)nn2c1=O]

The compound (150 mg) obtained in Reference Example 117 was treated by a method similar to that in Example 157 to give the title compound (187 mg).

MS (ESI) m/z; 398 [M+H]+

Example 165

2-[(R)-1-(2,3-dihydro-1H-indol-1-ylacetyl)pyrrolidin-2-yl]-7-(propan-2-yl)-5H-[1,3,4]thiadiazolo[3,2-a]pyrimidin-5-one

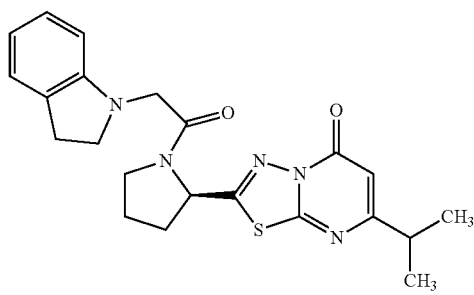 [SMILES: CC(C)c1cc(=O)n2nc([C@H]3CCCN3C(=O)CN3CCc4ccccc43)sc2n1]

To a solution (10.0 mL) of the compound (200 mg) obtained in Reference Example 114 and N,N-diisopropylethylamine (120 mg) in methylene chloride was added dropwise chloroacetyl chloride (90 mg) at room temperature. The reaction mixture was stirred at room temperature for 1 hr. Water was added to the reaction mixture, and the mixture was extracted twice with chloroform. The organic layer was dried over anhydrous magnesium sulfate, filtered and concentrated. The residue was purified by silica gel column chromatography (solvent; ethyl acetate/methanol=100/0-95/5) to give a viscous body (250 mg). To a solution (10.0 mL) of the obtained viscous body in THF were added indoline (100 mg) and sodium hydride (60% oil dispersion, 40 mg), and the reaction mixture was stirred with heating at 70° C. for 8 hr. The reaction mixture was cooled to room temperature, water was added thereto, and the mixture was extracted twice with ethyl acetate. The organic layer was dried over anhydrous magnesium sulfate, filtered and concentrated. The residue was purified by silica gel column chromatography (solvent; ethyl acetate/methanol=100/0-95/5) to give the title compound (36 mg).

MS (ESI) m/z; 424 [M+H]+

Example 166

2-{(R)-1-[(3,4-dihydroquinolin-1(2H)-yl)acetyl]pyrrolidin-2-yl}-7-(propan-2-yl)-5H-[1,3,4]thiadiazolo[3,2-a]pyrimidin-5-one

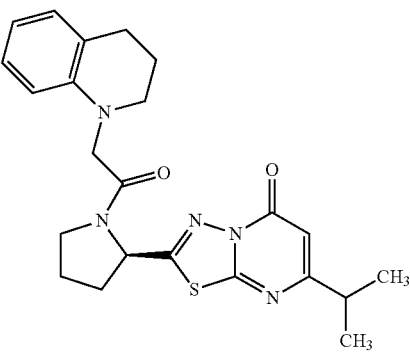 [SMILES: CC(C)c1cc(=O)n2nc([C@H]3CCCN3C(=O)CN3CCCc4ccccc43)sc2n1]

To a solution (10.0 mL) of the compound (200 mg) obtained in Reference Example 114 and N,N-diisopropylethylamine (110 mg) in methylene chloride was added dropwise chloroacetyl chloride (90 mg) at room temperature. After stirring at room temperature for 1 hr, water was added to the reaction mixture, and the mixture was extracted twice with chloroform. The organic layer was dried over anhydrous magnesium sulfate, filtered and concentrated. To a solution (10.0 mL) of the residue in acetonitrile were added potassium iodide (160 mg), potassium carbonate (130 mg) and 1,2,3,4-tetrahydroquinoline (130 mg), and the reaction mixture was stirred with heating at 80° C. for 3 hr. Water was added to the reaction mixture, and the mixture was extracted twice with chloroform. The organic layer was dried over anhydrous magnesium sulfate, filtered and concentrated. The residue was purified by NH silica gel column chromatography (solvent; ethyl acetate/methanol=100/0-95/5) to give the title compound (200 mg).

MS (ESI) m/z; 438 [M+H]+

Example 167

(R)-N-(1-phenylcyclopropyl)-2-[5-oxo-7-(propan-2-yl)-5H-[1,3,4]thiadiazolo[3,2-a]pyrimidin-2-yl]pyrrolidine-1-carboxamide

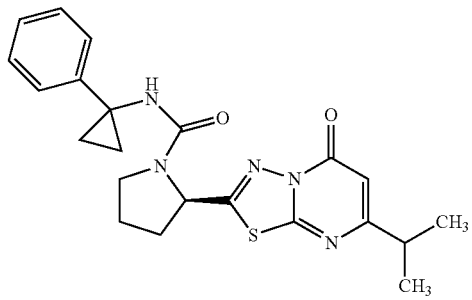 [SMILES: CC(C)c1cc(=O)n2nc([C@H]3CCCN3C(=O)NC3(c4ccccc4)CC3)sc2n1]

To a solution (10 mL) of triphosgene (100 mg) in methylene chloride was added pyridine (92 µL) at 0° C., and the reaction mixture was stirred for 30 min. The compound (150 mg) obtained in Reference Example 114 was added, and the reaction mixture was stirred at room temperature for 30 min. The solvent was evaporated under reduced pressure, methylene chloride (10 mL), 4-dimethylaminopyridine (350 mg) and 1-phenylcyclopropylamine (490 mg) were added at room temperature, and the reaction mixture was stirred at the same temperature for 1 hr. 1.0 mol/L Hydrochloric acid was added to the reaction mixture, and the mixture was extracted twice with chloroform. The organic layer was dried over anhydrous magnesium sulfate, filtered and concentrated. The residue was purified by silica gel column chromatography (solvent; ethyl acetate/methanol=100/0-95/5) to give the title compound (88 mg).

MS (ESI) m/z; 424 [M+H]+

Example 168

(R)-N-((R)-indan-1-yl)-2-[5-oxo-7-(propan-2-yl)-5H-[1,3,4]thiadiazolo[3,2-a]pyrimidin-2-yl]pyrrolidine-1-carboxamide

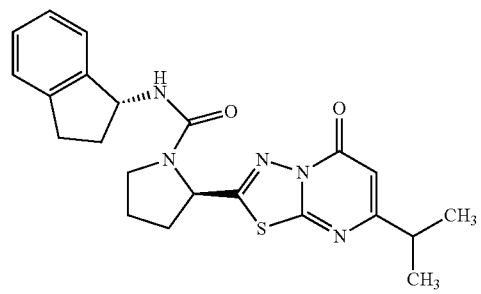 [SMILES: CC(C)c1cc(=O)n2nc([C@H]3CCCN3C(=O)N[C@@H]3CCc4ccccc43)sc2n1]

The compound (150 mg) obtained in Reference Example 114 was treated by a method similar to that in Example 167 to give the title compound (100 mg).

MS (ESI) m/z; 424 [M+H]+

Example 169

(R)-2-[5-oxo-7-(propan-2-yl)-5H-[1,3,4]thiadiazolo[3,2-a]pyrimidin-2-yl]-N-((R)-1,2,3,4-tetrahydronaphthalen-1-yl)pyrrolidine-1-carboxamide

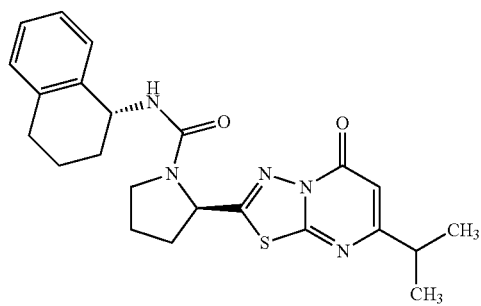 [SMILES: CC(C)c1cc(=O)n2nc([C@H]3CCCN3C(=O)N[C@@H]3CCCc4ccccc43)sc2n1]

The compound (150 mg) obtained in Reference Example 114 was treated by a method similar to that in Example 167 to give the title compound (43.0 mg).

MS (ESI) m/z; 438 [M+H]+

Example 170

2-[(R)-1-(2,3-dihydro-indole-1-carbonyl)pyrrolidin-2-yl]-7-(propan-2-yl)-5H-[1,3,4]thiadiazolo[3,2-a]pyrimidin-5-one

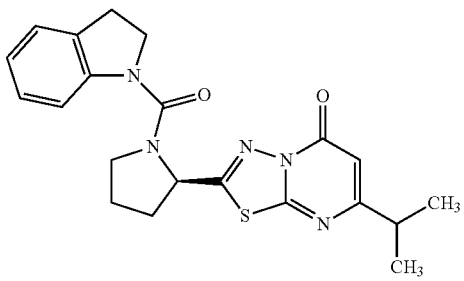 [SMILES: CC(C)c1cc(=O)n2nc([C@H]3CCCN3C(=O)N3CCc4ccccc43)sc2n1]

The compound (150 mg) obtained in Reference Example 114 was treated by a method similar to that in Example 167 to give the title compound (136 mg).
MS (ESI) m/z; 410 [M+H]$^+$ Example 171

(R)-2-(6,7-dimethyl-5-oxo-5H-[1,3,4]thiadiazolo[3,2-a]pyrimidin-2-yl)-N-((R)-1-phenylethyl)pyrrolidine-1-carboxamide

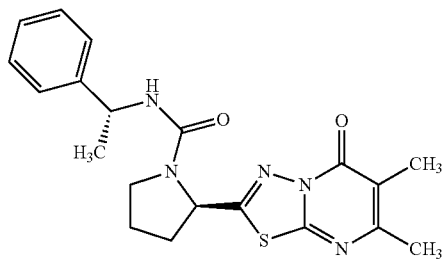 [SMILES: Cc1nc2sc([C@H]3CCCN3C(=O)N[C@H](C)c3ccccc3)nn2c(=O)c1C]

The compound (150 mg) obtained in Reference Example 116 was treated by a method similar to that in Example 167 to give the title compound (119 mg).
MS (ESI) m/z; 398 [M+H]$^+$ Example 172

(R)-2-(6,7-dimethyl-5-oxo-5H-[1,3,4]thiadiazolo[3,2-a]pyrimidin-2-yl)-N-(1-methyl-1-phenylethyl)pyrrolidine-1-carboxamide

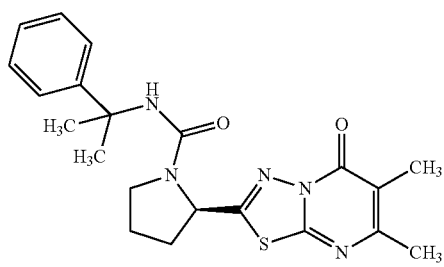 [SMILES: Cc1nc2sc([C@H]3CCCN3C(=O)NC(C)(C)c3ccccc3)nn2c(=O)c1C]

The compound (150 mg) obtained in Reference Example 116 was treated by a method similar to that in Example 167 to give the title compound (18.0 mg).
MS (ESI) m/z; 412 [M+H]$^+$ Example 173

(R)-2-(6,7-dimethyl-5-oxo-5H-[1,3,4]thiadiazolo[3,2-a]pyrimidin-2-yl)-N-(1-phenylcyclopropyl)pyrrolidine-1-carboxamide

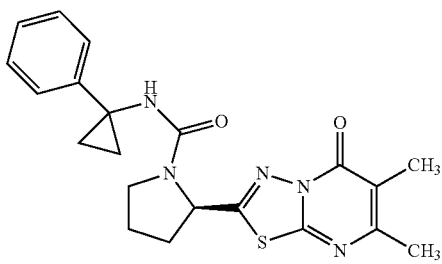 [SMILES: Cc1nc2sc([C@H]3CCCN3C(=O)NC3(c4ccccc4)CC3)nn2c(=O)c1C]

The compound (150 mg) obtained in Reference Example 116 was treated by a method similar to that in Example 167 to give the title compound (75.0 mg).
MS (ESI) m/z; 410 [M+H]$^+$ Example 174

(R)-2-(6,7-dimethyl-5-oxo-5H-[1,3,4]thiadiazolo[3,2-a]pyrimidin-2-yl)-N-((R)-indan-1-yl)pyrrolidine-1-carboxamide

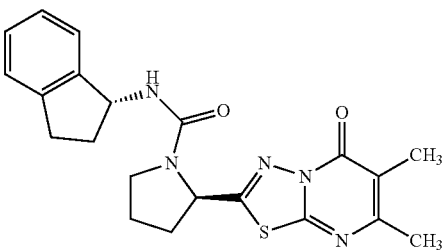 [SMILES: Cc1nc2sc([C@H]3CCCN3C(=O)N[C@@H]3CCc4ccccc43)nn2c(=O)c1C]

The compound (150 mg) obtained in Reference Example 116 was treated by a method similar to that in Example 167 to give the title compound (190 mg).
MS (ESI) m/z; 410 [M+H]$^+$

Example 175

(R)-2-(6,7-dimethyl-5-oxo-5H-[1,3,4]thiadiazolo[3,2-a]pyrimidin-2-yl)-N-(thieno[2,3-b]pyridin-3-yl)-pyrrolidine-1-carboxamide

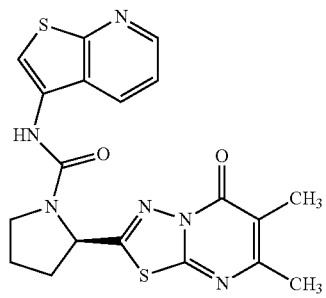 [SMILES: Cc1nc2sc([C@H]3CCCN3C(=O)Nc3csc4ncccc34)nn2c(=O)c1C]

The compound (150 mg) obtained in Reference Example 116 was treated by a method similar to that in Example 167 to give the title compound (10.5 mg).
MS (ESI) m/z; 427 [M+H]+

Example 176

2-(5-oxo-7-propyl-5H-[1,3,4]thiadiazolo[3,2-a]pyrimidin-2-yl)pyrazolidine-1-carboxylic acid phenyl ester

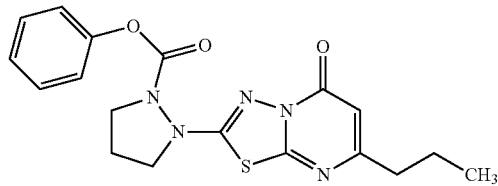 [SMILES: CCCc1cc(=O)n2nc(N3CCCN3C(=O)Oc3ccccc3)sc2n1]

To a solution (5.0 mL) of the compound (300 mg) obtained in Reference Example 122 in 1,4-dioxane were added N,N-diisopropylethylamine (0.76 mL) and pyrazolidine dihydrochloride (180 mg), and the mixture was stirred at room temperature for 1 hr. N,N-diisopropylethylamine (0.20 mL) and phenyl chloroformate (0.19 g) were added to the reaction mixture, and the reaction mixture was stirred at room temperature for 4 hr. After confirmation of the completion of the reaction, water and 1.0 mol/L hydrochloric acid were added, and the mixture was extracted twice with ethyl acetate. The organic layer was washed once with water, dried over anhydrous magnesium sulfate, filtered and concentrated. The residue was purified by silica gel column chromatography (solvent; ethyl acetate/methanol=100/0-95/5) and concentrated to give the title compound (210 mg).
MS (ESI) m/z; 386 [M+H]+

Example 177

(R)-2-[5-(4,4-difluorocyclohexyl)-7-oxo-6,7-dihydro[1,3]thiazolo[5,4-d]pyrimidin-2-yl]pyrrolidine-1-carboxylic acid 3-methylphenyl ester

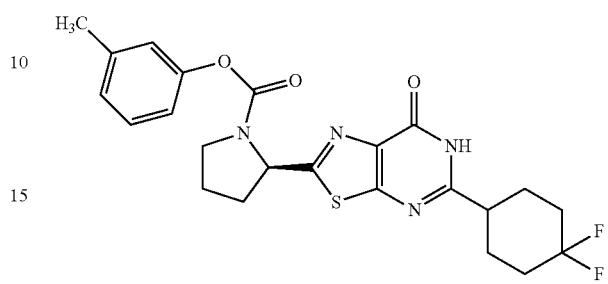

The compound (750 mg) obtained in Example 53 was treated is by a method similar to that in Example 86 to give the title compound (160 mg).
MS (ESI) m/z; 475 [M+H]+

Example 178

(R)-N-benzyl-1-(6-methyl-7-oxo-5-phenyl-6,7-dihydro[1,3]thiazolo[5,4-d]pyrimidin-2-yl)pyrrolidine-2-carboxamide

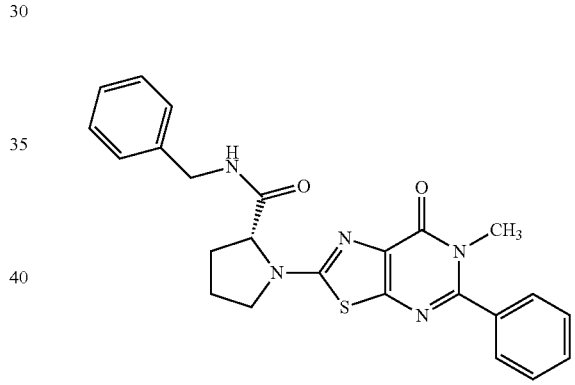

To a solution (350 mL) of the compound (35.0 g) obtained in Reference Example 268 in DMF were added (D)-proline (20.0 g) and cesium carbonate (86.2 g), and the reaction mixture was stirred with heating at 80° C. for 1 hr. The reaction mixture was cooled to room temperature, and acidified with 1.0 mol/L hydrochloric acid. Sodium chloride was added, and the mixture was extracted twice with chloroform. The organic layer was dried over anhydrous magnesium sulfate, and filtered. Chloroform was evaporated under reduced pressure from the filtrate, to the obtained mixture were added N,N-diisopropylethylamine (40 mL), benzylamine (24.6 g), EDC hydrochloride (44.1 g) and HOBt monohydrate (35.2 g), and the reaction mixture was stirred at room temperature overnight. Water was added, the mixture was extracted with ethyl acetate, and the organic layer was dried over anhydrous sodium sulfate, filtered and concentrated. The residue was purified by silica gel column chromatography (solvent; chloroform/methanol=100/0-90/10). To the obtained product was added ethyl acetate, and the solid was collected by filtration and dried to give the title compound (33.0 g).
MS (ESI) m/z; 446 [M+H]+

Example 179

(R)-N-benzyl-1-[5-(2-fluoropropan-2-yl)-6-methyl-7-oxo-6,7-dihydro-[1,3]thiazolo[5,4-d]pyrimidin-2-yl]pyrrolidine-2-carboxamide

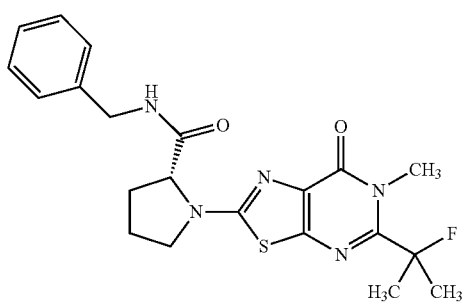 [SMILES: Cn1c(C(C)(C)F)nc2sc(N3CCC[C@@H]3C(=O)NCc3ccccc3)nc2c1=O]

The compound (157 mg) obtained in Reference Example 303 was treated by a method similar to that in Example 178 to give the title compound (170 mg).

MS (ESI) m/z; 430 [M+H]$^+$

Example 180

(R)-N-benzyl-1-(5, 6-dimethyl-7-oxo-6,7-dihydro-[1,3]thiazolo[5,4-d]pyrimidin-2-yl)pyrrolidine-2-carboxamide

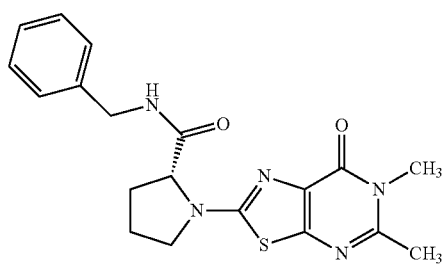 [SMILES: Cc1nc2sc(N3CCC[C@@H]3C(=O)NCc3ccccc3)nc2c(=O)n1C]

The compound (125 mg) obtained in Reference Example 305 was treated by a method similar to that in Example 178 to give the title compound (34 mg).

MS (ESI) m/z; 384 [M+H]$^+$

Example 181

(R)-N-benzyl-1-(5-ethyl-6-methyl-7-oxo-6,7-dihydro-[1,3]thiazolo[5,4-d]pyrimidin-2-yl)pyrrolidine-2-carboxamide

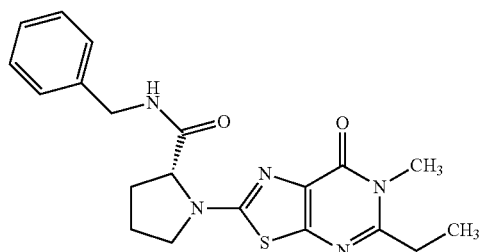

The compound (160 mg) obtained in Reference Example 304 was treated by a method similar to that in Example 178 to give the title compound (70 mg).

MS (ESI) m/z; 398 [M+H]$^+$

Example 182

(R)-1-(5-ethyl-6-methyl-7-oxo-6,7-dihydro-[1,3]thiazolo[5,4-d]pyrimidin-2-yl)-N-(2-fluorobenzyl)pyrrolidine-2-carboxamide

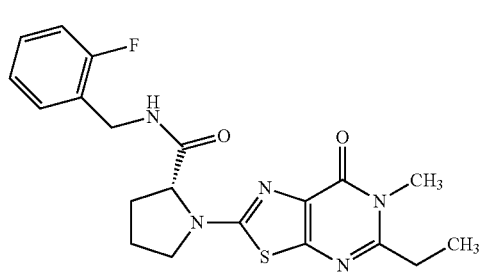 [SMILES: CCc1nc2sc(N3CCC[C@@H]3C(=O)NCc3ccccc3F)nc2c(=O)n1C]

The compound (337 mg) obtained in Reference Example 304 was treated by a method similar to that in Example 178 to give the title compound (450 mg).

MS (ESI) m/z; 416 [M+H]$^+$

Example 183

(R)-1-(5-ethyl-6-methyl-7-oxo-6,7-dihydro-[1,3]thiazolo[5,4-d]pyrimidin-2-yl)-N-(3-fluorobenzyl)pyrrolidine-2-carboxamide

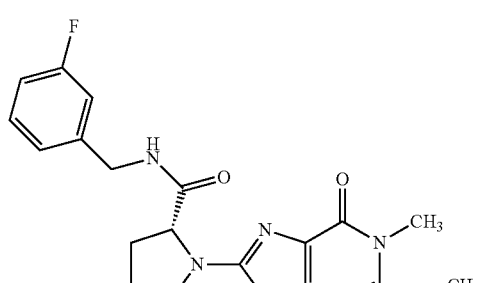

The compound (337 mg) obtained in Reference Example 304 was treated by a method similar to that in Example 178 to give the title compound (425 mg).
MS (ESI) m/z; 416 [M+H]+

Example 184

(R)-1-(5-ethyl-6-methyl-7-oxo-6,7-dihydro-[1,3]thiazolo[5,4-d]pyrimidin-2-yl)-N-(4-fluorobenzyl)pyrrolidine-2-carboxamide

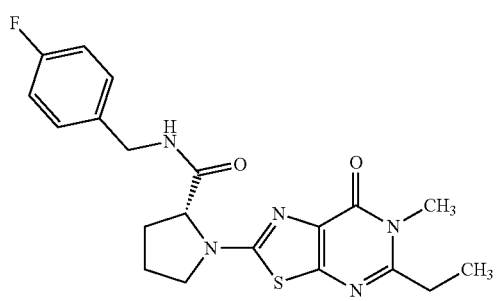 [SMILES: CCc1nc2sc(N3CCC[C@@H]3C(=O)NCc3ccc(F)cc3)nc2c(=O)n1C]

The compound (337 mg) obtained in Reference Example 304 was treated by a method similar to that in Example 178 to give the title compound (420 mg).
MS (ESI) m/z; 416 [M+H]+

Example 185

(R)-N-benzyl-1-(5,6-diethyl-7-oxo-6,7-dihydro-[1,3]thiazolo[5,4-d]pyrimidin-2-yl)pyrrolidine-2-carboxamide

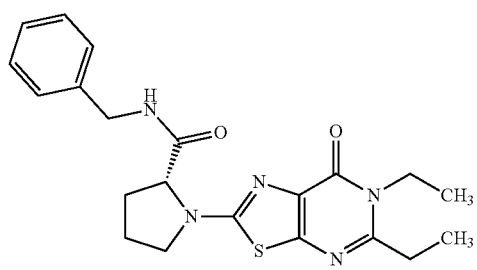 [SMILES: CCc1nc2sc(N3CCC[C@@H]3C(=O)NCc3ccccc3)nc2c(=O)n1CC]

The compound (839 mg) obtained in Reference Example 306 was treated by a method similar to that in Example 178 to give the title compound (659 mg).
MS (ESI) m/z; 412 [M+H]+

Example 186

(R)-N-benzyl-1-(6-cyclopropyl-5-methyl-7-oxo-6,7-dihydro-[1,3]thiazolo[5,4-d]pyrimidin-2-yl)pyrrolidine-2-carboxamide

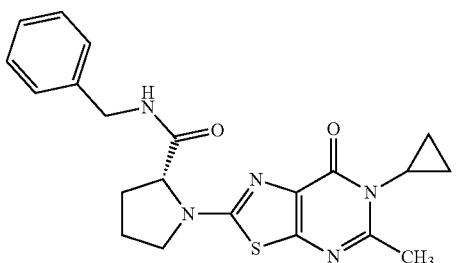

The compound (270 mg) obtained in Reference Example 307 was treated by a method similar to that in Example 178 to give the title compound (300 mg).
MS (ESI) m/z; 410 [M+H]+

Example 187

(R)-1-(6-cyclopropyl-5-methyl-7-oxo-6,7-dihydro-[1,3]thiazolo[5,4-d]pyrimidin-2-yl)-N-(2-fluorobenzyl)pyrrolidine-2-carboxamide

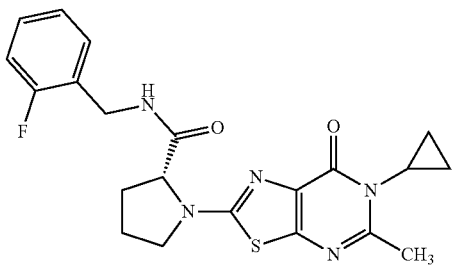 [SMILES: Cc1nc2sc(N3CCC[C@@H]3C(=O)NCc3ccccc3)nc2c(=O)n1C1CC1]

The compound (108 mg) obtained in Reference Example 307 was treated by a method similar to that in Example 178 to give the title compound (135 mg).
MS (ESI) m/z; 428 [M+H]+

Example 188

(R)-1-(6-cyclopropyl-5-methyl-7-oxo-6,7-dihydro-[1,3]thiazolo[5,4-d]pyrimidin-2-yl)-N-(3-fluorobenzyl)pyrrolidine-2-carboxamide

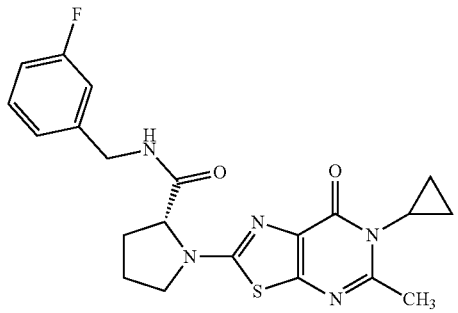 [SMILES: Cc1nc2sc(N3CCC[C@@H]3C(=O)NCc3cccc(F)c3)nc2c(=O)n1C1CC1]

The compound (108 mg) obtained in Reference Example 307 was treated by a method similar to that in Example 178 to give the title compound (135 mg).

MS (ESI) m/z; 428 [M+H]$^+$

Example 189

(R)-1-(6-cyclopropyl-5-methyl-7-oxo-6,7-dihydro-[1,3]thiazolo[5,4-d]pyrimidin-2-yl)-N-(4-fluorobenzyl)pyrrolidine-2-carboxamide

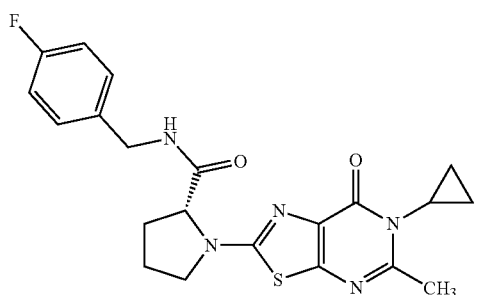

The compound (1.08 g) obtained in Reference Example 307 was treated by a method similar to that in Example 178 to give the title compound (875 mg).

MS (ESI) m/z; 428 [M+H]$^+$

Example 190

(R)-N-benzyl-1-(6-methyl-7-oxo-5-trifluoromethyl-6,7-dihydro-[1,3]thiazolo[5,4-d]pyrimidin-2-yl)pyrrolidine-2-carboxamide

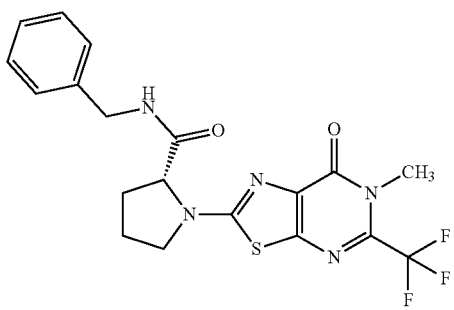 [SMILES: Cn1c(C(F)(F)F)nc2sc(N3CCC[C@@H]3C(=O)NCc3ccccc3)nc2c1=O]

The compound (120 mg) obtained in Reference Example 309 was treated by a method similar to that in Example 178 to give the title compound (85 mg).

MS (ESI) m/z; 438 [M+H]$^+$

Example 191

(R)-N-benzyl-1-[5-difluoromethyl-6-(2-methoxyethyl)-7-oxo-6,7-dihydro-[1,3]thiazolo[5,4-d]pyrimidin-2-yl]pyrrolidine-2-carboxamide

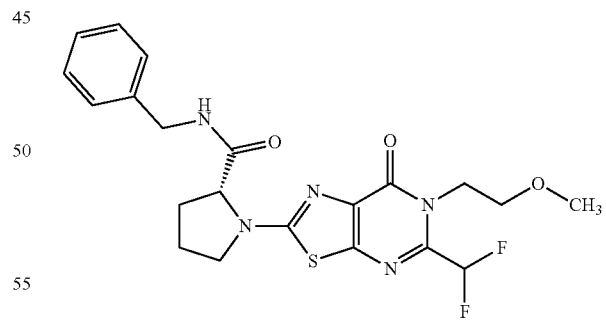

The compound (276 mg) obtained in Reference Example 313 was treated by a method similar to that in Example 178 to give the title compound (218 mg).

MS (ESI) m/z; 464 [M+H]$^+$

Example 192

(R)-N-benzyl-1-[5-difluoromethyl-7-oxo-6-(tetrahydro-2H-pyran-4-yl)-6,7-dihydro-[1,3]thiazolo[5,4-d]pyrimidin-2-yl]pyrrolidine-2-carboxamide

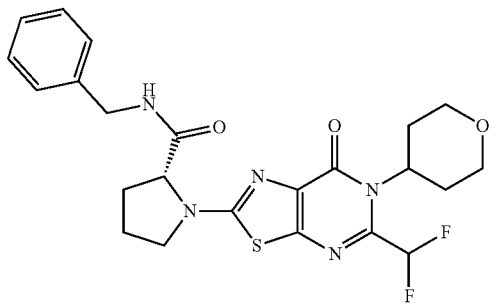 [SMILES: O=C(NCc1ccccc1)[C@H]1CCCN1c1nc2c(=O)n(C3CCOCC3)c(C(F)F)nc2s1]

The compound (254 mg) obtained in Reference Example 316 was treated by a method similar to that in Example 178 to give the title compound (73 mg).

MS (ESI) m/z; 490 [M+H]+

Example 193

(R)-1-[5-difluoromethyl-7-oxo-6-(tetrahydro-2H-pyran-4-yl)-6,7-dihydro-[1,3]thiazolo[5,4-d]pyrimidin-2-yl]-N-((R)-1-phenylethyl)pyrrolidine-2-carboxamide

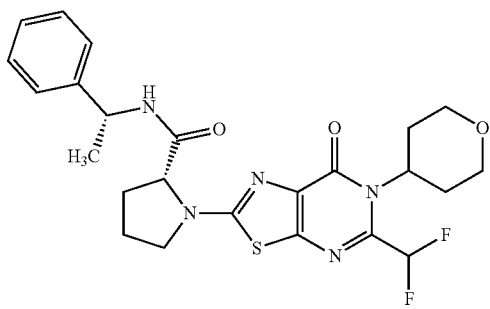 [SMILES: C[C@@H](NC(=O)[C@H]1CCCN1c1nc2c(=O)n(C3CCOCC3)c(C(F)F)nc2s1)c1ccccc1]

The compound (175 mg) obtained in Reference Example 316 was treated by a method similar to that in Example 178 to give the title compound (89 mg).

MS (ESI) m/z; 504 [M+H]+

Example 194

(R)-N-benzyl-1-[6-methyl-7-oxo-5-(pyridin-2-yl)-6,7-dihydro-[1,3]thiazolo[5,4-d]pyrimidin-2-yl]pyrrolidine-2-carboxamide

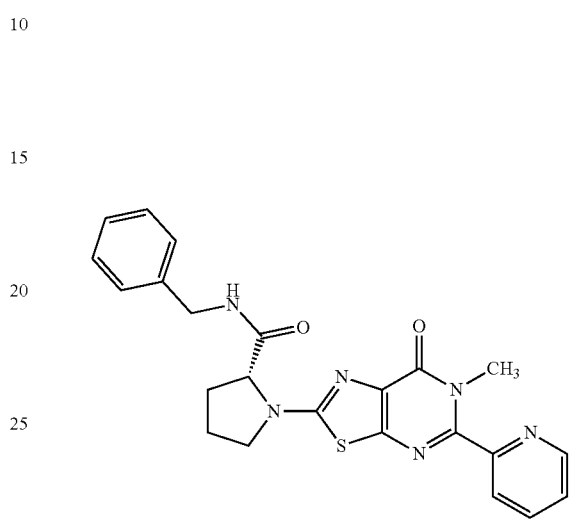

The compound (170 mg) obtained in Reference Example 326 was treated by a method similar to that in Example 178 to give the title compound (125 mg).

MS (ESI) m/z; 447 [M+H]+

Example 195

(R)-N-benzyl-1-(6-methyl-7-oxo-5-propyl-6,7-dihydro[1,3]thiazolo[5,4-d]pyrimidin-2-yl)pyrrolidine-2-carboxamide

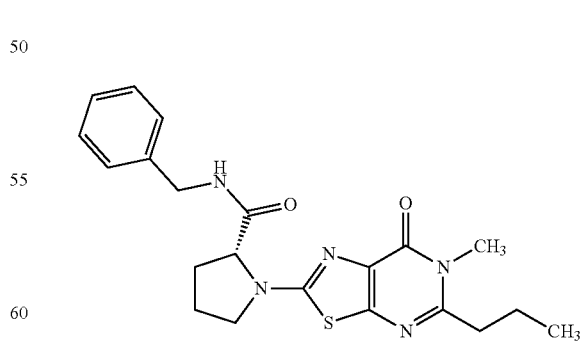

The compound (760 mg) obtained in Reference Example 333 was treated by a method similar to that in Example 178 to give the title compound (185 mg).

MS (ESI) m/z; 412 [M+H]+

Example 196

(R)-N-benzyl-1-[6-methyl-7-oxo-5-(propan-2-yl)-6,7-dihydro[1,3]thiazolo[5,4-d]pyrimidin-2-yl]pyrrolidine-2-carboxamide

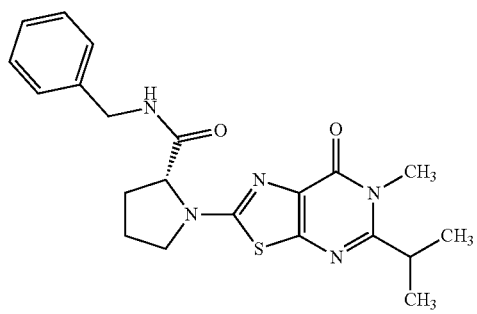 [SMILES: CC(C)c1nc2sc(N3CCC[C@@H]3C(=O)NCc3ccccc3)nc2c(=O)n1C]

The compound (1.96 g) obtained in Reference Example 334 was treated by a method similar to that in Example 178 to give the title compound (1.81 g).

MS (ESI) m/z; 412 [M+H]$^+$

Example 197

(R)-N-benzyl-1-(6-ethyl-5-methyl-7-oxo-6,7-dihydro[1,3]thiazolo[5,4-d]pyrimidin-2-yl)pyrrolidine-2-carboxamide

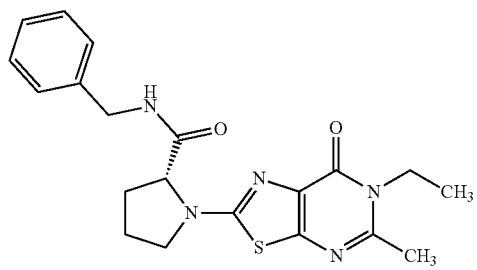 [SMILES: CCn1c(C)nc2sc(N3CCC[C@@H]3C(=O)NCc3ccccc3)nc2c1=O]

The compound (250 mg) obtained in Reference Example 335 was treated by a method similar to that in Example 178 to give the title compound (175 mg).

MS (ESI) m/z; 398 [M+H]$^+$

Example 198

(R)-N-benzyl-1-[5-methyl-7-oxo-6-(propan-2-yl)-6,7-dihydro[1,3]thiazolo[5,4-d]pyrimidin-2-yl]pyrrolidine-2-carboxamide

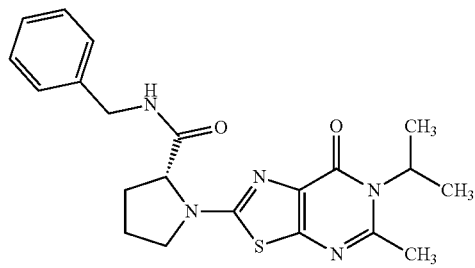 [SMILES: Cc1nc2sc(N3CCC[C@@H]3C(=O)NCc3ccccc3)nc2c(=O)n1C(C)C]

The compound (195 mg) obtained in Reference Example 336 was treated by a method similar to that in Example 178 to give the title compound (140 mg).

MS (ESI) m/z; 412 [M+H]$^+$

Example 199

(R)-N-benzyl-1-(6-cyclopentyl-5-methyl-7-oxo-6,7-dihydro[1,3]thiazolo[5,4-d]pyrimidin-2-yl)pyrrolidine-2-carboxamide

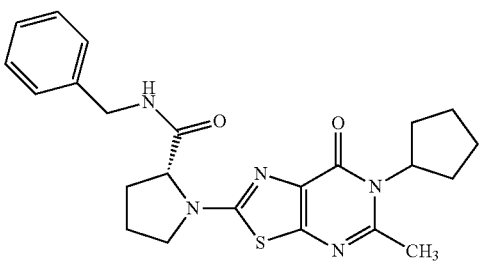 [SMILES: Cc1nc2sc(N3CCC[C@@H]3C(=O)NCc3ccccc3)nc2c(=O)n1C1CCCC1]

The compound (140 mg) obtained in Reference Example 337 was treated by a method similar to that in Example 178 to give the title compound (180 mg).

MS (ESI) m/z; 438 [M+H]$^+$

Example 200

(R)-N-benzyl-1-[5-methyl-7-oxo-6-(2,2,2-trifluoroethyl)-6,7-dihydro[1,3]thiazolo[5,4-d]pyrimidin-2-yl]pyrrolidine-2-carboxamide

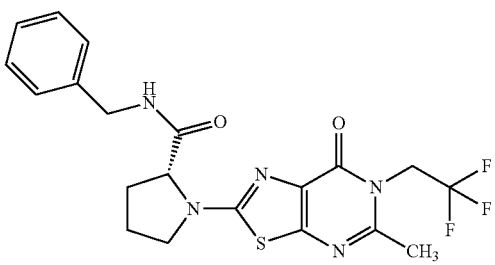 [SMILES: Cc1nc2sc(N3CCC[C@@H]3C(=O)NCc3ccccc3)nc2c(=O)n1CC(F)(F)F]

The compound (210 mg) obtained in Reference Example 338 was treated by a method similar to that in Example 178 to give the title compound (160 mg).
MS (ESI) m/z; 452 [M+H]$^+$ Example 201

(R)-N-benzyl-1-(5-methyl-7-oxo-6-phenyl-6,7-dihydro[1,3]thiazolo[5,4-d]pyrimidin-2-yl)pyrrolidine-2-carboxamide

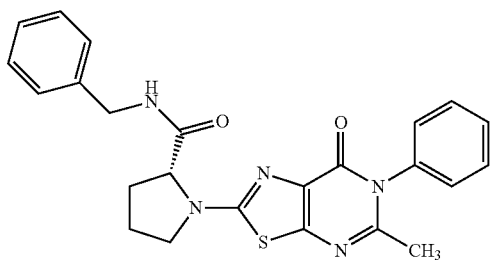 [SMILES: Cc1nc2sc(N3CCC[C@@H]3C(=O)NCc3ccccc3)nc2c(=O)n1-c1ccccc1]

The compound (215 mg) obtained in Reference Example 339 was treated by a method similar to that in Example 178 to give the title compound (230 mg).
MS (ESI) m/z; 446 [M+H]$^+$ Example 202

(R)-N-benzyl-1-[6-cyclopropyl-7-oxo-5-trifluoromethyl-6,7-dihydro[1,3]thiazolo[5,4-d]pyrimidin-2-yl]pyrrolidine-2-carboxamide

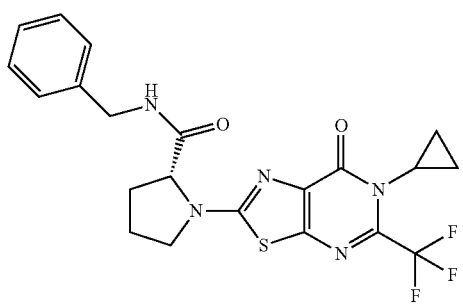 [SMILES: O=C(NCc1ccccc1)[C@H]1CCCN1c1nc2c(=O)n(C3CC3)c(C(F)(F)F)nc2s1]

The compound (320 mg) obtained in Reference Example 340 was treated by a method similar to that in Example 178 to give the title compound (300 mg).
MS (ESI) m/z; 464 [M+H]$^+$ Example 203

(R)-N-benzyl-1-[6-methyl-7-oxo-5-(2,4,6-trifluorophenyl)-6,7-dihydro[1,3]thiazolo[5,4-d]pyrimidin-2-yl]pyrrolidine-2-carboxamide

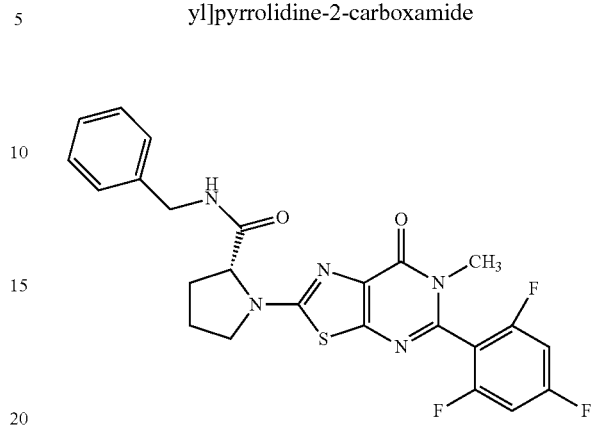

To a solution (5.0 mL) of the compound (249 mg) obtained in Reference Example 269 in DMF were added (D)-proline (119 mg) and potassium carbonate (380 mg), and the reaction mixture was stirred with heating at 80° C. for 3 hr. The reaction mixture was cooled to room temperature, and acidified with 1.0 mol/L hydrochloric acid. Sodium chloride was added, and the mixture was extracted twice with chloroform. The organic layer was dried over anhydrous sodium sulfate, and filtered. Chloroform was evaporated under reduced pressure from the filtrate, to the obtained mixture were added N,N-diisopropylethylamine (193 µL), benzylamine (150 µL), EDC hydrochloride (264 mg) and HOBt monohydrate (211 mg), and the reaction mixture was stirred at room temperature overnight. Water was added, and the mixture was extracted with ethyl acetate. The organic layer was dried over anhydrous sodium sulfate, filtered and concentrated. The residue was purified by silica gel column chromatography (solvent; ethyl acetate/methanol=100/0-90/10) to give the title compound (171 mg).
MS (ESI) m/z; 500 [M+H]$^+$ Example 204

(R)-N-benzyl-1-[5-(2,6-difluorophenyl)-6-methyl-7-oxo-6,7-dihydro[1,3]thiazolo[5,4-d]pyrimidin-2-yl]pyrrolidine-2-carboxamide

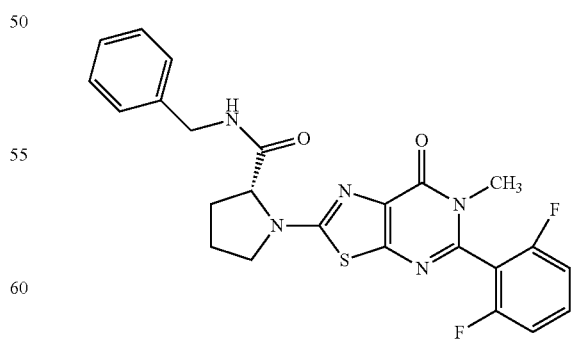

The compound (325 mg) obtained in Reference Example 270 was treated by a method similar to that in Example 203 to give the title compound (382 mg).
MS (ESI) m/z; 482 [M+H]$^+$

Example 205

(R)-N-benzyl-1-[5-methoxymethyl-7-oxo-6-(propan-2-yl)-6,7-dihydro[1,3]thiazolo[5,4-d]pyrimidin-2-yl]pyrrolidine-2-carboxamide

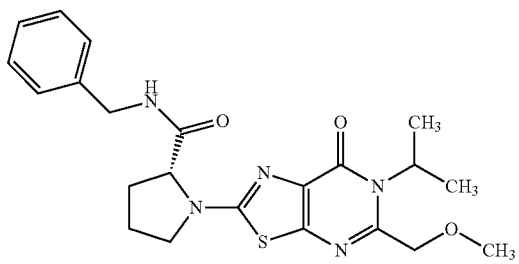 [SMILES: COCc1nc2sc(N3CCC[C@@H]3C(=O)NCc3ccccc3)nc2c(=O)n1C(C)C]

The compound (150 mg) obtained in Reference Example 272 was treated by a method similar to that in Example 203 to give the title compound (196 mg).
MS (ESI) m/z; 442 [M+H]+

Example 206

(R)-N-benzyl-1-[5-methyl-7-oxo-6-(tetrahydro-2H-pyran-4-yl)-6,7-dihydro[1,3]thiazolo[5,4-d]pyrimidin-2-yl]pyrrolidine-2-carboxamide

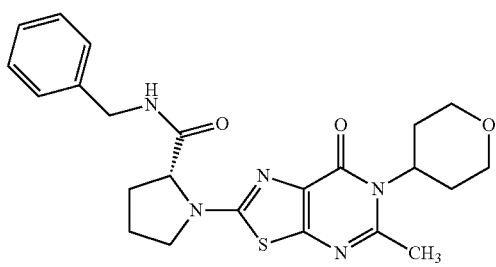 [SMILES: Cc1nc2sc(N3CCC[C@@H]3C(=O)NCc3ccccc3)nc2c(=O)n1C1CCOCC1]

The compound (350 mg) obtained in Reference Example 274 was treated by a method similar to that in Example 203 to give the title compound (200 mg).
MS (ESI) m/z; 454 [M+H]+

Example 207

(R)-N-benzyl-1-[6-(2-methoxy-2-methylpropyl)-5-methyl-7-oxo-6,7-dihydro[1,3]thiazolo[5,4-d]pyrimidin-2-yl]pyrrolidine-2-carboxamide

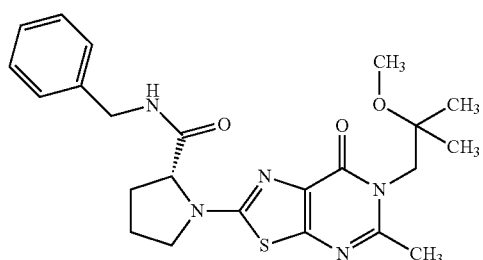

The compound (340 mg) obtained in Reference Example 275 was treated by a method similar to that in Example 203 to give the title compound (120 mg).
MS (ESI) m/z; 456 [M+H]+

Example 208

(R)-1-[5-(1,1-difluoro-2-methoxyethyl)-6-methyl-7-oxo-6,7-dihydro[1,3]thiazolo[5,4-d]pyrimidin-2-yl]-N-((R)-1-phenylethyl)pyrrolidine-2-carboxamide

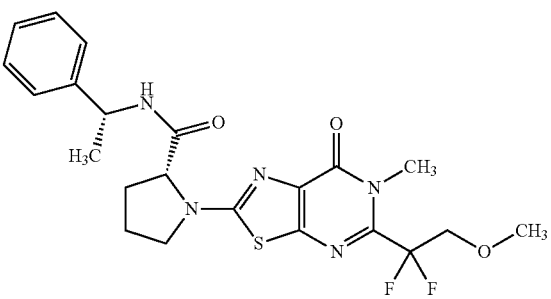 [SMILES: COCC(F)(F)c1nc2sc(N3CCC[C@@H]3C(=O)N[C@H](C)c3ccccc3)nc2c(=O)n1C]

The compound (84 mg) obtained in Reference Example 282 was treated by a method similar to that in Example 203 to give the title compound (87 mg).
MS (ESI) m/z; 478 [M+H]+

Example 209

(R)-N-benzyl-1-[6-methyl-5-(5-methyl-1,2,4-oxadiazol-3-yl)-7-oxo-6,7-dihydro[1,3]thiazolo[5,4-d]pyrimidin-2-yl]pyrrolidine-2-carboxamide

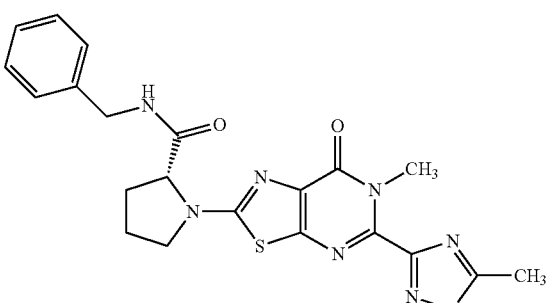

The compound (217 mg) obtained in Reference Example 285 was treated by a method similar to that in Example 203 to give the title compound (170 mg).
MS (ESI) m/z; 452 [M+H]+

Example 210

(R)-N-benzyl-1-[6-methyl-5-(5-methyl-1,3,4-oxadiazol-2-yl)-7-oxo-6,7-dihydro[1,3]thiazolo[5,4-d]pyrimidin-2-yl]pyrrolidine-2-carboxamide

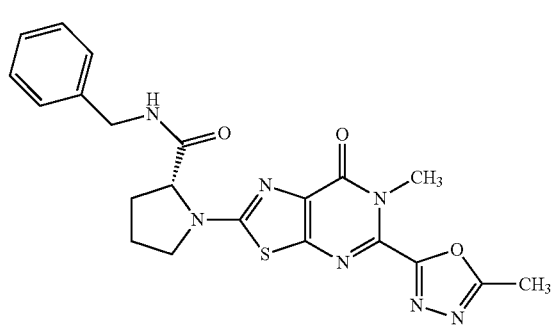 [SMILES: Cc1nnc(-c2nc3sc(N4CCC[C@@H]4C(=O)NCc4ccccc4)nc3c(=O)n2C)o1]

The compound (283 mg) obtained in Reference Example 286 was treated by a method similar to that in Example 203 to give the title compound (130 mg).
MS (ESI) m/z; 452 [M+H]+

Example 211

(R)-N-benzyl-1-[6-methyl-5-(3-methyl-1,2,4-oxadiazol-5-yl)-7-oxo-6,7-dihydro[1,3]thiazolo[5,4-d]pyrimidin-2-yl]pyrrolidine-2-carboxamide

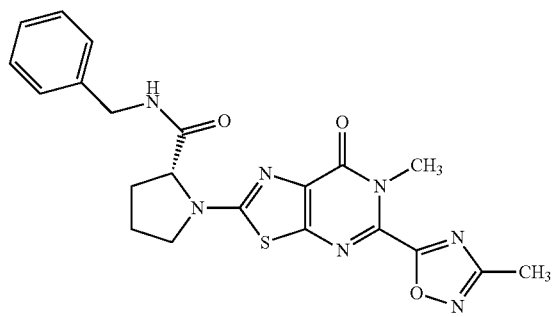 [SMILES: Cc1noc(-c2nc3sc(N4CCC[C@@H]4C(=O)NCc4ccccc4)nc3c(=O)n2C)n1]

The compound (160 mg) obtained in Reference Example 287 was treated by a method similar to that in Example 203 to give the title compound (114 mg).
MS (ESI) m/z; 452 [M+H]+

Example 212

(R)-1-[6-methyl-5-(3-methyl-[1,2,4]oxadiazol-5-yl)-7-oxo-6,7-dihydro[1,3]thiazolo[5,4-d]pyrimidin-2-yl]-N-((R)-1-phenylethyl)pyrrolidine-2-carboxamide

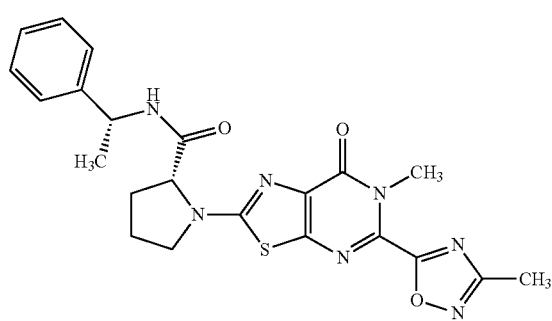 [SMILES: Cc1noc(-c2nc3sc(N4CCC[C@@H]4C(=O)N[C@H](C)c4ccccc4)nc3c(=O)n2C)n1]

The compound (133 mg) obtained in Reference Example 287 was treated by a method similar to that in Example 203 to give the title compound (159 mg).
MS (ESI) m/z; 466 [M+H]+

Example 213

(R)-N-(4-fluorobenzyl)-1-[6-methyl-5-(3-methyl-[1,2,4]oxadiazol-5-yl)-7-oxo-6,7-dihydro[1,3]thiazolo[5,4-d]pyrimidin-2-yl]pyrrolidine-2-carboxamide

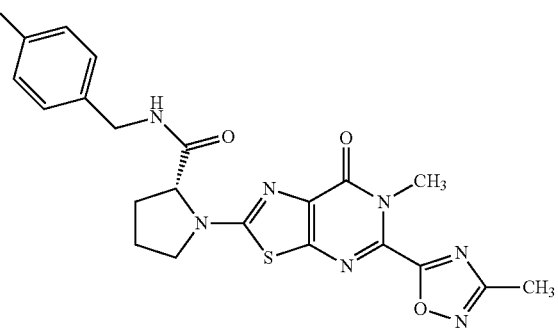

The compound (133 mg) obtained in Reference Example 287 was treated by a method similar to that in Example 203 to give the title compound (171 mg).
MS (ESI) m/z; 470 [M+H]+

Example 214

(R)-N-[(R)-1-(4-fluorophenyl)ethyl]-1-[6-methyl-5-(3-methyl-[1,2,4]oxadiazol-5-yl)-7-oxo-6,7-dihydro[1,3]thiazolo[5,4-d]pyrimidin-2-yl]pyrrolidine-2-carboxamide

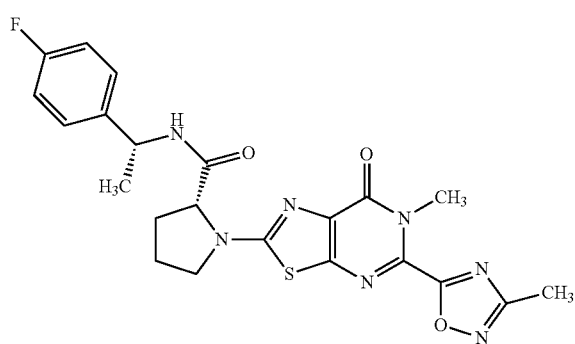 [SMILES: Cc1noc(-c2nc3sc(N4CCC[C@@H]4C(=O)N[C@H](C)c4ccc(F)cc4)nc3c(=O)n2C)n1]

The compound (133 mg) obtained in Reference Example 287 was treated by a method similar to that in Example 203 to give the title compound (177 mg).

MS (ESI) m/z; 484 [M+H]$^+$

Example 215

(R)-N-benzyl-1-[6-ethyl-5-(3-methyl-[1,2,4]oxadiazol-5-yl)-7-oxo-6,7-dihydro[1,3]thiazolo[5,4-d]pyrimidin-2-yl]pyrrolidine-2-carboxamide

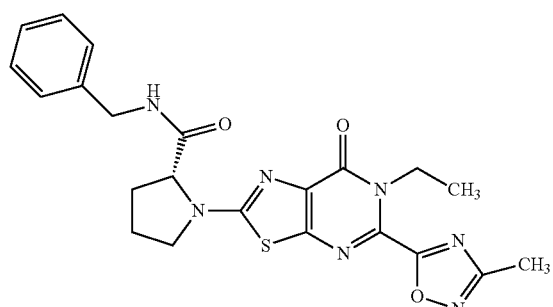

The compound (300 mg) obtained in Reference Example 288 was treated by a method similar to that in Example 203 to give the title compound (280 mg).

MS (ESI) m/z; 466 [M+H]$^+$

Example 216

(R)-1-[6-ethyl-5-(3-methyl-[1,2,4]oxadiazol-5-yl)-7-oxo-6,7-dihydro[1,3]thiazolo[5,4-d]pyrimidin-2-yl]-N-((R)-1-phenylethyl)pyrrolidine-2-carboxamide

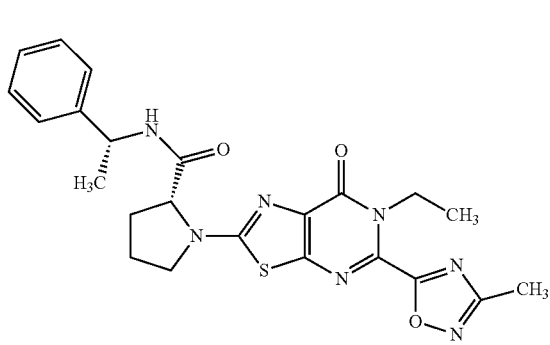 [SMILES: CCn1c(-c2nc(C)no2)nc2sc(N3CCC[C@@H]3C(=O)N[C@H](C)c3ccccc3)nc2c1=O]

The compound (160 mg) obtained in Reference Example 288 was treated by a method similar to that in Example 203 to give the title compound (170 mg).

MS (ESI) m/z; 480 [M+H]$^+$

Example 217

(R)-1-[6-ethyl-5-(3-methyl-[1,2,4]oxadiazol-5-yl)-7-oxo-6,7-dihydro[1,3]thiazolo[5,4-d]pyrimidin-2-yl]-N-(4-fluorobenzyl)pyrrolidine-2-carboxamide

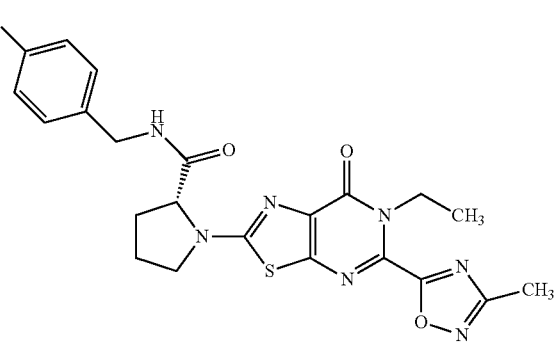

The compound (160 mg) obtained in Reference Example 288 was treated by a method similar to that in Example 203 to give the title compound (180 mg).

MS (ESI) m/z; 484 [M+H]$^+$

Example 218

(R)-1-[6-ethyl-5-(3-methyl-[1,2,4]oxadiazol-5-yl)-7-oxo-6,7-dihydro[1,3]thiazolo[5,4-d]pyrimidin-2-yl]-N-((R)-1-phenylethyl)-azetidine-2-carboxamide

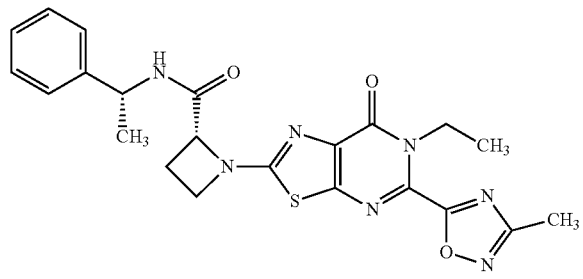 [SMILES: CCn1c(-c2nc(C)no2)nc2sc(N3CC[C@@H]3C(=O)N[C@H](C)c3ccccc3)nc2c1=O]

The compound (200 mg) obtained in Reference Example 288 was treated by a method similar to that in Example 203 to give the title compound (156 mg).

MS (ESI) m/z; 466 [M+H]$^+$

Example 219

(R)-N-benzyl-1-[5-(3-methyl-1,2,4-oxadiazol-5-yl)-7-oxo-6-(propan-2-yl)-6,7-dihydro[1,3]thiazolo[5,4-d]pyrimidin-2-yl]pyrrolidine-2-carboxamide

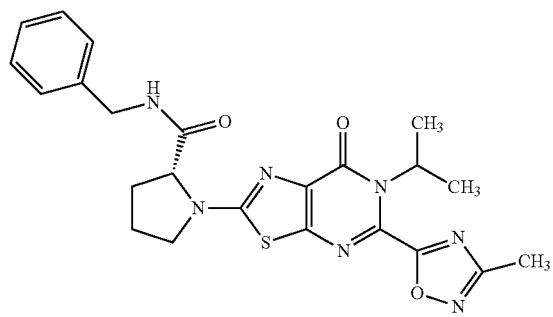 [SMILES: Cc1noc(-c2nc3sc(N4CCC[C@@H]4C(=O)NCc4ccccc4)nc3c(=O)n2C(C)C)n1]

The compound (170 mg) obtained in Reference Example 289 was treated by a method similar to that in Example 203 to give the title compound (213 mg).

MS (ESI) m/z; 480 [M+H]$^+$

Example 220

(R)-N-benzyl-1-[6-cyclopropyl-5-(3-methyl-1,2,4-oxadiazol-5-yl)-7-oxo-6,7-dihydro[1,3]thiazolo[5,4-d]pyrimidin-2-yl]pyrrolidine-2-carboxamide

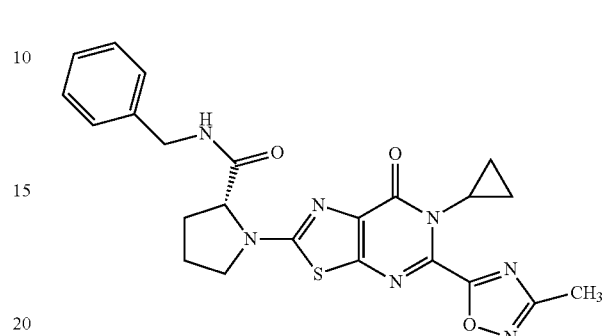

The compound (240 mg) obtained in Reference Example 290 was treated by a method similar to that in Example 203 to give the title compound (240 mg).

MS (ESI) m/z; 478 [M+H]$^+$

Example 221

(R)-N-benzyl-1-[6-(2,2-difluoroethyl)-5-(3-methyl-1,2,4-oxadiazol-5-yl)-7-oxo-6,7-dihydro[1,3]thiazolo[5,4-d]pyrimidin-2-yl]pyrrolidine-2-carboxamide

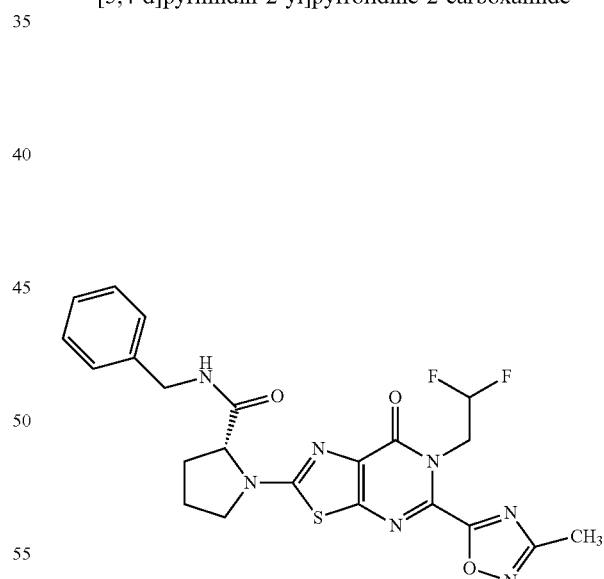

The compound (170 mg) obtained in Reference Example 291 was treated by a method similar to that in Example 203 to give the title compound (197 mg).

MS (ESI) m/z; 502 [M+H]$^+$

Example 222

(R)-N-benzyl-1-[6-(2-methoxyethyl)-5-(3-methyl-1,2,4-oxadiazol-5-yl)-7-oxo-6,7-dihydro[1,3]thiazolo[5,4-d]pyrimidin-2-yl]pyrrolidine-2-carboxamide

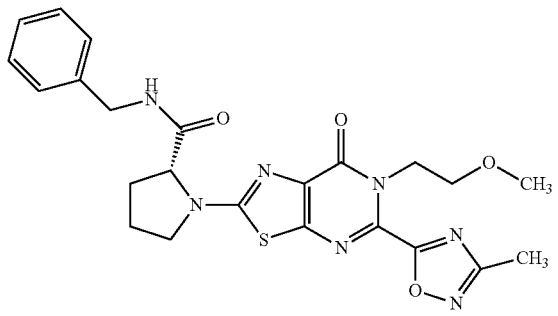 [SMILES: COCCn1c(-c2nc(C)no2)nc2sc(N3CCC[C@@H]3C(=O)NCc3ccccc3)nc2c1=O]

The compound (300 mg) obtained in Reference Example 292 was treated by a method similar to that in Example 203 to give the title compound (280 mg).

MS (ESI) m/z; 496 [M+H]$^+$

Example 223

(R)-N-benzyl-1-[5-(3-methyl-1,2,4-oxadiazol-5-yl)-7-oxo-6-(tetrahydro-2H-pyran-4-yl)-6,7-dihydro[1,3]thiazolo[5,4-d]pyrimidin-2-yl]pyrrolidine-2-carboxamide

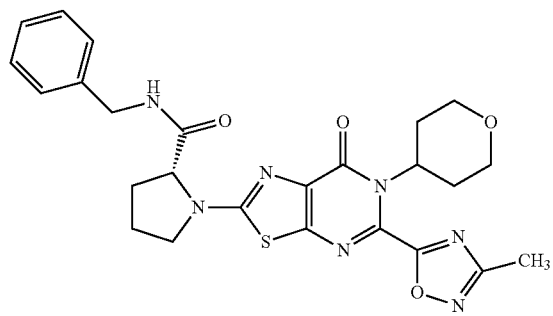 [SMILES: Cc1noc(-c2nc3sc(N4CCC[C@@H]4C(=O)NCc4ccccc4)nc3c(=O)n2C2CCOCC2)n1]

The compound (320 mg) obtained in Reference Example 293 was treated by a method similar to that in Example 203 to give the title compound (305 mg).

MS (ESI) m/z; 522 [M+H]$^+$

Example 224

(R)-N-benzyl-1-{6-[1-(methoxymethyl)cyclopropyl]-5-methyl-7-oxo-6,7-dihydro[1,3]thiazolo[5,4-d]pyrimidin-2-yl}pyrrolidine-2-carboxamide

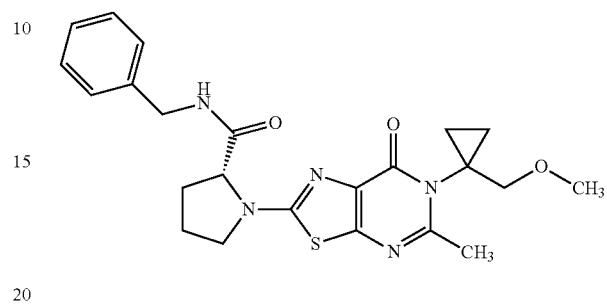

The compound (340 mg) obtained in Reference Example 296 was treated by a method similar to that in Example 203 to give the title compound (190 mg).

MS (ESI) m/z; 454 [M+H]$^+$

Example 225

(R)-N-benzyl-1-[5-(1-cyanocyclobutyl)-6-methyl-7-oxo-6,7-dihydro[1,3]thiazolo[5,4-d]pyrimidin-2-yl]pyrrolidine-2-carboxamide

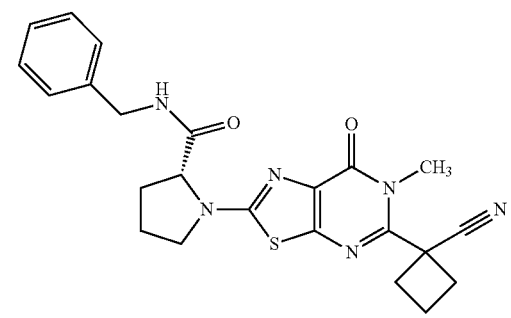 [SMILES: Cn1c(C2(C#N)CCC2)nc2sc(N3CCC[C@@H]3C(=O)NCc3ccccc3)nc2c1=O]

The compound (282 mg) obtained in Reference Example 298 was treated by a method similar to that in Example 203 to give the title compound (304 mg).

MS (ESI) m/z; 449 [M+H]$^+$

Example 226

(R)-N-benzyl-1-[5-(2-methoxypropan-2-yl)-6-methyl-7-oxo-6,7-dihydro[1,3]thiazolo[5,4-d]pyrimidin-2-yl]pyrrolidine-2-carboxamide

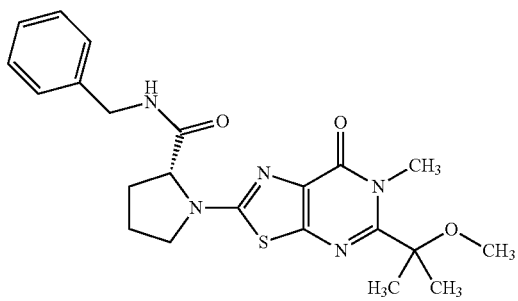 [SMILES: COC(C)(C)c1nc2sc(N3CCC[C@@H]3C(=O)NCc3ccccc3)nc2c(=O)n1C]

The compound (130 mg) obtained in Reference Example 299 was treated by a method similar to that in Example 203 to give the title compound (101 mg).
MS (ESI) m/z; 442 [M+H]$^+$

Example 227

(R)-N-benzyl-1-{6-[(3-methyloxetan-3-yl)methyl]-7-oxo-5-trifluoromethyl-6,7-dihydro[1,3]thiazolo[5,4-d]pyrimidin-2-yl}pyrrolidine-2-carboxamide

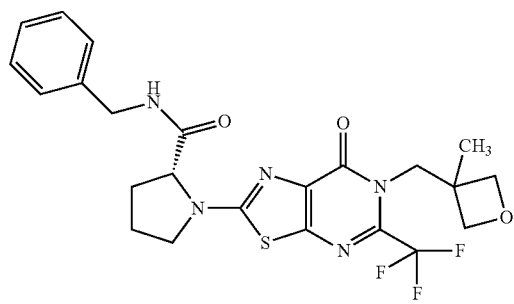 [SMILES: CC1(Cn2c(C(F)(F)F)nc3sc(N4CCC[C@@H]4C(=O)NCc4ccccc4)nc3c2=O)COC1]

The compound (270 mg) obtained in Reference Example 300 was treated by a method similar to that in Example 203 to give the title compound (120 mg).
MS (ESI) m/z; 508 [M+H]$^+$

Example 228

(R)-N-benzyl-1-(5-cyclopropyl-6-methyl-7-oxo-6,7-dihydro[1,3]thiazolo[5,4-d]pyrimidin-2-yl)pyrrolidine-2-carboxamide

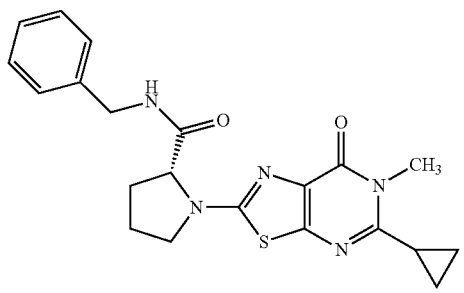 [SMILES: Cn1c(C2CC2)nc2sc(N3CCC[C@@H]3C(=O)NCc3ccccc3)nc2c1=O]

The compound (2.00 g) obtained in Reference Example 301 was treated by a method similar to that in Example 203 to give the title compound (2.35 g).
MS (ESI) m/z; 410 [M+H]$^+$

Example 229

(R)-1-(5,6-dimethyl-7-oxo-6,7-dihydro-[1,3]thiazolo[5,4-d]pyrimidin-2-yl)-N-(2-methylbenzyl)pyrrolidine-2-carboxamide

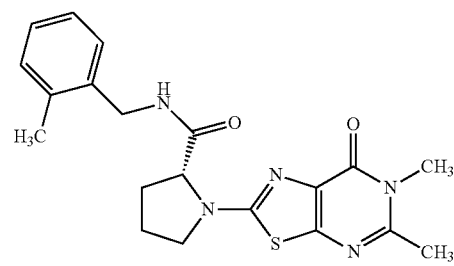 [SMILES: Cc1ccccc1CNC(=O)[C@H]1CCCN1c1nc2c(=O)n(C)c(C)nc2s1]

The compound (250 mg) obtained in Reference Example 305 was treated by a method similar to that in Example 203 to give the title compound (277 mg).
MS (ESI) m/z; 398 [M+H]$^+$

Example 230

(R)-1-(5-ethyl-6-methyl-7-oxo-6,7-dihydro-[1,3]thiazolo[5,4-d]pyrimidin-2-yl)-N-((R)-1-phenylethyl)pyrrolidine-2-carboxamide

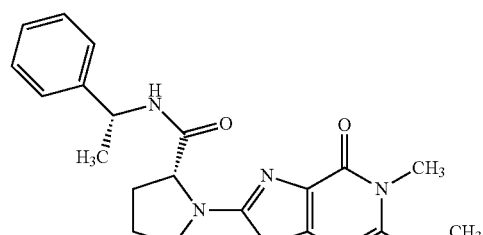

The compound (300 mg) obtained in Reference Example 304 was treated by a method similar to that in Example 203 to give the title compound (290 mg).
MS (ESI) m/z; 412 [M+H]$^+$ Example 231

(R)-1-(5-ethyl-6-methyl-7-oxo-6,7-dihydro-[1,3]thiazolo[5,4-d]pyrimidin-2-yl)-N-((S)-1-phenylethyl)pyrrolidine-2-carboxamide

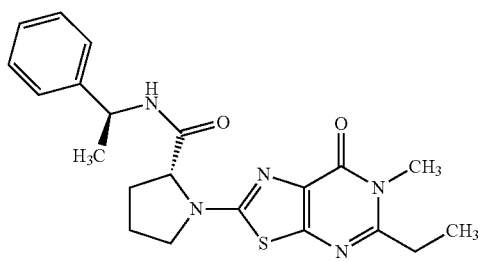 [SMILES: CCc1nc2sc(N3CCC[C@@H]3C(=O)N[C@@H](C)c3ccccc3)nc2c(=O)n1C]

The compound (300 mg) obtained in Reference Example 304 was treated by a method similar to that in Example 203 to give the title compound (283 mg).
MS (ESI) m/z; 412 [M+H]$^+$ Example 232

(R)-N-benzyl-2-{[N'-(5-ethyl-6-methyl-7-oxo-6,7-dihydro-[1,3]thiazolo[5,4-d]pyrimidin-2-yl)-N'-methyl]amino}propionamide

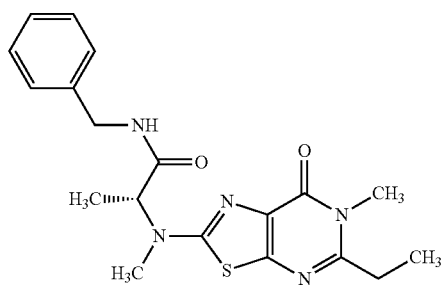 [SMILES: CCc1nc2sc(N(C)[C@H](C)C(=O)NCc3ccccc3)nc2c(=O)n1C]

The compound (300 mg) obtained in Reference Example 304 was treated by a method similar to that in Example 203 to give the title compound (33 mg).
MS (ESI) m/z; 386 [M+H]$^+$ Example 233

(R)-N-benzyl-1-(5-ethyl-6-methyl-7-oxo-6,7-dihydro-[1,3]thiazolo[5,4-d]pyrimidin-2-yl)azetidine-2-carboxamide

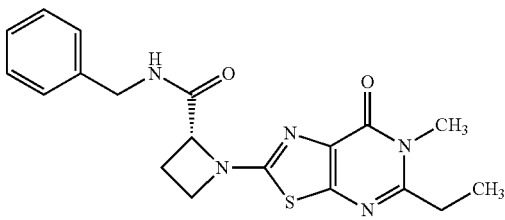 [SMILES: CCc1nc2sc(N3CC[C@@H]3C(=O)NCc3ccccc3)nc2c(=O)n1C]

The compound (250 mg) obtained in Reference Example 304 was treated by a method similar to that in Example 203 to give the title compound (307 mg).
MS (ESI) m/z; 384 [M+H]$^+$ Example 234

(R)-N-benzyl-1-(5-ethyl-6-methyl-7-oxo-6,7-dihydro-[1,3]thiazolo[5,4-d]pyrimidin-2-yl)piperidine-2-carboxamide

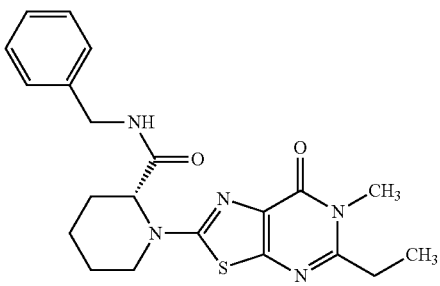 [SMILES: CCc1nc2sc(N3CCCC[C@@H]3C(=O)NCc3ccccc3)nc2c(=O)n1C]

The compound (800 mg) obtained in Reference Example 304 was treated by a method similar to that in Example 203 to give the title compound (59 mg).
MS (ESI) m/z; 412 [M+H]$^+$ Example 235

(R)-1-(5-ethyl-6-methyl-7-oxo-6,7-dihydro-[1,3]thiazolo[5,4-d]pyrimidin-2-yl)-N-(2-methylbenzyl)piperidine-2-carboxamide

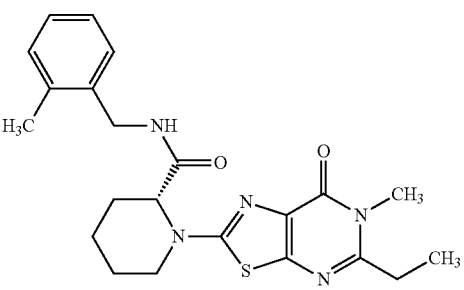 [SMILES: CCc1nc2sc(N3CCCC[C@@H]3C(=O)NCc3ccccc3C)nc2c(=O)n1C]

213

The compound (353 mg) obtained in Reference Example 304 was treated by a method similar to that in Example 203 to give the title compound (114 mg).

MS (ESI) m/z; 426 [M+H]$^+$

Example 236

(R)-N-benzyl-1-(5,6-diethyl-7-oxo-6,7-dihydro-[1,3]thiazolo[5,4-d]pyrimidin-2-yl)piperidine-2-carboxamide

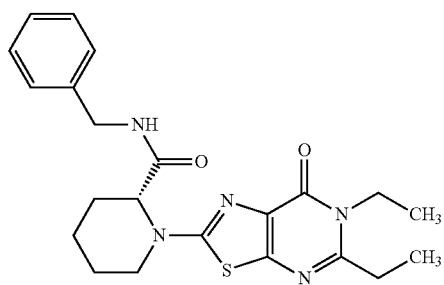 [SMILES: CCc1nc2sc(N3CCCC[C@@H]3C(=O)NCc3ccccc3)nc2c(=O)n1CC]

The compound (350 mg) obtained in Reference Example 306 was treated by a method similar to that in Example 203 to give the title compound (57 mg).

MS (ESI) m/z; 426 [M+H]$^+$

Example 237

(R)-1-(6-cyclopropyl-5-methyl-6,7-dihydro-[1,3]thiazolo[5,4-d]pyrimidin-2-yl)-N-(2-methylbenzyl)pyrrolidine-2-carboxamide

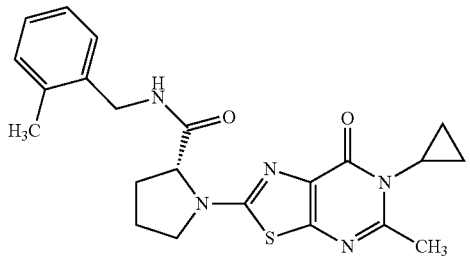 [SMILES: Cc1ccccc1CNC(=O)[C@H]1CCCN1c1nc2c(=O)n(C3CC3)c(C)nc2s1]

The compound (368 mg) obtained in Reference Example 307 was treated by a method similar to that in Example 203 to give the title compound (169 mg).

MS (ESI) m/z; 424 [M+H]$^+$

214

Example 238

(R)-N-benzyl-1-(6-cyclopentyl-7-oxo-6,7-dihydro-[1,3]thiazolo[5,4-d]pyrimidin-2-yl)pyrrolidine-2-carboxamide

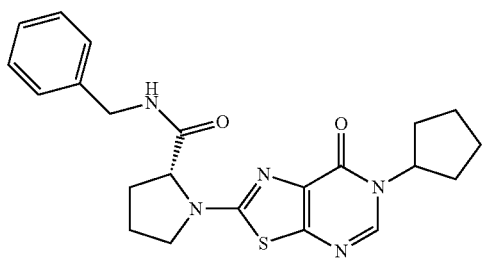 [SMILES: O=C(NCc1ccccc1)[C@H]1CCCN1c1nc2c(=O)n(C3CCCC3)cnc2s1]

The compound (300 mg) obtained in Reference Example 308 was treated by a method similar to that in Example 203 to give the title compound (340 mg).

MS (ESI) m/z; 424 [M+H]$^+$

Example 239

(R)-N-benzyl-1-(6-methyl-7-oxo-5-trifluoromethyl-6,7-dihydro-[1,3]thiazolo[5,4-d]pyrimidin-2-yl)piperidine-2-carboxamide

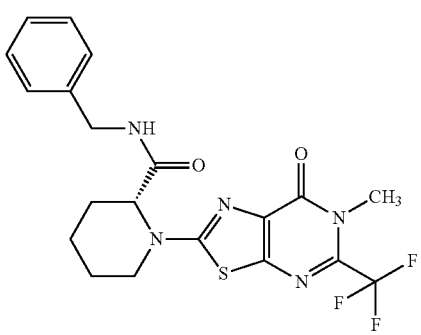 [SMILES: Cn1c(C(F)(F)F)nc2sc(N3CCCC[C@@H]3C(=O)NCc3ccccc3)nc2c1=O]

The compound (350 mg) obtained in Reference Example 309 was treated by a method similar to that in Example 203 to give the title compound (104 mg).

MS (ESI) m/z; 452 [M+H]$^+$

Example 240

(R)-N-benzyl-1-(6-ethyl-7-oxo-5-trifluoromethyl-6,7-dihydro-[1,3]thiazolo[5,4-d]pyrimidin-2-yl)pyrrolidine-2-carboxamide

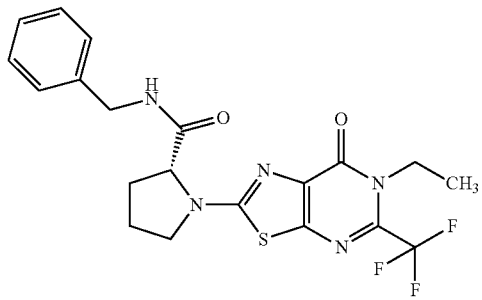 [SMILES: CCn1c(C(F)(F)F)nc2sc(N3CCC[C@@H]3C(=O)NCc3ccccc3)nc2c1=O]

The compound (250 mg) obtained in Reference Example 311 was treated by a method similar to that in Example 203 to give the title compound (256 mg).

MS (ESI) m/z; 452 [M+H]$^+$

Example 241

(R)-N-benzyl-1-[6-(2-methoxyethyl)-7-oxo-5-trifluoromethyl-6,7-dihydro-[1,3]thiazolo[5,4-d]pyrimidin-2-yl]pyrrolidine-2-carboxamide

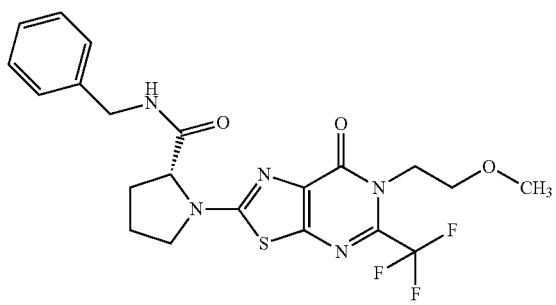 [SMILES: COCCn1c(C(F)(F)F)nc2sc(N3CCC[C@@H]3C(=O)NCc3ccccc3)nc2c1=O]

The compound (6.10 g) obtained in Reference Example 312 was treated by a method similar to that in Example 203 to give the title compound (5.30 g).

MS (ESI) m/z; 482 [M+H]$^+$

Example 242

(R)-1-[6-(2-methoxyethyl)-7-oxo-5-trifluoromethyl-6,7-dihydro-[1,3]thiazolo[5,4-d]pyrimidin-2-yl]-N-((R)-1-phenylethyl)pyrrolidine-2-carboxamide

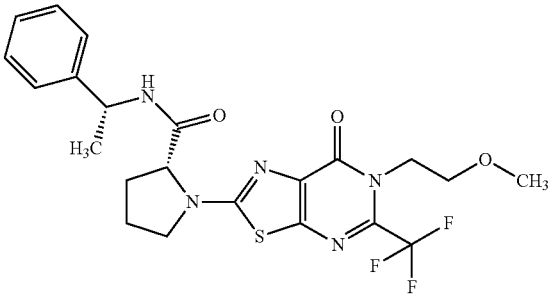 [SMILES: COCCn1c(C(F)(F)F)nc2sc(N3CCC[C@@H]3C(=O)N[C@H](C)c3ccccc3)nc2c1=O]

The compound (91 mg) obtained in Reference Example 312 was treated by a method similar to that in Example 203 to give the title compound (71 mg).

MS (ESI) m/z; 496 [M+H]$^+$

Example 243

(R)-N-benzyl-1-{6-[1-(methoxymethyl)cyclopropyl]-7-oxo-5-trifluoromethyl-6,7-dihydro-[1,3]thiazolo[5,4-d]pyrimidin-2-yl}pyrrolidine-2-carboxamide

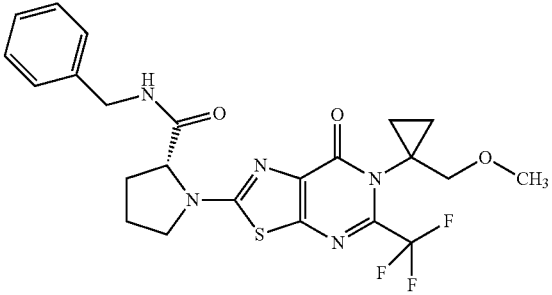 [SMILES: COCC1(n2c(C(F)(F)F)nc3sc(N4CCC[C@@H]4C(=O)NCc4ccccc4)nc3c2=O)CC1]

The compound (210 mg) obtained in Reference Example 314 was treated by a method similar to that in Example 203 to give the title compound (195 mg).

MS (ESI) m/z; 508 [M+H]$^+$

Example 244

(R)-N-benzyl-1-[7-oxo-6-(tetrahydro-2H-pyran-4-yl)-5-trifluoromethyl-6,7-dihydro-[1,3]thiazolo[5,4-d]pyrimidin-2-yl]pyrrolidine-2-carboxamide

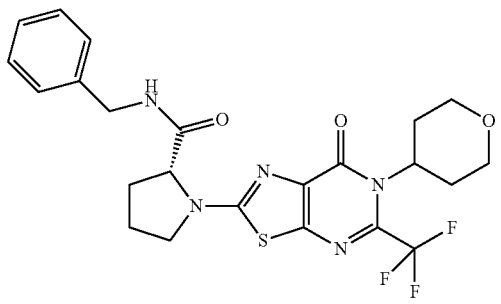 [SMILES: O=C(NCc1ccccc1)[C@H]1CCCN1c1nc2c(=O)n(C3CCOCC3)c(C(F)(F)F)nc2s1]

The compound (6.04 g) obtained in Reference Example 315 was treated by a method similar to that in Example 203 to give the title compound (6.51 g).
MS (ESI) m/z; 508 [M+H]$^+$

Example 245

(R)-N-1-[7-oxo-6-(tetrahydro-2H-pyran-4-yl)-5-trifluoromethyl-6,7-dihydro-[1,3]thiazolo[5,4-d]pyrimidin-2-yl]-N-((R)-1-phenylethyl)pyrrolidine-2-carboxamide

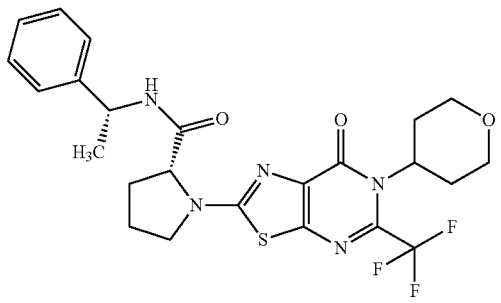 [SMILES: C[C@@H](NC(=O)[C@H]1CCCN1c1nc2c(=O)n(C3CCOCC3)c(C(F)(F)F)nc2s1)c1ccccc1]

The compound (12.0 g) obtained in Reference Example 315 was treated by a method similar to that in Example 203 to give the title compound (9.09 g).
MS (ESI) m/z; 522 [M+H]$^+$

Example 246

(R)-N-(4-fluorobenzyl)-1-[7-oxo-6-(tetrahydro-2H-pyran-4-yl)-5-trifluoromethyl-6,7-dihydro-[1,3]thiazolo[5,4-d]pyrimidin-2-yl]pyrrolidine-2-carboxamide

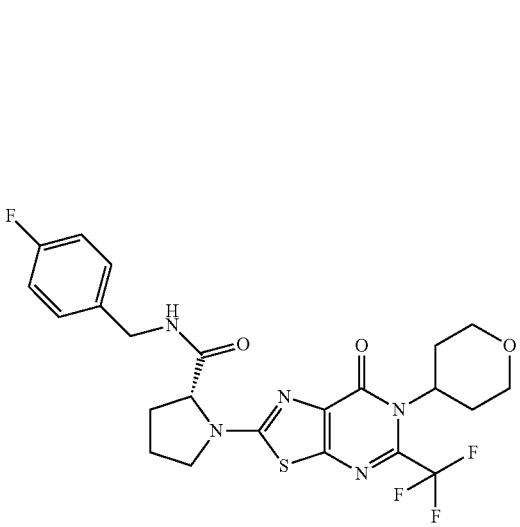 [SMILES: O=C(NCc1ccc(F)cc1)[C@H]1CCCN1c1nc2c(=O)n(C3CCOCC3)c(C(F)(F)F)nc2s1]

The compound (300 mg) obtained in Reference Example 315 was treated by a method similar to that in Example 203 to give the title compound (190 mg).
MS (ESI) m/z; 526 [M+H]$^+$

Example 247

(R)-N-benzyl-1-[7-oxo-6-(tetrahydro-2H-pyran-4-yl)-5-trifluoromethyl-6,7-dihydro-[1,3]thiazolo[5,4-d]pyrimidin-2-yl]azetidine-2-carboxamide

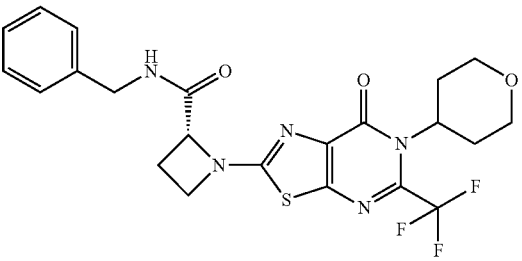 [SMILES: O=C(NCc1ccccc1)[C@H]1CCN1c1nc2c(=O)n(C3CCOCC3)c(C(F)(F)F)nc2s1]

The compound (185 mg) obtained in Reference Example 315 was treated by a method similar to that in Example 203 to give the title compound (100 mg).
MS (ESI) m/z; 494 [M+H]$^+$

Example 248

(R)-N-(2-methylbenzyl)-1-[7-oxo-6-(tetrahydro-2H-pyran-4-yl)-5-trifluoromethyl-6,7-dihydro-[1,3]thiazolo[5,4-d]pyrimidin-2-yl]azetidine-2-carboxamide

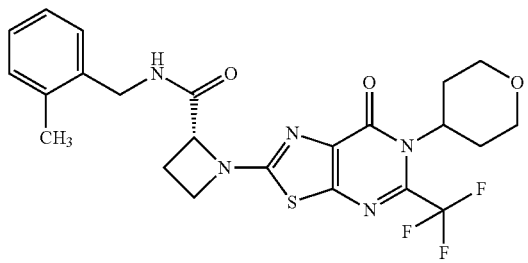 [SMILES: Cc1ccccc1CNC(=O)[C@H]1CCN1c1nc2c(=O)n(C3CCOCC3)c(C(F)(F)F)nc2s1]

The compound (185 mg) obtained in Reference Example 315 was treated by a method similar to that in Example 203 to give the title compound (95 mg).
MS (ESI) m/z; 508 [M+H]$^+$

Example 249

(R)-1-[7-oxo-6-(tetrahydro-2H-pyran-4-yl)-5-trifluoromethyl-6,7-dihydro-[1,3]thiazolo[5,4-d]pyrimidin-2-yl]-N-((R)-1-phenylethyl)azetidine-2-carboxamide

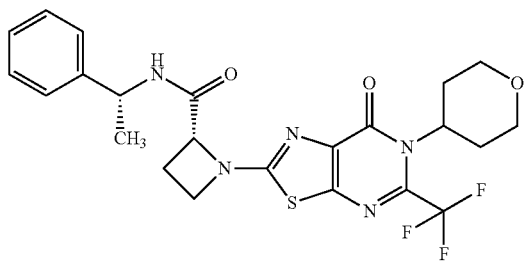 [SMILES: C[C@@H](NC(=O)[C@H]1CCN1c1nc2c(=O)n(C3CCOCC3)c(C(F)(F)F)nc2s1)c1ccccc1]

The compound (200 mg) obtained in Reference Example 315 was treated by a method similar to that in Example 203 to give the title compound (98 mg).
MS (ESI) m/z; 508 [M+H]$^+$

Example 250

(R)-N-benzyl-1-[7-oxo-6-((R)-tetrahydrofuran-3-yl)-5-trifluoromethyl-6,7-dihydro-[1,3]thiazolo[5,4-d]pyrimidine2-yl]pyrrolidine-2-carboxamide

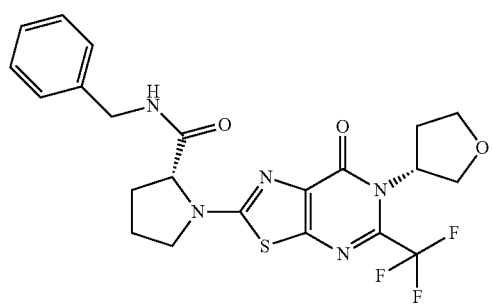 [SMILES: O=C(NCc1ccccc1)[C@H]1CCCN1c1nc2c(=O)n([C@@H]3CCOC3)c(C(F)(F)F)nc2s1]

The compound (380 mg) obtained in Reference Example 317 was treated by a method similar to that in Example 203 to give the title compound (330 mg).
MS (ESI) m/z; 494 [M+H]$^+$

Example 251

(R)-N-benzyl-1-[6-(oxetan-3-yl)-7-oxo-5-trifluoromethyl-6,7-dihydro-[1,3]thiazolo[5,4-d]pyrimidin-2-yl]pyrrolidine-2-carboxamide

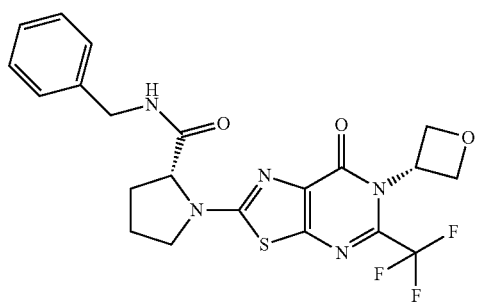

The compound (260 mg) obtained in Reference Example 318 was treated by a method similar to that in Example 203 to give the title compound (110 mg).
MS (ESI) m/z; 480 [M+H]$^+$

Example 252

(R)-N-benzyl-1-[7-oxo-6-(pyrrolidin-1-yl)-5-trifluoromethyl-6,7-dihydro-[1,3]thiazolo[5,4-d]pyrimidin-2-yl]pyrrolidine-2-carboxamide

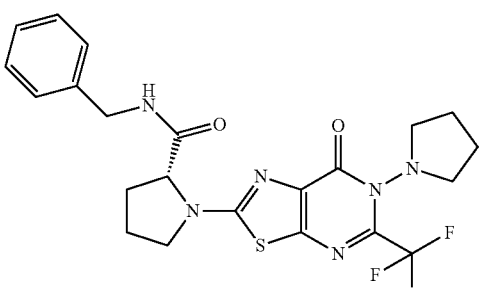

The compound (280 mg) obtained in Reference Example 319 was treated by a method similar to that in Example 203 to give the title compound (210 mg).
MS (ESI) m/z; 493 [M+H]$^+$

Example 253

(R)-N-benzyl-1-[6-(morpholin-4-yl)-7-oxo-5-trifluoromethyl-6,7-dihydro-[1,3]thiazolo[5,4-d]pyrimidin-2-yl]pyrrolidine-2-carboxamide

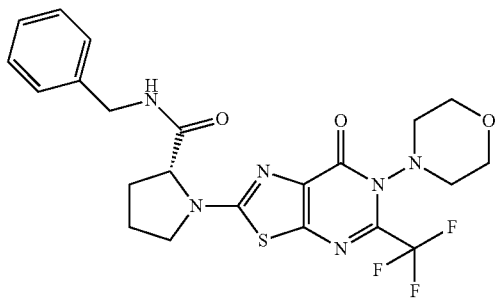 [SMILES: O=C(NCc1ccccc1)[C@H]1CCCN1c1nc2c(=O)n(N3CCOCC3)c(C(F)(F)F)nc2s1]

The compound (290 mg) obtained in Reference Example 320 was treated by a method similar to that in Example 203 to give the title compound (200 mg).
MS (ESI) m/z; 509 [M+H]$^+$

Example 254

(R)-N-benzyl-1-{5-difluoromethyl-7-oxo-6-[(tetrahydro-2H-pyran-4-yl)methyl]-6,7-dihydro-[1,3]thiazolo[5,4-d]pyrimidin-2-yl}pyrrolidine-2-carboxamide

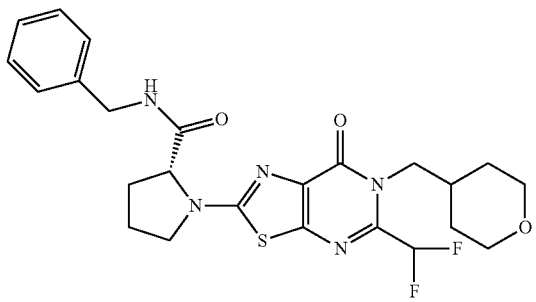 [SMILES: O=C(NCc1ccccc1)[C@H]1CCCN1c1nc2c(=O)n(CC3CCOCC3)c(C(F)F)nc2s1]

The compound (300 mg) obtained in Reference Example 328 was treated by a method similar to that in Example 203 to give the title compound (190 mg).
MS (ESI) m/z; 504 [M+H]$^+$

Example 255

(R)-1-{5-difluoromethyl-7-oxo-6-[(tetrahydro-2H-pyran-4-yl)methyl]-6,7-dihydro-[1,3]thiazolo[5,4-d]pyrimidin-2-yl}-N-((R)-1-phenylethyl)pyrrolidine-2-carboxamide

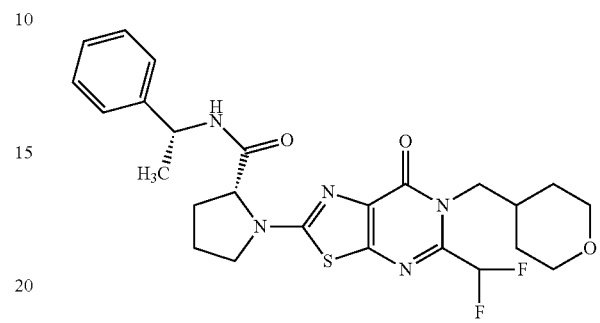

The compound (300 mg) obtained in Reference Example 328 was treated by a method similar to that in Example 203 to give the title compound (300 mg).
MS (ESI) m/z; 518 [M+H]$^+$

Example 256

(R)-N-benzyl-1-(6-cyclopentyl-5-methyl-7-oxo-6,7-dihydro-[1,3]thiazolo[5,4-d]pyrimidin-2-yl)azetidine-2-carboxamide

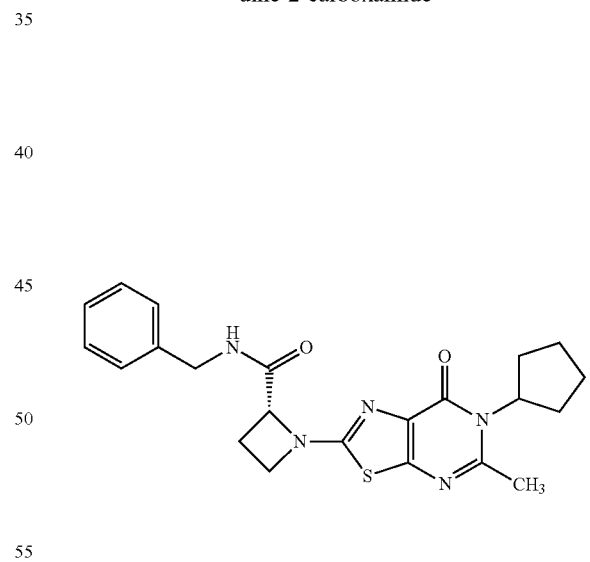

The compound (137 mg) obtained in Reference Example 337 was treated by a method similar to that in Example 203 to give the title compound (66 mg).
MS (ESI) m/z; 424 [M+H]$^+$

Example 257

(R)-N-benzyl-1-[6-methyl-7-oxo-5-((RS)-tetrahydro-furan-2-yl)-6,7-dihydro[1,3]thiazolo[5,4-d]pyrimidin-2-yl]pyrrolidine-2-carboxamide

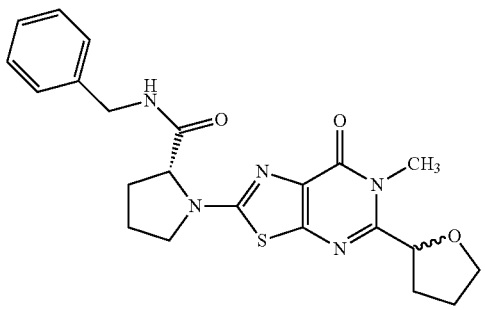

A mixture of the compound (260 mg) obtained in Reference Example 271, the compound (630 mg) obtained in Reference Example 341 and N,N-diisopropylethylamine (1.00 g) was heated at 150° C. for 4 hr. 1.0 mol/L Hydrochloric acid was added to the reaction mixture, and the mixture was extracted twice with chloroform. The organic layer was dried over anhydrous sodium sulfate, filtered and concentrated. The residue was purified by silica gel column chromatography (solvent; ethyl acetate/methanol=100/0-90/10), to the obtained product was added diethyl ether, and the solid was collected by filtration to give the title compound (115 mg).

MS (ESI) m/z; 440 [M+H]$^+$

Example 258

(R)-N-benzyl-1-[6-cyclopropyl-5-methoxymethyl-7-oxo-6,7-dihydro[1,3]thiazolo[5,4-d]pyrimidin-2-yl]pyrrolidine-2-carboxamide

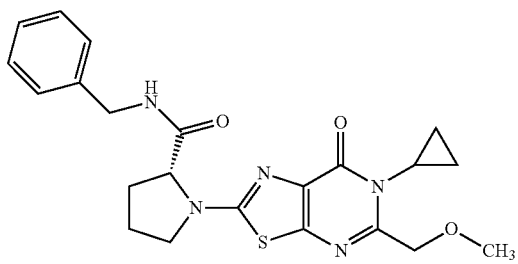 [SMILES: COCc1nc2sc(N3CCC[C@@H]3C(=O)NCc3ccccc3)nc2c(=O)n1C1CC1]

The compound (263 mg) obtained in Reference Example 273 was treated by a method similar to that in Example 257 to give the title compound (277 mg).

MS (ESI) m/z; 440 [M+H]$^+$

Example 259

(R)-N-benzyl-1-[6-methyl-7-oxo-5-(tetrahydro-2H-pyran-4-yl)-6,7-dihydro[1,3]thiazolo[5,4-d]pyrimidin-2-yl]pyrrolidine-2-carboxamide

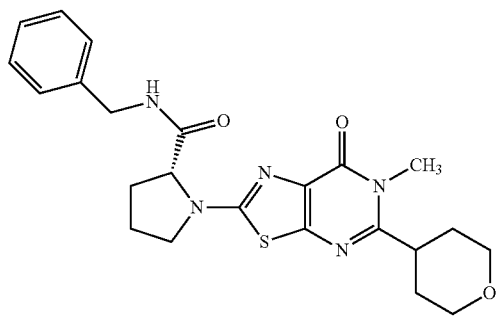 [SMILES: Cn1c(C2CCOCC2)nc2sc(N3CCC[C@@H]3C(=O)NCc3ccccc3)nc2c1=O]

The compound (200 mg) obtained in Reference Example 281 was treated by a method similar to that in Example 257 to give the title compound (215 mg).

MS (ESI) m/z; 454 [M+H]$^+$

Example 260

(R)-N-benzyl-1-[6-(2-methoxyethyl)-5-methyl-7-oxo-6,7-dihydro[1,3]thiazolo[5,4-d]pyrimidin-2-yl]pyrrolidine-2-carboxamide

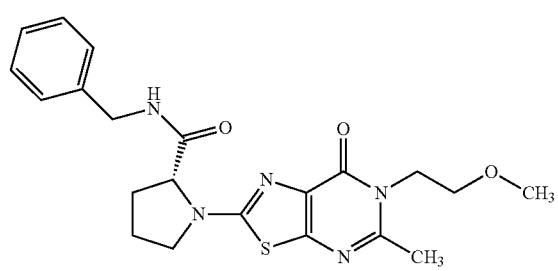 [SMILES: COCCn1c(C)nc2sc(N3CCC[C@@H]3C(=O)NCc3ccccc3)nc2c1=O]

The compound (300 mg) obtained in Reference Example 295 was treated by a method similar to that in Example 257 to give the title compound (100 mg).

MS (ESI) m/z; 428 [M+H]$^+$

Example 261

(R)-N-benzyl-1-[5-(1-cyanocyclopentyl)-6-methyl-7-oxo-6,7-dihydro[1,3]thiazolo[5,4-d]pyrimidin-2-yl]pyrrolidine-2-carboxamide

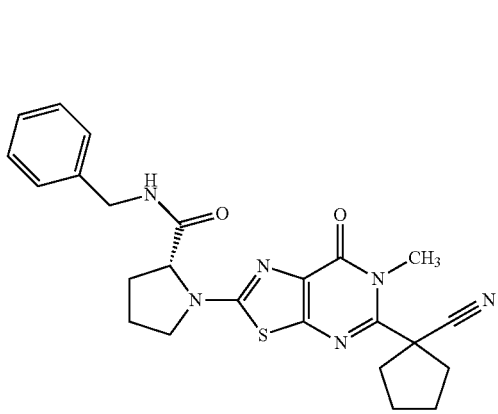 [SMILES: Cn1c(C2(C#N)CCCC2)nc2sc(N3CCC[C@@H]3C(=O)NCc3ccccc3)nc2c1=O]

The compound (155 mg) obtained in Reference Example 297 was treated by a method similar to that in Example 257 to give the title compound (140 mg).

MS (ESI) m/z; 463 [M+H]$^+$

Example 262

(R)-N-benzyl-1-(5-methoxymethyl-6-methyl-7-oxo-6,7-dihydro[1,3]thiazolo[5,4-d]pyrimidin-2-yl)pyrrolidine-2-carboxamide

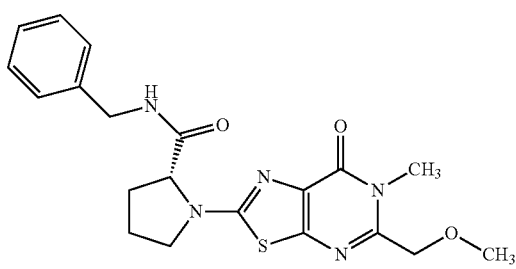 [SMILES: COCc1nc2sc(N3CCC[C@@H]3C(=O)NCc3ccccc3)nc2c(=O)n1C]

The compound (242 mg) obtained in Reference Example 302 was treated by a method similar to that in Example 257 to give the title compound (146 mg).

MS (ESI) m/z; 414 [M+H]$^+$

Example 263

(R)-N-benzyl-1-[6-methyl-7-oxo-5-((RS)-tetrahydrofuran-3-yl)-6,7-dihydro-[1,3]thiazolo[5,4-d]pyrimidin-2-yl]pyrrolidine-2-carboxamide

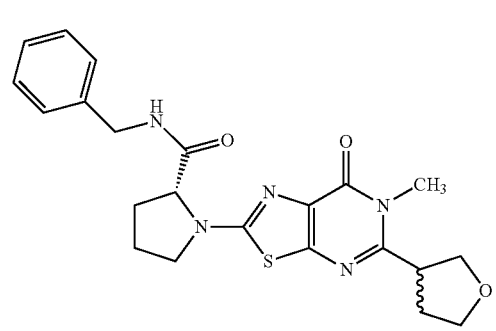 [SMILES: Cn1c(C2CCOC2)nc2sc(N3CCC[C@@H]3C(=O)NCc3ccccc3)nc2c1=O]

The compound (200 mg) obtained in Reference Example 322 was treated by a method similar to that in Example 257 to give the title compound (95 mg).

MS (ESI) m/z; 440 [M+H]$^+$

Example 264

(R)-N-benzyl-1-[6-(1-methylpiperidin-4-yl)-7-oxo-5-trifluoromethyl-6,7-dihydro-[1,3]thiazolo[5,4-d]pyrimidin-2-yl]pyrrolidine-2-carboxamide

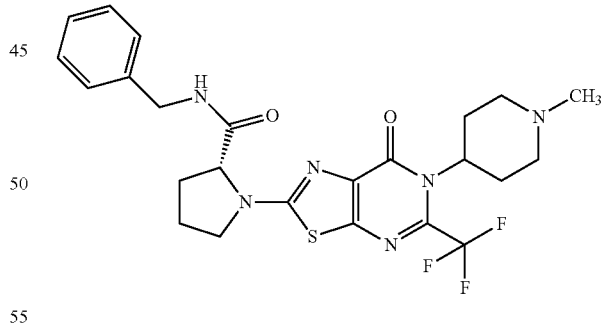

The compound (220 mg) obtained in Reference Example 332 was treated by a method similar to that in Example 257 to give the title compound (95 mg).

MS (ESI) m/z; 521 [M+H]$^+$

Example 265

(R)-N-[dideuterio(phenyl)methyl]-1-(6-methyl-7-oxo-5-phenyl-6,7-dihydro[1,3]thiazolo[5,4-d]pyrimidin-2-yl)pyrrolidine-2-carboxamide

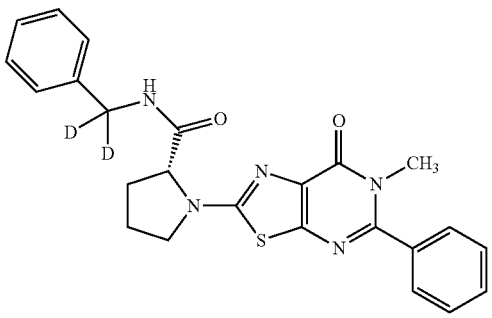 [SMILES: [2H]C([2H])(NC(=O)[C@H]1CCCN1c1nc2c(=O)n(C)c(-c3ccccc3)nc2s1)c1ccccc1]

To a solution (6.0 mL) of the compound (233 mg) obtained in Reference Example 268 in DMF were added (D)-proline (110 mg) and cesium carbonate (479 mg), and the reaction mixture was stirred with heating at 70° C. for 1 hr. The reaction mixture was cooled to 0° C., and neutralized with concentrated hydrochloric acid. N,N-diisopropylethylamine (223 μL), benzyl-α, α-D$_2$-amine (140 mg), EDC hydrochloride (245 mg) and HOBt monohydrate (196 mg) were added to the reaction mixture at room temperature, and the reaction mixture was stirred at room temperature overnight. Water was added to the reaction mixture, and the mixture was extracted three times with ethyl acetate. The combined organic layer was dried over anhydrous sodium sulfate, filtered and concentrated. The residue was purified by silica gel column chromatography (solvent; hexane/ethyl acetate=50/50-0/100) to give the title compound (210 mg).

MS (ESI) m/z; 448 [M+H]$^+$

Example 266

(R)-N-benzyl-1-[5-(1,1-difluoroethyl)-6-methyl-7-oxo-6,7-dihydro[1,3]thiazolo[5,4-d]pyrimidin-2-yl]pyrrolidine-2-carboxamide

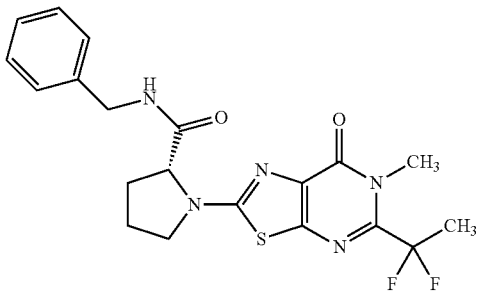

The compound (327 mg) obtained in Reference Example 276 was treated by a method similar to that in Example 265 to give the title compound (389 mg).

MS (ESI) m/z; 434 [M+H]$^+$

Example 267

(R)-1-[5-(1,1-difluoroethyl)-6-methyl-7-oxo-6,7-dihydro[1,3]thiazolo[5,4-d]pyrimidin-2-yl]-N-((R)-1-phenylethyl)pyrrolidine-2-carboxamide

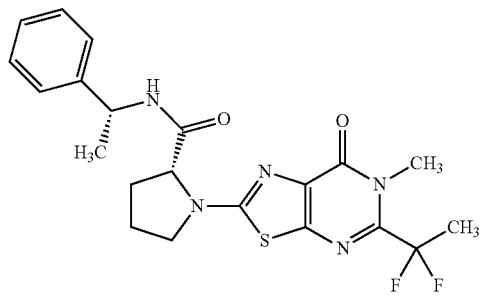 [SMILES: C[C@@H](NC(=O)[C@H]1CCCN1c1nc2c(=O)n(C)c(C(C)(F)F)nc2s1)c1ccccc1]

The compound (194 mg) obtained in Reference Example 276 was treated by a method similar to that in Example 265 to give the title compound (226 mg).

MS (ESI) m/z; 448 [M+H]$^+$

Example 268

(R)-N-benzyl-1-[5-(1-fluorocyclopropyl)-6-methyl-7-oxo-6,7-dihydro[1,3]thiazolo[5,4-d]pyrimidin-2-yl]pyrrolidine-2-carboxamide

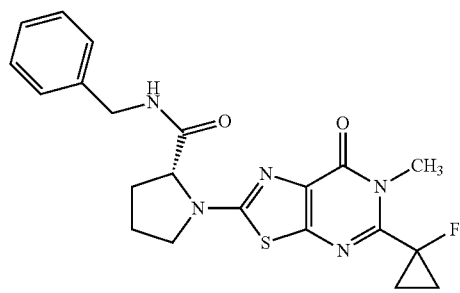 [SMILES: Cn1c(C2(F)CC2)nc2sc(N3CCC[C@@H]3C(=O)NCc3ccccc3)nc2c1=O]

The compound (220 mg) obtained in Reference Example 277 was treated by a method similar to that in Example 265 to give the title compound (225 mg).

MS (ESI) m/z; 428 [M+H]$^+$

Example 269

(R)-N-benzyl-1-[5-(1-chlorocyclopropyl)-6-methyl-7-oxo-6,7-dihydro[1,3]thiazolo[5,4-d]pyrimidin-2-yl]pyrrolidine-2-carboxamide

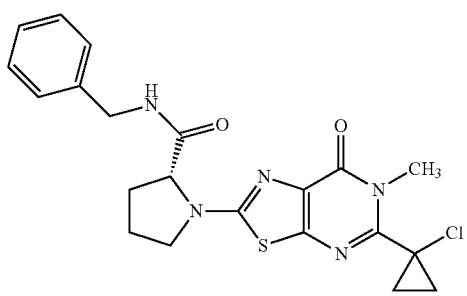 [SMILES: Cn1c(C2(Cl)CC2)nc2sc(N3CCC[C@@H]3C(=O)NCc3ccccc3)nc2c1=O]

The compound (54 mg) obtained in Reference Example 278 was treated by a method similar to that in Example 265 to give the title compound (54 mg).
MS (ESI) m/z; 444, 446 [M+H]$^+$

Example 270

(R)-1-[5-(1-fluorocyclopropyl)-6-methyl-7-oxo-6,7-dihydro[1,3]thiazolo[5,4-d]pyrimidin-2-yl]-N-((R)-1-phenylethyl)pyrrolidine-2-carboxamide

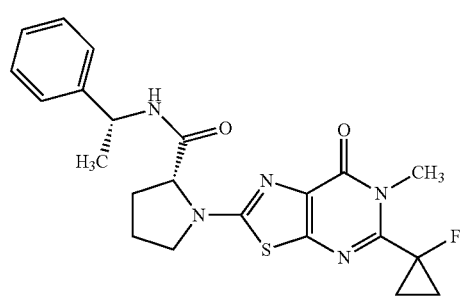 [SMILES: C[C@@H](NC(=O)[C@H]1CCCN1c1nc2c(=O)n(C)c(C3(F)CC3)nc2s1)c1ccccc1]

The compound (153 mg) obtained in Reference Example 277 was treated by a method similar to that in Example 265 to give the title compound (166 mg).
MS (ESI) m/z; 442 [M+H]$^+$

Example 271

(R)-1-[5-(1-chlorocyclopropyl)-6-methyl-7-oxo-6,7-dihydro[1,3]thiazolo[5,4-d]pyrimidin-2-yl]-N-((R)-1-phenylethyl)pyrrolidine-2-carboxamide

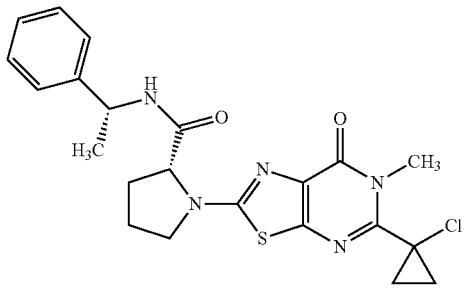 [SMILES: C[C@@H](NC(=O)[C@H]1CCCN1c1nc2c(=O)n(C)c(C3(Cl)CC3)nc2s1)c1ccccc1]

The compound (38 mg) obtained in Reference Example 278 was treated by a method similar to that in Example 265 to give the title compound (44 mg).
MS (ESI) m/z; 458, 460 [M+H]$^+$

Example 272

(R)-N-benzyl-1-[5-(1,1-difluoropropyl)-6-methyl-7-oxo-6,7-dihydro[1,3]thiazolo[5,4-d]pyrimidin-2-yl]pyrrolidine-2-carboxamide

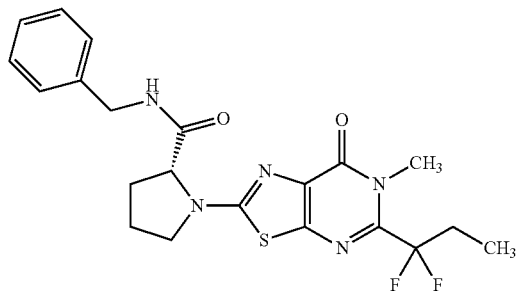 [SMILES: CCC(F)(F)c1nc2sc(N3CCC[C@@H]3C(=O)NCc3ccccc3)nc2c(=O)n1C]

The compound (254 mg) obtained in Reference Example 279 was treated by a method similar to that in Example 265 to give the title compound (303 mg).
MS (ESI) m/z; 448 [M+H]$^+$

Example 273

(R)-N-benzyl-1-{5-[difluoro(pyridin-2-yl)methyl]-6-methyl-7-oxo-6,7-dihydro[1,3]thiazolo[5,4-d]pyrimidin-2-yl}pyrrolidine-2-carboxamide

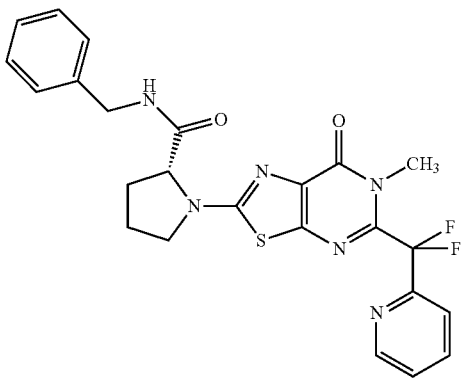 [SMILES: Cn1c(C(F)(F)c2ccccn2)nc2sc(N3CCC[C@@H]3C(=O)NCc3ccccc3)nc2c1=O]

The compound (500 mg) obtained in Reference Example 280 was treated by a method similar to that in Example 265 to give the title compound (472 mg).

MS (ESI) m/z; 497 [M+H]$^+$

Example 274

(R)-1-{5-[difluoro(pyridin-2-yl)methyl]-6-methyl-7-oxo-6,7-dihydro[1,3]thiazolo[5,4-d]pyrimidin-2-yl}-N-((R)-1-phenylethyl)pyrrolidine-2-carboxamide

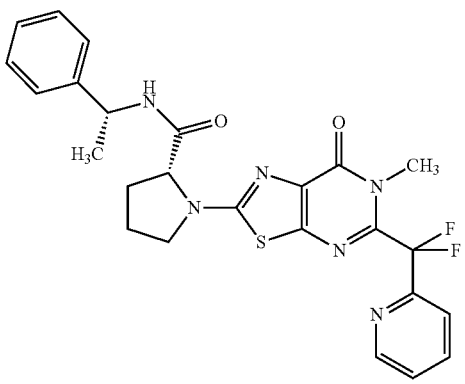 [SMILES: C[C@@H](NC(=O)[C@H]1CCCN1c1nc2c(=O)n(C)c(C(F)(F)c3ccccn3)nc2s1)c1ccccc1]

The compound (356 mg) obtained in Reference Example 280 was treated by a method similar to that in Example 265 to give the title compound (328 mg).

MS (ESI) m/z; 511 [M+H]$^+$

Example 275

(R)-N-benzyl-1-[5-(1,1-difluoro-2-methoxyethyl)-6-methyl-7-oxo-6,7-dihydro[1,3]thiazolo[5,4-d]pyrimidin-2-yl]pyrrolidine-2-carboxamide

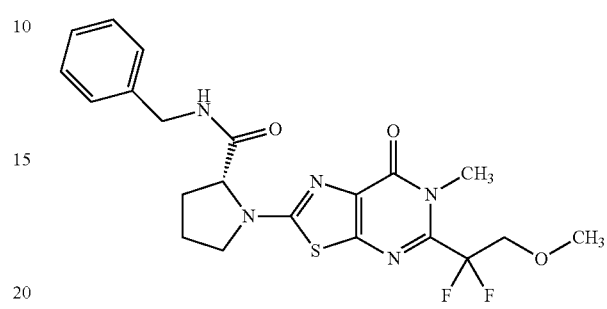

The compound (129 mg) obtained in Reference Example 282 was treated by a method similar to that in Example 265 to give the title compound (152 mg).

MS (ESI) m/z; 464 [M+H]$^+$

Example 276

(R)-N-benzyl-1-{6-ethyl-5-[2-(methylsulfonyl)phenyl]-7-oxo-6,7-dihydro[1,3]thiazolo[5,4-d]pyrimidin-2-yl}pyrrolidine-2-carboxamide

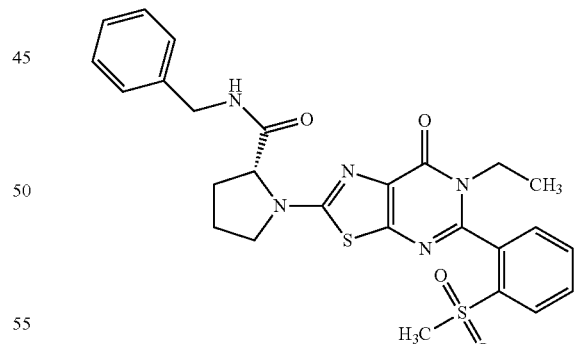

The compound (157 mg) obtained in Reference Example 283 was treated by a method similar to that in Example 265 to give the title compound (125 mg).

MS (ESI) m/z; 538 [M+H]$^+$

Example 277

1-{6-ethyl-5-[2-(methylsulfonyl)phenyl]-7-oxo-6,7-dihydro[1,3]thiazolo[5,4-d]pyrimidin-2-yl}-N-((R)-1-phenylethyl)pyrrolidine-2-carboxamide

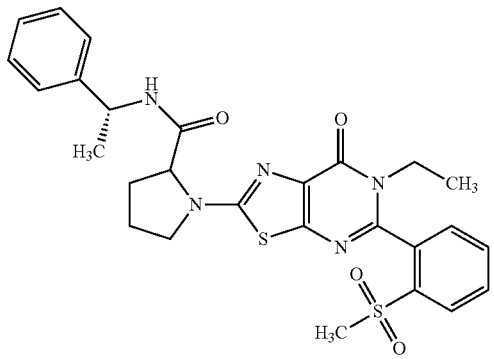 [SMILES: CCn1c(-c2ccccc2S(C)(=O)=O)nc2sc(N3CCCC3C(=O)N[C@H](C)c3ccccc3)nc2c1=O]

The compound (146 mg) obtained in Reference Example 283 was treated by a method similar to that in Example 265 to give the title compound (120 mg).

MS (ESI) m/z; 552 [M+H]$^+$

Example 278

(R)-1-(6-ethyl-7-oxo-5-pyrimidin-2-yl-6,7-dihydro[1,3]thiazolo[5,4-d]pyrimidin-2-yl)-N-((R)-1-phenylethyl) pyrrolidine-2-carboxamide

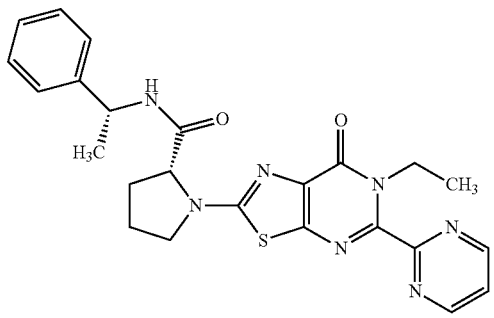 [SMILES: CCn1c(-c2ncccn2)nc2sc(N3CCC[C@@H]3C(=O)N[C@H](C)c3ccccc3)nc2c1=O]

The compound (251 mg) obtained in Reference Example 284 was treated by a method similar to that in Example 265 to give the title compound (117 mg).

MS (ESI) m/z; 476 [M+H]$^+$

Example 279

(R)-N-benzyl-1-[5-(1,1-difluoro-2-methoxyethyl)-6-ethyl-7-oxo-6,7-dihydro[1,3]thiazolo[5,4-d]pyrimidin-2-yl]pyrrolidine-2-carboxamide

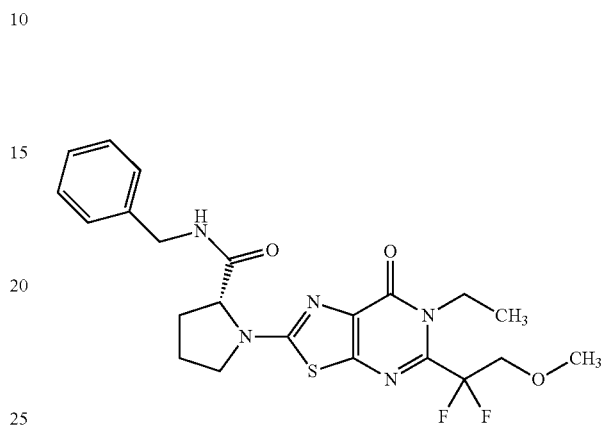

The compound (135 mg) obtained in Reference Example 294 was treated by a method similar to that in Example 265 to give the title compound (135 mg).

MS (ESI) m/z; 478 [M+H]$^+$

Example 280

(R)-N-benzyl-1-[6-ethyl-7-oxo-5-(pyridin-2-yl)-6,7-dihydro[1,3]thiazolo[5,4-d]pyrimidin-2-yl]pyrrolidine-2-carboxamide

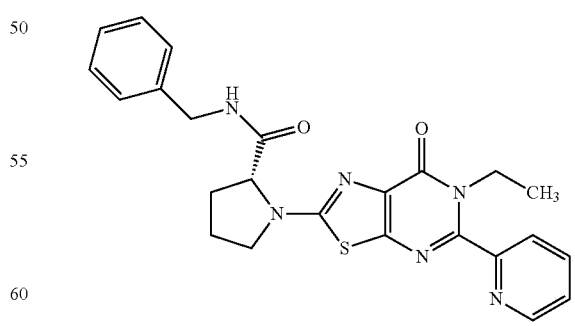

The compound (300 mg) obtained in Reference Example 330 was treated by a method similar to that in Example 265 to give the title compound (371 mg).

MS (ESI) m/z; 461 [M+H]$^+$

Example 281

(R)-N-benzyl-1-(5-difluoromethyl-6-methyl-7-oxo-6,7-dihydro-[1,3]thiazolo[5,4-d]pyrimidin-2-yl)pyrrolidine-2-carboxamide

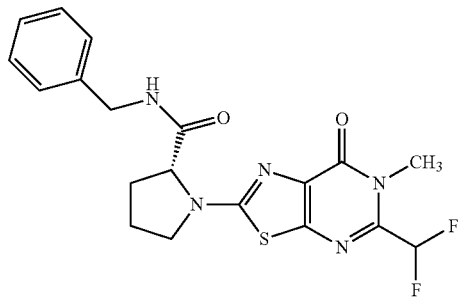

The compound (247 mg) obtained in Reference Example 310 was treated by a method similar to that in Example 265 to give the title compound (333 mg).
MS (ESI) m/z; 420 [M+H]$^+$

Example 282

(R)-1-(5-difluoromethyl-6-methyl-7-oxo-6,7-dihydro-[1,3]thiazolo[5,4-d]pyrimidin-2-yl)-N-((R)-1-phenylethyl)pyrrolidine-2-carboxamide

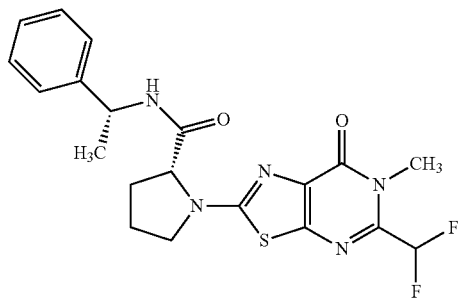 [SMILES: C[C@@H](NC(=O)[C@H]1CCCN1c1nc2c(=O)n(C)c(C(F)F)nc2s1)c1ccccc1]

The compound (200 mg) obtained in Reference Example 310 was treated by a method similar to that in Example 265 to give the title compound (253 mg).
MS (ESI) m/z; 434 [M+H]$^+$

Example 283

(R)-1-[5-difluoromethyl-6-(2-methoxyethyl)-7-oxo-6,7-dihydro-[1,3]thiazolo[5,4-d]pyrimidin-2-yl]-N-((R)-1-phenylethyl)pyrrolidine-2-carboxamide

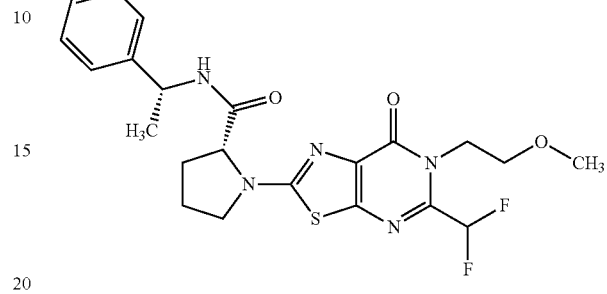

The compound (317 mg) obtained in Reference Example 313 was treated by a method similar to that in Example 265 to give the title compound (284 mg).
MS (ESI) m/z; 478 [M+H]$^+$

Example 284

(R)-1-[5-difluoromethyl-6-(2-methoxyethyl)-7-oxo-6,7-dihydro-[1,3]thiazolo[5,4-d]pyrimidin-2-yl]-N-(4-fluorobenzyl)pyrrolidine-2-carboxamide

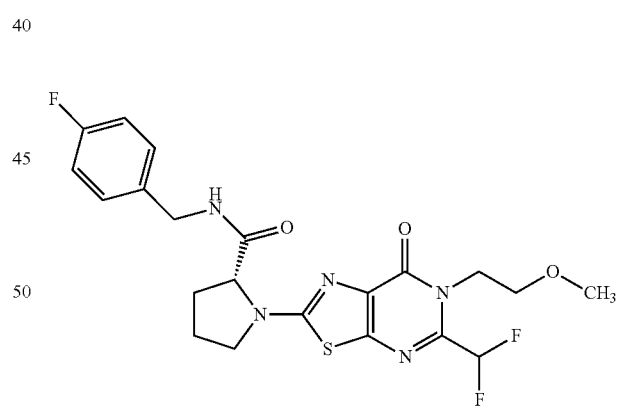

The compound (250 mg) obtained in Reference Example 313 was treated by a method similar to that in Example 265 to give the title compound (283 mg).
MS (ESI) m/z; 482 [M+H]$^+$

Example 285

(R)-N-benzyl-1-[6-ethyl-5-(3-fluoropyridin-4-yl)-7-oxo-6,7-dihydro-[1,3]thiazolo[5,4-d]pyrimidin-2-yl]pyrrolidine-2-carboxamide

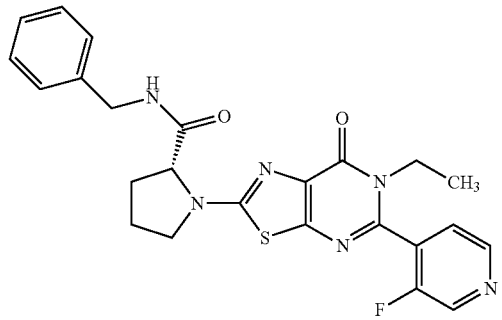 [SMILES: CCn1c(-c2ccncc2F)nc2sc(N3CCC[C@@H]3C(=O)NCc3ccccc3)nc2c1=O]

The compound (400 mg) obtained in Reference Example 323 was treated by a method similar to that in Example 265 to give the title compound (311 mg).

MS (ESI) m/z; 479 [M+H]$^+$

Example 286

(R)-N-benzyl-1-[6-ethyl-5-(4-fluoropyridin-2-yl)-7-oxo-6,7-dihydro-[1,3]thiazolo[5,4-d]pyrimidin-2-yl]pyrrolidine-2-carboxamide

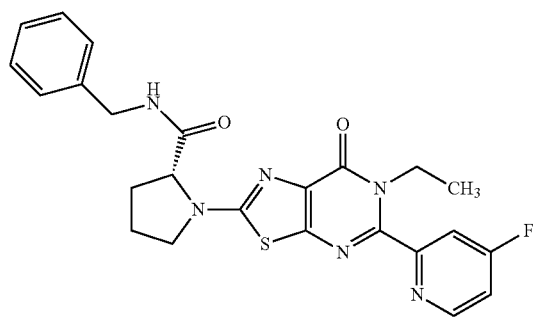 [SMILES: CCn1c(-c2cc(F)ccn2)nc2sc(N3CCC[C@@H]3C(=O)NCc3ccccc3)nc2c1=O]

The compound (200 mg) obtained in Reference Example 324 was treated by a method similar to that in Example 265 to give the title compound (114 mg).

MS (ESI) m/z; 479 [M+H]$^+$

Example 287

(R)-1-[6-ethyl-5-(4-fluoropyridin-2-yl)-7-oxo-6,7-dihydro-[1,3]thiazolo[5,4-d]pyrimidin-2-yl]-N-((R)-1-phenylethyl)pyrrolidine-2-carboxamide

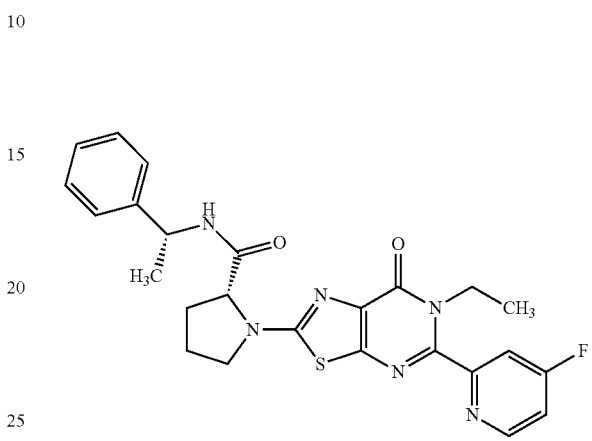

The compound (200 mg) obtained in Reference Example 324 was treated by a method similar to that in Example 265 to give the title compound (113 mg).

MS (ESI) m/z; 493 [M+H]$^+$

Example 288

(R)-N-benzyl-1-[5-(4-chloropyridin-2-yl)-6-ethyl-7-oxo-6,7-dihydro-[1,3]thiazolo[5,4-d]pyrimidin-2-yl]pyrrolidine-2-carboxamide

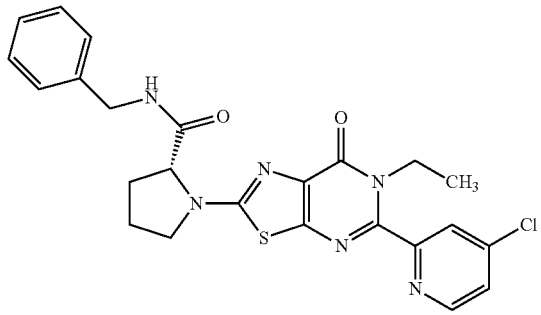 [SMILES: CCn1c(-c2cc(Cl)ccn2)nc2sc(N3CCC[C@@H]3C(=O)NCc3ccccc3)nc2c1=O]

The compound (140 mg) obtained in Reference Example 325 was treated by a method similar to that in Example 265 to give the title compound (147 mg).

MS (ESI) m/z; 495, 497 [M+H]$^+$

Example 289

(R)-N-benzyl-1-(5-difluoromethyl-6-ethyl-7-oxo-6,7-dihydro-[1,3]thiazolo[5,4-d]pyrimidin-2-yl)pyrrolidine-2-carboxamide

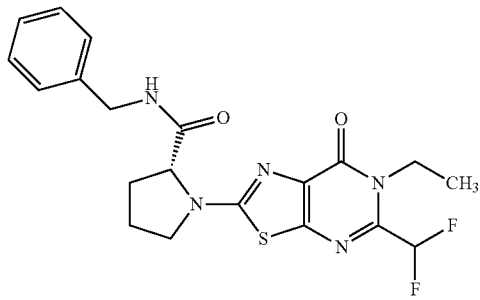 [SMILES: CCn1c(C(F)F)nc2sc(N3CCC[C@@H]3C(=O)NCc3ccccc3)nc2c1=O]

The compound (12.1 g) obtained in Reference Example 327 was treated by a method similar to that in Example 265 to give the title compound (12.4 g).

MS (ESI) m/z; 434 [M+H]$^+$

Example 290

(R)-1-(5-difluoromethyl-6-ethyl-7-oxo-6,7-dihydro-[1,3]thiazolo[5,4-d]pyrimidin-2-yl)-N-((R)-1-phenylethyl)pyrrolidine-2-carboxamide

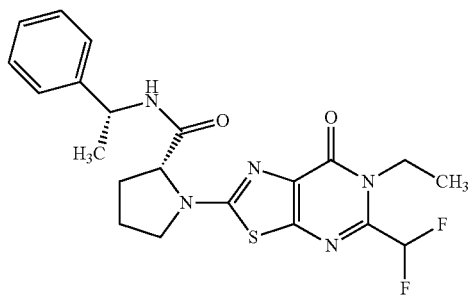 [SMILES: CCn1c(C(F)F)nc2sc(N3CCC[C@@H]3C(=O)N[C@H](C)c3ccccc3)nc2c1=O]

The compound (250 mg) obtained in Reference Example 327 was treated by a method similar to that in Example 265 to give the title compound (287 mg).

MS (ESI) m/z; 448 [M+H]$^+$

Example 291

(R)-1-(5-difluoromethyl-6-ethyl-7-oxo-6,7-dihydro-[1,3]thiazolo[5,4-d]pyrimidin-2-yl)-N-(4-fluorophenyl)pyrrolidine-2-carboxamide

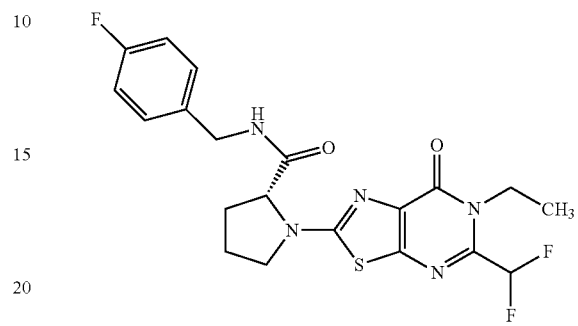

The compound (250 mg) obtained in Reference Example 327 was treated by a method similar to that in Example 265 to give the title compound (314 mg).

MS (ESI) m/z; 452 [M+H]$^+$

Example 292

(R)-N-benzyl-2-{[N'-(5-difluoromethyl-6-ethyl-7-oxo-6,7-dihydro-[1,3]thiazolo[5,4-d]pyrimidin-2-yl)-N'-methyl]amino}propionamide

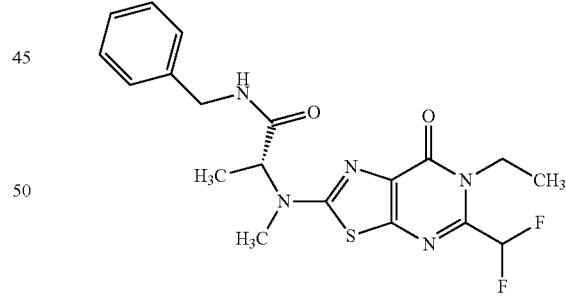

The compound (200 mg) obtained in Reference Example 327 was treated by a method similar to that in Example 265 to give the title compound (150 mg).

MS (ESI) m/z; 422 [M+H]$^+$

Example 293

(R)-N-benzyl-2-[N'-(5-difluoromethyl-6-ethyl-7-oxo-6,7-dihydro-[1,3]thiazolo[5,4-d]pyrimidin-2-yl)amino]propionamide

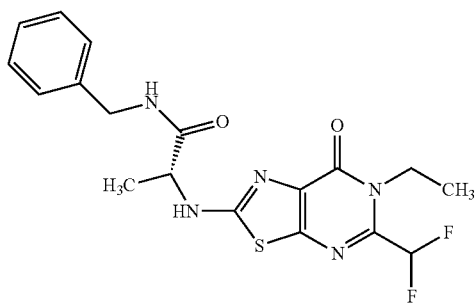 [SMILES: CCn1c(C(F)F)nc2sc(N[C@H](C)C(=O)NCc3ccccc3)nc2c1=O]

The compound (200 mg) obtained in Reference Example 327 was treated by a method similar to that in Example 265 to give the title compound (89 mg).

MS (ESI) m/z; 408 [M+H]$^+$

Example 294

(R)-N-benzyl-1-{6-[3-(N',N'-dimethylamino)propyl]-7-oxo-5-trifluoromethyl-6,7-dihydro-[1,3]thiazolo[5,4-d]pyrimidin-2-yl}pyrrolidine-2-carboxamide

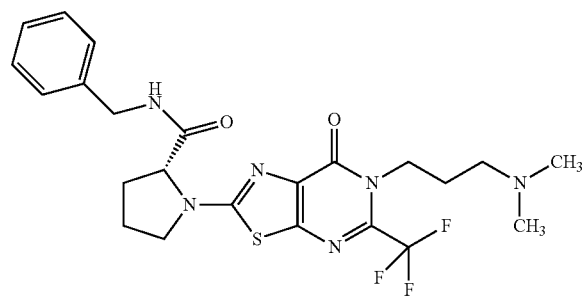 [SMILES: CN(C)CCCn1c(C(F)(F)F)nc2sc(N3CCC[C@@H]3C(=O)NCc3ccccc3)nc2c1=O]

The compound (190 mg) obtained in Reference Example 331 was treated by a method similar to that in Example 265 to give the title compound (90 mg).

MS (ESI) m/z; 509 [M+H]$^+$

Example 295

(R)-1-(6-methyl-7-oxo-5-phenyl-6,7-dihydro[1,3]thiazolo[5,4-d]pyrimidin-2-yl)-N-((R)-1-phenylethyl)pyrrolidine-2-carboxamide

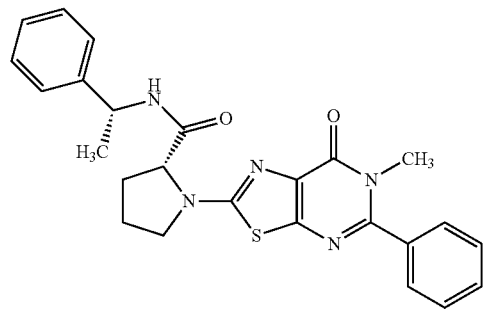 [SMILES: C[C@@H](NC(=O)[C@H]1CCCN1c1nc2c(=O)n(C)c(-c3ccccc3)nc2s1)c1ccccc1]

To a solution (3.0 mL) of the compound (172 mg) obtained in Reference Example 268 in DMF were added (D)-proline (89 mg) and potassium carbonate (143 mg), and the reaction mixture was heated at 70° C. for 3 hr. The reaction mixture was cooled to 0° C., and neutralized with concentrated hydrochloric acid (173 μL). N,N-diisopropylethylamine (135 μL), (R)-N-benzyl-1-phenylethylamine (139 μL), EDC hydrochloride (149 mg) and HOBt monohydrate (119 mg) were added to the reaction mixture at room temperature, and the reaction mixture was stirred at room temperature overnight. Water was added to the reaction mixture, and the mixture was extracted three times with ethyl acetate. The combined organic layer was dried over anhydrous sodium sulfate, filtered and concentrated. The residue was purified by NH silica gel column chromatography (solvent; hexane/ethyl acetate=70/30-0/100) to give the title compound (167 mg).

MS (ESI) m/z; 460 [M+H]$^+$

Example 296

(R)-N-benzyl-1-{6-[(oxetan-3-yl)methyl]-7-oxo-5-trifluoromethyl-6,7-dihydro-[1,3]thiazolo[5,4-d]pyrimidin-2-yl}pyrrolidine-2-carboxamide

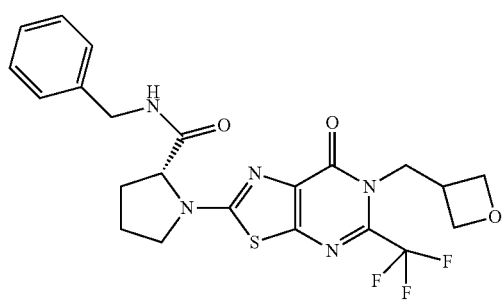 [SMILES: O=C(NCc1ccccc1)[C@H]1CCCN1c1nc2c(=O)n(CC3COC3)c(C(F)(F)F)nc2s1]

The compound (90 mg) obtained in Reference Example 321 was treated by a method similar to that in Example 295 to give the title compound (72 mg).

MS (ESI) m/z; 494 [M+H]$^+$

Example 297

(R)-1-{6-[(oxetan-3-yl)methyl]-7-oxo-5-trifluoromethyl-6,7-dihydro-[1,3]thiazolo[5,4-d]pyrimidin-2-yl}-N-((R)-1-phenylethyl) pyrrolidine-2-carboxamide

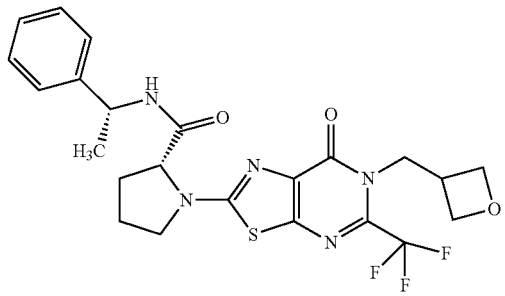 [SMILES: C[C@@H](NC(=O)[C@H]1CCCN1c1nc2c(=O)n(CC3COC3)c(C(F)(F)F)nc2s1)c1ccccc1]

The compound (90 mg) obtained in Reference Example 321 was treated by a method similar to that in Example 295 to give the title compound (59 mg).

MS (ESI) m/z; 508 [M+H]$^+$

Example 298

(R)-N-benzyl-1-[5-(3-fluoropyridin-2-yl)-6-methyl-7-oxo-6,7-dihydro-[1,3]thiazolo[5,4-d]pyrimidin-2-yl]pyrrolidine-2-carboxamide

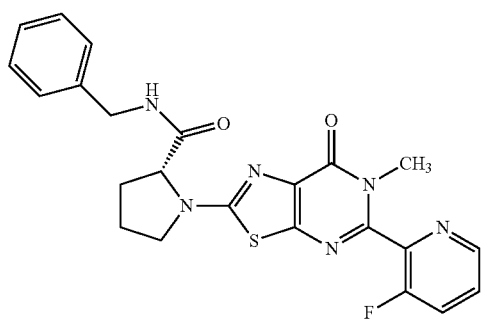 [SMILES: Cn1c(-c2ncccc2F)nc2sc(N3CCC[C@@H]3C(=O)NCc3ccccc3)nc2c1=O]

The compound (213 mg) obtained in Reference Example 329 was treated by a method similar to that in Example 295 to give the title compound (185 mg).

MS (ESI) m/z; 465 [M+H]$^+$

Example 299

(R)-N-[(R)-cyclopropyl(phenyl)methyl]-1-(5-difluoromethyl-6-ethyl-7-oxo-6,7-dihydro-[1,3]thiazolo[5,4-d]pyrimidin-2-yl)pyrrolidine-2-carboxamide

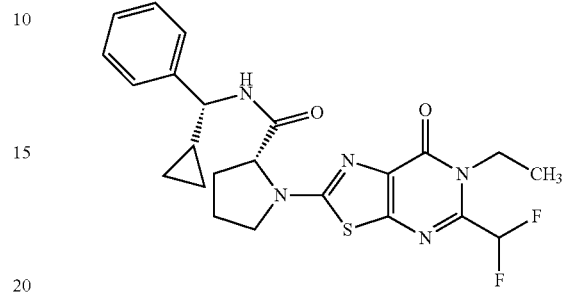

To a solution (4.0 mL) of the compound (200 mg) obtained in Reference Example 124 in DMF were added (R)-cyclopropylphenylmethylamine hydrochloride (160 mg), N,N-diisopropylethylamine (304 µL), EDC hydrochloride (167 mg) and HOBt monohydrate (133 mg), and the reaction mixture was stirred at room temperature overnight. Water was added to the reaction mixture, and the mixture was extracted twice with ethyl acetate. The organic layer was dried over anhydrous magnesium sulfate, filtered and concentrated. The residue was purified by silica gel column chromatography (solvent; hexane/ethyl acetate=70/30-20/80) to give the title compound (225 mg).

MS (ESI) m/z; 474 [M+H]$^+$

Example 300

(R)-1-(5-difluoromethyl-6-ethyl-7-oxo-6,7-dihydro-[1,3]thiazolo[5,4-d]pyrimidin-2-yl)-N-((S)-2-methoxy-1-phenylethyl)pyrrolidine-2-carboxamide

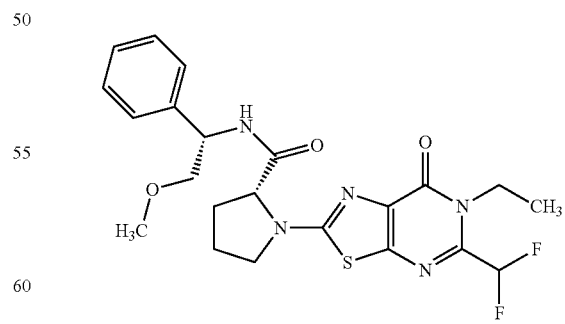

The compound (200 mg) obtained in Reference Example 124 was treated by a method similar to that in Example 299 to give the title compound (197 mg).

MS (ESI) m/z; 478 [M+H]$^+$

Example 301

(R)-1-(5-difluoromethyl-6-ethyl-7-oxo-6,7-dihydro-[1,3]thiazolo[5,4-d]pyrimidin-2-yl)pyrrolidine-N-((S)-2,2,2-trifluoro-1-phenylethyl)-2-carboxamide

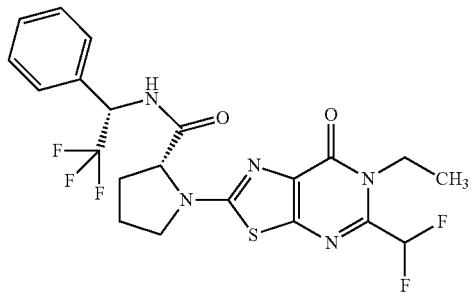 [SMILES: CCn1c(C(F)F)nc2sc(N3CCC[C@@H]3C(=O)N[C@@H](c3ccccc3)C(F)(F)F)nc2c1=O]

The compound (200 mg) obtained in Reference Example 124 was treated by a method similar to that in Example 299 to give the title compound (201 mg).

MS (ESI) m/z; 502 [M+H]$^+$

Example 302

(R)-N-(3-cyanobenzyl)-1-(5-difluoromethyl-6-ethyl-7-oxo-6,7-dihydro-[1,3]thiazolo[5,4-d]pyrimidin-2-yl)pyrrolidine-2-carboxamide

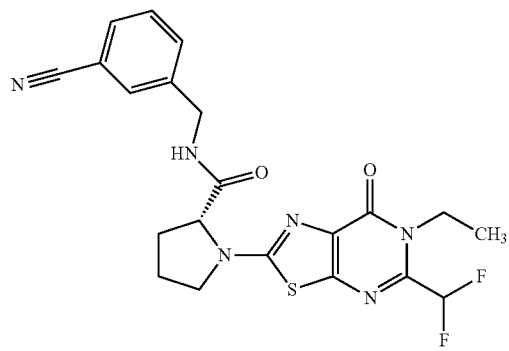 [SMILES: CCn1c(C(F)F)nc2sc(N3CCC[C@@H]3C(=O)NCc3cccc(C#N)c3)nc2c1=O]

To a solution (0.5 mL) of the compound (48 mg) obtained in Reference Example 124 in DMF were added 3-cyanobenzylamine (16 mg), EDC hydrochloride (35 mg), HOBt monohydrate (24 mg) and N,N-diisopropylethylamine (23 mg), and the reaction mixture was stirred at room temperature for 3 hr. After confirmation of the completion of the reaction, water was added to the reaction mixture, and the mixture was extracted twice with chloroform. The solvent was evaporated under reduced pressure, and the residue was purified by Waters XTerra® column (solvent; 10 mmol/L aqueous ammonium carbonate solution/methanol) to give the title compound (21 mg).

MS (ESI) m/z; 459 [M+H]$^+$

Example 303

(R)-1-(5-difluoromethyl-6-ethyl-7-oxo-6,7-dihydro-[1,3]thiazolo[5,4-d]pyrimidin-2-yl)-N-[(2,3-dihydrobenzofuran-5-yl)methyl]pyrrolidine-2-carboxamide

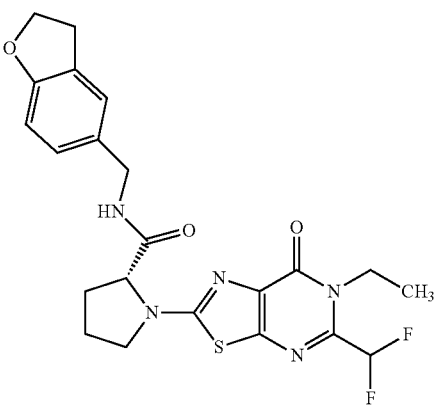 [SMILES: CCn1c(C(F)F)nc2sc(N3CCC[C@@H]3C(=O)NCc3ccc4c(c3)CCO4)nc2c1=O]

The compound (48 mg) obtained in Reference Example 124 was treated by a method similar to that in Example 302 to give the title compound (36 mg).

MS (ESI) m/z; 476 [M+H]$^+$

Example 304

(R)-N-[(benzo[1,3]dioxo-5-yl)methyl]-1-(5-difluoromethyl-6-ethyl-7-oxo-6,7-dihydro-[1,3]thiazolo[5,4-d]pyrimidin-2-yl)pyrrolidine-2-carboxamide

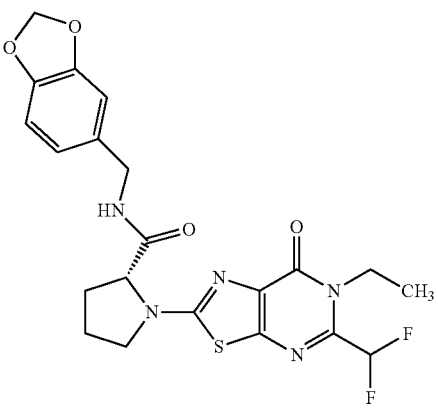 [SMILES: CCn1c(C(F)F)nc2sc(N3CCC[C@@H]3C(=O)NCc3ccc4c(c3)OCO4)nc2c1=O]

The compound (48 mg) obtained in Reference Example 124 was treated by a method similar to that in Example 302 to give the title compound (43 mg).

MS (ESI) m/z; 478 [M+H]$^+$

Example 305

(R)-1-(5-difluoromethyl-6-ethyl-7-oxo-6,7-dihydro-[1,3]thiazolo[5,4-d]pyrimidin-2-yl)-N-(3-fluorobenzyl)pyrrolidine-2-carboxamide

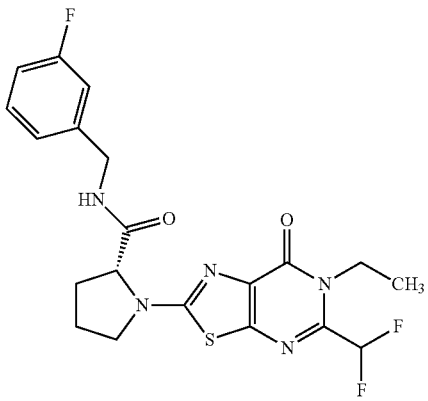 [SMILES: CCn1c(C(F)F)nc2sc(N3CCC[C@@H]3C(=O)NCc3cccc(F)c3)nc2c1=O]

The compound (48 mg) obtained in Reference Example 124 was treated by a method similar to that in Example 302 to give the title compound (43 mg).

MS (ESI) m/z; 452 [M+H]+

Example 306

(R)-1-(5-difluoromethyl-6-ethyl-7-oxo-6,7-dihydro-[1,3]thiazolo[5,4-d]pyrimidin-2-yl)-N-[4-(N',N'-dimethylamino)benzyl]pyrrolidine-2-carboxamide

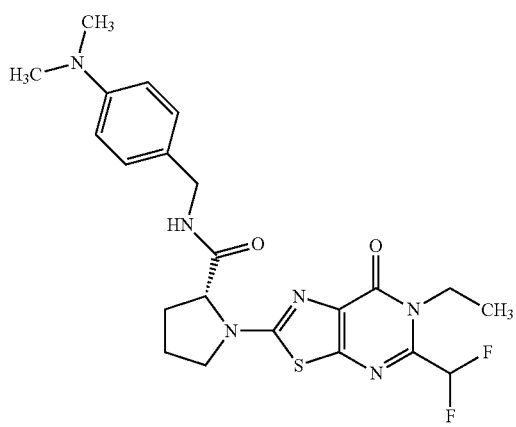 [SMILES: CCn1c(C(F)F)nc2sc(N3CCC[C@@H]3C(=O)NCc3ccc(N(C)C)cc3)nc2c1=O]

The compound (48 mg) obtained in Reference Example 124 was treated by a method similar to that in Example 302 to give the title compound (41 mg).

MS (ESI) m/z; 477 [M+H]+

Example 307

(R)-1-(5-difluoromethyl-6-ethyl-7-oxo-6,7-dihydro-[1,3]thiazolo[5,4-d]pyrimidin-2-yl)-N-[(furan-2-yl)methyl]pyrrolidine-2-carboxamide

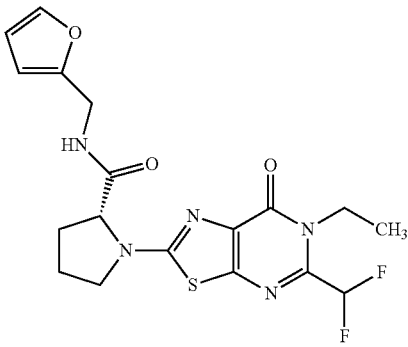 [SMILES: CCn1c(C(F)F)nc2sc(N3CCC[C@@H]3C(=O)NCc3ccco3)nc2c1=O]

The compound (48 mg) obtained in Reference Example 124 was treated by a method similar to that in Example 302 to give the title compound (43 mg).

MS (ESI) m/z; 424 [M+H]+

Example 308

(R)-1-(5-difluoromethyl-6-ethyl-7-oxo-6,7-dihydro-[1,3]thiazolo[5,4-d]pyrimidin-2-yl)-N-(4-methoxybenzyl)pyrrolidine-2-carboxamide

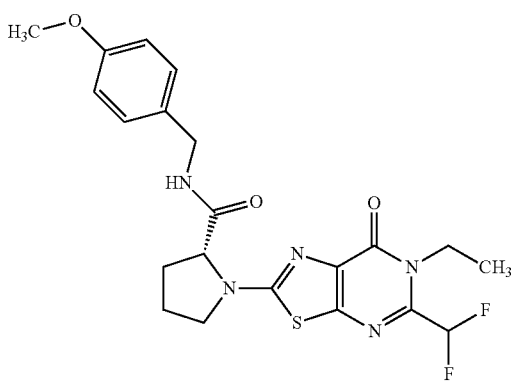 [SMILES: CCn1c(C(F)F)nc2sc(N3CCC[C@@H]3C(=O)NCc3ccc(OC)cc3)nc2c1=O]

The compound (48 mg) obtained in Reference Example 124 was treated by a method similar to that in Example 302 to give the title compound (43 mg).

MS (ESI) m/z; 464 [M+H]+

Example 309

(R)-1-(5-difluoromethyl-6-ethyl-7-oxo-6,7-dihydro-[1,3]thiazolo[5,4-d]pyrimidin-2-yl)-N-[(thiophen-2-yl)methyl]pyrrolidine-2-carboxamide

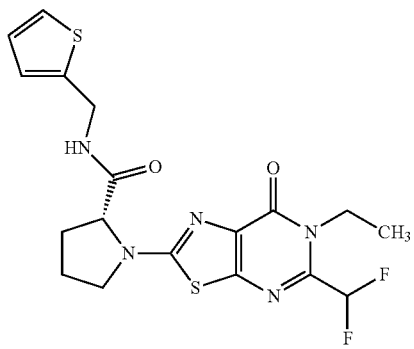 [SMILES: CCn1c(C(F)F)nc2sc(N3CCC[C@@H]3C(=O)NCc3cccs3)nc2c1=O]

The compound (48 mg) obtained in Reference Example 124 was treated by a method similar to that in Example 302 to give the title compound (46 mg).
MS (ESI) m/z; 440 [M+H]$^+$

Example 310

(R)-1-(5-difluoromethyl-6-ethyl-7-oxo-6,7-dihydro-[1,3]thiazolo[5,4-d]pyrimidin-2-yl)-N-(3,4-dimethoxybenzyl)pyrrolidine-2-carboxamide

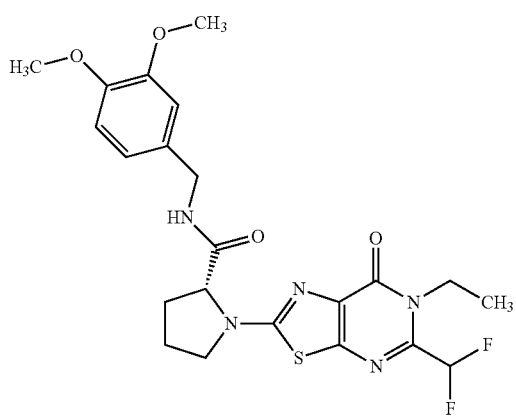 [SMILES: CCn1c(C(F)F)nc2sc(N3CCC[C@@H]3C(=O)NCc3ccc(OC)c(OC)c3)nc2c1=O]

The compound (48 mg) obtained in Reference Example 124 was treated by a method similar to that in Example 302 to give the title compound (29 mg).
MS (ESI) m/z; 494 [M+H]$^+$

Example 311

(R)-1-(5-difluoromethyl-6-ethyl-7-oxo-6,7-dihydro-[1,3]thiazolo[5,4-d]pyrimidin-2-yl)-N-[(5-methyl-isoxazol-3-yl)methyl]pyrrolidine-2-carboxamide

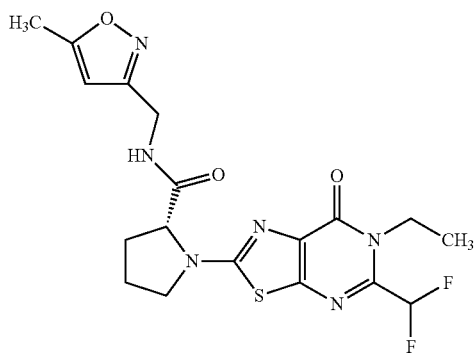 [SMILES: CCn1c(C(F)F)nc2sc(N3CCC[C@@H]3C(=O)NCc3cc(C)on3)nc2c1=O]

The compound (48 mg) obtained in Reference Example 124 was treated by a method similar to that in Example 302 to give the title compound (39 mg).
MS (ESI) m/z; 439 [M+H]$^+$

Example 312

(R)-1-(5-difluoromethyl-6-ethyl-7-oxo-6,7-dihydro-[1,3]thiazolo[5,4-d]pyrimidin-2-yl)-N-(2-fluorobenzyl)pyrrolidine-2-carboxamide

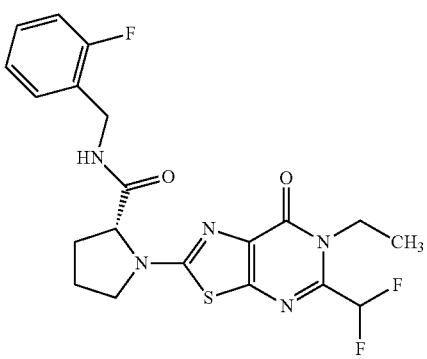 [SMILES: CCn1c(C(F)F)nc2sc(N3CCC[C@@H]3C(=O)NCc3ccccc3F)nc2c1=O]

The compound (48 mg) obtained in Reference Example 124 was treated by a method similar to that in Example 302 to give the title compound (44 mg).
MS (ESI) m/z; 452 [M+H]$^+$

Example 313

(R)-1-(5-difluoromethyl-6-ethyl-7-oxo-6,7-dihydro-[1,3]thiazolo[5,4-d]pyrimidin-2-yl)-N-[(2,5-dimethyl-2H-pyrazol-3-yl)methyl]pyrrolidine-2-carboxamide

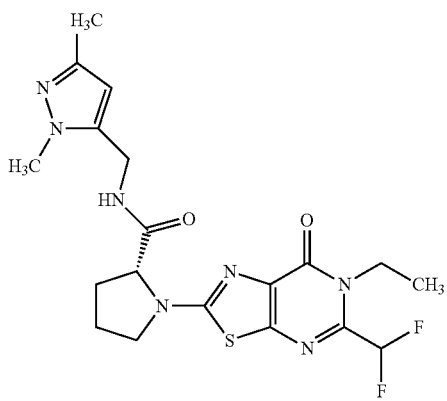 [SMILES: CCn1c(C(F)F)nc2sc(N3CCC[C@@H]3C(=O)NCc3cc(C)nn3C)nc2c1=O]

The compound (48 mg) obtained in Reference Example 124 was treated by a method similar to that in Example 302 to give the title compound (45 mg).

MS (ESI) m/z; 452 [M+H]+

Example 314

(R)-1-(5-difluoromethyl-6-ethyl-7-oxo-6,7-dihydro-[1,3]thiazolo[5,4-d]pyrimidin-2-yl)-N-[(1,3-thiazol-2-yl)methyl]pyrrolidine-2-carboxamide

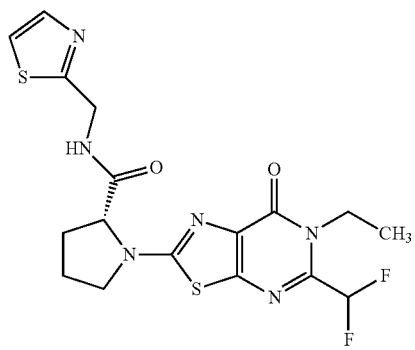 [SMILES: CCn1c(C(F)F)nc2sc(N3CCC[C@@H]3C(=O)NCc3nccs3)nc2c1=O]

The compound (48 mg) obtained in Reference Example 124 was treated by a method similar to that in Example 302 to give the title compound (44 mg).

MS (ESI) m/z; 441 [M+H]+

Example 315

(R)-1-(5-difluoromethyl-6-ethyl-7-oxo-6,7-dihydro-[1,3]thiazolo[5,4-d]pyrimidin-2-yl)-N-[3-(N',N'-dimethylamino) benzyl]pyrrolidine-2-carboxamide

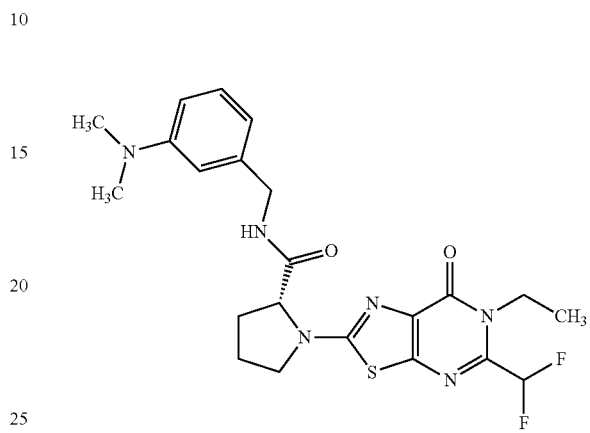

The compound (48 mg) obtained in Reference Example 124 was treated by a method similar to that in Example 302 to give the title compound (44 mg).

MS (ESI) m/z; 477 [M+H]+

Example 316

(R)-N-(4-cyanobenzyl)-1-(5-difluoromethyl-6-ethyl-7-oxo-6,7-dihydro-[1,3]thiazolo[5,4-d]pyrimidin-2-yl)pyrrolidine-2-carboxamide

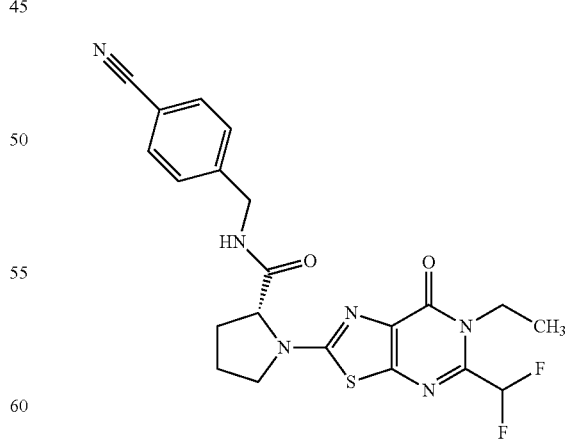

The compound (48 mg) obtained in Reference Example 124 was treated by a method similar to that in Example 302 to give the title compound (40 mg).

MS (ESI) m/z; 459 [M+H]+

Example 317

(R)-1-(5-difluoromethyl-6-ethyl-7-oxo-6,7-dihydro[1,3]thiazolo[5,4-d]pyrimidin-2-yl)-N-[2-(N',N'-dimethylamino)benzyl]pyrrolidine-2-carboxamide

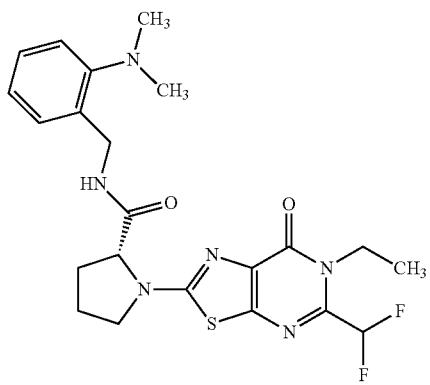 [SMILES: CCn1c(C(F)F)nc2sc(N3CCC[C@@H]3C(=O)NCc3ccccc3N(C)C)nc2c1=O]

The compound (48 mg) obtained in Reference Example 124 was treated by a method similar to that in Example 302 to give the title compound (47 mg).

MS (ESI) m/z; 477 [M+H]$^+$

Example 318

(R)-1-(5-difluoromethyl-6-ethyl-7-oxo-6,7-dihydro-[1,3]thiazolo[5,4-d]pyrimidin-2-yl)-N-{2-[(N',N'-dimethylamino)methyl]benzyl}pyrrolidine-2-carboxamide

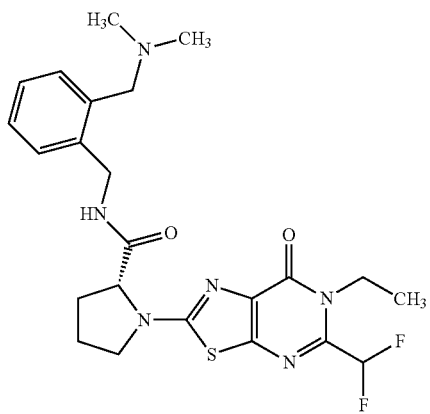 [SMILES: CCn1c(C(F)F)nc2sc(N3CCC[C@@H]3C(=O)NCc3ccccc3CN(C)C)nc2c1=O]

The compound (48 mg) obtained in Reference Example 124 was treated by a method similar to that in Example 302 to give the title compound (49 mg).

MS (ESI) m/z; 491 [M+H]$^+$

Example 319

(R)-1-(5-difluoromethyl-6-ethyl-7-oxo-6,7-dihydro-[1,3]thiazolo[5,4-d]pyrimidin-2-yl)-N-[2-(methoxymethyl)benzyl]pyrrolidine-2-carboxamide

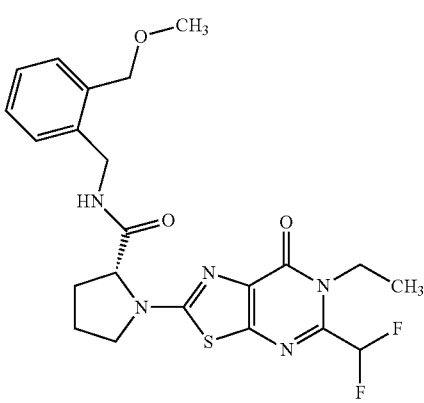 [SMILES: CCn1c(C(F)F)nc2sc(N3CCC[C@@H]3C(=O)NCc3ccccc3COC)nc2c1=O]

The compound (48 mg) obtained in Reference Example 124 was treated by a method similar to that in Example 302 to give the title compound (31 mg).

MS (ESI) m/z; 478 [M+H]$^+$

Example 320

(R)-1-(5-difluoromethyl-6-ethyl-7-oxo-6,7-dihydro-[1,3]thiazolo[5,4-d]pyrimidin-2-yl)-N-[4-(methoxymethyl)benzyl]pyrrolidine-2-carboxamide

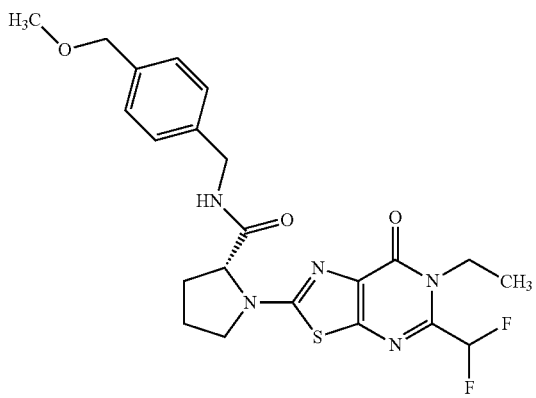 [SMILES: CCn1c(C(F)F)nc2sc(N3CCC[C@@H]3C(=O)NCc3ccc(COC)cc3)nc2c1=O]

The compound (48 mg) obtained in Reference Example 124 was treated by a method similar to that in Example 302 to give the title compound (48 mg).

MS (ESI) m/z; 478 [M+H]$^+$

Example 321

(R)-N-benzyl-1-{5-[(3-methoxyazetidin-1-yl)methyl]-6-methyl-7-oxo-6,7-dihydro[1,3]thiazolo[5,4-d]pyrimidin-2-yl}pyrrolidine-2-carboxamide

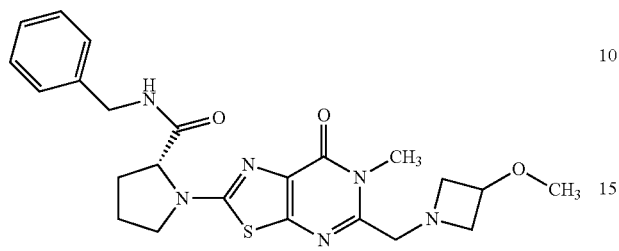

The compound (148 mg) obtained in Reference Example 355 was treated by a method similar to that in Example 178 to give the title compound (18 mg).
MS (ESI) m/z; 469 [M+H]$^+$

Example 322

(R)-N-benzyl-1-{6-methyl-5-[(morpholin-4-yl)methyl]-7-oxo-6,7-dihydro[1,3]thiazolo[5,4-d]pyrimidin-2-yl}pyrrolidine-2-carboxamide

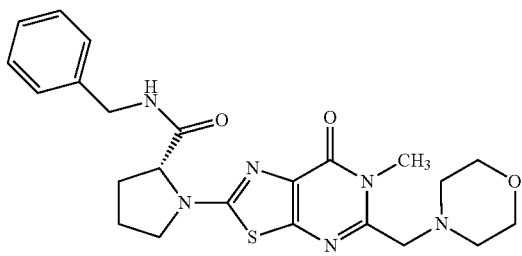 [SMILES: Cn1c(CN2CCOCC2)nc2sc(N3CCC[C@@H]3C(=O)NCc3ccccc3)nc2c1=O]

The compound (68 mg) obtained in Reference Example 351 was treated by a method similar to that in Example 257 to give the title compound (51 mg).
MS (ESI) m/z; 469 [M+H]$^+$

Example 323

(R)-N-benzyl-1-{5-[(N',N'-dimethylamino)methyl]-6-methyl-7-oxo-6,7-dihydro[1,3]thiazolo[5,4-d]pyrimidin-2-yl}pyrrolidine-2-carboxamide

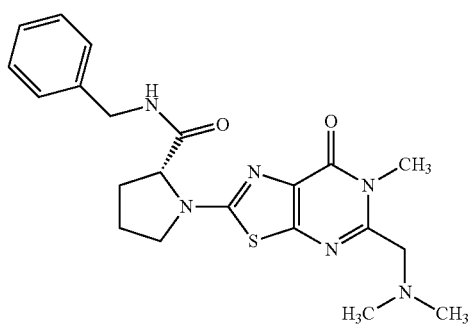 [SMILES: CN(C)Cc1nc2sc(N3CCC[C@@H]3C(=O)NCc3ccccc3)nc2c(=O)n1C]

The compound (306 mg) obtained in Reference Example 352 was treated by a method similar to that in Example 257 to give the title compound (252 mg).
MS (ESI) m/z; 427 [M+H]$^+$

Example 324

(R)-N-benzyl-1-{6-methyl-7-oxo-5-[(pyrrolidin-1-yl)methyl]-6,7-dihydro[1,3]thiazolo[5,4-d]pyrimidin-2-yl}pyrrolidine-2-carboxamide

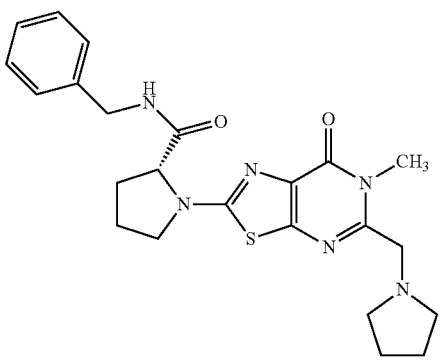 [SMILES: Cn1c(CN2CCCC2)nc2sc(N3CCC[C@@H]3C(=O)NCc3ccccc3)nc2c1=O]

The compound (346 mg) obtained in Reference Example 356 was treated by a method similar to that in Example 257 to give the title compound (217 mg).
MS (ESI) m/z; 453 [M+H]$^+$

Example 325

(R)-N-benzyl-1-{6-methyl-7-oxo-5-[(piperidin-1-yl)methyl]-6,7-dihydro[1,3]thiazolo[5,4-d]pyrimidin-2-yl}pyrrolidine-2-carboxamide

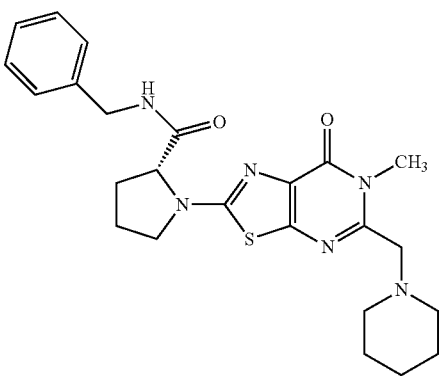 [SMILES: Cn1c(CN2CCCCC2)nc2sc(N3CCC[C@@H]3C(=O)NCc3ccccc3)nc2c1=O]

The compound (359 mg) obtained in Reference Example 357 was treated by a method similar to that in Example 257 to give the title compound (357 mg).
MS (ESI) m/z; 467 [M+H]$^+$

Example 326

(R)-N-benzyl-1-{5-[(N'-ethyl-N'-methylamino)methyl]-6-methyl-7-oxo-6,7-dihydro[1,3]thiazolo[5,4-d]pyrimidin-2-yl}pyrrolidine-2-carboxamide

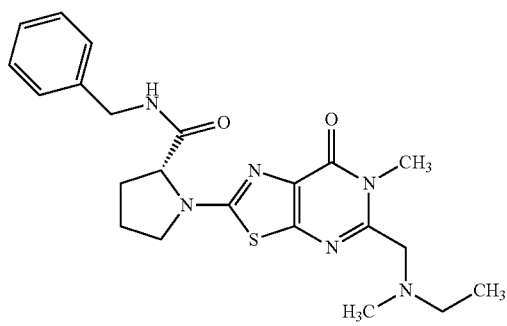 [SMILES: CCN(C)Cc1nc2sc(N3CCC[C@@H]3C(=O)NCc3ccccc3)nc2c(=O)n1C]

The compound (206 mg) obtained in Reference Example 353 was treated by a method similar to that in Example 295 to give the title compound (110 mg).

MS (ESI) m/z; 441 [M+H]$^+$

Example 327

(R)-1-{5-[(azetidin-1-yl)methyl]-6-methyl-7-oxo-6,7-dihydro[1,3]thiazolo[5,4-d]pyrimidin-2-yl}-N-benzylpyrrolidine-2-carboxamide

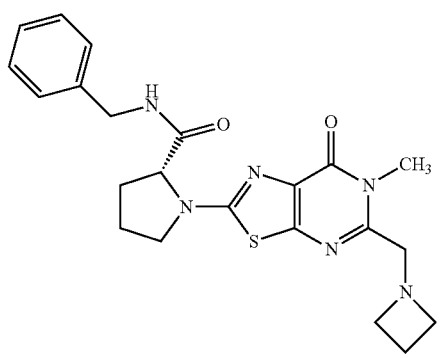 [SMILES: Cn1c(CN2CCC2)nc2sc(N3CCC[C@@H]3C(=O)NCc3ccccc3)nc2c1=O]

The compound (227 mg) obtained in Reference Example 354 was treated by a method similar to that in Example 295 to give the title compound (59 mg).

MS (ESI) m/z; 439 [M+H]$^+$

Example 328

(R)-N-benzyl-1-{5-[(1,3-dihydro-2H-isoindol-2-yl)methyl]-6-methyl-7-oxo-6,7-dihydro[1,3]thiazolo[5,4-d]pyrimidin-2-yl}pyrrolidine-2-carboxamide

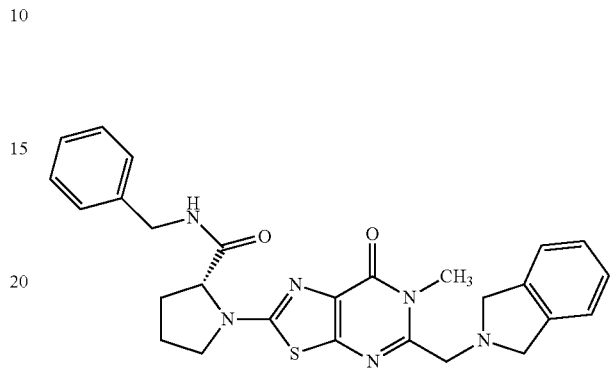

The compound (296 mg) obtained in Reference Example 358 was treated by a method similar to that in Example 295 to give the title compound (143 mg).

MS (ESI) m/z; 501 [M+H]$^+$

Example 329

(R)-N-benzyl-1-{5-[(N',N'-dimethylamino)methyl]-6-ethyl-7-oxo-6,7-dihydro[1,3]thiazolo[5,4-d]pyrimidin-2-yl}pyrrolidine-2-carboxamide

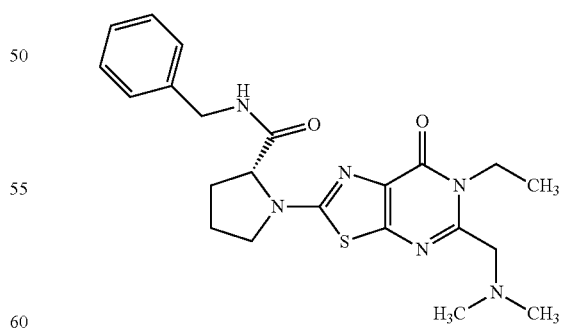

The compound (214 mg) obtained in Reference Example 359 was treated by a method similar to that in Example 295 to give the title compound (184 mg).

MS (ESI) m/z; 441 [M+H]$^+$

Example 330

(R)-N-benzyl-1-{6-ethyl-5-[(N'-ethyl-N'-methyl-amino)methyl]-7-oxo-6,7-dihydro[1,3]thiazolo[5,4-d]pyrimidin-2-yl}pyrrolidine-2-carboxamide

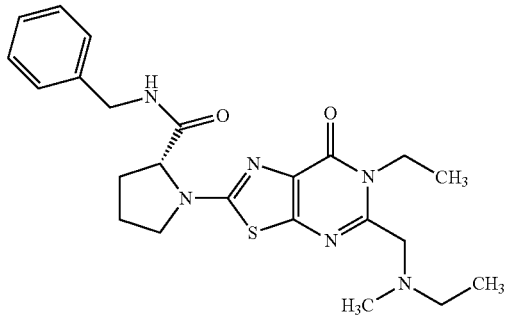 [SMILES: CCN(C)Cc1nc2sc(N3CCC[C@@H]3C(=O)NCc3ccccc3)nc2c(=O)n1CC]

The compound (267 mg) obtained in Reference Example 360 was treated by a method similar to that in Example 295 to give the title compound (134 mg).

MS (ESI) m/z; 455 [M+H]$^+$

Example 331

(R)-N-benzyl-1-{5-[(N',N'-dimethylamino)methyl]-7-oxo-6-(propan-2-yl)-6,7-dihydro[1,3]thiazolo[5,4-d]pyrimidin-2-yl}pyrrolidine-2-carboxamide

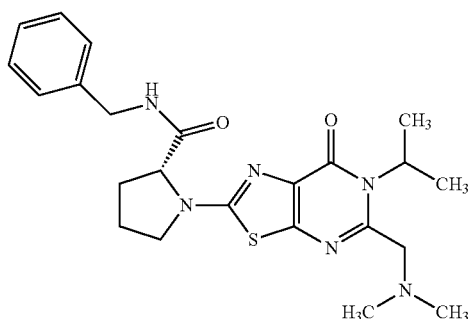

The compound (120 mg) obtained in Reference Example 361 was treated by a method similar to that in Example 295 to give the title compound (89 mg).

MS (ESI) m/z; 455 [M+H]$^+$

Example 332

(R)-N-benzyl-1-[5-{[N'-(2-methoxyethyl)-N'-methylamino]methyl}-7-oxo-6-(propan-2-yl)-6,7-dihydro[1,3]thiazolo[5,4-d]pyrimidin-2-yl]pyrrolidine-2-carboxamide

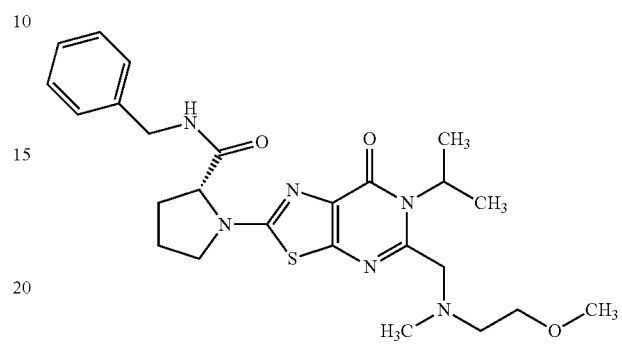

The compound (142 mg) obtained in Reference Example 362 was treated by a method similar to that in Example 295 to give the title compound (136 mg).

MS (ESI) m/z; 499 [M+H]$^+$

Example 333

(R)-N-benzyl-1-[6-methyl-5-{[N'-methyl-N'-(2,2,2-trifluoroethyl)amino]methyl}-7-oxo-6,7-dihydro[1,3]thiazolo[5,4-d]pyrimidin-2-yl]pyrrolidine-2-carboxamide

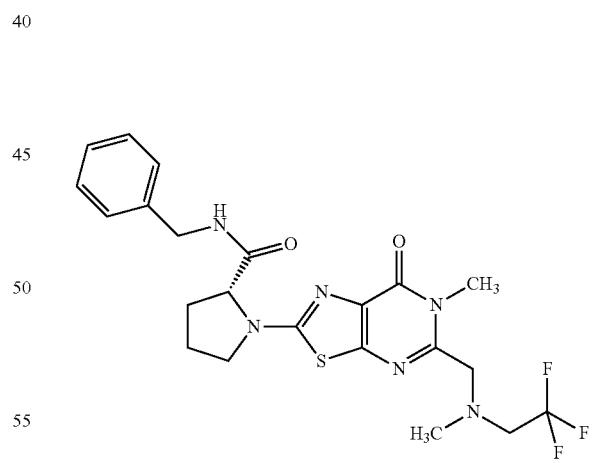

The compound (747 mg) obtained in Reference Example 363 was treated by a method similar to that in Example 295 to give the title compound (216 mg).

MS (ESI) m/z; 495 [M+H]$^+$

Example 334

(R)-N-benzyl-1-[6-(2-methoxyethyl)-5-(4-methyl-piperazin-1-yl)-7-oxo-6,7-dihydro[1,3]thiazolo[5,4-d]pyrimidin-2-yl]pyrrolidine-2-carboxamide hydrochloride

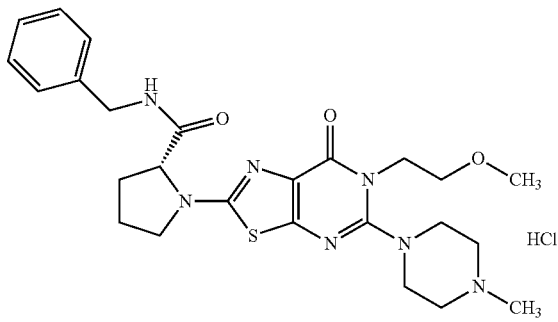 [SMILES: COCCn1c(N2CCN(C)CC2)nc2sc(N3CCC[C@@H]3C(=O)NCc3ccccc3)nc2c1=O ; Cl]

To a solution (4.0 mL) of the compound (174 mg) obtained in Reference Example 374 in DMF were added (D)-proline (81 mg) and cesium carbonate (344 mg), and the reaction mixture was heated at 80° C. for 2 hr. The reaction mixture was cooled to room temperature, and neutralized with concentrated hydrochloric acid (180 µL). N,N-diisopropylethylamine (163 µL), benzylamine (102 µL), EDC hydrochloride (180 mg) and HOBt monohydrate (143 mg) were added to the reaction mixture, and the reaction mixture was stirred at room temperature overnight. Water was added to the reaction mixture, and the mixture was extracted three times with ethyl acetate. The combined organic layer was dried over anhydrous sodium sulfate, filtered and concentrated. The residue was purified by silica gel column chromatography (solvent; chloroform/methanol=100/0-95/5). To a solution (2.0 mL) of the obtained product in ethyl acetate was added hydrogen chloride (4.0 mol/L ethyl acetate solution, 57 µL), and the mixture was stirred for 5 min. The solvent was evaporated under reduced pressure, to the residue was added ethyl acetate, and the solid was collected by filtration and dried to give the title compound (75 mg).
MS (ESI) m/z; 512 [M+H]$^+$

Example 335

(R)-N-benzyl-1-[5-(N',N'-dimethylamino)-6-methyl-7-oxo-6,7-dihydro[1,3]thiazolo[5,4-d]pyrimidin-2-yl]pyrrolidine-2-carboxamide

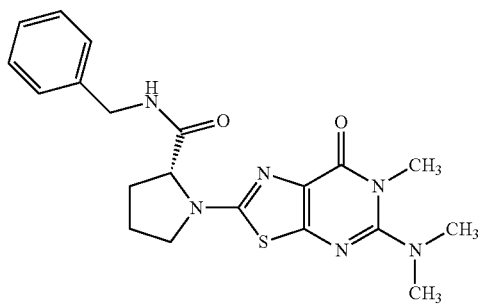 [SMILES: CN(C)c1nc2sc(N3CCC[C@@H]3C(=O)NCc3ccccc3)nc2c(=O)n1C]

The compound (278 mg) obtained in Reference Example 370 was treated by a method similar to that in Example 203 to give the title compound (241 mg).
MS (ESI) m/z; 413 [M+H]$^+$

Example 336

(R)-N-benzyl-1-[6-methyl-7-oxo-5-(pyrrolidin-1-yl)-6,7-dihydro[1,3]thiazolo[5,4-d]pyrimidin-2-yl]pyrrolidine-2-carboxamide

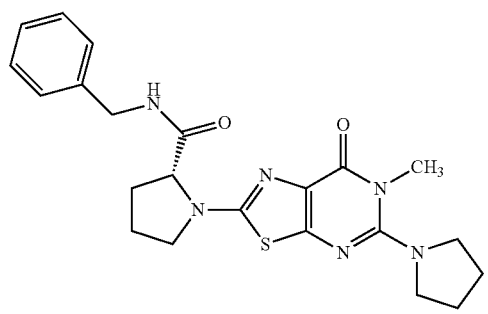 [SMILES: Cn1c(N2CCCC2)nc2sc(N3CCC[C@@H]3C(=O)NCc3ccccc3)nc2c1=O]

The compound (274 mg) obtained in Reference Example 371 was treated by a method similar to that in Example 203 to give the title compound (108 mg).
MS (ESI) m/z; 439 [M+H]$^+$

Example 337

(R)-N-benzyl-1-[6-methyl-7-oxo-5-(piperidin-1-yl)-6,7-dihydro[1,3]thiazolo[5,4-d]pyrimidin-2-yl]pyrrolidine-2-carboxamide

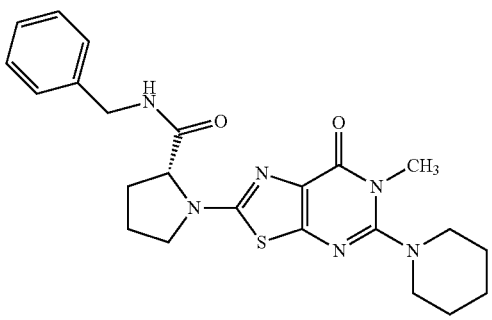 [SMILES: Cn1c(N2CCCCC2)nc2sc(N3CCC[C@@H]3C(=O)NCc3ccccc3)nc2c1=O]

The compound (205 mg) obtained in Reference Example 372 was treated by a method similar to that in Example 203 to give the title compound (96 mg).
MS (ESI) m/z; 453 [M+H]$^+$

Example 338

(R)-N-benzyl-1-[5-(3-methoxyazetidin-1-yl)-6-methyl-7-oxo-6,7-dihydro[1,3]thiazolo[5,4-d]pyrimidin-2-yl]pyrrolidine-2-carboxamide

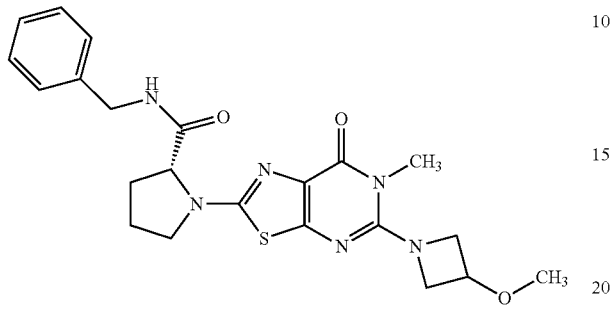

The compound (277 mg) obtained in Reference Example 373 was treated by a method similar to that in Example 203 to give the title compound (74 mg).

MS (ESI) m/z; 455 [M+H]$^+$

Example 339

(R)-N-benzyl-1-[6-methyl-5-(morpholin-4-yl)-7-oxo-6,7-dihydro[1,3]thiazolo[5,4-d]pyrimidin-2-yl]pyrrolidine-2-carboxamide

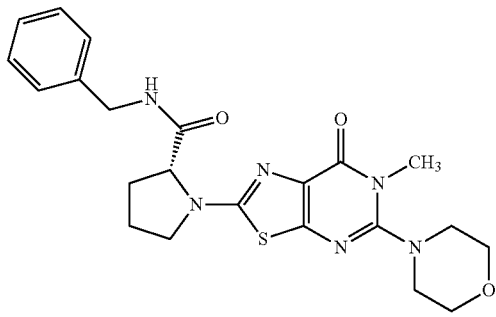 [SMILES: Cn1c(N2CCOCC2)nc2sc(N3CCC[C@@H]3C(=O)NCc3ccccc3)nc2c1=O]

The compound (214 mg) obtained in Reference Example 376 was treated by a method similar to that in Example 257 to give the title compound (166 mg).

MS (ESI) m/z; 455 [M+H]$^+$

Example 340

(R)-N-benzyl-1-{5-[N'-(4-methoxybenzyl)-N'-(propan-2-yl)amino]-6-methyl-7-oxo-6,7-dihydro[1,3]thiazolo[5,4-d]pyrimidin-2-yl}pyrrolidine-2-carboxamide

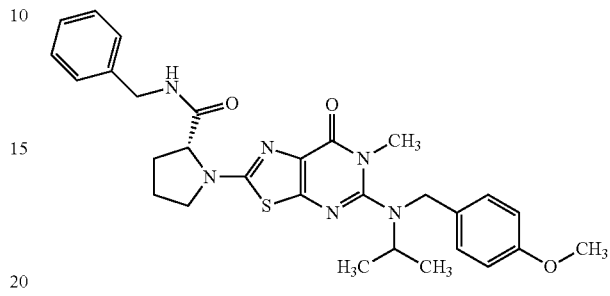

The compound (49.0 mg) obtained in Reference Example 379 was treated by a method similar to that in Example 203 to give the title compound (38.0 mg).

MS (ESI) m/z; 547 [M+H]$^+$

Example 341

(R)-N-benzyl-1-{6-methyl-7-oxo-5-[(propan-2-yl)amino]-6,7-dihydro[1,3]thiazolo[5,4-d]pyrimidin-2-yl}pyrrolidine-2-carboxamide

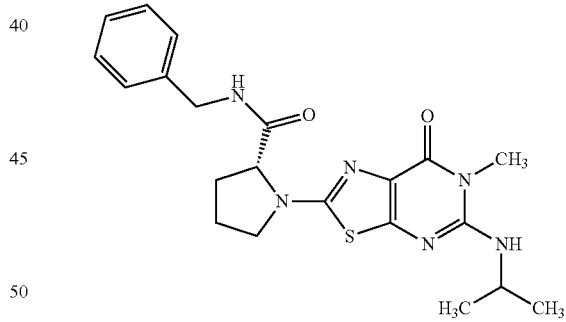

The compound (98 mg) obtained in Example 340 was dissolved in a mixture of trifluoroacetic acid/water/triethylsilane=90/5/5 (v/v) (2 mL), and the mixture was stirred with heating at 65° C. for 4 hr. The reaction mixture was concentrated, and the residue was purified by silica gel column chromatography (solvent; ethyl acetate/methanol=100/0-90/10). To the obtained product was added diisopropyl ether, and the solid was collected by filtration to give the title compound (80 mg).

MS (ESI) m/z; 427 [M+H]$^+$

Example 342

(R)-N-benzyl-1-{6-methyl-7-oxo-5-[(propan-2-yl)oxy]-6,7-dihydro[1,3]thiazolo[5,4-d]pyrimidin-2-yl}pyrrolidine-2-carboxamide

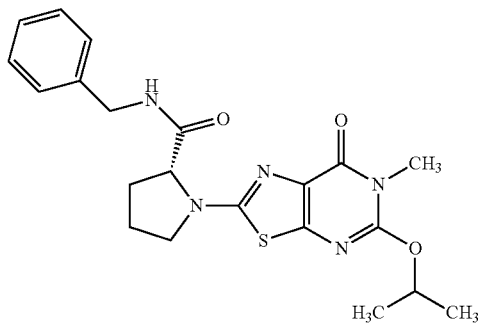 [SMILES: CC(C)Oc1nc2sc(N3CCC[C@@H]3C(=O)NCc3ccccc3)nc2c(=O)n1C]

The compound (207 mg) obtained in Reference Example 383 was treated by a method similar to that in Example 178 to give the title compound (160 mg).

MS (ESI) m/z; 428 [M+H]$^+$

Example 343

(R)-N-benzyl-1-[5-ethoxy-6-(2-methoxyethyl)-7-oxo-6,7-dihydro[1,3]thiazolo[5,4-d]pyrimidin-2-yl]pyrrolidine-2-carboxamide

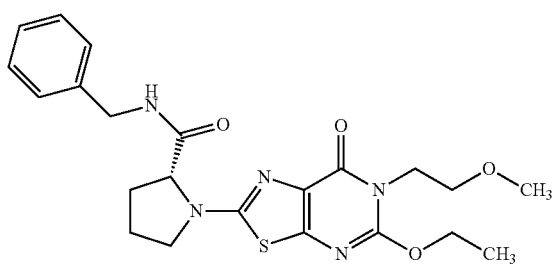 [SMILES: CCOc1nc2sc(N3CCC[C@@H]3C(=O)NCc3ccccc3)nc2c(=O)n1CCOC]

The compound (122 mg) obtained in Reference Example 384 was treated by a method similar to that in Example 178 to give the title compound (77 mg).

MS (ESI) m/z; 458 [M+H]$^+$

Example 344

(R)-N-benzyl-1-{6-(2-methoxyethyl)-7-oxo-5-[(propan-2-yl)oxy]-6,7-dihydro[1,3]thiazolo[5,4-d]pyrimidin-2-yl}pyrrolidine-2-carboxamide

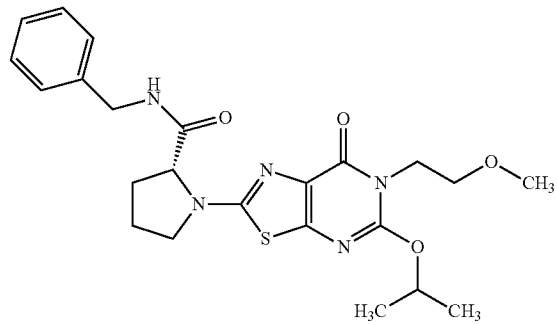 [SMILES: COCCn1c(OC(C)C)nc2sc(N3CCC[C@@H]3C(=O)NCc3ccccc3)nc2c1=O]

The compound (180 mg) obtained in Reference Example 385 was treated by a method similar to that in Example 178 to give the title compound (124 mg).

MS (ESI) m/z; 472 [M+H]$^+$

Example 345

(R)-N-benzyl-1-[5-(2-fluorophenyl)-6-methyl-7-oxo-6,7-dihydro[1,3]thiazolo[5,4-d]pyrimidin-2-yl]pyrrolidine-2-carboxamide

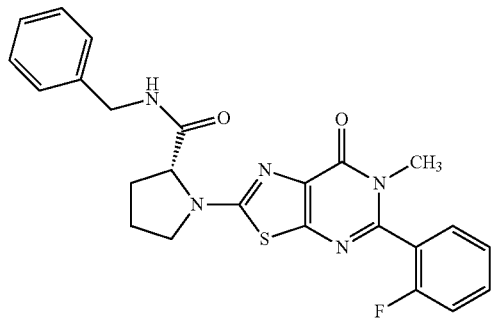 [SMILES: Cn1c(-c2ccccc2F)nc2sc(N3CCC[C@@H]3C(=O)NCc3ccccc3)nc2c1=O]

The compound (147 mg) obtained in Reference Example 389 was treated by a method similar to that in Example 203 to give the title compound (164 mg).

MS (ESI) m/z; 464 [M+H]$^+$

Example 346

(R)-N-benzyl-1-[5-(2-methoxyphenyl)-6-methyl-7-oxo-6,7-dihydro[1,3]thiazolo[5,4-d]pyrimidin-2-yl]pyrrolidine-2-carboxamide

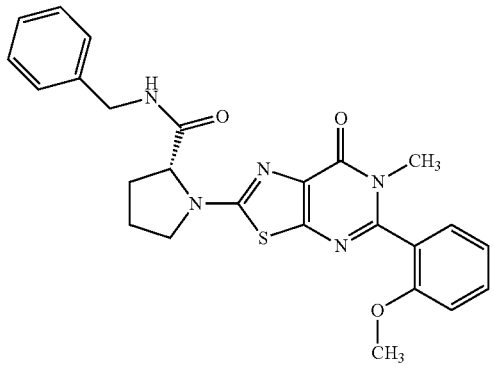 [SMILES: COc1ccccc1-c1nc2sc(N3CCC[C@@H]3C(=O)NCc3ccccc3)nc2c(=O)n1C]

The compound (326 mg) obtained in Reference Example 390 was treated by a method similar to that in Example 203 to give the title compound (250 mg).

MS (ESI) m/z; 476 [M+H]$^+$

Example 347

(R)-N-benzyl-1-[6-methyl-7-oxo-5-(2,3,4,5,6-pentadeuteriophenyl)-6,7-dihydro[1,3]thiazolo[5,4-d]pyrimidin-2-yl]pyrrolidine-2-carboxamide

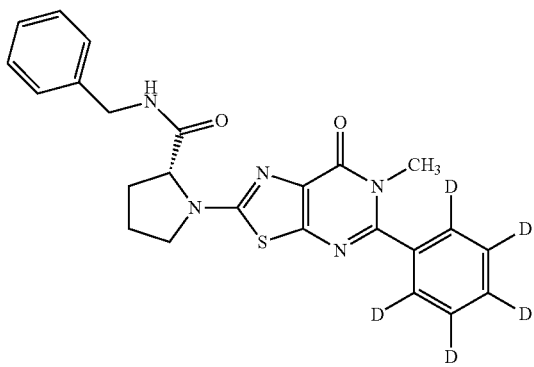 [SMILES: [2H]c1c([2H])c([2H])c(-c2nc3sc(N4CCC[C@@H]4C(=O)NCc4ccccc4)nc3c(=O)n2C)c([2H])c1[2H]]

The compound (350 mg) obtained in Reference Example 391 was treated by a method similar to that in Example 265 to give the title compound (363 mg).

MS (ESI) m/z; 451 [M+H]$^+$

Example 348

(S)-3-{2-[(R)-2-(benzylcarbamoyl)pyrrolidin-1-yl]-7-oxo-5-trifluoromethyl-7H-[1,3]thiazolo[5,4-d]pyrimidin-6-yl}pyrrolidine-1-carboxylic acid tert-butyl ester

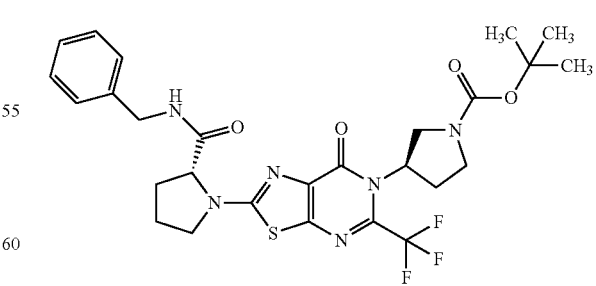

The compound (500 mg) obtained in Reference Example 413 was treated by a method similar to that in Example 203 to give the title compound (522 mg).

MS (ESI) m/z; 593 [M+H]$^+$

Example 349

(R)-3-{2-[(R)-2-(benzylcarbamoyl)pyrrolidin-1-yl]-7-oxo-5-trifluoromethyl-7H-[1,3]thiazolo[5,4-d]pyrimidin-6-yl}pyrrolidine-1-carboxylic acid tert-butyl ester The compound (500 mg) obtained in Reference Example 414 was treated by a method similar to that in Example 203 to give the title compound (486 mg).

MS (ESI) m/z; 593 [M+H]$^+$

Example 350

4-[{2-[(R)-2-(benzylcarbamoyl)pyrrolidin-1-yl]-7-oxo-5-trifluoromethyl-7H-[1,3]thiazolo[5,4-d]pyrimidin-6-yl}methyl]piperidine-1-carboxylic acid tert-butyl ester

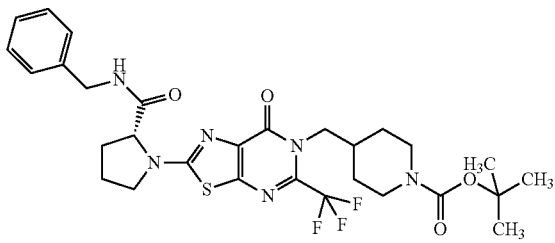 [SMILES: CC(C)(C)OC(=O)N1CCC(Cn2c(C(F)(F)F)nc3sc(N4CCC[C@@H]4C(=O)NCc4ccccc4)nc3c2=O)CC1]

The compound (2.40 g) obtained in Reference Example 415 was treated by a method similar to that in Example 203 to give the title compound (2.20 g).
MS (ESI) m/z; 521 [M+H-Boc]$^+$

Example 351

(RS)-3-[{2-[(R)-2-(benzylcarbamoyl)pyrrolidin-1-yl]-7-oxo-5-trifluoromethyl-7H-[1,3]thiazolo[5,4-d]pyrimidin-6-yl}methyl]pyrrolidine-1-carboxylic acid tert-butyl ester

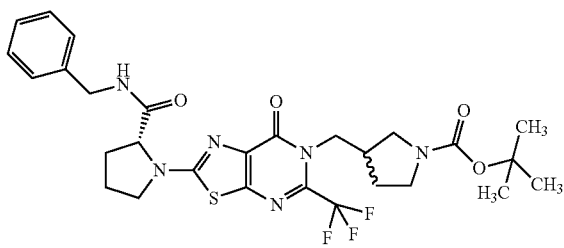 [SMILES: CC(C)(C)OC(=O)N1CCC(Cn2c(C(F)(F)F)nc3sc(N4CCC[C@@H]4C(=O)NCc4ccccc4)nc3c2=O)C1]

The compound (1.36 g) obtained in Reference Example 416 was treated by a method similar to that in Example 203 to give the title compound (1.27 g).
MS (ESI) m/z; 507 [M+H-Boc]$^+$

Example 352

(S)-2-[{2-[(R)-2-(benzylcarbamoyl)pyrrolidin-1-yl]-7-oxo-5-trifluoromethyl-7H-[1,3]thiazolo[5,4-d]pyrimidin-6-yl}methyl]pyrrolidine-1-carboxylic acid tert-butyl ester

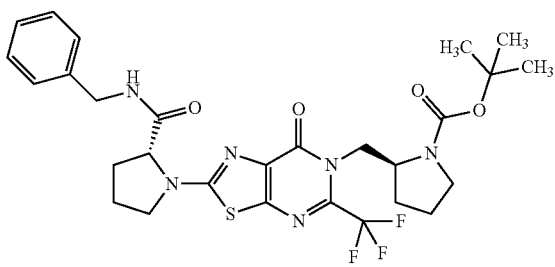 [SMILES: CC(C)(C)OC(=O)N1CCC[C@H]1Cn1c(C(F)(F)F)nc2sc(N3CCC[C@@H]3C(=O)NCc3ccccc3)nc2c1=O]

The compound (899 mg) obtained in Reference Example 417 was treated by a method similar to that in Example 203 to give the title compound (790 mg).
MS (ESI) m/z; 507 [M+H-Boc]$^+$

Example 353

(R)-2-[{2-[(R)-2-(benzylcarbamoyl)pyrrolidin-1-yl]-7-oxo-5-trifluoromethyl-7H-[1,3]thiazolo[5,4-d]pyrimidin-6-yl}methyl]pyrrolidine-1-carboxylic acid tert-butyl ester

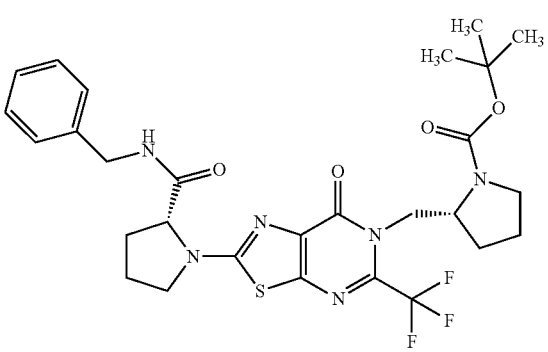 [SMILES: CC(C)(C)OC(=O)N1CCC[C@@H]1Cn1c(C(F)(F)F)nc2sc(N3CCC[C@@H]3C(=O)NCc3ccccc3)nc2c1=O]

The compound (1.30 g) obtained in Reference Example 418 was treated by a method similar to that in Example 203 to give the title compound (1.29 g).
MS (ESI) m/z; 507 [M+H-Boc]$^+$

Example 354

4-[{2-[N-((R)-1-benzylamino-1-oxopropan-2-yl)-N-methylamino]-7-oxo-5-trifluoromethyl-7H-[1,3]thiazolo[5,4-d]pyrimidin-6-yl}methyl]piperidine-1-carboxylic acid tert-butyl ester

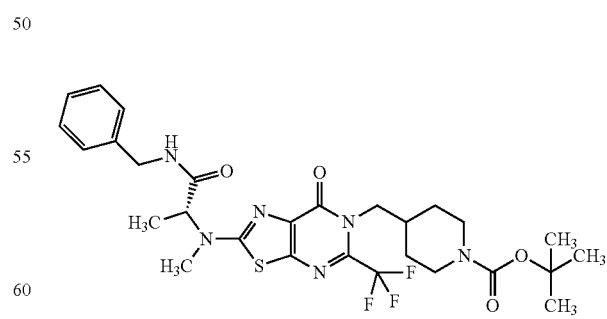

The compound (700 mg) obtained in Reference Example 415 was treated by a method similar to that in Example 265 to give the title compound (540 mg).
MS (ESI) m/z; 509 [M+H-Boc]$^+$

Example 355

N-[2-{2-[(R)-2-(benzylcarbamoyl)pyrrolidin-1-yl]-7-oxo-5-trifluoromethyl-7H-[1,3]thiazolo[5,4-d]pyrimidin-6-yl}ethyl]-N-methylcarbamic acid tert-butyl ester

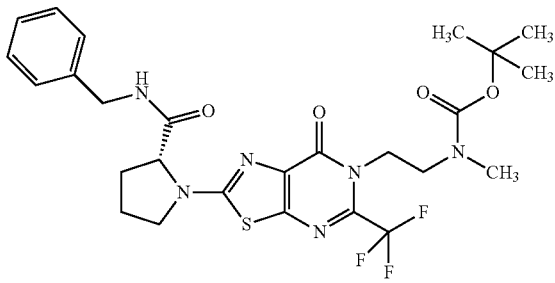 [SMILES: CN(CCn1c(C(F)(F)F)nc2sc(N3CCC[C@@H]3C(=O)NCc3ccccc3)nc2c1=O)C(=O)OC(C)(C)C]

The compound (250 mg) obtained in Reference Example 419 was treated by a method similar to that in Example 295 to give the title compound (256 mg).
MS (ESI) m/z; 581 [M+H]$^+$

Example 356

(R)-N-benzyl-1-[7-oxo-6-((S)-pyrrolidin-3-yl)-5-trifluoromethyl-6,7-dihydro[1,3]thiazolo[5,4-d]pyrimidin-2-yl]pyrrolidine-2-carboxamide

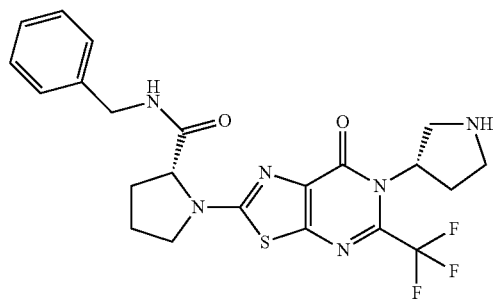 [SMILES: O=C(NCc1ccccc1)[C@H]1CCCN1c1nc2c(=O)n([C@H]3CCNC3)c(C(F)(F)F)nc2s1]

To a solution (7.5 mL) of the compound (469 mg) obtained in Example 348 in methylene chloride was added trifluoroacetic acid (7.5 mL), and the reaction mixture was stirred at room temperature for 2 hr. The reaction mixture was concentrated, aqueous sodium hydrogen carbonate solution was added, and the mixture was extracted three times with chloroform. The organic layer was dried over anhydrous sodium sulfate, filtered and concentrated. The residue was purified by NH silica gel column chromatography (solvent; ethyl acetate/methanol=100/0-95/5), to the obtained product was added (hexane-ethyl acetate=1:1), and the solid was collected by filtration and dried to give the title compound (296 mg).
MS (ESI) m/z; 493 [M+H]$^+$

Example 357

(R)-N-benzyl-1-[7-oxo-6-((R)-pyrrolidin-3-yl)-5-trifluoromethyl-6,7-dihydro[1,3]thiazolo[5,4-d]pyrimidin-2-yl]pyrrolidine-2-carboxamide

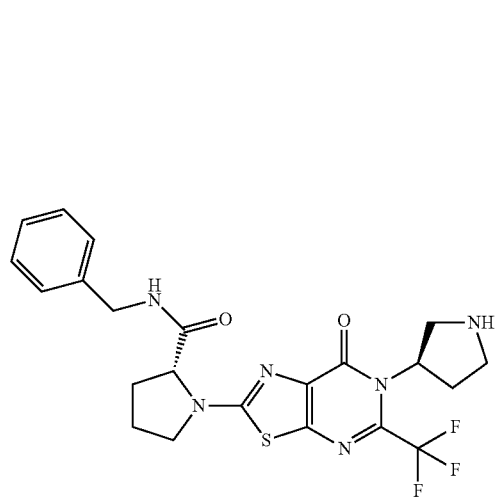 [SMILES: O=C(NCc1ccccc1)[C@H]1CCCN1c1nc2c(=O)n([C@@H]3CCNC3)c(C(F)(F)F)nc2s1]

The compound (485 mg) obtained in Example 349 was treated is by a method similar to that in Example 356 to give the title compound (319 mg).
MS (ESI) m/z; 493 [M+H]$^+$

Example 358

(R)-N-benzyl-1-{7-oxo-6-[(piperidin-4-yl)methyl]-5-trifluoromethyl-6,7-dihydro[1,3]thiazolo[5,4-d]pyrimidin-2-yl}pyrrolidine-2-carboxamide

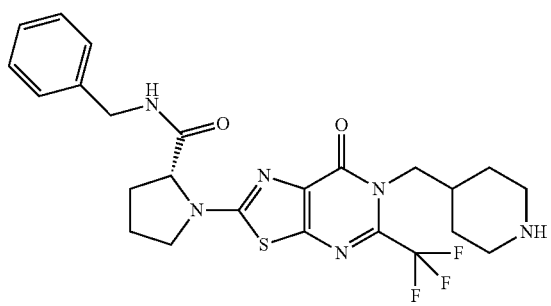 [SMILES: O=C(NCc1ccccc1)[C@H]1CCCN1c1nc2c(=O)n(CC3CCNCC3)c(C(F)(F)F)nc2s1]

The compound (2.20 g) obtained in Example 350 was treated by a method similar to that in Example 356 to give the title compound (1.75 g).
MS (ESI) m/z; 521 [M+H]$^+$

Example 359

(R)-N-benzyl-1-{7-oxo-6-[((RS)-pyrrolidin-3-yl)methyl]-5-trifluoromethyl-6,7-dihydro[1,3]thiazolo[5,4-d]pyrimidin-2-yl}pyrrolidine-2-carboxamide

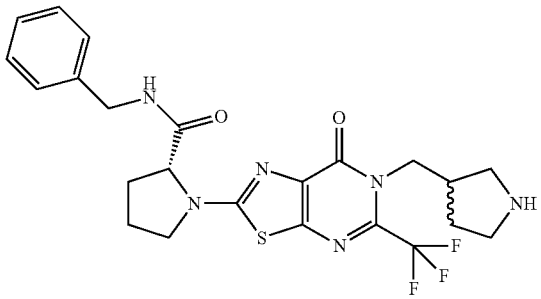 [SMILES: O=C(NCc1ccccc1)[C@H]1CCCN1c1nc2c(=O)n(CC3CCNC3)c(C(F)(F)F)nc2s1]

The compound (950 mg) obtained in Example 351 was treated by a method similar to that in Example 356 to give the title compound (800 mg).

MS (ESI) m/z; 507 [M+H]$^+$

Example 360

(R)-N-benzyl-1-{7-oxo-6-[((S)-pyrrolidin-2-yl)methyl]-5-trifluoromethyl-6,7-dihydro[1,3]thiazolo[5,4-d]pyrimidin-2-yl}pyrrolidine-2-carboxamide

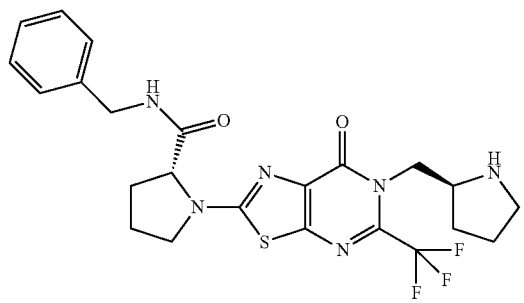 [SMILES: O=C(NCc1ccccc1)[C@H]1CCCN1c1nc2c(=O)n(C[C@@H]3CCCN3)c(C(F)(F)F)nc2s1]

The compound (799 mg) obtained in Example 352 was treated by a method similar to that in Example 356 to give the title compound (625 mg).

MS (ESI) m/z; 507 [M+H]$^+$

Example 361

(R)-N-benzyl-1-{7-oxo-6-((R)-pyrrolidin-2-yl)methyl}-5-trifluoromethyl-6,7-dihydro[1,3]thiazolo[5,4-d]pyrimidin-2-yl}pyrrolidine-2-carboxamide

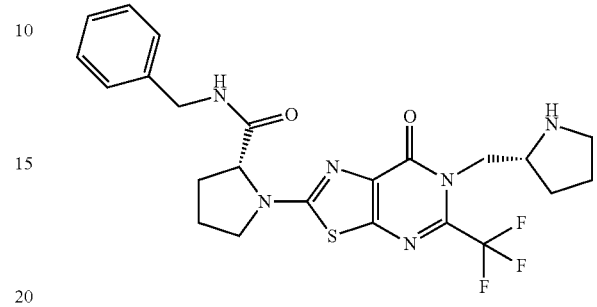

The compound (1.29 g) obtained in Example 353 was treated is by a method similar to that in Example 356 to give the title compound (653 mg).

MS (ESI) m/z; 507 [M+H]$^+$

Example 362

(R)-N-benzyl-2-[N'-methyl-N'-{7-oxo-6-[(piperidin-4-yl)methyl]-5-trifluoromethyl-6,7-dihydro[1,3]thiazolo[5,4-d]pyrimidin-2-yl}amino]propionamide

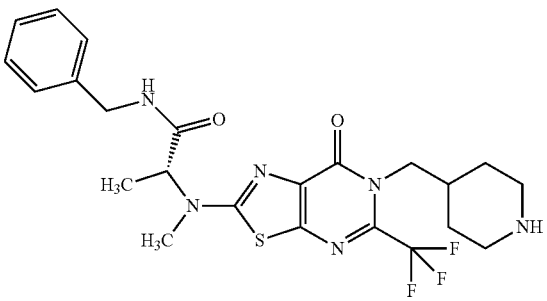 [SMILES: C[C@H](C(=O)NCc1ccccc1)N(C)c1nc2c(=O)n(CC3CCNCC3)c(C(F)(F)F)nc2s1]

The compound (540 mg) obtained in Example 354 was treated by a method similar to that in Example 356 to give the title compound (340 mg).

MS (ESI) m/z; 509 [M+H]$^+$

Example 363

(R)-N-benzyl-1-[6-(2-methylaminoethyl)-7-oxo-5-trifluoromethyl-6,7-dihydro[1,3]thiazolo[5,4-d]pyrimidin-2-yl]pyrrolidine-2-carboxamide

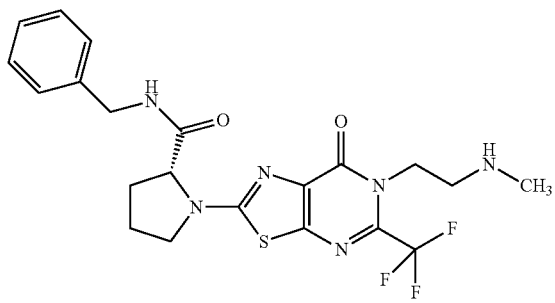 [SMILES: CNCCn1c(C(F)(F)F)nc2sc(N3CCC[C@@H]3C(=O)NCc3ccccc3)nc2c1=O]

The compound (256 mg) obtained in Example 355 was treated by a method similar to that in Example 356 to give the title compound (155 mg).

MS (ESI) m/z; 481 [M+H]$^+$

Example 364

(R)-N-benzyl-1-[6-((S)-1-methylpyrrolidin-3-yl)-7-oxo-5-trifluoromethyl-6,7-dihydro[1,3]thiazolo[5,4-d]pyrimidin-2-yl]pyrrolidine-2-carboxamide

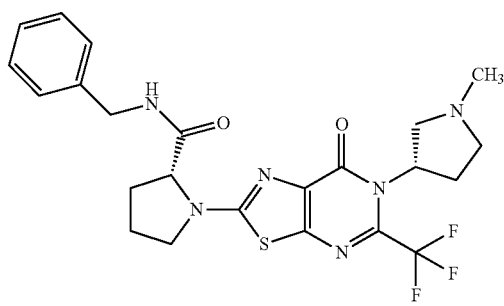 [SMILES: CN1CC[C@H](n2c(C(F)(F)F)nc3sc(N4CCC[C@@H]4C(=O)NCc4ccccc4)nc3c2=O)C1]

To a solution (7.0 mL) of the compound (247 mg) obtained in Example 356 in methylene chloride was added 35-38% aqueous formaldehyde solution (204 mg). The reaction mixture was stirred at room temperature for 1 hr, sodium triacetoxyborohydride (319 mg) was added to the reaction mixture, and the reaction mixture was stirred at room temperature for 17 hr. Saturated aqueous sodium hydrogen carbonate solution was added to the reaction mixture, and the mixture was extracted three times with methylene chloride. The organic layer was dried over anhydrous sodium sulfate, filtered and concentrated. The residue was purified by NH silica gel column chromatography (solvent; ethyl acetate/methanol=100/0-93/7), to the obtained product was added (hexane/ethyl acetate=1:1), and the solid was collected by filtration and dried to give the title compound (187 mg).

MS (ESI) m/z; 507 [M+H]$^+$

Example 365

(R)-N-benzyl-1-[6-((R)-1-methylpyrrolidin-3-yl)-7-oxo-5-trifluoromethyl-6,7-dihydro[1,3]thiazolo[5,4-d]pyrimidin-2-yl]pyrrolidine-2-carboxamide

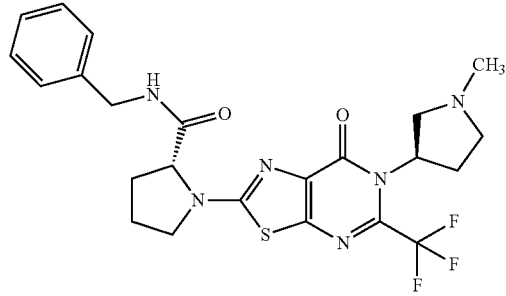 [SMILES: CN1CC[C@@H](n2c(C(F)(F)F)nc3sc(N4CCC[C@@H]4C(=O)NCc4ccccc4)nc3c2=O)C1]

The compound (174 mg) obtained in Example 357 was treated by a method similar to that in Example 364 to give the title compound (121 mg).

MS (ESI) m/z; 507 [M+H]$^+$

Example 366

(R)-N-benzyl-1-{6-[(1-methylpiperidin-4-yl)methyl]-7-oxo-5-trifluoromethyl-6,7-dihydro[1,3]thiazolo[5,4-d]pyrimidin-2-yl}pyrrolidine-2-carboxamide

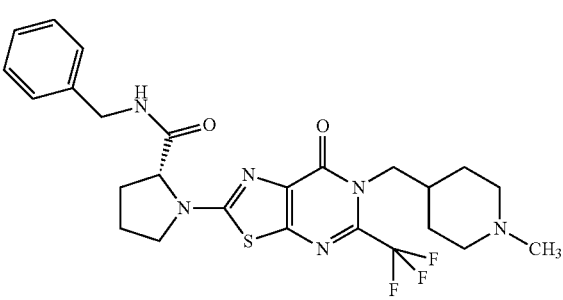 [SMILES: CN1CCC(Cn2c(C(F)(F)F)nc3sc(N4CCC[C@@H]4C(=O)NCc4ccccc4)nc3c2=O)CC1]

The compound (300 mg) obtained in Example 358 was treated by a method similar to that in Example 364 to give the title compound (180 mg).

MS (ESI) m/z; 535 [M+H]$^+$

Example 367

(R)-N-benzyl-1-[7-oxo-6-{[1-(propan-2-yl)piperidin-4-yl]methyl}-5-trifluoromethyl-6,7-dihydro[1,3]thiazolo[5,4-d]pyrimidin-2-yl]pyrrolidine-2-carboxamide

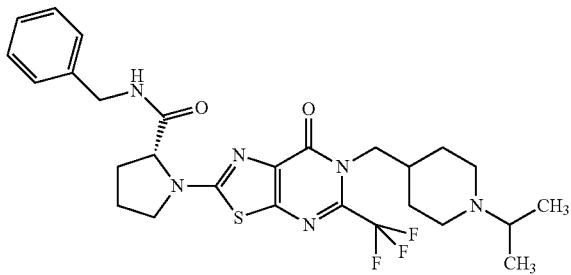 [SMILES: CC(C)N1CCC(Cn2c(C(F)(F)F)nc3sc(N4CCC[C@@H]4C(=O)NCc4ccccc4)nc3c2=O)CC1]

The compound (250 mg) obtained in Example 358 was treated by a method similar to that in Example 364 to give the title compound (78.0 mg).
MS (ESI) m/z; 563 [M+H]$^+$

Example 368

(R)-N-benzyl-1-{6-[((RS)-1-methylpyrrolidin-3-yl)methyl]-7-oxo-5-trifluoromethyl-6,7-dihydro[1,3]thiazolo[5,4-d]pyrimidin-2-yl}pyrrolidine-2-carboxamide

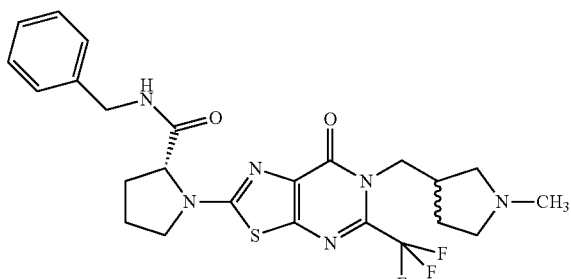

The compound (300 mg) obtained in Example 359 was treated by a method similar to that in Example 364 to give the title compound (250 mg).
MS (ESI) m/z; 521 [M+H]$^+$

Example 369

(R)-N-benzyl-1-{6-[((S)-1-methylpyrrolidin-2-yl)methyl]-7-oxo-5-trifluoromethyl-6,7-dihydro[1,3]thiazolo[5,4-d]pyrimidin-2-yl}pyrrolidine-2-carboxamide

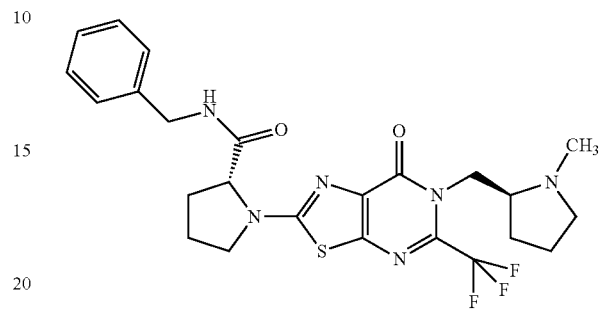

The compound (231 mg) obtained in Example 360 was treated by a method similar to that in Example 364 to give the title compound (202 mg).
MS (ESI) m/z; 521 [M+H]$^+$

Example 370

(R)-N-benzyl-1-{6-[((R)-1-methylpyrrolidin-2-yl)methyl]-7-oxo-5-trifluoromethyl-6,7-dihydro[1,3]thiazolo[5,4-d]pyrimidin-2-yl}pyrrolidine-2-carboxamide


The compound (300 mg) obtained in Example 361 was treated by a method similar to that in Example 364 to give the title compound (250 mg).
MS (ESI) m/z; 521 [M+H]$^+$

Example 371

(R)-N-benzyl-2-[N'-methyl-N'-{6-[(1-methylpiperidin-4-yl)methyl]-7-oxo-5-trifluoromethyl-6,7-dihydro[1,3]thiazolo[5,4-d]pyrimidin-2-yl}amino]propionamide

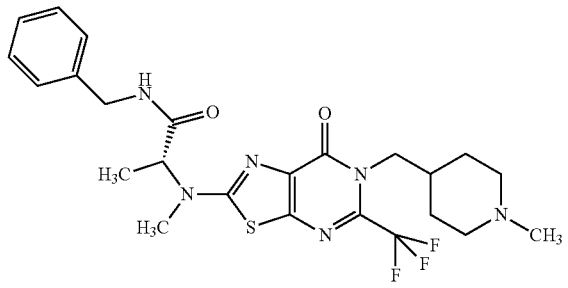 [SMILES: C[C@H](C(=O)NCc1ccccc1)N(C)c1nc2c(=O)n(CC3CCN(C)CC3)c(C(F)(F)F)nc2s1]

The compound (270 mg) obtained in Example 362 was treated by a method similar to that in Example 364 to give the title compound (160 mg).

MS (ESI) m/z; 523 [M+H]$^+$

Example 372

(R)-N-benzyl-1-{6-[2-(N',N'-dimethylamino)ethyl]-7-oxo-5-trifluoromethyl-6,7-dihydro[1,3]thiazolo[5,4-d]pyrimidin-2-yl}pyrrolidine-2-carboxamide

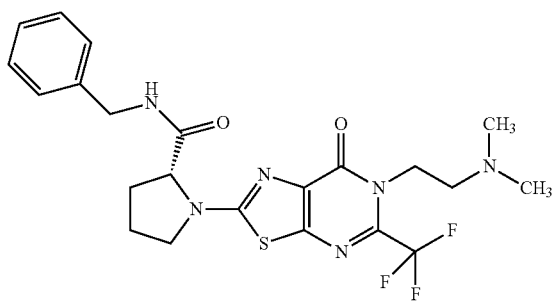 [SMILES: CN(C)CCn1c(C(F)(F)F)nc2sc(N3CCC[C@@H]3C(=O)NCc3ccccc3)nc2c1=O]

The compound (85.0 mg) obtained in Example 363 was treated by a method similar to that in Example 364 to give the title compound (75.0 mg).

MS (ESI) m/z; 495 [M+H]$^+$

Example 373

(R)-N-benzyl-1-[6-{2-[N'-methyl-N'-(2,2,2-trifluoroethyl)amino]ethyl}-7-oxo-5-trifluoromethyl-6,7-dihydro[1,3]thiazolo[5,4-d]pyrimidin-2-yl]pyrrolidine-2-carboxamide hydrochloride To a solution (6.0 mL) of the compound (300 mg) obtained in Example 363 in DMF were added N,N-diisopropylethylamine (240 mg) and 2,2,2-trifluoroethyl trifluoromethanesulfonate (220 mg) under ice-cooling, and the reaction mixture was stirred at room temperature for 10 hr. Water was added to the reaction mixture, and the mixture was extracted twice with ethyl acetate. The combined organic layer was washed with saturated brine, dried over anhydrous sodium sulfate, filtered and concentrated. The residue was purified by silica gel column chromatography (solvent; chloroform/methanol=99/1-95/5). To a solution of the obtained crude product (300 mg) in acetone was added hydrogen chloride (4.0 mol/L ethyl acetate solution, 0.15 mL), and the mixture was stirred at room temperature for 10 min. The solvent was evaporated under reduced pressure, to the obtained product was added hexane, and the solid was collected by filtration and dried to give the title compound (130 mg).

MS (ESI) m/z; 563 [M+H]$^+$

Example 374

N-[(R)-1-{2-[(R)-2-(benzylcarbamoyl)pyrrolidin-1-yl]-6-methyl-7-oxo-6,7-dihydro[1,3]thiazolo[5,4-d]pyrimidin-5-yl}ethyl]-N-methylcarbamic acid tert-butyl ester

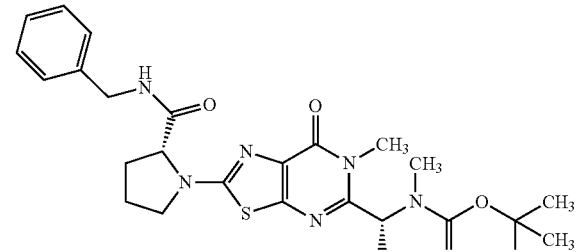

To a solution (2.8 mL) of the compound (162 mg) obtained in Reference Example 424 in DMF were added (D)-proline (72 mg) and potassium carbonate (116 mg), and the reaction mixture was heated at 80° C. for 2 hr. The reaction mixture was cooled to 0° C., and neutralized with concentrated hydrochloric acid (494 μL). N,N-diisopropylethylamine (110 µL), benzylamine (92 µL), EDC hydrochloride (120 mg) and HOBt monohydrate (96 mg) were added to the reaction mixture at room temperature, and the reaction mixture was stirred at room temperature overnight. Water was added to the reaction mixture, and the mixture was extracted three times with ethyl acetate. The combined organic layer was dried over anhydrous sodium sulfate, filtered and concentrated. The residue was purified by NH silica gel column chromatography (solvent; hexane/ethyl acetate=70/30-0/100) to give the title compound (195 mg).
MS (ESI) m/z; 527 [M+H]$^+$ Example 375

N-[(S)-1-{2-[(R)-2-(benzylcarbamoyl)pyrrolidin-1-yl]-6-methyl-7-oxo-6,7-dihydro[1,3]thiazolo[5,4-d]pyrimidin-5-yl}ethyl]-N-methylcarbamic acid tert-butyl ester

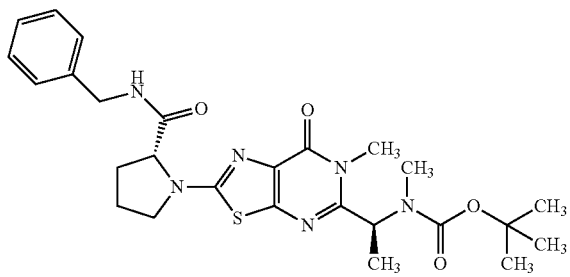 [SMILES: C[C@@H](c1nc2sc(N3CCC[C@@H]3C(=O)NCc3ccccc3)nc2c(=O)n1C)N(C)C(=O)OC(C)(C)C]

The compound (191 mg) obtained in Reference Example 425 was treated by a method similar to that in Example 374 to give the title compound (180 mg).
MS (ESI) m/z; 527 [M+H]$^+$ Example 376

(R)-N-benzyl-1-{5-[(R)-1-(N',N'-dimethylamino)ethyl]-6-methyl-7-oxo-6,7-dihydro[1,3]thiazolo[5,4-d]pyrimidin-2-yl}pyrrolidine-2-carboxamide

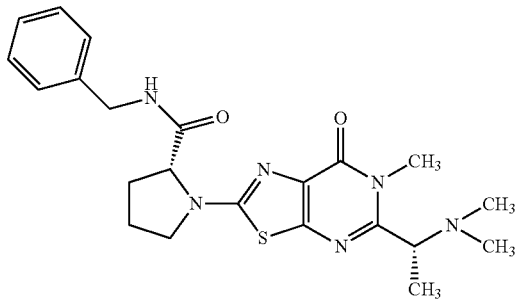 [SMILES: C[C@H](c1nc2sc(N3CCC[C@@H]3C(=O)NCc3ccccc3)nc2c(=O)n1C)N(C)C]

To a solution (0.5 mL) of the compound (100 mg) obtained in Example 374 in methylene chloride was added trifluoroacetic acid (1 mL), and the reaction mixture was stirred at room temperature for 3 hr. The reaction mixture was concentrated, to a solution (1.6 mL) of the residue in methylene chloride were added 35-38% aqueous formaldehyde solution (65 µL) and sodium triacetoxyborohydride (101 mg), and the reaction mixture was stirred at room temperature overnight. Saturated aqueous sodium hydrogen carbonate solution was added, and the mixture was extracted three times with chloroform. The organic layer was dried over anhydrous sodium sulfate, filtered and concentrated. The residue was purified by silica gel column chromatography (solvent; chloroform/methanol=100/0-90/10), and the obtained crude product was purified by reversed-phase HPLC (Capcelpak C18; 0.05% trifluoroacetic acid-water/acetonitrile=55/45-45/55). To the obtained product was added diisopropyl ether, and the solid was collected by filtration to give the title compound (38 mg).
MS (ESI) m/z; 441 [M+H]$^+$ Example 377

(R)-N-benzyl-1-{5-[(S)-1-(N',N'-dimethylamino)ethyl]-6-methyl-7-oxo-6,7-dihydro[1,3]thiazolo[5,4-d]pyrimidin-2-yl}pyrrolidine-2-carboxamide

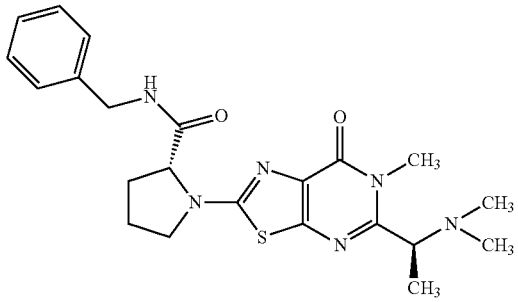 [SMILES: C[C@@H](c1nc2sc(N3CCC[C@@H]3C(=O)NCc3ccccc3)nc2c(=O)n1C)N(C)C]

The compound (95 mg) obtained in Example 375 was treated by a method similar to that in Example 376 to give the title compound (54 mg).
MS (ESI) m/z; 441 [M+H]$^+$ Example 378

N-[2-{2-[(R)-2-(benzylcarbamoyl)pyrrolidin-1-yl]-6-methyl-7-oxo-6,7-dihydro[1,3]thiazolo[5,4-d]pyrimidin-5-yl}-2,2-difluoroethyl]-N-methylcarbamic acid tert-butyl ester

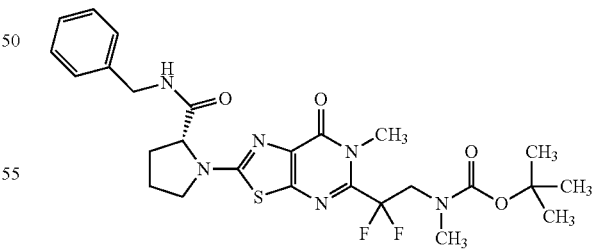

To a solution (4.0 mL) of the compound (246 mg) obtained in Reference Example 427 in DMF were added (D)-proline (101 mg) and potassium carbonate (201 mg), and the reaction mixture was heated at 70° C. for 2 hr. The reaction mixture was cooled to 0° C., and neutralized with concentrated hydrochloric acid (239 µL). N,N-diisopropylethylamine (202 µL), benzylamine (127 µL), EDC hydrochloride (222 mg) and HOBt monohydrate (178 mg) were added to the reaction mixture at room temperature, and the reaction mixture was stirred at room temperature for 8 hr. Water was added to the reaction mixture, and the mixture was extracted twice with ethyl acetate. The combined organic layer was dried over anhydrous sodium sulfate, filtered and is concentrated. The residue was purified by NH silica gel column chromatography (solvent; hexane/ethyl acetate=20/30-0/100) to give the title compound (286 mg).

MS (ESI) m/z; 563 [M+H]$^+$

Example 379

(R)-N-benzyl-1-{5-[1,1-difluoro-2-(methylamino) ethyl]-6-methyl-7-oxo-6,7-dihydro[1,3]thiazolo[5,4-d]pyrimidin-2-yl}pyrrolidine-2-carboxamide

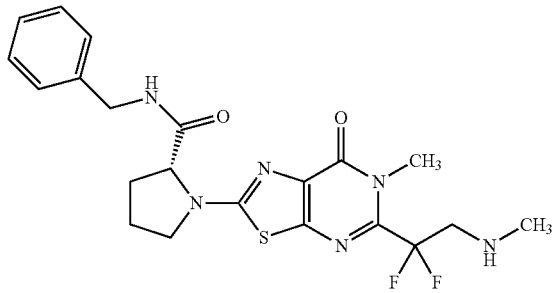 [SMILES: CNCC(F)(F)c1nc2sc(N3CCC[C@@H]3C(=O)NCc3ccccc3)nc2c(=O)n1C]

To a solution (1.0 mL) of the compound (286 mg) obtained in Example 378 in methylene chloride was added trifluoroacetic acid (2 mL), and the reaction mixture was stirred at room temperature for 6 hr. The reaction mixture was concentrated, aqueous sodium carbonate solution was added, and the mixture was extracted three times with chloroform. The organic layer was dried over anhydrous sodium sulfate, filtered and concentrated. The residue was purified by silica gel column chromatography (solvent; chloroform/methanol=100/0-90/10) to give the title compound (200 mg).

MS (ESI) m/z; 463 [M+H]$^+$

Example 380

(R)-N-benzyl-1-{5-[2-(N',N'-dimethylamino)-1,1-difluoroethyl]-6-methyl-7-oxo-6,7-dihydro[1,3]thiazolo[5,4-d]pyrimidin-2-yl}pyrrolidine-2-carboxamide

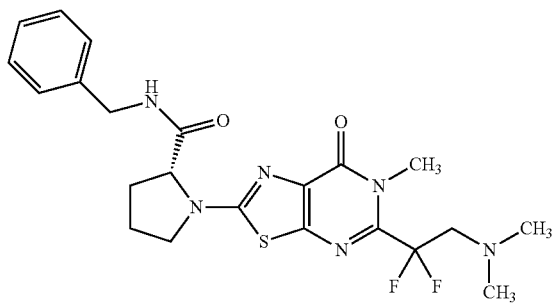 [SMILES: CN(C)CC(F)(F)c1nc2sc(N3CCC[C@@H]3C(=O)NCc3ccccc3)nc2c(=O)n1C]

To a solution (1.8 mL) of the compound (100 mg) obtained in Example 379 in methylene chloride was added 35-38% aqueous formaldehyde solution (74 μL). The reaction mixture was stirred at room temperature for 1.5 hr, sodium triacetoxyborohydride (114 mg) was added to the reaction mixture, and the reaction mixture was stirred at room temperature overnight. Saturated aqueous sodium hydrogen carbonate solution was added to the reaction mixture, and the mixture was extracted three times with methylene chloride. The organic layer was dried over anhydrous sodium sulfate, filtered and concentrated. The residue was purified by silica gel column chromatography (solvent; chloroform/methanol=100/0-90/10), to the obtained product was added diisopropyl ether, and the solid was collected by filtration to give the title compound (94 mg).

MS (ESI) m/z; 477 [M+H]$^+$

Example 381

(R)-N-benzyl-1-[6-((S)-1-hydroxypropan-2-yl)-7-oxo-5-trifluoromethyl-6,7-dihydro[1,3]thiazolo[5,4-d]pyrimidin-2-yl]pyrrolidine-2-carboxamide

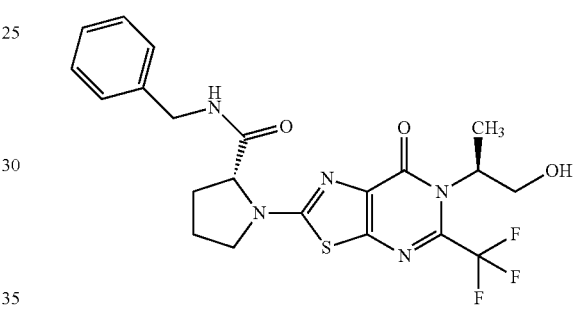

To a solution (4 mL) of the compound (260 mg) obtained in Reference Example 434 in DMF were added (D)-proline (132 mg) and potassium carbonate (211 mg), and the reaction mixture was heated at 80° C. for 2.5 hr. The reaction mixture was cooled to room temperature, and acidified with 1.0 mol/L hydrochloric acid. Sodium chloride was added, and the mixture was extracted twice with chloroform. The organic layer was dried over anhydrous sodium sulfate, and filtered. Chloroform was evaporated under reduced pressure from the filtrate, to the obtained mixture were added N,N-diisopropylethylamine (199 μL), benzylamine (125 μL), EDC hydrochloride (219 mg) and HOBt monohydrate (175 mg), and the reaction mixture was stirred at room temperature for 17 hr. Water was added, and the mixture was extracted with ethyl acetate. The organic layer was dried over anhydrous sodium sulfate, filtered and concentrated. The residue was purified by silica gel column chromatography (solvent; chloroform/methanol=100/0-90/10). To the obtained product was added ethyl acetate/hexane=3/1, and the solid was collected by filtration to give the title compound (218.8 mg).

MS (ESI) m/z; 482 [M+H]$^+$

Example 382

(R)-N-benzyl-1-[6-((R)-1-hydroxypropan-2-yl)-7-oxo-5-trifluoromethyl-6,7-dihydro[1,3]thiazolo[5,4-d]pyrimidin-2-yl]pyrrolidine-2-carboxamide

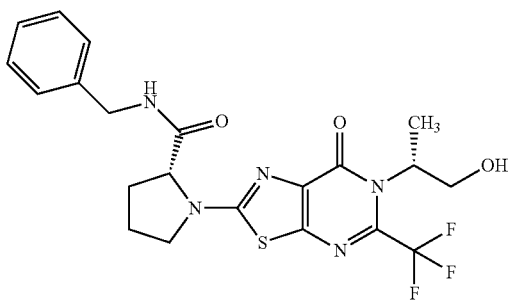 [SMILES: C[C@H](CO)n1c(C(F)(F)F)nc2sc(N3CCC[C@@H]3C(=O)NCc3ccccc3)nc2c1=O]

The compound (92 mg) obtained in Reference Example 435 was treated by a method similar to that in Example 381 to give the title compound (102 mg).
MS (ESI) m/z; 482 [M+H]$^+$

Example 383

(R)-N-benzyl-1-{6-[(S)-1-(N',N'-dimethylamino)propan-2-yl]-7-oxo-5-trifluoromethyl-6,7-dihydro[1,3]thiazolo[5,4-d]pyrimidin-2-yl}pyrrolidine-2-carboxamide

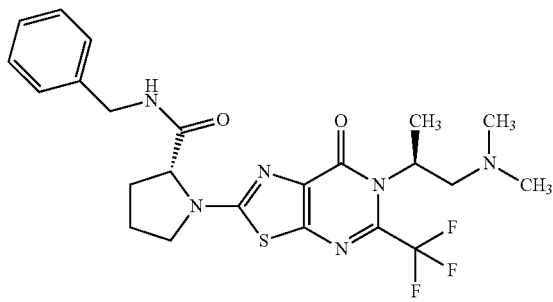 [SMILES: C[C@@H](CN(C)C)n1c(C(F)(F)F)nc2sc(N3CCC[C@@H]3C(=O)NCc3ccccc3)nc2c1=O]

To a solution (8.0 mL) of the compound (215 mg) obtained in Example 381 and triethylamine (106 μL) in methylene chloride was added dropwise methanesulfonyl chloride (52 μL) under ice-cooling. After stirring at room temperature for 1.5 hr, the reaction mixture was concentrated. The obtained crude product was dissolved in acetonitrile (6.5 mL), and sodium iodide (134 mg) and dimethylamine (2.0 mol/L THF solution, 4.47 mL) were added. After stirring with heating at 65° C. for 2 hr, the reaction mixture was concentrated. To the residue was added saturated aqueous sodium hydrogen carbonate solution, and the mixture was extracted twice with methylene chloride. The organic layer was dried over anhydrous sodium sulfate, filtered and concentrated. The residue was purified by silica gel column chromatography (solvent; ethyl acetate/methanol=100/0-93/7). To the obtained product was added ethyl acetate/hexane=1/1, and the solid was collected by filtration to give the title compound (123 mg).
MS (ESI) m/z; 509 [M+H]$^+$

Example 384

(R)-N-benzyl-1-{6-[(R)-1-(N',N'-dimethylamino)propan-2-yl]-7-oxo-5-trifluoromethyl-6,7-dihydro[1,3]thiazolo[5,4-d]pyrimidin-2-yl}pyrrolidine-2-carboxamide hydrochloride

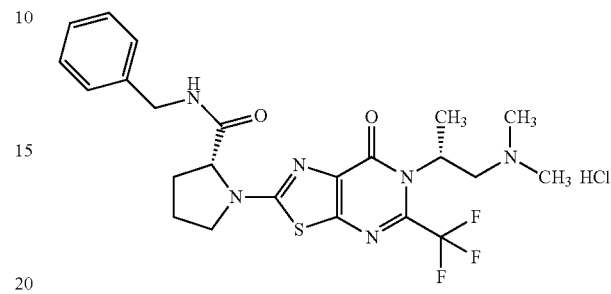

To a solution (2.0 mL) of the compound (100 mg) obtained in Example 382 and triethylamine (76 μL) in methylene chloride was added dropwise methanesulfonyl chloride (38 μL) under ice-cooling. After stirring at room temperature for 2 hr, the reaction mixture was concentrated. The obtained crude product was dissolved in acetonitrile (3.0 mL), and sodium iodide (62 mg) and dimethylamine (2.0 mol/L THF solution, 2.08 mL) were added. After stirring with heating at 65° C. for 2 hr, the reaction mixture was concentrated. To the residue was added saturated aqueous sodium hydrogen carbonate solution, and the mixture was extracted twice with methylene chloride. The organic layer was dried over anhydrous sodium sulfate, filtered and concentrated. The residue was purified by silica gel column chromatography (solvent; ethyl acetate/methanol=100/0-93/7). The obtained product was dissolved in ethyl acetate (2.0 mL), hydrogen chloride (4.0 mol/L ethyl acetate solution, 39 μL) was added, and the mixture was stirred for 30 min. The solvent was evaporated under reduced pressure, and the precipitated solid was collected by filtration to give the title compound (42 mg).
MS (ESI) m/z; 509 [M+H]$^+$

Example 385

(R)-N-benzyl-1-[5-(2-hydroxyethyl)-6-methyl-7-oxo-6,7-dihydro[1,3]thiazolo[5,4-d]pyrimidin-2-yl]pyrrolidine-2-carboxamide

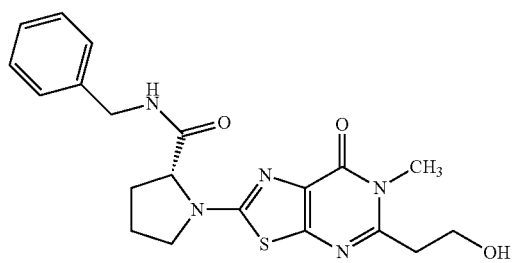 [SMILES: Cn1c(CCO)nc2sc(N3CCC[C@@H]3C(=O)NCc3ccccc3)nc2c1=O]

To a solution (18 mL) of the compound (750 mg) obtained in Reference Example 445 in DMF were added (D)-proline (480 mg) and potassium carbonate (760 mg), and the mixture was heated at 80° C. for 1 hr. After cooling to 0° C.,

287 concentrated hydrochloric acid (920 μL) was added and the mixture was neutralized. N,N-diisopropylethylamine (540 mg), benzylamine (600 mg), EDC hydrochloride (800 mg) and HOBt monohydrate (640 mg) were added to the reaction mixture at room temperature, and the reaction mixture was stirred at room temperature overnight. Water was added to the reaction mixture, and the mixture was extracted three times with ethyl acetate. The combined organic layer was dried over anhydrous sodium sulfate, filtered and concentrated. The residue was purified by silica gel column chromatography (solvent; chloroform/methanol=100/0-90/10) to give the title compound (620 mg).

MS (ESI) m/z; 414 [M+H]+

Example 386

(R)-N-benzyl-1-[6-ethyl-5-(2-hydroxyethyl)-7-oxo-6,7-dihydro[1,3]thiazolo[5,4-d]pyrimidin-2-yl]pyrrolidine-2-carboxamide

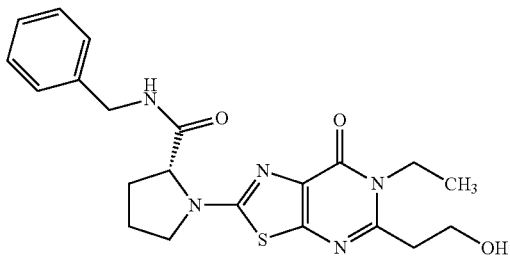 [SMILES: CCn1c(CCO)nc2sc(N3CCC[C@@H]3C(=O)NCc3ccccc3)nc2c1=O]

The compound (543 mg) obtained in Reference Example 446 was treated by a method similar to that in Example 385 to give the title compound (623 mg).

MS (ESI) m/z; 428 [M+H]+

Example 387

(R)-N-benzyl-1-[5-(2-hydroxyethyl)-7-oxo-6-(propan-2-yl)-6,7-dihydro[1,3]thiazolo[5,4-d]pyrimidin-2-yl]pyrrolidine-2-carboxamide

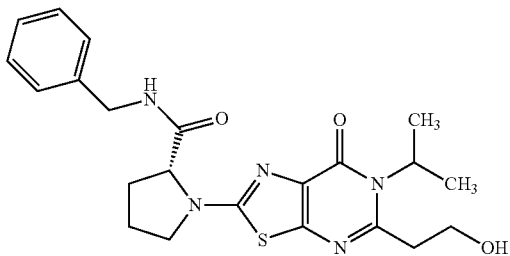 [SMILES: CC(C)n1c(CCO)nc2sc(N3CCC[C@@H]3C(=O)NCc3ccccc3)nc2c1=O]

The compound (446 mg) obtained in Reference Example 447 was treated by a method similar to that in Example 385 to give the title compound (577 mg).

MS (ESI) m/z; 442 [M+H]+

288

Example 388

(R)-N-benzyl-1-{5-[2-(N',N'-dimethylamino)ethyl]-6-methyl-7-oxo-6,7-dihydro[1,3]thiazolo[5,4-d]pyrimidin-2-yl}pyrrolidine-2-carboxamide

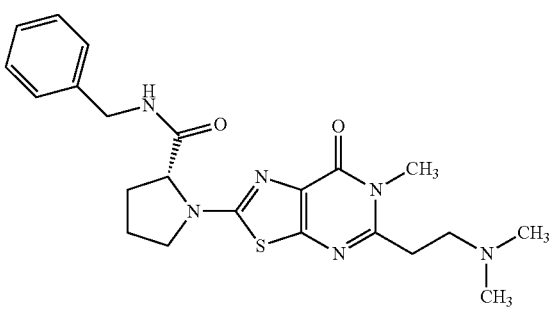 [SMILES: CN(C)CCc1nc2sc(N3CCC[C@@H]3C(=O)NCc3ccccc3)nc2c(=O)n1C]

To a solution (8.0 mL) of the compound (480 mg) obtained in Example 385 and triethylamine (141 mg) in methylene chloride was added dropwise methanesulfonyl chloride (146 mg) under ice-cooling. Under ice-cooling, the reaction mixture was stirred for 1 hr. Chloroform was added to the reaction mixture, and the mixture was washed with water. The organic layer was dried over anhydrous sodium sulfate, filtered and concentrated. The obtained crude product was dissolved in acetonitrile (5.0 mL), and sodium iodide (90 mg) and dimethylamine (2.0 mol/L THF solution, 3.0 mL) were added. The reaction mixture was stirred with heating at 65° C. for 2 hr, and concentrated. To the residue was added saturated aqueous sodium hydrogen carbonate solution, and the mixture was extracted three times with methylene chloride. The organic layer was dried over anhydrous sodium sulfate, filtered and concentrated. The residue was purified by silica gel column chromatography (solvent; chloroform/methanol=100/0-90/10). To the obtained product were added ethyl acetate and hexane, and the solid was collected by filtration and dried to give the title compound (110 mg).

MS (ESI) m/z; 441 [M+H]+

Example 389

(R)-N-benzyl-1-{6-methyl-7-oxo-5-[2-(2-piperidin-1-yl)ethyl]-6,7-dihydro[1,3]thiazolo[5,4-d]pyrimidin-2-yl}pyrrolidine-2-carboxamide

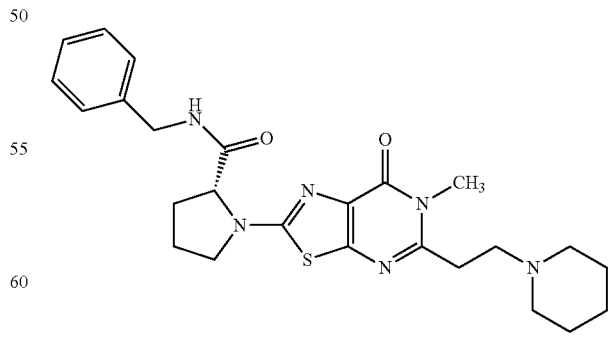

The compound (240 mg) obtained in Example 385 was treated by a method similar to that in Example 388 to give the title compound (105 mg).

MS (ESI) m/z; 481 [M+H]+

Example 390

(R)-N-benzyl-1-{5-[2-(N',N'-dimethylamino)ethyl]-6-ethyl-7-oxo-6,7-dihydro[1,3]thiazolo[5,4-d]pyrimidin-2-yl}pyrrolidine-2-carboxamide hydrochloride

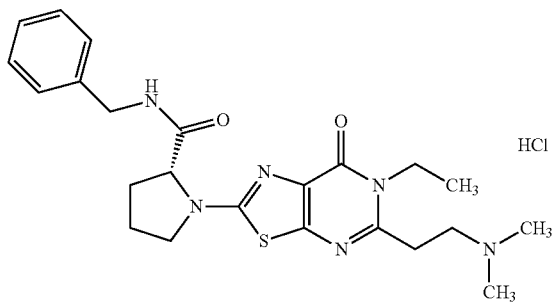 [SMILES: CCn1c(CCN(C)C)nc2sc(N3CCC[C@@H]3C(=O)NCc3ccccc3)nc2c1=O ; Cl]

To a solution (1.0 mL) of the compound (60 mg) obtained in Example 386 and triethylamine (23 μL) in methylene chloride was added dropwise methanesulfonyl chloride (12 μL) under ice-cooling. Under ice-cooling, the mixture was stirred for 1.5 hr, diluted with ethyl acetate and washed with water. The organic layer was dried over anhydrous sodium sulfate, filtered and concentrated. The obtained crude product was dissolved in acetonitrile (1.0 mL), and sodium iodide (21 mg) and dimethylamine (2.0 mol/L THF solution, 700 μL) were added. After stirring with heating at 65° C. for 3 hr, the reaction mixture was concentrated. Saturated aqueous sodium hydrogen carbonate solution was added, and the mixture was extracted three times with methylene chloride. The organic layer was dried over anhydrous sodium sulfate, filtered and concentrated. The residue was purified by NH silica gel column chromatography (solvent; ethyl acetate/methanol=100/0-90/10). The obtained product was dissolved in ethyl acetate (2.0 mL), and hydrogen chloride (4.0 mol/L ethyl acetate solution, 31 μL) was added. The precipitated solid was collected by filtration to give the title compound (43 mg).

MS (ESI) m/z; 455 [M+H]$^+$

Example 391

(R)-N-benzyl-1-{5-[2-(N',N'-dimethylamino)ethyl]-7-oxo-6-(propan-2-yl)-6,7-dihydro[1,3]thiazolo[5,4-d]pyrimidin-2-yl}pyrrolidine-2-carboxamide hydrochloride

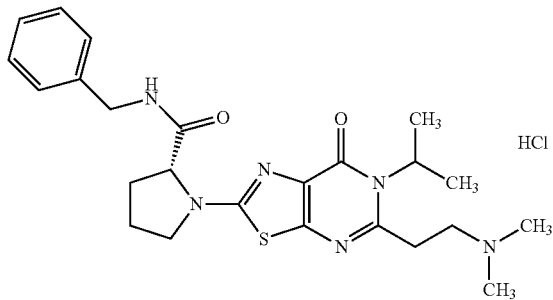 [SMILES: CC(C)n1c(CCN(C)C)nc2sc(N3CCC[C@@H]3C(=O)NCc3ccccc3)nc2c1=O ; Cl]

The compound (100 mg) obtained in Example 387 was treated is by a method similar to that in Example 390 to give the title compound (73 mg).

MS (ESI) m/z; 469 [M+H]$^+$

Example 392

(R)-N-benzyl-1-{5-[2-(methylamino)ethyl]-7-oxo-6-(propan-2-yl)-6,7-dihydro[1,3]thiazolo[5,4-d]pyrimidin-2-yl}pyrrolidine-2-carboxamide hydrochloride

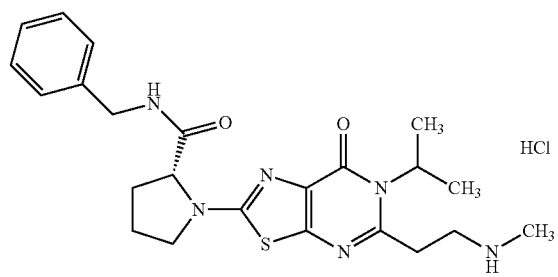 [SMILES: CNCCc1nc2sc(N3CCC[C@@H]3C(=O)NCc3ccccc3)nc2c(=O)n1C(C)C ; Cl]

The compound (100 mg) obtained in Example 387 was treated by a method similar to that in Example 390 to give the title compound (37 mg).

MS (ESI) m/z; 455 [M+H]$^+$

Example 393

(R)-N-benzyl-1-[6-ethyl-5-(3-hydroxypropyl)-7-oxo-6,7-dihydro[1,3]thiazolo[5,4-d]pyrimidin-2-yl]pyrrolidine-2-carboxamide

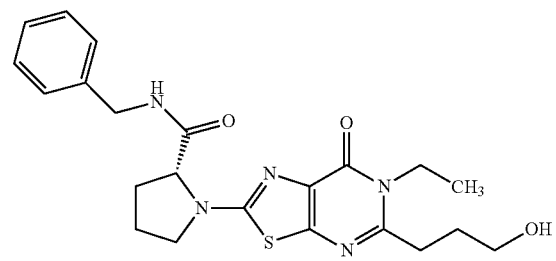 [SMILES: CCn1c(CCCO)nc2sc(N3CCC[C@@H]3C(=O)NCc3ccccc3)nc2c1=O]

To a solution (10 mL) of the compound (476 mg) obtained in Reference Example 451 in DMF were added (D)-proline (273 mg) and potassium carbonate (437 mg), and the reaction mixture was heated at 80° C. for 1 hr. The reaction mixture was cooled to 0° C., and neutralized with concentrated hydrochloric acid (527 μL). N,N-diisopropylethylamine (413 μL), benzylamine (345 μL), EDC hydrochloride (454 mg) and HOBt monohydrate (363 mg) were added to the reaction mixture at room temperature, and the reaction mixture was stirred at room temperature overnight. Water was added to the reaction mixture, and the mixture was extracted three times with chloroform. The organic layer was dried over anhydrous sodium sulfate, filtered and concentrated. The residue was purified by NH silica gel column chromatography (solvent; ethyl acetate/methanol=100/0-95/5). To the obtained product was added diisopropyl ether, and the solid was collected by filtration to give the title compound (574 mg).

MS (ESI) m/z; 442 [M+H]$^+$

Example 394

(R)-N-benzyl-1-{5-[3-(1,3-dioxo-1,3-dihydroisoindol-2-yl)propyl]-6-ethyl-7-oxo-6,7-dihydro[1,3]thiazolo[5,4-d]pyrimidin-2-yl}pyrrolidine-2-carboxamide

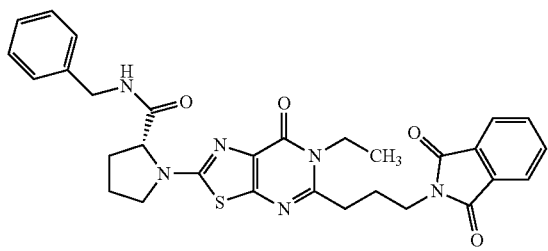 [SMILES: CCn1c(CCCN2C(=O)c3ccccc3C2=O)nc2sc(N3CCC[C@@H]3C(=O)NCc3ccccc3)nc2c1=O]

To a solution of the compound (50 mg) obtained in Example 393 in THF (1 mL) were added phthalimido (24 mg), triphenylphosphine (58 mg) and diisopropyl azodicarboxylate (1.9 mol/L toluene solution, 116 μL). The reaction mixture was stirred at room temperature for 1 hr, and concentrated. The residue was purified by NH silica gel column chromatography (solvent; hexane/ethyl acetate=50/50-0/100) to give the title compound (57 mg).

MS (ESI) m/z; 571 [M+H]$^+$

Example 395

(R)-N-benzyl-1-{5-[3-(N',N'-dimethylamino)propyl]-6-ethyl-7-oxo-6,7-dihydro[1,3]thiazolo[5,4-d]pyrimidin-2-yl}pyrrolidine-2-carboxamide

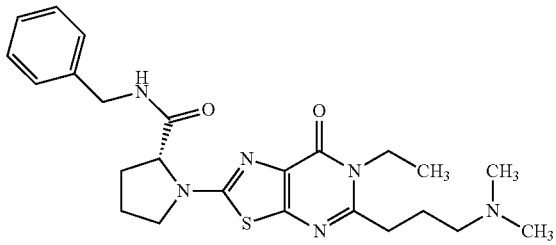 [SMILES: CCn1c(CCCN(C)C)nc2sc(N3CCC[C@@H]3C(=O)NCc3ccccc3)nc2c1=O]

To a solution of the compound (57 mg) obtained in Example 394 in ethanol (1.0 mL) was added hydrazine monohydrate (49 μL), and the reaction mixture was stirred at room temperature for 6 hr. The reaction mixture was concentrated, to the residue was added methylene chloride, and the insoluble material was filtered off. The filtrate was concentrated, and the obtained crude product was dissolved in methylene chloride (1.5 mL). 35-38% Aqueous formaldehyde solution (86 μL) was added, and the reaction mixture was stirred at room temperature for 30 min. Sodium triacetoxyborohydride (106 mg) was added to the reaction mixture, and the reaction mixture was stirred at room temperature overnight. Saturated aqueous sodium hydrogen carbonate solution was added to the reaction mixture, and the mixture was extracted three times with methylene chloride. The organic layer was dried over anhydrous sodium sulfate, filtered and concentrated. The residue was purified by NH silica gel column chromatography (solvent; ethyl acetate/methanol=100/0-90/10). The obtained product was dissolved in ethyl acetate (1 mL), and hydrogen chloride (4.0 mol/L ethyl acetate solution, 30 μL) was added. The precipitated solid was collected by filtration to give the title compound (18 mg).

MS (ESI) m/z; 469 [M+H]$^+$

Example 396

(R)-N-benzyl-1-[6-(2-hydroxyethyl)-7-oxo-5-trifluoromethyl-6,7-dihydro[1,3]thiazolo[5,4-d]pyrimidin-2-yl]pyrrolidine-2-carboxamide

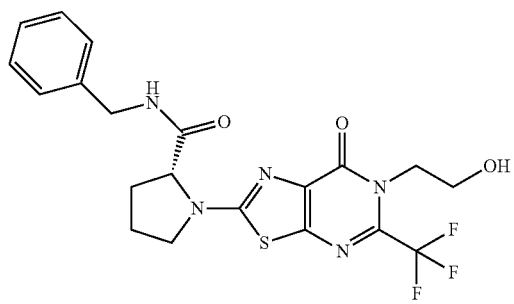 [SMILES: O=C(NCc1ccccc1)[C@H]1CCCN1c1nc2c(=O)n(CCO)c(C(F)(F)F)nc2s1]

To a solution (9 mL) of the compound (468 mg) obtained in Reference Example 453 in DMF were added (D)-proline (247 mg) and potassium carbonate (395 mg), and the reaction mixture was heated at 80° C. for 1 hr. The reaction mixture was cooled to room temperature, and acidified with 1.0 mol/L hydrochloric acid. Sodium chloride was added, and the mixture was extracted five times with chloroform. The organic layer was dried over anhydrous sodium sulfate, and filtered. Chloroform was evaporated under reduced pressure from the filtrate, to the obtained mixture were added N,N-diisopropylethylamine (374 μL), benzylamine (312 μL), EDC hydrochloride (412 mg) and HOBt monohydrate (329 mg), and the reaction mixture was stirred at room temperature overnight. Water was added, and the mixture was extracted five times with chloroform. The organic layer was dried over anhydrous sodium sulfate, filtered and concentrated. The residue was purified by NH silica gel column chromatography (solvent; hexane/ethyl acetate=70/30-0/100) to give the title compound (479 mg).

MS (ESI) m/z; 468 [M+H]$^+$

Example 397

(R)-N-benzyl-1-[5-(1-hydroxy-2-methylpropan-2-yl)-6-methyl-7-oxo-6,7-dihydro[1,3]thiazolo[5,4-d]pyrimidin-2-yl]pyrrolidine-2-carboxamide

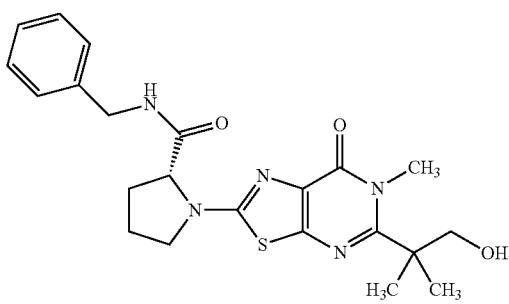 [SMILES: Cn1c(C(C)(C)CO)nc2sc(N3CCC[C@@H]3C(=O)NCc3ccccc3)nc2c1=O]

To a solution (3.0 mL) of the compound (156 mg) obtained in Reference Example 457 in DMF solution (3.0 mL) were added (D)-proline (79 mg) and potassium carbonate (126 mg), and the reaction mixture was heated at 70° C. for 3 hr. The reaction mixture was cooled to 0° C., and neutralized with concentrated hydrochloric acid (150 μL). N,N-diisopropylethylamine (119 μL), benzylamine (100 μL), EDC hydrochloride (131 mg) and HOBt monohydrate (105 mg) were added to the reaction mixture at room temperature, and the reaction mixture was stirred at room temperature overnight. Water was added to the reaction mixture, and the mixture was extracted twice with methylene chloride. The combined organic layer was dried over anhydrous sodium sulfate, filtered and concentrated. The residue was purified by NH silica gel column chromatography (solvent; ethyl acetate/methanol=100/0-95/5) to give the title compound (189 mg).

MS (ESI) m/z; 442 [M+H]$^+$

Example 398

(R)-N-benzyl-1-{5-[2-(hydroxymethyl)phenyl]-6-methyl-7-oxo-6,7-dihydro[1,3]thiazolo[5,4-d]pyrimidin-2-yl}pyrrolidine-2-carboxamide

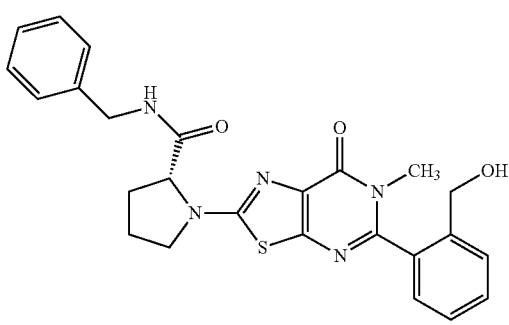 [SMILES: Cn1c(-c2ccccc2CO)nc2sc(N3CCC[C@@H]3C(=O)NCc3ccccc3)nc2c1=O]

To a solution (5 mL) of the compound (340 mg) obtained in Reference Example 461 in DMF were added (D)-proline (181 mg) and potassium carbonate (580 mg), and the reaction mixture was heated at 80° C. for 1.5 hr. The reaction mixture was cooled to room temperature, and acidified with 1.0 mol/L hydrochloric acid. Sodium chloride was added, and the mixture was extracted twice with chloroform. The organic layer was dried over anhydrous magnesium sulfate, and filtered. Chloroform was evaporated under reduced pressure from the filtrate, to the obtained mixture were added N,N-diisopropylethylamine (295 μL), benzylamine (230 μL), EDC hydrochloride (403 mg) and HOBt monohydrate (322 mg), and the reaction mixture was stirred at room temperature overnight. Water was added, and the mixture was extracted with ethyl acetate. The organic layer was dried over anhydrous magnesium sulfate, filtered and concentrated. The residue was purified by silica gel column chromatography (solvent; chloroform/methanol=100/0-97/3) to give the title compound (375.2 mg).

MS (ESI) m/z; 476 [M+H]$^+$

Example 399

(R)-N-benzyl-1-{5-[3-(hydroxymethyl)phenyl]-6-methyl-7-oxo-6,7-dihydro[1,3]thiazolo[5,4-d]pyrimidin-2-yl}pyrrolidine-2-carboxamide

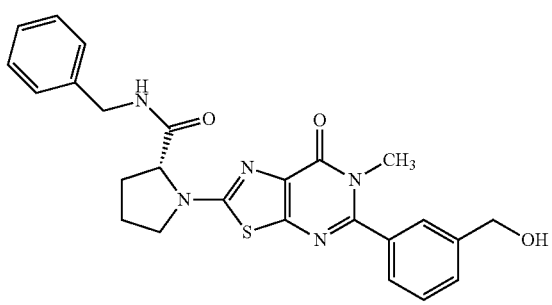 [SMILES: Cn1c(-c2cccc(CO)c2)nc2sc(N3CCC[C@@H]3C(=O)NCc3ccccc3)nc2c1=O]

The compound (192 mg) obtained in Reference Example 462 was treated by a method similar to that in Example 398 to give the title compound (142 mg).

MS (ESI) m/z; 476 [M+H]$^+$

Example 400

(R)-N-benzyl-1-{5-[4-(hydroxymethyl)phenyl]-6-methyl-7-oxo-6,7-dihydro[1,3]thiazolo[5,4-d]pyrimidin-2-yl}pyrrolidine-2-carboxamide

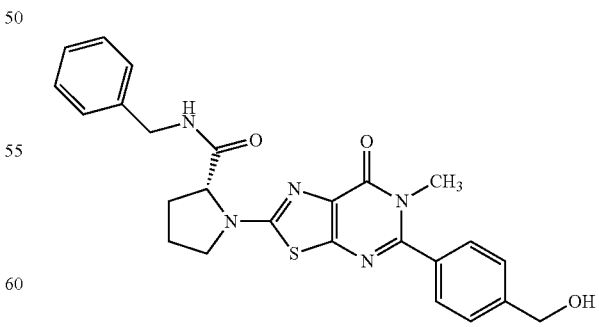

The compound (136 mg) obtained in Reference Example 463 was treated by a method similar to that in Example 398 to give the title compound (155 mg).

MS (ESI) m/z; 476 [M+H]$^+$

Example 401

(R)-N-benzyl-1-[5-{2-[(N',N'-dimethylamino)methyl]phenyl}-6-methyl-7-oxo-6,7-dihydro[1,3]thiazolo[5,4-d]pyrimidin-2-yl]pyrrolidine-2-carboxamide

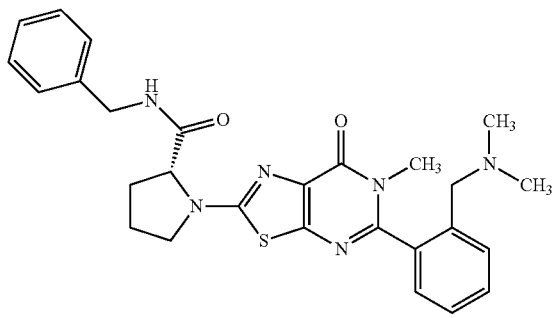 [SMILES: CN(C)Cc1ccccc1-c1nc2sc(N3CCC[C@@H]3C(=O)NCc3ccccc3)nc2c(=O)n1C]

To a solution (3.0 mL) of the compound (150 mg) obtained in Example 398 and triethylamine (100 μL) in methylene chloride was added dropwise methanesulfonyl chloride (37 μL) under ice-cooling, and the reaction mixture was stirred under ice-cooling for 30 min. Dimethylamine (2.0 mol/L THF solution, 1.6 mL) was added, and the reaction mixture was stirred with heating at room temperature for 2 hr, and concentrated. To the residue was added saturated aqueous sodium hydrogen carbonate solution, and the mixture was extracted three times with methylene chloride. The organic layer was dried over anhydrous magnesium sulfate, filtered and concentrated. The residue was purified by silica gel column chromatography (solvent; chloroform/methanol=100/0-97/3) to give the title compound (154 mg).

MS (ESI) m/z; 503 [M+H]$^+$

Example 402

(R)-N-benzyl-1-[5-{3-[(N',N'-dimethylamino)methyl]phenyl}-6-methyl-7-oxo-6,7-dihydro[1,3]thiazolo[5,4-d]pyrimidin-2-yl]pyrrolidine-2-carboxamide

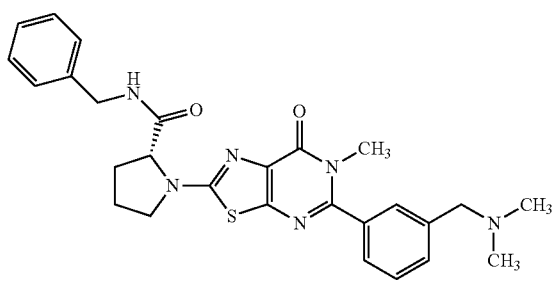 [SMILES: CN(C)Cc1cccc(-c2nc3sc(N4CCC[C@@H]4C(=O)NCc4ccccc4)nc3c(=O)n2C)c1]

The compound (142 mg) obtained in Example 399 was treated by a method similar to that in Example 401 to give the title compound (60 mg).

MS (ESI) m/z; 503 [M+H]$^+$

Example 403

(R)-N-benzyl-1-[5-{4-[(N',N'-dimethylamino)methyl]phenyl}-6-methyl-7-oxo-6,7-dihydro[1,3]thiazolo[5,4-d]pyrimidin-2-yl]pyrrolidine-2-carboxamide

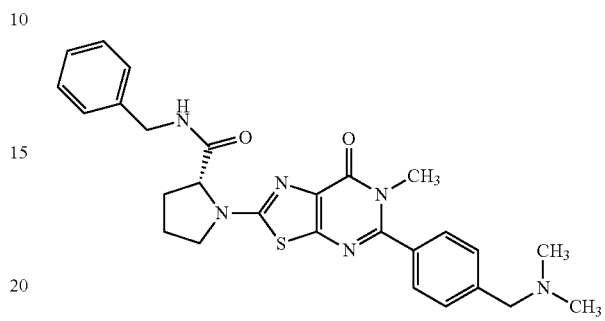

The compound (155 mg) obtained in Example 400 was treated by a method similar to that in Example 401 to give the title compound (74 mg).

MS (ESI) m/z; 503 [M+H]$^+$

Example 404

N-{[2-{2-[(R)-2-(benzylcarbamoyl)pyrrolidin-1-yl]-6-methyl-7-oxo-6,7-dihydro[1,3]thiazolo[5,4-d]pyrimidin-5-yl}oxy]ethyl}-N-methylcarbamic acid tert-butyl ester

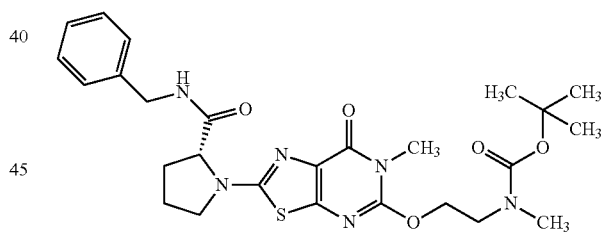

To a solution (9.5 mL) of the compound (1.61 g) obtained in Reference Example 465 in DMF were added (D)-proline (690 mg) and cesium carbonate (3.0 g), and the reaction mixture was heated at 70° C. for 2 hr. The reaction mixture was cooled to 0° C., and neutralized with concentrated hydrochloric acid. N,N-diisopropylethylamine (1.4 mL), benzylamine (880 μL), EDC hydrochloride (1.53 g) and HOBt monohydrate (1.23 g) were added to the reaction mixture at room temperature, and the reaction mixture was stirred at room temperature for 3 days. Water was added to the reaction mixture, and the mixture was extracted three times with ethyl acetate. The combined organic layer was dried over anhydrous magnesium sulfate, filtered and concentrated. The residue was purified by NH silica gel column chromatography (solvent; hexane/ethyl acetate=50/50-0/100) to give the title compound (542 mg).

MS (ESI) m/z; 543 [M+H]$^+$

Example 405

(R)-N-benzyl-1-[6-methyl-5-(2-methylaminoethoxy)-7-oxo-6,7-dihydro[1,3]thiazolo[5,4-d]pyrimidin-2-yl]pyrrolidine-2-carboxamide

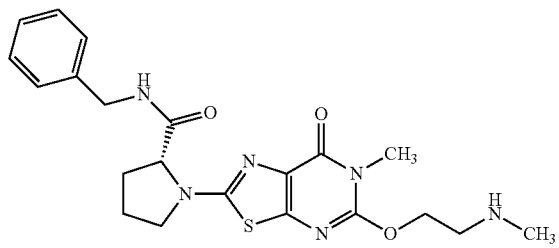 [SMILES: CNCCOc1nc2sc(N3CCC[C@@H]3C(=O)NCc3ccccc3)nc2c(=O)n1C]

To a solution (2.0 mL) of the compound (200 mg) obtained in Example 404 in methylene chloride was added trifluoroacetic acid (2 mL), and the reaction mixture was stirred at room temperature for 2 hr. The reaction mixture was concentrated, aqueous sodium hydrogen carbonate solution was added, and the mixture was extracted twice with chloroform. The organic layer was dried over anhydrous magnesium sulfate, filtered and concentrated. The residue was purified by silica gel column chromatography (solvent; chloroform/methanol=100/0-90/10) to give the title compound (75 mg).

MS (ESI) m/z; 443 [M+H]$^+$

Example 406

(R)-N-benzyl-1-{5-[2-(N',N'-dimethylamino)ethoxy]-6-methyl-7-oxo-6,7-dihydro[1,3]thiazolo[5,4-d]pyrimidin-2-yl}pyrrolidine-2-carboxamide

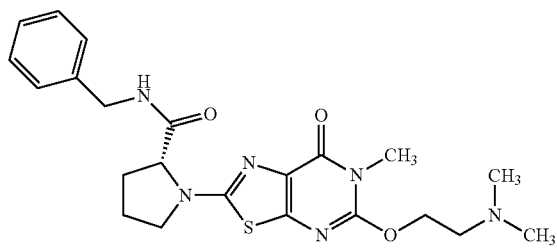 [SMILES: CN(C)CCOc1nc2sc(N3CCC[C@@H]3C(=O)NCc3ccccc3)nc2c(=O)n1C]

To a solution (1.5 mL) of the compound (73 mg) obtained in Example 405 in methylene chloride was added 35-38% aqueous formaldehyde solution (57 μL). The reaction mixture was stirred at room temperature for 10 min, sodium triacetoxyborohydride (87 mg) was added to the reaction mixture, and the reaction mixture was stirred at room temperature for 2 hr. Saturated aqueous sodium hydrogen carbonate solution was added, and the mixture was extracted three times with methylene chloride. The organic layer was dried over anhydrous magnesium sulfate, filtered and concentrated. The residue was purified by silica gel column chromatography (solvent; chloroform/methanol=100/0-90/10) to give the title compound (45 mg).

MS (ESI) m/z; 457 [M+H]$^+$

Example 407

(R)-N-benzyl-1-[5-{2-[N-methyl-N-(propan-2-yl)amino]ethoxy}-6-methyl-7-oxo-6,7-dihydro[1,3]thiazolo[5,4-d]pyrimidin-2-yl]pyrrolidine-2-carboxamide

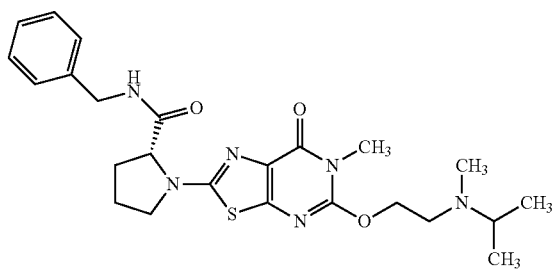 [SMILES: CC(C)N(C)CCOc1nc2sc(N3CCC[C@@H]3C(=O)NCc3ccccc3)nc2c(=O)n1C]

The compound (47 mg) obtained in Example 405 and acetone (31 μL) were treated by a method similar to that in Example 406 to give the title compound (21 mg).

MS (ESI) m/z; 485 [M+H]$^+$

Example 408

(R)-N-benzyl-1-[5-((1RS)-1-hydroxyethyl)-6-methyl-7-oxo-6,7-dihydro[1,3]thiazolo[5,4-d]pyrimidin-2-yl]pyrrolidine-2-carboxamide

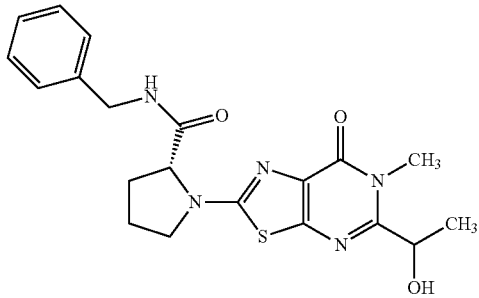 [SMILES: CC(O)c1nc2sc(N3CCC[C@@H]3C(=O)NCc3ccccc3)nc2c(=O)n1C]

To a solution (2 mL) of the compound (63 mg) obtained in Reference Example 477 in DMF were added (D)-proline (44 mg) and potassium carbonate (79 mg), and the reaction mixture was heated at 80° C. for 1 hr. The reaction mixture was cooled to room temperature, acidified with 1.0 mol/L hydrochloric acid, sodium chloride was added, and the mixture was extracted three times with chloroform. The organic layer was dried over magnesium sulfate, filtered and concentrated. The obtained residue was dissolved in DMF (2.0 mL), N,N-diisopropylethylamine (51 μL), benzylamine (31 μL), EDC hydrochloride (56 mg) and HOBt monohydrate (44 mg) were added, and the reaction mixture was stirred at room temperature for 2 hr. 0.5 mol/L Hydrochloric acid was added, and the mixture was extracted with ethyl acetate. The organic layer was washed with saturated brine, dried over anhydrous sodium sulfate, filtered and concentrated. The residue was purified by silica gel column chromatography (solvent; chloroform/methanol=100/0-95/5) to give the title compound (46 mg).

MS (ESI) m/z; 414 [M+H]$^+$

Example 409

(R)-N-benzyl-1-[5-(1-hydroxycyclopropyl)-6-methyl-7-oxo-6,7-dihydro[1,3]thiazolo[5,4-d]pyrimidin-2-yl]pyrrolidine-2-carboxamide

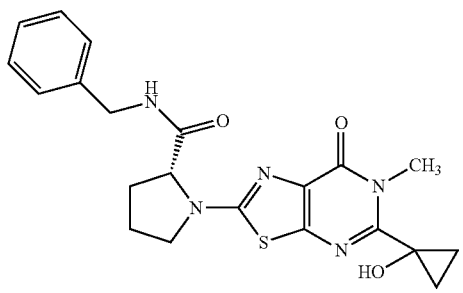 [SMILES: Cn1c(C2(O)CC2)nc2sc(N3CCC[C@@H]3C(=O)NCc3ccccc3)nc2c1=O]

The compound (260 mg) obtained in Reference Example 478 was treated by a method similar to that in Example 408 to give the title compound (70 mg).

MS (ESI) m/z; 426 [M+H]$^+$

Example 410

(R)-N-benzyl-1-[5-(1-hydroxycyclobutyl)-6-methyl-7-oxo-6,7-dihydro[1,3]thiazolo[5,4-d]pyrimidin-2-yl]pyrrolidine-2-carboxamide

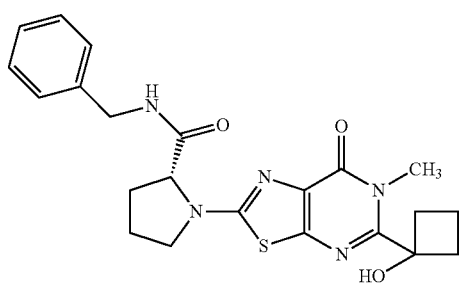 [SMILES: Cn1c(C2(O)CCC2)nc2sc(N3CCC[C@@H]3C(=O)NCc3ccccc3)nc2c1=O]

The compound (156 mg) obtained in Reference Example 479 was treated by a method similar to that in Example 408 to give the title compound (100 mg).

MS (ESI) m/z; 440 [M+H]$^+$

Example 411

(R)-1-(5-acetyl-6-methyl-7-oxo-6,7-dihydro[1,3]thiazolo[5,4-d]pyrimidin-2-yl)-N-benzylpyrrolidine-2-carboxamide

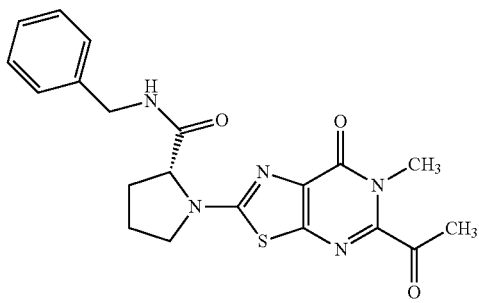 [SMILES: CC(=O)c1nc2sc(N3CCC[C@@H]3C(=O)NCc3ccccc3)nc2c(=O)n1C]

To a solution (2 mL) of the compound (100 mg) obtained in Example 408 in chloroform was added manganese dioxide (210 mg), and the reaction mixture was stirred at 60° C. for 9 hr. Manganese dioxide (210 mg) was added, and the reaction mixture was heated at 60° C. for 4 hr. The reaction mixture was filtered through diatomaceous earth, the filtrate was concentrated, and the residue was purified by NH silica gel column chromatography (solvent; hexane/ethyl acetate=50/50-0/100). To the obtained product was added diisopropyl ether, and the solid was collected by filtration to give the title compound (78 mg).

MS (ESI) m/z; 412 [M+H]$^+$

Example 412

(R)-N-benzyl-1-[5-(1-methoxycyclopropyl)-6-methyl-7-oxo-6,7-dihydro[1,3]thiazolo[5,4-d]pyrimidin-2-yl]pyrrolidine-2-carboxamide

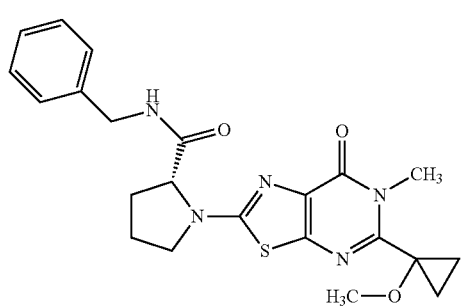 [SMILES: COC1(c2nc3sc(N4CCC[C@@H]4C(=O)NCc4ccccc4)nc3c(=O)n2C)CC1]

The compound (200 mg) obtained in Reference Example 482 was treated by a method similar to that in Example 408 to give the title compound (220 mg).

MS (ESI) m/z; 440 [M+H]$^+$

Example 413

(R)-N-benzyl-1-[5-(1-methoxycyclobutyl)-6-methyl-7-oxo-6,7-dihydro[1,3]thiazolo[5,4-d]pyrimidin-2-yl]pyrrolidine-2-carboxamide

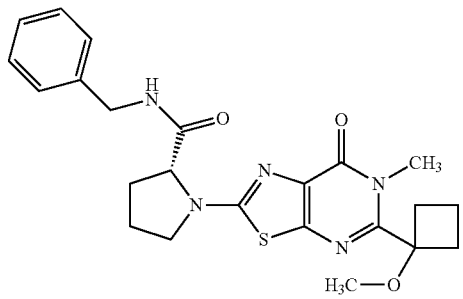 [SMILES: COC1(c2nc3sc(N4CCC[C@@H]4C(=O)NCc4ccccc4)nc3c(=O)n2C)CCC1]

The compound (383 mg) obtained in Reference Example 483 was treated by a method similar to that in Example 408 to give the title compound (280 mg).

MS (ESI) m/z; 454 [M+H]$^+$

Example 414

(R)-N-benzyl-1-[6-(2,4-dimethoxybenzyl)-5-(2-fluoropropan-2-yl)-7-oxo-6,7-dihydro[1,3]thiazolo[5,4-d]pyrimidin-2-yl]pyrrolidine-2-carboxamide

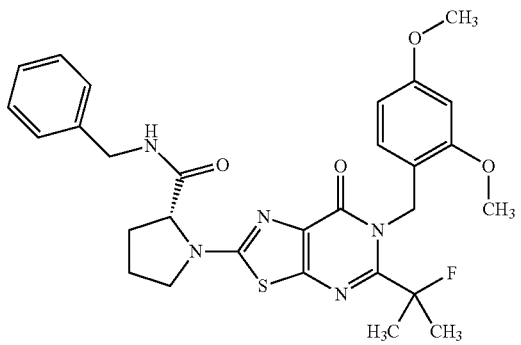 [SMILES: COc1ccc(Cn2c(C(C)(C)F)nc3sc(N4CCC[C@@H]4C(=O)NCc4ccccc4)nc3c2=O)c(OC)c1]

To a solution (10.0 mL) of the compound (400 mg) obtained in Reference Example 558 in DMF were added (D)-proline (162 mg) and cesium carbonate (704 mg), and the reaction mixture was stirred with heating at 70° C. for 1 hr. The reaction mixture was cooled to room temperature, and neutralized with 1.0 mol/L hydrochloric acid. To the obtained mixture were added N,N-diisopropylethylamine (0.327 mL), benzylamine (0.206 mL), EDC hydrochloride (360 mg) and HOBt monohydrate (288 mg), and the reaction mixture was stirred at room temperature overnight. Water was added, and the mixture was extracted three times with ethyl acetate. The organic layer was dried over anhydrous sodium sulfate, filtered and concentrated. The residue was purified by silica gel column chromatography (solvent; hexane/ethyl acetate=70/30-20/80) to give the title compound (474 mg).

MS (ESI) m/z; 566 [M+H]$^+$

Example 415

(R)-N-benzyl-1-[6-(2,4-dimethoxybenzyl)-5-(2-fluoropropan-2-yl)-7-oxo-6,7-dihydro[1,3]thiazolo[5,4-d]pyrimidin-2-yl]piperidine-2-carboxamide

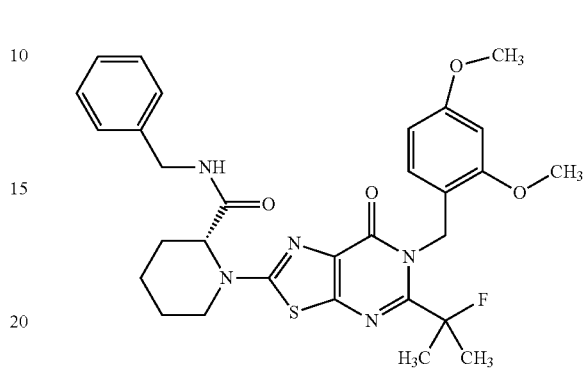

The compound (300 mg) obtained in Reference Example 558 was treated by a method similar to that in Example 178 to give the title compound (62 mg).

MS (ESI) m/z; 580 [M+H]$^+$

Example 416

(R)-N-benzyl-1-[6-(2,4-dimethoxybenzyl)-5-(propan-2-yl)-7-oxo-6,7-dihydro[1,3]thiazolo[5,4-d]pyrimidin-2-yl]azetidine-2-carboxamide

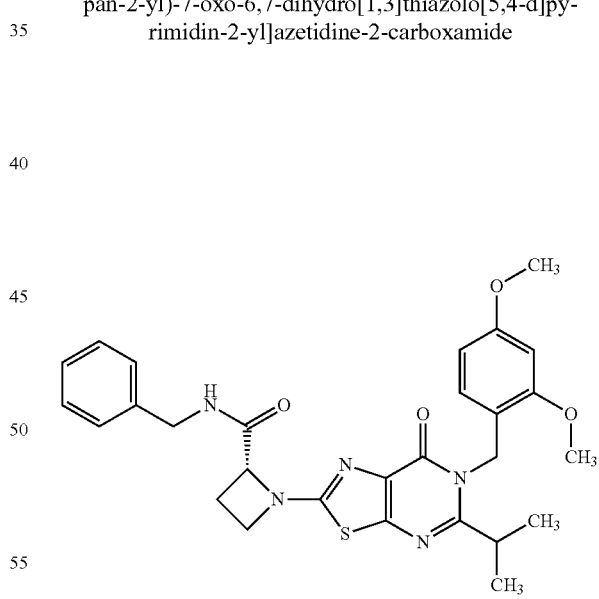

The compound (500 mg) obtained in Reference Example 560 was treated by a method similar to that in Example 178 to give the title compound (500 mg).

MS (ESI) m/z; 534 [M+H]$^+$

Example 417

(R)-N-benzyl-1-[6-(2,4-dimethoxybenzyl)-5-(propan-2-yl)-7-oxo-6,7-dihydro[1,3]thiazolo[5,4-d]pyrimidin-2-yl]piperidine-2-carboxamide

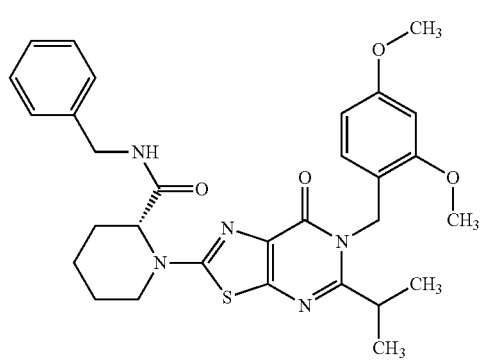 [SMILES: COc1ccc(Cn2c(C(C)C)nc3sc(N4CCCC[C@@H]4C(=O)NCc4ccccc4)nc3c2=O)c(OC)c1]

The compound (500 mg) obtained in Reference Example 560 was treated by a method similar to that in Example 178 to give the title compound (111 mg).

MS (ESI) m/z; 562 [M+H]$^+$

Example 418

(R)-N-benzyl-2-{N'-[6-(2,4-dimethoxybenzyl)-5-(propan-2-yl)-7-oxo-6,7-dihydro[1,3]thiazolo[5,4-d]pyrimidin-2-yl]-N'-methylamino}propionamide

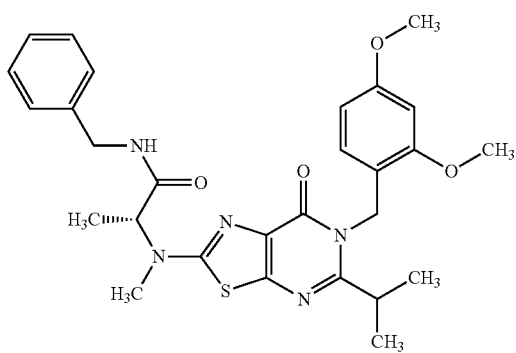 [SMILES: COc1ccc(Cn2c(C(C)C)nc3sc(N(C)[C@H](C)C(=O)NCc4ccccc4)nc3c2=O)c(OC)c1]

The compound (500 mg) obtained in Reference Example 560 was treated by a method similar to that in Example 178 to give the title compound (352 mg).

MS (ESI) m/z; 536 [M+H]$^+$

Example 419

(R)-N-benzyl-1-[6-(2,4-dimethoxybenzyl)-7-oxo-5-phenyl-6,7-dihydro[1,3]thiazolo[5,4-d]pyrimidin-2-yl]pyrrolidine-2-carboxamide

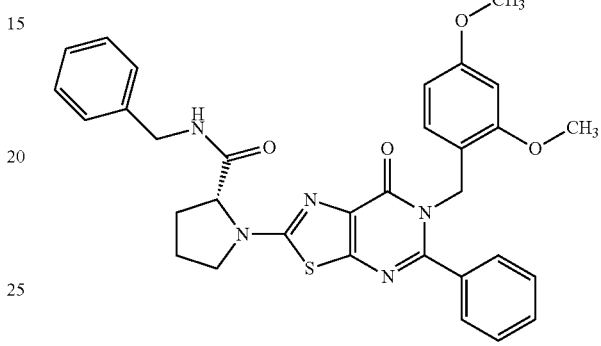

The compound (160 mg) obtained in Reference Example 562 was treated by a method similar to that in Example 178 to give the title compound (146 mg).

MS (ESI) m/z; 582 [M+H]$^+$

Example 420

(R)-1-[6-(2,4-dimethoxybenzyl)-7-oxo-5-phenyl-6,7-dihydro[1,3]thiazolo[5,4-d]pyrimidin-2-yl]-N-((R)-1-phenylethyl)pyrrolidine-2-carboxamide

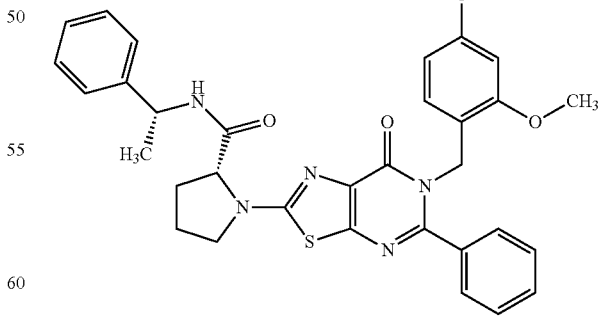

The compound (160 mg) obtained in Reference Example 562 was treated by a method similar to that in Example 178 to give the title compound (144 mg).

MS (ESI) m/z; 596 [M+H]$^+$

Example 421

(R)-N-benzyl-1-[6-(2,4-dimethoxybenzyl)-5-(2-fluorophenyl)-7-oxo-6,7-dihydro[1,3]thiazolo[5,4-d]pyrimidin-2-yl]pyrrolidine-2-carboxamide

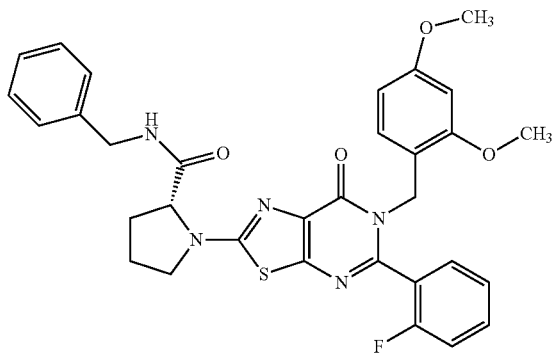 [SMILES: COc1ccc(Cn2c(-c3ccccc3F)nc3sc(N4CCC[C@@H]4C(=O)NCc4ccccc4)nc3c2=O)c(OC)c1]

The compound (391 mg) obtained in Reference Example 563 was treated by a method similar to that in Example 178 to give the title compound (298 mg).

MS (ESI) m/z; 600 [M+H]$^+$

Example 422

(R)-1-[6-(2,4-dimethoxybenzyl)-5-(2-fluorophenyl)-7-oxo-6,7-dihydro[1,3]thiazolo[5,4-d]pyrimidin-2-yl]-N-((R)-1-phenylethyl)pyrrolidine-2-carboxamide

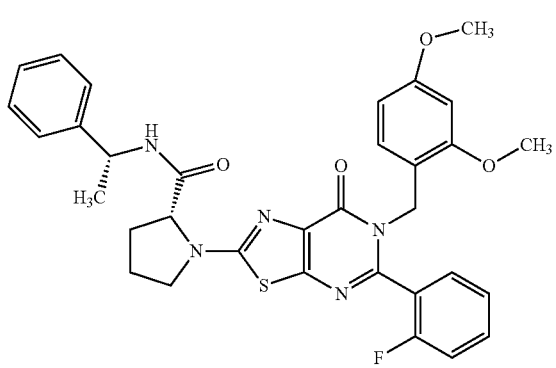 [SMILES: COc1ccc(Cn2c(-c3ccccc3F)nc3sc(N4CCC[C@@H]4C(=O)N[C@H](C)c4ccccc4)nc3c2=O)c(OC)c1]

The compound (391 mg) obtained in Reference Example 563 was treated by a method similar to that in Example 178 to give the title compound (348 mg).

MS (ESI) m/z; 614 [M+H]$^+$

Example 423

(R)-N-benzyl-1-[6-(2, 4-dimethoxybenzyl)-5-(2-fluorophenyl)-7-oxo-6,7-dihydro[1,3]thiazolo[5,4-d]pyrimidin-2-yl]azetidine-2-carboxamide

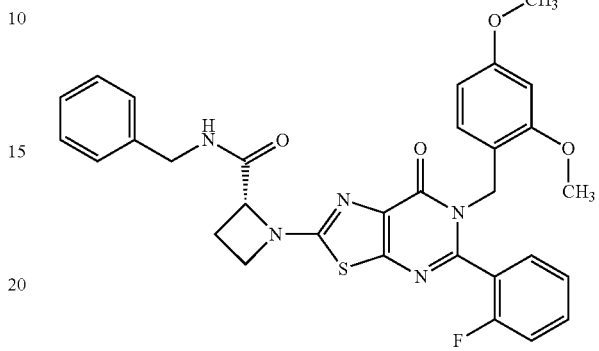

The compound (570 mg) obtained in Reference Example 563 was treated by a method similar to that in Example 178 to give the title compound (45 mg).

MS (ESI) m/z; 586 [M+H]$^+$

Example 424

(R)-N-benzyl-1-[6-(2, 4-dimethoxybenzyl)-5-(2-fluorophenyl)-7-oxo-6,7-dihydro[1,3]thiazolo[5,4-d]pyrimidin-2-yl]piperidine-2-carboxamide

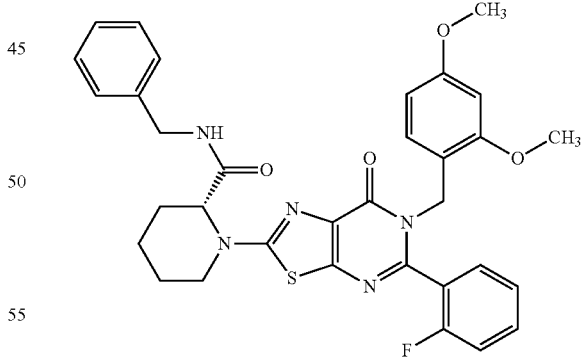

The compound (300 mg) obtained in Reference Example 563 was treated by a method similar to that in Example 178 to give the title compound (95 mg).

MS (ESI) m/z; 614 [M+H]$^+$

Example 425

(R)-N-benzyl-1-[5-(2-chlorophenyl)-6-(2,4-dimethoxybenzyl)-7-oxo-6,7-dihydro[1,3]thiazolo[5,4-d]pyrimidin-2-yl]pyrrolidine-2-carboxamide

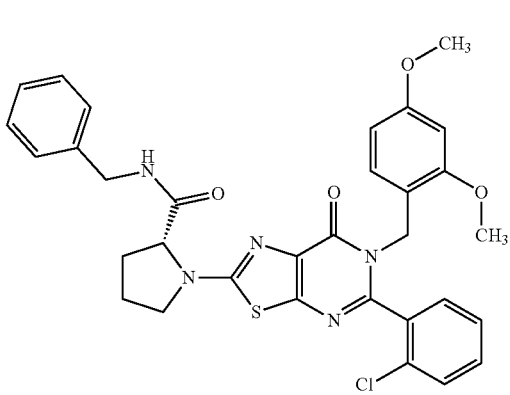 [SMILES: COc1ccc(Cn2c(-c3ccccc3Cl)nc3sc(N4CCC[C@@H]4C(=O)NCc4ccccc4)nc3c2=O)c(OC)c1]

The compound (274 mg) obtained in Reference Example 564 was treated by a method similar to that in Example 178 to give the title compound (200 mg).

MS (ESI) m/z; 616, 618 [M+H]$^+$

Example 426

(R)-N-benzyl-1-[6-(2,4-dimethoxybenzyl)-5-(2-methoxyphenyl)-7-oxo-6,7-dihydro[1,3]thiazolo[5,4-d]pyrimidin-2-yl]pyrrolidine-2-carboxamide

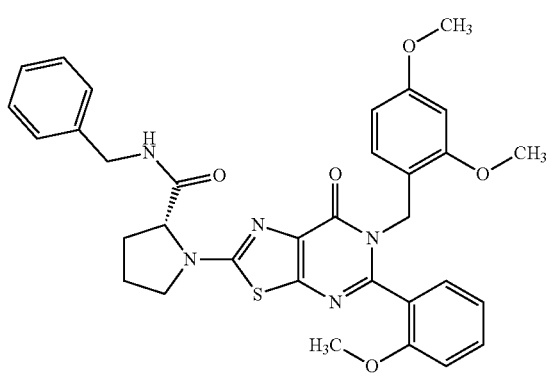 [SMILES: COc1ccc(Cn2c(-c3ccccc3OC)nc3sc(N4CCC[C@@H]4C(=O)NCc4ccccc4)nc3c2=O)c(OC)c1]

The compound (159 mg) obtained in Reference Example 565 was treated by a method similar to that in Example 178 to give the title compound (100 mg).

MS (ESI) m/z; 612 [M+H]$^+$

Example 427

(R)-N-benzyl-1-[6-(2,4-dimethoxybenzyl)-5-(2-methoxyphenyl)-7-oxo-6,7-dihydro[1,3]thiazolo[5,4-d]pyrimidin-2-yl]-N-((R)-1-phenylethyl)pyrrolidine-2-carboxamide

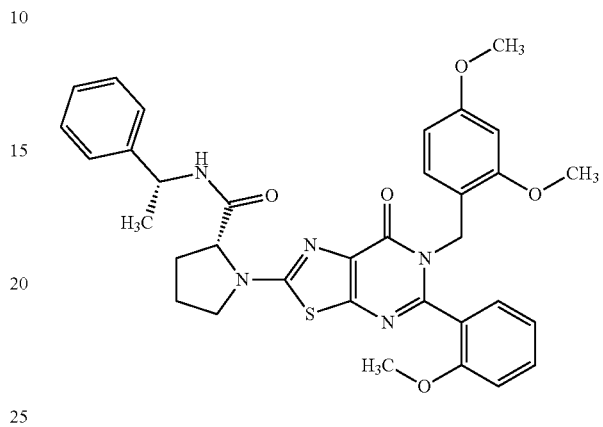

The compound (159 mg) obtained in Reference Example 565 was treated by a method similar to that in Example 178 to give the title compound (116 mg).

MS (ESI) m/z; 626 [M+H]$^+$

Example 428

(R)-N-benzyl-1-{6-(2,4-dimethoxybenzyl)-7-oxo-5-[2-(trifluoromethoxy)phenyl]-6,7-dihydro[1,3]thiazolo[5,4-d]pyrimidin-2-yl}pyrrolidine-2-carboxamide

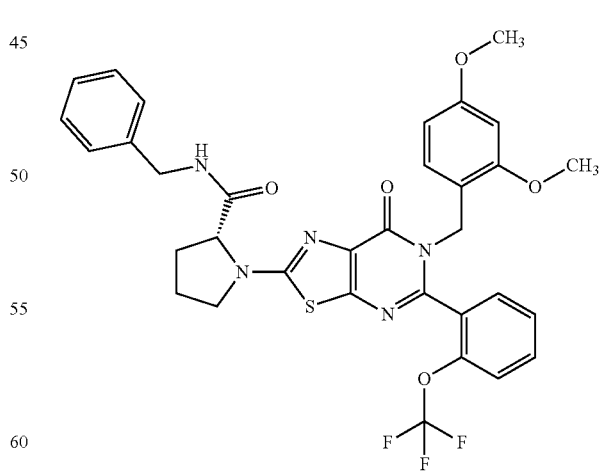

The compound (645 mg) obtained in Reference Example 566 was treated by a method similar to that in Example 178 to give the title compound (485 mg).

MS (ESI) m/z; 666 [M+H]$^+$

Example 429

(R)-N-benzyl-1-[6-(2,4-dimethoxybenzyl)-5-(2-methylphenyl)-7-oxo-6,7-dihydro[1,3]thiazolo[5,4-d]pyrimidin-2-yl]pyrrolidine-2-carboxamide

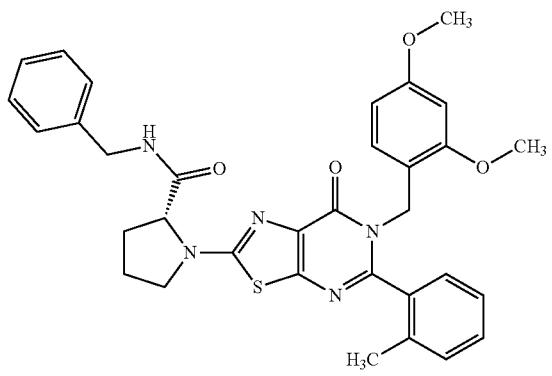 [SMILES: COc1ccc(Cn2c(-c3ccccc3C)nc3sc(N4CCC[C@@H]4C(=O)NCc4ccccc4)nc3c2=O)c(OC)c1]

The compound (652 mg) obtained in Reference Example 567 was treated by a method similar to that in Example 178 to give the title compound (507 mg).

MS (ESI) m/z; 596 [M+H]$^+$

Example 430

(R)-N-benzyl-1-[5-(2,4-difluorophenyl)-6-(2,4-dimethoxybenzyl)-7-oxo-6,7-dihydro[1,3]thiazolo[5,4-d]pyrimidin-2-yl]pyrrolidine-2-carboxamide

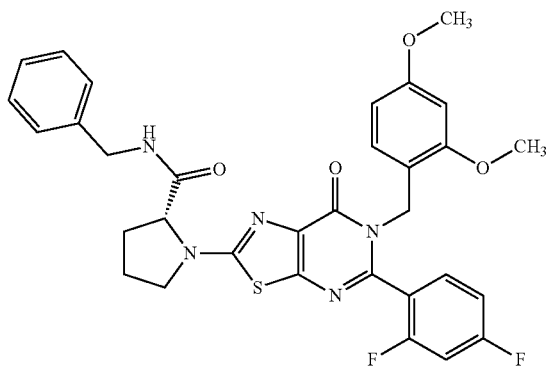 [SMILES: COc1ccc(Cn2c(-c3ccc(F)cc3F)nc3sc(N4CCC[C@@H]4C(=O)NCc4ccccc4)nc3c2=O)c(OC)c1]

The compound (287 mg) obtained in Reference Example 568 was treated by a method similar to that in Example 178 to give the title compound (285 mg).

MS (ESI) m/z; 618 [M+H]$^+$

Example 431

(R)-1-[5-(2,4-difluorophenyl)-6-(2,4-dimethoxybenzyl)-7-oxo-6,7-dihydro[1,3]thiazolo[5,4-d]pyrimidin-2-yl]-N-((R)-1-phenylethyl)pyrrolidine-2-carboxamide

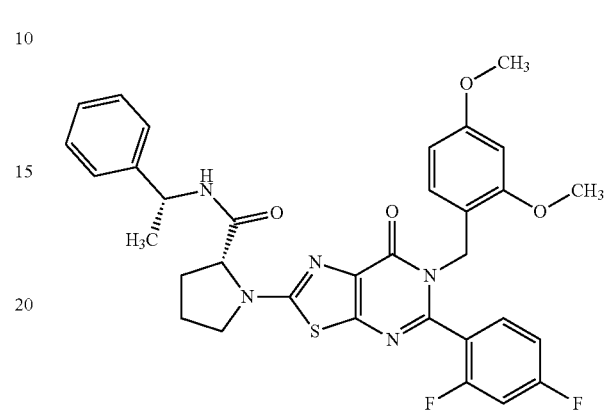

The compound (287 mg) obtained in Reference Example 568 was treated by a method similar to that in Example 178 to give the title compound (300 mg).

MS (ESI) m/z; 632 [M+H]$^+$

Example 432

(R)-N-benzyl-1-[6-(2,4-dimethoxybenzyl)-5-(5-methylthiophen-2-yl)-7-oxo-6,7-dihydro[1,3]thiazolo[5,4-d]pyrimidin-2-yl]pyrrolidine-2-carboxamide

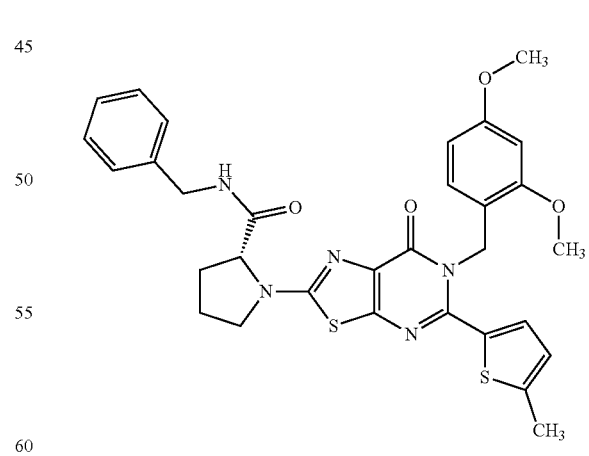

The compound (265 mg) obtained in Reference Example 577 was treated by a method similar to that in Example 178 to give the title compound (304 mg).

MS (ESI) m/z; 602 [M+H]$^+$

Example 433

(R)-N-benzyl-1-[6-(2,4-dimethoxybenzyl)-5-(3-fluoro-5-methylthiophen-2-yl)-7-oxo-6,7-dihydro[1,3]thiazolo[5,4-d]pyrimidin-2-yl]pyrrolidine-2-carboxamide

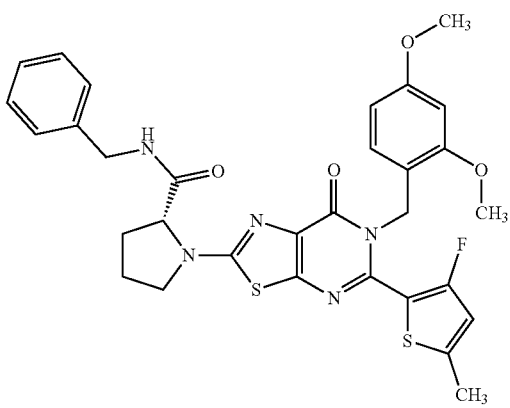 [SMILES: COc1ccc(Cn2c(-c3sc(C)cc3F)nc3sc(N4CCC[C@@H]4C(=O)NCc4ccccc4)nc3c2=O)c(OC)c1]

The compound (408 mg) obtained in Reference Example 583 was treated by a method similar to that in Example 178 to give the title compound (442 mg).

MS (ESI) m/z; 620 [M+H]$^+$

Example 434

(R)-N-benzyl-1-[5-(3-benzenesulfonyl-1,1-difluoro-propyl)-6-(2,4-dimethoxybenzyl)-7-oxo-6,7-dihydro[1,3]thiazolo[5,4-d]pyrimidin-2-yl]pyrrolidine-2-carboxamide

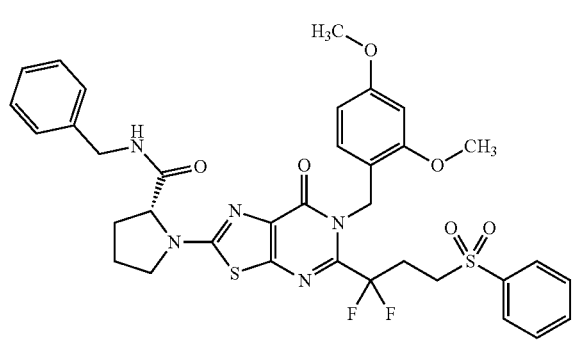 [SMILES: COc1ccc(Cn2c(C(F)(F)CCS(=O)(=O)c3ccccc3)nc3sc(N4CCC[C@@H]4C(=O)NCc4ccccc4)nc3c2=O)c(OC)c1]

The compound (440 mg) obtained in Reference Example 585 was treated by a method similar to that in Example 178 to give the title compound (359 mg).

MS (ESI) m/z; 724 [M+H]$^+$

Example 435

(R)-N-benzyl-1-[5-(1-chlorocyclopropyl)-6-(2,4-dimethoxybenzyl)-7-oxo-6,7-dihydro[1,3]thiazolo[5,4-d]pyrimidin-2-yl]azetidine-2-carboxamide

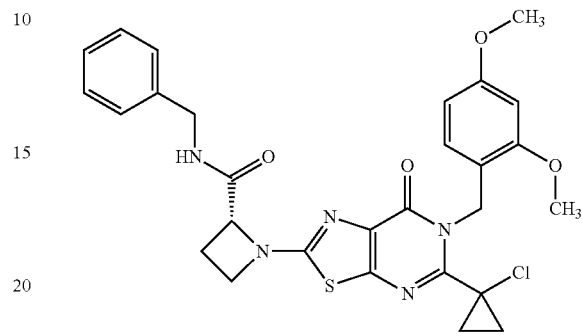

The compound (240 mg) obtained in Reference Example 586 was treated by a method similar to that in Example 178 to give the title compound (191 mg).

MS (ESI) m/z; 566 [M+H]$^+$

Example 436

(R)-N-benzyl-1-[5-(1-chlorocyclopropyl)-6-(2,4-dimethoxybenzyl)-7-oxo-6,7-dihydro[1,3]thiazolo[5,4-d]pyrimidin-2-yl]piperidine-2-carboxamide

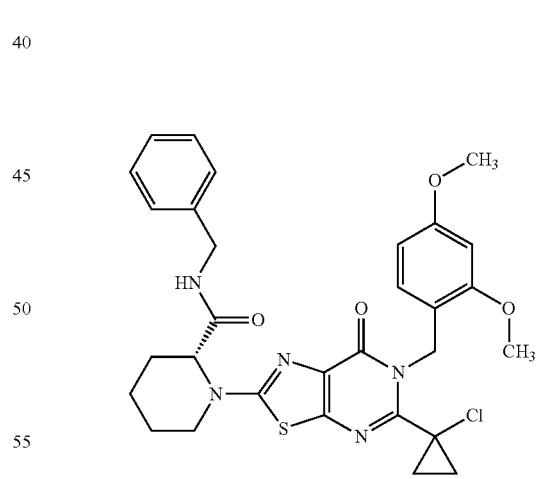

The compound (300 mg) obtained in Reference Example 586 was treated by a method similar to that in Example 178 to give the title compound (171 mg).

MS (ESI) m/z; 594 [M+H]$^+$

Example 437

(R)-N-benzyl-1-[5-(3-fluorophenyl)-6-(4-methoxybenzyl)-7-oxo-6,7-dihydro[1,3]thiazolo[5,4-d]pyrimidin-2-yl]pyrrolidine-2-carboxamide

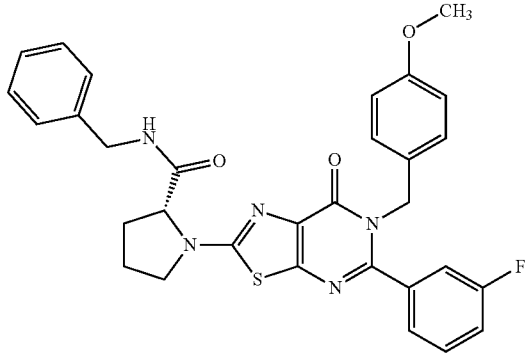 [SMILES: COc1ccc(Cn2c(-c3cccc(F)c3)nc3sc(N4CCC[C@@H]4C(=O)NCc4ccccc4)nc3c2=O)cc1]

The compound (165 mg) obtained in Reference Example 591 was treated by a method similar to that in Example 178 to give the title compound (129 mg).

MS (ESI) m/z; 570 [M+H]$^+$

Example 438

(R)-N-benzyl-1-[5-(4-fluorophenyl)-6-(4-methoxybenzyl)-7-oxo-6,7-dihydro[1,3]thiazolo[5,4-d]pyrimidin-2-yl]pyrrolidine-2-carboxamide

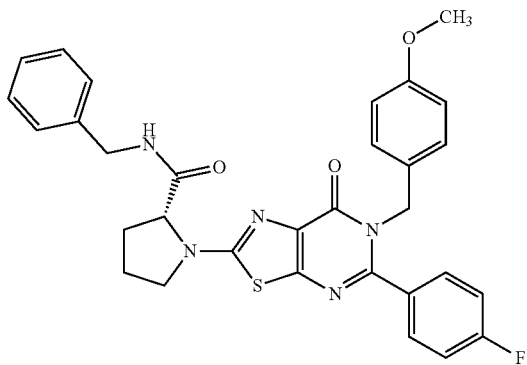 [SMILES: COc1ccc(Cn2c(-c3ccc(F)cc3)nc3sc(N4CCC[C@@H]4C(=O)NCc4ccccc4)nc3c2=O)cc1]

The compound (101 mg) obtained in Reference Example 592 was treated by a method similar to that in Example 178 to give the title compound (63 mg).

MS (ESI) m/z; 570 [M+H]$^+$

Example 439

(R)-N-benzyl-1-[5-(2,5-difluorophenyl)-6-(4-methoxybenzyl)-7-oxo-6,7-dihydro[1,3]thiazolo[5,4-d]pyrimidin-2-yl]pyrrolidine-2-carboxamide

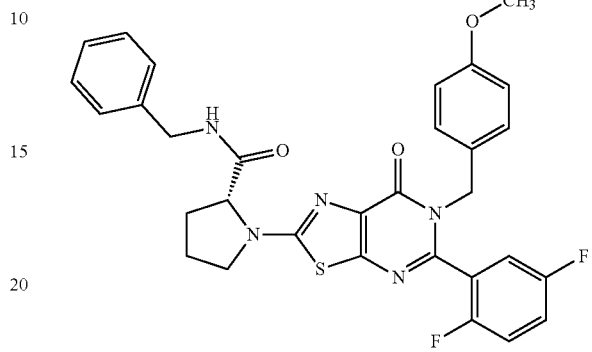

The compound (284 mg) obtained in Reference Example 594 was treated by a method similar to that in Example 178 to give the title compound (294 mg).

MS (ESI) m/z; 588 [M+H]$^+$

Example 440

(R)-N-benzyl-1-[5-(3, 4-difluorophenyl)-6-(4-methoxybenzyl)-7-oxo-6,7-dihydro[1,3]thiazolo[5,4-d]pyrimidin-2-yl]pyrrolidine-2-carboxamide

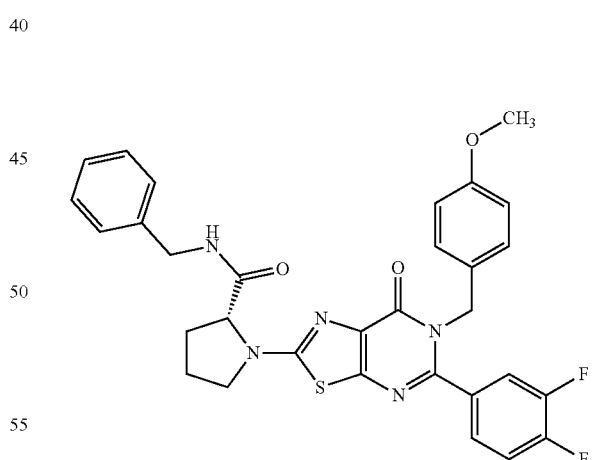

The compound (300 mg) obtained in Reference Example 595 was treated by a method similar to that in Example 178 to give the title compound (197 mg).

MS (ESI) m/z; 588 [M+H]$^+$

Example 441

(R)-N-benzyl-1-[5-(3, 5-difluorophenyl)-6-(4-methoxybenzyl)-7-oxo-6,7-dihydro[1,3]thiazolo[5,4-d]pyrimidin-2-yl]pyrrolidine-2-carboxamide

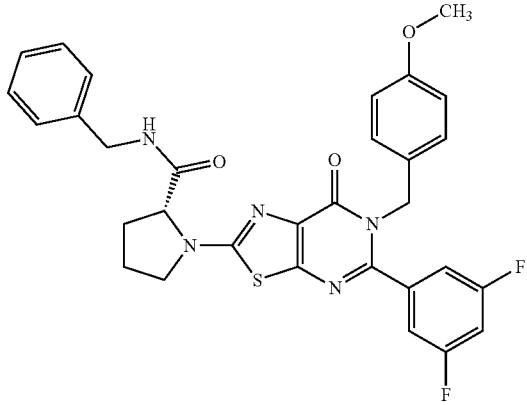 [SMILES: COc1ccc(Cn2c(-c3cc(F)cc(F)c3)nc3sc(N4CCC[C@@H]4C(=O)NCc4ccccc4)nc3c2=O)cc1]

The compound (225 mg) obtained in Reference Example 596 was treated by a method similar to that in Example 178 to give the title compound (143 mg).
MS (ESI) m/z; 588 [M+H]$^+$

Example 442

(R)-N-benzyl-1-[5-(4-fluoro-2-methoxyphenyl)-6-(4-methoxybenzyl)-7-oxo-6,7-dihydro[1,3]thiazolo[5,4-d]pyrimidin-2-yl]pyrrolidine-2-carboxamide

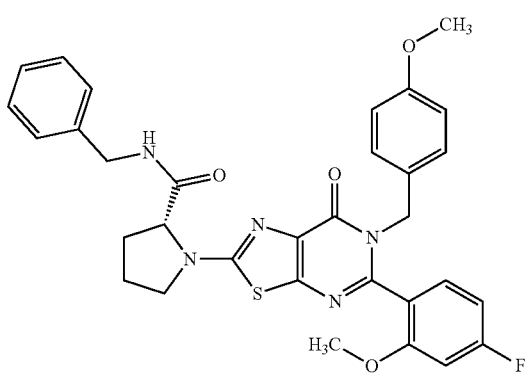 [SMILES: COc1ccc(Cn2c(-c3ccc(F)cc3OC)nc3sc(N4CCC[C@@H]4C(=O)NCc4ccccc4)nc3c2=O)cc1]

The compound (159 mg) obtained in Reference Example 597 was treated by a method similar to that in Example 178 to give the title compound (136 mg).
MS (ESI) m/z; 600 [M+H]$^+$

Example 443

(R)-N-benzyl-1-[5-(2-ethylphenyl)-6-(4-methoxybenzyl)-7-oxo-6,7-dihydro[1,3]thiazolo[5,4-d]pyrimidin-2-yl]pyrrolidine-2-carboxamide

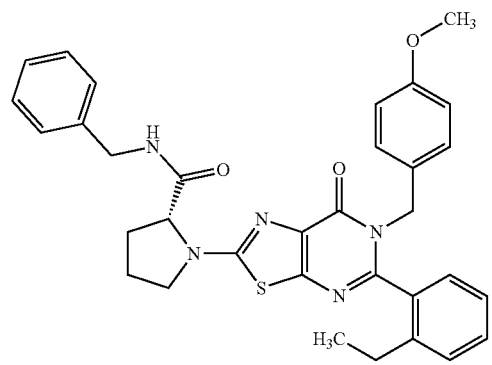 [SMILES: CCc1ccccc1-c1nc2sc(N3CCC[C@@H]3C(=O)NCc3ccccc3)nc2c(=O)n1Cc1ccc(OC)cc1]

The compound (238 mg) obtained in Reference Example 598 was treated by a method similar to that in Example 178 to give the title compound (254 mg).
MS (ESI) m/z; 580 [M+H]$^+$

Example 444

(R)-N-benzyl-1-{6-(4-methoxybenzyl)-7-oxo-5-[2-(trifluoromethyl)phenyl]-6,7-dihydro[1,3]thiazolo[5,4-d]pyrimidin-2-yl}pyrrolidine-2-carboxamide

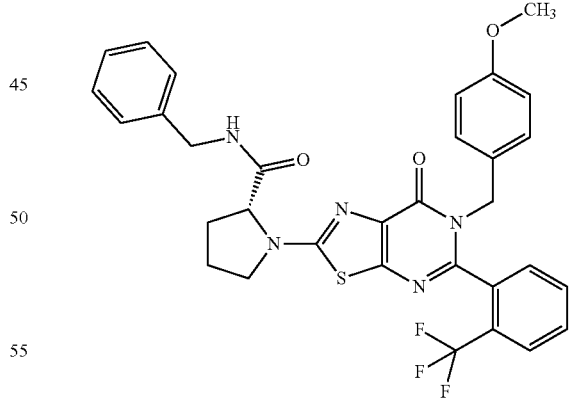

The compound (164 mg) obtained in Reference Example 599 was treated by a method similar to that in Example 178 to give the title compound (130 mg).
MS (ESI) m/z; 620 [M+H]$^+$

Example 445

(R)-N-benzyl-1-[6-(2,4-dimethoxybenzyl)-5-ethyl-7-oxo-6,7-dihydro[1,3]thiazolo[5,4-d]pyrimidin-2-yl]pyrrolidine-2-carboxamide

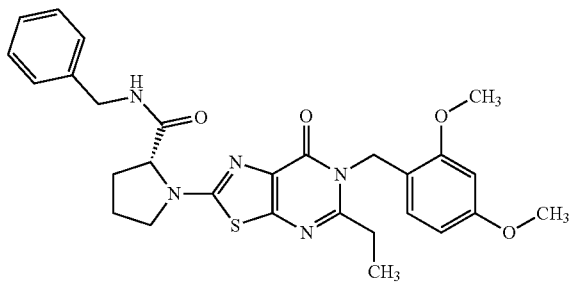 [SMILES: CCc1nc2sc(N3CCC[C@@H]3C(=O)NCc3ccccc3)nc2c(=O)n1Cc1ccc(OC)cc1OC]

The compound (341 mg) obtained in Reference Example 559 was treated by a method similar to that in Example 203 to give the title compound (418 mg).

MS (ESI) m/z; 534 [M+H]$^+$

Example 446

(R)-N-benzyl-1-[5-(5-chloro-2-fluorophenyl)-6-(2,4-dimethoxybenzyl)-7-oxo-6,7-dihydro[1,3]thiazolo[5,4-d]pyrimidin-2-yl]pyrrolidine-2-carboxamide

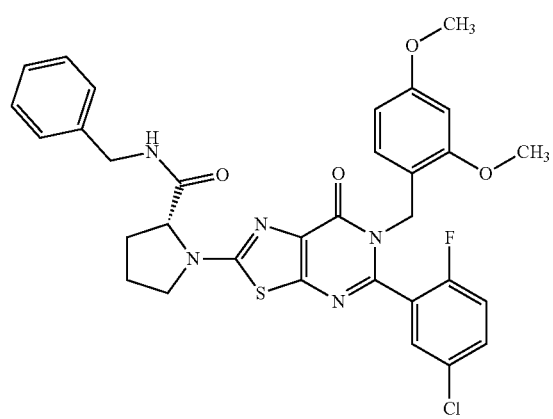 [SMILES: COc1ccc(Cn2c(-c3cc(Cl)ccc3F)nc3sc(N4CCC[C@@H]4C(=O)NCc4ccccc4)nc3c2=O)c(OC)c1]

The compound (511 mg) obtained in Reference Example 569 was treated by a method similar to that in Example 203 to give the title compound (515 mg).

MS (ESI) m/z; 634, 636 [M+H]$^+$

Example 447

(R)-N-benzyl-2-{N'-[6-(2,4-dimethoxybenzyl)-5-(1-methoxycyclopropyl)-7-oxo-6,7-dihydro[1,3]thiazolo[5,4-d]pyrimidin-2-yl]-N'-methylamino}propionamide

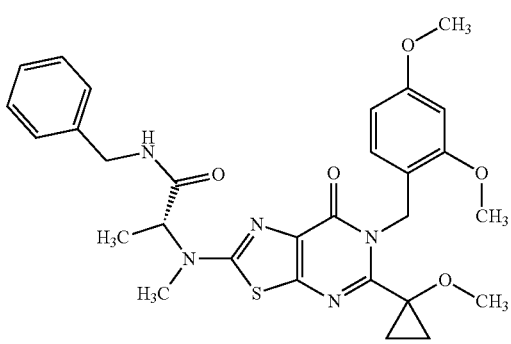 [SMILES: COc1ccc(Cn2c(C3(OC)CC3)nc3sc(N(C)[C@H](C)C(=O)NCc4ccccc4)nc3c2=O)c(OC)c1]

The compound (300 mg) obtained in Reference Example 578 was treated by a method similar to that in Example 203 to give the title compound (259 mg).

MS (ESI) m/z; 564 [M+H]$^+$

Example 448

(R)-N-benzyl-1-{6-(2,4-dimethoxybenzyl)-5-[1-(fluoromethyl)cyclopropyl]-7-oxo-6,7-dihydro[1,3]thiazolo[5,4-d]pyrimidin-2-yl}pyrrolidine-2-carboxamide

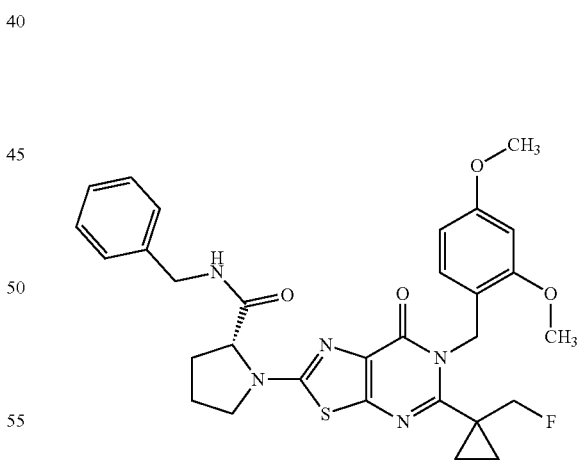

The compound (400 mg) obtained in Reference Example 579 was treated by a method similar to that in Example 203 to give the title compound (467 mg).

MS (ESI) m/z; 578 [M+H]$^+$

Example 449

(R)-N-benzyl-1-{6-(2,4-dimethoxybenzyl)-5-[1-(methoxymethyl)cyclopropyl]-7-oxo-6,7-dihydro[1,3]thiazolo[5,4-d]pyrimidin-2-yl}pyrrolidine-2-carboxamide

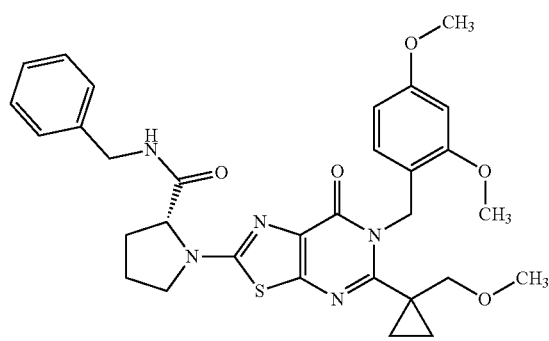 [SMILES: COCC1(c2nc3sc(N4CCC[C@@H]4C(=O)NCc4ccccc4)nc3c(=O)n2Cc2ccc(OC)cc2OC)CC1]

The compound (400 mg) obtained in Reference Example 580 was treated by a method similar to that in Example 203 to give the title compound (480 mg).

MS (ESI) m/z; 590 [M+H]$^+$

Example 450

(R)-N-benzyl-1-[6-(2,4-dimethoxybenzyl)-5-(2-fluoro-5-methylphenyl)-7-oxo-6,7-dihydro[1,3]thiazolo[5,4-d]pyrimidin-2-yl]pyrrolidine-2-carboxamide

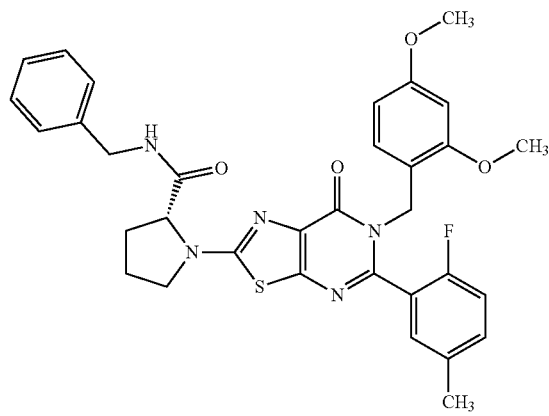 [SMILES: COc1ccc(Cn2c(-c3cc(C)ccc3F)nc3sc(N4CCC[C@@H]4C(=O)NCc4ccccc4)nc3c2=O)c(OC)c1]

The compound (525 mg) obtained in Reference Example 581 was treated by a method similar to that in Example 203 to give the title compound (542 mg).

MS (ESI) m/z; 614 [M+H]$^+$

Example 451

(R)-N-benzyl-1-[6-(2,4-dimethoxybenzyl)-5-(3-fluoropyridin-2-yl)-7-oxo-6,7-dihydro[1,3]thiazolo[5,4-d]pyrimidin-2-yl]pyrrolidine-2-carboxamide

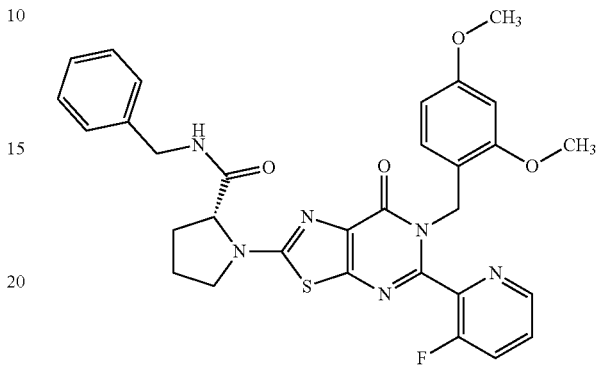

The compound (342 mg) obtained in Reference Example 582 was treated by a method similar to that in Example 203 to give the title compound (355 mg).

MS (ESI) m/z; 601 [M+H]$^+$

Example 452

(R)-N-benzyl-1-[5-(3-chloro-2-fluorophenyl)-6-(2,4-dimethoxybenzyl)-7-oxo-6,7-dihydro[1,3]thiazolo[5,4-d]pyrimidin-2-yl]pyrrolidine-2-carboxamide

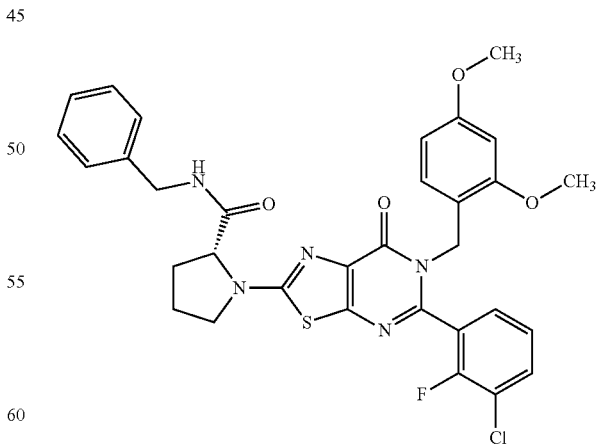

The compound (570 mg) obtained in Reference Example 587 was treated by a method similar to that in Example 203 to give the title compound (431 mg).

MS (ESI) m/z; 634, 636 [M+H]$^+$

Example 453

(R)-N-benzyl-1-[6-(2,4-dimethoxybenzyl)-7-oxo-5-trifluoromethyl-6,7-dihydro[1,3]thiazolo[5,4-d]pyrimidin-2-yl]pyrrolidine-2-carboxamide

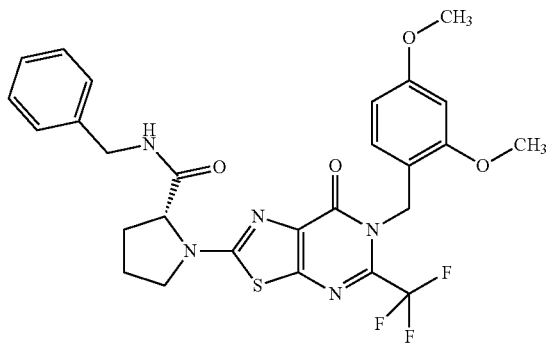 [SMILES: COc1ccc(Cn2c(C(F)(F)F)nc3sc(N4CCC[C@@H]4C(=O)NCc4ccccc4)nc3c2=O)c(OC)c1]

The compound (528 mg) obtained in Reference Example 588 was treated by a method similar to that in Example 203 to give the title compound (534 mg).

MS (ESI) m/z; 574 [M+H]$^+$

Example 454

(R)-1-[6-(2,4-dimethoxybenzyl)-7-oxo-5-trifluoromethyl-6,7-dihydro-[1,3]thiazolo[5,4-d]pyrimidin-2-yl]-N-((R)-1-phenylethyl)pyrrolidine-2-carboxamide

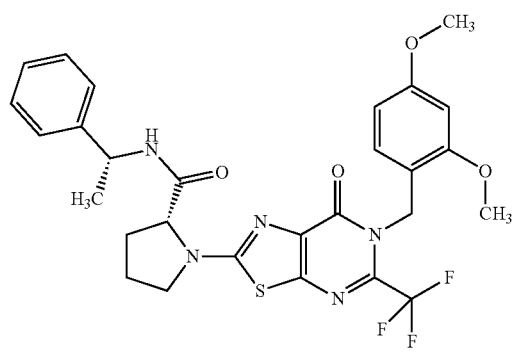 [SMILES: COc1ccc(Cn2c(C(F)(F)F)nc3sc(N4CCC[C@@H]4C(=O)N[C@H](C)c4ccccc4)nc3c2=O)c(OC)c1]

The compound (415 mg) obtained in Reference Example 588 was treated by a method similar to that in Example 203 to give the title compound (455 mg).

MS (ESI) m/z; 588 [M+H]$^+$

Example 455

(R)-N-benzyl-1-[5-(2,3-difluorophenyl)-6-(4-methoxybenzyl)-7-oxo-6,7-dihydro[1,3]thiazolo[5,4-d]pyrimidin-2-yl]pyrrolidine-2-carboxamide

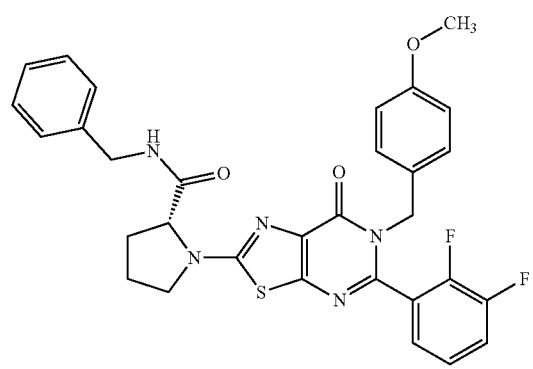 [SMILES: COc1ccc(Cn2c(-c3cccc(F)c3F)nc3sc(N4CCC[C@@H]4C(=O)NCc4ccccc4)nc3c2=O)cc1]

The compound (187 mg) obtained in Reference Example 593 was treated by a method similar to that in Example 203 to give the title compound (220 mg).

MS (ESI) m/z; 588 [M+H]$^+$

Example 456

(R)-N-benzyl-1-[6-(2,4-dimethoxybenzyl)-5-methoxymethyl-7-oxo-6,7-dihydro[1,3]thiazolo[5,4-d]pyrimidin-2-yl]pyrrolidine-2-carboxamide

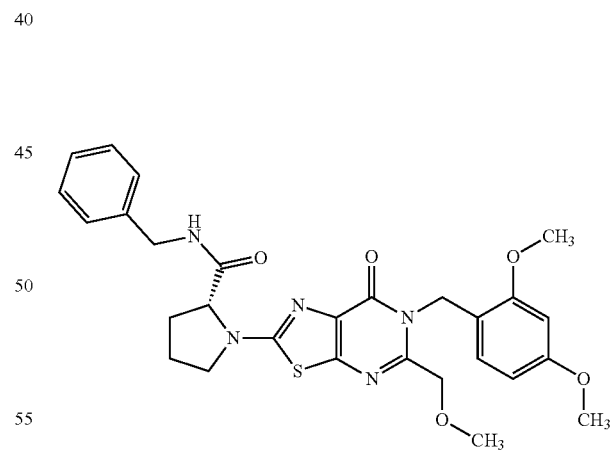

The compound (282 mg) obtained in Reference Example 561 was treated by a method similar to that in Example 265 to give the title compound (219 mg).

MS (ESI) m/z; 550 [M+H]$^+$

Example 457

(R)-1-[6-(2,4-dimethoxybenzyl)-5-(2-fluoropropan-2-yl)-7-oxo-6,7-dihydro[1,3]thiazolo[5,4-d]pyrimidin-2-yl]-N-((R)-1-phenylethyl)pyrrolidine-2-carboxamide

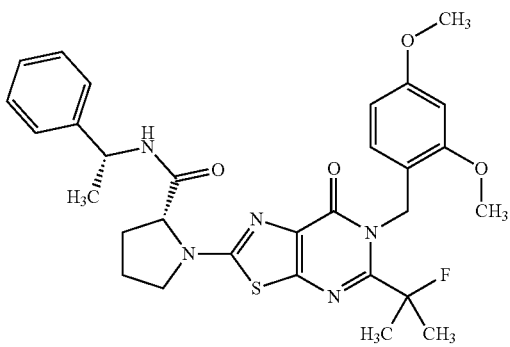 [SMILES: COc1ccc(Cn2c(C(C)(C)F)nc3sc(N4CCC[C@@H]4C(=O)N[C@H](C)c4ccccc4)nc3c2=O)c(OC)c1]

The compound (200 mg) obtained in Reference Example 558 was treated by a method similar to that in Example 265 to give the title compound (232 mg).
MS (ESI) m/z; 580 [M+H]$^+$

Example 458

(R)-N-benzyl-2-{N'-[6-(2,4-dimethoxybenzyl)-5-(2-fluoropropan-2-yl)-7-oxo-6,7-dihydro[1,3]thiazolo[5,4-d]pyrimidin-2-yl]-N'-methylamino}propionamide

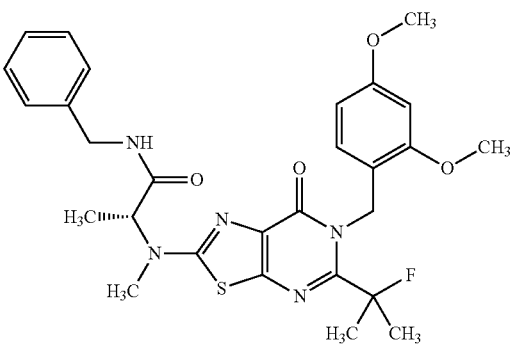 [SMILES: COc1ccc(Cn2c(C(C)(C)F)nc3sc(N(C)[C@H](C)C(=O)NCc4ccccc4)nc3c2=O)c(OC)c1]

The compound (300 mg) obtained in Reference Example 558 was treated by a method similar to that in Example 265 to give the title compound (271 mg).
MS (ESI) m/z; 554 [M+H]$^+$

Example 459

(R)-N-benzyl-1-[6-(2,4-dimethoxybenzyl)-5-(1-fluorocyclopropyl)-7-oxo-6,7-dihydro[1,3]thiazolo[5,4-d]pyrimidin-2-yl]pyrrolidine-2-carboxamide

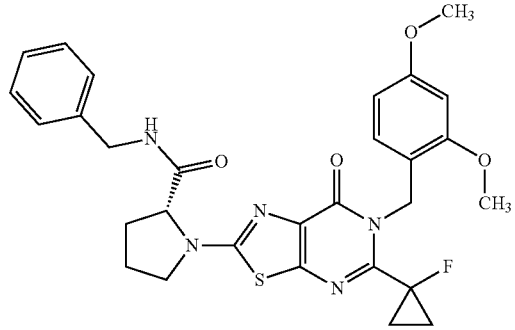 [SMILES: COc1ccc(Cn2c(C3(F)CC3)nc3sc(N4CCC[C@@H]4C(=O)NCc4ccccc4)nc3c2=O)c(OC)c1]

The compound (369 mg) obtained in Reference Example 570 was treated by a method similar to that in Example 265 to give the title compound (457 mg).
MS (ESI) m/z; 564 [M+H]$^+$

Example 460

(R)-1-[6-(2,4-dimethoxybenzyl)-5-(1-fluorocyclopropyl)-7-oxo-6,7-dihydro[1,3]thiazolo[5,4-d]pyrimidin-2-yl]-N-((R)-1-phenylethyl)pyrrolidine-2-carboxamide

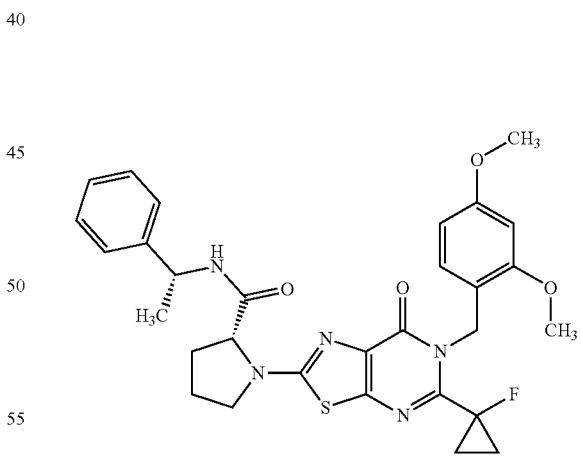

The compound (255 mg) obtained in Reference Example 570 was treated by a method similar to that in Example 265 to give the title compound (296 mg).
MS (ESI) m/z; 578 [M+H]$^+$

Example 461

(R)-N-benzyl-1-[5-(1-chlorocyclopropyl)-6-(2,4-dimethoxybenzyl)-7-oxo-6,7-dihydro[1,3]thiazolo[5,4-d]pyrimidin-2-yl]pyrrolidine-2-carboxamide

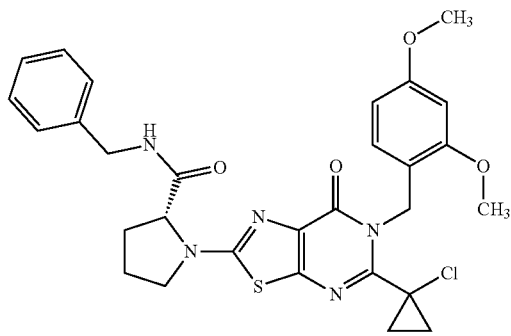

The compound (127 mg) obtained in Reference Example 586 was treated by a method similar to that in Example 265 to give the title compound (117 mg).

MS (ESI) m/z; 581 [M+H]⁺

Example 462

(R)-1-[5-(1-chlorocyclopropyl)-6-(2,4-dimethoxybenzyl)-7-oxo-6,7-dihydro[1,3]thiazolo[5,4-d]pyrimidin-2-yl]-N-((R)-1-phenylethyl)pyrrolidine-2-carboxamide

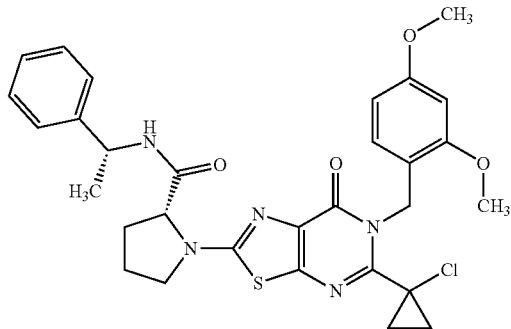 [SMILES: COc1ccc(Cn2c(C3(F)CC3)nc3sc(N4CCC[C@@H]4C(=O)N[C@H](C)c4ccccc4)nc3c2=O)c(OC)c1]

The compound (88 mg) obtained in Reference Example 586 was treated by a method similar to that in Example 265 to give the title compound (76 mg).

MS (ESI) m/z; 595 [M+H]⁺

Example 463

(R)-N-benzyl-1-[5-(1,1-difluoroethyl)-6-(2,4-dimethoxybenzyl)-7-oxo-6,7-dihydro[1,3]thiazolo[5,4-d]pyrimidin-2-yl]pyrrolidine-2-carboxamide

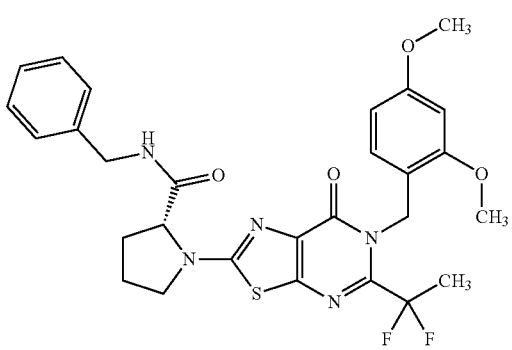 [SMILES: COc1ccc(Cn2c(C(C)(F)F)nc3sc(N4CCC[C@@H]4C(=O)NCc4ccccc4)nc3c2=O)c(OC)c1]

The compound (528 mg) obtained in Reference Example 571 was treated by a method similar to that in Example 265 to give the title compound (498 mg).

MS (ESI) m/z; 570 [M+H]⁺

Example 464

(R)-1-[5-(1,1-difluoroethyl)-6-(2,4-dimethoxybenzyl)-7-oxo-6,7-dihydro[1,3]thiazolo[5,4-d]pyrimidin-2-yl]-N-((R)-1-phenylethyl)pyrrolidine-2-carboxamide

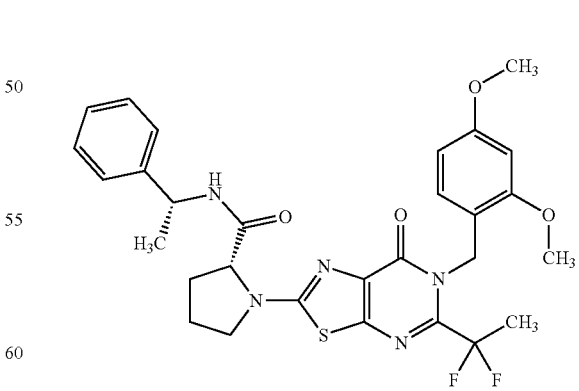

The compound (570 mg) obtained in Reference Example 571 was treated by a method similar to that in Example 265 to give the title compound (596 mg).

MS (ESI) m/z; 584 [M+H]⁺

Example 465

(R)-N-benzyl-1-[5-(1,1-difluoro-2-methoxyethyl)-6-(2,4-dimethoxybenzyl)-7-oxo-6,7-dihydro[1,3]thiazolo[5,4-d]pyrimidin-2-yl]pyrrolidine-2-carboxamide

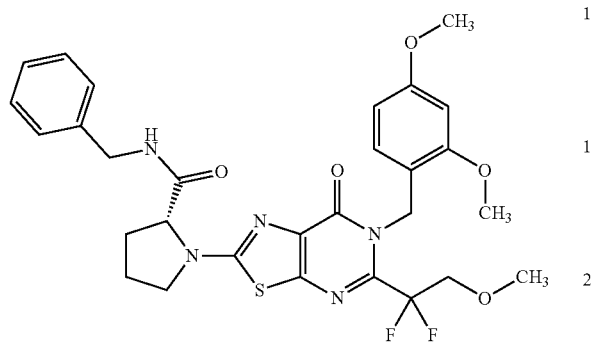

The compound (1.05 g) obtained in Reference Example 572 was treated by a method similar to that in Example 265 to give the title compound (956 mg).

MS (ESI) m/z; 600 [M+H]$^+$

Example 466

(R)-1-[5-(1,1-difluoro-2-methoxyethyl)-6-(2,4-dimethoxybenzyl)-7-oxo-6,7-dihydro[1,3]thiazolo[5,4-d]pyrimidin-2-yl]-N-((R)-1-phenylethyl)pyrrolidine-2-carboxamide

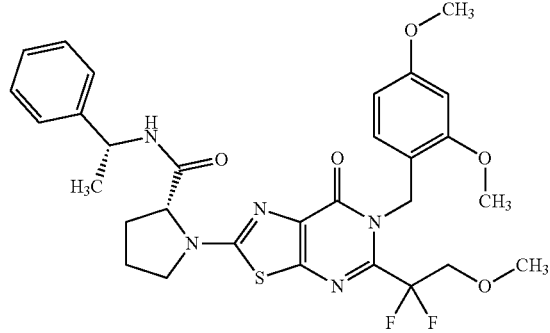 [SMILES: COCC(F)(F)c1nc2sc(N3CCC[C@@H]3C(=O)N[C@H](C)c3ccccc3)nc2c(=O)n1Cc1ccc(OC)cc1OC]

The compound (250 mg) obtained in Reference Example 572 was treated by a method similar to that in Example 265 to give the title compound (198 mg).

MS (ESI) m/z; 614 [M+H]$^+$

Example 467

(R)-N-benzyl-1-{6-(2,4-dimethoxybenzyl)-7-oxo-5-[1-(trifluoromethyl)cyclopropyl]-6,7-dihydro[1,3]thiazolo[5,4-d]pyrimidin-2-yl}pyrrolidine-2-carboxamide

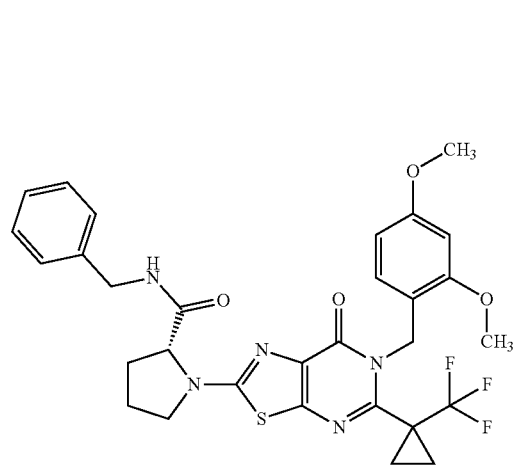 [SMILES: COc1ccc(Cn2c(C3(C(F)(F)F)CC3)nc3sc(N4CCC[C@@H]4C(=O)NCc4ccccc4)nc3c2=O)c(OC)c1]

The compound (600 mg) obtained in Reference Example 573 was treated by a method similar to that in Example 265 to give the title compound (636 mg).

MS (ESI) m/z; 614 [M+H]$^+$

Example 468

(R)-N-benzyl-2-[N'-{6-(2,4-dimethoxybenzyl)-7-oxo-5-[1-(trifluoromethyl)cyclopropyl]-6,7-dihydro[1,3]thiazolo[5,4-d]pyrimidin-2-yl}-N'-methylamino]propionamide

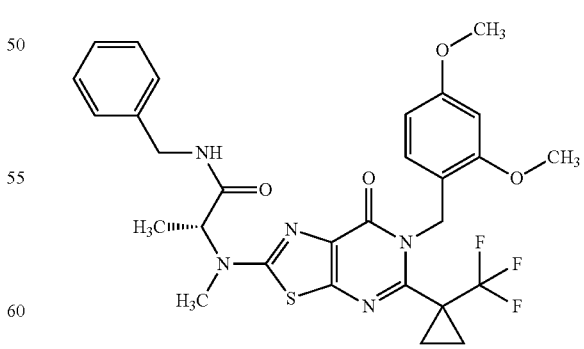

The compound (470 mg) obtained in Reference Example 573 was treated by a method similar to that in Example 265 to give the title compound (351 mg).

MS (ESI) m/z; 602 [M+H]$^+$

Example 469

(R)-N-benzyl-1-{5-[difluoro(phenyl)methyl]-6-(2,4-dimethoxybenzyl)-7-oxo-6,7-dihydro[1,3]thiazolo[5,4-d]pyrimidin-2-yl}pyrrolidine-2-carboxamide

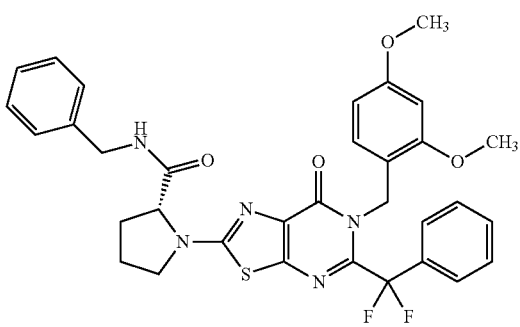 [SMILES: COc1ccc(Cn2c(C(F)(F)c3ccccc3)nc3sc(N4CCC[C@@H]4C(=O)NCc4ccccc4)nc3c2=O)c(OC)c1]

The compound (187 mg) obtained in Reference Example 574 was treated by a method similar to that in Example 265 to give the title compound (190 mg).

MS (ESI) m/z; 632 [M+H]$^+$

Example 470

(R)-1-[5-(difluoro(phenyl)methyl)-6-(2,4-dimethoxybenzyl)-7-oxo-6,7-dihydro[1,3]thiazolo[5,4-d]pyrimidin-2-yl]-N-((R)-1-phenylethyl)pyrrolidine-2-carboxamide

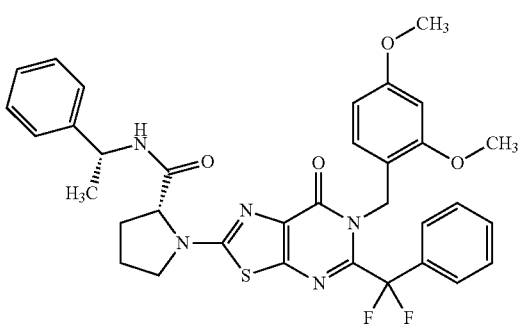 [SMILES: COc1ccc(Cn2c(C(F)(F)c3ccccc3)nc3sc(N4CCC[C@@H]4C(=O)N[C@H](C)c4ccccc4)nc3c2=O)c(OC)c1]

The compound (91 mg) obtained in Reference Example 574 was treated by a method similar to that in Example 265 to give the title compound (86 mg).

MS (ESI) m/z; 646 [M+H]$^+$

Example 471

(R)-N-benzyl-1-[6-(2,4-dimethoxybenzyl)-5-(2-fluoro-3-methoxyphenyl)-7-oxo-6,7-dihydro[1,3]thiazolo[5,4-d]pyrimidin-2-yl]pyrrolidine-2-carboxamide

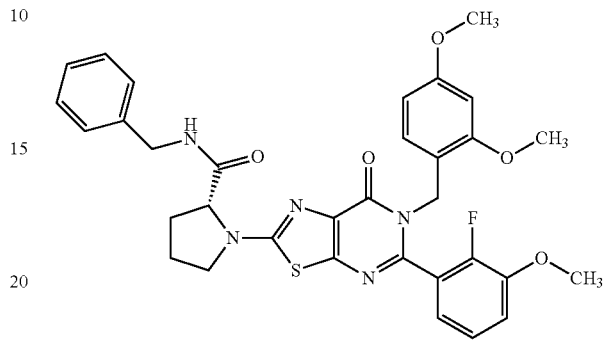

The compound (695 mg) obtained in Reference Example 575 was treated by a method similar to that in Example 265 to give the title compound (666 mg).

MS (ESI) m/z; 630 [M+H]$^+$

Example 472

(R)-N-benzyl-1-[6-(2,4-dimethoxybenzyl)-5-(2-fluoro-3-methylphenyl)-7-oxo-6,7-dihydro[1,3]thiazolo[5,4-d]pyrimidin-2-yl]pyrrolidine-2-carboxamide

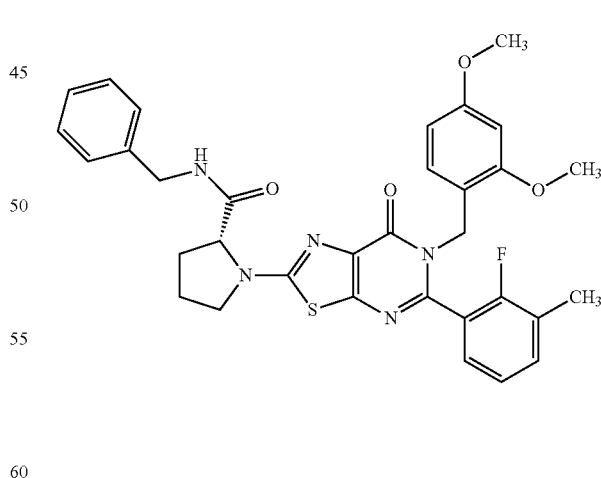

The compound (607 mg) obtained in Reference Example 576 was treated by a method similar to that in Example 265 to give the title compound (642 mg).

MS (ESI) m/z; 614 [M+H]$^+$

Example 473

(R)-N-benzyl-1-[6-(2,4-dimethoxybenzyl)-7-oxo-5-pentafluoroethyl-6,7-dihydro[1,3]thiazolo[5,4-d]pyrimidin-2-yl]pyrrolidine-2-carboxamide

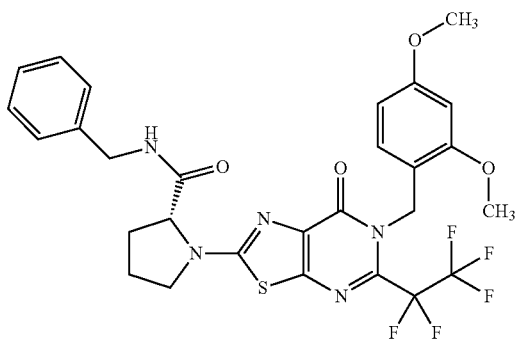 [SMILES: COc1ccc(Cn2c(C(F)(F)C(F)(F)F)nc3sc(N4CCC[C@@H]4C(=O)NCc4ccccc4)nc3c2=O)c(OC)c1]

The compound (115 mg) obtained in Reference Example 584 was treated by a method similar to that in Example 265 to give the title compound (90 mg).

MS (ESI) m/z; 624 [M+H]$^+$

Example 474

(R)-1-[6-(2,4-dimethoxybenzyl)-7-oxo-5-pentafluoroethyl-6,7-dihydro[1,3]thiazolo[5,4-d]pyrimidin-2-yl]-N-((R)-1-phenylethyl)pyrrolidine-2-carboxamide

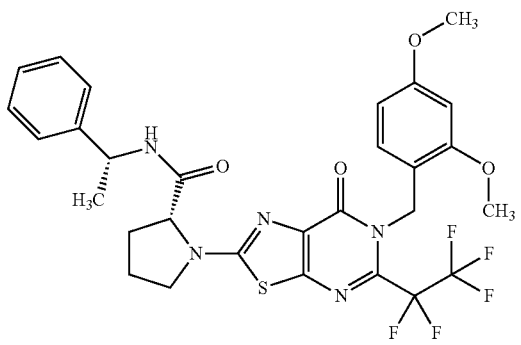 [SMILES: COc1ccc(Cn2c(C(F)(F)C(F)(F)F)nc3sc(N4CCC[C@@H]4C(=O)N[C@H](C)c4ccccc4)nc3c2=O)c(OC)c1]

The compound (115 mg) obtained in Reference Example 584 was treated by a method similar to that in Example 265 to give the title compound (94 mg).

MS (ESI) m/z; 638 [M+H]$^+$

Example 475

(R)-N-benzyl-2-{N'-[6-(2,4-dimethoxybenzyl)-7-oxo-5-phenyl-6,7-dihydro[1,3]thiazolo[5,4-d]pyrimidin-2-yl]-N'-methylamino}propionamide

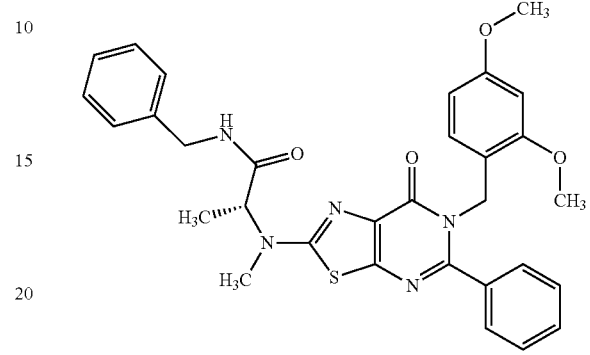

The compound (554 mg) obtained in Reference Example 562 was treated by a method similar to that in Example 265 to give the title compound (296 mg).

MS (ESI) m/z; 570 [M+H]$^+$

Example 476

(R)-N-benzyl-2-{N'-[6-(2,4-dimethoxybenzyl)-5-(2-fluorophenyl)-7-oxo-6,7-dihydro[1,3]thiazolo[5,4-d]pyrimidin-2-yl]-N'-methylamino}propionamide

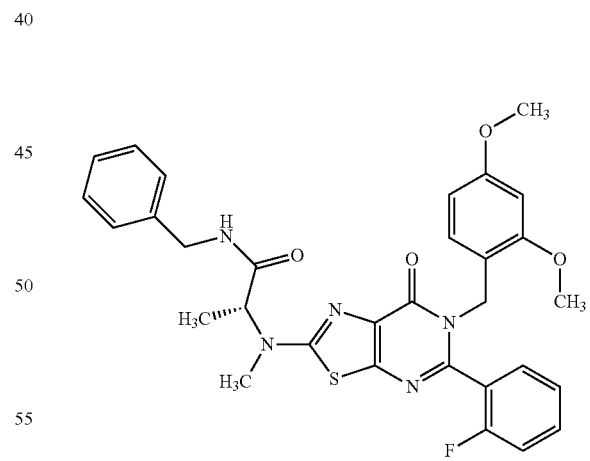

The compound (850 mg) obtained in Reference Example 563 was treated by a method similar to that in Example 265 to give the title compound (550 mg).

MS (ESI) m/z; 588 [M+H]$^+$

Example 477

(R)-N-benzyl-2-{N'-[5-(1-chlorocyclopropyl)-6-(2,4-dimethoxybenzyl)-7-oxo-6,7-dihydro[1,3]thiazolo[5,4-d]pyrimidin-2-yl]-N'-methylamino}propionamide

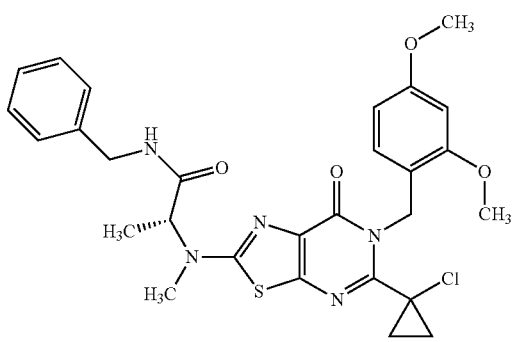

The compound (575 mg) obtained in Reference Example 586 was treated by a method similar to that in Example 265 to give the title compound (368 mg).

MS (ESI) m/z; 568 [M+H]$^+$

Example 478

(R)-N-benzyl-2-{N'-[6-(2,4-dimethoxybenzyl)-5-(1-fluorocyclopropyl)-7-oxo-6,7-dihydro[1,3]thiazolo[5,4-d]pyrimidin-2-yl]-N'-methylamino}propionamide

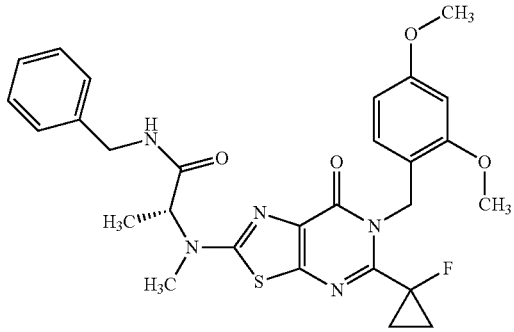 [SMILES: COc1ccc(Cn2c(C3(F)CC3)nc3sc(N(C)[C@H](C)C(=O)NCc4ccccc4)nc3c2=O)c(OC)c1]

The compound (770 mg) obtained in Reference Example 570 was treated by a method similar to that in Example 265 to give the title compound (699 mg).

MS (ESI) m/z; 552 [M+H]$^+$

Example 479

(R)-N-benzyl-1-[5-difluoromethyl-6-(2,4-dimethoxybenzyl)-7-oxo-6,7-dihydro[1,3]thiazolo[5,4-d]pyrimidin-2-yl]pyrrolidine-2-carboxamide

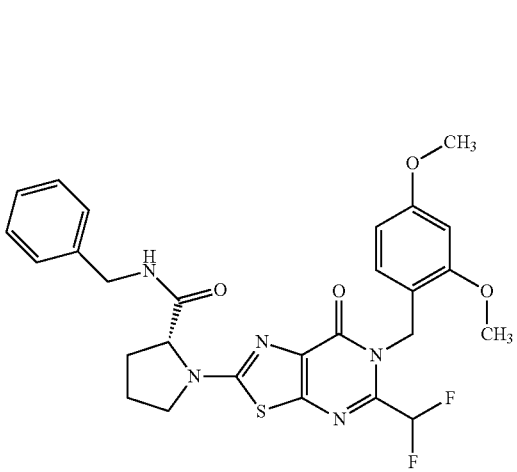 [SMILES: COc1ccc(Cn2c(C(F)F)nc3sc(N4CCC[C@@H]4C(=O)NCc4ccccc4)nc3c2=O)c(OC)c1]

The compound (1.60 g) obtained in Reference Example 589 was treated by a method similar to that in Example 265 to give the title compound (1.75 g).

MS (ESI) m/z; 556 [M+H]$^+$

Example 480

(R)-1-[5-difluoromethyl-6-(2,4-dimethoxybenzyl)-7-oxo-6,7-dihydro[1,3]thiazolo[5,4-d]pyrimidin-2-yl]-N-((R)-1-phenylethyl)pyrrolidine-2-carboxamide

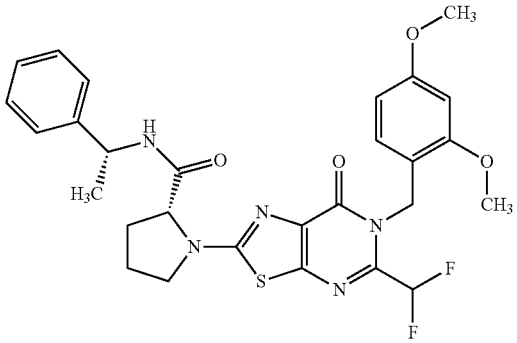 [SMILES: COc1ccc(Cn2c(C(F)F)nc3sc(N4CCC[C@@H]4C(=O)N[C@H](C)c4ccccc4)nc3c2=O)c(OC)c1]

The compound (1.20 g) obtained in Reference Example 589 was treated by a method similar to that in Example 265 to give the title compound (1.37 g).

MS (ESI) m/z; 570 [M+H]$^+$

Example 481

(R)-1-[6-(4-methoxybenzyl)-7-oxo-5-phenyl-6,7-dihydro[1,3]thiazolo[5,4-d]pyrimidin-2-yl]-N-[dideuterio(phenyl)methyl]pyrrolidine-2-carboxamide

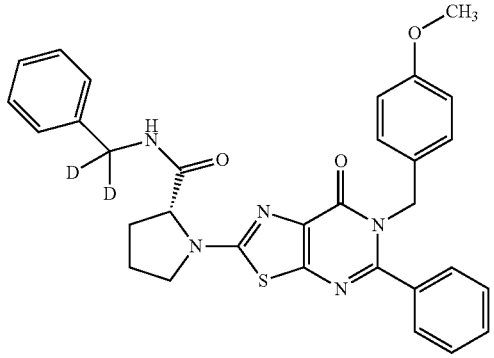 [SMILES: [2H]C([2H])(NC(=O)[C@H]1CCCN1c1nc2c(=O)n(Cc3ccc(OC)cc3)c(-c3ccccc3)nc2s1)c1ccccc1]

The compound (350 mg) obtained in Reference Example 590 was treated by a method similar to that in Example 265 to give the title compound (410 mg).
MS (ESI) m/z; 554 [M+H]$^+$

Example 482

(R)-N-benzyl-1-[5-(2-fluoropropan-2-yl)-7-oxo-6,7-dihydro[1,3]thiazolo[5,4-d]pyrimidin-2-yl]pyrrolidine-2-carboxamide

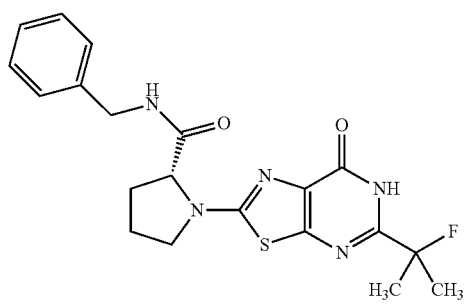 [SMILES: CC(C)(F)c1nc2sc(N3CCC[C@@H]3C(=O)NCc3ccccc3)nc2c(=O)[nH]1]

The compound (460 mg) obtained in Example 414 was dissolved in a mixture (5.0 mL) of trifluoroacetic acid/water/triethylsilane=90/5/5 (v/v) under ice-cooling, and the mixture was stirred at room temperature for 2.5 hr. The reaction mixture was concentrated, and the residue was purified by silica gel column chromatography (solvent; chloroform/methanol=100/0-90/10) to give the title compound (304 mg).
MS (ESI) m/z; 416 [M+H]$^+$

Example 483

(R)-N-benzyl-1-[5-(2-fluoropropan-2-yl)-7-oxo-6,7-dihydro[1,3]thiazolo[5,4-d]pyrimidin-2-yl]piperidine-2-carboxamide

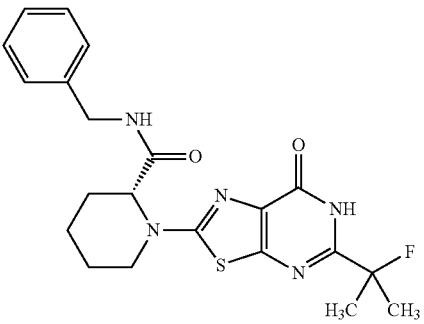 [SMILES: CC(C)(F)c1nc2sc(N3CCCC[C@@H]3C(=O)NCc3ccccc3)nc2c(=O)[nH]1]

The compound (61 mg) obtained in Example 415 was treated by a method similar to that in Example 482 to give the title compound (14 mg).
MS (ESI) m/z; 430 [M+H]$^+$

Example 484

(R)-N-benzyl-1-[5-(propan-2-yl)-7-oxo-6,7-dihydro[1,3]thiazolo[5,4-d]pyrimidin-2-yl]azetidine-2-carboxamide

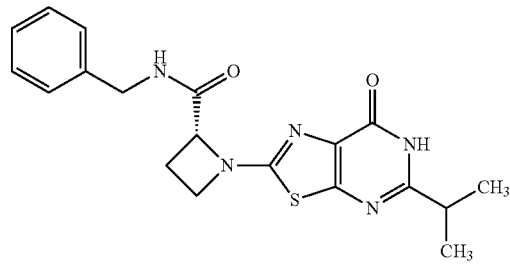 [SMILES: CC(C)c1nc2sc(N3CC[C@@H]3C(=O)NCc3ccccc3)nc2c(=O)[nH]1]

The compound (450 mg) obtained in Example 416 was treated by a method similar to that in Example 482 to give the title compound (240 mg).
MS (ESI) m/z; 384 [M+H]$^+$ Example 485

(R)-N-benzyl-1-[5-(propan-2-yl)-7-oxo-6,7-dihydro[1,3]thiazolo[5,4-d]pyrimidin-2-yl]piperidine-2-carboxamide

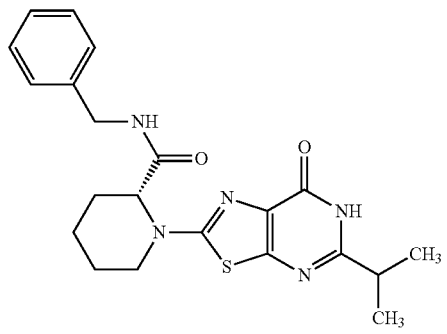 [SMILES: CC(C)c1nc2sc(N3CCCC[C@@H]3C(=O)NCc3ccccc3)nc2c(=O)[nH]1]

The compound (110 mg) obtained in Example 417 was treated by a method similar to that in Example 482 to give the title compound (39 mg).

MS (ESI) m/z; 412 [M+H]+

Example 486

(R)-N-benzyl-2-{N'-[5-(propan-2-yl)-7-oxo-6,7-dihydro[1,3]thiazolo[5,4-d]pyrimidin-2-yl]-N'-methylamino}propionamide

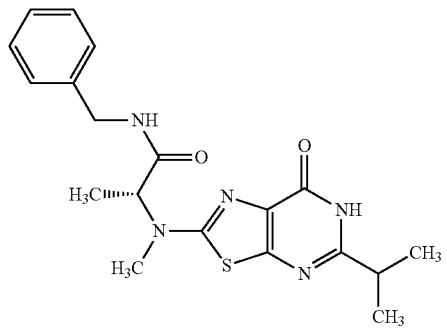 [SMILES: CC(C)c1nc2sc(N(C)[C@H](C)C(=O)NCc3ccccc3)nc2c(=O)[nH]1]

The compound (350 mg) obtained in Example 418 was treated by a method similar to that in Example 482 to give the title compound (175 mg).

MS (ESI) m/z; 386 [M+H]+

Example 487

(R)-N-benzyl-1-(7-oxo-5-phenyl-6,7-dihydro[1,3]thiazolo[5,4-d]pyrimidin-2-yl)pyrrolidine-2-carboxamide

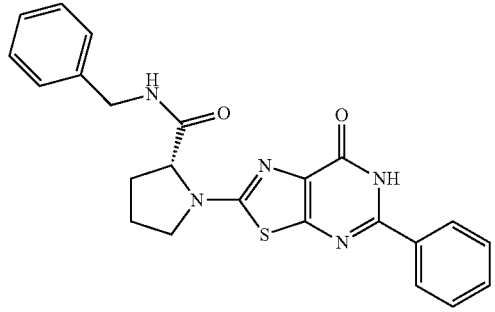 [SMILES: O=C(NCc1ccccc1)[C@H]1CCCN1c1nc2c(=O)[nH]c(-c3ccccc3)nc2s1]

The compound (143 mg) obtained in Example 419 was treated by a method similar to that in Example 482 to give the title compound (98 mg).

MS (ESI) m/z; 432 [M+H]+

Example 488

(R)-1-(7-oxo-5-phenyl-6,7-dihydro[1,3]thiazolo[5,4-d]pyrimidin-2-yl)-N-((R)-1-phenylethyl)pyrrolidine-2-carboxamide

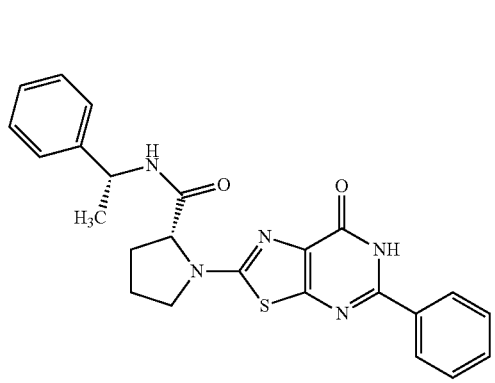 [SMILES: C[C@@H](NC(=O)[C@H]1CCCN1c1nc2c(=O)[nH]c(-c3ccccc3)nc2s1)c1ccccc1]

The compound (138 mg) obtained in Example 420 was treated by a method similar to that in Example 482 to give the title compound (84 mg).

MS (ESI) m/z; 446 [M+H]+

Example 489

(R)-N-benzyl-1-[5-(2-fluorophenyl)-7-oxo-6,7-di-hydro[1,3]thiazolo[5,4-d]pyrimidin-2-yl]pyrrolidine-2-carboxamide

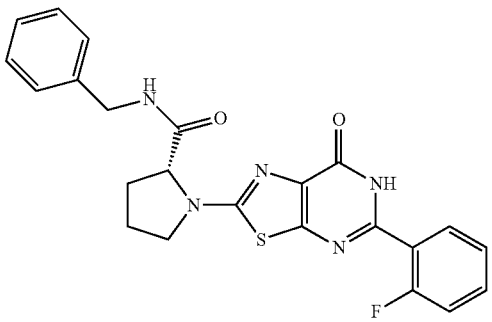 [SMILES: O=C(NCc1ccccc1)[C@H]1CCCN1c1nc2c(=O)[nH]c(-c3ccccc3F)nc2s1]

The compound (19.9 g) obtained in Example 421 was treated by a method similar to that in Example 482 to give the title compound (13.9 g).

MS (ESI) m/z; 450 [M+H]$^+$

Example 490

(R)-1-[5-(2-fluorophenyl)-7-oxo-6,7-dihydro[1,3]thiazolo[5,4-d]pyrimidin-2-yl]-N-((R)-1-phenyl-ethyl)pyrrolidine-2-carboxamide

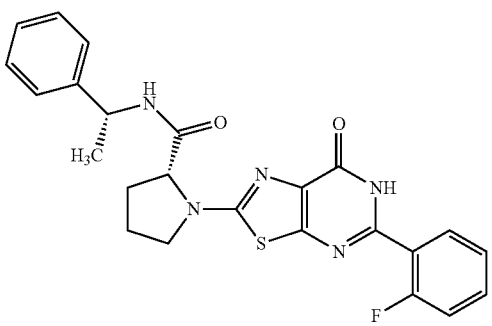 [SMILES: C[C@@H](NC(=O)[C@H]1CCCN1c1nc2c(=O)[nH]c(-c3ccccc3F)nc2s1)c1ccccc1]

The compound (339 mg) obtained in Example 422 was treated by a method similar to that in Example 482 to give the title compound (196 mg).

MS (ESI) m/z; 464 [M+H]$^+$

Example 491

(R)-N-benzyl-1-[5-(2-fluorophenyl)-7-oxo-6,7-di-hydro[1,3]thiazolo[5,4-d]pyrimidin-2-yl]azetidine-2-carboxamide

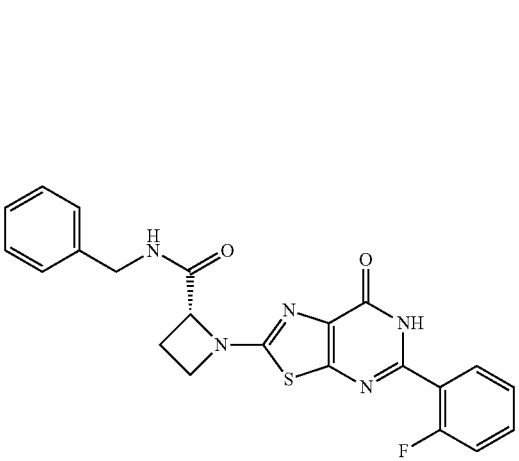 [SMILES: O=C(NCc1ccccc1)[C@H]1CCN1c1nc2c(=O)[nH]c(-c3ccccc3F)nc2s1]

The compound (44 mg) obtained in Example 423 was treated by a method similar to that in Example 482 to give the title compound (25 mg).

MS (ESI) m/z; 436 [M+H]$^+$

Example 492

(R)-N-benzyl-1-[5-(2-fluorophenyl)-7-oxo-6,7-di-hydro[1,3]thiazolo[5,4-d]pyrimidin-2-yl]piperidine-2-carboxamide

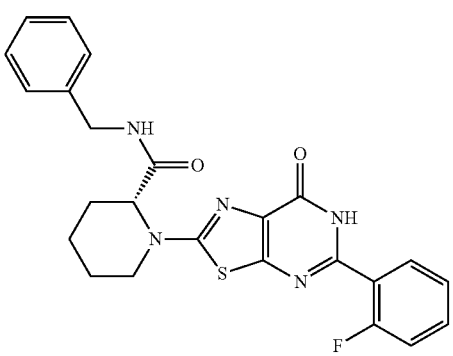 [SMILES: O=C(NCc1ccccc1)[C@H]1CCCCN1c1nc2c(=O)[nH]c(-c3ccccc3F)nc2s1]

The compound (92 mg) obtained in Example 424 was treated by a method similar to that in Example 482 to give the title compound (34 mg).

MS (ESI) m/z; 464 [M+H]$^+$

Example 493

(R)-N-benzyl-1-[5-(2-chlorophenyl)-7-oxo-6,7-di-hydro[1,3]thiazolo[5,4-d]pyrimidin-2-yl]pyrrolidine-2-carboxamide

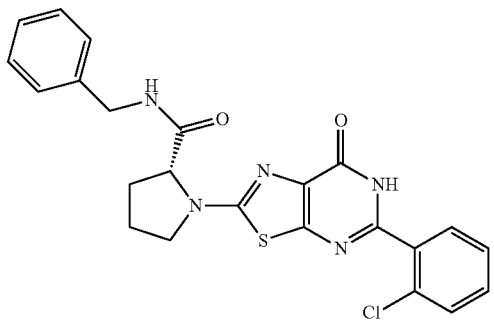 [SMILES: O=C(NCc1ccccc1)[C@H]1CCCN1c1nc2c(=O)[nH]c(-c3ccccc3Cl)nc2s1]

The compound (197 mg) obtained in Example 425 was treated by a method similar to that in Example 482 to give the title compound (137 mg).

MS (ESI) m/z; 466, 468 [M+H]$^+$

Example 494

(R)-N-benzyl-1-[5-(2-methoxyphenyl)-7-oxo-6,7-dihydro[1,3]thiazolo[5,4-d]pyrimidin-2-yl]pyrrolidine-2-carboxamide

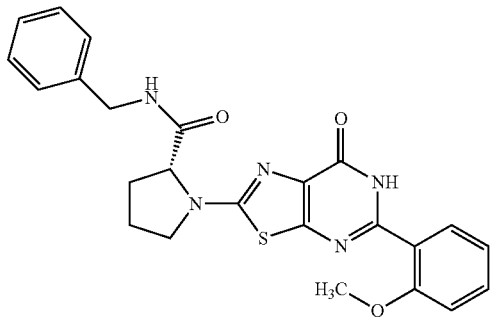 [SMILES: COc1ccccc1-c1nc2sc(N3CCC[C@@H]3C(=O)NCc3ccccc3)nc2c(=O)[nH]1]

The compound (93 mg) obtained in Example 426 was treated by a method similar to that in Example 482 to give the title compound (41 mg).

MS (ESI) m/z; 462 [M+H]$^+$

Example 495

(R)-1-[5-(2-methoxyphenyl)-7-oxo-6,7-dihydro[1,3]thiazolo[5,4-d]pyrimidin-2-yl]-N-((R)-1-phenyl-ethyl)pyrrolidine-2-carboxamide

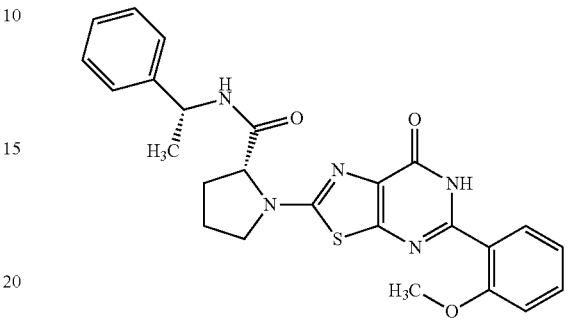

The compound (111 mg) obtained in Example 427 was treated by a method similar to that in Example 482 to give the title compound (63 mg).

MS (ESI) m/z; 476 [M+H]$^+$

Example 496

(R)-N-benzyl-1-{7-oxo-5-[2-(trifluoromethoxy)phe-nyl]-6,7-dihydro[1,3]thiazolo[5,4-d]pyrimidin-2-yl}pyrrolidine-2-carboxamide

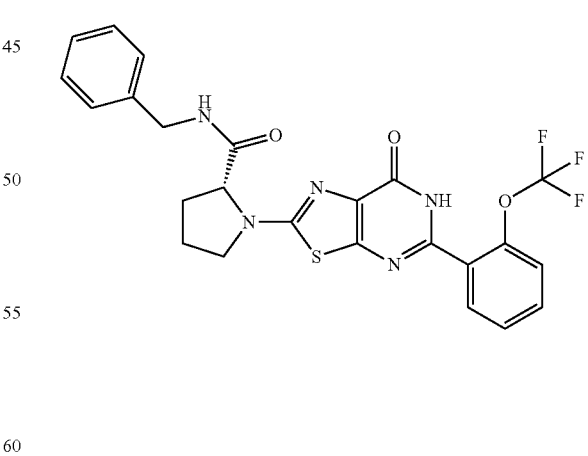

The compound (482 mg) obtained in Example 428 was treated by a method similar to that in Example 482 to give the title compound (285 mg).

MS (ESI) m/z; 516 [M+H]$^+$

Example 497

(R)-N-benzyl-1-[5-(2-methylphenyl)-7-oxo-6,7-dihydro[1,3]thiazolo[5,4-d]pyrimidin-2-yl]pyrrolidine-2-carboxamide

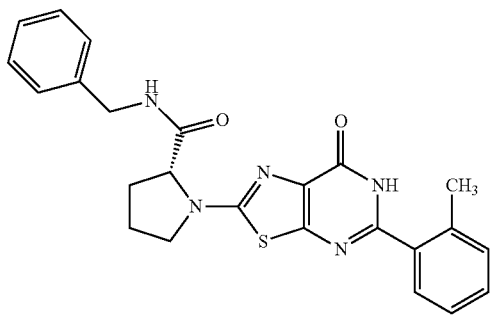 [SMILES: Cc1ccccc1-c1nc2sc(N3CCC[C@@H]3C(=O)NCc3ccccc3)nc2c(=O)[nH]1]

The compound (498 mg) obtained in Example 429 was treated by a method similar to that in Example 482 to give the title compound (340 mg)
MS (ESI) m/z; 446 [M+H]$^+$

Example 498

(R)-N-benzyl-1-[5-(2,4-difluorophenyl)-7-oxo-6,7-dihydro[1,3]thiazolo[5,4-d]pyrimidin-2-yl]pyrrolidine-2-carboxamide

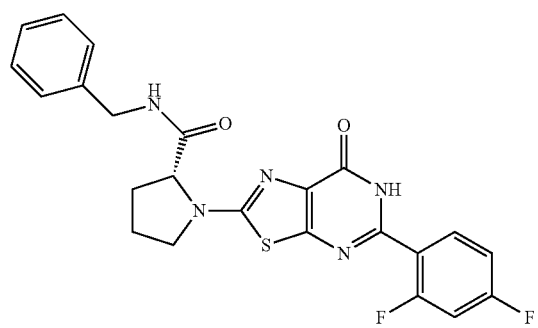 [SMILES: O=C(NCc1ccccc1)[C@H]1CCCN1c1nc2c(=O)[nH]c(-c3ccc(F)cc3F)nc2s1]

The compound (270 mg) obtained in Example 430 was treated by a method similar to that in Example 482 to give the title compound (195 mg).
MS (ESI) m/z; 468 [M+H]$^+$

Example 499

(R)-1-[5-(2,4-difluorophenyl)-7-oxo-6,7-dihydro[1,3]thiazolo[5,4-d]pyrimidin-2-yl]N-((R)-1-phenylethyl)pyrrolidine-2-carboxamide

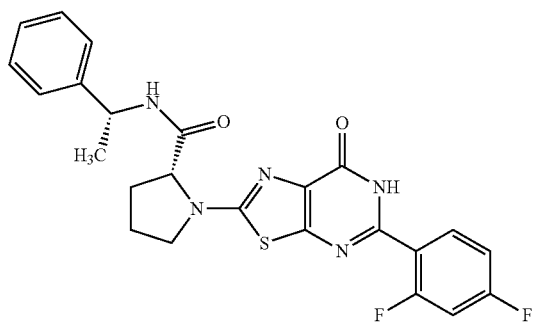 [SMILES: C[C@@H](NC(=O)[C@H]1CCCN1c1nc2c(=O)[nH]c(-c3ccc(F)cc3F)nc2s1)c1ccccc1]

The compound (285 mg) obtained in Example 431 was treated by a method similar to that in Example 482 to give the title compound (179 mg).
MS (ESI) m/z; 482 [M+H]$^+$

Example 500

(R)-N-benzyl-1-[5-(5-methylthiophen-2-yl)-7-oxo-6,7-dihydro[1,3]thiazolo[5,4-d]pyrimidin-2-yl]pyrrolidine-2-carboxamide

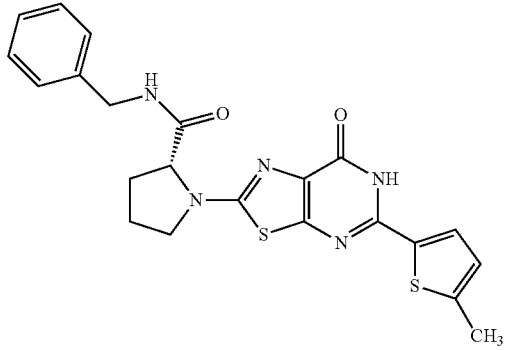 [SMILES: Cc1ccc(-c2nc3sc(N4CCC[C@@H]4C(=O)NCc4ccccc4)nc3c(=O)[nH]2)s1]

The compound (300 mg) obtained in Example 432 was treated by a method similar to that in Example 482 to give the title compound (218 mg).
MS (ESI) m/z; 452 [M+H]$^+$

Example 501

(R)-N-benzyl-1-[5-(3-fluoro-5-methylthiophen-2-yl)-7-oxo-6,7-dihydro[1,3]thiazolo[5,4-d]pyrimidin-2-yl]pyrrolidine-2-carboxamide

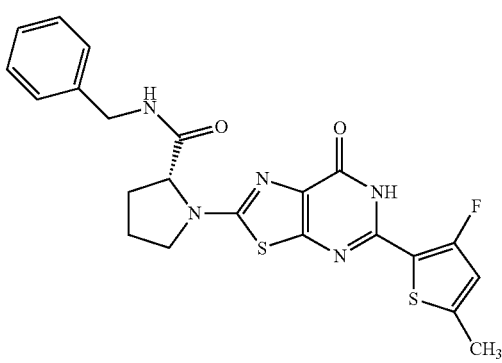 [SMILES: Cc1cc(F)c(-c2nc3sc(N4CCC[C@@H]4C(=O)NCc4ccccc4)nc3c(=O)[nH]2)s1]

The compound (440 mg) obtained in Example 433 was treated by a method similar to that in Example 482 to give the title compound (319 mg).

MS (ESI) m/z; 470 [M+H]$^+$

Example 502

(R)-N-benzyl-1-[5-(1-chlorocyclopropyl)-7-oxo-6,7-dihydro[1,3]thiazolo[5,4-d]pyrimidin-2-yl]azetidine-2-carboxamide

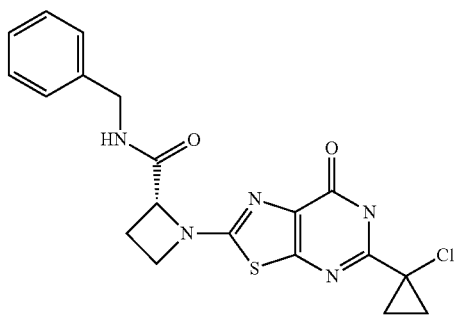 [SMILES: O=C(NCc1ccccc1)[C@H]1CCN1c1nc2c(=O)[nH]c(C3(Cl)CC3)nc2s1]

The compound (180 mg) obtained in Example 435 was treated by a method similar to that in Example 482 to give the title compound (104 mg).

MS (ESI) m/z; 416 [M+H]$^+$

Example 503

(R)-N-benzyl-1-[5-(1-chlorocyclopropyl)-7-oxo-6,7-dihydro[1,3]thiazolo[5,4-d]pyrimidin-2-yl]piperidine-2-carboxamide

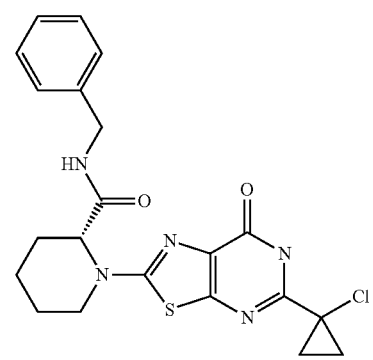 [SMILES: O=C(NCc1ccccc1)[C@H]1CCCCN1c1nc2c(=O)[nH]c(C3(Cl)CC3)nc2s1]

The compound (160 mg) obtained in Example 436 was treated by a method similar to that in Example 482 to give the title compound (50.0 mg).

MS (ESI) m/z; 444 [M+H]$^+$

Example 504

(R)-N-benzyl-1-(5-ethyl-7-oxo-6,7-dihydro[1,3]thiazolo[5,4-d]pyrimidin-2-yl)pyrrolidine-2-carboxamide

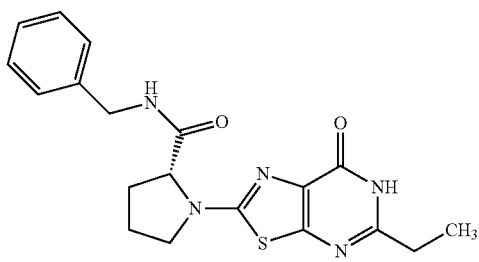 [SMILES: CCc1nc2sc(N3CCC[C@@H]3C(=O)NCc3ccccc3)nc2c(=O)[nH]1]

The compound (418 mg) obtained in Example 445 was treated by a method similar to that in Example 482 to give the title compound (220 mg).

MS (ESI) m/z; 384 [M+H]$^+$

Example 505: (R)-N-benzyl-1-[5-(5-chloro-2-fluo-rophenyl)-7-oxo-6,7-dihydro[1,3]thiazolo[5,4-d]pyrimidin-2-yl]pyrrolidine-2-carboxamide

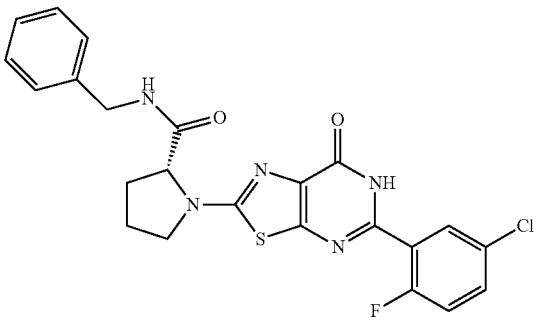 [SMILES: O=C(NCc1ccccc1)[C@H]1CCCN1c1nc2c(=O)[nH]c(-c3cc(Cl)ccc3F)nc2s1]

The compound (515 mg) obtained in Example 446 was treated by a method similar to that in Example 482 to give the title compound (254 mg).

MS (ESI) m/z; 484, 486 [M+H]$^+$

Example 506

(R)-N-benzyl-2-{N'-[5-(1-methoxycyclopropyl)-7-oxo-6,7-dihydro[1,3]thiazolo[5,4-d]pyrimidin-2-yl]-N'-methylamino}propionamide

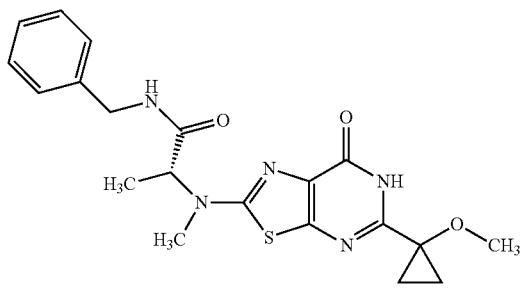 [SMILES: COC1(c2nc3sc(N(C)[C@H](C)C(=O)NCc4ccccc4)nc3c(=O)[nH]2)CC1]

The compound (259 mg) obtained in Example 447 was treated by a method similar to that in Example 482 to give the title compound (100 mg).

MS (ESI) m/z; 414 [M+H]$^+$

Example 507

(R)-N-benzyl-1-{5-[1-(fluoromethyl)cyclopropyl]-7-oxo-6,7-dihydro[1,3]thiazolo[5,4-d]pyrimidin-2-yl}pyrrolidine-2-carboxamide

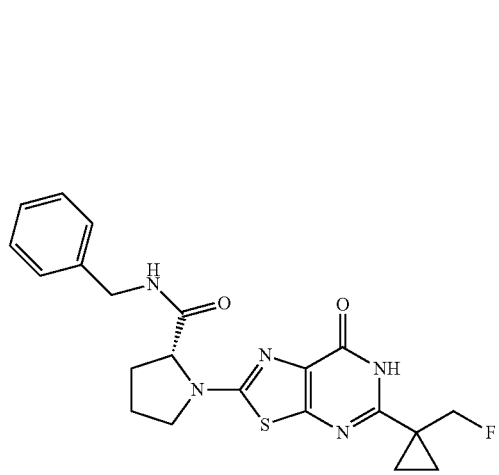 [SMILES: O=C(NCc1ccccc1)[C@H]1CCCN1c1nc2c(=O)[nH]c(C3(CF)CC3)nc2s1]

The compound (467 mg) obtained in Example 448 was treated by a method similar to that in Example 482 to give the title compound (230 mg).

MS (ESI) m/z; 428 [M+H]$^+$

Example 508

(R)-N-benzyl-1-{5-[1-(methoxymethyl)cyclopropyl]-7-oxo-6,7-dihydro[1,3]thiazolo[5,4-d]pyrimidin-2-yl}pyrrolidine-2-carboxamide

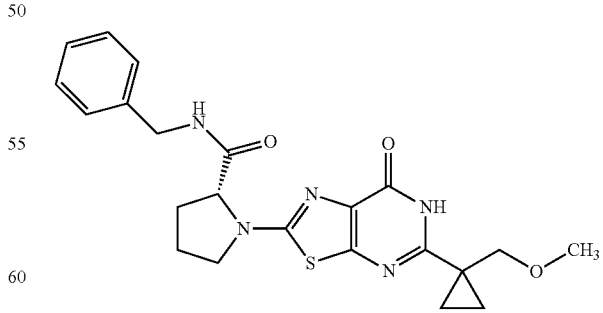

The compound (480 mg) obtained in Example 449 was treated by a method similar to that in Example 482 to give the title compound (320 mg).

MS (ESI) m/z; 440 [M+H]$^+$

Example 509

(R)-N-benzyl-1-[5-(2-fluoro-5-methylphenyl)-7-oxo-6,7-dihydro[1,3]thiazolo[5,4-d]pyrimidin-2-yl]pyrrolidine-2-carboxamide

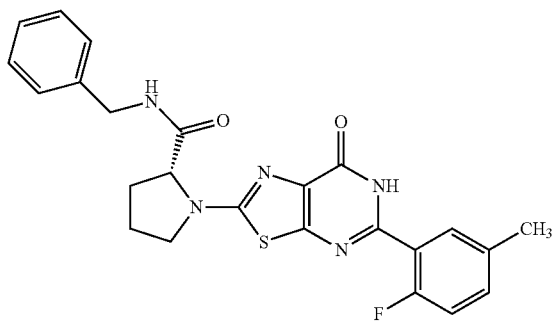 [SMILES: Cc1ccc(F)c(-c2nc3sc(N4CCC[C@@H]4C(=O)NCc4ccccc4)nc3c(=O)[nH]2)c1]

The compound (541 mg) obtained in Example 450 was treated by a method similar to that in Example 482 to give the title compound (229 mg).
MS (ESI) m/z; 464 [M+H]+

Example 510

(R)-N-benzyl-1-[5-(3-fluoropyridin-2-yl)-7-oxo-6,7-dihydro[1,3]thiazolo[5,4-d]pyrimidin-2-yl]pyrrolidine-2-carboxamide

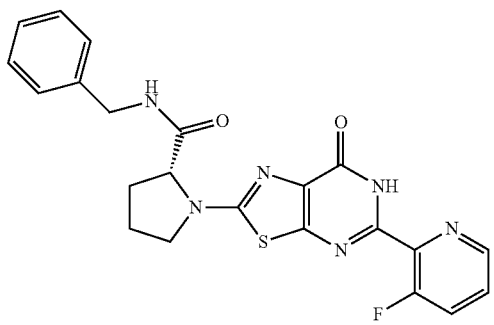 [SMILES: O=C(NCc1ccccc1)[C@H]1CCCN1c1nc2c(=O)[nH]c(-c3ncccc3F)nc2s1]

The compound (344 mg) obtained in Example 451 was treated by a method similar to that in Example 482 to give the title compound (181 mg).
MS (ESI) m/z; 451 [M+H]+

Example 511

(R)-N-benzyl-1-(5-methoxymethyl-7-oxo-6,7-dihydro[1,3]thiazolo[5,4-d]pyrimidin-2-yl)pyrrolidine-2-carboxamide

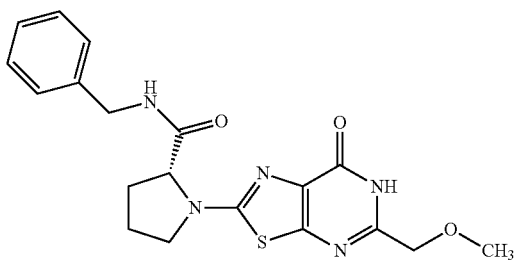 [SMILES: COCc1nc2sc(N3CCC[C@@H]3C(=O)NCc3ccccc3)nc2c(=O)[nH]1]

The compound (180 mg) obtained in Example 456 was treated by a method similar to that in Example 482 to give the title compound (147 mg).
MS (ESI) m/z; 400 [M+H]+

Example 512

(R)-1-[5-(2-fluoropropan-2-yl)-7-oxo-6,7-dihydro-[1,3]thiazolo[5,4-d]pyrimidin-2-yl]-N-((R)-1-phenylethyl)pyrrolidine-2-carboxamide

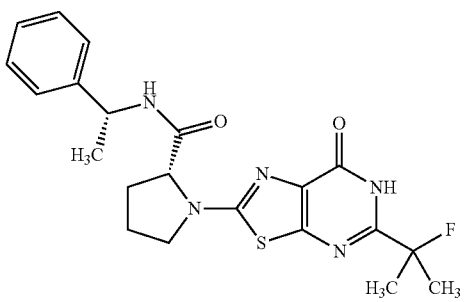 [SMILES: C[C@@H](NC(=O)[C@H]1CCCN1c1nc2c(=O)[nH]c(C(C)(C)F)nc2s1)c1ccccc1]

The compound (220 mg) obtained in Example 457 was treated by a method similar to that in Example 482 to give the title compound (153 mg).
MS (ESI) m/z; 430 [M+H]+

Example 513

(R)-N-benzyl-2-{N'-[5-(2-fluoropropan-2-yl)-7-oxo-6,7-dihydro[1,3]thiazolo[5,4-d]pyrimidin-2-yl]-N'-methylamino}propionamide

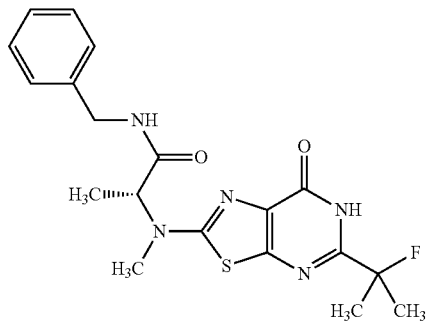 [SMILES: C[C@H](C(=O)NCc1ccccc1)N(C)c1nc2c(=O)[nH]c(C(C)(C)F)nc2s1]

The compound (259 mg) obtained in Example 458 was treated by a method similar to that in Example 482 to give the title compound (176 mg).

MS (ESI) m/z; 404 [M+H]$^+$

Example 514

(R)-N-benzyl-1-[5-(1-fluorocyclopropyl)-7-oxo-6,7-dihydro[1,3]thiazolo[5,4-d]pyrimidin-2-yl]pyrrolidine-2-carboxamide

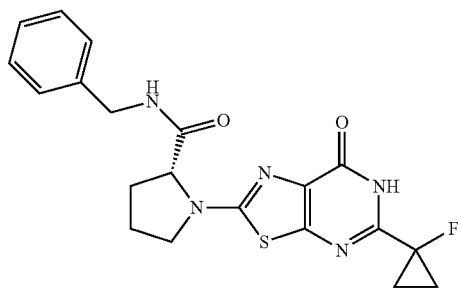 [SMILES: O=C(NCc1ccccc1)[C@H]1CCCN1c1nc2c(=O)[nH]c(C3(F)CC3)nc2s1]

The compound (457 mg) obtained in Example 459 was treated by a method similar to that in Example 482 to give the title compound (260 mg).

MS (ESI) m/z; 414 [M+H]$^+$

Example 515

(R)-1-[5-(1-fluorocyclopropyl)-7-oxo-6,7-dihydro[1,3]thiazolo[5,4-d]pyrimidin-2-yl]pyrrolidine-2-carboxamide

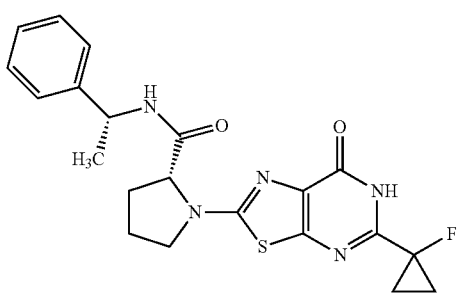 [SMILES: C[C@@H](NC(=O)[C@H]1CCCN1c1nc2c(=O)[nH]c(C3(F)CC3)nc2s1)c1ccccc1]

The compound (296 mg) obtained in Example 460 was treated by a method similar to that in Example 482 to give the title compound (172 mg).

MS (ESI) m/z; 428 [M+H]$^+$

Example 516

(R)-N-benzyl-1-[5-(1-chlorocyclopropyl)-7-oxo-6,7-dihydro[1,3]thiazolo[5,4-d]pyrimidin-2-yl]pyrrolidine-2-carboxamide

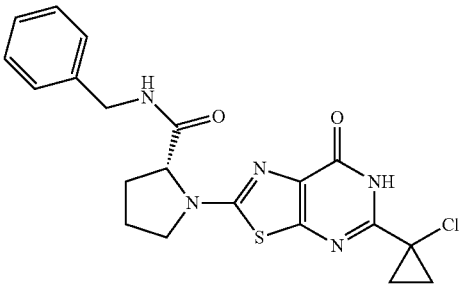 [SMILES: O=C(NCc1ccccc1)[C@H]1CCCN1c1nc2c(=O)[nH]c(C3(Cl)CC3)nc2s1]

The compound (117 mg) obtained in Example 461 was treated by a method similar to that in Example 482 to give the title compound (48 mg).

MS (ESI) m/z; 430 [M+H]$^+$

Example 517

(R)-1-[5-(1-chlorocyclopropyl)-7-oxo-6,7-dihydro[1,3]thiazolo[5,4-d]pyrimidin-2-yl]-N-((R)-1-phenylethyl)pyrrolidine-2-carboxamide

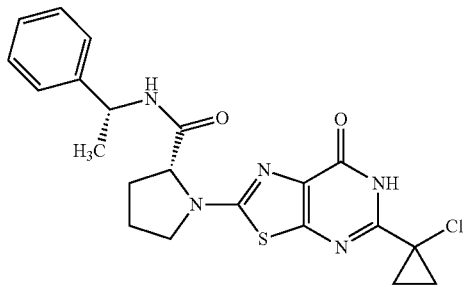 [SMILES: C[C@@H](NC(=O)[C@H]1CCCN1c1nc2c(=O)[nH]c(C3(Cl)CC3)nc2s1)c1ccccc1]

The compound (76 mg) obtained in Example 462 was treated by a method similar to that in Example 482 to give the title compound (42 mg).

MS (ESI) m/z; 444 [M+H]$^+$

Example 518

(R)-N-benzyl-1-[5-(1,1-difluoroethyl)-7-oxo-6,7-dihydro[1,3]thiazolo[5,4-d]pyrimidin-2-yl]pyrrolidine-2-carboxamide

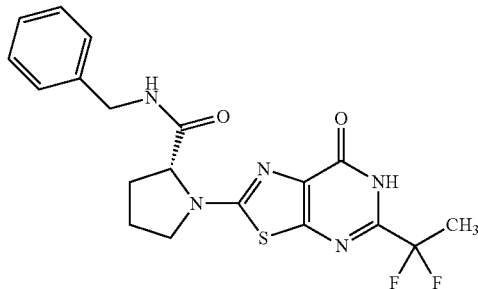 [SMILES: CC(F)(F)c1nc2sc(N3CCC[C@@H]3C(=O)NCc3ccccc3)nc2c(=O)[nH]1]

The compound (478 mg) obtained in Example 463 was treated by a method similar to that in Example 482 to give the title compound (338 mg).

MS (ESI) m/z; 420 [M+H]$^+$

Example 519

(R)-1-[5-(1,1-difluoroethyl)-7-oxo-6,7-dihydro[1,3]thiazolo[5,4-d]pyrimidin-2-yl]-N-((R)-1-phenylethyl)pyrrolidine-2-carboxamide

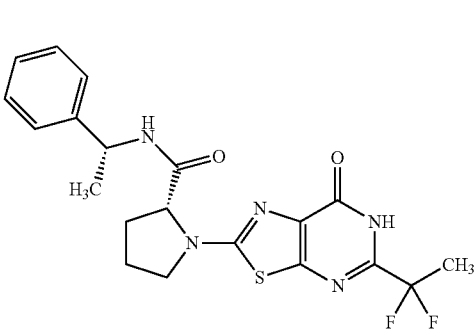 [SMILES: C[C@@H](NC(=O)[C@H]1CCCN1c1nc2c(=O)[nH]c(C(C)(F)F)nc2s1)c1ccccc1]

The compound (575 mg) obtained in Example 464 was treated by a method similar to that in Example 482 to give the title compound (381 mg).

MS (ESI) m/z; 434 [M+H]$^+$

Example 520

(R)-N-benzyl-1-[5-(1,1-difluoro-2-methoxyethyl)-7-oxo-6,7-dihydro[1,3]thiazolo[5,4-d]pyrimidin-2-yl]pyrrolidine-2-carboxamide

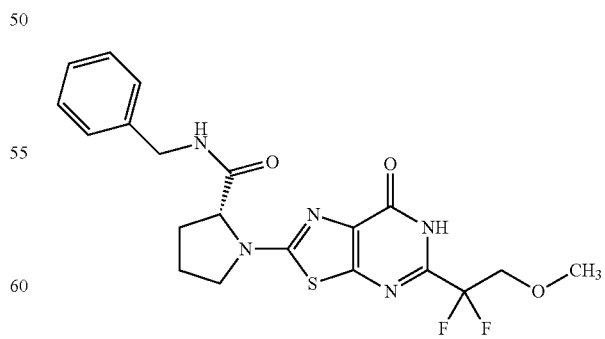

The compound (955 mg) obtained in Example 465 was treated by a method similar to that in Example 482 to give the title compound (649 mg).

MS (ESI) m/z; 450 [M+H]$^+$

Example 521

(R)-1-[5-(1,1-difluoro-2-methoxyethyl)-7-oxo-6,7-dihydro[1,3]thiazolo[5,4-d]pyrimidin-2-yl]-N-((R)-1-phenylethyl)pyrrolidine-2-carboxamide

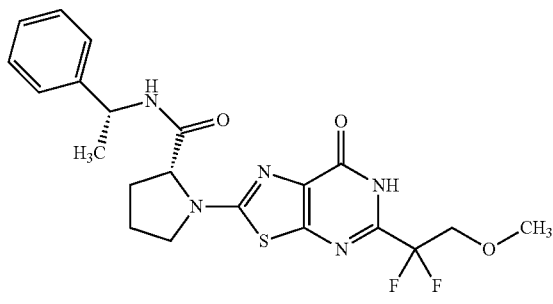 [SMILES: COCC(F)(F)c1nc2sc(N3CCC[C@@H]3C(=O)N[C@H](C)c3ccccc3)nc2c(=O)[nH]1]

The compound (175 mg) obtained in Example 466 was treated by a method similar to that in Example 482 to give the title compound (130 mg).
MS (ESI) m/z; 464 [M+H]⁺

Example 522

(R)-N-benzyl-1-{7-oxo-5-[1-(trifluoromethyl)cyclopropyl]-6,7-dihydro[1,3]thiazolo[5,4-d]pyrimidin-2-yl}pyrrolidine-2-carboxamide

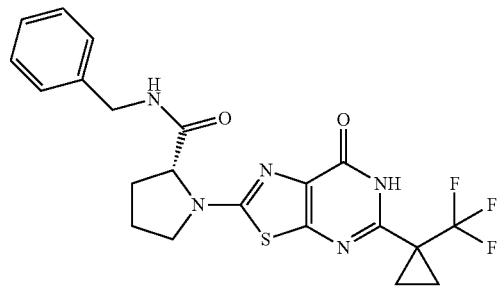 [SMILES: O=C(NCc1ccccc1)[C@H]1CCCN1c1nc2c(=O)[nH]c(C3(C(F)(F)F)CC3)nc2s1]

The compound (620 mg) obtained in Example 467 was treated by a method similar to that in Example 482 to give the title compound (427 mg).
MS (ESI) m/z; 464 [M+H]⁺

Example 523

(R)-N-benzyl-2-[N'-methyl-N'-{7-oxo-5-[1-(trifluoromethyl)cyclopropyl]-6,7-dihydro[1,3]thiazolo[5,4-d]pyrimidin-2-yl}amino]propionamide

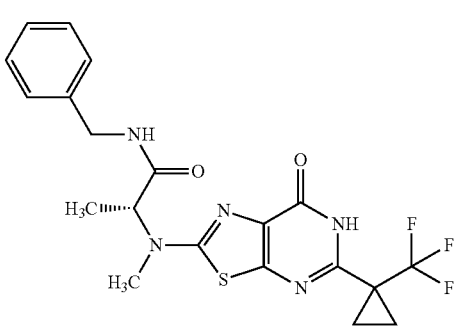 [SMILES: C[C@H](C(=O)NCc1ccccc1)N(C)c1nc2c(=O)[nH]c(C3(C(F)(F)F)CC3)nc2s1]

The compound (233 mg) obtained in Example 468 was treated by a method similar to that in Example 482 to give the title compound (210 mg).
MS (ESI) m/z; 452 [M+H]⁺

Example 524

(R)-N-benzyl-1-{5-[difluoro(phenyl)methyl]-7-oxo-6,7-dihydro[1,3]thiazolo[5,4-d]pyrimidin-2-yl}pyrrolidine-2-carboxamide

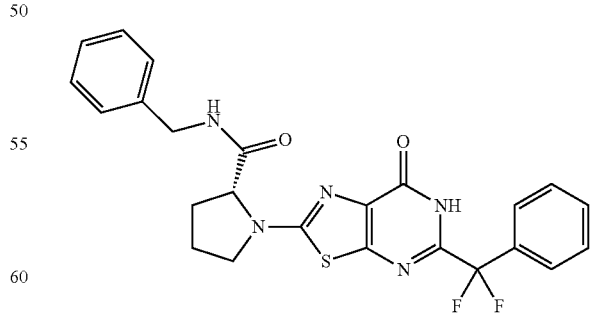

The compound (190 mg) obtained in Example 469 was treated by a method similar to that in Example 482 to give the title compound (118 mg).
MS (ESI) m/z; 482 [M+H]⁺

Example 525

(R)-1-[5-(difluoro(phenyl)methyl)-7-oxo-6,7-di-hydro-[1,3]thiazolo[5,4-d]pyrimidin-2-yl]-N-((R)-1-phenylethyl)pyrrolidine-2-carboxamide

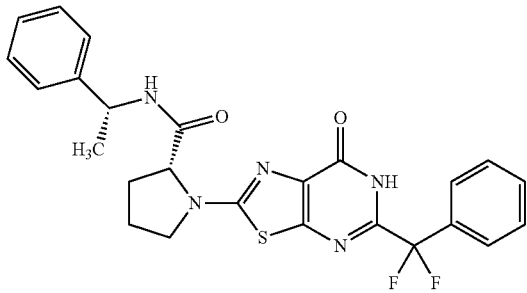 [SMILES: C[C@@H](NC(=O)[C@H]1CCCN1c1nc2c(=O)[nH]c(C(F)(F)c3ccccc3)nc2s1)c1ccccc1]

The compound (85 mg) obtained in Example 470 was treated by a method similar to that in Example 482 to give the title compound (51 mg).
MS (ESI) m/z; 496 [M+H]$^+$

Example 526

(R)-N-benzyl-1-[5-(2-fluoro-3-methoxyphenyl)-7-oxo-6,7-dihydro[1,3]thiazolo[5,4-d]pyrimidin-2-yl]pyrrolidine-2-carboxamide

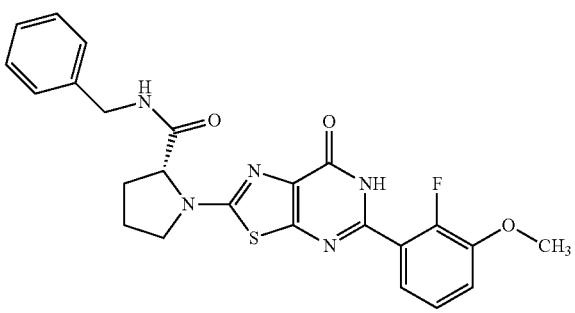 [SMILES: COc1cccc(-c2nc3sc(N4CCC[C@@H]4C(=O)NCc4ccccc4)nc3c(=O)[nH]2)c1F]

The compound (640 mg) obtained in Example 471 was treated by a method similar to that in Example 482 to give the title compound (409 mg).
MS (ESI) m/z; 480 [M+H]$^+$

Example 527

(R)-N-benzyl-1-[5-(2-fluoro-3-methylphenyl)-7-oxo-6,7-dihydro[1,3]thiazolo[5,4-d]pyrimidin-2-yl]pyrrolidine-2-carboxamide

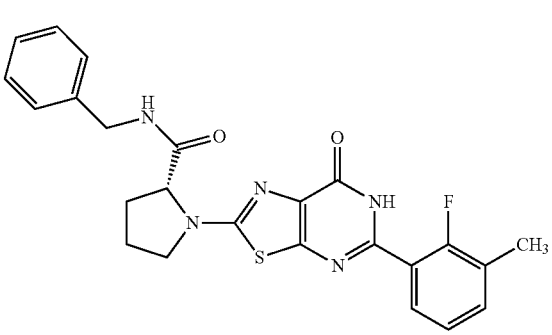 [SMILES: Cc1cccc(-c2nc3sc(N4CCC[C@@H]4C(=O)NCc4ccccc4)nc3c(=O)[nH]2)c1F]

The compound (620 mg) obtained in Example 472 was treated by a method similar to that in Example 482 to give the title compound (419 mg).
MS (ESI) m/z; 464 [M+H]$^+$

Example 528

(R)-N-benzyl-1-[7-oxo-5-pentafluoroethyl-6,7-dihydro[1,3]thiazolo[5,4-d]pyrimidin-2-yl]pyrrolidine-2-carboxamide

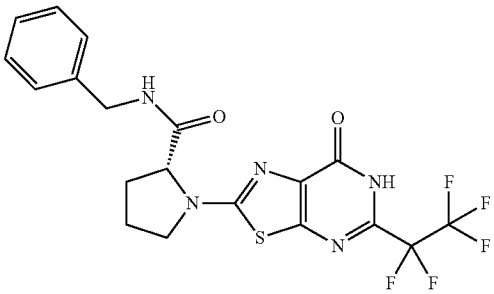 [SMILES: O=C(NCc1ccccc1)[C@H]1CCCN1c1nc2c(=O)[nH]c(C(F)(F)C(F)(F)F)nc2s1]

The compound (89 mg) obtained in Example 473 was treated by a method similar to that in Example 482 to give the title compound (60 mg).
MS (ESI) m/z; 474 [M+H]$^+$

Example 529

(R)-1-(7-oxo-5-pentafluoroethyl-6,7-dihydro-[1,3]thiazolo[5,4-d]pyrimidin-2-yl)-N-((R)-1-phenylethyl)pyrrolidine-2-carboxamide

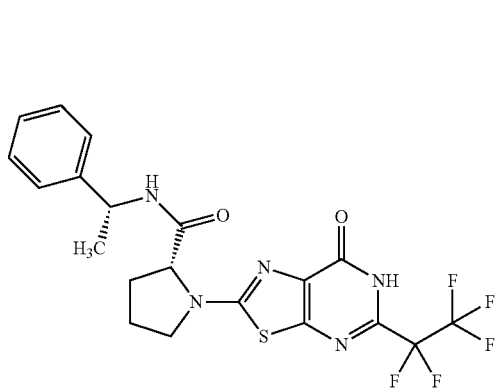 [SMILES: C[C@@H](NC(=O)[C@H]1CCCN1c1nc2c(=O)[nH]c(C(F)(F)C(F)(F)F)nc2s1)c1ccccc1]

The compound (90 mg) obtained in Example 474 was treated by a method similar to that in Example 482 to give the title compound (54 mg).
MS (ESI) m/z; 488 [M+H]$^+$

Example 530

(R)-N-benzyl-1-[5-(3-benzenesulfonyl-1,1-difluoropropyl)-7-oxo-6,7-dihydro-[1,3]thiazolo[5,4-d]pyrimidin-2-yl]pyrrolidine-2-carboxamide

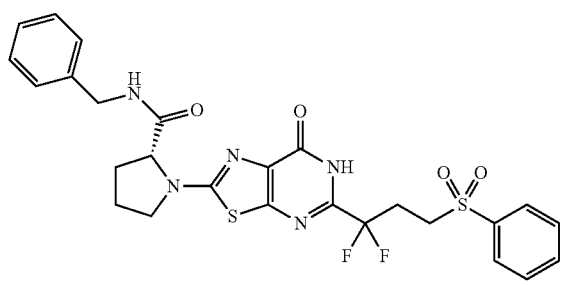 [SMILES: O=C(NCc1ccccc1)[C@H]1CCCN1c1nc2c(=O)[nH]c(C(F)(F)CCS(=O)(=O)c3ccccc3)nc2s1]

The compound (340 mg) obtained in Example 434 was treated by a method similar to that in Example 482 to give the title compound (248 mg).
MS (ESI) m/z; 574 [M+H]$^+$

Example 531

(R)-N-benzyl-2-[N'-methyl-N'-(7-oxo-5-phenyl-6,7-dihydro[1,3]thiazolo[5,4-d]pyrimidin-2-yl)amino]propionamide

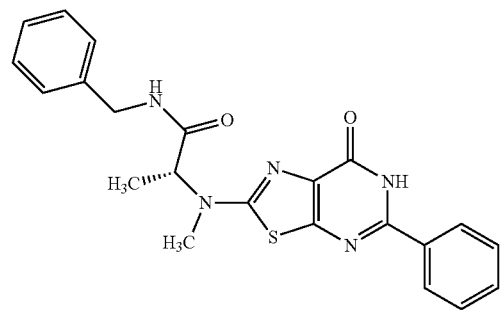 [SMILES: C[C@H](C(=O)NCc1ccccc1)N(C)c1nc2c(=O)[nH]c(-c3ccccc3)nc2s1]

The compound (280 mg) obtained in Example 475 was treated by a method similar to that in Example 482 to give the title compound (150 mg).
MS (ESI) m/z; 420 [M+H]$^+$

Example 532

(R)-N-benzyl-2-{N'-[5-(2-fluorophenyl)-7-oxo-6,7-dihydro[1,3]thiazolo[5,4-d]pyrimidin-2-yl]-N'-methylamino}propionamide

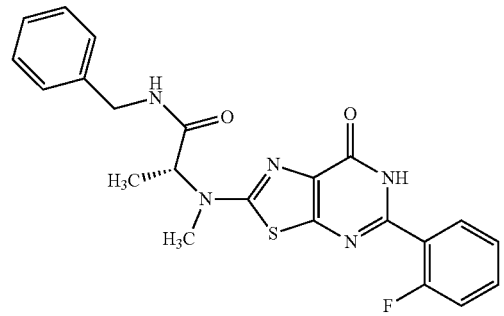 [SMILES: C[C@H](C(=O)NCc1ccccc1)N(C)c1nc2c(=O)[nH]c(-c3ccccc3F)nc2s1]

The compound (550 mg) obtained in Example 476 was treated by a method similar to that in Example 482 to give the title compound (318 mg).
MS (ESI) m/z; 438 [M+H]$^+$

Example 533

(R)-N-benzyl-2-{N'-[5-(1-chlorocyclopropyl)-7-oxo-6,7-dihydro[1,3]thiazolo[5,4-d]pyrimidin-2-yl]-N'-methylamino}propionamide

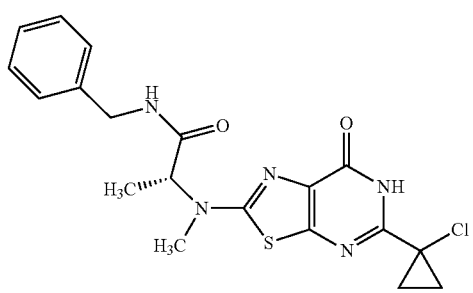 [SMILES: C[C@H](C(=O)NCc1ccccc1)N(C)c1nc2c(=O)[nH]c(C3(Cl)CC3)nc2s1]

The compound (350 mg) obtained in Example 477 was treated by a method similar to that in Example 482 to give the title compound (196 mg).

MS (ESI) m/z; 418 [M+H]$^+$

Example 534

(R)-N-benzyl-2-{N'-[5-(1-fluorocyclopropyl)-7-oxo-6,7-dihydro[1,3]thiazolo[5,4-d]pyrimidin-2-yl]-N'-methylamino}propionamide

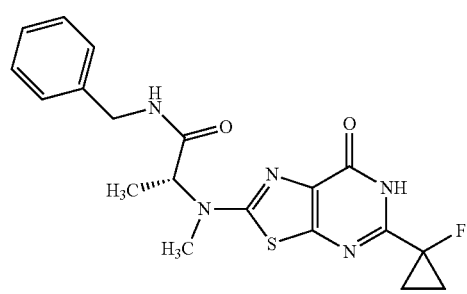 [SMILES: C[C@H](C(=O)NCc1ccccc1)N(C)c1nc2c(=O)[nH]c(C3(F)CC3)nc2s1]

The compound (680 mg) obtained in Example 478 was treated by a method similar to that in Example 482 to give the title compound (410 mg).

MS (ESI) m/z; 402 [M+H]$^+$

Example 535

(R)-N-benzyl-1-[5-(3-chloro-2-fluorophenyl)-7-oxo-6,7-dihydro[1,3]thiazolo[5,4-d]pyrimidin-2-yl]pyrrolidine-2-carboxamide

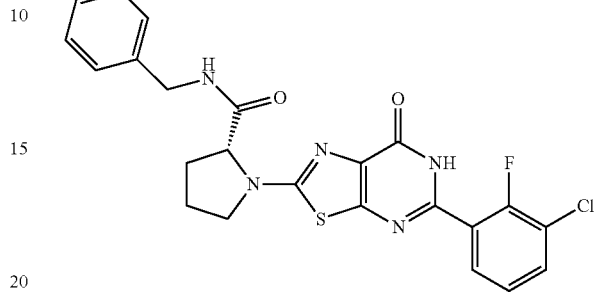

The compound (431 mg) obtained in Example 452 was treated by a method similar to that in Example 482 to give the title compound (257 mg).

MS (ESI) m/z; 484, 486 [M+H]$^+$

Example 536

(R)-N-benzyl-1-(7-oxo-5-trifluoromethyl-6,7-dihydro[1,3]thiazolo[5,4-d]pyrimidin-2-yl)pyrrolidine-2-carboxamide

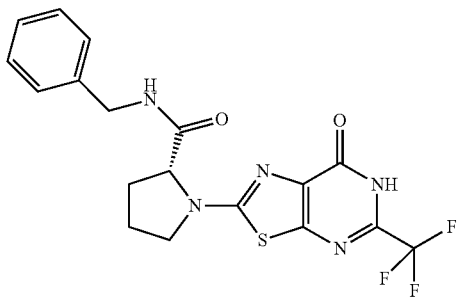 [SMILES: O=C(NCc1ccccc1)[C@H]1CCCN1c1nc2c(=O)[nH]c(C(F)(F)F)nc2s1]

The compound (534 mg) obtained in Example 453 was treated by a method similar to that in Example 482 to give the title compound (309 mg).

MS (ESI) m/z; 424 [M+H]$^+$

Example 537

(R)-1-(7-oxo-5-trifluoromethyl-6,7-dihydro[1,3]thiazolo[5,4-d]pyrimidin-2-yl)-N-((R)-1-phenylethyl)pyrrolidine-2-carboxamide

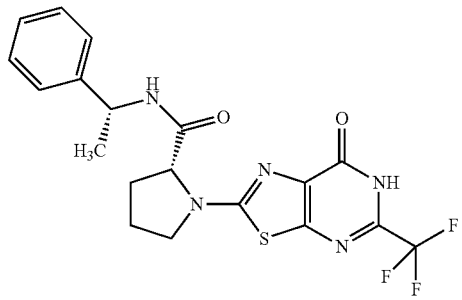 [SMILES: C[C@@H](NC(=O)[C@H]1CCCN1c1nc2c(=O)[nH]c(C(F)(F)F)nc2s1)c1ccccc1]

The compound (455 mg) obtained in Example 454 was treated by a method similar to that in Example 482 to give the title compound (253 mg).

MS (ESI) m/z; 438 [M+H]$^+$

Example 538

(R)-1-(5-difluoromethyl-7-oxo-6,7-dihydro[1,3]thiazolo[5,4-d]pyrimidin-2-yl)-N-((R)-1-phenylethyl)pyrrolidine-2-carboxamide

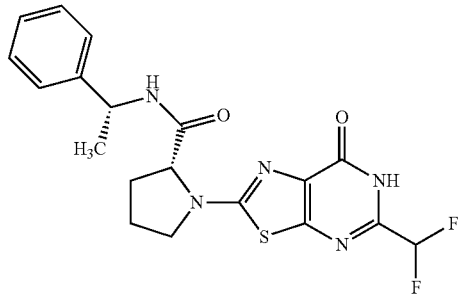 [SMILES: C[C@@H](NC(=O)[C@H]1CCCN1c1nc2c(=O)[nH]c(C(F)F)nc2s1)c1ccccc1]

The compound (1.30 g) obtained in Example 480 was treated by a method similar to that in Example 482 to give the title compound (900 mg).

MS (ESI) m/z; 420 [M+H]$^+$

Example 539

(R)-N-benzyl-1-(5-difluoromethyl-7-oxo-6,7-dihydro[1,3]thiazolo[5,4-d]pyrimidin-2-yl)pyrrolidine-2-carboxamide

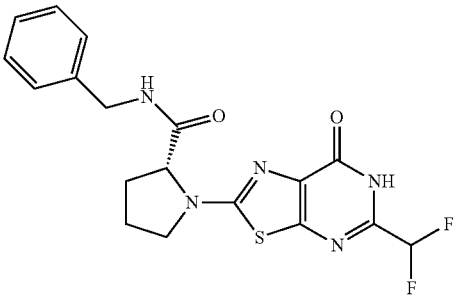 [SMILES: O=C(NCc1ccccc1)[C@H]1CCCN1c1nc2c(=O)[nH]c(C(F)F)nc2s1]

The compound (1.70 g) obtained in Example 479 was treated by a method similar to that in Example 482 to give the title compound (1.29 g).

MS (ESI) m/z; 406 [M+H]$^+$

Example 540

(R)-N-benzyl-1-[5-(3-fluorophenyl)-7-oxo-6,7-dihydro[1,3]thiazolo[5,4-d]pyrimidin-2-yl]pyrrolidine-2-carboxamide

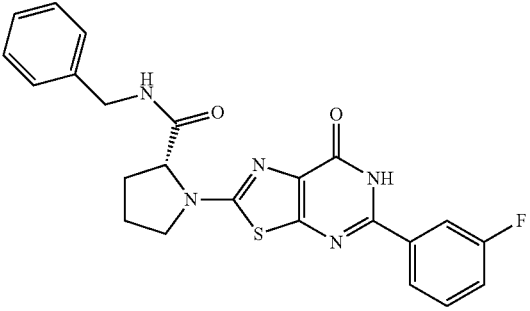 [SMILES: O=C(NCc1ccccc1)[C@H]1CCCN1c1nc2c(=O)[nH]c(-c3cccc(F)c3)nc2s1]

The compound (125 mg) obtained in Example 437 was treated by a method similar to that in Example 482 to give the title compound (96 mg).

MS (ESI) m/z; 450 [M+H]$^+$

Example 541

(R)-N-benzyl-1-[5-(4-fluorophenyl)-7-oxo-6,7-di-hydro[1,3]thiazolo[5,4-d]pyrimidin-2-yl]pyrrolidine-2-carboxamide

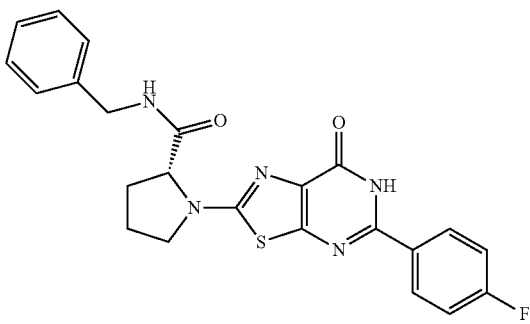 [SMILES: O=C(NCc1ccccc1)[C@H]1CCCN1c1nc2c(=O)[nH]c(-c3ccc(F)cc3)nc2s1]

The compound (56 mg) obtained in Example 438 was treated by a method similar to that in Example 482 to give the title compound (23 mg).

MS (ESI) m/z; 450 [M+H]+

Example 542

(R)-N-benzyl-1-[5-(2,5-difluorophenyl)-7-oxo-6,7-dihydro[1,3]thiazolo[5,4-d]pyrimidin-2-yl]pyrrolidine-2-carboxamide

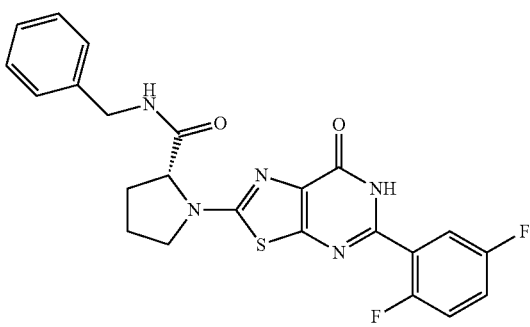 [SMILES: O=C(NCc1ccccc1)[C@H]1CCCN1c1nc2c(=O)[nH]c(-c3cc(F)ccc3F)nc2s1]

The compound (285 mg) obtained in Example 439 was treated by a method similar to that in Example 482 to give the title compound (160 mg).

MS (ESI) m/z; 468 [M+H]+

Example 543

(R)-N-benzyl-1-[5-(3,4-difluorophenyl)-7-oxo-6,7-dihydro[1,3]thiazolo[5,4-d]pyrimidin-2-yl]pyrrolidine-2-carboxamide

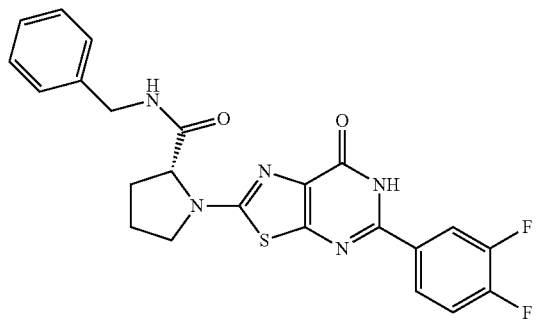 [SMILES: O=C(NCc1ccccc1)[C@H]1CCCN1c1nc2c(=O)[nH]c(-c3ccc(F)c(F)c3)nc2s1]

The compound (194 mg) obtained in Example 440 was treated by a method similar to that in Example 482 to give the title compound (91 mg).

MS (ESI) m/z; 468 [M+H]+

Example 544

(R)-N-benzyl-1-[5-(3,5-difluorophenyl)-7-oxo-6,7-dihydro[1,3]thiazolo[5,4-d]pyrimidin-2-yl]pyrrolidine-2-carboxamide The compound (140 mg) obtained in Example 441 was treated by a method similar to that in Example 482 to give the title compound (62 mg).

MS (ESI) m/z; 468 [M+H]+

Example 545

(R)-N-benzyl-1-[5-(4-fluoro-2-methoxyphenyl)-7-oxo-6,7-dihydro[1,3]thiazolo[5,4-d]pyrimidin-2-yl]pyrrolidine-2-carboxamide

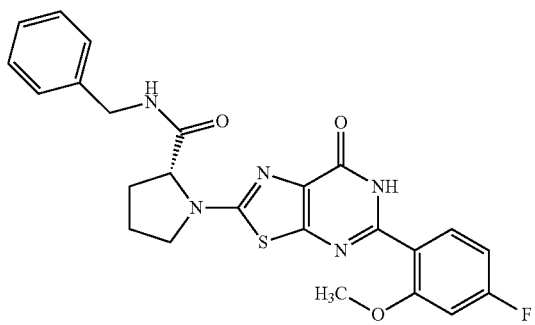 [SMILES: COc1cc(F)ccc1-c1nc2sc(N3CCC[C@@H]3C(=O)NCc3ccccc3)nc2c(=O)[nH]1]

The compound (118 mg) obtained in Example 442 was treated by a method similar to that in Example 482 to give the title compound (83 mg).

MS (ESI) m/z; 480 [M+H]+

Example 546

(R)-N-benzyl-1-[5-(2-ethylphenyl)-7-oxo-6,7-dihydro[1,3]thiazolo[5,4-d]pyrimidin-2-yl]pyrrolidine-2-carboxamide

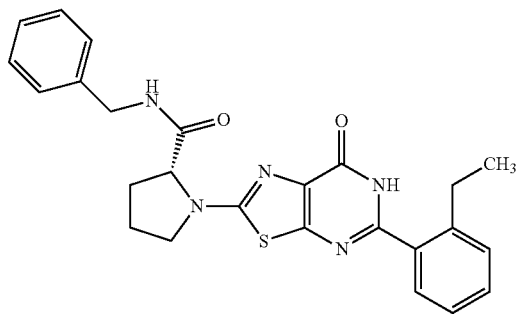 [SMILES: CCc1ccccc1-c1nc2sc(N3CCC[C@@H]3C(=O)NCc3ccccc3)nc2c(=O)[nH]1]

The compound (248 mg) obtained in Example 443 was treated by a method similar to that in Example 482 to give the title compound (116 mg).

MS (ESI) m/z; 460 [M+H]+

Example 547

(R)-N-benzyl-1-{7-oxo-5-[2-(trifluoromethyl)phenyl]-6,7-dihydro[1,3]thiazolo[5,4-d]pyrimidin-2-yl}pyrrolidine-2-carboxamide

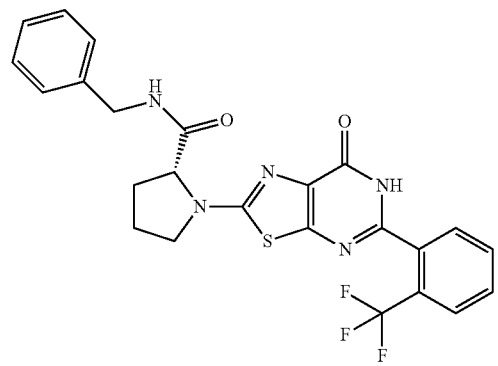 [SMILES: O=C(NCc1ccccc1)[C@H]1CCCN1c1nc2c(=O)[nH]c(-c3ccccc3C(F)(F)F)nc2s1]

The compound (125 mg) obtained in Example 444 was treated by a method similar to that in Example 482 to give the title compound (70 mg).

MS (ESI) m/z; 500 [M+H]+

Example 548

(R)-N-benzyl-1-[5-(2,3-difluorophenyl)-7-oxo-6,7-dihydro[1,3]thiazolo[5,4-d]pyrimidin-2-yl]pyrrolidine-2-carboxamide

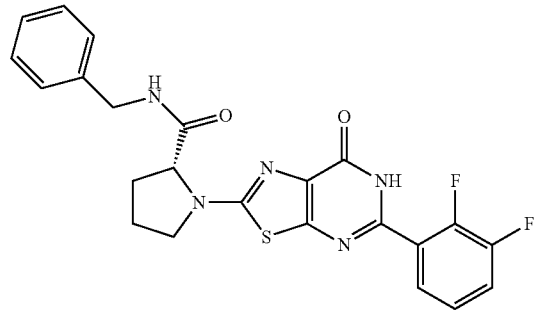

The compound (219 mg) obtained in Example 455 was treated by a method similar to that in Example 482 to give the title compound (141 mg).

MS (ESI) m/z; 468 [M+H]+

Example 549

(R)-N-[dideuterio(phenyl)methyl]-1-(7-oxo-5-phenyl-6,7-dihydro[1,3]thiazolo[5,4-d]pyrimidin-2-yl)pyrrolidine-2-carboxamide

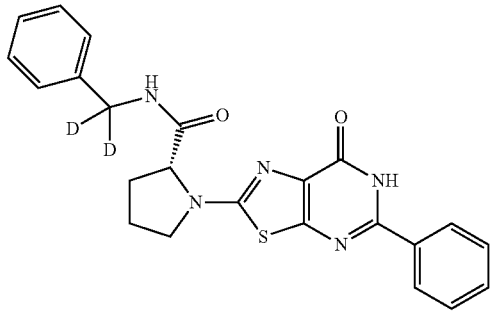 [SMILES: [2H]C([2H])(NC(=O)[C@H]1CCCN1c1nc2c(=O)[nH]c(-c3ccccc3)nc2s1)c1ccccc1]

The compound (410 mg) obtained in Example 481 was treated by a method similar to that in Example 482 to give the title compound (305 mg).

MS (ESI) m/z; 434 [M+H]$^+$

Example 550

(R)-N-benzyl-1-{6-(4-methoxybenzyl)-7-oxo-5-[(R)-2-(trifluoromethyl)pyrrolidin-1-yl]-6,7-dihydro[1,3]thiazolo[5,4-d]pyrimidin-2-yl}pyrrolidine-2-carboxamide

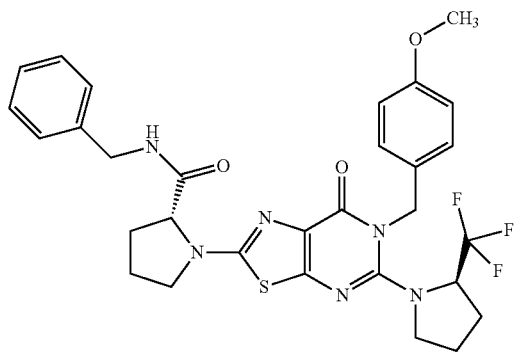 [SMILES: COc1ccc(Cn2c(N3CCC[C@@H]3C(F)(F)F)nc3sc(N4CCC[C@@H]4C(=O)NCc4ccccc4)nc3c2=O)cc1]

The compound (280 mg) obtained in Reference Example 602 was treated by a method similar to that in Example 178 to give the title compound (200 mg).

MS (ESI) m/z; 613 [M+H]$^+$

Example 551

(R)-N-benzyl-1-{6-(4-methoxybenzyl)-7-oxo-5-[(S)-2-(trifluoromethyl)pyrrolidin-1-yl]-6,7-dihydro[1,3]thiazolo[5,4-d]pyrimidin-2-yl}pyrrolidine-2-carboxamide

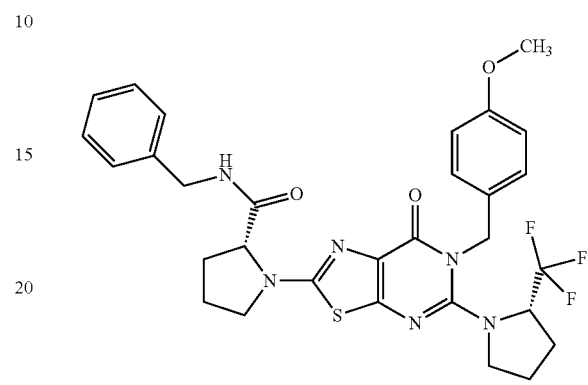

The compound (360 mg) obtained in Reference Example 603 was treated by a method similar to that in Example 178 to give the title compound (220 mg).

MS (ESI) m/z; 613 [M+H]$^+$

Example 552

(R)-N-benzyl-1-{7-oxo-5-((R)-2-[(trifluoromethyl)pyrrolidin-1-yl]-6, 7-dihydro[1,3]thiazolo[5,4-d]pyrimidin-2-yl}pyrrolidine-2-carboxamide

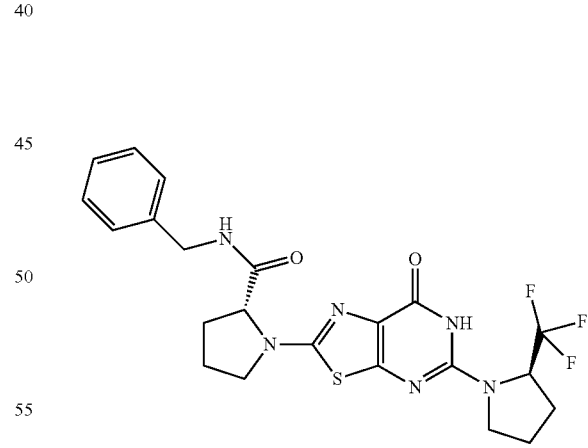

The compound (200 mg) obtained in Example 550 was treated by a method similar to that in Example 482 to give the title compound (115 mg).

MS (ESI) m/z; 493 [M+H]$^+$

Example 553

(R)-N-benzyl-1-{7-oxo-5-[(S)-2-(trifluoromethyl)pyrrolidin-1-yl]-6, 7-dihydro[1,3]thiazolo[5,4-d]pyrimidin-2-yl}pyrrolidine-2-carboxamide

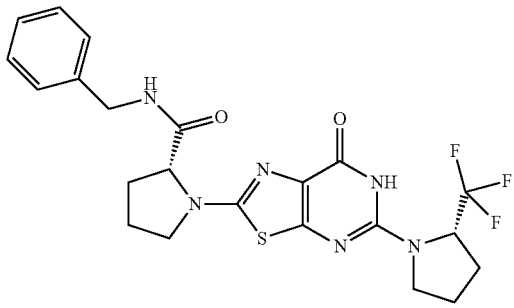 [SMILES: O=C(NCc1ccccc1)[C@H]1CCCN1c1nc2c(=O)[nH]c(N3CCC[C@H]3C(F)(F)F)nc2s1]

The compound (220 mg) obtained in Example 551 was treated by a method similar to that in Example 482 to give the title compound (100 mg).

MS (ESI) m/z; 493 [M+H]⁺

Example 554

(R)-N-benzyl-1-[6-(4-methoxybenzyl)-7-oxo-5-(2,2,2-trifluoroethoxy)-6,7-dihydro[1,3]thiazolo[5,4-d]pyrimidin-2-yl]pyrrolidine-2-carboxamide

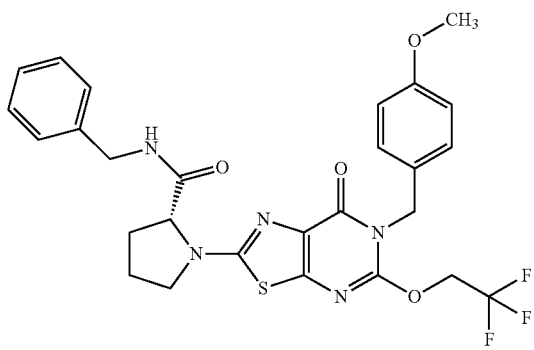 [SMILES: COc1ccc(Cn2c(OCC(F)(F)F)nc3sc(N4CCC[C@@H]4C(=O)NCc4ccccc4)nc3c2=O)cc1]

The compound (168 mg) obtained in Reference Example 605 was treated by a method similar to that in Example 178 to give the title compound (83 mg)

MS (ESI) m/z; 574 [M+H]⁺

Example 555

(R)-N-benzyl-1-[7-oxo-5-(2,2,2-trifluoroethoxy)-6, 7-dihydro[1,3]thiazolo[5,4-d]pyrimidin-2-yl]pyrrolidine-2-carboxamide

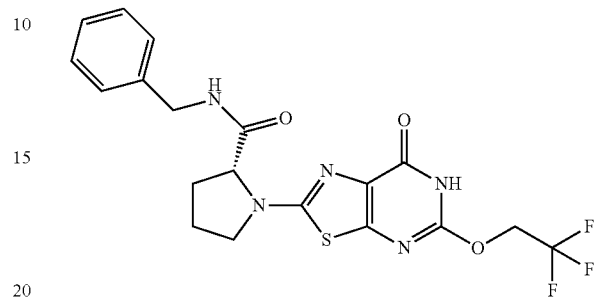

The compound (60 mg) obtained in Example 554 was treated by a method similar to that in Example 482 to give the title compound (31 mg).

MS (ESI) m/z; 454 [M+H]⁺

Example 556

(R)-N-benzyl-1-[5-(1,1-difluoroethyl)-7-oxo-6-(trideuteriomethyl)-6,7-dihydro[1,3]thiazolo[5,4-d]pyrimidin-2-yl]pyrrolidine-2-carboxamide

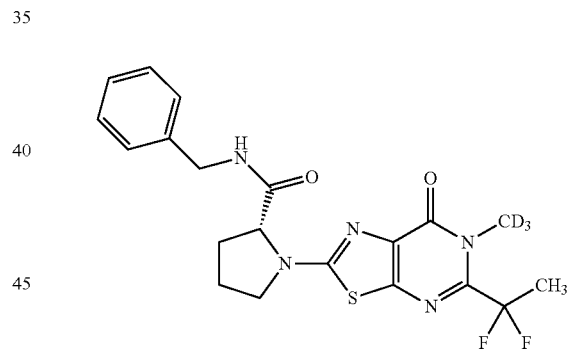

To a solution (5 mL) of the compound (230 mg) obtained in Example 518 in DMF were successively added potassium carbonate (114 mg) and trideuteriomethyl iodide (77 μL) at room temperature, and the reaction mixture was stirred at room temperature for 3 hr. Water was added to the reaction mixture, and the mixture was extracted with ethyl acetate. The organic layer was washed successively with water and saturated brine, dried over anhydrous sodium sulfate, filtered and concentrated under reduced pressure. The obtained residue was purified by silica gel column chromatography (solvent; hexane/ethyl acetate=60/40-20/80) to give the title compound (128 mg).

MS (ESI) m/z; 437 [M+H]⁺

Example 557

(R)-N-benzyl-1-[5-difluoromethyl-7-oxo-6-(trideuteriomethyl)-6,7-dihydro[1,3]thiazolo[5,4-d]pyrimidin-2-yl]pyrrolidine-2-carboxamide

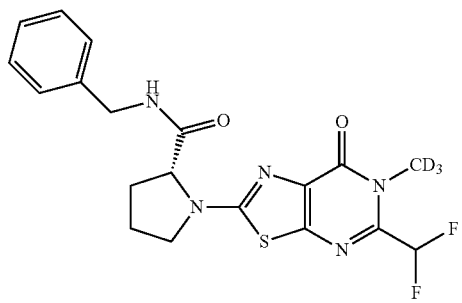 [SMILES: [2H]C([2H])([2H])n1c(C(F)F)nc2sc(N3CCC[C@@H]3C(=O)NCc3ccccc3)nc2c1=O]

The compound (110 mg) obtained in Example 539 was treated by a method similar to that in Example 556 to give the title compound (57 mg).
MS (ESI) m/z; 423 [M+H]$^+$ Example 558

(R)-N-benzyl-1-[5-(1,1-difluoro-2-methoxyethyl)-7-oxo-6-(trideuteriomethyl)-6,7-dihydro[1,3]thiazolo[5,4-d]pyrimidin-2-yl]pyrrolidine-2-carboxamide

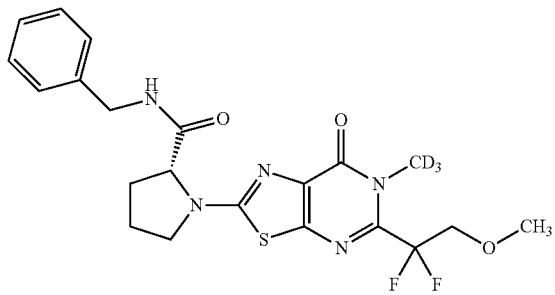

The compound (640 mg) obtained in Example 520 was treated by a method similar to that in Example 556 to give the title compound (227 mg).
MS (ESI) m/z; 467 [M+H]$^+$ Example 559

(R)-N-benzyl-1-[7-oxo-5-phenyl-6-(trideuteriomethyl)-6,7-dihydro[1,3]thiazolo[5,4-d]pyrimidin-2-yl]pyrrolidine-2-carboxamide

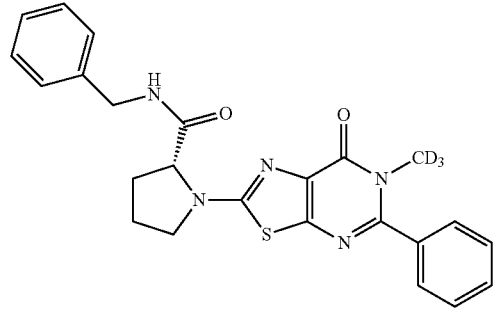 [SMILES: [2H]C([2H])([2H])n1c(-c2ccccc2)nc2sc(N3CCC[C@@H]3C(=O)NCc3ccccc3)nc2c1=O]

The compound (294 mg) obtained in Example 487 was treated by a method similar to that in Example 556 to give the title compound (45 mg).
MS (ESI) m/z; 449 [M+H]$^+$ Example 560

N-[dideuterio(phenyl)methyl]-1-[7-oxo-5-phenyl-6-(trideuteriomethyl)-6,7-dihydro[1,3]thiazolo[5,4-d]pyrimidin-2-yl]pyrrolidine-2-carboxamide

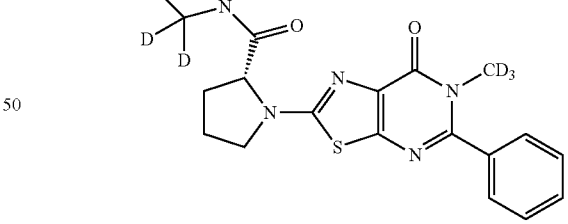

The compound (185 mg) obtained in Example 549 was treated by a method similar to that in Example 556 to give the title compound (26 mg).
MS (ESI) m/z; 451 [M+H]$^+$

Example 561

(R)-N-benzyl-1-[6-methyl-5-(5-methylthiophen-2-yl)-7-oxo-6,7-dihydro[1,3]thiazolo[5,4-d]pyrimidin-2-yl]pyrrolidine-2-carboxamide

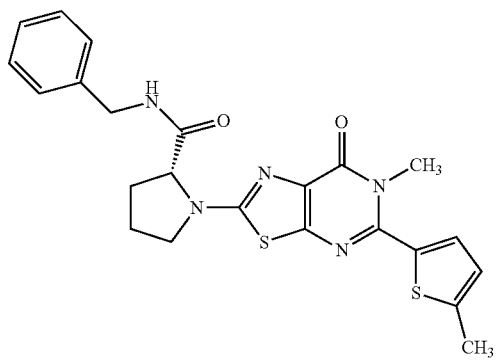 [SMILES: Cc1ccc(-c2nc3sc(N4CCC[C@@H]4C(=O)NCc4ccccc4)nc3c(=O)n2C)s1]

The compound (110 mg) obtained in Example 500 was treated by a method similar to that in Example 556 to give the title compound (42 mg).

MS (ESI) m/z; 466 [M+H]$^+$

Example 562

(R)-N-benzyl-1-[5-(3-fluoro-5-methylthiophen-2-yl)-6-methyl-7-oxo-6,7-dihydro[1,3]thiazolo[5,4-d]pyrimidin-2-yl]pyrrolidine-2-carboxamide

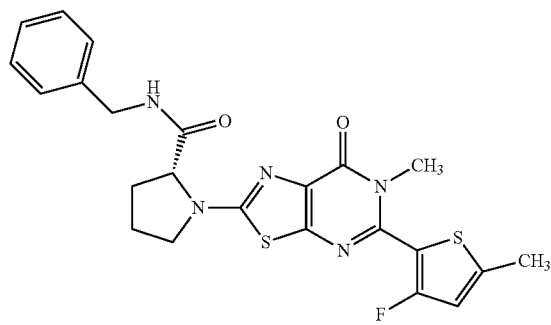 [SMILES: Cc1cc(F)c(-c2nc3sc(N4CCC[C@@H]4C(=O)NCc4ccccc4)nc3c(=O)n2C)s1]

The compound (159 mg) obtained in Example 501 was treated by a method similar to that in Example 556 to give the title compound (23 mg).

MS (ESI) m/z; 484 [M+H]$^+$

Example 563

(R)-N-benzyl-1-[5-(1-fluoromethylcyclopropyl)-6-methyl-7-oxo-6,7-dihydro[1,3]thiazolo[5,4-d]pyrimidin-2-yl]pyrrolidine-2-carboxamide

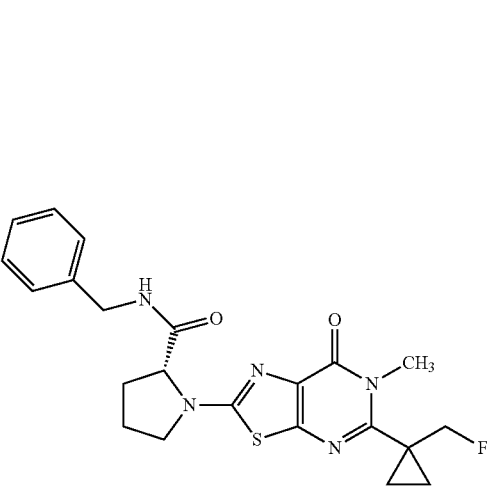 [SMILES: Cn1c(C2(CF)CC2)nc2sc(N3CCC[C@@H]3C(=O)NCc3ccccc3)nc2c1=O]

The compound (200 mg) obtained in Example 507 was treated by a method similar to that in Example 556 to give the title compound (130 mg).

MS (ESI) m/z; 442 [M+H]$^+$

Example 564

(R)-N-benzyl-1-{5-[1-(methoxymethyl)cyclopropyl]-6-methyl-7-oxo-6,7-dihydro[1,3]thiazolo[5,4-d]pyrimidin-2-yl}pyrrolidine-2-carboxamide

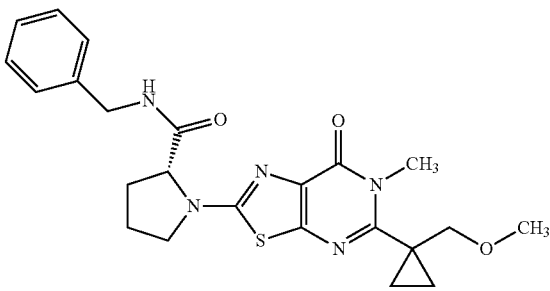 [SMILES: COCC1(c2nc3sc(N4CCC[C@@H]4C(=O)NCc4ccccc4)nc3c(=O)n2C)CC1]

The compound (290 mg) obtained in Example 508 was treated by a method similar to that in Example 556 to give the title compound (110 mg).

MS (ESI) m/z; 454 [M+H]$^+$

Example 565

(R)-N-benzyl-1-[5-methoxymethyl-7-oxo-6-(tetra-hydro-2H-pyran-4-yl)-6,7-dihydro[1,3]thiazolo[5,4-d]pyrimidin-2-yl]pyrrolidine-2-carboxamide

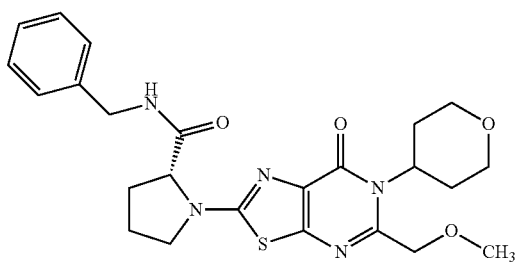 [SMILES: COCc1nc2sc(N3CCC[C@@H]3C(=O)NCc3ccccc3)nc2c(=O)n1C1CCOCC1]

To a solution (10 mL) of the compound (190 mg) obtained in Reference Example 610 in DMF were added (D)-proline (130 mg) and potassium carbonate (230 mg), and the reaction mixture was stirred with heating at 80° C. for 1.5 hr. The reaction mixture was cooled to room temperature, acidified with 1.0 mol/L hydrochloric acid, and extracted twice with chloroform. The organic layer was dried over magnesium sulfate, filtered and concentrated. To the obtained residue were added benzylamine (85 mg), EDC hydrochloride (150 mg), HOBt monohydrate (120 mg) and N,N-diisopropylethylamine (100 mg), and the reaction mixture was stirred at room temperature for 15 hr. 0.5 mol/L Hydrochloric acid was added, and the mixture was extracted with ethyl acetate. The organic layer was washed with saturated brine, dried over anhydrous sodium sulfate, filtered and concentrated. The residue was purified by NH silica gel column chromatography (solvent; hexane/ethyl acetate=50/50-0/100) to give the title compound (120 mg).

MS (ESI) m/z; 484 [M+H]$^+$

Example 566

(R)-N-benzyl-1-[6-methyl-7-oxo-5-(pyrazol-1-yl)-6,7-dihydro[1,3]thiazolo[5,4-d]pyrimidin-2-yl]pyrrolidine-2-carboxamide

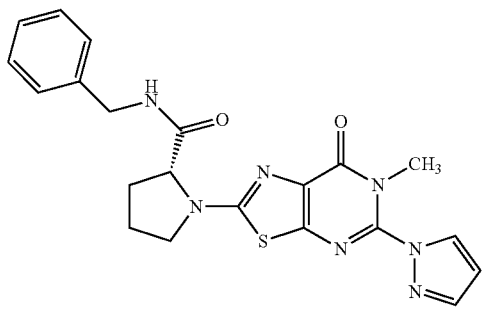 [SMILES: Cn1c(-n2cccn2)nc2sc(N3CCC[C@@H]3C(=O)NCc3ccccc3)nc2c1=O]

To a solution (3 mL) of the compound (99 mg) obtained in Reference Example 613 in DMF were added (D)-proline (58 mg) and cesium carbonate (273 mg), and the reaction mixture was stirred with heating at 90° C. for 1 hr. The reaction mixture was cooled to room temperature, acidified with 1.0 mol/L hydrochloric acid, and extracted twice with chloroform. The organic layer was dried over magnesium sulfate, filtered and concentrated. To a solution of the obtained residue in DMF (2.0 mL) were added benzylamine (73 µL), EDC hydrochloride (128 mg), HOBt monohydrate (103 mg) and N,N-diisopropylethylamine (120 µL), and the reaction mixture was stirred at room temperature for 3 hr. 0.5 mol/L Hydrochloric acid was added, and the mixture was extracted with ethyl acetate. The organic layer was washed with saturated aqueous sodium hydrogen carbonate solution and saturated brine, dried over anhydrous magnesium sulfate, filtered and concentrated. The residue was purified by silica gel column chromatography (solvent; ethyl acetate/methanol=100/0-95/5) to give the title compound (11.6 mg).

MS (ESI) m/z; 436 [M+H]$^+$

Example 567

[(3S,5R)-5-benzylcarbamoyl-1-(6-methyl-7-oxo-5-phenyl-6,7-dihydro[1,3]thiazolo[5,4-d]pyrimidin-2-yl)pyrrolidin-3-yl]carbamic acid tert-butyl ester

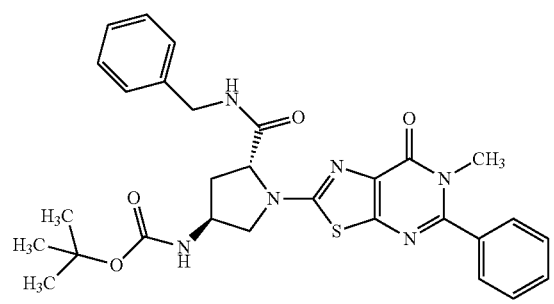 [SMILES: Cn1c(-c2ccccc2)nc2sc(N3C[C@@H](NC(=O)OC(C)(C)C)C[C@@H]3C(=O)NCc3ccccc3)nc2c1=O]

To a solution (3.4 mL) of the compound (200 mg) obtained in Reference Example 268 in DMF were added (2R,4S)-4-[(tert-butoxycarbonyl)amino]pyrrolidine-2-carboxylic acid (226 mg) and cesium carbonate (533 mg), and the reaction mixture was heated at 70° C. for 2.5 hr. The reaction mixture was cooled to room temperature, acidified with 1.0 mol/L hydrochloric acid, and extracted three times with chloroform. The organic layer was dried over magnesium sulfate, filtered and concentrated. To a solution of the obtained residue in DMF (2.0 mL) were added benzylamine (107 µL), EDC hydrochloride (188 mg), HOBt monohydrate (150 mg) and N,N-diisopropylethylamine (171 µL), and the reaction mixture was stirred at room temperature overnight. 1.0 mol/L Hydrochloric acid was added, and the mixture was extracted twice with ethyl acetate. The organic layer was washed with saturated brine, dried over anhydrous sodium sulfate, filtered and concentrated. The residue was purified by NH silica gel column chromatography (solvent; hexane/ethyl acetate=50/50-0/100) to give the title compound (237 mg).

MS (ESI) m/z; 561 [M+H]$^+$

Example 568

[(3R,5R)-5-benzylcarbamoyl-1-(6-methyl-7-oxo-5-phenyl-6,7-dihydro[1,3]thiazolo[5,4-d]pyrimidin-2-yl)-pyrrolidin-3-yl]carbamic acid tert-butyl ester

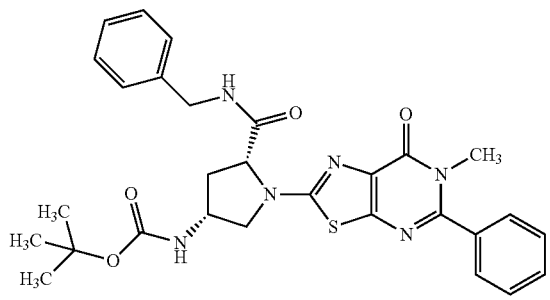 [SMILES: Cn1c(-c2ccccc2)nc2sc(N3C[C@H](NC(=O)OC(C)(C)C)C[C@@H]3C(=O)NCc3ccccc3)nc2c1=O]

The compound (200 mg) and (2R,4R)-4-[(tert-butoxycarbonyl)amino]pyrrolidine-2-carboxylic acid (226 mg) obtained in Reference Example 268 was treated by a method similar to that in Example 567 to give the title compound (227 mg).
MS (ESI) m/z; 561 [M+H]$^+$

Example 569

(2R,4S)-4-amino-1-(6-methyl-7-oxo-5-phenyl-6,7-dihydro[1,3]thiazolo[5,4-d]pyrimidin-2-yl)pyrrolidine-2-carboxamide hydrochloride

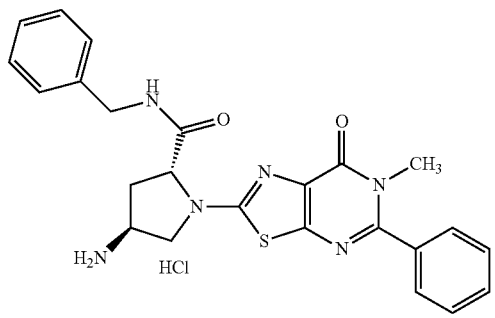 [SMILES: Cn1c(-c2ccccc2)nc2sc(N3C[C@@H](N)C[C@@H]3C(=O)NCc3ccccc3)nc2c1=O ; Cl]

To a solution (3.9 mL) of the compound (179 mg) obtained in Example 567 in methanol was added hydrogen chloride (4.0 mol/L ethyl acetate solution, 0.8 mL), and the reaction mixture was stirred at room temperature for 3 hr. The resultant solid was collected by filtration, and dried to give the title compound (151 mg).
MS (ESI) m/z; 461 [M+H]$^+$

Example 570

(2R,4R)-4-amino-1-(6-methyl-7-oxo-5-phenyl-6,7-dihydro[1,3]thiazolo[5,4-d]pyrimidin-2-yl)pyrrolidine-2-carboxamide hydrochloride

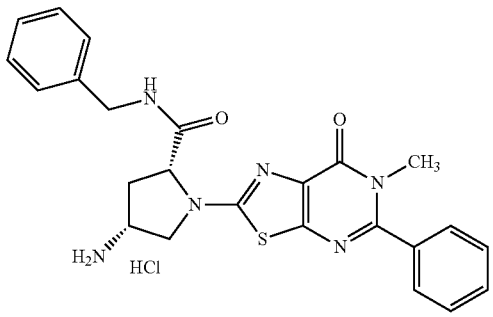 [SMILES: Cn1c(-c2ccccc2)nc2sc(N3C[C@H](N)C[C@@H]3C(=O)NCc3ccccc3)nc2c1=O ; Cl]

The compound (189 mg) obtained in Example 568 was treated by a method similar to that in Example 569 to give the title compound (178 mg)
MS (ESI) m/z; 461 [M+H]$^+$

Example 571

(R)-N-benzyl-1-(5-cyclopropyl-6-methyl-7-oxo-6,7-dihydro[1,3]thiazolo[5,4-d]pyrimidin-2-yl)-piperidine-2-carboxamide

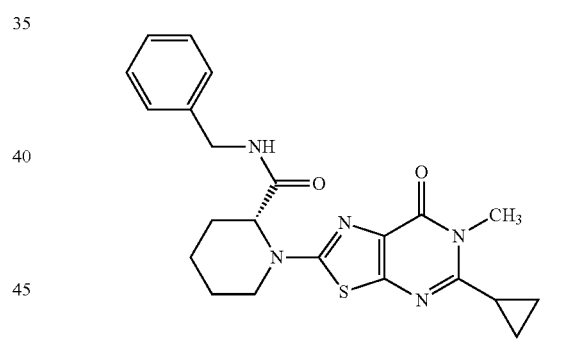

To a solution (4 mL) of the compound (250 mg) obtained in Reference Example 617 in DMF were added (R)-piperidine-2-carboxylic acid (339 mg) and potassium carbonate (326 mg), and the reaction mixture was stirred with heating at 120° C. for 5 hr. The reaction mixture was cooled to room temperature, and acidified with 1.0 mol/L hydrochloric acid. Sodium chloride was added, and the mixture was extracted three times with chloroform. The organic layer was dried over sodium sulfate, filtered and concentrated. To the obtained residue were added N,N-diisopropylethylamine (228 µL), benzylamine (143 µL), EDC hydrochloride (251 mg) and HOBt monohydrate (201 mg), and the reaction mixture was stirred at room temperature overnight. Ethyl acetate was added to the reaction mixture, and the mixture was washed with water and saturated brine. The organic layer was dried over anhydrous sodium sulfate, filtered and concentrated. The residue was purified by silica gel column chromatography (solvent; hexane/ethyl acetate=70/30-0/100), and the obtained crude product was purified by reversed-phase HPLC (Capcelpak C18; 0.05% trifluoroacetic acid-water/acetonitrile=55/45-45/55). To the obtained product was added ethyl acetate/diethyl ether, and the solid was collected by filtration to give the title compound (213 mg).

MS (ESI) m/z; 424 [M+H]+

Example 572

(R)-N-benzyl-1-(5-cyclopropyl-6-methyl-7-oxo-6,7-dihydro[1,3]thiazolo[5,4-d]pyrimidin-2-yl)-4,4-difluoropyrrolidine-2-carboxamide

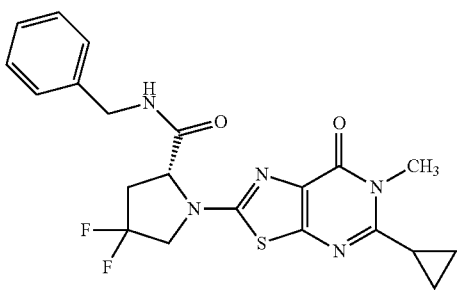 [SMILES: Cn1c(C2CC2)nc2sc(N3CC(F)(F)C[C@@H]3C(=O)NCc3ccccc3)nc2c1=O]

A mixed solution of the compound (62 mg) obtained in Reference Example 617, the compound (121 mg) obtained in Reference Example 618 and N,N-diisopropylethylamine (2.0 mL) was stirred with heating at 120° C. for 12 hr. The reaction mixture was cooled to room temperature, acidified with 1.0 mol/L hydrochloric acid, and extracted with chloroform. The organic layer was dried over magnesium sulfate, filtered and concentrated. The residue was purified by silica gel column chromatography (solvent; ethyl acetate/methanol=100/0-95/5), and the obtained crude product was purified by reversed-phase HPLC (Capcelpak C18; 0.05% trifluoroacetic acid-water/acetonitrile=55/45-45/55). To the obtained product was added diethyl ether, and the solid was collected by filtration and dried to give the title compound (15.5 mg).

MS (ESI) m/z; 446 [M+H]+

Example 573

(R)-N-benzyl-1-[5-(1-cyanocyclopropyl)-6-methyl-7-oxo-6,7-dihydro[1,3]thiazolo[5,4-d]pyrimidin-2-yl]pyrrolidine-2-carboxamide

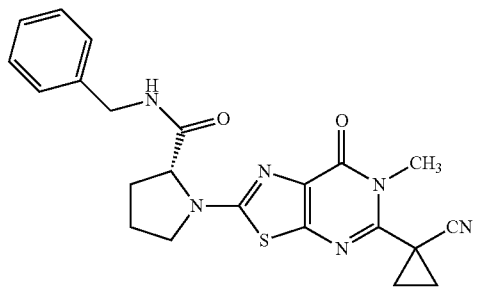 [SMILES: Cn1c(C2(C#N)CC2)nc2sc(N3CCC[C@@H]3C(=O)NCc3ccccc3)nc2c1=O]

To a solution (1.8 mL) of the compound (84 mg) obtained in Reference Example 621 in methylene chloride were added trimethylsilyl trifluoromethanesulfonate (101 μL) and triethylamine (130 μL), and the reaction mixture was stirred at room temperature for 1 hr. Saturated aqueous sodium hydroxide solution was added to the reaction mixture, and the mixture was extracted twice with ethyl acetate. The organic layer was dried over anhydrous sodium sulfate, filtered and concentrated. The residue was purified by silica gel column chromatography (solvent; ethyl acetate/methanol=100/0-90/10) to give the title compound (56.8 mg).

MS (ESI) m/z; 435 [M+H]+

Example 574

6-methyl-2-[(R)-2-(2-phenoxyacetyl)pyrrolidin-1-yl]-5-(tetrahydro-2H-pyran-4-yl)[1,3]thiazolo[5,4-d]pyrimidin-7(6H)-one

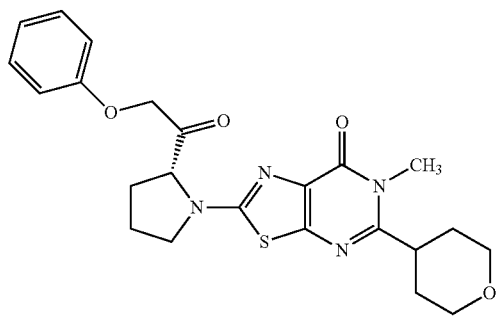 [SMILES: Cn1c(C2CCOCC2)nc2sc(N3CCC[C@@H]3C(=O)COc3ccccc3)nc2c1=O]

To a solution (3 mL) of oxalyl chloride (63 μL) in methylene chloride was added dimethyl sulfoxide (100 μL) at −78° C., and the reaction mixture was stirred for 5 min. A solution (6.0 mL) of the compound (0.30 g) obtained in Reference Example 125 in methylene chloride and triethylamine (0.46 mL) were added at −78° C., and the reaction mixture was stirred for 1 hr, allowing the mixture to gradually warm to room temperature. Water was added, and the mixture was extracted once with ethyl acetate. The organic layer was washed once with water, dried over anhydrous magnesium sulfate, filtered and concentrated. The residue was purified by silica gel column chromatography (solvent; ethyl acetate/methanol=100/0-95/5) to give the title compound (0.19 g).

MS (ESI) m/z; 455 [M+H]+

Example 575

5-ethyl-6-methyl-2-[(R)-2-(2-phenoxyacetyl)pyrrolidin-1-yl][1,3]thiazolo[5,4-d]pyrimidin-7(6H)-one

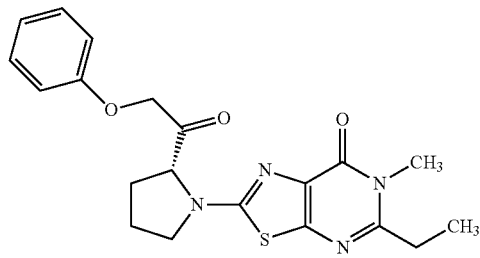 [SMILES: CCc1nc2sc(N3CCC[C@@H]3C(=O)COc3ccccc3)nc2c(=O)n1C]

The compound (80 mg) obtained in Reference Example 126 was treated by a method similar to that in Example 574 to give the title compound (33 mg).

MS (ESI) m/z; 399 [M+H]+

Example 576

5-methyl-2-[(R)-2-(2-phenoxyacetyl)pyrrolidin-1-yl]-6-(tetrahydro-2H-pyran-4-yl)[1,3]thiazolo[5,4-d]pyrimidin-7(6H)-one

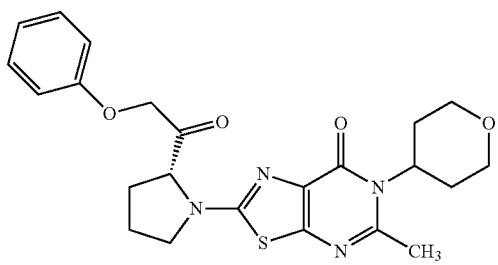 [SMILES: Cc1nc2sc(N3CCC[C@@H]3C(=O)COc3ccccc3)nc2c(=O)n1C1CCOCC1]

The compound (170 mg) obtained in Reference Example 127 was treated by a method similar to that in Example 574 to give the title compound (110 mg).

MS (ESI) m/z; 455 [M+H]$^+$

Example 577

6-methyl-5-[(morpholin-4-yl)methyl]-2-[(R)-2-(2-phenoxyacetyl)pyrrolidin-1-yl][1,3]thiazolo[5,4-d]pyrimidin-7(6H)-one

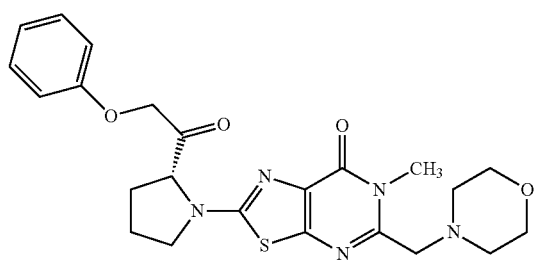 [SMILES: Cn1c(CN2CCOCC2)nc2sc(N3CCC[C@@H]3C(=O)COc3ccccc3)nc2c1=O]

The compound (127 mg) obtained in Reference Example 128 was treated by a method similar to that in Example 574 to give the title compound (42.0 mg).

MS (ESI) m/z; 470 [M+H]$^+$

Example 578

5-(3-methoxyazetidin-1-yl)-6-methyl-2-[(R)-2-(2-phenoxyacetyl)pyrrolidin-1-yl][1,3]thiazolo[5,4-d]pyrimidin-7(6H)-one

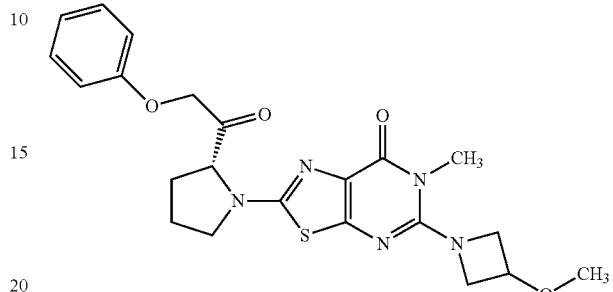

The compound (90 mg) obtained in Reference Example 129 was treated by a method similar to that in Example 574 to give the title compound (20 mg).

MS (ESI) m/z; 456 [M+H]$^+$

Example 579

5-ethyl-6-methyl-2-[(R)-2-(2-phenylaminoacetyl)pyrrolidin-1-yl][1,3]thiazolo[5,4-d]pyrimidin-7(6H)-one

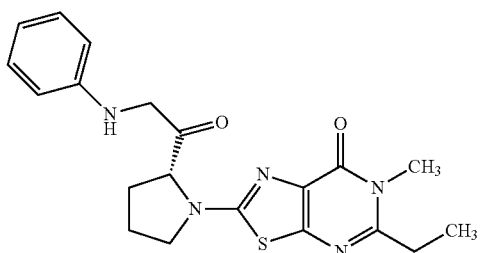

is To a solution (2.0 mL) of oxalyl chloride (52 μL) in methylene chloride was added dimethyl sulfoxide (86 μL) at −78° C., and the reaction mixture was stirred for 10 min. A solution (4 mL) of the compound (200 mg) obtained in Reference Example 130 in methylene chloride and triethylamine (350 μL) were added at −78° C., and the reaction mixture was stirred for 1 hr, allowing the mixture to gradually warm to room temperature. Water was added, and the mixture was extracted once with ethyl acetate. The organic layer was washed once with water, dried over anhydrous magnesium sulfate, filtered and concentrated. The residue was purified by silica gel column chromatography (solvent; ethyl acetate/methanol=100/0-95/5) to give the title compound (6.0 mg).

MS (ESI) m/z; 398 [M+H]$^+$

Example 580

6-(2,4-dimethoxybenzyl)-5-(2-fluorophenyl)-2-[(R)-2-(2-phenoxyacetyl)pyrrolidin-1-yl][1,3]thiazolo[5,4-d]pyrimidin-7(6H)-one

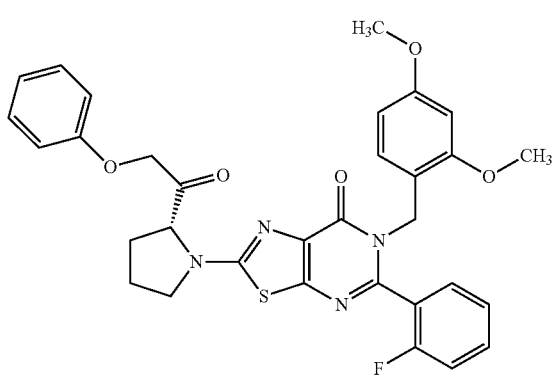 [SMILES: COc1ccc(Cn2c(-c3ccccc3F)nc3sc(N4CCC[C@@H]4C(=O)COc4ccccc4)nc3c2=O)c(OC)c1]

To a solution (4 mL) of oxalyl chloride (0.13 mL) in methylene chloride was added dimethyl sulfoxide (0.22 mL) at −78° C., and the reaction mixture was stirred for 5 min. A solution (8 mL) of the compound (0.43 g) obtained in Reference Example 131 in methylene chloride and triethylamine (1.0 mL) were added at −78° C., and the reaction mixture was stirred for 1 hr, allowing the mixture to gradually warm to room temperature. Water was added, and the mixture was extracted once with ethyl acetate. The organic layer was washed once with water, dried over anhydrous magnesium sulfate, filtered and concentrated. The residue was purified by silica gel column chromatography (solvent; chloroform/methanol=100/0-95/5) to give the title compound (0.25 g).

MS (ESI) m/z; 601 [M+H]$^+$

Example 581

5-(2-fluorophenyl)-2-[(R)-2-(2-phenoxyacetyl)pyrrolidin-1-yl][1,3]thiazolo[5,4-d]pyrimidin-7(6H)-one

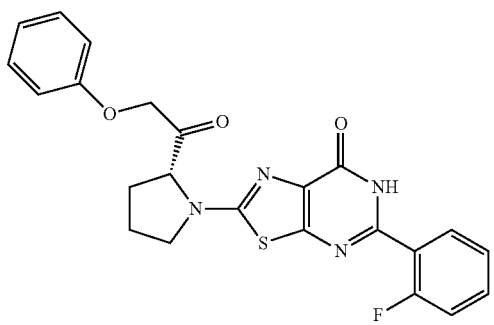 [SMILES: O=C(COc1ccccc1)[C@H]1CCCN1c1nc2c(=O)[nH]c(-c3ccccc3F)nc2s1]

To a solution (5 mL) of the compound (0.25 g) obtained in Example 580 in methylene chloride were added water (0.5 mL) and trifluoroacetic acid (5.0 mL) at room temperature, and the reaction mixture was stirred for 1 hr. The reaction mixture was neutralized with saturated aqueous sodium hydrogen carbonate solution, and extracted once with chloroform. The organic layer was washed once with water, dried over anhydrous magnesium sulfate, filtered and concentrated. The residue was purified by silica gel column chromatography (solvent; chloroform/methanol=100/0-95/5). Ethyl acetate was added to the obtained product, and the solid was collected by filtration to give the title compound (0.17 g).

MS (ESI) m/z; 451 [M+H]$^+$

Example 582

(R)-N-benzyl-1-[5-(2,6-difluorophenyl)-6-(2,4-dimethoxybenzyl)-7-oxo-6,7-dihydro[1,3]thiazolo[5,4-d]pyrimidin-2-yl]pyrrolidine-2-carboxamide

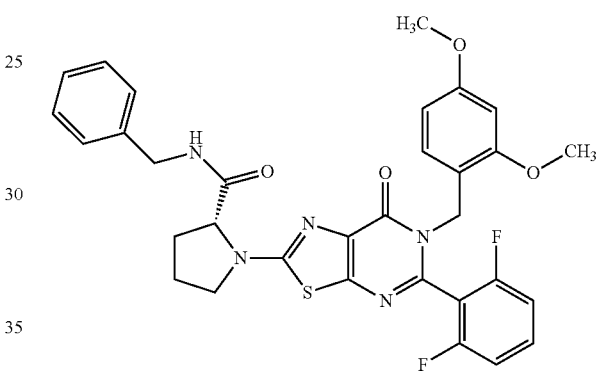

To a solution (30.0 mL) of the compound (3.00 g) obtained in Reference Example 635 in N-methylpyrrolidone were added (D)-proline (1.45 g) and potassium carbonate (3.47 g), and the reaction mixture was stirred with heating at 80° C. for 1 hr. The reaction mixture was cooled to room temperature, and acidified with 1.0 mol/L hydrochloric acid. Sodium chloride was added, and the mixture was extracted twice with chloroform. The organic layer was dried over anhydrous magnesium sulfate, and filtered. Chloroform was evaporated under reduced pressure from the filtrate, to the obtained mixture were added N,N-diisopropylethylamine (1.63 mL), benzylamine (981 mg), EDC hydrochloride (1.80 g) and HOBt monohydrate (1.50 g), and the reaction mixture was stirred at room temperature overnight. Water was added, and the mixture was extracted with ethyl acetate. The organic layer was dried over anhydrous sodium sulfate, filtered and concentrated. To the residue was added diisopropyl ether, and the solid was collected by filtration and dried to give the title compound (3.80 g).

MS (ESI) m/z; 618 [M+H]$^+$

Example 583

(R)-N-benzyl-1-[5-(2,6-difluorophenyl)-7-oxo-6,7-dihydro[1,3]thiazolo[5,4-d]pyrimidin-2-yl]pyrrolidine-2-carboxamide

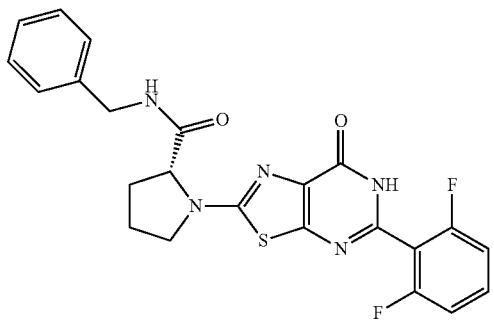 [SMILES: O=C(NCc1ccccc1)[C@H]1CCCN1c1nc2c(=O)[nH]c(-c3c(F)cccc3F)nc2s1]

The compound (3.78 g) obtained in Example 582 was treated by a method similar to that in Example 482 to give the title compound (2.52 g).

MS (ESI) m/z; 468 [M+H]+

Example 584

(RS)-2-[5-(3-methyl-[1,2,4]oxadiazol-5-yl)-7-oxo-6,7-dihydro[1,3]thiazolo[5,4-d]pyrimidin-2-yl]pyrrolidine-1-carboxylic acid benzyl ester

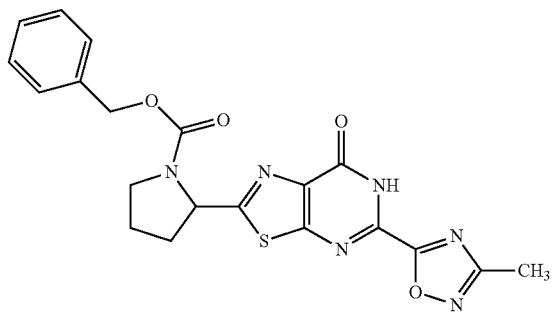 [SMILES: Cc1noc(-c2nc3sc(C4CCCN4C(=O)OCc4ccccc4)nc3c(=O)[nH]2)n1]

15s To a solution (5.00 mL) of the compound (0.47 g) obtained in Reference Example 66 in methylene chloride were added chlorotrimethylsilane (0.66 mL) and triethylamine (2.20 mL), and the reaction mixture was stirred at room temperature for 2 hr. Chlorotrimethylsilane (0.66 mL) and triethylamine (2.20 mL) were added, and the mixture was stirred for 3 days. Water was added to the reaction mixture, and the mixture was extracted twice with chloroform. The organic layer was dried over anhydrous magnesium sulfate, filtered and concentrated. The residue was purified by silica gel column chromatography (solvent; chloroform/methanol=100/0-95/5) to give the title compound (0.31 g).

MS (ESI) m/z; 439 [M+H]+

Example 585

(R)-N-benzyl-1-[5-(3-methyl-[1,2,4]oxadiazol-5-yl)-7-oxo-6,7-dihydro[1,3]thiazolo[5,4-d]pyrimidin-2-yl]pyrrolidine-2-carboxamide

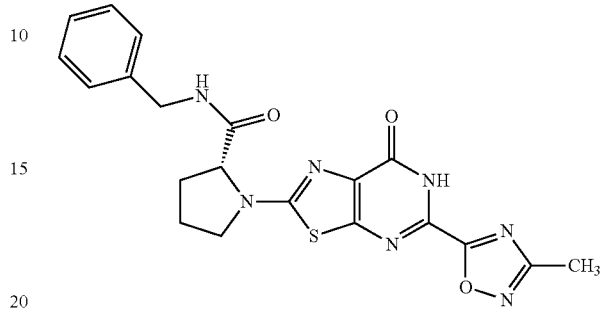

To a solution (20 mL) of the compound (0.2 g) obtained in Reference Example 643 in methylene chloride was added mCPBA is (69-75%, 0.18 g) at 0° C., and the reaction mixture was stirred at room temperature for 1 hr. After confirmation of the completion of the reaction, water and aqueous sodium thiosulfate solution were added to the reaction mixture, and the mixture was extracted twice with chloroform. The organic layer was washed once with water, dried over anhydrous magnesium sulfate, filtered and concentrated. The residue was washed with ethyl acetate, filtered, and dried to give a white solid. To the obtained solid were added N,N-diisopropylethylamine (3.7 mL) and the compound (0.52 g) obtained in Reference Example 341, and the reaction mixture was stirred at 160° C. for 5 hr. After confirmation of the completion of the reaction, water and chloroform were added to the reaction mixture, and the mixture was neutralized with 1.0 mol/L hydrochloric acid and extracted twice with chloroform. The organic layer was washed once with water, dried over anhydrous magnesium sulfate, filtered and concentrated. The residue was purified by silica gel column chromatography (solvent; chloroform/methanol=100/0-90/10) to give the title compound (60 mg).

MS (ESI) m/z; 438 [M+H]+

Example 586

(R)-N-benzyl-1-[7-oxo-5-(1,1,1-trifluoro-2-methylpropan-2-yl)-6,7-dihydro[1,3]thiazolo[5,4-d]pyrimidin-2-yl]pyrrolidine-2-carboxamide

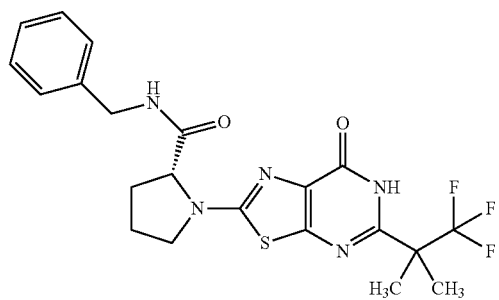 [SMILES: CC(C)(c1nc2sc(N3CCC[C@@H]3C(=O)NCc3ccccc3)nc2c(=O)[nH]1)C(F)(F)F]

A mixture of the compound (180 mg) obtained in Reference Example 654 and the compound (2.8 mL) obtained in Reference Example 341 was stirred with heating at 150° C. for 4 hr. The compound (2.56 g) obtained in Reference Example 341 and N,N-diisopropylethylamine (1.4 mL) were added, and the reaction mixture was stirred with heating at 150° C. for 12 hr. The reaction mixture was cooled to room temperature, and ethyl acetate was added. The mixture was neutralized with 1.0 mol/L hydrochloric acid, and extracted twice with ethyl acetate. The organic layer was dried over anhydrous magnesium sulfate, filtered and concentrated. The residue was purified by silica gel column chromatography (solvent; ethyl acetate/methanol=100/0-90/10). To the obtained product was added diisopropyl ether, and the solid was collected by filtration to give the title compound (50 mg).
MS (ESI) m/z; 466 [M+H]$^+$ Example 587

(R)-N-benzyl-1-(5-tert-butyl-7-oxo-6,7-dihydro[1,3]thiazolo[5,4-d]pyrimidin-2-yl)pyrrolidine-2-carboxamide

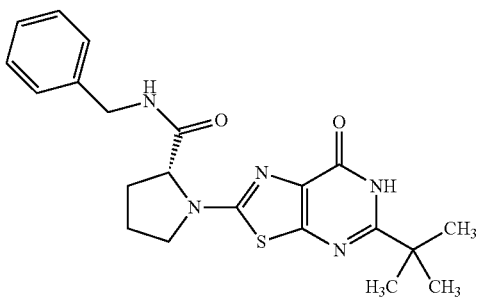 [SMILES: CC(C)(C)c1nc2sc(N3CCC[C@@H]3C(=O)NCc3ccccc3)nc2c(=O)[nH]1]

To a mixture of the compound (150 mg) obtained in Reference Example 655 and potassium carbonate (144 mg) in DMF (4.3 mL) was added dropwise benzyl bromide (75 µL) at 0° C. The reaction mixture was stirred at room temperature overnight, and water (20 mL) was added at 0° C. The precipitated solid was collected by filtration, dissolved in chloroform/methanol (100/1), and the obtained solution was dried over anhydrous sodium sulfate, filtered and concentrated. To the residue was added hexane/diethyl ether=10/1, and the solid was collected by filtration. To a solution (2.5 mL) of the obtained solid in DMF were added (D)-proline (80 mg) and cesium carbonate (377 mg), and the reaction mixture was heated at 75° C. for 1 hr. The reaction mixture was cooled to room temperature, acidified with 1.0 mol/L hydrochloric acid, and extracted twice with chloroform. The organic layer was dried over anhydrous sodium sulfate, filtered and concentrated. To the obtained residue were added N,N-diisopropylethylamine (121 µL), benzylamine (76 µL), EDC hydrochloride (133 mg) and HOBt monohydrate (106 mg), and the reaction mixture was stirred at room temperature for 18 hr. 1.0 mol/L Hydrochloric acid was added and the mixture was extracted twice with ethyl acetate. The organic layer was washed with saturated brine, dried over anhydrous sodium sulfate, filtered and concentrated. The residue was purified by NH silica gel column chromatography (solvent; hexane/ethyl acetate=95/5-55/45). The obtained product was dissolved in a mixture (2.878 mL) of trifluoroacetic acid/water/triethylsilane=90/5/5 (v/v), and the reaction mixture was stirred at room temperature for 1 hr, and concentrated. The residue was purified by silica gel column chromatography (solvent; ethyl acetate/methanol=100/0-95/5) and purified by to reversed-phase HPLC (Capcelpak C18; 0.05% trifluoroacetic acid-water/acetonitrile=55/45-45/55). To the obtained product was added hexane-ethyl acetate mixed solvent (1:1), and the solid was collected by filtration to give the title compound (121 mg)
MS (ESI) m/z; 412 [M+H]$^+$ Example 588

2-[(R)-2-(benzylcarbamoyl)pyrrolidin-1-yl]-10-oxo-5,7,8,10-tetrahydro-6H-pyrazino[1,2-a][1,3]thiazolo[5,4-d]pyrimidine-6-carboxylic acid tert-butyl ester

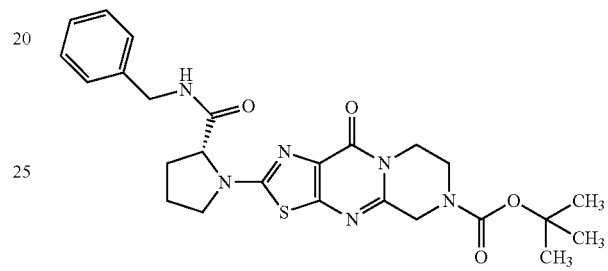

To a solution (22 mL) of the compound (1070 mg) obtained in Reference Example 661 in DMF were added (D)-proline (499 mg) and potassium carbonate (998 mg), and the reaction mixture was heated at 70° C. for 1.5 hr. The reaction mixture was cooled to 0° C., and neutralized with concentrated hydrochloric acid (1.2 mL). N,N-diisopropylethylamine (1.01 mL), benzylamine (631 µL), EDC hydrochloride (1010 mg) and HOBt monohydrate (781 mg) were added at room temperature, and the reaction mixture was stirred at room temperature overnight. Water was added to the reaction mixture, and the mixture was extracted three times with ethyl acetate. The combined organic layer was dried over anhydrous sodium sulfate, filtered and concentrated. The residue was purified by NH silica gel column chromatography (solvent; ethyl acetate/methanol=100/0-90/10) to give the title compound (536.4 mg).
MS (ESI) m/z; 511 [M+H]$^+$ Example 589

(R)-N-benzyl-1-(10-oxo-5,7,8,10-tetrahydro-6H-pyrazino[1,2-a][1,3]thiazolo[5,4-d]pyrimidin-2-yl)pyrrolidine-2-carboxamide

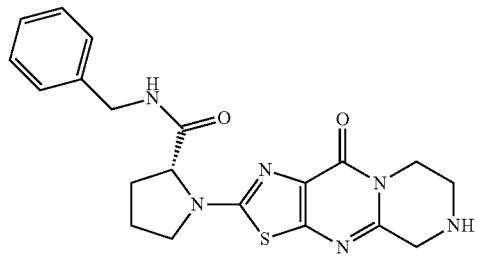 [SMILES: O=C(NCc1ccccc1)[C@H]1CCCN1c1nc2c(=O)n3c(nc2s1)CNCC3]

To a solution (2.3 mL) of the compound (535 mg) obtained in Example 588 in methylene chloride was added trifluoroacetic acid (4.6 mL), and the reaction mixture was stirred at room temperature for 1.5 hr, and concentrated. The residue was diluted with water and chloroform, and the mixture was adjusted to pH 9 with 2 mol/L aqueous sodium carbonate solution, and the mixture was extracted twice with chloroform. The combined organic layer was washed with saturated brine, dried over anhydrous sodium sulfate, filtered and concentrated. The residue was purified by NH silica gel column chromatography (solvent; chloroform/methanol=100/0-93/7) and silica gel column chromatography (solvent; chloroform/methanol=100/0-85/15), to the obtained product was added hexane/ethyl acetate=1/1, and the solid was collected by filtration to give the title compound (340.5 mg).

MS (ESI) m/z; 411 [M+H]$^+$

Example 590

(R)-N-benzyl-1-(6-methyl-10-oxo-5,7,8,10-tetrahydro-6H-pyrazino[1,2-a][1,3]thiazolo[5,4-d]pyrimidin-2-yl)pyrrolidine-2-carboxamide

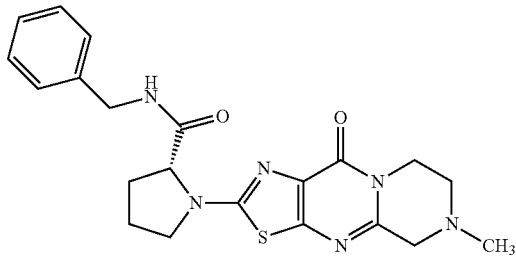 [SMILES: CN1CCn2c(nc3sc(N4CCC[C@@H]4C(=O)NCc4ccccc4)nc3c2=O)C1]

To a solution (1.5 mL) of the compound (80 mg) obtained in Example 589 in methylene chloride was added 35-38% aqueous formaldehyde solution (67 µL). The reaction mixture was stirred at room temperature for 1 hr, sodium triacetoxyborohydride (103 mg) was added to the reaction mixture, and the reaction mixture was stirred at room temperature for 1 hr. Saturated aqueous sodium hydrogen carbonate solution was added, and the mixture was extracted twice with methylene chloride. The combined organic layer was washed with saturated brine, dried over anhydrous sodium sulfate, filtered and concentrated. The residue was purified by silica gel column chromatography (solvent; chloroform/methanol=100/0-93/7), to the obtained product was added diethyl ether, and the solid was collected by filtration to give the title compound (76.6 mg).

MS (ESI) m/z; 425 [M+H]$^+$

Example 591

(R)-N-benzyl-1-[10-oxo-6-(propan-2-yl)-5,7,8,10-tetrahydro-6H-pyrazino[1,2-a][1,3]thiazolo[5,4-d]pyrimidin-2-yl]pyrrolidine-2-carboxamide

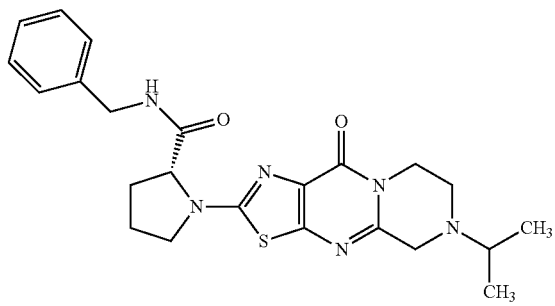 [SMILES: CC(C)N1CCn2c(nc3sc(N4CCC[C@@H]4C(=O)NCc4ccccc4)nc3c2=O)C1]

The compound (80 mg) and acetone (57 µL) obtained in Example 589 was treated by a method similar to that in Example 590 to give the title compound (67.7 mg).

MS (ESI) m/z; 453 [M+H]$^+$

Example 592

(R)-N-benzyl-1-[10-oxo-6-(2,2,2-trifluoroethyl)-5,7,8,10-tetrahydro-6H-pyrazino[1,2-a][1,3]thiazolo[5,4-d]pyrimidin-2-yl]pyrrolidine-2-carboxamide

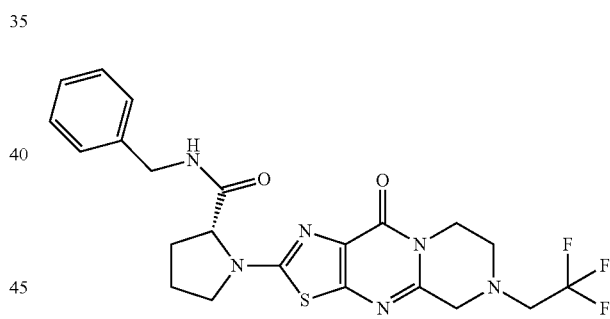

To a solution (1.5 mL) of the compound (85 mg) obtained in Example 589 in DMF were added N,N-diisopropylethylamine (108 µL) and 2,2,2-trifluoroethyl trifluoromethanesulfonate (72 mg) under ice-cooling, and the reaction mixture was stirred at room temperature for 14 hr. Water was added to the reaction mixture, and the mixture was extracted twice with chloroform. The combined organic layer was washed with saturated brine, dried over anhydrous sodium sulfate, filtered and concentrated. The residue was purified by silica gel column chromatography (solvent; ethyl acetate/methanol=99/1-85/15), to the obtained product was added hexane/ethyl acetate=10/1, and the solid was collected by filtration to give the title compound (38.2 mg).

MS (ESI) m/z; 493 [M+H]$^+$

Example 593

(R)-N-benzyl-1-[6-(2,2-difluoroethyl)-10-oxo-5,7,8,10-tetrahydro-6H-pyrazino[1,2-a][1,3]thiazolo[5,4-d]pyrimidin-2-yl]pyrrolidine-2-carboxamide

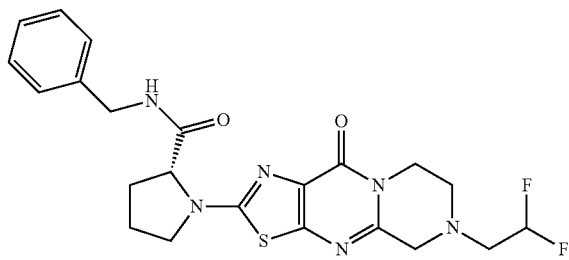 [SMILES: O=C(NCc1ccccc1)[C@H]1CCCN1c1nc2c(=O)n3c(nc2s1)CN(CC(F)F)CC3]

To a solution of the compound (90 mg) obtained in Example 589 in dichloroethane-methylene chloride mixture (1.5 mL-1.0 mL) were added, under ice-cooling, N,N-diisopropylethylamine (76 μL) and difluoroethyl trifluoromethanesulfonate (56 mg), and the reaction mixture was stirred at room temperature for 24 hr. Water was added to the reaction mixture, and the mixture was extracted twice with chloroform. The combined organic layer was washed with saturated brine, dried over anhydrous sodium sulfate, filtered and concentrated. The residue was purified by silica gel column chromatography (solvent; ethyl acetate/methanol=99/1-85/15), to the obtained product was added hexane/ethyl acetate=10/1, and the solid was collected by filtration to give the title compound (80.8 mg).

MS (ESI) m/z; 475 [M+H]$^+$

Example 594

[(S)-2-{2-[(R)-2-(benzylcarbamoyl)pyrrolidin-1-yl]-5-hydroxymethyl-7-oxo-7H-[1,3]thiazolo[5,4-d]pyrimidin-6-yl}propyl]carbamic acid tert-butyl ester

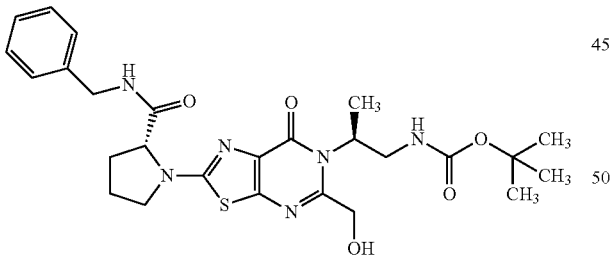

To a solution (8 mL) of the compound (500 mg) obtained in Reference Example 670 in DMF were added (D)-proline (215 mg) and potassium carbonate (343 mg), and the reaction mixture was stirred with heating at 80° C. for 1.5 hr. The reaction mixture was cooled to 0° C., and neutralized with concentrated hydrochloric acid (414 μL). N,N-diisopropylethylamine (325 μL), benzylamine (272 μL), EDC hydrochloride (357 mg) and HOBt monohydrate (252 mg) were added at room temperature, and the reaction mixture was stirred at room temperature overnight. Water was added to the reaction mixture, the precipitate was collected by filtration, and the filtrate was extracted once with ethyl acetate. The precipitate was dissolved in ethyl acetate, and the combined organic layer was dried over anhydrous magnesium sulfate, filtered and concentrated. The residue was purified by silica gel column chromatography (solvent; ethyl acetate/methanol=100/0-94/6), to the obtained product was added hexane/ethyl acetate=1/1, and the solid was collected by filtration to give the title compound (275.3 mg).

MS (ESI) m/z; 543 [M+H]$^+$

Example 595

[(R)-2-{2-[(R)-2-(benzylcarbamoyl)pyrrolidin-1-yl]-5-hydroxymethyl-7-oxo-7H-[1,3]thiazolo[5,4-d]pyrimidin-6-yl}propyl]carbamic acid tert-butyl ester

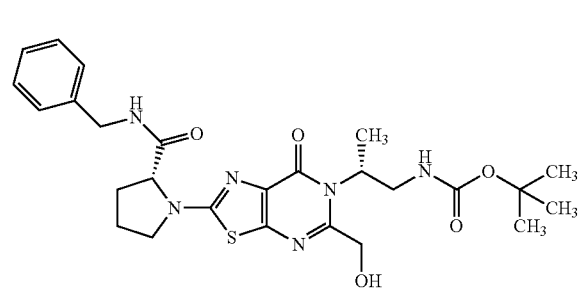 [SMILES: C[C@H](CNC(=O)OC(C)(C)C)n1c(CO)nc2sc(N3CCC[C@@H]3C(=O)NCc3ccccc3)nc2c1=O]

The compound (635 mg) obtained in Reference Example 671 was treated by a method similar to that in Example 594 to give the title compound (363.5 mg).

MS (ESI) m/z; 543 [M+H]$^+$

Example 596

[(S)-2-{2-[(R)-2-(benzylcarbamoyl)pyrrolidin-1-yl]-5-[(methylsulfonyl)oxymethyl]-7-oxo-7H-[1,3]thiazolo[5,4-d]pyrimidin-6-yl}propyl]carbamic acid tert-butyl ester

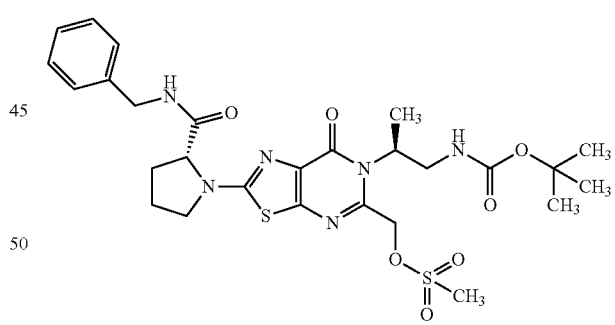

To a solution (8 mL) of the compound (170 mg) obtained in Example 594 and triethylamine (48 μL) in methylene chloride was added dropwise methanesulfonyl chloride (26 μL) under ice-cooling, and the reaction mixture was stirred at room temperature for 1 hr. Triethylamine (48 μL) and methanesulfonyl chloride (26 μL) were added, and the reaction mixture was further stirred for 1 hr. Saturated aqueous sodium hydrogen carbonate solution was added, and the mixture was extracted twice with methylene chloride. The combined organic layer was washed with saturated brine, dried over anhydrous sodium sulfate, filtered and concentrated. The residue was purified by silica gel column chromatography (solvent; chloroform/methanol=95/5), to the obtained product was added diethyl ether, and the solid was collected by filtration to give the title compound (333.6 mg).

MS (ESI) m/z; 621 [M+H]+

Example 597

[(R)-2-{2-[(R)-2-(benzylcarbamoyl)pyrrolidin-1-yl]-5-[(methylsulfonyl)oxymethyl]-7-oxo-7H-[1,3]thiazolo[5,4-d]pyrimidin-6-yl}propyl]carbamic acid tert-butyl ester

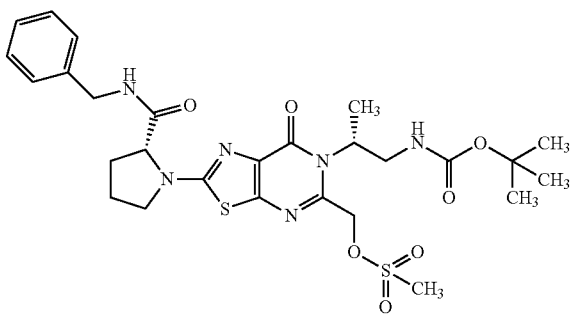 [SMILES: C[C@H](CNC(=O)OC(C)(C)C)n1c(COS(C)(=O)=O)nc2sc(N3CCC[C@@H]3C(=O)NCc3ccccc3)nc2c1=O]

The compound (362 mg) obtained in Example 595 was treated by a method similar to that in Example 596 to give the title compound (390 mg).

MS (ESI) m/z; 621 [M+H]+

Example 598

(R)-N-benzyl-1-[(S)-8-methyl-10-oxo-5,7,8,10-tetrahydro-6H-pyrazino[1,2-a][1,3]thiazolo[5,4-d]pyrimidin-2-yl]pyrrolidine-2-carboxamide

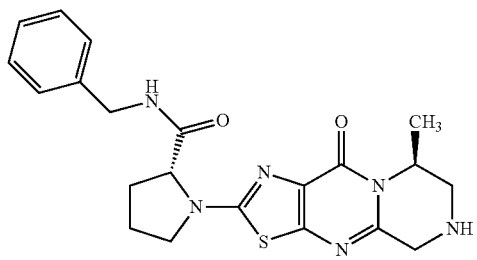 [SMILES: C[C@H]1CNCc2nc3sc(N4CCC[C@@H]4C(=O)NCc4ccccc4)nc3c(=O)n21]

To a solution (1 mL) of the compound (305 mg) obtained in Example 596 in methylene chloride was added dropwise trifluoroacetic acid (1 mL) under ice-cooling. The reaction mixture was stirred at room temperature for 1.5 hr, and concentrated under reduced pressure. The residue was diluted with water (3 mL) and THF (3 mL). Under ice-cooling, the reaction mixture was adjusted to pH 9-10 with saturated aqueous sodium hydrogen carbonate solution, stirred at room temperature for 2 hr, and extracted twice with chloroform. The combined organic layer was dried over anhydrous magnesium sulfate, filtered and concentrated. The residue was purified by silica gel column chromatography (solvent; chloroform/methanol=98/2-88/12) to give the title compound (199 mg).

MS (ESI) m/z; 425 [M+H]+

Example 599

(R)-N-benzyl-1-[(R)-8-methyl-10-oxo-5,7,8,10-tetrahydro-6H-pyrazino[1,2-a][1,3]thiazolo[5,4-d]pyrimidin-2-yl]pyrrolidine-2-carboxamide

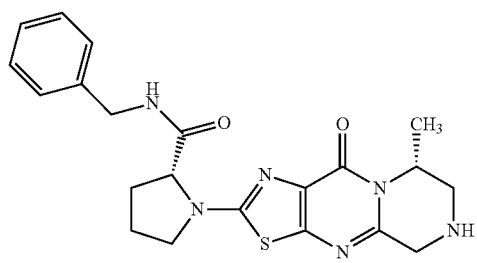 [SMILES: C[C@@H]1CNCc2nc3sc(N4CCC[C@@H]4C(=O)NCc4ccccc4)nc3c(=O)n21]

The compound (390 mg) obtained in Example 597 was treated by a method similar to that in Example 598 to give the title compound (211 mg).

MS (ESI) m/z; 425 [M+H]+

Example 600

(R)-N-benzyl-1-[(S)-6,8-dimethyl-10-oxo-5,7,8,10-tetrahydro-6H-pyrazino[1,2-a][1,3]thiazolo[5,4-d]pyrimidin-2-yl]pyrrolidine-2-carboxamide

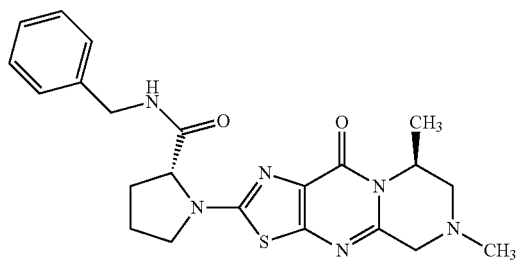 [SMILES: C[C@H]1CN(C)Cc2nc3sc(N4CCC[C@@H]4C(=O)NCc4ccccc4)nc3c(=O)n21]

To a solution (2 mL) of the compound (85 mg) obtained in Example 598 in methylene chloride was added dropwise 35% aqueous formaldehyde solution (69 mg), and the reaction mixture was stirred at room temperature for 1 hr. Sodium triacetoxyborohydride (106 mg) was added, and the reaction mixture was stirred at room temperature for 1 hr. Saturated aqueous sodium hydrogen carbonate solution was added, and the mixture was extracted twice with methylene chloride. The combined organic layer was dried over anhydrous sodium sulfate, filtered and concentrated. The residue was purified by NH silica gel column chromatography (solvent; chloroform/methanol=100/0-92/8), to the obtained product was added hexane/diethyl ether (1/2), and the solid was collected by filtration to give the title compound (50 mg).

MS (ESI) m/z; 439 [M+H]+

Example 601

(R)-N-benzyl-1-[(R)-6,8-dimethyl-10-oxo-5,7,8,10-tetrahydro-6H-pyrazino[1,2-a][1,3]thiazolo[5,4-d]pyrimidin-2-yl]pyrrolidine-2-carboxamide

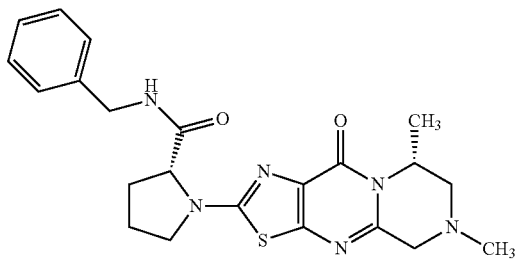 [SMILES: C[C@@H]1CN(C)Cc2nc3sc(N4CCC[C@@H]4C(=O)NCc4ccccc4)nc3c(=O)n21]

The compound (100 mg) obtained in Example 599 was treated by a method similar to that in Example 600 to give the title compound (39.4 mg).
MS (ESI) m/z; 439 [M+H]$^+$

Example 602

(R)-N-benzyl-1-(5-methyl-9-oxo-5,6,7,9-tetrahydroimidazo[1,2-a][1,3]thiazolo[5,4-d]pyrimidin-2-yl)pyrrolidine-2-carboxamide

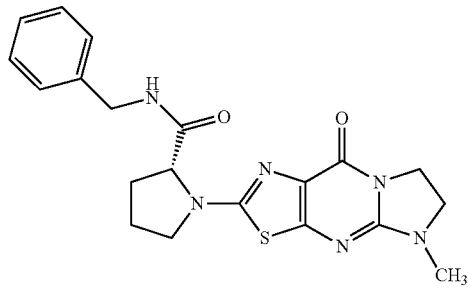 [SMILES: Cn1ccn2c(=O)c3nc(N4CCC[C@@H]4C(=O)NCc4ccccc4)sc3nc12]

To a solution (11 mL) of the compound (305 mg) obtained in Reference Example 675 in N-methylpyrrolidone were added (D)-proline (390 mg) and potassium carbonate (624 mg), and the reaction mixture was stirred with heating at 130° C. for 2 hr. (D)-proline (260 mg) and potassium carbonate (468 mg) were added, and the reaction mixture was stirred with heating at 130° C. for 2 hr. The reaction mixture was cooled to 0° C., acidified with 1.0 mol/L hydrochloric acid, and extracted 4 times with chloroform and 2 times with chloroform/methanol (10/1). The organic layer was dried over magnesium sulfate, filtered and concentrated. To the obtained residue were added N,N-diisopropylethylamine (295 µL), benzylamine (185 µL), EDC hydrochloride (324 mg) and HOBt monohydrate (259 mg), and the reaction mixture was stirred at room temperature overnight. Water was added, and the mixture was extracted 4 times with ethyl acetate and 2 times with ethyl acetate/methanol (10/1). The organic layer was washed with saturated aqueous sodium hydrogen carbonate solution, and saturated brine, dried over anhydrous sodium sulfate, filtered and concentrated. The residue was purified by NH silica gel column chromatography (solvent; ethyl acetate/methanol=100/0-90/10). To the obtained product was added hexane/ethyl acetate (1/1), and the solid was collected by filtration to give the title compound (131.2 mg).
MS (ESI) m/z; 411 [M+H]$^+$

Example 603

(R)-N-benzyl-1-(5-methyl-9-oxo-5,9-dihydroimidazo[1,2-a][1,3]thiazolo[5,4-d]pyrimidin-2-yl)pyrrolidine-2-carboxamide

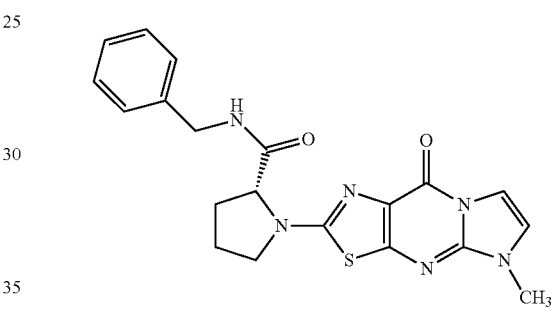

To a solution (1.5 mL) of the compound (30 mg) obtained in Reference Example 678 in N-methylpyrrolidone were added (D)-proline (26 mg) and potassium carbonate (46 mg), and the reaction mixture was stirred with heating at 130° C. for 2 hr. The reaction mixture was cooled to 0° C., acidified with 1.0 mol/L hydrochloric acid, and extracted 2 times with chloroform and 3 times with chloroform/methanol (5/1). The organic layer was dried over magnesium sulfate, filtered and concentrated. To the obtained residue were added N,N-diisopropylethylamine (29 µL), benzylamine (18 µL), EDC hydrochloride (32 mg) and HOBt monohydrate (26 mg), and the reaction mixture was stirred at room temperature overnight. Water was added, and the mixture was extracted three times with ethyl acetate. To the aqueous layer was added sodium chloride, and the mixture was extracted twice with ethyl acetate. The organic layer was washed with saturated aqueous sodium hydrogen carbonate solution, and saturated brine, dried over anhydrous sodium sulfate, filtered and concentrated. The residue was purified by silica gel column chromatography (solvent; ethyl acetate/methanol=99/1-90/10). To the obtained product was added hexane/ethyl acetate (1/2), and the solid was collected by filtration to give the title compound (15.8 mg).
MS (ESI) m/z; 409 [M+H]$^+$

Example 604

(R)-N-benzyl-1-(5,5-difluoro-9-oxo-5,6,7,9-tetrahydropyrrolo[1,2-a][1,3]thiazolo[5,4-d]pyrimidin-2-yl)pyrrolidine-2-carboxamide

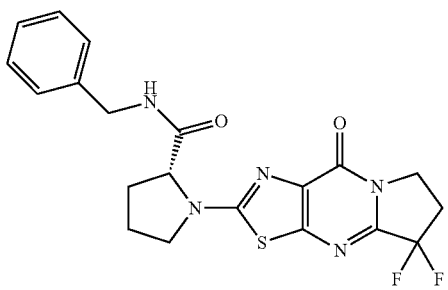 [SMILES: O=C(NCc1ccccc1)[C@H]1CCCN1c1nc2c(=O)n3c(nc2s1)C(F)(F)CC3]

To a solution (2.0 mL) of the compound (38 mg) obtained in Reference Example 683 in DMF were added (D)-proline (23 mg) and cesium carbonate (97 mg), and the reaction mixture was stirred with heating at 70° C. for 1 hr. The reaction mixture was cooled to 0° C., and neutralized with concentrated hydrochloric acid (49 µL). N,N-diisopropylethylamine (45 µL), benzylamine (28 µL), EDC hydrochloride (50 mg) and HOBt monohydrate (40 mg) were successively added, and the reaction mixture was stirred at room temperature overnight. Water was added to the reaction mixture, and the mixture was extracted three times with ethyl acetate. The combined organic layer was washed with saturated brine, dried over anhydrous sodium sulfate, filtered and concentrated under reduced pressure. The obtained residue was purified by silica gel column chromatography (solvent; hexane/ethyl acetate=40/60-0/100) to give the title compound (29.7 mg).
MS (ESI) m/z; 432 [M+H]$^+$

Example 605

(R)-N-benzyl-1-(5,5-difluoro-10-oxo-5,7,8,10-tetrahydro-6H-pyrido[1,2-a][1,3]thiazolo[5,4-d]pyrimidin-2-yl)pyrrolidine-2-carboxamide

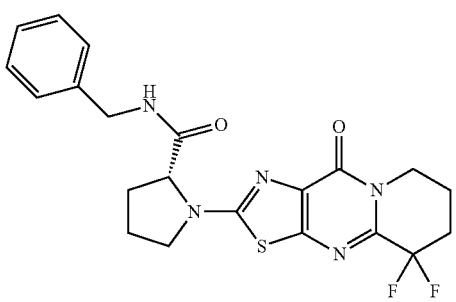 [SMILES: O=C(NCc1ccccc1)[C@H]1CCCN1c1nc2c(=O)n3c(nc2s1)C(F)(F)CCC3]

To a solution (2.0 mL) of the compound (61 mg) obtained in Reference Example 689 in DMF were added (D)-proline (34 mg) and cesium carbonate (148 mg), and the reaction mixture was stirred with heating at 70° C. for 1 hr. The reaction mixture was cooled to 0° C., and neutralized with concentrated hydrochloric acid (74 µL). N,N-diisopropylethylamine (69 µL), benzylamine (43 µL), EDC hydrochloride (76 mg) and HOBt monohydrate (60 mg) were successively added, and the reaction mixture was stirred at room temperature for 5 hr. Water was added to the reaction mixture, and the mixture was extracted three times with ethyl acetate. The combined organic layer was washed with saturated brine, dried over anhydrous sodium sulfate, filtered and concentrated under reduced pressure. The obtained residue was purified by silica gel column chromatography (solvent; hexane/ethyl acetate=40/60-0/100) to give the title compound (56.9 mg).
MS (ESI) m/z; 446 [M+H]$^+$

Example 606

(R)-N-benzyl-1-[5-(2-hydroxypropan-2-yl)-7-oxo-6,7-dihydro[1,3]thiazolo[5,4-d]pyrimidin-2-yl]pyrrolidine-2-carboxamide

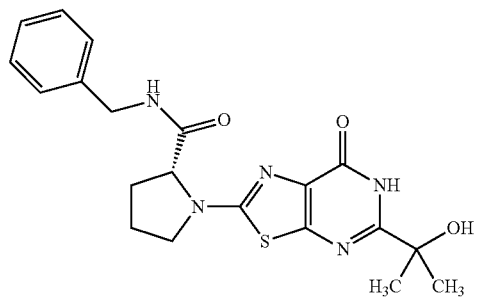 [SMILES: CC(C)(O)c1nc2sc(N3CCC[C@@H]3C(=O)NCc3ccccc3)nc2c(=O)[nH]1]

To a solution of the compound (1000 mg) obtained in Example 482 in acetonitrile-water mixture (40 mL-40 mL) was added sodium hydrogen carbonate (2.10 g), and the reaction mixture was stirred with heating at 80° C. for 6 hr. The reaction mixture was allowed to cool to room temperature, 1.0 mol/L hydrochloric acid (25 mL) was added, and the mixture was extracted twice with chloroform. The organic layer was washed with water, dried over anhydrous magnesium sulfate, filtered and concentrated. The residue was purified by silica gel column chromatography (solvent; chloroform/methanol=100/0-95/5). Ethyl acetate was added to the obtained product, and the solid was collected by filtration and dried to give the title compound (660 mg).
MS (ESI) m/z; 414 [M+H]$^+$

Example 607

(R)-N-benzyl-1-[5-(2-methoxypropan-2-yl)-7-oxo-6,7-dihydro[1,3]thiazolo[5,4-d]pyrimidin-2-yl]pyrrolidine-2-carboxamide

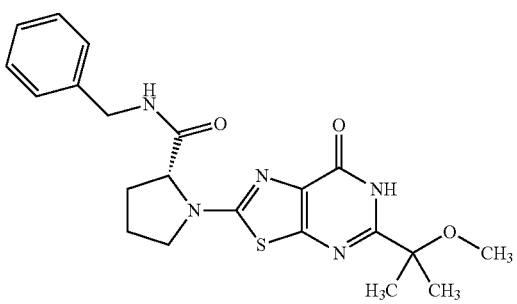 [SMILES: COC(C)(C)c1nc2sc(N3CCC[C@@H]3C(=O)NCc3ccccc3)nc2c(=O)[nH]1]

To a solution (30 mL) of the compound (600 mg) obtained in Example 482 in methanol was added potassium carbonate (4.00 g), and the reaction mixture was heated under reflux overnight. The reaction mixture was allowed to cool to room temperature, ethyl acetate and water were added, and the mixture was neutralized with 1.0 mol/L hydrochloric acid and extracted twice with ethyl acetate. The organic layer was washed with water, dried over anhydrous magnesium sulfate, filtered and concentrated. The residue was purified by silica gel column chromatography (solvent; ethyl acetate/hexane=50/50-100/0) to give the title compound (360 mg).

MS (ESI) m/z; 428 [M+H]+

Example 608

[(2R,3S)-2-benzylcarbamoyl-1-(6-methyl-7-oxo-5-phenyl-6,7-dihydro[1,3]thiazolo[5,4-d]pyrimidin-2-yl)pyrrolidin-3-yl]carbamic acid benzyl ester

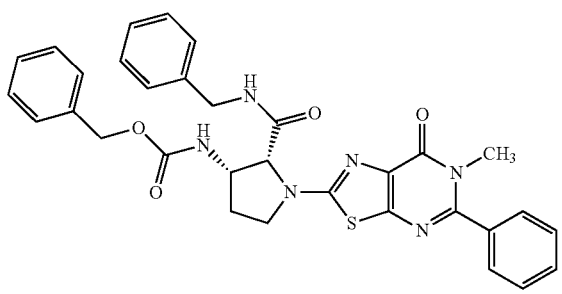 [SMILES: Cn1c(-c2ccccc2)nc2sc(N3CC[C@H](NC(=O)OCc4ccccc4)[C@@H]3C(=O)NCc3ccccc3)nc2c1=O]

A mixture of the compound (250 mg) obtained in Reference Example 691, the compound (600 mg) obtained in Reference Example 696 and N,N-diisopropylethylamine (0.68 mL) in 1,4-dioxane (2.5 mL) was stirred with heating at 120° C. overnight. The reaction mixture was cooled to room temperature, acidified with 1.0 mol/L hydrochloric acid, and extracted with ethyl acetate. The organic layer was dried over magnesium sulfate, filtered and concentrated. The residue was purified by silica gel column chromatography (solvent; hexane/ethyl acetate=50/50-0/100) to give the title compound (320 mg).

MS (ESI) m/z; 595 [M+H]+

Example 609

[(2R,3R)-2-benzylcarbamoyl-1-(6-methyl-7-oxo-5-phenyl-6,7-dihydro[1,3]thiazolo[5,4-d]pyrimidin-2-yl)pyrrolidin-3-yl]carbamic acid benzyl ester

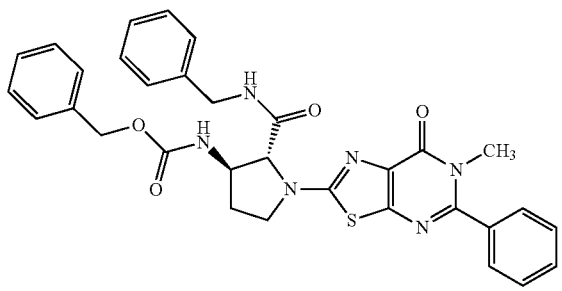 [SMILES: Cn1c(-c2ccccc2)nc2sc(N3CC[C@@H](NC(=O)OCc4ccccc4)[C@@H]3C(=O)NCc3ccccc3)nc2c1=O]

The compound (0.25 g) obtained in Reference Example 691, the compound (440 mg) obtained in Reference Example 697 were treated by a method similar to that in Example 608 to give the title compound (0.36 g).

MS (ESI) m/z; 595 [M+H]+

Example 610

(2R,3S)-3-amino-N-benzyl-1-(6-methyl-7-oxo-5-phenyl-6,7-dihydro[1,3]thiazolo[5,4-d]pyrimidin-2-yl)pyrrolidine-2-carboxamide

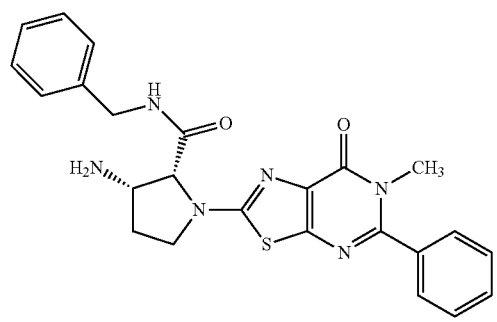 [SMILES: Cn1c(-c2ccccc2)nc2sc(N3CC[C@H](N)[C@@H]3C(=O)NCc3ccccc3)nc2c1=O]

To a solution (3.0 mL) of the compound (300 mg) obtained in Example 608 in methylene chloride was added trimethylsilyl iodide (150 μL), and the reaction mixture was stirred at room temperature for 2 hr. To the reaction mixture were added water and ethyl acetate, and the mixture was extracted 3 times with 1.0 mol/L hydrochloric acid. The aqueous layer was neutralized with saturated aqueous sodium hydrogen carbonate solution, and extracted twice with chloroform. The organic layer was dried over anhydrous magnesium sulfate, filtered and concentrated. The residue was purified by silica gel column chromatography (solvent; chloroform/methanol=100/0-95/5). To the obtained product was added diisopropyl ether, the solid was collected by is filtration, and dried to give the title compound (95.0 mg).

MS (ESI) m/z; 461 [M+H]+

Example 611

(2R,3R)-3-amino-N-benzyl-1-(6-methyl-7-oxo-5-phenyl-6,7-dihydro[1,3]thiazolo[5,4-d]pyrimidin-2-yl)pyrrolidine-2-carboxamide

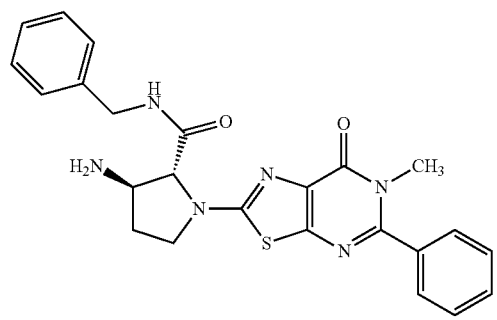 [SMILES: Cn1c(-c2ccccc2)nc2sc(N3CC[C@@H](N)[C@@H]3C(=O)NCc3ccccc3)nc2c1=O]

The compound (320 mg) obtained in Example 609 was treated by a method similar to that in Example 610 to give the title compound (80.0 mg).

MS (ESI) m/z; 461 [M+H]$^+$

Example 612

(R)-N-benzyl-1-(5,7-diethyl-4-oxo-4,5-dihydro[1,3]thiazolo[4,5-d]pyridazin-2-yl)pyrrolidine-2-carboxamide

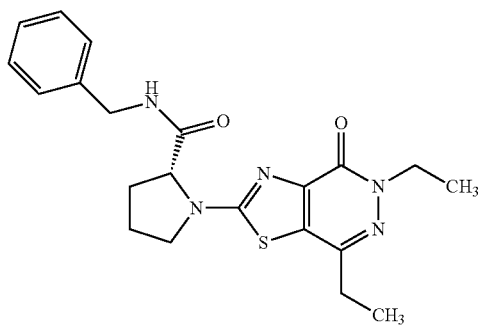 [SMILES: CCc1nn(CC)c(=O)c2nc(N3CCC[C@@H]3C(=O)NCc3ccccc3)sc12]

To a solution (13 mL) of the compound (300 mg) obtained in Reference Example 709 in N-methylpyrrolidone were added (D)-proline (240 mg) and potassium carbonate (440 mg), and the reaction mixture was stirred with heating at 70° C. for 2 hr. The reaction mixture was cooled to room temperature, acidified with 1.0 mol/L hydrochloric acid, and extracted twice with chloroform. The organic layer was dried over anhydrous sodium sulfate, filtered and concentrated. To a solution of the obtained residue in N-methylpyrrolidone were added N,N-diisopropylethylamine (210 mg), benzylamine (170 mg), EDC hydrochloride (300 mg) and HOBt monohydrate (240 mg), and the reaction mixture was stirred at room temperature for 6 hr. To the reaction mixture was added saturated aqueous sodium hydrogen carbonate solution, and the mixture was extracted twice with ethyl acetate. The combined organic layer was washed 3 times with saturated brine, dried over anhydrous sodium sulfate, filtered and concentrated. The residue was purified by silica gel column chromatography (solvent; ethyl acetate=100) to give the title compound (170 mg).

MS (ESI) m/z; 412 [M+H]$^+$

Example 613

(R)-N-benzyl-1-[7-ethyl-4-oxo-5-(tetrahydro-2H-pyran-4-yl)-4,5-dihydro[1,3]thiazolo[4,5-d]pyridazin-2-yl]pyrrolidine-2-carboxamide

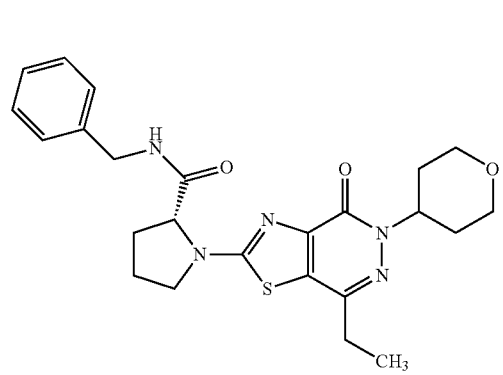 [SMILES: CCc1nn(C2CCOCC2)c(=O)c2nc(N3CCC[C@@H]3C(=O)NCc3ccccc3)sc12]

The compound (350 mg) obtained in Reference Example 710 was treated by a method similar to that in Example 612 to give the title compound (150 mg).

MS (ESI) m/z; 468 [M+H]$^+$

Example 614

(R)-N-benzyl-1-(7-cyclopropyl-5-ethyl-4-oxo-4,5-dihydro[1,3]thiazolo[4,5-d]pyridazin-2-yl)pyrrolidine-2-carboxamide

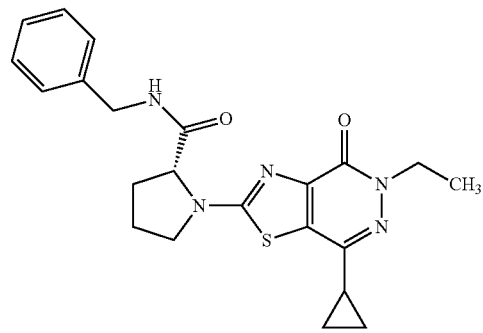 [SMILES: CCn1nc(C2CC2)c2sc(N3CCC[C@@H]3C(=O)NCc3ccccc3)nc2c1=O]

The compound (300 mg) obtained in Reference Example 711 was treated by a method similar to that in Example 612 to give the title compound (340 mg).

MS (ESI) m/z; 424 [M+H]$^+$

Example 615

(R)-N-benzyl-1-(5-ethyl-7-methyl-4-oxo-4,5-di-hydro[1,3]thiazolo[4,5-d]pyridazin-2-yl)pyrrolidine-2-carboxamide

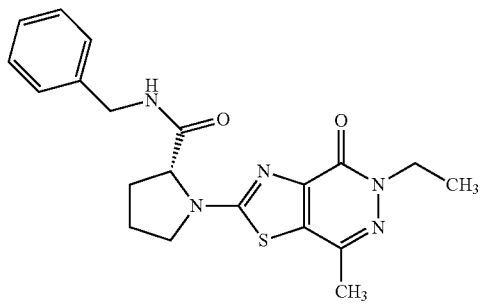 [SMILES: CCn1nc(C)c2sc(N3CCC[C@@H]3C(=O)NCc3ccccc3)nc2c1=O]

The compound (400 mg) obtained in Reference Example 712 was treated by a method similar to that in Example 612 to give the title compound (420 mg).

MS (ESI) m/z; 398 [M+H]$^+$

Example 616

(R)-N-benzyl-1-(5-cyclohexyl-7-methyl-4-oxo-4,5-dihydro[1,3]thiazolo[4,5-d]pyridazin-2-yl)pyrrolidine-2-carboxamide

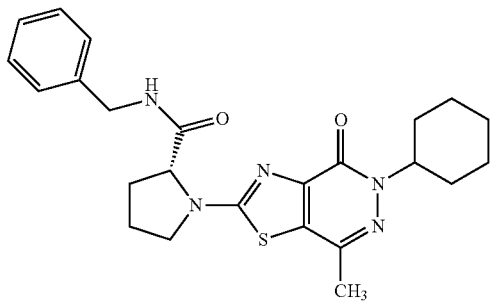 [SMILES: Cc1nn(C2CCCCC2)c(=O)c2nc(N3CCC[C@@H]3C(=O)NCc3ccccc3)sc12]

The compound (350 mg) obtained in Reference Example 713 was treated by a method similar to that in Example 612 to give the title compound (230 mg).

MS (ESI) m/z; 452 [M+H]$^+$

Example 617

(R)-N-benzyl-1-(4-oxo-7-trifluoromethyl-4,5-di-hydro[1,3]thiazolo[4,5-c]pyridin-2-yl)pyrrolidine-2-carboxamide

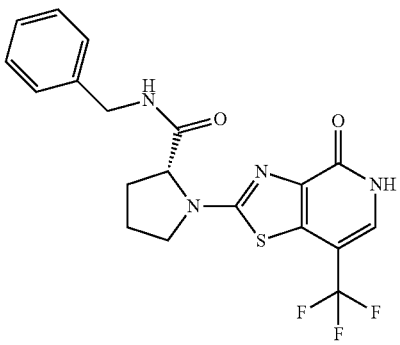 [SMILES: O=C(NCc1ccccc1)[C@H]1CCCN1c1nc2c(=O)[nH]cc(C(F)(F)F)c2s1]

To a solution (1.4 mL) of the compound (50.0 mg) obtained in Reference Example 736 in DMF were added potassium carbonate (46 mg) and 4-methoxybenzyl chloride (27 μL), and the reaction mixture was stirred with heating at 70° C. for 2 hr. The reaction mixture was cooled to 0° C., water was added, and the mixture was extracted twice with ethyl acetate. The organic layer was dried over anhydrous magnesium sulfate, filtered and concentrated. The residue was purified by silica gel column chromatography (solvent; hexane/ethyl acetate=80/20-40/60). To a solution (0.70 mL) of the obtained product (31.9 mg) in DMF were added (D)-proline (12 mg) and cesium carbonate (58 mg), and the reaction mixture was stirred with heating at 70° C. for 1.5 hr. The reaction mixture was cooled to room temperature, acidified with 1.0 mol/L hydrochloric acid, and extracted twice with chloroform. The organic layer was dried over anhydrous sodium sulfate, filtered and concentrated. To the obtained residue were added N,N-diisopropylethylamine (19 μL), benzylamine (12 μL), EDC hydrochloride (21 mg) and HOBt monohydrate (16 mg), and the reaction mixture was stirred at room temperature overnight. 1.0 mol/L Hydrochloric acid was added, and the mixture was extracted twice with ethyl acetate. The organic layer was washed with saturated brine, dried over anhydrous sodium sulfate, filtered and concentrated. The obtained residue was dissolved in a mixture (0.72 mL) of trifluoroacetic acid/water/triethylsilane=90/5/5 (v/v), and the reaction mixture was stirred at 80° C. for 4 days, cooled to room temperature, and concentrated. The residue was purified by silica gel column chromatography (solvent; ethyl acetate/methanol=100/0-90/10). To the obtained product was added hexane-diethyl ether mixed solvent (1:1), and the solid was collected by filtration to give the title compound (16.0 mg).

MS (ESI) m/z; 423 [M+H]$^+$

Example 618

(R)-N-benzyl-1-[4-oxo-6-(propan-2-yl)-7-trifluoromethyl-4,5-dihydro[1,3]thiazolo[4,5-c]pyridin-2-yl]pyrrolidine-2-carboxamide

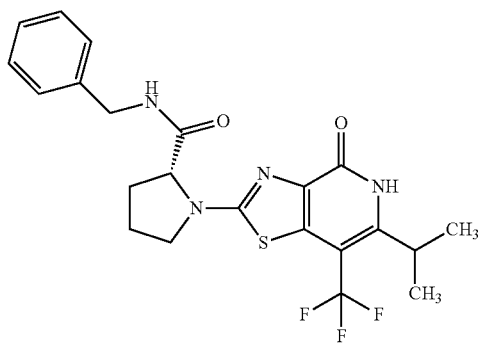 [SMILES: CC(C)c1[nH]c(=O)c2nc(N3CCC[C@@H]3C(=O)NCc3ccccc3)sc2c1C(F)(F)F]

To a solution (1.9 mL) of the compound (77.0 mg) obtained in Reference Example 737 in DMF were added potassium carbonate (63 mg) and 4-methoxybenzyl chloride (37 μL), and the reaction mixture was stirred with heating at 80° C. for 2 hr. The reaction mixture was cooled to 0° C., water was added, and the mixture was extracted twice with ethyl acetate. The organic layer was dried over anhydrous magnesium sulfate, filtered and concentrated. The residue was purified by silica gel column chromatography (solvent; hexane/ethyl acetate=90/10-75/25). To a solution (1.20 mL) of the obtained product (60.0 mg) in DMF were added (D)-proline (23 mg) and cesium carbonate (106 mg), and the reaction mixture was stirred with heating at 70° C. is for 1.5 hr. The reaction mixture was cooled to room temperature, acidified with 1.0 mol/L hydrochloric acid, and extracted twice with chloroform. The organic layer was dried over anhydrous sodium sulfate, filtered and concentrated. To the obtained residue were added N,N-diisopropylethylamine (34 μL), benzylamine (21 μL), EDC hydrochloride (37 mg) and HOBt monohydrate (30 mg), and the reaction mixture was stirred at room temperature overnight. 1 mol/L Hydrochloric acid was added, and the mixture was extracted twice with ethyl acetate. The organic layer was washed with saturated brine, dried over anhydrous sodium sulfate, filtered and concentrated. To a solution (0.70 mL) of the obtained residue in methylene chloride were added trifluoroacetic acid (175 μL) and triethylsilane (42 μL), and the reaction mixture was stirred at room temperature for 1 hr. The reaction mixture was concentrated, and the residue was purified by silica gel column chromatography (solvent; chloroform/methanol=100/0-92/8). To the obtained product was added hexane-diethyl ether mixed solvent (4:1), and the solid was collected by filtration to give the title compound (53.5 mg).

MS (ESI) m/z; 465 [M+H]$^+$

Example 619

(R)-N-benzyl-1-[4-oxo-6-(propan-2-yl)-4,5-dihydro[1,3]thiazolo[4,5-c]pyridin-2-yl]pyrrolidine-2-carboxamide

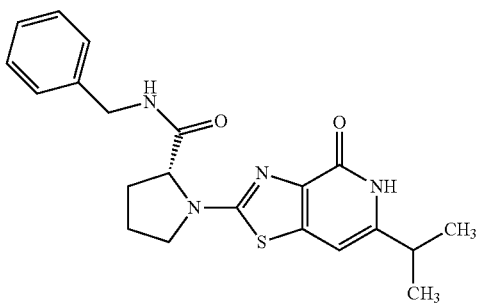 [SMILES: CC(C)c1cc2sc(N3CCC[C@@H]3C(=O)NCc3ccccc3)nc2c(=O)[nH]1]

The compound (261 mg) obtained in Reference Example 738 was treated by a method similar to that in Example 618 to give the title compound (254 mg).

MS (ESI) m/z; 397 [M+H]$^+$

Example 620

(R)-N-benzyl-1-(6-cyclopropyl-4-oxo-4,5-dihydro[1,3]thiazolo[4,5-c]pyridin-2-yl)pyrrolidine-2-carboxamide

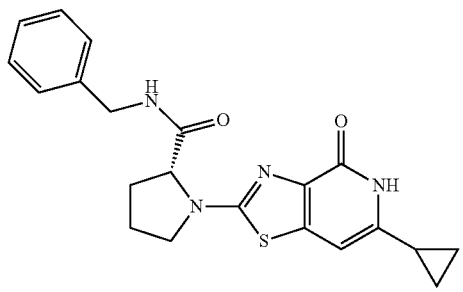 [SMILES: O=C(NCc1ccccc1)[C@H]1CCCN1c1nc2c(=O)[nH]c(C3CC3)cc2s1]

The compound (245 mg) obtained in Reference Example 739 was treated by a method similar to that in Example 618 to give the title compound (143 mg).

MS (ESI) m/z; 395 [M+H]$^+$

Example 621

(R)-N-benzyl-1-[6-(2-fluorophenyl)-4-oxo-4,5-di-hydro[1,3]thiazolo[4,5-c]pyridin-2-yl]pyrrolidine-2-carboxamide

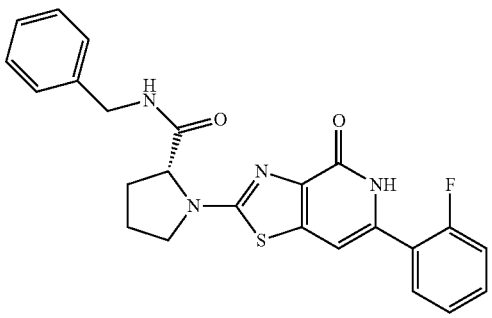 [SMILES: O=C(NCc1ccccc1)[C@H]1CCCN1c1nc2c(=O)[nH]c(-c3ccccc3F)cc2s1]

The compound (158 mg) obtained in Reference Example 740 was treated by a-method similar to that in Example 618 to give the title compound (113 mg)

MS (ESI) m/z; 449 [M+H]$^+$

Example 622

(R)-N-benzyl-1-[7-chloro-4-oxo-6-(propan-2-yl)-4,5-dihydro[1,3]thiazolo[4,5-c]pyridin-2-yl]pyrrolidine-2-carboxamide

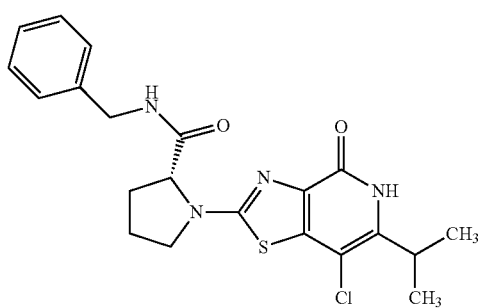 [SMILES: CC(C)c1[nH]c(=O)c2nc(N3CCC[C@@H]3C(=O)NCc3ccccc3)sc2c1Cl]

To a solution (3.3 mL) of the compound (168 mg) obtained in Example 619 in DMF was added a solution (0.5 mL) of N-chlorosuccinimide (85 mg) in DMF at 0° C., and the reaction mixture was stirred at 60° C. for 1 hr. The reaction mixture was allowed to cool to room temperature, aqueous sodium thiosulfate solution was added and the mixture was stirred at room temperature for 10 min, and extracted twice with ethyl acetate. The organic layer was dried over anhydrous sodium sulfate, filtered and concentrated. The residue was purified by silica gel column chromatography (solvent; chloroform/methanol=100/0-95/5). To the obtained product was added hexane-ethyl acetate mixed solvent (1:1), and the solid was collected by filtration to give the title compound (105 mg).

MS (ESI) m/z; 431, 433 [M+H]$^+$

Example 623

(R)-N-benzyl-1-(7-chloro-6-cyclopropyl-4-oxo-4,5-dihydro[1,3]thiazolo[4,5-c]pyridin-2-yl)pyrrolidine-2-carboxamide

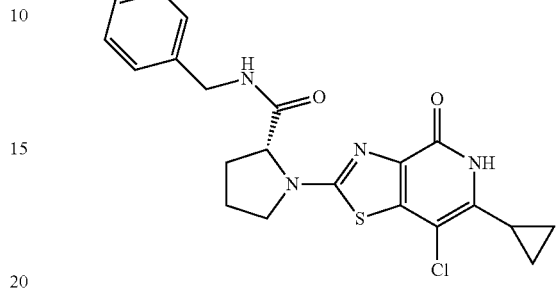

The compound (105 mg) obtained in Example 620 was treated by a method similar to that in Example 622 to give the title compound (25.4 mg).

MS (ESI) m/z; 429, 431 [M+H]$^+$

Example 624

(R)-N-benzyl-1-[7-chloro-6-(2-fluorophenyl)-4-oxo-4,5-dihydro[1,3]thiazolo[4,5-c]pyridin-2-yl]pyrrolidine-2-carboxamide

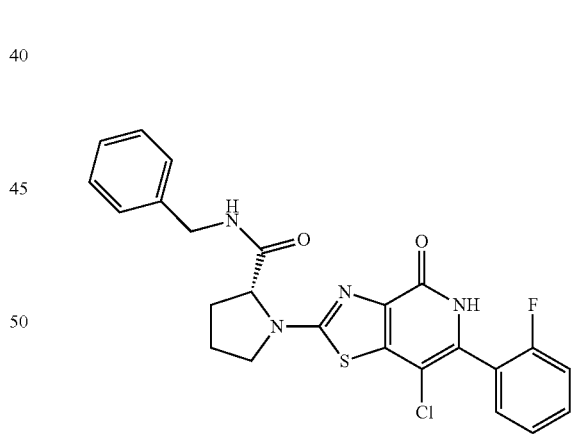

The compound (110 mg) obtained in Example 621 was treated by a method similar to that in Example 622 to give the title compound (45.1 mg).

MS (ESI) m/z; 483, 485 [M+H]$^+$

Example 625

(R)-N-benzyl-1-[6-(2-fluoropropan-2-yl)-4-oxo-4,5-dihydro[1,3]thiazolo[4,5-c]pyridin-2-yl]pyrrolidine-2-carboxamide

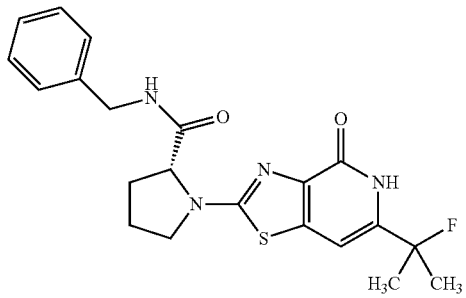 [SMILES: CC(C)(F)c1cc2sc(N3CCC[C@@H]3C(=O)NCc3ccccc3)nc2c(=O)[nH]1]

To a solution (4.8 mL) of the compound (130 mg) obtained in Reference Example 747 in methylene chloride were added trifluoroacetic acid (480 μL) and triethylsilane (77 μL), and the reaction mixture was stirred at room temperature for 1.5 hr. Hexane was added, and the precipitated solid was collected by filtration. The obtained solid was purified by NH silica gel column chromatography (solvent; ethyl acetate/methanol=99/1-88/12). To the obtained product was added hexane-ethyl acetate mixed solvent (2:1), and the solid was collected by filtration, and dried to give the title compound (60.9 mg).

MS (ESI) m/z; 415 [M+H]$^+$

Example 626

(R)-N-benzyl-1-[7-chloro-6-(2-fluoropropan-2-yl)-4-oxo-4,5-dihydro[1,3]thiazolo[4,5-c]pyridin-2-yl]pyrrolidine-2-carboxamide

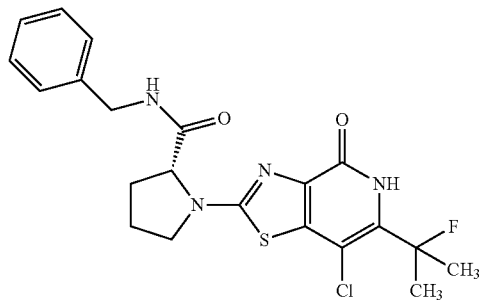 [SMILES: CC(C)(F)c1[nH]c(=O)c2nc(N3CCC[C@@H]3C(=O)NCc3ccccc3)sc2c1Cl]

The compound (52 mg) obtained in Example 625 was treated by a method similar to that in Example 622 to give the title compound (25.5 mg).

MS (ESI) m/z; 449, 451 [M+H]$^+$

Example 627

(R)-N-benzyl-1-[6-(1-ethoxyvinyl)-5-(4-methoxybenzyl)-4-oxo-4,5-dihydro[1,3]thiazolo[4,5-c]pyridin-2-yl]pyrrolidine-2-carboxamide

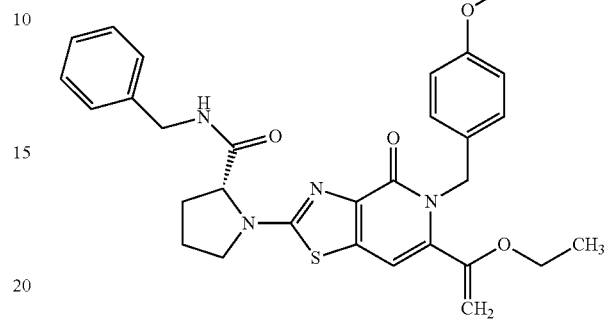

To a solution (1.3 mL) of the compound (62 mg) obtained in Reference Example 133 in chloroform were added N,N-diisopropylethylamine (36 μL), benzylamine (22 μL), EDC hydrochloride (39 mg) and HOBt monohydrate (31 mg), and the reaction mixture was stirred at room temperature for 20 hr. Water was added, and the mixture was extracted twice with chloroform. The organic layer was dried over anhydrous sodium sulfate, filtered and concentrated. The residue was purified by silica gel column chromatography (solvent; ethyl acetate/methanol=100/0-95/5) to give the title compound (45.1 mg).

MS (ESI) m/z; 545 [M+H]$^+$

Example 628

(R)-N-benzyl-1-[6-(1-ethoxycyclopropyl)-5-(4-methoxybenzyl)-4-oxo-4,5-dihydro[1,3]thiazolo[4,5-c]pyridin-2-yl]pyrrolidine-2-carboxamide

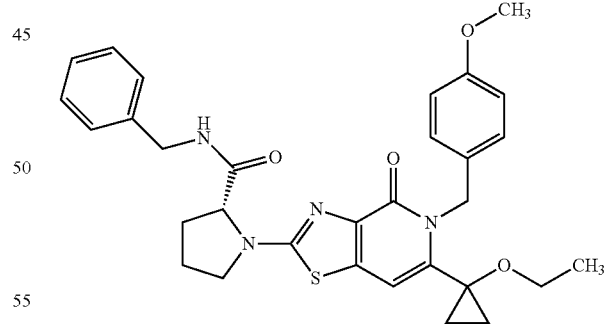

(1) To a solution (0.5 mL) of methyl iodide (106 mg) in toluene was added diethylzinc (1.0 mol/L toluene solution, 287 μL) at 0° C., and the reaction mixture was stirred at the same temperature for 10 min. A solution (0.5 mL) of the compound (43 mg) obtained in Example 627 in toluene was added, and the reaction mixture was stirred with heating at 50° C. for 12 hr. Dichloroethane (0.5 mL) was further added, and the reaction mixture was stirred with heating at 70° C. for 12 hr. The reaction mixture was cooled to 0° C., methylene iodide (106 mg) and diethylzinc (1.0 mol/L toluene solution, 287 µL) were added, and the reaction mixture was stirred with heating at 50° C. for 12 hr.

(2) Separately, to diethyl zinc (1.0 mol/L toluene solution, 215 µL) was added trifluoroacetic acid (18 µL) at 0° C., and the mixture was stirred for 15 min, and methylene iodide (63 mg) was added to give a mixture. The mixture was added to the reaction mixture described in (1) at 0° C. The reaction mixture was stirred at room temperature for 16 hr, saturated aqueous sodium hydrogen carbonate solution and chloroform were added at 0° C., and the mixture was filtered through diatomaceous earth. The filtrate was extracted twice with chloroform, and the organic layer was dried over anhydrous sodium sulfate, filtered and concentrated. The residue was purified by silica gel column chromatography (solvent; ethyl acetate/methanol=100/0-95/5) to give the title compound (14.0 mg).

MS (ESI) m/z; 559 [M+H]$^+$

Example 629

(R)-N-benzyl-1-[6-(1-ethoxycyclopropyl)-4-oxo-4,5-dihydro[1,3]thiazolo[4,5-c]pyridin-2-yl]pyrrolidine-2-carboxamide

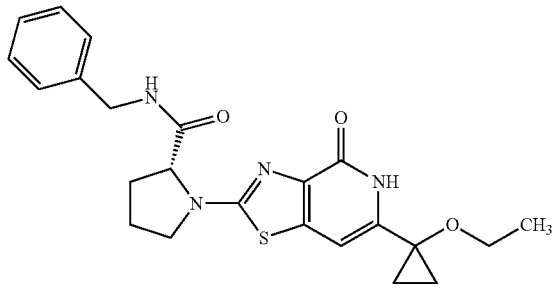 [SMILES: CCOC1(c2cc3sc(N4CCC[C@@H]4C(=O)NCc4ccccc4)nc3c(=O)[nH]2)CC1]

The compound (14 mg) obtained in Example 628 was dissolved in a mixture (556 µL) of trifluoroacetic acid/water/triethylsilane=90/5/5 (v/v), and the mixture was stirred at 60° C. for 6 days, cooled to room temperature, and concentrated. The residue was purified by silica gel column chromatography (solvent; ethyl acetate/methanol=100/0-88/12) to give the title compound (2.5 mg).

MS (ESI) m/z; 439 [M+H]$^+$

Example 630

(R)-N-benzyl-1-(4-oxo-6-trifluoromethyl-4,5-dihydro[1,3]thiazolo[4,5-c]pyridin-2-yl)pyrrolidine-2-carboxamide

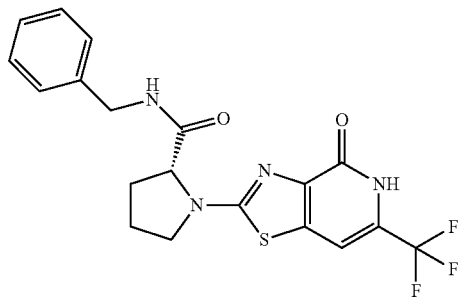 [SMILES: O=C(NCc1ccccc1)[C@H]1CCCN1c1nc2c(=O)[nH]c(C(F)(F)F)cc2s1]

(1) To a mixture (2 mL) of the compound (180 mg) obtained in Reference Example 754 and potassium carbonate (296 mg) in DMF was added 4-methoxybenzyl bromide (229 µL), and the reaction mixture was stirred at room temperature for 1.5 hr. Water was added to the reaction mixture, and the mixture was extracted twice with ethyl acetate. The combined organic layer was washed with saturated brine, dried over anhydrous sodium sulfate, filtered and concentrated. The residue was purified by silica gel column chromatography (solvent; hexane/ethyl acetate=90/10-70/30) to give a product (314 mg).

(2) The obtained product was dissolved in methylene chloride (9 mL), and mCPBA (69-75%, 172 mg) was added under ice-cooling. The reaction mixture was stirred under ice-cooling for 1 hr, aqueous sodium thiosulfate solution and saturated aqueous sodium hydrogen carbonate solution were added, and the mixture was extracted twice with methylene chloride. The aqueous layer was filtered through diatomaceous earth, and extracted twice with methylene chloride. The combined organic layer was dried over anhydrous sodium sulfate, filtered and concentrated. To the residue was added hexane/ethyl acetate=4/1, and the solid was collected by filtration, crude product (278 mg).

(3) The obtained crude product was dissolved in N-methylpyrrolidone (6 mL), (D)-proline (125 mg) and potassium carbonate (224 mg) were added, and the reaction mixture was stirred with heating at 90° C. for 3 hr. The reaction mixture was cooled to room temperature, diluted with chloroform, and acidified with 1.0 mol/L hydrochloric acid. Saturated brine was added, and the mixture was extracted twice with chloroform. The combined organic layer was washed with saturated brine, dried over anhydrous sodium sulfate, filtered and concentrated. To a solution of the obtained residue in N-methylpyrrolidone were added N,N-diisopropylethylamine (141 µL), benzylamine (89 µL), EDC hydrochloride (156 mg) and HOBt monohydrate (124 mg), and the reaction mixture was stirred at room temperature for 21 hr. Water was added to the reaction mixture, and the mixture was extracted twice with ethyl acetate. The combined organic layer was washed with saturated brine, dried over anhydrous sodium sulfate, filtered and concentrated. The residue was purified by silica gel column chromatography (solvent; hexane/ethyl acetate=70/30-35/75) to give a product (233 mg).

(4) The obtained product was dissolved in a mixture (4.0 mL) of trifluoroacetic acid/water/triethylsilane=90/5/5 (v/v), and the mixture was stirred with heating at 50° C. for 1.5 hr. The reaction mixture was concentrated and the residue was purified by silica gel column chromatography (solvent; hexane/ethyl acetate=40/60-0/100), to the obtained product was added diethyl ether, and the solid was collected by filtration to give the title compound (166 mg).

MS (ESI) m/z; 423 [M+H]$^+$

Example 631

(R)-N-benzyl-1-(5-methyl-4-oxo-6-trifluoromethyl-4,5-dihydro[1,3]thiazolo[4,5-c]pyridin-2-yl)pyrrolidine-2-carboxamide

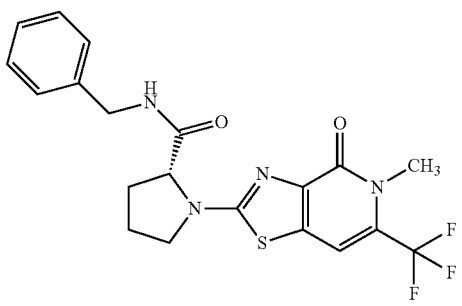 [SMILES: Cn1c(C(F)(F)F)cc2sc(N3CCC[C@@H]3C(=O)NCc3ccccc3)nc2c1=O]

To a solution (1.5 mL) of the compound (60 mg) obtained in Example 630 in DMF was added potassium carbonate (29 mg), iodomethane (13 μL) was added under ice-cooling, and the reaction mixture was stirred at room temperature for 4 hr. To the reaction mixture were added saturated aqueous ammonium chloride solution and water, and the mixture was extracted twice with ethyl acetate. The combined organic layer was washed with saturated brine, dried over anhydrous sodium sulfate, filtered and concentrated under reduced pressure. The obtained residue was purified by NH silica gel column chromatography (solvent; hexane/ethyl acetate=60/40-0/100) to give the title compound (24 mg).

MS (ESI) m/z; 437 [M+H]$^+$

Example 632

(R)-N-benzyl-1-(7-chloro-4-oxo-6-trifluoromethyl-4,5-dihydro[1,3]thiazolo[4,5-c]pyridin-2-yl)pyrrolidine-2-carboxamide

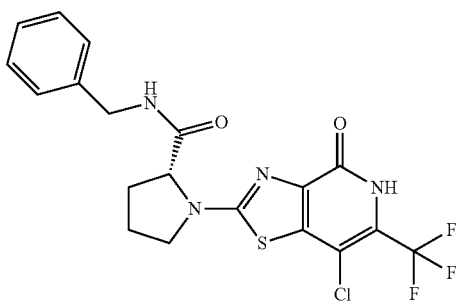 [SMILES: O=C(NCc1ccccc1)[C@H]1CCCN1c1nc2c(=O)[nH]c(C(F)(F)F)c(Cl)c2s1]

(1) To a mixture (1.8 mL) of the compound (195 mg) obtained in Reference Example 756 and potassium carbonate (179 mg) in DMF was added 4-methoxybenzyl chloride (106 μL), and the reaction mixture was stirred with heating at 70° C. for 2.5 hr. Water was added to the reaction mixture, and the mixture was extracted twice with ethyl acetate. The combined organic layer was washed with saturated brine, dried over anhydrous sodium sulfate, filtered and concentrated. The residue was purified by silica gel column chromatography (solvent; hexane/ethyl acetate=92/8-80/20) to give a product (238 mg).

(2) The obtained product was dissolved in methylene chloride (7.5 mL), mCPBA (69-75%, 151 mg) was added under ice-cooling, and the reaction mixture was stirred under ice-cooling for 1.5 hr. Aqueous sodium thiosulfate solution and saturated aqueous sodium hydrogen carbonate solution were added, and the mixture was extracted twice with methylene chloride. The combined organic layer was washed with saturated brine, dried over anhydrous sodium sulfate, filtered and concentrated to give a crude product (234 mg).

(3) The obtained product was dissolved in DMF (5.8 mL), (D)-proline (121 mg) and potassium carbonate (218 mg) were added, and the reaction mixture was stirred with heating at 85° C. for 3.5 hr. The reaction mixture was ice-cooled, diluted with chloroform, acidified with 1.0 mol/L hydrochloric acid, and extracted twice with chloroform. The combined organic layer was dried over anhydrous sodium sulfate, and filtered. Chloroform was evaporated under reduced pressure from the filtrate, to the obtained mixture were added N,N-diisopropylethylamine (138 μL), benzylamine (86 μL), EDC hydrochloride (151 mg) and HOBt monohydrate (121 mg), and the reaction mixture was stirred at room temperature for 18 hr. Water was added to the reaction mixture, and the mixture was extracted twice with ethyl acetate. The combined organic layer was washed with saturated brine, dried over anhydrous sodium sulfate, filtered and concentrated. The residue was purified by silica gel column chromatography (solvent; hexane/ethyl acetate=70/30-30/70) to give a product (263 mg).

(4) The obtained product was dissolved in a mixture (3.2 mL) of trifluoroacetic acid/water/triethylsilane=90/5/5 (v/v), and stirred with heating at 50° C. for 1 hr. The reaction mixture was concentrated, and the obtained residue was purified by silica gel column chromatography (solvent; hexane/ethyl acetate=40/60-0/100). To the obtained product was added hexane/ethyl acetate=3/1, and the solid was collected by filtration to give the title compound (187 mg).

MS (ESI) m/z; 457 [M+H]$^+$

Example 633

(R)-N-benzyl-1-(7-cyclopropyl-4-oxo-6-trifluoromethyl-4,5-dihydro[1,3]thiazolo[4,5-c]pyridin-2-yl)pyrrolidine-2-carboxamide

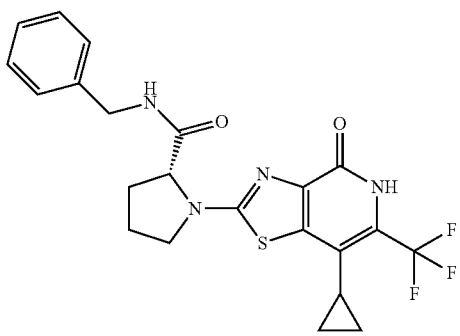 [SMILES: O=C(NCc1ccccc1)[C@H]1CCCN1c1nc2c(=O)[nH]c(C(F)(F)F)c(C3CC3)c2s1]

(1) To a mixture (5.2 mL) of the compound (720 mg) obtained in Reference Example 757 and potassium carbonate (508 mg) in DMF was added 4-methoxybenzyl bromide (300 μL), and the reaction mixture was stirred at room temperature for 30 min and stirred with heating at 70° C. for 3 hr. The reaction mixture was ice-cooled, neutralized with 1.0 mol/L hydrochloric acid and diluted with water. The precipitated solid was filtered, and washed with water. The obtained solid was dissolved in chloroform/methanol=10/1, and the obtained solution was dried over anhydrous sodium sulfate, filtered and concentrated under reduced pressure. To the obtained solid were added hexane/diethyl ether=5/1, and the solid was collected by filtration to give a product (888 mg).

(2) The obtained product (400 mg) was dissolved in 1,4-dioxane (4 mL), cyclopropylboronic acid (201 mg), dichlorobis(tricyclohexylphosphine)palladium(II) (115 mg), cesium carbonate (763 mg) were successively added, and the reaction mixture was heated under reflux for 6 hr. After confirmation of the completion of the reaction, the reaction mixture was cooled to room temperature, diluted with ethyl acetate and filtered through diatomaceous earth. The filtrate was washed successively with water and saturated brine, dried over anhydrous sodium sulfate, filtered and concentrated. The obtained residue was purified by silica gel column chromatography (solvent; hexane/ethyl acetate=98/2-90/10) to give a product (234 mg).

(3) The obtained product was dissolved in methylene chloride (7 mL), mCPBA (69-75%, 140 mg) was added under ice-cooling, and the reaction mixture was stirred under ice-cooling for 1.5 hr. Aqueous sodium thiosulfate solution and saturated aqueous sodium hydrogen carbonate solution were added, and the mixture was extracted twice with methylene chloride. The combined organic layer was washed with saturated brine, dried over anhydrous sodium sulfate, filtered and concentrated to give a crude product (193 mg).

(4) The obtained product was dissolved in DMF (4.5 mL), (D)-proline (95 mg) and potassium carbonate (171 mg) were added, and the reaction mixture was stirred with heating at 90° C. for 2.5 hr. The reaction mixture was ice-cooled, diluted with chloroform, acidified with 1.0 mol/L hydrochloric acid, and extracted twice with chloroform. The combined organic layer was dried over anhydrous sodium sulfate, and filtered. Chloroform was evaporated under reduced pressure from the filtrate, to the obtained mixture were added N,N-diisopropylethylamine (108 µL), benzylamine (68 µL), EDC hydrochloride (118 mg) and HOBt monohydrate (95 mg), and the reaction mixture was stirred at room temperature for 16 hr. Water was added to the reaction mixture, and the mixture was extracted twice with ethyl acetate. The combined organic layer was washed with saturated brine, dried over anhydrous sodium sulfate, filtered and concentrated. The residue was purified by silica gel column chromatography (solvent; hexane/ethyl acetate=80/20-40/60) to give a product (195 mg).

(5) The obtained product was dissolved in a mixture (3.2 mL) of trifluoroacetic acid/water/triethylsilane=90/5/5 (v/v), and stirred with heating at 50° C. for 1.5 hr. The reaction mixture was concentrated, and the obtained residue was purified by silica gel column chromatography (solvent; hexane/ethyl acetate=40/60-0/100). To the obtained product was added hexane/ethyl acetate=5/1, and the solid was collected by filtration to give the title compound (130 mg).

MS (ESI) m/z; 463 [M+H]$^+$

Example 634

(R)-N-benzyl-1-(5-oxo-7-propyl-5H-[1,3,4]thiadiazolo[3,2-a]pyrimidin-2-yl)pyrrolidine-2-carboxamide

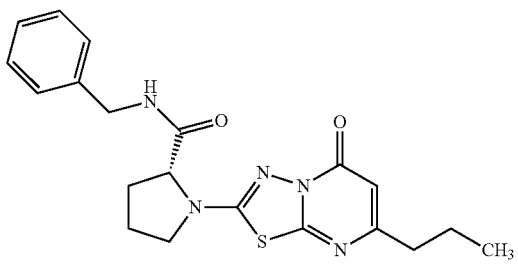 [SMILES: CCCc1cc(=O)n2nc(N3CCC[C@@H]3C(=O)NCc3ccccc3)sc2n1]

A mixture of the compound (1.38 g) obtained in Reference Example 763, the compound (1.21 g) obtained in Reference Example 341 and triethylamine (1.6 g) in THF (100 mL) was stirred with heating at 100° C. for 1 hr. After confirmation of the completion of the reaction, water (20 mL) were added to the reaction mixture, and the mixture was extracted twice with ethyl acetate. The organic layer was washed once with water, dried over anhydrous magnesium sulfate, filtered and concentrated. The residue was purified by silica gel column chromatography (solvent; ethyl acetate/methanol=100/0-90/10). To the obtained product was added diisopropyl ether, and the solid was collected by filtration to give the title compound (1.7 g).

MS (ESI) m/z; 398 [M+H]$^+$

Example 635

(R)-N-benzyl-1-(5-oxo-7-propyl-5H-[1,3,4]thiadiazolo[3,2-a]pyrimidin-2-yl) piperidine-2-carboxamide

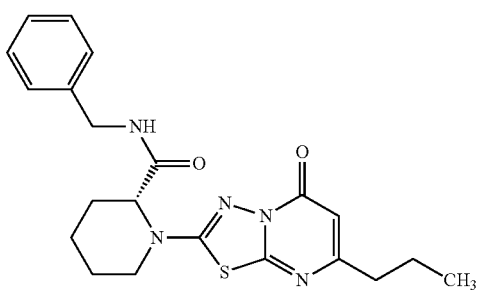 [SMILES: CCCc1cc(=O)n2nc(N3CCCC[C@@H]3C(=O)NCc3ccccc3)sc2n1]

The compound (600 mg) obtained in Reference Example 763 was treated by a method similar to that in Example 634 to give the title compound (298 mg).

MS (ESI) m/z; 412 [M+H]$^+$

Example 636

(R)-1-(7-methyl-5-oxo-5H-[1,3,4]thiadiazolo[3,2-a]pyrimidin-2-yl)-N-(1-methyl-1-phenylethyl)pyrrolidine-2-carboxamide

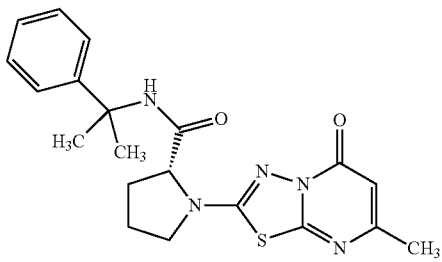 [SMILES: Cc1cc(=O)n2nc(N3CCC[C@@H]3C(=O)NC(C)(C)c3ccccc3)sc2n1]

The compound (870 mg) obtained in Reference Example 764 was treated by a method similar to that in Example 634 to give the title compound (840 mg).
MS (ESI) m/z; 398 [M+H]$^+$

Example 637

(R)-N-benzyl-1-(7-ethyl-5-oxo-5H-[1,3,4]thiadiazolo[3,2-a]pyrimidin-2-yl)pyrrolidine-2-carboxamide

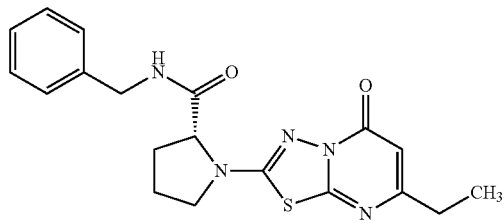 [SMILES: CCc1cc(=O)n2nc(N3CCC[C@@H]3C(=O)NCc3ccccc3)sc2n1]

The compound (150 mg) obtained in Reference Example 765 was treated by a method similar to that in Example 634 to give the title compound (187 mg).
MS (ESI) m/z; 384 [M+H]$^+$

Example 638

(R)-N-benzyl-1-(5-oxo-7-phenyl-5H-[1,3,4]thiadiazolo[3,2-a]pyrimidin-2-yl)pyrrolidine-2-carboxamide

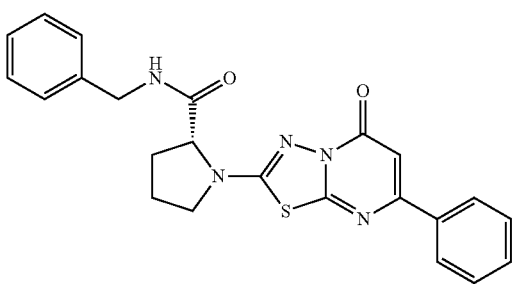 [SMILES: O=C(NCc1ccccc1)[C@H]1CCCN1c1nn2c(=O)cc(-c3ccccc3)nc2s1]

The compound (150 mg) obtained in Reference Example 766 was treated by a method similar to that in Example 634 to give the title compound (158 mg).
MS (ESI) m/z; 432 [M+H]$^+$

Example 639

(R)-N-benzyl-1-(5-oxo-6,7,8,9-tetrahydro-5H-[1,3,4]thiadiazolo[2,3-b]quinazolin-2-yl)pyrrolidine-2-carboxamide

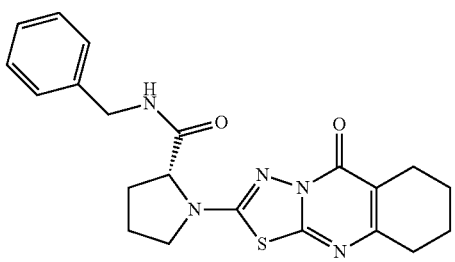 [SMILES: O=C(NCc1ccccc1)[C@H]1CCCN1c1nn2c(=O)c3c(nc2s1)CCCC3]

The compound (400 mg) obtained in Reference Example 770 was treated by a method similar to that in Example 634 to give the title compound (400 mg).
MS (ESI) m/z; 410 [M+H]$^+$

Example 640

(R)-N-benzyl-1-(6-fluoro-5-oxo-7-propyl-5H-[1,3,4]thiadiazolo[3,2-a]pyrimidin-2-yl)pyrrolidine-2-carboxamide

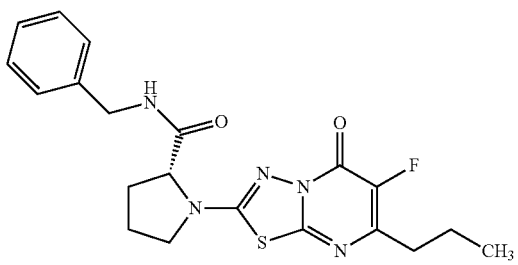 [SMILES: CCCc1nc2sc(N3CCC[C@@H]3C(=O)NCc3ccccc3)nn2c(=O)c1F]

The compound (400 mg) obtained in Reference Example 772 was treated by a method similar to that in Example 634 to give the title compound (424 mg).
MS (ESI) m/z; 416 [M+H]$^+$

Example 641

(R)-N-benzyl-1-(6-fluoro-5-oxo-7-propyl-5H-[1,3,4]thiadiazolo[3,2-a]pyrimidin-2-yl)piperidine-2-carboxamide

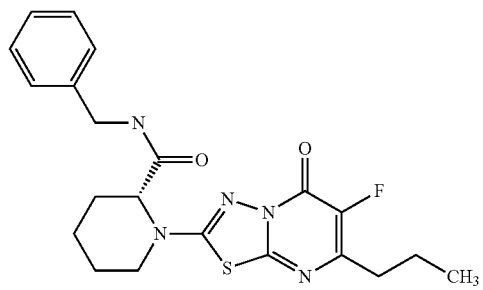 [SMILES: CCCc1nc2sc(N3CCCC[C@@H]3C(=O)NCc3ccccc3)nn2c(=O)c1F]

The compound (400 mg) obtained in Reference Example 772 was treated by a method similar to that in Example 634 to give the title compound (367 mg).
MS (ESI) m/z; 430 [M+H]$^+$

Example 642

(R)-N-benzyl-1-(5-oxo-7-trifluoromethyl-5H-[1,3,4]thiadiazolo[3,2-a]pyrimidin-2-yl)pyrrolidine-2-carboxamide

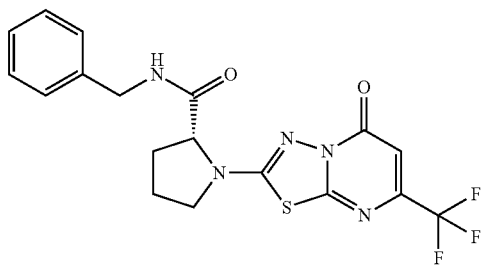 [SMILES: O=C(NCc1ccccc1)[C@H]1CCCN1c1nn2c(=O)cc(C(F)(F)F)nc2s1]

The compound (150 mg) obtained in Reference Example 774 was treated by a method similar to that in Example 634 to give the title compound (159 mg).
MS (ESI) m/z; 424 [M+H]$^+$

Example 643

(R)-N-benzyl-1-(5-oxo-5H-[1,3,4]thiadiazolo[2,3-b]quinazolin-2-yl)pyrrolidine-2-carboxamide

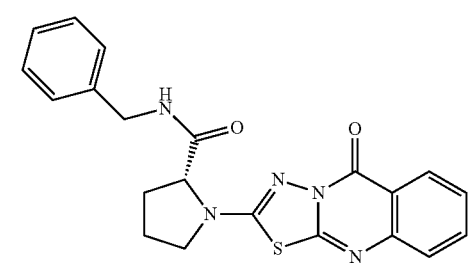 [SMILES: O=C(NCc1ccccc1)[C@H]1CCCN1c1nn2c(=O)c3ccccc3nc2s1]

The compound (300 mg) obtained in Reference Example 775 was treated by a method similar to that in Example 634 to give the title compound (300 mg).
MS (ESI) m/z; 406 [M+H]$^+$

Example 644

(R)-N-benzyl-1-(6-chloro-7-ethyl-5-oxo-5H-[1,3,4]thiadiazolo[3,2-a]pyrimidin-2-yl)piperidine-2-carboxamide

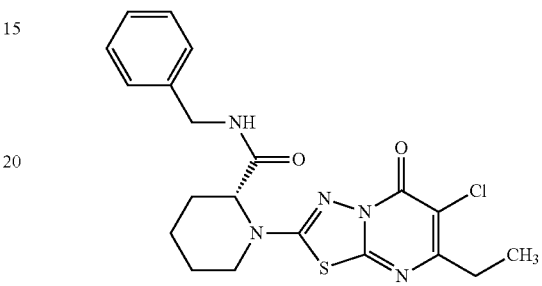

To a solution (1.5 mL) of the compound (0.29 g) obtained in Reference Example 778 in THF were added the compound (0.25 g) obtained in Reference Example 758 and N,N-diisopropylethylamine (0.51 mL), and the reaction mixture was heated under reflux for 10 hr. After confirmation of the completion of the reaction, water was added to the reaction mixture, and the mixture was extracted twice with chloroform. The organic layer was dried over anhydrous magnesium sulfate, filtered and concentrated and the residue was purified by NH silica gel column chromatography (solvent; hexane/ethyl acetate=80/20-0/100). To the obtained product was added diisopropyl ether, and the solid was collected by filtration to give the title compound (0.21 g).
MS (ESI) m/z; 432 [M+H]$^+$

Example 645

(R)-N-benzyl-4-(7-ethyl-5-oxo-5H-[1,3,4]thiadiazolo[3,2-a]pyrimidin-2-yl)morpholine-3-carboxamide

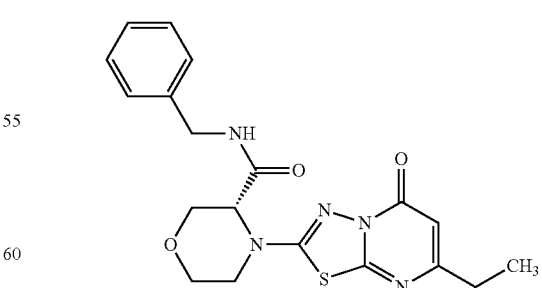

The compound (101 mg) obtained in Reference Example 765 was treated by a method similar to that in Example 644 to give the title compound (63.0 mg).
MS (ESI) m/z; 400 [M+H]$^+$

Example 646

(R)-N-benzyl-1-(6,7-dimethyl-5-oxo-5H-[1,3,4]thiadiazolo[3,2-a]pyrimidin-2-yl)pyrrolidine-2-carboxamide

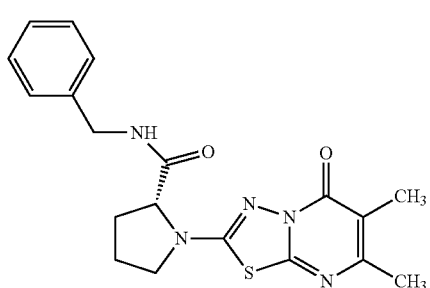

The compound (200 mg) obtained in Reference Example 767 was treated by a method similar to that in Example 644 to give the title compound (185 mg).

MS (ESI) m/z; 384 [M+H]$^+$

Example 647

(R)-N-benzyl-1-[7-methyl-5-oxo-6-(propan-2-yl)-5H-[1,3,4]thiadiazolo[3,2-a]pyrimidin-2-yl]pyrrolidine-2-carboxamide

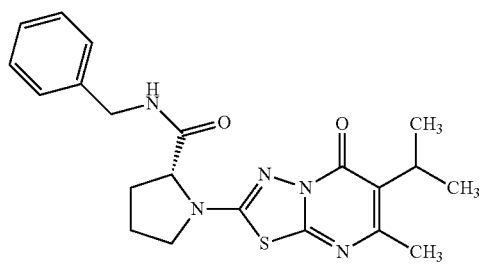 [SMILES: Cc1nc2sc(N3CCC[C@@H]3C(=O)NCc3ccccc3)nn2c(=O)c1C(C)C]

The compound (300 mg) obtained in Reference Example 768 was treated by a method similar to that in Example 644 to give the title compound (319 mg).

MS (ESI) m/z; 412 [M+H]$^+$

Example 648

(R)-N-benzyl-1-(7-methyl-5-oxo-6-phenyl-5H-[1,3,4]thiadiazolo[3,2-a]pyrimidin-2-yl)pyrrolidine-2-carboxamide

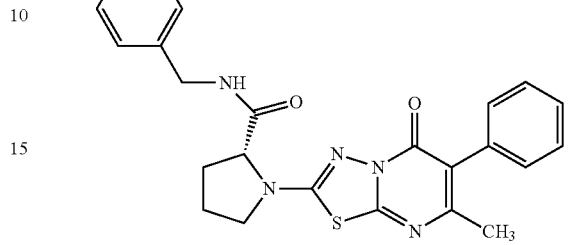

The compound (150 mg) obtained in Reference Example 769 was treated by a method similar to that in Example 644 to give the title compound (130 mg).

MS (ESI) m/z; 446 [M+H]$^+$

Example 649

(R)-N-benzyl-1-(7-ethyl-6-fluoro-5-oxo-5H-[1,3,4]thiadiazolo[3,2-a]pyrimidin-2-yl)pyrrolidine-2-carboxamide

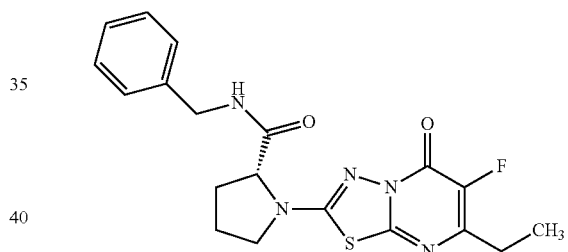

The compound (500 mg) obtained in Reference Example 771 was treated by a method similar to that in Example 644 to give the title compound (570 mg).

MS (ESI) m/z; 402 [M+H]$^+$

Example 650

(R)-N-benzyl-1-(7-ethyl-6-fluoro-5-oxo-5H-[1,3,4]thiadiazolo[3,2-a]pyrimidin-2-yl)-4,4-difluoropyrrolidine-2-carboxamide

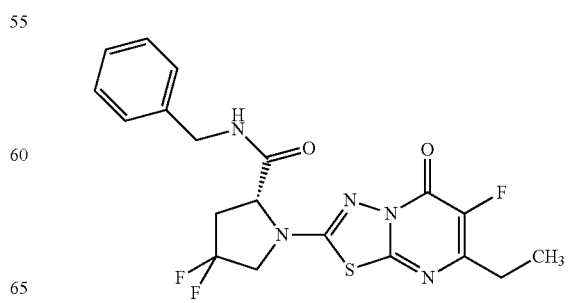

The compound (184 mg) obtained in Reference Example 771 was treated by a method similar to that in Example 644 to give the title compound (109 mg).

MS (ESI) m/z; 438 [M+H]$^+$

Example 651

(R)-1-(6-fluoro-5-oxo-7-propyl-5H-[1,3,4]thiadiazolo[3,2-a]pyrimidin-2-yl)-N-(1-phenylcyclopropyl)pyrrolidine-2-carboxamide

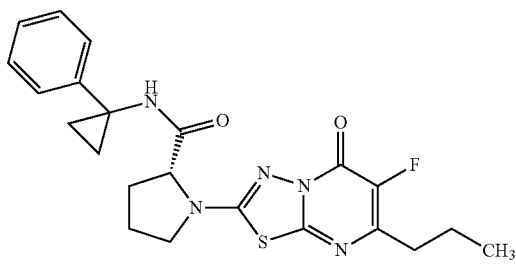 [SMILES: CCCc1nc2sc(N3CCC[C@@H]3C(=O)NC3(c4ccccc4)CC3)nn2c(=O)c1F]

The compound (200 mg) obtained in Reference Example 772 was treated by a method similar to that in Example 644 to give the title compound (141 mg).

MS (ESI) m/z; 442 [M+H]$^+$

Example 652

(R)-N-benzyl-1-[5-oxo-7-(propan-2-yl)-5H-[1,3,4]thiadiazolo[3,2-a]pyrimidin-2-yl]pyrrolidine-2-carboxamide

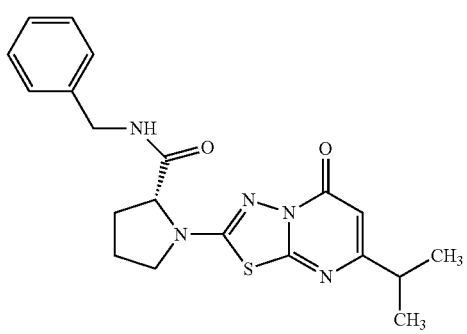 [SMILES: CC(C)c1cc(=O)n2nc(N3CCC[C@@H]3C(=O)NCc3ccccc3)sc2n1]

The compound (1.90 g) obtained in Reference Example 773 was treated by a method similar to that in Example 644 to give the title compound (1.83 g).

MS (ESI) m/z; 398 [M+H]$^+$

Example 653

(R)-1-[5-oxo-7-(propan-2-yl)-5H-[1,3,4]thiadiazolo[3,2-a]pyrimidin-2-yl]-N-[(pyridin-2-yl)methyl]pyrrolidine-2-carboxamide

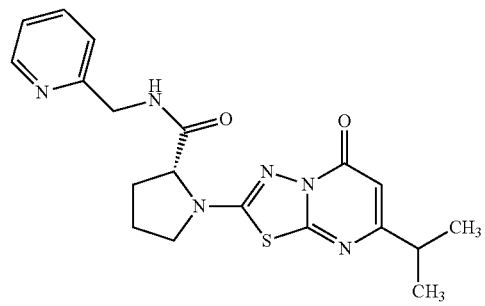 [SMILES: CC(C)c1cc(=O)n2nc(N3CCC[C@@H]3C(=O)NCc3ccccn3)sc2n1]

The compound (342 mg) obtained in Reference Example 773 was treated by a method similar to that in Example 644 to give the title compound (432 mg).

MS (ESI) m/z; 399 [M+H]$^+$

Example 654

(R)-1-(5-oxo-5H-[1,3,4]thiadiazolo[2,3-b]quinazolin-2-yl)-N-[(pyridin-2-yl)methyl]pyrrolidine-2-carboxamide

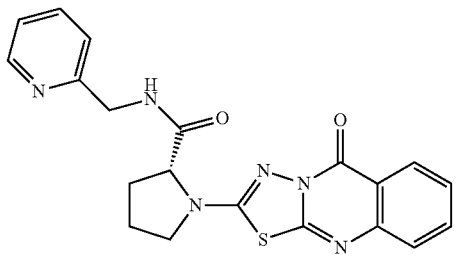 [SMILES: O=C(NCc1ccccn1)[C@H]1CCCN1c1nn2c(=O)c3ccccc3nc2s1]

The compound (200 mg) obtained in Reference Example 775 was treated by a method similar to that in Example 644 to give the title compound (240 mg).

MS (ESI) m/z; 407 [M+H]$^+$

Example 655

(R)-1-(5-oxo-5H-[1,3,4]thiadiazolo[2,3-b]quinazolin-2-yl)-N-(1-phenylcyclopropyl)pyrrolidine-2-carboxamide The compound (200 mg) obtained in Reference Example 775 was treated by a method similar to that in Example 644 to give the title compound (223 mg).
MS (ESI) m/z; 432 [M+H]+

Example 656

(R)-N-benzyl-1-(6-methyl-8-oxo-8H-[1,3,4]thiadiazolo[3,2-a]thieno[2,3-d]pyrimidin-2-yl)pyrrolidine-2-carboxamide

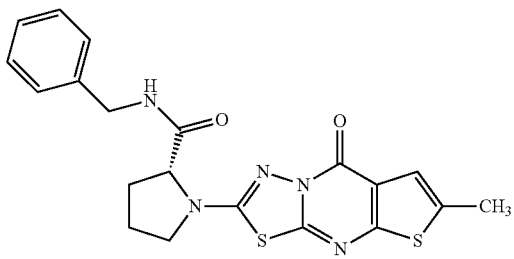 [SMILES: Cc1cc2c(=O)n3nc(N4CCC[C@@H]4C(=O)NCc4ccccc4)sc3nc2s1]

The compound (300 mg) obtained in Reference Example 776 was treated by a method similar to that in Example 644 to give the title compound (356 mg).
MS (ESI) m/z; 426 [M+H]+

Example 657

(R)-N-benzyl-1-(6-chloro-7-methyl-5-oxo-5H-[1,3,4]thiadiazolo[3,2-a]pyrimidin-2-yl)pyrrolidine-2-carboxamide

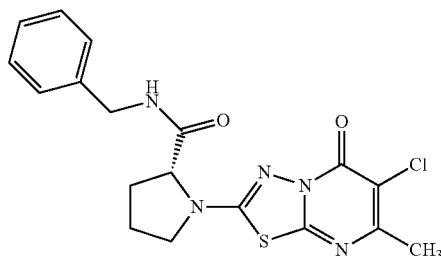

The compound (246 mg) obtained in Reference Example 779 was treated by a method similar to that in Example 644 to give the title compound (278 mg).
MS (ESI) m/z; 404, 406 [M+H]+

Example 658

(R)-N-benzyl-1-[6-chloro-5-oxo-7-(propan-2-yl)-5H-[1,3,4]thiadiazolo[3,2-a]pyrimidin-2-yl]pyrrolidine-2-carboxamide

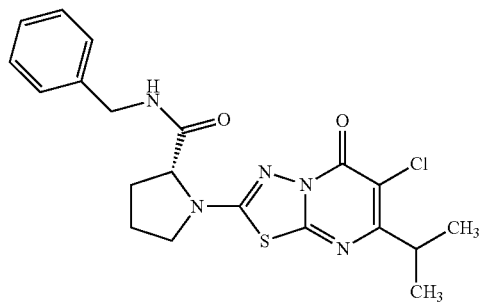

The compound (200 mg) obtained in Reference Example 780 was treated by a method similar to that in Example 644 to give the title compound (227 mg).
MS (ESI) m/z; 432, 434 [M+H]+

Example 659

(R)-N-benzyl-1-[6-chloro-5-oxo-7-(propan-2-yl)-5H-[1,3,4]thiadiazolo[3,2-a]pyrimidin-2-yl]piperidine-2-carboxamide

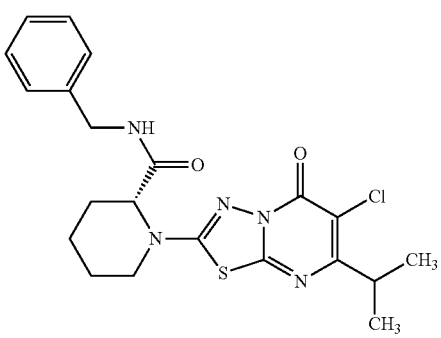 [SMILES: CC(C)c1nc2sc(N3CCCC[C@@H]3C(=O)NCc3ccccc3)nn2c(=O)c1Cl]

The compound (150 mg) obtained in Reference Example 780 was treated by a method similar to that in Example 644 to give the title compound (182 mg).
MS (ESI) m/z; 446, 448 [M+H]+

Example 660

(R)-N-benzyl-1-(9-oxo-9H-pyrido[2,3-d][1,3,4]thiadiazolo[3,2-a]pyrimidin-2-yl)pyrrolidine-2-carboxamide hydrochloride

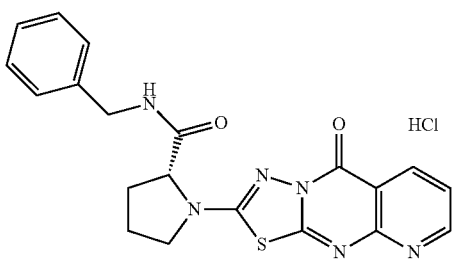 [SMILES: O=C(NCc1ccccc1)[C@H]1CCCN1c1nn2c(=O)c3cccnc3nc2s1 ; Cl]

To a solution (5.0 mL) of the compound (0.16 g) obtained in Reference Example 777 in DMF were added the compound (0.14 g) obtained in Reference Example 341 and N,N-diisopropylethylamine (0.23 g), and the reaction mixture was stirred with heating at 80° C. for 1 hr. After confirmation of the completion of the reaction, water was added to the reaction mixture, and the mixture was extracted twice with chloroform. The organic layer was dried over anhydrous magnesium sulfate, filtered and concentrated and the residue was purified by silica gel column chromatography (solvent; chloroform/methanol=100/0-95/5). The obtained product was dissolved in methanol (5 mL), hydrogen chloride (4.0 mol/L ethyl acetate solution, 1.0 mL) was added, and the mixture was stirred at room temperature for 10 min. The solvent was evaporated under reduced pressure, to the obtained product was added ethyl acetate, and the solid was collected by filtration to give the title compound (56 mg).

MS (ESI) m/z; 407 [M+H]$^+$

Example 661

(1SR,2RS,5RS)-N-benzyl-3-(7-methyl-5-oxo-5H-[1,3,4]thiadiazolo[3,2-a]pyrimidin-2-yl)-3-azabicyclo[3.1.0]hexane-2-carboxamide

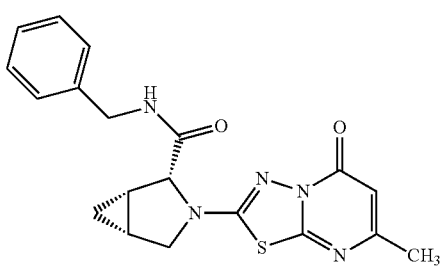 [SMILES: Cc1cc(=O)n2nc(N3C[C@@H]4C[C@@H]4[C@@H]3C(=O)NCc3ccccc3)sc2n1]

To a solution (10 mL) of the compound (0.97 g) obtained in Reference Example 764 in DMF were added cis-3-azabicyclo[3.1.0]hexane-2-carboxylic acid (0.5 g) and triethylamine (1.2 g), and the reaction mixture was stirred with heating at 80° C. for 1 hr, and cooled to room temperature. Benzylamine (0.43 g), EDC hydrochloride (1.13 g), HOBt monohydrate (0.9 g) and N,N-diisopropylethylamine (0.77 g) were added, and the reaction mixture was stirred at 60° C. for 1 hr. After confirmation of the completion of the reaction, water was added to the reaction mixture, and the mixture was extracted twice with ethyl acetate. The organic layer was washed once with saturated aqueous sodium hydrogen carbonate solution, dried over anhydrous magnesium sulfate, filtered and concentrated. The residue was purified by silica gel column chromatography (solvent; chloroform/methanol=100/0-90/10). To the obtained product was added diisopropyl ether, and the solid was collected by filtration to give the title compound (0.52 g).

MS (ESI) m/z; 382 [M+H]$^+$

Example 662

(R)-1-(7-ethyl-6-fluoro-5-oxo-5H-[1,3,4]thiadiazolo[3,2-a]pyrimidin-2-yl)-N-[(pyridin-2-yl)methyl]pyrrolidine-2-carboxamide

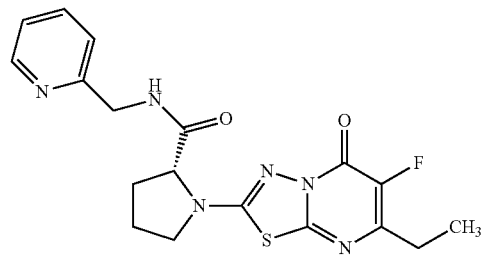 [SMILES: CCc1nc2sc(N3CCC[C@@H]3C(=O)NCc3ccccn3)nn2c(=O)c1F]

To a solution (1.4 mL) of the compound (180 mg) obtained in Reference Example 134 in DMF were added (pyridin-2-yl)methylamine (0.065 mL), EDC hydrochloride (166 mg), HOBt monohydrate (132 mg) and N,N-diisopropylethylamine (0.15 mL), and the reaction mixture was stirred at room temperature for 4 hr. After confirmation of the completion of the reaction, water was added to the reaction mixture, and the mixture was extracted twice with chloroform. The organic layer was dried over anhydrous magnesium sulfate, filtered and concentrated. The residue was purified by NH silica gel column chromatography (solvent; ethyl acetate/methanol=100/0-90/10). To the obtained product was added diisopropyl ether, and the solid was collected by filtration to give the title compound (175 mg).

MS (ESI) m/z; 403 [M+H]$^+$

Example 663

(R)-1-(7-ethyl-6-fluoro-5-oxo-5H-[1,3,4]thiadiazolo[3,2-a]pyrimidin-2-yl)-N-[(5-methylpyridin-2-yl)methyl]pyrrolidine-2-carboxamide

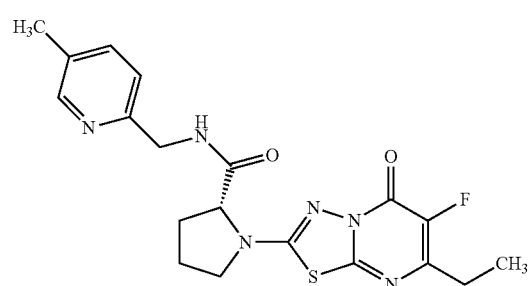

The compound (180 mg) obtained in Reference Example 134 was treated by a method similar to that in Example 662 to give the title compound (63 mg).

MS (ESI) m/z; 417 [M+H]+

Example 664

(R)-1-(7-ethyl-6-fluoro-5-oxo-5H-[1,3,4]thiadiazolo[3,2-a]pyrimidin-2-yl)-N-[(4-methylpyridin-2-yl)methyl]pyrrolidine-2-carboxamide

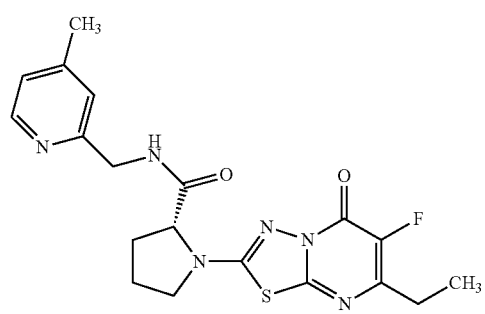 [SMILES: CCc1nc2sc(N3CCC[C@@H]3C(=O)NCc3cc(C)ccn3)nn2c(=O)c1F]

The compound (180 mg) obtained in Reference Example 134 was treated by a method similar to that in Example 662 to give the title compound (125 mg).

MS (ESI) m/z; 417 [M+H]+

Example 665

(R)-1-(7-ethyl-6-fluoro-5-oxo-5H-[1,3,4]thiadiazolo[3,2-a]pyrimidin-2-yl)-N-[(6-methylpyridin-2-yl)methyl]pyrrolidine-2-carboxamide

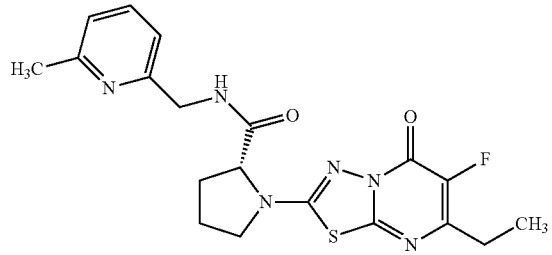 [SMILES: CCc1nc2sc(N3CCC[C@@H]3C(=O)NCc3cccc(C)n3)nn2c(=O)c1F]

The compound (180 mg) obtained in Reference Example 134 was treated by a method similar to that in Example 662 to give the title compound (152 mg).

MS (ESI) m/z; 417 [M+H]+

Example 666:

(R)-1-(7-ethyl-6-fluoro-5-oxo-5H-[1,3,4]thiadiazolo[3,2-a]pyrimidin-2-yl)-N-[(5-fluoropyridin-2-yl)methyl]pyrrolidine-2-carboxamide

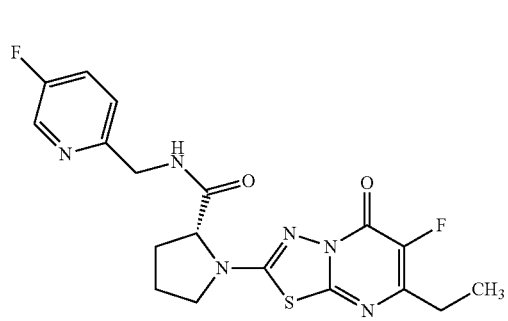 [SMILES: CCc1nc2sc(N3CCC[C@@H]3C(=O)NCc3ccc(F)cn3)nn2c(=O)c1F]

The compound (180 mg) obtained in Reference Example 134 was treated by a method similar to that in Example 662 to give the title compound (133 mg).

MS (ESI) m/z; 421 [M+H]+

Example 667

(R)-1-(7-methyl-5-oxo-5H-[1,3,4]thiadiazolo[3,2-a]pyrimidin-2-yl)-N-(4-trifluoromethylbenzyl)pyrrolidine-2-carboxamide

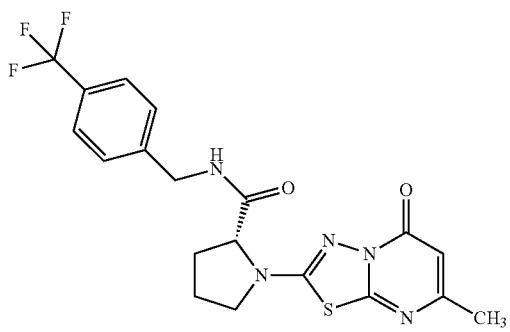 [SMILES: Cc1cc(=O)n2nc(N3CCC[C@@H]3C(=O)NCc3ccc(C(F)(F)F)cc3)sc2n1]

The compound (200 mg) obtained in Reference Example 135 was treated by a method similar to that in Example 662 to give the title compound (135 mg).

MS (ESI) m/z; 438 [M+H]+

Example 668

(R)-N-(4-fluorobenzyl)-1-(7-methyl-5-oxo-5H-[1,3,4]thiadiazolo[3,2-a]pyrimidin-2-yl)pyrrolidine-2-carboxamide

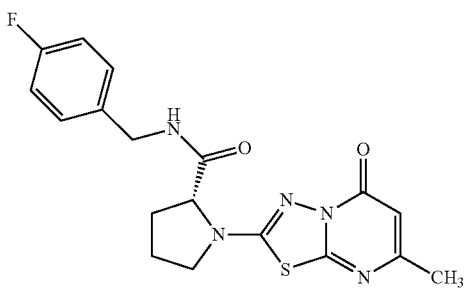 [SMILES: Cc1cc(=O)n2nc(N3CCC[C@@H]3C(=O)NCc3ccc(F)cc3)sc2n1]

The compound (200 mg) obtained in Reference Example 135 was treated by a method similar to that in Example 662 to give the title compound (115 mg).
MS (ESI) m/z; 388 [M+H]$^+$

Example 669

(R)-N-(7-methyl-5-oxo-5H-[1,3,4]thiadiazolo[3,2-a]pyrimidin-2-yl)-N-((R)-1,2,3,4-tetrahydronaphthalen-1-yl)pyrrolidine-2-carboxamide

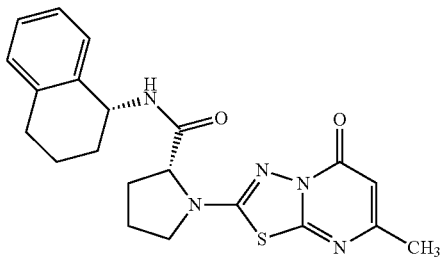 [SMILES: Cc1cc(=O)n2nc(N3CCC[C@@H]3C(=O)N[C@@H]3CCCc4ccccc43)sc2n1]

The compound (200 mg) obtained in Reference Example 135 was treated by a method similar to that in Example 662 to give the title compound (135 mg).
MS (ESI) m/z; 410 [M+H]$^+$

Example 670

(R)-1-(7-methyl-5-oxo-5H-[1,3,4]thiadiazolo[3,2-a]pyrimidin-2-yl)-N-(1-phenylcyclopropyl)pyrrolidine-2-carboxamide

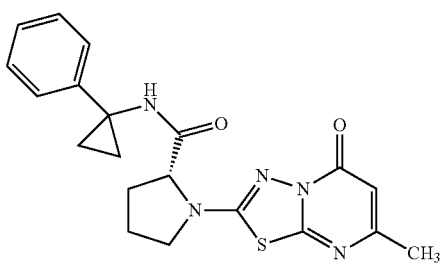 [SMILES: Cc1cc(=O)n2nc(N3CCC[C@@H]3C(=O)NC3(c4ccccc4)CC3)sc2n1]

The compound (200 mg) obtained in Reference Example 135 was treated by a method similar to that in Example 662 to give the title compound (135 mg).
MS (ESI) m/z; 396 [M+H]$^+$

Example 671

(R)-1-(7-ethyl-6-fluoro-5-oxo-5H-[1,3,4]thiadiazolo[3,2-a]pyrimidin-2-yl)-N-(2-fluorobenzyl)pyrrolidine-2-carboxamide

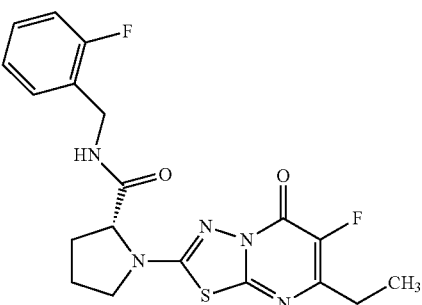

To a solution (0.5 mL) of the compound (37.0 mg) obtained in Reference Example 134 in DMF were added 2-fluorobenzylamine (16 mg), EDC hydrochloride (35 mg), HOBt monohydrate (24 mg) and N,N-diisopropylethylamine (23 mg), and the reaction mixture was stirred at room temperature for 3 hr. After confirmation of the completion of the reaction, water was added to the reaction mixture, and the mixture was extracted twice with chloroform. The organic layer was concentrated, and the residue was purified by Waters XTerra® column (solvent; 10 mmol/L aqueous ammonium carbonate solution/methanol) to give the title compound (25.8 mg).
MS (ESI) m/z; 420 [M+H]$^+$

Example 672

(R)-1-(7-ethyl-6-fluoro-5-oxo-5H-[1,3,4]thiadiazolo[3,2-a]pyrimidin-2-yl)-N-(3-fluorobenzyl)pyrrolidine-2-carboxamide

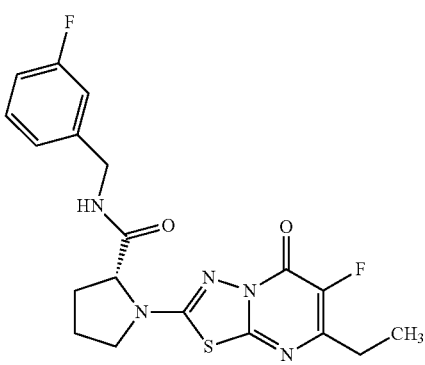 [SMILES: CCc1nc2sc(N3CCC[C@@H]3C(=O)NCc3cccc(F)c3)nn2c(=O)c1F]

The compound (37.0 mg) obtained in Reference Example 134 was treated by a method similar to that in Example 671 to give the title compound (36.3 mg).
MS (ESI) m/z; 420 [M+H]$^+$

Example 673

(R)-N-(3,5-difluorobenzyl)-1-(7-ethyl-6-fluoro-5-oxo-5H-[1,3,4]thiadiazolo[3,2-a]pyrimidin-2-yl)pyrrolidine-2-carboxamide

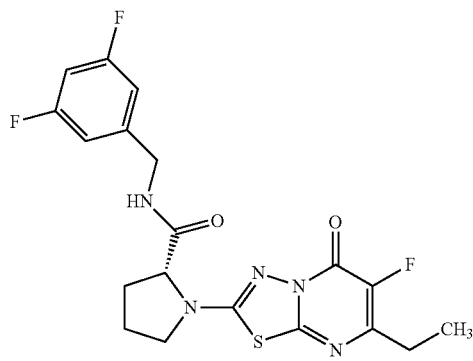 [SMILES: CCc1nc2sc(N3CCC[C@@H]3C(=O)NCc3cc(F)cc(F)c3)nn2c(=O)c1F]

The compound (37.0 mg) obtained in Reference Example 134 was treated by a method similar to that in Example 671 to give the title compound (35.4 mg).
MS (ESI) m/z; 438 [M+H]+

Example 674

(R)-N-(2,4-difluorobenzyl)-1-(7-ethyl-6-fluoro-5-oxo-5H-[1,3,4]thiadiazolo[3,2-a]pyrimidin-2-yl)pyrrolidine-2-carboxamide

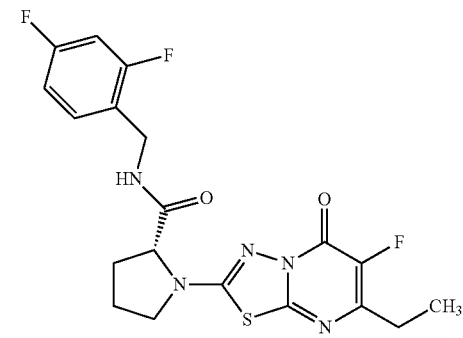 [SMILES: CCc1nc2sc(N3CCC[C@@H]3C(=O)NCc3ccc(F)cc3F)nn2c(=O)c1F]

The compound (37.0 mg) obtained in Reference Example 134 was treated by a method similar to that in Example 671 to give the title compound (28.4 mg).
MS (ESI) m/z; 438 [M+H]+

Example 675

(R)-N-(2,3-difluorobenzyl)-1-(7-ethyl-6-fluoro-5-oxo-5H-[1,3,4]thiadiazolo[3,2-a]pyrimidin-2-yl)pyrrolidine-2-carboxamide

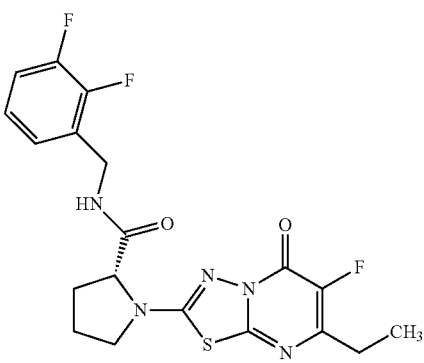 [SMILES: CCc1nc2sc(N3CCC[C@@H]3C(=O)NCc3cccc(F)c3F)nn2c(=O)c1F]

The compound (37.0 mg) obtained in Reference Example 134 was treated by a method similar to that in Example 671 to give the title compound (29.7 mg).
MS (ESI) m/z; 438 [M+H]+

Example 676

(R)-N-(4-chlorobenzyl)-1-(7-ethyl-6-fluoro-5-oxo-5H-[1,3,4]thiadiazolo[3,2-a]pyrimidin-2-yl)pyrrolidine-2-carboxamide

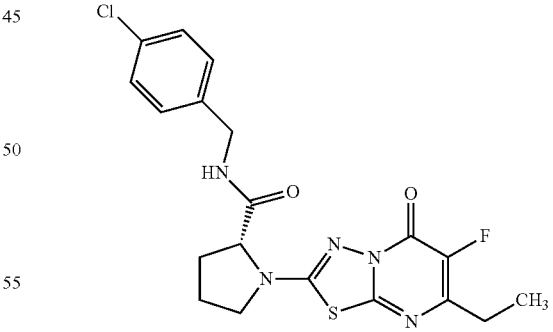

The compound (37.0 mg) obtained in Reference Example 134 was treated by a method similar to that in Example 671 to give the title compound (32.0 mg).
MS (ESI) m/z; 436, 438 [M+H]+

Example 677

(R)-N-(3-chlorobenzyl)-1-(7-ethyl-6-fluoro-5-oxo-5H-[1,3,4]thiadiazolo[3,2-a]pyrimidin-2-yl)pyrrolidine-2-carboxamide

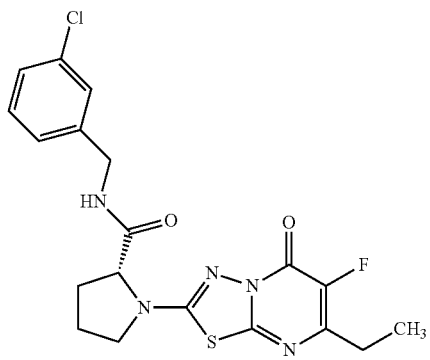 [SMILES: CCc1nc2sc(N3CCC[C@@H]3C(=O)NCc3cccc(Cl)c3)nn2c(=O)c1F]

The compound (37.0 mg) obtained in Reference Example 134 was treated by a method similar to that in Example 671 to give the title compound (32.5 mg).
MS (ESI) m/z; 436, 438 [M+H]$^+$

Example 678

(R)-N-(2-chlorobenzyl)-1-(7-ethyl-6-fluoro-5-oxo-5H-[1,3,4]thiadiazolo[3,2-a]pyrimidin-2-yl)pyrrolidine-2-carboxamide

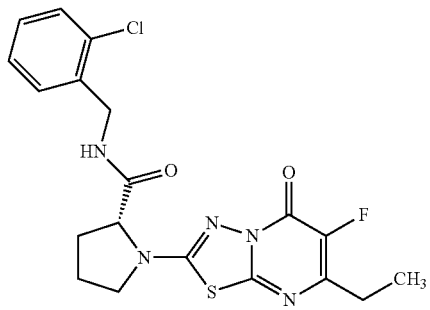 [SMILES: CCc1nc2sc(N3CCC[C@@H]3C(=O)NCc3ccccc3Cl)nn2c(=O)c1F]

The compound (37.0 mg) obtained in Reference Example 134 was treated by a method similar to that in Example 671 to give the title compound (25.5 mg).
MS (ESI) m/z; 436, 438 [M+H]$^+$

Example 679

(R)-N-(3,4-dichlorobenzyl)-1-(7-ethyl-6-fluoro-5-oxo-5H-[1,3,4]thiadiazolo[3,2-a]pyrimidin-2-yl)pyrrolidine-2-carboxamide

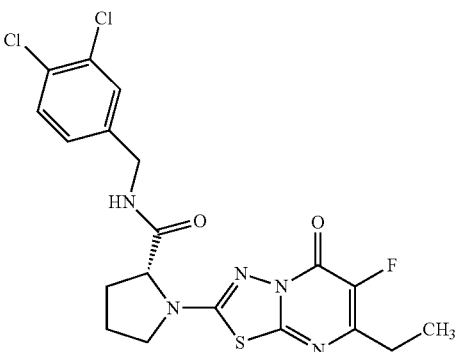

The compound (37.0 mg) obtained in Reference Example 134 was treated by a method similar to that in Example 671 to give the title compound (17.4 mg).
MS (ESI) m/z; 470, 472 [M+H]$^+$

Example 680

(R)-N-(2,3-dichlorobenzyl)-1-(7-ethyl-6-fluoro-5-oxo-5H-[1,3,4]thiadiazolo[3,2-a]pyrimidin-2-yl)pyrrolidine-2-carboxamide

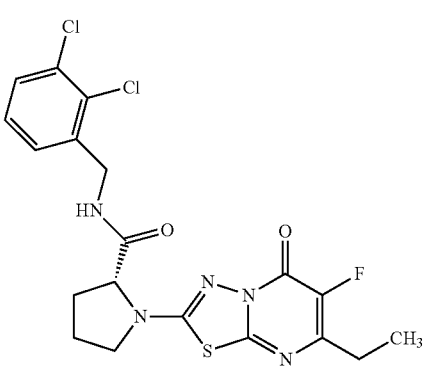 [SMILES: CCc1nc2sc(N3CCC[C@@H]3C(=O)NCc3cccc(Cl)c3Cl)nn2c(=O)c1F]

The compound (37.0 mg) obtained in Reference Example 134 was treated by a method similar to that in Example 671 to give the title compound (36.9 mg).
MS (ESI) m/z; 470, 472 [M+H]$^+$

Example 681

(R)-1-(7-ethyl-6-fluoro-5-oxo-5H-[1,3,4]thiadiazolo[3,2-a]pyrimidin-2-yl)-N-(4-methoxybenzyl)pyrrolidine-2-carboxamide

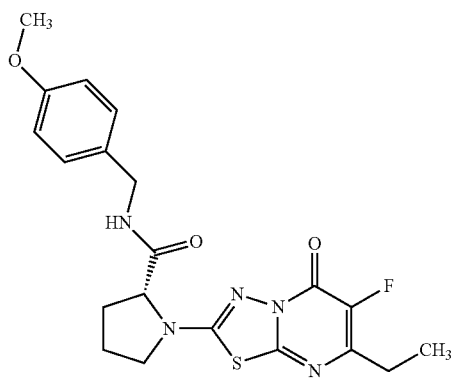 [SMILES: CCc1nc2sc(N3CCC[C@@H]3C(=O)NCc3ccc(OC)cc3)nn2c(=O)c1F]

The compound (37.0 mg) obtained in Reference Example 134 was treated by a method similar to that in Example 671 to give the title compound (14.4 mg).

MS (ESI) m/z; 432 [M+H]$^+$

Example 682

(R)-1-(7-ethyl-6-fluoro-5-oxo-5H-[1,3,4]thiadiazolo[3,2-a]pyrimidin-2-yl)-N-(3-methoxybenzyl)pyrrolidine-2-carboxamide

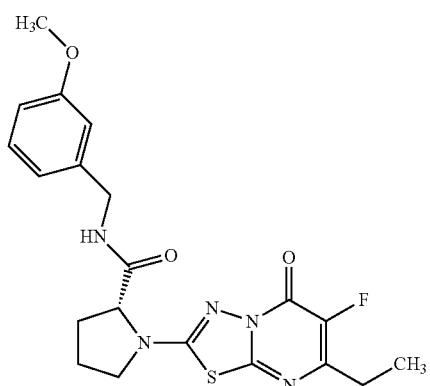

The compound (37.0 mg) obtained in Reference Example 134 was treated by a method similar to that in Example 671 to give the title compound (19.4 mg).

MS (ESI) m/z; 432 [M+H]$^+$

Example 683

(R)-1-(7-ethyl-6-fluoro-5-oxo-5H-[1,3,4]thiadiazolo[3,2-a]pyrimidin-2-yl)-N-(2-methoxybenzyl)pyrrolidine-2-carboxamide

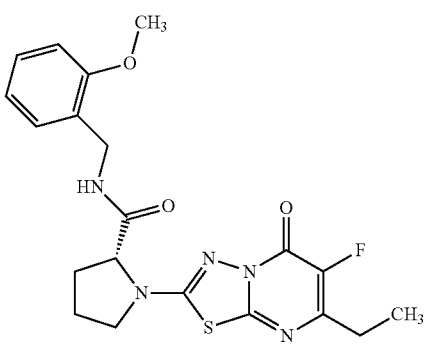 [SMILES: CCc1nc2sc(N3CCC[C@@H]3C(=O)NCc3ccccc3OC)nn2c(=O)c1F]

The compound (37.0 mg) obtained in Reference Example 134 was treated by a method similar to that in Example 671 to give the title compound (6.10 mg).

MS (ESI) m/z; 432 [M+H]$^+$

Example 684

(R)-1-(7-ethyl-6-fluoro-5-oxo-5H-[1,3,4]thiadiazolo[3,2-a]pyrimidin-2-yl)-N-[(pyrimidin-2-yl)methyl]pyrrolidine-2-carboxamide

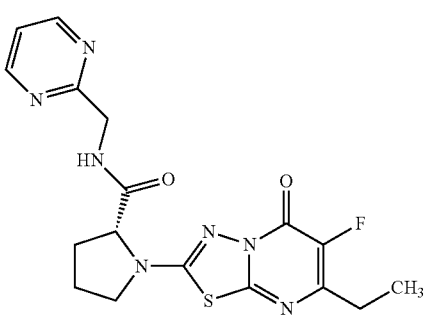 [SMILES: CCc1nc2sc(N3CCC[C@@H]3C(=O)NCc3ncccn3)nn2c(=O)c1F]

The compound (37.0 mg) obtained in Reference Example 134 was treated by a method similar to that in Example 671 to give the title compound (26.8 mg).

MS (ESI) m/z; 404 [M+H]$^+$

Example 685

(R)-1-(7-ethyl-6-fluoro-5-oxo-5H-[1,3,4]thiadiazolo[3,2-a]pyrimidin-2-yl)-N-[(5-methylpyrazin-2-yl)methyl]pyrrolidine-2-carboxamide

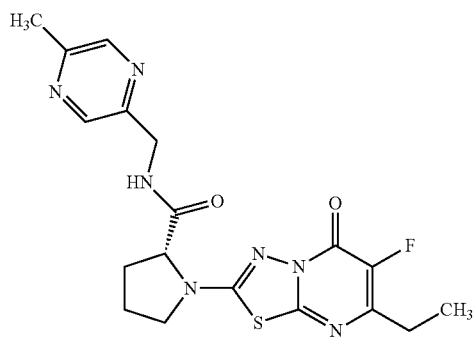 [SMILES: CCc1nc2sc(N3CCC[C@@H]3C(=O)NCc3cnc(C)cn3)nn2c(=O)c1F]

The compound (37.0 mg) obtained in Reference Example 134 was treated by a method similar to that in Example 671 to give the title compound (23.0 mg).

MS (ESI) m/z; 418 [M+H]⁺

Example 686

(R)-1-(7-ethyl-6-fluoro-5-oxo-5H-[1,3,4]thiadiazolo[3,2-a]pyrimidin-2-yl)-N-[([1,2,4]triazolo[4,3-a]pyridin-3-yl)methyl]pyrrolidine-2-carboxamide

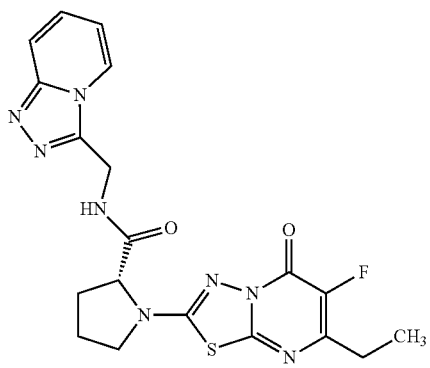 [SMILES: CCc1nc2sc(N3CCC[C@@H]3C(=O)NCc3nnc4ccccn34)nn2c(=O)c1F]

The compound (37.0 mg) obtained in Reference Example 134 was treated by a method similar to that in Example 671 to give the title compound (20.0 mg).

MS (ESI) m/z; 443 [M+H]⁺

Example 687

(R)-1-(7-ethyl-6-fluoro-5-oxo-5H-[1,3,4]thiadiazolo[3,2-a]pyrimidin-2-yl)-N-(4-fluorobenzyl)pyrrolidine-2-carboxamide

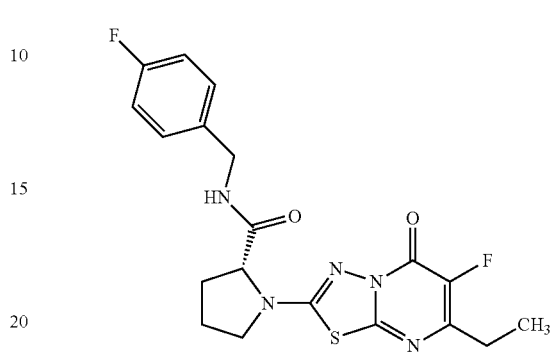

The compound (37.0 mg) obtained in Reference Example 134 was treated by a method similar to that in Example 671 to give the title compound (4.30 mg).

MS (ESI) m/z; 420 [M+H]⁺

Example 688

(R)-N-(2,4-dichlorobenzyl)-1-(7-ethyl-6-fluoro-5-oxo-5H-[1,3,4]thiadiazolo[3,2-a]pyrimidin-2-yl)pyrrolidine-2-carboxamide

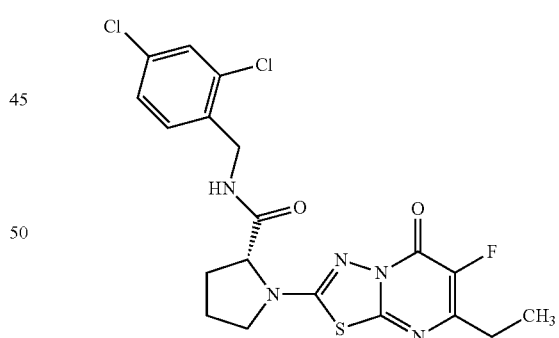

The compound (37.0 mg) obtained in Reference Example 134 was treated by a method similar to that in Example 671 to give the title compound (22.4 mg).

MS (ESI) m/z; 470, 472 [M+H]⁺

Example 689

(R)-N-(2,6-dichlorobenzyl)-1-(7-ethyl-6-fluoro-5-oxo-5H-[1,3,4]thiadiazolo[3,2-a]pyrimidin-2-yl)pyrrolidine-2-carboxamide

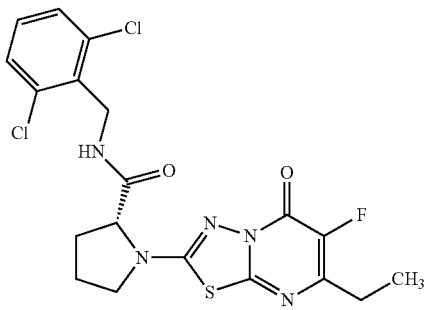 [SMILES: CCc1nc2sc(N3CCC[C@@H]3C(=O)NCc3c(Cl)cccc3Cl)nn2c(=O)c1F]

The compound (37.0 mg) obtained in Reference Example 134 was treated by a method similar to that in Example 671 to give the title compound (1.0 mg).

MS (ESI) m/z; 470, 472 [M+H]+

Example 690

(R)-N-benzyl-1-[6-fluoro-5-oxo-7-(propan-2-yl)-5H-[1,3,4]thiadiazolo[3,2-a]pyrimidin-2-yl]pyrrolidine-2-carboxamide

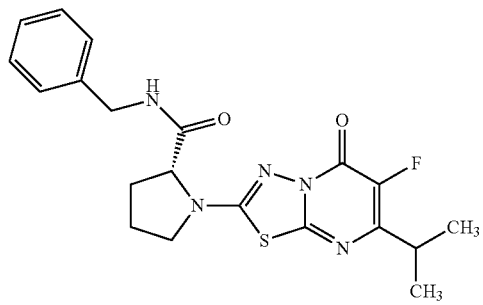 [SMILES: CC(C)c1nc2sc(N3CCC[C@@H]3C(=O)NCc3ccccc3)nn2c(=O)c1F]

To a solution (52 mL) of the compound (1.83 g) obtained in Example 652 in acetonitrile was added 1-chloromethyl-4-fluoro-1,4-diazoniabicyclo[2.2.2]octane bistetrafluoroborate (3.26 g) at room temperature, and the reaction mixture was stirred at room temperature for 7 hr. After confirmation of the completion of the reaction, chloroform was added, and the mixture was washed twice with water, dried over anhydrous sodium sulfate, filtered and concentrated. The residue was purified by NH silica gel column chromatography (solvent; hexane/ethyl acetate=50/50-0/100) to give the title compound (131 mg).

MS (ESI) m/z; 416 [M+H]+

Example 691

(R)-N-benzyl-1-(6-fluoro-7-methyl-5-oxo-5H-[1,3,4]thiadiazolo[3,2-a]pyrimidin-2-yl)pyrrolidine-2-carboxamide

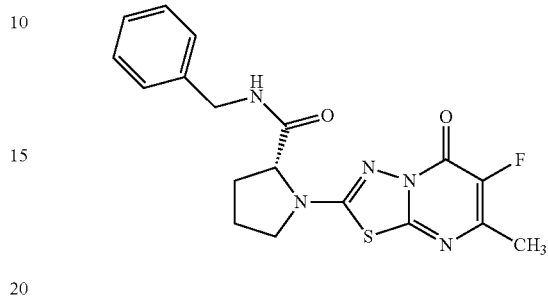

(1) The compound (1200 mg) obtained in Reference Example 764 was treated by a method similar to that in Example 634 to give (R)-N-benzyl-1-(7-methyl-5-oxo-5H-[1,3,4]thiadiazolo[3,2-a]pyrimidin-2-yl)pyrrolidine-2-carboxamide (1200 mg).

MS (ESI) m/z; 370 [M+H]+

(2) The compound (360 mg) obtained in (1) was treated by a method similar to that in Example 690 to give the title compound (33.0 mg).

MS (ESI) m/z; 388 [M+H]+

Example 692

(R)-N-benzyl-1-(6-chloro-5-oxo-7-propyl-5H-[1,3,4]thiadiazolo[3,2-a]pyrimidin-2-yl)pyrrolidine-2-carboxamide

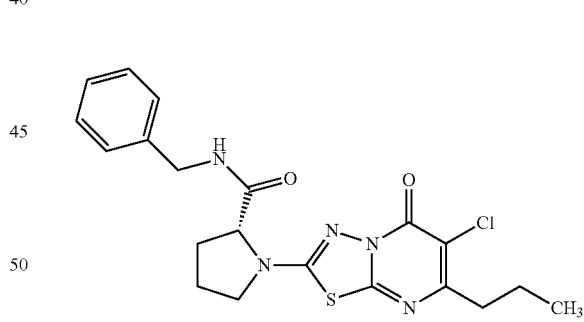

A mixture of the compound (0.40 g) obtained in Example 634 and N-chlorosuccinimide (0.14 g) in acetonitrile (10 mL) was stirred with heating at 80° C. for 5 hr. After confirmation of the completion of the reaction, the reaction mixture was cooled to room temperature, chloroform was added, and the mixture was washed twice with water. The organic layer was dried over anhydrous magnesium sulfate, filtered and concentrated. The residue was purified by silica gel column chromatography (solvent; ethyl acetate/methanol=100/0-90/10) to give the title compound (0.3 g).

MS (ESI) m/z; 432, 434 [M+H]+

Example 693

(R)-N-benzyl-1-(6-chloro-5-oxo-7-propyl-5H-[1,3,4]thiadiazolo[3,2-a]pyrimidin-2-yl)piperidine-2-carboxamide

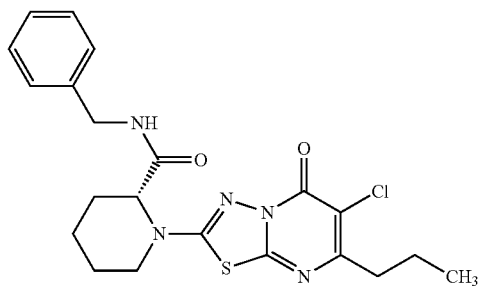 [SMILES: CCCc1nc2sc(N3CCCC[C@@H]3C(=O)NCc3ccccc3)nn2c(=O)c1Cl]

The compound (190 mg) obtained in Example 635 was treated by a method similar to that in Example 692 to give the title compound (97 mg).
MS (ESI) m/z; 446, 448 [M+H]+

Example 694

(1SR,2RS,5RS)-N-benzyl-3-(6-chloro-7-methyl-5-oxo-5H-[1,3,4]thiadiazolo[3,2-a]pyrimidin-2-yl)-3-azabicyclo[3.1.0]hexane-2-carboxamide

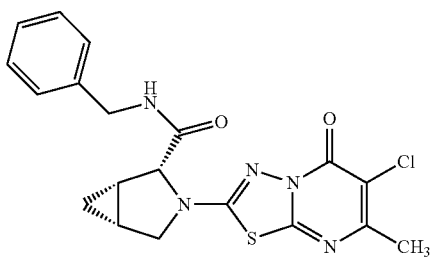 [SMILES: Cc1nc2sc(N3C[C@@H]4C[C@@H]4[C@@H]3C(=O)NCc3ccccc3)nn2c(=O)c1Cl]

The compound (300 mg) obtained in Example 661 was treated by a method similar to that in Example 692 to give the title compound (217 mg).
MS (ESI) m/z; 416, 418 [M+H]+

Example 695

(R)-N-benzyl-1-(6-chloro-7-ethyl-5-oxo-5H-[1,3,4]thiadiazolo[3,2-a]pyrimidin-2-yl)pyrrolidine-2-carboxamide

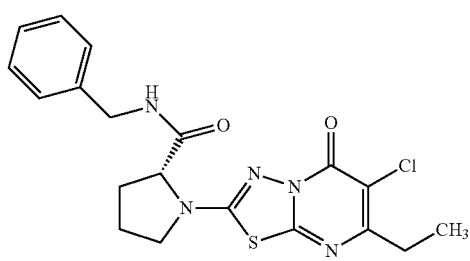 [SMILES: CCc1nc2sc(N3CCC[C@@H]3C(=O)NCc3ccccc3)nn2c(=O)c1Cl]

The compound (299 mg) obtained in Example 637 was treated by a method similar to that in Example 692 to give the title compound (291 mg).
MS (ESI) m/z; 418, 420 [M+H]+

Example 696

(R)-1-[6-chloro-5-oxo-7-(propan-2-yl)-5H-[1,3,4]thiadiazolo[3,2-a]pyrimidin-2-yl]-N-[(pyridin-2-yl)methyl]pyrrolidine-2-carboxamide hydrochloride

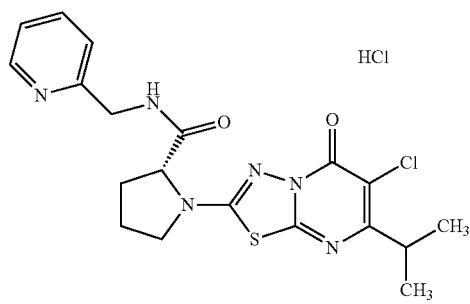 [SMILES: CC(C)c1nc2sc(N3CCC[C@@H]3C(=O)NCc3ccccn3)nn2c(=O)c1Cl ; Cl]

A mixture of the compound (200 mg) obtained in Example 653 and N-chlorosuccinimide (148 mg) in acetonitrile (3.6 mL) was stirred with heating at 60° C. for 23 hr. After confirmation of the completion of the reaction, the reaction mixture was cooled to room temperature, chloroform was added, and the mixture was washed twice with water. The organic layer was dried over anhydrous magnesium sulfate, filtered and concentrated. The residue was purified by silica gel column chromatography (solvent; ethyl acetate/methanol=100/0-90/10). The obtained residue was dissolved in ethyl acetate (8 mL), hydrogen chloride (4.0 mol/L ethyl acetate solution, 0.1 mL) was added, and the mixture was stirred at room temperature for 10 min, and concentrated under reduced pressure to give the title compound (48 mg).
MS (ESI) m/z; 433, 435 [M+H]+

Example 697

(R)-N-benzyl-1-(6-bromo-7-methyl-5-oxo-5H-[1,3,4]thiadiazolo[3,2-a]pyrimidin-2-yl)pyrrolidine-2-carboxamide

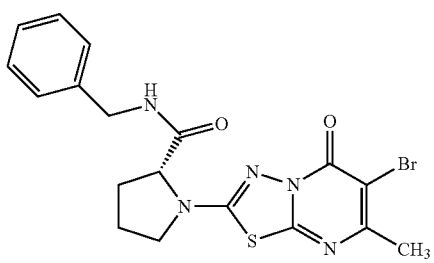 [SMILES: Cc1nc2sc(N3CCC[C@@H]3C(=O)NCc3ccccc3)nn2c(=O)c1Br]

A mixture of (R)-N-benzyl-1-(7-methyl-5-oxo-5H-[1,3,4]thiadiazolo[3,2-a]pyrimidin-2-yl)pyrrolidine-2-carboxamide (2.83 g) obtained by a method of Example 691(1) and N-bromosuccinimide (1.4 g) in acetonitrile (50 mL) was stirred with heating at 80° C. for 3 hr. After confirmation of the completion of the reaction, the reaction mixture was cooled to room temperature, chloroform was added, and the mixture was washed once with water. The organic layer was dried over anhydrous magnesium sulfate, filtered and concentrated. Ethyl acetate was added to the obtained product, and the solid was collected by filtration to give the title compound (2.85 g).

MS (ESI) m/z; 448, 450 [M+H]$^+$

Example 698

(R)-N-benzyl-1-[6-(3,6-dihydro-2H-pyran-4-yl)-7-methyl-5-oxo-5H-[1,3,4]thiadiazolo[3,2-a]pyrimidin-2-yl]pyrrolidine-2-carboxamide

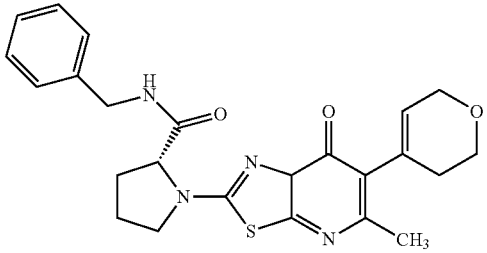 [SMILES: CC1=C(C2=CCOCC2)C(=O)C2N=C(N3CCC[C@@H]3C(=O)NCc3ccccc3)SC2=N1]

To the compound (0.40 g) obtained in Example 697 in THF (10 mL)-water (5.0 mL) mixed solvent were added 4-(4,4,5,5-tetramethyl-[1,3,2]dioxaborolan-2-yl)-3,6-dihydro-2H-pyran (0.56 g), tetrakis(triphenylphosphine)palladium(0) (60 mg) and sodium carbonate (0.30 g) at room temperature, and the reaction mixture was stirred with heating at 100° C. for 4 hr. After confirmation of the completion of the reaction, the reaction mixture was cooled to room temperature, chloroform (200 mL) was added, and the mixture was washed once with water. The organic layer was dried over anhydrous magnesium sulfate, filtered and concentrated. The residue was purified by silica gel column chromatography (solvent; ethyl acetate/methanol=100/0-90/10) to give the title compound (0.21 g).

MS (ESI) m/z; 452 [M+H]$^+$

Example 699

(R)-N-benzyl-1-(7-ethyl-5-oxo-5H-[1,3,4]thiadiazolo[3,2-a]pyridin-2-yl)pyrrolidine-2-carboxamide

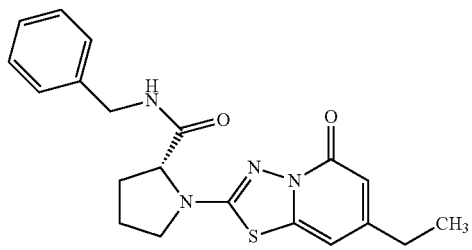 [SMILES: CCc1cc(=O)n2nc(N3CCC[C@@H]3C(=O)NCc3ccccc3)sc2c1]

To a solution (2 mL) of the compound (0.56 g) obtained in Reference Example 785 in pyridine were added the compound (1.29 g) obtained in Reference Example 341 and N,N-diisopropylethylamine (3.7 mL), and the reaction mixture was stirred for 5 hr at 140° C. After confirmation of the completion of the reaction, chloroform was added, and the mixture was washed once with 0.5 mol/L hydrochloric acid, and further washed once with saturated sodium hydrogen carbonate. The organic layer was dried over anhydrous sodium sulfate, filtered and concentrated. The residue was purified by silica gel column chromatography (solvent; ethyl acetate/methanol=100/0-95/5) to give the title compound (0.32 g).

MS (ESI) m/z; 383 [M+H]$^+$

Example 700

(R)-N-benzyl-1-(7-methyl-5-oxo-5H-[1,3,4]thiadiazolo[3,2-a]pyridin-2-yl)pyrrolidine-2-carboxamide

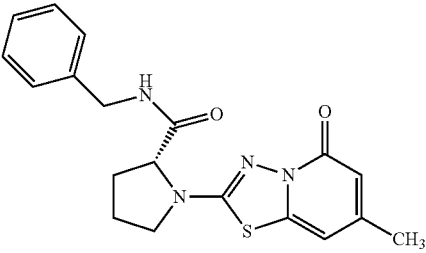 [SMILES: Cc1cc(=O)n2nc(N3CCC[C@@H]3C(=O)NCc3ccccc3)sc2c1]

The compound (300 mg) obtained in Reference Example 786 was treated by a method similar to that in Example 699 to give the title compound (75.0 mg).

MS (ESI) m/z; 369 [M+H]$^+$

Example 701

(R)-N-benzyl-1-(6,8-dichloro-7-ethyl-5-oxo-5H-[1,3,4]thiadiazolo[3,2-a]pyridin-2-yl)pyrrolidine-2-carboxamide

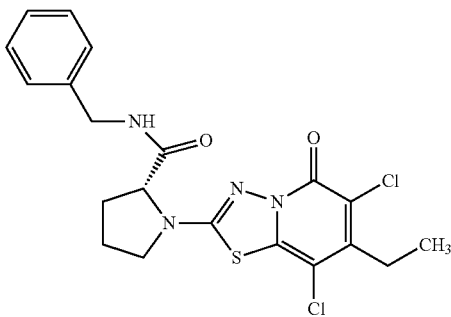 [SMILES: CCc1c(Cl)c(=O)n2nc(N3CCC[C@@H]3C(=O)NCc3ccccc3)sc2c1Cl]

A mixture of the compound (330 mg) obtained in Example 699 and N-chlorosuccinimide (115 mg) in acetonitrile (9 mL) was stirred with heating at 80° C. for 2 hr. After confirmation of the completion of the reaction, the reaction mixture was cooled to room temperature, and concentrated. The residue was purified by Capcellpak C18 UG80 30×250 mm (solvent; 0.05% trifluoroacetic acid acetonitrile/water). The solution of the obtained product was extracted with chloroform, and the organic layer was dried over anhydrous sodium sulfate, filtered and concentrated to give the title compound (30.0 mg).

MS (ESI) m/z; 451, 453 [M+H]$^+$

Example 702

(R)-N-benzyl-1-(6,8-dichloro-7-methyl-5-oxo-5H-[1,3,4]thiadiazolo[3,2-a]pyridin-2-yl)pyrrolidine-2-carboxamide

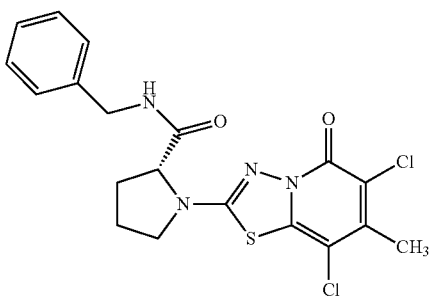 [SMILES: Cc1c(Cl)c(=O)n2nc(N3CCC[C@@H]3C(=O)NCc3ccccc3)sc2c1Cl]

The compound (100 mg) obtained in Example 700 was treated by a method similar to that in Example 701 to give the title compound (20.0 mg).

MS (ESI) m/z; 437, 439 [M+H]$^+$

Example 703

(R)-N-benzyl-1-(2-ethyl-3-methyl-4-oxo-3,4-dihydropyrido[3,2-d]pyrimidin-6-yl)pyrrolidine-2-carboxamide

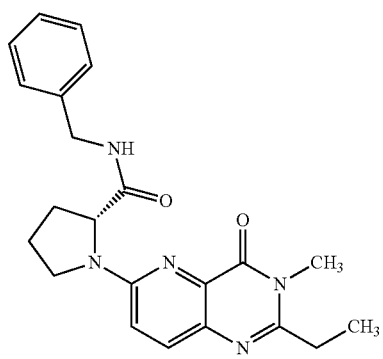 [SMILES: CCc1nc2ccc(N3CCC[C@@H]3C(=O)NCc3ccccc3)nc2c(=O)n1C]

A mixture of the compound (0.16 g) obtained in Reference Example 790, N,N-diisopropylethylamine (1.1 mL) and the compound (0.44 g) obtained in Reference Example 341 in pyridine (0.6 mL) was stirred at 135° C. for 8 hr. After confirmation of the completion of the reaction, the solvent was evaporated under reduced pressure. The residue was purified by silica gel column chromatography (solvent; ethyl acetate/methanol=100/0-95/5) to give the title compound (170 mg).

MS (ESI) m/z; 392 [M+H]$^+$

Example 704

(R)-N-benzyl-1-(2,3-dimethyl-4-oxo-3,4-dihydropyrido[3,2-d]pyrimidin-6-yl)pyrrolidine-2-carboxamide

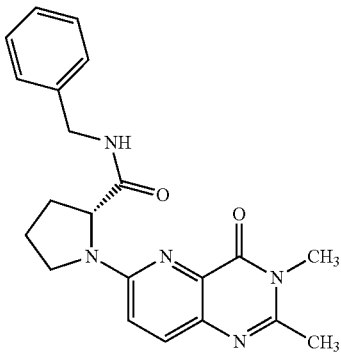 [SMILES: Cc1nc2ccc(N3CCC[C@@H]3C(=O)NCc3ccccc3)nc2c(=O)n1C]

The compound (60 mg) obtained in Reference Example 791 was treated by a method similar to that in Example 703 to give the title compound (55 mg).

MS (ESI) m/z; 378 [M+H]$^+$

Example 705

(R)-N-benzyl-1-(3-ethyl-2-methyl-4-oxo-3,4-dihydropyrido[3,2-d]pyrimidin-6-yl)pyrrolidine-2-carboxamide

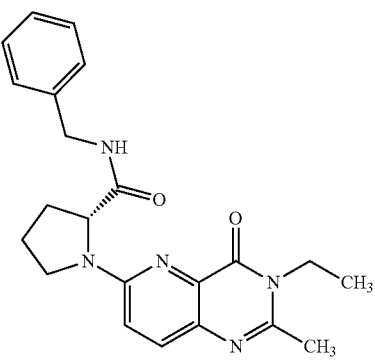 [SMILES: CCn1c(C)nc2ccc(N3CCC[C@@H]3C(=O)NCc3ccccc3)nc2c1=O]

The compound (1.56 g) obtained in Reference Example 792 was treated by a method similar to that in Example 703 to give the title compound (1.57 g).

MS (ESI) m/z; 392 [M+H]$^+$

Example 706

(R)-N-benzyl-1-[2-methyl-4-oxo-3-(2,2,2-trifluoro-ethyl)-3,4-dihydropyrido[3,2-d]pyrimidin-6-yl]pyrrolidine-2-carboxamide

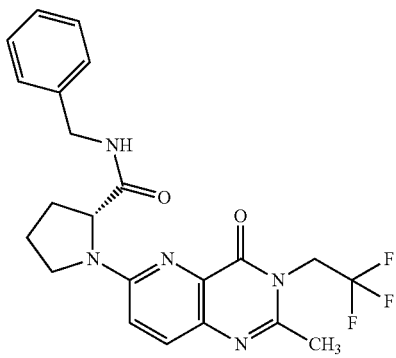 [SMILES: Cc1nc2ccc(N3CCC[C@@H]3C(=O)NCc3ccccc3)nc2c(=O)n1CC(F)(F)F]

The compound (132 mg) obtained in Reference Example 793 was treated by a method similar to that in Example 703 to give the title compound (141 mg).
MS (ESI) m/z; 446 [M+H]$^+$

Example 707

(R)-N-benzyl-1-(3-methyl-4-oxo-2-trifluoromethyl-3,4-dihydropyrido[3,2-d]pyrimidin-6-yl)pyrrolidine-2-carboxamide

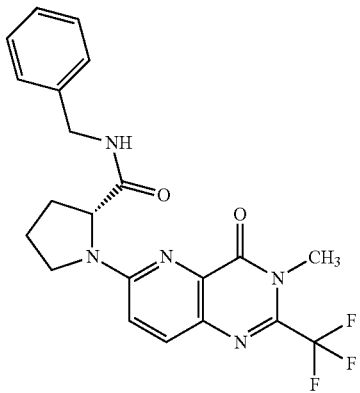 [SMILES: Cn1c(C(F)(F)F)nc2ccc(N3CCC[C@@H]3C(=O)NCc3ccccc3)nc2c1=O]

The compound (230 mg) obtained in Reference Example 794 was treated by a method similar to that in Example 703 to give the title compound (312 mg).
MS (ESI) m/z; 432 [M+H]$^+$

Example 708

(R)-N-benzyl-1-(3-ethyl-4-oxo-2-trifluoromethyl-3,4-dihydropyrido[3,2-d]pyrimidin-6-yl)pyrrolidine-2-carboxamide

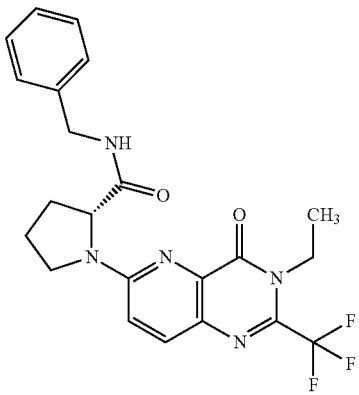 [SMILES: CCn1c(C(F)(F)F)nc2ccc(N3CCC[C@@H]3C(=O)NCc3ccccc3)nc2c1=O]

The compound (201 mg) obtained in Reference Example 795 was treated by a method similar to that in Example 703 to give the title compound (224 mg).
MS (ESI) m/z; 446 [M+H]$^+$

Example 709

(R)-N-benzyl-1-[3-(2,4-dimethoxybenzyl)-4-oxo-2-(propan-2-yl)-3,4-dihydropyrido[3,2-d]pyrimidin-6-yl]pyrrolidine-2-carboxamide

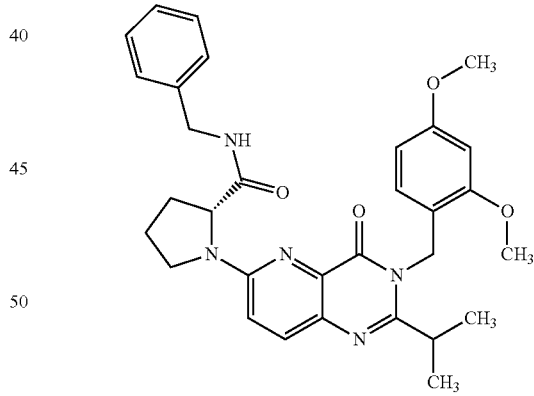

A mixture of the compound (160 mg) obtained in Reference Example 800, N,N-diisopropylethylamine (2.50 mL) and the compound (0.35 g) obtained in Reference Example 341 was stirred with heating at 140° C. for 3 hr. After confirmation of the completion of the reaction, ethyl acetate was added, and the reaction mixture was acidified with 1.0 mol/L hydrochloric acid. The organic layer was washed with water, dried over anhydrous magnesium sulfate, filtered and concentrated. To the residue was added diisopropyl ether, and the solid was collected by filtration and dried to give the title compound (250 mg).
MS (ESI) m/z; 542 [M+H]$^+$

Example 710

(R)-N-benzyl-1-[3-(2,4-dimethoxybenzyl)-2-(2-fluorophenyl)-4-oxo-3,4-dihydropyrido[3,2-d]pyrimidin-6-yl]pyrrolidine-2-carboxamide

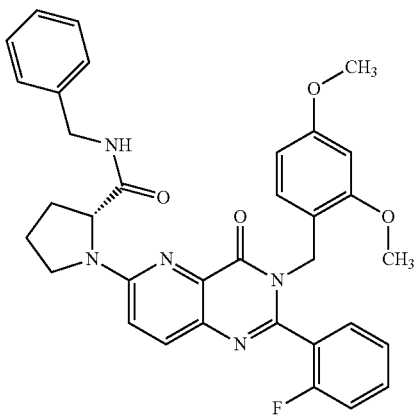 [SMILES: COc1ccc(Cn2c(-c3ccccc3F)nc3ccc(N4CCC[C@@H]4C(=O)NCc4ccccc4)nc3c2=O)c(OC)c1]

The compound (300 mg) obtained in Reference Example 801 was treated by a method similar to that in Example 709 to give the title compound (360 mg).

MS (ESI) m/z; 594 [M+H]+

Example 711

(R)-N-benzyl-1-[2-(1-chlorocyclopropyl)-4-oxo-3,4-dihydropyrido[3,2-d]pyrimidin-6-yl]pyrrolidine-2-carboxamide

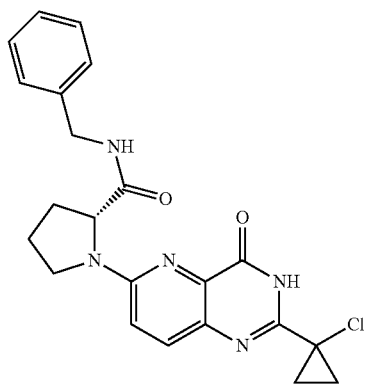 [SMILES: O=C(NCc1ccccc1)[C@H]1CCCN1c1ccc2nc(C3(Cl)CC3)[nH]c(=O)c2n1]

The compound (200 mg) obtained in Reference Example 802 was treated by a method similar to that in Example 709 to give the title compound (180 mg).

MS (ESI) m/z; 424, 426 [M+H]+

Example 712

(R)-N-benzyl-1-[4-oxo-2-(propan-2-yl)-3,4-dihydropyrido[3,2-d]pyrimidin-6-yl]pyrrolidine-2-carboxamide

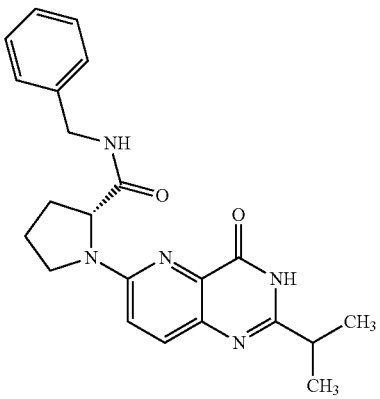 [SMILES: CC(C)c1nc2ccc(N3CCC[C@@H]3C(=O)NCc3ccccc3)nc2c(=O)[nH]1]

To the compound (250 mg) obtained in Example 709 was added a mixed solution of triethylsilane (0.11 mL) and trifluoroacetic acid (2.0 mL), and the reaction mixture was stirred at room temperature for 2 hr. The solvent was evaporated under reduced pressure, chloroform was added, and the mixture was washed with saturated aqueous sodium hydrogen carbonate solution. The organic layer was dried over anhydrous magnesium sulfate, filtered and concentrated. The residue was purified by silica gel column chromatography (solvent; ethyl acetate/methanol=100/0-95/5) to give the title compound (130 mg).

MS (ESI) m/z; 392 [M+H]+

Example 713

(R)-N-benzyl-1-[2-(2-fluorophenyl)-4-oxo-3,4-dihydropyrido[3,2-d]pyrimidin-6-yl]pyrrolidine-2-carboxamide

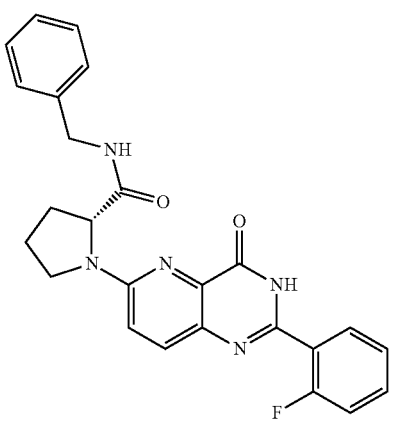 [SMILES: O=C(NCc1ccccc1)[C@H]1CCCN1c1ccc2nc(-c3ccccc3F)[nH]c(=O)c2n1]

The compound (360 mg) obtained in Example 710 was treated by a method similar to that in Example 712 to give the title compound (186 mg).

MS (ESI) m/z; 444 [M+H]+

Example 714

(R)-N-benzyl-1-(4-oxo-2-phenyl-4H-pyrimido[1,2-b]pyridazin-7-yl)pyrrolidine-2-carboxamide

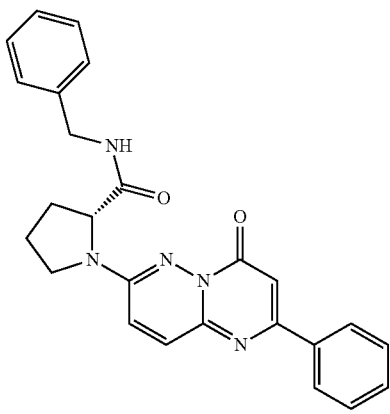 [SMILES: O=C(NCc1ccccc1)[C@H]1CCCN1c1ccc2nc(-c3ccccc3)cc(=O)n2n1]

To a solution (6 mL) of the compound (0.20 g) obtained in Reference Example 806 in THF were added the compound (0.28 g) obtained in Reference Example 341 and triethylamine (0.24 g), and the reaction mixture was stirred with heating at 100° C. for 8 hr. After confirmation of the completion of the reaction, water was added to the reaction mixture, and the mixture was extracted once with chloroform. The organic layer was dried over anhydrous magnesium sulfate, filtered and concentrated. The residue was purified by silica gel column chromatography (solvent; ethyl acetate/methanol=100/0-90/10) to give the title compound (0.30 g).

MS (ESI) m/z; 426 [M+H]$^+$

Example 715

(R)-N-benzyl-1-(3-fluoro-4-oxo-2-propyl-4H-pyrimido[1,2-b]pyridazin-7-yl)pyrrolidine-2-carboxamide

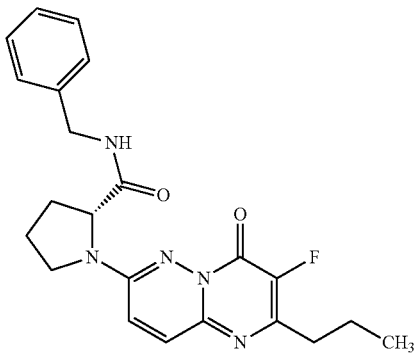 [SMILES: CCCc1nc2ccc(N3CCC[C@@H]3C(=O)NCc3ccccc3)nn2c(=O)c1F]

To a solution (10 mL) of the compound (0.40 g) obtained in Reference Example 807 in THF were added the compound (0.60 g) obtained in Reference Example 341 and N,N-diisopropylethylamine (0.86 g), and the reaction mixture was stirred with heating at 100° C. for 8 hr. After confirmation of the completion of the reaction, the reaction mixture was cooled to room temperature, water was added to the reaction mixture, and the mixture was extracted once with chloroform. The organic layer was dried over anhydrous magnesium sulfate, filtered and concentrated. The residue was purified by silica gel column chromatography (solvent; ethyl acetate/methanol=100/0-90/10). Ethyl acetate was added to the obtained product, and the solid was collected by filtration to give the title compound (0.46 g).

MS (ESI) m/z; 410 [M+H]$^+$

Example 716

(R)-N-benzyl-1-(2-ethyl-3-fluoro-4-oxo-4H-pyrimido[1,2-b]pyridazin-7-yl)pyrrolidine-2-carboxamide

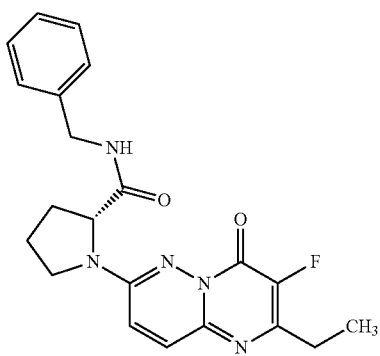 [SMILES: CCc1nc2ccc(N3CCC[C@@H]3C(=O)NCc3ccccc3)nn2c(=O)c1F]

The compound (400 mg) obtained in Reference Example 808 was treated by a method similar to that in Example 715 to give the title compound (440 mg).

MS (ESI) m/z; 396 [M+H]$^+$

Example 717

(R)-N-benzyl-1-(4-oxo-2-propyl-4H-pyrimido[1,2-b]pyridazin-7-yl)pyrrolidine-2-carboxamide

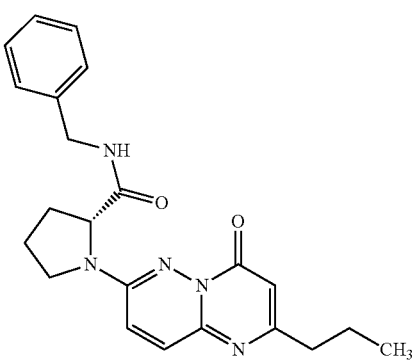 [SMILES: CCCc1cc(=O)n2nc(N3CCC[C@@H]3C(=O)NCc3ccccc3)ccc2n1]

The compound (600 mg) obtained in Reference Example 803 was treated by a method similar to that in Example 715 to give the title compound (586 mg).

MS (ESI) m/z; 392 [M+H]$^+$

Example 718

(R)-1-(4-oxo-2-propyl-4H-pyrimido[1,2-b]pyridazin-7-yl)-N-(1-phenylcyclopropyl)pyrrolidine-2-carboxamide

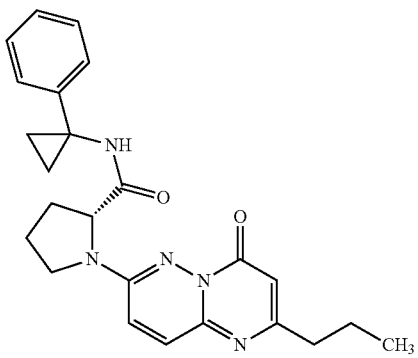 [SMILES: CCCc1cc(=O)n2nc(N3CCC[C@@H]3C(=O)NC3(c4ccccc4)CC3)ccc2n1]

The compound (300 mg) obtained in Reference Example 803 was treated by a method similar to that in Example 715 to give the title compound (360 mg).

MS (ESI) m/z; 418 [M+H]$^+$

Example 719

(R)-N-benzyl-1-(2-ethyl-4-oxo-4H-pyrimido[1,2-b]pyridazin-7-yl)pyrrolidine-2-carboxamide

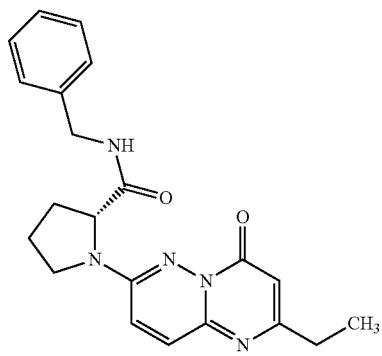 [SMILES: CCc1cc(=O)n2nc(N3CCC[C@@H]3C(=O)NCc3ccccc3)ccc2n1]

The compound (400 mg) obtained in Reference Example 804 was treated by a method similar to that in Example 715 to give the title compound (306 mg).

MS (ESI) m/z; 378 [M+H]$^+$

Example 720

(R)-N-benzyl-1-[4-oxo-2-(propan-2-yl)-4H-pyrimido[1,2-b]pyridazin-7-yl]pyrrolidine-2-carboxamide

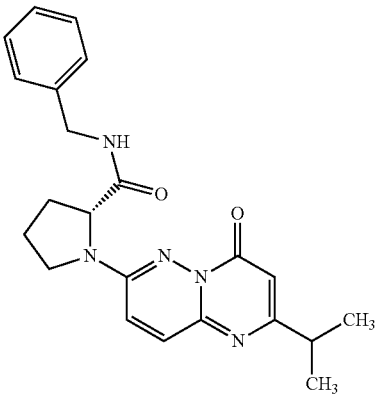 [SMILES: CC(C)c1cc(=O)n2nc(N3CCC[C@@H]3C(=O)NCc3ccccc3)ccc2n1]

The compound (300 mg) obtained in Reference Example 805 was treated by a method similar to that in Example 715 to give the title compound (83 mg).

MS (ESI) m/z; 392 [M+H]$^+$

Example 721

(R)-1-(4-oxo-2-phenyl-4H-pyrimido[1,2-b]pyridazin-7-yl)-N-(1-phenylcyclopropyl)pyrrolidine-2-carboxamide

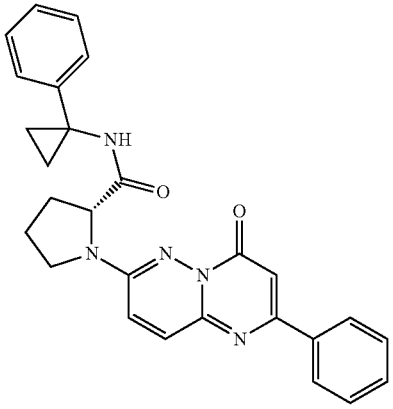 [SMILES: O=C(NC1(c2ccccc2)CC1)[C@H]1CCCN1c1ccc2nc(-c3ccccc3)cc(=O)n2n1]

The compound (200 mg) obtained in Reference Example 806 was treated by a method similar to that in Example 715 to give the title compound (260 mg).

MS (ESI) m/z; 452 [M+H]$^+$

Example 722

(R)-N-benzyl-1-[3-fluoro-4-oxo-2-(propan-2-yl)-4H-pyrimido[1,2-b]pyridazin-7-yl]pyrrolidine-2-carboxamide

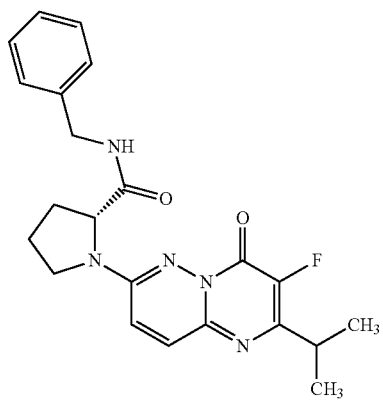

To a solution (10 mL) of the compound (1.02 g) obtained is in Example 720 in acetonitrile was added 1-chloromethyl-4-fluoro-1,4-diazoniabicyclo[2.2.2]octane bistetrafluoroborate (1.10 g) at room temperature, and the reaction mixture was stirred at 80° C. for 6 hr. After confirmation of the completion of the reaction, chloroform was added, and the mixture was washed once with water. The organic layer was dried over anhydrous magnesium sulfate, filtered and concentrated. The residue was purified by silica gel column chromatography (solvent; ethyl acetate/methanol=100/0-90/10). To the obtained product was added hexane, and the solid was collected by filtration to give the title compound (116 mg)

MS (ESI) m/z; 410 $[M+H]^+$

Example 723

(R)-N-benzyl-1-(3-chloro-4-oxo-2-propyl-4H-pyrimido[1,2-b]pyridazin-7-yl)pyrrolidine-2-carboxamide

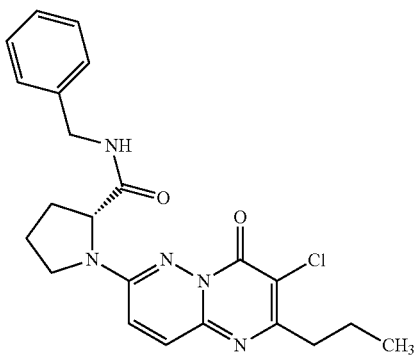

To a solution (10 mL) of the compound (200 mg) obtained in Example 717 in acetonitrile was added N-chlorosuccinimide (63 mg) at room temperature, and the reaction mixture was stirred with heating at 80° C. for 5 hr. After confirmation of the completion of the reaction, the reaction mixture was cooled to room temperature, chloroform was added, and the mixture was washed once with water. The organic layer was dried over anhydrous magnesium sulfate, filtered and concentrated. The residue was purified by silica gel column chromatography (solvent; ethyl acetate/methanol=100/0-90/10). Ethyl acetate was added to the obtained product, and the solid was collected by filtration to give the title compound (126 mg).

MS (ESI) m/z; 426, 428 $[M+H]^+$

Example 724

(R)-1-(3-chloro-4-oxo-2-propyl-4H-pyrimido[1,2-b]pyridazin-7-yl)-N-(1-phenylcyclopropyl)pyrrolidine-2-carboxamide

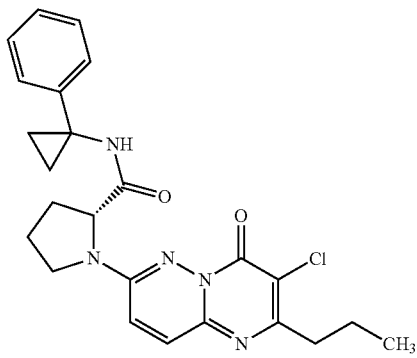 [SMILES: CCCc1nc2ccc(N3CCC[C@@H]3C(=O)NC3(c4ccccc4)CC3)nn2c(=O)c1Cl]

The compound (300 mg) obtained in Example 718 was treated by a method similar to that in Example 723 to give the title compound (200 mg).

MS (ESI) m/z; 452, 454 $[M+H]^+$

Example 725

(R)-N-benzyl-1-(3-chloro-2-ethyl-4-oxo-4H-pyrimido[1,2-b]pyridazin-7-yl)pyrrolidine-2-carboxamide

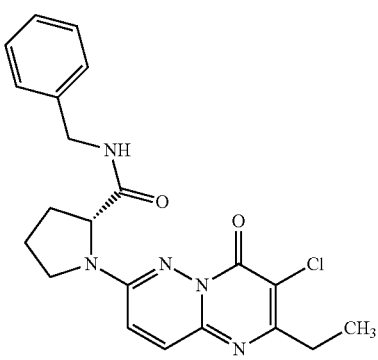

The compound (200 mg) obtained in Example 719 was treated by a method similar to that in Example 723 to give the title compound (129 mg).

MS (ESI) m/z; 412, 414 $[M+H]^+$

Example 726

(R)-N-benzyl-1-[3-chloro-4-oxo-2-(propan-2-yl)-4H-pyrimido[1,2-b]pyridazin-7-yl]pyrrolidine-2-carboxamide

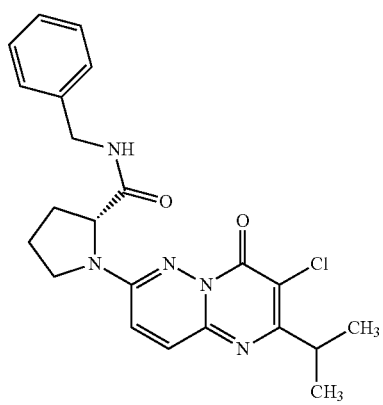 [SMILES: CC(C)c1nc2ccc(N3CCC[C@@H]3C(=O)NCc3ccccc3)nn2c(=O)c1Cl]

The compound (1.10 g) obtained in Example 720 was treated by a method similar to that in Example 723 to give the title compound (890 mg).
MS (ESI) m/z; 426, 428 [M+H]$^+$

Example 727

(R)-N-benzyl-1-[6-(4-methoxybenzyl)-7-oxo-5-(piperidin-1-yl)-6,7-dihydro[1,3]thiazolo[5,4-d]pyrimidin-2-yl]pyrrolidine-2-carboxamide

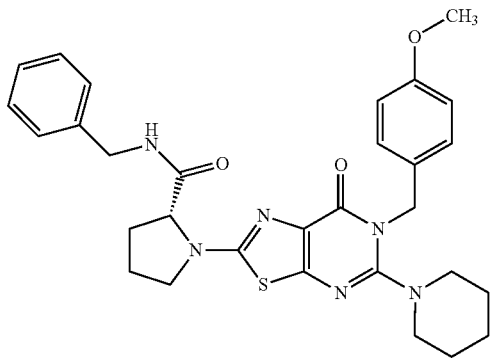 [SMILES: COc1ccc(Cn2c(N3CCCCC3)nc3sc(N4CCC[C@@H]4C(=O)NCc4ccccc4)nc3c2=O)cc1]

To a solution (40.0 mL) of the compound (2.00 g) obtained in Reference Example 637 in N-methylpyrrolidone were added (D)-proline (1.65 g) and potassium carbonate (3.96 g), and the reaction mixture was stirred with heating at 100° C. for 2 hr. The reaction mixture was cooled to room temperature, and acidified with 1.0 mol/L hydrochloric acid. Sodium chloride was added, and the mixture was extracted twice with chloroform. The organic layer was dried over anhydrous magnesium sulfate, and filtered. Chloroform was evaporated under reduced pressure from the filtrate, to the obtained mixture were added N,N-diisopropylethylamine (1.24 mL), benzylamine (775 mg), EDC hydrochloride (1.37 g) and HOBt monohydrate (1.10 g), and the reaction mixture was stirred at room temperature overnight. Water was added, and the mixture was extracted with ethyl acetate. The organic layer was dried over anhydrous sodium sulfate, filtered and concentrated. The residue was purified by silica gel column chromatography (solvent; hexane/ethyl acetate=70/30-10/90) to give the title compound (2.39 g).
MS (ESI) m/z; 559 [M+H]$^+$

Example 728

(R)-N-benzyl-1-[7-oxo-5-(piperidin-1-yl)-6,7-dihydro[1,3]thiazolo[5,4-d]pyrimidin-2-yl]pyrrolidine-2-carboxamide

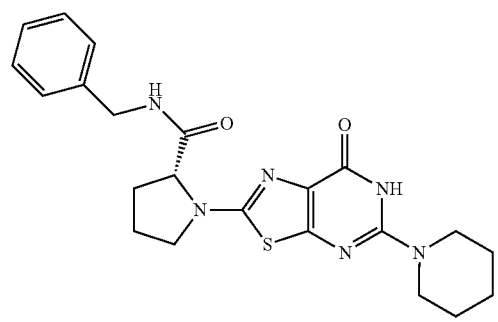 [SMILES: O=C(NCc1ccccc1)[C@H]1CCCN1c1nc2c(=O)[nH]c(N3CCCCC3)nc2s1]

The compound (2.39 g) obtained in Example 727 was treated by a method similar to that in Example 482 to give the title compound (1.35 g).
MS (ESI) m/z; 439 [M+H]$^+$

Reference Example 1

[(R)-1-(benzyloxycarbonyl)pyrrolidine-2-carbonyl]aminocyanoacetic acid ethyl ester

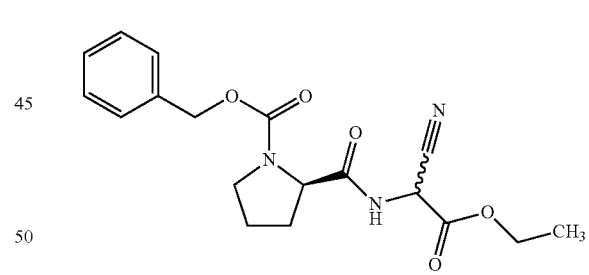

To a solution (500 mL) of N-carbobenzoxy-D-proline (32 g) in THF were added triethylamine (28.5 g) and isobutyl chloroformate (18.4 g) at 0° C., and the reaction mixture was stirred at room temperature for 30 min. A solution (30 mL) of 2-amino-2-cyanoacetic acid ethyl ester (15.7 g) in THF was added at room temperature, and the reaction mixture was stirred overnight. Water was added to the reaction mixture, and the mixture was extracted three times with ethyl acetate. The organic layer was dried over anhydrous magnesium sulfate, filtered and concentrated. The residue was purified by silica gel column chromatography (solvent; hexane/ethyl acetate=70/30-20/80) to give the title compound (40.6 g).
MS (ESI) m/z; 360 [M+H]$^+$

Reference Example 2

{(R)-2-[N-(tert-butoxycarbonyl)-N-methylamino]propionyl}aminocyanoacetic acid ethyl ester

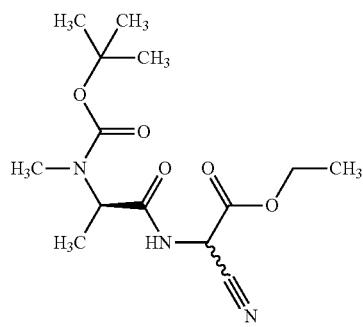 [SMILES: CCOC(=O)C(C#N)NC(=O)[C@@H](C)N(C)C(=O)OC(C)(C)C]

N-(tert-butylcarbonyl)-N-methyl-D-alanine (5.00 g) was treated by a method similar to that in Reference Example 1 to give the title compound (7.44 g).

MS (ESI) m/z; 314 [M+H]$^+$

Reference Example 3

5-amino-2-[(R)-1-(benzyloxycarbonyl)pyrrolidin-2-yl]-1,3-thiazole-4-carboxylic acid ethyl ester 4-toluenesulfonate

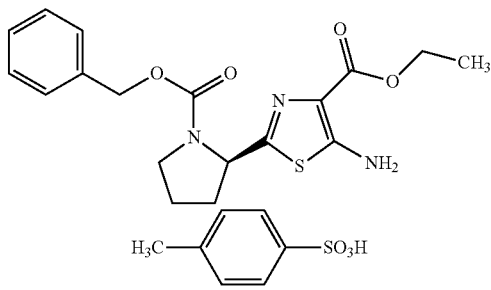

A mixture of the compound (40.6 g) obtained in Reference Example 1, pyridine (46 mL), and Lawesson reagent (27.5 g) in toluene (600 mL) was stirred with heating at 100° C. for 8 hr. The reaction mixture was allowed to cool and water was added, and the mixture was extracted three times with ethyl acetate. The organic layer was dried over anhydrous magnesium sulfate, filtered and concentrated. The residue was purified by NH silica gel column chromatography (solvent; hexane/ethyl acetate=70/30-20/80) to give the title compound in a free form (16.0 g). To a solution (300 mL) of the obtained free form in acetonitrile was added 4-toluenesulfonic acid monohydrate (8.1 g), and the mixture was stirred at room temperature for 30 min. The solvent was evaporated under reduced pressure, and the obtained crystal was washed with ethyl acetate, collected by filtration and dried to give the title compound (14.0 g).

MS (ESI) m/z; 376 [M+H]$^+$

Reference Example 4

5-amino-2-{(R)-1-[N-(tert-butoxycarbonyl)-N-methylamino]ethyl}-1,3-thiazole-4-carboxylic acid ethyl ester

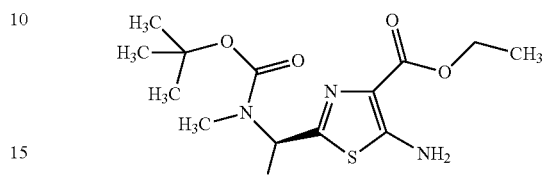

A mixture of the compound (7.44 g) obtained in Reference Example 2 pyridine (14.4 mL), and Lawesson reagent (8.63 g) in 1,4-dioxane (150 mL) was stirred with heating at 100° C. for 24 hr. The reaction mixture was allowed to cool, and the solvent was evaporated under reduced pressure. The residue was dissolved in chloroform, adsorbed to NH silica gel, and the solvent was evaporated. Ethyl acetate was added to the residue, and the mixture was filtered and washed. The filtrate was concentrated under reduced pressure, and the residue was purified by NH silica gel column chromatography (solvent; hexane/ethyl acetate=70/30-20/80) to give the title compound (1.27 g).

MS (ESI) m/z; 330 [M+H]$^+$

Reference Example 5

5-amino-2-[(R)-1-(benzyloxycarbonyl)pyrrolidin-2-yl]-1,3-thiazole-4-carboxylic acid

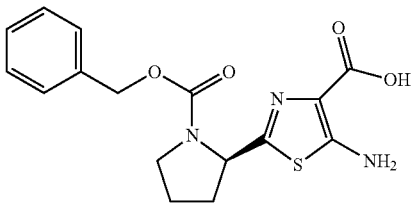 [SMILES: Nc1sc([C@H]2CCCN2C(=O)OCc2ccccc2)nc1C(=O)O]

A suspension (400 mL) of the compound (18.6 g) obtained in Reference Example 3 in chloroform was alkalified with saturated aqueous sodium hydrogen carbonate solution and dissolved. The aqueous layer was separated, extracted twice with chloroform and the combined organic layer was dried over anhydrous magnesium sulfate, filtered and concentrated. To a solution (140 mL) of the residue in ethanol was added 1.0 mol/L sodium hydroxide (140 mL), and the reaction mixture was stirred with heating at 90° C. for 2 hr. The reaction mixture was allowed to cool to room temperature, neutralized with 1.0 mol/L hydrochloric acid, and extracted twice with chloroform. The organic layer was dried over anhydrous magnesium sulfate, filtered and concentrated to give the title compound (11.2 g).

MS (ESI) m/z; 348 [M+H]$^+$

Reference Example 6

5-amino-2-{(R)-1-[N-(tert-butoxycarbonyl)-N-methylamino]ethyl}-1,3-thiazole-4-carboxylic acid

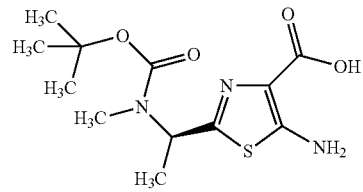 [SMILES: C[C@H](c1nc(C(=O)O)c(N)s1)N(C)C(=O)OC(C)(C)C]

To a solution (70.0 mL) of the compound (1.27 g) obtained in Reference Example 4 in ethanol was added 1.0 mol/L aqueous sodium hydroxide solution (15.5 mL), and the reaction mixture was stirred with heating at 80° C. for 3 hr. The reaction mixture was allowed to cool to room temperature, neutralized with 1.0 mol/L hydrochloric acid, and extracted once with chloroform. The organic layer was dried over anhydrous magnesium sulfate, filtered and concentrated to give the title compound (1.12 g).

MS (ESI) m/z; 302 [M+H]$^+$

Reference Example 7

(R)-2-[5-amino-4-(methylcarbamoyl)-1,3-thiazol-2-yl]pyrrolidine-1-carboxylic acid benzyl ester

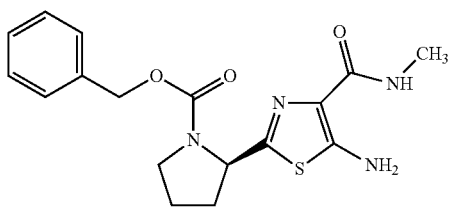 [SMILES: CNC(=O)c1nc([C@H]2CCCN2C(=O)OCc2ccccc2)sc1N]

To a solution (15 mL) of the compound (1.53 g) obtained in Reference Example 5 in DMF were added N,N-diisopropylethylamine (4.6 g), methylamine hydrochloride (1.2 g), EDC hydrochloride (3.4 g) and HOBt monohydrate (2.7 g), and the reaction mixture was stirred at room temperature overnight. Water was added to the reaction mixture, and the mixture was extracted three times with ethyl acetate. The organic layer was dried over anhydrous magnesium sulfate, filtered and concentrated. The residue was purified by silica gel column chromatography (solvent; hexane/ethyl acetate=70/30-20/80) to give the title compound (1.1 g).

MS (ESI) m/z; 361 [M+H]$^+$

Reference Example 8

(R)-2-{5-amino-4-[(propan-2-yl)carbamoyl]-1,3-thiazol-2-yl}pyrrolidine-1-carboxylic acid benzyl ester

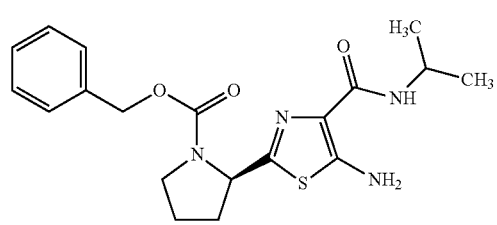 [SMILES: CC(C)NC(=O)c1nc([C@H]2CCCN2C(=O)OCc2ccccc2)sc1N]

The compound (3.60 g) obtained in Reference Example 5 was treated by a method similar to that in Reference Example 7 to give the title compound (2.45 g).

MS (ESI) m/z; 389 [M+H]$^+$

Reference Example 9

(R)-2-{5-amino-4-[(tetrahydro-2H-pyran-4-yl)carbamoyl]-1,3-thiazol-2-yl}pyrrolidine-1-carboxylic acid benzyl ester

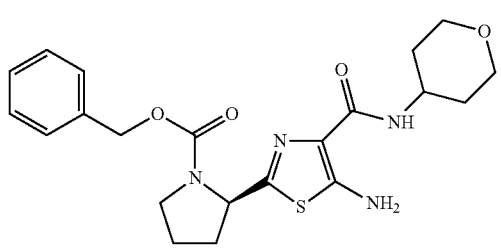 [SMILES: Nc1sc([C@H]2CCCN2C(=O)OCc2ccccc2)nc1C(=O)NC1CCOCC1]

The compound (500 mg) obtained in Reference Example 5 was treated by a method similar to that in Reference Example 7 to give the title compound (766 mg).

MS (ESI) m/z; 431 [M+H]$^+$

Reference Example 10

(R)-2-{4-(methylcarbamoyl)-5-[(3-methyl-[1,2,4]oxadiazole-5-carbonyl)amino]-1,3-thiazol-2-yl}pyrrolidine-1-carboxylic acid benzyl ester

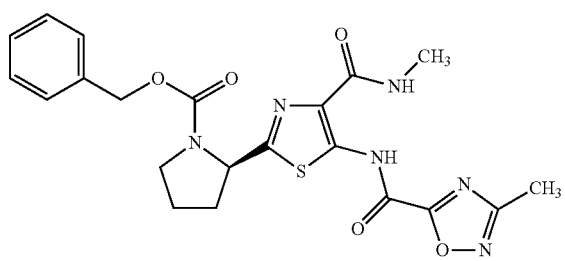 [SMILES: CNC(=O)c1nc([C@H]2CCCN2C(=O)OCc2ccccc2)sc1NC(=O)c1nc(C)no1]

To a solution (50 mL) of 3-methyl-[1,2,4]oxadiazole-5-carboxylic acid ethyl ester (9.45 g) in ethanol was added an aqueous solution (20 mL) of potassium hydroxide (4.0 g) at room temperature, and the reaction mixture was stirred for 2 hr. The solvent was evaporated under reduced pressure, acetonitrile was added to the residue, and the solid was collected by filtration, and dried to give 3-methyl-[1,2,4]oxadiazole-5-carboxylic acid potassium salt (9.38 g). To a solution (60 mL) of the obtained 3-methyl-[1,2,4]oxadiazole-5-carboxylic acid potassium salt (2.8 g) in acetonitrile were added oxalyl chloride (1.4 mL) and DMF (one drop), and the reaction mixture was stirred at room temperature for 2 hr. The reaction mixture was added dropwise to a solution (90 mL) of the compound (2.44 g) obtained in Reference Example 7 and triethylamine (3.8 mL) in methylene chloride under ice-cooling, and the mixture was stirred at room temperature for 2 hr. Water was added to the reaction mixture, and the mixture was extracted twice with chloroform. The organic layer was dried over anhydrous magnesium sulfate, filtered and concentrated. The residue was purified by silica gel column chromatography (solvent; hexane/ethyl acetate=70/30-20/80) to give the title compound (1.68 g).

MS (ESI) m/z; 471 [M+H]+

Reference Example 11

(R)-2-{4-(methylcarbamoyl)-5-[(5-methyl-[1,2,4]oxadiazole-3-carbonyl)amino]-1,3-thiazol-2-yl}pyrrolidine-1-carboxylic acid benzyl ester

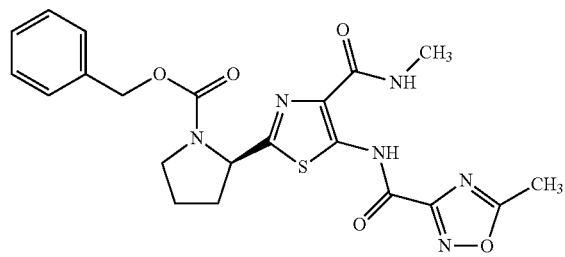 [SMILES: CNC(=O)c1nc([C@H]2CCCN2C(=O)OCc2ccccc2)sc1NC(=O)c1noc(C)n1]

The compound (1500 mg) obtained in Reference Example 7 was treated by a method similar to that in Reference Example 10 to give the title compound (760 mg).

MS (ESI) m/z; 471 [M+H]+

Reference Example 12

(R)-2-{4-(methylcarbamoyl)-5-[(5-methyl-[1,3,4]oxadiazole-2-carbonyl)amino]-1,3-thiazol-2-yl}pyrrolidine-1-carboxylic acid benzyl ester

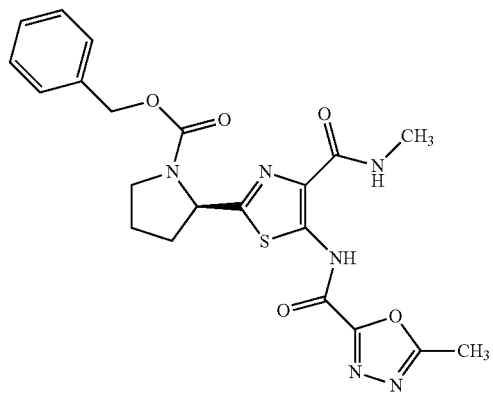 [SMILES: CNC(=O)c1nc([C@H]2CCCN2C(=O)OCc2ccccc2)sc1NC(=O)c1nnc(C)o1]

The compound (2400 mg) obtained in Reference Example 7 was treated by a method similar to that in Reference Example 10 to give the title compound (1800 mg).

MS (ESI) m/z; 471 [M+H]+

Reference Example 13

(R)-2-{5-[(2-chloroacetyl)amino]-4-(methylcarbamoyl)-1,3-thiazol-2-yl}pyrrolidine-1-carboxylic acid benzyl ester

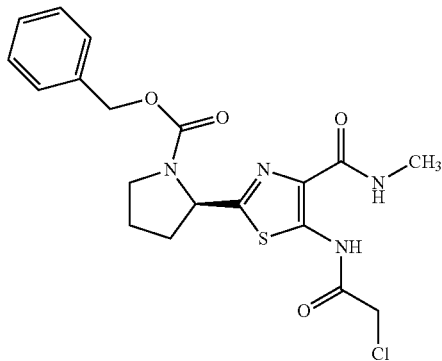 [SMILES: CNC(=O)c1nc([C@H]2CCCN2C(=O)OCc2ccccc2)sc1NC(=O)CCl]

To a solution (10 mL) of the compound (830 mg) obtained in Reference Example 7 and N,N-diisopropylethylamine (0.48 mL) in methylene chloride was added dropwise chloroacetyl chloride (0.22 mL) under ice-cooling. The reaction mixture was stirred at room temperature for 2 hr. Water was added to the reaction mixture, and the mixture was extracted twice with chloroform. The organic layer was dried over anhydrous magnesium sulfate, filtered and concentrated. The residue was purified by silica gel column chromatography (solvent; hexane/ethyl acetate=90/10-20/80) to give the title compound (775 mg).

MS (ESI) m/z; 437 [M+H]+

Reference Example 14

(R)-2-{5-(acetylamino)-4-[(tetrahydro-2H-pyran-4-yl)carbamoyl]-1,3-thiazol-2-yl}pyrrolidine-1-carboxylic acid benzyl ester

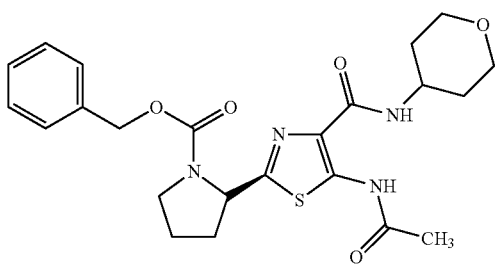

The compound (766 mg) obtained in Reference Example 9 was treated by a method similar to that in Reference Example 13 to give the title compound (285 mg).

MS (ESI) m/z; 473 [M+H]$^+$

Reference Example 15

(R)-2-{4-(methylcarbamoyl)-5-[(tetrahydro-2H-pyran-4-carbonyl)amino]-1,3-thiazol-2-yl}pyrrolidine-1-carboxylic acid benzyl ester

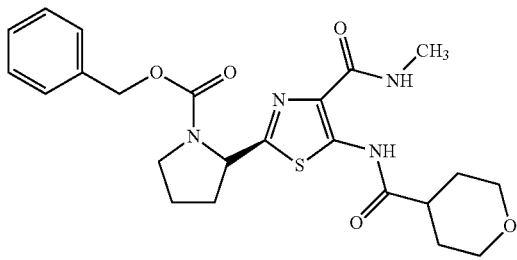

To a solution (30 mL) of tetrahydro-2H-pyran-4-carboxylic acid (1.36 g) in acetonitrile were added oxalyl chloride (0.88 mL) and DMF (one drop), and the reaction mixture was stirred at room temperature for 2 hr. The reaction mixture was added dropwise to a solution (60 mL) of the compound (1.5 g) obtained in Reference Example 7 and triethylamine (2.4 mL) in methylene chloride under ice-cooling, and the mixture was stirred at room temperature for 2 hr. Water was added to the reaction mixture, and the mixture was extracted twice with chloroform. The organic layer was dried over anhydrous magnesium sulfate, filtered and concentrated. The residue was purified by silica gel column chromatography (solvent; hexane/ethyl acetate=70/30-20/80) to give the title compound (1.96 g).

MS (ESI) m/z; 473 [M+H]$^+$

Reference Example 16

6-methyl-5-(3-methyl-[1,2,4]oxadiazol-5-yl)-2-((R)-pyrrolidin-2-yl)-6H-[1,3]thiazolo[5,4-d]pyrimidin-7-one

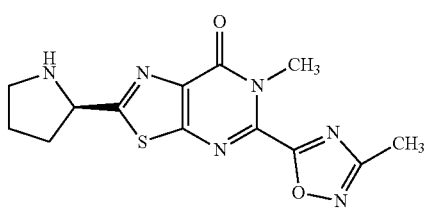 [SMILES: Cc1noc(-c2nc3sc([C@H]4CCCN4)nc3c(=O)n2C)n1]

To a solution (30 mL) of the compound (0.80 g) obtained in Example 1 in acetonitrile was added trimethylsilyl iodide (0.38 mL), and the reaction mixture was stirred at room temperature for 3 hr. Water and 1.0 mol/L hydrochloric acid were added to the reaction mixture, and the mixture was washed with ethyl acetate, neutralized with saturated aqueous sodium hydrogen carbonate solution, and extracted twice with chloroform. The organic layer was dried over anhydrous magnesium sulfate, filtered and concentrated. The residue was purified by silica gel column chromatography (solvent; chloroform/methanol=100/0-95/5) to give the title compound (0.40 g).

MS (ESI) m/z; 319 [M+H]$^+$

Reference Example 17

6-methyl-5-(5-methyl-[1,2,4]oxadiazol-3-yl)-2-((R)-pyrrolidin-2-yl)-6H-[1,3]thiazolo[5,4-d]pyrimidin-7-one

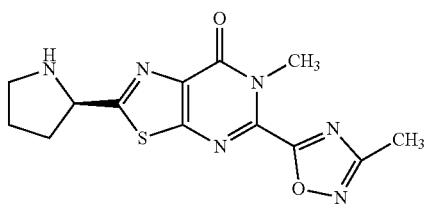 [SMILES: Cc1noc(-c2nc3sc([C@H]4CCCN4)nc3c(=O)n2C)n1]

The compound (700 mg) obtained in Example 2 was treated by a method similar to that in Reference Example 16 to give the title compound (330 mg).

MS (ESI) m/z; 319 [M+H]$^+$

Reference Example 18

6-methyl-5-(5-methyl-[1,3,4]oxadiazol-2-yl)-2-((R)-pyrrolidin-2-yl)-6H-[1,3]thiazolo[5,4-d]pyrimidin-7-one

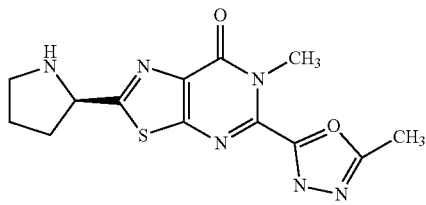

The compound (1300 mg) obtained in Example 3 was treated by a method similar to that in Reference Example 16 to give the title compound (470 mg).
MS (ESI) m/z; 319 [M+H]$^+$

Reference Example 19

6-methyl-2-((R)-pyrrolidin-2-yl)-5-(tetrahydro-2H-pyran-4-yl)-6H-[1,3]thiazolo[5,4-d]pyrimidin-7-one

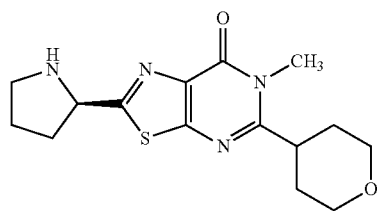 [SMILES: Cn1c(C2CCOCC2)nc2sc([C@H]3CCCN3)nc2c1=O]

The compound (1600 mg) obtained in Example 5 was treated by a method similar to that in Reference Example 16 to give the title compound (720 mg).
MS (ESI) m/z; 321 [M+H]$^+$

Reference Example 20

6-(propan-2-yl)-2-((R)-pyrrolidin-2-yl)-5-trifluoromethyl-6H-[1,3]thiazolo[5,4-d]pyrimidin-7-one

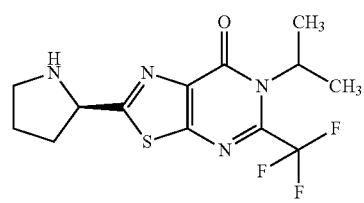 [SMILES: CC(C)n1c(C(F)(F)F)nc2sc([C@H]3CCCN3)nc2c1=O]

To a solution (10 mL) of the compound (2.46 g) obtained in Example 6 in methylene chloride was added 30% hydrogen bromide-acetic acid solution (9.3 mL), and the reaction mixture was stirred at room temperature for 2 hr. Water and 1.0 mol/L hydrochloric acid were added to the reaction mixture, and the mixture was washed with ethyl acetate, neutralized with 1.0 mol/L aqueous sodium hydroxide solution, and extracted twice with chloroform. The organic layer was dried over anhydrous magnesium sulfate, filtered and concentrated. The residue was purified by silica gel column chromatography (solvent; ethyl acetate/methanol=100/0-95/5) to give the title compound (1.30 g).
MS (ESI) m/z; 333 [M+H]$^+$

Reference Example 21

5-ethyl-6-methyl-2-((R)-pyrrolidin-2-yl)-6H-[1,3]thiazolo[5,4-d]pyrimidin-7-one

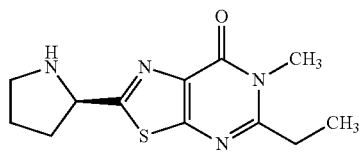 [SMILES: CCc1nc2sc([C@H]3CCCN3)nc2c(=O)n1C]

The compound (100 mg) obtained in Example 7 was treated by a method similar to that in Reference Example 16 to give the title compound (23 mg).
MS (ESI) m/z; 265 [M+H]$^+$

Reference Example 22

6-methyl-5-[(morpholin-4-yl)methyl]-2-((R)-pyrrolidin-2-yl)-6H-[1,3]thiazolo[5,4-d]pyrimidin-7-one

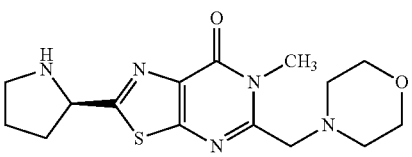 [SMILES: Cn1c(CN2CCOCC2)nc2sc([C@H]3CCCN3)nc2c1=O]

The compound (275 mg) obtained in Example 8 was treated by a method similar to that in Reference Example 16 to give the title compound (43 mg).
MS (ESI) m/z; 336 [M+H]$^+$

Reference Example 23

5-methyl-2-((R)-pyrrolidin-2-yl)-6-(tetrahydro-2H-pyran-4-yl)-6H-[1,3]thiazolo[5,4-d]pyrimidin-7-one

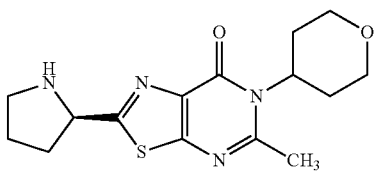 [SMILES: Cc1nc2sc([C@H]3CCCN3)nc2c(=O)n1C1CCOCC1]

To a solution (5.0 mL) of the compound (202 mg) obtained in Reference Example 14 in acetic acid was added concentrated sulfuric acid (2.0 mL), and the reaction mixture was stirred with heating at 125° C. for 25 hr. The reaction mixture was cooled to room temperature, neutralized with saturated aqueous sodium hydrogen carbonate solution, and extracted twice with chloroform. The organic layer was dried over anhydrous magnesium sulfate, filtered and concentrated. The residue was purified by silica gel column chromatography (solvent; chloroform/methanol=100/0-95/5) to give the title compound (60 mg).

MS (ESI) m/z; 321 [M+H]+

Reference Example 24

(R)-2-{5-amino-4-[(2,4-dimethoxybenzyl)carbamoyl]-1,3-thiazol-2-yl}pyrrolidine-1-carboxylic acid benzyl ester

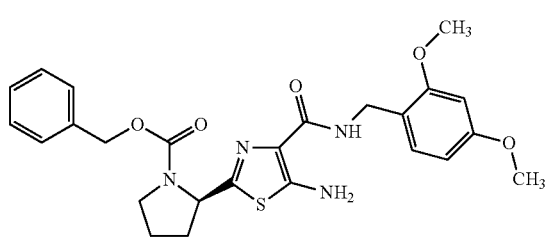 [SMILES: COc1ccc(CNC(=O)c2nc([C@H]3CCCN3C(=O)OCc3ccccc3)sc2N)c(OC)c1]

To a solution (120 mL) of the compound (11.16 g) obtained in Reference Example 5 in DMF were added N,N-diisopropylethylamine (6.3 g), 2,4-dimethoxybenzylamine (8.1 g), to EDC hydrochloride (9.3 g) and HOBt monohydrate (7.4 g), and the reaction mixture was stirred at room temperature overnight. Water was added to the reaction mixture, and the mixture was extracted three times with ethyl acetate. The organic layer was dried over anhydrous magnesium sulfate, filtered and concentrated. The residue was purified by silica gel column chromatography (solvent; hexane/ethyl acetate=70/30-20/80) to give the title compound (16.0 g).

MS (ESI) m/z; 497 [M+H]+

Reference Example 25

N-[(R)-1-{5-amino-4-[(2,4-dimethoxybenzyl)carbamoyl]-1,3-thiazol-2-yl}ethyl]-N-methylcarbamic acid tert-butyl ester

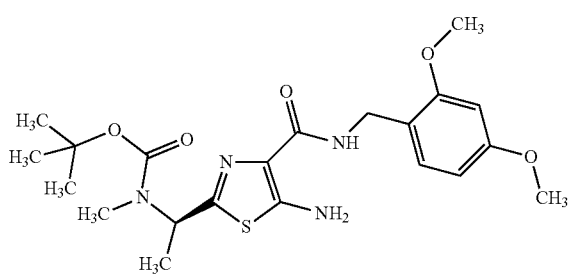 [SMILES: COc1ccc(CNC(=O)c2nc([C@@H](C)N(C)C(=O)OC(C)(C)C)sc2N)c(OC)c1]

The compound (1.12 g) obtained in Reference Example 6 was treated by a method similar to that in Reference Example 24 to give the title compound (1.46 g).

MS (ESI) m/z; 451 [M+H]+

Reference Example 26

(R)-2-{4-[(2,4-dimethoxybenzyl)carbamoyl]-5-(2-methylpropanoyl)amino-1,3-thiazol-2-yl}pyrrolidine-1-carboxylic acid benzyl ester

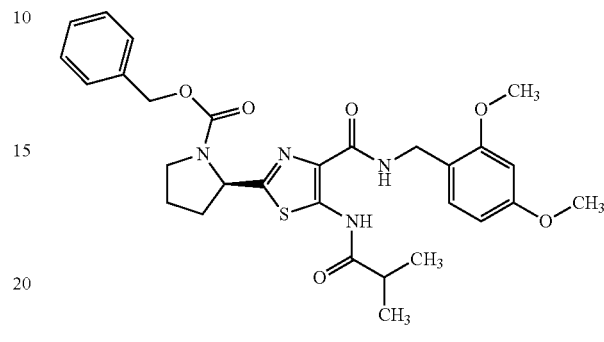

To a solution (30 mL) of the compound (1500 mg) obtained is in Reference Example 24 in methylene chloride were added triethylamine (630 μL) and isobutyryl chloride (380 μL) at room temperature. The reaction mixture was stirred at room temperature for 1.5 hr. Water was added to the reaction mixture, and the mixture was extracted with chloroform. The combined organic layer was dried over anhydrous magnesium sulfate, filtered and concentrated to give the title compound (1800 mg).

MS (ESI) m/z; 567 [M+H]+

Reference Example 27

(R)-2-{5-[(cyclopropylcarbonyl)amino]-4-[(2,4-dimethoxybenzyl)carbamoyl]-1,3-thiazol-2-yl}pyrrolidine-1-carboxylic acid benzyl ester

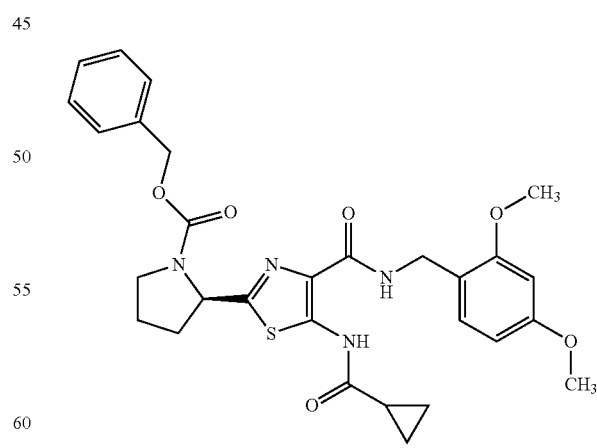

The compound (1.00 g) obtained in Reference Example 24 was treated by a method similar to that in Reference Example 26 to give the title compound (1.28 g).

MS (ESI) m/z; 565 [M+H]+

Reference Example 28

(R)-2-{5-benzoylamino-4-[(2,4-dimethoxybenzyl)carbamoyl]-1,3-thiazol-2-yl}pyrrolidine-1-carboxylic acid benzyl ester

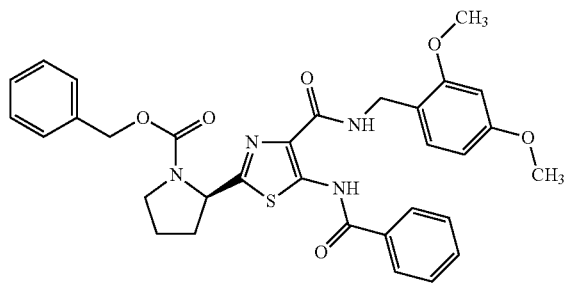 [SMILES: COc1ccc(CNC(=O)c2nc([C@H]3CCCN3C(=O)OCc3ccccc3)sc2NC(=O)c2ccccc2)c(OC)c1]

The compound (1.50 g) obtained in Reference Example 24 was treated by a method similar to that in Reference Example 26 to give the title compound (1.74 g).
MS (ESI) m/z; 601 [M+H]$^+$

Reference Example 29

(R)-2-{4-[(2,4-dimethoxybenzyl)carbamoyl]-5-[(2-fluorobenzoyl)amino]-1,3-thiazol-2-yl}pyrrolidine-1-carboxylic acid benzyl ester

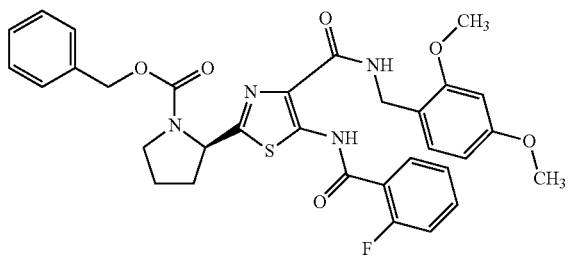 [SMILES: COc1ccc(CNC(=O)c2nc([C@H]3CCCN3C(=O)OCc3ccccc3)sc2NC(=O)c2ccccc2F)c(OC)c1]

The compound (2.00 g) obtained in Reference Example 24 was treated by a method similar to that in Reference Example 26 to give the title compound (1.90 g).
MS (ESI) m/z; 619 [M+H]$^+$

Reference Example 30

(R)-2-{5-[(2,4-difluorobenzoyl)amino]-4-[(2,4-dimethoxybenzyl)carbamoyl]-1,3-thiazol-2-yl}pyrrolidine-1-carboxylic acid benzyl ester

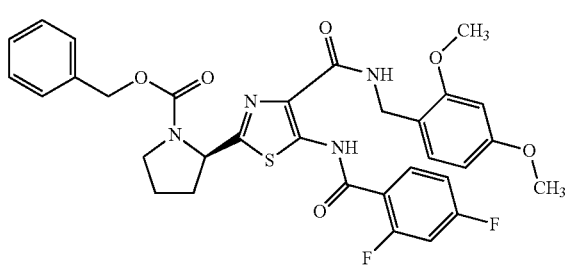 [SMILES: COc1ccc(CNC(=O)c2nc([C@H]3CCCN3C(=O)OCc3ccccc3)sc2NC(=O)c2ccc(F)cc2F)c(OC)c1]

The compound (1.50 g) obtained in Reference Example 24 was treated by a method similar to that in Reference Example 26 to give the title compound (1.47 g).
MS (ESI) m/z; 637 [M+H]$^+$

Reference Example 31

(R)-2-{4-[(2,4-dimethoxybenzyl)carbamoyl]-5-[2-(trifluoromethoxy)benzoylamino]-1,3-thiazol-2-yl}pyrrolidine-1-carboxylic acid benzyl ester

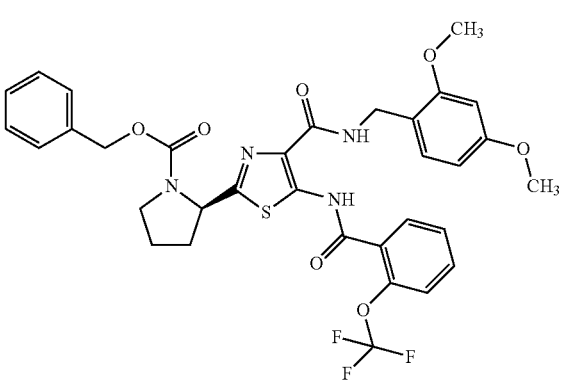 [SMILES: COc1ccc(CNC(=O)c2nc([C@H]3CCCN3C(=O)OCc3ccccc3)sc2NC(=O)c2ccccc2OC(F)(F)F)c(OC)c1]

The compound (1.50 g) obtained in Reference Example 24 was treated by a method similar to that in Reference Example 26 to give the title compound (1.90 g).
MS (ESI) m/z; 685 [M+H]$^+$

Reference Example 32

(R)-2-{4-[(2,4-dimethoxybenzyl)carbamoyl]-5-[(2-methylbenzoyl)amino]-1,3-thiazol-2-yl}pyrrolidine-1-carboxylic acid benzyl ester

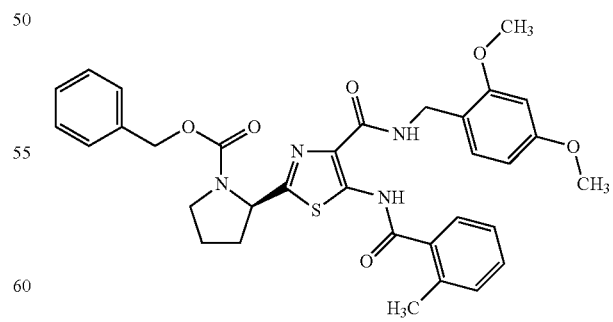

The compound (1.50 g) obtained in Reference Example 24 was treated by a method similar to that in Reference Example 26 to give the title compound (1.45 g).
MS (ESI) m/z; 615 [M+H]$^+$

Reference Example 33

(R)-2-{4-[(2,4-dimethoxybenzyl)carbamoyl]-5-[(2-methoxybenzoyl)amino]-1,3-thiazol-2-yl}pyrrolidine-1-carboxylic acid benzyl ester

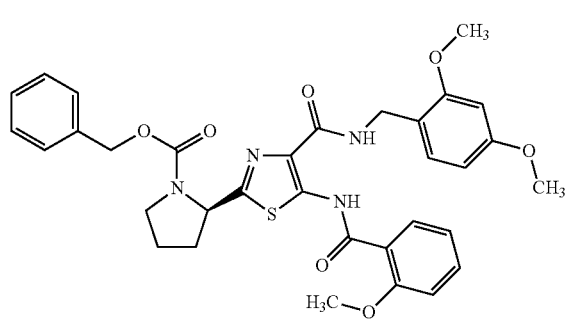 [SMILES: COc1ccc(CNC(=O)c2nc([C@H]3CCCN3C(=O)OCc3ccccc3)sc2NC(=O)c2ccccc2OC)c(OC)c1]

The compound (1.50 g) obtained in Reference Example 24 was treated by a method similar to that in Reference Example 26 to give the title compound (1.90 g).

MS (ESI) m/z; 631 [M+H]$^+$

Reference Example 34

N-[(R)-1-{4-[(2,4-dimethoxybenzyl)carbamoyl]-5-[(propan-2-yl)amino]-1,3-thiazol-2-yl}ethyl]-N-methylcarbamic acid tert-butyl ester

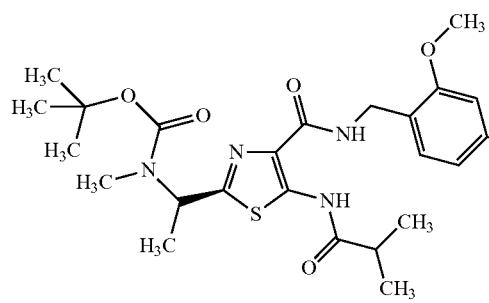

The compound (700 mg) obtained in Reference Example 25 was treated by a method similar to that in Reference Example 26 to give the title compound (800 mg).

MS (ESI) m/z; 521 [M+H]$^+$

Reference Example 35

(R)-2-[4-[(2,4-dimethoxybenzyl)carbamoyl]-5-{[(1-fluorocyclopropyl)carbonyl]amino}-1,3-thiazol-2-yl]pyrrolidine-1-carboxylic acid benzyl ester

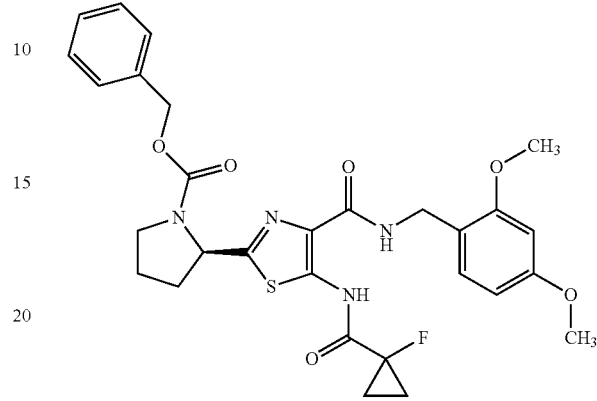

To a solution (10 mL) of 1-fluorocyclopropylcarboxylic acid (540 mg) in methylene chloride were added oxalyl chloride (440 μL) and DMF (one drop), and the reaction mixture was stirred at room temperature for 2 hr. The reaction mixture was added dropwise to a solution (20 mL) of the compound (2.0 g) obtained in Reference Example 24 and triethylamine (2.3 mL) in methylene chloride under ice-cooling, and the mixture was stirred at room temperature for 7 hr. Water was added to the reaction mixture, and the mixture was extracted twice with chloroform. The organic layer was dried over anhydrous magnesium sulfate, filtered and concentrated. The residue was purified by silica gel column chromatography (solvent; hexane/ethyl acetate=70/30-20/80) to give the title compound (1.8 g).

MS (ESI) m/z; 583 [M+H]$^+$

Reference Example 36

(R)-2-[5-{[(1-chlorocyclopropyl)carbonyl]amino}-4-[(2,4-dimethoxybenzyl)carbamoyl]-1,3-thiazol-2-yl]pyrrolidine-1-carboxylic acid benzyl ester

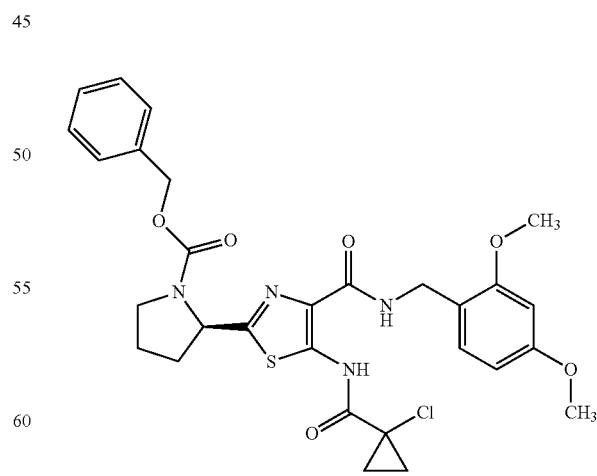

The compound (200 mg) obtained in Reference Example 24 was treated by a method similar to that in Reference Example 35 to give the title compound (180 mg).

MS (ESI) m/z; 599 [M+H]$^+$

Reference Example 37

(R)-2-{5-[(2,2-difluoropropionyl)amino]-4-[(2,4-dimethoxybenzyl)carbamoyl]-1,3-thiazol-2-yl}pyrrolidine-1-carboxylic acid benzyl ester

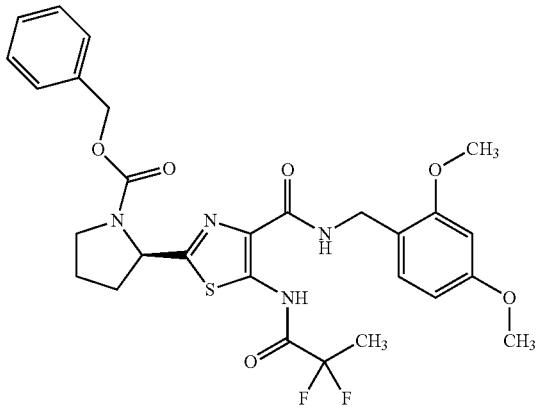 [SMILES: COc1ccc(CNC(=O)c2nc([C@H]3CCCN3C(=O)OCc3ccccc3)sc2NC(=O)C(C)(F)F)c(OC)c1]

The compound (312 mg) obtained in Reference Example 24 was treated by a method similar to that in Reference Example 35 to give the title compound (207 mg).

MS (ESI) m/z; 589 [M+H]$^+$

Reference Example 38

(R)-2-[5-{[(4,4-difluorocyclohexane)carbonyl]amino}-4-[(2,4-dimethoxybenzyl)carbamoyl]-1,3-thiazol-2-yl]pyrrolidine-1-carboxylic acid benzyl ester

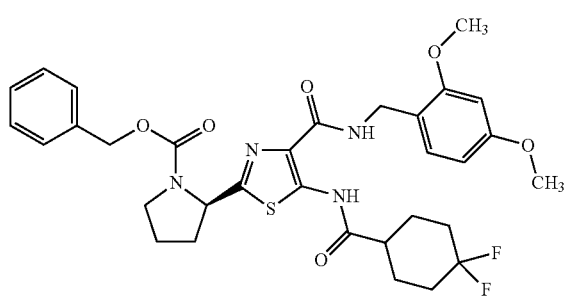 [SMILES: COc1ccc(CNC(=O)c2nc([C@H]3CCCN3C(=O)OCc3ccccc3)sc2NC(=O)C2CCC(F)(F)CC2)c(OC)c1]

The compound (1.50 g) obtained in Reference Example 24 was treated by a method similar to that in Reference Example 35 to give the title compound (1.90 g).

MS (ESI) m/z; 643 [M+H]$^+$

Reference Example 39

(R)-2-[4-[(2,4-dimethoxybenzyl)carbamoyl]-5-{[(1-fluorocyclohexane)carbonyl]amino}-1,3-thiazol-2-yl]pyrrolidine-1-carboxylic acid benzyl ester

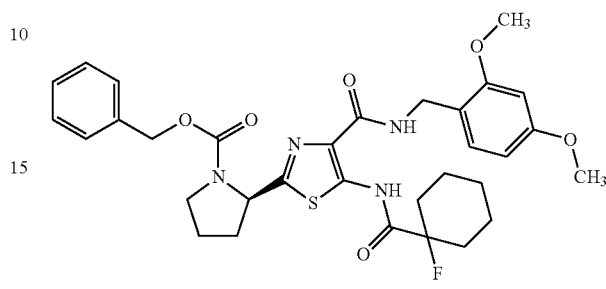

The compound (1.50 g) obtained in Reference Example 24 was treated by a method similar to that in Reference Example 35 to give the title compound (1.34 g).

MS (ESI) m/z; 625 [M+H]$^+$

Reference Example 40

(R)-2-[5-{[(3,3-difluorocyclobutane)carbonyl]amino}-4-[(2,4-dimethoxybenzyl)carbamoyl]-1,3-thiazol-2-yl]pyrrolidine-1-carboxylic acid benzyl ester

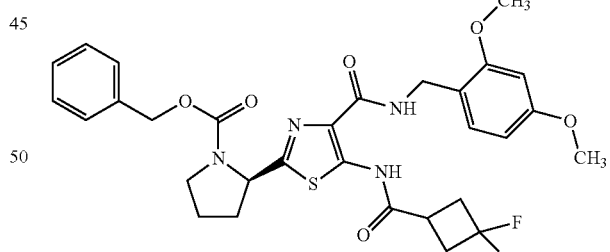

The compound (1.50 g) obtained in Reference Example 24 was treated by a method similar to that in Reference Example 35 to give the title compound (1.68 g).

MS (ESI) m/z; 615 [M+H]$^+$

Reference Example 41

(R)-2-[4-[(2, 4-dimethoxybenzyl)carbamoyl]-5-{[(1-ethoxycyclopropyl)carbonyl]amino}-1,3-thiazol-2-yl]pyrrolidine-1-carboxylic acid benzyl ester

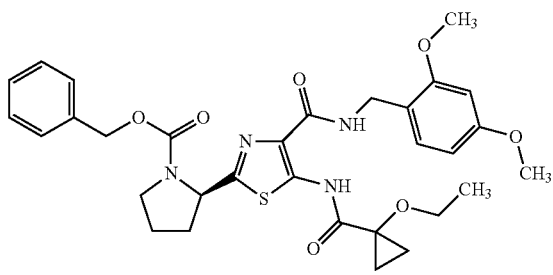 [SMILES: CCOC1(C(=O)Nc2sc([C@H]3CCCN3C(=O)OCc3ccccc3)nc2C(=O)NCc2ccc(OC)cc2OC)CC1]

The compound (2.00 g) obtained in Reference Example 24 was treated by a method similar to that in Reference Example 35 to give the title compound (1.40 g).

MS (ESI) m/z; 609 [M+H]$^+$

Reference Example 42

(R)-2-[5-{[(1-cyanocyclopropyl) carbonyl]amino}-4-[(2,4-dimethoxybenzyl)carbamoyl]-1,3-thiazol-2-yl]pyrrolidine-1-carboxylic acid benzyl ester

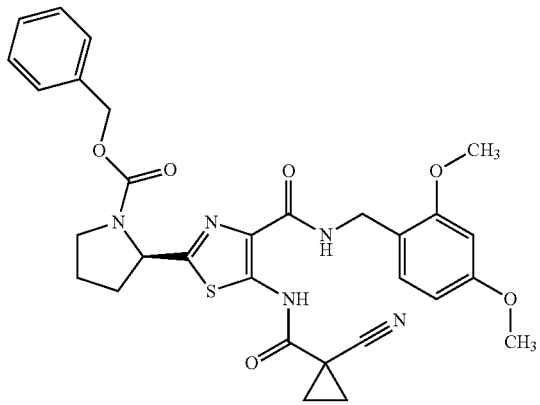 [SMILES: COc1ccc(CNC(=O)c2nc([C@H]3CCCN3C(=O)OCc3ccccc3)sc2NC(=O)C2(C#N)CC2)c(OC)c1]

The compound (3.50 g) obtained in Reference Example 24 was treated by a method similar to that in Reference Example 35 to give the title compound (4.10 g).

MS (ESI) m/z; 590 [M+H]$^+$

Reference Example 43

(R)-2-{5-[(2-cyano-2-methylpropionyl)amino]-4-[(2,4-dimethoxybenzyl)carbamoyl]-1,3-thiazol-2-yl}pyrrolidine-1-carboxylic acid benzyl ester

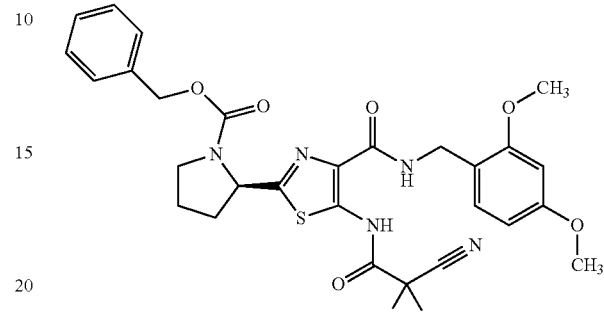

The compound (700 mg) obtained in Reference Example 24 was treated by a method similar to that in Reference Example 35 to give the title compound (583 mg).

MS (ESI) m/z; 592 [M+H]$^+$

Reference Example 44

(R)-2-{4-[(2,4-dimethoxybenzyl)carbamoyl]-5-[{[1-(fluoromethyl)cyclopropyl]carbonyl}amino]-1,3-thiazol-2-yl}pyrrolidine-1-carboxylic acid benzyl ester

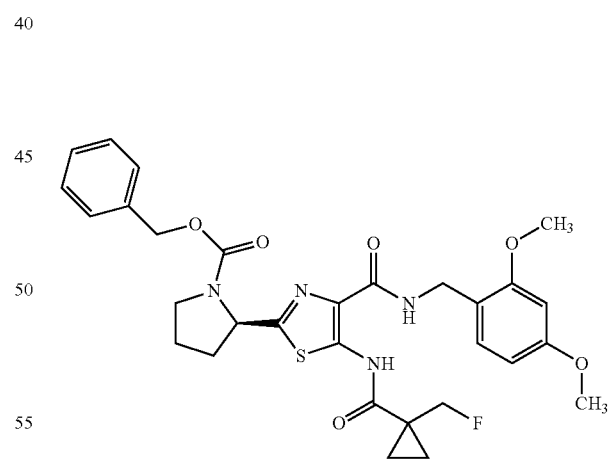

The compound (500 mg) obtained in Reference Example 24 was treated by a method similar to that in Reference Example 35 to give the title compound (379 mg).

MS (ESI) m/z; 597 [M+H]$^+$

Reference Example 45

(R)-2-[4-[(2,4-dimethoxybenzyl)carbamoyl]-5-{[1-(trifluoromethyl)cyclopropylcarbonyl]amino}-1,3-thiazol-2-yl]pyrrolidine-1-carboxylic acid benzyl ester

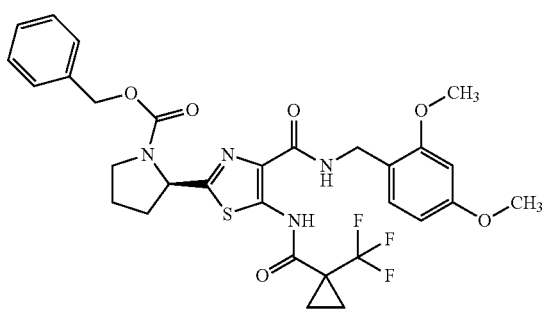 [SMILES: COc1ccc(CNC(=O)c2nc([C@H]3CCCN3C(=O)OCc3ccccc3)sc2NC(=O)C2(C(F)(F)F)CC2)c(OC)c1]

The compound (1.50 g) obtained in Reference Example 24 was treated by a method similar to that in Reference Example 35 to give the title compound (1.46 g)

MS (ESI) m/z; 633 [M+H]$^+$

Reference Example 46

N-[(R)-1-{5-{[(1-chlorocyclopropyl)carbonyl]amino}-4-[(2,4-dimethylbenzyl)carbamoyl]-1,3-thiazol-2-yl}ethyl]-N-methylcarbamic acid tert-butyl ester

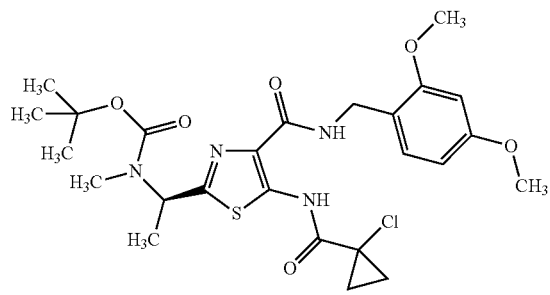 [SMILES: COc1ccc(CNC(=O)c2nc([C@@H](C)N(C)C(=O)OC(C)(C)C)sc2NC(=O)C2(Cl)CC2)c(OC)c1]

The compound (700 mg) obtained in Reference Example 25 was treated by a method similar to that in Reference Example 35 to give the title compound (815 mg).

MS (ESI) m/z; 553, 555 [M+H]$^+$

Reference Example 47

(R)-2-{4-[(2,4-dimethoxybenzyl)carbamoyl]-5-[(2,2,2-trifluoroacetyl)amino]-1,3-thiazol-2-yl}pyrrolidine-1-carboxylic acid benzyl ester

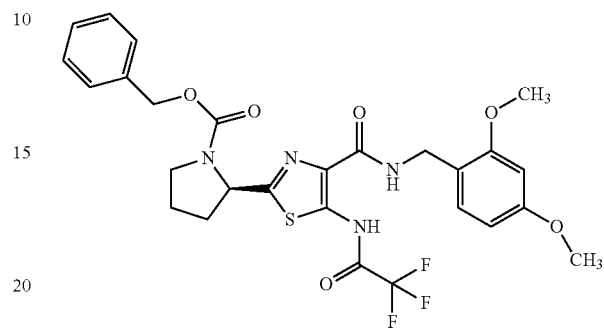

To a solution (10 mL) of the compound (486 mg) obtained in Reference Example 24 in methylene chloride were added dropwise trifluoroacetic anhydride (165 μL) and pyridine (158 μL), and the reaction mixture was stirred at room temperature for 5 hr. The reaction mixture was concentrated under reduced pressure, and the residue was dissolved in chloroform. The solution was washed with 1.0 mol/L hydrochloric acid and saturated aqueous sodium hydrogen carbonate solution, dried over anhydrous magnesium sulfate, filtered and concentrated to give the title compound (580 mg).

MS (ESI) m/z; 593 [M+H]$^+$

Reference Example 48

(R)-2-{5-[(2,2-difluoroacetyl)amino]-4-[(2,4-dimethoxybenzyl)carbamoyl]-1,3-thiazol-2-yl}pyrrolidine-1-carboxylic acid benzyl ester

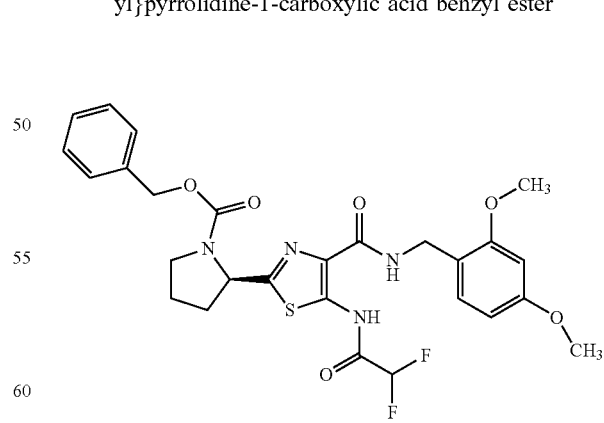

The compound (497 mg) obtained in Reference Example 24 was treated by a method similar to that in Reference Example 47 to give the title compound (567 mg).

MS (ESI) m/z; 575 [M+H]$^+$

Reference Example 49

N-{(R)-1-[6-(2,4-dimethoxybenzyl)-7-oxo-5-(propan-2-yl)-6,7-dihydro[1,3]thiazolo[5,4-d]pyrimidin-2-yl]ethyl}-N-methylcarbamic acid tert-butyl ester

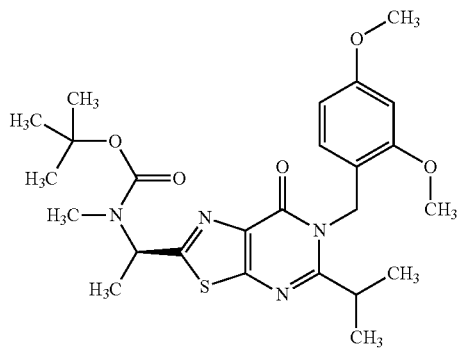 [SMILES: COc1ccc(Cn2c(C(C)C)nc3sc([C@@H](C)N(C)C(=O)OC(C)(C)C)nc3c2=O)c(OC)c1]

The compound (800 mg) obtained in Reference Example 34 was treated by a method similar to that in Example 42 to give the title compound (740 mg).

MS (ESI) m/z; 503 [M+H]$^+$

Reference Example 50

N-{(R)-1-[5-(1-chlorocyclopropyl)-6-(2,4-dimethoxybenzyl)-7-oxo-6,7-dihydro[1,3]thiazolo[5,4-d]pyrimidin-2-yl]ethyl}-N-methylcarbamic acid tert-butyl ester

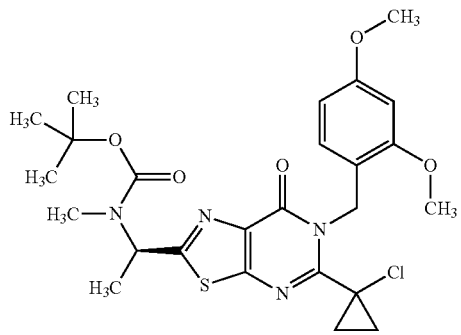 [SMILES: COc1ccc(Cn2c(C3(Cl)CC3)nc3sc([C@@H](C)N(C)C(=O)OC(C)(C)C)nc3c2=O)c(OC)c1]

The compound (815 mg) obtained in Reference Example 46 was treated by a method similar to that in Example 42 to give the title compound (765 mg).

MS (ESI) m/z; 535, 537 [M+H]$^+$

Reference Example 51

(R)-2-{4-[(2,4-dimethoxybenzyl)carbamoyl]-5-[{[1-(methoxymethyl)cyclopropyl]carbonyl}amino]-1,3-thiazol-2-yl}pyrrolidine-1-carboxylic acid benzyl ester

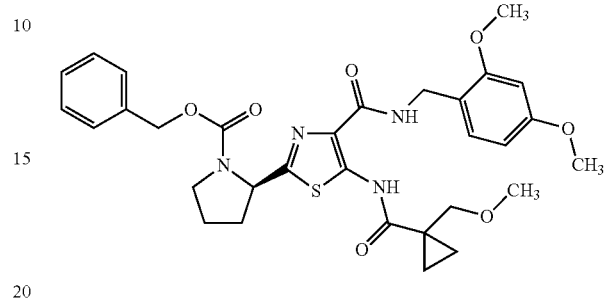

The compound (2.50 g) obtained in Reference Example 24 was treated by a method similar to that in Reference Example 35 to give the title compound (2.50 g).

MS (ESI) m/z; 609 [M+H]$^+$

Reference Example 52

2-(R)-(pyrrolidin-2-yl)-5-[1-(methoxymethyl)cyclopropyl]-6H-[1,3]thiazolo[5,4-d]pyrimidin-7-one

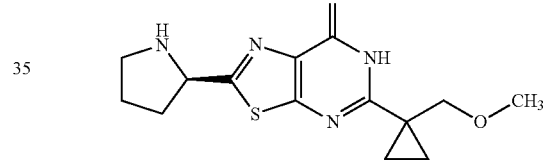

To a solution (30 mL) of the compound (2.30 g) obtained in Example 95 in acetonitrile was added trimethylsilyl iodide (0.84 mL), and the reaction mixture was stirred at room temperature overnight. To the reaction mixture were added water and ethyl acetate, and the mixture was extracted 3 times with 1.0 mol/L hydrochloric acid. The aqueous layer was neutralized with saturated aqueous sodium hydrogen carbonate solution, and extracted 3 times with chloroform. The organic layer was dried over anhydrous magnesium sulfate, filtered and concentrated to give the title compound (1.00 g).

MS (ESI) m/z; 307 [M+H]$^+$

Reference Example 53

2-(R)-(pyrrolidin-2-yl)-5-[1-(trifluoromethyl)cyclopropyl]-6H-[1,3]thiazolo[5,4-d]pyrimidin-7-one

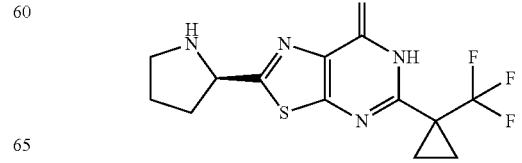

The compound (320 mg) obtained in Example 60 was treated by a method similar to that in Reference Example 52 to give the title compound (120 mg).
MS (ESI) m/z; 331 [M+H]⁺

Reference Example 54

(R)-2-[6-(2,4-dimethoxybenzyl)-5-mercapto-7-oxo-6,7-dihydro[1,3]thiazolo[5,4-d]pyrimidin-2-yl]pyrrolidine-1-carboxylic acid benzyl ester

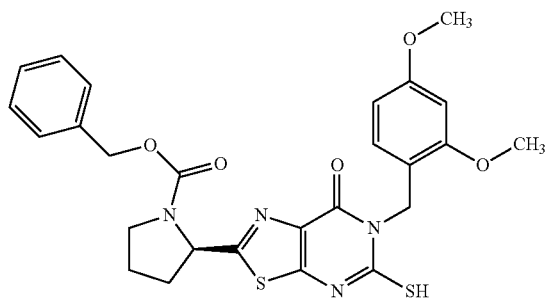 [SMILES: COc1ccc(Cn2c(S)nc3sc([C@H]4CCCN4C(=O)OCc4ccccc4)nc3c2=O)c(OC)c1]

To a solution (10 mL) of the compound (1.48 g) obtained in Reference Example 24 in ethanol was added potassium ethyl xanthogenate (1.43 g), and the reaction mixture was heated under reflux for 17 hr. The reaction mixture was cooled to room temperature, 1.0 mol/L hydrochloric acid was added, and the mixture was extracted twice with ethyl acetate. The combined organic layer was washed with saturated brine, dried over anhydrous magnesium sulfate, filtered and concentrated to give the title compound (1.56 g).
MS (ESI) m/z; 539 [M+H]⁺

Reference Example 55

(R)-2-[6-(2,4-dimethoxybenzyl)-5-methylsulfanyl-7-oxo-6,7-dihydro[1,3]thiazolo[5,4-d]pyrimidin-2-yl]pyrrolidine-1-carboxylic acid benzyl ester

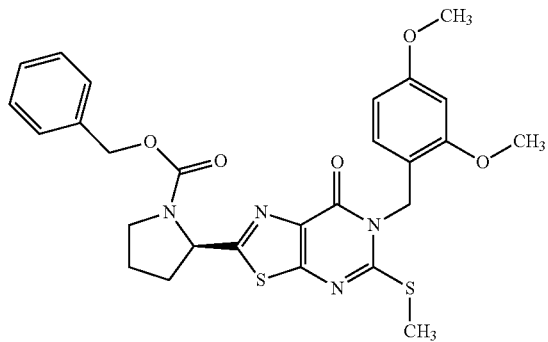 [SMILES: COc1ccc(Cn2c(SC)nc3sc([C@H]4CCCN4C(=O)OCc4ccccc4)nc3c2=O)c(OC)c1]

To a solution (20 mL) of the compound (1.53 g) obtained in Reference Example 54 in DMF was added potassium carbonate (590 mg) and methyl iodide (0.27 mL) at 0° C., and the reaction mixture was stirred at room temperature for 3 hr. Water was added to the reaction mixture, and the mixture was extracted twice with ethyl acetate. The combined organic layer was washed with saturated brine, dried over anhydrous magnesium sulfate, filtered and concentrated. The residue was purified by NH silica gel column chromatography (solvent; hexane/ethyl acetate=70/30-50/50) to give the title compound (1.13 g).
MS (ESI) m/z; 553 [M+H]⁺

Reference Example 56

(R)-2-[6-(2,4-dimethoxybenzyl)-5-((RS)-methylsulfinyl)-7-oxo-6,7-dihydro[1,3]thiazolo[5,4-d]pyrimidin-2-yl]pyrrolidine-1-carboxylic acid benzyl ester

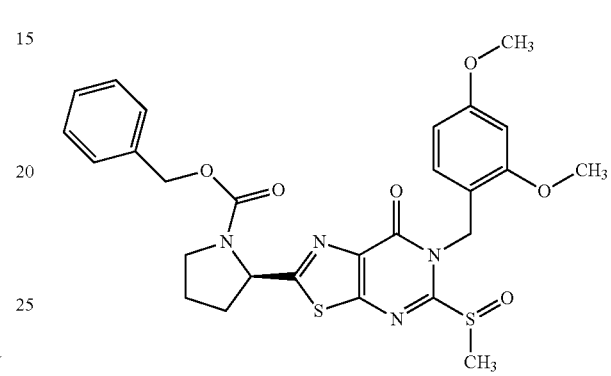

To a solution (5.0 mL) of the compound (300 mg) obtained in Reference Example 55 in methylene chloride was added mCPBA (69-75%, 147 mg) under ice-cooling. The reaction mixture was stirred under ice-cooling for 2 hr. To the reaction mixture were added aqueous sodium thiosulfate solution and saturated aqueous sodium hydrogen carbonate solution, and the mixture was extracted with chloroform. The organic layer was dried over anhydrous magnesium sulfate, filtered and concentrated. The residue was purified by silica gel column chromatography (solvent; hexane/ethyl acetate=50/50-0/100) to give the title compound (192 mg).
MS (ESI) m/z; 569 [M+H]⁺

Reference Example 57

(R)-2-{4-[(2,4-dimethoxybenzyl)carbamoyl]-5-(propionylamino)-1,3-thiazol-2-yl}pyrrolidine-1-carboxylic acid benzyl ester

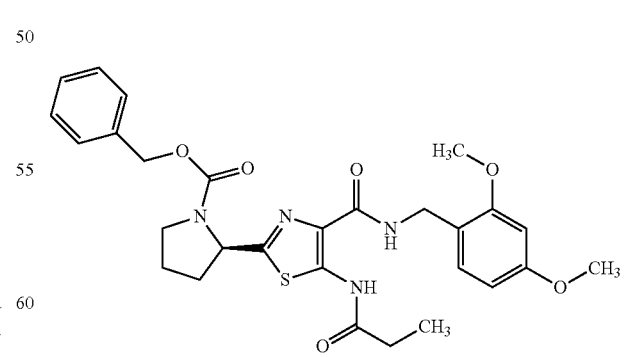

The compound (1.00 g) obtained in Reference Example 24 was treated by a method similar to that in Reference Example 26 to give the title compound (0.92 g).
MS (ESI) m/z; 553 [M+H]⁺

Reference Example 58

(R)-2-[4-[(2,4-dimethoxybenzyl)carbamoyl]-5-{[(1-methylcyclopropyl) carbonyl]amino}-1,3-thiazol-2-yl]pyrrolidine-1-carboxylic acid benzyl ester

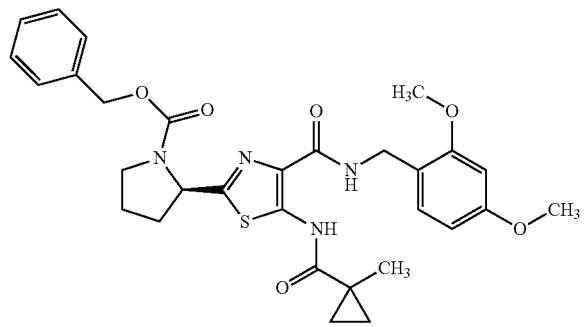 [SMILES: COc1ccc(CNC(=O)c2nc([C@H]3CCCN3C(=O)OCc3ccccc3)sc2NC(=O)C2(C)CC2)c(OC)c1]

The compound (1.50 g) obtained in Reference Example 24 was treated by a method similar to that in Reference Example 35 to give the title compound (1.27 g).

MS (ESI) m/z; 579 [M+H]⁺

Reference Example 59

(R)-2-{4-[(2,4-dimethoxybenzyl)carbamoyl]-5-[(3-methyloxetane-3-carbonyl)amino]-1,3-thiazol-2-yl}pyrrolidine-1-carboxylic acid benzyl ester

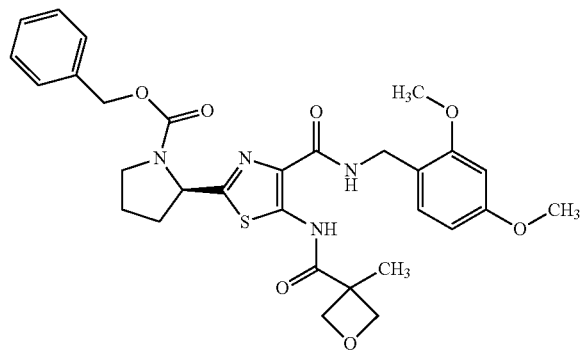 [SMILES: COc1ccc(CNC(=O)c2nc([C@H]3CCCN3C(=O)OCc3ccccc3)sc2NC(=O)C2(C)COC2)c(OC)c1]

To a solution (50.0 mL) of 3-methyloxetane-3-carboxylic acid (1.00 g) in DMF were added the compound (2.80 g) obtained in Reference Example 24, N,N-diisopropylethylamine (2.50 mL) and HATU (3.30 g), and the reaction mixture was stirred at room temperature for 6 days. Water was added to the reaction mixture, and the mixture was extracted twice with ethyl acetate. The organic layer was dried over anhydrous magnesium sulfate, filtered and concentrated. The residue was purified by silica gel column chromatography (solvent; hexane/ethyl acetate=90/10-40/60) to give the title compound (2.10 g).

MS (ESI) m/z; 595 [M+H]⁺

Reference Example 60

6-(2,4-dimethoxybenzyl)-5-ethyl-2-((R)-pyrrolidin-2-yl)-6H-[1,3]thiazolo[5,4-d]pyrimidin-7-one

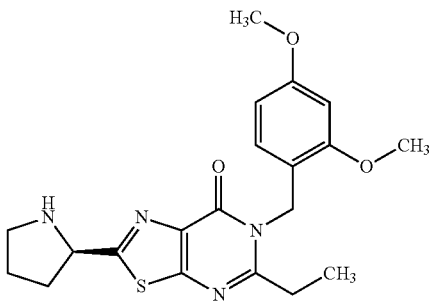 [SMILES: CCc1nc2sc([C@H]3CCCN3)nc2c(=O)n1Cc1ccc(OC)cc1OC]

To a solution (70 mL) of the compound (700 mg) obtained in Example 108 in acetonitrile was added trimethylsilyl iodide (0.38 mL), and the reaction mixture was stirred at room temperature overnight. To the reaction mixture were added water and ethyl acetate, and the mixture was extracted 3 times with 1.0 mol/L hydrochloric acid. The aqueous layer was neutralized with saturated aqueous sodium hydrogen carbonate solution, and extracted 3 times with chloroform. The organic layer was dried over anhydrous magnesium sulfate, filtered and concentrated. The residue was purified by silica gel column chromatography (solvent; chloroform/methanol=100/0-95/5) to give the title compound (480 mg).

MS (ESI) m/z; 401 [M+H]⁺

Reference Example 61

6-(2,4-dimethoxybenzyl)-5-(1-methylcyclopropyl)-2-((R)-pyrrolidin-2-yl)-6H-[1,3]thiazolo[5,4-d]pyrimidin-7-one

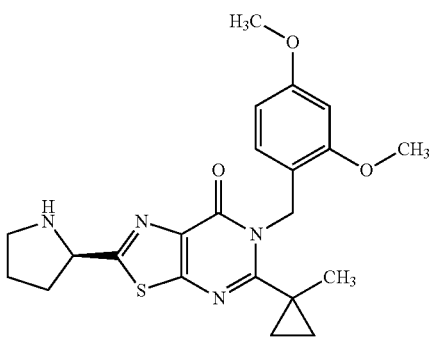 [SMILES: COc1ccc(Cn2c(C3(C)CC3)nc3sc([C@H]4CCCN4)nc3c2=O)c(OC)c1]

The compound (548 mg) obtained in Example 109 was treated by a method similar to that in Reference Example 60 to give the title compound (320 mg).

MS (ESI) m/z; 427 [M+H]⁺

Reference Example 62

6-(2,4-dimethoxybenzyl)-5-(3-methyloxetan-3-yl)-2-((R)-pyrrolidin-2-yl)-6H-[1,3]thiazolo[5,4-d]pyrimidin-7-one

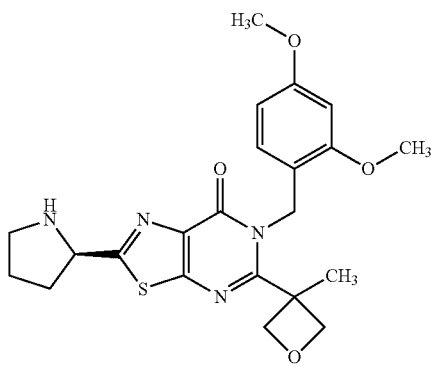 [SMILES: COc1ccc(Cn2c(C3(C)COC3)nc3sc([C@H]4CCCN4)nc3c2=O)c(OC)c1]

To a solution (10.0 mL) of the compound (650 mg) obtained in Example 110 in methanol was added 10% palladium hydroxide carbon (200 mg), and the reaction mixture was stirred under a hydrogen atmosphere at room temperature overnight. The reaction mixture was filtered through diatomaceous earth, and the filtrate was concentrated. The residue was purified by silica gel column chromatography (solvent; chloroform/methanol=100/0-95/5) to give the title compound (70.0 mg).

MS (ESI) m/z; 443 [M+H]$^+$

Reference Example 63

(R)-2-{4-[(2,4-dimethoxybenzyl)carbamoyl]-5-[(2-fluoro-2-methylpropionyl)amino]-1,3-thiazol-2-yl}pyrrolidine-1-carboxylic acid benzyl ester

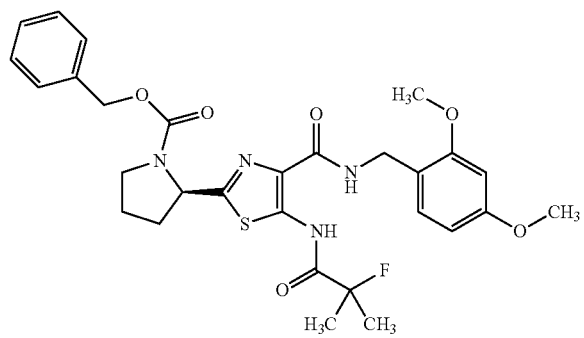 [SMILES: COc1ccc(CNC(=O)c2nc([C@H]3CCCN3C(=O)OCc3ccccc3)sc2NC(=O)C(C)(C)F)c(OC)c1]

The compound (2.0 g) obtained in Reference Example 24 was treated by a method similar to that in Reference Example 35 to give the title compound (2.0 g).

MS (ESI) m/z; 585 [M+H]$^+$

Reference Example 64

(R)-2-{4-carbamoyl-5-[(2-fluoro-2-methylpropionyl)amino]-1,3-thiazol-2-yl}pyrrolidine-1-carboxylic acid benzyl ester

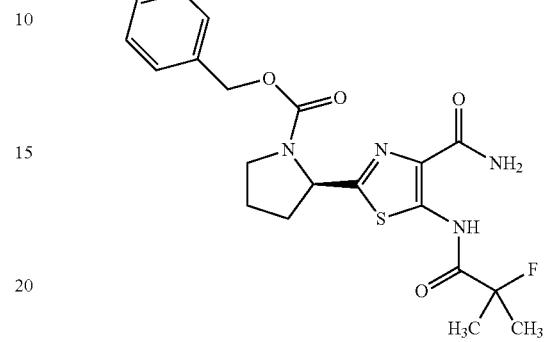

To the compound (2.0 g) obtained in Reference Example 63 was added a mixture of triethylsilane (3.3 m), water (3.3 mL) and trifluoroacetic acid (60 mL), and the reaction mixture was stirred at room temperature for 2 hr. The solvent was evaporated under reduced pressure, to the residue were added chloroform and saturated aqueous sodium hydrogen carbonate solution, and the mixture was extracted twice with chloroform. The organic layer was dried over anhydrous magnesium sulfate, filtered and concentrated. The residue was purified by silica gel column chromatography (solvent; hexane/ethyl acetate=70/30-50/50) to give the title compound (1.3 g).

MS (ESI) m/z; 435 [M+H]$^+$

Reference Example 65

(RS)-2-(5-amino-4-carbamoyl-1,3-thiazol-2-yl)pyrrolidine-1-carboxylic acid benzyl ester

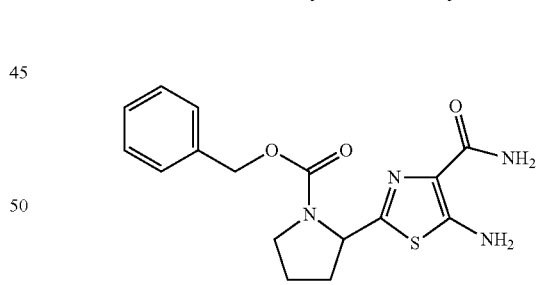

The compound (1.0 g) obtained in Reference Example 24 was added to a mixed solvent of triethylsilane (2.0 mL) and trifluoroacetic acid (18 mL), and the reaction mixture was stirred at room temperature for 1 hr. The solvent was evaporated under reduced pressure, ethyl acetate and saturated aqueous sodium hydrogen carbonate solution were added to the residue, and the mixture was extracted twice with ethyl acetate. The organic layer was dried over anhydrous magnesium sulfate, filtered and concentrated. The residue was purified by silica gel column chromatography (solvent; hexane/ethyl acetate=70/30-20/80) to give the title compound (0.47 g).

MS (ESI) m/z; 347 [M+H]$^+$

Reference Example 66

(RS)-2-{4-carbamoyl-5-[(3-methyl-[1,2,4]oxadiazole-5-carbonyl)amino]-1,3-thiazol-2-yl}pyrrolidine-1-carboxylic acid benzyl ester

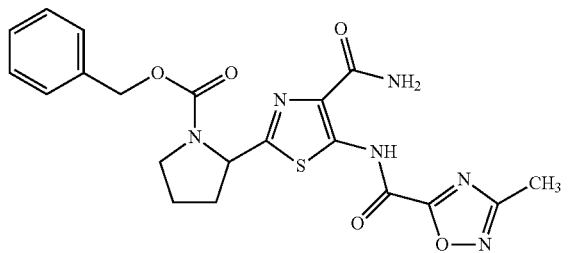 [SMILES: Cc1noc(C(=O)Nc2sc(C3CCCN3C(=O)OCc3ccccc3)nc2C(N)=O)n1]

To a solution (50 mL) of 3-methyl-[1,2,4]oxadiazole-5-carboxylic acid ethyl ester (9.45 g) in ethanol was added an aqueous solution (20 mL) of potassium hydroxide (4.0 g) at room temperature, and the reaction mixture was stirred at the same temperature for 2 hr. The solvent was evaporated under reduced pressure, acetonitrile was added to the residue, and the solid was collected by filtration, and dried to give 3-methyl-[1,2,4]oxadiazole-5-carboxylic acid potassium salt (9.38 g). To a solution (10 mL) of the obtained 3-methyl-[1,2,4]oxadiazole-5-carboxylic acid potassium salt (0.71 g) in acetonitrile were added oxalyl chloride (0.36 mL) and DMF (one drop), and the reaction mixture was stirred at room temperature for 30 min. The reaction mixture was added dropwise to a solution (10 mL) of the compound (0.34 g) obtained in Reference Example 65 in pyridine under ice-cooling, and the mixture was stirred at room temperature for 1 hr. The reaction mixture was neutralized with 1.0 mol/L hydrochloric acid, and extracted is twice with ethyl acetate. The organic layer was dried over anhydrous magnesium sulfate, filtered and concentrated. The residue was purified by silica gel column chromatography (solvent; hexane/ethyl acetate=70/30-0/100) to give the title compound (0.47 g).

MS (ESI) m/z; 457 [M+H]$^+$

Reference Example 67

(R)-2-{5-[(1-acetoxycyclopropylcarbonyl)amino]-4-[(2,4-dimethoxybenzyl)carbamoyl]-1,3-thiazol-2-yl}pyrrolidine-1-carboxylic acid benzyl ester

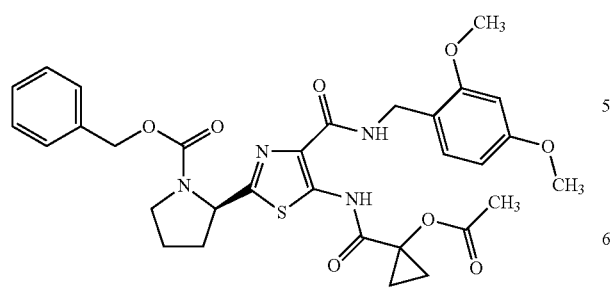

The compound (5.50 g) obtained in Reference Example 24 was treated by a method similar to that in Reference Example 35 to give the title compound (6.38 g).

MS (ESI) m/z; 623 [M+H]$^+$

Reference Example 68

5-(1-methoxycyclopropyl)-2-((R)-pyrrolidin-2-yl)-6H-[1,3]thiazolo[5,4-d]pyrimidin-7-one

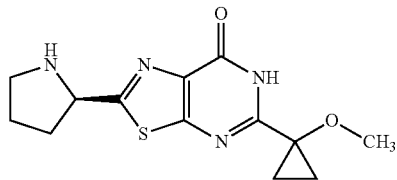 [SMILES: COC1(c2nc3sc([C@H]4CCCN4)nc3c(=O)[nH]2)CC1]

The compound (2.20 g) obtained in Example 123 was treated by a method similar to that in Reference Example 52 to give the title compound (0.88 g).

MS (ESI) m/z; 293 [M+H]$^+$

Reference Example 69

2-tert-butyl-5-nitro-3H-pyrimidin-4-one

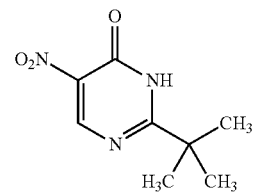

To nitroethyl acetate (2.0 g) was added N,N-dimethylformamide dimethyl acetal (3.6 g), and the reaction mixture was stirred at room temperature for 1 hr and stirred with heating at 100° C. for 1.5 hr. The reaction mixture was cooled to room temperature and the solvent was evaporated under reduced pressure. To the residue were added ethanol (40 mL), pivalamidine hydrochloride (2.3 g) and triethylamine (2.4 mL) at room temperature, and the reaction mixture was stirred with heating at 100° C. for 8 hr. The reaction mixture was cooled to room temperature and the solvent was evaporated. The residue was purified by silica gel column chromatography (solvent; chloroform/methanol=100/0-90/10) to give the title compound (1.33 g).

MS (ESI) m/z; 198 [M+H]$^+$

Reference Example 70

5-amino-2-tert-butyl-3H-pyrimidin-4-one

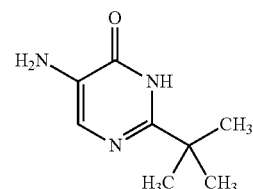

To a mixture of the compound (1.33 g) obtained in Reference Example 69 in methanol-chloroform (20 mL-10 mL) was added 10% palladium carbon (100 mg), and the reaction mixture was stirred under a hydrogen atmosphere at room temperature for 8 hr. After confirmation of the completion of the reaction, the reaction mixture was filtered through diatomaceous earth, and the filtrate was concentrated under reduced pressure to give the title compound (1.20 g).

MS (ESI) m/z; 168 [M+H]+

Reference Example 71

5-amino-6-bromo-2-tert-butyl-3H-pyrimidin-4-one

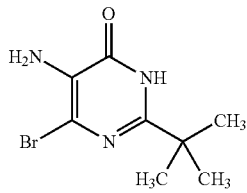

To a solution (30 mL) of the compound (1.20 g) obtained in Reference Example 70 in DMF was added a solution (5 mL) of N-bromosuccinimide (1.32 g) in DMF at 0° C. The reaction mixture was stirred at 0° C. for 1 hr. To the reaction mixture was added aqueous sodium thiosulfate solution, and the mixture was extracted twice with ethyl acetate. The organic layer was dried over anhydrous magnesium sulfate, filtered and concentrated. The residue was purified by silica gel column chromatography (solvent; hexane/ethyl acetate=80/20-30/70) to give the title compound (580 mg).

MS (ESI) m/z; 246, 248 [M+H]+

Reference Example 72

(R)-2-[(4-bromo-2-tert-butyl-6-oxo-1,6-dihydropyrimidin-5-yl)carbamoyl]pyrrolidine-1-carboxylic acid benzyl ester

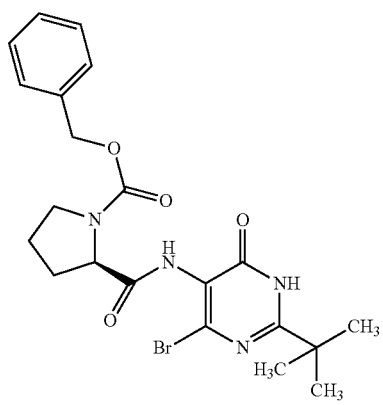 [SMILES: CC(C)(C)c1nc(Br)c(NC(=O)[C@H]2CCCN2C(=O)OCc2ccccc2)c(=O)[nH]1]

To a solution (10 mL) of N-carbobenzoxy-D-proline (650 mg) in methylene chloride were added oxalyl chloride (220 μL) and DMF (one drop), and the reaction mixture was stirred at room temperature for 2 hr. The reaction mixture was added dropwise to a solution (20 mL) of the compound (580 mg) obtained in Reference Example 71 and triethylamine (1.7 mL) in methylene chloride under ice-cooling, and the mixture was stirred at room temperature for 2 hr. Water was added to the reaction mixture, and the mixture was extracted twice with chloroform. The organic layer was dried over anhydrous magnesium sulfate, filtered and concentrated. To the residue was added diisopropyl ether, and the solid was collected by filtration and dried to give the title compound (960 mg).

MS (ESI) m/z; 477, 479 [M+H]+

Reference Example 73

(R)-2-{[4-bromo-2-tert-butyl-6-(4-methoxybenzyloxy)pyrimidin-5-yl]carbamoyl}pyrrolidine-1-carboxylic acid benzyl ester

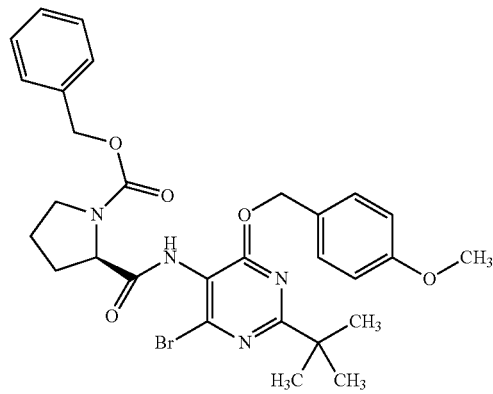

To a solution (20 mL) of the compound (960 mg) obtained in Reference Example 72 in THF were added 4-methoxybenzyl alcohol (420 mg), triphenylphosphine (790 mg) and a solution (1.6 mL) of diisopropyl azodicarboxylate in 1.9 mol/L toluene at room temperature, and the reaction mixture was stirred at the same temperature for 2 hr. The solvent was evaporated under reduced pressure, and the residue was purified by silica gel column chromatography (solvent; hexane/ethyl acetate=70/30-50/50) to give the title compound (1.46 g)

MS (ESI) m/z; 597, 599 [M+H]+

Reference Example 74

(R)-2-(5-tert-butyl-7-thioxo-6,7-dihydro[1,3]thiazolo[5,4-d]pyrimidin-2-yl)pyrrolidine-1-carboxylic acid benzyl ester

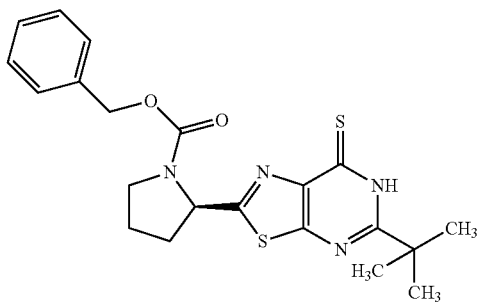 [SMILES: CC(C)(C)c1nc2sc([C@H]3CCCN3C(=O)OCc3ccccc3)nc2c(=S)[nH]1]

To a solution (10 mL) of the compound (1.46 g) obtained in Reference Example 73 in toluene were added pyridine (0.83 mL) and Lawesson reagent (0.49 g), and the reaction mixture was stirred with heating at 100° C. for 8 hr. Pyridine (0.43 mL) and Lawesson reagent (0.25 g) were further added, and the reaction mixture was stirred with heating at 100° C. for 2 hr. The reaction mixture was allowed to cool to and the solvent was evaporated under reduced pressure. The residue was purified by NH silica gel column chromatography (solvent; chloroform/methanol=100/0-95/5) to give the title compound (0.41 g).

MS (ESI) m/z; 429 [M+H]$^+$

Reference Example 75

(R)-2-(5-tert-butyl-7-methylsulfanyl-[1,3]thiazolo[5,4-d]pyrimidin-2-yl)pyrrolidine-1-carboxylic acid benzyl ester

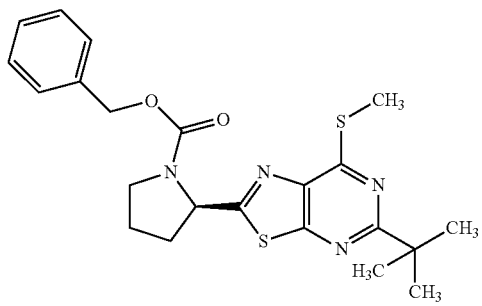 [SMILES: CSc1nc(C(C)(C)C)nc2sc([C@H]3CCCN3C(=O)OCc3ccccc3)nc12]

To a solution (5.0 mL) of the compound (410 mg) obtained in Reference Example 74 in DMF were added potassium carbonate (200 mg) and methyl iodide (90 μL) at 0° C., and the reaction mixture was stirred for 1 hr. To the reaction mixture were added water and aqueous sodium thiosulfate solution, and the mixture was extracted twice with ethyl acetate. The organic layer was dried over anhydrous magnesium sulfate, filtered and concentrated to give the title compound (380 mg).

MS (ESI) m/z; 443 [M+H]$^+$

Reference Example 76

(R)-2-(5-tert-butyl-7-methylsulfonyl-[1,3]thiazolo[5,4-d]pyrimidin-2-yl)pyrrolidine-1-carboxylic acid benzyl ester

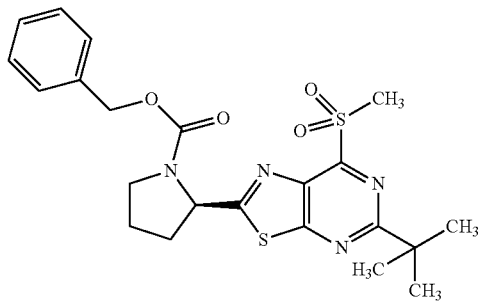 [SMILES: CC(C)(C)c1nc(S(C)(=O)=O)c2nc([C@H]3CCCN3C(=O)OCc3ccccc3)sc2n1]

To a solution (10 mL) of the compound (380 mg) obtained in Reference Example 75 in methylene chloride was added mCPBA (69-75%, 440 mg) under ice-cooling. The reaction mixture was stirred under ice-cooling for 2 hr. To the reaction mixture were added aqueous sodium thiosulfate solution and saturated aqueous sodium hydrogen carbonate solution, and the mixture was extracted with chloroform. The organic layer was dried over anhydrous magnesium sulfate, filtered and concentrated. The residue was purified by silica gel column chromatography (solvent; hexane/ethyl acetate=80/20-50/50) to give the title compound (400 mg).

MS (ESI) m/z; 475 [M+H]$^+$

Reference Example 77

(R)-2-[5-tert-butyl-7-(4-methoxybenzyloxy)-[1,3]thiazolo[5,4-d]pyrimidin-2-yl]pyrrolidine-1-carboxylic acid benzyl ester

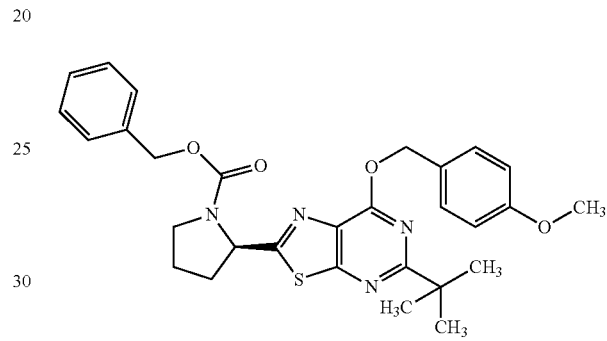

A solution (2.0 mL) of the compound (400 mg) obtained in Reference Example 76 in DMF was added to a solution (5.0 mL) of 4-methoxybenzyl alcohol (150 mg) and sodium hydride (60% oil dispersion, 41 mg) in DMF at 0° C., and the reaction mixture was stirred for 1 hr. Water was added to the reaction mixture, and the mixture was extracted twice with ethyl acetate. The organic layer was dried over anhydrous magnesium sulfate, filtered and concentrated. The residue was purified by silica gel column chromatography (solvent; hexane/ethyl acetate=70/30-50/50) to give the title compound (350 mg).

MS (ESI) m/z; 533 [M+H]$^+$

Reference Example 78

5-tert-butyl-2-((R)-pyrrolidin-2-yl)-6H-[1,3]thiazolo[5,4-d]pyrimidin-7-one

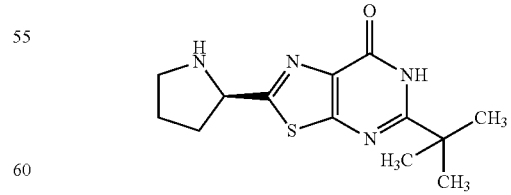

To a solution (10 mL) of the compound (350 mg) obtained in Reference Example 77 in acetonitrile was added trimethylsilyl iodide (380 μL) at room temperature, and the reaction mixture was stirred for 2 hr. To the reaction mixture were added water and ethyl acetate, and the mixture was extracted 3 times with 1.0 mol/L hydrochloric acid. The aqueous layer was neutralized with saturated aqueous sodium hydrogen carbonate solution, and extracted 3 times with chloroform. The organic layer was dried over anhydrous magnesium sulfate, filtered and concentrated to give the title compound (120 mg).
MS (ESI) m/z; 279 [M+H]$^+$ Reference Example 79 pyrazolidine-1-carboxylic acid phenyl ester

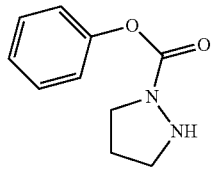 [SMILES: O=C(Oc1ccccc1)N1CCCN1]

To a solution (100 mL) of pyrazolidine dihydrochloride (3.0 g) in methylene chloride were added triethylamine (8.7 mL) and phenyl chloroformate (2.9 g) at 0° C., and the reaction mixture was stirred at the same temperature for 1 hr. Water was added to the reaction mixture, and the mixture was extracted twice with chloroform. The organic layer was dried over anhydrous magnesium sulfate, filtered and concentrated. The residue was purified by silica gel column chromatography (solvent; chloroform/methanol=100/0-95/5) to give the title compound (2.58 g).
MS (ESI) m/z; 193 [M+H]$^+$ Reference Example 80

2-phenyl-1-(pyrazolidin-1-yl)ethanone

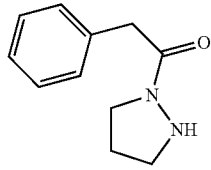 [SMILES: O=C(Cc1ccccc1)N1CCCN1]

Pyrazolidine dihydrochloride (3.0 g) was treated by a method similar to that in Reference Example 79 to give the title compound (1.58 g).
MS (ESI) m/z; 191 [M+H]$^+$ Reference Example 81

1-(pyrazolidin-1-yl)-2-(3-methylphenyl)ethanone

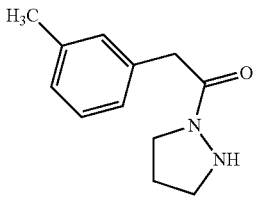

To a solution (30 mL) of 3-methylphenylacetic acid (2.8 g) in methylene chloride were added oxalyl chloride (1.6 mL) and DMF (one drop), and the reaction mixture was stirred at room temperature for 2 hr. The reaction mixture was added dropwise to a solution (100 mL) of pyrazolidine dihydrochloride (3.0 g) and triethylamine (11.5 mL) in methylene chloride at 0° C., and the mixture was stirred for 1 hr. Water was added to the reaction mixture, and the mixture was extracted twice with chloroform. The organic layer was dried over anhydrous magnesium sulfate, filtered and concentrated. The residue was purified by silica gel column chromatography (solvent; chloroform/methanol=100/0-95/5) to give the title compound (1.63 g).
MS (ESI) m/z; 205 [M+H]$^+$ Reference Example 82 pyrazolidine-1-carboxylic acid 3-methylphenyl ester

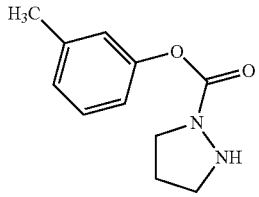

To a solution of triphosgene (3.0 g) in toluene (30 mL) were added m-cresol (2.7 g) and pyridine (2.6 mL) under ice-cooling, and the reaction mixture was stirred at room temperature for 30 min. The solvent was evaporated under reduced pressure, and the residue was dissolved in methylene chloride and added to a solution (100 mL) of pyrazolidine dihydrochloride (3.0 g) and triethylamine (10.1 mL) in methylene chloride at 0° C., and the reaction mixture was stirred for 1 hr. Water was added to the reaction mixture, and the mixture was extracted twice with chloroform. The organic layer was dried over anhydrous magnesium sulfate, filtered and concentrated. The residue was purified by silica gel column chromatography (solvent; chloroform/methanol=100/0-95/5) to give the title compound (1.0 g).
MS (ESI) m/z; 207 [M+H]$^+$ Reference Example 83

5-amino-2-bromo-1,3-thiazole-4-carboxylic acid

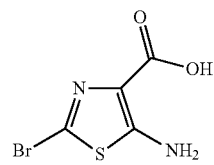

To a solution (15 mL) of 2-bromo-5-[(tert-butoxycarbonyl)amino]-1,3-thiazole-4-carboxylic acid (3.2 g) synthesized by the method described in US 2011/005996 A1 in methylene chloride was added trifluoroacetic acid (30 mL) at room temperature, and the reaction mixture was stirred at the same temperature was stirred for 2 hr. The solvent was evaporated under reduced pressure to give the title compound (2.15 g).
MS (ESI) m/z; 223, 225 [M+H]$^+$

Reference Example 84

5-amino-2-bromo-N-(2,4-dimethoxybenzyl)-1,3-thiazole-4-carboxamide

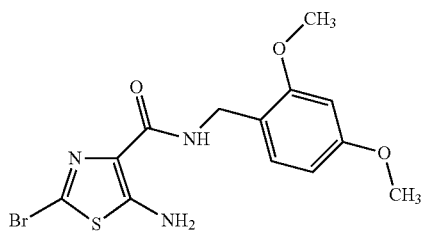 [SMILES: COc1ccc(CNC(=O)c2nc(Br)sc2N)c(OC)c1]

To a solution (30 mL) of the compound (2.15 g) obtained is in Reference Example 83 in DMF were added N,N-diisopropylethylamine (2.60 mL), 2,4-dimethoxybenzylamine (2.50 g), EDC hydrochloride (2.90 g) and HOBt monohydrate (2.30 g), and the reaction mixture was stirred at room temperature for 3 hr. Water was added to the reaction mixture, and the mixture was extracted three times with ethyl acetate. The organic layer was dried over anhydrous magnesium sulfate, filtered and concentrated. The residue was purified by silica gel column chromatography (solvent; hexane/ethyl acetate=70/30-20/80) to give the title compound (2.78 g)

MS (ESI) m/z; 372, 374 [M+H]$^+$

Reference Example 85

2-bromo-N-(2,4-dimethoxybenzyl)-5-[(2-fluorobenzoyl)amino]-1,3-thiazole-4-carboxamide

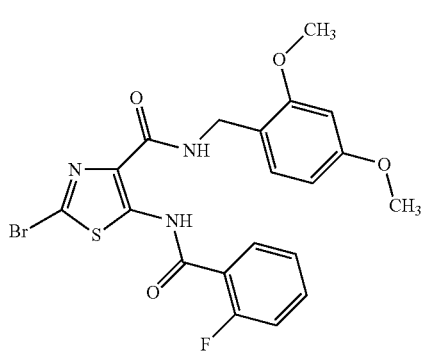 [SMILES: COc1ccc(CNC(=O)c2nc(Br)sc2NC(=O)c2ccccc2F)c(OC)c1]

To a solution (30 mL) of the compound (2.78 g) obtained in Reference Example 84 in methylene chloride were added triethylamine (1.60 mL) and 2-fluorobenzoyl chloride (1.30 g) at room temperature, and the reaction mixture was stirred at the same temperature overnight. Water was added to the reaction mixture, and the mixture was extracted with chloroform. The combined organic layer was dried over anhydrous magnesium sulfate, filtered and concentrated. The residue was purified by silica gel column chromatography (solvent; hexane/ethyl acetate=70/30-40/60) to give the title compound (2.88 g).

MS (ESI) m/z; 494, 496 [M+H]$^+$

Reference Example 86

2-bromo-N-(2,4-dimethoxybenzyl)-5-{[(1-methoxycyclopropyl)carbonyl]amino}-1,3-thiazole-4-carboxamide

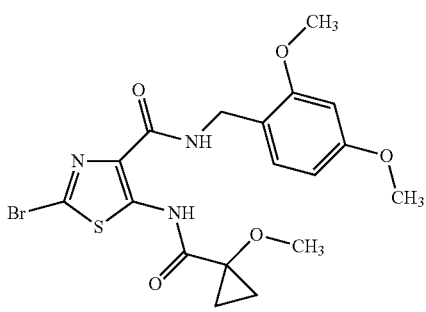 [SMILES: COc1ccc(CNC(=O)c2nc(Br)sc2NC(=O)C2(OC)CC2)c(OC)c1]

To a solution (10 mL) of 1-methoxycyclopropanecarboxylic acid (1.07 g) in methylene chloride were added oxalyl chloride (780 µL) and DMF (one drop), and the reaction mixture was stirred at room temperature for 2 hr. The reaction mixture was added dropwise to a solution (20 mL) of the compound (1.9 g) obtained in Reference Example 84 and triethylamine (3.6 mL) in methylene chloride under ice-cooling. The reaction mixture was stirred at room temperature overnight. Water was added to the reaction mixture, and the mixture was extracted twice with chloroform. The organic layer was dried over anhydrous magnesium sulfate, filtered and concentrated. The residue was purified by silica gel column chromatography (solvent; hexane/ethyl acetate=70/30-40/60) to give the title compound (2.00 g).

MS (ESI) m/z; 470, 472 [M+H]$^+$

Reference Example 87

2-bromo-6-(2,4-dimethoxybenzyl)-5-(2-fluorophenyl)-6H-[1,3]thiazolo[5,4-d]pyrimidin-7-one

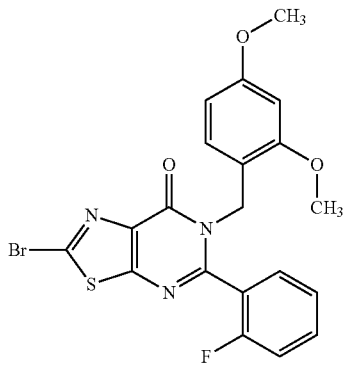 [SMILES: COc1ccc(Cn2c(-c3ccccc3F)nc3sc(Br)nc3c2=O)c(OC)c1]

To a solution (50 mL) of the compound (2.88 g) obtained in Reference Example 85 in methylene chloride were added chlorotrimethylsilane (15.0 mL) and triethylamine (50.0 mL), and the reaction mixture was stirred at room temperature overnight. Water and 1.0 mol/L hydrochloric acid were added to the reaction mixture, and the mixture was extracted twice with chloroform. The organic layer was dried over anhydrous magnesium sulfate, filtered and concentrated.

Reference Example 88

2-bromo-6-(2,4-dimethoxybenzyl)-5-(1-methoxycyclopropyl)-6H-[1,3]thiazolo[5,4-d]pyrimidin-7-one

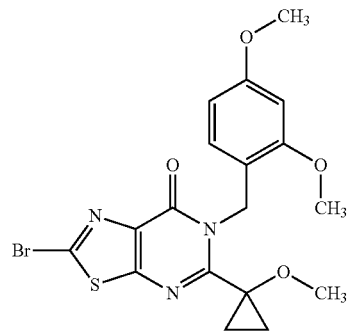 [SMILES: COc1ccc(Cn2c(C3(OC)CC3)nc3sc(Br)nc3c2=O)c(OC)c1]

The compound (1.70 g) obtained in Reference Example 86 was treated by a method similar to that in Reference Example 87 to give the title compound (0.68 g).

MS (ESI) m/z; 452, 454 [M+H]$^+$

Reference Example 89

2-bromo-N-(2,4-dimethoxybenzyl)-5-[(2-fluoro-2-methylpropionyl)amino]-1,3-thiazole-4-carboxamide

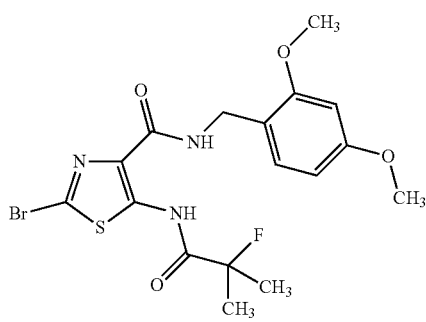 [SMILES: COc1ccc(CNC(=O)c2nc(Br)sc2NC(=O)C(C)(C)F)c(OC)c1]

The compound (1.90 g) obtained in Reference Example 84 was treated by a method similar to that in Reference Example 86 to give the title compound (2.10 g).

MS (ESI) m/z; 460, 462 [M+H]$^+$

Reference Example 90

2-bromo-5-[(2-fluoro-2-methylpropionyl)amino]-1,3-thiazole-4-carboxamide

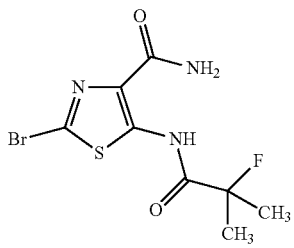 [SMILES: CC(C)(F)C(=O)Nc1sc(Br)nc1C(N)=O]

To the compound (1.90 g) obtained in Reference Example 89 was added a mixture of triethylsilane (4.20 mL), water (4.20 mL) and trifluoroacetic acid (60 mL), and the reaction mixture was stirred at room temperature for 1 hr. The reaction mixture was neutralized with saturated aqueous sodium hydrogen carbonate solution, and extracted twice with chloroform. The organic layer was dried over anhydrous magnesium sulfate, filtered and concentrated. The residue was purified by silica gel column chromatography (solvent; hexane/ethyl acetate=80/20-40/60) to give the title compound (1.00 g).

MS (ESI) m/z; 310, 312 [M+H]$^+$

Reference Example 91

2-bromo-5-(2-fluoropropan-2-yl)-6H-[1,3]thiazolo[5,4-d]pyrimidin-7-one

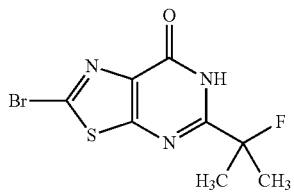

To a solution (20 mL) of the compound (1.00 g) obtained in Reference Example 90 in methylene chloride were added chlorotrimethylsilane (16.4 mL) and triethylamine (54.0 mL), and the reaction mixture was stirred at room temperature 14 days. Water and 1.0 mol/L hydrochloric acid were added to the reaction mixture, and the mixture was extracted twice with chloroform. The organic layer was dried over anhydrous magnesium sulfate, filtered and concentrated. The residue was purified by silica gel column chromatography (solvent; chloroform/methanol=100/0-95/5) to give the title compound (0.55 g).

MS (ESI) m/z; 292, 294 [M+H]$^+$

The residue was purified by silica gel column chromatography (solvent; hexane/ethyl acetate=70/30-50/50) to give the title compound (1.41 g).

MS (ESI) m/z; 476, 478 [M+H]$^+$

Reference Example 92

3-amino-2-methoxy-6-iodopyridine

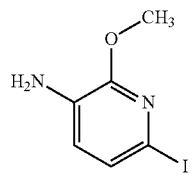

To a solution (40 mL) of 3-amino-2-methoxypyridine (5.00 g) in DMF was added a solution (20 mL) of N-iodosuccinimide (9.97 g) in DMF at 0° C. The reaction mixture was stirred at 0° C. for 2.5 hr. A solution (5.0 mL) of N-iodosuccinimide (1.81 g) in DMF was added, and the reaction mixture was stirred at room temperature for 14 hr. Aqueous sodium thiosulfate solution was added, and the mixture was stirred at room temperature for 10 min, and extracted twice with ethyl acetate. The organic layer was dried over anhydrous sodium sulfate, filtered and concentrated. The residue was purified by NH silica gel column chromatography (solvent; hexane/ethyl acetate=90/10-70/30) to give the title compound (2.54 g).

MS (ESI) m/z; 251 [M+H]$^+$

Reference Example 93

3-amino-4-chloro-2-methoxy-6-iodopyridine

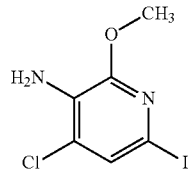

To a solution (25 mL) of the compound (2.54 g) obtained in Reference Example 92 in DMF was added a solution (10 mL) of N-chlorosuccinimide (1.63 g) in DMF at 0° C., and the reaction mixture was stirred with heating at 70° C. for 1.5 hr. The reaction mixture was cooled to 0° C., aqueous sodium thiosulfate solution was added, and the mixture was stirred at room temperature for 10 min, and extracted twice with ethyl acetate. The organic layer was dried over anhydrous sodium sulfate, filtered and concentrated. The residue was purified by silica gel column chromatography (solvent; hexane/ethyl acetate=90/10-75/25) to give the title compound (1.75 g).

MS (ESI) m/z; 285 [M+H]$^+$

Reference Example 94

3-amino-4-chloro-6-(2-fluorophenyl)-2-methoxypyridine

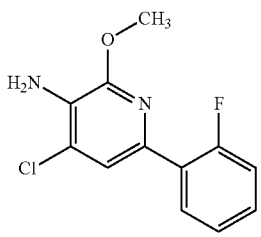 [SMILES: COc1nc(-c2ccccc2F)cc(Cl)c1N]

To a solution (3.52 mL) of the compound (500 mg) obtained in Reference Example 93 in toluene were added [1,1-bis(diphenylphosphino)ferrocene]dichloropalladium (II) methylene chloride adduct (72 mg), a solution (1.76 mL) of 2-fluorophenylboronic acid (295 mg) in ethanol and a 2.0 mol/L aqueous solution (3.52 mL) of sodium carbonate, and the reaction mixture was stirred with heating at 105° C. for 30 min. The reaction mixture was cooled to room temperature, water was added, and the mixture was extracted twice with ethyl acetate. The organic layer was dried over anhydrous sodium sulfate, filtered and concentrated. The residue was purified by silica gel column chromatography (solvent; hexane/ethyl acetate=98/2-88/12) to give the title compound (416 mg)

MS (ESI) m/z; 253 [M+H]$^+$

Reference Example 95

(R)-2-{[4-chloro-6-(2-fluorophenyl)-2-methoxypyridin-3-yl]carbamoyl}pyrrolidine-1-carboxylic acid benzyl ester To a solution (8.8 mL) of N-carbobenzoxy-D-proline (1.18 g) in methylene chloride were added dropwise oxalyl chloride (407 µL) and DMF (one drop) under ice-cooling. The reaction mixture was stirred at room temperature for 1 hr, and added dropwise to a solution (8.80 mL) of the compound (600 mg) obtained in Reference Example 94 and pyridine (955 µL) in methylene chloride under ice-cooling. The reaction mixture was stirred under ice-cooling for 1 hr. The reaction mixture was acidified with 1.0 mol/L hydrochloric acid (7 mL), and the mixture was diluted with water, and extracted twice with methylene chloride. The combined organic layer was washed with saturated brine, dried over anhydrous sodium sulfate, filtered and concentrated. The residue was purified by silica gel column chromatography (solvent; hexane/ethyl acetate=85/15-50/50), to the obtained

Reference Example 96

(R)-2-{[4-chloro-2-(4-methoxybenzyloxy)-6-(trifluoromethyl)pyridin-3-yl]carbamoyl}pyrrolidine-1-carboxylic acid benzyl ester

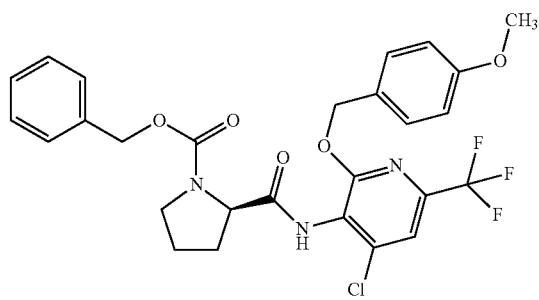 [SMILES: COc1ccc(COc2nc(C(F)(F)F)cc(Cl)c2NC(=O)[C@H]2CCCN2C(=O)OCc2ccccc2)cc1]

A 1.9 mol/L solution (5.64 mL) of diisopropyl azodicarboxylate in toluene was added dropwise to a solution (35 mL) of triphenylphosphine (2.81 g) in THF at room temperature. The reaction mixture was stirred at room temperature for 15 min, and a solution (5.0 mL) of 4-chloro-3-nitro-6-(trifluoromethyl)pyridin-2-ol (2.00 g) synthesized by the method described in US 2007/197478 A1 in THF and 4-methoxybenzyl alcohol (1.23 mL) were added dropwise to the reaction mixture at room temperature. The reaction mixture was stirred at room temperature for 1 hr, and concentrated under reduced pressure. To the residue was added hexane/diethyl ether=2/1, and the precipitated solid was filtered off. The filtrate was concentrated, and the residue was purified by NH silica gel column chromatography (solvent; hexane/ethyl acetate=95/5-85/15) to give a product (1.28 g).

A mixture of the obtained product (817 mg), ammonium chloride (145 mg) and iron powder (503 mg) in methanol (15 mL), THF (15 mL) and water (7.5 mL) was stirred with heating at 70° C. is for 3 hr. The reaction mixture was cooled to room temperature, filtered through diatomaceous earth, and the filtrate was concentrated. The residue was dissolved in ethyl acetate, and washed with water and saturated brine. The organic layer was dried over anhydrous sodium sulfate, filtered and concentrated. The residue was purified by NH silica gel column chromatography (solvent; hexane/ethyl acetate=95/5-85/15) to give a product (666 mg).

The obtained product (255 mg) was treated by a method similar to that in Reference Example 95 to give the title compound (272 mg).

MS (ESI) m/z; 564 [M+H]$^+$

Reference Example 97

(R)-2-[6-(2-fluorophenyl)-4-methoxy-[1,3]thiazolo[4,5-c]pyridin-2-yl]pyrrolidine-1-carboxylic acid benzyl ester

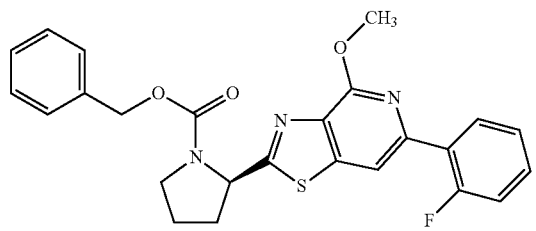 [SMILES: COc1nc(-c2ccccc2F)cc2sc([C@H]3CCCN3C(=O)OCc3ccccc3)nc12]

To a solution (6.9 mL) of the compound (600 mg) obtained in Reference Example 95 in toluene were added pyridine (579 μL) and Lawesson reagent (351 mg), and the reaction mixture was stirred with heating at 110° C. for 16 hr. The reaction mixture was allowed to cool, diluted with chloroform, acidified with 1.0 mol/L hydrochloric acid, and extracted twice with chloroform. The combined organic layer was washed with saturated brine, dried over anhydrous sodium sulfate, filtered and concentrated. The residue was purified by silica gel column chromatography (solvent; hexane/ethyl acetate=90/10-65/35) to give the title compound (339 mg).

MS (ESI) m/z; 464 [M+H]$^+$

Reference Example 98

(R)-2-[4-(4-methoxybenzyloxy)-6-trifluoromethyl-[1,3]thiazolo[4,5-c]pyridin-2-yl]pyrrolidine-1-carboxylic acid benzyl ester

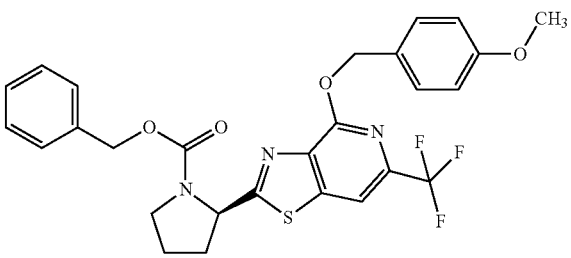 [SMILES: COc1ccc(COc2nc(C(F)(F)F)cc3sc([C@H]4CCCN4C(=O)OCc4ccccc4)nc23)cc1]

The compound (252 mg) obtained in Reference Example 96 was treated by a method similar to that in Reference Example 97 to give the title compound (82 mg).

MS (ESI) m/z; 544 [M+H]$^+$

Reference Example 99

(R)-1-(2-nitrophenylsulfonyl)pyrrolidine-2-carboxylic acid

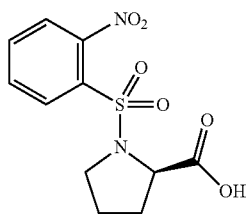 [SMILES: O=C(O)[C@H]1CCCN1S(=O)(=O)c1ccccc1[N+](=O)[O-]]

To a solution (90 mL) of D-proline (5.0 g) in 1.0 mol/L aqueous sodium hydroxide was added 2-nitrobenzenesulfonyl chloride (9.62 g) at 0° C., and the reaction mixture was stirred at the same temperature for 8 hr. To the reaction mixture was added 1.0 mol/L hydrochloric acid (90 mL), and the mixture was extracted twice with chloroform. The organic layer was dried over anhydrous magnesium sulfate, filtered and concentrated to give the title compound (11.1 g).

MS (ESI) m/z; 301 [M+H]$^+$

Reference Example 100

(R)-1-(2-nitrophenylsulfonyl)piperidine-2-carboxylic acid

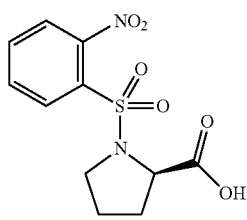 [SMILES: O=C(O)[C@H]1CCCN1S(=O)(=O)c1ccccc1[N+](=O)[O-]]

(R)-piperidine-2-carboxylic acid (4.0 g) was treated by a method similar to that in Reference Example 99 to give the title compound (3.6 g).

MS (ESI) m/z; 315 [M+H]$^+$

Reference Example 101

2-[(R)-1-(2-nitrophenylsulfonyl)pyrrolidine-2-carbonyl]hydrazinecarbothioamide

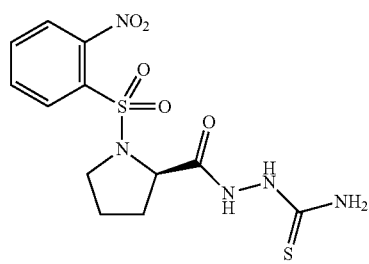 [SMILES: NC(=S)NNC(=O)[C@H]1CCCN1S(=O)(=O)c1ccccc1[N+](=O)[O-]]

To a solution (110 mL) of the compound (11.1 g) obtained in Reference Example 99 in DMF were added N,N-diisopropylethylamine (5.8 g), thiosemicarbazide (3.4 g), EDC hydrochloride (8.5 g) and HOBt monohydrate (6.8 g) at room temperature, and the reaction mixture was stirred overnight. Water was added to the reaction mixture, and the mixture was extracted three times with ethyl acetate. The organic layer was dried over anhydrous magnesium sulfate, filtered and concentrated. The residue was purified by silica gel column chromatography (solvent; chloroform/methanol=100/0-90/10) to give the title compound (6.81 g).

MS (ESI) m/z; 374 [M+H]$^+$

Reference Example 102

2-[(R)-1-(2-nitrophenylsulfonyl)piperidine-2-carbonyl]hydrazinecarbothioamide

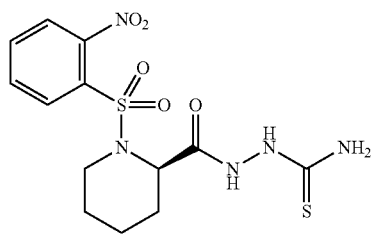 [SMILES: NC(=S)NNC(=O)[C@H]1CCCCN1S(=O)(=O)c1ccccc1[N+](=O)[O-]]

The compound (4.1 g) obtained in Reference Example 100 was treated by a method similar to that in Reference Example 101 to give the title compound (1.75 g).

MS (ESI) m/z; 388 [M+H]$^+$

Reference Example 103

2-amino-5-[(R)-1-(2-nitrophenylsulfonyl)pyrrolidin-2-yl]-[1,3,4]thiadiazole

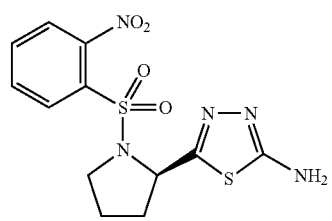 [SMILES: Nc1nnc([C@H]2CCCN2S(=O)(=O)c2ccccc2[N+](=O)[O-])s1]

To a solution (120 mL) of the compound (5.80 g) obtained in Reference Example 101 in toluene was added methansulfonic acid (2.30 g) at room temperature, and the reaction mixture was heated under reflux for 2 hr. The reaction mixture was cooled to room temperature, chloroform and water were added, and the mixture was neutralized with 1.0 mol/L aqueous sodium hydroxide solution, and extracted twice with chloroform. The organic layer was dried over anhydrous magnesium sulfate, filtered and concentrated. The residue was purified by silica gel column chromatography (solvent; ethyl acetate/methanol=100/0-90/10) to give the title compound (4.27 g).

MS (ESI) m/z; 356 [M+H]$^+$

Reference Example 104

2-amino-5-[(R)-1-(2-nitrophenylsulfonyl)piperidin-2-yl]-[1,3,4]thiadiazole

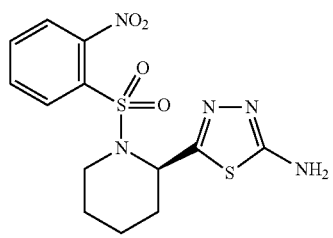 [SMILES: Nc1nnc([C@H]2CCCCN2S(=O)(=O)c2ccccc2[N+](=O)[O-])s1]

The compound (1.75 g) obtained in Reference Example 102 was treated by a method similar to that in Reference Example 103 to give the title compound (0.72 g).

MS (ESI) m/z; 370 [M+H]$^+$

Reference Example 105

2-{(R)-1-[(2-nitrophenyl)sulfonyl]pyrrolidin-2-yl}-7-(propan-2-yl)-5H-[1,3,4]thiadiazolo[3,2-a]pyrimidin-5-one

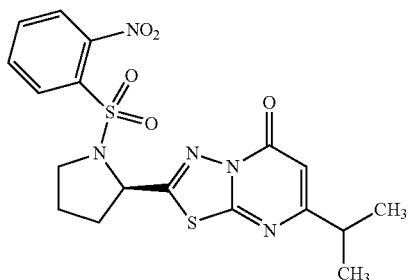

To a solution (25 mL) of the compound (5.50 g) obtained is in Reference Example 103 in concentrated sulfuric acid was added methyl 4-methyl-3-oxopentanoate (3.20 g) at room temperature, and the reaction mixture was stirred with heating at 800° C. for 10 hr. The reaction mixture was cooled to room temperature, water was added thereto, and the mixture was extracted twice with chloroform. The organic layer was dried over anhydrous magnesium sulfate, filtered and concentrated. The residue was purified by silica gel column chromatography (solvent; ethyl acetate/methanol=100/0-95/5) to give the title compound (5.10 g).

MS (ESI) m/z; 450 [M+H]$^+$

Reference Example 106

7-ethyl-2-{(R)-1-[(2-nitrophenyl)sulfonyl]pyrrolidin-2-yl}-5H-[1,3,4]thiadiazolo[3,2-a]pyrimidin-5-one

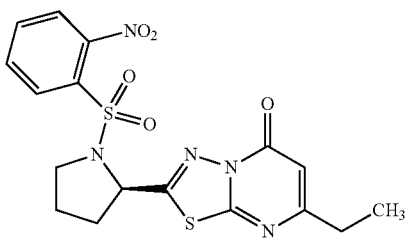 [SMILES: CCc1cc(=O)n2nc([C@H]3CCCN3S(=O)(=O)c3ccccc3[N+](=O)[O-])sc2n1]

The compound (2.00 g) obtained in Reference Example 103 was treated by a method similar to that in Reference Example 105 to give the title compound (2.15 g).

MS (ESI) m/z; 436 [M+H]$^+$

Reference Example 107

6,7-dimethyl-2-{(R)-1-[(2-nitrophenyl)sulfonyl]pyrrolidin-2-yl}-5H-[1,3,4]thiadiazolo[3,2-a]pyrimidin-5-one

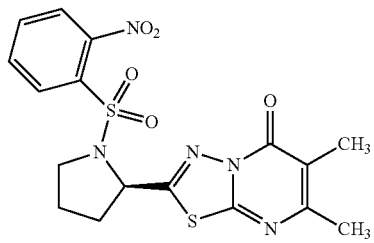 [SMILES: Cc1nc2sc([C@H]3CCCN3S(=O)(=O)c3ccccc3[N+](=O)[O-])nn2c(=O)c1C]

The compound (2.00 g) obtained in Reference Example 103 was treated by a method similar to that in Reference Example 105 to give the title compound (3.40 g).

MS (ESI) m/z; 436 [M+H]$^+$

Reference Example 108

6-ethyl-7-methyl-2-{(R)-1-[(2-nitrophenyl)sulfonyl]pyrrolidin-2-yl}-5H-[1,3,4]thiadiazolo[3,2-a]pyrimidin-5-one

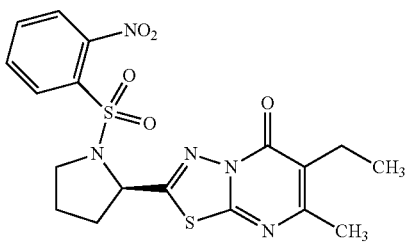 [SMILES: CCc1c(C)nc2sc([C@H]3CCCN3S(=O)(=O)c3ccccc3[N+](=O)[O-])nn2c1=O]

The compound (8.58 g) obtained in Reference Example 103 was treated by a method similar to that in Reference Example 105 to give the title compound (9.80 g).

MS (ESI) m/z; 450 [M+H]$^+$

Reference Example 109

2-{(R)-1-[(2-nitrophenyl)sulfonyl]pyrrolidin-2-yl}-6,7,8,9-tetrahydro-5H-[1,3,4]thiadiazolo[2,3-b]quinazolin-5-one

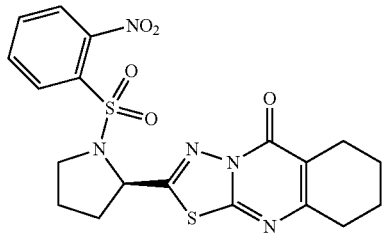 [SMILES: O=c1c2c(nc3sc([C@H]4CCCN4S(=O)(=O)c4ccccc4[N+](=O)[O-])nn13)CCCC2]

The compound (2.00 g) obtained in Reference Example 103 was treated by a method similar to that in Reference Example 105 to give the title compound (2.15 g).

MS (ESI) m/z; 462 [M+H]$^+$

Reference Example 110

2-{(R)-1-[(2-nitrophenyl) sulfonyl]piperidin-2-yl}-7-(propan-2-yl)-5H-[1,3,4]thiadiazolo[3,2-a]pyrimidin-5-one

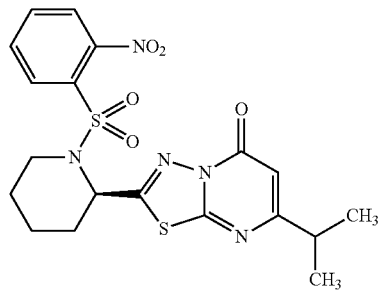 [SMILES: CC(C)c1cc(=O)n2nc([C@H]3CCCCN3S(=O)(=O)c3ccccc3[N+](=O)[O-])sc2n1]

The compound (0.72 g) obtained in Reference Example 104 was treated by a method similar to that in Reference Example 105 to give the title compound (0.81 g).

MS (ESI) m/z; 464 [M+H]$^+$

Reference Example 111

6-chloro-2-{(R)-1-[(2-nitrophenyl) sulfonyl]pyrrolidin-2-yl}-7-(propan-2-yl)-5H-[1,3,4]thiadiazolo[3,2-a]pyrimidin-5-one

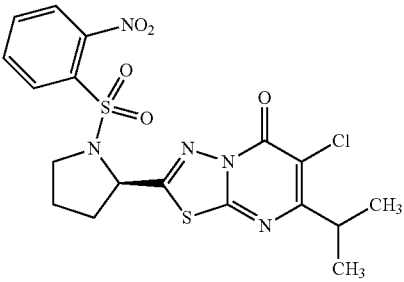 [SMILES: CC(C)c1nc2sc([C@H]3CCCN3S(=O)(=O)c3ccccc3[N+](=O)[O-])nn2c(=O)c1Cl]

To a solution (50 mL) of the compound (2.0 g) obtained in Reference Example 105 in acetonitrile was added N-chlorosuccinimide (0.6 g) at room temperature, and the reaction mixture was stirred with heating at 80° C. for 3 hr. The reaction mixture was cooled to room temperature, water was added thereto, and the mixture was extracted twice with chloroform. The organic layer was dried over anhydrous magnesium sulfate, filtered and concentrated. The residue was purified by silica gel column chromatography (solvent; ethyl acetate/methanol=100/0-95/5) to give the title compound (2.2 g)

MS (ESI) m/z; 484, 486 [M+H]$^+$

Reference Example 112

2-bromo-5-[(R)-1-(2-nitrophenylsulfonyl)-pyrrolidin-2-yl]-[1,3,4]thiadiazole

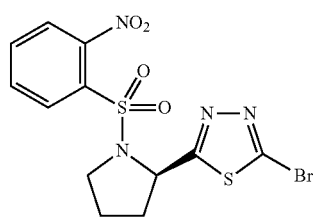 [SMILES: O=[N+]([O-])c1ccccc1S(=O)(=O)N1CCC[C@@H]1c1nnc(Br)s1]

To a solution (100 mL) of the compound (4.28 g) obtained in Reference Example 103 in acetonitrile were added isoamyl nitrite (2.10 g) and copper(II) bromide (3.30 g) at 0° C., and the reaction mixture was stirred at room temperature for 3 hr. To the reaction mixture were added water and aqueous ammonia, and the mixture was extracted twice with ethyl acetate. The organic layer was dried over anhydrous magnesium sulfate, filtered and concentrated. The residue was purified by silica gel column chromatography (solvent; hexane/ethyl acetate=80/20-50/50) to give the title compound (3.74 g).

MS (ESI) m/z; 419, 421 [M+H]$^+$

Reference Example 113

7-fluoro-2-{(R)-1-[(2-nitrophenyl)sulfonyl]pyrrolidin-2-yl}-5H-[1,3,4]thiadiazolo[2,3-b]quinazolin-5-one

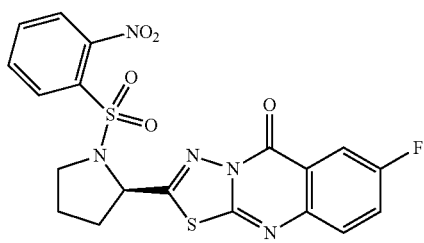 [SMILES: O=c1c2cc(F)ccc2nc2sc([C@H]3CCCN3S(=O)(=O)c3ccccc3[N+](=O)[O-])nn12]

A mixture of the compound (3.50 g) obtained in Reference Example 112 and methyl 2-amino-5-fluorobenzoate (1.42 g) was stirred with heating at 160° C. for 30 min. The reaction mixture was cooled to room temperature, dissolved in chloroform and purified by silica gel column chromatography (solvent; chloroform/methanol=100/0-95/5) to give the title compound (2.86 g).

MS (ESI) m/z; 476 [M+H]$^+$

Reference Example 114

7-(propan-2-yl)-2-[(R)-pyrrolidin-2-yl]-5H-[1,3,4]thiadiazolo[3,2-a]pyrimidin-5-one

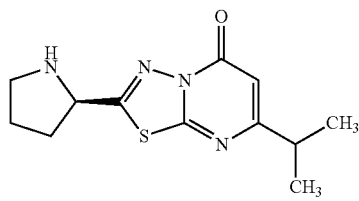 [SMILES: CC(C)c1cc(=O)n2nc([C@H]3CCCN3)sc2n1]

To a solution (120 mL) of the compound (5.10 g) obtained in Reference Example 105 in acetonitrile were added cesium carbonate (5.60 g) and 4-methylbenzenethiol (1.70 g) at room temperature, and the reaction mixture was stirred for 1 hr. The reaction mixture was cooled to room temperature, water and ethyl acetate were added, and the mixture was extracted 3 times with 1.0 mol/L hydrochloric acid. The aqueous layer was neutralized with saturated aqueous sodium hydrogen carbonate solution, and extracted twice with chloroform. The organic layer was dried over anhydrous magnesium sulfate, filtered and concentrated. The residue was purified by silica gel column chromatography (solvent; ethyl acetate/methanol=100/0-95/5) to give the title compound (2.47 g).

MS (ESI) m/z; 265 [M+H]$^+$

Reference Example 115

7-ethyl-2-[(R)-pyrrolidin-2-yl]-5H-[1,3,4]thiadiazolo[3,2-a]pyrimidin-5-one

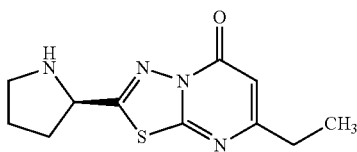

The compound (2.13 g) obtained in Reference Example 106 was treated by a method similar to that in Reference Example 114 to give the title compound (1.09 g).

MS (ESI) m/z; 251 [M+H]$^+$

Reference Example 116

6,7-dimethyl-2-[(R)-pyrrolidin-2-yl]-5H-[1,3,4]thiadiazolo[3,2-a]pyrimidin-5-one

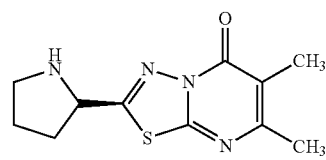

The compound (9.80 g) obtained in Reference Example 107 was treated by a method similar to that in Reference Example 114 to give the title compound (4.50 g).

MS (ESI) m/z; 251 [M+H]$^+$

Reference Example 117

6-ethyl-7-methyl-2-[(R)-pyrrolidin-2-yl]-5H-[1,3,4]thiadiazolo[3,2-a]pyrimidin-5-one

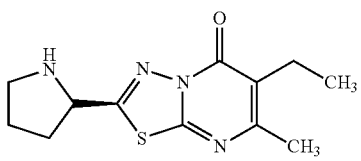

The compound (1.74 g) obtained in Reference Example 108 was treated by a method similar to that in Reference Example 114 to give the title compound (0.83 g).

MS (ESI) m/z; 265 [M+H]$^+$

Reference Example 118

2-[(R)-pyrrolidin-2-yl]-6,7,8,9-tetrahydro-5H-[1,3,4]thiadiazolo[2,3-b]quinazolin-5-one

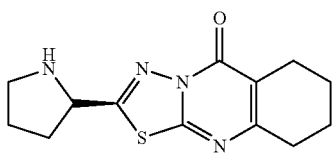

The compound (2.15 g) obtained in Reference Example 109 was treated by a method similar to that in Reference Example 114 to give the title compound (1.05 g).
MS (ESI) m/z; 277 [M+H]$^+$

Reference Example 119

2-[(R)-piperidin-2-yl]-7-(propan-2-yl)-5H-[1,3,4]thiadiazolo[3,2-a]pyrimidin-5-one

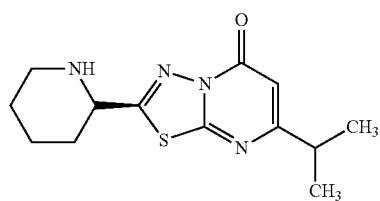

The compound (0.81 g) obtained in Reference Example 110 was treated by a method similar to that in Reference Example 114 to give the title compound (0.27 g).
MS (ESI) m/z; 279 [M+H]$^+$

Reference Example 120

6-chloro-7-(propan-2-yl)-2-[(R)-pyrrolidin-2-yl]-5H-[1,3,4]thiadiazolo[3,2-a]pyrimidin-5-one

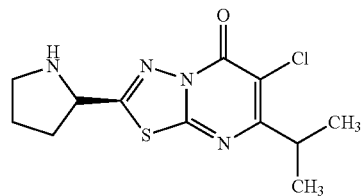

The compound (2.20 g) obtained in Reference Example 111 was treated by a method similar to that in Reference Example 114 to give the title compound (0.88 g).
MS (ESI) m/z; 299, 301 [M+H]$^+$

Reference Example 121

7-fluoro-2-[(R)-pyrrolidin-2-yl]-5H-[1,3,4]thiadiazolo[2,3-b]quinazolin-5-one

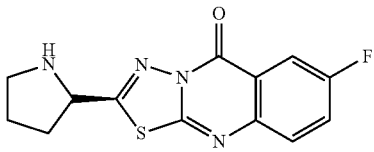

The compound (3.00 g) obtained in Reference Example 113 was treated by a method similar to that in Reference Example 114 to give the title compound (1.65 g).
MS (ESI) m/z; 291 [M+H]$^+$

Reference Example 122

2-bromo-7-propyl-5H-[1,3,4]thiadiazolo[3,2-a]pyrimidin-5-one

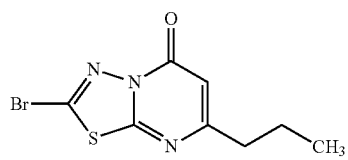

A mixture of 2-amino-5-bromo[1,3,4]thiadiazole (10 g) and ethyl 3-oxohexanoate (10.6 g) in polyphosphoric acid (60 g) was stirred with heating at 100° C. for 5 hr. After confirmation of the completion of the reaction, the reaction mixture was cooled to room temperature, dissolved by adding water, and the mixture was extracted twice with chloroform. The organic layer was washed once with water, dried over anhydrous magnesium sulfate, filtered and concentrated. The residue was purified by silica gel column chromatography (solvent; hexane/ethyl acetate=80/20-50/50), and concentrated. To the obtained product was added diisopropyl ether, and the solid was collected by filtration to give the title compound (6.2 g).
MS (ESI) m/z; 274, 276 [M+H]$^+$

Reference Example 123

(R)-1-[5-difluoromethyl-6-ethyl-7-oxo-6,7-dihydro[1,3]thiazolo[5,4-d]pyrimidin-2-yl]pyrrolidine-2-carboxylic acid tert-butyl ester

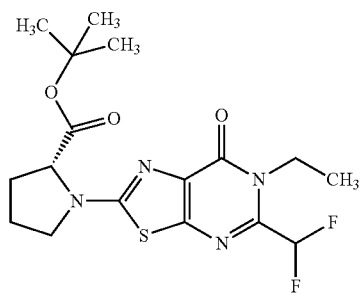 [SMILES: CCn1c(C(F)F)nc2sc(N3CCC[C@@H]3C(=O)OC(C)(C)C)nc2c1=O]

To the compound (5.39 g) obtained in Reference Example 327 were added (D)-proline tert-butyl ester (3.78 g) and N,N-diisopropylethylamine (3.85 mL), and the reaction mixture was heated at 120° C. for 1 hr. 15% Aqueous citric acid solution was added to the reaction mixture, and the mixture was extracted twice with ethyl acetate. The organic layer was dried over anhydrous sodium sulfate, filtered and concentrated. The residue was purified by silica gel column chromatography (solvent; hexane/ethyl acetate=90/10-50/50) to give the title compound (5.96 g).

MS (ESI) m/z; 401 [M+H]$^+$

Reference Example 124

(R)-1-[5-difluoromethyl-6-ethyl-7-oxo-6,7-dihydro[1,3]thiazolo[5,4-d]pyrimidin-2-yl]pyrrolidine-2-carboxylic acid

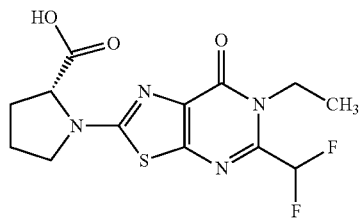 [SMILES: CCn1c(C(F)F)nc2sc(N3CCC[C@@H]3C(=O)O)nc2c1=O]

To a solution (38 mL) of the compound (5.96 g) obtained in Reference Example 123 in methylene chloride was added trifluoroacetic acid (38 mL), and the reaction mixture was stirred at room temperature for 2 hr. The reaction mixture was concentrated, azeotroped with toluene, and diisopropyl ether was added to the residue. The solid was collected by filtration to give the title compound (4.25 g).

MS (ESI) m/z; 345 [M+H]$^+$

Reference Example 125

2-[(R)-2-((RS)-1-hydroxy-2-phenoxyethyl)pyrrolidin-1-yl]-6-methyl-5-(tetrahydro-2H-pyran-4-yl)[1,3]thiazolo[5,4-d]pyrimidin-7(6H)-one

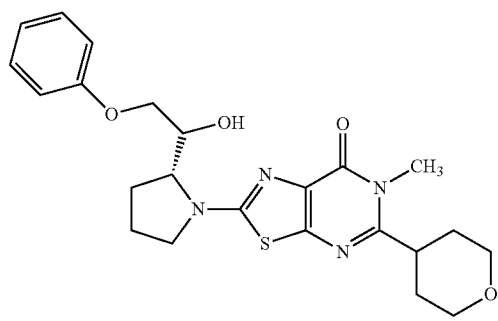

To the compound (0.39 g) obtained in Reference Example 281 were added the compound (1.0 g) obtained in Reference Example 625 and N,N-diisopropylethylamine (2.2 mL), and the reaction mixture was stirred with heating at 120° C. for 8 hr. After cooling to room temperature, chloroform was added, and the mixture was neutralized with 1.0 mol/L hydrochloric acid. The chloroform layer was washed once with water, dried over anhydrous magnesium sulfate, filtered and concentrated. The residue was purified by silica gel column chromatography (solvent; ethyl acetate/methanol=100/0-95/5). Ethyl acetate was added to the obtained product, and the solid was collected by filtration to give the title compound (0.36 g).

MS (ESI) m/z; 457 [M+H]$^+$

Reference Example 126

5-ethyl-2-[(R)-2-((RS)-1-hydroxy-2-phenoxyethyl)pyrrolidin-1-yl]-6-methyl[1,3]thiazolo[5,4-d]pyrimidin-7(6H)-one

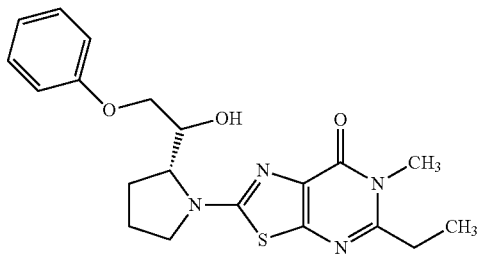 [SMILES: CCc1nc2sc(N3CCC[C@@H]3C(O)COc3ccccc3)nc2c(=O)n1C]

The compound (300 mg) obtained in Reference Example 304 was treated by a method similar to that in Reference Example 125 to give the title compound (149 mg).

MS (ESI) m/z; 401 [M+H]$^+$

Reference Example 127

2-[(R)-2-((RS)-1-hydroxy-2-phenoxyethyl)pyrrolidin-1-yl]-5-methyl-6-(tetrahydro-2H-pyran-4-yl)[1,3]thiazolo[5,4-d]pyrimidin-7(6H)-one

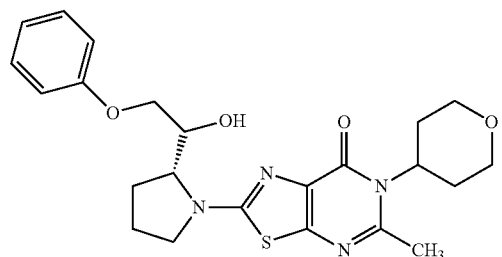

The compound (190 mg) obtained in Reference Example 274 was treated by a method similar to that in Reference Example 125 to give the title compound (180 mg).

MS (ESI) m/z; 457 [M+H]$^+$

Reference Example 128

2-[(R)-2-((RS)-1-hydroxy-2-phenoxyethyl)pyrrolidin-1-yl]-6-methyl-5-[(morpholin-4-yl)methyl][1,3]thiazolo[5,4-d]pyrimidin-7(6H)-one

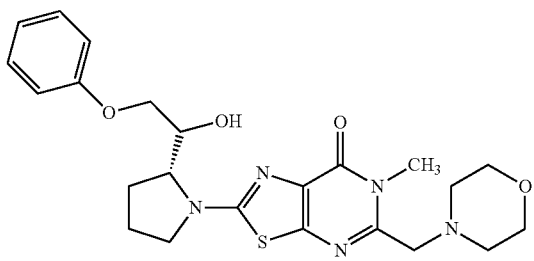 [SMILES: Cn1c(CN2CCOCC2)nc2sc(N3CCC[C@@H]3C(O)COc3ccccc3)nc2c1=O]

The compound (200 mg) obtained in Reference Example 351 was treated by a method similar to that in Reference Example 125 to give the title compound (137 mg).
MS (ESI) m/z; 472 [M+H]$^+$

Reference Example 129

2-[(R)-2-((RS)-1-hydroxy-2-phenoxyethyl)pyrrolidin-1-yl]-5-(3-methoxyazetidin-1-yl)-6-methyl[1,3]thiazolo[5,4-d]pyrimidin-7(6H)-one

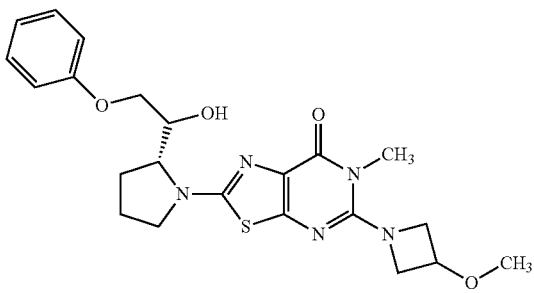 [SMILES: COC1CN(c2nc3sc(N4CCC[C@@H]4C(O)COc4ccccc4)nc3c(=O)n2C)C1]

The compound (200 mg) obtained in Reference Example 373 was treated by a method similar to that in Reference Example 125 to give the title compound (100 mg).
MS (ESI) m/z; 458 [M+H]$^+$

Reference Example 130

5-ethyl-2-{(R)-2-[(RS)-(1-hydroxy-2-phenylamino)ethyl]pyrrolidin-1-yl}-6-methyl[1,3]thiazolo[5,4-d]pyrimidin-7(6H)-one

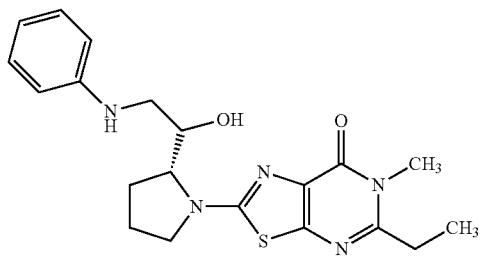 [SMILES: CCc1nc2sc(N3CCC[C@@H]3C(O)CNc3ccccc3)nc2c(=O)n1C]

To the compound (600 mg) obtained in Reference Example 304 were added the compound (1.4 g) obtained in Reference Example 629 and N,N-diisopropylethylamine (4.0 mL), and the reaction mixture was stirred with heating at 120° C. for 8 hr. The reaction mixture was cooled to room temperature, chloroform was added, and the mixture was neutralized with 1.0 mol/L hydrochloric acid. The chloroform layer was washed once with water, dried over anhydrous magnesium sulfate, filtered and concentrated. The residue was purified by silica gel column chromatography (solvent; ethyl acetate/methanol=100/0-95/5). Ethyl acetate was added to the obtained product, and the solid was collected by filtration to give the title compound (284 mg)
MS (ESI) m/z; 400 [M+H]$^+$

Reference Example 131

6-(2,4-dimethoxybenzyl)-5-(2-fluorophenyl)-2-[(R)-2-((RS)-1-hydroxy-2-phenoxyethyl)pyrrolidin-1-yl][1,3]thiazolo[5,4-d]pyrimidin-7(6H)-one

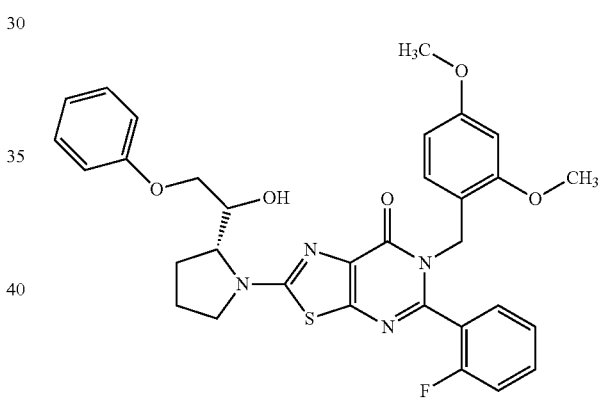

To the compound (0.38 g) obtained in Reference Example 563 were added the compound (0.4 g) obtained in Reference Example 625 and N,N-diisopropylethylamine (3.0 mL), and the reaction mixture was stirred with heating at 140° C. for 4 hr. The reaction mixture was cooled to room temperature, chloroform was added, and the mixture was neutralized with 1.0 mol/L hydrochloric acid. The chloroform layer was washed once with water, dried over anhydrous magnesium sulfate, filtered and concentrated. The residue was purified by silica gel column chromatography (solvent; hexane/ethyl acetate=50/50-20/80) to give the title compound (0.43 g).
MS (ESI) m/z; 603 [M+H]$^+$

Reference Example 132

(R)-1-[6-(1-ethoxyvinyl)-5-(4-methoxybenzyl)-4-oxo-4,5-dihydro[1,3]thiazolo[4,5-c]pyridin-2-yl]pyrrolidine-2-carboxylic acid tert-butyl ester

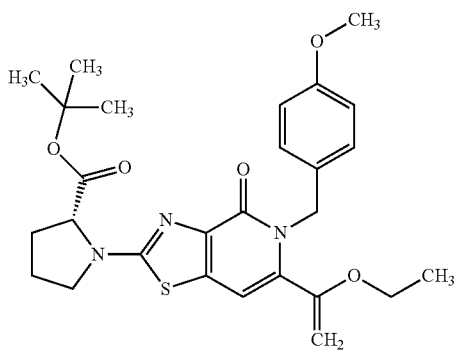 [SMILES: C=C(OCC)c1cc2sc(N3CCC[C@@H]3C(=O)OC(C)(C)C)nc2c(=O)n1Cc1ccc(OC)cc1]

To a solution (0.60 mL) of the compound (85 mg) obtained in Reference Example 752 in DMF were added dichlorobis(triphenylphosphine)palladium(II) (2.3 mg) and (1-ethoxyethenyl)tributylstannan (64 mg), and the reaction mixture was stirred with heating at 90° C. for 1.5 hr. The reaction mixture was cooled to room temperature, aqueous potassium fluoride solution was added, and the precipitated solid was filtered off. The filtrate was extracted twice with ethyl acetate, the organic layer was dried over anhydrous sodium sulfate, filtered and concentrated. The residue was purified by silica gel column chromatography (solvent; hexane/ethyl acetate=70/30-0/100) to give the title compound (82.0 mg).

MS (ESI) m/z; 512 [M+H]$^+$

Reference Example 133

(R)-1-[6-(1-ethoxyvinyl)-5-(4-methoxybenzyl)-4-oxo-4,5-dihydro[1,3]thiazolo[4,5-c]pyridin-2-yl]pyrrolidine-2-carboxylic acid

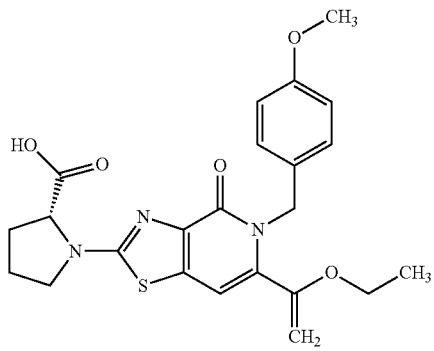 [SMILES: C=C(OCC)c1cc2sc(N3CCC[C@@H]3C(=O)O)nc2c(=O)n1Cc1ccc(OC)cc1]

To a solution of methyl iodide (335 mg) in toluene (0.35 mL) was added diethylzinc (1.1 mol/L toluene solution, 569 μL) at 0° C., and the reaction mixture was stirred for 15 min. A solution of the compound (80 mg) obtained in Reference Example 132 in toluene (1.75 mL) was added, and the reaction mixture was stirred with heating at 80° C. for 2 hr. The reaction mixture was cooled to room temperature, 1.0 mol/L hydrochloric to acid was added, and the mixture was extracted twice with chloroform. The organic layer was dried over anhydrous sodium sulfate, filtered and concentrated. To the obtained product was added diethyl ether, and the solid was collected by filtration, and dried to give the title compound (63.5 mg).

MS (ESI) m/z; 456 [M+H]$^+$

Reference Example 134

(R)-N-benzyl-1-(7-ethyl-6-fluoro-5-oxo-5H-[1,3,4]thiadiazolo[3,2-a]pyrimidin-2-yl)pyrrolidine-2-carboxylic acid

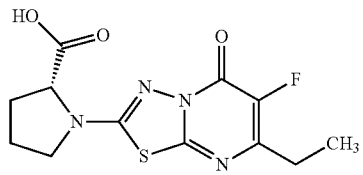 [SMILES: CCc1nc2sc(N3CCC[C@@H]3C(=O)O)nn2c(=O)c1F]

To a solution (80 mL) of the compound (4.6 g) obtained in Reference Example 771 in THF were added D-proline-tert-butyl ester (3.8 g) and triethylamine (8.3 g), and the reaction mixture was heated under reflux for 4 hr. After confirmation of the completion of the reaction, water (20 mL) was added to the reaction mixture, and the mixture was extracted twice with ethyl acetate. The organic layer was washed once with water, dried over anhydrous magnesium sulfate, filtered and concentrated. To the residue were added methylene chloride (30 mL) and trifluoroacetic acid (39 mL), and the reaction mixture was stirred at room temperature for 4 hr. After confirmation of the completion of the reaction, the solvent was evaporated under reduced pressure. To the obtained product was added diisopropyl ether, and the solid was collected by filtration to give the title compound (4.1 g).

MS (ESI) m/z; 313 [M+H]$^+$

Reference Example 135

(R)-N-benzyl-1-(7-methyl-5-oxo-5H-[1,3,4]thiadiazolo[3,2-a]pyrimidin-2-yl)pyrrolidine-2-carboxylic acid

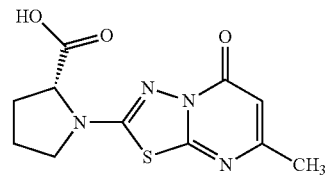 [SMILES: Cc1cc(=O)n2nc(N3CCC[C@@H]3C(=O)O)sc2n1]

The compound (1000 mg) obtained in Reference Example 764 was treated by a method similar to that in Reference Example 134 to give the title compound (850 mg).

MS (ESI) m/z; 281 [M+H]$^+$

Reference Example 136

5-amino-N-methyl-2-methylsulfanyl-1,3-thiazole-4-carboxamide

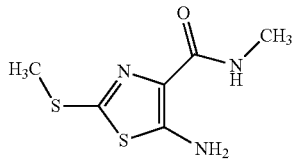

To a solution (520 mL) of 5-amino-2-methylsulfanyl-1,3-thiazole-4-carboxylic acid (52.0 g) in DMF were added EDC hydrochloride (78.5 g), HOBt monohydrate (63.0 g), N,N-diisopropylethylamine (72.0 mL) and methylamine (12 mol/L aqueous solution, 46.0 mL), and the reaction mixture was stirred at room temperature overnight. Water was added to the reaction mixture, and the mixture was extracted three times with ethyl acetate. The organic layer was dried over anhydrous magnesium sulfate, filtered and concentrated. To the residue was added hexane, and the solid was collected by filtration and dried to give the title compound (56.8 g).
MS (ESI) m/z; 204 [M+H]$^+$

Reference Example 137

5-amino-N-ethyl-2-methylsulfanyl-1,3-thiazole-4-carboxamide

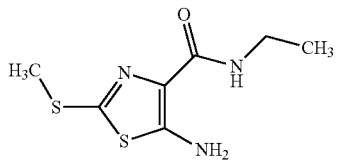

5-Amino-2-methylsulfanyl-1,3-thiazole-4-carboxylic acid (8.97 g) was treated by a method similar to that in Reference Example 136 to give the title compound (8.87 g).
MS (ESI) m/z; 218 [M+H]$^+$

Reference Example 138

5-amino-2-methylsulfanyl-N-(propan-2-yl)-1,3-thiazole-4-carboxamide

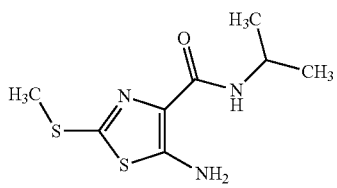

5-Amino-2-methylsulfanyl-1,3-thiazole-4-carboxylic acid (1.50 g) was treated by a method similar to that in Reference Example 136 to give the title compound (1.70 g).
MS (ESI) m/z; 232 [M+H]$^+$

Reference Example 139

5-amino-N-cyclopropyl-2-methylsulfanyl-1,3-thiazole-4-carboxamide

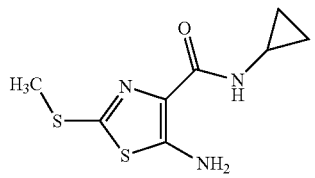

5-Amino-2-methylsulfanyl-1,3-thiazole-4-carboxylic acid (5.00 g) was treated by a method similar to that in Reference Example 136 to give the title compound (5.59 g).
MS (ESI) m/z; 230 [M+H]$^+$

Reference Example 140

5-amino-N-cyclopentyl-2-methylsulfanyl-1,3-thiazole-4-carboxamide

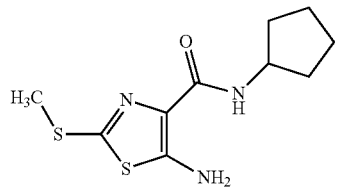 [SMILES: CSc1nc(C(=O)NC2CCCC2)c(N)s1]

5-Amino-2-methylsulfanyl-1,3-thiazole-4-carboxylic acid (2.00 g) was treated by a method similar to that in Reference Example 136 to give the title compound (2.75 g).
MS (ESI) m/z; 258 [M+H]$^+$

Reference Example 141

5-amino-N-(2-methoxyethyl)-2-methylsulfanyl-1,3-thiazole-4-carboxamide

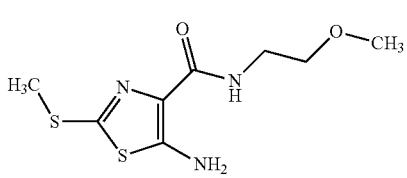

5-Amino-2-methylsulfanyl-1,3-thiazole-4-carboxylic acid (3.00 g) was treated by a method similar to that in Reference Example 136 to give the title compound (3.97 g).
MS (ESI) m/z; 248 [M+H]$^+$

Reference Example 142

5-amino-N-[1-(methoxymethyl)cyclopropyl]-2-methylsulfanyl-1,3-thiazole-4-carboxamide

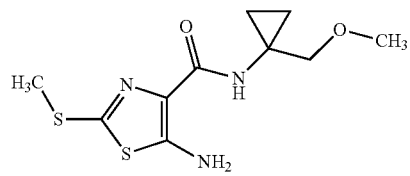

5-Amino-2-methylsulfanyl-1,3-thiazole-4-carboxylic acid (900 mg) was treated by a method similar to that in Reference Example 136 to give the title compound (1.10 g).

MS (ESI) m/z; 274 [M+H]$^+$

Reference Example 143

5-amino-2-methylsulfanyl-N-(tetrahydro-2H-pyran-4-yl)-1,3-thiazole-4-carboxamide

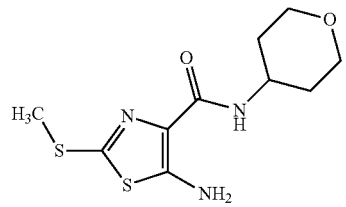 [SMILES: CSc1nc(C(=O)NC2CCOCC2)c(N)s1]

5-Amino-2-methylsulfanyl-1,3-thiazole-4-carboxylic acid (1.50 g) was treated by a method similar to that in Reference Example 136 to give the title compound (2.15 g).

MS (ESI) m/z; 274 [M+H]$^+$

Reference Example 144

5-amino-N-[(3-methyloxetan-3-yl)methyl]-2-methylsulfanyl-1,3-thiazole-4-carboxamide

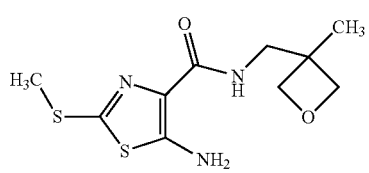 [SMILES: CSc1nc(C(=O)NCC2(C)COC2)c(N)s1]

5-Amino-2-methylsulfanyl-1,3-thiazole-4-carboxylic acid (940 mg) was treated by a method similar to that in Reference Example 136 to give the title compound (800 mg).

MS (ESI) m/z; 274 [M+H]$^+$

Reference Example 145

5-amino-2-methylsulfanyl-N-[(tetrahydro-2H-pyran-4-yl)methyl]-1,3-thiazole-4-carboxamide

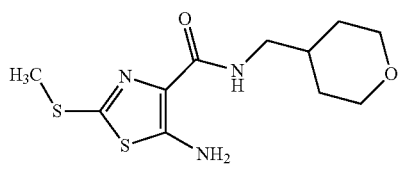 [SMILES: CSc1nc(C(=O)NCC2CCOCC2)c(N)s1]

5-Amino-2-methylsulfanyl-1,3-thiazole-4-carboxylic acid (800 mg) was treated by a method similar to that in Reference Example 136 to give the title compound (1.04 g).

MS (ESI) m/z; 288 [M+H]$^+$

Reference Example 146

5-amino-N-(2-methoxy-2-methylpropyl)-2-methylsulfanyl-1,3-thiazole-4-carboxamide

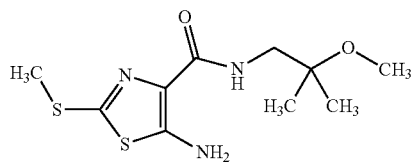

5-Amino-2-methylsulfanyl-1,3-thiazole-4-carboxylic acid (850 mg) was treated by a method similar to that in Reference Example 136 to give the title compound (1.20 g).

MS (ESI) m/z; 276 [M+H]$^+$

Reference Example 147

5-amino-N-(2,2-difluoroethyl)-2-methylsulfanyl-1,3-thiazole-4-carboxamide

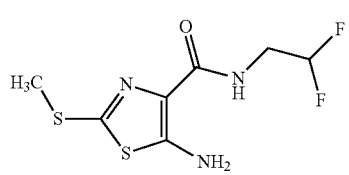

5-Amino-2-methylsulfanyl-1,3-thiazole-4-carboxylic acid (1.50 g) was treated by a method similar to that in Reference Example 136 to give the title compound (1.87 g).

MS (ESI) m/z; 254 [M+H]$^+$

Reference Example 148

5-amino-2-methylsulfanyl-N-(2,2,2-trifluoroethyl)-1,3-thiazole-4-carboxamide

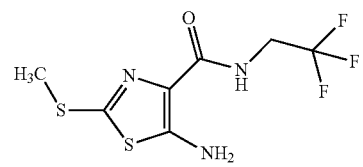

5-Amino-2-methylsulfanyl-1,3-thiazole-4-carboxylic acid (300 mg) was treated by a method similar to that in Reference Example 136 to give the title compound (355 mg).

MS (ESI) m/z; 272 [M+H]$^+$

Reference Example 149

5-amino-2-methylsulfanyl-N-phenyl-1,3-thiazole-4-carboxamide

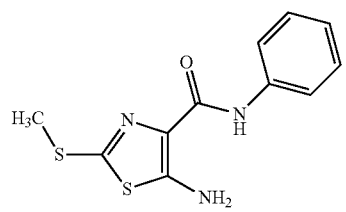 [SMILES: CSc1nc(C(=O)Nc2ccccc2)c(N)s1]

5-Amino-2-methylsulfanyl-1,3-thiazole-4-carboxylic acid (1.00 g) was treated by a method similar to that in Reference Example 136 to give the title compound (1.32 g).

MS (ESI) m/z; 266 [M+H]$^+$

Reference Example 150

5-amino-2-methylsulfanyl-N-((R)-tetrahydrofuran-3-yl)-1,3-thiazole-4-carboxamide

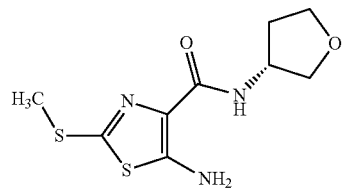

5-Amino-2-methylsulfanyl-1,3-thiazole-4-carboxylic acid (730 mg) was treated by a method similar to that in Reference Example 136 to give the title compound (750 mg).

MS (ESI) m/z; 260 [M+H]$^+$

Reference Example 151

5-amino-2-methylsulfanyl-N-(oxetan-3-yl)-1,3-thiazole-4-carboxamide

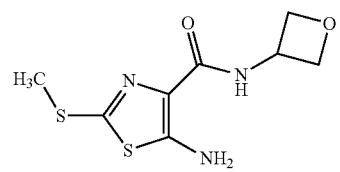

5-Amino-2-methylsulfanyl-1,3-thiazole-4-carboxylic acid (1.74 g) was treated by a method similar to that in Reference Example 136 to give the title compound (1.80 g).

MS (ESI) m/z; 246 [M+H]$^+$

Reference Example 152

5-amino-N-(1-methylpiperidin-4-yl)-2-methylsulfanyl-1,3-thiazole-4-carboxamide

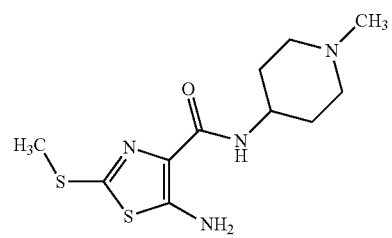

5-Amino-2-methylsulfanyl-1,3-thiazole-4-carboxylic acid (800 mg) was treated by a method similar to that in Reference Example 136 to give the title compound (1.10 g).

MS (ESI) m/z; 287 [M+H]$^+$

Reference Example 153

5-amino-N-[3-(N',N'-dimethylamino)propyl]-2-methylsulfanyl-1,3-thiazole-4-carboxamide

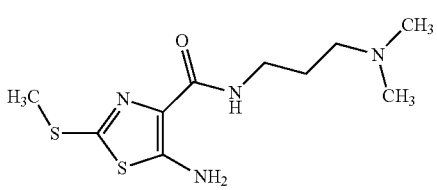

5-Amino-2-methylsulfanyl-1,3-thiazole-4-carboxylic acid (600 mg) was treated by a method similar to that in Reference Example 136 to give the title compound (330 mg).

MS (ESI) m/z; 275 [M+H]$^+$

Reference Example 154

5-amino-2-methylsulfanyl-N-(pyrrolidin-1-yl)-1,3-thiazole-4-carboxamide

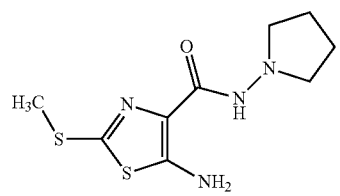

5-Amino-2-methylsulfanyl-1,3-thiazole-4-carboxylic acid (900 mg) was treated by a method similar to that in Reference Example 136 to give the title compound (950 mg).

MS (ESI) m/z; 259 [M+H]+

Reference Example 155

5-amino-2-methylsulfanyl-N-(morpholin-4-yl)-1,3-thiazole-4-carboxamide

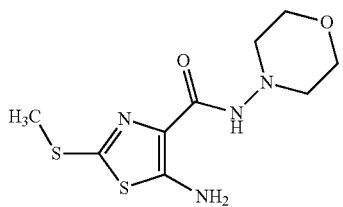

5-Amino-2-methylsulfanyl-1,3-thiazole-4-carboxylic acid (800 mg) was treated by a method similar to that in Reference Example 136 to give the title compound (1.10 g).

MS (ESI) m/z; 275 [M+H]+

Reference Example 156

5-(benzoylamino)-N-methyl-2-methylsulfanyl-1,3-thiazole-4-carboxamide

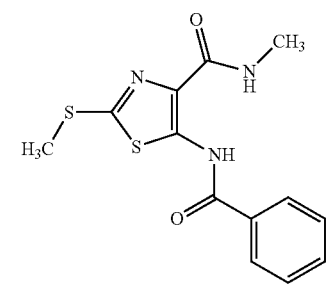 [SMILES: CNC(=O)c1nc(SC)sc1NC(=O)c1ccccc1]

To a solution (700 mL) of the compound (25.0 g) obtained in Reference Example 136 in methylene chloride were added triethylamine (35.0 mL) and benzoyl chloride (24.2 g) at 0° C., and the reaction mixture was stirred at room temperature overnight. To the reaction mixture were added water and saturated aqueous sodium hydrogen carbonate solution, and the mixture was extracted with chloroform. The combined organic layer was dried over anhydrous magnesium sulfate, filtered and concentrated. To the residue was added diisopropyl ether, and the solid was collected by filtration and dried to give the title compound (24.2 g).

MS (ESI) m/z; 308 [M+H]+

Reference Example 157

N-methyl-2-methylsulfanyl-5-[(2,4,6-trifluorobenzoyl)amino]-1,3-thiazole-4-carboxamide

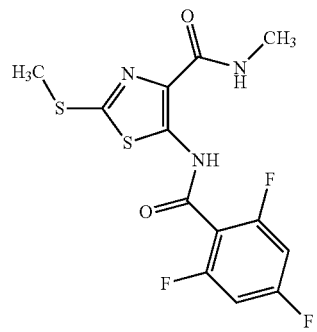 [SMILES: CNC(=O)c1nc(SC)sc1NC(=O)c1c(F)cc(F)cc1F]

The compound (203 mg) obtained in Reference Example 136 was treated by a method similar to that in Reference Example 156 to give the title compound (138 mg).

MS (ESI) m/z; 362 [M+H]+

Reference Example 158

5-[(2,6-difluorobenzoyl)amino]-N-methyl-2-methylsulfanyl-1,3-thiazole-4-carboxamide

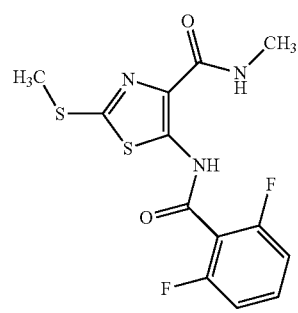 [SMILES: CNC(=O)c1nc(SC)sc1NC(=O)c1c(F)cccc1F]

The compound (291 mg) obtained in Reference Example 136 was treated by a method similar to that in Reference Example 156 to give the title compound (418 mg)

MS (ESI) m/z; 344 [M+H]+

Reference Example 159

5-[(cyclopropylcarbonyl)amino]-N-methyl-2-methylsulfanyl-1,3-thiazole-4-carboxamide

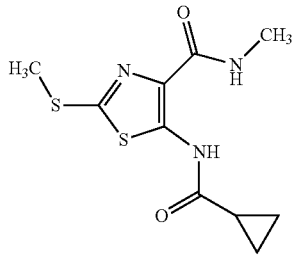 [SMILES: CNC(=O)c1nc(SC)sc1NC(=O)C1CC1]

The compound (3.50 g) obtained in Reference Example 136 was treated by a method similar to that in Reference Example 156 to give the title compound (4.64 g)
MS (ESI) m/z; 272 [M+H]$^+$

Reference Example 160

5-[(methoxyacetyl)amino]-N-methyl-2-methylsulfanyl-1,3-thiazole-4-carboxamide

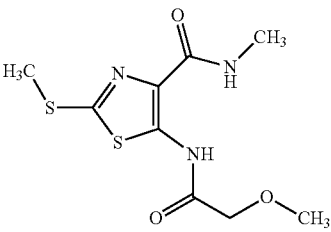

The compound (500 mg) obtained in Reference Example 136 was treated by a method similar to that in Reference Example 156 to give the title compound (697 mg)
MS (ESI) m/z; 276 [M+H]$^+$

Reference Example 161

N-methyl-2-methylsulfanyl-5-{[((RS)-tetrahydrofuran-2-yl)carbonyl]amino}-1,3-thiazole-4-carboxamide

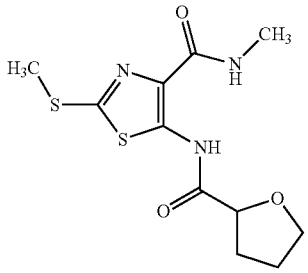 [SMILES: CNC(=O)c1nc(SC)sc1NC(=O)C1CCCO1]

The compound (500 mg) obtained in Reference Example 136 was treated by a method similar to that in Reference Example 156 to give the title compound (760 mg)
MS (ESI) m/z; 302 [M+H]$^+$

Reference Example 162

N-(4-ethylcarbamoyl-2-methylsulfanyl-1,3-thiazol-5-yl)pyridine-2-carboxamide

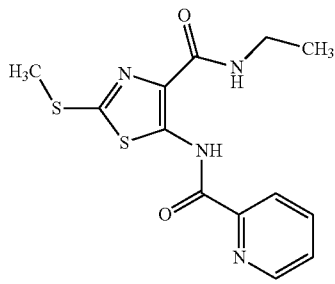 [SMILES: CCNC(=O)c1nc(SC)sc1NC(=O)c1ccccn1]

The compound (500 mg) obtained in Reference Example 137 was treated by a method similar to that in Reference Example 156 to give the title compound (715 mg)
MS (ESI) m/z; 323 [M+H]$^+$

Reference Example 163

5-[(methoxyacetyl)amino]-2-methylsulfanyl-N-(propan-2-yl)-1,3-thiazole-4-carboxamide

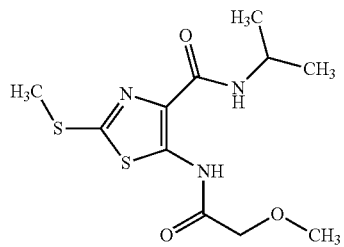

The compound (820 mg) obtained in Reference Example 138 was treated by a method similar to that in Reference Example 156 to give the title compound (881 mg)
MS (ESI) m/z; 304 [M+H]$^+$

Reference Example 164

N-cyclopropyl-5-[(methoxyacetyl)amino]-2-methylsulfanyl-1,3-thiazole-4-carboxamide

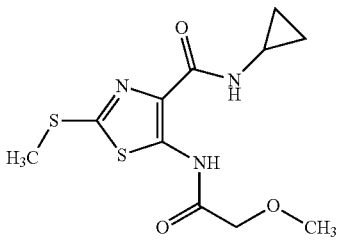

The compound (700 mg) obtained in Reference Example 139 was treated by a method similar to that in Reference Example 156 to give the title compound (897 mg)
MS (ESI) m/z; 302 [M+H]+

Reference Example 165

5-(acetylamino)-N-(2-methoxyethyl)-2-methylsulfanyl-1,3-thiazole-4-carboxamide

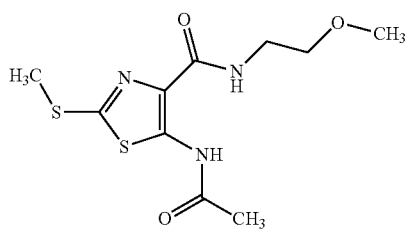

The compound (500 mg) obtained in Reference Example 141 was treated by a method similar to that in Reference Example 156 to give the title compound (360 mg)
MS (ESI) m/z; 290 [M+H]+

Reference Example 166

5-(acetylamino)-N-[1-(methoxymethyl)cyclopropyl]-2-methylsulfanyl-1,3-thiazole-4-carboxamide

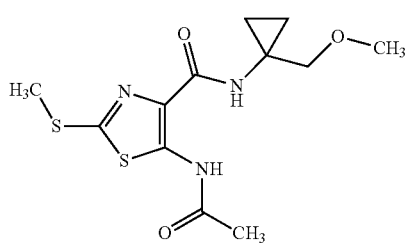

The compound (600 mg) obtained in Reference Example 142 was treated by a method similar to that in Reference Example 156 to give the title compound (600 mg)
MS (ESI) m/z; 316 [M+H]+

Reference Example 167

5-(acetylamino)-2-methylsulfanyl-N-(tetrahydro-2H-pyran-4-yl)-1,3-thiazole-4-carboxamide

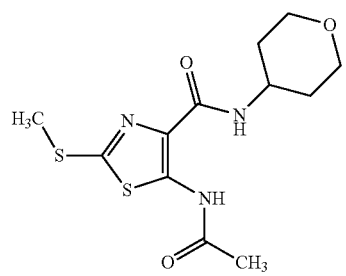 [SMILES: CSc1nc(C(=O)NC2CCOCC2)c(NC(C)=O)s1]

The compound (2.15 g) obtained in Reference Example 143 was treated by a method similar to that in Reference Example 156 to give the title compound (1.60 g)
MS (ESI) m/z; 316 [M+H]+

Reference Example 168

5-(acetylamino)-N-(2-methoxy-2-methylpropyl)-2-methylsulfanyl-1,3-thiazole-4-carboxamide

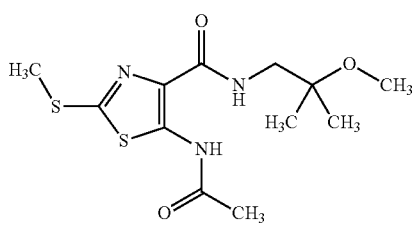

The compound (600 mg) obtained in Reference Example 146 was treated by a method similar to that in Reference Example 156 to give the title compound (570 mg)
MS (ESI) m/z; 318 [M+H]+

Reference Example 169

N-methyl-2-methylsulfanyl-5-{[(tetrahydro-2H-pyran-4-yl)carbonyl]amino}-1,3-thiazole-4-carboxamide

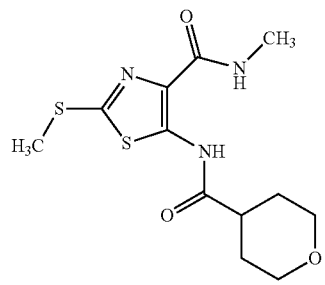 [SMILES: CNC(=O)c1nc(SC)sc1NC(=O)C1CCOCC1]

To a solution (2.00 mL) of tetrahydro-2H-carboxylic acid (585 mg) in methylene chloride were added oxalyl chloride (762 μL) and DMF (one drop), and the reaction mixture was stirred at room temperature for 2 hr. The reaction mixture was concentrated under reduced pressure, and the residue was dissolved in methylene chloride (1.00 mL) and added dropwise to a solution (3.00 mL) of the compound (500 mg) obtained in Reference Example 136 and triethylamine (697 μL) in methylene chloride under ice-cooling, and the mixture was stirred at room temperature for 30 min. Water was added to the reaction mixture, and the mixture was extracted twice with chloroform. The organic layer was dried over anhydrous sodium sulfate, filtered and concentrated. The residue was purified by silica gel column chromatography (solvent; hexane/ethyl acetate=70/30-20/80) to give the title compound (555 mg)
MS (ESI) m/z; 316 [M+H]+

Reference Example 170

5-{[(1-cyanocyclopentyl)carbonyl]amino}-N-methyl-2-methylsulfanyl-1,3-thiazole-4-carboxamide

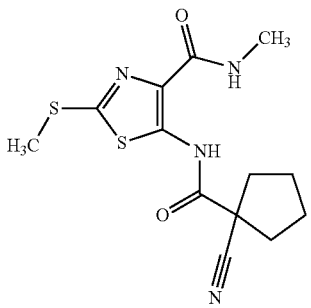 [SMILES: CNC(=O)c1nc(SC)sc1NC(=O)C1(C#N)CCCC1]

The compound (404 mg) obtained in Reference Example 136 was treated by a method similar to that in Reference Example 169 to give the title compound (561 mg)
MS (ESI) m/z; 325 [M+H]$^+$

Reference Example 171

5-{[(1-cyanocyclobutyl)carbonyl]amino}-N-methyl-2-methylsulfanyl-1,3-thiazole-4-carboxamide

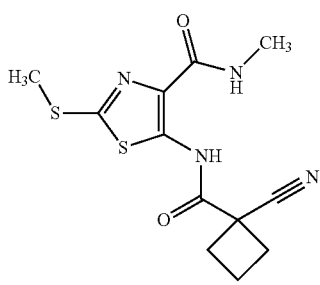 [SMILES: CNC(=O)c1nc(SC)sc1NC(=O)C1(C#N)CCC1]

The compound (203 mg) obtained in Reference Example 136 was treated by a method similar to that in Reference Example 169 to give the title compound (309 mg)
MS (ESI) m/z; 311 [M+H]$^+$

Reference Example 173

5-[(2,2-difluoropropanoyl)amino]-N-methyl-2-methylsulfanyl-1,3-thiazole-4-carboxamide

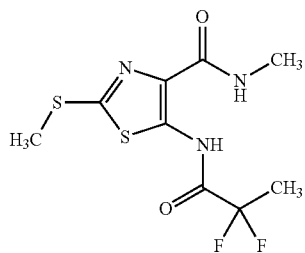 [SMILES: CNC(=O)c1nc(SC)sc1NC(=O)C(C)(F)F]

The compound (820 mg) obtained in Reference Example 136 was treated by a method similar to that in Reference Example 169 to give the title compound (555 mg)
MS (ESI) m/z; 296 [M+H]$^+$

Reference Example 174

5-{[(1-fluorocyclopropyl)carbonyl]amino}-N-methyl-2-methylsulfanyl-1,3-thiazole-4-carboxamide

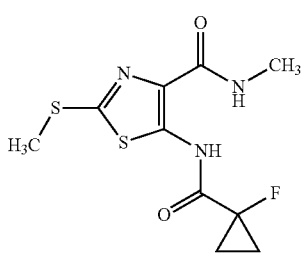 [SMILES: CNC(=O)c1nc(SC)sc1NC(=O)C1(F)CC1]

The compound (300 mg) obtained in Reference Example 136 was treated by a method similar to that in Reference Example 169 to give the title compound (490 mg)
MS (ESI) m/z; 290 [M+H]$^+$

Reference Example 175

5-{[(1-chlorocyclopropyl)carbonyl]amino}-N-methyl-2-methylsulfanyl-1,3-thiazole-4-carboxamide

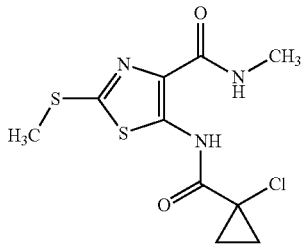

The compound (73 mg) obtained in Reference Example 136 was treated by a method similar to that in Reference Example 169 to give the title compound (98 mg)
MS (ESI) m/z; 306 [M+H]$^+$

Reference Example 176

5-[(2,2-difluorobutanoyl)amino]-N-methyl-2-methylsulfanyl-1,3-thiazole-4-carboxamide

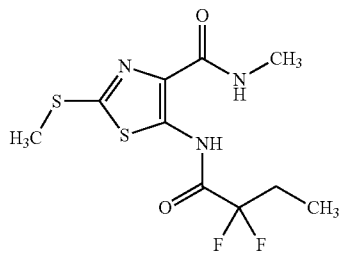 [SMILES: CCC(F)(F)C(=O)Nc1sc(SC)nc1C(=O)NC]

The compound (500 mg) obtained in Reference Example 136 was treated by a method similar to that in Reference Example 169 to give the title compound (282 mg)
MS (ESI) m/z; 310 [M+H]$^+$

Reference Example 177

5-{[difluoro(pyridin-2-yl)acetyl]amino}-N-methyl-2-methylsulfanyl-1,3-thiazole-4-carboxamide

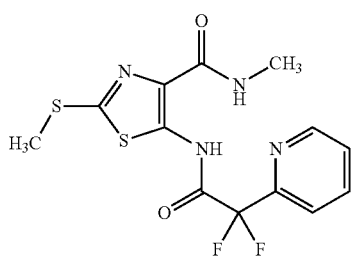 [SMILES: CNC(=O)c1nc(SC)sc1NC(=O)C(F)(F)c1ccccn1]

The compound (500 mg) obtained in Reference Example 136 was treated by a method similar to that in Reference Example 169 to give the title compound (827 mg)
MS (ESI) m/z; 359 [M+H]$^+$

Reference Example 178

5-[(2-methoxy-2-methylpropanoyl)amino]-N-methyl-2-methylsulfanyl-1,3-thiazole-4-carboxamide

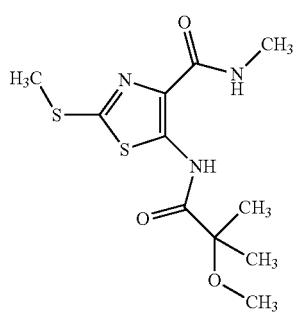

The compound (241 mg) obtained in Reference Example 136 was treated by a method similar to that in Reference Example 169 to give the title compound (243 mg)
MS (ESI) m/z; 304 [M+H]$^+$

Reference Example 179

N-ethyl-2-methylsulfanyl-5-{[2-(methylsulfonyl)benzoyl]amino}-1,3-thiazole-4-carboxamide

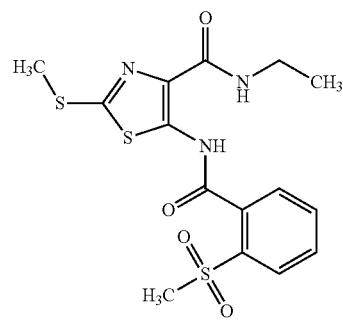 [SMILES: CCNC(=O)c1nc(SC)sc1NC(=O)c1ccccc1S(C)(=O)=O]

The compound (500 mg) obtained in Reference Example 137 was treated by a method similar to that in Reference Example 169 to give the title compound (320 mg)
MS (ESI) m/z; 400 [M+H]$^+$

Reference Example 180

N-(4-ethylcarbamoyl-2-methylsulfanyl-1,3-thiazol-5-yl)pyrimidine-2-carboxamide

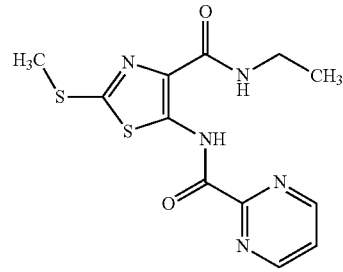 [SMILES: CCNC(=O)c1nc(SC)sc1NC(=O)c1ncccn1]

The compound (639 mg) obtained in Reference Example 137 was treated by a method similar to that in Reference Example 169 to give the title compound (547 mg)
MS (ESI) m/z; 324 [M+H]$^+$

Reference Example 181

5-[(2-fluoro-2-methylpropanoyl)amino]-N-methyl-2-methylsulfanyl-1,3-thiazole-4-carboxamide

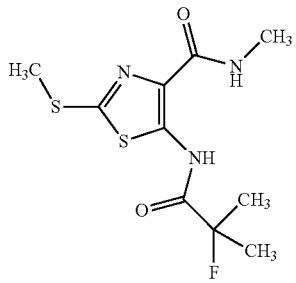

The compound (3.00 g) obtained in Reference Example 136 was treated by a method similar to that in Reference Example 169 to give the title compound (3.49 g)
MS (ESI) m/z; 292 [M+H]$^+$

Reference Example 182

5-methyl-N-(4-methylcarbamoyl-2-methylsulfanyl-1,3-thiazol-5-yl)-1,2,4-oxadiazole-3-carboxamide

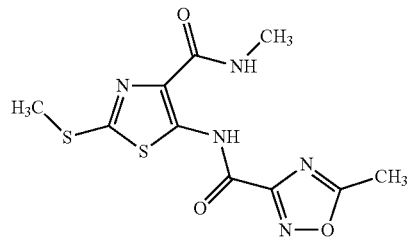

To a solution (50 mL) of 3-methyl-[1,2,4]oxadiazole-5-carboxylic acid ethyl ester (9.45 g) in ethanol was added an aqueous solution (20 mL) of potassium hydroxide (4.0 g) at room temperature, and the reaction mixture was stirred for 2 hr The solvent was evaporated under reduced pressure, acetonitrile was added to the residue, and the solid was collected by filtration, and dried to give 3-methyl-[1,2,4]oxadiazole-5-carboxylic acid potassium salt (9.38 g). To a solution (10 mL) of the obtained 3-methyl-[1,2,4]oxadiazole-5-carboxylic acid potassium salt (360 mg) in acetonitrile were added oxalyl chloride (310 μL) and DMF (one drop). The reaction mixture was stirred at room temperature for 2 hr and added dropwise to a solution (30 mL) of the compound (450 mg) obtained in Reference Example 136 and triethylamine (670 mg) in methylene chloride under ice-cooling, and the mixture was stirred at room temperature for 2 hr. Water was added to the reaction mixture, and the mixture was extracted twice with chloroform. The organic layer was dried over anhydrous magnesium sulfate, filtered and concentrated. The residue was purified by silica gel column chromatography (solvent; hexane/ethyl acetate=70/30-20/80) to give the title compound (300 mg)
MS (ESI) m/z; 314 [M+H]$^+$

Reference Example 183

5-methyl-N-(4-methylcarbamoyl-2-methylsulfanyl-1,3-thiazol-5-yl)-1,3,4-oxadiazole-2-carboxamide

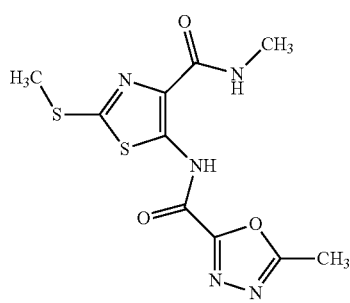

The compound (1.09 g) obtained in Reference Example 136 was treated by a method similar to that in Reference Example 182 to give the title compound (808 mg)
MS (ESI) m/z; 314 [M+H]$^+$

Reference Example 184

3-methyl-N-(4-methylcarbamoyl-2-methylsulfanyl-1,3-thiazol-5-yl)-1,2,4-oxadiazole-5-carboxamide

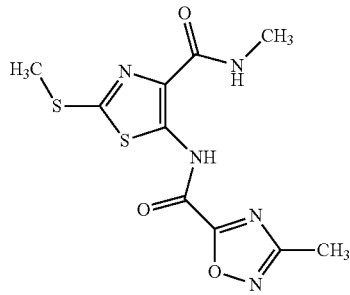

The compound (5.60 g) obtained in Reference Example 136 was treated by a method similar to that in Reference Example 182 to give the title compound (5.83 g)
MS (ESI) m/z; 314 [M+H]$^+$

Reference Example 185

N-(4-ethylcarbamoyl-2-methylsulfanyl-1,3-thiazol-5-yl)-3-methyl-1,2,4-oxadiazole-5-carboxamide

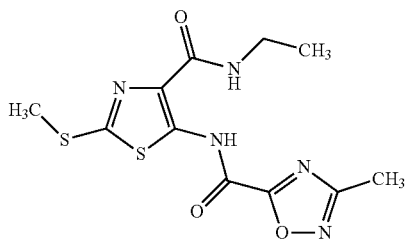

The compound (1.51 g) obtained in Reference Example 137 was treated by a method similar to that in Reference Example 182 to give the title compound (582 mg)

MS (ESI) m/z; 328 [M+H]+

Reference Example 186

3-methyl-N-[2-methylsulfanyl-4-(propan-2-yl)car-bamoyl-1,3-thiazol-5-yl]-1,2,4-oxadiazole-5-carbox-amide

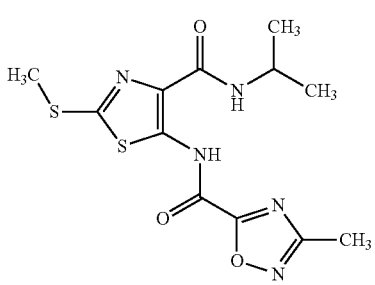

The compound (850 mg) obtained in Reference Example 138 was treated by a method similar to that in Reference Example 182 to give the title compound (794 mg)

MS (ESI) m/z; 342 [M+H]+

Reference Example 187

N-(4-cyclopropylcarbamoyl-2-methylsulfanyl-1,3-thiazol-5-yl)-3-methyl-1,2,4-oxadiazole-5-carbox-amide

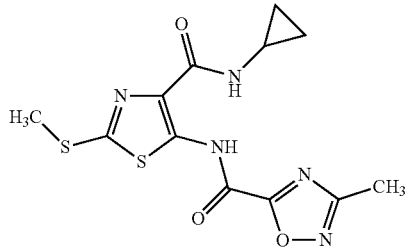

The compound (1.20 g) obtained in Reference Example 139 was treated by a method similar to that in Reference Example 182 to give the title compound (400 mg)

MS (ESI) m/z; 340 [M+H]+

Reference Example 188

N-[4-(2,2-difluoroethyl)carbamoyl-2-methylsulfa-nyl-1,3-thiazol-5-yl]-3-methyl-1,2,4-oxadiazole-5-carboxamide

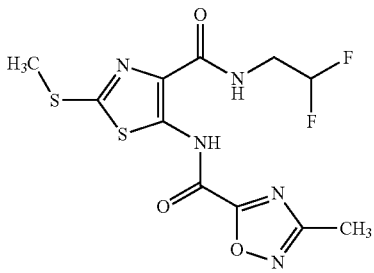 [SMILES: CSc1nc(C(=O)NCC(F)F)c(NC(=O)c2nc(C)no2)s1]

The compound (1.20 g) obtained in Reference Example 147 was treated by a method similar to that in Reference Example 182 to give the title compound (1.52 g)

MS (ESI) m/z; 364 [M+H]+

Reference Example 189

N-[4-(2-methoxyethyl)carbamoyl-2-methylsulfanyl-1,3-thiazol-5-yl]-3-methyl-1,2,4-oxadiazole-5-car-boxamide

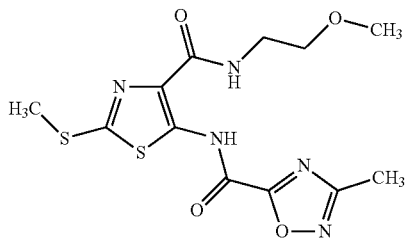

The compound (1.30 g) obtained in Reference Example 141 was treated by a method similar to that in Reference Example 182 to give the title compound (700 mg)

MS (ESI) m/z; 358 [M+H]+

Reference Example 190

3-methyl-N-[2-methylsulfanyl-4-(tetrahydro-2H-pyran-4-yl)carbamoyl-1,3-thiazol-5-yl]-1,2,4-oxadi-azole-5-carboxamide

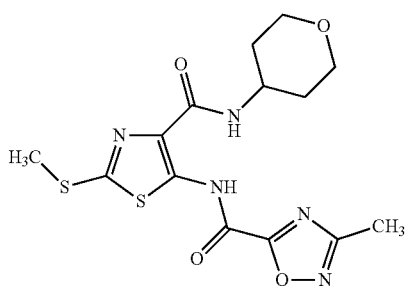

The compound (1.20 g) obtained in Reference Example 143 was treated by a method similar to that in Reference Example 182 to give the title compound (1.05 g)

MS (ESI) m/z; 384 [M+H]⁺

Reference Example 191

5-[(2,2-difluoro-3-methoxypropanoyl)amino]-N-ethyl-2-methylsulfanyl-1,3-thiazole-4-carboxamide

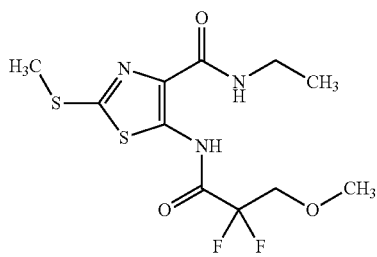

The compound (300 mg) obtained in Reference Example 137 was treated by a method similar to that in Reference Example 182 to give the title compound (136 mg)

MS (ESI) m/z; 340 [M+H]⁺

Reference Example 192

5-[(2,2-difluoro-3-methoxypropanoyl)amino]-N-methyl-2-methylsulfanyl-1,3-thiazole-4-carboxamide

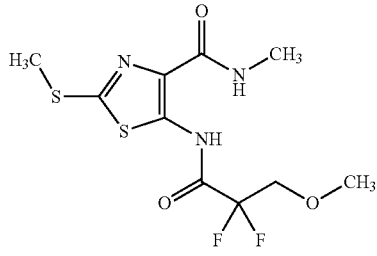

The compound (1.76 g) obtained in Reference Example 136 was treated by a method similar to that in Reference Example 182 to give the title compound (165 mg)

MS (ESI) m/z; 326 [M+H]⁺

Reference Example 194

N-[(3-methyloxetan-3-yl)methyl]-2-methylsulfanyl-5-[(trifluoroacetyl)amino]-1,3-thiazole-4-carboxamide

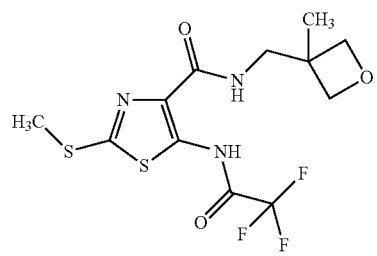 [SMILES: CSc1nc(C(=O)NCC2(C)COC2)c(NC(=O)C(F)(F)F)s1]

To a solution (15 mL) of the compound (650 mg) obtained in Reference Example 144 in methylene chloride were added pyridine (230 mg) and difluoroacetic anhydride (550 mg) under ice-cooling, and the reaction mixture was stirred at 0° C. for 1 hr. Water was added to the reaction mixture, and the mixture was extracted twice with chloroform. The combined organic layer was washed with aqueous citric acid solution and saturated brine, dried over anhydrous sodium sulfate, filtered and concentrated to give the title compound (750 mg)

MS (ESI) m/z; 370 [M+H]⁺

Reference Example 195

6-methyl-2-methylsulfanyl-5-phenyl[1,3]thiazolo[5,4-d]pyrimidin-7(6H)-one

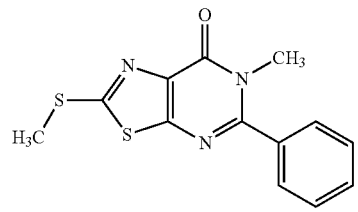 [SMILES: CSc1nc2c(=O)n(C)c(-c3ccccc3)nc2s1]

To a solution (900 mL) of the compound (43.6 g) obtained in Reference Example 156 in methylene chloride were added chlorotrimethylsilane (90.0 mL) and triethylamine (297 mL), and the reaction mixture was stirred at room temperature overnight. The reaction mixture was poured into water (1000 mL), and the mixture was extracted three times with chloroform. The organic layer was dried over anhydrous magnesium sulfate, filtered and concentrated. To the residue was added ethyl acetate, and the solid was collected by filtration, and dried to give the title compound (37.7 g)

MS (ESI) m/z; 290 [M+H]⁺

Reference Example 196

6-methyl-2-methylsulfanyl-5-(2,4,6-trifluorophenyl)[1,3]thiazolo[5,4-d]pyrimidin-7(6H)-one

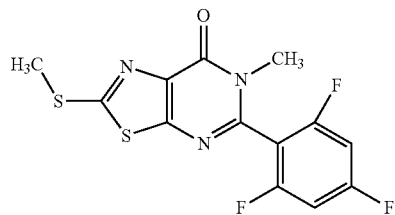 [SMILES: CSc1nc2c(=O)n(C)c(-c3c(F)cc(F)cc3F)nc2s1]

The compound (117 mg) obtained in Reference Example 157 was treated by a method similar to that in Reference Example 195 to give the title compound (97 mg)

MS (ESI) m/z; 344 [M+H]$^+$

Reference Example 197

5-(2,6-difluorophenyl)-6-methyl-2-methylsulfanyl[1,3]thiazolo[5,4-d]pyrimidin-7(6H)-one

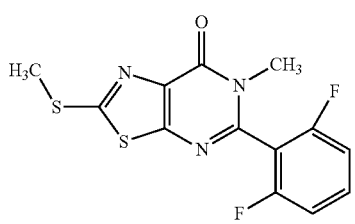 [SMILES: CSc1nc2c(=O)n(C)c(-c3c(F)cccc3F)nc2s1]

The compound (181 mg) obtained in Reference Example 158 was treated by a method similar to that in Reference Example 195 to give the title compound (175 mg)

MS (ESI) m/z; 326 [M+H]$^+$

Reference Example 198

6-methyl-2-methylsulfanyl-5-((RS)-tetrahydrofuran-2-yl)[1,3]thiazolo[5,4-d]pyrimidin-7(6H)-one

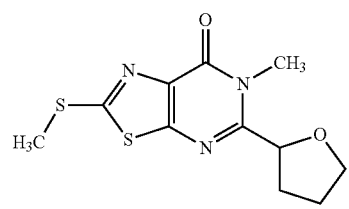 [SMILES: CSc1nc2c(=O)n(C)c(C3CCCO3)nc2s1]

The compound (740 mg) obtained in Reference Example 161 was treated by a method similar to that in Reference Example 195 to give the title compound (600 mg)

MS (ESI) m/z; 284 [M+H]$^+$

Reference Example 199

6-ethyl-2-methylsulfanyl-5-(pyridin-2-yl)[1,3]thiazolo[5,4-d]pyrimidin-7(6H)-one

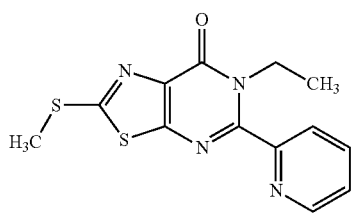 [SMILES: CCn1c(-c2ccccn2)nc2sc(SC)nc2c1=O]

The compound (700 mg) obtained in Reference Example 162 was treated by a method similar to that in Reference Example 195 to give the title compound (647 mg)

MS (ESI) m/z; 305 [M+H]$^+$

Reference Example 200

5-methoxymethyl-2-methylsulfanyl-6-(propan-2-yl)[1,3]thiazolo[5,4-d]pyrimidin-7(6H)-one

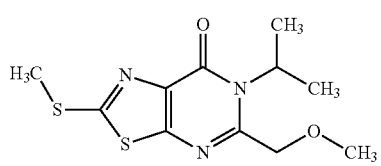

The compound (680 mg) obtained in Reference Example 163 was treated by a method similar to that in Reference Example 195 to give the title compound (582 mg)

MS (ESI) m/z; 286 [M+H]$^+$

Reference Example 201

6-cyclopropyl-5-methoxymethyl-2-methylsulfanyl[1,3]thiazolo[5,4-d]pyrimidin-7(6H)-one

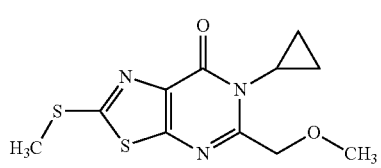

The compound (897 mg) obtained in Reference Example 164 was treated by a method similar to that in Reference Example 195 to give the title compound (772 mg)

MS (ESI) m/z; 284 [M+H]$^+$

Reference Example 202

5-methyl-2-methylsulfanyl-6-(tetrahydro-2H-pyran-4-yl)[1,3]thiazolo[5,4-d]pyrimidin-7(6H)-one

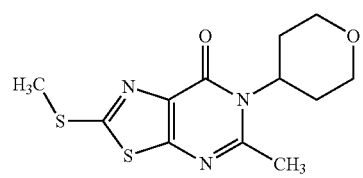 [SMILES: CSc1nc2c(=O)n(C3CCOCC3)c(C)nc2s1]

The compound (1.60 g) obtained in Reference Example 167 was treated by a method similar to that in Reference Example 195 to give the title compound (1.16 g)

MS (ESI) m/z; 298 [M+H]$^+$

Reference Example 203

6-(2-methoxy-2-methylpropyl)-5-methyl-2-methylsulfanyl[1,3]thiazolo[5,4-d]pyrimidin-7(6H)-one

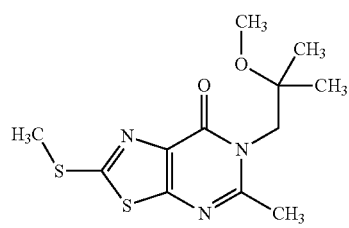 [SMILES: COC(C)(C)Cn1c(C)nc2sc(SC)nc2c1=O]

The compound (560 mg) obtained in Reference Example 168 was treated by a method similar to that in Reference Example 195 to give the title compound (320 mg)

MS (ESI) m/z; 300 [M+H]$^+$

Reference Example 204

5-(1,1-difluoroethyl)-6-methyl-2-methylsulfanyl[1,3]thiazolo[5,4-d]pyrimidin-7(6H)-one

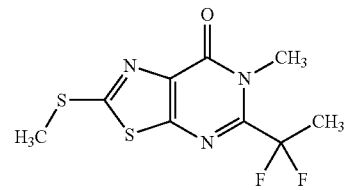 [SMILES: CSc1nc2c(=O)n(C)c(C(C)(F)F)nc2s1]

The compound (550 mg) obtained in Reference Example 173 was treated by a method similar to that in Reference Example 195 to give the title compound (507 mg)

MS (ESI) m/z; 278 [M+H]$^+$

Reference Example 205

5-(1-fluorocyclopropyl)-6-methyl-2-methylsulfanyl[1,3]thiazolo[5,4-d]pyrimidin-7(6H)-one

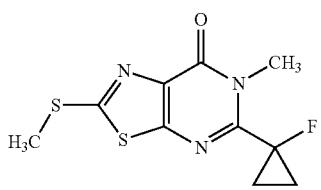 [SMILES: CSc1nc2c(=O)n(C)c(C3(F)CC3)nc2s1]

The compound (384 mg) obtained in Reference Example 174 was treated by a method similar to that in Reference Example 195 to give the title compound (346 mg)

MS (ESI) m/z; 272 [M+H]$^+$

Reference Example 206

5-(1-chlorocyclopropyl)-6-methyl-2-methylsulfanyl[1,3]thiazolo[5,4-d]pyrimidin-7(6H)-one

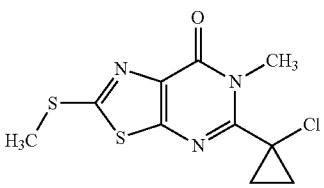 [SMILES: CSc1nc2c(=O)n(C)c(C3(Cl)CC3)nc2s1]

The compound (96 mg) obtained in Reference Example 175 was treated by a method similar to that in Reference Example 195 to give the title compound (86 mg)

MS (ESI) m/z; 288, 290 [M+H]$^+$

Reference Example 207

5-(1,1-difluoropropyl)-6-methyl-2-methylsulfanyl[1,3]thiazolo[5,4-d]pyrimidin-7(6H)-one

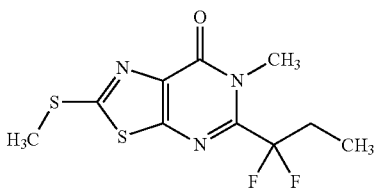 [SMILES: CCC(F)(F)c1nc2sc(SC)nc2c(=O)n1C]

The compound (280 mg) obtained in Reference Example 176 was treated by a method similar to that in Reference Example 195 to give the title compound (240 mg)

MS (ESI) m/z; 292 [M+H]$^+$

Reference Example 208

5-[difluoro(pyridin-2-yl)methyl]-6-methyl-2-methyl-sulfanyl[1,3]thiazolo[5,4-d]pyrimidin-7(6H)-one

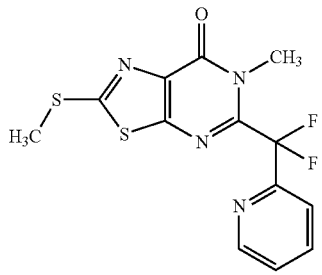 [SMILES: CSc1nc2c(=O)n(C)c(C(F)(F)c3ccccn3)nc2s1]

The compound (825 mg) obtained in Reference Example 177 was treated by a method similar to that in Reference Example 195 to give the title compound (772 mg)

MS (ESI) m/z; 341 [M+H]$^+$

Reference Example 209

6-methyl-2-methylsulfanyl-5-(tetrahydro-2H-pyran-4-yl)[1,3]thiazolo[5,4-d]pyrimidin-7(6H)-one

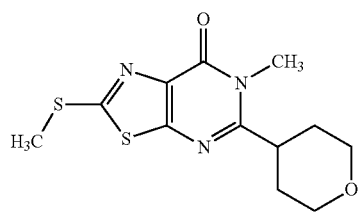 [SMILES: CSc1nc2c(=O)n(C)c(C3CCOCC3)nc2s1]

The compound (691 mg) obtained in Reference Example 169 was treated by a method similar to that in Reference Example 195 to give the title compound (615 mg)

MS (ESI) m/z; 298 [M+H]$^+$

Reference Example 210

5-(1,1-difluoro-2-methoxyethyl)-6-methyl-2-methyl-sulfanyl[1,3]thiazolo[5,4-d]pyrimidin-7(6H)-one

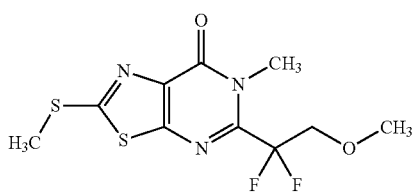

The compound (165 mg) obtained in Reference Example 192 was treated by a method similar to that in Reference Example 195 to give the title compound (122 mg)

MS (ESI) m/z; 308 [M+H]$^+$

Reference Example 211

6-ethyl-2-methylsulfanyl-5-[2-(methylsulfonyl)phenyl][1,3]thiazolo[5,4-d]pyrimidin-7(6H)-one

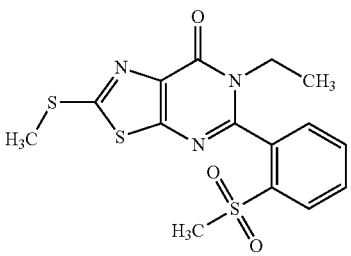 [SMILES: CCn1c(-c2ccccc2S(C)(=O)=O)nc2sc(SC)nc2c1=O]

The compound (310 mg) obtained in Reference Example 179 was treated by a method similar to that in Reference Example 195 to give the title compound (261 mg)

MS (ESI) m/z; 382 [M+H]$^+$

Reference Example 212

6-ethyl-2-methylsulfanyl-5-(pyrimidin-2-yl)[1,3]thiazolo[5,4-d]pyrimidin-7(6H)-one

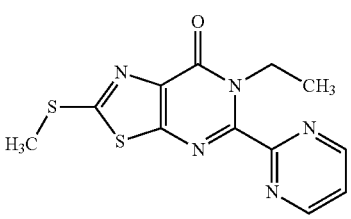 [SMILES: CCn1c(-c2ncccn2)nc2sc(SC)nc2c1=O]

The compound (535 mg) obtained in Reference Example 180 was treated by a method similar to that in Reference Example 195 to give the title compound (500 mg)

MS (ESI) m/z; 306 [M+H]$^+$

Reference Example 213

6-methyl-5-(5-methyl-1,2,4-oxadiazol-3-yl)-2-methylsulfanyl[1,3]thiazolo[5,4-d]pyrimidin-7(6H)-one

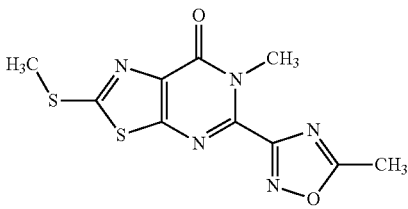

The compound (300 mg) obtained in Reference Example 182 was treated by a method similar to that in Reference Example 195 to give the title compound (220 mg)

MS (ESI) m/z; 296 [M+H]$^+$

Reference Example 214

6-methyl-5-(5-methyl-1,3,4-oxadiazol-2-yl)-2-methylsulfanyl[1,3]thiazolo[5,4-d]pyrimidin-7(6H)-one

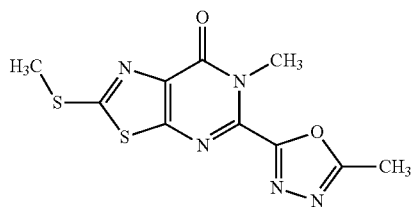

The compound (400 mg) obtained in Reference Example 183 was treated by a method similar to that in Reference Example 195 to give the title compound (310 mg)
MS (ESI) m/z; 296 [M+H]$^+$

Reference Example 215

6-methyl-5-(3-methyl-1,2,4-oxadiazol-5-yl)-2-methylsulfanyl[1,3]thiazolo[5,4-d]pyrimidin-7(6H)-one

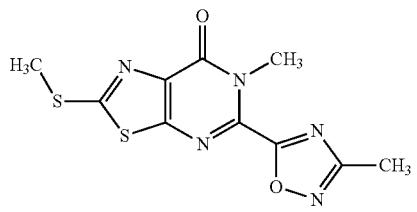

The compound (191 mg) obtained in Reference Example 184 was treated by a method similar to that in Reference Example 195 to give the title compound (171 mg)
MS (ESI) m/z; 296 [M+H]$^+$

Reference Example 216

6-ethyl-5-(3-methyl-1,2,4-oxadiazol-5-yl)-2-methylsulfanyl[1,3]thiazolo[5,4-d]pyrimidin-7(6H)-one

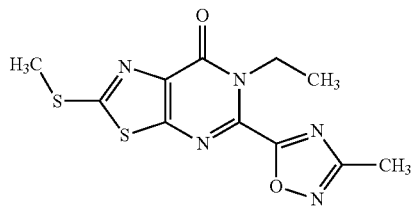

The compound (1.25 g) obtained in Reference Example 185 was treated by a method similar to that in Reference Example 195 to give the title compound (830 mg)
MS (ESI) m/z; 310 [M+H]$^+$

Reference Example 217

5-(3-methyl-1,2,4-oxadiazol-5-yl)-2-methylsulfanyl-6-(propan-2-yl)[1,3]thiazolo[5,4-d]pyrimidin-7(6H)-one

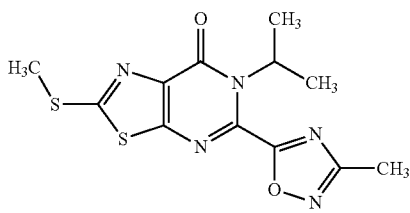

The compound (790 mg) obtained in Reference Example 186 was treated by a method similar to that in Reference Example 195 to give the title compound (279 mg)
MS (ESI) m/z; 324 [M+H]$^+$

Reference Example 218

6-cyclopropyl-5-(3-methyl-1,2,4-oxadiazol-5-yl)-2-methylsulfanyl[1,3]thiazolo[5,4-d]pyrimidin-7(6H)-one

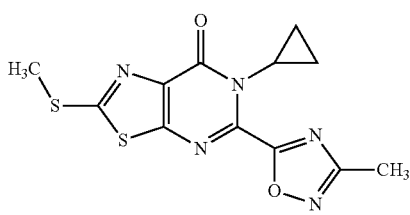

The compound (400 mg) obtained in Reference Example 187 was treated by a method similar to that in Reference Example 195 to give the title compound (290 mg)
MS (ESI) m/z; 322 [M+H]$^+$

Reference Example 219

6-(2,2-difluoroethyl)-5-(3-methyl-1,2,4-oxadiazol-5-yl)-2-methylsulfanyl[1,3]thiazolo[5,4-d]pyrimidin-7(6H)-one

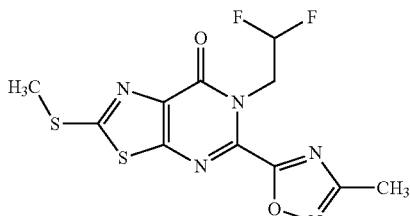

The compound (1.52 g) obtained in Reference Example 188 was treated by a method similar to that in Reference Example 195 to give the title compound (1.31 g)
MS (ESI) m/z; 346 [M+H]$^+$

Reference Example 220

6-(2-methoxyethyl)-5-(3-methyl-1,2,4-oxadiazol-5-yl)-2-methylsulfanyl[1,3]thiazolo[5,4-d]pyrimidin-7(6H)-one

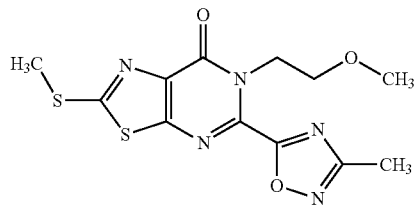

The compound (700 mg) obtained in Reference Example 189 was treated by a method similar to that in Reference Example 195 to give the title compound (460 mg)
MS (ESI) m/z; 340 [M+H]$^+$

Reference Example 221

5-(3-methyl-1,2,4-oxadiazol-5-yl)-2-methylsulfanyl-6-(tetrahydro-2H-pyran-4-yl)[1,3]thiazolo[5,4-d]pyrimidin-7(6H)-one

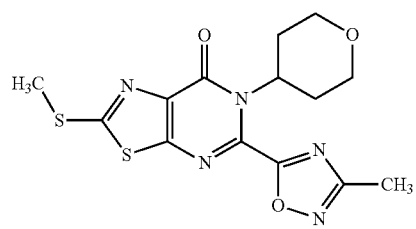

The compound (1.05 g) obtained in Reference Example 190 was treated by a method similar to that in Reference Example 195 to give the title compound (410 mg)
MS (ESI) m/z; 366 [M+H]$^+$

Reference Example 222

5-(1,1-difluoro-2-methoxyethyl)-6-ethyl-2-methylsulfanyl[1,3]thiazolo[5,4-d]pyrimidin-7(6H)-one

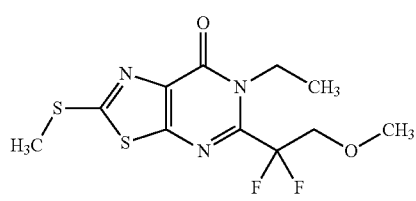

The compound (135 mg) obtained in Reference Example 191 was treated by a method similar to that in Reference Example 195 to give the title compound (106 mg)
MS (ESI) m/z; 322 [M+H]$^+$

Reference Example 223

5-(2-fluoropropan-2-yl)-6-methyl-2-methylsulfanyl[1,3]thiazolo[5,4-d]pyrimidin-7(6H)-one

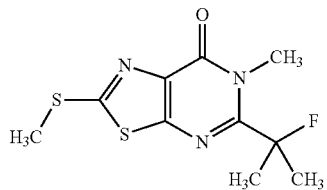 [SMILES: CSc1nc2c(=O)n(C)c(C(C)(C)F)nc2s1]

The compound (300 mg) obtained in Reference Example 181 was treated by a method similar to that in Reference Example 195 to give the title compound (238 mg)
MS (ESI) m/z; 274 [M+H]$^+$

Reference Example 224

1-(6-methyl-2-methylsulfanyl-7-oxo-6,7-dihydro[1,3]thiazolo[5,4-d]pyrimidin-5-yl)cyclopentanecarbonitrile

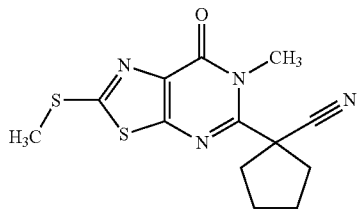 [SMILES: CSc1nc2c(=O)n(C)c(C3(C#N)CCCC3)nc2s1]

To a solution (10 mL) of the compound (561 mg) obtained in Reference Example 170 in dichloroethane were added trimethylsilyl trifluoromethanesulfonate (376 µL) and triethylamine (482 µL). The reaction mixture was stirred at room temperature for 1 hr, trimethylsilyl trifluoromethanesulfonate (376 µL) and triethylamine (482 µL) were added, and the reaction mixture was further stirred at room temperature overnight. 1.0 mol/L Hydrochloric acid was added to the reaction mixture, and the mixture was extracted twice with chloroform. The organic layer was dried over anhydrous sodium sulfate, filtered and concentrated. The residue was purified by silica gel column chromatography (solvent; hexane/ethyl acetate=80/20-30/70) to give the title compound (287 mg)
MS (ESI) m/z; 307 [M+H]$^+$

Reference Example 225

6-(2-methoxyethyl)-5-methyl-2-methylsulfanyl[1,3]thiazolo[5,4-d]pyrimidin-7(6H)-one

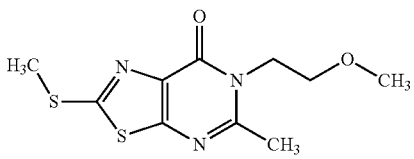

The compound (360 mg) obtained in Reference Example 165 was treated by a method similar to that in Reference Example 224 to give the title compound (360 mg)

MS (ESI) m/z; 272 [M+H]$^+$

Reference Example 226

6-[1-(methoxymethyl)cyclopropyl]-5-methyl-2-methylsulfanyl[1,3]thiazolo[5,4-d]pyrimidin-7(6H)-one

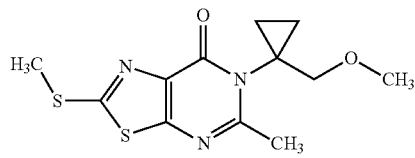

The compound (600 mg) obtained in Reference Example 166 was treated by a method similar to that in Reference Example 224 to give the title compound (360 mg)

MS (ESI) m/z; 298 [M+H]$^+$

Reference Example 227

1-[6-methyl-2-methylsulfanyl-7-oxo-6,7-dihydro[1,3]thiazolo[5,4-d]pyrimidin-5-yl]cyclobutanecarbonitrile

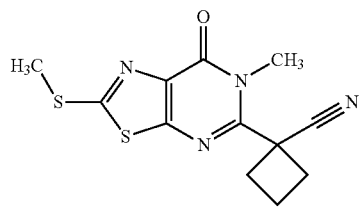 [SMILES: CSc1nc2c(=O)n(C)c(C3(C#N)CCC3)nc2s1]

The compound (309 mg) obtained in Reference Example 171 was treated by a method similar to that in Reference Example 224 to give the title compound (253 mg)

MS (ESI) m/z; 293 [M+H]$^+$

Reference Example 228

5-(2-methoxypropan-2-yl)-6-methyl-2-methylsulfanyl[1,3]thiazolo[5,4-d]pyrimidin-7(6H)-one

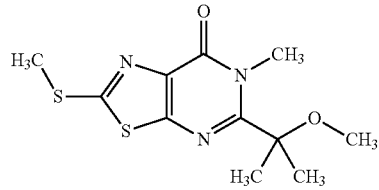

The compound (243 mg) obtained in Reference Example 178 was treated by a method similar to that in Reference Example 224 to give the title compound (171 mg)

MS (ESI) m/z; 287 [M+H]$^+$

Reference Example 229

6-[(3-methyloxetan-3-yl)methyl]-2-methylsulfanyl-5-trifluoromethyl[1,3]thiazolo[5,4-d]pyrimidin-7(6H)-one

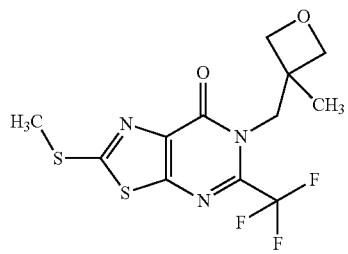 [SMILES: CSc1nc2c(=O)n(CC3(C)COC3)c(C(F)(F)F)nc2s1]

To a solution (20 mL) of the compound (610 mg) obtained in Reference Example 194 in dichloroethane were added trifluoroacetic anhydride (1.80 g) and triethylamine (1.70 g), and the reaction mixture was stirred at room temperature for 4 hr. Aqueous citric acid solution was added, and the mixture was extracted twice with chloroform. The organic layer was washed with saturated aqueous sodium hydrogen carbonate solution, dried over anhydrous sodium sulfate, filtered and concentrated. The residue was purified by silica gel column chromatography (solvent; hexane/ethyl acetate=80/20-60/40) to give the title compound (450 mg)

MS (ESI) m/z; 352 [M+H]$^+$

Reference Example 230

5-cyclopropyl-6-methyl-2-methylsulfanyl[1,3]thiazolo[5,4-d]pyrimidin-7(6H)-one

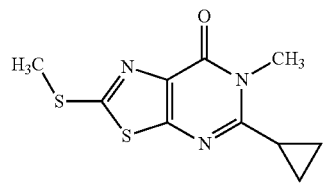 [SMILES: CSc1nc2c(=O)n(C)c(C3CC3)nc2s1]

To a solution (20 mL) of the compound (600 mg) obtained in Reference Example 159 in dichloroethane were added hexamethyldisilasane (4.70 mL), iodine (2.79 g) and N,N-diisopropylethylamine (2.0 mL), and the reaction mixture was stirred with heating at 80° C. for 17 hr. The reaction mixture was cooled to room temperature, 2 mol/L hydrochloric acid was added, and the mixture was extracted twice with chloroform. The organic layer was washed with aqueous sodium thiosulfate solution, dried over anhydrous sodium sulfate, filtered and concentrated. The residue was purified by silica gel column chromatography (solvent; hexane/ethyl acetate=80/20-60/40) to give the title compound (420 mg)

MS (ESI) m/z; 254 [M+H]$^+$

Reference Example 231

5-methoxymethyl-6-methyl-2-methylsulfanyl[1,3]thiazolo[5,4-d]pyrimidin-7(6H)-one

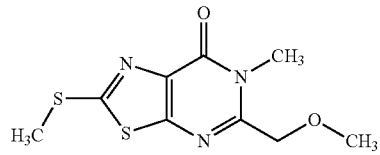

The compound (338 mg) obtained in Reference Example 160 was treated by a method similar to that in Reference Example 230 to give the title compound (257 mg)

MS (ESI) m/z; 258 [M+H]+

Reference Example 232

5-ethyl-6-methyl-2-methylsulfanyl[1,3]thiazolo[5,4-d]pyrimidin-7(6H)-one

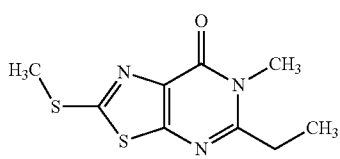

The compound (1.50 g) obtained in Reference Example 136 was added to trimethyl orthopropionate (3.96 g) and the mixture was heated at 120° C. for 4 hr. Acetic anhydride (3.49 mL) was added, and the reaction mixture was further heated at 120° C. for 8 hr. Acetic anhydride (1.00 mL) was added, and the reaction mixture was further heated at 120° C. for 6 hr. The reaction mixture was cooled to room temperature, ethyl acetate was added to the resultant solid, and the solid was collected by filtration to give the title compound (1.23 g)

MS (ESI) m/z; 242 [M+H]+

Reference Example 233

5,6-dimethyl-2-methylsulfanyl[1,3]thiazolo[5,4-d]pyrimidin-7(6H)-one

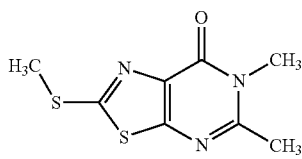

The compound (800 mg) obtained in Reference Example 136 was treated by a method similar to that in Reference Example 232 to give the title compound (444 mg)

MS (ESI) m/z; 228 [M+H]+

Reference Example 234

5,6-diethyl-2-methylsulfanyl[1,3]thiazolo[5,4-d]pyrimidin-7(6H)-one

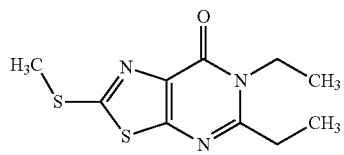 [SMILES: CCc1nc2sc(SC)nc2c(=O)n1CC]

The compound (2.00 g) obtained in Reference Example 137 was treated by a method similar to that in Reference Example 232 to give the title compound (1.55 g)

MS (ESI) m/z; 256 [M+H]+

Reference Example 235

6-cyclopropyl-5-methyl-2-methylsulfanyl[1,3]thiazolo[5,4-d]pyrimidin-7(6H)-one

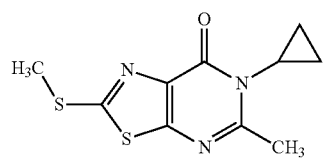

The compound (19.5 g) obtained in Reference Example 139 was treated by a method similar to that in Reference Example 232 to give the title compound (8.72 g)

MS (ESI) m/z; 254 [M+H]+

Reference Example 236

6-cyclopentyl-2-methylsulfanyl[1,3]thiazolo[5,4-d]pyrimidin-7(6H)-one

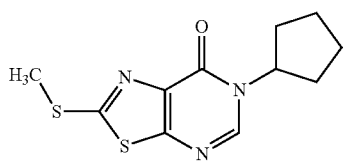 [SMILES: CSc1nc2c(=O)n(C3CCCC3)cnc2s1]

The compound (600 mg) obtained in Reference Example 140 was treated by a method similar to that in Reference Example 232 to give the title compound (360 mg)

MS (ESI) m/z; 268 [M+H]+

Reference Example 237

6-methyl-2-methylsulfanyl-5-propyl[1,3]thiazolo[5,4-d]pyrimidin-7(6H)-one

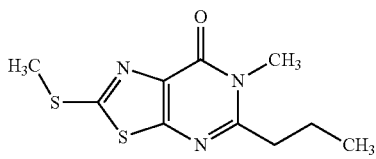 [SMILES: CCCc1nc2sc(SC)nc2c(=O)n1C]

The compound (1.20 g) obtained in Reference Example 136 was treated by a method similar to that in Reference Example 232 to give the title compound (1.20 g)

MS (ESI) m/z; 256 [M+H]$^+$

Reference Example 238

6-methyl-2-methylsulfanyl-5-(propan-2-yl)[1,3]thiazolo[5,4-d]pyrimidin-7(6H)-one

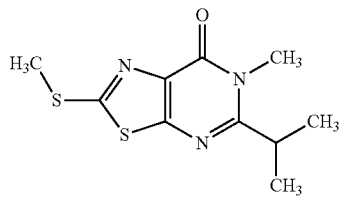

The compound (2.00 g) obtained in Reference Example 136 was treated by a method similar to that in Reference Example 232 to give the title compound (2.00 g)

MS (ESI) m/z; 256 [M+H]$^+$

Reference Example 239

6-ethyl-5-methyl-2-methylsulfanyl[1,3]thiazolo[5,4-d]pyrimidin-7(6H)-one

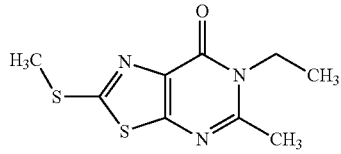

The compound (740 mg) obtained in Reference Example 137 was treated by a method similar to that in Reference Example 232 to give the title compound (480 mg)

MS (ESI) m/z; 242 [M+H]$^+$

Reference Example 240

5-methyl-2-methylsulfanyl-6-(propan-2-yl)[1,3]thiazolo[5,4-d]pyrimidin-7(6H)-one

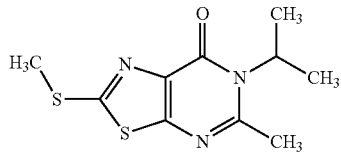 [SMILES: CSc1nc2c(=O)n(C(C)C)c(C)nc2s1]

The compound (840 mg) obtained in Reference Example 138 was treated by a method similar to that in Reference Example 232 to give the title compound (400 mg)

MS (ESI) m/z; 256 [M+H]$^+$

Reference Example 241

6-cyclopentyl-5-methyl-2-methylsulfanyl[1,3]thiazolo[5,4-d]pyrimidin-7(6H)-one

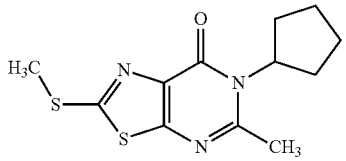

The compound (1.37 g) obtained in Reference Example 140 was treated by a method similar to that in Reference Example 232 to give the title compound (325 mg)

MS (ESI) m/z; 282 [M+H]$^+$

Reference Example 242

5-methyl-2-methylsulfanyl-6-(2,2,2-trifluoroethyl)[1,3]thiazolo[5,4-d]pyrimidin-7(6H)-one

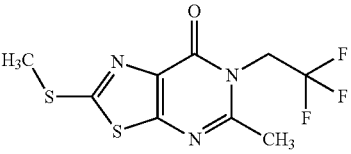 [SMILES: CSc1nc2c(=O)n(CC(F)(F)F)c(C)nc2s1]

The compound (355 mg) obtained in Reference Example 148 was treated by a method similar to that in Reference Example 232 to give the title compound (190 mg)

MS (ESI) m/z; 296 [M+H]$^+$

Reference Example 243

5-methyl-2-methylsulfanyl-6-phenyl[1,3]thiazolo[5,4-d]pyrimidin-7(6H)-one

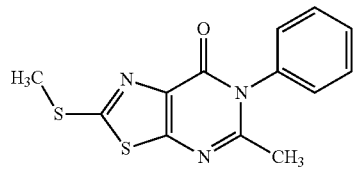 [SMILES: CSc1nc2c(=O)n(-c3ccccc3)c(C)nc2s1]

The compound (1.32 g) obtained in Reference Example 149 was treated by a method similar to that in Reference Example 232 to give the title compound (1.45 g)
MS (ESI) m/z; 290 [M+H]$^+$

Reference Example 244

6-methyl-2-methylsulfanyl-5-trifluoromethyl[1,3]thiazolo[5,4-d]pyrimidin-7(6H)-one

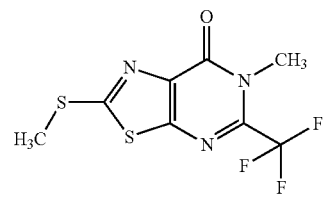 [SMILES: CSc1nc2c(=O)n(C)c(C(F)(F)F)nc2s1]

To a solution (50 mL) of the compound (2.50 g) obtained in Reference Example 136 in methylene chloride was added dropwise trifluoroacetic anhydride. The reaction mixture was stirred for 30 min, pyridine (4.96 mL) was added dropwise, and the reaction mixture was stirred at room temperature overnight The reaction mixture was concentrated under reduced pressure, and the residue was dissolved in ethyl acetate. The solution was washed with 1.0 mol/L hydrochloric acid, dried over anhydrous sodium sulfate, filtered and concentrated. The residue was purified by silica gel column chromatography (solvent; hexane/ethyl acetate=100/0-60/40) to give the title compound (3.25 g)
MS (ESI) m/z; 282 [M+H]$^+$

Reference Example 245

5-difluoromethyl-6-methyl-2-methylsulfanyl[1,3]thiazolo[5,4-d]pyrimidin-7(6H)-one

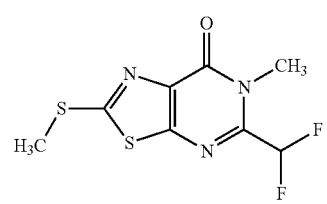 [SMILES: CSc1nc2c(=O)n(C)c(C(F)F)nc2s1]

The compound (1.00 g) obtained in Reference Example 136 was treated by a method similar to that in Reference Example 244 to give the title compound (1.08 g)
MS (ESI) m/z; 264 [M+H]$^+$

Reference Example 246

6-ethyl-2-methylsulfanyl-5-trifluoromethyl[1,3]thiazolo[5,4-d]pyrimidin-7(6H)-one

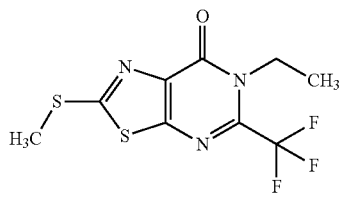 [SMILES: CCn1c(C(F)(F)F)nc2sc(SC)nc2c1=O]

The compound (2.50 g) obtained in Reference Example 137 was treated by a method similar to that in Reference Example 244 to give the title compound (2.83 g)
MS (ESI) m/z; 296 [M+H]$^+$

Reference Example 247

6-(2-methoxyethyl)-2-methylsulfanyl-5-trifluoromethyl[1,3]thiazolo[5,4-d]pyrimidin-7(6H)-one

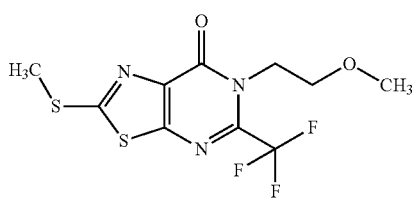

The compound (500 mg) obtained in Reference Example 141 was treated by a method similar to that in Reference Example 244 to give the title compound (570 mg)
MS (ESI) m/z; 326 [M+H]$^+$

Reference Example 248

5-difluoromethyl-6-(2-methoxyethyl)-2-methylsulfanyl[1,3]thiazolo[5,4-d]pyrimidin-7(6H)-one

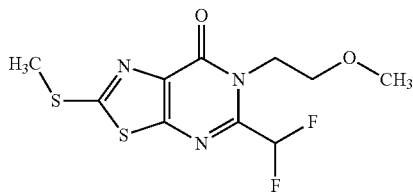

The compound (300 mg) obtained in Reference Example 141 was treated by a method similar to that in Reference Example 244 to give the title compound (260 mg)
MS (ESI) m/z; 308 [M+H]$^+$

Reference Example 249

6-[1-(methoxymethyl)cyclopropyl]-2-methylsulfanyl-5-trifluoromethyl[1,3]thiazolo[5,4-d]pyrimidin-7(6H)-one

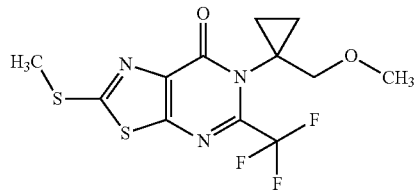

The compound (500 mg) obtained in Reference Example 142 was treated by a method similar to that in Reference Example 244 to give the title compound (270 mg)

MS (ESI) m/z; 352 [M+H]$^+$

Reference Example 250

2-methylsulfanyl-6-(tetrahydro-2H-pyran-4-yl)-5-trifluoromethyl[1,3]thiazolo[5,4-d]pyrimidin-7(6H)-one

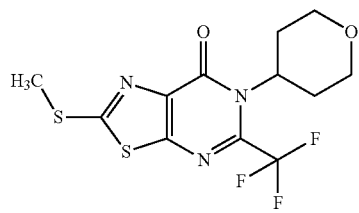

The compound (600 mg) obtained in Reference Example 143 was treated by a method similar to that in Reference Example 244 to give the title compound (497 mg)

MS (ESI) m/z; 352 [M+H]$^+$

Reference Example 251

5-difluoromethyl-2-methylsulfanyl-6-(tetrahydro-2H-pyran-4-yl)[1,3]thiazolo[5,4-d]pyrimidin-7(6H)-one

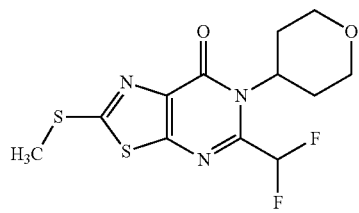 [SMILES: CSc1nc2c(=O)n(C3CCOCC3)c(C(F)F)nc2s1]

The compound (300 mg) obtained in Reference Example 143 was treated by a method similar to that in Reference Example 244 to give the title compound (104 mg)

MS (ESI) m/z; 334 [M+H]$^+$

Reference Example 252

2-methylsulfanyl-6-((R)-tetrahydrofuran-3-yl)-5-trifluoromethyl[1,3]thiazolo[5,4-d]pyrimidin-7(6H)-one

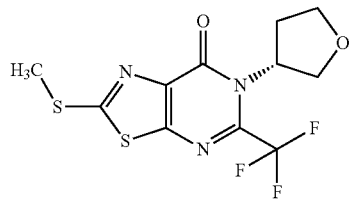 [SMILES: CSc1nc2c(=O)n([C@@H]3CCOC3)c(C(F)(F)F)nc2s1]

The compound (750 mg) obtained in Reference Example 150 was treated by a method similar to that in Reference Example 244 to give the title compound (840 mg)

MS (ESI) m/z; 338 [M+H]$^+$

Reference Example 253

2-methylsulfanyl-6-(oxetan-3-yl)-5-trifluoromethyl[1,3]thiazolo[5,4-d]pyrimidin-7(6H)-one

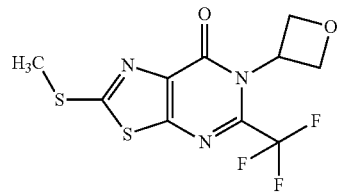 [SMILES: CSc1nc2c(=O)n(C3COC3)c(C(F)(F)F)nc2s1]

The compound (400 mg) obtained in Reference Example 151 was treated by a method similar to that in Reference Example 244 to give the title compound (190 mg)

MS (ESI) m/z; 324 [M+H]$^+$

Reference Example 254

6-(1-methylpiperidin-4-yl)-2-methylsulfanyl-5-trifluoromethyl[1,3]thiazolo[5,4-d]pyrimidin-7(6H)-one

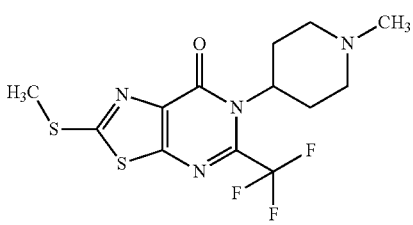

The compound (500 mg) obtained in Reference Example 152 was treated by a method similar to that in Reference Example 244 to give the title compound (600 mg)

MS (ESI) m/z; 365 [M+H]$^+$

Reference Example 255

2-methylsulfanyl-6-(pyrrolidin-1-yl)-5-trifluoromethyl[1,3]thiazolo[5,4-d]pyrimidin-7(6H)-one

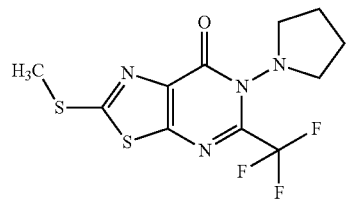 [SMILES: CSc1nc2c(=O)n(N3CCCC3)c(C(F)(F)F)nc2s1]

The compound (850 mg) obtained in Reference Example 154 was treated by a method similar to that in Reference Example 244 to give the title compound (360 mg)

MS (ESI) m/z; 337 [M+H]$^+$

Reference Example 256

2-methylsulfanyl-6-(morpholin-4-yl)-5-trifluoromethyl[1,3]thiazolo[5,4-d]pyrimidin-7(6H)-one

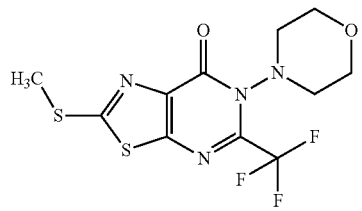 [SMILES: CSc1nc2c(=O)n(N3CCOCC3)c(C(F)(F)F)nc2s1]

The compound (1.10 g) obtained in Reference Example 155 was treated by a method similar to that in Reference Example 244 to give the title compound (560 mg)

MS (ESI) m/z; 353 [M+H]$^+$

Reference Example 257

6-cyclopropyl-2-methylsulfanyl-5-trifluoromethyl[1,3]thiazolo[5,4-d]pyrimidin-7(6H)-one

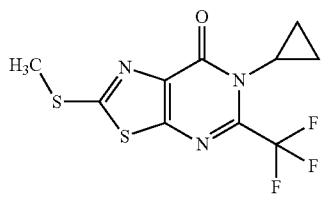 [SMILES: CSc1nc2c(=O)n(C3CC3)c(C(F)(F)F)nc2s1]

The compound (500 mg) obtained in Reference Example 139 was treated by a method similar to that in Reference Example 244 to give the title compound (370 mg)

MS (ESI) m/z; 308 [M+H]$^+$

Reference Example 258

2-methylsulfanyl-6-[(oxetan-3-yl)methyl]-5-trifluoromethyl[1,3]thiazolo[5,4-d]pyrimidin-7(6H)-one

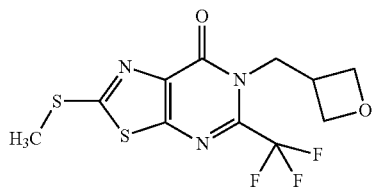 [SMILES: CSc1nc2c(=O)n(CC3COC3)c(C(F)(F)F)nc2s1]

To a solution (20 mL) of 3-nitromethylene-oxetane (1.14 g) in DMF was added 20% palladium hydroxide carbon (50% hydrate, 500 mg), and the reaction mixture was stirred under a hydrogen atmosphere, at room temperature for 8 hr. 20% Palladium hydroxide carbon (50% hydrate, 1.00 g) was added, and the reaction mixture was further stirred at room temperature for 9 hr. The reaction mixture was filtered through diatomaceous earth, and washed with DMF (40 mL). To the filtrate were added 5-amino-2-methylsulfanyl-1,3-thiazole-4-carboxylic acid (1.89 g), N,N-diisopropylethylamine (2.60 mL), EDC hydrochloride (2.85 g) and HOBt monohydrate (2.28 g), and the reaction mixture was stirred at room temperature overnight. To the reaction mixture were added water and chloroform, the mixture was filtered through diatomaceous earth, and the filtrate was extracted with chloroform. The combined organic layer was dried over anhydrous sodium sulfate, filtered and concentrated. The residue was purified by silica gel column chromatography (solvent; hexane/ethyl acetate=70/30-0/100) to give a crude product (461 mg) This was dissolved in methylene chloride (16 mL), triethylamine (2.48 mL) and trifluoroacetic anhydride (1.98 mL) were added, and the reaction mixture was stirred at room temperature overnight. To the reaction mixture was added 15% aqueous citric acid solution, and the mixture was extracted twice with chloroform. The combined organic layer was washed with saturated aqueous sodium hydrogen carbonate solution, dried over anhydrous sodium sulfate, filtered and concentrated The residue was purified by NH silica gel column chromatography (solvent; hexane/ethyl acetate=90/10-50/50) to give the title compound (147 mg)

MS (ESI) m/z; 338 [M+H]$^+$

Reference Example 259

6-[3-(N,N-dimethylamino)propyl]-2-methylsulfanyl-5-trifluoromethyl[1,3]thiazolo[5,4-d]pyrimidin-7(6H)-one

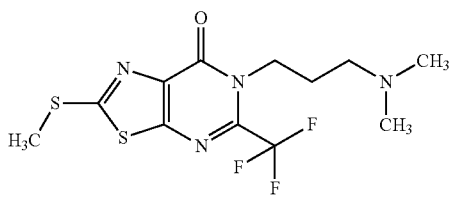

To a solution (8.0 mL) of the compound (330 mg) obtained in Reference Example 153 in methylene chloride were added trifluoroacetic anhydride (300 mg) and pyridine (115 mg) under ice-cooling, and the reaction mixture was stirred at room temperature for 2 hr. Trifluoroacetic anhydride (1.26 g) and triethylamine (1.22 g) were added, and the reaction mixture was stirred at room temperature overnight. Saturated aqueous sodium hydrogen carbonate solution was added to the reaction mixture, and the mixture was extracted twice with chloroform The organic layer was washed with saturated brine, dried over anhydrous sodium sulfate, filtered and concentrated. The residue was purified by NH silica gel column chromatography (solvent; hexane/ethyl acetate=80/20-50/50) to give the title compound (420 mg)

MS (ESI) m/z; 353 [M+H]+

Reference Example 260

6-methyl-2-methylsulfanyl-5-((RS)-tetrahydrofuran-3-yl)[1,3]thiazolo[5,4-d]pyrimidin-7(6H)-one

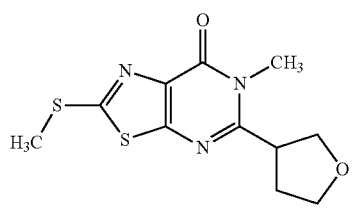 [SMILES: CSc1nc2c(=O)n(C)c(C3CCOC3)nc2s1]

To a solution (2.0 mL) of (RS)-tetrahydrofuran-3-carboxylic acid (400 mg) in methylene chloride were added oxalyl chloride (700 mg) and DMF (one drop) under ice-cooling The reaction mixture was stirred at room temperature for 2 hr, and concentrated. The residue was dissolved in methylene chloride, and added dropwise to a solution (3.0 mL) of the compound (840 mg) obtained in Reference Example 136 and triethylamine (510 mg) in methylene chloride under ice-cooling, and the reaction mixture was stirred at room temperature for 1.5 hr. To the reaction mixture were added water and saturated aqueous sodium hydrogen carbonate solution, and the mixture was extracted twice with chloroform. The organic layer was dried over anhydrous sodium sulfate, filtered and concentrated. To a solution (20 mL) of the obtained crude product in dichloroethane were added triethylamine (5.4 g) and chlorotrimethylsilane (1.9 g), and the reaction mixture was stirred at room temperature for 5.5 hr. Water was added to the reaction mixture, and the mixture was extracted twice with chloroform. The organic layer was dried over anhydrous sodium sulfate, filtered and concentrated. The residue was purified by silica gel column chromatography (solvent; hexane/ethyl acetate=70/30-0/100) to give the title compound (470 mg)

MS (ESI) m/z; 284 [M+H]+

Reference Example 261

6-ethyl-5-(3-fluoropyridin-4-yl)-2-methylsulfanyl[1,3]thiazolo[5,4-d]pyrimidin-7(6H)-one

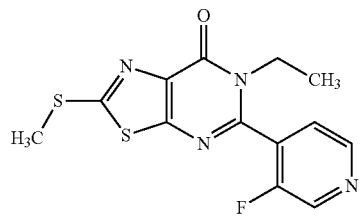 [SMILES: CCn1c(-c2ccncc2F)nc2sc(SC)nc2c1=O]

The compound (500 mg) obtained in Reference Example 137 was treated by a method similar to that in Reference Example 260 to give the title compound (354 mg)

MS (ESI) m/z; 323 [M+H]+

Reference Example 262

6-ethyl-5-(4-fluoropyridin-2-yl)-2-methylsulfanyl[1,3]thiazolo[5,4-d]pyrimidin-7(6H)-one

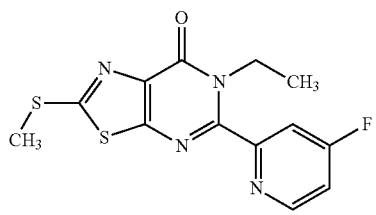 [SMILES: CCn1c(-c2cc(F)ccn2)nc2sc(SC)nc2c1=O]

Reference Example 263

5-(4-chloropyridin-2-yl)-6-ethyl-2-methylsulfanyl[1,3]thiazolo[5,4-d]pyrimidin-7(6H)-one

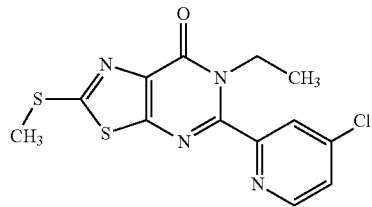 [SMILES: CCn1c(-c2cc(Cl)ccn2)nc2sc(SC)nc2c1=O]

To a solution (26 mL) of 4-fluoropyridine-2-carboxylic acid (650 mg) in methylene chloride were added oxalyl chloride (779 μL) and DMF (one drop) under ice-cooling. The mixture was stirred at room temperature overnight, and concentrated. The residue was dissolved in methylene chloride, and added dropwise to a solution (12 mL) of the compound (500 mg) obtained in Reference Example 137 and triethylamine (641 μL) in methylene chloride under ice-cooling, and the reaction mixture was stirred at room temperature for 3.5 hr. To the reaction mixture were added water and saturated aqueous sodium hydrogen carbonate solution, and the mixture was extracted 4 times with chlo- Reference Example 264

6-methyl-2-methylsulfanyl-5-(pyridin-2-yl)[1,3]thiazolo[5,4-d]pyrimidin-7(6H)-one

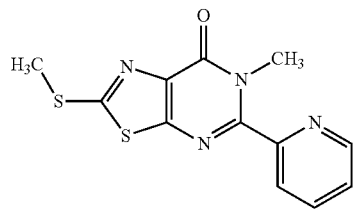 [SMILES: CSc1nc2c(=O)n(C)c(-c3ccccn3)nc2s1]

To a solution (20 mL) of the compound (1.00 g) obtained in Reference Example 136 in DMF were added EDC hydrochloride (1.28 g), HOBt monohydrate (0.98 g), N,N-diisopropylethylamine (0.86 mL) and pyridine-2-carboxylic acid (0.79 g), and the reaction mixture was stirred at room temperature overnight. Water was added to the reaction mixture, and the mixture was extracted three times with ethyl acetate, and the organic layer was dried over anhydrous magnesium sulfate, filtered and concentrated. To the residue was added hexane, and the solid was collected by filtration, and dried to give a solid (1.67 g). To a solution (13 mL) of the obtained solid (0.42 g) in dichloroethane were added triethylamine (2.85 mL) and chlorotrimethylsilane (0.86 mL), and the reaction mixture was stirred at room temperature overnight. Water was added to the reaction mixture, and the mixture was extracted twice with chloroform. The organic layer was dried over anhydrous magnesium sulfate, filtered and concentrated. To the residue was added diethyl ether, and the solid was collected by filtration, and dried to give the title compound (265 mg) m/z; 291 [M+H]$^+$ Reference Example 265

5-difluoromethyl-6-ethyl-2-methylsulfanyl[1,3]thiazolo[5,4-d]pyrimidin-7(6H)-one

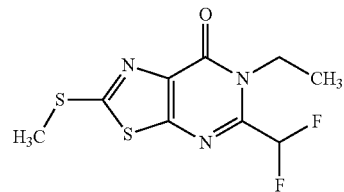 [SMILES: CCn1c(C(F)F)nc2sc(SC)nc2c1=O]

To a solution (300 mL) of the compound (12.9 g) obtained in Reference Example 137 in methylene chloride was added dropwise under ice-cooling difluoroacetic anhydride (46.7 g), and the reaction mixture was stirred for 1 hr. Pyridine (24.1 mL) was added, and the reaction mixture was stirred for 2 hr. The reaction mixture was concentrated and the residue was dissolved in ethyl acetate, and washed with saturated aqueous sodium hydrogen carbonate solution. The organic layer was dried over anhydrous sodium sulfate, filtered and concentrated. The obtained crude product was dissolved in methylene chloride (250 mL), triethylamine (20.9 mL) and chlorotrimethylsilane (6.32 mL) were added, and the reaction mixture was stirred at room temperature for 2 hr. Water was added to the reaction mixture, and the mixture was extracted three times with chloroform, and the extracted organic layer was dried over anhydrous sodium sulfate, filtered and concentrated. The obtained residue was purified by silica gel column chromatography (solvent; hexane/ethyl acetate=70/30-40/60) to give the title compound (12.3 g).

MS (ESI) m/z; 278 [M+H]$^+$

Reference Example 266

5-difluoromethyl-2-methylsulfanyl-6-[(tetrahydro-2H-pyran-4-yl)methyl][1,3]thiazolo[5,4-d]pyrimidin-7(6H)-one

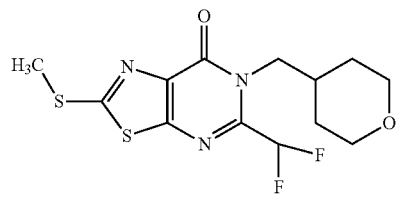 [SMILES: CSc1nc2c(=O)n(CC3CCOCC3)c(C(F)F)nc2s1]

The compound (1.37 g) obtained in Reference Example 145 was treated by a method similar to that in Reference Example 265 to give the title compound (1.05 g).

MS (ESI) m/z; 348 [M+H]$^+$

Reference Example 267

5-(3-fluoropyridin-2-yl)-6-methyl-2-methylsulfanyl[1,3]thiazolo[5,4-d]pyrimidin-7(6H)-one

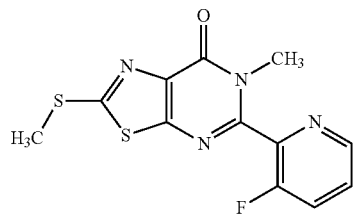 [SMILES: CSc1nc2c(=O)n(C)c(-c3ncccc3F)nc2s1]

To a solution (10 mL) of the compound (484 mg) obtained in Reference Example 136 in DMF were added HATU (2.72 g), N,N-diisopropylethylamine (2.34 mL) and 3-fluoropyridine-2-carboxylic acid (840 mg), and the reaction mixture was stirred at room temperature for 2 hr. HATU (2.72 g), N,N-diisopropylethylamine (2.34 mL) and 3-fluoropyridine-2-carboxylic acid (840 mg) were added, and the reaction mixture was stirred at room temperature for 3 days. Water was added to the reaction mixture, and the mixture was extracted three times with ethyl acetate, and the organic layer was dried over anhydrous magnesium sulfate, filtered and concentrated. To a solution (20 mL) of the obtained crude product in dichloroethane were added triethylamine (6.66 mL) and chlorotrimethylsilane (3.02 mL), and the reaction mixture was stirred at room temperature for 2 hr. Triethylamine (6.66 mL) and chlorotrimethylsilane (3.02 mL) were added, and the reaction mixture was stirred at room temperature for 3 days. Water was added to the reaction mixture, and the mixture was extracted twice with chloroform. The organic layer was dried over anhydrous magnesium sulfate, filtered and concentrated. The residue was purified by silica gel column chromatography (solvent; hexane/ethyl acetate=70/30-0/100) to give the title compound (543 mg)
MS (ESI) m/z; 309 [M+H]$^+$

Reference Example 268

6-methyl-2-methylsulfinyl-5-phenyl[1,3]thiazolo[5,4-d]pyrimidin-7(6H)-one

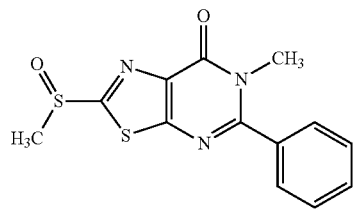 [SMILES: Cn1c(-c2ccccc2)nc2sc(S(C)=O)nc2c1=O]

To a solution (800 mL) of the compound (37.7 g) obtained in Reference Example 195 in methylene chloride was added mCPBA (69-75%, 33.0 g) under ice-cooling, and the reaction mixture was stirred under ice-cooling for 1 hr. To the reaction mixture were added aqueous sodium thiosulfate solution and saturated aqueous sodium hydrogen carbonate solution, and the mixture was extracted three times with chloroform. The organic layer was dried over anhydrous sodium sulfate, filtered and concentrated to give the title compound (39.4 g).
MS (ESI) m/z; 306 [M+H]$^+$

Reference Example 269

6-methyl-2-methylsulfinyl-5-(2,4,6-trifluorophenyl)[1,3]thiazolo[5,4-d]pyrimidin-7(6H)-one

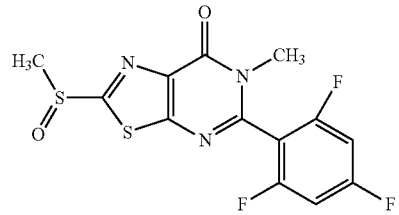 [SMILES: Cn1c(-c2c(F)cc(F)cc2F)nc2sc(S(C)=O)nc2c1=O]

The compound (240 mg) obtained in Reference Example 196 was treated by a method similar to that in Reference Example 268 to give the title compound (252 mg)
MS (ESI) m/z; 360 [M+H]$^+$

Reference Example 270

5-(2,6-difluorophenyl)-6-methyl-2-methylsulfinyl[1,3]thiazolo[5,4-d]pyrimidin-7(6H)-one

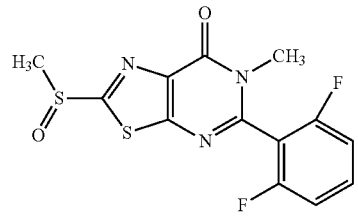

The compound (321 mg) obtained in Reference Example 197 was treated by a method similar to that in Reference Example 268 to give the title compound (329 mg)
MS (ESI) m/z; 342 [M+H]$^+$

Reference Example 271

6-methyl-2-((RS)-methylsulfinyl)-5-((RS)-tetrahydrofuran-2-yl)[1,3]thiazolo[5,4-d]pyrimidin-7(6H)-one

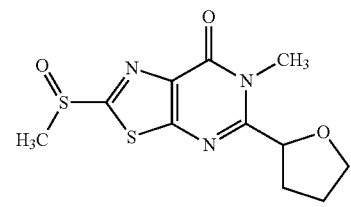 [SMILES: Cn1c(C2CCCO2)nc2sc(S(C)=O)nc2c1=O]

The compound (600 mg) obtained in Reference Example 198 was treated by a method similar to that in Reference Example 268 to give the title compound (550 mg)
MS (ESI) m/z; 300 [M+H]$^+$

Reference Example 272

5-methoxymethyl-2-methylsulfinyl-6-(propan-2-yl)[1,3]thiazolo[5,4-d]pyrimidin-7(6H)-one

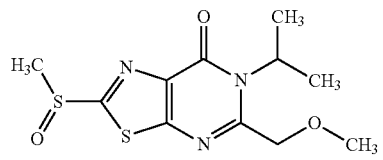

The compound (370 mg) obtained in Reference Example 200 was treated by a method similar to that in Reference Example 268 to give the title compound (376 mg)

MS (ESI) m/z; 302 [M+H]$^+$

Reference Example 273

6-cyclopropyl-5-methoxymethyl-2-methylsulfinyl[1,3]thiazolo[5,4-d]pyrimidin-7(6H)-one

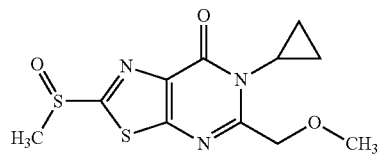 [SMILES: COCc1nc2sc(S(C)=O)nc2c(=O)n1C1CC1]

The compound (772 mg) obtained in Reference Example 201 was treated by a method similar to that in Reference Example 268 to give the title compound (773 mg)

MS (ESI) m/z; 300 [M+H]$^+$

Reference Example 274

5-methyl-2-methylsulfinyl-6-(tetrahydro-2H-pyran-4-yl)[1,3]thiazolo[5,4-d]pyrimidin-7(6H)-one

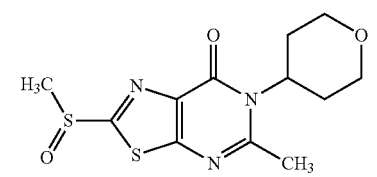 [SMILES: Cc1nc2sc(S(C)=O)nc2c(=O)n1C1CCOCC1]

The compound (400 mg) obtained in Reference Example 202 was treated by a method similar to that in Reference Example 268 to give the title compound (350 mg)

MS (ESI) m/z; 314 [M+H]$^+$

Reference Example 275

6-(2-methoxy-2-methylpropyl)-5-methyl-2-methylsulfinyl[1,3]thiazolo[5,4-d]pyrimidin-7(6H)-one

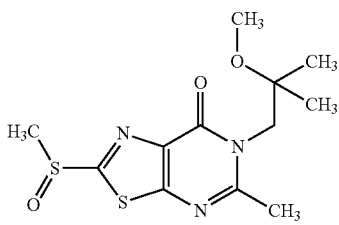 [SMILES: COC(C)(C)Cn1c(C)nc2sc(S(C)=O)nc2c1=O]

The compound (320 mg) obtained in Reference Example 203 was treated by a method similar to that in Reference Example 268 to give the title compound (340 mg)

MS (ESI) m/z; 316 [M+H]$^+$

Reference Example 276

5-(1,1-difluoroethyl)-6-methyl-2-methylsulfinyl[1,3]thiazolo[5,4-d]pyrimidin-7(6H)-one

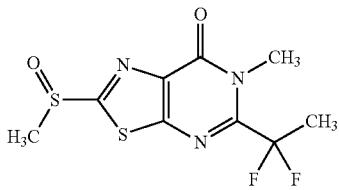 [SMILES: Cn1c(C(C)(F)F)nc2sc(S(C)=O)nc2c1=O]

The compound (490 mg) obtained in Reference Example 204 was treated by a method similar to that in Reference Example 268 to give the title compound (522 mg)

MS (ESI) m/z; 294 [M+H]$^+$

Reference Example 277

5-(1-fluorocyclopropyl)-6-methyl-2-methylsulfinyl[1,3]thiazolo[5,4-d]pyrimidin-7(6H)-one

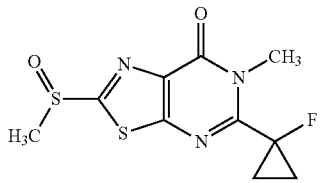 [SMILES: Cn1c(C2(F)CC2)nc2sc(S(C)=O)nc2c1=O]

The compound (350 mg) obtained in Reference Example 205 was treated by a method similar to that in Reference Example 268 to give the title compound (466 mg)

MS (ESI) m/z; 288 [M+H]$^+$

Reference Example 278

5-(1-chlorocyclopropyl)-6-methyl-2-methylsulfinyl[1,3]thiazolo[5,4-d]pyrimidin-7(6H)-one

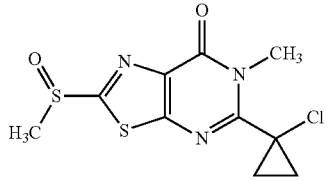 [SMILES: Cn1c(C2(Cl)CC2)nc2sc(S(C)=O)nc2c1=O]

The compound (86 mg) obtained in Reference Example 175 was treated by a method similar to that in Reference Example 268 to give the title compound (92 mg)
MS (ESI) m/z; 304, 306 [M+H]+

Reference Example 279

5-(1,1-difluoropropyl)-6-methyl-2-methylsulfinyl[1,3]thiazolo[5,4-d]pyrimidin-7(6H)-one

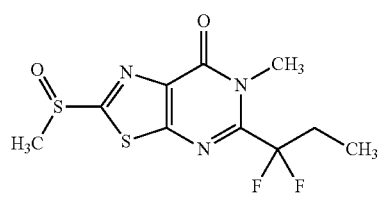 [SMILES: CCC(F)(F)c1nc2sc(S(C)=O)nc2c(=O)n1C]

The compound (240 mg) obtained in Reference Example 207 was treated by a method similar to that in Reference Example 268 to give the title compound (254 mg)
MS (ESI) m/z; 308 [M+H]+

Reference Example 280

5-[difluoro(pyridin-2-yl)methyl]-6-methyl-2-methylsulfinyl[1,3]thiazolo[5,4-d]pyrimidin-7(6H)-one

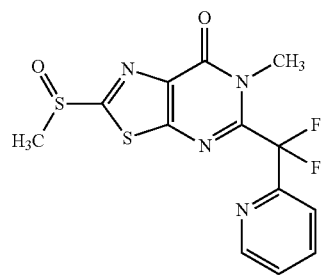 [SMILES: Cn1c(C(F)(F)c2ccccn2)nc2sc(S(C)=O)nc2c1=O]

The compound (770 mg) obtained in Reference Example 208 was treated by a method similar to that in Reference Example 268 to give the title compound (857 mg)
MS (ESI) m/z; 357 [M+H]+

Reference Example 281

6-methyl-2-methylsulfinyl-5-(tetrahydro-2H-pyran-4-yl)[1,3]thiazolo[5,4-d]pyrimidin-7(6H)-one

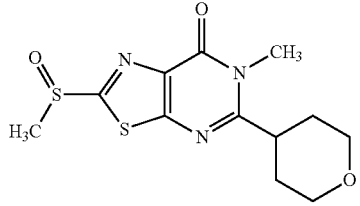

The compound (615 mg) obtained in Reference Example 209 was treated by a method similar to that in Reference Example 268 to give the title compound (651 mg)
MS (ESI) m/z; 314 [M+H]+

Reference Example 282

5-(1,1-difluoro-2-methoxyethyl)-6-methyl-2-methylsulfinyl[1,3]thiazolo[5,4-d]pyrimidin-7(6H)-one

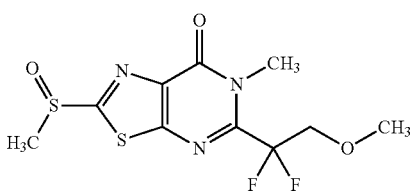 [SMILES: COCC(F)(F)c1nc2sc(S(C)=O)nc2c(=O)n1C]

The compound (1.04 g) obtained in Reference Example 210 was treated by a method similar to that in Reference Example 268 to give the title compound (1.08 g).
MS (ESI) m/z; 324 [M+H]+

Reference Example 283

6-ethyl-2-methylsulfinyl-5-[2-(methylsulfonyl)phenyl][1,3]thiazolo[5,4-d]pyrimidin-7(6H)-one

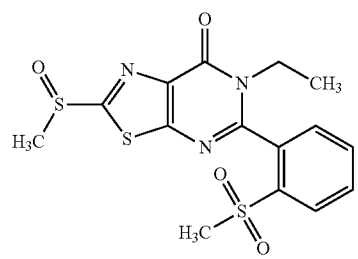 [SMILES: CCn1c(-c2ccccc2S(C)(=O)=O)nc2sc(S(C)=O)nc2c1=O]

The compound (260 mg) obtained in Reference Example 211 was treated by a method similar to that in Reference Example 268 to give the title compound (303 mg)
MS (ESI) m/z; 398 [M+H]+

Reference Example 284

6-ethyl-2-methylsulfinyl-5-(pyrimidin-2-yl)[1,3]thiazolo[5,4-d]pyrimidin-7(6H)-one

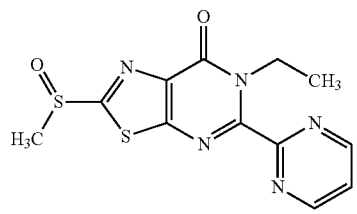 [SMILES: CCn1c(-c2ncccn2)nc2sc(S(C)=O)nc2c1=O]

The compound (500 mg) obtained in Reference Example 212 was treated by a method similar to that in Reference Example 268 to give the title compound (550 mg)

MS (ESI) m/z; 322 [M+H]$^+$

Reference Example 285

6-methyl-5-(5-methyl-1,2,4-oxadiazol-3-yl)-2-methylsulfinyl[1,3]thiazolo[5,4-d]pyrimidin-7(6H)-one

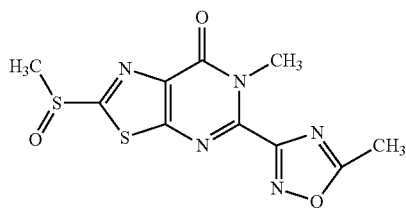

The compound (220 mg) obtained in Reference Example 213 was treated by a method similar to that in Reference Example 268 to give the title compound (217 mg)

MS (ESI) m/z; 312 [M+H]$^+$

Reference Example 286

6-methyl-5-(5-methyl-1,3,4-oxadiazol-2-yl)-2-methylsulfinyl[1,3]thiazolo[5,4-d]pyrimidin-7(6H)-one

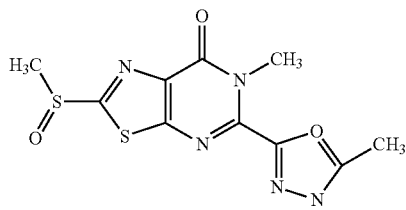

The compound (310 mg) obtained in Reference Example 214 was treated by a method similar to that in Reference Example 268 to give the title compound (283 mg)

MS (ESI) m/z; 312 [M+H]$^+$

Reference Example 287

6-methyl-5-(3-methyl-1,2,4-oxadiazol-5-yl)-2-methylsulfinyl[1,3]thiazolo[5,4-d]pyrimidin-7(6H)-one

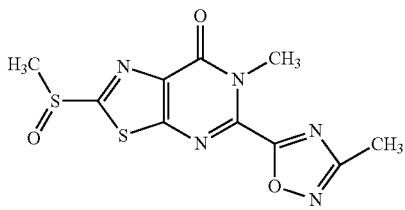

The compound (171 mg) obtained in Reference Example 215 was treated by a method similar to that in Reference Example 268 to give the title compound (166 mg)

MS (ESI) m/z; 312 [M+H]$^+$

Reference Example 288

6-ethyl-5-(3-methyl-1,2,4-oxadiazol-5-yl)-2-methylsulfinyl[1,3]thiazolo[5,4-d]pyrimidin-7(6H)-one

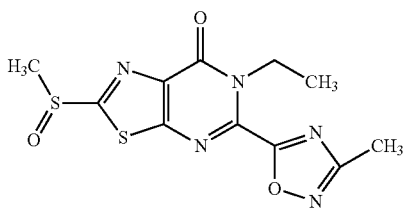

The compound (830 mg) obtained in Reference Example 216 was treated by a method similar to that in Reference Example 268 to give the title compound (830 mg)

MS (ESI) m/z; 326 [M+H]$^+$

Reference Example 289

5-(3-methyl-1,2,4-oxadiazol-5-yl)-2-methylsulfinyl-6-(propan-2-yl)[1,3]thiazolo[5,4-d]pyrimidin-7(6H)-one

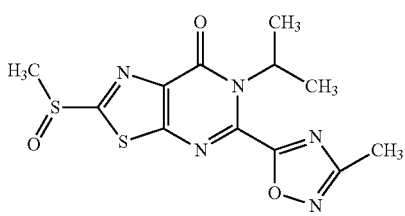

The compound (170 mg) obtained in Reference Example 217 was treated by a method similar to that in Reference Example 268 to give the title compound (213 mg)

MS (ESI) m/z; 340 [M+H]$^+$

Reference Example 290

6-(cyclopropyl)-5-(3-methyl-1,2,4-oxadiazol-5-yl)-2-methylsulfinyl[1,3]thiazolo[5,4-d]pyrimidin-7(6H)-one

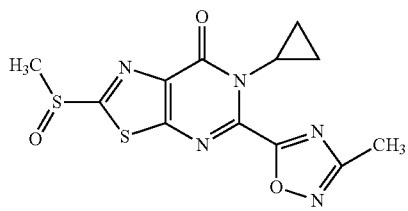

The compound (290 mg) obtained in Reference Example 218 was treated by a method similar to that in Reference Example 268 to give the title compound (240 mg)
MS (ESI) m/z; 338 [M+H]+

Reference Example 291

6-(2,2-difluoroethyl)-5-(3-methyl-1,2,4-oxadiazol-5-yl)-2-methylsulfinyl[1,3]thiazolo[5,4-d]pyrimidin-7(6H)-one

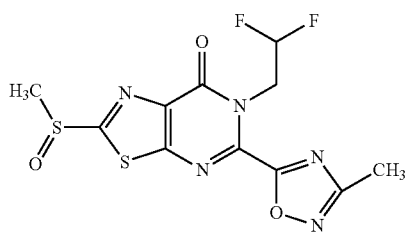

The compound (1.30 g) obtained in Reference Example 219 was treated by a method similar to that in Reference Example 268 to give the title compound (1.25 g).
MS (ESI) m/z; 362 [M+H]+

Reference Example 292

6-(2-methoxyethyl)-5-(3-methyl-1,2,4-oxadiazol-5-yl)-2-methylsulfinyl[1,3]thiazolo[5,4-d]pyrimidin-7(6H)-one

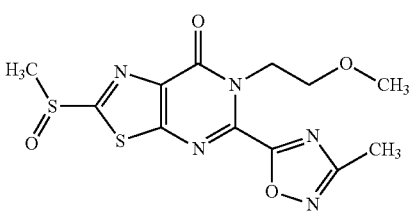

The compound (460 mg) obtained in Reference Example 220 was treated by a method similar to that in Reference Example 268 to give the title compound (420 mg)
MS (ESI) m/z; 356 [M+H]+

Reference Example 293

5-(3-methyl-1,2,4-oxadiazol-5-yl)-2-methylsulfinyl-6-(tetrahydro-2H-pyran-4-yl)[1,3]thiazolo[5,4-d]pyrimidin-7(6H)-one

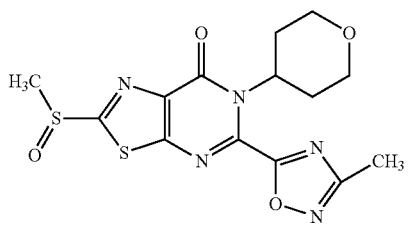

The compound (410 mg) obtained in Reference Example 221 was treated by a method similar to that in Reference Example 268 to give the title compound (320 mg)
MS (ESI) m/z; 382 [M+H]+

Reference Example 294

5-(1,1-difluoro-2-methoxyethyl)-6-ethyl-2-methylsulfinyl[1,3]thiazolo[5,4-d]pyrimidin-7(6H)-one

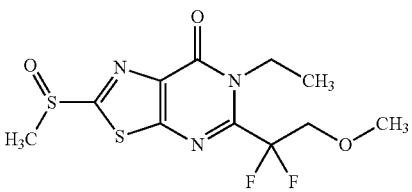 [SMILES: CCn1c(C(F)(F)COC)nc2sc(S(C)=O)nc2c1=O]

The compound (135 mg) obtained in Reference Example 222 was treated by a method similar to that in Reference Example 268 to give the title compound (135 mg)
MS (ESI) m/z; 338 [M+H]+

Reference Example 295

6-(2-methoxyethyl)-5-methyl-2-methylsulfinyl[1,3]thiazolo[5,4-d]pyrimidin-7(6H)-one

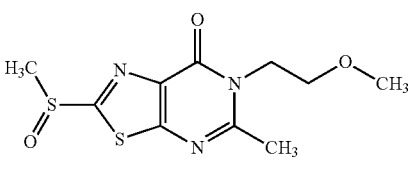

The compound (350 mg) obtained in Reference Example 225 was treated by a method similar to that in Reference Example 268 to give the title compound (300 mg)
MS (ESI) m/z; 288 [M+H]+

Reference Example 296

6-[1-(methoxymethyl)cyclopropyl]-5-methyl-2-methylsulfinyl[1,3]thiazolo[5,4-d]pyrimidin-7(6H)-one

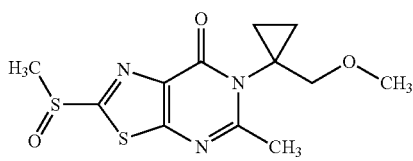

The compound (340 mg) obtained in Reference Example 226 was treated by a method similar to that in Reference Example 268 to give the title compound (340 mg)

MS (ESI) m/z; 314 [M+H]$^+$

Reference Example 297

1-[6-methyl-2-methylsulfinyl-7-oxo-6,7-dihydro[1,3]thiazolo[5,4-d]pyrimidin-5-yl]cyclopentanecarbonitrile

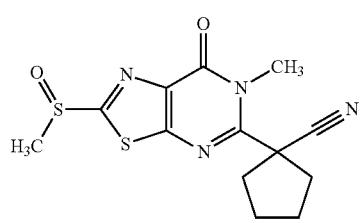 [SMILES: Cn1c(C2(C#N)CCCC2)nc2sc(S(C)=O)nc2c1=O]

The compound (287 mg) obtained in Reference Example 224 was treated by a method similar to that in Reference Example 268 to give the title compound (315 mg)

MS (ESI) m/z; 323 [M+H]$^+$

Reference Example 298

1-[6-methyl-2-methylsulfinyl-7-oxo-6,7-dihydro[1,3]thiazolo[5,4-d]pyrimidin-5-yl]cyclobutanecarbonitrile

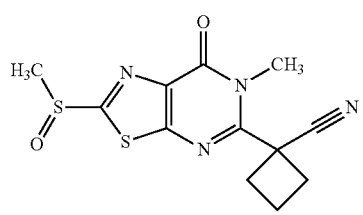 [SMILES: Cn1c(C2(C#N)CCC2)nc2sc(S(C)=O)nc2c1=O]

The compound (253 mg) obtained in Reference Example 227 was treated by a method similar to that in Reference Example 268 to give the title compound (282 mg)

MS (ESI) m/z; 309 [M+H]$^+$

Reference Example 299

5-(2-methoxypropan-2-yl)-6-methyl-2-methylsulfinyl[1,3]thiazolo[5,4-d]pyrimidin-7(6H)-one

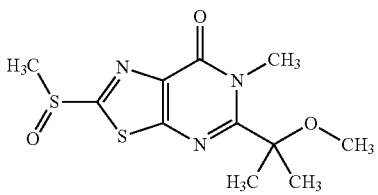 [SMILES: COC(C)(C)c1nc2sc(S(C)=O)nc2c(=O)n1C]

The compound (171 mg) obtained in Reference Example 228 was treated by a method similar to that in Reference Example 268 to give the title compound (130 mg)

MS (ESI) m/z; 302 [M+H]$^+$

Reference Example 300

6-[(3-methyloxetan-3-yl)methyl]-2-methylsulfinyl-5-trifluoromethyl[1,3]thiazolo[5,4-d]pyrimidin-7(6H)-one

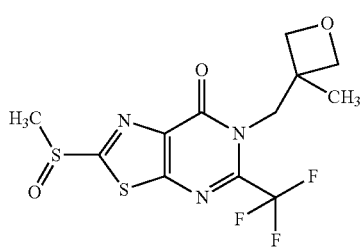 [SMILES: CS(=O)c1nc2c(=O)n(CC3(C)COC3)c(C(F)(F)F)nc2s1]

The compound (430 mg) obtained in Reference Example 229 was treated by a method similar to that in Reference Example 268 to give the title compound (280 mg)

MS (ESI) m/z; 368 [M+H]$^+$

Reference Example 301

5-cyclopropyl-6-methyl-2-methylsulfinyl[1,3]thiazolo[5,4-d]pyrimidin-7(6H)-one

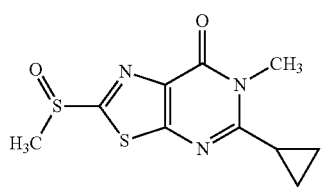 [SMILES: Cn1c(C2CC2)nc2sc(S(C)=O)nc2c1=O]

The compound (3.58 g) obtained in Reference Example 230 was treated by a method similar to that in Reference Example 268 to give the title compound (3.19 g).

MS (ESI) m/z; 270 [M+H]$^+$

Reference Example 302

5-methoxymethyl-6-methyl-2-methylsulfinyl[1,3]thiazolo[5,4-d]pyrimidin-7(6H)-one

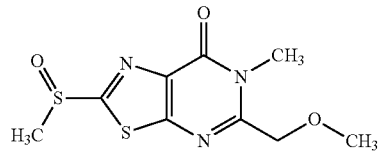

The compound (250 mg) obtained in Reference Example 231 was treated by a method similar to that in Reference Example 268 to give the title compound (249 mg)

MS (ESI) m/z; 274 [M+H]$^+$

Reference Example 303

5-(2-fluoropropan-2-yl)-6-methyl-2-methylsulfinyl[1,3]thiazolo[5,4-d]pyrimidin-7(6H)-one

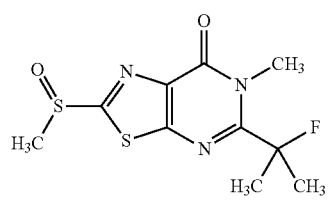

The compound (220 mg) obtained in Reference Example 223 was treated by a method similar to that in Reference Example 268 to give the title compound (167 mg)

MS (ESI) m/z; 290 [M+H]$^+$

Reference Example 304

5-ethyl-6-methyl-2-methylsulfinyl[1,3]thiazolo[5,4-d]pyrimidin-7(6H)-one

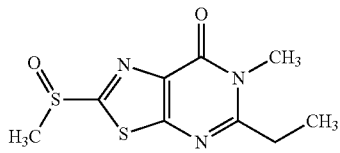

The compound (600 mg) obtained in Reference Example 232 was treated by a method similar to that in Reference Example 268 to give the title compound (594 mg)

MS (ESI) m/z; 258 [M+H]$^+$

Reference Example 305

5,6-dimethyl-2-methylsulfinyl[1,3]thiazolo[5,4-d]pyrimidin-7(6H)-one

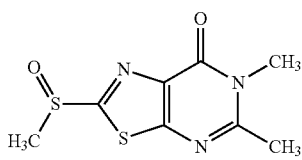

The compound (834 mg) obtained in Reference Example 233 was treated by a method similar to that in Reference Example 268 to give the title compound (728 mg)

MS (ESI) m/z; 244 [M+H]$^+$

Reference Example 306

5,6-diethyl-2-methylsulfinyl[1,3]thiazolo[5,4-d]pyrimidin-7(6H)-one

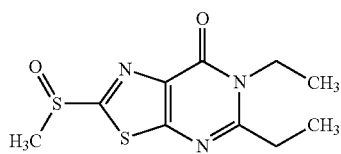 [SMILES: CCc1nc2sc(S(C)=O)nc2c(=O)n1CC]

The compound (773 mg) obtained in Reference Example 234 was treated by a method similar to that in Reference Example 268 to give the title compound (733 mg)

MS (ESI) m/z; 272 [M+H]$^+$

Reference Example 307

6-cyclopropyl-5-methyl-2-methylsulfinyl[1,3]thiazolo[5,4-d]pyrimidin-7(6H)-one

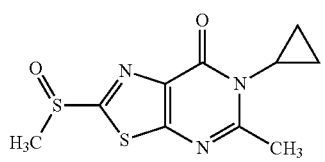 [SMILES: Cc1nc2sc(S(C)=O)nc2c(=O)n1C1CC1]

The compound (12.0 g) obtained in Reference Example 235 was treated by a method similar to that in Reference Example 268 to give the title compound (11.0 g).

MS (ESI) m/z; 270 [M+H]$^+$

Reference Example 308

6-cyclopentyl-2-methylsulfinyl[1,3]thiazolo[5,4-d]pyrimidin-7(6H)-one

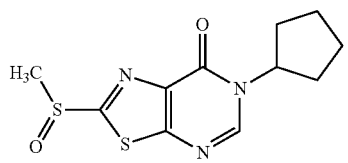 [SMILES: CS(=O)c1nc2c(=O)n(C3CCCC3)cnc2s1]

The compound (360 mg) obtained in Reference Example 236 was treated by a method similar to that in Reference Example 268 to give the title compound (400 mg)

MS (ESI) m/z; 284 [M+H]+

Reference Example 309

6-methyl-2-methylsulfinyl-5-trifluoromethyl[1,3]thiazolo[5,4-d]pyrimidin-7(6H)-one

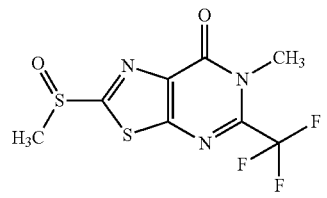 [SMILES: Cn1c(C(F)(F)F)nc2sc(S(C)=O)nc2c1=O]

The compound (3.25 g) obtained in Reference Example 244 was treated by a method similar to that in Reference Example 268 to give the title compound (2.30 g)

MS (ESI) m/z; 298 [M+H]+

Reference Example 310

5-difluoromethyl-6-methyl-2-methylsulfinyl[1,3]thiazolo[5,4-d]pyrimidin-7(6H)-one

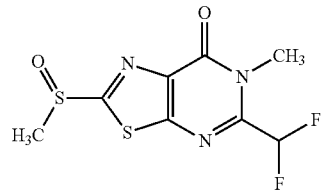 [SMILES: Cn1c(C(F)F)nc2sc(S(C)=O)nc2c1=O]

The compound (1.08 g) obtained in Reference Example 245 was treated by a method similar to that in Reference Example 268 to give the title compound (1.15 g).

MS (ESI) m/z; 280 [M+H]+

Reference Example 311

6-ethyl-2-methylsulfinyl-5-trifluoromethyl[1,3]thiazolo[5,4-d]pyrimidin-7(6H)-one

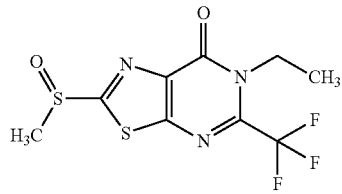 [SMILES: CCn1c(C(F)(F)F)nc2sc(S(C)=O)nc2c1=O]

The compound (1.43 g) obtained in Reference Example 246 was treated by a method similar to that in Reference Example 268 to give the title compound (1.45 g).

MS (ESI) m/z; 312 [M+H]+

Reference Example 312

6-(2-methoxyethyl)-2-methylsulfinyl-5-trifluoromethyl[1,3]thiazolo[5,4-d]pyrimidin-7(6H)-one

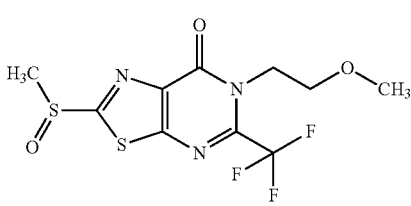 [SMILES: COCCn1c(C(F)(F)F)nc2sc(S(C)=O)nc2c1=O]

The compound (560 mg) obtained in Reference Example 247 was treated by a method similar to that in Reference Example 268 to give the title compound (530 mg)

MS (ESI) m/z; 342 [M+H]+

Reference Example 313

5-difluoromethyl-6-(2-methoxyethyl)-2-methylsulfinyl[1,3]thiazolo[5,4-d]pyrimidin-7(6H)-one

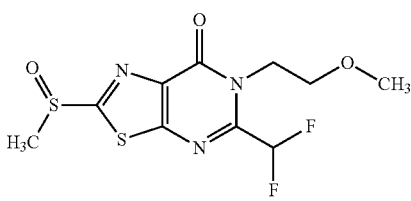

The compound (250 mg) obtained in Reference Example 248 was treated by a method similar to that in Reference Example 268 to give the title compound (276 mg)

MS (ESI) m/z; 324 [M+H]+

Reference Example 314

6-[1-(methoxymethyl)cyclopropyl]-2-methylsulfinyl-5-trifluoromethyl[1,3]thiazolo[5,4-d]pyrimidin-7(6H)-one

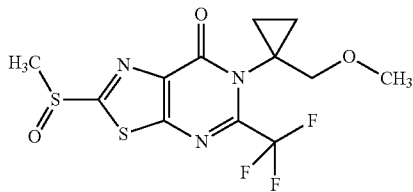 [SMILES: COCC1(n2c(C(F)(F)F)nc3sc(S(C)=O)nc3c2=O)CC1]

The compound (270 mg) obtained in Reference Example 249 was treated by a method similar to that in Reference Example 268 to give the title compound (220 mg)

MS (ESI) m/z; 368 [M+H]$^+$

Reference Example 315

2-methylsulfinyl-6-(tetrahydro-2H-pyran-4-yl)-5-trifluoromethyl[1,3]thiazolo[5,4-d]pyrimidin-7(6H)-one

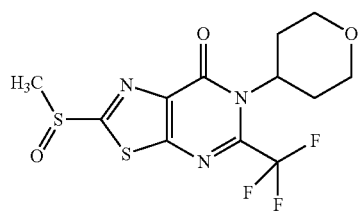 [SMILES: CS(=O)c1nc2c(=O)n(C3CCOCC3)c(C(F)(F)F)nc2s1]

The compound (894 mg) obtained in Reference Example 250 was treated by a method similar to that in Reference Example 268 to give the title compound (935 mg)

MS (ESI) m/z; 368 [M+H]$^+$

Reference Example 316

5-difluoromethyl-2-methylsulfinyl-6-(tetrahydro-2H-pyran-4-yl)[1,3]thiazolo[5,4-d]pyrimidin-7(6H)-one

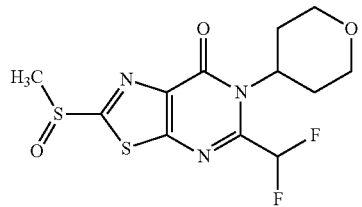 [SMILES: CS(=O)c1nc2c(=O)n(C3CCOCC3)c(C(F)F)nc2s1]

The compound (170 mg) obtained in Reference Example 251 was treated by a method similar to that in Reference Example 268 to give the title compound (182 mg)

MS (ESI) m/z; 350 [M+H]$^+$

Reference Example 317

2-((RS)-methylsulfinyl)-6-((R)-tetrahydrofuran-3-yl)-5-trifluoromethyl[1,3]thiazolo[5,4-d]pyrimidin-7(6H)-one

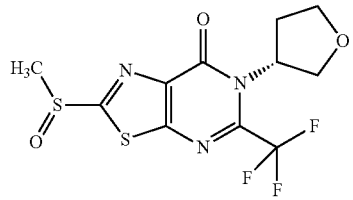 [SMILES: CS(=O)c1nc2c(=O)n([C@@H]3CCOC3)c(C(F)(F)F)nc2s1]

The compound (840 mg) obtained in Reference Example 252 was treated by a method similar to that in Reference Example 268 to give the title compound (780 mg)

MS (ESI) m/z; 354 [M+H]$^+$

Reference Example 318

2-methylsulfinyl-6-(oxetan-3-yl)-5-trifluoromethyl[1,3]thiazolo[5,4-d]pyrimidin-7(6H)-one

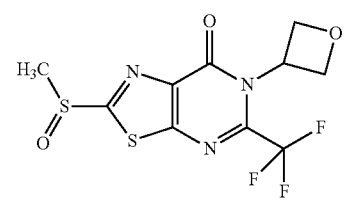 [SMILES: CS(=O)c1nc2c(=O)n(C3COC3)c(C(F)(F)F)nc2s1]

The compound (390 mg) obtained in Reference Example 253 was treated by a method similar to that in Reference Example 268 to give the title compound (260 mg)

MS (ESI) m/z; 340 [M+H]$^+$

Reference Example 319

2-methylsulfinyl-6-(pyrrolidin-1-yl)-5-trifluoromethyl[1,3]thiazolo[5,4-d]pyrimidin-7(6H)-one

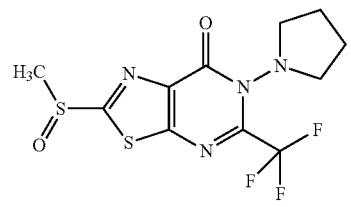 [SMILES: CS(=O)c1nc2c(=O)n(N3CCCC3)c(C(F)(F)F)nc2s1]

The compound (330 mg) obtained in Reference Example 255 was treated by a method similar to that in Reference Example 268 to give the title compound (280 mg)

MS (ESI) m/z; 353 [M+H]$^+$

Reference Example 320

2-methylsulfinyl-6-(morpholin-4-yl)-5-trifluoromethyl[1,3]thiazolo[5,4-d]pyrimidin-7(6H)-one

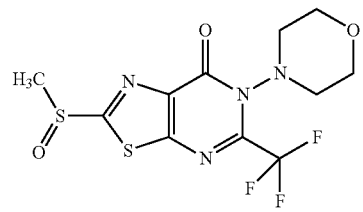 [SMILES: CS(=O)c1nc2c(=O)n(N3CCOCC3)c(C(F)(F)F)nc2s1]

The compound (560 mg) obtained in Reference Example 256 was treated by a method similar to that in Reference Example 268 to give the title compound (580 mg)

MS (ESI) m/z; 369 [M+H]$^+$

Reference Example 321

2-methylsulfinyl-6-[(oxetan-3-yl)methyl]-5-trifluoromethyl[1,3]thiazolo[5,4-d]pyrimidin-7(6H)-one

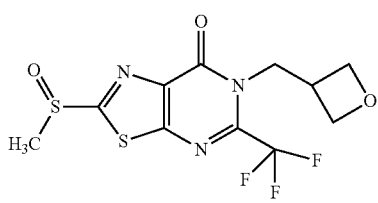 [SMILES: CS(=O)c1nc2c(=O)n(CC3COC3)c(C(F)(F)F)nc2s1]

The compound (160 mg) obtained in Reference Example 258 was treated by a method similar to that in Reference Example 268 to give the title compound (179 mg)

MS (ESI) m/z; 354 [M+H]$^+$

Reference Example 322

6-methyl-2-((RS)-methylsulfinyl)-5-((RS)-tetrahydrofuran-3-yl)[1,3]thiazolo[5,4-d]pyrimidin-7(6H)-one

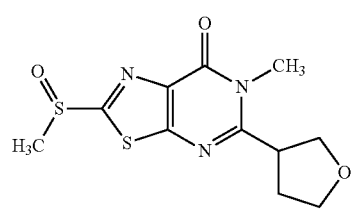 [SMILES: Cn1c(C2CCOC2)nc2sc(S(C)=O)nc2c1=O]

The compound (450 mg) obtained in Reference Example 260 was treated by a method similar to that in Reference Example 268 to give the title compound (440 mg)

MS (ESI) m/z; 300 [M+H]$^+$

Reference Example 323

6-ethyl-5-(3-fluoropyridin-4-yl)-2-methylsulfinyl[1,3]thiazolo[5,4-d]pyrimidin-7(6H)-one

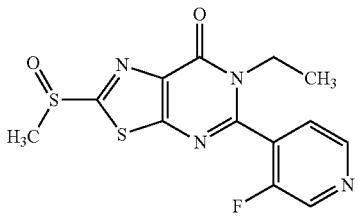 [SMILES: CCn1c(-c2ccncc2F)nc2sc(S(C)=O)nc2c1=O]

The compound (340 mg) obtained in Reference Example 261 was treated by a method similar to that in Reference Example 268 to give the title compound (418 mg)

MS (ESI) m/z; 339 [M+H]$^+$

Reference Example 324

6-ethyl-5-(4-fluoropyridin-2-yl)-2-methylsulfinyl[1,3]thiazolo[5,4-d]pyrimidin-7(6H)-one

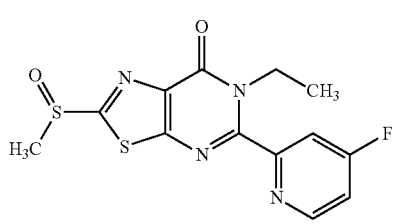 [SMILES: CCn1c(-c2cc(F)ccn2)nc2sc(S(C)=O)nc2c1=O]

The compound (380 mg) obtained in Reference Example 262 was treated by a method similar to that in Reference Example 268 to give the title compound (400 mg)

MS (ESI) m/z; 339 [M+H]$^+$

Reference Example 325

5-(4-chloropyridin-2-yl)-6-ethyl-2-methylsulfinyl[1,3]thiazolo[5,4-d]pyrimidin-7(6H)-one

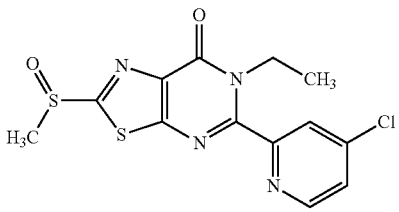 [SMILES: CCn1c(-c2cc(Cl)ccn2)nc2sc(S(C)=O)nc2c1=O]

The compound (130 mg) obtained in Reference Example 263 was treated by a method similar to that in Reference Example 268 to give the title compound (140 mg)

MS (ESI) m/z; 355, 357 [M+H]$^+$

Reference Example 326

6-methyl-2-methylsulfinyl-5-(pyridin-2-yl)[1,3]thi-azolo[5,4-d]pyrimidin-7(6H)-one

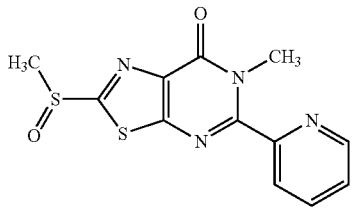 [SMILES: Cn1c(-c2ccccn2)nc2sc(S(C)=O)nc2c1=O]

The compound (260 mg) obtained in Reference Example 264 is was treated by a method similar to that in Reference Example 268 to give the title compound (170 mg)

MS (ESI) m/z; 307 [M+H]$^+$

Reference Example 327

5-difluoromethyl-6-ethyl-2-methylsulfinyl[1,3]thi-azolo[5,4-d]pyrimidin-7(6H)-one

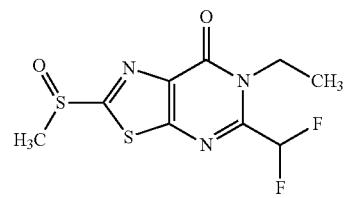 [SMILES: CCn1c(C(F)F)nc2sc(S(C)=O)nc2c1=O]

The compound (960 mg) obtained in Reference Example 265 was treated by a method similar to that in Reference Example 268 to give the title compound (878 mg)

MS (ESI) m/z; 294 [M+H]$^+$

Reference Example 328

5-difluoromethyl-2-methylsulfinyl-6-[(tetrahydro-2H-pyran-4-yl)methyl][1,3]thiazolo[5,4-d]pyrimi-din-7(6H)-one

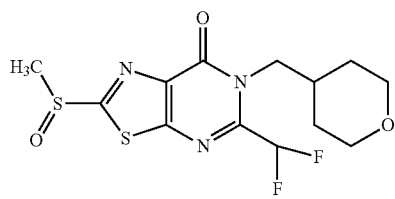 [SMILES: CS(=O)c1nc2c(=O)n(CC3CCOCC3)c(C(F)F)nc2s1]

The compound (1.00 g) obtained in Reference Example 266 was treated by a method similar to that in Reference Example 268 to give the title compound (1.05 g).

MS (ESI) m/z; 364 [M+H]$^+$

Reference Example 329

5-(3-fluoropyridin-2-yl)-6-methyl-2-methylsulfinyl [1,3]thiazolo[5,4-d]pyrimidin-7(6H)-one

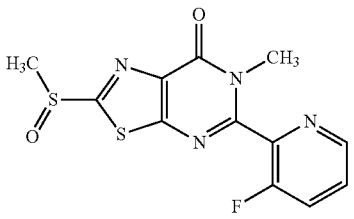 [SMILES: Cn1c(-c2ncccc2F)nc2sc(S(C)=O)nc2c1=O]

The compound (200 mg) obtained in Reference Example 267 was treated by a method similar to that in Reference Example 268 to give the title compound (214 mg)

MS (ESI) m/z; 325 [M+H]$^+$

Reference Example 330

6-ethyl-2-methylsulfinyl-5-(pyridin-2-yl)[1,3]thi-azolo[5,4-d]pyrimidin-7(6H)-one

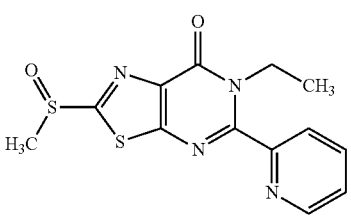 [SMILES: CCn1c(-c2ccccn2)nc2sc(S(C)=O)nc2c1=O]

To a solution (12 mL) of the compound (630 mg) obtained in Reference Example 199 in methylene chloride was added trifluoroacetic acid (337 µL) under ice-cooling, and the reaction mixture was stirred at the same temperature for 10 min. Under ice-cooling, mCPBA (69-75%, 551 mg) was added, and the reaction mixture was stirred at room temperature overnight. After confirmation of the completion of the reaction, aqueous sodium thiosulfate solution and saturated aqueous sodium hydrogen carbonate solution were added to the reaction mixture, and the mixture was extracted three times with methylene chloride. The organic layer was dried over anhydrous sodium sulfate, filtered and concentrated to give the title compound (674 mg)

MS (ESI) m/z; 321 [M+H]$^+$

Reference Example 331

6-[3-(N,N-dimethylamino)propyl]-2-methylsulfinyl-5-trifluoromethyl[1,3]thiazolo[5,4-d]pyrimidin-7(6H)-one

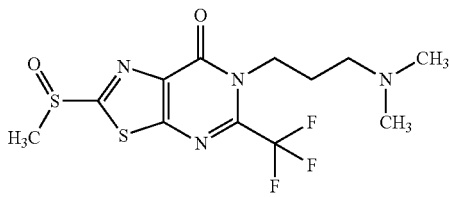 [SMILES: CN(C)CCCn1c(C(F)(F)F)nc2sc(S(C)=O)nc2c1=O]

The compound (420 mg) obtained in Reference Example 259 was treated by a method similar to that in Reference Example 330 to give the title compound (190 mg)
MS (ESI) m/z; 369 [M+H]$^+$

Reference Example 332

6-(1-methylpiperidin-4-yl)-2-methylsulfinyl-5-trifluoromethyl[1,3]thiazolo[5,4-d]pyrimidin-7(6H)-one

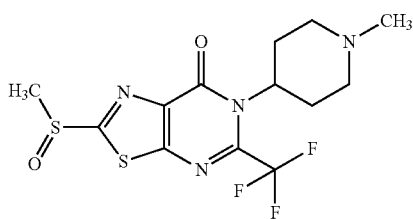

To a solution (5.0 mL) of the compound (500 mg) obtained in Reference Example 254 in methanol was added hydrogen chloride (2 mol/L ethanol solution), and the reaction mixture was stirred at room temperature for 30 min. The solvent was evaporated under reduced pressure. To a solution (5.0 mL) of the residue in methanol was added an aqueous solution (15 mL) of ozone (2.55 g), and the reaction mixture was stirred at room temperature for 2 hr, and stirred with heating at 50° C. for 1 hr. The reaction mixture was cooled to room temperature, and aqueous potassium carbonate solution was added to the reaction mixture, and the mixture was extracted 4 times with chloroform. The organic layer was dried over anhydrous sodium sulfate, filtered and concentrated to give the title compound (220 mg)
MS (ESI) m/z; 381 [M+H]$^+$

Reference Example 333

6-methyl-2-methylsulfonyl-5-propyl[1,3]thiazolo[5,4-d]pyrimidin-7(6H)-one

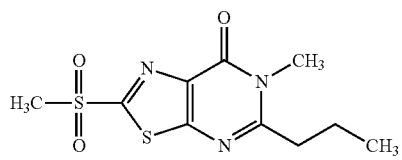 [SMILES: CCCc1nc2sc(S(C)(=O)=O)nc2c(=O)n1C]

To a solution (8.0 mL) of the compound (400 mg) obtained in Reference Example 237 in methylene chloride was added mCPBA (69-75%, 1.04 g) under ice-cooling, and the reaction mixture was stirred at room temperature for 6 hr. To the reaction mixture were added aqueous sodium thiosulfate solution and saturated aqueous sodium hydrogen carbonate solution, and the mixture was extracted with chloroform. The organic layer was dried over anhydrous sodium sulfate, filtered and concentrated. The residue was purified by silica gel column chromatography (solvent; hexane/ethyl acetate=70/30-0/100) to give the title compound (495 mg)
MS (ESI) m/z; 288 [M+H]$^+$

Reference Example 334

6-methyl-2-methylsulfonyl-5-(propan-2-yl)[1,3]thiazolo[5,4-d]pyrimidin-7(6H)-one

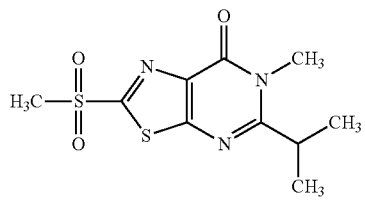

The compound (2.00 g) obtained in Reference Example 238 was treated by a method similar to that in Reference Example 333 to give the title compound (1.96 g).
MS (ESI) m/z; 288 [M+H]$^+$

Reference Example 335

6-ethyl-5-methyl-2-methylsulfonyl[1,3]thiazolo[5,4-d]pyrimidin-7(6H)-one

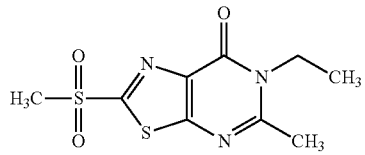

The compound (480 mg) obtained in Reference Example 239 was treated by a method similar to that in Reference Example 333 to give the title compound (520 mg)
MS (ESI) m/z; 274 [M+H]$^+$

Reference Example 336

5-methyl-2-methylsulfonyl-6-(propan-2-yl)[1,3]thiazolo[5,4-d]pyrimidin-7(6H)-one

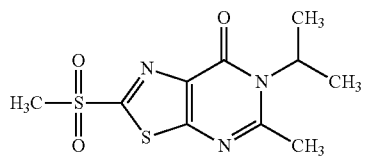

The compound (380 mg) obtained in Reference Example 240 was treated by a method similar to that in Reference Example 333 to give the title compound (395 mg)

MS (ESI) m/z; 288 [M+H]+

Reference Example 337

6-cyclopentyl-5-methyl-2-methylsulfonyl[1,3]thiazolo[5,4-d]pyrimidin-7(6H)-one

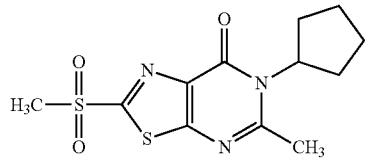

The compound (325 mg) obtained in Reference Example 241 was treated by a method similar to that in Reference Example 333 to give the title compound (285 mg)

MS (ESI) m/z; 314 [M+H]+

Reference Example 338

5-methyl-2-methylsulfonyl-6-(2,2,2-trifluoroethyl)[1,3]thiazolo[5,4-d]pyrimidin-7(6H)-one

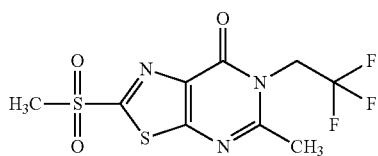 [SMILES: Cc1nc2sc(S(C)(=O)=O)nc2c(=O)n1CC(F)(F)F]

The compound (190 mg) obtained in Reference Example 242 was treated by a method similar to that in Reference Example 333 to give the title compound (210 mg)

MS (ESI) m/z; 328 [M+H]+

Reference Example 339

5-methyl-2-methylsulfonyl-6-phenyl[1,3]thiazolo[5,4-d]pyrimidin-7(6H)-one

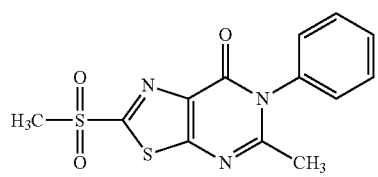 [SMILES: Cc1nc2sc(S(C)(=O)=O)nc2c(=O)n1-c1ccccc1]

The compound (190 mg) obtained in Reference Example 243 was treated by a method similar to that in Reference Example 333 to give the title compound (215 mg)

MS (ESI) m/z; 322 [M+H]+

Reference Example 340

6-cyclopropyl-2-methylsulfonyl-5-trifluoromethyl[1,3]thiazolo[5,4-d]pyrimidin-7(6H)-one

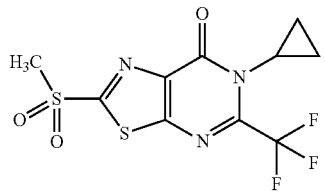 [SMILES: CS(=O)(=O)c1nc2c(=O)n(C3CC3)c(C(F)(F)F)nc2s1]

The compound (370 mg) obtained in Reference Example 257 was treated by a method similar to that in Reference Example 333 to give the title compound (320 mg)

MS (ESI) m/z; 340 [M+H]+

Reference Example 341

(R)-N-benzylpyrrolidine-2-carboxamide hydrochloride

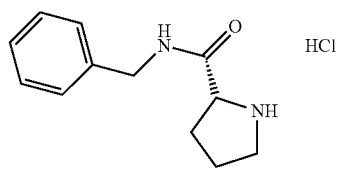

To a solution (40 mL) of N-(tert-butoxycarbonyl)-D-proline (4.0 g) in DMF were added benzylamine (2.0 g), EDC hydrochloride (5.4 g), HOBt monohydrate (4.3 g) and diisopropylethylamine (3.6 g), and the reaction mixture was stirred at room temperature for 1 hr. After confirmation of the completion of the reaction, water (200 mL) were added to the reaction mixture, and the mixture was extracted twice with ethyl acetate. The organic layer was washed once with water, dried over anhydrous magnesium sulfate, filtered and concentrated. The residue was purified by silica gel column chromatography (solvent; hexane/ethyl acetate=80/20-50/50). The obtained product was dissolved in methanol (100 mL), hydrogen chloride (4.0 mol/L 1,4-dioxane solution, 50 mL) was added, and the reaction mixture was stirred at room temperature for 2 hr. After confirmation of the completion of the reaction, the solvent was evaporated, and ethyl acetate was added to the residue, and the solid was collected by filtration to give the title compound (3.8 g).

MS (ESI) m/z; 205 [M+H]+

Reference Example 342

5-[(2-chloroacetyl)amino]-N-methyl-2-methylsulfanyl-1,3-thiazole-4-carboxamide

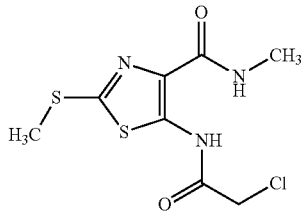

The compound (3.00 g) obtained in Reference Example 136 was treated by a method similar to that in Reference Example 156 to give the title compound (2.95 g).

MS (ESI) m/z; 280, 282 [M+H]$^+$

Reference Example 343

5-[(2-chloroacetyl)amino]-N-ethyl-2-methylsulfanyl-1,3-thiazole-4-carboxamide

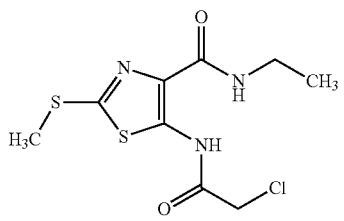 [SMILES: CCNC(=O)c1nc(SC)sc1NC(=O)CCl]

The compound (4.00 g) obtained in Reference Example 137 was treated by a method similar to that in Reference Example 156 to give the title compound (5.62 g).

MS (ESI) m/z; 294, 296 [M+H]$^+$

Reference Example 344

5-[(2-chloroacetyl)amino]-2-methylsulfanyl-N-(propan-2-yl)-1,3-thiazole-4-carboxamide

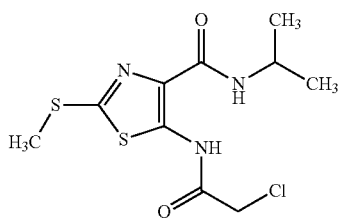 [SMILES: CSc1nc(C(=O)NC(C)C)c(NC(=O)CCl)s1]

The compound (4.00 g) obtained in Reference Example 138 was treated by a method similar to that in Reference Example 156 to give the title compound (3.54 g).

MS (ESI) m/z; 308, 310 [M+H]$^+$

Reference Example 345

5-chloromethyl-6-methyl-2-methylsulfanyl[1,3]thiazolo[5,4-d]pyrimidin-7(6H)-one

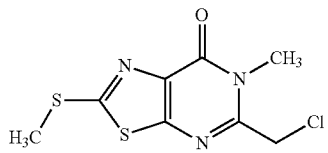

The compound (1.69 g) obtained in Reference Example 342 was treated by a method similar to that in Reference Example 195 to give the title compound (1.00 g).

MS (ESI) m/z; 262, 264 [M+H]$^+$

Reference Example 346

5-chloromethyl-6-ethyl-2-methylsulfanyl[1,3]thiazolo[5,4-d]pyrimidin-7(6H)-one

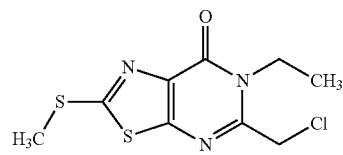 [SMILES: CCn1c(CCl)nc2sc(SC)nc2c1=O]

The compound (5.62 g) obtained in Reference Example 343 was treated by a method similar to that in Reference Example 195 to give the title compound (4.07 g)

MS (ESI) m/z; 276, 278 [M+H]$^+$

Reference Example 347

5-chloromethyl-2-methylsulfanyl-6-(propan-2-yl)[1,3]thiazolo[5,4-d]pyrimidin-7(6H)-one

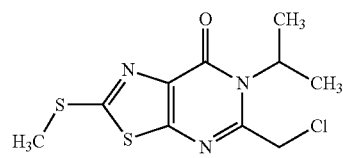 [SMILES: CSc1nc2c(=O)n(C(C)C)c(CCl)nc2s1]

The compound (4.00 g) obtained in Reference Example 344 was treated by a method similar to that in Reference Example 195 to give the title compound (250 mg)

MS (ESI) m/z; 290, 292 [M+H]$^+$

Reference Example 348

5-chloromethyl-6-methyl-2-methylsulfinyl[1,3]thi-azolo[5,4-d]pyrimidin-7(6H)-one

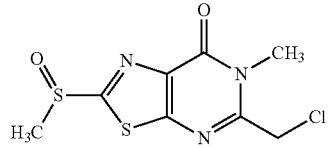 [SMILES: Cn1c(CCl)nc2sc(S(C)=O)nc2c1=O]

The compound (121 mg) obtained in Reference Example 345 was treated by a method similar to that in Reference Example 268 to give the title compound (94 mg)

MS (ESI) m/z; 278, 280 [M+H]+

Reference Example 349

5-chloromethyl-6-ethyl-2-methylsulfinyl[1,3]thi-azolo[5,4-d]pyrimidin-7(6H)-one

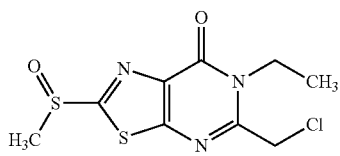 [SMILES: CCn1c(CCl)nc2sc(S(C)=O)nc2c1=O]

The compound (4.07 g) obtained in Reference Example 346 was treated by a method similar to that in Reference Example 268 to give the title compound (4.26 g)

MS (ESI) m/z; 292, 294 [M+H]+

Reference Example 350

5-chloromethyl-2-methylsulfinyl-6-(propan-2-yl)[1,3]thiazolo[5,4-d]pyrimidin-7(6H)-one

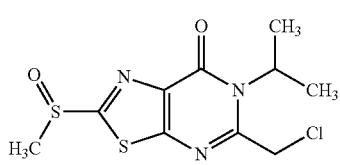 [SMILES: CC(C)n1c(CCl)nc2sc(S(C)=O)nc2c1=O]

The compound (250 mg) obtained in Reference Example 347 was treated by a method similar to that in Reference Example 268 to give the title compound (252 mg)

MS (ESI) m/z; 306, 308 [M+H]+

Reference Example 351

6-methyl-2-methylsulfinyl-5-[(morpholin-4-yl)methyl][1,3]thiazolo[5,4-d]pyrimidin-7(6H)-one

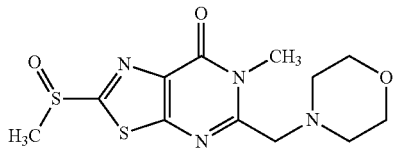 [SMILES: Cn1c(CN2CCOCC2)nc2sc(S(C)=O)nc2c1=O]

To a solution (30 mL) of the compound (600 mg) obtained in Reference Example 348 in acetonitrile were added potassium carbonate (600 mg), potassium iodide (430 mg) and morpholine (290 μL), and the reaction mixture was stirred at 80° C. for 2 hr. Water was added to the reaction mixture, and the mixture was extracted twice with chloroform. The organic layer was dried over anhydrous magnesium sulfate, filtered and concentrated. The residue was purified by silica gel column chromatography (solvent; ethyl acetate/methanol=100/0-95/5) to give the title compound (690 mg)

MS (ESI) m/z; 329 [M+H]+

Reference Example 352

5-[(N,N-dimethylamino)methyl]-6-methyl-2-methylsulfinyl[1,3]thiazolo[5,4-d]pyrimidin-7(6H)-one

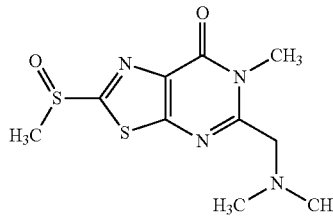

The compound (300 mg) obtained in Reference Example 348 was treated by a method similar to that in Reference Example 351 to give the title compound (360 mg)

MS (ESI) m/z; 287 [M+H]+

Reference Example 353

5-[(N-ethyl-N-methyl-amino)methyl]-6-methyl-2-methylsulfinyl[1,3]thiazolo[5,4-d]pyrimidin-7(6H)-one

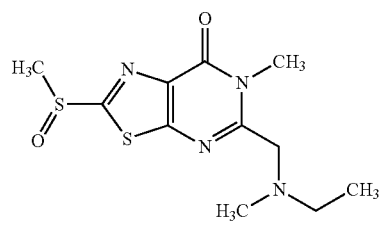 [SMILES: CCN(C)Cc1nc2sc(S(C)=O)nc2c(=O)n1C]

The compound (200 mg) obtained in Reference Example 348 was treated by a method similar to that in Reference Example 351 to give the title compound (206 mg)

MS (ESI) m/z; 301 [M+H]+

Reference Example 354

5-[(azetidin-1-yl)methyl]-6-methyl-2-methylsulfinyl[1,3]thiazolo[5,4-d]pyrimidin-7(6H)-one

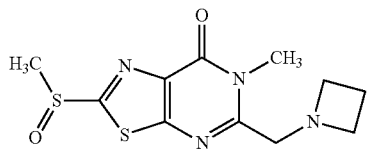 [SMILES: Cn1c(CN2CCC2)nc2sc(S(C)=O)nc2c1=O]

The compound (200 mg) obtained in Reference Example 348 was treated by a method similar to that in Reference Example 351 to give the title compound (227 mg)

MS (ESI) m/z; 299 [M+H]$^+$

Reference Example 355

5-[(3-methoxyazetidin-1-yl)methyl]-6-methyl-2-methylsulfinyl[1,3]thiazolo[5,4-d]pyrimidin-7(6H)-one

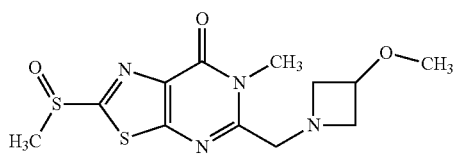

The compound (200 mg) obtained in Reference Example 348 was treated by a method similar to that in Reference Example 351 to give the title compound (155 mg)

MS (ESI) m/z; 329 [M+H]$^+$

Reference Example 356

6-methyl-2-methylsulfinyl-5-[(pyrrolidin-1-yl)methyl][1,3]thiazolo[5,4-d]pyrimidin-7(6H)-one

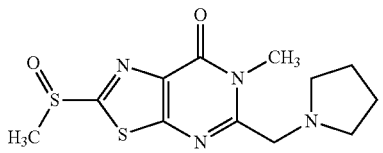 [SMILES: Cn1c(CN2CCCC2)nc2sc(S(C)=O)nc2c1=O]

The compound (300 mg) obtained in Reference Example 348 was treated by a method similar to that in Reference Example 351 to give the title compound (363 mg)

MS (ESI) m/z; 313 [M+H]$^+$

Reference Example 357

6-methyl-2-methylsulfinyl-5-[(piperidin-1-yl)methyl][1,3]thiazolo[5,4-d]pyrimidin-7(6H)-one

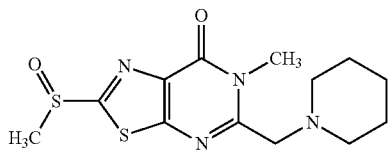 [SMILES: Cn1c(CN2CCCCC2)nc2sc(S(C)=O)nc2c1=O]

The compound (300 mg) obtained in Reference Example 348 was treated by a method similar to that in Reference Example 351 to give the title compound (366 mg)

MS (ESI) m/z; 327 [M+H]$^+$

Reference Example 358

5-[(1,3-dihydro-2H-isoindol-2-yl)methyl]-6-methyl-2-methylsulfinyl[1,3]thiazolo[5,4-d]pyrimidin-7(6H)-one

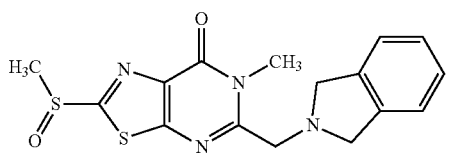 [SMILES: Cn1c(CN2Cc3ccccc3C2)nc2sc(S(C)=O)nc2c1=O]

The compound (200 mg) obtained in Reference Example 348 was treated by a method similar to that in Reference Example 351 to give the title compound (296 mg)

MS (ESI) m/z; 361 [M+H]$^+$

Reference Example 359

5-[(N,N-dimethylamino)methyl]-6-ethyl-2-methylsulfinyl[1,3]thiazolo[5,4-d]pyrimidin-7(6H)-one

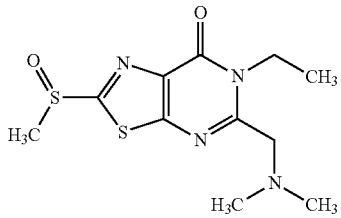 [SMILES: CCn1c(CN(C)C)nc2sc(S(C)=O)nc2c1=O]

The compound (200 mg) obtained in Reference Example 349 was treated by a method similar to that in Reference Example 351 to give the title compound (214 mg)

MS (ESI) m/z; 301 [M+H]$^+$

Reference Example 360

6-ethyl-5-[(N-ethyl-N-methylamino)methyl]-2-methylsulfinyl[1,3]thiazolo[5,4-d]pyrimidin-7(6H)-one

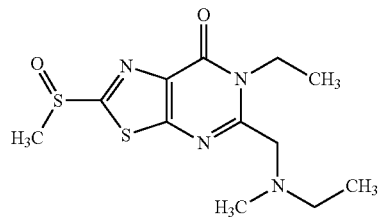 [SMILES: CCN(C)Cc1nc2sc(S(C)=O)nc2c(=O)n1CC]

The compound (200 mg) obtained in Reference Example 349 was treated by a method similar to that in Reference Example 351 to give the title compound (267 mg)
MS (ESI) m/z; 315 [M+H]$^+$

Reference Example 361

5-[(N,N-dimethylamino)methyl]-2-methylsulfinyl-6-(propan-2-yl)[1,3]thiazolo[5,4-d]pyrimidin-7(6H)-one

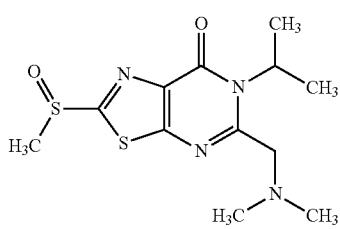 [SMILES: CC(C)n1c(CN(C)C)nc2sc(S(C)=O)nc2c1=O]

The compound (126 mg) obtained in Reference Example 350 was treated by a method similar to that in Reference Example 351 to give the title compound (120 mg)
MS (ESI) m/z; 315 [M+H]$^+$

Reference Example 362

5-{[(N-(2-methoxyethyl)-N-methylamino]methyl}-2-methylsulfinyl-6-(propan-2-yl)[1,3]thiazolo[5,4-d]pyrimidin-7(6H)-one

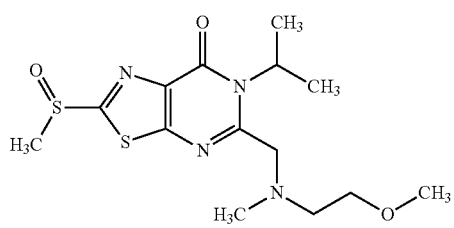 [SMILES: COCCN(C)Cc1nc2sc(S(C)=O)nc2c(=O)n1C(C)C]

The compound (126 mg) obtained in Reference Example 350 was treated by a method similar to that in Reference Example 351 to give the title compound (142 mg)
MS (ESI) m/z; 359 [M+H]$^+$

Reference Example 363

6-methyl-2-methylsulfinyl-5-{[N-methyl-N-(2,2,2-trifluoroethyl)amino]methyl}[1,3]thiazolo[5,4-d]pyrimidin-7(6H)-one

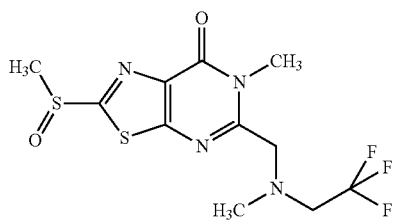 [SMILES: CN(Cc1nc2sc(S(C)=O)nc2c(=O)n1C)CC(F)(F)F]

To a solution (2.0 mL) of the compound (200 mg) obtained in Reference Example 348 in DMF were added N-methyl-N-(2,2,2-trifluoroethyl)amine hydrochloride (215 mg) and N,N-diisopropylethylamine (439 μL), and the reaction mixture was stirred with heating at 60° C. for 5 hr. Water was added to the reaction mixture, and the mixture was extracted three times with ethyl acetate. The organic layer was dried over anhydrous sodium sulfate, filtered and concentrated to give the title compound (747 mg).
MS (ESI) m/z; 355 [M+H]$^+$

Reference Example 364

5-mercapto-6-methyl-2-methylsulfanyl[1,3]thiazolo[5,4-d]pyrimidin-7(6H)-one

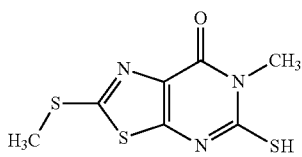

To a solution (1.0 mL) of 5-amino-2-methylsulfanyl-1,3-thiazole-4-carboxylic acid ethyl ester (100 mg) in ethanol were added methyl isothiocyanate (50 mg) and DBU (137 μL), and the reaction mixture was stirred with heating at 80° C. for 5 hr. The reaction mixture was cooled to 0° C., acetic acid and water were added, and the precipitated solid was filtered, and dried to give the title compound (68.0 mg).
MS (ESI) m/z; 246 [M+H]$^+$

Reference Example 365

5-mercapto-6-(2-methoxyethyl)-2-methylsulfanyl[1,3]thiazolo[5,4-d]pyrimidin-7(6H)-one

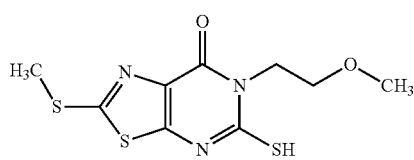

5-Amino-2-methylsulfanyl-1,3-thiazole-4-carboxylic acid ethyl ester (5.00 g) was treated by a method similar to that in Reference Example 364 to give the title compound (4.87 g).
MS (ESI) m/z; 290 [M+H]+

Reference Example 366

5-chloro-6-methyl-2-methylsulfanyl[1,3]thiazolo[5,4-d]pyrimidin-7(6H)-one

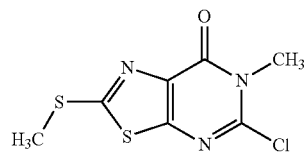

To a solution (40 mL) of the compound (5.03 g) obtained in Reference Example 364 in DMF was added phosphorus oxychloride (2.8 mL) under ice-cooling. The reaction mixture was stirred with heating at 70° C. for 3 hr, and added to water. The precipitated solid was collected by filtration, and dried to give the title compound (3.44 g).
MS (ESI) m/z; 248, 250 [M+H]+

Reference Example 367

5-chloro-6-(2-methoxyethyl)-2-methylsulfanyl[1,3]thiazolo[5,4-d]pyrimidin-7(6H)-one

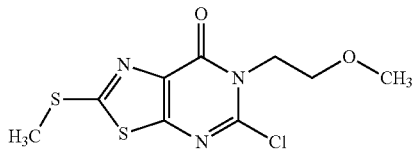

The compound (2.00 g) obtained in Reference Example 365 was treated by a method similar to that in Reference Example 366 to give the title compound (1.50 g).
MS (ESI) m/z; 292, 294 [M+H]+

Reference Example 368

5-chloro-6-methyl-2-methylsulfinyl[1,3]thiazolo[5,4-d]pyrimidin-7(6H)-one

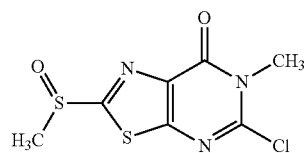

The compound (2.78 g) obtained in Reference Example 366 was treated by a method similar to that in Reference Example 268 to give the title compound (2.22 g).
MS (ESI) m/z; 264, 266 [M+H]+

Reference Example 369

5-chloro-6-(2-methoxyethyl)-2-methylsulfinyl[1,3]thiazolo[5,4-d]pyrimidin-7(6H)-one

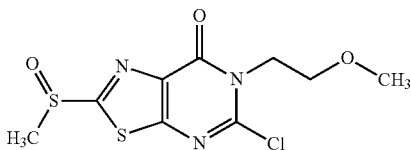

The compound (300 mg) obtained in Reference Example 367 was treated by a method similar to that in Reference Example 268 to give the title compound (173 mg).
MS (ESI) m/z; 308, 310 [M+H]+

Reference Example 370

5-(N,N-dimethylamino)-6-methyl-2-methylsulfinyl[1,3]thiazolo[5,4-d]pyrimidin-7(6H)-one

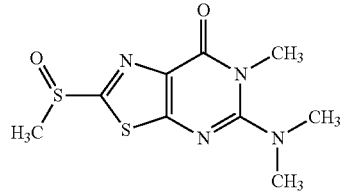

To a solution (10 mL) of the compound (250 mg) obtained in Reference Example 368 in THF were added triethylamine (400 μL) and a 50% aqueous dimethylamine solution (120 μL), and the reaction mixture was stirred with heating at 50° C. for 2.5 hr. To the reaction mixture was added 1.0 mol/L hydrochloric acid, and the mixture was extracted twice with chloroform. The organic layer was dried over anhydrous magnesium sulfate, filtered and concentrated to give the title compound (300 mg).
MS (ESI) m/z; 273 [M+H]+

Reference Example 371

6-methyl-2-methylsulfinyl-5-(pyrrolidin-1-yl)[1,3]thiazolo[5,4-d]pyrimidin-7(6H)-one

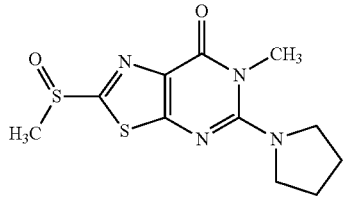 [SMILES: Cn1c(N2CCCC2)nc2sc(S(C)=O)nc2c1=O]

The compound (250 mg) obtained in Reference Example 368 was treated by a method similar to that in Reference Example 370 to give the title compound (277 mg).
MS (ESI) m/z; 299 [M+H]+

Reference Example 372

6-methyl-2-methylsulfinyl-5-(piperidin-1-yl)[1,3]thiazolo[5,4-d]pyrimidin-7(6H)-one

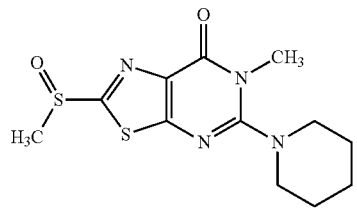 [SMILES: Cn1c(N2CCCCC2)nc2sc(S(C)=O)nc2c1=O]

The compound (250 mg) obtained in Reference Example 368 was treated by a method similar to that in Reference Example 370 to give the title compound (210 mg).
MS (ESI) m/z; 313 [M+H]$^+$

Reference Example 373

5-(3-methoxyazetidin-1-yl)-6-methyl-2-methylsulfinyl[1,3]thiazolo[5,4-d]pyrimidin-7(6H)-one

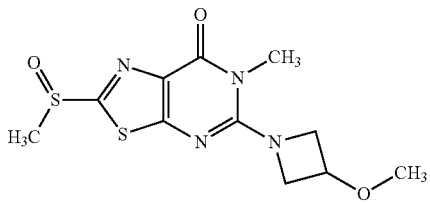

The compound (250 mg) obtained in Reference Example 368 was treated by a method similar to that in Reference Example 370 to give the title compound (283 mg).
MS (ESI) m/z; 315 [M+H]$^+$

Reference Example 374

6-(2-methoxyethyl)-5-(4-methylpiperazin-1-yl)-2-methylsulfinyl[1,3]thiazolo[5,4-d]pyrimidin-7(6H)-one

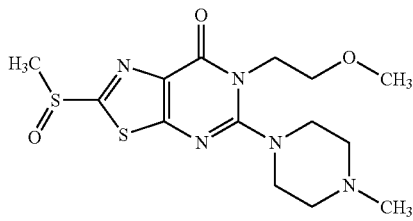 [SMILES: COCCn1c(N2CCN(C)CC2)nc2sc(S(C)=O)nc2c1=O]

The compound (168 mg) obtained in Reference Example 369 was treated by a method similar to that in Reference Example 370 to give the title compound (179 mg).
MS (ESI) m/z; 372 [M+H]$^+$

Reference Example 375

6-methyl-2-methylsulfanyl-5-(morpholin-4-yl)[1,3]thiazolo[5,4-d]pyrimidin-7(6H)-one

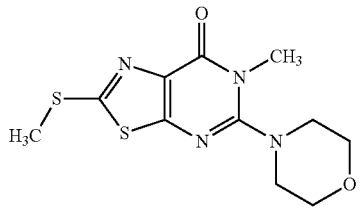 [SMILES: CSc1nc2c(=O)n(C)c(N3CCOCC3)nc2s1]

To a solution (10 mL) of the compound (268 mg) obtained in Reference Example 366 in THF were added morpholine (110 μL) and triethylamine (450 μL), and the reaction mixture was stirred with heating at 50° C. for 1.5 hr. The reaction mixture was cooled to room temperature, and water was added to the reaction mixture, and the mixture was extracted three times with ethyl acetate. The organic layer was dried over anhydrous magnesium sulfate, filtered and concentrated. The residue was purified by silica gel column chromatography (solvent; chloroform/methanol=100/0-95/5) to give the title compound (211 mg).
MS (ESI) m/z; 299 [M+H]$^+$

Reference Example 376

6-methyl-2-methylsulfinyl-5-(morpholin-4-yl)[1,3]thiazolo[5,4-d]pyrimidin-7(6H)-one

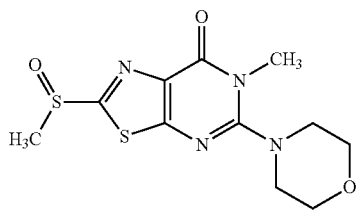 [SMILES: Cn1c(N2CCOCC2)nc2sc(S(C)=O)nc2c1=O]

The compound (198 mg) obtained in Reference Example 375 was treated by a method similar to that in Reference Example 268 to give the title compound (218 mg).
MS (ESI) m/z; 315 [M+H]$^+$

Reference Example 377

6-methyl-2-methylsulfanyl-5-[(propan-2-yl)amino][1,3]thiazolo[5,4-d]pyrimidin-7(6H)-one

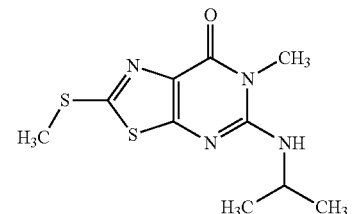

The compound (600 mg) obtained in Reference Example 366 was treated by a method similar to that in Reference Example 375 to give the title compound (624 mg).
MS (ESI) m/z; 271 [M+H]$^+$ Reference Example 378

6-methyl-2-methylsulfonyl-5-[(propan-2-yl)amino][1,3]thiazolo[5,4-d]pyrimidin-7(6H)-one

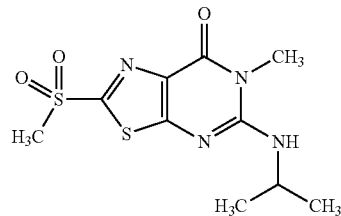

To a solution (2.00 mL) of the compound (319 mg) obtained in Reference Example 377 in trifluoroacetic acid was added 30% hydrogen peroxide water (285 μL) under ice-cooling. The mixture was stirred at room temperature for 2.5 hr, and the reaction mixture was ice-cooled, and water was added. The precipitated solid was collected by filtration, washed with water and dried to give the title compound (333 mg).
MS (ESI) m/z; 303 [M+H]$^+$ Reference Example 379

5-{N-(4-methoxybenzyl)-N-[(propan-2-yl)amino]}-6-methyl-2-methylsulfonyl-[1,3]thiazolo[5,4-d]pyrimidin-7(6H)-one

To a solution (2 mL) of the compound (303 mg) obtained in Reference Example 378 in DMF was added sodium hydride (60% oil dispersion, 48 mg), and the reaction mixture was stirred for 5 min. 4-Methoxybenzyl chloride (540 μL) was added dropwise, and the reaction mixture was stirred at room temperature overnight. Sodium hydride (60% oil dispersion, 48 mg) and 4-methoxybenzyl chloride (540 μL) were added, and the reaction mixture was stirred at room temperature overnight, and stirred with heating at 65° C. for 7 hr. To the reaction mixture was added 1 mol/L hydrochloric acid, and the mixture was extracted three times with ethyl acetate. The combined organic layer was dried over anhydrous sodium sulfate, filtered and concentrated. The residue was purified by silica gel column chromatography (solvent; hexane/ethyl acetate=80/20-0/100) to give the title compound (49 mg).
MS (ESI) m/z; 423 [M+H]$^+$ Reference Example 380

6-methyl-2-methylsulfanyl-5-[(propan-2-yl)oxy][1,3]thiazolo[5,4-d]pyrimidin-7(6H)-one

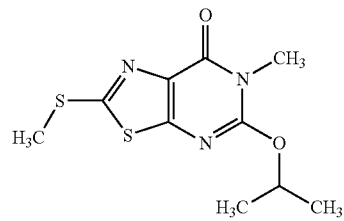 [SMILES: CSc1nc2c(=O)n(C)c(OC(C)C)nc2s1]

To a solution (10 mL) of the compound (300 mg) obtained in Reference Example 366 and 2-propanol (110 μL) in DMF was added sodium hydride (60% oil dispersion, 58 mg) under ice-cooling. The reaction mixture was stirred at room temperature for 1.5 hr, water was added, and the mixture was extracted twice with ethyl acetate. The organic layer was dried over anhydrous magnesium sulfate, filtered and concentrated. The residue was purified by silica gel column chromatography (solvent; hexane/ethyl acetate=80/20-50/50) to give the title compound (236 mg).
MS (ESI) m/z; 272 [M+H]$^+$ Reference Example 381

5-ethoxy-6-(2-methoxyethyl)-2-methylsulfanyl[1,3]thiazolo[5,4-d]pyrimidin-7(6H)-one

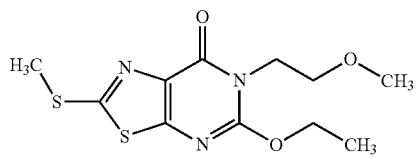

The compound (400 mg) obtained in Reference Example 367 was treated by a method similar to that in Reference Example 380 to give the title compound (194 mg).
MS (ESI) m/z; 302 [M+H]$^+$ Reference Example 382

6-(2-methoxyethyl)-2-methylsulfanyl-5-[(propan-2-yl)oxy][1,3]thiazolo[5,4-d]pyrimidin-7(6H)-one

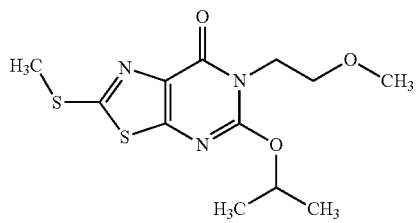

The compound (400 mg) obtained in Reference Example 367 was treated by a method similar to that in Reference Example 380 to give the title compound (288 mg).
MS (ESI) m/z; 316 [M+H]$^+$

Reference Example 383

6-methyl-2-methylsulfinyl-5-[(propan-2-yl)oxy][1,3]thiazolo[5,4-d]pyrimidin-7(6H)-one

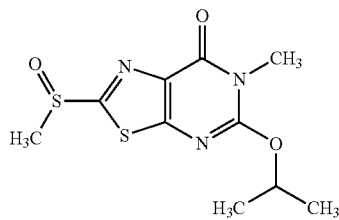

The compound (220 mg) obtained in Reference Example 380 was treated by a method similar to that in Reference Example 268 to give the title compound (209 mg).

MS (ESI) m/z; 288 [M+H]$^+$

Reference Example 384

5-ethoxy-6-(2-methoxyethyl)-2-methylsulfinyl[1,3]thiazolo[5,4-d]pyrimidin-7(6H)-one

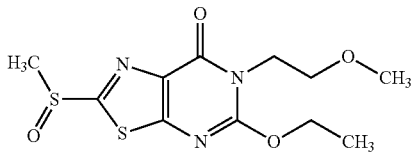

The compound (180 mg) obtained in Reference Example 381 was treated by a method similar to that in Reference Example 268 to give the title compound (129 mg).

MS (ESI) m/z; 318 [M+H]$^+$

Reference Example 385

6-(2-methoxyethyl)-2-methylsulfinyl-5-[(propan-2-yl)oxy][1,3]thiazolo[5,4-d]pyrimidin-7(6H)-one

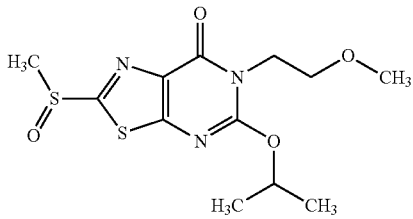 [SMILES: COCCn1c(OC(C)C)nc2sc(S(C)=O)nc2c1=O]

The compound (282 mg) obtained in Reference Example 382 was treated by a method similar to that in Reference Example 268 to give the title compound (191 mg).

MS (ESI) m/z; 332 [M+H]$^+$

Reference Example 386

5-(2-fluorophenyl)-6-methyl-2-methylsulfanyl[1,3]thiazolo[5,4-d]pyrimidin-7(6H)-one

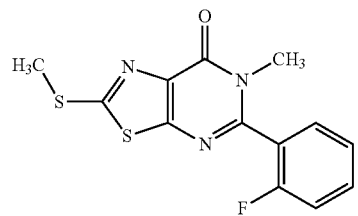 [SMILES: CSc1nc2c(=O)n(C)c(-c3ccccc3F)nc2s1]

To a solution (16 mL) of the compound (496 mg) obtained in Reference Example 366 in dimethoxyethane were successively added 2-fluorophenylboronic acid (336 mg), tetrakis(triphenylphosphine)palladium(0) (116 mg), and an aqueous solution (4.0 mL) of sodium carbonate (848 mg) at room temperature, and the reaction mixture was stirred at 100° C. for 5 hr. After confirmation of the completion of the reaction, the reaction mixture was cooled to room temperature, and diluted with methylene chloride. The organic layer was washed with saturated brine, and the aqueous layer was extracted with methylene chloride. The organic layers were combined, dried over anhydrous magnesium sulfate, filtered and concentrated. The obtained residue was purified by silica gel column chromatography (solvent; hexane/ethyl acetate=90/10-50/50) to give the title compound (142 mg).

MS (ESI) m/z; 308 [M+H]$^+$

Reference Example 387

5-(2-methoxyphenyl)-6-methyl-2-methylsulfanyl[1,3]thiazolo[5,4-d]pyrimidin-7(6H)-one

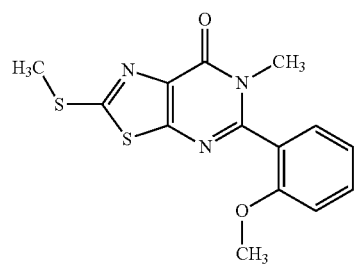 [SMILES: COc1ccccc1-c1nc2sc(SC)nc2c(=O)n1C]

The compound (496 mg) obtained in Reference Example 366 was treated by a method similar to that in Reference Example 386 to give the title compound (263 mg).

MS (ESI) m/z; 320 [M+H]$^+$

Reference Example 388

6-methyl-2-methylsulfanyl-5-(2,3,4,5,6-pentadeuteriophenyl)[1,3]thiazolo[5,4-d]pyrimidin-7(6H)-one

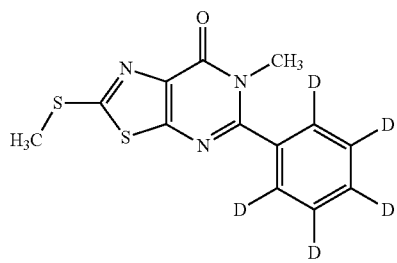 [SMILES: [2H]c1c([2H])c([2H])c(-c2nc3sc(SC)nc3c(=O)n2C)c([2H])c1[2H]]

The compound (800 mg) obtained in Reference Example 366 was treated by a method similar to that in Reference Example 386 to give the title compound (307 mg).
MS (ESI) m/z; 295 [M+H]$^+$

Reference Example 389

5-(2-fluorophenyl)-6-methyl-2-methylsulfinyl[1,3]thiazolo[5,4-d]pyrimidin-7(6H)-one

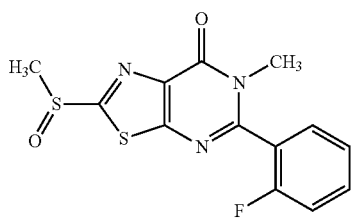

The compound (141 mg) obtained in Reference Example 386 was treated by a method similar to that in Reference Example 268 to give the title compound (147 mg).
MS (ESI) m/z; 324 [M+H]$^+$

Reference Example 390

5-(2-methoxyphenyl)-6-methyl-2-methylsulfinyl[1,3]thiazolo[5,4-d]pyrimidin-7(6H)-one

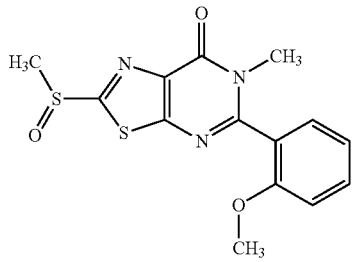 [SMILES: COc1ccccc1-c1nc2sc(S(C)=O)nc2c(=O)n1C]

The compound (258 mg) obtained in Reference Example 387 was treated by a method similar to that in Reference Example 268 to give the title compound (326 mg).
MS (ESI) m/z; 336 [M+H]$^+$

Reference Example 391

6-methyl-2-methylsulfinyl-5-(2,3,4,5,6-pentadeuteriophenyl)[1,3]thiazolo[5,4-d]pyrimidin-7(6H)-one

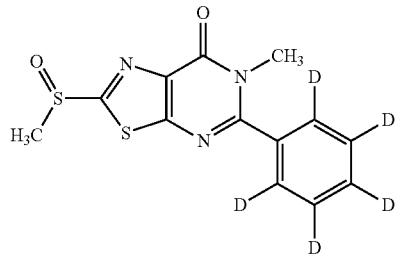 [SMILES: [2H]c1c([2H])c([2H])c(-c2nc3sc(S(C)=O)nc3c(=O)n2C)c([2H])c1[2H]]

The compound (298 mg) obtained in Reference Example 388 was treated by a method similar to that in Reference Example 268 to give the title compound (352 mg).
MS (ESI) m/z; 311 [M+H]$^+$

Reference Example 392

(S)-3-{[(5-amino-2-methylsulfanyl-1,3-thiazol-4-yl)carbonyl]amino}pyrrolidine-1-carboxylic acid tert-butyl ester

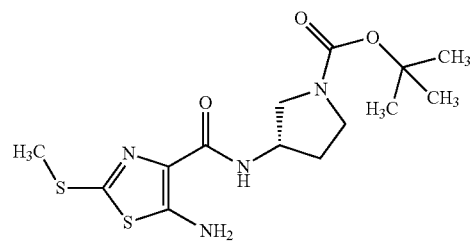 [SMILES: CSc1nc(C(=O)N[C@H]2CCN(C(=O)OC(C)(C)C)C2)c(N)s1]

5-Amino-2-methylsulfanyl-1,3-thiazole-4-carboxylic acid (0.92 g) was treated by a method similar to that in Reference Example 136 to give the title compound (1.84 g).
MS (ESI) m/z; 359 [M+H]$^+$

Reference Example 393

(R)-3-{[(5-amino-2-methylsulfanyl-1,3-thiazol-4-yl)carbonyl]amino}pyrrolidine-1-carboxylic acid tert-butyl ester

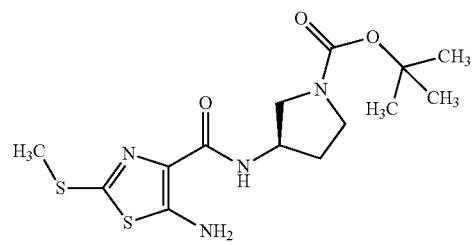 [SMILES: CSc1nc(C(=O)N[C@@H]2CCN(C(=O)OC(C)(C)C)C2)c(N)s1]

5-Amino-2-methylsulfanyl-1,3-thiazole-4-carboxylic acid (0.60 g) was treated by a method similar to that in Reference Example 136 to give the title compound (1.12 g).
MS (ESI) m/z; 359 [M+H]$^+$

Reference Example 394

4-[{[(5-amino-2-methylsulfanyl-1,3-thiazol-4-yl)carbonyl]amino}methyl]piperidine-1-carboxylic acid tert-butyl ester

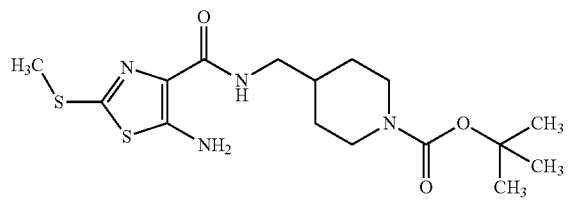 [SMILES: CSc1nc(C(=O)NCC2CCN(C(=O)OC(C)(C)C)CC2)c(N)s1]

5-Amino-2-methylsulfanyl-1,3-thiazole-4-carboxylic acid (2.00 g) was treated by a method similar to that in Reference Example 136 to give the title compound (3.90 g).
MS (ESI) m/z; 287 [M+H-Boc]+

Reference Example 395

(RS)-3-[{[(5-amino-2-methylsulfanyl-1,3-thiazol-4-yl)carbonyl]amino}methyl]pyrrolidine-1-carboxylic acid tert-butyl ester

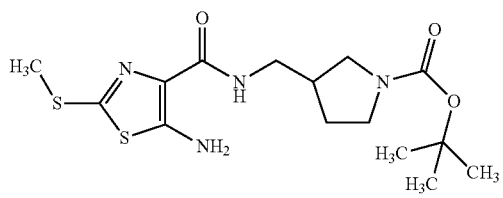 [SMILES: CSc1nc(C(=O)NCC2CCN(C(=O)OC(C)(C)C)C2)c(N)s1]

5-Amino-2-methylsulfanyl-1,3-thiazole-4-carboxylic acid (0.85 g) was treated by a method similar to that in Reference Example 136 to give the title compound (1.54 g).
MS (ESI) m/z; 273 [M+H-Boc]+

Reference Example 396

(S)-2-[{[(5-amino-2-methylsulfanyl-1,3-thiazol-4-yl)carbonyl]amino}methyl]pyrrolidine-1-carboxylic acid tert-butyl ester

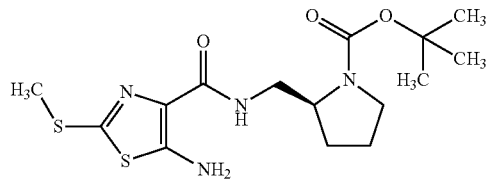 [SMILES: CSc1nc(C(=O)NC[C@@H]2CCCN2C(=O)OC(C)(C)C)c(N)s1]

5-Amino-2-methylsulfanyl-1,3-thiazole-4-carboxylic acid (864 mg) was treated by a method similar to that in Reference Example 136 to give the title compound (1.64 g).
MS (ESI) m/z; 373 [M+H]+

Reference Example 397

(R)-2-[{[(5-amino-2-methylsulfanyl-1,3-thiazol-4-yl)carbonyl]amino}methyl]pyrrolidine-1-carboxylic acid tert-butyl ester

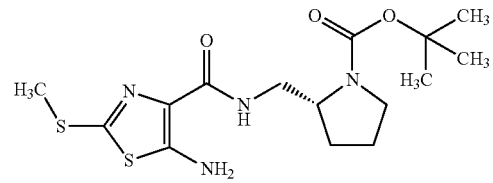 [SMILES: CSc1nc(C(=O)NC[C@H]2CCCN2C(=O)OC(C)(C)C)c(N)s1]

5-Amino-2-methylsulfanyl-1,3-thiazole-4-carboxylic acid (750 mg) was treated by a method similar to that in Reference Example 136 to give the title compound (1.32 g).
MS (ESI) m/z; 373 [M+H]+

Reference Example 398

N-[{2-[(5-amino-2-methylsulfanyl-1,3-thiazol-4-yl)carbonyl]amino}ethyl]-N-methylcarbamic acid tert-butyl ester

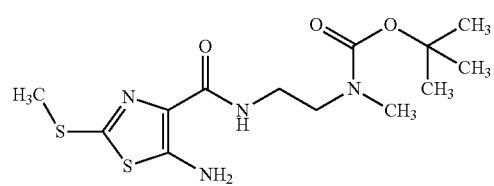 [SMILES: CSc1nc(C(=O)NCCN(C)C(=O)OC(C)(C)C)c(N)s1]

5-Amino-2-methylsulfanyl-1,3-thiazole-4-carboxylic acid (2.19 g) was treated by a method similar to that in Reference Example 136 to give the title compound (3.80 g).
MS (ESI) m/z; 347 [M+H]+

Reference Example 399

(S)-3-{[(2-methylsulfanyl-5-[(trifluoroacetyl)amino]-1,3-thiazol-4-yl)carbonyl]amino}pyrrolidine-1-carboxylic acid tert-butyl ester

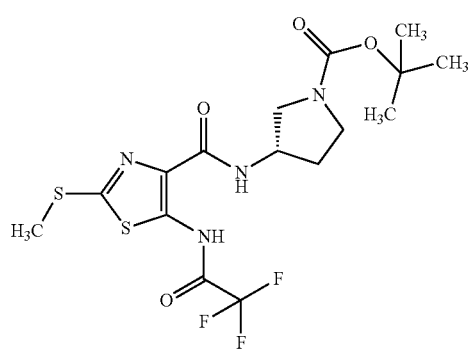 [SMILES: CSc1nc(C(=O)N[C@H]2CCN(C(=O)OC(C)(C)C)C2)c(NC(=O)C(F)(F)F)s1]

The compound (1.80 g) obtained in Reference Example 392 was treated by a method similar to that in Reference Example 194 to give the title compound (2.05 g).

MS (ESI) m/z; 355 [M+H-Boc]+

Reference Example 400

(R)-3-{[(2-methylsulfanyl-5-[(trifluoroacetyl)amino]-1,3-thiazol-4-yl) carbonyl]amino}pyrrolidine-1-carboxylic acid tert-butyl ester

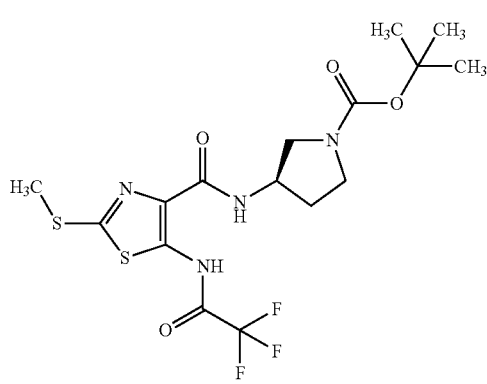 [SMILES: CSc1nc(C(=O)N[C@@H]2CCN(C(=O)OC(C)(C)C)C2)c(NC(=O)C(F)(F)F)s1]

The compound (1.07 g) obtained in Reference Example 393 was treated by a method similar to that in Reference Example 194 to give the title compound (1.66 g).

MS (ESI) m/z; 355 [M+H-Boc]+

Reference Example 401

4-[{[(2-methylsulfanyl-5-[(trifluoroacetyl)amino]-1,3-thiazol-4-yl)carbonyl]amino}methyl]piperidine-1-carboxylic acid tert-butyl ester

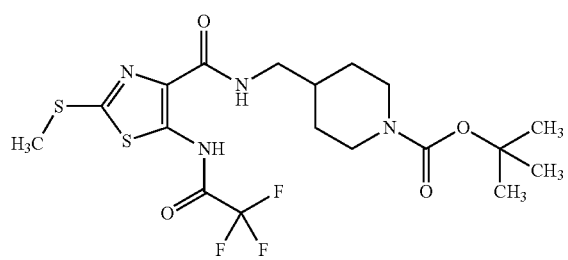 [SMILES: CSc1nc(C(=O)NCC2CCN(C(=O)OC(C)(C)C)CC2)c(NC(=O)C(F)(F)F)s1]

The compound (3.90 g) obtained in Reference Example 394 was treated by a method similar to that in Reference Example 194 to give the title compound (4.05 g).

MS (ESI) m/z; 383 [M+H-Boc]+

Reference Example 402

(RS)-3-[{[(2-methylsulfanyl-5-[(trifluoroacetyl)amino]-1,3-thiazol-4-yl)carbonyl]amino}methyl]pyrrolidine-1-carboxylic acid tert-butyl ester

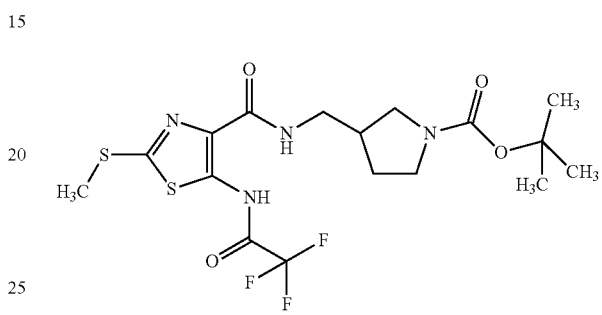

The compound (1.50 g) obtained in Reference Example 395 was treated by a method similar to that in Reference Example 194 to give the title compound (1.70 g).

MS (ESI) m/z; 369 [M+H-Boc]+

Reference Example 403

(S)-2-[{[(2-methylsulfanyl-5-[(trifluoroacetyl)amino]-1,3-thiazol-4-yl)carbonyl]amino}methyl]pyrrolidine-1-carboxylic acid tert-butyl ester

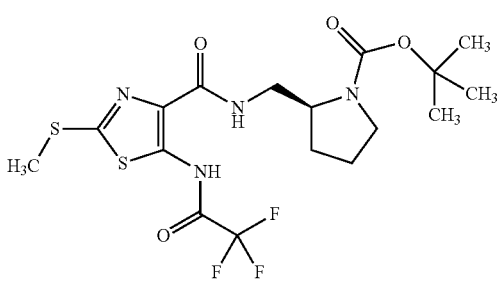 [SMILES: CSc1nc(C(=O)NC[C@@H]2CCCN2C(=O)OC(C)(C)C)c(NC(=O)C(F)(F)F)s1]

The compound (825 mg) obtained in Reference Example 396 was treated by a method similar to that in Reference Example 194 to give the title compound (990 mg).

MS (ESI) m/z; 369 [M+H-Boc]+

Reference Example 404

(R)-2-[{[{2-methylsulfanyl-5-[(trifluoroacetyl)amino]-1,3-thiazol-4-yl}carbonyl]amino}methyl]pyrrolidine-1-carboxylic acid tert-butyl ester

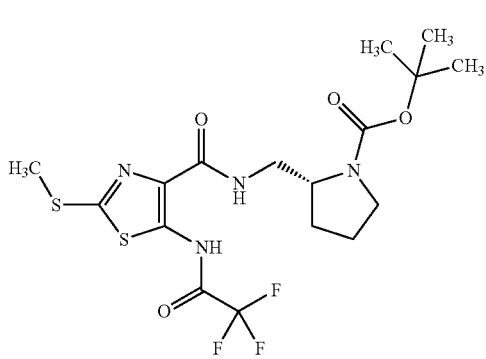 [SMILES: CSc1nc(C(=O)NC[C@H]2CCCN2C(=O)OC(C)(C)C)c(NC(=O)C(F)(F)F)s1]

The compound (1.32 g) obtained in Reference Example 397 was treated by a method similar to that in Reference Example 194 to give the title compound (1.31 g).

MS (ESI) m/z; 369 [M+H-Boc]$^+$

Reference Example 405

N-methyl-N-[2-{[{2-methylsulfanyl-5-[(trifluoroacetyl)amino]-1,3-thiazol-4-yl}carbonyl]amino}ethyl]carbamic acid tert-butyl ester

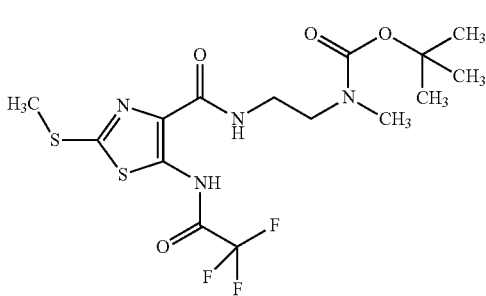 [SMILES: CSc1nc(C(=O)NCCN(C)C(=O)OC(C)(C)C)c(NC(=O)C(F)(F)F)s1]

The compound (1.50 g) obtained in Reference Example 398 was treated by a method similar to that in Reference Example 194 to give the title compound (1.84 g).

MS (ESI) m/z; 343 [M+H-Boc]$^+$

Reference Example 406

(S)-3-(2-methylsulfanyl-7-oxo-5-trifluoromethyl-7H-[1,3]thiazolo[5,4-d]pyrimidin-6-yl)pyrrolidine-1-carboxylic acid tert-butyl ester

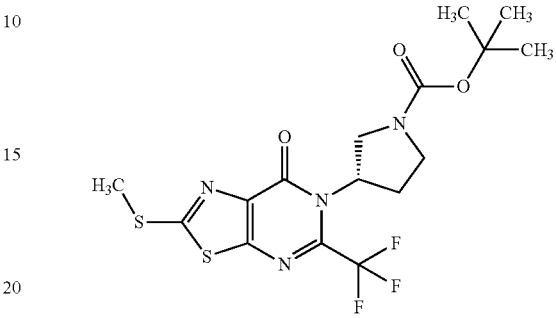

The compound (2.00 g) obtained in Reference Example 399 was treated by a method similar to that in Reference Example 229 to give the title compound (1.16 g).

MS (ESI) m/z; 337 [M+H-Boc]$^+$

Reference Example 407

(R)-3-(2-methylsulfanyl-7-oxo-5-trifluoromethyl-7H-[1,3]thiazolo[5,4-d]pyrimidin-6-yl)pyrrolidine-1-carboxylic acid tert-butyl ester

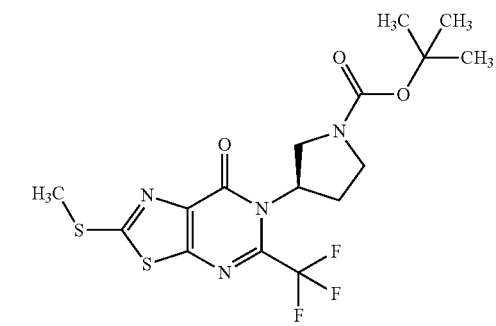 [SMILES: CSc1nc2c(=O)n([C@@H]3CCN(C(=O)OC(C)(C)C)C3)c(C(F)(F)F)nc2s1]

The compound (1.66 g) obtained in Reference Example 400 was treated by a method similar to that in Reference Example 229 to give the title compound (911 mg).

MS (ESI) m/z; 337 [M+H-Boc]$^+$

Reference Example 408

4-[(2-methylsulfanyl-7-oxo-5-trifluoromethyl-7H-[1,3]thiazolo[5,4-d]pyrimidin-6-yl)methyl]piperidine-1-carboxylic acid tert-butyl ester

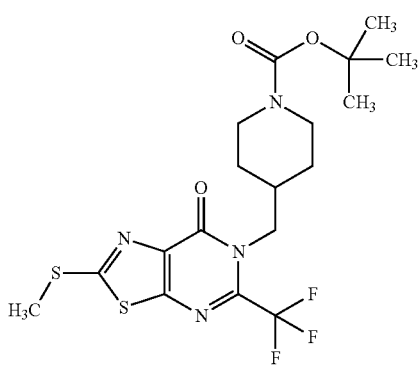 [SMILES: CSc1nc2c(=O)n(CC3CCN(C(=O)OC(C)(C)C)CC3)c(C(F)(F)F)nc2s1]

The compound (4.05 g) obtained in Reference Example 401 was treated by a method similar to that in Reference Example 229 to give the title compound (2.76 g).
MS (ESI) m/z; 365 [M+H-Boc]$^+$

Reference Example 409

(RS)-3-[(2-methylsulfanyl-7-oxo-5-trifluoromethyl-7H-[1,3]thiazolo[5,4-d]pyrimidin-6-yl)methyl]pyrrolidine-1-carboxylic acid tert-butyl ester

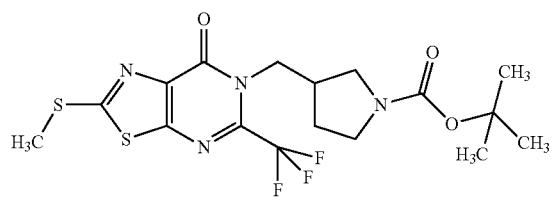 [SMILES: CSc1nc2c(=O)n(CC3CCN(C(=O)OC(C)(C)C)C3)c(C(F)(F)F)nc2s1]

The compound (1.70 g) obtained in Reference Example 402 was treated by a method similar to that in Reference Example 229 to give the title compound (1.43 g).
MS (ESI) m/z; 351 [M+H-Boc]$^+$

Reference Example 410

(S)-2-[(2-methylsulfanyl-7-oxo-5-trifluoromethyl-7H-[1,3]thiazolo[5,4-d]pyrimidin-6-yl)methyl]pyrrolidine-1-carboxylic acid tert-butyl ester

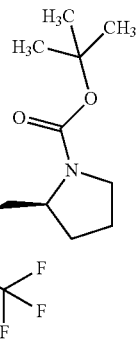

The compound (984 mg) obtained in Reference Example 403 was treated by a method similar to that in Reference Example 229 to give the title compound (802 mg).
MS (ESI) m/z; 351 [M+H-Boc]$^+$

Reference Example 411

(R)-2-[(2-methylsulfanyl-7-oxo-5-trifluoromethyl-7H-[1,3]thiazolo[5,4-d]pyrimidin-6-yl)methyl]pyrrolidine-1-carboxylic acid tert-butyl ester

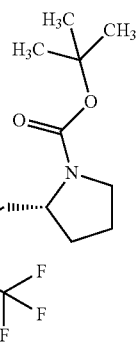

The compound (1.31 g) obtained in Reference Example 404 was treated by a method similar to that in Reference Example 229 to give the title compound (1.15 g).
MS (ESI) m/z; 351 [M+H-Boc]$^+$

Reference Example 412

N-methyl-N-[2-(2-methylsulfanyl-7-oxo-5-trifluoromethyl-7H-[1,3]thiazolo[5,4-d]pyrimidin-6-yl)ethyl]carbamic acid tert-butyl ester

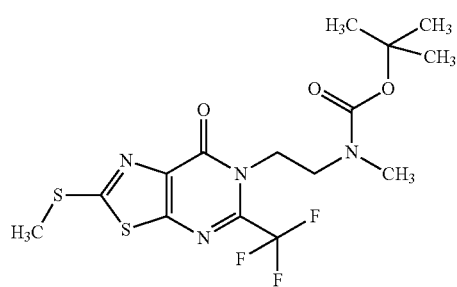 [SMILES: CSc1nc2c(=O)n(CCN(C)C(=O)OC(C)(C)C)c(C(F)(F)F)nc2s1]

The compound (1.00 g) obtained in Reference Example 405 was treated by a method similar to that in Reference Example 229 to give the title compound (440 mg).

MS (ESI) m/z; 325 [M+H-Boc]⁺

Reference Example 413

(S)-3-[2-((RS)-methylsulfinyl)-7-oxo-5-trifluoromethyl-7H-[1,3]thiazolo[5,4-d]pyrimidin-6-yl]pyrrolidine-1-carboxylic acid tert-butyl ester

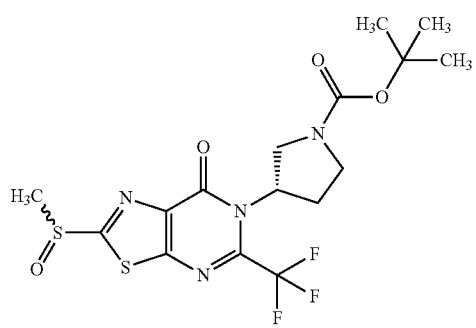 [SMILES: CS(=O)c1nc2c(=O)n([C@H]3CCN(C(=O)OC(C)(C)C)C3)c(C(F)(F)F)nc2s1]

The compound (1.01 g) obtained in Reference Example 406 was treated by a method similar to that in Reference Example 268 to give the title compound (1.02 g).

MS (ESI) m/z; 453 [M+H]⁺

Reference Example 414

(R)-3-[2-((RS)-methylsulfinyl)-7-oxo-5-trifluoromethyl-7H-[1,3]thiazolo[5,4-d]pyrimidin-6-yl]pyrrolidine-1-carboxylic acid tert-butyl ester

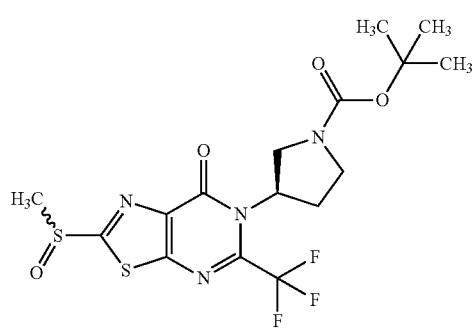 [SMILES: CS(=O)c1nc2c(=O)n([C@@H]3CCN(C(=O)OC(C)(C)C)C3)c(C(F)(F)F)nc2s1]

The compound (900 mg) obtained in Reference Example 407 was treated by a method similar to that in Reference Example 268 to give the title compound (939 mg).

MS (ESI) m/z; 453 [M+H]⁺

Reference Example 415

4-[(2-methylsulfinyl-7-oxo-5-trifluoromethyl-7H-[1,3]thiazolo[5,4-d]pyrimidin-6-yl)methyl]piperidine-1-carboxylic acid tert-butyl ester

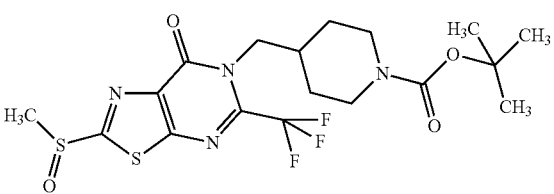 [SMILES: CS(=O)c1nc2c(=O)n(CC3CCN(C(=O)OC(C)(C)C)CC3)c(C(F)(F)F)nc2s1]

The compound (2.75 g) obtained in Reference Example 408 was treated by a method similar to that in Reference Example 268 to give the title compound (2.40 g).

MS (ESI) m/z; 381 [M+H-Boc]⁺

Reference Example 416

(RS)-3-{[2-((RS)-methylsulfinyl)-7-oxo-5-trifluoromethyl-7H-[1,3]thiazolo[5,4-d]pyrimidin-6-yl]methyl}pyrrolidine-1-carboxylic acid tert-butyl ester

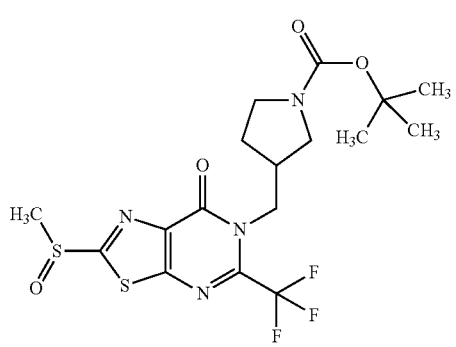 [SMILES: CS(=O)c1nc2c(=O)n(CC3CCN(C(=O)OC(C)(C)C)C3)c(C(F)(F)F)nc2s1]

The compound (1.40 g) obtained in Reference Example 409 was treated by a method similar to that in Reference Example 268 to give the title compound (1.36 g).

MS (ESI) m/z; 367 [M+H-Boc]$^+$

Reference Example 417

(S)-2-{[2-((RS)-methylsulfinyl)-7-oxo-5-trifluoromethyl-7H-[1,3]thiazolo[5,4-d]pyrimidin-6-yl]methyl}pyrrolidine-1-carboxylic acid tert-butyl ester

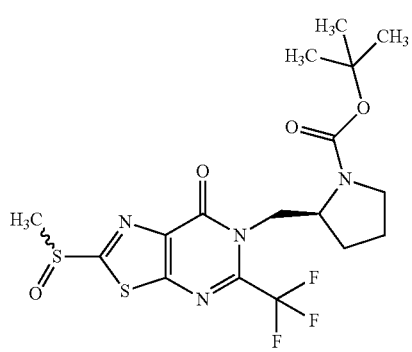 [SMILES: CS(=O)c1nc2c(=O)n(C[C@@H]3CCCN3C(=O)OC(C)(C)C)c(C(F)(F)F)nc2s1]

The compound (791 mg) obtained in Reference Example 410 was treated by a method similar to that in Reference Example 268 to give the title compound (899 mg).

MS (ESI) m/z; 367 [M+H-Boc]$^+$

Reference Example 418

(R)-2-{[2-((RS)-methylsulfinyl)-7-oxo-5-trifluoromethyl-7H-[1,3]thiazolo[5,4-d]pyrimidin-6-yl]methyl}pyrrolidine-1-carboxylic acid tert-butyl ester

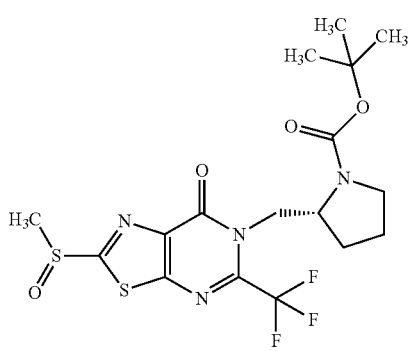 [SMILES: CS(=O)c1nc2c(=O)n(C[C@H]3CCCN3C(=O)OC(C)(C)C)c(C(F)(F)F)nc2s1]

The compound (1.15 g) obtained in Reference Example 411 was treated by a method similar to that in Reference Example 268 to give the title compound (1.30 g).

MS (ESI) m/z; 367 [M+H-Boc]$^+$

Reference Example 419

N-methyl-N-[2-(2-methylsulfinyl-7-oxo-5-trifluoromethyl-7H-[1,3]thiazolo[5,4-d]pyrimidin-6-yl)ethyl]carbamic acid tert-butyl ester

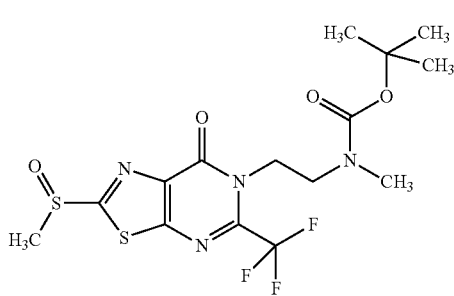 [SMILES: CN(CCn1c(C(F)(F)F)nc2sc(S(C)=O)nc2c1=O)C(=O)OC(C)(C)C]

The compound (440 mg) obtained in Reference Example 412 was treated by a method similar to that in Reference Example 268 to give the title compound (449 mg).

MS (ESI) m/z; 341 [M+H-Boc]$^+$

Reference Example 420

N-methyl-N-{(R)-1-[(4-methylcarbamoyl-2-methyl-sulfanyl-1,3-thiazol-5-yl)amino]-1-oxo-propan-2-yl}carbamic acid tert-butyl ester

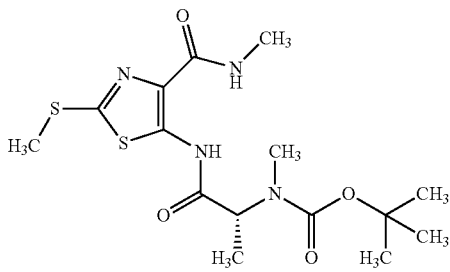 [SMILES: CNC(=O)c1nc(SC)sc1NC(=O)[C@@H](C)N(C)C(=O)OC(C)(C)C]

To a solution of (R)-2-[N-(tert-butoxycarbonyl)-N-methylamino]-propionic acid (430 mg) in DMF were added the compound (287 mg) obtained in Reference Example 136, N,N-diisopropylethylamine (884 μL) and HATU (1.07 g), and the reaction mixture was stirred at room temperature for 6 days. Water was added to the reaction mixture, and the mixture was extracted three times with ethyl acetate. The organic layer was dried over anhydrous sodium sulfate, filtered and concentrated. The residue was purified by silica gel column chromatography (solvent; hexane/ethyl acetate=90/10-40/60) to give the title compound (302 mg).

MS (ESI) m/z; 389 [M+H]$^+$

Reference Example 421

N-methyl-N-{(S)-1-[(4-methylcarbamoyl-2-methyl-sulfanyl-1,3-thiazol-5-yl)amino]-1-oxopropan-2-yl}carbamic acid tert-butyl ester

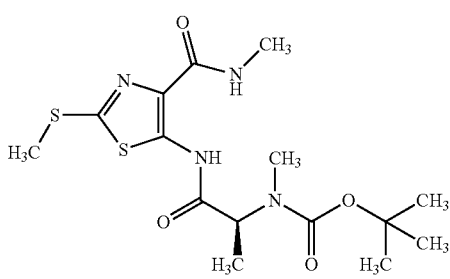 [SMILES: CNC(=O)c1nc(SC)sc1NC(=O)[C@H](C)N(C)C(=O)OC(C)(C)C]

(S)-2-[(N-tert-butoxycarbonyl)-N-methylamino]-propionic acid (601 mg) was treated by a method similar to that in Reference Example 420 to give the title compound (415 mg).

MS (ESI) m/z; 389 [M+H]$^+$

Reference Example 422

N-methyl-N-[(R)-1-(6-methyl-2-methylsulfanyl-7-oxo-6,7-dihydro[1,3]thiazolo[5,4-d]pyrimidin-5-yl)ethyl]carbamic acid tert-butyl ester

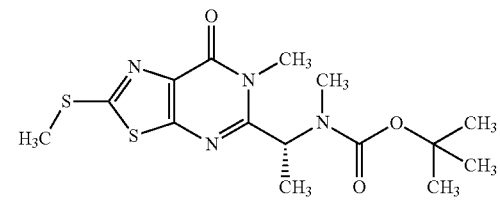 [SMILES: CSc1nc2c(=O)n(C)c([C@@H](C)N(C)C(=O)OC(C)(C)C)nc2s1]

To a solution (3 mL) of the compound (302 mg) obtained in Reference Example 420 in methylene chloride were added chlorotrimethylsilane (491 μL) and triethylamine (1.62 mL), and the reaction mixture was stirred at room temperature overnight. 1.0 mol/L Hydrochloric acid was added to the reaction mixture, and the mixture was extracted twice with chloroform. The organic layer was dried over anhydrous sodium sulfate, filtered and concentrated. The residue was purified by silica gel column chromatography (solvent; hexane/ethyl acetate=95/5-50/50) to give the title compound (239 mg).

MS (ESI) m/z; 371 [M+H]$^+$

Reference Example 423

N-methyl-N-[(S)-1-(6-methyl-2-methylsulfanyl-7-oxo-6,7-dihydro[1,3]thiazolo[5,4-d]pyrimidin-5-yl)ethyl]carbamic acid tert-butyl ester

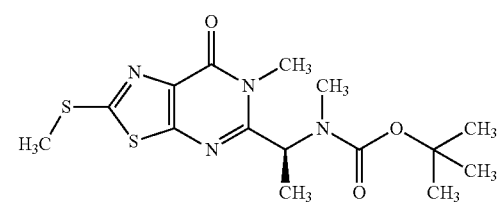 [SMILES: CSc1nc2c(=O)n(C)c([C@H](C)N(C)C(=O)OC(C)(C)C)nc2s1]

The compound (415 mg) obtained in Reference Example 421 was treated by a method similar to that in Reference Example 422 to give the title compound (332 mg).

MS (ESI) m/z; 371 [M+H]$^+$

Reference Example 424

N-methyl-N-[(R)-1-(6-methyl-2-((RS)-methylsulfinyl)-7-oxo-6,7-dihydro[1,3]thiazolo[5,4-d]pyrimidin-5-yl)ethyl]carbamic acid tert-butyl ester

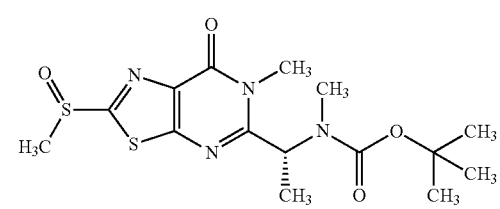 [SMILES: C[C@H](c1nc2sc(S(C)=O)nc2c(=O)n1C)N(C)C(=O)OC(C)(C)C]

To a solution (2.2 mL) of the compound (160 mg) obtained in Reference Example 422 in methylene chloride was added mCPBA (69-75%, 109 mg) under ice-cooling, and the reaction mixture was stirred under ice-cooling for 30 min. To the reaction mixture were added aqueous sodium thiosulfate solution and saturated aqueous sodium hydrogen carbonate solution, and the mixture was extracted three times with chloroform. The organic layer was dried over anhydrous sodium sulfate, filtered and concentrated to give the title compound (162 mg).

MS (ESI) m/z; 387 [M+H]$^+$

Reference Example 425

N-methyl-N-[(S)-1-(6-methyl-2-((RS)-methylsulfinyl)-7-oxo-6,7-dihydro[1,3]thiazolo[5,4-d]pyrimidin-5-yl)ethyl]carbamic acid tert-butyl ester

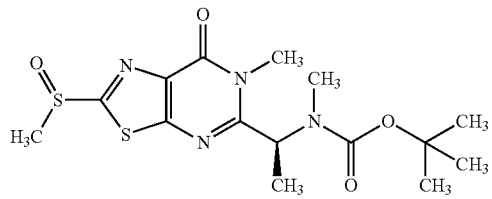 [SMILES: C[C@@H](c1nc2sc(S(C)=O)nc2c(=O)n1C)N(C)C(=O)OC(C)(C)C]

The compound (170 mg) obtained in Reference Example 423 was treated by a method similar to that in Reference Example 424 to give the title compound (191 mg).

MS (ESI) m/z; 387 [M+H]$^+$

Reference Example 426

N-[2,2-difluoro-2-(6-methyl-2-methylsulfanyl-7-oxo-6,7-dihydro[1,3]thiazolo[5,4-d]pyrimidin-5-yl)ethyl]-N-methylcarbamic acid tert-butyl ester

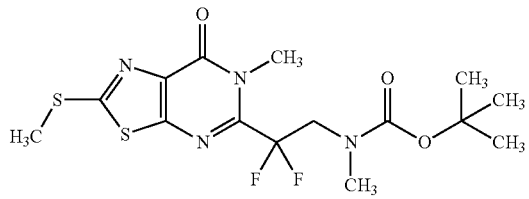 [SMILES: CSc1nc2c(=O)n(C)c(C(F)(F)CN(C)C(=O)OC(C)(C)C)nc2s1]

To a solution (4 mL) of 3-[(tert-butoxycarbonyl)amino]-2,2-difluoropropionic acid potassium salt (350 mg) in THF were added methyl iodide (182 µL) and sodium hydride (60% oil dispersion, 117 mg) under ice-cooling, and the reaction mixture was stirred at room temperature overnight. Water was added, and the mixture was washed with hexane, and the aqueous layer was acidified with 1.0 mol/L hydrochloric acid, and extracted twice with ethyl acetate. The organic layer was washed with saturated brine, dried over anhydrous sodium sulfate, filtered and concentrated. To a solution (3.0 mL) of the residue in DMF were added the compound (202 mg) obtained in Reference Example 136, N,N-diisopropylethylamine (433 µL) and HATU (529 mg), and the reaction mixture was stirred at room temperature overnight. The reaction mixture was diluted with ethyl acetate, washed with saturated brine, dried over anhydrous sodium sulfate, filtered and concentrated. The obtained crude product was dissolved in dichloroethane solution (4.5 mL), triethylamine (2.08 mL) and chlorotrimethylsilane (628 µL) were added, and the reaction mixture was stirred at room temperature overnight. Water was added to the reaction mixture, and the mixture was extracted with ethyl acetate. The organic layer was washed with water and saturated brine, dried over anhydrous sodium sulfate, filtered and concentrated. The residue was purified by silica gel column chromatography (solvent; hexane/ethyl acetate=100/0-50/50) to give the title compound (393 mg).

MS (ESI) m/z; 407 [M+H]$^+$

Reference Example 427

N-[2,2-difluoro-2-(6-methyl-2-methylsulfinyl-7-oxo-6,7-dihydro[1,3]thiazolo[5,4-d]pyrimidin-5-yl)ethyl]-N-methylcarbamic acid tert-butyl ester

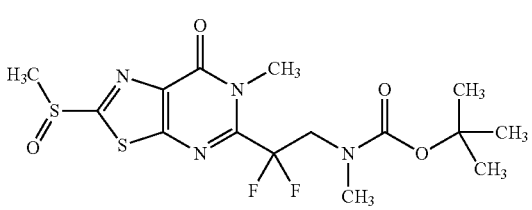 [SMILES: CN(CC(F)(F)c1nc2sc(S(C)=O)nc2c(=O)n1C)C(=O)OC(C)(C)C]

To a solution (2.4 mL) of the compound (240 mg) obtained in Reference Example 426 in methylene chloride was added mCPBA (69-75%, 149 mg) under ice-cooling. The reaction mixture was stirred under ice-cooling for 1 hr, aqueous sodium thiosulfate solution and saturated aqueous sodium hydrogen carbonate solution were added to the reaction mixture, and the mixture was extracted three times with chloroform. The organic layer was dried over anhydrous sodium sulfate, filtered and concentrated to give the title compound (246 mg).

MS (ESI) m/z; 423 [M+H]$^+$

Reference Example 428

5-amino-N-[(S)-1-hydroxypropan-2-yl]-2-methylsulfanyl-1,3-thiazole-4-carboxamide

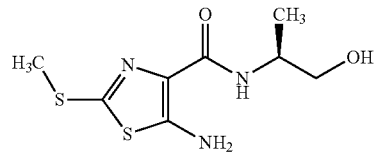

To a solution (11 mL) of 5-amino-2-methylsulfanyl-1,3-thiazole-4-carboxylic acid (500 mg) in DMF were added N,N-diisopropylethylamine (0.64 mL), (S)-2-aminopropanol (0.24 mL), EDC hydrochloride (706 mg) and HOBt monohydrate (563 mg), and the reaction mixture was stirred at room temperature for 20 hr. Water was added to the reaction mixture, and the mixture was extracted three times with chloroform. The organic layer was dried over anhydrous magnesium sulfate, filtered and concentrated. The residue was purified by silica gel column chromatography (solvent; hexane/ethyl acetate=50/50-0/100) to give the title compound (595 mg).

MS (ESI) m/z; 248 [M+H]+

Reference Example 429

5-amino-N-[(R)-1-hydroxypropan-2-yl]-2-methyl-sulfanyl-1,3-thiazole-4-carboxamide

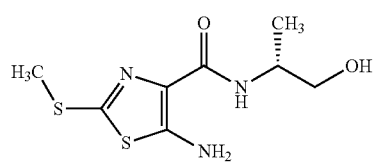

5-Amino-2-methylsulfanyl-1,3-thiazole-4-carboxylic acid (500 mg) was treated by a method similar to that in Reference Example 428 to give the title compound (556 mg).

MS (ESI) m/z; 248 [M+H]+

Reference Example 430 trifluoroacetic acid (S)-2-{[{2-methylsulfanyl-5-[(trifluoroacetyl)amino]-1,3-thiazol-4-yl}carbonyl]amino}propyl ester

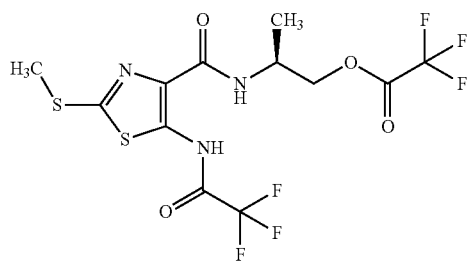 [SMILES: CSc1nc(C(=O)N[C@@H](C)COC(=O)C(F)(F)F)c(NC(=O)C(F)(F)F)s1]

To a solution (15 mL) of the compound (593 mg) obtained in Reference Example 428 in methylene chloride were added pyridine (424 μL) and trifluoroacetic anhydride (666 μL) under ice-cooling, and the reaction mixture was stirred at room temperature for 3 hr. 1.0 mol/L Hydrochloric acid was added to the reaction mixture, and the mixture was extracted twice with methylene chloride. The organic layer was washed with saturated brine, dried over anhydrous sodium sulfate, filtered and concentrated to give the title compound (1.05 g).

MS (ESI) m/z; 440 [M+H]+

Reference Example 431 trifluoroacetic acid (R)-2-{[{2-methylsulfanyl-5-[(trifluoroacetyl)amino]-1,3-thiazol-4-yl}carbonyl]amino}propyl ester

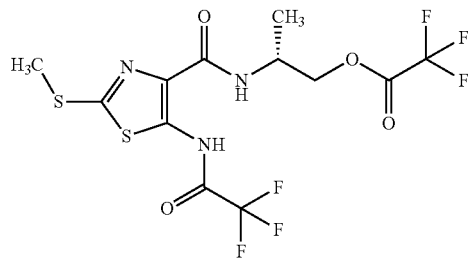 [SMILES: CSc1nc(C(=O)N[C@H](C)COC(=O)C(F)(F)F)c(NC(=O)C(F)(F)F)s1]

The compound (305 mg) obtained in Reference Example 429 was treated by a method similar to that in Reference Example 430 to give the title compound (572 mg).

MS (ESI) m/z; 440 [M+H]+

Reference Example 432

6-((S)-1-hydroxypropan-2-yl)-2-methylsulfanyl-5-trifluoromethyl-6H-[1,3]thiazolo[5,4-d]pyrimidin-7-one

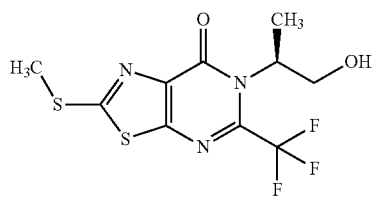 [SMILES: CSc1nc2c(=O)n([C@@H](C)CO)c(C(F)(F)F)nc2s1]

To a solution (19 mL) of the compound (1.05 g) obtained in Reference Example 430 in dichloroethane were added trifluoroacetic anhydride (2.67 mL) and triethylamine (3.34 mL), and the reaction mixture was stirred at room temperature for 3 days. Water was added to the reaction mixture, and the mixture was extracted twice with chloroform. The combined organic layer was washed with 1.0 mol/L hydrochloric acid and saturated brine, dried over anhydrous sodium sulfate, filtered and concentrated. The residue was diluted with methanol (15 mL), sodium hydrogen carbonate (1010 mg) was added under ice-cooling, and the reaction mixture was stirred at 0° C. for 30 min. To the reaction mixture was added saturated aqueous ammonium chloride solution, methanol was evaporated under reduced pressure, and the obtained mixture was extracted twice with ethyl acetate. The combined organic layer was washed with saturated brine, dried over anhydrous sodium sulfate, filtered and concentrated. The residue was purified by NH silica gel column chromatography (solvent; ethyl acetate), to the obtained product was added diethyl ether/hexane=8/1, and the solid was collected by filtration to give the title compound (470 mg).

MS (ESI) m/z; 326 [M+H]+

Reference Example 433

6-((R)-1-hydroxypropan-2-yl)-2-methylsulfanyl-5-trifluoromethyl-6H-[1,3]thiazolo[5,4-d]pyrimidin-7-one

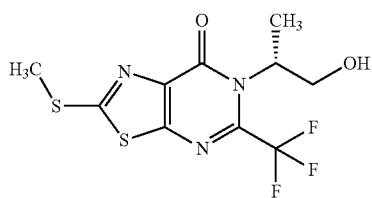 [SMILES: CSc1nc2c(=O)n([C@H](C)CO)c(C(F)(F)F)nc2s1]

The compound (572 mg) obtained in Reference Example 431 was treated by a method similar to that in Reference Example 432 to give the title compound (265 mg).
MS (ESI) m/z; 326 [M+H]$^+$

Reference Example 434

6-((S)-1-hydroxypropan-2-yl)-2-((RS)-methylsulfinyl)-5-trifluoromethyl-6H-[1,3]thiazolo[5,4-d]pyrimidin-7-one

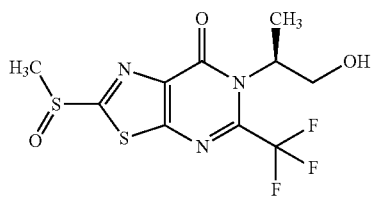 [SMILES: C[C@@H](CO)n1c(C(F)(F)F)nc2sc(S(C)=O)nc2c1=O]

To a solution (10 mL) of the compound (250 mg) obtained in Reference Example 432 in methylene chloride was added mCPBA (69-75%, 208 mg) under ice-cooling. The reaction mixture was stirred under ice-cooling for 2 hr, aqueous sodium thiosulfate solution and saturated aqueous sodium hydrogen carbonate solution were added to the reaction mixture, and the mixture was extracted twice with chloroform. The organic layer was dried over anhydrous sodium sulfate, filtered and concentrated to give the title compound (261 mg).
MS (ESI) m/z; 342 [M+H]$^+$

Reference Example 435

6-((R)-1-hydroxypropan-2-yl)-2-((RS)-methylsulfinyl)-5-trifluoromethyl-6H-[1,3]thiazolo[5,4-d]pyrimidin-7-one

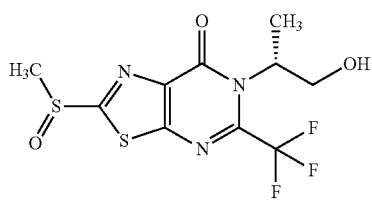 [SMILES: C[C@H](CO)n1c(C(F)(F)F)nc2sc(S(C)=O)nc2c1=O]

The compound (100 mg) obtained in Reference Example 433 was treated by a method similar to that in Reference Example 434 to give the title compound (92.3 mg).
MS (ESI) m/z; 342 [M+H]$^+$

Reference Example 436

N-methyl-5-[(3-methoxypropionyl)amino]-2-methylsulfanyl-1,3-thiazole-4-carboxamide

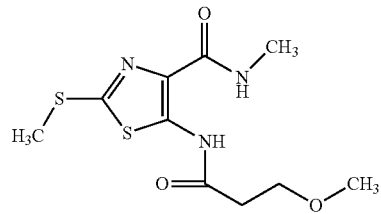

To a solution (5.0 mL) of 3-methoxypropionic acid (875 mg) in methylene chloride were added oxalyl chloride (1.42 mL) and DMF (one drop), and the reaction mixture was stirred at room temperature for 2 hr. The reaction mixture was concentrated under reduced pressure, and the residue was dissolved in methylene chloride (1.0 mL) and added dropwise to a solution (10 mL) of the compound (1.3 g) obtained in Reference Example 136 and triethylamine (1.22 g) in methylene chloride under ice-cooling. The reaction mixture was stirred at room temperature for 1.5 hr, water was added to the reaction mixture, and the mixture was extracted twice with chloroform. The organic layer was dried over anhydrous sodium sulfate, filtered and concentrated. The residue was purified by silica gel column chromatography (solvent; hexane/ethyl acetate=50/50-20/80) to give the title compound (1.4 g).
MS (ESI) m/z; 290 [M+H]$^+$

Reference Example 437

N-ethyl-5-[(3-methoxypropionyl)amino]-2-methylsulfanyl-1,3-thiazole-4-carboxamide

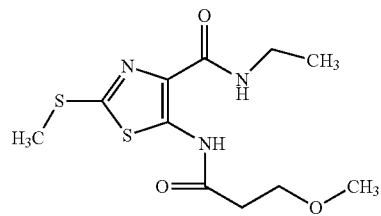

The compound (1.0 g) obtained in Reference Example 137 was treated by a method similar to that in Reference Example 436 to give the title compound (1.63 g).
MS (ESI) m/z; 304 [M+H]$^+$

Reference Example 438

5-[(3-methoxypropionyl)amino]-2-methylsulfanyl-N-(propan-2-yl)-1,3-thiazole-4-carboxamide

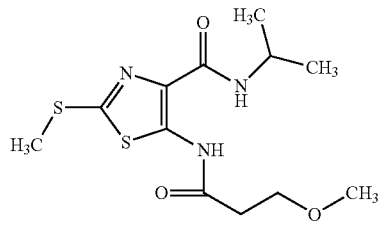

The compound (1.06 g) obtained in Reference Example 138 was treated by a method similar to that in Reference Example 436 to give the title compound (1.89 g).
MS (ESI) m/z; 318 [M+H]$^+$

Reference Example 439

5-(2-methoxyethyl)-6-methyl-2-methylsulfanyl-6H-[1,3]thiazolo[5,4-d]pyrimidin-7-one

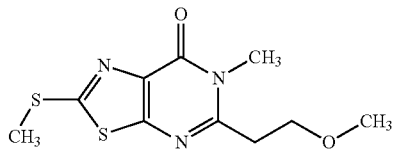

To a solution (20 mL) of the compound (1.4 g) obtained in Reference Example 436 in dichloroethane were added chlorotrimethylsilane (2.65 g) and triethylamine (7.4 g), and the reaction mixture was stirred at room temperature overnight. 1.0 mol/L Hydrochloric acid was added to the reaction mixture, and the mixture was extracted twice with chloroform. The organic layer was dried over anhydrous sodium sulfate, filtered and concentrated. The residue was purified by silica gel column chromatography (solvent; hexane/ethyl acetate=50/50-0/100) to give the title compound (990 mg).
MS (ESI) m/z; 272 [M+H]$^+$

Reference Example 440

6-ethyl-5-(2-methoxyethyl)-2-methylsulfanyl-6H-[1,3]thiazolo[5,4-d]pyrimidin-7-one

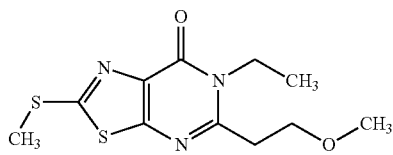

The compound (1.63 g) obtained in Reference Example 437 was treated by a method similar to that in Reference Example 439 to give the title compound (856 mg).
MS (ESI) m/z; 286 [M+H]$^+$

Reference Example 441

5-(2-methoxyethyl)-2-methylsulfanyl-6-(propan-2-yl)-6H-[1,3]thiazolo[5,4-d]pyrimidin-7-one

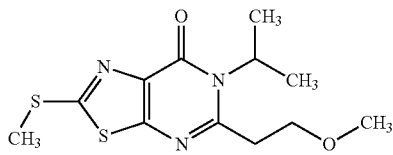

The compound (1.89 g) obtained in Reference Example 438 was treated by a method similar to that in Reference Example 439 to give the title compound (622 mg).
MS (ESI) m/z; 300 [M+H]$^+$

Reference Example 442

5-(2-hydroxyethyl)-6-methyl-2-methylsulfanyl-6H-[1,3]thiazolo[5,4-d]pyrimidin-7-one

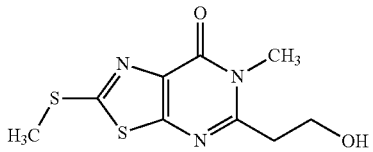 [SMILES: CSc1nc2c(=O)n(C)c(CCO)nc2s1]

A solution (18 mL) of the compound (980 mg) obtained in Reference Example 439 in methylene chloride was ice-cooled, and 1.0 mol/L boron tribromide methylene chloride solution (4.0 mL) was added dropwise. The reaction mixture was stirred at room temperature for 1 hr, to the ice-cooled reaction mixture was added saturated aqueous sodium hydrogen carbonate solution, and the mixture was extracted three times with methylene chloride. The organic layer was dried over anhydrous sodium sulfate, filtered and concentrated. To the residue was added hexane, and the solid was collected by filtration, and dried to give the title compound (835 mg).
MS (ESI) m/z; 258 [M+H]$^+$

Reference Example 443

6-ethyl-5-(2-hydroxyethyl)-2-methylsulfanyl-6H-[1,3]thiazolo[5,4-d]pyrimidin-7-one

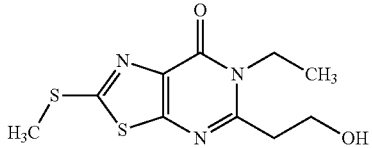 [SMILES: CCn1c(CCO)nc2sc(SC)nc2c1=O]

The compound (856 mg) obtained in Reference Example 440 was treated by a method similar to that in Reference Example 442 to give the title compound (758 mg).
MS (ESI) m/z; 272 [M+H]$^+$

Reference Example 444

5-(2-hydroxyethyl)-2-methylsulfanyl-6-(propan-2-yl)-6H-[1,3]thiazolo[5,4-d]pyrimidin-7-one

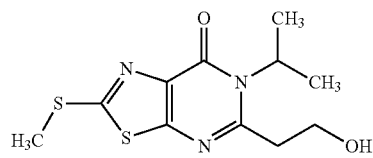

The compound (622 mg) obtained in Reference Example 441 was treated by a method similar to that in Reference Example 442 to give the title compound (500 mg).

MS (ESI) m/z; 286 [M+H]$^+$

Reference Example 445

5-(2-hydroxyethyl)-6-methyl-2-methylsulfinyl-6H-[1,3]thiazolo[5,4-d]pyrimidin-7-one

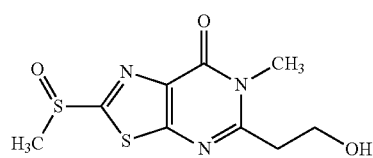 [SMILES: Cn1c(CCO)nc2sc(S(C)=O)nc2c1=O]

To a solution (18 mL) of the compound (820 mg) obtained in Reference Example 442 in methylene chloride was added mCPBA (69-75%, 880 mg) under ice-cooling. The reaction mixture was stirred under ice-cooling for 3 hr, to the reaction mixture were added aqueous sodium thiosulfate solution and saturated aqueous sodium hydrogen carbonate solution, and the mixture was extracted three times with chloroform. The organic layer was dried over anhydrous sodium sulfate, filtered and concentrated. The obtained residue was purified by silica gel column chromatography (solvent; chloroform/methanol=100/0-90/10) to give the title compound (750 mg).

MS (ESI) m/z; 274 [M+H]$^+$

Reference Example 446

6-ethyl-5-(2-hydroxyethyl)-2-methylsulfinyl-6H-[1,3]thiazolo[5,4-d]pyrimidin-7-one

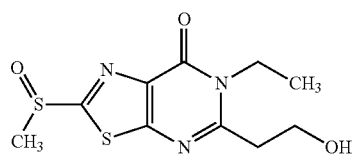 [SMILES: CCn1c(CCO)nc2sc(S(C)=O)nc2c1=O]

The compound (758 mg) obtained in Reference Example 443 was treated by a method similar to that in Reference Example 445 to give the title compound (543 mg).

MS (ESI) m/z; 288 [M+H]$^+$

Reference Example 447

5-(2-hydroxyethyl)-2-methylsulfinyl-6-(propan-2-yl)-6H-[1,3]thiazolo[5,4-d]pyrimidin-7-one

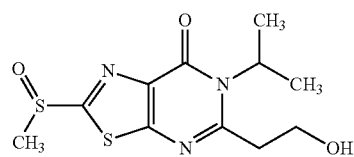 [SMILES: CC(C)n1c(CCO)nc2sc(S(C)=O)nc2c1=O]

The compound (500 mg) obtained in Reference Example 444 was treated by a method similar to that in Reference Example 445 to give the title compound (446 mg).

MS (ESI) m/z; 302 [M+H]$^+$

Reference Example 448

N-ethyl-5-[(4-methoxybutyryl)amino]-2-methylsulfanyl-1,3-thiazole-4-carboxamide

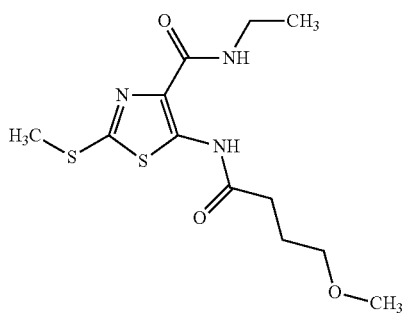

To a solution (3.5 mL) of 4-methoxybutyric acid (761 mg) is in methylene chloride were added oxalyl chloride (3.5 mL) and DMF (one drop), and the reaction mixture was stirred at room temperature for 2 hr. The reaction mixture was concentrated under reduced pressure, and the residue was dissolved in methylene chloride (1 mL), and added dropwise to a solution (9.0 mL) of the compound (1.0 g) obtained in Reference Example 137 and triethylamine (1.28 mL) in methylene chloride under ice-cooling. The reaction mixture was stirred at room temperature for 1 hr, to the reaction mixture were added water and saturated aqueous sodium hydrogen carbonate solution, and the mixture was extracted twice with chloroform. The organic layer was dried over anhydrous sodium sulfate, filtered and concentrated to give the title compound (1.7 g).

MS (ESI) m/z; 318 [M+H]$^+$

Reference Example 449

6-ethyl-5-(3-methoxypropyl)-2-methylsulfanyl-6H-[1,3]thiazolo[5,4-d]pyrimidin-7-one

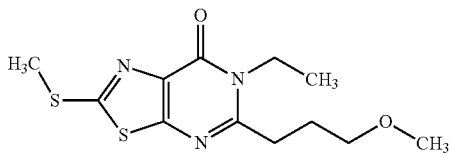

To a solution (20 mL) of the compound (1.7 g) obtained in Reference Example 448 in dichloroethane were added chlorotrimethylsilane (2.91 mL) and triethylamine (9.62 mL), and the reaction mixture was stirred at room temperature overnight. Water was added to the reaction mixture, and the mixture was extracted twice with ethyl acetate. The organic layer was dried over anhydrous sodium sulfate, filtered and concentrated. The residue was purified by silica gel column chromatography (solvent; hexane/ethyl acetate=70/30-0/100) to give the title compound (1.163 g).

MS (ESI) m/z; 300 [M+H]$^+$

Reference Example 450

6-ethyl-5-(3-hydroxypropyl)-2-methylsulfanyl-6H-[1,3]thiazolo[5,4-d]pyrimidin-7-one

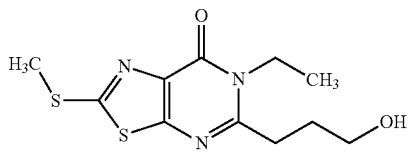 [SMILES: CCn1c(CCCO)nc2sc(SC)nc2c1=O]

To a solution (25 mL) of the compound (1.16 g) obtained in Reference Example 449 in methylene chloride was added dropwise 1.0 mol/L boron tribromide methylene chloride solution (3.87 mL) under ice-cooling. The reaction mixture was stirred under ice-cooling for 1 hr, to the ice-cooled reaction mixture was added saturated aqueous sodium hydrogen carbonate solution, and the mixture was extracted three times with methylene chloride. The organic layer was dried over anhydrous sodium sulfate, filtered and concentrated. The residue was purified by silica gel column chromatography (solvent; hexane/ethyl acetate=70/30-0/100) to give the title compound (643 mg).

MS (ESI) m/z; 286 [M+H]$^+$

Reference Example 451

6-ethyl-5-(3-hydroxypropyl)-2-methylsulfinyl-6H-[1,3]thiazolo[5,4-d]pyrimidin-7-one

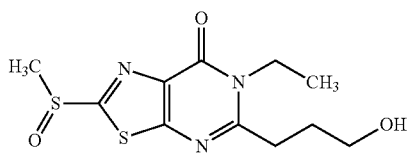 [SMILES: CCn1c(CCCO)nc2sc(S(C)=O)nc2c1=O]

To a solution (10 mL) of the compound (643 mg) obtained in Reference Example 450 in methylene chloride was added mCPBA (69-75%, 569 mg) under ice-cooling. The reaction mixture was stirred under ice-cooling for 2 hr, to the reaction mixture were added aqueous sodium thiosulfate solution and saturated aqueous sodium hydrogen carbonate solution, and the mixture was extracted three times with chloroform. The organic layer was dried over anhydrous sodium sulfate, filtered and concentrated to give the title compound (476 mg).

MS (ESI) m/z; 302 [M+H]$^+$

Reference Example 452

6-(2-hydroxyethyl)-2-methylsulfanyl-5-trifluoromethyl-6H-[1,3]thiazolo[5,4-d]pyrimidin-7-one

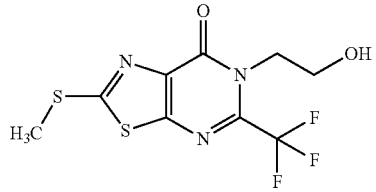 [SMILES: CSc1nc2c(=O)n(CCO)c(C(F)(F)F)nc2s1]

A solution (12 mL) of the compound (600 mg) obtained in Reference Example 247 in methylene chloride was ice-cooled, and 1.0 mol/L boron tribromide methylene chloride solution (1.84 mL) was added dropwise. The reaction mixture was stirred under ice-cooling for 1 hr, to the reaction mixture was added saturated aqueous sodium hydrogen carbonate solution, and the mixture was extracted three times with methylene chloride. The organic layer was dried over anhydrous sodium sulfate, filtered and concentrated. The residue was purified by silica gel column chromatography (solvent; hexane/ethyl acetate=80/20-30/70) to give the title compound (622 mg).

MS (ESI) m/z; 312 [M+H]$^+$

Reference Example 453

6-(2-hydroxyethyl)-2-methylsulfinyl-5-trifluoromethyl-6H-[1,3]thiazolo[5,4-d]pyrimidin-7-one

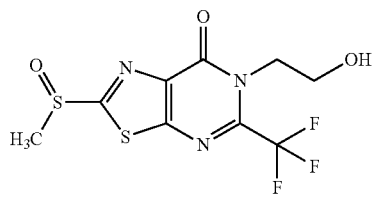 [SMILES: CS(=O)c1nc2c(=O)n(CCO)c(C(F)(F)F)nc2s1]

To a solution (10 mL) of the compound (621 mg) obtained in Reference Example 452 in methylene chloride was added mCPBA (69-75%, 482 mg) under ice-cooling. The reaction mixture was stirred under ice-cooling for 1 hr, to the reaction mixture were added aqueous sodium thiosulfate solution and saturated aqueous sodium hydrogen carbonate solution, and the mixture was extracted 4 times with methylene chloride. The organic layer was dried over anhydrous sodium sulfate, filtered and concentrated to give the title compound (468 mg).

MS (ESI) m/z; 328 [M+H]$^+$

Reference Example 454

5-[(3-methoxy-2,2-dimethyl-propionyl)amino]-2-methylsulfanyl-N-methyl-1,3-thiazole-4-carboxamide

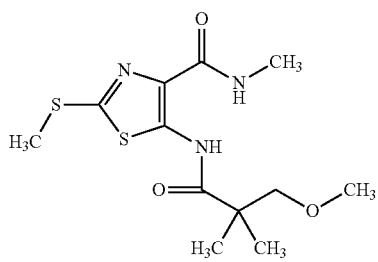

To a solution (4.0 mL) of 3-methoxy-2,2-dimethyl-propionic acid (1.06 g) in methylene chloride were added oxalyl chloride (1.36 mL) and DMF (one drop), and the reaction mixture was stirred at room temperature for 2 hr. The reaction mixture was concentrated under reduced pressure, and the residue was dissolved in methylene chloride (1.0 mL), and added dropwise to a solution (8 mL) of the compound (1.16 g) obtained in Reference Example 136 and triethylamine (1.6 mL) in methylene chloride under ice-cooling. The reaction mixture was stirred at room temperature for 2 hr, water was added to the reaction mixture, and the mixture was extracted twice with chloroform. The organic layer was washed with saturated aqueous sodium hydrogen carbonate solution, dried over anhydrous sodium sulfate, filtered and concentrated to give the title compound (2.20 g).

MS (ESI) m/z; 318 [M+H]$^+$

Reference Example 455

5-(1-methoxy-2-methylpropan-2-yl)-6-methyl-2-methylsulfanyl-6H-[1,3]thiazolo[5,4-d]pyrimidin-7-one

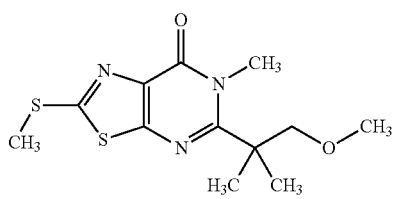

To a solution (25 mL) of the compound (2.20 g) obtained in Reference Example 454 in methylene chloride were added chlorotrimethylsilane (3.62 mL) and triethylamine (12.0 mL), and the reaction mixture was stirred at room temperature overnight. Trimethylsilyl trifluoromethanesulfonate (5.20 mL) and triethylamine (12.0 mL) were added, and the reaction mixture was stirred at room temperature for 7 days. Water was added to the reaction mixture, and the mixture was extracted twice with chloroform. The organic layer was dried over anhydrous sodium sulfate, filtered and concentrated. The residue was purified by silica gel column chromatography (solvent; hexane/ethyl acetate=100/0-50/50) to give the title compound (322 mg).

MS (ESI) m/z; 300 [M+H]$^+$

Reference Example 456

5-(1-hydroxy-2-methylpropan-2-yl)-6-methyl-2-methylsulfanyl-6H-[1,3]thiazolo[5,4-d]pyrimidin-7-one

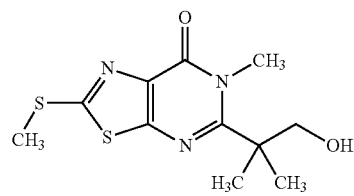 [SMILES: CSc1nc2c(=O)n(C)c(C(C)(C)CO)nc2s1]

To a solution (6.0 mL) of the compound (322 mg) obtained in Reference Example 455 in methylene chloride was added dropwise 1.0 mol/L boron tribromide methylene chloride solution (1.08 mL) under ice-cooling, and the reaction mixture was stirred under ice-cooling for 2 hr, and at room temperature for 7 hr. To the reaction mixture was added saturated aqueous sodium hydrogen carbonate solution, and the mixture was extracted three times with methylene chloride. The organic layer was dried over anhydrous sodium sulfate, filtered and concentrated. The residue was purified by silica gel column chromatography (solvent; hexane/ethyl acetate=70/30-0/100) to give the title compound (261 mg).

MS (ESI) m/z; 286 [M+H]$^+$

Reference Example 457

5-(1-hydroxy-2-methylpropan-2-yl)-2-methylsulfinyl-6-methyl-6H-[1,3]thiazolo[5,4-d]pyrimidin-7-one

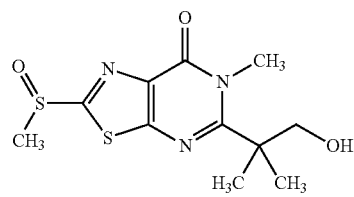 [SMILES: Cn1c(C(C)(C)CO)nc2sc(S(C)=O)nc2c1=O]

To a solution (2.3 mL) of the compound (130 mg) obtained in Reference Example 456 in methylene chloride was added mCPBA (69-75%, 115 mg) under ice-cooling. The reaction mixture was stirred under ice-cooling for 30 min, to the reaction mixture were added aqueous sodium thiosulfate solution and saturated aqueous sodium hydrogen carbonate solution, and the mixture was extracted three times with chloroform. The organic layer was dried over anhydrous sodium sulfate, filtered and concentrated to give the title compound (156 mg).

MS (ESI) m/z; 302 [M+H]$^+$

Reference Example 458

5-[2-(hydroxymethyl) phenyl]-6-methyl-2-methyl-sulfanyl-6H-[1,3]thiazolo[5,4-d]pyrimidin-7-one

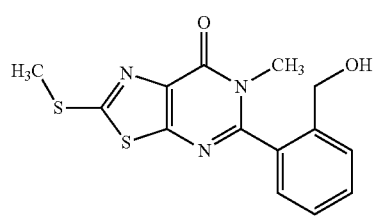 [SMILES: CSc1nc2c(=O)n(C)c(-c3ccccc3CO)nc2s1]

To a solution (16 mL) of the compound (496 mg) obtained in Reference Example 366 in dimethoxyethane were successively added (2-hydroxymethylphenyl)boronic acid (365 mg), tetrakis(triphenylphosphine)palladium(0) (116 mg) and aqueous solution (4.0 mL) of sodium carbonate (848 mg) at room temperature, and the reaction mixture was stirred at 100° C. for 4 hr. After confirmation of the completion of the reaction, the reaction mixture was cooled to room temperature, and extracted with chloroform. The organic layer was washed with saturated brine, dried over anhydrous magnesium sulfate, filtered and concentrated. The obtained residue was purified by silica gel column chromatography (solvent; chloroform/methanol=100/0-97/3) to give the title compound (210.7 mg).

MS (ESI) m/z; 320 [M+H]$^+$

Reference Example 459

5-[3-(hydroxymethyl)phenyl]-6-methyl-2-methylsul-fanyl-6H-[1,3]thiazolo[5,4-d]pyrimidin-7-one

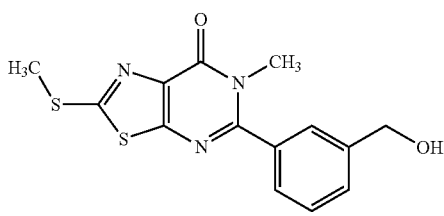 [SMILES: CSc1nc2c(=O)n(C)c(-c3cccc(CO)c3)nc2s1]

The compound (496 mg) obtained in Reference Example 366 was treated by a method similar to that in Reference Example 458 to give the title compound (198 mg).

MS (ESI) m/z; 320 [M+H]$^+$

Reference Example 460

5-[4-(hydroxymethyl)phenyl]-6-methyl-2-methylsul-fanyl-6H-[1,3]thiazolo[5,4-d]pyrimidin-7-one

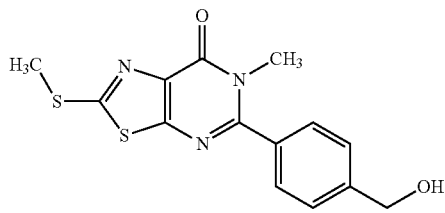 [SMILES: CSc1nc2c(=O)n(C)c(-c3ccc(CO)cc3)nc2s1]

The compound (496 mg) obtained in Reference Example 366 was treated by a method similar to that in Reference Example 458 to give the title compound (164 mg).

MS (ESI) m/z; 320 [M+H]$^+$

Reference Example 461

5-[2-(hydroxymethyl)phenyl]-6-methyl-2-methyl-sulfinyl-6H-[1,3]thiazolo[5,4-d]pyrimidin-7-one

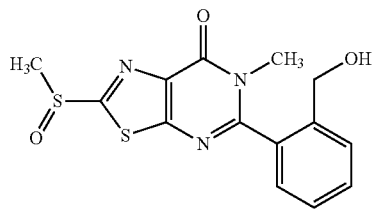 [SMILES: Cn1c(-c2ccccc2CO)nc2sc(S(C)=O)nc2c1=O]

To a solution (10 mL) of the compound (335 mg) obtained in Reference Example 458 in methylene chloride was added mCPBA (69-75%, 217 mg) under ice-cooling. The reaction mixture was stirred under ice-cooling for 6 hr, to the reaction mixture were added aqueous sodium thiosulfate solution and saturated aqueous sodium hydrogen carbonate solution, and the mixture was extracted three times with chloroform. The organic layer was dried over anhydrous magnesium sulfate, filtered and concentrated to give the title compound (340 mg).

MS (ESI) m/z; 336 [M+H]$^+$

Reference Example 462

5-[3-(hydroxymethyl)phenyl]-6-methyl-2-methyl-sulfinyl-6H-[1,3]thiazolo[5,4-d]pyrimidin-7-one

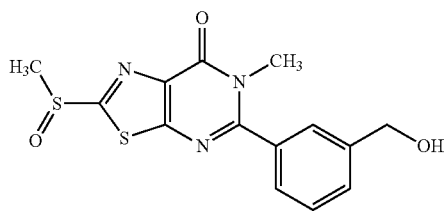 [SMILES: Cn1c(-c2cccc(CO)c2)nc2sc(S(C)=O)nc2c1=O]

The compound (187 mg) obtained in Reference Example 459 was treated by a method similar to that in Reference Example 461 to give the title compound (192 mg).

MS (ESI) m/z; 336 [M+H]$^+$

Reference Example 463

5-[4-(hydroxymethyl)phenyl]-6-methyl-2-methyl-sulfinyl-6H-[1,3]thiazolo[5,4-d]pyrimidin-7-one

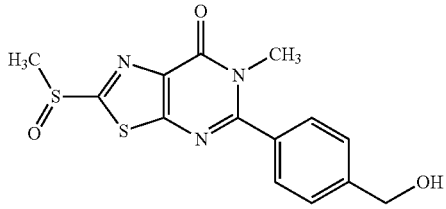 [SMILES: Cn1c(-c2ccc(CO)cc2)nc2sc(S(C)=O)nc2c1=O]

The compound (152 mg) obtained in Reference Example 460 was treated by a method similar to that in Reference Example 461 to give the title compound (136 mg).
MS (ESI) m/z; 336 [M+H]$^+$

Reference Example 464

N-methyl-N-{2-[(6-methyl-2-methylsulfanyl-7-oxo-6,7-dihydro[1,3]thiazolo[5,4-d]pyrimidin-5-yl)oxy]ethyl}carbamic acid tert-butyl ester

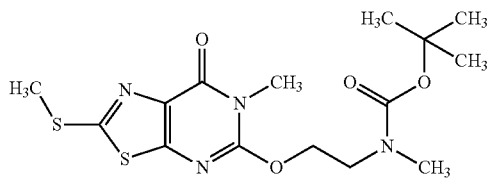 [SMILES: CSc1nc2c(=O)n(C)c(OCCN(C)C(=O)OC(C)(C)C)nc2s1]

To a solution (80 mL) of the compound (2.0 g) obtained in Reference Example 366 and (2-hydroxyethyl)-methyl-carbamic acid tert-butyl ester (1.70 g) in DMF was added sodium hydride (60% oil dispersion, 400 mg) under ice-cooling. The reaction mixture was stirred at room temperature for 3 hr, water was added, and the mixture was extracted twice with ethyl acetate. The organic layer was dried over anhydrous magnesium sulfate, filtered and concentrated. The residue was purified by silica gel column chromatography (solvent; hexane/ethyl acetate=50/50-30/70), to the obtained product was added hexane, and the solid was collected by filtration, and dried to give the title compound (1.66 g).
MS (ESI) m/z; 387 [M+H]$^+$

Reference Example 465

N-methyl-N-{2-[(6-methyl-2-methylsulfinyl-7-oxo-6,7-dihydro[1,3]thiazolo[5,4-d]pyrimidin-5-yl)oxy]ethyl}carbamic acid tert-butyl ester

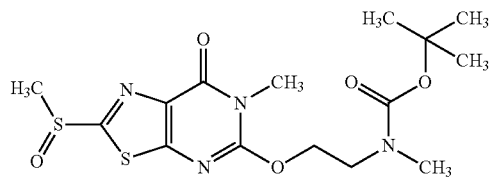 [SMILES: CN(CCOc1nc2sc(S(C)=O)nc2c(=O)n1C)C(=O)OC(C)(C)C]

To a solution (40 mL) of the compound (1.65 g) obtained in Reference Example 464 in methylene chloride was added mCPBA (69-75%, 1.17 g) under ice-cooling. The reaction mixture was stirred under ice-cooling for 1 hr, to the reaction mixture were added aqueous sodium thiosulfate solution and saturated aqueous sodium hydrogen carbonate solution, and the mixture was extracted twice with chloroform. The organic layer was dried over anhydrous sodium sulfate, filtered and concentrated to give the title compound (1.63 g).
MS (ESI) m/z; 403 [M+H]$^+$

Reference Example 466

1-acetoxycyclopropanecarboxylic acid

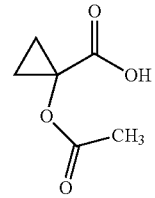

A mixed solution of 1-hydroxycyclopropanecarboxylic acid (0.78 g) and acetic anhydride (3.1 mL) was stirred with heating at 140° C. for 2 hr. The reaction mixture was cooled to room temperature, water (5.0 mL) was added, and the solvent was evaporated under reduced pressure. To the obtained product was added diisopropyl ether, and the solid was collected by filtration to give the title compound (0.33 g).
MS (ESI) m/z; 145 [M+H]$^+$

Reference Example 467

1-acetoxycyclobutanecarboxylic acid

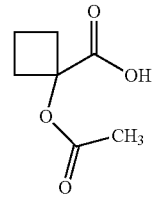

1-hydroxycyclobutanecarboxylic acid (1.0 g) was treated by a method similar to that in Reference Example 466 to give the title compound (1.3 g).
MS (ESI) m/z; 159 [M+H]+

Reference Example 468 acetic acid (RS)-1-[(4-methylcarbamoyl-2-methylsulfanyl-1,3-thiazol-5-yl)amino]-1-oxopropan-2-yl ester

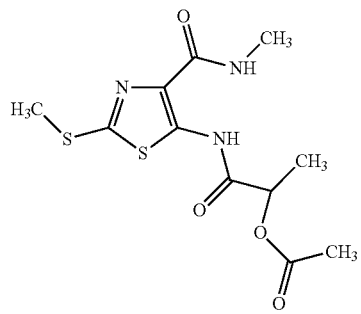 [SMILES: CNC(=O)c1nc(SC)sc1NC(=O)C(C)OC(C)=O]

To a solution (3.0 mL) of 2-acetoxypropionic acid (936 mg) in methylene chloride were added oxalyl chloride (1.2 mL) and DMF (one drop), and the reaction mixture was stirred at room temperature for 2 hr. The reaction mixture was concentrated under reduced pressure, and the residue was dissolved in methylene chloride (2.0 mL) and added dropwise to a solution (5.0 mL) of the compound (800 mg) obtained in Reference Example 136 and triethylamine (1.1 mL) in methylene chloride under ice-cooling. The reaction mixture was stirred at room temperature for 5 hr, to the reaction mixture was added water, and the mixture was extracted twice with ethyl acetate. The organic layer was dried over anhydrous sodium sulfate, filtered and concentrated. The residue was purified by silica gel column chromatography (solvent; hexane/ethyl acetate=70/30-20/80) to give the title compound (1.06 g).
MS (ESI) m/z; 318 [M+H]+

Reference Example 469 acetic acid 1-[(4-methylcarbamoyl-2-methylsulfanyl-1,3-thiazol-5-yl)carbamoyl]cyclopropyl ester

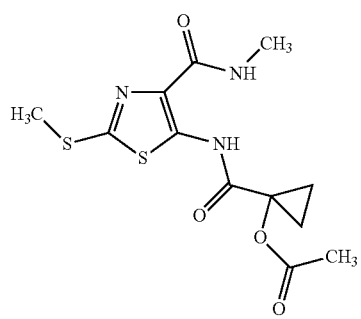 [SMILES: CNC(=O)c1nc(SC)sc1NC(=O)C1(OC(C)=O)CC1]

The compound (0.33 g) obtained in Reference Example 466 was treated by a method similar to that in Reference Example 468 to give the title compound (0.6 g).
MS (ESI) m/z; 330 [M+H]+

Reference Example 470 acetic acid 1-[(4-methylcarbamoyl-2-methylsulfanyl-1,3-thiazol-5-yl)carbamoyl]cyclobutyl ester

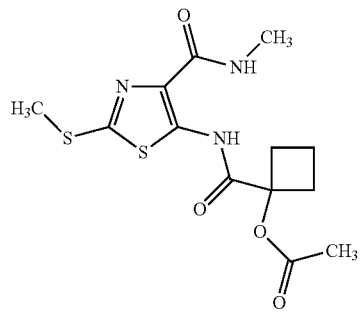 [SMILES: CNC(=O)c1nc(SC)sc1NC(=O)C1(OC(C)=O)CCC1]

The compound (1.3 g) obtained in Reference Example 467 was treated by a method similar to that in Reference Example 468 to give the title compound (2.06 g).
MS (ESI) m/z; 344 [M+H]+

Reference Example 471 acetic acid (RS)-1-[6-methyl-2-methylsulfanyl-7-oxo-6,7-dihydro[1,3]thiazolo[5,4-d]pyrimidin-5-yl] ethyl ester

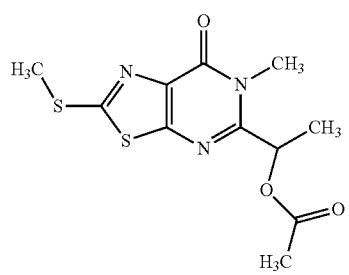 [SMILES: CSc1nc2c(=O)n(C)c(C(C)OC(C)=O)nc2s1]

To a solution (21 mL) of the compound (1.06 g) obtained in Reference Example 468 in dichloroethane were added chlorotrimethylsilane (2.11 mL) and triethylamine (6.98 mL), and the reaction mixture was heated at 80° C. for 9 hr. The reaction mixture was cooled to room temperature, 1.0 mol/L hydrochloric acid was added to the reaction mixture, and the mixture was extracted twice with chloroform. The organic layer was dried over anhydrous sodium sulfate, filtered and concentrated. The residue was purified by silica gel column chromatography (solvent; hexane/ethyl acetate=70/30-0/100) to give the title compound (869 mg).
MS (ESI) m/z; 300 [M+H]+

Reference Example 472 acetic acid 1-(6-methyl-2-methylsulfanyl-7-oxo-6,7-dihydro[1,3]thiazolo[5,4-d]pyrimidin-5-yl)cyclopropyl ester

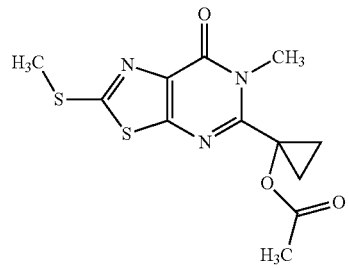

The compound (0.6 g) obtained in Reference Example 469 was treated by a method similar to that in Reference Example 471 to give the title compound (0.53 g).
MS (ESI) m/z; 312 [M+H]$^+$

Reference Example 473 acetic acid 1-(6-methyl-2-methylsulfanyl-7-oxo-6,7-dihydro[1,3]thiazolo[5,4-d]pyrimidin-5-yl)cyclobutyl ester

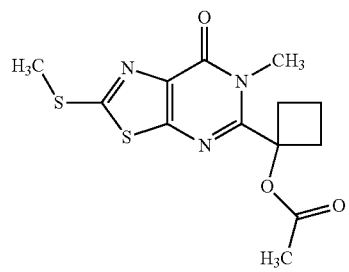 [SMILES: CSc1nc2c(=O)n(C)c(C3(OC(C)=O)CCC3)nc2s1]

To a solution (60 mL) of the compound (2.06 g) obtained in Reference Example 470 in methylene chloride were added trimethylsilyl trifluoromethanesulfonate (4.0 g) and triethylamine (3.7 g), and the reaction mixture was stirred at room temperature for 3 hr. Trimethylsilyl trifluoromethanesulfonate (4.0 g) and triethylamine (3.7 g) were added, and the reaction mixture was stirred at room temperature for 2 hr. 1.0 mol/L Hydrochloric acid was added to the reaction mixture, and the mixture was extracted twice with chloroform. The organic layer was dried over anhydrous magnesium sulfate, filtered and concentrated. The residue was purified by silica gel column chromatography (solvent; hexane/ethyl acetate=70/30-40/60) to give the title compound (660 mg).
MS (ESI) m/z; 326 [M+H]$^+$

Reference Example 474

5-((RS)-1-hydroxyethyl)-6-methyl-2-methylsulfanyl-6H-[1,3]thiazolo[5,4-d]pyrimidin-7-one

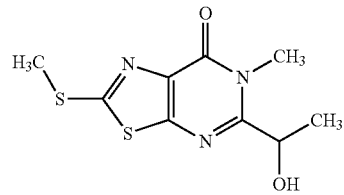 [SMILES: CSc1nc2c(=O)n(C)c(C(C)O)nc2s1]

To a solution (1.2 mL) of the compound (100 mg) obtained in Reference Example 471 in methanol was added 1.0 mol/L aqueous sodium hydroxide solution (0.4 mL), and the reaction mixture was stirred at room temperature overnight. 1.0 mol/L Hydrochloric acid were added to the reaction mixture, and the mixture was extracted three times with chloroform. The organic layer was dried over anhydrous sodium sulfate, filtered and concentrated. The residue was purified by silica gel column chromatography (solvent; hexane/ethyl acetate=70/30-0/100) to give the title compound (49 mg).
MS (ESI) m/z; 258 [M+H]$^+$

Reference Example 475

5-(1-hydroxycyclopropyl)-6-methyl-2-methylsulfanyl-6H-[1,3]thiazolo[5,4-d]pyrimidin-7-one

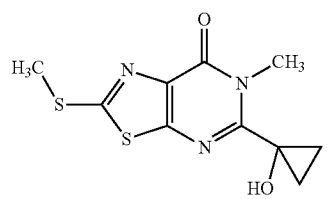 [SMILES: CSc1nc2c(=O)n(C)c(C3(O)CC3)nc2s1]

The compound (0.53 g) obtained in Reference Example 472 was treated by a method similar to that in Reference Example 474 to give the title compound (0.37 g).
MS (ESI) m/z; 270 [M+H]$^+$

Reference Example 476

5-(1-hydroxycyclobutyl)-6-methyl-2-methylsulfanyl-6H-[1,3]thiazolo[5,4-d]pyrimidin-7-one

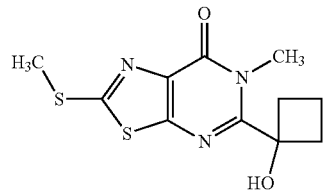 [SMILES: CSc1nc2c(=O)n(C)c(C3(O)CCC3)nc2s1]

The compound (660 mg) obtained in Reference Example 473 was treated by a method similar to that in Reference Example 474 to give the title compound (550 mg).
MS (ESI) m/z; 284 [M+H]$^+$

Reference Example 477

5-((RS)-1-hydroxyethyl)-6-methyl-2-((RS)-methyl-sulfinyl)-6H-[1,3]thiazolo[5,4-d]pyrimidin-7-one

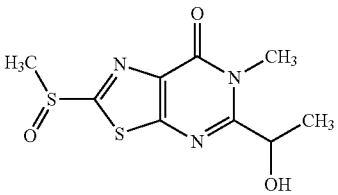 [SMILES: CC(O)c1nc2sc(S(C)=O)nc2c(=O)n1C]

To a solution (1 mL) of the compound (49 mg) obtained in Reference Example 474 in methylene chloride was added mCPBA (69-75%, 48 mg) under ice-cooling. The reaction mixture was stirred under ice-cooling for 1 hr, to the reaction mixture were added aqueous sodium thiosulfate solution and saturated aqueous sodium hydrogen carbonate solution, and the mixture was extracted three times with chloroform. The organic layer was dried over anhydrous sodium sulfate, filtered and concentrated to give the title compound (63 mg).
MS (ESI) m/z; 274 [M+H]$^+$

Reference Example 478

5-(1-hydroxycyclopropyl)-6-methyl-2-methylsulfinyl-6H-[1,3]thiazolo[5,4-d]pyrimidin-7-one

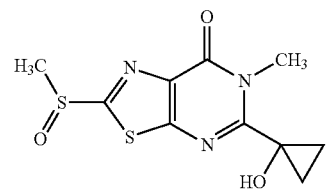 [SMILES: Cn1c(C2(O)CC2)nc2sc(S(C)=O)nc2c1=O]

The compound (0.37 g) obtained in Reference Example 475 was treated by a method similar to that in Reference Example 477 to give the title compound (318 mg).
MS (ESI) m/z; 286 [M+H]$^+$

Reference Example 479

5-(1-hydroxycyclobutyl)-6-methyl-2-methylsulfinyl-6H-[1,3]thiazolo[5,4-d]pyrimidin-7-one

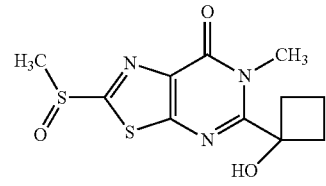 [SMILES: Cn1c(C2(O)CCC2)nc2sc(S(C)=O)nc2c1=O]

The compound (150 mg) obtained in Reference Example 476 was treated by a method similar to that in Reference Example 477 to give the title compound (156 mg).
MS (ESI) m/z; 300 [M+H]$^+$

Reference Example 480

5-(1-methoxycyclopropyl)-6-methyl-2-methylsulfanyl-6H-[1,3]thiazolo[5,4-d]pyrimidin-7-one

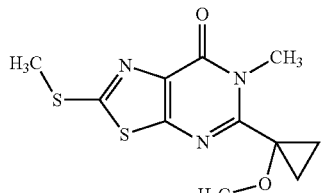

To a solution (40 mL) of the compound (1.14 g) obtained in Reference Example 475 in DMF were added methyl iodide (0.9 g) and sodium hydride (60% oil dispersion, 170 mg) at 0° C., and the reaction mixture was stirred at room temperature for 1 hr. Water was added at 0° C., and the mixture was extracted with ethyl acetate. The organic layer was washed with water, dried over anhydrous magnesium sulfate, filtered and concentrated is under reduced pressure. The obtained residue was purified by silica gel column chromatography (solvent; hexane/ethyl acetate=80/20-40/60) to give the title compound (0.64 g).
MS (ESI) m/z; 284 [M+H]$^+$

Reference Example 481

5-(1-methoxycyclobutyl)-6-methyl-2-methylsulfanyl-6H-[1,3]thiazolo[5,4-d]pyrimidin-7-one

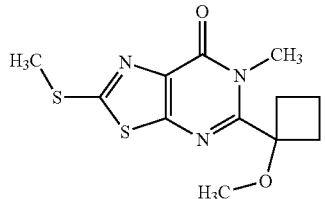

The compound (400 mg) obtained in Reference Example 476 was treated by a method similar to that in Reference Example 480 to give the title compound (386 mg).
MS (ESI) m/z; 298 [M+H]$^+$

Reference Example 482

5-(1-methoxycyclopropyl)-6-methyl-2-methylsulfinyl-6H-[1,3]thiazolo[5,4-d]pyrimidin-7-one

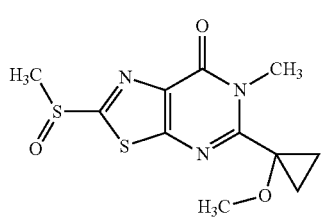 [SMILES: COC1(c2nc3sc(S(C)=O)nc3c(=O)n2C)CC1]

The compound (0.64 g) obtained in Reference Example 480 was treated by a method similar to that in Reference Example 477 to give the title compound (0.64 g).

MS (ESI) m/z; 300 [M+H]⁺

Reference Example 483

5-(1-methoxycyclobutyl)-6-methyl-2-methylsulfinyl-6H-[1,3]thiazolo[5,4-d]pyrimidin-7-one

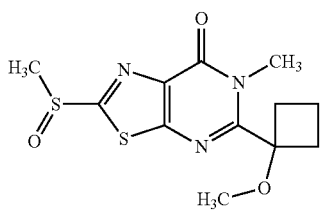 [SMILES: COC1(c2nc3sc(S(C)=O)nc3c(=O)n2C)CCC1]

The compound (386 mg) obtained in Reference Example 481 was treated by a method similar to that in Reference Example 477 to give the title compound (383 mg).

MS (ESI) m/z; 314 [M+H]⁺

Reference Example 484

5-amino-N-(2,4-dimethoxybenzyl)-2-methylsulfanyl-1,3-thiazole-4-carboxamide

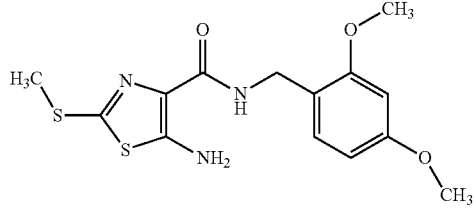

To a solution (600 mL) of 5-amino-2-methylsulfanyl-1,3-thiazole-4-carboxylic acid (23.0 g) in DMF were added EDC hydrochloride (34.8 g), HOBt monohydrate (27.8 g), N,N-diisopropylethylamine (31.6 mL) and 2,4-dimethoxybenzylamine (27.2 mL), and the reaction mixture was stirred at room temperature overnight. Water was added to the reaction mixture, and the mixture was extracted three times with ethyl acetate. The organic layer was dried over anhydrous magnesium sulfate, filtered and concentrated. The residue was purified by silica gel column chromatography (solvent; hexane/ethyl acetate=90/10-50/50) to give the title compound (39.9 g).

MS (ESI) m/z; 340 [M+H]⁺

Reference Example 485

N-(2,4-dimethoxybenzyl)-5-[(2-methylpropanoyl)amino]-2-methylsulfanyl-1,3-thiazole-4-carboxamide

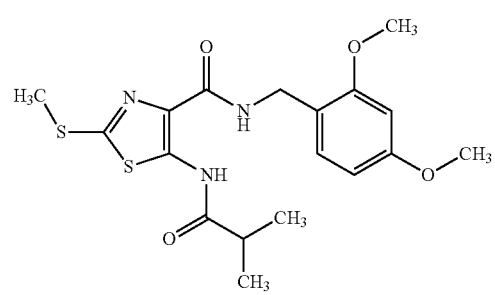

The compound (2.00 g) obtained in Reference Example 484 was treated by a method similar to that in Reference Example 156 to give the title compound (2.34 g).

MS (ESI) m/z; 410 [M+H]⁺

Reference Example 486

N-(2,4-dimethoxybenzyl)-2-methylsulfanyl-5-(propanoylamino)-1,3-thiazole-4-carboxamide

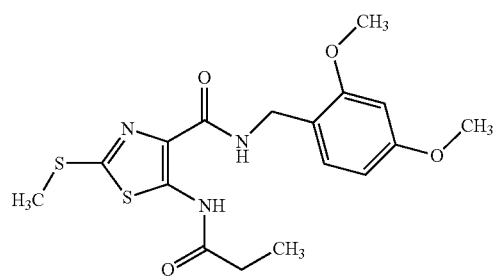

The compound (1.70 g) obtained in Reference Example 484 was treated by a method similar to that in Reference Example 156 to give the title compound (1.98 g).

MS (ESI) m/z; 396 [M+H]⁺

Reference Example 487

N-(2,4-dimethoxybenzyl)-5-[(methoxyacetyl)amino]-2-methylsulfanyl-1,3-thiazole-4-carboxamide

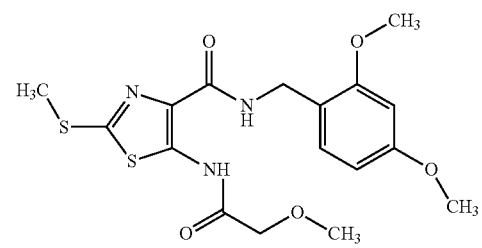

The compound (6.72 g) obtained in Reference Example 484 was treated by a method similar to that in Reference Example 156 to give the title compound (7.82 g).
MS (ESI) m/z; 412 [M+H]⁺

Reference Example 488

5-(benzoylamino)-N-(2,4-dimethoxybenzyl)-2-methylsulfanyl-1,3-thiazole-4-carboxamide

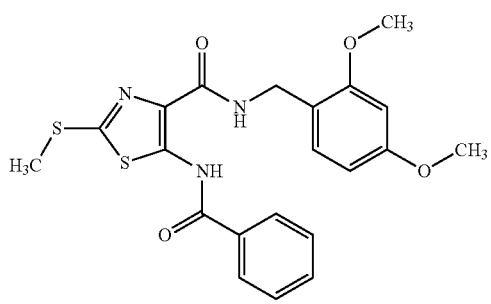

The compound (500 mg) obtained in Reference Example 484 was treated by a method similar to that in Reference Example is 156 to give the title compound (413 mg).
MS (ESI) m/z; 444 [M+H]⁺

Reference Example 489

N-(2,4-dimethoxybenzyl)-5-[(2-fluorobenzoyl)amino]-2-methylsulfanyl-1,3-thiazole-4-carboxamide

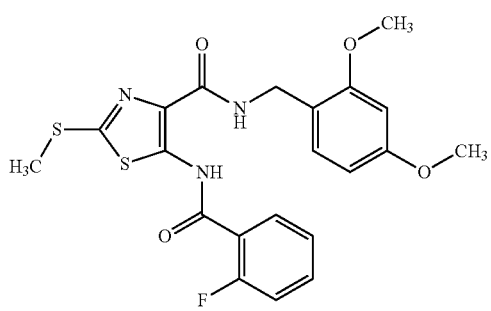

The compound (2.00 g) obtained in Reference Example 484 was treated by a method similar to that in Reference Example 156 to give the title compound (2.65 g).
MS (ESI) m/z; 462 [M+H]⁺

Reference Example 490

5-[(2-chlorobenzoyl)amino]-N-(2,4-dimethoxybenzyl)-2-methylsulfanyl-1,3-thiazole-4-carboxamide

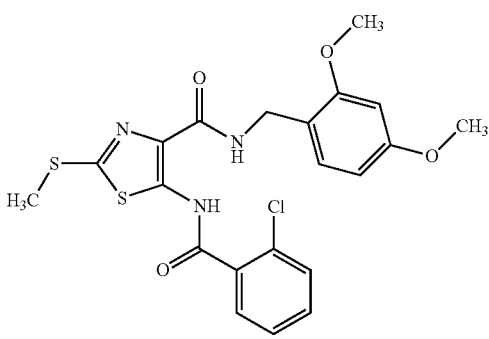

The compound (500 mg) obtained in Reference Example 484 was treated by a method similar to that in Reference Example 156 to give the title compound (1.02 g).
MS (ESI) m/z; 478, 480 [M+H]⁺

Reference Example 491

N-(2,4-dimethoxybenzyl)-5-[(2-methoxybenzoyl)amino]-2-methylsulfanyl-1,3-thiazole-4-carboxamide

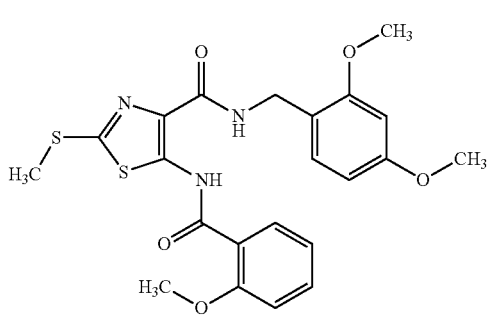

The compound (500 mg) obtained in Reference Example 484 was treated by a method similar to that in Reference Example 156 to give the title compound (577 mg).
MS (ESI) m/z; 474 [M+H]⁺

Reference Example 492

N-(2,4-dimethoxybenzyl)-2-methylsulfanyl-5-{[2-(trifluoromethoxy)benzoyl]amino}-1,3-thiazole-4-carboxamide

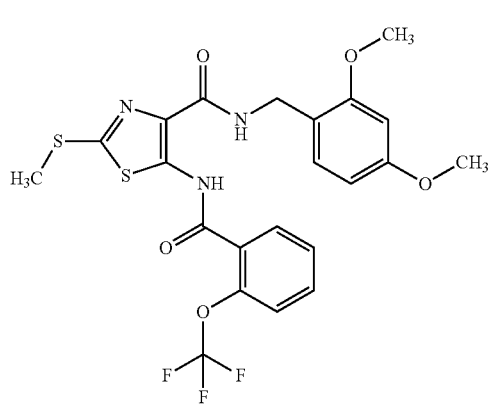

The compound (500 mg) obtained in Reference Example 484 was treated by a method similar to that in Reference Example 156 to give the title compound (918 mg).
MS (ESI) m/z; 528 [M+H]$^+$

Reference Example 493

N-(2,4-dimethoxybenzyl)-5-[(2-methylbenzoyl)amino]-2-methylsulfanyl-1,3-thiazole-4-carboxamide

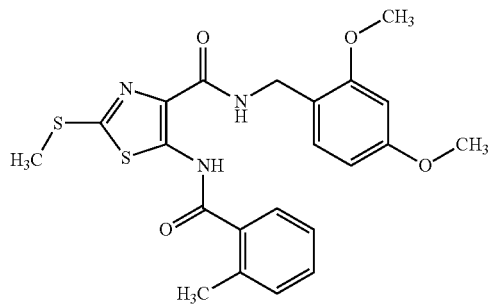

The compound (500 mg) obtained in Reference Example 484 was treated by a method similar to that in Reference Example 156 to give the title compound (867 mg).
MS (ESI) m/z; 458 [M+H]$^+$

Reference Example 494

5-[(2,4-difluorobenzoyl)amino]-N-(2,4-dimethoxybenzyl)-2-methylsulfanyl-1,3-thiazole-4-carboxamide

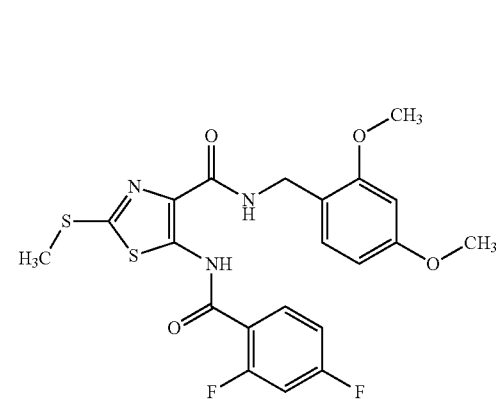

The compound (600 mg) obtained in Reference Example 484 was treated by a method similar to that in Reference Example 156 to give the title compound (690 mg).
MS (ESI) m/z; 480 [M+H]$^+$

Reference Example 495

5-[(5-chloro-2-fluorobenzoyl)amino]-N-(2,4-dimethoxybenzyl)-2-methylsulfanyl-1,3-thiazole-4-carboxamide

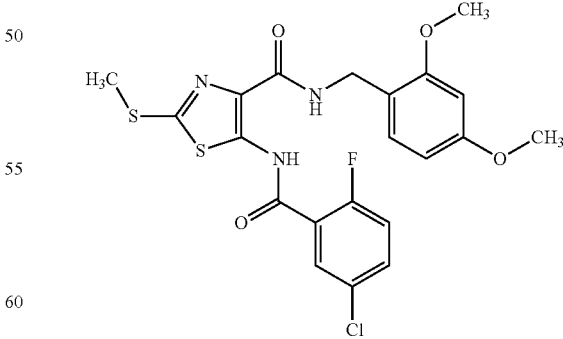

The compound (500 mg) obtained in Reference Example 484 was treated by a method similar to that in Reference Example 156 to give the title compound (506 mg).
MS (ESI) m/z; 496, 498 [M+H]$^+$

Reference Example 496

N-(2,4-dimethoxybenzyl)-5-[(2-fluoro-2-methylpropanoyl)amino]-2-methylsulfanyl-1,3-thiazole-4-carboxamide

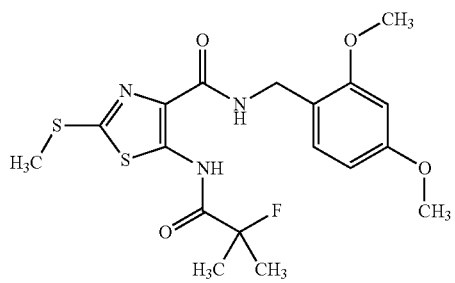

To a solution (11.0 mL) of 2-fluoro-2-methylpropionic acid (625 mg) in methylene chloride were added oxalyl chloride (498 μL) and DMF (one drop), and the reaction mixture was stirred at room temperature for 4 hr. The obtained solution was added dropwise to a solution (30.0 mL) of the compound (1.00 g) obtained in Reference Example 484 and triethylamine (1.23 mL) in methylene chloride under ice-cooling, and the reaction mixture was stirred at room temperature overnight. Water was added to the reaction mixture, and the mixture was extracted three times with methylene chloride. The organic layer was dried over anhydrous sodium sulfate, filtered and concentrated. The residue was purified by silica gel column chromatography (solvent; hexane/ethyl acetate=100/0-70/30) to give the title compound (1.25 g).

MS (ESI) m/z; 428 [M+H]$^+$

Reference Example 497

5-[(2,2-difluoropropanoyl)amino]-N-(2,4-dimethoxybenzyl)-2-methylsulfanyl-1,3-thiazole-4-carboxamide

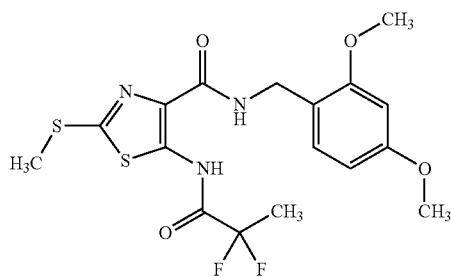

The compound (2.31 g) obtained in Reference Example 484 was treated by a method similar to that in Reference Example 169 to give the title compound (1.12 g).

MS (ESI) m/z; 432 [M+H]$^+$

Reference Example 498

5-[(2,2-difluoro-3-methoxypropanoyl)amino]-N-(2,4-dimethoxybenzyl)-2-methylsulfanyl-1,3-thiazole-4-carboxamide

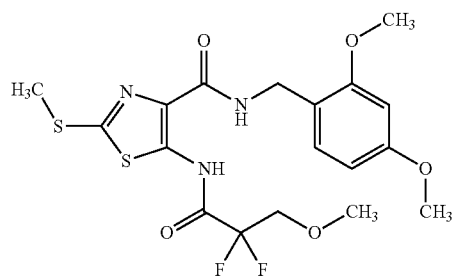

To a solution (20 mL) of 2,2-difluoro-3-methoxypropionic acid methyl ester (2.00 g) in ethanol was added 1.0 mol/L aqueous sodium hydroxide solution (13 mL) at room temperature, and the reaction mixture was stirred at 50° C. for 2 hr. The solvent was evaporated under reduced pressure to give 2,2-difluoro-3-methoxypropionic acid potassium salt. To a solution (40 mL) of the obtained 2,2-difluoro-3-methoxypropionic acid potassium salt in methylene chloride were added oxalyl chloride (2.2 mL) and DMF (one drop), and the reaction mixture was stirred at room temperature for 6 hr. The solvent was evaporated under reduced pressure. The obtained acid chloride in methylene chloride solution (20 mL) and triethylamine (2.72 mL) were added to a solution (50 mL) of the compound (4.41 g) obtained in Reference Example 484 in methylene chloride at room temperature, and the reaction mixture was stirred overnight. Water was added to the reaction mixture, and the mixture was extracted twice with chloroform. The organic layer was dried over anhydrous magnesium sulfate, filtered and concentrated. The residue was purified by silica gel column chromatography (solvent; hexane/ethyl acetate=100/0-50/50) to give the title compound (2.51 g).

MS (ESI) m/z; 462 [M+H]$^+$

Reference Example 499

N-(2,4-dimethoxybenzyl)-2-methylsulfanyl-5-[{[1-(trifluoromethyl)cyclopropyl]carbonyl}amino]-1,3-thiazole-4-carboxamide

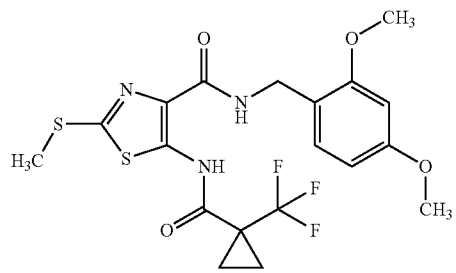

The compound (800 mg) obtained in Reference Example 484 was treated by a method similar to that in Reference Example 169 to give the title compound (787 mg).

MS (ESI) m/z; 476 [M+H]$^+$

Reference Example 500

5-{[difluoro(phenyl)acetyl]amino}-N-(2,4-dimethoxybenzyl)-2-methylsulfanyl-1,3-thiazole-4-carboxamide

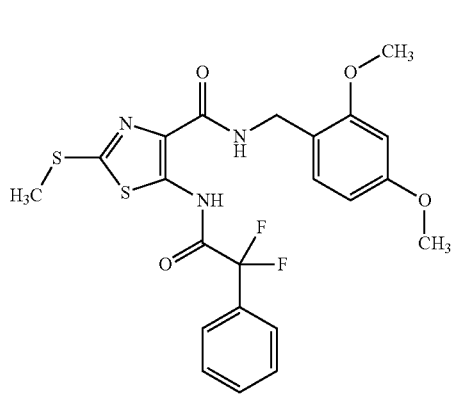

The compound (576 mg) obtained in Reference Example 484 was treated by a method similar to that in Reference Example 169 to give the title compound (332 mg).
MS (ESI) m/z; 494 [M+H]$^+$

Reference Example 501

N-(2,4-dimethoxybenzyl)-5-[(2-fluoro-3-methoxybenzoyl)amino]-2-methylsulfanyl-1,3-thiazole-4-carboxamide

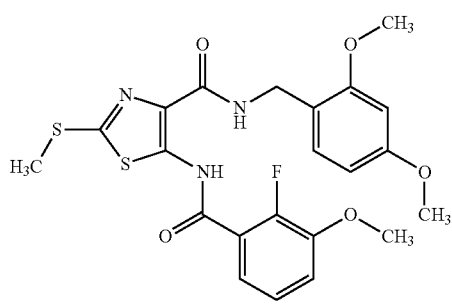

The compound (500 mg) obtained in Reference Example 484 was treated by a method similar to that in Reference Example 169 to give the title compound (850 mg).
MS (ESI) m/z; 492 [M+H]$^+$

Reference Example 502

N-(2,4-dimethoxybenzyl)-5-[(2-fluoro-3-methylbenzoyl)amino]-2-methylsulfanyl-1,3-thiazole-4-carboxamide

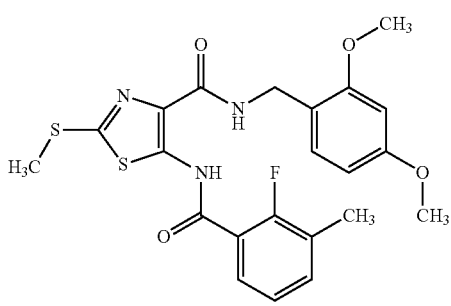

The compound (500 mg) obtained in Reference Example 484 was treated by a method similar to that in Reference Example 169 to give the title compound (700 mg).
MS (ESI) m/z; 476 [M+H]$^+$

Reference Example 503

N-(2,4-dimethoxybenzyl)-2-methylsulfanyl-5-{[(5-methylthiophen-2-yl)carbonyl]amino}-1,3-thiazole-4-carboxamide

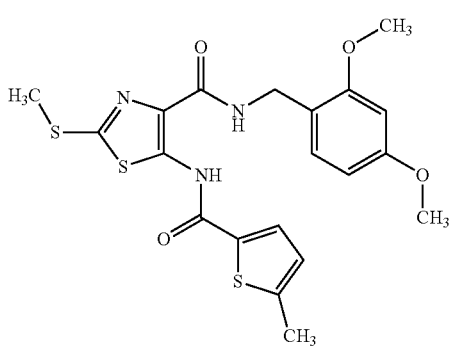

The compound (600 mg) obtained in Reference Example 484 was treated by a method similar to that in Reference Example 169 to give the title compound (310 mg).
MS (ESI) m/z; 464 [M+H]$^+$

Reference Example 504

N-(2,4-dimethoxybenzyl)-5-{[(1-methoxycyclopropyl)carbonyl]amino}-2-methylsulfanyl-1,3-thiazole-4-carboxamide

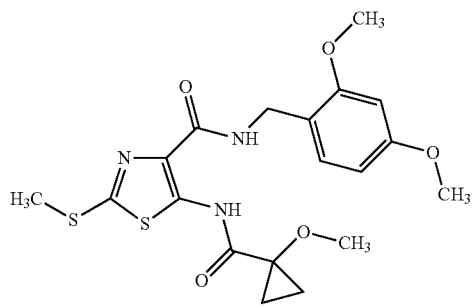

The compound (1.00 g) obtained in Reference Example 484 was treated by a method similar to that in Reference Example 169 to give the title compound (1.27 g).
MS (ESI) m/z; 438 [M+H]+

Reference Example 505

N-(2,4-dimethoxybenzyl)-5-[{[1-(fluoromethyl)cyclopropyl]carbonyl}amino]-2-methylsulfanyl-1,3-thiazole-4-carboxamide

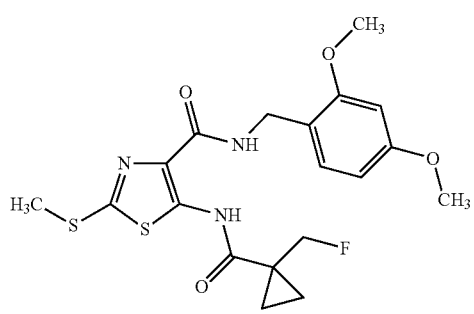

The compound (700 mg) obtained in Reference Example 484 was treated by a method similar to that in Reference Example 169 to give the title compound (670 mg).
MS (ESI) m/z; 440 [M+H]+

Reference Example 506

N-(2,4-dimethoxybenzyl)-5-[{[1-(fluoromethyl)cyclopropyl]carbonyl}amino]-2-methylsulfanyl-1,3-thiazole-4-carboxamide

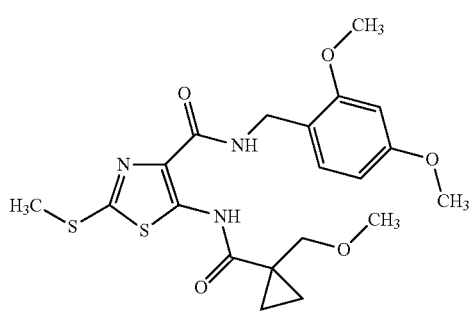

The compound (1.45 g) obtained in Reference Example 484 was treated by a method similar to that in Reference Example 169 to give the title compound (1.90 g).
MS (ESI) m/z; 452 [M+H]+

Reference Example 507

N-(2,4-dimethoxybenzyl)-5-[(2-fluoro-5-methylbenzoyl)amino]-2-methylsulfanyl-1,3-thiazole-4-carboxamide

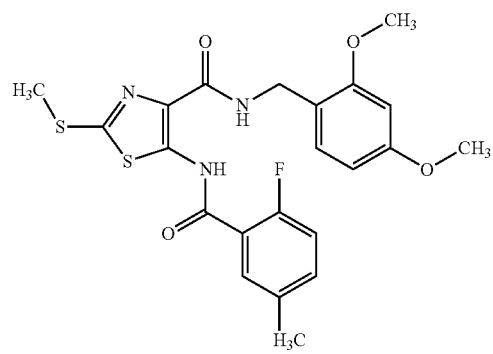

To a solution (5.0 mL) of the compound (500 mg) obtained in Reference Example 484 and 2-fluoro-5-methylbenzoic acid (227 mg) in DMF were added HATU (1.40 g) and N,N-diisopropylethylamine (1.03 mL), and the reaction mixture was stirred at room temperature overnight. HATU (1.40 g) and N,N-diisopropylethylamine (1.03 mL) were added, and the reaction mixture was stirred at room temperature for 5 hr. 2-Fluoro-5-methylbenzoic acid (554 mg), HATU (1.40 g) and N,N-diisopropylethylamine (1.03 mL) were further added, and the reaction mixture was stirred at room temperature overnight. To the reaction mixture was added saturated aqueous sodium hydrogen carbonate solution, and the mixture was extracted with ethyl acetate. The organic layer was washed with saturated brine, dried over anhydrous magnesium sulfate, filtered and concentrated. The residue was purified by NH silica gel column chromatography (solvent; hexane/ethyl acetate=80/20) to give the title compound (466 mg).
MS (ESI) m/z; 476 [M+H]+

Reference Example 508

N-[4-(2,4-dimethoxybenzyl)carbamoyl-2-methylsulfanyl-1,3-thiazol-5-yl]-3-fluoropyridine-2-carboxamide

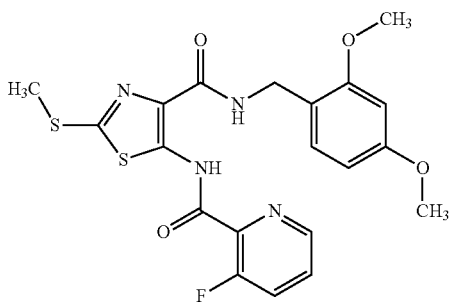

The compound (500 mg) obtained in Reference Example 484 was treated by a method similar to that in Reference Example 507 to give the title compound (371 mg), MS (ESI) m/z; 463 [M+H]$^+$

Reference Example 509

N-(2,4-dimethoxybenzyl)-5-{[(3-fluoro-5-methylthiophen-2-yl)carbonyl]amino}-2-methylsulfanyl-1,3-thiazole-4-carboxamide

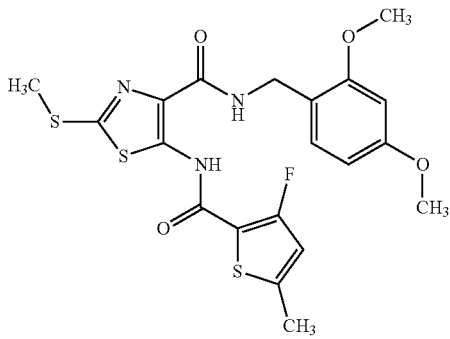

To a solution (48 mL) of 5-methylthiophene-2-carboxylic acid (3.00 g) in THF was added dropwise n-butyllithium (2.69 mol/L hexane solution, 17.3 mL) at −78° C. over 5 min. The reaction mixture was stirred at −78° C. for 1 hr, and a solution (48 mL) of N-fluorobenzenesulfoneamide (7.98 g) in THF was added dropwise over 15 min. The reaction mixture was stirred at −78° C. for 4 hr, allowed to warm to room temperature over 2 hr and stirred at room temperature overnight. The reaction mixture was adjusted to pH 2 with 2.0 mol/L hydrochloric acid, and extracted twice with diethyl ether. The organic layer was dried over anhydrous magnesium sulfate, filtered and concentrated. The residue was purified by carboxylic acid-carrying silica gel column chromatography (solvent; hexane/ethyl acetate=92/8-40/60), to the obtained product was added hexane/ethyl acetate=3/1, and the solid was collected by filtration to give 3-fluoro-5-methylthiophene-2-carboxylic acid (1.20 g), to a solution (15 mL) of the obtained 3-fluoro-5-methylthiophene-2-carboxylic acid (566 mg) in THF, sodium hydride (60% oil dispersion, 138 mg) was added under ice-cooling. The reaction mixture was stirred at room temperature for 10 min, concentrated under reduced pressure, and the residue was washed with diethyl ether. The obtained solid was dried under reduced pressure, diluted with acetonitrile (5.5 mL), oxalyl chloride (296 μL) and DMF (one drop) were added thereto, and the reaction mixture was stirred at 50° C. for 2 hr. Oxalyl chloride (296 μL) was further added, and the mixture was stirred at 50° C. for 3 hr. The reaction mixture was concentrated under reduced pressure, and the residue was dissolved in methylene chloride (2 mL), and added dropwise to a solution (6 mL) of the compound (600 mg) obtained in Reference Example 484 and triethylamine (986 μL) in methylene chloride at room temperature. The reaction mixture was stirred at room temperature overnight, to the reaction mixture were added ethyl acetate and water, and the insoluble material was filtered off through diatomaceous earth. The filtrate was extracted twice with ethyl acetate, and the organic layer was dried over anhydrous sodium sulfate, filtered and concentrated. The residue was purified by NH silica gel column chromatography (solvent; hexane/ethyl acetate=90/10-55/45), to the obtained product was added diethyl ether/hexane=1/2, and the solid was collected by filtration to give the title compound (444 mg).

MS (ESI) m/z; 482 [M+H]$^+$

Reference Example 510

5-[(4-benzenesulfonyl-2,2-difluorobutyryl)amino]-2-methylsulfanyl-N-(2,4-dimethoxyphenyl)-1,3-thiazole-4-carboxamide

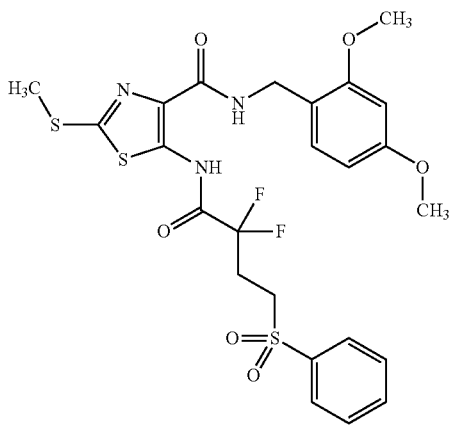

The compound (316 mg) obtained in Reference Example 484 was treated by a method similar to that in Reference Example 182 to give the title compound (501 mg).

MS (ESI) m/z; 586 [M+H]$^+$

Reference Example 511

N-(2,4-dimethoxybenzyl)-2-methylsulfanyl-5-[(2,2,3,3,3-pentafluoropropanoyl)amino]-1,3-thiazole-4-carboxamide

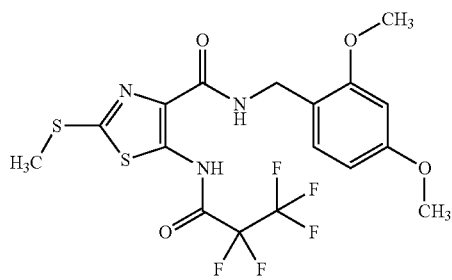

The compound (500 mg) obtained in Reference Example 484 was treated by a method similar to that in Reference Example 194 to give the title compound (700 mg).

MS (ESI) m/z; 486 [M+H]$^+$

Reference Example 512

N-(2,4-dimethoxybenzyl)-5-{[(1-fluorocyclopropyl)carbonyl]amino}-2-methylsulfanyl-1,3-thiazole-4-carboxamide

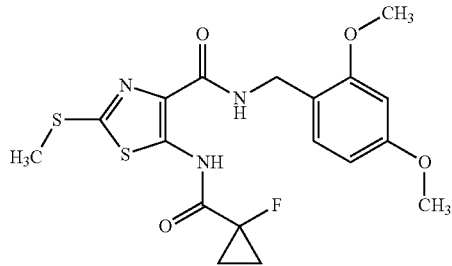

To a solution of the compound (2.10 g) obtained in Reference Example 484 in methylene chloride (30 mL) was added a solution (5.0 mL) of 1-fluorocyclopropanecarboxylic acid (4-fluorophenyl) ester (2.04 g) synthesized by the method described in WO 2011/148922A1 in methylene chloride. To the reaction mixture was added dropwise DBU (1.85 mL), and the reaction mixture was stirred at room temperature overnight. Water was added to the reaction mixture, and the mixture was extracted twice with methylene chloride. The combined organic layer was washed with saturated aqueous sodium hydrogen carbonate solution, dried over anhydrous sodium sulfate, filtered and concentrated. The residue was purified by silica gel (solvent; hexane/ethyl acetate=80/20) and NH silica gel column chromatography (solvent; hexane/ethyl acetate=80/20) to give the title compound (3.64 g).

MS (ESI) m/z; 426 [M+H]$^+$

Reference Example 513

5-{[(1-chlorocyclopropyl)carbonyl]amino}-N-(2,4-dimethoxybenzyl)-2-methylsulfanyl-1,3-thiazole-4-carboxamide

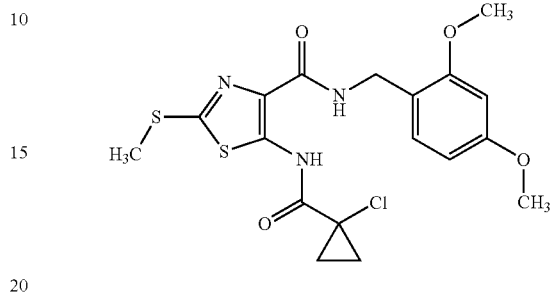

To a solution (125 mL) of 4,4'-dichlorobutyrophenone (25.0 g) in chloroform was added sulfuryl chloride (15.1 mL), and the reaction mixture was stirred with heating at 50° C. for 18 hr. Sulfuryl chloride (4.04 mL) was added, and the reaction mixture was stirred with heating at 50° C. overnight. The reaction mixture was neutralized with aqueous sodium hydrogen carbonate solution under ice-cooling and extracted twice with chloroform. The organic layer was dried over anhydrous sodium sulfate, filtered and concentrated. The residue was purified by silica gel column chromatography (solvent; hexane/ethyl acetate=100/0-93/7) to give 2,4-dichloro-1-(4-chlorophenyl)butan-1-one (27.7 g). To a solution (195 mL) of the obtained 2,4-dichloro-1-(4-chlorophenyl)butan-1-one (27.7 g) in tert-butanol was added potassium tert-butoxide (19.8 g) at 0° C., and the reaction mixture was stirred with heating at 50° C. for 15 min. The solvent was evaporated under reduced pressure, hexane was added, and the mixture was washed with water. The organic layer was dried over anhydrous sodium sulfate, filtered and concentrated. The residue was purified by silica gel column chromatography (solvent; hexane/diethyl ether=100/0-93/7) to give (1-chlorocyclopropyl)-(4-chlorophenyl)-methanone (22.6 g). To a solution (200 mL) of the obtained (1-chlorocyclopropyl)-(4-chlorophenyl)-methanone (21.1 g) in chloroform was added mCPBA (69-75%, 52.4 g), and the reaction mixture was heated under reflux for 2 days. mCPBA (69-75%, 26.2 g) was added, and the reaction mixture was heated under reflux for 2 days, mCPBA (69-75%, 13.1 g) was added, and the reaction mixture was heated under reflux overnight. The reaction mixture was allowed to cool to room temperature, aqueous sodium thiosulfate solution was added, and the mixture was stirred at room temperature for 15 min. The separated organic layer was washed with aqueous sodium hydrogen carbonate solution, dried over anhydrous sodium sulfate, filtered and concentrated. The residue was purified by silica gel column chromatography (solvent; hexane/ethyl acetate=100/0-90/10) to give 1-chlorocyclopropanecarboxylic acid (4-chlorophenyl) ester (13.3 g). In the following, 1-chlorocyclopropanecarboxylic acid (4-chlorophenyl) ester (1.26 g) and the compound (1.00 g) is obtained in Reference Example 484 were treated by a method similar to that in Reference Example 512 to give the title compound (1.54 g).

MS (ESI) m/z; 442 [M+H]$^+$

Reference Example 514

6-(2,4-dimethoxybenzyl)-5-(2-fluoropropan-2-yl)-2-methylsulfanyl[1,3]thiazolo[5,4-d]pyrimidin-7(6H)-one

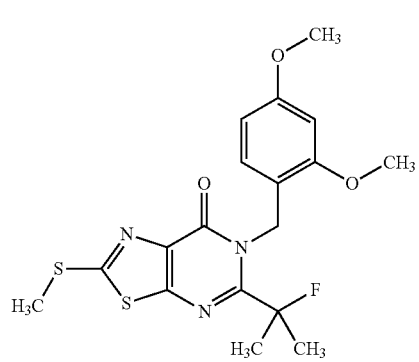

To a solution (5.00 mL) of the compound (1.00 g) obtained in Reference Example 496 in N,N-dimethylformamide were added N,O-bis(trimethylsilyl)acetamide (2.86 mL) and triethylamine (1.63 mL), and the reaction mixture was stirred at room temperature for 2 hr. To the reaction mixture was added water (50.0 mL), and the resultant solid was collected by filtration and dried to give the title compound (900 mg).

MS (ESI) m/z; 410 [M+H]$^+$

Reference Example 515

6-(2,4-dimethoxybenzyl)-5-ethyl-2-methylsulfanyl[1,3]thiazolo[5,4-d]pyrimidin-7(6H)-one

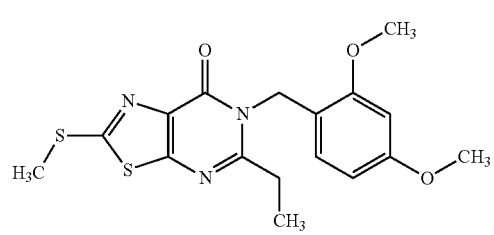

The compound (970 mg) obtained in Reference Example 486 was treated by a method similar to that in Reference Example 195 to give the title compound (750 mg).

MS (ESI) m/z; 378 [M+H]$^+$

Reference Example 516

6-(2,4-dimethoxybenzyl)-2-methylsulfanyl-5-(propan-2-yl)[1,3]thiazolo[5,4-d]pyrimidin-7(6H)-one

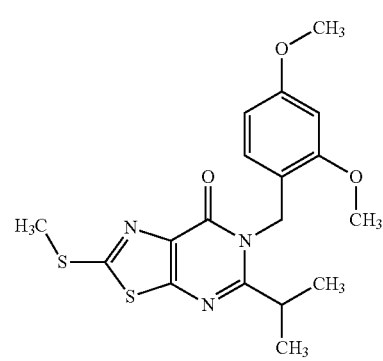

The compound (2.33 g) obtained in Reference Example 485 was treated by a method similar to that in Reference Example 195 to give the title compound (1.96 g).

MS (ESI) m/z; 392 [M+H]$^+$

Reference Example 517

6-(2,4-dimethoxybenzyl)-5-methoxymethyl-2-methylsulfanyl[1,3]thiazolo[5,4-d]pyrimidin-7(6H)-one

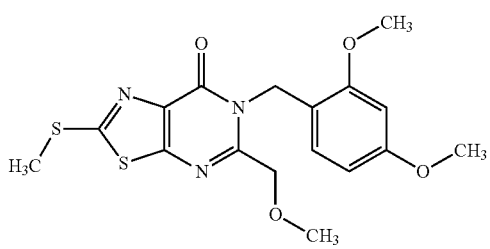

The compound (7.81 g) obtained in Reference Example 487 was treated by a method similar to that in Reference Example 195 to give the title compound (4.00 g).

MS (ESI) m/z; 394 [M+H]$^+$

Reference Example 518

6-(2,4-dimethoxybenzyl)-2-methylsulfanyl-5-phenyl[1,3]thiazolo[5,4-d]pyrimidin-7(6H)-one

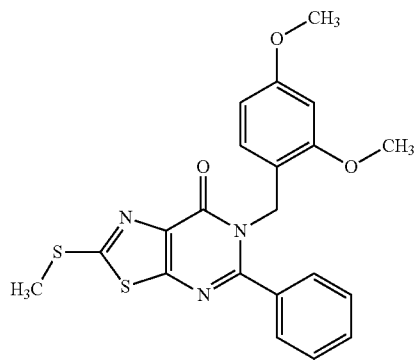

The compound (410 mg) obtained in Reference Example 488 was treated by a method similar to that in Reference Example 195 to give the title compound (366 mg).

MS (ESI) m/z; 426 [M+H]$^+$

Reference Example 519

6-(2,4-dimethoxybenzyl)-5-(2-fluorophenyl)-2-methylsulfanyl[1,3]thiazolo[5,4-d]pyrimidin-7(6H)-one

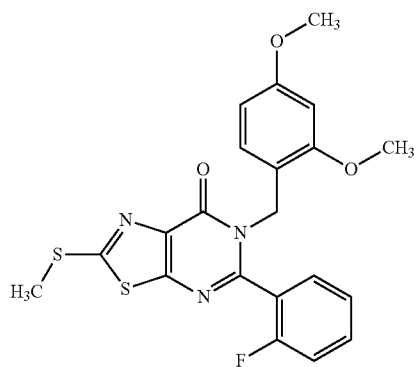

The compound (2.65 g) obtained in Reference Example 489 was treated by a method similar to that in Reference Example is 195 to give the title compound (2.30 g).

MS (ESI) m/z; 444 [M+H]$^+$

Reference Example 520

5-(2-chlorophenyl)-6-(2,4-dimethoxybenzyl)-2-methylsulfanyl[1,3]thiazolo[5,4-d]pyrimidin-7(6H)-one

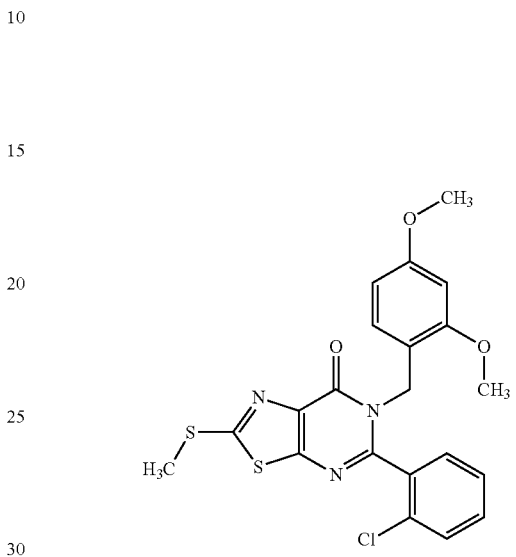

The compound (1.00 g) obtained in Reference Example 490 was treated by a method similar to that in Reference Example 195 to give the title compound (456 mg).

MS (ESI) m/z; 460, 462 [M+H]$^+$

Reference Example 521

6-(2,4-dimethoxybenzyl)-5-(2-methoxyphenyl)-2-methylsulfanyl[1,3]thiazolo[5,4-d]pyrimidin-7(6H)-one

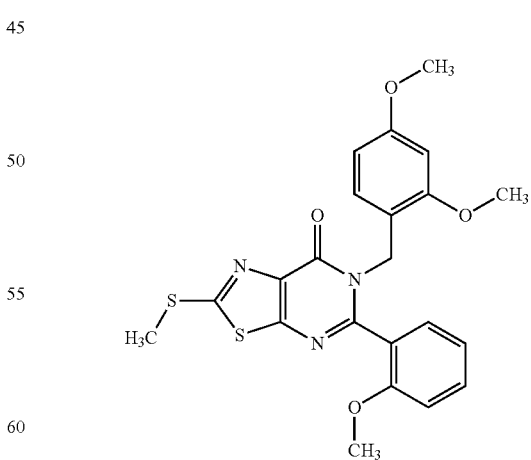

The compound (570 mg) obtained in Reference Example 491 was treated by a method similar to that in Reference Example 195 to give the title compound (312 mg).

MS (ESI) m/z; 456 [M+H]$^+$

Reference Example 522

6-(2,4-dimethoxybenzyl)-2-methylsulfanyl-5-[2-(trifluoromethoxy)phenyl][1,3]thiazolo[5,4-d]pyrimidin-7(6H)-one

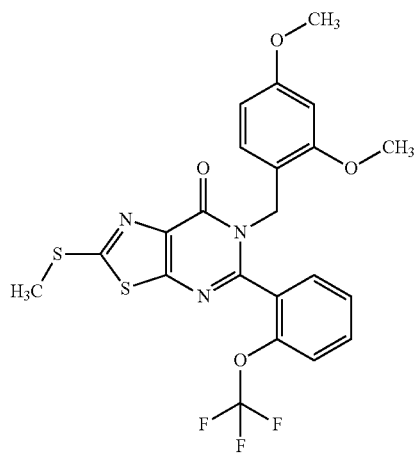

The compound (897 mg) obtained in Reference Example 492 was treated by a method similar to that in Reference Example 195 to give the title compound (603 mg).

MS (ESI) m/z; 510 [M+H]$^+$

Reference Example 523

6-(2,4-dimethoxybenzyl)-5-(2-methylphenyl)-2-methylsulfanyl[1,3]thiazolo[5,4-d]pyrimidin-7(6H)-one

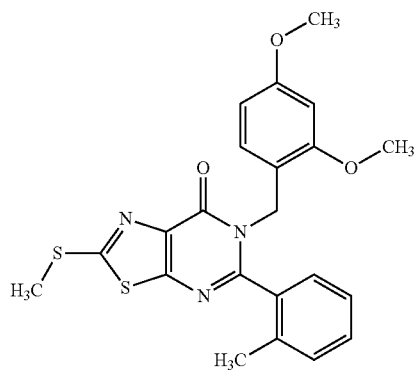

The compound (844 mg) obtained in Reference Example 493 was treated by a method similar to that in Reference Example 195 to give the title compound (588 mg).

MS (ESI) m/z; 440 [M+H]$^+$

Reference Example 524

5-(2,4-difluorophenyl)-6-(2,4-dimethoxybenzyl)-2-methylsulfanyl[1,3]thiazolo[5,4-d]pyrimidin-7(6H)-one

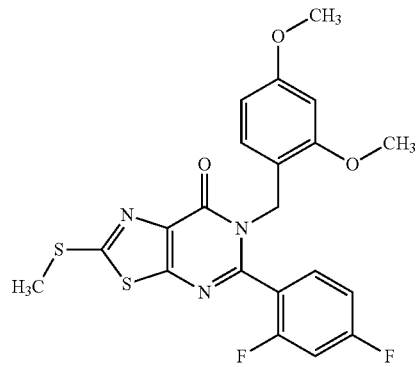 [SMILES: COc1ccc(Cn2c(-c3ccc(F)cc3F)nc3sc(SC)nc3c2=O)c(OC)c1]

The compound (689 mg) obtained in Reference Example 494 was treated by a method similar to that in Reference Example 195 to give the title compound (540 mg).

MS (ESI) m/z; 462 [M+H]$^+$

Reference Example 525

5-(5-chloro-2-fluorophenyl)-6-(2, 4-dimethoxybenzyl)-2-methylsulfanyl[1,3]thiazolo[5,4-d]pyrimidin-7(6H)-one

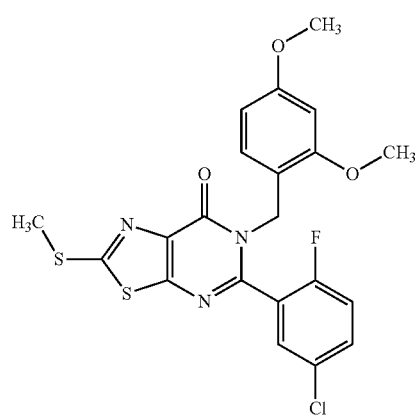

The compound (505 mg) obtained in Reference Example 495 was treated by a method similar to that in Reference Example 195 to give the title compound (464 mg).

MS (ESI) m/z; 478, 480 [M+H]$^+$

Reference Example 526

6-(2,4-dimethoxybenzyl)-5-(1-fluorocyclopropyl)-2-methylsulfanyl[1,3]thiazolo[5,4-d]pyrimidin-7(6H)-one

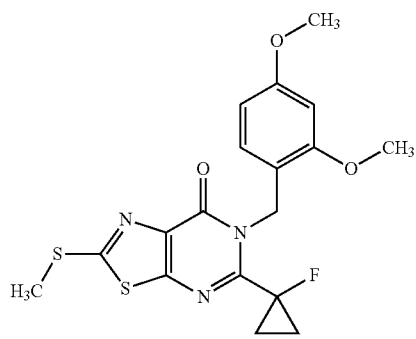

The compound (3.64 g) obtained in Reference Example 512 was treated by a method similar to that in Reference Example 195 to give the title compound (2.31 g).

MS (ESI) m/z; 408 [M+H]$^+$

Reference Example 527

5-(1,1-difluoroethyl)-6-(2,4-dimethoxybenzyl)-2-methylsulfanyl[1,3]thiazolo[5,4-d]pyrimidin-7(6H)-one

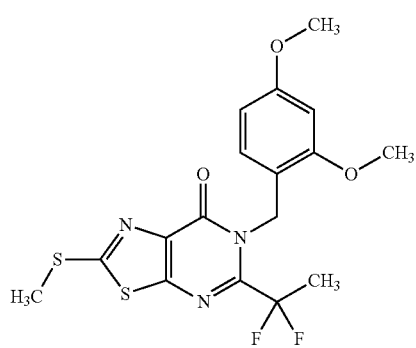

The compound (1.12 g) obtained in Reference Example 497 was treated by a method similar to that in Reference Example 195 to give the title compound (978 mg).

MS (ESI) m/z; 414 [M+H]$^+$

Reference Example 528

5-(1,1-difluoro-2-methoxyethyl)-6-(2,4-dimethoxybenzyl)-2-methylsulfanyl[1,3]thiazolo[5,4-d]pyrimidin-7(6H)-one

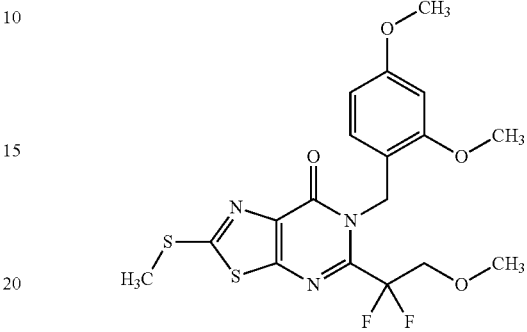

The compound (2.50 g) obtained in Reference Example 498 was treated by a method similar to that in Reference Example 195 to give the title compound (2.01 g).

MS (ESI) m/z; 444 [M+H]$^+$

Reference Example 529

6-(2,4-dimethoxybenzyl)-2-methylsulfanyl-5-[1-(trifluoromethyl)cyclopropyl][1,3]thiazolo[5,4-d]pyrimidin-7(6H)-one

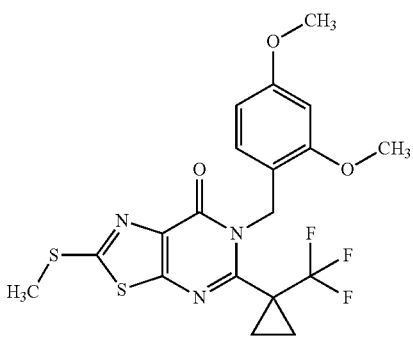

The compound (787 mg) obtained in Reference Example 499 was treated by a method similar to that in Reference Example 195 to give the title compound (587 mg).

MS (ESI) m/z; 458 [M+H]$^+$

Reference Example 530

5-[difluoro(phenyl)methyl]-6-(2,4-dimethoxyben-zyl)-2-methylsulfanyl[1,3]thiazolo[5,4-d]pyrimidin-7(6H)-one

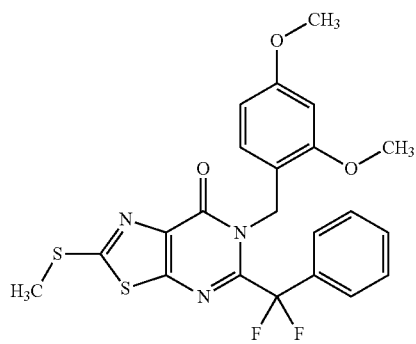 [SMILES: COc1ccc(Cn2c(C(F)(F)c3ccccc3)nc3sc(SC)nc3c2=O)c(OC)c1]

The compound (330 mg) obtained in Reference Example 500 was treated by a method similar to that in Reference Example 195 to give the title compound (256 mg)
MS (ESI) m/z; 476 [M+H]$^+$

Reference Example 531

6-(2,4-dimethoxybenzyl)-5-(2-fluoro-3-methoxyphe-nyl)-2-methylsulfanyl[1,3]thiazolo[5,4-d]pyrimidin-7(6H)-one

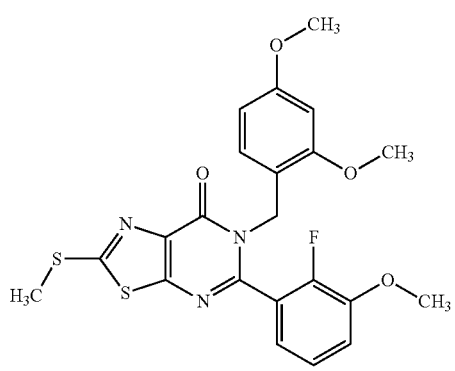

The compound (850 mg) obtained in Reference Example 501 was treated by a method similar to that in Reference Example 195 to give the title compound (617 mg).
MS (ESI) m/z; 474 [M+H]$^+$

Reference Example 532

6-(2,4-dimethoxybenzyl)-5-(2-fluoro-3-methylphe-nyl)-2-methylsulfanyl[1,3]thiazolo[5,4-d]pyrimidin-7(6H)-one

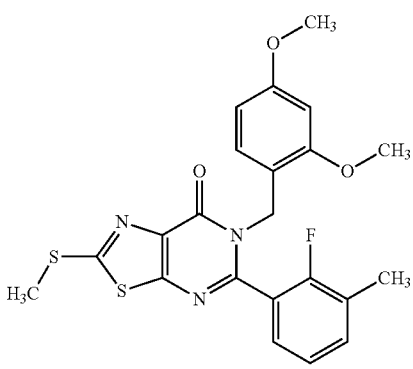

The compound (700 mg) obtained in Reference Example 502 was treated by a method similar to that in Reference Example 195 to give the title compound (544 mg).
MS (ESI) m/z; 458 [M+H]$^+$

Reference Example 533

6-(2,4-dimethoxybenzyl)-2-methylsulfanyl-5-(5-methylthiophen-2-yl)[1,3]thiazolo[5,4-d]pyrimidin-7(6H)-one

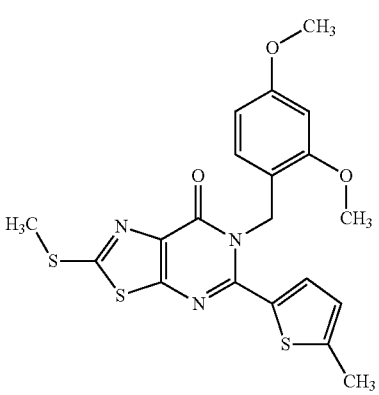

The compound (305 mg) obtained in Reference Example 503 was treated by a method similar to that in Reference Example 195 to give the title compound (255 mg).
MS (ESI) m/z; 446 [M+H]$^+$

Reference Example 534

6-(2,4-dimethoxybenzyl)-5-(1-methoxycyclopropyl)-2-methylsulfanyl[1,3]thiazolo[5,4-d]pyrimidin-7(6H)-one

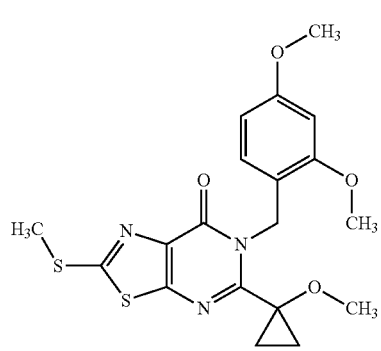

The compound (1.27 g) obtained in Reference Example 504 was treated by a method similar to that in Reference Example 195 to give the title compound (1.20 g).

MS (ESI) m/z; 420 [M+H]$^+$

Reference Example 535

6-(2,4-dimethoxybenzyl)-5-[1-(fluoromethyl)cyclopropyl]-2-methylsulfanyl[1,3]thiazolo[5,4-d]pyrimidin-7(6H)-one

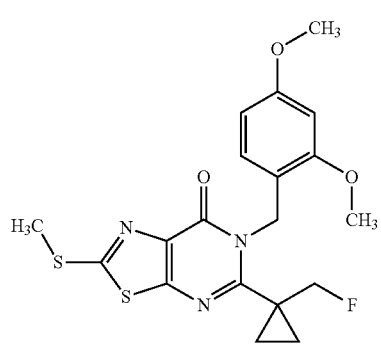 [SMILES: COc1ccc(Cn2c(C3(CF)CC3)nc3sc(SC)nc3c2=O)c(OC)c1]

The compound (670 mg) obtained in Reference Example 505 was treated by a method similar to that in Reference Example 195 to give the title compound (630 mg).

MS (ESI) m/z; 422 [M+H]$^+$

Reference Example 536

6-(2,4-dimethoxybenzyl)-5-[1-(methoxymethyl)cyclopropyl]-2-methylsulfanyl[1,3]thiazolo[5,4-d]pyrimidin-7(6H)-one

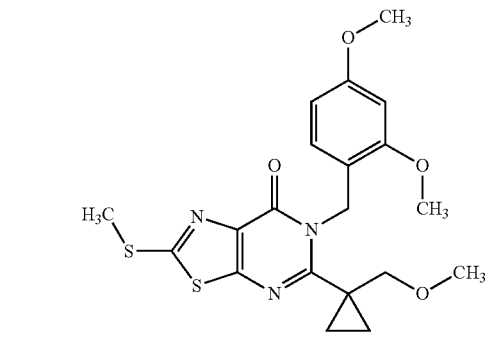

The compound (1.90 g) obtained in Reference Example 506 was treated by a method similar to that in Reference Example 195 to give the title compound (1.70 g).

MS (ESI) m/z; 434 [M+H]$^+$

Reference Example 537

6-(2,4-dimethoxybenzyl)-5-(2-fluoro-5-methylphenyl)-2-methylsulfanyl[1,3]thiazolo[5,4-d]pyrimidin-7(6H)-one

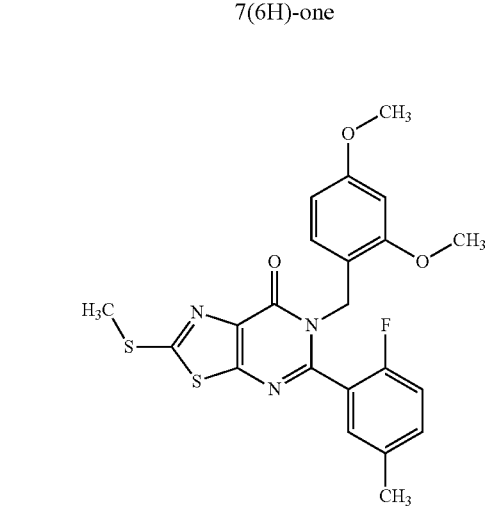

The compound (465 mg) obtained in Reference Example 507 was treated by a method similar to that in Reference Example 195 to give the title compound (477 mg).

MS (ESI) m/z; 458 [M+H]$^+$

Reference Example 538

6-(2,4-dimethoxybenzyl)-5-(3-fluoropyridin-2-yl)-2-methylsulfanyl[1,3]thiazolo[5,4-d]pyrimidin-7(6H)-one

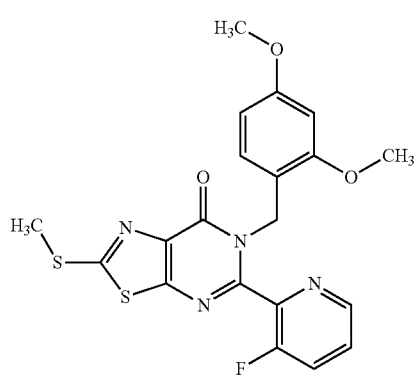

The compound (709 mg) obtained in Reference Example 508 was treated by a method similar to that in Reference Example 195 to give the title compound (610 mg).
MS (ESI) m/z; 445 [M+H]$^+$

Reference Example 539

6-(2,4-dimethoxybenzyl)-5-(3-fluoro-5-methylthiophen-2-yl)-2-methylsulfanyl[1,3]thiazolo[5,4-d]pyrimidin-7(6H)-one

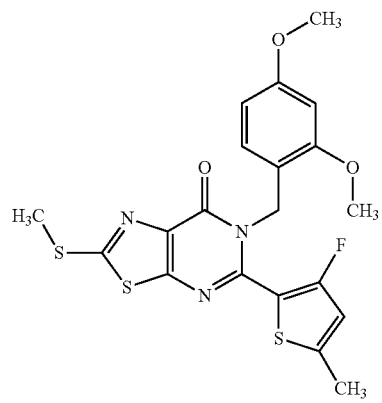

The compound (440 mg) obtained in Reference Example 509 was treated by a method similar to that in Reference Example 195 to give the title compound (429 mg).
MS (ESI) m/z; 464 [M+H]$^+$

Reference Example 540

6-(2,4-dimethoxybenzyl)-2-methylsulfanyl-5-pentafluoroethyl[1,3]thiazolo[5,4-d]pyrimidin-7(6H)-one

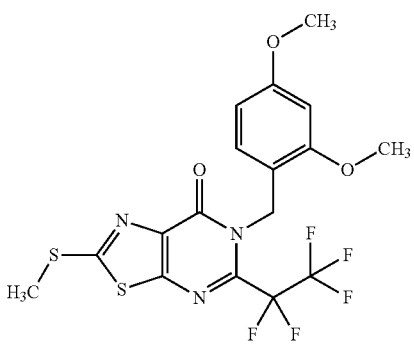

The compound (640 mg) obtained in Reference Example 511 was treated by a method similar to that in Reference Example 195 to give the title compound (343 mg).
MS (ESI) m/z; 468 [M+H]$^+$

Reference Example 541

5-(3-benzenesulfonyl-1,1-difluoropropyl)-6-(2,4-dimethoxybenzyl)-2-methylsulfanyl[1,3]thiazolo[5,4-d]pyrimidin-7(6H)-one

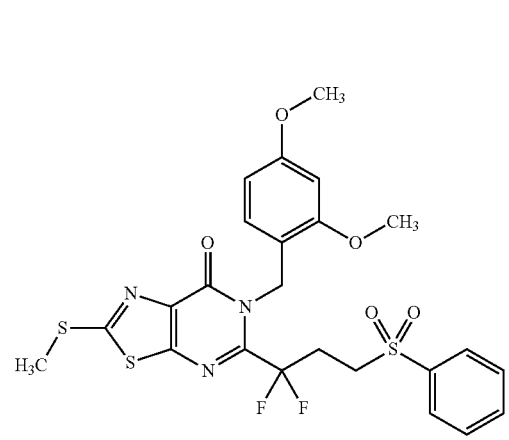 [SMILES: COc1ccc(Cn2c(C(F)(F)CCS(=O)(=O)c3ccccc3)nc3sc(SC)nc3c2=O)c(OC)c1]

The compound (487 mg) obtained in Reference Example 510 was treated by a method similar to that in Reference Example 195 to give the title compound (439 mg).
MS (ESI) m/z; 568 [M+H]$^+$

Reference Example 542

5-(1-chlorocyclopropyl)-6-(2,4-dimethoxybenzyl)-2-methylsulfanyl[1,3]thiazolo[5,4-d]pyrimidin-7 (H)-one

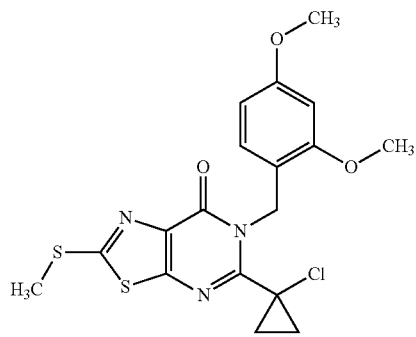

The compound (1.53 g) obtained in Reference Example 513 was treated by a method similar to that in Reference Example 195 to give the title compound (989 mg).

MS (ESI) m/z; 424 [M+H]$^+$

Reference Example 543

5-difluoromethyl-6-(2,4-dimethoxybenzyl)-2-methylsulfanyl[1,3]thiazolo[5,4-d]pyrimidin-7(6H)-one

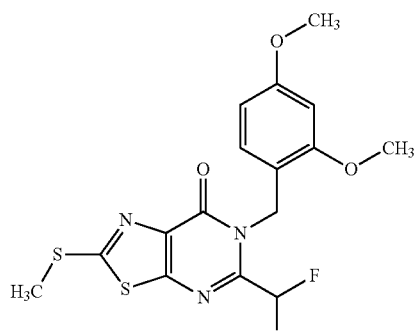

The compound (10.0 g) obtained in Reference Example 484 was treated by a method similar to that in Reference Example 244 to give the title compound (10.1 g).

MS (ESI) m/z; 400 [M+H]$^+$

Reference Example 544

5-(3-chloro-2-fluorophenyl)-6-(2,4-dimethoxybenzyl)-2-methylsulfanyl[1,3]thiazolo[5,4-d]pyrimidin-7(6H)-one

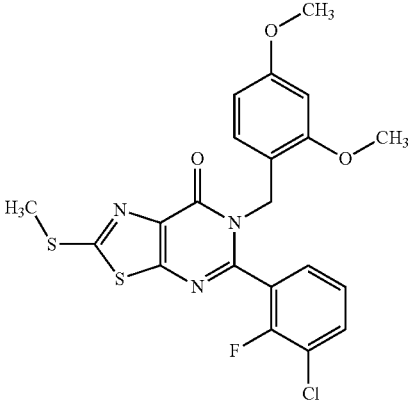

The compound (500 mg) obtained in Reference Example 484 was treated by a method similar to that in Reference Example 260 to give the title compound (576 mg).

MS (ESI) m/z; 478, 480 [M+H]$^+$

Reference Example 545

6-(2,4-dimethoxybenzyl)-2-methylsulfanyl-5-trifluoromethyl[1,3]thiazolo[5,4-d]pyrimidin-7(6H)-one

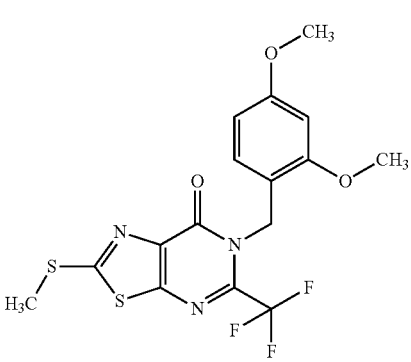

The compound (1.50 g) obtained in Reference Example 484 was treated by a method similar to that in Reference Example 265 to give the title compound (1.32 g).

MS (ESI) m/z; 418 [M+H]$^+$

Reference Example 546

6-(4-methoxybenzyl)-2-methylsulfanyl-5-sulfanyl[1,3]thiazolo[5,4-d]pyrimidin-7(6H)-one

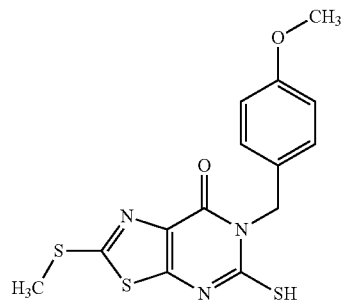

To a solution (27 mL) of 5-amino-2-methylsulfanyl-1,3-thiazole-4-carboxylic acid ethyl ester (2.84 g) in ethanol were added (4-methoxybenzyl) isothiocyanate (3.50 g) and DBU (3.89 mL), and the reaction mixture was stirred at room temperature for 30 min, and stirred with heating at 80° C. for 13 hr. The reaction mixture was cooled to 0° C., and acetic acid (2.0 mL) was added. Ethanol was evaporated under reduced pressure, water was added to the obtained mixture, and the mixture was extracted three times with chloroform. The combined organic layer was washed with saturated brine, dried over anhydrous magnesium sulfate, filtered and concentrated. The residue was purified by silica gel column chromatography (solvent; chloroform/methanol=100/0-85/15), to the obtained product was added hexane/ethyl acetate=1/2, and the solid was collected by filtration to give the title compound (1.68 g).

MS (ESI) m/z; 352 [M+H]$^+$

Reference Example 547

5-chloro-6-(4-methoxybenzyl)-2-methylsulfanyl[1,3]thiazolo[5,4-d]pyrimidin-7(6H)-one

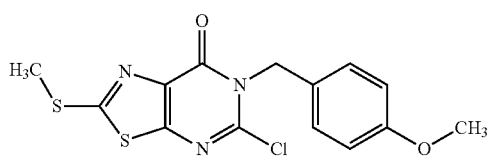

To a solution of the compound (1.40 g) obtained in Reference Example 546 in 1,2-dichloroethane/DMF (12 mL/1.5 mL) was added oxalyl chloride (512 μL) under ice-cooling. The reaction mixture was stirred with heating at 60° C. for 2 hr, and the reaction mixture was cooled to 0° C., and saturated aqueous sodium hydrogen carbonate solution was added. Dichloroethane was evaporated under reduced pressure, the obtained mixture was diluted with ethyl acetate, and the insoluble material was removed by filtration. The filtrate was extracted twice with ethyl acetate, the combined organic layer was washed with saturated brine, dried over anhydrous sodium sulfate, filtered and concentrated. To the residue was added hexane/ethyl is acetate=1/3, and the solid was collected by filtration to give the title compound (1.10 g).

MS (ESI) m/z; 354 [M+H]$^+$

Reference Example 548

6-(4-methoxybenzyl)-2-methylsulfanyl-5-phenyl[1,3]thiazolo[5,4-d]pyrimidin-7(6H)-one

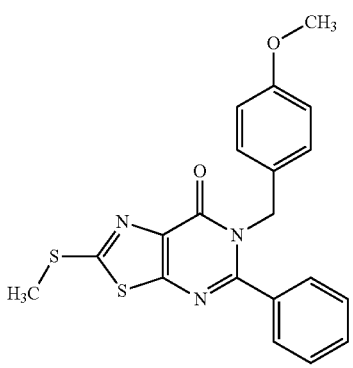 [SMILES: COc1ccc(Cn2c(-c3ccccc3)nc3sc(SC)nc3c2=O)cc1]

To a solution (12 mL) of the compound (855 mg) obtained in Reference Example 547 in DME were successively added phenylboronic acid (737 mg), tetrakis(triphenylphosphine)palladium(O) (280 mg) and an aqueous solution (3 mL) of sodium carbonate (1.03 g) at room temperature, and the reaction mixture was stirred with heating at 100° C. for 2.5 hr. After confirmation of the completion of the reaction, the reaction mixture was cooled to room temperature, water was added, and the mixture was extracted three times with methylene chloride. The combined organic layer was washed with saturated brine, dried over anhydrous sodium sulfate, filtered and concentrated. The obtained residue was purified by silica gel column chromatography (solvent; hexane/ethyl acetate=100/0-70/30) to give the title compound (736 mg).

MS (ESI) m/z; 396 [M+H]$^+$

Reference Example 549

5-(3-fluorophenyl)-6-(4-methoxybenzyl)-2-methylsulfanyl[1,3]thiazolo[5,4-d]pyrimidin-7(6H)-one

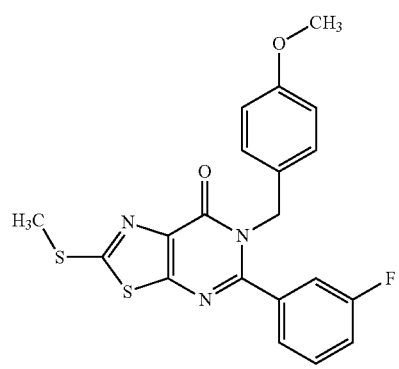 [SMILES: COc1ccc(Cn2c(-c3cccc(F)c3)nc3sc(SC)nc3c2=O)cc1]

The compound (140 mg) obtained in Reference Example 547 was treated by a method similar to that in Reference Example 548 to give the title compound (134 mg).

MS (ESI) m/z; 414 [M+H]$^+$

Reference Example 550

5-(4-fluorophenyl)-6-(4-methoxybenzyl)-2-methyl-sulfanyl[1,3]thiazolo[5,4-d]pyrimidin-7(6H)-one

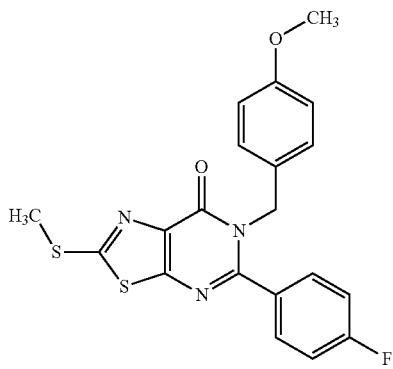 [SMILES: COc1ccc(Cn2c(-c3ccc(F)cc3)nc3sc(SC)nc3c2=O)cc1]

The compound (140 mg) obtained in Reference Example 547 was treated by a method similar to that in Reference Example 548 to give the title compound (96 mg).

MS (ESI) m/z; 414 [M+H]$^+$

Reference Example 551

5-(2,3-difluorophenyl)-6-(4-methoxybenzyl)-2-methylsulfanyl[1,3]thiazolo[5,4-d]pyrimidin-7(6H)-one

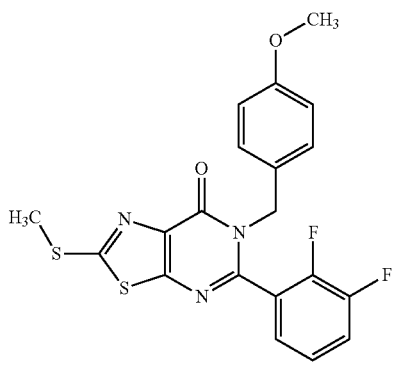 [SMILES: COc1ccc(Cn2c(-c3cccc(F)c3F)nc3sc(SC)nc3c2=O)cc1]

The compound (200 mg) obtained in Reference Example 547 was treated by a method similar to that in Reference Example 548 to give the title compound (184 mg).

MS (ESI) m/z; 432 [M+H]$^+$

Reference Example 552

5-(2,5-difluorophenyl)-6-(4-methoxybenzyl)-2-methylsulfanyl[1,3]thiazolo[5,4-d]pyrimidin-7(6H)-one

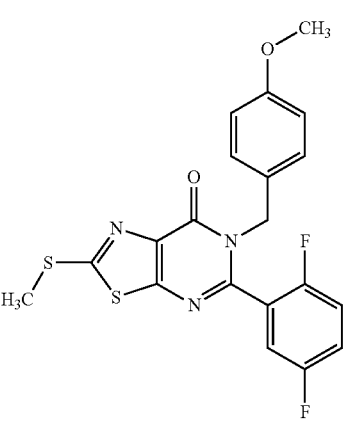 [SMILES: COc1ccc(Cn2c(-c3cc(F)ccc3F)nc3sc(SC)nc3c2=O)cc1]

The compound (400 mg) obtained in Reference Example 547 was treated by a method similar to that in Reference Example 548 to give the title compound (301 mg).

MS (ESI) m/z; 432 [M+H]$^+$

Reference Example 553

5-(3,4-difluorophenyl)-6-(4-methoxybenzyl)-2-methylsulfanyl[1,3]thiazolo[5,4-d]pyrimidin-7(6H)-one

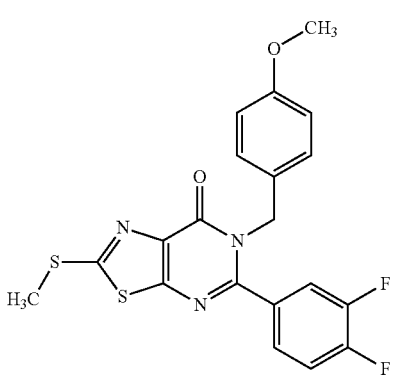 [SMILES: COc1ccc(Cn2c(-c3ccc(F)c(F)c3)nc3sc(SC)nc3c2=O)cc1]

The compound (350 mg) obtained in Reference Example 547 was treated by a method similar to that in Reference Example 548 to give the title compound (306 mg).

MS (ESI) m/z; 432 [M+H]$^+$

Reference Example 554

5-(3,5-difluorophenyl)-6-(4-methoxybenzyl)-2-methylsulfanyl[1,3]thiazolo[5,4-d]pyrimidin-7(6H)-one

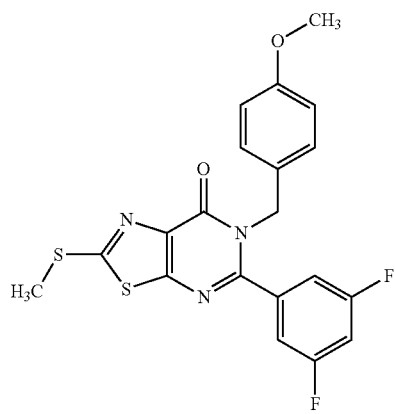 [SMILES: COc1ccc(Cn2c(-c3cc(F)cc(F)c3)nc3sc(SC)nc3c2=O)cc1]

The compound (350 mg) obtained in Reference Example 547 was treated by a method similar to that in Reference Example 548 to give the title compound (196 mg).
MS (ESI) m/z; 432 [M+H]$^+$

Reference Example 555

5-(4-fluoro-2-methoxyphenyl)-6-(4-methoxybenzyl)-2-methylsulfanyl[1,3]thiazolo[5,4-d]pyrimidin-7(6H)-one

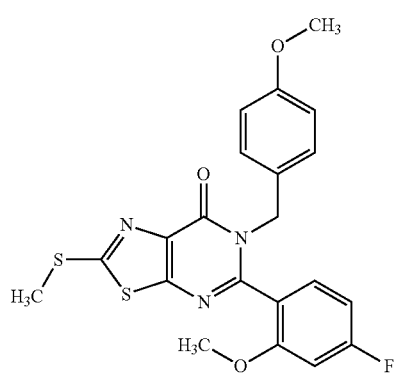 [SMILES: COc1ccc(Cn2c(-c3ccc(F)cc3OC)nc3sc(SC)nc3c2=O)cc1]

The compound (140 mg) obtained in Reference Example 547 was treated by a method similar to that in Reference Example 548 to give the title compound (153 mg).
MS (ESI) m/z; 444 [M+H]$^+$

Reference Example 556

5-(2-ethylphenyl)-6-(4-methoxybenzyl)-2-methylsulfanyl[1,3]thiazolo[5,4-d]pyrimidin-7(6H)-one

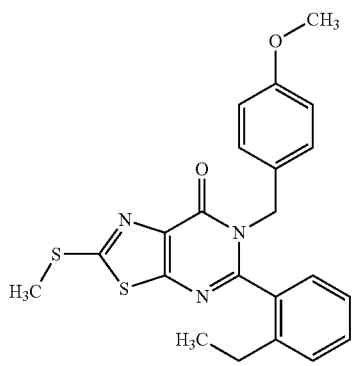 [SMILES: CCc1ccccc1-c1nc2sc(SC)nc2c(=O)n1Cc1ccc(OC)cc1]

The compound (350 mg) obtained in Reference Example 547 was treated by a method similar to that in Reference Example 548 to give the title compound (427 mg).
MS (ESI) m/z; 424 [M+H]$^+$

Reference Example 557

6-(4-methoxybenzyl)-2-methylsulfanyl-5-[2-(trifluoromethyl)phenyl][1,3]thiazolo[5,4-d]pyrimidin-7(6H)-one

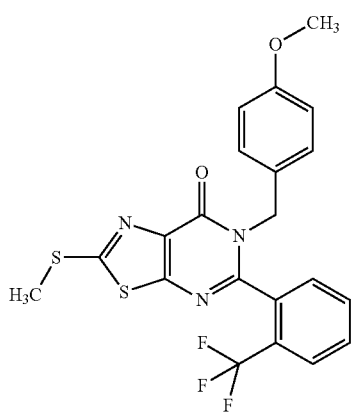 [SMILES: COc1ccc(Cn2c(-c3ccccc3C(F)(F)F)nc3sc(SC)nc3c2=O)cc1]

The compound (300 mg) obtained in Reference Example 547 was treated by a method similar to that in Reference Example 548 to give the title compound (181 mg).
MS (ESI) m/z; 464 [M+H]$^+$

Reference Example 558

6-(2,4-dimethoxybenzyl)-5-(2-fluoropropan-2-yl)-2-methylsulfinyl[1,3]thiazolo[5,4-d]pyrimidin-7(6H)-one

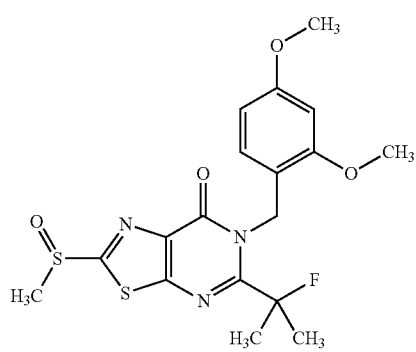

To a solution (10.0 mL) of the compound (570 mg) obtained in Reference Example 514 in methylene chloride was added mCPBA (69-75%, 377 mg) under ice-cooling, and the reaction mixture was stirred at room temperature for 4 hr. To the reaction mixture was added aqueous sodium thiosulfate solution, and the mixture was extracted three times with methylene chloride. The organic layer was washed with saturated aqueous sodium hydrogen carbonate solution, dried over anhydrous sodium sulfate, filtered and concentrated to give the title compound (631 mg).
MS (ESI) m/z; 426 [M+H]$^+$

Reference Example 559

6-(2,4-dimethoxybenzyl)-5-ethyl-2-methylsulfinyl[1,3]thiazolo[5,4-d]pyrimidin-7(6H)-one

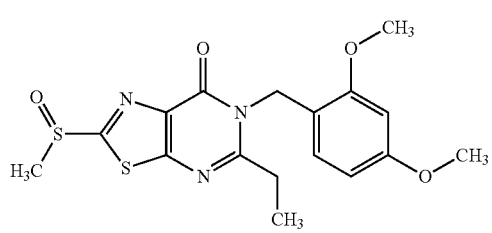

The compound (360 mg) obtained in Reference Example 515 was treated by a method similar to that in Reference Example 268 to give the title compound (341 mg).
MS (ESI) m/z; 394 [M+H]$^+$

Reference Example 560

6-(2,4-dimethoxybenzyl)-2-methylsulfinyl-5-(propan-2-yl)[1,3]thiazolo[5,4-d]pyrimidin-7(6H)-one

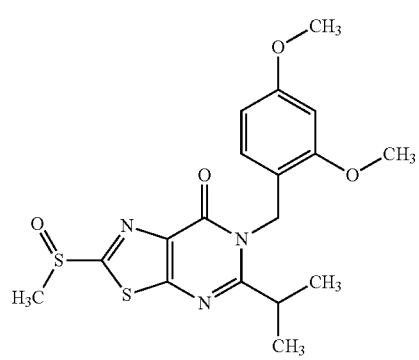

The compound (1.94 g) obtained in Reference Example 516 was treated by a method similar to that in Reference Example 268 to give the title compound (1.79 g).
MS (ESI) m/z; 408 [M+H]$^+$

Reference Example 561

6-(2,4-dimethoxybenzyl)-5-methoxymethyl-2-methylsulfinyl[1,3]thiazolo[5,4-d]pyrimidin-7(6H)-one

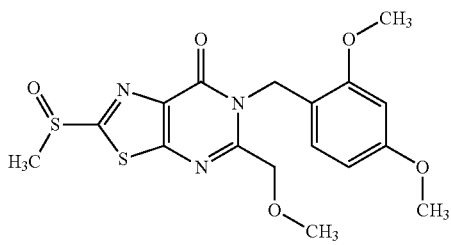

The compound (200 mg) obtained in Reference Example 517 was treated by a method similar to that in Reference Example 268 to give the title compound (282 mg).
MS (ESI) m/z; 410 [M+H]$^+$

Reference Example 562

6-(2,4-dimethoxybenzyl)-2-methylsulfinyl-5-phenyl[1,3]thiazolo[5,4-d]pyrimidin-7(6H)-one

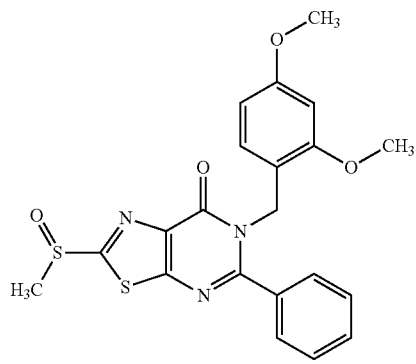

The compound (360 mg) obtained in Reference Example 518 was treated by a method similar to that in Reference Example 268 to give the title compound (326 mg).

MS (ESI) m/z; 442 [M+H]$^+$

Reference Example 563

6-(2,4-dimethoxybenzyl)-5-(2-fluorophenyl)-2-methylsulfinyl[1,3]thiazolo[5,4-d]pyrimidin-7(6H)-one

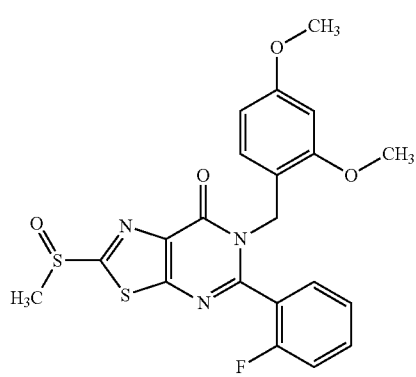

The compound (2.30 g) obtained in Reference Example 519 was treated by a method similar to that in Reference Example 268 to give the title compound (2.10 g).

MS (ESI) m/z; 460 [M+H]$^+$

Reference Example 564

5-(2-chlorophenyl)-6-(2,4-dimethoxybenzyl)-2-methylsulfinyl[1,3]thiazolo[5,4-d]pyrimidin-7(6H)-one

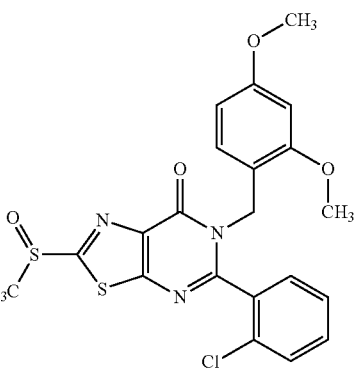

The compound (450 mg) obtained in Reference Example 520 was treated by a method similar to that in Reference Example 268 to give the title compound (288 mg).

MS (ESI) m/z; 476, 478 [M+H]$^+$

Reference Example 565

6-(2,4-dimethoxybenzyl)-5-(2-methoxyphenyl)-2-methylsulfinyl[1,3]thiazolo[5,4-d]pyrimidin-7(6H)-one

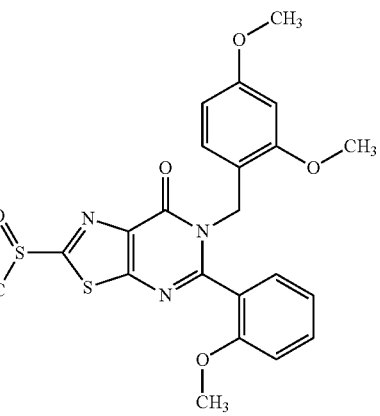

The compound (309 mg) obtained in Reference Example 521 was treated by a method similar to that in Reference Example 268 to give the title compound (329 mg).

MS (ESI) m/z; 472 [M+H]$^+$

Reference Example 566

6-(2,4-dimethoxybenzyl)-2-methylsulfinyl-5-[2-(trifluoromethoxy)phenyl][1,3]thiazolo[5,4-d]pyrimidin-7(6H)-one

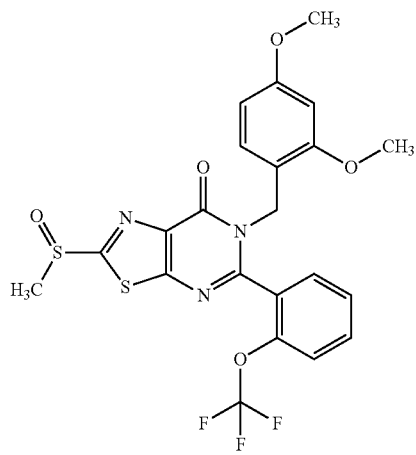

The compound (595 mg) obtained in Reference Example 522 was treated by a method similar to that in Reference Example 268 to give the title compound (649 mg).

MS (ESI) m/z; 526 [M+H]$^+$

Reference Example 567

6-(2,4-dimethoxybenzyl)-5-(2-methylphenyl)-2-methylsulfinyl[1,3]thiazolo[5,4-d]pyrimidin-7(6H)-one

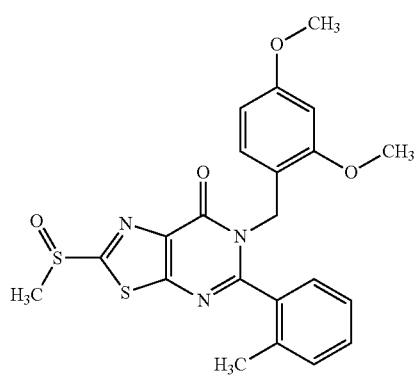

The compound (575 mg) obtained in Reference Example 523 was treated by a method similar to that in Reference Example 268 to give the title compound (673 mg).

MS (ESI) m/z; 456 [M+H]$^+$

Reference Example 568

5-(2,4-difluorophenyl)-6-(2,4-dimethoxybenzyl)-2-methylsulfinyl[1,3]thiazolo[5,4-d]pyrimidin-7(6H)-one

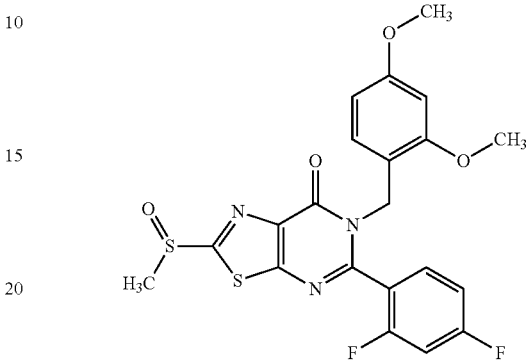

The compound (534 mg) obtained in Reference Example 524 was treated by a method similar to that in Reference Example 268 to give the title compound (580 mg).

MS (ESI) m/z; 478 [M+H]$^+$

Reference Example 569

5-(5-chloro-2-fluorophenyl)-6-(2,4-dimethoxybenzyl)-2-methylsulfinyl[1,3]thiazolo[5,4-d]pyrimidin-7(6H)-one

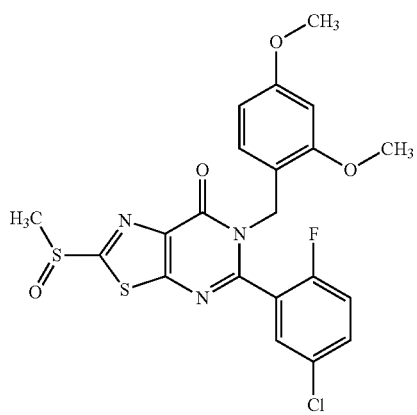 [SMILES: COc1ccc(Cn2c(-c3cc(Cl)ccc3F)nc3sc(S(C)=O)nc3c2=O)c(OC)c1]

The compound (461 mg) obtained in Reference Example 525 was treated by a method similar to that in Reference Example 268 to give the title compound (511 mg).

MS (ESI) m/z; 494, 496 [M+H]$^+$

Reference Example 570

6-(2,4-dimethoxybenzyl)-5-(1-fluorocyclopropyl)-2-methylsulfinyl[1,3]thiazolo[5,4-d]pyrimidin-7(6H)-one

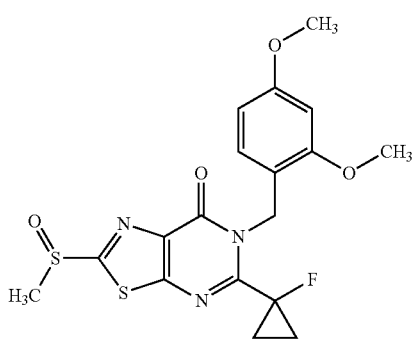

The compound (2.30 g) obtained in Reference Example 526 was treated by a method similar to that in Reference Example 268 to give the title compound (2.37 g).

MS (ESI) m/z; 424 [M+H]$^+$

Reference Example 571

5-(1,1-difluoroethyl)-6-(2,4-dimethoxybenzyl)-2-methylsulfinyl[1,3]thiazolo[5,4-d]pyrimidin-7(6H)-one

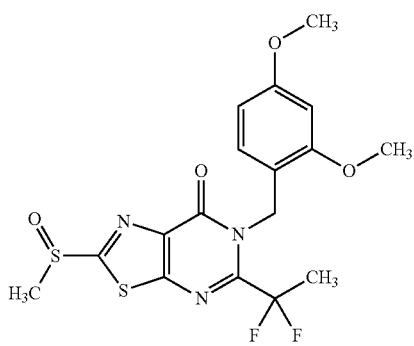

The compound (967 mg) obtained in Reference Example 527 was treated by a method similar to that in Reference Example 268 to give the title compound (1.10 g).

MS (ESI) m/z; 430 [M+H]$^+$

Reference Example 572

5-(1,1-difluoro-2-methoxyethyl)-6-(2,4-dimethoxybenzyl)-2-methylsulfinyl[1,3]thiazolo[5,4-d]pyrimidin-7(6H)-one

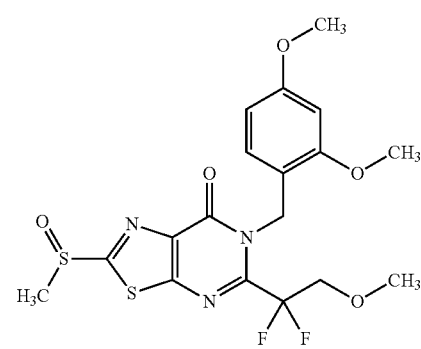

The compound (400 mg) obtained in Reference Example 528 was treated by a method similar to that in Reference Example 268 to give the title compound (500 mg).

MS (ESI) m/z; 460 [M+H]$^+$

Reference Example 573

6-(2,4-dimethoxybenzyl)-2-methylsulfinyl-5-[1-(trifluoromethyl)cyclopropyl][1,3]thiazolo[5,4-d]pyrimidin-7(6H)-one

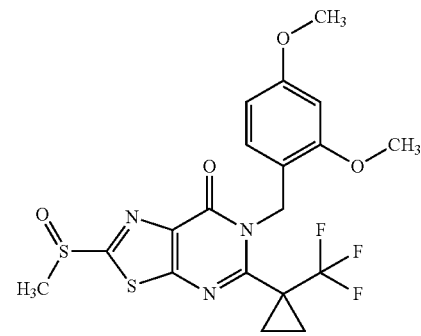

The compound (420 mg) obtained in Reference Example 529 was treated by a method similar to that in Reference Example 268 to give the title compound (472 mg).

MS (ESI) m/z; 474 [M+H]$^+$

Reference Example 574

5-[difluoro(phenyl)methyl]-6-(2,4-dimethoxybenzyl)-2-methylsulfinyl[1,3]thiazolo[5,4-d]pyrimidin-7(6H)-one

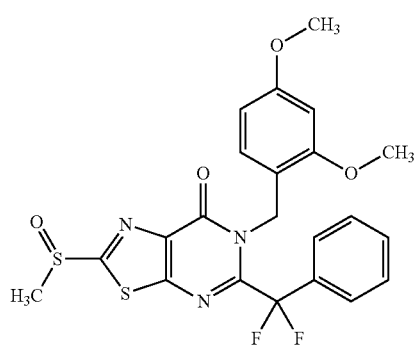 [SMILES: COc1ccc(Cn2c(C(F)(F)c3ccccc3)nc3sc(S(C)=O)nc3c2=O)c(OC)c1]

The compound (256 mg) obtained in Reference Example 530 was treated by a method similar to that in Reference Example 268 to give the title compound (279 mg).

MS (ESI) m/z; 492 [M+H]$^+$

Reference Example 575

6-(2,4-dimethoxybenzyl)-5-(2-fluoro-3-methoxyphenyl)-2-methylsulfinyl[1,3]thiazolo[5,4-d]pyrimidin-7(6H)-one

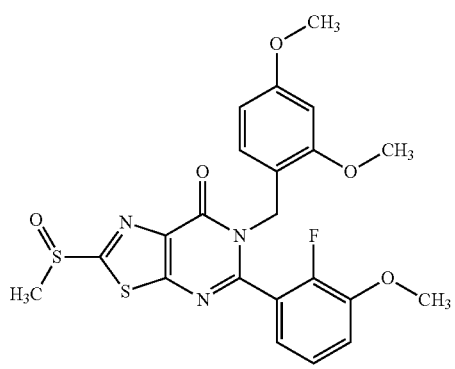

The compound (600 mg) obtained in Reference Example 531 was treated by a method similar to that in Reference Example 268 to give the title compound (695 mg).

MS (ESI) m/z; 490 [M+H]$^+$

Reference Example 576

6-(2,4-dimethoxybenzyl)-5-(2-fluoro-3-methylphenyl)-2-methylsulfinyl[1,3]thiazolo[5,4-d]pyrimidin-7(6H)-one

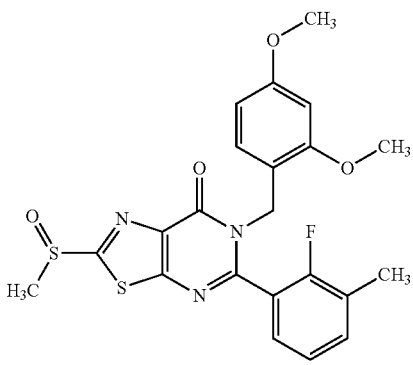

The compound (525 mg) obtained in Reference Example 532 was treated by a method similar to that in Reference Example 268 to give the title compound (607 mg).

MS (ESI) m/z; 474 [M+H]$^+$

Reference Example 577

6-(2,4-dimethoxybenzyl)-2-methylsulfinyl-5-(5-methylthiophen-2-yl)[1,3]thiazolo[5,4-d]pyrimidin-7(6H)-one

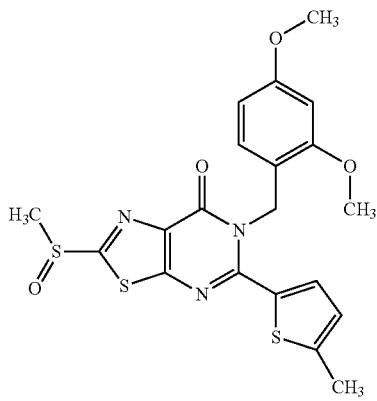 [SMILES: COc1ccc(Cn2c(-c3ccc(C)s3)nc3sc(S(C)=O)nc3c2=O)c(OC)c1]

The compound (253 mg) obtained in Reference Example 533 was treated by a method similar to that in Reference Example 268 to give the title compound (267 mg).

MS (ESI) m/z; 462 [M+H]$^+$

Reference Example 578

6-(2,4-dimethoxybenzyl)-5-(1-methoxycyclopropyl)-2-methylsulfinyl[1,3]thiazolo[5,4-d]pyrimidin-7(6H)-one

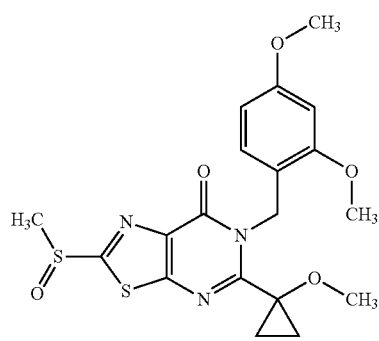 [SMILES: COc1ccc(Cn2c(C3(OC)CC3)nc3sc(S(C)=O)nc3c2=O)c(OC)c1]

The compound (1.20 g) obtained in Reference Example 534 was treated by a method similar to that in Reference Example 268 to give the title compound (890 mg).

MS (ESI) m/z; 871 [2M+H]$^+$

Reference Example 579

6-(2,4-dimethoxybenzyl)-5-[1-(fluoromethyl)cyclopropyl]-2-methylsulfinyl[1,3]thiazolo[5,4-d]pyrimidin-7(6H)-one

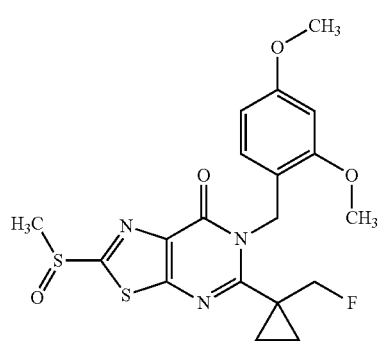 [SMILES: COc1ccc(Cn2c(C3(CF)CC3)nc3sc(S(C)=O)nc3c2=O)c(OC)c1]

The compound (630 mg) obtained in Reference Example 535 was treated by a method similar to that in Reference Example 268 to give the title compound (490 mg).

MS (ESI) m/z; 875 [2M+H]$^+$

Reference Example 580

6-(2,4-dimethoxybenzyl)-5-[1-(methoxymethyl)cyclopropyl]-2-methylsulfinyl[1,3]thiazolo[5,4-d]pyrimidin-7(6)-one

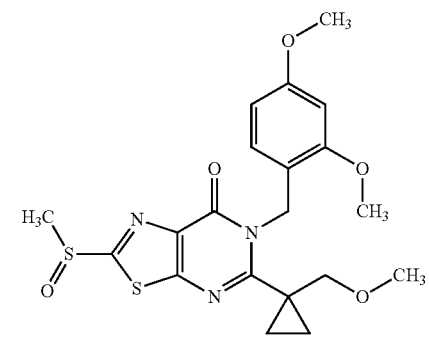 [SMILES: COCC1(c2nc3sc(S(C)=O)nc3c(=O)n2Cc2ccc(OC)cc2OC)CC1]

The compound (1.70 g) obtained in Reference Example 536 was treated by a method similar to that in Reference Example 268 to give the title compound (1.47 g).

MS (ESI) m/z; 899 [2M+H]$^+$

Reference Example 581

6-(2,4-dimethoxybenzyl)-5-(2-fluoro-5-methylphenyl)-2-methylsulfinyl[1,3]thiazolo[5,4-d]pyrimidin-7(6H)-one

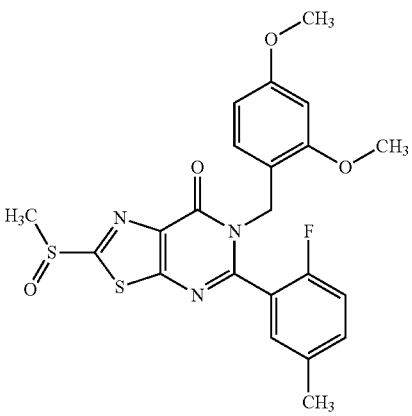 [SMILES: COc1ccc(Cn2c(-c3cc(C)ccc3F)nc3sc(S(C)=O)nc3c2=O)c(OC)c1]

The compound (477 mg) obtained in Reference Example 537 was treated by a method similar to that in Reference Example 268 to give the title compound (525 mg).

MS (ESI) m/z; 474 [M+H]$^+$

Reference Example 582

6-(2,4-dimethoxybenzyl)-5-(3-fluoropyridin-2-yl)-2-methylsulfinyl[1,3]thiazolo[5,4-d]pyrimidin-7(6H)-one

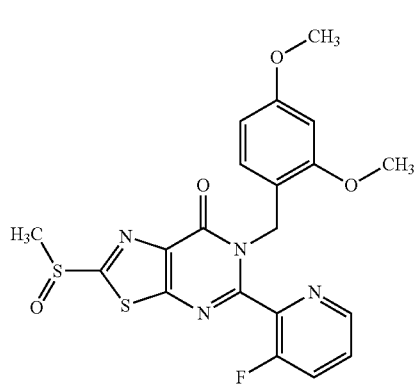 [SMILES: COc1ccc(Cn2c(-c3ncccc3F)nc3sc(S(C)=O)nc3c2=O)c(OC)c1]

The compound (300 mg) obtained in Reference Example 538 was treated by a method similar to that in Reference Example 268 to give the title compound (357 mg).
MS (ESI) m/z; 461 [M+H]$^+$

Reference Example 583

6-(2,4-dimethoxybenzyl)-5-(3-fluoro-5-methylthiophen-2-yl)-2-methylsulfinyl[1,3]thiazolo[5,4-d]pyrimidin-7(6H)-one

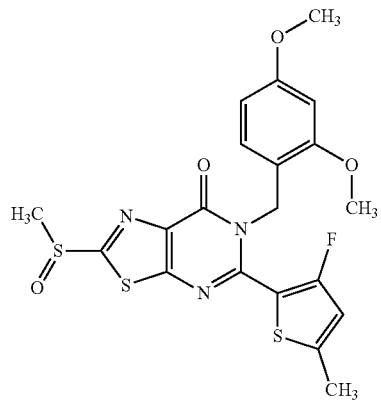 [SMILES: COc1ccc(Cn2c(-c3sc(C)cc3F)nc3sc(S(C)=O)nc3c2=O)c(OC)c1]

The compound (375 mg) obtained in Reference Example 539 was treated by a method similar to that in Reference Example 268 to give the title compound (411 mg).
MS (ESI) m/z; 480 [M+H]$^+$

Reference Example 584

6-(2,4-dimethoxybenzyl)-2-methylsulfinyl-5-pentafluoroethyl[1,3]thiazolo[5,4-d]pyrimidin-7(6H)-one

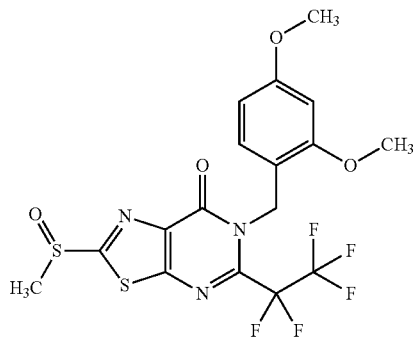

The compound (343 mg) obtained in Reference Example 540 was treated by a method similar to that in Reference Example 268 to give the title compound (233 mg).
MS (ESI) m/z; 484 [M+H]$^+$

Reference Example 585

5-(3-benzenesulfonyl-1,1-difluoropropyl)-6-(2,4-dimethoxybenzyl)-2-methylsulfinyl[1,3]thiazolo[5,4-d]pyrimidin-7(6H)-one

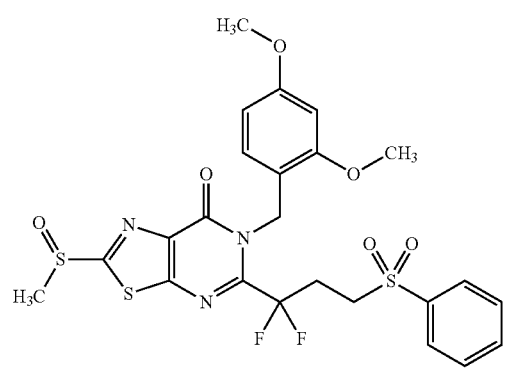 [SMILES: COc1ccc(Cn2c(C(F)(F)CCS(=O)(=O)c3ccccc3)nc3sc(S(C)=O)nc3c2=O)c(OC)c1]

The compound (400 mg) obtained in Reference Example 541 was treated by a method similar to that in Reference Example 268 to give the title compound (441 mg).
MS (ESI) m/z; 584 [M+H]$^+$ Reference Example 586

5-(1-chlorocyclopropyl)-6-(2,4-dimethoxybenzyl)-2-methylsulfinyl[1,3]thiazolo[5,4-d]pyrimidin-7(6H)-one

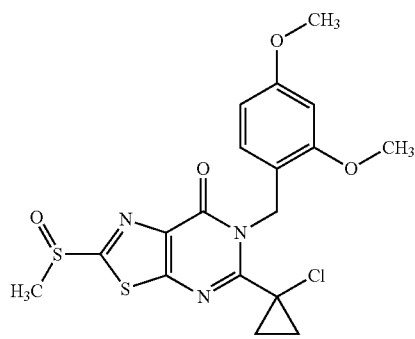

The compound (988 mg) obtained in Reference Example 542 was treated by a method similar to that in Reference Example 268 to give the title compound (1.18 g).
MS (ESI) m/z; 440 [M+H]$^+$ Reference Example 587

5-(3-chloro-2-fluorophenyl)-6-(2,4-dimethoxybenzyl)-2-methylsulfinyl[1,3]thiazolo[5,4-d]pyrimidin-7(6H)-one

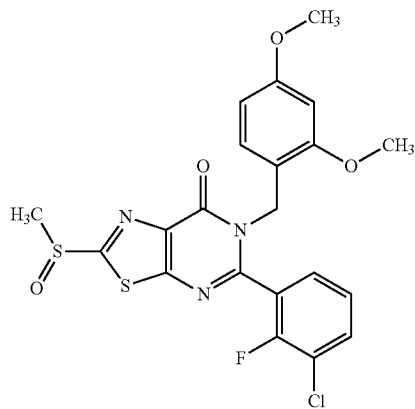 [SMILES: COc1ccc(Cn2c(-c3cccc(Cl)c3F)nc3sc(S(C)=O)nc3c2=O)c(OC)c1]

The compound (576 mg) obtained in Reference Example 544 was treated by a method similar to that in Reference Example 268 to give the title compound (576 mg).
MS (ESI) m/z; 494, 496 [M+H]$^+$ Reference Example 588

6-(2,4-dimethoxybenzyl)-2-methylsulfinyl-5-trifluoromethyl[1,3]thiazolo[5,4-d]pyrimidin-7(6H)-one

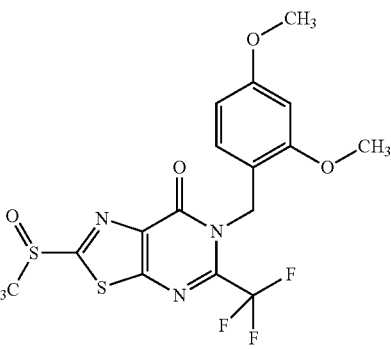

The compound (500 mg) obtained in Reference Example 545 was treated by a method similar to that in Reference Example 268 to give the title compound (528 mg).
MS (ESI) m/z; 434 [M+H]$^+$ Reference Example 589

5-difluoromethyl-6-(2,4-dimethoxybenzyl)-2-methylsulfinyl[1,3]thiazolo[5,4-d]pyrimidin-7(6H)-one

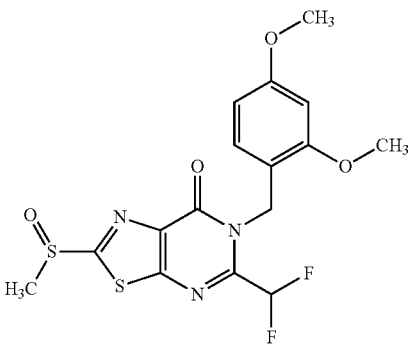

The compound (140 mg) obtained in Reference Example 543 was treated by a method similar to that in Reference Example 268 to give the title compound (167 mg).
MS (ESI) m/z; 416 [M+H]$^+$

Reference Example 590

6-(4-methoxybenzyl)-2-methylsulfinyl-5-phenyl[1,3]thiazolo[5,4-d]pyrimidin-7(6H)-one

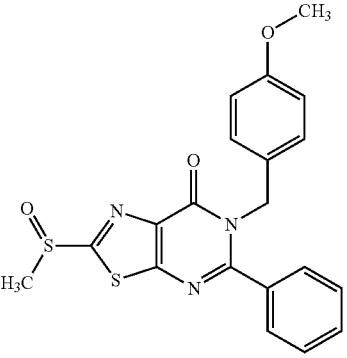

The compound (736 mg) obtained in Reference Example 548 was treated by a method similar to that in Reference Example 268 to give the title compound (834 mg)
MS (ESI) m/z; 412 [M+H]$^+$

Reference Example 591

5-(3-fluorophenyl)-6-(4-methoxybenzyl)-2-methylsulfinyl[1,3]thiazolo[5,4-d]pyrimidin-7(6H)-one

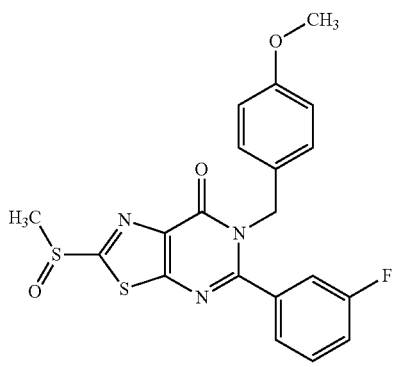 [SMILES: COc1ccc(Cn2c(-c3cccc(F)c3)nc3sc(S(C)=O)nc3c2=O)cc1]

The compound (205 mg) obtained in Reference Example 549 was treated by a method similar to that in Reference Example 268 to give the title compound (127 mg).
MS (ESI) m/z; 430 [M+H]$^+$

Reference Example 592

5-(4-fluorophenyl)-6-(4-methoxybenzyl)-2-methylsulfinyl[1,3]thiazolo[5,4-d]pyrimidin-7(6H)-one

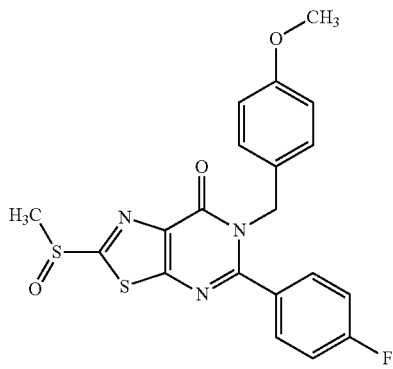 [SMILES: COc1ccc(Cn2c(-c3ccc(F)cc3)nc3sc(S(C)=O)nc3c2=O)cc1]

The compound (92 mg) obtained in Reference Example 550 was treated by a method similar to that in Reference Example 268 to give the title compound (107 mg).
MS (ESI) m/z; 430 [M+H]$^+$

Reference Example 593

5-(2,3-difluorophenyl)-6-(4-methoxybenzyl)-2-methylsulfinyl[1,3]thiazolo[5,4-d]pyrimidin-7(6H)-one

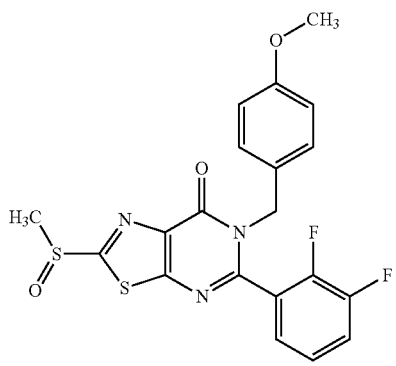 [SMILES: COc1ccc(Cn2c(-c3cccc(F)c3F)nc3sc(S(C)=O)nc3c2=O)cc1]

The compound (184 mg) obtained in Reference Example 551 was treated by a method similar to that in Reference Example 268 to give the title compound (189 mg).
MS (ESI) m/z; 448 [M+H]$^+$

Reference Example 594

5-(2,5-difluorophenyl)-6-(4-methoxybenzyl)-2-methylsulfinyl[1,3]thiazolo[5,4-d]pyrimidin-7(6H)-one

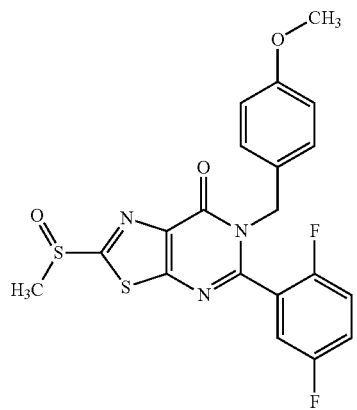

The compound (295 mg) obtained in Reference Example 552 was treated by a method similar to that in Reference Example 268 to give the title compound (289 mg).

MS (ESI) m/z; 448 [M+H]$^+$

Reference Example 595

5-(3,4-difluorophenyl)-6-(4-methoxybenzyl)-2-methylsulfinyl[1,3]thiazolo[5,4-d]pyrimidin-7(6H)-one

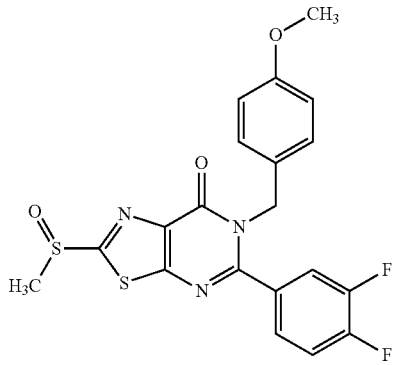 [SMILES: COc1ccc(Cn2c(-c3ccc(F)c(F)c3)nc3sc(S(C)=O)nc3c2=O)cc1]

The compound (300 mg) obtained in Reference Example 553 was treated by a method similar to that in Reference Example 268 to give the title compound (317 mg).

MS (ESI) m/z; 448 [M+H]$^+$

Reference Example 596

5-(3,5-difluorophenyl)-6-(4-methoxybenzyl)-2-methylsulfinyl[1,3]thiazolo[5,4-d]pyrimidin-7(6H)-one

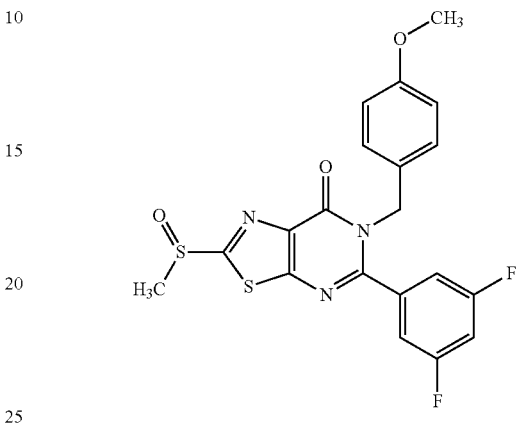

The compound (191 mg) obtained in Reference Example 554 was treated by a method similar to that in Reference Example 268 to give the title compound (232 mg).

MS (ESI) m/z; 448 [M+H]$^+$

Reference Example 597

5-(4-fluoro-2-methoxyphenyl)-6-(4-methoxybenzyl)-2-methylsulfinyl[1,3]thiazolo[5,4-d]pyrimidin-7(6H)-one

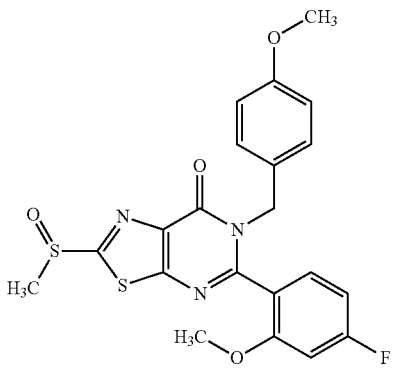 [SMILES: COc1ccc(Cn2c(-c3ccc(F)cc3OC)nc3sc(S(C)=O)nc3c2=O)cc1]

The compound (150 mg) obtained in Reference Example 555 was treated by a method similar to that in Reference Example 268 to give the title compound (164 mg).

MS (ESI) m/z; 460 [M+H]$^+$

Reference Example 598

5-(2-ethylphenyl)-6-(4-methoxybenzyl)-2-methyl-sulfinyl[1,3]thiazolo[5,4-d]pyrimidin-7(6H)-one

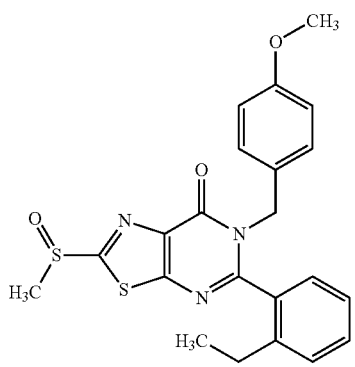 [SMILES: CCc1ccccc1-c1nc2sc(S(C)=O)nc2c(=O)n1Cc1ccc(OC)cc1]

The compound (424 mg) obtained in Reference Example 556 was treated by a method similar to that in Reference Example 268 to give the title compound (244 mg).

MS (ESI) m/z; 440 [M+H]$^+$

Reference Example 599

6-(4-methoxybenzyl)-2-methylsulfinyl-5-[2-(trifluoromethyl)phenyl][1,3]thiazolo[5,4-d]pyrimidin-7(6H)-one

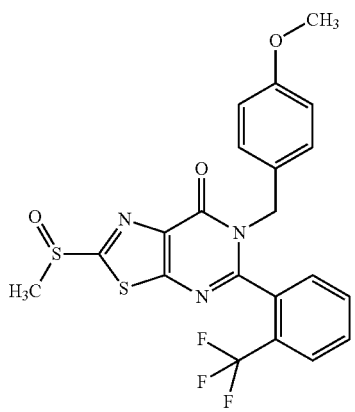 [SMILES: COc1ccc(Cn2c(-c3ccccc3C(F)(F)F)nc3sc(S(C)=O)nc3c2=O)cc1]

The compound (150 mg) obtained in Reference Example 557 was treated by a method similar to that in Reference Example 268 to give the title compound (174 mg).

MS (ESI) m/z; 480 [M+H]$^+$

Reference Example 600

6-(4-methoxybenzyl)-2-methylsulfanyl-5-[(R)-2-(trifluoromethyl)pyrrolidin-1-yl][1,3]thiazolo[5,4-d]pyrimidin-7(6H)-one

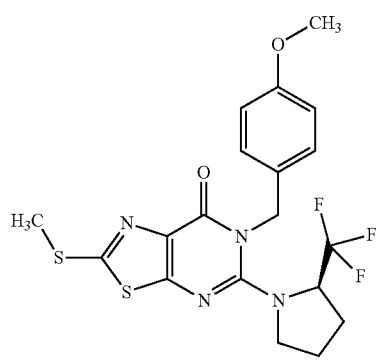 [SMILES: COc1ccc(Cn2c(N3CCC[C@@H]3C(F)(F)F)nc3sc(SC)nc3c2=O)cc1]

A mixture of the compound (500 mg) obtained in Reference Example 547, (R)-2-trifluoromethylpyrrolidine (300 mg) and N,N-diisopropylethylamine (3.50 mL) was stirred with heating at 150° C. for 1 hr. (R)-2-trifluoromethylpyrrolidine (600 mg) was added, and the reaction mixture was stirred with heating at 150° C. for 8 hr. The reaction mixture was allowed to cool, ethyl acetate and hydrochloric acid were added, and the mixture was extracted with ethyl acetate. The combined organic layer was washed with saturated brine, dried over anhydrous magnesium sulfate, filtered and concentrated. The residue was purified by silica gel column chromatography (solvent; hexane/ethyl acetate) to give the title compound (380 mg).

MS (ESI) m/z; 457 [M+H]$^+$

Reference Example 601

6-(4-methoxybenzyl)-2-methylsulfanyl-5-[(S)-2-(trifluoromethyl)pyrrolidin-1-yl][1,3]thiazolo[5,4-d]pyrimidin-7(6H)-one

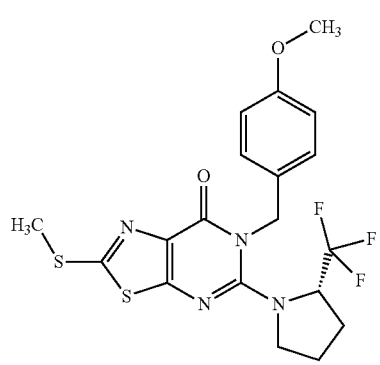 [SMILES: COc1ccc(Cn2c(N3CCC[C@H]3C(F)(F)F)nc3sc(SC)nc3c2=O)cc1]

The compound (500 mg) obtained in Reference Example 547 was treated by a method similar to that in Reference Example 600 to give the title compound (500 mg).

MS (ESI) m/z; 457 [M+H]$^+$

Reference Example 602

6-(4-methoxybenzyl)-2-((RS)-methylsulfinyl)-5-[(R)-2-(trifluoromethyl)pyrrolidin-1-yl][1,3]thiazolo[5,4-d]pyrimidin-7(6H)-one

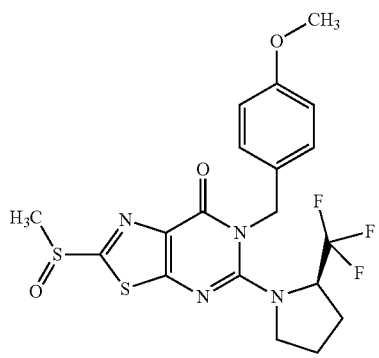 [SMILES: COc1ccc(Cn2c(N3CCC[C@@H]3C(F)(F)F)nc3sc(S(C)=O)nc3c2=O)cc1]

The compound (380 mg) obtained in Reference Example 600 was treated by a method similar to that in Reference Example 268 to give the title compound (280 mg).

MS (ESI) m/z; 473 [M+H]$^+$

Reference Example 603

6-(4-methoxybenzyl)-2-((RS)-methylsulfinyl)-5-[(S)-2-(trifluoromethyl) pyrrolidin-1-yl][1,3]thiazolo[5,4-d]pyrimidin-7(6H)-one

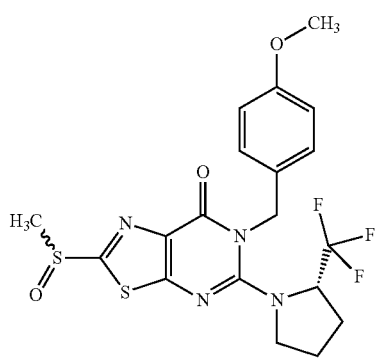 [SMILES: COc1ccc(Cn2c(N3CCC[C@H]3C(F)(F)F)nc3sc(S(C)=O)nc3c2=O)cc1]

The compound (500 mg) obtained in Reference Example 601 was treated by a method similar to that in Reference Example 268 to give the title compound (360 mg).

MS (ESI) m/z; 473 [M+H]$^+$

Reference Example 604

6-(4-methoxybenzyl)-2-methylsulfanyl-5-(2,2,2-trifluoroethoxy)-6H-thiazolo[5,4-d]pyrimidin-7-one

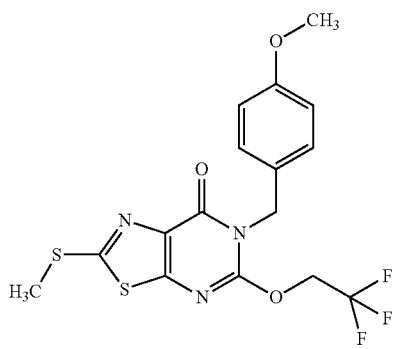 [SMILES: COc1ccc(Cn2c(OCC(F)(F)F)nc3sc(SC)nc3c2=O)cc1]

To a solution (10 mL) of the compound (350 mg) obtained in Reference Example 547 in DMF was added sodium hydride (60% oil dispersion, 59 mg), 2,2,2-trifluoroethanol (107 µL) was added, and the reaction mixture was stirred at room temperature for 1.5 hr. Water was added to the reaction mixture, and the mixture was extracted twice with ethyl acetate. The combined organic layer was washed with water and saturated brine, dried over anhydrous magnesium sulfate, filtered and concentrated. The residue was purified by silica gel column chromatography (solvent; hexane/ethyl acetate=90/10-70/30) to give the title compound (176 mg).

MS (ESI) m/z; 418 [M+H]$^+$

Reference Example 605

2-methylsulfinyl-6-(4-methoxybenzyl)-5-(2,2,2-trifluoroethoxy)-6H-thiazolo[5,4-d]pyrimidin-7-one

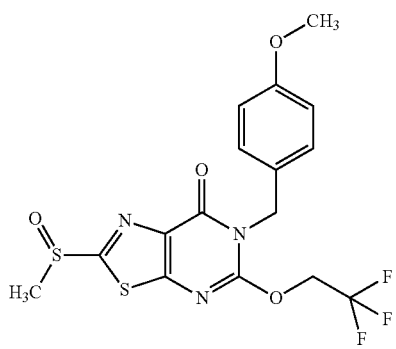 [SMILES: COc1ccc(Cn2c(OCC(F)(F)F)nc3sc(S(C)=O)nc3c2=O)cc1]

The compound (172 mg) obtained in Reference Example 604 was treated by a method similar to that in Reference Example 268 to give the title compound (173 mg).

MS (ESI) m/z; 434 [M+H]$^+$

Reference Example 606

N-[2-methylsulfanyl-4-(tetrahydro-2H-pyran-4-yl)carbamoyl-1,3-thiazol-5-yl]oxamic acid ethyl ester

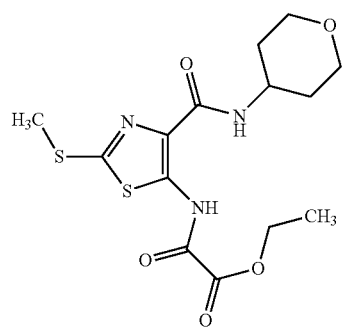 [SMILES: CCOC(=O)C(=O)Nc1sc(SC)nc1C(=O)NC1CCOCC1]

To a solution (20 mL) of the compound (1.35 g) obtained in Reference Example 143 in methylene chloride were added triethylamine (700 mg) and ethyl chloroglyoxylate (710 mg) under ice-cooling, and the reaction mixture was stirred at 0° C. for 1 hr. Water was added to the reaction mixture, and the mixture was extracted with chloroform. The combined organic layer was dried over anhydrous sodium sulfate, filtered and concentrated. The residue was purified by silica gel column chromatography (solvent; hexane/ethyl acetate=50/50-20/80) to give the title compound (1.15 g).

MS (ESI) m/z; 374 [M+H]$^+$

Reference Example 607

2-methylsulfanyl-7-oxo-6-(tetrahydro-2H-pyran-4-yl)-6,7-dihydro[1,3]thiazolo[5,4-d]pyrimidine-5-carboxylic acid ethyl ester

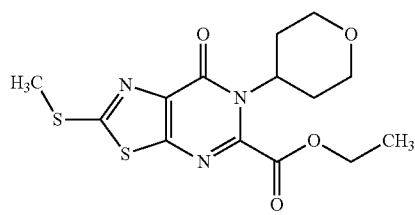 [SMILES: CCOC(=O)c1nc2sc(SC)nc2c(=O)n1C1CCOCC1]

To a solution (20 mL) of the compound (1.15 g) obtained in Reference Example 606 in dichloroethane were added chlorotrimethylsilane (3.35 g) and triethylamine (9.4 g), and the reaction mixture was stirred at room temperature for 3 days. 1.0 mol/L Hydrochloric acid was added to the reaction mixture, and the mixture was extracted twice with chloroform. The organic layer was dried over anhydrous sodium sulfate, filtered and concentrated. The residue was purified by silica gel column chromatography (solvent; hexane/ethyl acetate=50/50-20/80) to give the title compound (950 mg).

MS (ESI) m/z; 356 [M+H]$^+$

Reference Example 608

5-hydroxymethyl-2-methylsulfanyl-6-(tetrahydro-2H-pyran-4-yl)[1,3]thiazolo[5,4-d]pyrimidin-7(6H)-one

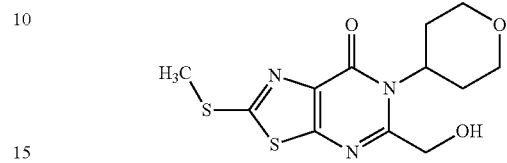

To a solution (40 mL) of the compound (950 mg) obtained in Reference Example 607 in THF was added lithium aluminum hydride (100 mg) under ice-cooling. The reaction mixture was stirred at room temperature for 1 hr, to the reaction mixture were added methanol and water. The mixture was extracted with chloroform, and the organic layer was dried over anhydrous sodium sulfate, filtered and concentrated. To the residue was added diisopropyl ether, and the solid was collected by filtration, and dried to give the title compound (550 mg).

MS (ESI) m/z; 314 [M+H]$^+$

Reference Example 609

5-methoxymethyl-2-methylsulfanyl-6-(tetrahydro-2H-pyran-4-yl)[1,3]thiazolo[5,4-d]pyrimidin-7(6H)-one

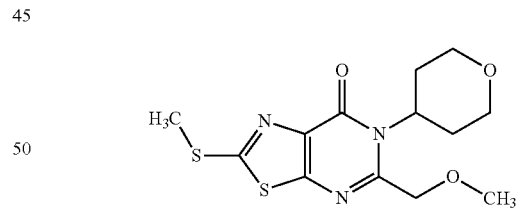

To a solution (20 mL) of the compound (550 mg) obtained in Reference Example 608 in DMF were added sodium hydride (60% oil dispersion, 95 mg) and methyl iodide (300 mg) under ice-cooling. The reaction mixture was stirred at 0° C. for 1 hr, and water was added to the reaction mixture. The mixture was extracted with ethyl acetate, and the organic layer was dried over anhydrous sodium sulfate, filtered and concentrated. The residue was purified by silica gel column chromatography (solvent; hexane/ethyl acetate=50/50-0/100) to give the title compound (210 mg).

MS (ESI) m/z; 328 [M+H]$^+$

Reference Example 610

5-methoxymethyl-2-methylsulfinyl-6-(tetrahydro-2H-pyran-4-yl)[1,3]thiazolo[5,4-d]pyrimidin-7(6H)-one

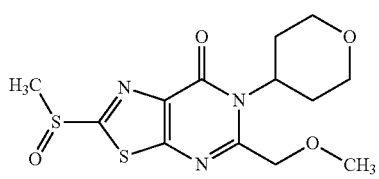

To a solution (8 mL) of the compound (210 mg) obtained in Reference Example 609 in methylene chloride was added mCPBA (69-75%, 165 mg) under ice-cooling. The reaction mixture was stirred at room temperature for 1.5 hr, to the reaction mixture is were added aqueous sodium thiosulfate solution and saturated aqueous sodium hydrogen carbonate solution, and the mixture was extracted with methylene chloride. The organic layer was dried over anhydrous sodium sulfate, filtered and concentrated to give the title compound (190 g).
MS (ESI) m/z; 344 [M+H]$^+$

Reference Example 611

5-hydrazine-6-methyl-2-methylsulfanyl[1,3]thiazolo[5,4-d]pyrimidin-7(6H)-one

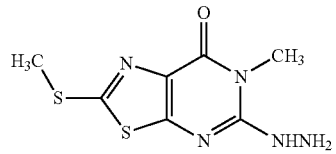

To a solution (5 mL) of the compound (300 mg) obtained in Reference Example 366 in THF was added hydrazine monohydrate (0.11 mL), and the reaction mixture was stirred at room temperature for 2 hr. Water was added to the reaction mixture, and the resultant solid was collected by filtration and dried to give the title compound (121 mg).
MS (ESI) m/z; 244 [M+H]$^+$

Reference Example 612

6-methyl-2-methylsulfanyl-5-(pyrazol-1-yl)[1,3]thiazolo[5,4-d]pyrimidin-7(6H)-one

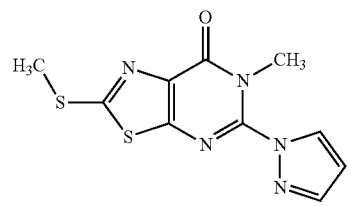 [SMILES: CSc1nc2c(=O)n(C)c(-n3cccn3)nc2s1]

To a solution (8.0 mL) of the compound (110 mg) obtained in Reference Example 611 in ethanol were added 1,1,3,3-tetramethoxypropane (0.082 mL) and concentrated hydrochloric acid (0.057 mL), and the reaction mixture was heated under reflux for 1.5 hr. Under ice-cooling, the reaction mixture was neutralized with saturated sodium hydrogen carbonate, and the mixture was extracted with ethyl acetate. The organic layer was dried over anhydrous magnesium sulfate, filtered and concentrated. The obtained residue was purified by silica gel column chromatography (solvent; hexane/ethyl acetate=80/20-50/50) to give the title compound (93 mg).
MS (ESI) m/z; 280 [M+H]$^+$

Reference Example 613

6-methyl-2-methylsulfinyl-5-(pyrazol-1-yl)[1,3]thiazolo[5,4-d]pyrimidin-7(6H)-one

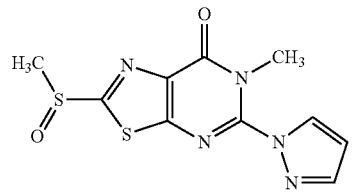 [SMILES: Cn1c(-n2cccn2)nc2sc(S(C)=O)nc2c1=O]

To a solution (3.0 mL) of the compound (90 mg) obtained in Reference Example 612 in methylene chloride was added mCPBA (69-75%, 95 mg) under ice-cooling. The reaction mixture was stirred under ice-cooling for 1 hr, to the reaction mixture were added aqueous sodium thiosulfate solution and saturated aqueous sodium hydrogen carbonate solution, and the mixture was extracted with chloroform. The organic layer was dried over anhydrous sodium sulfate, filtered and concentrated to give the title compound (105 mg).
MS (ESI) m/z; 296 [M+H]$^+$

Reference Example 614

5-amino-N-methyl-1,3-thiazole-4-carboxamide

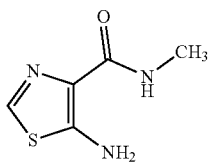

To a solution (500 mL) of ethyl 2-amino-2-cyanoacetate (51.2 g) in diisopropyl ether was added 40% methylamine methanol solution (62.1 mL) under ice-cooling, and the reaction mixture was stirred at room temperature for 1.5 hr. The resultant solid was collected by filtration, washed with diisopropyl ether-ethanol (2:1), and dried to give 2-amino-2-cyano-N-methylacetamido (28.7 g).

A mixture of acetic anhydride (50 mL) and formic acid (24 mL) was stirred with heating at 60° C. for 3 hr. The obtained mixed acid anhydride was added to a solution (190 mL) of 2-amino-2-cyano-N-methylacetamide (20.0 g) in THF under ice-cooling, and the reaction mixture was stirred at room temperature for 2 hr. The solvent was evaporated, ethyl acetate was added to the residue, and the precipitated solid was collected by filtration, washed with ethyl acetate and diisopropyl ether, and dried to give 2-cyano-2-formamide-N-methylacetamide (15.6 g).

A mixture (18 mL) of 2-cyano-2-formamide-N-methylacetamide (1.00 g) and Lawesson reagent (1.43 g) in 1,4-dioxane was stirred with heating at 80° C. for 7 hr. The solvent was evaporated under reduced pressure, and the residue was dissolved in chloroform, and washed with saturated aqueous sodium hydrogen carbonate solution. The separated aqueous is layer was extracted twice with chloroform. The combined organic layer was dried over anhydrous sodium sulfate, filtered and concentrated. The residue was purified by NH silica gel column chromatography (solvent; hexane/ethyl acetate=70/30-20/80) to give the title compound (244 mg).

MS (ESI) m/z; 158 [M+H]$^+$

Reference Example 615

5-[(cyclopropylcarbonyl)amino]-N-methyl-1,3-thiazole-4-carboxamide

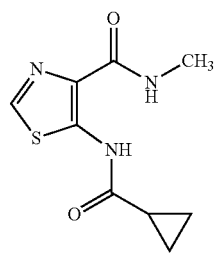

To a solution (12 mL) of the compound (1.20 g) obtained in Reference Example 614 in methylene chloride were added N,N-diisopropylethylamine (1.99 mL) and cyclopropylcarbonyl chloride (838 μL) at room temperature, and the reaction mixture was stirred at room temperature overnight. Cyclopropylcarbonyl chloride (800 μL) was added, and the reaction mixture was stirred at room temperature for 2 hr. Water was added to the reaction mixture, and the mixture was extracted with chloroform. The combined organic layer was dried over anhydrous sodium sulfate, filtered and concentrated. The residue was purified by silica gel column chromatography (solvent; hexane/ethyl acetate=80/20-20/80) to give the title compound (1.59 g).

MS (ESI) m/z; 226 [M+H]$^+$

Reference Example 616

5-cyclopropyl-6-methyl[1,3]thiazolo[5,4-d]pyrimidin-7(6H)-one

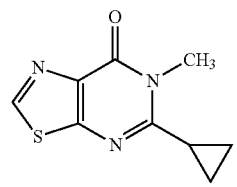

To a solution (42 mL) of the compound (1.49 g) obtained in Reference Example 615 in dichloroethane were added chlorotrimethylsilane (4.18 mL) and triethylamine (13.7 mL), and the reaction mixture was stirred with heating at 80° C. for 5 hr. The reaction mixture was cooled to room temperature, water was added to the reaction mixture, and the mixture was extracted twice with chloroform. The organic layer was dried over anhydrous sodium sulfate, filtered and concentrated. The residue was purified by silica gel column chromatography (solvent; hexane/ethyl acetate=70/30-0/100) to give the title compound (1.30 g).

MS (ESI) m/z; 208 [M+H]$^+$

Reference Example 617

2-bromo-5-cyclopropyl-6-methyl[1,3]thiazolo[5,4-d]pyrimidin-7(6H)-one

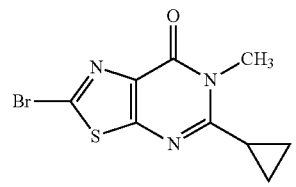

A mixture of the compound (1.30 g) obtained in Reference Example 616 and N-bromosuccinimide (1.12 g) in acetonitrile (24 mL) was heated under reflux for 2 hr. N-bromosuccinimide (2.24 g) was added, and the reaction mixture was further heated under reflux for 12 hr. Ethyl acetate was added to the reaction mixture, and the mixture was washed with aqueous sodium thiosulfate solution and saturated brine, and the organic layer was dried over sodium sulfate, filtered and concentrated. The residue was purified by silica gel column chromatography (solvent; hexane/ethyl acetate=80/20-20/80) to give the title compound (1.26 g).

MS (ESI) m/z; 286, 288 [M+H]$^+$

Reference Example 618

(R)-N-benzyl-4,4-difluoropyrrolidine-2-carboxamidehydrochloride

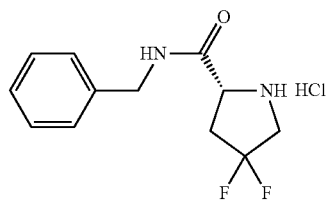 [SMILES: O=C(NCc1ccccc1)[C@H]1CC(F)(F)CN1 ; Cl]

To a solution (2.4 mL) of (R)N-(tert-butoxycarbonyl)-4,4-difluoropyrrolidine-2-carboxylic acid (300 mg) described in WO 2011/130383 in DMF were added benzylamine (131 μL), EDC hydrochloride (341 mg), HOBt monohydrate (273 mg) and N,N-diisopropylethylamine (0.31 mL), and the reaction mixture was stirred at room temperature for 1 hr. After confirmation of the completion of the reaction, water was added to the reaction mixture, and the mixture was extracted twice with ethyl acetate. The organic layer was washed once with water, dried over anhydrous magnesium sulfate, filtered and concentrated. The residue was purified by silica gel column chromatography (solvent; hexane/ethyl acetate=80/20-50/50). The obtained product was dissolved in methanol (7.0 mL), hydrogen chloride (4.0 mol/L 1,4-dioxane solution, 1.5 mL) was added, and the mixture was stirred at room temperature overnight. The solvent was evaporated, ethyl acetate was added to the residue, and the solid was collected by filtration, and dried to give the title compound (243 mg).

MS (ESI) m/z; 241 [M+H]$^+$

Reference Example 619

5-amino-2-bromo-N-methyl-1,3-thiazole-4-carboxamide

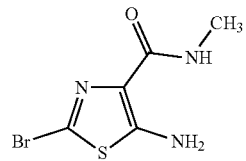

To a solution (12 mL) of the compound (317 mg) obtained in Reference Example 614 in acetonitrile was added N-bromosuccinimide (360 mg), and the reaction mixture was stirred at 0° C. for 30 min. The solvent was evaporated under reduced pressure, and the residue was purified by silica gel column chromatography (solvent; hexane/ethyl acetate=90/10-50/50) to give the title compound (373 mg).

MS (ESI) m/z; 236, 238 [M+H]$^+$

Reference Example 620

5-amino-2-[(R)-2-(benzylcarbamoyl)pyrrolidin-1-yl]-N-methyl-1,3-thiazole-4-carboxamide

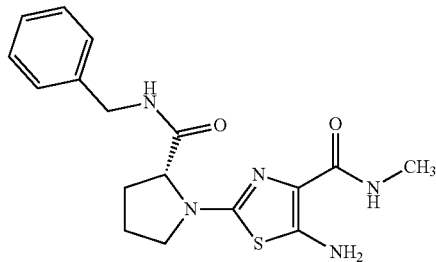 [SMILES: CNC(=O)c1nc(N2CCC[C@@H]2C(=O)NCc2ccccc2)sc1N]

A mixed solution of the compound (2.57 g) obtained in Reference Example 619, the compound (5.24 g) obtained in Reference Example 341 and N,N-diisopropylethylamine (22 mL) was stirred with heating at 120° C. for 3 hr. The reaction mixture was concentrated and the residue was purified by silica gel column chromatography (solvent; ethyl acetate/methanol=100/0-90/10) and concentrated to give the title compound (2.92 g).

MS (ESI) m/z; 360 [M+H]$^+$

Reference Example 621

2-[(R)-2-(benzylcarbamoyl)pyrrolidin-1-yl]-5-{[(1-cyanocyclopropyl)carbonyl]amino}-N-methyl-1,3-thiazole-4-carboxamide

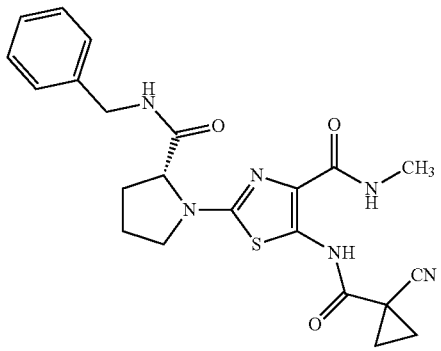 [SMILES: CNC(=O)c1nc(N2CCC[C@@H]2C(=O)NCc2ccccc2)sc1NC(=O)C1(C#N)CC1]

To a solution (0.7 mL) of the compound (128 mg) obtained in Reference Example 620 in DMF were added 1-cyanocyclopropanecarboxylic acid (43 mg), EDC hydrochloride (106 mg), HOBt monohydrate (84 mg) and N,N-diisopropylethylamine (0.095 mL), and the reaction mixture was stirred at room temperature for 1 hr. 1-Cyanocyclopropanecarboxylic acid (43 mg), EDC hydrochloride (106 mg), HOBt monohydrate (84 mg) and N,N-diisopropylethylamine (0.095 mL) were added, and the reaction mixture was stirred overnight. Water was added to the reaction mixture, and the mixture was extracted three times with ethyl acetate. The organic layer was dried over anhydrous sodium sulfate, filtered and concentrated. The residue was purified by silica gel column chromatography (solvent; ethyl acetate/methanol=100/0-90/10) to give the title compound (89 mg).

MS (ESI) m/z; 453 [M+H]$^+$

Reference Example 622

(R)-2-(2-phenoxyacetyl)pyrrolidine-1-carboxylic acid tert-butyl ester

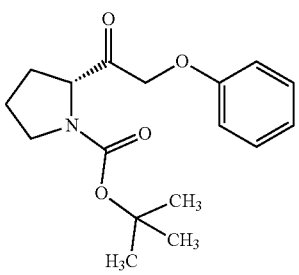 [SMILES: CC(C)(C)OC(=O)N1CCC[C@@H]1C(=O)COc1ccccc1]

To a solution (30 mL) of (R)-N-(tert-butoxycarbonyl)-2-(2-chloroacetyl)-pyrrolidine (2.6 g) synthesized by the method described in Tetrahedron Lett. 1997, 3175-3178 in DMF were added potassium carbonate (1.8 g), potassium iodide (2.1 g) and phenol (1.18 g) at room temperature, and the reaction mixture was stirred at room temperature overnight. After confirmation of the completion of the reaction, water was added to the reaction mixture, and the mixture was extracted twice with ethyl acetate. The organic layer was washed once with water, dried over anhydrous magnesium sulfate, filtered and concentrated. The residue was purified by silica gel column chromatography (solvent; hexane/ethyl acetate=90/10-80/20) to give the title compound (2.3 g).

MS (ESI) m/z; 306 [M+H]$^+$

Reference Example 623 and Reference Example 624

(R)-2-((RS)-1-hydroxy-2-phenoxyethyl)pyrrolidine-1-carboxylic acid tert-butyl ester

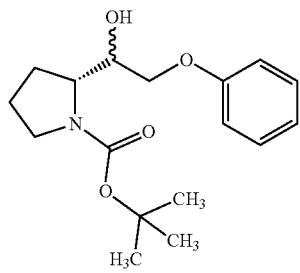 [SMILES: CC(C)(C)OC(=O)N1CCC[C@@H]1C(O)COc1ccccc1]

To a solution (40 mL) of the compound (2.3 g) obtained in Reference Example 622 in methanol was added sodium borohydride (0.57 g) at 0° C., and the reaction mixture was stirred at room temperature for 1 hr. After confirmation of the completion of the reaction, water was added to the reaction mixture, and the mixture was neutralized with 1.0 mol/L hydrochloric acid and extracted twice with ethyl acetate. The organic layer was washed once with water, dried over anhydrous magnesium sulfate, filtered and concentrated. The residue was purified by silica gel column chromatography (solvent; chloroform/methanol=100/0-95/5) to give the title compound (TLC using silica gel (eluent chloroform/methanol=90:10) as a less polar compound (Reference Example 623; 1.64 g), and a highly-polar compound (Reference Example 624; 0.62 g)).

Reference Example 623 (ESI) m/z; 308 [M+H]$^+$
Reference Example 624 (ESI) m/z; 308 [M+H]$^+$ Reference Example 625

(RS)-2-phenoxy-1-((R)-pyrrolidin-2-yl)ethanol trifluoroacetate

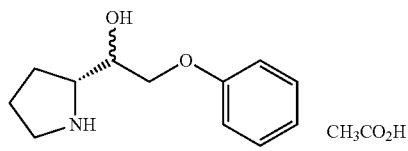

To a solution (20 mL) of the compound (1.64 g) obtained in Reference Example 623 in methylene chloride were added trifluoroacetic acid (20 mL) and water (2 drops) at room temperature, and the reaction mixture was stirred at room temperature for 1 hr. After confirmation of the completion of the reaction, the solvent was evaporated under reduced pressure to give the title compound (1.7 g).

MS (ESI) m/z; 208 [M+H]$^+$

Reference Example 626

(R)-2-[(2-phenylamino)acetyl]pyrrolidine-1-carboxylic acid tert-butyl ester

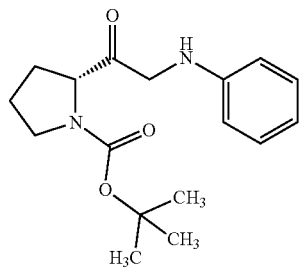 [SMILES: CC(C)(C)OC(=O)N1CCC[C@@H]1C(=O)CNc1ccccc1]

To a solution (30 mL) of (R)-N-(tert-butoxycarbonyl)-2-(2-chloroacetyl)-pyrrolidine (3.0 g) synthesized by the method described in Tetrahedron Lett. 1997, 3175-3178 in DMF were added potassium carbonate (2.0 g), potassium iodide (2.4 g) and aniline (1.35 g) at room temperature, and the reaction mixture was stirred at room temperature overnight. After confirmation of the completion of the reaction, water was added to the reaction mixture, and the mixture was extracted twice with ethyl acetate. The organic layer was washed once with water, dried over anhydrous magnesium sulfate, filtered and concentrated. The residue was purified by silica gel column chromatography (solvent; hexane/ethyl acetate=90/10-80/20) to give the title compound (2.16 g).

MS (ESI) m/z; 305 [M+H]$^+$

Reference Example 627 and Reference Example 628

(R)-2-[(RS)-1-hydroxy-2-(phenylamino)ethyl]pyrrolidine-1-carboxylic acid tert-butyl ester

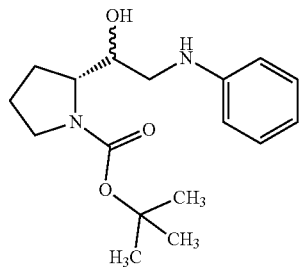 [SMILES: CC(C)(C)OC(=O)N1CCC[C@@H]1C(O)CNc1ccccc1]

To a solution (40 mL) of the compound (2.16 g) obtained in Reference Example 626 in methanol was added sodium borohydride (0.54 g) at 0° C., and the reaction mixture was stirred at room temperature for 1 hr. After confirmation of the completion of the reaction, water was added to the reaction mixture, and the mixture was neutralized with 1.0 mol/L hydrochloric acid, and extracted once with ethyl acetate. The organic layer was washed once with water, dried over anhydrous magnesium sulfate, filtered and concentrated. The residue was purified by silica gel column chromatography (solvent; hexane/ethyl acetate=90/10-70/30) to give the title compound (TLC using silica gel (eluent hexane/ethyl acetate=50:50) as a less polar compound (Reference Example 627; 1.36 g), and a highly-polar compound (Reference Example 628; 0.69 g)).

Reference Example 627 (ESI) m/z; 307 [M+H]+
Reference Example 628 (ESI) m/z; 307 [M+H]+

Reference Example 629

(RS)-2-phenylamino-1-((R)-pyrrolidin-2-yl)ethanol trifluoroacetate

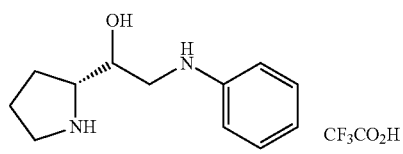

To a solution (20 mL) of the compound (1.36 g) obtained in Reference Example 627 in methylene chloride were added trifluoroacetic acid (20 mL) and water (2 drops) at room temperature, and the reaction mixture was stirred at room temperature for 1 hr. After confirmation of the completion of the reaction, the solvent was evaporated under reduced pressure to give the title compound (1.4 g).

MS (ESI) m/z; 207 [M+H]+

Reference Example 633

5-[(2,6-difluorobenzoyl)amino]-N-(2,4-dimethoxybenzyl)-2-methylsulfanyl-1,3-thiazole-4-carboxamide

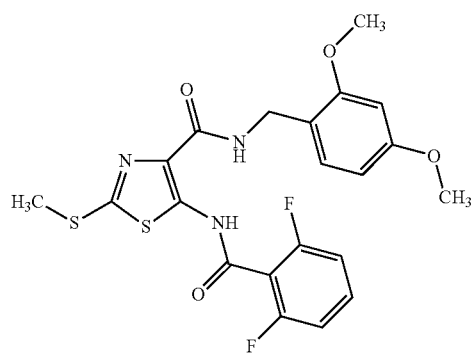

To a solution (6 mL) of the compound (600 mg) obtained in Reference Example 484 and triethylamine (820 mL) in methylene chloride was added 2,6-difluorobenzoyl chloride (0.33 mL) at 0° C., and the reaction mixture was stirred for 1 hr at room temperature. Water was added to the reaction mixture, and the mixture was extracted twice with ethyl acetate, organic layer was dried over anhydrous magnesium sulfate, filtered and concentrated. The residue was purified by silica gel column chromatography (solvent; hexane/ethyl acetate=90/10-60/40) to give the title compound (681 mg).

MS (ESI) m/z; 480 [M+H]+

Reference Example 634

5-(2,6-difluorophenyl)-6-(2,4-dimethoxybenzyl)-2-methylsulfanyl[1,3]thiazolo[5,4-d]pyrimidin-7(6H)-one

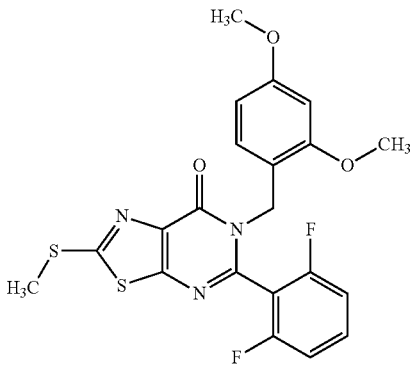

The compound (6.72 g) obtained in Reference Example 633 was treated by a method similar to that in Reference Example 514 to give the title compound (6.17 g).

MS (ESI) m/z; 462 [M+H]+

Reference Example 635

5-(2,6-difluorophenyl)-6-(2,4-dimethoxybenzyl)-2-methylsulfinyl[1,3]thiazolo[5,4-d]pyrimidin-7(6H)-one

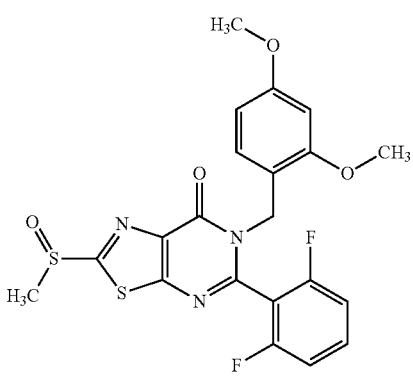

The compound (6.12 g) obtained in Reference Example 634 was treated by a method similar to that in Reference Example 268 to give the title compound (5.79 g).

MS (ESI) m/z; 478 [M+H]+

Reference Example 636

6-(4-methoxybenzyl)-2-methylsulfanyl-5-(piperidin-1-yl)[1,3]thiazolo[5,4-d]pyrimidin-7(6H)-one

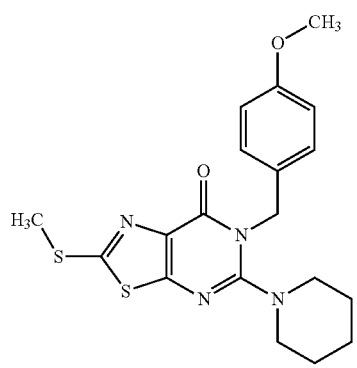 [SMILES: COc1ccc(Cn2c(N3CCCCC3)nc3sc(SC)nc3c2=O)cc1]

To a solution (50.0 mL) of the compound (5.00 g) obtained in Reference Example 547 in N-methylpyrrolidone were added piperidine (2.09 mL) and N,N-diisopropylethylamine (4.89 mL), and the reaction mixture was stirred with heating at 60° C. for 1 hr. The reaction mixture was allowed to cool, water was added, and the mixture was extracted with ethyl acetate. The organic layer was washed with saturated brine, dried over anhydrous magnesium sulfate, filtered and concentrated. The residue was purified by silica gel column chromatography (solvent; hexane/ethyl acetate=50/50-20/80) to give the title compound (5.70 g).

MS (ESI) m/z; 403 [M+H]$^+$

Reference Example 637

6-(4-methoxybenzyl)-2-methylsulfinyl-5-(piperidin-1-yl)[1,3]thiazolo[5,4-d]pyrimidin-7(6H)-one

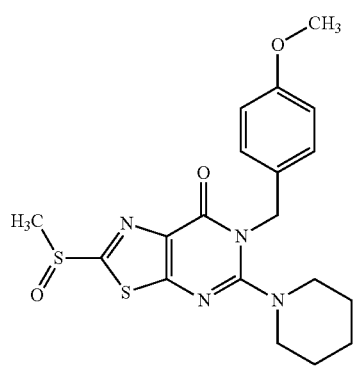 [SMILES: COc1ccc(Cn2c(N3CCCCC3)nc3sc(S(C)=O)nc3c2=O)cc1]

The compound (5.70 g) obtained in Reference Example 636 was treated by a method similar to that in Reference Example 268 to give the title compound (5.19 g).

MS (ESI) m/z; 419 [M+H]$^+$

Reference Example 641

5-amino-2-methylsulfanyl-1,3-thiazole-4-carboxamide

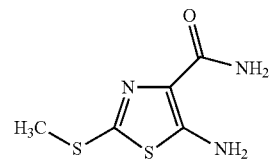

To trifluoroacetic acid (20 mL) were added triethylsilane (5.7 mL) and the compound (2.0 g) obtained in Reference Example 484, and the mixture was stirred at room temperature for 1 hr. After confirmation of the completion of the reaction, chloroform and water were added to the reaction mixture, and the mixture was neutralized with saturated aqueous sodium hydrogen carbonate solution and extracted twice with chloroform. The organic layer was washed once with water, dried over anhydrous magnesium sulfate, filtered and concentrated. The residue was purified by silica gel column chromatography (solvent; chloroform/methanol=100/0-90/10) to give the title compound (0.9 g).

MS (ESI) m/z; 190 [M+H]$^+$

Reference Example 642

5-[(3-methyl-[1,2,4]oxadiazole-5-carbonyl)amino]-2-methylsulfanyl-1,3-thiazole-4-carboxamide

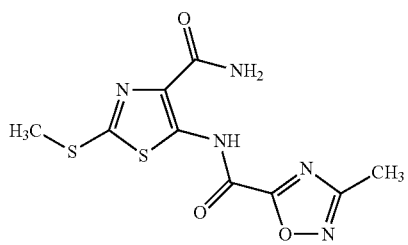

To a solution (50 mL) of 3-methyl-[1,2,4]oxadiazole-5-carboxylic acid ethyl ester (9.45 g) in ethanol was added an aqueous solution (20 mL) of potassium hydroxide (4.0 g) at room temperature, and the reaction mixture was stirred for 2 hr. The solvent was evaporated under reduced pressure, to the residue was added acetonitrile, and the solid was collected by filtration, and dried to give 3-methyl-[1,2,4]oxadiazole-5-carboxylic acid potassium salt (9.38 g). To a solution of the obtained 3-methyl-[1,2,4]oxadiazole-5-carboxylic acid potassium salt (3.6 g) in acetonitrile were added oxalyl chloride (1.84 mL) and DMF (2 drops) at 0° C., and the reaction mixture was stirred at room temperature for 1 hr. The solution was added to a solution (40 mL) of the compound (1.35 g) obtained in Reference Example 641 in pyridine at 0° C., and the reaction mixture was stirred at room temperature for 3 hr. After confirmation of the completion of the reaction, ethyl acetate and water were added to the reaction mixture, and the mixture was neutralized with 6.0 mol/L hydrochloric acid at room temperature, and the mixture was extracted twice with ethyl acetate. The organic layer was washed once with water, dried over anhydrous magnesium sulfate, filtered and concentrated. The residue was washed with ethyl acetate and diisopropyl ether, collected by filtration, and dried to give the title compound (1.2 g).

MS (ESI) m/z; 300 [M+H]+

Reference Example 643

5-(3-methyl-[1,2,4]oxadiazol-5-yl)-2-methylsulfanyl[1,3]thiazolo[5,4-d]pyrimidin-7(6H)-one

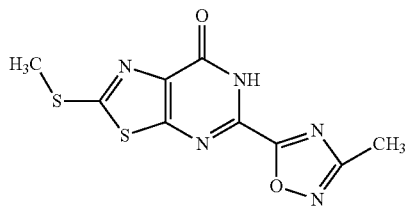

To a solution (50 mL) of the compound (1.2 g) obtained in Reference Example 642 in methylene chloride were added chlorotrimethylsilane (5.1 mL) and triethylamine (17 mL), and the reaction mixture was stirred at room temperature for 2 days. After confirmation of the completion of the reaction, water was added to the reaction mixture, and the mixture was extracted twice with chloroform. The organic layer was washed once with water, dried over anhydrous magnesium sulfate, filtered and concentrated. The residue was purified by silica gel column chromatography (solvent; chloroform/methanol=100/0-90/10) to give the title compound (0.83 g).

MS (ESI) m/z; 282 [M+H]+

Reference Example 644

5-nitro-2-(1,1,1-trifluoro-2-methylpropan-2-yl)-3H-pyrimidin-4-one

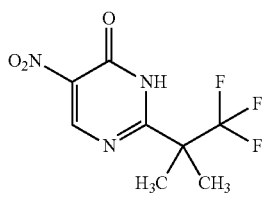 [SMILES: CC(C)(c1ncc([N+](=O)[O-])c(=O)[nH]1)C(F)(F)F]

To nitroethyl acetate (3.9 g) was added dimethylformamide dimethylacetal (7.0 g), and the reaction mixture was stirred at room temperature for 30 min and stirred with heating at 100° C. for 2 hr. The reaction mixture was cooled to room temperature and the solvent was evaporated under reduced pressure. To the residue were added ethanol (30 mL), 3,3,3-trifluoro-2,2-dimethylpropionamidine hydrochloride (7.8 g) (synthesized by the method described in US2011/3786) and triethylamine (5.8 mL) at room temperature, and the reaction mixture was stirred with heating at 100° C. for 10 hr. The reaction mixture was cooled to room temperature, water and 1.0 mol/L hydrochloric acid were added to acidify the mixture, and the mixture was extracted twice with chloroform. The organic layer was dried over anhydrous magnesium sulfate, filtered and concentrated. The residue was purified by silica gel column chromatography (solvent; ethyl acetate/methanol=100/0-90/10) to give the title compound (1.46 g).

MS (ESI) m/z; 252 [M+H]+

Reference Example 645

2-tert-butyl-5-nitro-3H-pyrimidin-4-one

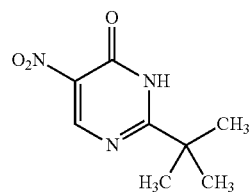

2,2-dimethylpropionamidine hydrochloride (2.30 g) was treated by a method similar to that in Reference Example 644 to give the title compound (1.33 g).

MS (ESI) m/z; 198 [M+H]+

Reference Example 646

5-amino-2-(1,1,1-trifluoro-2-methylpropan-2-yl)-3H-pyrimidin-4-one

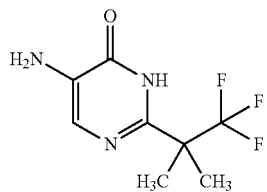

To a mixed solution of the compound (1.46 g) obtained in Reference Example 644 in methanol-chloroform (20 mL-10 mL) was added 10% palladium carbon (0.2 g), and the reaction mixture was stirred under a hydrogen atmosphere at room temperature for 2 hr. After confirmation of the completion of the reaction, the reaction mixture was filtered through diatomaceous earth, and the filtrate was concentrated under reduced pressure to give the title compound (1.28 g).

MS (ESI) m/z; 222 [M+H]+

Reference Example 647

5-amino-2-tert-butyl-3H-pyrimidin-4-one

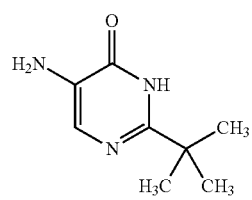

The compound (1.33 g) obtained in Reference Example 645 was treated by a method similar to that in Reference Example 646 to give the title compound (1.20 g).

MS (ESI) m/z; 168 [M+H]+

Reference Example 648

5-amino-6-bromo-2-(1,1,1-trifluoro-2-methylpropan-2-yl)-3H-pyrimidin-4-one

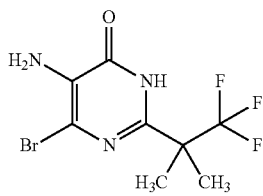

To a solution (13 mL) of the compound (1.28 g) obtained in Reference Example 646 in DMF was added a solution (5 mL) of N-bromosuccinimide (1.0 g) in DMF at 0° C. The reaction mixture was stirred at 0° C. for 1 hr, to the reaction mixture was added aqueous sodium thiosulfate solution, and the mixture was extracted twice with ethyl acetate. The organic layer was dried over anhydrous magnesium sulfate, filtered and concentrated. The residue was purified by silica gel column chromatography (solvent; hexane/ethyl acetate=80/20-30/70) to give the title compound (1.07 g).

MS (ESI) m/z; 300, 302 [M+H]$^+$

Reference Example 649

5-amino-6-bromo-2-tert-butyl-3H-pyrimidin-4-one

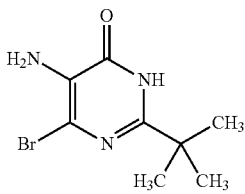

The compound (1.20 g) obtained in Reference Example 647 was treated by a method similar to that in Reference Example 648 to give the title compound (580 mg).
MS (ESI) m/z; 246, 248 [M+H]$^+$

Reference Example 650

2-thioxo-5-(1,1,1-trifluoro-2-methylpropan-2-yl)-1,6-dihydro-2H-[1,3]thiazolo[5,4-d]pyrimidin-7(6H)-one

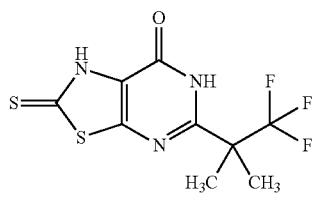

A solution (10 mL) of the compound (1.07 g) obtained in Reference Example 648 and potassium ethyl xanthogenate (1.15 g) in DMF was stirred with heating at 140° C. for 3 hr. The reaction mixture was cooled to room temperature, and acetic acid (10 mL) and water (20 mL) were added. The precipitated solid was collected by filtration, washed with water and diisopropyl ether, and dried under reduced pressure to give the title compound (0.54 g).

MS (ESI) m/z; 296 [M+H]$^+$

Reference Example 651

5-tert-butyl-2-thioxo-1,6-dihydro-2H-[1,3]thiazolo[5,4-d]pyrimidin-7(6H)-one

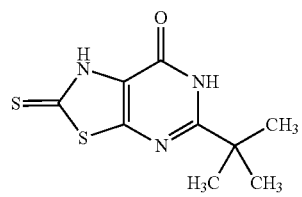

The compound (640 mg) obtained in Reference Example 649 was treated by a method similar to that in Reference Example 650 to give the title compound (630 mg).
MS (ESI) m/z; 242 [M+H]$^+$

Reference Example 652

2-methylsulfanyl-5-(2,2,2-trifluoro-1,1-dimethyl-ethyl)[1,3]thiazolo[5,4-d]pyrimidin-7(6H)-one

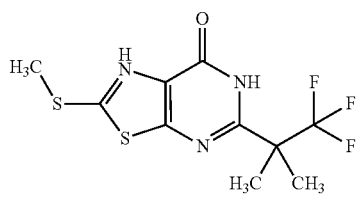

To a solution (5 mL) of the compound (200 mg) obtained in Reference Example 650 in DMF were added sodium hydrogen carbonate (70 mg) and methyl iodide (47 μL) at 0° C. The reaction mixture was stirred at room temperature for 2 hr, and sodium hydrogen carbonate (35 mg) and methyl iodide (23 μL) were added at room temperature. The reaction mixture was stirred at room temperature for 1 hr stirred, water (20 mL) was added, and the resultant solid was collected by filtration, and dried to give the title compound (176 mg).

MS (ESI) m/z; 310 [M+H]$^+$

Reference Example 653

5-tert-butyl-2-methylsulfanyl[1,3]thiazolo[5,4-d]pyrimidin-7(6H)-one

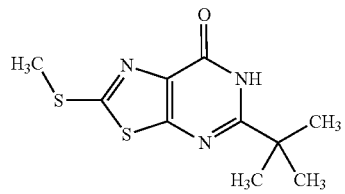

The compound (625 mg) obtained in Reference Example 651 was treated by a method similar to that in Reference Example 652 to give the title compound (658 mg).
MS (ESI) m/z; 256 [M+H]$^+$

Reference Example 654

2-methylsulfonyl-5-(1,1,1-trifluoro-2-methylpropan-2-yl)[1,3]thiazolo[5,4-d]pyrimidin-7(6H)-one

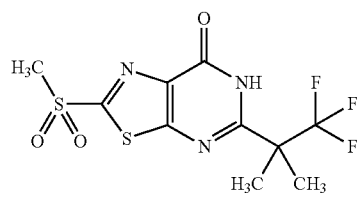 [SMILES: CC(C)(c1nc2sc(S(C)(=O)=O)nc2c(=O)[nH]1)C(F)(F)F]

To a solution (1.4 mL) of the compound (176 mg) obtained in Reference Example 652 in trifluoroacetic acid was added 30% is aqueous hydrogen peroxide solution (140 μL) under ice-cooling. The reaction mixture was stirred at room temperature for 1 hr, water (20 mL) was added, and the resultant solid was filtered and dried to give the title compound (180 mg).
MS (ESI) m/z; 342 [M+H]$^+$

Reference Example 655

5-tert-butyl-2-methylsulfonyl[1,3]thiazolo[5,4-d]pyrimidin-7(6H)-one

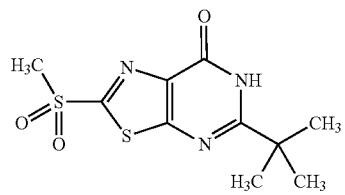 [SMILES: CC(C)(C)c1nc2sc(S(C)(=O)=O)nc2c(=O)[nH]1]

The compound (650 mg) obtained in Reference Example 653 was treated by a method similar to that in Reference Example 654 to give the title compound (688 mg).
MS (ESI) m/z; 288 [M+H]$^+$

Reference Example 656

{2-[(5-amino-2-methylsulfanyl-1,3-thiazole-4-carbonyl)amino]ethyl}carbamic acid tert-butyl ester

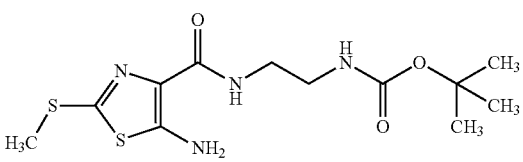 [SMILES: CSc1nc(C(=O)NCCNC(=O)OC(C)(C)C)c(N)s1]

To a solution (70 mL) of 5-amino-2-methylsulfanyl-1,3-thiazole-4-carboxylic acid (3.00 g) in DMF were added N,N-diisopropylethylamine (4.1 mL), (2-aminoethyl)-carbamic acid tert-butyl ester (3.76 mL), EDC hydrochloride (4.54 g) and HOBt monohydrate (3.63 g), and the reaction mixture was stirred at room temperature for 3 days. Water was added to the reaction mixture, and the mixture was extracted three times with ethyl acetate. The organic layer was dried over anhydrous magnesium sulfate, filtered and concentrated. The residue was purified by silica gel column chromatography (solvent; hexane/ethyl acetate=70/30-30/70) to give the title compound (4.48 g).
MS (ESI) m/z; 233 [M+H-Boc]$^+$

Reference Example 657

{2-[{5-[(2-chloroacetyl)amino]-2-methylsulfanyl-1,3-thiazole-4-carbonyl}amino]ethyl}carbamic acid tert-butyl ester

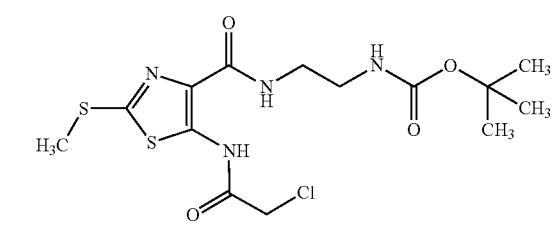 [SMILES: CSc1nc(C(=O)NCCNC(=O)OC(C)(C)C)c(NC(=O)CCl)s1]

To a solution (40 mL) of the compound (2.67 g) obtained in Reference Example 656 in methylene chloride were added triethylamine (3.36 mL) and chloroacetyl chloride (958 μL) at room temperature. The reaction mixture was stirred at room temperature for 15 hr, chloroacetyl chloride (180 μL) was added, and the reaction mixture was stirred at room temperature for 1 hr. Water was added to the reaction mixture, and the mixture was extracted with ethyl acetate. The combined organic layer was dried over anhydrous sodium sulfate, collected by collected by filtration and concentrated. To the residue was added hexane/ethyl acetate=2/1 and the precipitated solid was filtered, and dried under reduced pressure to give the title compound (2.31 g).
MS (ESI) m/z; 308 [M+H-Boc]$^+$

Reference Example 658

[2-(5-chloromethyl-2-methylsulfanyl-7-oxo-7H-[1,3]thiazolo[5,4-d]pyrimidin-6-yl)ethyl]carbamic acid tert-butyl ester

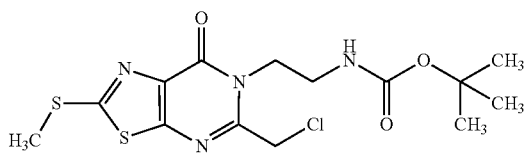 [SMILES: CSc1nc2c(=O)n(CCNC(=O)OC(C)(C)C)c(CCl)nc2s1]

To a solution (50 mL) of the compound (2.27 g) obtained in Reference Example 657 in dichloroethane were added chlorotrimethylsilane (3.51 mL) and triethylamine (11.60 mL), and the reaction mixture was stirred at room temperature for 1.5 hr. Water was added to the reaction mixture, and the mixture was extracted twice with ethyl acetate. The organic layer was dried over anhydrous sodium sulfate, filtered and concentrated. The residue was purified by silica gel column chromatography (solvent; hexane/ethyl acetate=80/20-50/50) to give the title compound (1.89 g).
MS (ESI) m/z; 391 [M+H]$^+$

Reference Example 659

6-(2-aminoethyl)-5-chloromethyl-2-methylsulfanyl[1,3]thiazolo[5,4-d]pyrimidin-7(6H)-one hydrochloride

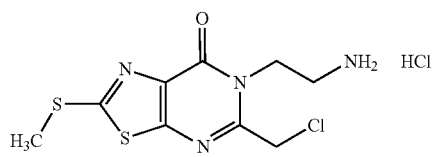 [SMILES: CSc1nc2c(=O)n(CCN)c(CCl)nc2s1 ; Cl]

To a solution (40 mL) of the compound (1.565 g) obtained in Reference Example 658 in ethyl acetate was added hydrogen chloride (4.0 mol/L ethyl acetate solution, 9 mL), and the reaction mixture was stirred with heating at 40° C. for 5 hr. The reaction mixture was cooled to room temperature, to the resultant solid were added ethyl acetate, chloroform and diethyl ether, and the solid was collected by filtration to give the title compound (1.268 g).
MS (ESI) m/z; 291 [M+H]$^+$

Reference Example 660

2-methylsulfanyl-10-oxo-5,7,8,10-tetrahydro-6H-pyrazino[1,2-a][1,3]thiazolo[5,4-d]pyrimidine-6-carboxylic acid tert-butyl ester

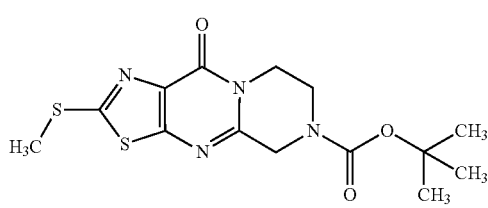 [SMILES: CSc1nc2c(=O)n3c(nc2s1)CN(C(=O)OC(C)(C)C)CC3]

To a mixed solution of the compound (1250 mg) obtained in Reference Example 659 in THF/water (35 mL/35 mL) was added sodium hydrogen carbonate (963 mg) under ice-cooling, and the reaction mixture was stirred at room temperature for 2.5 hr. To the reaction mixture was added di-tert-butyl dicarbonate (917 mg), and the reaction mixture was stirred at room temperature for 14 hr. THF was evaporated under reduced pressure, and the mixture was extracted twice with ethyl acetate. The combined organic layer was washed with saturated brine, dried over anhydrous sodium sulfate, filtered and concentrated. The residue was purified by silica gel column chromatography (solvent; hexane/ethyl acetate=80/20-20/80), to the obtained product was added hexane/ethyl acetate=2/1, and the solid was collected by filtration to give the title compound (1182 mg).
MS (ESI) m/z; 355 [M+H]$^+$

Reference Example 661

2-methylsulfinyl-10-oxo-5,7,8,10-tetrahydro-6H-pyrazino[1,2-a][1,3]thiazolo[5,4-d]pyrimidine-6-carboxylic acid tert-butyl ester

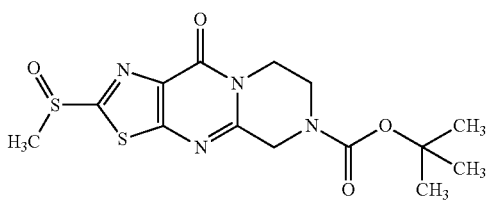 [SMILES: CS(=O)c1nc2c(=O)n3c(nc2s1)CN(C(=O)OC(C)(C)C)CC3]

To a solution (5 mL) of the compound (235 mg) obtained in Reference Example 660 in methylene chloride was added mCPBA (69-75%, 168 mg) under ice-cooling. The reaction mixture was stirred at room temperature for 1.5 hr, to the reaction mixture were added aqueous sodium thiosulfate solution and saturated aqueous sodium hydrogen carbonate solution, and the mixture was extracted with methylene chloride. The organic layer was dried over anhydrous sodium sulfate, filtered and concentrated. To the obtained residue were added hexane/diethyl ether=1/1, and the solid was collected by filtration, and dried to give the title compound (244.6 mg).
MS (ESI) m/z; 371 [M+H]$^+$

Reference Example 662

{(S)-2-[(5-amino-2-methylsulfanyl-1,3-thiazole-4-carbonyl)amino]propyl}carbamic acid tert-butyl ester

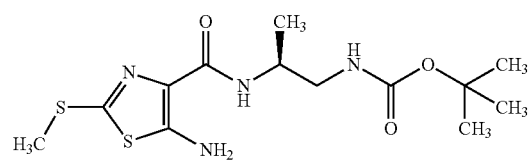 [SMILES: CSc1nc(C(=O)N[C@@H](C)CNC(=O)OC(C)(C)C)c(N)s1]

To a solution (33 mL) of 5-amino-2-methylsulfanyl-1,3-thiazole-4-carboxylic acid (1.50 g) in DMF were added ((S)-2-aminopropyl)-carbamic acid tert-butyl ester (1.65 g) synthesized by the method described in US2010/22518A1, N,N-diisopropylethylamine (1.92 mL), EDC hydrochloride (2.12 g) and HOBt monohydrate (1.49 g), and the reaction mixture was stirred at room temperature for 3 days. Water was added to the reaction mixture, and the mixture was extracted three times with ethyl acetate. The organic layer was dried over anhydrous magnesium sulfate, filtered and concentrated. The residue was purified by silica gel column chromatography (solvent; hexane/ethyl acetate=70/30-20/80) to give the title compound (2.29 g).

MS (ESI) m/z; 347 [M+H]$^+$

Reference Example 663

{(R)-2-[(5-amino-2-methylsulfanyl-1,3-thiazole-4-carbonyl)amino]propyl}carbamic acid tert-butyl ester

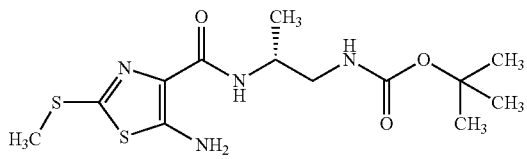 [SMILES: CSc1nc(C(=O)N[C@H](C)CNC(=O)OC(C)(C)C)c(N)s1]

5-Amino-2-methylsulfanyl-1,3-thiazole-4-carboxylic acid (1.50 g) and ((R)-2-aminopropyl)-carbamic acid tert-butyl ester (1.65 g) synthesized by the method described in US2010/22518A1 were treated by a method similar to that in Reference Example 662 to give the title compound (2.70 g).

MS (ESI) m/z; 347 [M+H]$^+$

Reference Example 664

{(S)-2-[{5-[(acetyloxy)acetylamino]-2-methylsulfanyl-1,3-thiazole-4-carbonyl}amino]propyl}carbamic acid tert-butyl ester

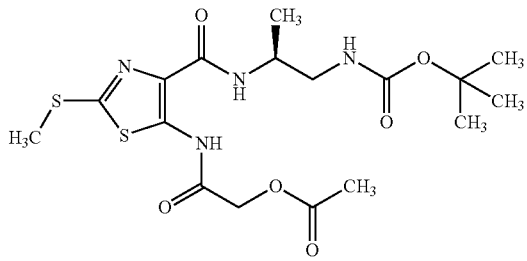 [SMILES: CSc1nc(C(=O)N[C@@H](C)CNC(=O)OC(C)(C)C)c(NC(=O)COC(C)=O)s1]

To a solution (27 mL) of the compound (1.88 g) obtained in Reference Example 662 in methylene chloride were added triethylamine (1.89 mL) and acetoxyacetyl chloride (758 μL) at 0° C., and the reaction mixture was stirred at room temperature for 1.5 hr. Water was added to the reaction mixture, and the mixture was extracted with chloroform, and the organic layer was dried over anhydrous sodium sulfate, filtered and concentrated. The residue was purified by silica gel column chromatography (solvent; hexane/ethyl acetate=60/40-20/80) to give the title compound (2.82 g).

MS (ESI) m/z; 447 [M+H]$^+$

Reference Example 665

{(R)-2-[{5-[(acetyloxy)acetylamino]-2-methylsulfanyl-1,3-thiazole-4-carbonyl}amino]propyl}carbamic acid tert-butyl ester

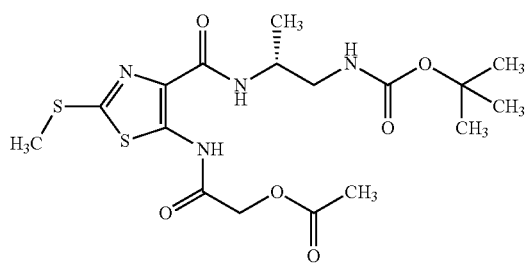 [SMILES: CSc1nc(C(=O)N[C@H](C)CNC(=O)OC(C)(C)C)c(NC(=O)COC(C)=O)s1]

The compound (2.86 g) obtained in Reference Example 663 was treated by a method similar to that in Reference Example 664 to give the title compound (3.39 g).

MS (ESI) m/z; 447 [M+H]$^+$

Reference Example 666

[(S)-2-{5-[(acetyloxy)methyl]-2-methylsulfanyl-7-oxo-7H-[1,3]thiazolo[5,4-d]pyrimidin-6-yl}propyl] carbamic acid tert-butyl ester

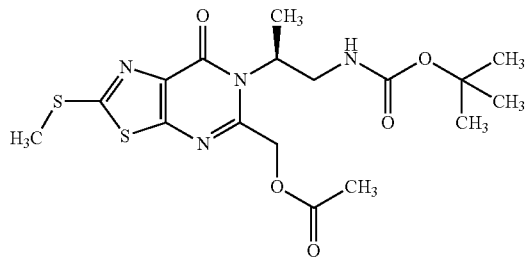 [SMILES: CSc1nc2c(=O)n([C@@H](C)CNC(=O)OC(C)(C)C)c(COC(C)=O)nc2s1]

To a solution (34 mL) of the compound (2.82 g) obtained in Reference Example 664 in dichloroethane were added chlorotrimethylsilane (5.15 mL) and triethylamine (17.0 mL) at 0° C., and the reaction mixture was stirred at room temperature for 3 hr. Water was added to the reaction mixture, and the mixture was extracted twice with chloroform. The organic layer was dried over anhydrous sodium sulfate, filtered and concentrated. The residue was purified by silica gel column chromatography (solvent; hexane/ethyl acetate=70/30-30/70) to give the title compound (2.16 g).

MS (ESI) m/z; 429 [M+H]$^+$

Reference Example 667

[(R)-2-{5-[(acetyloxy)methyl]-2-methylsulfanyl-7-oxo-7H-[1,3]thiazolo[5,4-d]pyrimidin-6-yl}propyl]carbamic acid tert-butyl ester

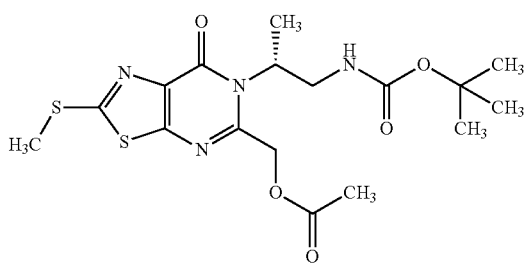 [SMILES: CSc1nc2c(=O)n([C@H](C)CNC(=O)OC(C)(C)C)c(COC(C)=O)nc2s1]

The compound (3.39 g) obtained in Reference Example 665 was treated by a method similar to that in Reference Example 666 to give the title compound (3.02 g).
MS (ESI) m/z; 429 [M+H]$^+$

Reference Example 668

[(S)-2-(5-hydroxymethyl-2-methylsulfanyl-7-oxo-7H-[1,3]thiazolo[5,4-d]pyrimidin-6-yl)propyl]carbamic acid tert-butyl ester

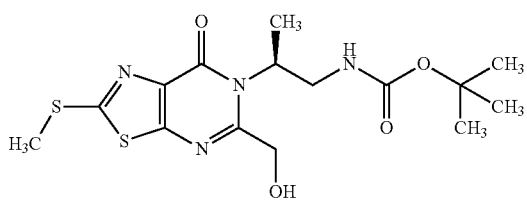 [SMILES: CSc1nc2c(=O)n([C@@H](C)CNC(=O)OC(C)(C)C)c(CO)nc2s1]

To a mixed solution of the compound (2160 mg) obtained in Reference Example 666 in methanol/THF (52 mL/26 mL) was added 1.0 mol/L aqueous sodium hydroxide solution (5.29 mL) under ice-cooling, and the mixture was stirred under ice-cooling for is 1 hr. To the reaction mixture was added saturated aqueous ammonium chloride solution, and methanol and THF were evaporated under reduced pressure. The obtained mixture was diluted with water, and extracted twice with ethyl acetate. The combined organic layer was washed with saturated brine, dried over anhydrous magnesium sulfate, filtered and concentrated. To the residue was added hexane/ethyl acetate=2/1, and the solid was collected by filtration to give the title compound (1621 mg).
MS (ESI) m/z; 387 [M+H]$^+$

Reference Example 669

[(R)-2-(5-hydroxymethyl-2-methylsulfanyl-7-oxo-7H-[1,3]thiazolo[5,4-d]pyrimidin-6-yl)propyl]carbamic acid tert-butyl ester

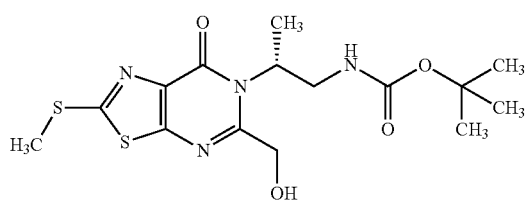 [SMILES: CSc1nc2c(=O)n([C@H](C)CNC(=O)OC(C)(C)C)c(CO)nc2s1]

The compound (3.02 g) obtained in Reference Example 667 was treated by a method similar to that in Reference Example 668 to give the title compound (1.99 g).
MS (ESI) m/z; 387 [M+H]$^+$

Reference Example 670

{(S)-2-[5-hydroxymethyl-2-((RS)-methylsulfinyl)-7-oxo-7H-[1,3]thiazolo[5,4-d]pyrimidin-6-yl]propyl}carbamic acid tert-butyl ester

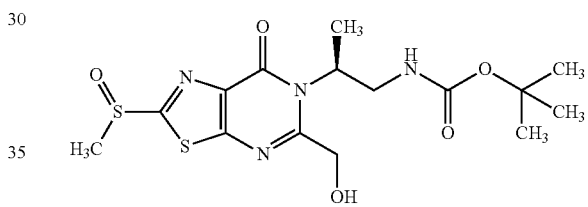

To a solution (31 mL) of the compound (1320 mg) obtained in Reference Example 668 in methylene chloride was added mCPBA (69-75%, 864 mg) under ice-cooling, and the reaction mixture was stirred at 0° C. for 1.5 hr. To the reaction mixture were added aqueous sodium thiosulfate solution, and saturated aqueous sodium hydrogen carbonate solution, and the mixture was extracted with methylene chloride. The organic layer was dried over anhydrous sodium sulfate, filtered and concentrated to give the title compound (1489 mg).
MS (ESI) m/z; 403 [M+H]$^+$

Reference Example 671

{(R)-2-[5-hydroxymethyl-2-((RS)-methylsulfinyl)-7-oxo-7H-[1,3]thiazolo[5,4-d]pyrimidin-6-yl]propyl}carbamic acid tert-butyl ester

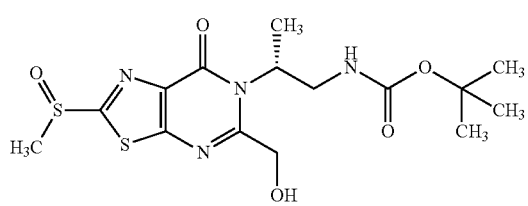 [SMILES: C[C@H](CNC(=O)OC(C)(C)C)n1c(CO)nc2sc(S(C)=O)nc2c1=O]

The compound (600 mg) obtained in Reference Example 669 was treated by a method similar to that in Reference Example 670 to give the title compound (636.9 mg).
MS (ESI) m/z; 403 [M+H]+

Reference Example 672

5-chloro-2-methylsulfanyl[1,3]thiazolo[5,4-d]pyrimidin-7(6H)-one

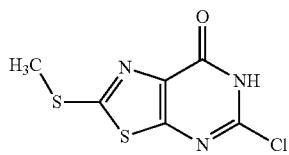

A mixed solution of the compound (600 mg) obtained in Reference Example 547 in trifluoroacetic acid/triethylsilane/water (15 mL/832 µL/832 µL) was stirred with heating at 50° C. for 2 hr, and the reaction mixture was concentrated under reduced pressure. To the residue was added ethyl acetate, and the solid was collected by filtration to give the title compound (365 mg).
MS (ESI) m/z; 234 [M+H]+

Reference Example 673

5-[N-(2-hydroxyethyl)-N-methylamino]-2-methyl-sulfanyl[1,3]thiazolo[5,4-d]pyrimidin-7(6H)-one

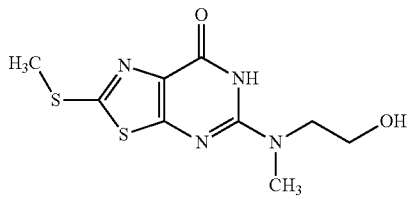 [SMILES: CSc1nc2c(=O)[nH]c(N(C)CCO)nc2s1]

A mixture of the compound (375 mg) obtained in Reference Example 672, N-methylaminoethanol (282 µL) in ethanol was heated under reflux for 18 hr. The reaction mixture was diluted with water, and adjusted to pH 2 with 1.0 mol/L hydrochloric acid. The precipitated solid was collected by filtration, washed with water, 2-propanol and diethyl ether, and dried to give the title compound (400 mg).
MS (ESI) m/z; 273 [M+H]+

Reference Example 674

5-methyl-2-methylsulfanyl-6,7-dihydroimidazo[1,2-a][1,3]thiazolo[5,4-d]pyrimidin-9(5H)-one

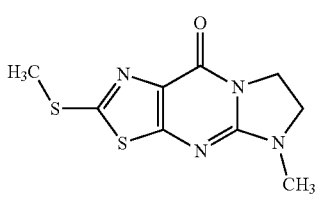

A mixture of the compound (395 mg) obtained in Reference Example 673 and concentrated sulfuric acid (3.5 mL) was stirred with heating at 60° C. for 4 hr. The reaction mixture was cooled to 0° C., and poured into ice water. The mixture was alkalified with saturated aqueous sodium hydrogen carbonate solution, and extracted twice with chloroform. The combined organic layer was washed with saturated brine, dried over anhydrous sodium sulfate, filtered and concentrated to give the title compound (350 mg).
MS (ESI) m/z; 255 [M+H]+

Reference Example 675

5-methyl-2-(methylsulfinyl)-6,7-dihydro-imidazo[1,2-a][1,3]thiazolo[5,4-d]pyrimidin-9(5H)-one

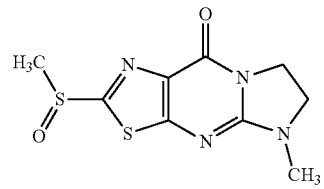 [SMILES: CN1CCn2c1nc1sc(S(C)=O)nc1c2=O]

To a solution (5 mL) of the compound (85 mg) obtained in Reference Example 674 in methylene chloride was added mCPBA (69-75%, 91 mg) under ice-cooling, and the mixture was stirred at 0° C. for 1.5 hr. To the reaction mixture were added aqueous sodium thiosulfate solution and saturated aqueous sodium hydrogen carbonate solution, and the mixture was extracted with methylene chloride. The organic layer was dried over anhydrous sodium sulfate, filtered and concentrated to give the title compound (90 mg).
MS (ESI) m/z; 271 [M+H]+

Reference Example 676

5-[N-(2,2-dimethoxyethyl)-N-methylamino]-2-methylsulfanyl[1,3]thiazolo[5,4-d]pyrimidin-7(6H)-one

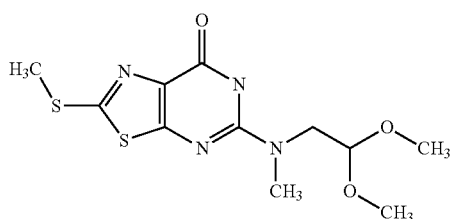

A mixture of the compound (160 mg) obtained in Reference Example 672 and methylamine dimethyl acetal (189 µL) in ethanol (2.4 mL) was heated under reflux for 20 hr. Ethanol was evaporated under reduced pressure, and the obtained mixture was diluted with water, and adjusted to pH 2 with 1.0 mol/L hydrochloric acid. The precipitated solid was collected by filtration, washed with water, 2-propanol and diethyl ether, and dried to give the title compound (196.6 mg).
MS (ESI) m/z; 317 [M+H]+

Reference Example 677

5-methyl-2-(methylsulfanyl)imidazo[1,2-a][1,3]thi-
azolo[5,4-d]pyrimidin-9 (5H)-one

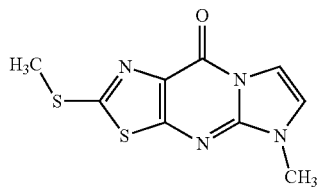

To the compound (195 mg) obtained in Reference Example 676 was added concentrated sulfuric acid (3.0 mL), and the reaction mixture was stirred at room temperature for 20 hr and stirred with heating at 60° C. for 3 hr. The reaction mixture was cooled to 0° C., and poured into ice water. The mixture was extracted 3 times with ethyl acetate. The combined organic layer was washed with saturated brine, dried over anhydrous sodium sulfate, filtered and concentrated. To the residue was added hexane/ethyl acetate (1/1), and the solid was collected by filtration to give the title compound (37.7 mg).

MS (ESI) m/z; 253 [M+H]$^+$

Reference Example 678

5-methyl-2-(methylsulfinyl)imidazo[1,2-a][1,3]thi-
azolo[5,4-d]pyrimidin-9(5H)-one

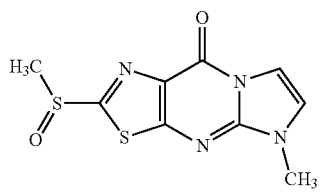

To a solution (6.0 mL) of the compound (32 mg) obtained in Reference Example 677 in methylene chloride was added mCPBA (69-75%, 34 mg) under ice-cooling. The reaction mixture was stirred at 0° C. for 1 hr, to the reaction mixture were added aqueous sodium thiosulfate solution and saturated aqueous sodium hydrogen carbonate solution, and the mixture was extracted with methylene chloride. The organic layer was dried over anhydrous sodium sulfate, filtered and concentrated to give the title compound (31.6 mg).

MS (ESI) m/z; 269 [M+H]$^+$

Reference Example 679

5-[3-(tert-butyl-diphenyl-silanyloxy)-1,1-difluoro-
propyl]-6-(2,4-dimethoxybenzyl)-2-methylsulfanyl
[1,3]thiazolo[5,4-d]pyrimidin-7(6H)-one

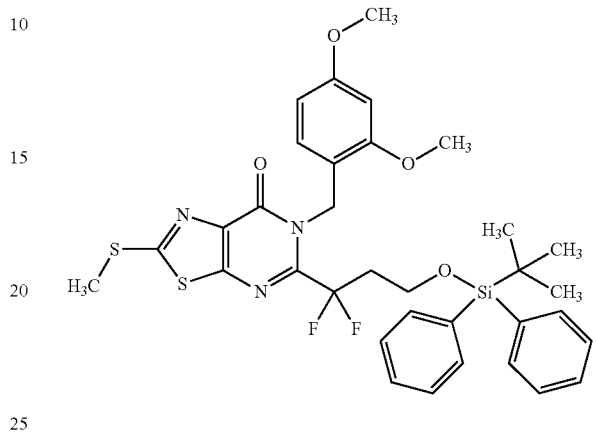

To a solution (1.0 mL) of 4-(tert-butyldiphenylsilanyloxy)-2,2-difluorobutyric acid ethyl ester (U.S. Pat. No. 5,712,279A) (105 mg) in ethanol was added 1.0 mol/L aqueous sodium hydroxide solution (258 µL), and the mixture was stirred at 50° C. for 3.5 hr. The reaction mixture was concentrated under reduced pressure, to the residue was added methanol and the solvent was evaporated twice by azeotropy under reduced pressure. To the obtained 4-(tert-butyldiphenylsilanyloxy)-2,2-difluorobutyric acid sodium salt was added methylene chloride (3.0 mL), to the resultant suspension were added oxalyl chloride (44 µL) and DMF (one drop) under ice-cooling, and the reaction mixture was stirred at room temperature for 2 hr. The reaction mixture was concentrated under reduced pressure, to the residue was added methylene chloride (1 mL). A solution (2.0 mL) of the compound (88 mg) obtained in Reference Example 484 in methylene chloride and triethylamine (144 µL) was added dropwise at room temperature. The reaction mixture was stirred at room temperature overnight, water was added to the reaction mixture, and the mixture was extracted twice with methylene chloride. The organic layer was washed with saturated brine, dried over anhydrous sodium sulfate, filtered and concentrated under reduced pressure. The residue was purified by silica gel column chromatography (solvent; hexane/ethyl acetate=100/0-70/30) to give amide intermediate (106.1 mg). To a solution (2.0 mL) of amide intermediate (106 mg) in methylene chloride were added chlorotrimethylsilane (191 µL) and triethylamine (631 µL), and the reaction mixture was stirred at room temperature for 28 hr. Under ice-cooling, water was added to the reaction mixture, and the mixture was extracted twice with methylene chloride. The organic layer was washed with saturated brine, dried over anhydrous sodium sulfate, filtered and concentrated under reduced pressure. The residue was purified by silica gel column chromatography (solvent; hexane/ethyl acetate=90/10-70/30) to give the title compound (97.8 mg).

MS (APCI) m/z; 682 [M+H]$^+$

Reference Example 680

5-(1,1-difluoro-3-hydroxypropyl)-6-(2,4-dimethoxybenzyl)-2-methylsulfanyl[1,3]thiazolo[5,4-d]pyrimidin-7(6H)-one

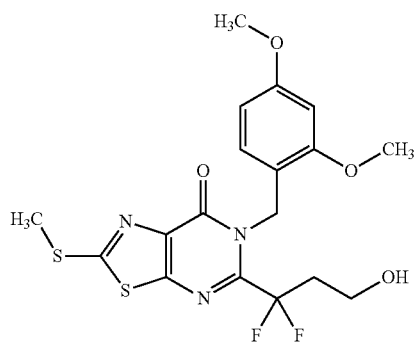

To a solution (2.0 mL) of the compound (95 mg) obtained in Reference Example 679 in THF were successively added acetic acid (24 µL) and 1.0 mol/L tetrabutylammonium fluoride THF solution (279 µL) at room temperature, and the reaction mixture was stirred at room temperature for 2 hr. Water was added to the reaction mixture, and the mixture was extracted three times with ethyl acetate. The combined organic layer was washed with saturated brine, dried over anhydrous sodium sulfate, filtered and concentrated under reduced pressure. The obtained residue was purified by silica gel column chromatography (solvent; chloroform/methanol=100/0-90/10) to give the title compound (64.8 mg).

MS (ESI) m/z; 444 [M+H]$^+$

Reference Example 681

5-(1,1-difluoro-3-hydroxypropyl)-2-methylsulfanyl[1,3]thiazolo[5,4-d]pyrimidin-7(6H)-one

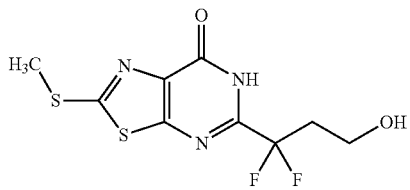 [SMILES: CSc1nc2c(=O)[nH]c(C(F)(F)CCO)nc2s1]

To the compound (64 mg) obtained in Reference Example 680 was added a mixture of trifluoroacetic acid (900 µL), triethylsilane (50 µL) and water (50 µL) under ice-cooling, and the reaction mixture was stirred at room temperature for 3 hr. The reaction mixture was concentrated under reduced pressure, methanol was added, and concentrated twice by azeotropy under reduced pressure. The obtained residue was purified by silica gel column chromatography (solvent; chloroform/methanol=100/0-90/10) to give the title compound (32.4 mg).

MS (ESI) m/z; 294 [M+H]$^+$

Reference Example 682

5,5-difluoro-2-methylsulfanyl-6,7-dihydro-pyrrolo[1,2-a][1,3]thiazolo[5,4-d]pyrimidin-9(5H)-one

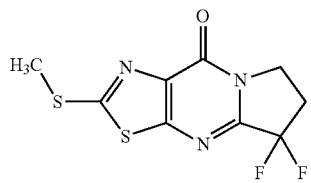 [SMILES: CSc1nc2c(=O)n3c(nc2s1)C(F)(F)CC3]

To a solution (2.0 mL) of the compound (40 mg) obtained in Reference Example 681 in DMF were successively added triethylamine (95 µL) and methyltriphenoxyphosphonium iodide (154 mg) under ice-cooling, and the reaction mixture was stirred at room temperature overnight. To the reaction mixture was added methanol (0.5 mL), and the mixture was diluted with ethyl acetate, and washed successively with 20% aqueous sodium carbonate solution and saturated brine. The organic layer was dried over anhydrous sodium sulfate, filtered and concentrated under reduced pressure. The obtained residue was purified by silica gel column chromatography (solvent; hexane/ethyl acetate=90/10-50/50) to give the title compound (37.6 mg).

MS (ESI) m/z; 276 [M+H]$^+$

Reference Example 683

5,5-difluoro-2-methylsulfinyl-6,7-dihydro-pyrrolo[1,2-a][1,3]thiazolo[5,4-d]pyrimidin-9(5H)-one

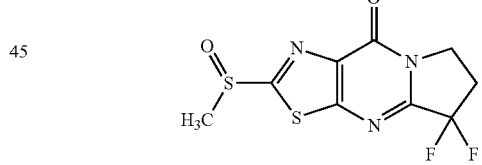

To a solution (2.0 mL) of the compound (37 mg) obtained in Reference Example 682 in methylene chloride was added mCPBA (69-75%, 34 mg) under ice-cooling, and the reaction mixture was stirred at room temperature for 2 hr. To the reaction mixture was added aqueous sodium thiosulfate solution, and the mixture was extracted three times with methylene chloride. The organic layer was washed with saturated aqueous sodium hydrogen carbonate solution, dried over anhydrous sodium sulfate, filtered and concentrated under reduced pressure to give the title compound as a crude product (38.5 mg).

MS (ESI) m/z; 292 [M+H]$^+$

Reference Example 684

5-[{5-[tert-butyl(diphenyl)silanyloxy]-2,2-difluoropentanoyl}amino]-N-(2,4-dimethoxybenzyl)-2-methylsulfanyl-1,3-thiazole-4-carboxamide

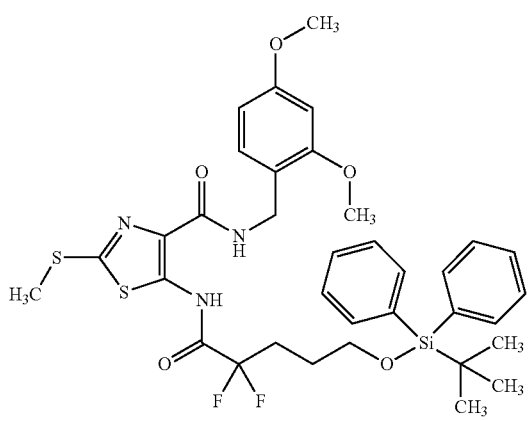 [SMILES: COc1ccc(CNC(=O)c2nc(SC)sc2NC(=O)C(F)(F)CCCO[Si](c2ccccc2)(c2ccccc2)C(C)(C)C)c(OC)c1]

To a solution (15 mL) of 2,2-difluoropentanedioic acid-5-benzyl ester-1-ethyl ester (840 mg) synthesized by the method described in Journal of Fluorine Chemistry 2003, 121, 105-107 in methanol was added 10% palladium carbon (100 mg), and the reaction mixture was stirred for 3 hr under 1 atm hydrogen atmosphere. The reaction mixture was filtered through diatomaceous earth, and the filtrate was concentrated under reduced pressure to give 2,2-difluoropentanedioic acid-1-ethyl ester as a crude product (610 mg). To a mixed solution of the obtained 2,2-difluoropentanedioic acid-1-ethyl ester (610 mg) in THF (10 mL) and methylene chloride (5.0 mL) was added borane dimethylsulfide complex (402 μL), and the reaction mixture was stirred for 17 hr with heating under reflux. After cooling to room temperature, the reaction mixture was concentrated under reduced pressure, methylene chloride was added and the mixture was concentrated twice by azeotropy under reduced pressure. The residue containing the obtained alcohol was dissolved in DMF (10 mL), tert-butyldiphenylsilyl chloride (915 μL) and imidazole (479 mg) were successively added, and the reaction mixture was stirred at room temperature overnight. Water was added to the reaction mixture, and the mixture was extracted twice with diethyl ether. The organic layer was washed with saturated brine, dried over anhydrous sodium sulfate, filtered and concentrated under reduced pressure. The residue was purified by silica gel column chromatography (solvent; hexane/ethyl acetate=100/0-90/10) to give the corresponding silyl ether (788 mg). The obtained silyl ether (710 mg) was dissolved in ethanol (3.4 mL), 1.0 mol/L aqueous sodium hydroxide solution (1.69 mL) was added, and the reaction mixture was stirred at 50° C. for 2 hr. The reaction mixture was concentrated under reduced pressure, methanol was added to the residue, and the mixture was further concentrated twice by azeotropy under reduced pressure. To the residue was added methylene chloride (5.0 mL), to the resultant suspension were added oxalyl chloride (715 μL) and DMF (one drop) under ice-cooling, and the reaction mixture was stirred at room temperature for 3 hr. The reaction mixture was concentrated under reduced pressure, to the residue was added methylene chloride (5.0 mL), and a solution (5.0 mL) of the compound (574 mg) obtained in Reference Example 484 in methylene chloride and triethylamine (2.36 mL) were added dropwise at room temperature. The reaction mixture was stirred at room temperature overnight, water was added to the reaction mixture, and the mixture was extracted twice with methylene chloride. The organic layer was washed with saturated brine, dried over anhydrous sodium sulfate, filtered and concentrated under reduced pressure. The residue was purified by silica gel column chromatography (solvent; hexane/ethyl acetate=100/0-70/30) to give the title compound (1.13 g).

MS (APCI) m/z; 714 [M+H]$^+$

Reference Example 685

5-{4-[tert-butyl(diphenyl)silanyloxy]-1,1-difluorobutyl}-6-(2,4-dimethoxybenzyl)-2-methylsulfanyl[1,3]thiazolo[5,4-d]pyrimidin-7(6H)-one

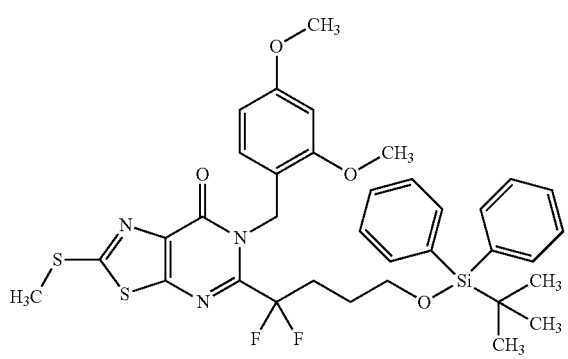 [SMILES: COc1ccc(Cn2c(C(F)(F)CCCO[Si](c3ccccc3)(c3ccccc3)C(C)(C)C)nc3sc(SC)nc3c2=O)c(OC)c1]

To a solution (10 mL) of the compound (1.13 g) obtained in Reference Example 684 in methylene chloride were added chlorotrimethylsilane (1.92 mL) and triethylamine (6.36 mL), and the reaction mixture was stirred at room temperature for 3 days. Under ice-cooling, water was added to the reaction mixture, and the mixture was extracted three times with methylene chloride. The organic layer was washed with saturated brine, dried over anhydrous sodium sulfate, filtered and concentrated under reduced pressure. The residue was is purified by silica gel column chromatography (solvent; hexane/ethyl acetate=90/10-70/30) to give the title compound (991 mg).

MS (APCI) m/z; 696 [M+H]$^+$

Reference Example 686

5-(1,1-difluoro-4-hydroxybutyl)-6-(2,4-dimethoxybenzyl)-2-methylsulfanyl[1,3]thiazolo[5,4-d]pyrimidin-7(6H)-one

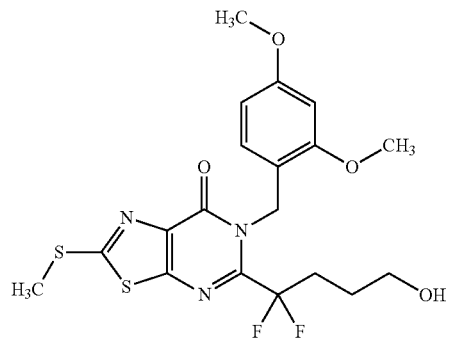 [SMILES: COc1ccc(Cn2c(C(F)(F)CCCO)nc3sc(SC)nc3c2=O)c(OC)c1]

To a solution (10 mL) of the compound (980 mg) obtained in Reference Example 685 in THF were successively added acetic acid (484 μL) and 1.0 mol/L solution (5.64 mL) of tetrabutylammonium fluoride in THF at room temperature, and the reaction mixture was stirred at room temperature overnight. Water was added to the reaction mixture, and the mixture was extracted three times with ethyl acetate. The combined organic layer was washed successively with saturated brine, dried over anhydrous sodium sulfate, filtered and concentrated under reduced pressure. The obtained residue was purified by silica gel column chromatography (solvent; hexane/ethyl acetate=70/30-20/80) to give the title compound (658 mg).
MS (APCI) m/z; 458 [M+H]$^+$ Reference Example 687

5-(1,1-difluoro-4-hydroxybutyl)-2-methylsulfanyl[1,3]thiazolo[5,4-d]pyrimidin-7(6H)-one

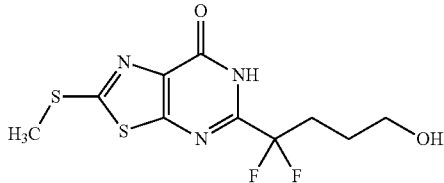 [SMILES: CSc1nc2c(=O)[nH]c(C(F)(F)CCCO)nc2s1]

To a solution of the compound (640 mg) obtained in Reference Example 686 in methylene chloride (2 mL) were successively added triethylsilane (250 μl), water (250 μL) and trifluoroacetic acid (4.5 mL) under ice-cooling, and the reaction mixture was stirred at room temperature for 4 hr. The reaction mixture was concentrated under reduced pressure, methanol was added, and the mixture was further concentrated twice by azeotropy under reduced pressure. The obtained residue was purified by silica gel column chromatography (solvent; chloroform/methanol=100/0-90/10) to give the title compound (69.8 mg).
MS (ESI) m/z; 308 [M+H]$^+$ Reference Example 688

5,5-difluoro-2-methylsulfanyl-5,6,7,8-tetrahydro-10H-pyrido[1,2-a][1,3]thiazolo[5,4-d]pyrimidin-10-one

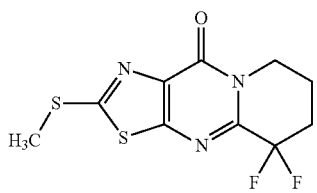 [SMILES: CSc1nc2c(=O)n3c(nc2s1)C(F)(F)CCC3]

To a solution (2.0 mL) of the compound (69 mg) obtained in Reference Example 687 in DMF were successively added triethylamine (157 μL) and methyltriphenoxyphosphonium iodide (254 mg) under ice-cooling, and the reaction mixture was stirred at room temperature for 7 hr. To the reaction mixture was added methanol (0.50 mL), and the mixture was further stirred for 10 min. The reaction mixture was diluted with ethyl acetate, and washed successively with 20% aqueous sodium carbonate solution and saturated brine. The organic layer was dried over anhydrous sodium sulfate, filtered and concentrated under reduced pressure. The obtained residue was purified by silica gel column chromatography (solvent; hexane/ethyl acetate=90/10-50/50) to give the title compound (57 mg).
MS (ESI) m/z; 290 [M+H]$^+$ Reference Example 689

5,5-difluoro-2-methylsulfinyl-5,6,7,8-tetrahydro-10H-pyrido[1,2-a][1,3]thiazolo[5,4-d]pyrimidin-10-one

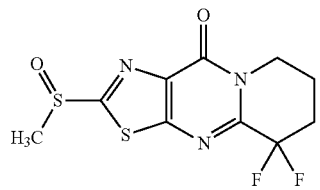 [SMILES: CS(=O)c1nc2c(=O)n3c(nc2s1)C(F)(F)CCC3]

To a solution (2.0 mL) of the compound (57 mg) obtained in Reference Example 688 in methylene chloride was added mCPBA (69-75%, 53 mg) under ice-cooling. The reaction mixture was stirred at room temperature for 2.5 hr, to the reaction mixture was added aqueous sodium thiosulfate solution, and the mixture was extracted twice with methylene chloride. The organic layer was washed with saturated aqueous sodium hydrogen carbonate solution, dried over anhydrous sodium sulfate, filtered and concentrated under reduced pressure to give the title compound as a crude product (61.3 mg).
MS (ESI) m/z; 306 [M+H]$^+$ Reference Example 690

N-methyl-5-benzoylamino-2-bromo-1,3-thiazole-4-carboxamide

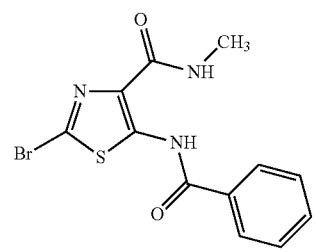 [SMILES: CNC(=O)c1nc(Br)sc1NC(=O)c1ccccc1]

To a solution (20 mL) of the compound (1.76 g) obtained in Reference Example 619 in methylene chloride were added triethylamine (2.10 mL) and benzoyl chloride (1.30 g) at 0° C., and the reaction mixture was stirred at room temperature overnight. 1.0 mol/L Aqueous sodium hydroxide solution (10.0 mL) was added to the reaction mixture. The mixture was stirred at room temperature for 30 min and extracted 4 times with chloroform. The organic layer was dried over anhydrous magnesium sulfate, filtered and concentrated. To the residue was added ethyl acetate, and the solid was collected by filtration, and dried to give the title compound (2.20 g).
MS (ESI) m/z; 340, 342 [M+H]$^+$

Reference Example 691

2-bromo-6-methyl-5-phenyl[1,3]thiazolo[5,4-d]pyrimidin-7(6H)-one

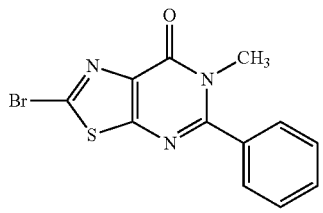 [SMILES: Cn1c(-c2ccccc2)nc2sc(Br)nc2c1=O]

To a solution (150 mL) of the compound (2.20 g) obtained in Reference Example 690 in methylene chloride were added chlorotrimethylsilane (4.10 mL) and triethylamine (13.6 mL), and the reaction mixture was stirred at room temperature overnight. The reaction mixture was added to water (200 mL), and the mixture was extracted twice with chloroform. The organic layer was dried over anhydrous magnesium sulfate, filtered and concentrated. The residue was purified by silica gel column chromatography (solvent; hexane/ethyl acetate=70/30-20/80) to give the title compound (1.36 g).

MS (ESI) m/z; 322, 324 [M+H]$^+$

Reference Example 692

(2R,3S)-3-[(benzyloxycarbonyl)amino]pyrrolidine-1,2-dicarboxylic acid 1-tert-butyl-2-ethyl ester

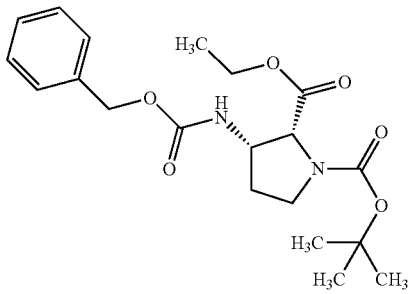 [SMILES: CCOC(=O)[C@H]1[C@@H](NC(=O)OCc2ccccc2)CCN1C(=O)OC(C)(C)C]

(1) To a solution (100 mL) of (2R,3S)-N-(tert-butoxycarbonyl)-3-hydroxypyrrolidine-2-carboxylic acid ethyl ester (2.80 g) synthesized by the method described in J. Chem. Soc., Perkin Trans. 1 1993, 1313-1317 in THF were added 4-nitrobenzoic acid (3.60 g), triphenylphosphine (6.30 g) and diethyl azodicarboxylate 2.2 mol/L toluene solution (10.8 mL) at room temperature, and the reaction mixture was stirred overnight. The solvent was evaporated under reduced pressure, and the residue was purified by silica gel column chromatography (solvent; hexane/ethyl acetate=90/10-60/40) and further by NH silica gel column chromatography (solvent; hexane/ethyl acetate=95/5-80/20) to give (2R,3R)-(N-tert-butoxycarbonyl)-3-(4-nitrophenylcarbonyloxy)-pyrrolidine-2-carboxylic acid ethyl ester (3.40 g).

(2) To a solution (60 mL) of the obtained (2R,3R)-N-(tert-butoxycarbonyl)-3-(4-nitrophenylcarbonyloxy)-pyrrolidine-2-carboxylic acid ethyl ester (0.73 g) in ethanol was added sodium azide (0.43 g) at room temperature, and the reaction mixture was stirred at 45° C. overnight. The reaction mixture was cooled to room temperature, water was added, and the mixture was extracted twice with ethyl acetate. The organic layer was dried over anhydrous magnesium sulfate, filtered and concentrated. The residue was purified by silica gel column chromatography (solvent; hexane/ethyl acetate=70/30-40/60) to give (2R,3R)-N-(tert-butoxycarbonyl)-3-hydroxypyrrolidine-2-carboxylic acid ethyl ester (0.45 g).

(3) To a solution (70 mL) of the obtained (2R,3R)-N-(tert-butoxycarbonyl)-3-hydroxypyrrolidine-2-carboxylic acid ethyl ester (1.73 g) in THF were added diphenylphosphoryl azide (2.40 g), triphenylphosphine (2.30 g) and diethyl azodicarboxylate 2.2 mol/L toluene solution (4.0 mL) at room temperature, and the reaction mixture was stirred overnight. The solvent was evaporated under reduced pressure, and the residue was purified by silica gel column chromatography (solvent; hexane/ethyl acetate=90/10-80/20) to give (2R,3S)-3-azidopyrrolidine-N-(tert-butoxycarbonyl)-2-carboxylic acid ethyl ester (1.66 g).

(4) To a solution (80 mL) of the obtained (2R,3S)-3-azidopyrrolidine-N-(tert-butoxycarbonyl)-2-carboxylic acid ethyl ester (1.66 g) in methanol was added tin(II) chloride (3.33 g) at room temperature, and the reaction mixture was stirred overnight. The solvent was evaporated under reduced pressure, and a solution (50 mL) of the residue in acetone was slowly added to an aqueous solution (50 mL) of sodium hydrogen carbonate (4.90 g) at 0° C., an acetone solution (50 mL) of N-(carbobenzoxy)succinimide (1.75 g) was added, and the reaction mixture was stirred at room temperature overnight. Water was added, and the mixture was filtered through diatomaceous earth, and the filtrate was and the mixture was extracted twice with ethyl acetate. The organic layer was dried over anhydrous magnesium sulfate, filtered and concentrated. The residue was purified by silica gel column chromatography (solvent; hexane/ethyl acetate=90/10-40/60) to give the title compound (1.78 g).

MS (ESI) m/z; 393 [M+H]$^+$

Reference Example 693

(2R,3S)-3-[(benzyloxycarbonyl)amino]-1-(tert-butoxycarbonyl)pyrrolidine-2-carboxylic acid tert-butyl ester

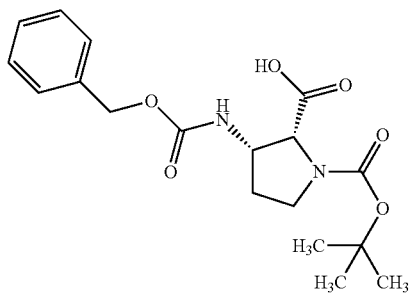 [SMILES: CC(C)(C)OC(=O)N1CC[C@H](NC(=O)OCc2ccccc2)[C@@H]1C(=O)O]

To a mixed solution of the compound (1.78 g) obtained in Reference Example 692 in methanol-water (48 mL-16 mL)

were added lithium hydroxide monohydrate (1.90 g) and 30% hydrogen peroxide (1.83 mL) at 0° C., and the reaction mixture was stirred at room temperature overnight. Aqueous sodium thiosulfate solution was added, and the reaction mixture was stirred at room temperature for 10 min. The reaction mixture was neutralized with 1.0 mol/L hydrochloric acid, and extracted twice with chloroform. The organic layer was dried over anhydrous magnesium sulfate, filtered and concentrated to give the title compound (1.50 g).

MS (ESI) m/z; 365 [M+H]$^+$

Reference Example 694

(2R,3S)-2-benzylcarbamoyl-3-[(benzyloxycarbonyl)amino]pyrrolidine-1-carboxylic acid tert-butyl ester

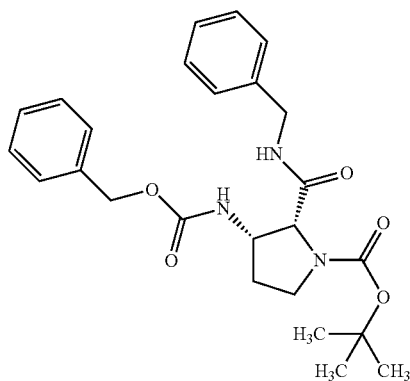 [SMILES: CC(C)(C)OC(=O)N1CC[C@H](NC(=O)OCc2ccccc2)[C@@H]1C(=O)NCc1ccccc1]

To a solution (10 mL) of the compound (0.60 g) obtained in Reference Example 693 in DMF were added benzylamine (0.36 g), EDC hydrochloride (0.64 g), HOBt monohydrate (0.51 g) and N,N-diisopropylethylamine (0.58 mL), and the reaction mixture was stirred at room temperature overnight. Water was added to the reaction mixture, and the mixture was extracted twice with ethyl acetate. The organic layer was washed once with water, dried over anhydrous magnesium sulfate, filtered and concentrated. The residue was purified by silica gel column chromatography (solvent; hexane/ethyl acetate=80/20-50/50) to give the title compound (0.60 g).

MS (ESI) m/z; 454 [M+H]$^+$

Reference Example 695

(2R,3R)-2-benzylcarbamoyl-3-[(benzyloxycarbonyl)amino]pyrrolidine-1-carboxylic acid tert-butyl ester

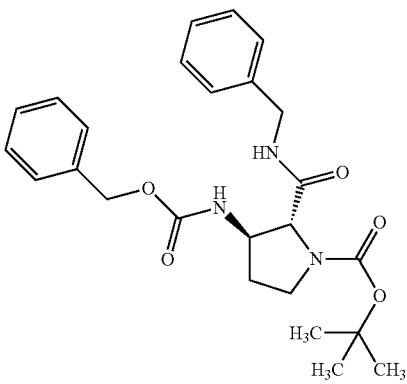 [SMILES: CC(C)(C)OC(=O)N1CC[C@@H](NC(=O)OCc2ccccc2)[C@@H]1C(=O)NCc1ccccc1]

(2R,3R)-N-(tert-butoxycarbonyl)-3-[(benzyloxycarbonyl)amino]pyrrolidine-2-carboxylic acid (0.70 g) synthesized by the method described in Org. Lett. 2002, 4, 3317-3319 was treated by a method similar to that in Reference Example 694 to give the title compound (0.60 g).

MS (ESI) m/z; 454 [M+H]$^+$

Reference Example 696

[(2R,3S)-2-(benzylcarbamoyl)pyrrolidin-3-yl]carbamic acid benzyl ester trifluoroacetate

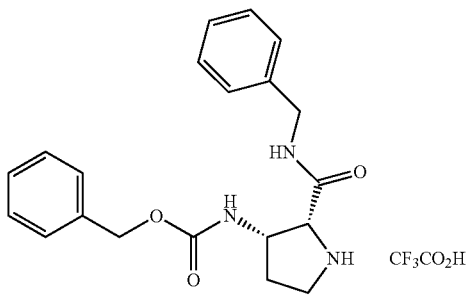 [SMILES: O=C(N[C@H]1CCN[C@H]1C(=O)NCc1ccccc1)OCc1ccccc1 ; "CF3CO2H"]

To a solution (6.0 mL) of the compound (0.60 g) obtained in Reference Example 694 in methylene chloride was added trifluoroacetic acid (6.0 mL), and the reaction mixture was stirred at room temperature for 3 hr. After confirmation of the completion of the reaction, the solvent was evaporated to give the title compound (0.60 g).

MS (ESI) m/z; 354 [M+H]$^+$

Reference Example 697

[(2R,3R)-2-(benzylcarbamoyl)pyrrolidin-3-yl]carbamic acid benzyl ester trifluoroacetate

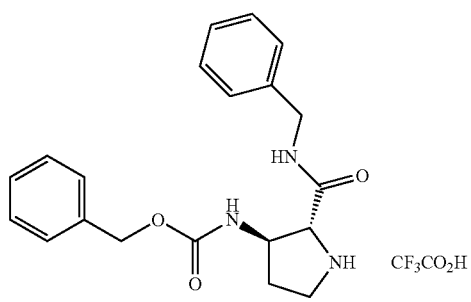 [SMILES: O=C(N[C@@H]1CCN[C@H]1C(=O)NCc1ccccc1)OCc1ccccc1 ; "CF3CO2H"]

The compound (0.60 g) obtained in Reference Example 695 was treated by a method similar to that in Reference Example 696 to give the title compound (0.62 g).
MS (ESI) m/z; 354 [M+H]$^+$ Reference Example 698

2-amino-5-propionyl-1,3-thiazole-4-carboxylic acid ethyl ester

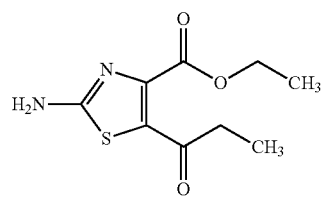

Sodium (3.18 g) was added to ethanol (60 mL) a little by little at room temperature, and the mixture was stirred until it was dissolved. A solution (30 mL) of 2-butanone (10.0 g) in ethanol was added dropwise to the reaction mixture under ice-cooling, and the reaction mixture was stirred for 10 min and a solution (30 mL) of diethyl oxalate (20.2 g) in ethanol was added. The reaction mixture was stirred with heating at 70° C. for 2.5 hr, allowed to cool, and ethanol was evaporated under reduced pressure. The residue was diluted with water, acidified with 1.0 mol/L hydrochloric acid, and extracted twice with chloroform. The combined organic layer was dried over anhydrous sodium sulfate, filtered and concentrated to give 2,4-dioxohexanoic acid ethyl ester (17.0 g).

To a solution of 2,4-dioxohexanoic acid ethyl ester (17.0 g) in carbon tetrachloride (30 mL) was added dropwise sulfuryl chloride (13.3 g) under ice-cooling. The reaction mixture was stirred at room temperature for 1 hr, carbon tetrachloride was evaporated under reduced pressure, and the obtained residue was added to a mixture of thiourea (6.70 g) in ethanol (40 mL). The reaction mixture was stirred at room temperature for 4 hr, and ethanol was evaporated under reduced pressure. Water was added to the reaction mixture, and the mixture was extracted twice with ethyl acetate. The combined organic layer was washed with saturated aqueous sodium hydrogen carbonate solution and saturated brine, dried over anhydrous sodium sulfate, filtered and concentrated. The residue was purified by silica gel column chromatography (solvent; hexane/ethyl acetate=80/20-50/50), to the obtained product was added a mixture of ethyl acetate and diisopropyl ether, and the solid was collected by filtration to give the title compound (4.40 g).
MS (ESI) m/z; 229 [M+H]$^+$ Reference Example 699

2-amino-5-(cyclopropylcarbonyl)-1,3-thiazole-4-carboxylic acid ethyl ester

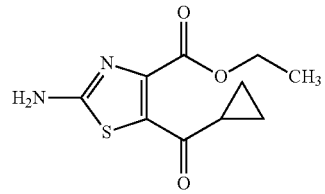 [SMILES: CCOC(=O)c1nc(N)sc1C(=O)C1CC1]

4-Cyclopropyl-2,4-dioxobutyric acid ethyl ester (10.5 g) was prepared from 1-cyclopropylethanone (2.87 g) by a method is similar to that in Reference Example 698, and treated by a method similar to that in Reference Example 698 to give the title compound (2.10 g).
MS (ESI) m/z; 241 [M+H]$^+$ Reference Example 700

5-acetyl-2-amino-1,3-thiazole-4-carboxylic acid ethyl ester

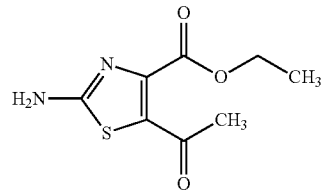

2,4-dioxopentanoic acid ethyl ester (7.85 g) was treated by a method similar to that in Reference Example 698 to give the title compound (5.00 g).
MS (ESI) m/z; 215 [M+H]$^+$ Reference Example 701

2-amino-5-propionyl-1,3-thiazole-4-carboxylic acid

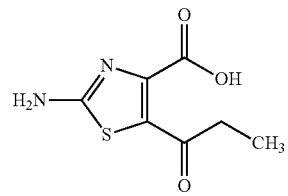

To a mixture of the compound (4.40 g) obtained in Reference Example 698 in ethanol (20 mL) was added 2.5 mol/L aqueous sodium hydroxide solution (20 mL), and the reaction mixture was stirred at room temperature for 2 hr. Ethanol was evaporated under reduced pressure, water was added, and the mixture was acidified with 1.0 mol/L hydrochloric acid. The precipitated solid was collected by filtration, and washed with water to give the title compound (3.55 g).

MS (ESI) m/z; 201 [M+H]$^+$

Reference Example 702

2-amino-5-(cyclopropylcarbonyl)-1,3-thiazole-4-carboxylic acid

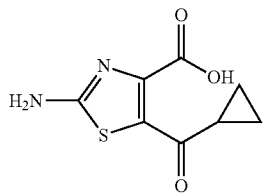 [SMILES: Nc1nc(C(=O)O)c(C(=O)C2CC2)s1]

The compound (2.10 g) obtained in Reference Example 699 was treated by a method similar to that in Reference Example 701 to give the title compound (1.50 g).

MS (ESI) m/z; 213 [M+H]$^+$

Reference Example 703

5-acetyl-2-amino-1,3-thiazole-4-carboxylic acid

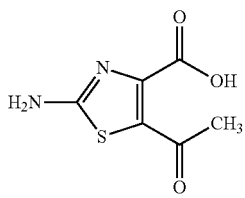

The compound (3.65 g) obtained in Reference Example 700 was treated by a method similar to that in Reference Example 701 to give the title compound (2.48 g).

MS (ESI) m/z; 187 [M+H]$^+$

Reference Example 704

2-amino-5,7-diethyl-5H-[1,3]thiazolo[4,5-d]pyridazin-4-one

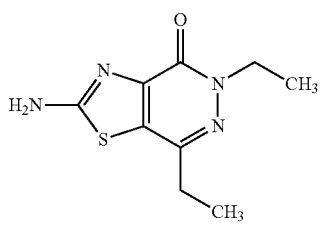

To a mixture of the compound (1.00 g) obtained in Reference Example 701 in toluene (10 mL)/N-methylpyrrolidone (4.0 mL) was added ethylhydrazine (0.75 g), and the reaction mixture was stirred with heating at 120° C. for 3 hr. The reaction mixture was allowed to cool, toluene was evaporated under reduced pressure, and water was added. The precipitated solid was collected by filtration, washed with water and diisopropyl ether, and dried to give the title compound (1.05 g).

MS (ESI) m/z; 225 [M+H]$^+$

Reference Example 705

2-amino-7-ethyl-5-(tetrahydro-2H-pyran-4-yl)-5H-[1,3]thiazolo[4,5-d]pyridazin-4-one

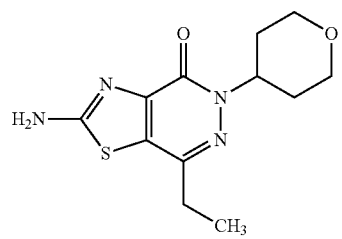

The compound (1.00 g) obtained in Reference Example 701 was treated by a method similar to that in Reference Example 704 to give the title compound (940 mg).

MS (ESI) m/z; 281 [M+H]$^+$

Reference Example 706

2-amino-7-cyclopropyl-5-ethyl-5H-[1,3]thiazolo[4,5-d]pyridazin-4-one

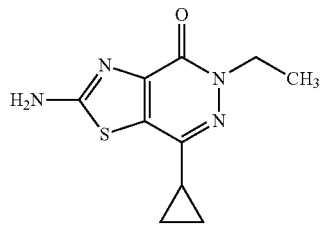 [SMILES: CCn1nc(C2CC2)c2sc(N)nc2c1=O]

The compound (1.50 g) obtained in Reference Example 702 was treated by a method similar to that in Reference Example 704 to give the title compound (1.15 g).

MS (ESI) m/z; 237 [M+H]$^+$

Reference Example 707

2-amino-5-ethyl-7-methyl-5H-[1,3]thiazolo[4,5-d]pyridazin-4-one

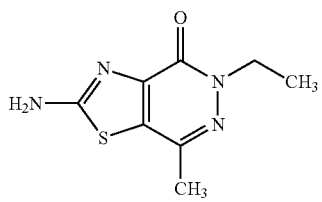

The compound (2.48 g) obtained in Reference Example 703 was treated by a method similar to that in Reference Example 704 to give the title compound (1.55 g).
MS (ESI) m/z; 211 [M+H]+

Reference Example 708

2-amino-5-cyclohexyl-7-methyl-5H-[1,3]thiazolo[4,5-d]pyridazin-4-one

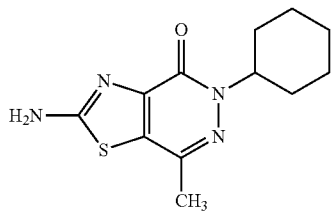 [SMILES: Cc1nn(C2CCCCC2)c(=O)c2nc(N)sc12]

The compound (1.20 g) obtained in Reference Example 703 was treated by a method similar to that in Reference Example 704 to give the title compound (1.19 g).
MS (ESI) m/z; 265 [M+H]+

Reference Example 709

2-bromo-5,7-diethyl-5H-[1,3]thiazolo[4,5-d]pyridazin-4-one

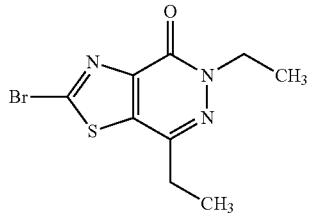

tert-Butyl nitrite (690 mg) was added dropwise to a mixture of copper(II) bromide (1.25 g) in acetonitrile (16 mL) at room temperature, and the compound (1.00 g) obtained in Reference Example 704 was added a little by little at 50° C. The reaction mixture was stirred with heating at 50° C. for 30 min, and concentrated under reduced pressure. Water and 1.0 mol/L hydrochloric acid were added, and the mixture was extracted twice with chloroform. The combined organic layer was washed with saturated brine, dried over anhydrous sodium sulfate, filtered and concentrated. The residue was purified by silica gel column chromatography (solvent; hexane/ethyl acetate=80/20-50/50) to give the title compound (1.15 g).
MS (ESI) m/z; 288, 290 [M+H]+

Reference Example 710

2-bromo-7-ethyl-5-(tetrahydro-2H-pyran-4-yl)-5H-[1,3]thiazolo[4,5-d]pyridazin-4-one

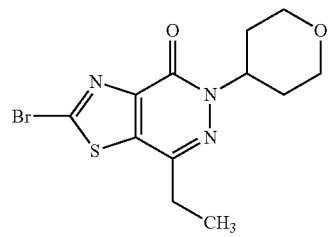 [SMILES: CCc1nn(C2CCOCC2)c(=O)c2nc(Br)sc12]

The compound (940 mg) obtained in Reference Example 705 was treated by a method similar to that in Reference Example 709 to give the title compound (830 mg).
MS (ESI) m/z; 344, 346 [M+H]+

Reference Example 711

2-bromo-7-cyclopropyl-5-ethyl-5H-[1,3]thiazolo[4,5-d]pyridazin-4-one

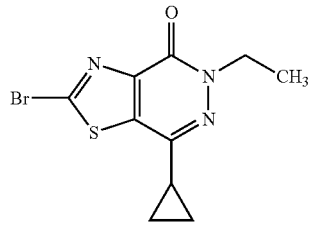 [SMILES: CCn1nc(C2CC2)c2sc(Br)nc2c1=O]

The compound (1.15 g) obtained in Reference Example 706 was treated by a method similar to that in Reference Example 709 to give the title compound (1.12 g).
MS (ESI) m/z; 300, 302 [M+H]+

Reference Example 712

2-bromo-5-ethyl-7-methyl-5H-[1,3]thiazolo[4,5-d]pyridazin-4-one

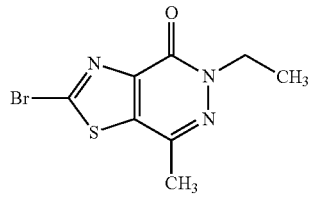

The compound (1.55 g) obtained in Reference Example 707 was treated by a method similar to that in Reference Example 709 to give the title compound (1.69 g).

MS (ESI) m/z; 274, 276 [M+H]⁺

Reference Example 713

2-bromo-5-cyclohexyl-7-methyl-5H-[1,3]thiazolo[4,5-d]pyridazin-4-one

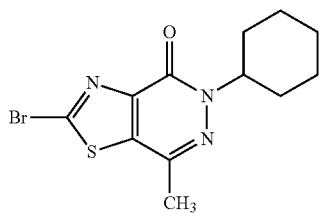

The compound (1.18 g) obtained in Reference Example 708 was treated by a method similar to that in Reference Example 709 to give the title compound (1.17 g).

MS (ESI) m/z; 328, 330 [M+H]⁺

Reference Example 714

3-amino-2-methoxy-5-(trifluoromethyl)pyridine

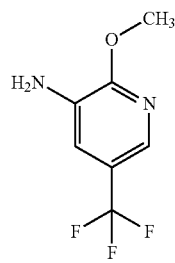

To a solution (20 mL) of 2-chloro-3-nitro-5-trifluoromethylpyridine (5.53 g) in methanol was added 28% sodium methoxide methanol solution (5.18 g) at 5° C., and the reaction mixture was stirred for 10 min. The reaction mixture was added to ice water, and resultant solid was filtered and dried to give 2-methoxy-3-nitro-5-trifluoromethylpyridine (5.13 g). To a solution (30 mL) of the obtained 2-methoxy-3-nitro-5-trifluoromethylpyridine (4.00 g) in methanol was added 10% palladium carbon (400 mg), and the mixture was stirred at under a hydrogen atmosphere at room temperature for 1.5 hr. The reaction mixture was filtered through diatomaceous earth, and the filtrate was evaporated under reduced pressure. The residue was purified by silica gel column chromatography (solvent; hexane/ethyl acetate=0/100) to give the title compound (3.25 g).

MS (ESI) m/z; 193 [M+H]⁺

Reference Example 715

3-amino-6-bromo-2-methoxy-5-(trifluoromethyl)pyridine

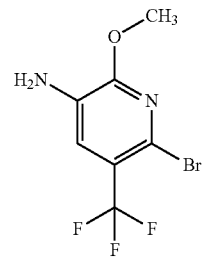

To a solution (32 mL) of the compound (3.25 g) obtained in Reference Example 714 in DMF was added a solution (15 mL) of N-bromosuccinimide (3.31 g) in DMF at −40° C., and the mixture was stirred at −25° C. for 2 hr. Aqueous sodium thiosulfate solution was added, and the mixture was stirred at room temperature for 10 min and extracted twice with ethyl acetate. The organic layer was dried over anhydrous sodium sulfate, filtered and concentrated. The residue was purified by silica gel column chromatography (solvent; hexane/ethyl acetate=95/5-60/40) to give the title compound (4.40 g).

MS (ESI) m/z; 271, 273 [M+H]⁺

Reference Example 716

3-amino-6-bromo-2-methoxypyridine

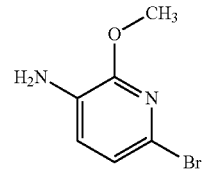

3-Amino-2-methoxypyridine (9.85 g) was treated by a method similar to that in Reference Example 715 to give the title compound (12.6 g).

MS (ESI) m/z; 203, 205 [M+H]⁺

Reference Example 717

3-amino-2-methoxy-6-iodopyridine

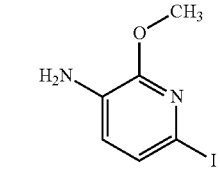

To a solution (40 mL) of 3-amino-2-methoxypyridine (5.00 g) in DMF was added a solution (20 mL) of N-iodosuccinimide (9.97 g) in DMF at 0° C. The reaction mixture was stirred at 0° C. for 2.5 hr, a solution (5.0 mL) of N-iodosuccinimide (1.81 g) in DMF was added, and the reaction mixture was stirred at room temperature for 14 hr. Aqueous sodium thiosulfate solution was added, and the mixture was stirred at room temperature for 10 min and extracted twice with ethyl acetate. The organic layer was dried over anhydrous sodium sulfate, filtered and concentrated. The residue was purified by NH silica gel column chromatography (solvent; hexane/ethyl acetate=90/10-70/30) to give the title compound (2.54 g).

MS (ESI) m/z; 251 [M+H]$^+$

Reference Example 718

3-amino-6-bromo-4-chloro-2-methoxy-5-(trifluoromethyl)pyridine

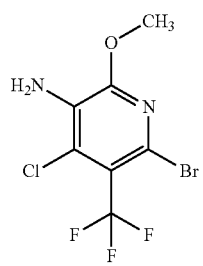

To a solution (32 mL) of the compound (4.40 g) obtained in Reference Example 715 in DMF was added a solution (13 mL) of N-chlorosuccinimide (2.60 g) in DMF at 0° C., and the reaction mixture was stirred for 2 hr. Aqueous sodium thiosulfate solution was added, and the mixture was stirred at room temperature for 10 min and extracted twice with ethyl acetate. The organic layer was dried over anhydrous sodium sulfate, filtered and concentrated. The residue was purified by silica gel column chromatography (solvent; hexane/ethyl acetate=95/5-60/40) to give the title compound (4.62 g).

MS (ESI) m/z; 305, 307, 309 [M+H]$^+$

Reference Example 719

3-amino-6-bromo-4-chloro-2-methoxypyridine

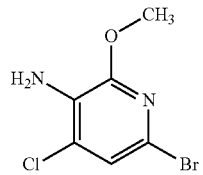

The compound (12.6 g) obtained in Reference Example 716 was treated by a method similar to that in Reference Example 718 to give the title compound (9.60 g).

MS (ESI) m/z; 237, 239 [M+H]$^+$

Reference Example 720

3-amino-4-chloro-2-methoxy-6-iodopyridine

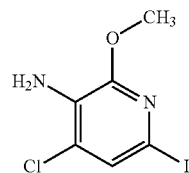

The compound (2.54 g) obtained in Reference Example 717 was treated by a method similar to that in Reference Example 718 to give the title compound (1.75 g).

MS (ESI) m/z; 285 [M+H]$^+$

Reference Example 721

3-amino-4-chloro-2-methoxy-5-trifluoromethylpyridine

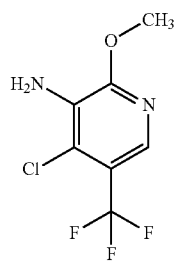

Reference Example 722

3-amino-4-chloro-2-methoxy-6-(propan-2-yl)-5-(trifluoromethyl)pyridine

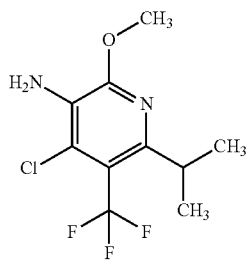 [SMILES: COc1nc(C(C)C)c(C(F)(F)F)c(Cl)c1N]

To a solution (39 mL) of the compound (1.50 g) obtained in Reference Example 718 in 1,4-dioxane were added [1,1-bis(diphenylphosphino)ferrocene]dichloropalladium(II) methylene chloride adduct (80 mg) and diisopropylzinc 1.0 mol/L toluene solution (5.89 mL), and the reaction mixture was stirred with heating at 80° C. for 15 hr. The reaction mixture was cooled to room temperature, aqueous ammonium chloride solution was added, and the mixture was extracted twice with ethyl acetate. The organic layer was dried over anhydrous sodium sulfate, filtered and concentrated. The residue was purified by silica gel column chromatography (solvent; hexane/ethyl acetate=95/5-85/15) to give Reference Example 721 (3-amino-4-chloro-2-methoxy-5-trifluoromethylpyridine, 382 mg) and Reference Example 722 (3-amino-4-chloro-2-methoxy-6-(propan-2-yl)-5-trifluoromethylpyridine, 285 mg).

Reference Example 721 (ESI) m/z; 227, 229 [M+H]$^+$

Reference Example 722 (ESI) m/z; 269, 271 [M+H]$^+$

Reference Example 723

3-amino-4-chloro-2-methoxy-6-(propan-2-yl)pyridine

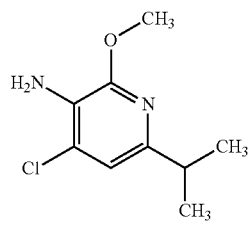

The compound (1.50 g) obtained in Reference Example 719 was treated by a method similar to that in Reference Example 722 to give the title compound (705 mg).

MS (ESI) m/z; 201, 203 [M+H]$^+$

Reference Example 724

3-amino-4-chloro-6-cyclopropyl-2-methoxypyridine

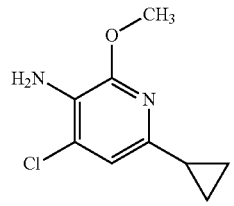

To a solution (5.98 mL) of the compound (710 mg) obtained in Reference Example 719 in toluene were added [1,1-bis(diphenylphosphino)ferrocene]dichloropalladium (II) methylene chloride adduct (122 mg), a solution (2.99 mL) of cyclopropylboronic acid (308 mg) in ethanol and 2.0 mol/L aqueous sodium carbonate solution (5.98 mL), and the reaction mixture was stirred with heating at 100° C. for 2 hr. The reaction mixture was cooled to room temperature, water was added, and the mixture was extracted twice with ethyl acetate. The organic layer was dried over anhydrous sodium sulfate, filtered and concentrated. The residue was purified by silica gel column chromatography (solvent; hexane/ethyl acetate=100/0-80/20) to give the title compound (338 mg).

MS (ESI) m/z; 199, 201 [M+H]$^+$

Reference Example 725

3-amino-4-chloro-6-(2-fluorophenyl)-2-methoxypyridine

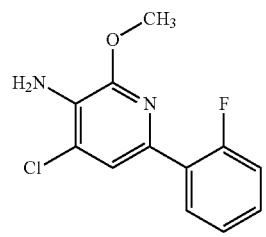 [SMILES: COc1nc(-c2ccccc2F)cc(Cl)c1N]

The compound (500 mg) obtained in Reference Example 720 was treated by a method similar to that in Reference Example 724 to give the title compound (416 mg).

MS (ESI) m/z; 253 [M+H]$^+$

Reference Example 726

2-mercapto-7-trifluoromethyl-5H-[1,3]thiazolo[4,5-c]pyridin-4-one

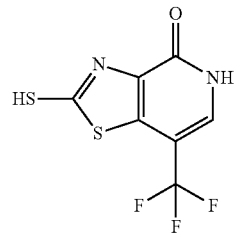 [SMILES: O=c1[nH]cc(C(F)(F)F)c2sc(S)nc12]

A solution (2.0 mL) of the compound (380 mg) obtained in Reference Example 721 and potassium ethyl xanthogenate (807 mg) in DMF was stirred with heating at 130° C. for 3 hr. The reaction mixture was cooled to room temperature, acetic acid (0.48 mL) and water were added, and the mixture was extracted twice with ethyl acetate. The organic layer was dried over anhydrous sodium sulfate, filtered and concentrated. To the residue was added 25% hydrogen bromide-acetic acid solution (3.0 mL), and the reaction mixture was stirred with heating at 70° C. for 1 hr. The reaction mixture was cooled to 0° C., water was added, and the precipitated solid was collected by filtration and dried to give the title compound (249 mg).

MS (ESI) m/z; 253 [M+H]$^+$

Reference Example 727

2-mercapto-6-(propan-2-yl)-7-trifluoromethyl-5H-[1,3]thiazolo[4,5-c]pyridin-4-one

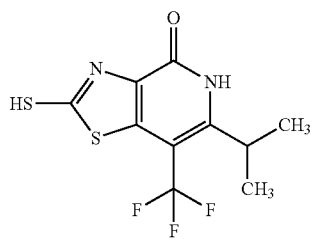 [SMILES: CC(C)c1[nH]c(=O)c2nc(S)sc2c1C(F)(F)F]

The compound (282 mg) obtained in Reference Example 722 was treated by a method similar to that in Reference Example 726 to give the title compound (250 mg).

MS (ESI) m/z; 295 [M+H]+

Reference Example 728

2-mercapto-6-(propan-2-yl)-5H-[1,3]thiazolo[4,5-c]pyridin-4-one

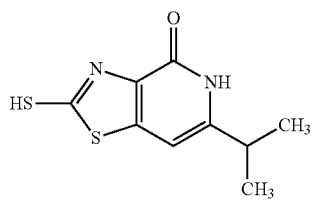

The compound (700 mg) obtained in Reference Example 723 was treated by a method similar to that in Reference Example 726 to give the title compound (631 mg).

MS (ESI) m/z; 227 [M+H]+

Reference Example 729

6-cyclopropyl-2-mercapto-5H-[1,3]thiazolo[4,5-c]pyridin-4-one

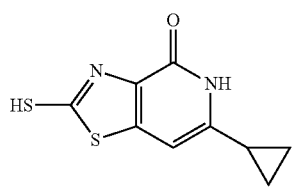 [SMILES: O=c1[nH]c(C2CC2)cc2sc(S)nc12]

The compound (338 mg) obtained in Reference Example 724 was treated by a method similar to that in Reference Example 726 to give the title compound (293 mg).

MS (ESI) m/z; 225 [M+H]+

Reference Example 730

6-(2-fluorophenyl)-2-mercapto-5H-[1,3]thiazolo[4,5-c]pyridin-4-one

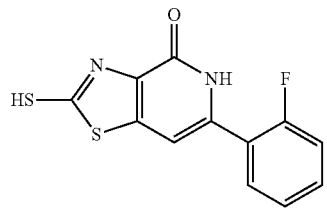 [SMILES: O=c1[nH]c(-c2ccccc2F)cc2sc(S)nc12]

The compound (410 mg) obtained in Reference Example 725 was treated by a method similar to that in Reference Example 726 to give the title compound (378 mg).

MS (ESI) m/z; 279 [M+H]+

Reference Example 731

2-methylsulfanyl-7-trifluoromethyl-5H-[1,3]thiazolo[4,5-c]pyridin-4-one

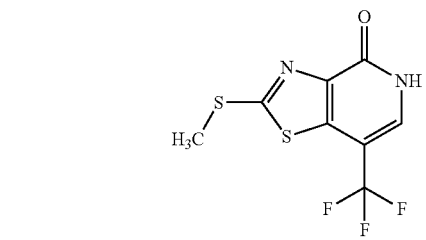

To a solution (4.3 mL) of the compound (246 mg) obtained in Reference Example 726 in DMF were added sodium hydrogen carbonate (98 mg) and methyl iodide (67 μL) at 0° C. The reaction mixture was stirred at room temperature for 3 hr, water (20 mL) was added, and the mixture was extracted twice with ethyl acetate. The organic layer was dried over anhydrous sodium sulfate, filtered and concentrated. The residue was purified by silica gel column chromatography (solvent; chloroform/methanol=100/0-90/10) to give the title compound (53.0 mg).

MS (ESI) m/z; 267 [M+H]+

Reference Example 732

2-methylsulfanyl-6-(propan-2-yl)-7-trifluoromethyl-5H-[1,3]thiazolo[4,5-c]pyridin-4-one

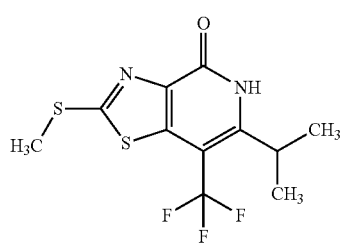 [SMILES: CSc1nc2c(=O)[nH]c(C(C)C)c(C(F)(F)F)c2s1]

The compound (248 mg) obtained in Reference Example 727 was treated by a method similar to that in Reference Example 731 to give the title compound (88.0 mg).
MS (ESI) m/z; 309 [M+H]+

Reference Example 733

2-methylsulfanyl-6-(propan-2-yl)-5H-[1,3]thiazolo[4,5-c]pyridin-4-one

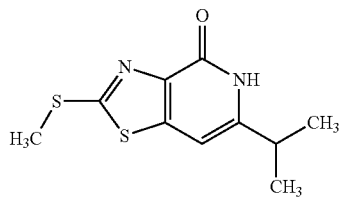

The compound (628 mg) obtained in Reference Example 728 was treated by a method similar to that in Reference Example 731 to give the title compound (398 mg).
MS (ESI) m/z; 241 [M+H]+

Reference Example 734

6-cyclopropyl-2-methylsulfanyl-5H-[1,3]thiazolo[4,5-c]pyridin-4-one

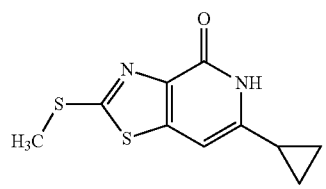

The compound (290 mg) obtained in Reference Example 729 was treated by a method similar to that in Reference Example 731 to give the title compound (295 mg).
MS (ESI) m/z; 239 [M+H]+

Reference Example 735

6-(2-fluorophenyl)-2-methylsulfanyl-5H-[1,3]thiazolo[4,5-c]pyridin-4-one

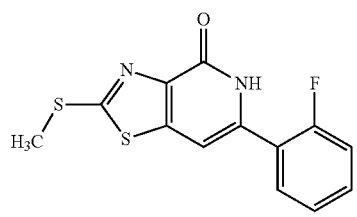 [SMILES: CSc1nc2c(=O)[nH]c(-c3ccccc3F)cc2s1]

The compound (375 mg) obtained in Reference Example 730 was treated by a method similar to that in Reference Example 731 to give the title compound (337 mg).
MS (ESI) m/z; 293 [M+H]+

Reference Example 736

2-methylsulfonyl-7-trifluoromethyl-5H-[1,3]thiazolo[4,5-c]pyridin-4-one

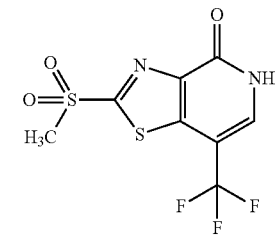 [SMILES: CS(=O)(=O)c1nc2c(=O)[nH]cc(C(F)(F)F)c2s1]

To a solution (400 μL) of the compound (53.0 mg) obtained in Reference Example 731 in trifluoroacetic acid was added 30% aqueous hydrogen peroxide solution (80 μL) under ice-cooling. The reaction mixture was stirred at room temperature for 1 hr, water (20 mL) was added, and the mixture was extracted twice with chloroform. The organic layer was dried over anhydrous sodium sulfate, filtered and concentrated. The residue was is purified by silica gel column chromatography (solvent; hexane/ethyl acetate=50/50-0/100) to give the title compound (51.4 mg).
MS (ESI) m/z; 299 [M+H]+

Reference Example 737

2-methylsulfonyl-6-(propan-2-yl)-7-trifluoromethyl-5H-[1,3]thiazolo[4,5-c]pyridin-4-one

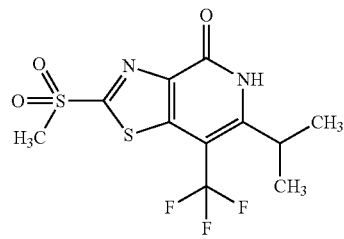 [SMILES: CC(C)c1[nH]c(=O)c2nc(S(C)(=O)=O)sc2c1C(F)(F)F]

The compound (88.0 mg) obtained in Reference Example 732 was treated by a method similar to that in Reference Example 736 to give the title compound (78.4 mg).
MS (ESI) m/z; 341 [M+H]+

Reference Example 738

2-methylsulfonyl-6-(propan-2-yl)-5H-[1,3]thiazolo[4,5-c]pyridin-4-one

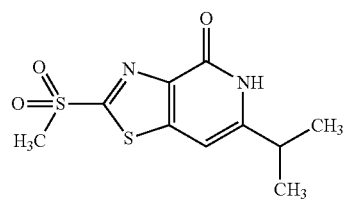 [SMILES: CC(C)c1cc2sc(S(C)(=O)=O)nc2c(=O)[nH]1]

The compound (297 mg) obtained in Reference Example 733 was treated by a method similar to that in Reference Example 736 to give the title compound (314 mg).
MS (ESI) m/z; 273 [M+H]+

Reference Example 739

6-cyclopropyl-2-methylsulfonyl-5H-[1,3]thiazolo[4,5-c]pyridin-4-one

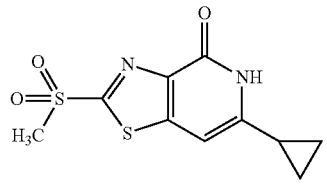 [SMILES: CS(=O)(=O)c1nc2c(=O)[nH]c(C3CC3)cc2s1]

The compound (292 mg) obtained in Reference Example 734 was treated by a method similar to that in Reference Example 736 to give the title compound (250 mg)
MS (ESI) m/z; 271 [M+H]+

Reference Example 740

6-(2-fluorophenyl)-2-methylsulfonyl-5H-[1,3]thiazolo[4,5-c]pyridin-4-one

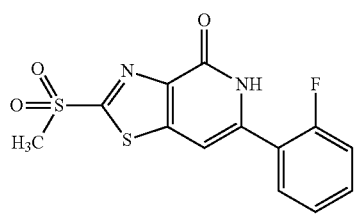 [SMILES: CS(=O)(=O)c1nc2c(=O)[nH]c(-c3ccccc3F)cc2s1]

The compound (150 mg) obtained in Reference Example 735 was treated by a method similar to that in Reference Example 736 to give the title compound (165 mg).
MS (ESI) m/z; 325 [M+H]+

Reference Example 741

3-amino-4-chloro-6-(propen-2-yl)-2-methoxypyridine

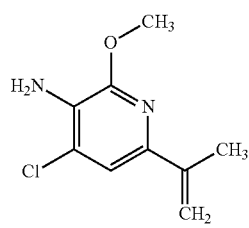

The compound (4.00 g) obtained in Reference Example 719 was treated by a method similar to that in Reference Example 724 to give the title compound (3.35 g).
MS (ESI) m/z; 199, 201 [M+H]+

Reference Example 742

2-methylsulfanyl-6-(propen-2-yl)-5H-[1,3]thiazolo[4,5-c]pyridin-4-one

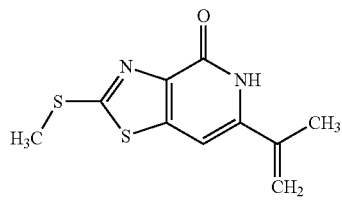

A solution (20 mL) of the compound (3.35 g) obtained in Reference Example 741 and potassium ethyl xanthogenate (8.11 g) in DMF was stirred with heating at 130° C. for 4 hr. The reaction mixture was cooled to room temperature, acetic acid (7.0 mL) and water were added, and the precipitated solid was collected by filtration and dried. To the obtained solid was added 25% hydrogen bromide-acetic acid solution (25 mL), and the reaction mixture was stirred with heating at 70° C. for 1 hr. The reaction mixture was cooled to 0° C., water was added, and the precipitated solid was collected by filtration and dried. To a solution (85 mL) of the obtained solid in DMF were added sodium hydrogen carbonate (1.70 g) and methyl iodide (1.05 mL) at 0° C. The reaction mixture was stirred at room temperature for 3 hr, and added to aqueous ammonium chloride solution. The precipitated solid was purified by silica gel column chromatography (solvent; ethyl acetate/methanol=100/0-90/10) to give the title compound (302 mg).
MS (ESI) m/z; 239 [M+H]+

Reference Example 743

6-(2-hydroxypropan-2-yl)-2-methylsulfanyl-5H-[1,3]thiazolo[4,5-c]pyridin-4-one

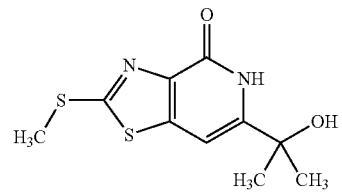

To a mixed solution of the compound (150 mg) obtained in Reference Example 742 in 1,4-dioxane-water (5.0 mL-2.5 mL) was added methansulfonic acid (2.5 mL), and the reaction mixture was stirred with heating at 80° C. for 2 days. The reaction mixture was cooled to room temperature, extracted twice with chloroform, and the organic layer was dried over anhydrous sodium sulfate, filtered and concentrated. The residue was purified by silica gel column chromatography (solvent; ethyl acetate/methanol=100/0-93/7) to give the title compound (28 mg).
MS (ESI) m/z; 257 [M+H]+

Reference Example 744

6-(2-hydroxypropan-2-yl)-4-(4-methoxybenzyloxy)-2-methylsulfanyl-[1,3]thiazolo[4,5-c]pyridine

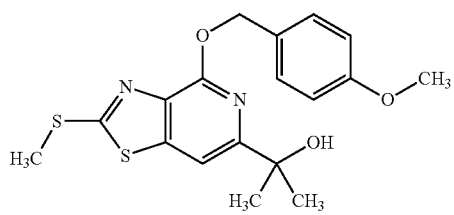

To a solution (7.0 mL) of the compound (231 mg) obtained in Reference Example 743 in DMF were added potassium carbonate (249 mg) and 4-methoxybenzyl chloride (147 μL), and the reaction mixture was stirred with heating at 80° C. for 2 hr. The reaction mixture was cooled to 0° C., water was added, and the mixture was extracted twice with ethyl acetate. The organic layer was dried over anhydrous magnesium sulfate, filtered and concentrated. The residue was purified by NH silica gel column chromatography (solvent; hexane/ethyl acetate=95/5-60/40) to give the title compound (338 mg).

MS (ESI) m/z; 377 [M+H]$^+$

Reference Example 745

6-(2-fluoropropan-2-yl)-4-(4-methoxybenzyloxy)-2-methylsulfanyl-[1,3]thiazolo[4,5-c]pyridine

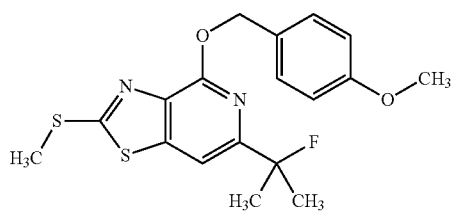

To a solution (15 mL) of the compound (335 mg) obtained in Reference Example 744 in methylene chloride was added a solution (5.0 mL) of N,N-diethylaminosulfur trifluoride (175 μL) in methylene chloride at −25° C., and the reaction mixture was stirred at −20° C. for 1 hr. Saturated aqueous sodium hydrogen carbonate solution was added, and the mixture was extracted twice with chloroform. The organic layer was dried over anhydrous magnesium sulfate, filtered and concentrated. The residue was purified by silica gel column chromatography (solvent; hexane/ethyl acetate=100/0-85/15) to give the title compound (305 mg).

MS (ESI) m/z; 379 [M+H]$^+$

Reference Example 746

6-(2-fluoropropan-2-yl)-4-(4-methoxybenzyloxy)-2-methylsulfinyl-[1,3]thiazolo[4,5-c]pyridine

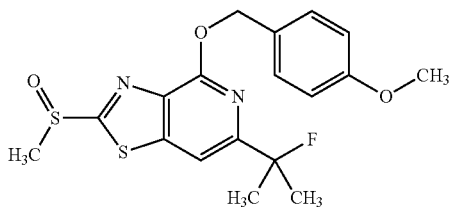

To a solution (11 mL) of the compound (311 mg) obtained in Reference Example 745 in methylene chloride was added mCPBA (69-75%, 226 mg) under ice-cooling. The reaction mixture was stirred under ice-cooling for 1.5 hr, to the reaction mixture were added aqueous sodium thiosulfate solution and saturated aqueous sodium hydrogen carbonate solution, and the mixture was extracted twice with chloroform. The organic layer was dried over anhydrous sodium sulfate, filtered and concentrated. To the obtained residue was added hexane-diethyl ether mixed solvent (1:1), and the solid was collected by filtration, and dried to give the title compound (320 mg).

MS (ESI) m/z; 395 [M+H]$^+$

Reference Example 747

(R)-N-benzyl-1-[6-(2-fluoropropan-2-yl)-4-(4-methoxybenzyloxy)-[1,3]thiazolo[4,5-c]pyridin-2-yl]pyrrolidine-2-carboxamide

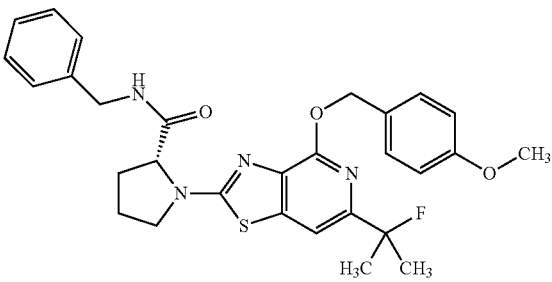 [SMILES: COc1ccc(COc2nc(C(C)(C)F)cc3sc(N4CCC[C@@H]4C(=O)NCc4ccccc4)nc23)cc1]

To a solution (3.0 mL) of the compound (124 mg) obtained in Reference Example 746 in DMF were added (D)-proline (54 mg) and cesium carbonate (256 mg), and the reaction mixture was heated at 70° C. for 1.5 hr. The reaction mixture was cooled to room temperature, acidified with 1.0 mol/L hydrochloric acid, and extracted twice with chloroform. The organic layer was dried over anhydrous sodium sulfate, filtered and concentrated. To the obtained residue were added N,N-diisopropylethylamine (82 μL), benzylamine (52 μL), EDC hydrochloride (90 mg) and HOBt monohydrate (72 mg), and the reaction mixture was stirred at room temperature for 3 hr. Water was added, and the mixture was extracted twice with ethyl acetate. The organic layer was washed with saturated brine, dried over anhydrous sodium sulfate, filtered and concentrated. The residue was purified by silica gel column chromatography (solvent; hexane/ethyl acetate=85/15-20/80) to give the title compound (133 mg).

MS (ESI) m/z; 535 [M+H]$^+$

Reference Example 748

6-bromo-2-mercapto-5H-[1,3]thiazolo[4,5-c]pyridin-4-one

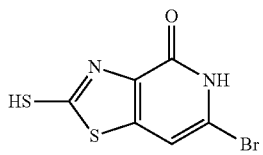 [SMILES: O=c1[nH]c(Br)cc2sc(S)nc12]

The compound (2.00 g) obtained in Reference Example 719 was treated by a method similar to that in Reference Example 726 to give the title compound (1.20 g).
MS (ESI) m/z; 263, 265 [M+H]+

Reference Example 749

6-bromo-2-methylsulfanyl-5H-[1,3]thiazolo[4,5-c]pyridin-4-one

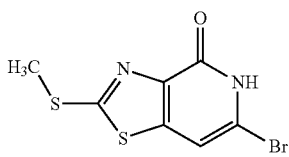

The compound (1.20 g) obtained in Reference Example 748 was treated by a method similar to that in Reference Example 731 to give the title compound (959 mg).
MS (ESI) m/z; 277, 279 [M+H]+

Reference Example 750

6-bromo-5-(4-methoxybenzyl)-2-methylsulfanyl-5H-[1,3]thiazolo[4,5-c]pyridin-4-one

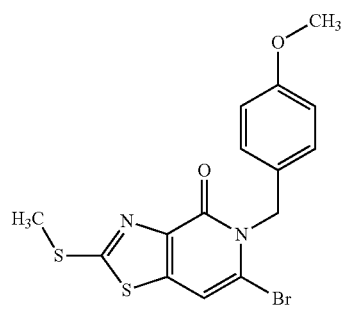

To a solution (19.4 mL) of the compound (955 mg) obtained in Reference Example 749 in DMF were added potassium carbonate (952 mg) and 4-methoxybenzyl chloride (563 μL), and the reaction mixture was stirred with heating at 70° C. for 2 hr. The reaction mixture was cooled to 0° C., water was added, and the mixture was extracted twice with ethyl acetate. The organic layer was dried over anhydrous magnesium sulfate, filtered and concentrated. The residue was purified by NH silica gel column chromatography (solvent; hexane/ethyl acetate=95/5-40/60) to give the title compound (299 mg).
MS (ESI) m/z; 397, 399 [M+H]+

Reference Example 751

6-bromo-5-(4-methoxybenzyl)-2-methylsulfinyl-5H-[1,3]thiazolo[4,5-c]pyridin-4-one

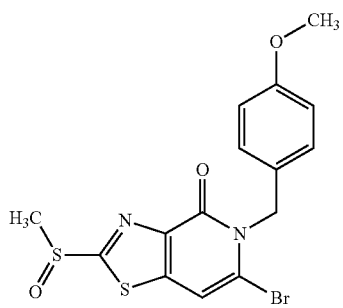

To a solution (10 mL) of the compound (195 mg) obtained in Reference Example 750 in methylene chloride was added mCPBA (69-75%, 120 mg) under ice-cooling. The reaction mixture was stirred under ice-cooling for 1 hr, to the reaction mixture were added aqueous sodium thiosulfate solution and saturated aqueous sodium hydrogen carbonate solution, and the mixture was extracted three times with chloroform. The organic layer was dried over anhydrous sodium sulfate, filtered and concentrated to give the title compound (204 mg).
MS (ESI) m/z; 413, 415 [M+H]+

Reference Example 752

(R)-1-[6-bromo-5-(4-methoxybenzyl)-4-oxo-4,5-dihydro[1,3]thiazolo[4,5-c]pyridin-2-yl]pyrrolidine-2-carboxylic acid tert-butyl ester

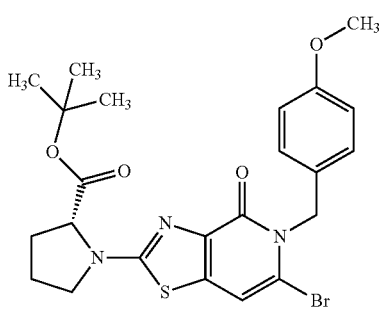 [SMILES: COc1ccc(Cn2c(Br)cc3sc(N4CCC[C@@H]4C(=O)OC(C)(C)C)nc3c2=O)cc1]

A mixed solution of the compound (150 mg) obtained in Reference Example 751, D-proline-tert-butyl ester (124 mg) and N,N-diisopropylethylamine (1.26 mL) was stirred with heating at 140° C. for 9 hr. D-proline-tert-butyl ester (248 mg) and N-methylpyrrolidone (200 μL) were added, and the reaction mixture was stirred with heating at 140° C. for 4 hr. The reaction mixture was cooled to room temperature, acidified with 1.0 mol/L hydrochloric acid, and extracted twice with ethyl acetate. The organic layer was dried over anhydrous sodium sulfate, filtered and concentrated and the residue was purified by silica gel column chromatography (solvent; hexane/ethyl acetate=90/10-40/60). To the obtained product was added hexane-diethyl ether mixed solvent (1:1), and the solid was collected by filtration and dried to give the title compound (86.6 mg).

MS (ESI) m/z; 520, 522 [M+H]$^+$

Reference Example 753

3-amino-4-chloro-2-hydroxy-6-trifluoromethylpyridine

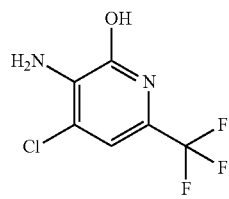 [SMILES: Nc1c(Cl)cc(C(F)(F)F)nc1O]

A mixture of 4-chloro-3-nitro-6-trifluoromethylpyridin-2-ol (1.50 g) synthesized by the method described in US 2007/197478 A1, ammonium chloride (397 mg) and iron powder (1.38 g) in methanol (20 mL), THF (20 mL) and water (10 mL) was stirred at 70° C. for 2.5 hr. The reaction mixture was cooled to room temperature, filtered through diatomaceous earth, and the filtrate was concentrated. The residue was diluted with ethyl acetate, and filtered again through diatomaceous earth. The filtrate was washed with water and saturated brine, and the organic layer was dried over anhydrous sodium sulfate, filtered and concentrated. To the obtained solid was added hexane/ethyl acetate=2/1, and the solid was collected by filtration to give the title compound (1.21 g).

MS (ESI) m/z; 213 [M+H]$^+$

Reference Example 754

4-hydroxy-2-mercapto-6-trifluoromethyl-[1,3]thiazolo[4,5-c]pyridine

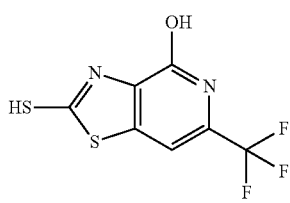 [SMILES: Oc1nc(C(F)(F)F)cc2sc(S)nc12]

The compound (700 mg) obtained in Reference Example 753 was treated by a method similar to that in Reference Example 726 to give the title compound (716 mg).

MS (ESI) m/z; 253 [M+H]$^+$

Reference Example 755

2-methylsulfanyl-6-trifluoromethyl-5H-[1,3]thiazolo[4,5-c]pyridin-4-one

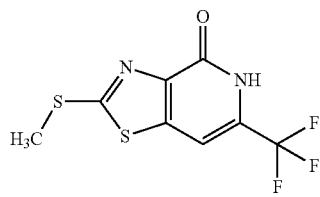 [SMILES: CSc1nc2c(=O)[nH]c(C(F)(F)F)cc2s1]

To a mixture of the compound (600 mg) obtained in Reference Example 754 and sodium hydrogen carbonate (240 mg) in DMF (8 mL)/THF (4 mL) was added dropwise iodomethane (163 μL) at −10° C. The reaction mixture was stirred at −10° C. for 30 min and stirred at room temperature for 1.5 hr. The reaction mixture was acidified with 1.0 mol/L hydrochloric acid, and water was added. The precipitated solid was collected by filtration, washed with water, and dissolved in ethyl acetate/methanol=5/1. The solution was dried over anhydrous sodium sulfate, filtered and concentrated under reduced pressure. The obtained residue was purified by NH silica gel column chromatography (solvent; hexane/ethyl acetate=60/40-0/100) to give the title compound (24 mg).

MS (ESI) m/z; 266 [M+H]$^+$

Reference Example 756

7-chloro-2-methylsulfanyl-6-trifluoromethyl-5H-[1,3]thiazolo[4,5-c]pyridin-4-one

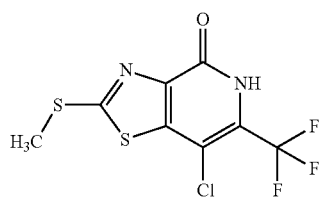 [SMILES: CSc1nc2c(=O)[nH]c(C(F)(F)F)c(Cl)c2s1]

A mixture (5.3 mL) of the compound (530 mg) obtained in Reference Example 755 and N-chlorosuccinimide (372 mg) in DMF was stirred with heating at 70° C. for 2 hr. N-chlorosuccinimide (53 mg) was added, and the mixture was further stirred with heating for 1 hr. The reaction mixture was ice-cooled, water was added, and the mixture was extracted twice with ethyl acetate. The combined organic layer was washed with saturated brine, dried over anhydrous sodium sulfate, filtered and concentrated under reduced pressure. The obtained residue was purified by silica gel column chromatography (solvent; hexane/ethyl acetate=90/10-40/60) to give the title compound (197 mg)

MS (ESI) m/z; 301 [M+H]$^+$

Reference Example 757

7-iodo-2-methylsulfanyl-6-trifluoromethyl-5H-[1,3]thiazolo[4,5-c]pyridin-4-one

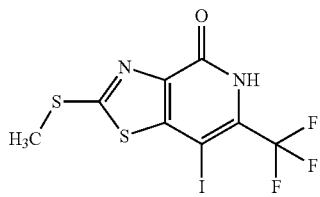 [SMILES: CSc1nc2c(=O)[nH]c(C(F)(F)F)c(I)c2s1]

To a solution (5.5 mL) of the compound (550 mg) obtained in Reference Example 755 in DMF was added N-iodosuccinimide (511 mg). The reaction mixture was stirred at room temperature for 1 hr and stirred with heating at 70° C. for 2 hr. N-iodosuccinimide (139 mg) was added, and the mixture was further stirred with heating for 2 hr. The reaction mixture was ice-cooled, and diluted with water. The precipitated solid was collected by filtration, washed with water, and dissolved in ethyl acetate/methanol=5/1. The obtained solution was dried over anhydrous sodium sulfate, filtered and concentrated under reduced pressure. To the obtained solid were added hexane/diethyl ether=3/1, and the solid was collected by filtration to give the title compound (725 mg).

MS (ESI) m/z; 393 [M+H]$^+$

Reference Example 758

(R)-N-benzylpiperidine-2-carboxamide hydrochloride

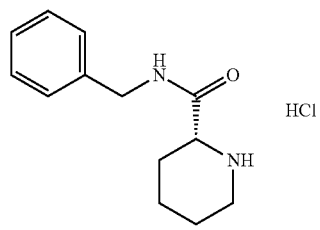 [SMILES: O=C(NCc1ccccc1)[C@H]1CCCCN1 ; Cl]

(R)-N-(tert-butoxycarbonyl)-piperidine-2-carboxylic acid (7.63 g) was treated by a method similar to that in Reference Example 341 to give the title compound (6.74 g).

MS (ESI) m/z; 219 [M+H]$^+$

Reference Example 759

(R)-N-benzylmorpholine-3-carboxamide hydrochloride

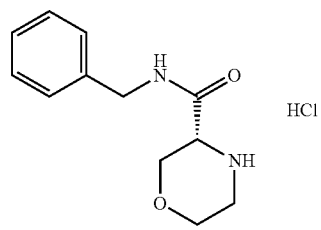 [SMILES: O=C(NCc1ccccc1)[C@H]1COCCN1 ; Cl]

(R)-N-(tert-butoxycarbonyl)-morpholine-3-carboxylic acid (581 mg) was treated by a method similar to that in Reference Example 341 to give the title compound (430 mg).

MS (ESI) m/z; 221 [M+H]$^+$

Reference Example 760

(R)-N-[(pyridin-2-yl)methyl]pyrrolidine-2-carboxamidehydrochloride

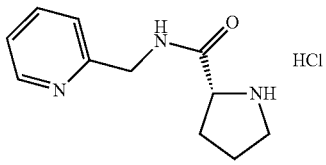 [SMILES: O=C(NCc1ccccn1)[C@H]1CCCN1 ; Cl]

N-(tert-butoxycarbonyl)-D-proline (5.00 g) was treated by is a method similar to that in Reference Example 341 to give the title compound (5.04 g).

MS (ESI) m/z; 206 [M+H]$^+$

Reference Example 761

(R)-N-(1-phenylcyclopropyl)pyrrolidine-2-carboxamidehydrochloride

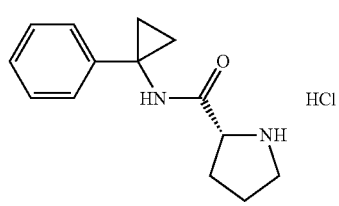 [SMILES: O=C(NC1(c2ccccc2)CC1)[C@H]1CCCN1 ; Cl]

N-(tert-butoxycarbonyl)-D-proline (3.00 g) was treated by a method similar to that in Reference Example 341 to give the title compound (3.21 g).

MS (ESI) m/z; 231 [M+H]$^+$

Reference Example 762

(R)-N-(1-methyl-1-phenylethyl)pyrrolidine-2-carboxamidehydrochloride

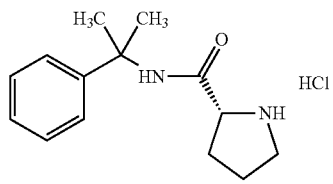 [SMILES: CC(C)(NC(=O)[C@H]1CCCN1)c1ccccc1 ; Cl]

N-(tert-butoxycarbonyl)-D-proline (6.82 g) was treated by a method similar to that in Reference Example 341 to give the title compound (8.60 g).
MS (ESI) m/z; 233 [M+H]$^+$

Reference Example 763

2-bromo-7-propyl-5H-[1,3,4]thiadiazolo[3,2-a]pyrimidin-5-one

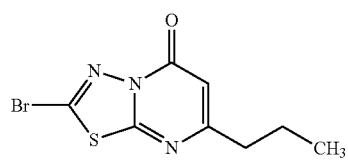

2-Amino-5-bromo[1,3,4]thiadiazole (10 g) and 3-oxohexanoic acid ethyl ester (10.6 g) were added to polyphosphoric acid (60 g), and the reaction mixture was stirred with heating at 100° C. for 5 hr. After confirmation of the completion of the reaction, the reaction mixture was cooled to room temperature, water was added, and the mixture was dissolved, and extracted twice with chloroform. The organic layer was washed once with water, dried over anhydrous magnesium sulfate, filtered and concentrated. The residue was purified by silica gel column chromatography (solvent; hexane/ethyl acetate=80/20-50/50). To the obtained product was added diisopropyl ether, and the solid was collected by filtration to give the title compound (6.2 g).
MS (ESI) m/z; 274, 276 [M+H]$^+$

Reference Example 764

2-bromo-7-methyl-5H-[1,3,4]thiadiazolo[3,2-a]pyrimidin-5-one

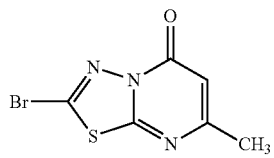

2-Amino-5-bromo[1,3,4]thiadiazole (27.6 g) was treated by a method similar to that in Reference Example 763 to give the title compound (24.6 g).
MS (ESI) m/z; 246, 248 [M+H]$^+$

Reference Example 765

2-bromo-7-ethyl-5H-[1,3,4]thiadiazolo[3,2-a]pyrimidin-5-one

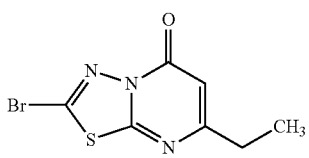

2-Amino-5-bromo[1,3,4]thiadiazole (3.60 g) was treated by a method similar to that in Reference Example 763 to give the title compound (2.60 g).
MS (ESI) m/z; 260, 262 [M+H]$^+$

Reference Example 766

2-bromo-7-phenyl-5H-[1,3,4]thiadiazolo[3,2-a]pyrimidin-5-one

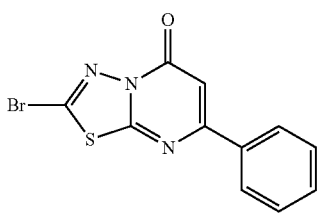 [SMILES: O=c1cc(-c2ccccc2)nc2sc(Br)nn12]

2-Amino-5-bromo[1,3,4]thiadiazole (3.60 g) was treated by a method similar to that in Reference Example 763 to give the title compound (410 mg).
MS (ESI) m/z; 308, 310 [M+H]$^+$

Reference Example 767

2-bromo-6,7-dimethyl-5H-[1,3,4]thiadiazolo[3,2-a]pyrimidin-5-one

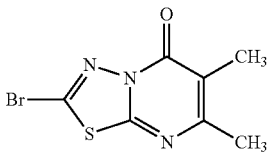

2-Amino-5-bromo[1,3,4]thiadiazole (1000 mg) was treated by a method similar to that in Reference Example 763 to give the title compound (540 mg).
MS (ESI) m/z; 260, 262 [M+H]$^+$

Reference Example 768

2-bromo-7-methyl-6-(propan-2-yl)-5H-[1,3,4]thiadiazolo[3,2-a]pyrimidin-5-one

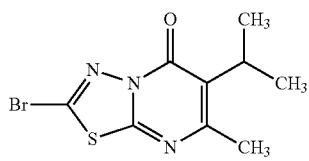

2-Amino-5-bromo[1,3,4]thiadiazole (5.00 g) was treated by a method similar to that in Reference Example 763 to give the title compound (2.69 g).

MS (ESI) m/z; 288, 290 [M+H]$^+$

Reference Example 769

2-bromo-7-methyl-6-phenyl-5H-[1,3,4]thiadiazolo[3,2-a]pyrimidin-5-one

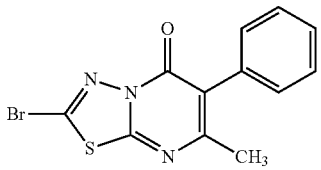

2-Amino-5-bromo[1,3,4]thiadiazole (1.00 g) was treated by a method similar to that in Reference Example 763 to give the title compound (369 mg).

MS (ESI) m/z; 322, 324 [M+H]$^+$

Reference Example 770

2-bromo-6,7,8,9-tetrahydro-5H-[1,3,4]thiadiazolo[2,3-b]quinazolin-5-one

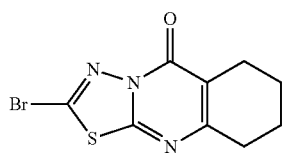 [SMILES: O=c1c2c(nc3sc(Br)nn13)CCCC2]

2-Amino-5-bromo[1,3,4]thiadiazole (4.70 g) was treated by a method similar to that in Reference Example 763 to give the title compound (5.70 g).

MS (ESI) m/z; 286, 288 [M+H]$^+$

Reference Example 771

2-bromo-7-ethyl-6-fluoro-5H-[1,3,4]thiadiazolo[3,2-a]pyrimidin-5-one

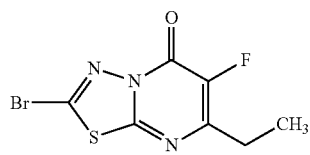

To a solution (56 mL) of 3-oxo-pentanoic acid methyl ester (3.67 g) in acetonitrile was added 1-chloromethyl-4-fluoro-1,4-diazoniabicyclo[2.2.2]octane bistetrafluoroborate (10.0 g) at room temperature, and the reaction mixture was stirred with heating at 80° C. for 8 hr. The reaction mixture was cooled to room temperature, diethyl ether was added, and the mixture was washed twice with water. The organic layer was dried over anhydrous sodium sulfate, filtered and concentrated to give 2-fluoro-3-oxo-pentanoic acid methyl ester (3.24 g). The obtained 2-fluoro-3-oxo-pentanoic acid methyl ester (3.24 g) and 2-amino-5-bromo[1,3,4]thiadiazole (3.28 g) were added to polyphosphoric acid (18.4 g), and the reaction mixture was stirred with heating at 100° C. for 5 hr. The reaction mixture was cooled to room temperature, water was added, and the mixture was extracted twice with chloroform. The organic layer was washed once with water, dried over anhydrous sodium sulfate, filtered and concentrated. The residue was purified by silica gel column chromatography (solvent; hexane/ethyl acetate=80/20-50/50) to give the title compound (1.14 g).

MS (ESI) m/z; 278, 280 [M+H]$^+$

Reference Example 772

2-bromo-6-fluoro-7-propyl-5H-[1,3,4]thiadiazolo[3,2-a]pyrimidin-5-one

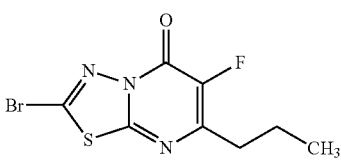

2-Amino-5-bromo[1,3,4]thiadiazole (4.00 g) was treated by a method similar to that in Reference Example 771 to give the title compound (1.10 g).

MS (ESI) m/z; 292, 294 [M+H]$^+$

Reference Example 773

2-bromo-7-(propan-2-yl)-5H-[1,3,4]thiadiazolo[3,2-a]pyrimidin-5-one

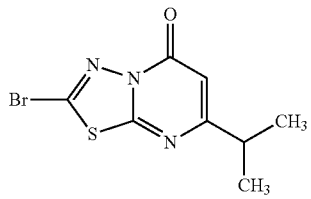

2-Amino-5-bromo[1,3,4]thiadiazole (10 g) and 4-methyl-3-oxopentanoic acid methyl ester (9.6 g) were added to concentrated sulfuric acid (60 mL), and the reaction mixture was stirred at room temperature for 2 hr and stirred with heating at 60° C. for 4 hr. After confirmation of the completion of the reaction, the reaction mixture was cooled to room temperature, diluted with water, and neutralized with 1.0 mol/L aqueous sodium hydroxide solution. The mixture was extracted twice with chloroform, and the organic layer was washed once with water, dried over anhydrous sodium sulfate, filtered and concentrated. The residue was purified by silica gel column chromatography (solvent; hexane/ethyl acetate=80/20-50/50) to give the title compound (10.9 g).
MS (ESI) m/z; 274, 276 [M+H]+

Reference Example 774

2-bromo-7-trifluoromethyl-5H-[1,3,4]thiadiazolo[3,2-a]pyrimidin-5-one

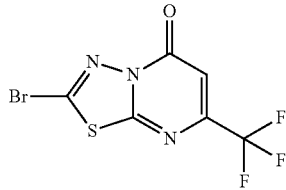 [SMILES: O=c1cc(C(F)(F)F)nc2sc(Br)nn12]

2-Amino-5-bromo[1,3,4]thiadiazole (3.60 g) was treated by a method similar to that in Reference Example 773 to give the title compound (757 mg).
MS (ESI) m/z; 300, 302 [M+H]+

Reference Example 775

2-bromo-5H-[1,3,4]thiadiazolo[2,3-b]quinazolin-5-one

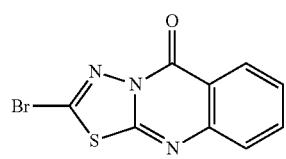 [SMILES: O=c1c2ccccc2nc2sc(Br)nn12]

To a solution (30 mL) of 2-amino-5-bromo[1,3,4]thiadiazole (3.0 g) in acetic acid was added anthranilic acid (1.7 g) at room temperature, and the reaction mixture was heated under reflux for 5 hr. After confirmation of the completion of the reaction, the reaction mixture was cooled to room temperature, and the resultant solid was washed with diisopropyl ether, and collected by filtration. The obtained solid was dissolved in chloroform, and the solution was washed once with saturated aqueous sodium hydrogen carbonate solution. The organic layer was concentrated under reduced pressure, to the resultant solid was added ethyl acetate, and the insoluble material was filtered off. The filtrate was concentrated, and the residue was purified by silica gel column chromatography (solvent; hexane/ethyl acetate=80/20-50/50) to give the title compound (0.6 g).
MS (ESI) m/z; 282, 284 [M+H]+

Reference Example 776

2-bromo-6-methyl-8H-[1,3,4]thiadiazolo[3,2-a]thieno[2,3-d]pyrimidin-8-one

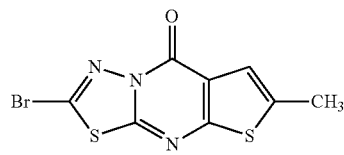

A mixture of 2,5-dibromo[1,3,4]thiadiazole (2.0 g) and 2-amino-5-methylthiophene-3-carboxylic acid ethyl ester (1.5 g) was stirred with heating at 160° C. for 30 min. After confirmation of the completion of the reaction, the reaction mixture was cooled to room temperature, dissolved in chloroform (200 mL), washed once with 1.0 mol/L hydrochloric acid (30 mL), and washed once with water. The organic layer was dried over anhydrous magnesium sulfate, filtered and concentrated and the residue was purified by silica gel column chromatography (solvent; chloroform/methanol=100/0-90/10). To the obtained product was added diisopropyl ether, and the solid was collected by filtration to give the title compound (0.9 g).
MS (ESI) m/z; 302, 304 [M+H]+

Reference Example 777

2-bromo-9H-pyrido[2,3-d][1,3,4]thiadiazolo[3,2-a]pyrimidin-9-one

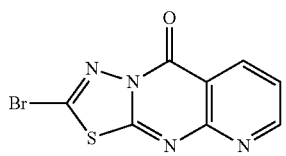 [SMILES: O=c1c2cccnc2nc2sc(Br)nn12]

A mixture of 2-amino-5-bromo[1,3,4]thiadiazole (2.8 g) and 2-chloropyridine-3-carboxylic acid (2.6 g) was stirred with heating at 200° C. for 1 hr. After confirmation of the completion of the reaction, the reaction mixture was cooled to room temperature, dissolved in chloroform (200 mL), washed once with saturated aqueous sodium hydrogen carbonate solution, and washed once with water. The organic layer was dried over anhydrous magnesium sulfate, filtered and concentrated and the residue was purified by silica gel column chromatography (solvent; chloroform/methanol=100/0-90/10). Ethyl acetate was added to the obtained product, and the solid was collected by filtration to give the title compound (0.16 g).
MS (ESI) m/z; 283, 285 [M+H]⁺

Reference Example 778

2-bromo-6-chloro-7-ethyl-5H-[1,3,4]thiadiazolo[3,2-a]pyrimidin-5-one

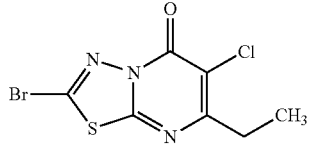

To a solution (22 mL) of the compound (1.7 g) obtained in Reference Example 765 in acetonitrile was added N-chlorosuccinimide (850 mg) at room temperature, and the reaction mixture was stirred with heating at 60° C. for 7 hr. After confirmation of the completion of the reaction, the reaction mixture was cooled to room temperature, chloroform was added, and the mixture was washed twice with water. The organic layer was dried over anhydrous sodium sulfate, filtered and concentrated. The residue was purified by silica gel column chromatography (solvent; chloroform) to give the title compound (1.2 g).
MS (ESI) m/z; 294, 296 [M+H]⁺

Reference Example 779

2-bromo-6-chloro-7-methyl-5H-[1,3,4]thiadiazolo[3,2-a]pyrimidin-5-one

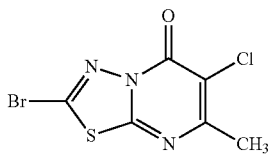

The compound (500 mg) obtained in Reference Example 764 was treated by a method similar to that in Reference Example 778 to give the title compound (516 mg).
MS (ESI) m/z; 280, 282 [M+H]⁺

Reference Example 780

2-bromo-6-chloro-7-(propan-2-yl)-5H-[1,3,4]thiadiazolo[3,2-a]pyrimidin-5-one

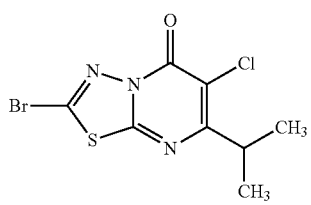

The compound (1350 mg) obtained in Reference Example 773 was treated by a method similar to that in Reference Example 778 to give the title compound (574 mg).
MS (ESI) m/z; 308, 310 [M+H]⁺

Reference Example 781

(EZ)-2-ethylpropene-1,3-dicarboxylic acid diethyl ester

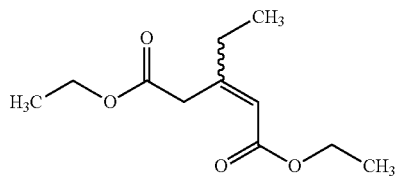

To a solution (30 mL) of ethyl 2-pentynoate (10.0 g) and ethyl acetoacetate (10 mL) in ethanol was added dropwise 20% sodium ethoxide ethanol solution (6.1 mL) at 80° C. over 1 hr, and the reaction mixture was stirred at the same temperature for 6 hr. The reaction mixture was cooled to room temperature, diethyl ether was added, and the mixture was washed once with 1.0 mol/L hydrochloric acid and once with water. The organic layer was dried over anhydrous magnesium sulfate, filtered and concentrated. The residue was purified by silica gel column chromatography (solvent; hexane/ethyl acetate=90/10-80/20) to give the title compound (12.8 g, cis:trans=>4:1).
MS (ESI) m/z; 215 [M+H]⁺

Reference Example 782

4-ethyl-2H-pyran-2,6(3H)-dione

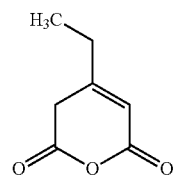

To the compound (12.8 g) obtained in Reference Example 781 was added aqueous sodium hydroxide solution (11.9 g/67 mL), and the reaction mixture was stirred with heating at 80° C. for 4 hr. The reaction mixture was cooled to room temperature, and washed once with diethyl ether. The aqueous layer was acidified with concentrated hydrochloric acid (25 mL), and extracted 3 times with diethyl ether. The organic layer was dried over anhydrous magnesium sulfate, filtered and concentrated. To the residue was added acetic anhydride (10.6 mL), and the reaction mixture was stirred with heating at 80° C. for 3 hr, acetic anhydride (3.0 mL) were added, and the mixture was further stirred with heating for 2 hr. The reaction mixture was cooled to room temperature, and the solvent was evaporated under reduced pressure. The residue was evaporated under reduced pressure at 12 mmHg (160-170° C.) to give the title compound (6.5 g).
MS (ESI) m/z; 141 [M+H]⁺

Reference Example 783

7-ethyl-2-methylsulfanyl-5H-[1,3,4]thiadiazolo[3,2-a]pyridin-5-one

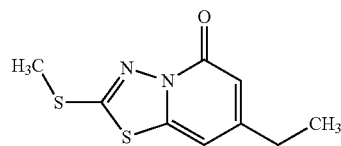

To a solution (10 mL) of methyl dithiocarbazate (1.3 g) in THF was added the compound (1.5 g) obtained in Reference Example 782, and the reaction mixture was stirred at room temperature for 3 hr. The solvent was evaporated under reduced pressure, 85% phosphoric acid (10 mL) was added, and the mixture was stirred at 120° C. for 2 hr. After confirmation of the completion of the reaction, chloroform was added, and the mixture was washed once with water. The organic layer was dried over anhydrous sodium sulfate, filtered and concentrated. The residue was purified by silica gel column chromatography (solvent; chloroform/methanol=100/0-90/10) and the solvent was evaporated under reduced pressure to give the title compound (2.3 g).

MS (ESI) m/z; 227 [M+H]$^+$

Reference Example 784

7-methyl-2-methylsulfanyl-5H-[1,3,4]thiadiazolo[3,2-a]pyridin-5-one

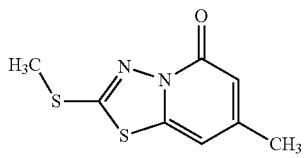

Methyl dithiocarbazate (970 mg) was treated by a method similar to that in Reference Example 783 to give the title compound (1115 mg).

MS (ESI) m/z; 213 [M+H]$^+$

Reference Example 785

7-ethyl-2-methylsulfonyl-5H-[1,3,4]thiadiazolo[3,2-a]pyridin-5-one

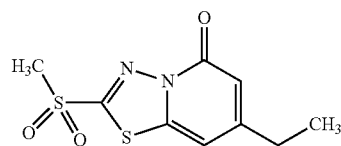 [SMILES: CCc1cc(=O)n2nc(S(C)(=O)=O)sc2c1]

To a solution (20 mL) of the compound (1.0 g) obtained in Reference Example 783 in methylene chloride was added mCPBA (69-75%, 3.52 g) at 0° C., and the reaction mixture was stirred at room temperature for 4 hr. mCPBA (69-75%, 0.8 g) was added, and the reaction mixture was stirred at room temperature for 4 hr. Aqueous sodium thiosulfate solution and chloroform were added, and the mixture was washed once with water, and once with saturated aqueous sodium hydrogen carbonate solution. The organic layer was dried over anhydrous sodium sulfate, filtered and concentrated. The residue was purified by silica gel column chromatography (solvent; chloroform/methanol=100/0-95/5), and the solvent was evaporated under reduced pressure to give the title compound (0.56 g).

MS (ESI) m/z; 259 [M+H]$^+$ to Reference Example 786

7-methyl-2-methylsulfonyl-5H-[1,3,4]thiadiazolo[3,2-a]pyridin-5-one

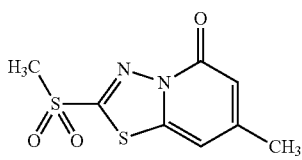

The compound (550 mg) obtained in Reference Example 784 was treated by a method similar to that in Reference Example 785 to give the title compound (300 mg).

MS (ESI) m/z; 245 [M+H]$^+$

Reference Example 787

3-amino-6-bromopyridine-N-methyl-2-carboxamide

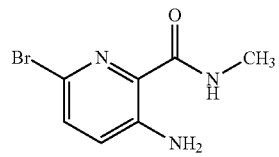

To a solution (5 mL) of 3-amino-6-bromopyridine-2-carboxylic acid (280 mg) synthesized by the method described in WO 2008/106692 A1 and WO 2005/97805 A1 in DMF were added aqueous methylamine solution (0.16 mL), EDC hydrochloride (320 mg), HOBt monohydrate (255 mg) and N,N-diisopropylethylamine (0.225 mL), and the reaction mixture was stirred at room temperature overnight. After confirmation of the completion of the reaction, water was added to the reaction mixture, and the mixture was extracted twice with ethyl acetate. The organic layer was washed once with water, dried over anhydrous magnesium sulfate, filtered and concentrated. The residue was purified by silica gel column chromatography (solvent; hexane/ethyl acetate=80/20-50/50) to give the title compound (260 mg).

MS (ESI) m/z; 230, 232 [M+H]$^+$

Reference Example 788

3-amino-6-bromopyridine-N-ethyl-2-carboxamide

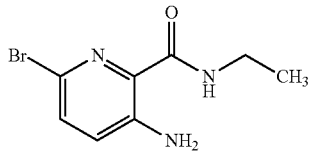

3-Amino-6-bromopyridine-2-carboxylic acid (280 mg) was treated by a method similar to that in Reference Example 787 to give the title compound (295 mg).

MS (ESI) m/z; 244, 246 [M+H]$^+$

Reference Example 789

3-amino-6-bromopyridine-N-(2,2,2-trifluoroethyl)-2-carboxamide

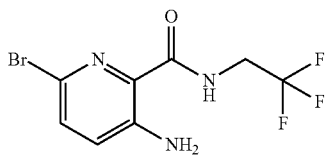 [SMILES: Nc1ccc(Br)nc1C(=O)NCC(F)(F)F]

3-Amino-6-bromopyridine-2-carboxylic acid (350 mg) was treated by a method similar to that in Reference Example 787 to give the title compound (459 mg).

MS (ESI) m/z; 298, 300 [M+H]$^+$

Reference Example 790

6-bromo-2-ethyl-3-methylpyrido[3,2-d]pyrimidin-4(3H)-one

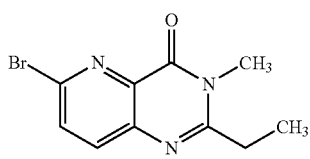

A mixture of the compound (260 mg) obtained in Reference Example 787, trimethyl orthopropionate (2.2 mL) and acetic anhydride (2.2 mL) was heated under reflux for 20 hr. The reaction mixture was allowed to cool to room temperature, and the solvent was evaporated under reduced pressure. The residue was purified by silica gel column chromatography (solvent; hexane/ethyl acetate=90/20-70/30) to give the title compound (160 mg).

MS (ESI) m/z; 268, 270 [M+H]$^+$

Reference Example 791

6-bromo-2,3-dimethylpyrido[3,2-d]pyrimidin-4(3H)-one

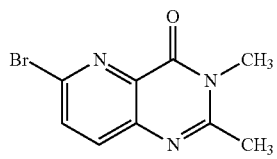

The compound (70 mg) obtained in Reference Example 787 was treated by a method similar to that in Reference Example 790 to give the title compound (60 mg).

MS (ESI) m/z; 254, 256 [M+H]$^+$

Reference Example 792

6-bromo-3-ethyl-2-methylpyrido[3,2-d]pyrimidin-4(3H)-one

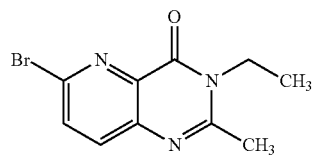

The compound (295 mg) obtained in Reference Example 788 was treated by a method similar to that in Reference Example 790 to give the title compound (200 mg).

MS (ESI) m/z; 268, 270 [M+H]$^+$

Reference Example 793

6-bromo-2-methyl-3-(2,2,2-trifluoroethyl)pyrido[3,2-d]pyrimidin-4(3H)-one

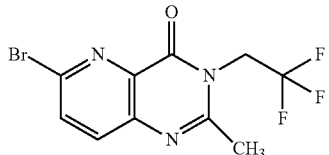

The compound (250 mg) obtained in Reference Example 789 was treated by a method similar to that in Reference Example 790 to give the title compound (162 mg).

MS (ESI) m/z; 322, 324 [M+H]$^+$

Reference Example 794

6-bromo-3-methyl-2-(trifluoromethyl)pyrido[3,2-d]pyrimidin-4(3H)-one

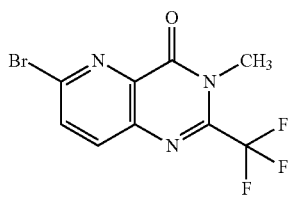 [SMILES: Cn1c(C(F)(F)F)nc2ccc(Br)nc2c1=O]

A mixture of the compound (200 mg) obtained in Reference Example 787, trifluoroacetic anhydride (0.6 mL) and pyridine (0.35 mL) was heated under reflux for 8 hr. The reaction mixture was allowed to cool to room temperature, and the solvent was evaporated under reduced pressure. The residue was purified by silica gel column chromatography (solvent; hexane/ethyl acetate=90/20-70/30) to give the title compound (230 mg).
MS (ESI) m/z; 308, 310 [M+H]$^+$ Reference Example 795

6-bromo-3-ethyl-2-(trifluoromethyl)pyrido[3,2-d]pyrimidin-4(3H)-one

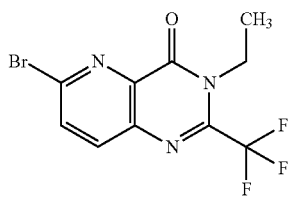

The compound (145 mg) obtained in Reference Example 788 was treated by a method similar to that in Reference Example 794 to give the title compound (210 mg).
MS (ESI) m/z; 322, 324 [M+H]$^+$ Reference Example 796

3-amino-6-bromo-N-(2,4-dimethoxybenzyl)pyridine-2-carboxamide

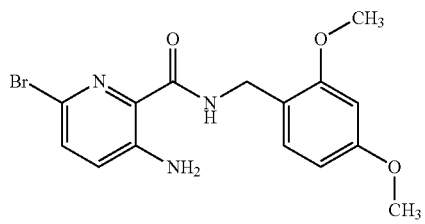 [SMILES: COc1ccc(CNC(=O)c2nc(Br)ccc2N)c(OC)c1]

To a solution (30 mL) of 3-amino-6-bromopyridine-2-carboxylic acid (3.00 g) in DMF were added N,N-diisopropylethylamine (3.6 mL), 2,4-dimethoxybenzylamine (3.50 g), EDC hydrochloride (4.00 g) and HOBt monohydrate (3.20 g), and the reaction mixture was stirred at room temperature overnight. Water was added to the reaction mixture, and the mixture was extracted three times with ethyl acetate. The organic layer was dried over anhydrous magnesium sulfate, filtered and concentrated. The residue was purified by silica gel column chromatography (solvent; hexane/ethyl acetate=70/30-20/80) to give the title compound (5.00 g).
MS (ESI) m/z; 366, 368 [M+H]$^+$ Reference Example 797

6-bromo-N-(2,4-dimethoxybenzyl)-3-[(2-methylpropanoyl)amino]pyridine-2-carboxamide

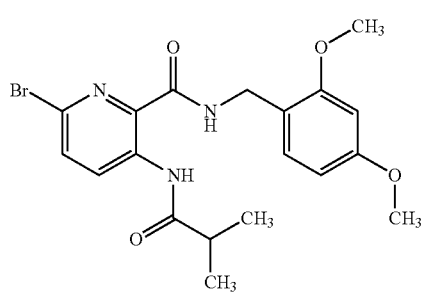 [SMILES: COc1ccc(CNC(=O)c2nc(Br)ccc2NC(=O)C(C)C)c(OC)c1]

To a solution (20 mL) of the compound (1000 mg) obtained in Reference Example 796 in methylene chloride were added triethylamine (760 µL) and isobutyryl chloride (350 mg) at room temperature. The reaction mixture was stirred at room temperature for 4 hr, water was added to the reaction mixture, and the mixture was extracted with chloroform. The combined organic layer was dried over anhydrous magnesium sulfate, filtered and concentrated. To the crude product was added diisopropyl ether, and the solid was collected by filtration, and dried to give the title compound (1140 mg).
MS (ESI) m/z; 436, 438 [M+H]$^+$ Reference Example 798

6-bromo-N-(2,4-dimethoxybenzyl)-3-[(2-fluorobenzoyl)amino]pyridine-2-carboxamide

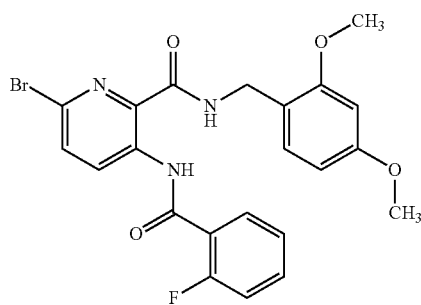 [SMILES: COc1ccc(CNC(=O)c2nc(Br)ccc2NC(=O)c2ccccc2F)c(OC)c1]

The compound (1000 mg) obtained in Reference Example 796 was treated by a method similar to that in Reference Example 797 to give the title compound (1330 mg).
MS (ESI) m/z; 488, 490 [M+H]$^+$

Reference Example 799

6-bromo-3-{[(1-chlorocyclopropyl)carbonyl]amino}-N-(2,4-dimethoxybenzyl)pyridine-2-carboxamide

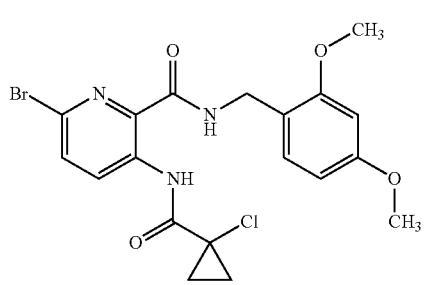 [SMILES: COc1ccc(CNC(=O)c2nc(Br)ccc2NC(=O)C2(Cl)CC2)c(OC)c1]

To a solution (10 mL) of 1-chlorocyclopropanecarboxylic acid (660 mg) in methylene chloride were added oxalyl chloride (470 μL) and DMF (one drop), and the reaction mixture was stirred at room temperature for 2 hr. The reaction mixture was added dropwise to a solution (20 mL) of the compound (1000 mg) obtained in Reference Example 796 and triethylamine (1.60 mL) in methylene chloride under ice-cooling. The reaction mixture was stirred at room temperature overnight, water was added to the reaction mixture, and the mixture was extracted twice with chloroform. The organic layer was dried over anhydrous magnesium sulfate, filtered and concentrated. The residue was purified by silica gel column chromatography (solvent; chloroform) to give the title compound (1280 mg).

MS (ESI) m/z; 468, 470 [M+H]$^+$

Reference Example 800

6-bromo-3-(2,4-dimethoxybenzyl)-2-(propan-2-yl)pyrido[3,2-d]pyrimidin-4 (3H)-one

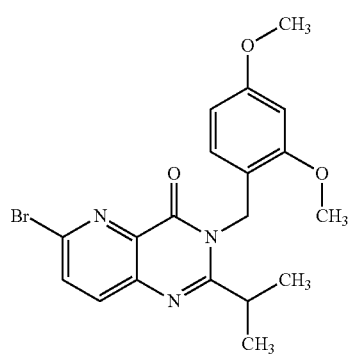 [SMILES: COc1ccc(Cn2c(C(C)C)nc3ccc(Br)nc3c2=O)c(OC)c1]

To a solution (10 mL) of the compound (1.14 g) obtained in Reference Example 797 in methylene chloride were added chlorotrimethylsilane (3.30 mL) and triethylamine (11.0 mL), and the reaction mixture was stirred at room temperature overnight. Water and 1.0 mol/L hydrochloric acid were added to the reaction mixture, and the mixture was extracted twice with chloroform. The organic layer was dried over anhydrous magnesium sulfate, filtered and concentrated. The residue was purified by silica gel column chromatography (solvent; hexane/ethyl acetate=70/30-0/100) to give the title compound (0.80 g).

MS (ESI) m/z; 418, 420 [M+H]$^+$

Reference Example 801

6-bromo-3-(2,4-dimethoxybenzyl)-2-(2-fluorophenyl)pyrido[3,2-d]pyrimidin-4 (3H)-one

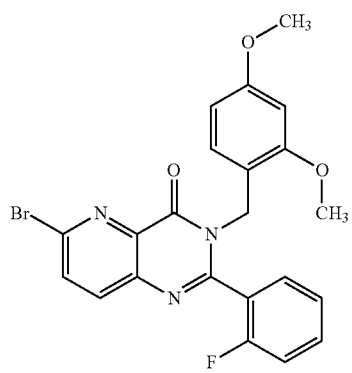 [SMILES: COc1ccc(Cn2c(-c3ccccc3F)nc3ccc(Br)nc3c2=O)c(OC)c1]

The compound (1.33 g) obtained in Reference Example 798 was treated by a method similar to that in Reference Example 800 to give the title compound (1.07 g).

MS (ESI) m/z; 470, 472 [M+H]$^+$

Reference Example 802

6-bromo-2-(1-chlorocyclopropyl)pyrido[3,2-d]pyrimidin-4 (3H)-one

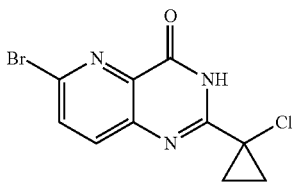 [SMILES: O=c1[nH]c(C2(Cl)CC2)nc2ccc(Br)nc12]

To the compound (1.20 g) obtained in Reference Example 799 was added a mixed solution of triethylsilane (0.70 mL) and trifluoroacetic acid (12.0 mL), and the reaction mixture was stirred at room temperature overnight. The solvent was evaporated under reduced pressure, chloroform was added, and the mixture was washed with saturated aqueous sodium hydrogen carbonate solution. The organic layer was dried over anhydrous magnesium sulfate, filtered and concentrated. To the residue was added diisopropyl ether, and the solid was collected by filtration and dried to give the title compound (570 mg).

MS (ESI) m/z; 300, 302 [M+H]$^+$

Reference Example 803

7-chloro-2-propyl-4H-pyrimido[1,2-b]pyridazin-4-one

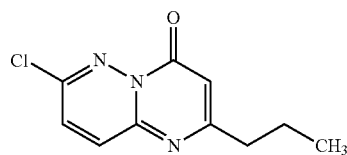

3-Oxo-hexanoic acid ethyl ester (5.90 g) and 3-amino-6-chloropyridazine (4.00 g) were added to polyphosphoric acid (40 g), and the reaction mixture was stirred with heating at 120° C. for 3 hr. After confirmation of the completion of the reaction, the reaction mixture was cooled to room temperature, and water (200 mL) was added. The mixture was extracted twice with chloroform. The organic layer was washed once with water, dried over anhydrous magnesium sulfate, filtered and concentrated. The residue was purified by silica gel column chromatography (solvent; ethyl acetate/methanol=100/0-95/5) and the solvent was evaporated under reduced pressure. To the obtained product was added diisopropyl ether, and the solid was collected by filtration to give the title compound (2.37 g).
MS (ESI) m/z; 224, 226 [M+H]$^+$ Reference Example 804

7-chloro-2-ethyl-4H-pyrimido[1,2-b]pyridazin-4-one

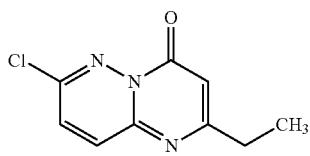

3-Amino-6-chloropyridazine (3.00 g) was treated by a method similar to that in Reference Example 803 to give the title compound (1.62 g).
MS (ESI) m/z; 210, 212 [M+H]$^+$ Reference Example 805

7-chloro-2-(propan-2-yl)-4H-pyrimido[1,2-b]pyridazin-4-one

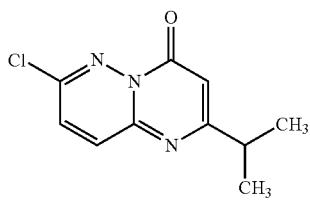

3-Amino-6-chloropyridazine (6.00 g) was treated by a method similar to that in Reference Example 803 to give the title compound (940 mg).
MS (ESI) m/z; 224, 226 [M+H]$^+$ Reference Example 806

7-chloro-2-phenyl-4H-pyrimido[1,2-b]pyridazin-4-one

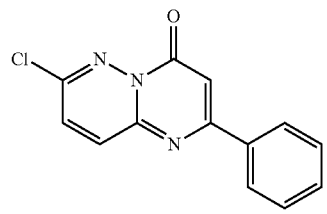 [SMILES: O=c1cc(-c2ccccc2)nc2ccc(Cl)nn12]

3-Amino-6-chloropyridazine (5.00 g) was treated by a method similar to that in Reference Example 803 to give the title compound (900 mg).
MS (ESI) m/z; 258, 260 [M+H]$^+$ Reference Example 807

7-chloro-3-fluoro-2-propyl-4H-pyrimido[1,2-b]pyridazin-4-one

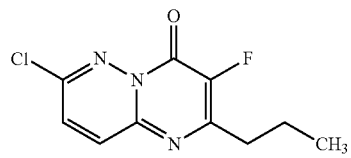 [SMILES: CCCc1nc2ccc(Cl)nn2c(=O)c1F]

To a solution (140 mL) of 3-oxo-hexanoic acid ethyl ester (10.2 g) in acetonitrile was added 1-chloromethyl-4-fluoro-1,4-diazoniabicyclo[2.2.2]octane bistetrafluoroborate (25.0 g) at room temperature, and the reaction mixture was stirred with heating at 100° C. for 6 hr. The reaction mixture was cooled to room temperature, ethyl acetate was added, and the mixture was washed once with water. The organic layer was dried over anhydrous magnesium sulfate, filtered and concentrated. The residue was purified by silica gel column chromatography (solvent; hexane/ethyl acetate=90/10-80/20) to give 2-fluoro-3-oxo-hexanoic acid ethyl ester (8.40 g). A mixture of the obtained 2-fluoro-3-oxo-hexanoic acid ethyl ester (4.1 g), 3-amino-6-chloropyridazine (2.70 g) and polyphosphoric acid (30 g) was stirred with heating at 120° C. for 3 hr. After confirmation of the completion of the reaction, the reaction mixture was cooled to room temperature, and water (200 mL) was added. The precipitated solid was collected by filtration, washed once with water, and dissolved in chloroform. The obtained solution was dried over anhydrous magnesium sulfate, filtered and concentrated. To the obtained product was added diisopropyl ether, and the solid was collected by filtration to give the title compound (1.74 g).
MS (ESI) m/z; 242, 244 [M+H]$^+$

Reference Example 808

7-chloro-2-ethyl-3-fluoro-4H-pyrimido[1,2-b]pyridazin-4-one

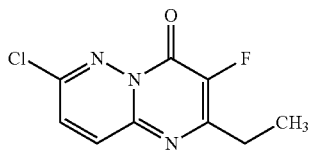

3-Amino-6-chloropyridazine (3.00 g) was treated by a method similar to that in Reference Example 807 to give the title compound (2.08 g).

MS (ESI) m/z; 228, 230 $[M+H]^+$

Pharmacological Experiment

KAT-II Inhibitory Test

Test Compound

The compounds described in the above-mentioned Examples were used for the KAT-II inhibitory test.

Preparation of Human Recombinant KAT-II

Human recombinant KAT-II was prepared as follows.

His tag and maltose binding protein tag were added to the N-terminal of a gene encoding human KAT-II (Genbank accession number: AF481738.1), and the obtained gene was incorporated into pET32 (Merck Nihon Millipore), which is an *Escherichia coli* expression vector. Human recombinant KAT-II produced by BL21(DE3) *Escherichia coli* (Merck Nihon Millipore, 69450) transformed using the plasmid was purified using an amylose resin column (New England Biolabs, #800-21 L).

Test Method

The inhibitory action of the test compound on human recombinant KAT-II was determined by the following method.

To a reaction mixture (45 μL) containing 3.0 μmol/L kynurenine, 10 μmol/L pyridoxal phosphate, 2.0 ng/μL human recombinant KAT-II, and 150 mmol/L tris(hydroxymethyl)aminomethane-acetate buffer (pH 8.0) was added a 10% dimethyl sulfoxide solution (5 μL) of each test compound prepared, and the mixture was reacted at 37° C. for 1 hr. After the reaction, 50% trichloroacetic acid (5 μL) was added to terminate the reaction.

The resultant kynurenic acid was quantified as follows by high performance liquid chromatography. An enzyme reaction mixture was separated by an octadecylsilane reversed-phase column (SC-50DS, Eicom Corporation; mobile phase: 250 mmol/L zinc acetate, 50 mmol/L sodium acetate, and 5.0% acetonitrile (pH 6.2)) incubated at 30° C., and kynurenic acid was quantified using a fluorescence detector (RF-20Axs, Shimadzu Corporation) at excitation wavelength 354 nm, detection wavelength 460 nm. The analytical curve was drawn every time by an external standard method. Each test compound was tested by dual measurement at each concentration. The kynurenic acid level in the presence of a test compound at each concentration was converted into % relative to kynurenic acid resulting from a reaction with an enzyme alone as 100%, and the obtained values were fitted to S-curve to determine $IC_{50}$.

Results

The $IC_{50}$ values of respective test compounds are shown in the following Table 1-Table 3.

TABLE 1

| test compound (Example No.) | KAT-II inhibitory test $IC_{50}$ (μmol/L) |
| --- | --- |
| 8 | 0.61 |
| 9 | 0.25 |
| 11 | 6.2 |
| 12 | 0.13 |
| 13 | 0.56 |
| 14 | 0.057 |
| 15 | 1.1 |
| 17 | 1.6 |
| 19 | 0.043 |
| 28 | 0.025 |
| 32 | 0.40 |
| 36 | 0.018 |
| 63 | 0.015 |
| 65 | 0.025 |
| 67 | 0.014 |
| 69 | 0.040 |
| 74 | 0.084 |
| 80 | 0.0086 |
| 85 | 0.17 |
| 94 | 0.0061 |
| 96 | 0.019 |
| 97 | 0.013 |
| 98 | 0.037 |
| 104 | 0.073 |
| 105 | 0.065 |
| 106 | 0.069 |
| 107 | 0.046 |
| 111 | 0.27 |
| 114 | 0.029 |
| 116 | 0.014 |
| 120 | 0.0047 |
| 131 | 0.11 |
| 132 | 0.051 |
| 133 | 0.15 |
| 134 | 0.23 |
| 135 | 0.023 |
| 137 | 0.069 |
| 138 | 0.39 |
| 140 | 0.077 |
| 142 | 0.98 |
| 143 | 2.2 |
| 144 | 0.72 |
| 145 | 1.5 |
| 146 | 0.14 |
| 148 | 0.23 |
| 149 | 0.16 |
| 153 | 0.048 |
| 155 | 0.32 |
| 157 | 0.47 |
| 158 | 0.17 |
| 160 | 5.2 |
| 166 | 0.19 |
| 167 | 0.090 |
| 168 | 0.41 |
| 170 | 0.88 |
| 171 | 1.8 |
| 172 | 0.84 |
| 175 | 3.7 |
| 176 | 0.52 |
| 178 | 0.012 |
| 183 | 0.032 |
| 190 | 0.026 |
| 191 | 0.031 |
| 194 | 0.076 |

TABLE 2

| test compound (Example No.) | KAT-II inhibitory test $IC_{50}$ (μmol/L) |
| --- | --- |
| 203 | 0.014 |
| 204 | 0.0070 |
| 211 | 0.0073 |
| 213 | 0.016 |

TABLE 2-continued

| test compound (Example No.) | KAT-II inhibitory test IC$_{50}$ (μmol/L) |
|---|---|
| 221 | 0.0048 |
| 227 | 0.072 |
| 229 | 0.021 |
| 233 | 0.12 |
| 236 | 0.24 |
| 238 | 0.016 |
| 244 | 0.011 |
| 251 | 0.040 |
| 252 | 0.019 |
| 253 | 0.089 |
| 254 | 0.011 |
| 258 | 0.18 |
| 259 | 0.0043 |
| 264 | 0.16 |
| 265 | 0.0054 |
| 267 | 0.022 |
| 268 | 0.0088 |
| 273 | 0.0056 |
| 281 | 0.027 |
| 294 | 0.17 |
| 298 | 0.026 |
| 299 | 0.46 |
| 300 | 0.18 |
| 301 | 2.6 |
| 304 | 0.021 |
| 307 | 0.12 |
| 309 | 0.061 |
| 311 | 0.34 |
| 313 | 1.1 |
| 314 | 0.61 |
| 321 | 0.070 |
| 322 | 0.020 |
| 323 | 0.078 |
| 328 | 0.017 |
| 333 | 0.049 |
| 335 | 0.0056 |
| 337 | 0.0044 |
| 339 | 0.0079 |
| 341 | 0.011 |
| 345 | 0.0087 |
| 347 | 0.016 |
| 363 | 0.12 |
| 366 | 0.15 |
| 372 | 0.039 |
| 373 | 0.0080 |
| 376 | 0.014 |
| 396 | 0.076 |
| 406 | 0.37 |
| 411 | 0.015 |
| 414 | 0.043 |
| 482 | 0.0097 |
| 486 | 0.015 |
| 489 | 0.0060 |
| 499 | 0.0071 |
| 500 | 0.041 |
| 501 | 0.017 |
| 524 | 0.0040 |
| 530 | 0.019 |
| 532 | 0.017 |
| 536 | 0.0069 |
| 539 | 0.022 |
| 553 | 0.043 |

TABLE 3

| test compound (Example No.) | KAT-II inhibitory test IC$_{50}$ (μmol/L) |
|---|---|
| 555 | 1.1 |
| 559 | 0.016 |
| 560 | 0.011 |
| 565 | 0.010 |
| 572 | 0.086 |
| 573 | 0.035 |
| 575 | 0.019 |
| 578 | 0.028 |
| 579 | 0.010 |
| 583 | 0.0090 |
| 585 | 0.012 |
| 590 | 0.28 |
| 593 | 0.051 |
| 601 | 0.14 |
| 602 | 0.031 |
| 603 | 0.0049 |
| 605 | 0.0082 |
| 606 | 0.0076 |
| 611 | 0.57 |
| 612 | 0.052 |
| 613 | 0.022 |
| 614 | 0.016 |
| 616 | 0.073 |
| 617 | 0.24 |
| 623 | 0.022 |
| 624 | 0.015 |
| 626 | 0.015 |
| 629 | 0.047 |
| 631 | 0.055 |
| 635 | 0.97 |
| 636 | 1.5 |
| 638 | 0.029 |
| 639 | 0.049 |
| 642 | 0.078 |
| 645 | 1.6 |
| 647 | 0.058 |
| 648 | 0.046 |
| 650 | 2.2 |
| 653 | 0.19 |
| 655 | 0.029 |
| 656 | 0.044 |
| 661 | 3.9 |
| 664 | 0.56 |
| 669 | 7.3 |
| 678 | 0.019 |
| 684 | 11 |
| 685 | 2.2 |
| 686 | 32 |
| 688 | 0.029 |
| 698 | 0.067 |
| 699 | 0.23 |
| 701 | 0.05 |
| 703 | 0.11 |
| 706 | 0.17 |
| 707 | 0.68 |
| 711 | 0.19 |
| 712 | 0.062 |
| 713 | 0.088 |
| 714 | 0.59 |
| 718 | 0.31 |
| 720 | 0.55 |
| 722 | 0.089 |
| 728 | 0.024 |
| — | — |

INDUSTRIAL APPLICABILITY

Compound (I) or a pharmacologically acceptable salt thereof of the present invention shows a KAT-II inhibitory action. Therefore, compound (I) or a pharmacologically acceptable salt thereof of the present invention is useful for the prophylaxis or treatment of various diseases (e.g., schizophrenia) involving KAT-II.

This application is based on a patent application No. 2014-089185 filed in Japan, the contents of which are incorporated in full herein.

The invention claimed is:
1. A compound represented by the formula (I):

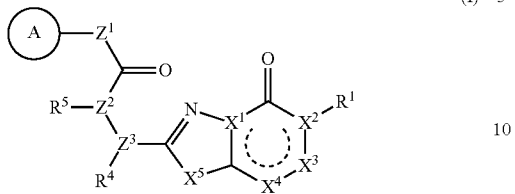
(I)

wherein ring A is an optionally substituted aromatic group,
one of $X^1$ and $X^2$ is a carbon atom, and the other is a nitrogen atom,
$X^3$ is a nitrogen atom, or $CR^2$,
$X^4$ is a nitrogen atom, or $CR^3$,
$X^5$ is a sulfur atom, or —CH=CH—,
$Z^1$ is an oxygen atom, —C($R^6$)($R^7$)—, —NH—, —C($R^6$)($R^7$)—NH—, —NH—C($R^6$)($R^7$)—, —C($R^6$)($R^7$)—O—, or —O—C($R^6$)($R^7$)—, or is a single bond directly linking the adjacent carbonyl group to ring A
one of $Z^2$ and $Z^3$ is CH and the other is a nitrogen atom, or both are nitrogen atoms,
$R^1$ is a hydrogen atom, optionally substituted alkyl, optionally substituted cycloalkyl, optionally substituted aryl, an optionally substituted nonaromatic heterocyclic group, or a halogen atom,
$R^2$ is a hydrogen atom, optionally substituted alkyl, optionally substituted cycloalkyl, optionally substituted amino, optionally substituted aryl, an optionally substituted nonaromatic heterocyclic group, optionally substituted heteroaryl, optionally substituted alkoxy, or optionally substituted cycloalkoxy,
or, $R^1$ and $R^2$ are bonded to each other to form, together with the adjacent $X^2$ and carbon atom, an optionally substituted ring,
$R^3$ is a hydrogen atom, optionally substituted alkyl, optionally substituted cycloalkyl, or a halogen atom,
$R^4$ and $R^5$ are each independently a hydrogen atom, or optionally substituted alkyl,
or, $R^4$ and $R^5$ are bonded to each other to form, together with the adjacent $Z^2$ and $Z^3$, an optionally substituted nitrogen-containing non-aromatic heterocycle,
$R^6$ and $R^7$ are each independently a hydrogen atom, optionally substituted alkyl, or optionally substituted cycloalkyl,
or, $R^6$ and $R^7$ are bonded to each other to form, together with the adjacent carbon atom, an optionally substituted cycloalkane,
a part represented by the following formula in the aforementioned formula (I):

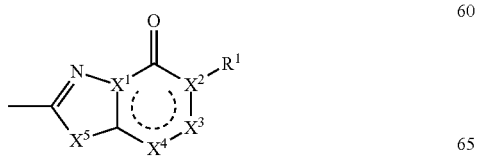

is
(A) when $X^1$ is a carbon atom and $X^2$ is a nitrogen atom, a group represented by the following formula (i-a):

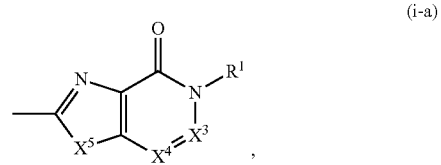
(i-a)

and
(B) when $X^1$ is a nitrogen atom and $X^2$ is a carbon atom, a group represented by the following formula (i-b):

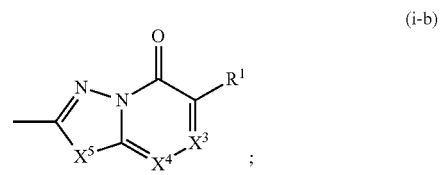
(i-b)

;

provided (a) when a part represented by the following formula in the aforementioned formula (I):

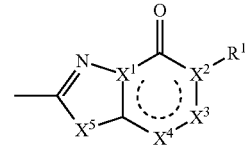

is a group represented by the formula (ii-a):

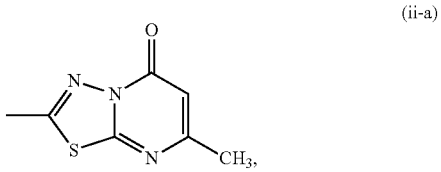
(ii-a)

(a-1) $Z^2$ is a nitrogen atom, and $Z^3$ is CH or a nitrogen atom;
(a-2) $Z^2$ is CH, and $Z^3$ is a nitrogen atom, and a part represented by the following formula in the formula (I):

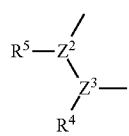

is a group represented by the formula (v-x):

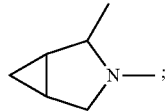
(v-x)

or (a-3) $Z^2$ is CH, and $Z^3$ is a nitrogen atom, and a part represented by the following formula in the formula (I):

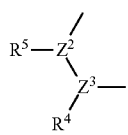

is a group represented by the formula (v-y):

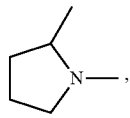
(v-y)

and a part represented by the following formula in the formula (I):

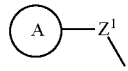

is a group represented by the formula (iii-a), (iii-b), or (iii-c):

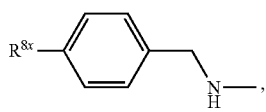
(iii-a)

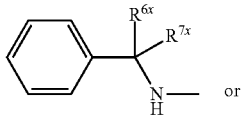
(iii-b)

or

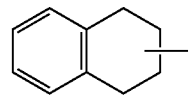
(iii-c)

wherein $R^{6x}$ and $R^{7x}$ are each optionally substituted alkyl or $R^{6x}$ and $R^{7x}$ are bonded to each other to form, together with the adjacent carbon atom, an optionally substituted cycloalkane, $R^{8x}$ is halogenoalkyl, or a fluorine atom, and (b) when a part represented by the following formula in the aforementioned formula (I):

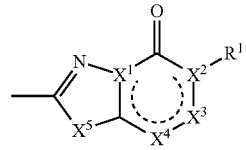

is a group represented by the formula (ii-b):

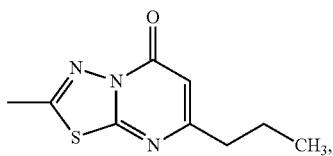
(ii-b)

(b-1) $Z^2$ is a nitrogen atom, and $Z^3$ is CH or a nitrogen atom; or (b-2) $Z^2$ is CH, and $Z^3$ is a nitrogen atom, $R^4$ and $R^5$ are bonded to each other to form, together with the adjacent $Z^2$ and $Z^3$, an optionally substituted nitrogen-containing non-aromatic heterocycle, and a part represented by the following formula in the formula (I):

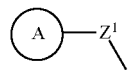

is a group represented by the formula (iii-d):

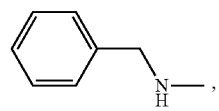
(iii-d)

or a pharmacologically acceptable salt thereof.

2. The compound according to claim 1, wherein, in the formula (I), the part represented by the following formula:

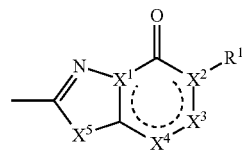

is a group represented by the formula (iv-a), (iv-b), (iv-c), (iv-d), (iv-e), (iv-f), or (iv-g):

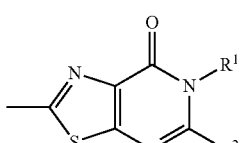
(iv-a)

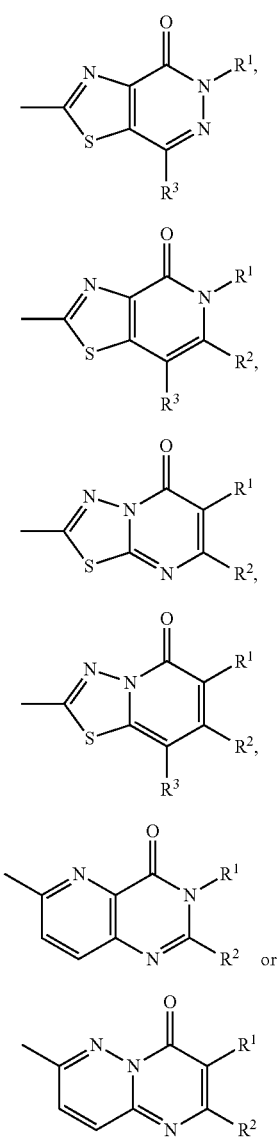

or a pharmacologically acceptable salt thereof.

3. The compound according to claim 2, wherein
ring A is a 5- to 11-membered monocyclic or bicyclic aromatic group optionally containing, besides carbon atom, 1-4 hetero atoms selected from the group consisting of oxygen atom, sulfur atom and nitrogen atom, wherein said aromatic group is optionally substituted by the same or different 1, 2 or 3 groups selected from the group consisting of (1) alkyl optionally substituted by the same or different 1-7 groups selected from the group consisting of amino optionally substituted by 1 or 2 alkyls, alkoxy, and a halogen atom; (2) cyano; (3) amino optionally substituted by 1 or 2 alkyls; (4) alkoxy optionally substituted by 1-7 halogen atoms; and (5) a halogen atom, $R^1$ is (a) a hydrogen atom; (b) alkyl optionally substituted by the same or different 1-7 groups selected from the group consisting of amino (wherein said amino is optionally substituted by the same or different 1 or 2 groups selected from the group consisting of alkyl, halogenoalkyl, and alkoxycarbonyl), hydroxy, alkoxy, a halogen atom, phenyl, alkoxyphenyl, and a 4- to 7-membered monocyclic nonaromatic heterocyclic group containing, besides carbon atom, 1 or 2 hetero atoms selected from the group consisting of oxygen atom, sulfur atom and nitrogen atom, wherein said nonaromatic heterocyclic group is optionally substituted by the same or different 1, 2 or 3 groups selected from the group consisting of alkyl, and alkoxycarbonyl; (c) cycloalkyl optionally substituted by 1, 2 or 3 alkoxyalkyls; (d) a halogen atom; (e) phenyl; or (f) a 4- to 7-membered monocyclic nonaromatic heterocyclic group containing, besides carbon atom, 1 or 2 hetero atoms selected from the group consisting of oxygen atom, sulfur atom and nitrogen atom, wherein said nonaromatic heterocyclic group is optionally substituted by the same or different 1, 2 or 3 groups selected from the group consisting of alkyl, and alkoxycarbonyl, $R^2$ is (a) a hydrogen atom; (b) alkyl optionally substituted by the same or different 1-7 groups selected from the group consisting of alkylidene, cyano, amino (wherein said amino is optionally substituted by the same or different 1 or 2 groups selected from the group consisting of alkyl, alkoxyalkyl, halogenoalkyl, and alkoxycarbonyl), hydroxy, alkoxy, alkylsulfonyloxy, oxo, phenylsulfonyl, a halogen atom, phenyl, 5- to 11-membered monocyclic or bicyclic heteroaryl containing, besides carbon atom, 1-4 hetero atoms selected from the group consisting of oxygen atom, sulfur atom and nitrogen atom, wherein said heteroaryl is optionally substituted by 1 or 2 oxos, and a 4- to 7-membered monocyclic nonaromatic heterocyclic group containing, besides carbon atom, 1 or 2 hetero atoms selected from the group consisting of oxygen atom, sulfur atom and nitrogen atom, wherein said nonaromatic heterocyclic group is optionally substituted by alkoxy; (c) cycloalkyl optionally substituted by the same or different 1, 2 or 3 groups selected from the group consisting of alkyl, alkoxyalkyl, halogenoalkyl, cyano, hydroxy, alkoxy, alkanoyloxy, and a halogen atom; (d) amino optionally substituted by the same or different 1 or 2 groups selected from the group consisting of alkyl and alkoxyphenylalkyl; (e) alkoxy optionally substituted by the same or different 1, 2 or 3 groups selected from the group consisting of amino (wherein said amino is optionally substituted by the same or different 1 or 2 groups selected from the group consisting of alkyl, and alkoxycarbonyl), and a halogen atom; (f) cycloalkoxy optionally substituted by alkyl; (g) phenyl optionally substituted by the same or different 1, 2 or 3 groups selected from the group consisting of alkyl., wherein said alkyl is optionally substituted by the same or different 1, 2 or 3 groups selected from the group consisting of alkylamino, dialkylamino, hydroxy, and a halogen atom, alkoxy optionally substituted by 1, 2 or 3 halogen atoms, alkylsulfonyl, and a halogen atom; (h) 5- to 6-membered monocyclic heteroaryl containing, besides carbon atom, 1-4 hetero atoms selected from the group consisting of oxygen atom, sulfur atom and nitrogen atom, wherein said heteroaryl is optionally substituted by the same or different 1, 2 or 3 groups selected from the group consisting of alkyl, alkoxy, and a halogen atom; or (i) a 4- to 7-membered monocyclic nonaromatic heterocyclic group containing, besides carbon atom, 1 or 2 hetero atoms selected from the group consisting of oxygen atom, sulfur atom and nitrogen atom, wherein said nonaromatic heterocyclic group is optionally substituted by the same or different 1, 2 or 3 groups selected from the group consisting of alkyl, halogenoalkyl, and alkoxy, or, $R^1$ and $R^2$ are bonded to each other to form, together with the adjacent $X^2$ and carbon atom, a ring selected from the group consisting of 4- to 7-membered ($C_4$-$C_7$) cycloalkene, benzene, a 4- to 7-membered monocyclic non-aromatic heterocycle containing, besides carbon atom, 1 or 2 hetero atoms selected from the group consisting of oxygen atom, sulfur atom and nitrogen atom, and 5- to 6-membered monocyclic heteroarene containing, besides carbon atom, 1-4 hetero atoms selected from the group consisting of oxygen atom, sulfur atom and nitrogen atom, wherein said ring is optionally substituted by the same or different 1, 2 or 3 groups selected from the group consisting of alkyl, halogenoalkyl, alkoxycarbonyl, and a halogen atom, $R^3$ is (a) a hydrogen atom; (b) alkyl optionally substituted by 1, 2 or 3 halogen atoms; (c) cycloalkyl; or (d) a halogen atom, $R^4$ and $R^5$ are each independently a hydrogen atom, or alkyl, or, $R^4$ and $R^5$ are bonded to each other to form, together with the adjacent $Z^2$ and $Z^3$, 4- to 12-membered monocyclic or bicyclic nitrogen-containing non-aromatic heterocycle containing, besides carbon atom, at least one nitrogen atom and 1-4 hetero atoms selected from the group consisting of oxygen atom, sulfur atom and nitrogen atom, wherein said nitrogen-containing non-aromatic heterocycle is optionally substituted by the same or different 1, 2 or 3 groups selected from the group consisting of amino optionally substituted by a group selected from the group consisting of alkoxycarbonyl and phenylalkoxycarbonyl, and a halogen atom, and $R^6$ and $R^7$ are each independently (a) a hydrogen atom; (b) alkyl optionally substituted by the same or different 1, 2 or 3 groups selected from the group consisting of alkoxy, and a halogen atom; or (c) cycloalkyl, or, $R^6$ and $R^7$ are bonded to each other to form, together with the adjacent carbon atom, cycloalkane, or a pharmacologically acceptable salt thereof.

4. The compound according to claim 3, wherein, in the formula (I), the part represented by the following formula:

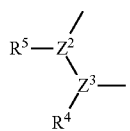

is a group represented by the formula (v):

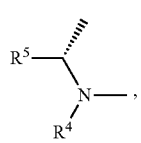

or a pharmacologically acceptable salt thereof.

5. The compound according to claim 4, wherein $Z^1$ is —C($R^6$)($R^7$)—NH—, or a pharmacologically acceptable salt thereof.

6. The compound according to claim 3, wherein, in the formula (I), the part represented by the following formula:

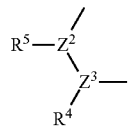

is a group represented by the formula (vi):

or a pharmacologically acceptable salt thereof.

7. The compound according to claim 6, wherein $R^4$ and $R^5$ are bonded to each other to form, together with the adjacent nitrogen atom and carbon atom, pyrrolidine, or a pharmacologically acceptable salt thereof.

8. The compound according to claim 5, wherein, in the formula (I), the part represented by the following formula:

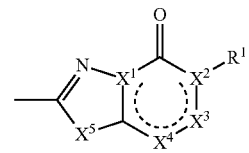

is a group represented by the following formula (iv-a), (iv-b), (iv-c), (iv-d), or (iv-e):

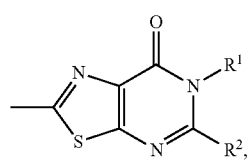

(iv-a)

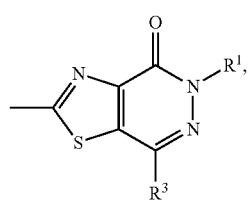

(iv-b)

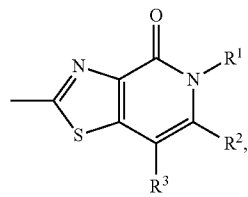

(iv-c)

-continued

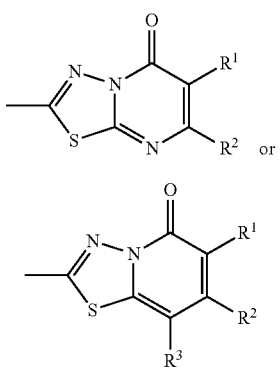

or a pharmacologically acceptable salt thereof.

9. The compound according to claim 8, wherein the part represented by the following formula:

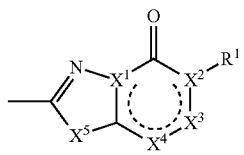

is a group represented by the formula (iv-a), (iv-c), or (iv-d), or a pharmacologically acceptable salt thereof.

10. The compound according to claim 8, wherein the part represented by the following formula:

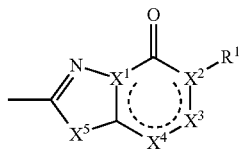

is a group represented by the formula (iv-a), or a pharmacologically acceptable salt thereof.

11. The compound according to claim 1, wherein, in the formula (I), the part represented by the following formula:

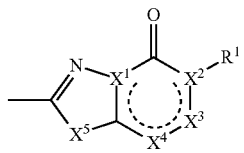

is a cyclic group represented by the following formula:

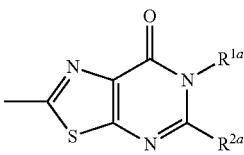

wherein
$R^{1a}$ is (a) a hydrogen atom; (b) alkyl optionally substituted by 1-7 groups selected from the group consisting of amino (wherein said amino is optionally substituted by 1 or 2 groups selected from the group consisting of alkyl, halogenoalkyl, and alkoxycarbonyl), hydroxy, alkoxy, a halogen atom, phenyl, alkoxyphenyl, and a 4- to 7-membered monocyclic nonaromatic heterocyclic group containing, besides carbon atom, 1 or 2 hetero atoms selected from the group consisting of oxygen atom and nitrogen atom, wherein said nonaromatic heterocyclic group is optionally substituted by 1, 2 or 3 groups selected from the group consisting of alkyl, and alkoxycarbonyl (c) cycloalkyl; (d) phenyl; or (e) a 4- to 7-membered monocyclic nonaromatic heterocyclic group containing, besides carbon atom, 1 or 2 hetero atoms selected from the group consisting of oxygen atom and nitrogen atom, wherein said nonaromatic heterocyclic group is optionally substituted by 1, 2 or 3 groups selected from the group consisting of alkyl, and alkoxycarbonyl, $R^{2a}$ is (a) a hydrogen atom; (b) alkyl optionally substituted by 1-7 groups selected from the group consisting of cyano, amino (wherein said amino is optionally substituted by 1 or 2 groups selected from the group consisting of alkyl, alkoxyalkyl, halogenoalkyl, and alkoxycarbonyl), hydroxy, alkoxy, alkylsulfonyloxy, oxo, phenylsulfonyl, a halogen atom, phenyl, pyridyl, isoindolyl optionally substituted by 1 or 2 oxos, and a 4- to 7-membered monocyclic nonaromatic heterocyclic group containing, besides carbon atom, 1 or 2 hetero atoms selected from the group consisting of oxygen atom, and nitrogen atom, wherein said nonaromatic heterocyclic group is optionally substituted by alkoxy; (c) cycloalkyl optionally substituted by 1, 2 or 3 groups selected from the group consisting of alkyl, alkoxyalkyl, halogenoalkyl, cyano, hydroxy, alkoxy, alkanoyloxy, and a halogen atom; (d) amino optionally substituted by 1 or 2 groups selected from the group consisting of alkyl and alkoxyphenyl; (e) alkoxy optionally substituted by 1, 2 or 3 groups selected from the group consisting of amino (wherein said amino is optionally substituted by 1 or 2 groups selected from the group consisting of alkyl, and alkoxycarbonyl), and a halogen atom; (f) cycloalkoxy optionally substituted by alkyl; (g) phenyl optionally substituted by 1, 2 or 3 groups selected from the group consisting of alkyl, wherein said alkyl is optionally substituted by 1, 2 or 3 groups selected from the group consisting of alkylamino, dialkylamino, hydroxy, and a halogen atom, alkoxy optionally substituted by 1, 2 or 3 halogen atoms, alkylsulfonyl, and a halogen atom; (h) 5- to 6-membered monocyclic heteroaryl containing, besides carbon atom, 1, 2 or 3 hetero atoms selected from the group consisting of oxygen atom, sulfur atom and nitrogen atom, wherein said heteroaryl is optionally substituted by 1, 2 or 3 groups selected from the group consisting of alkyl, alkoxy, and a halogen atom; or (i) a 4- to 7-membered monocyclic nonaromatic heterocyclic group containing, besides carbon atom, 1 or 2 hetero atoms selected from the group consisting of oxygen atom, and nitrogen atom, wherein said nonaromatic heterocyclic group is optionally substituted by 1, 2 or 3 groups selected from the group consisting of alkyl, halogenoalkyl, and alkoxy, or $R^{1a}$ and $R^{2a}$ are bonded to each other to form, together with the adjacent nitrogen atom and carbon atom, (a) a 4- to 7-membered monocyclic nitrogen-containing non-aromatic heterocycle containing 1 or 2 nitrogen atoms besides carbon atom, wherein said nitrogen-containing non-aromatic heterocycle is optionally substituted by 1, 2 or 3 groups selected from the group consisting of alkyl, halogenoalkyl, alkoxycarbonyl, and a halogen atom; or (b) 5- to 6-membered monocyclic nitrogen-containing heteroarene containing, besides carbon atom, at least one nitrogen atom and 1 or 2 hetero atoms selected from the group consisting of sulfur atom and nitrogen atom, wherein said nitrogen-containing heteroarene is optionally substituted by 1, 2 or 3 groups selected from the group consisting of alkyl, halogenoalkyl, alkoxycarbonyl, and a halogen atom, and the part represented by the following formula:

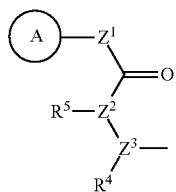

is a group represented by the following formula:

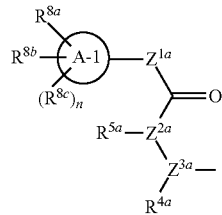

wherein ring A-1 is $C_6$-$C_{11}$ monocyclic or bicyclic aryl, or 5- to 11-membered monocyclic or bicyclic heteroaryl containing, besides carbon atom, 1, 2 or 3 hetero atoms selected from the group consisting of oxygen atom, sulfur atom and nitrogen atom, $Z^{1a}$ is an oxygen atom, —C($R^{6a}$)($R^{7a}$)—, —NH—, —C($R^{6a}$)($R^{7a}$)—, —NH—, —NH——C($R^{6a}$)($R^{7a}$)—, —C($R^{6a}$)($R^{7a}$)—O—, or —O—C($R^{6a}$)($R^{7a}$)—, or is a single bond directly linking the adjacent carbonyl group to ring A, (a) one of $Z^{2a}$ and $Z^{3a}$ is CH and the other is a nitrogen atom, or (b) both of them are nitrogen atoms, $R^{4a}$ and $R^{5a}$ are each independently a hydrogen atom, or alkyl, or, $R^{4a}$ and $R^{5a}$ are bonded to each other to form, together with the adjacent $Z^{2a}$ and $Z^{3a}$, 4- to 7-membered monocyclic nitrogen-containing non-aromatic heterocycle containing, besides carbon atom, at least one nitrogen atom and 1 or 2 hetero atoms selected from the group consisting of oxygen atom, and nitrogen atom, wherein said nitrogen-containing non-aromatic heterocycle is optionally substituted by 1, 2 or 3 groups selected from the group consisting of amino optionally substituted by a group selected from the group consisting of alkoxycarbonyl and phenylalkoxycarbonyl, and a halogen atom, and $R^{6a}$ and $R^{7a}$ are each independently (a) a hydrogen atom; (b) alkyl optionally substituted by 1, 2 or 3 groups selected from the group consisting of alkoxy, and a halogen atom; or (c) cycloalkyl, or $R^{6a}$ and $R^{7a}$ are bonded to each other to form, together with the adjacent carbon atom, cycloalkane, $R^{8a}$, $R^{8b}$ and $R^{8c}$ are each independently (a) a hydrogen atom; (b) alkyl optionally substituted by 1, 2 or 3 groups selected from the group consisting of alkylamino, dialkylamino, alkoxy, and a halogen atom; (c) cyano; (d) amino optionally substituted by 1 or 2 alkyls; (e) alkoxy optionally substituted by 1-7 halogen atoms; or (f) a halogen atom, and n is 0 or 1, or a pharmacologically acceptable salt thereof.

12. The compound according to claim 11, wherein $Z^{2a}$ is CH, and $Z^{3a}$ is a nitrogen atom, or a pharmacologically acceptable salt thereof.

13. The compound according to claim 11, wherein $Z^{2a}$ is a nitrogen atom, and $Z^{3a}$ is CH, or a pharmacologically acceptable salt thereof.

14. The compound according to claim 12, wherein ring A-1 is phenyl, indanyl, tetrahydronaphthyl, furyl, thienyl, pyrazolyl, isoxazolyl, thiazolyl, dihydrobenzofuranyl, benzodioxolanyl, or tetrahydroquinolyl, $Z^{1a}$ is an oxygen atom, —C($R^{6a}$)($R^{7a}$)—, —NH—, —C($R^{6a}$)($R^{7a}$)—, —NH—, —NH—C($R^{6a}$)($R^{7a}$)—, —C($R^{6a}$)($R^{7a}$)—O—, or —O—C($R^{6a}$)($R^{7a}$)—, $R^{1a}$ is (a) a hydrogen atom; (b) alkyl optionally substituted by 1-7 groups selected from the group consisting of amino (wherein said amino is optionally substituted by 1 or 2 groups selected from the group consisting of alkyl, halogenoalkyl, and alkoxycarbonyl), hydroxy, alkoxy, a halogen atom, phenyl, alkoxyphenyl, and a nonaromatic heterocyclic group selected from the group consisting of pyrrolidyl, piperidyl, oxetanyl, and tetrahydropyranyl, wherein said nonaromatic heterocyclic group is optionally substituted by 1, 2 or 3 groups selected from the group consisting of alkyl, and alkoxycarbonyl; (c) cycloalkyl; (d) phenyl; or (e) a nonaromatic heterocyclic group selected from the group consisting of pyrrolidyl, piperidyl, morpholinyl, oxetanyl, tetrahydrofuranyl, and tetrahydropyranyl, wherein said nonaromatic heterocyclic group is optionally substituted by 1, 2 or 3 groups selected from the group consisting of alkyl, and alkoxycarbonyl, $R^{2a}$ is (a) a hydrogen atom; (b) alkyl optionally substituted by 1-7 groups selected from the group consisting of cyano, amino (wherein said amino is optionally substituted by 1 or 2 groups selected from the group consisting of alkyl, alkoxyalkyl, halogenoalkyl, and alkoxycarbonyl), hydroxy, alkoxy, alkylsulfonyloxy, oxo, phenylsulfonyl, a halogen atom, phenyl, pyridyl, isoindolyl optionally substituted by 1 or 2 oxos, and a monocyclic nonaromatic heterocyclic group selected from the group consisting of azetidinyl, pyrrolidyl, piperidyl, and morpholinyl, wherein said nonaromatic heterocyclic group is optionally substituted by alkoxy; (c) cycloalkyl optionally substituted by 1, 2 or 3 groups selected from the group consisting of alkyl, alkoxyalkyl, halogenoalkyl, cyano, hydroxy, alkoxy, and a halogen atom; (d) amino optionally substituted by 1 or 2 groups selected from the group consisting of alkyl and alkoxyphenyl; (e) alkoxy optionally substituted by 1, 2 or 3 groups selected from the group consisting of amino (wherein said amino is optionally substituted by 1 or 2 groups selected from the group consisting of alkyl, and alkoxycarbonyl), and a halogen atom; (f) cycloalkoxy optionally substituted by alkyl; (g) phenyl optionally substituted by 1, 2 or 3 groups selected from the group consisting of alkyl, wherein said alkyl is optionally substituted by 1, 2 or 3 groups selected from the group consisting of alkylamino, dialkylamino, hydroxy, and a halogen atom, alkoxy optionally substituted by 1, 2 or 3 halogen atoms, alkylsulfonyl, and a halogen atom; (h) heteroaryl selected from the group consisting of thienyl, pyrazolyl, oxadiazolyl, pyridyl, and pyrimidinyl, wherein said heteroaryl is optionally substituted by 1, 2 or 3 groups selected from the group consisting of alkyl, alkoxy, and a halogen atom; or (i) a nonaromatic heterocyclic group selected from the group consisting of azetidinyl, pyrrolidyl, piperidyl, tetrahydrofuryl, tetrahydropyranyl, piperazinyl, and morpholinyl, wherein said nonaromatic heterocyclic group is optionally substituted by 1, 2 or 3 groups selected from the group consisting of alkyl, halogenoalkyl, and alkoxy, Or $R^{1a}$ and $R^{2a}$ are bonded to each other to form, together with the adjacent nitrogen atom and carbon atom, a nitrogen-containing non-aromatic heterocycle selected from the group consisting of pyrrolidine, piperidine, dihydroimidazole, imidazolidine, and piperazine, wherein said nitrogen-containing non-aromatic heterocycle is optionally substituted by 1, 1, 2 or 3 groups selected from the group consisting of alkyl, halogenoalkyl, alkoxycarbonyl, and a halogen atom, $R^{4a}$ and $R^{5a}$ are each alkyl, or $R^{4a}$ and $R^{5a}$ are bonded to each other to form, together with the adjacent $Z^{2a}$ and $Z^{3a}$, a nitrogen-containing non-aromatic heterocycle selected from the group consisting of azetidine, pyrrolidine, and piperidine, wherein said nitrogen-containing non-aromatic heterocycle is optionally substituted by 1, 2 or 3 groups selected from the group consisting of amino optionally substituted by one group selected from the group consisting of alkoxycarbonyl and phenylalkoxycarbonyl, and a halogen atom, $R^{6a}$ and $R^{7a}$ are each independently a hydrogen atom, or alkyl, $R^{8a}$, $R^{8b}$, $R^{8c}$ are each independently (a) a hydrogen atom; (b) alkyl optionally substituted by one group selected from the group consisting of dialkylamino, and alkoxy; (c) cyano; (d) amino optionally substituted by 1 or 2 alkyls; (e) alkoxy; or (f) a halogen atom, and n is 1, or a pharmacologically acceptable salt thereof.

15. The compound according to claim 11, wherein the part represented by the following formula:

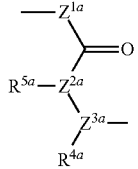

is a group represented by the following formula:

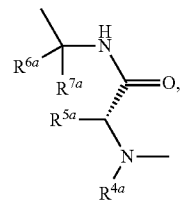

or a pharmacologically acceptable salt thereof.

16. The compound according to claim 15, wherein $R^{4a}$ and $R^{5a}$ are bonded to each other to form, together with the adjacent nitrogen atom and carbon atom, pyrrolidine, and $R^{6a}$ and $R^{7a}$ are each a hydrogen atom, or a pharmacologically acceptable salt thereof.

17. The compound according to claim 15, wherein $R^{4a}$ is $C_1$-$C_6$ alkyl, $R^{5a}$ is $C_1$-$C_6$ alkyl, and $R^{6a}$ and $R^{7a}$ are each a hydrogen atom, or a pharmacologically acceptable salt thereof.

18. The compound according to claim 11, wherein the part represented by the following formula:

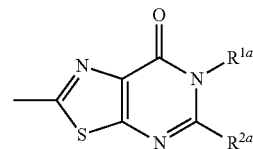

is a cyclic group represented by the formula:

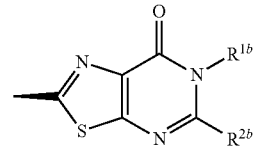

wherein $R^{1b}$ is (a) a hydrogen atom; (b) alkyl optionally substituted by 1-7 groups selected from the group consisting of amino (wherein said amino is optionally substituted by 1 or 2 groups selected from the group consisting of alkyl, halogenoalkyl, and alkoxycarbonyl), hydroxy, alkoxy, a halogen atom, phenyl, alkoxyphenyl, and a 4- to 7-membered monocyclic nonaromatic heterocyclic group containing, besides carbon atom, 1 or 2 hetero atoms selected from the group consisting of oxygen atom and nitrogen atom, said nonaromatic heterocyclic group is optionally substituted by 1, 2 or 3 groups selected from the group consisting of alkyl, and alkoxycarbonyl; (c) cycloalkyl; (d) phenyl; or (e) a 4- to 7-membered monocyclic nonaromatic heterocyclic group containing, besides carbon atom, 1 or 2 hetero atoms selected from the group consisting of oxygen atom and nitrogen atom, wherein said nonaromatic heterocyclic group is optionally substituted by 1, 2 or 3 groups selected from the group consisting of alkyl, and alkoxycarbonyl, $R^{2b}$ is (a) a hydrogen atom; (b) alkyl optionally substituted by 1-7 groups selected from the group consisting of cyano, amino (wherein said amino is optionally substituted by 1 or 2 groups selected from the group consisting of alkyl, alkoxyalkyl, halogenoalkyl, and alkoxycarbonyl), hydroxy, alkoxy, alkylsulfonyloxy, oxo, phenylsulfonyl, a halogen atom, phenyl, pyridyl, isoindolyl optionally substituted by 1 or 2 oxos, and a 4- to 7-membered monocyclic nonaromatic heterocyclic group containing, besides carbon atom, 1 or 2 hetero atoms selected from the group consisting of oxygen atom, and nitrogen atom, wherein said nonaromatic heterocyclic group is optionally substituted by alkoxy; (c) cycloalkyl optionally substituted by 1, 2 or 3 groups selected from the group consisting of alkyl, alkoxyalkyl, halogenoalkyl, cyano, hydroxy, alkoxy, alkanoyloxy, and a halogen atom; (d) amino optionally substituted by 1 or 2 groups selected from the group consisting of alkyl and alkoxyphenyl; (e) alkoxy optionally substituted by 1, 2 or 3 groups selected from the group consisting of amino (wherein said amino is optionally substituted by 1 or 2 groups selected from the group consisting of alkyl, and alkoxycarbonyl), and a halogen atom; (f) cycloalkoxy optionally substituted by alkyl; (g) phenyl optionally substituted by 1, 2 or 3 groups selected from the group consisting of alkyl, wherein said alkyl is optionally substituted by 1, 2 or 3 groups selected from the group consisting of alkylamino, dialkylamino, hydroxy, and a halogen atom, alkoxy optionally substituted by 1, 2 or 3 halogen atoms, alkylsulfonyl, and a halogen atom; (h) 5- to 6-membered monocyclic heteroaryl containing, besides carbon atom, 1, 2 or 3 hetero atoms selected from the group consisting of oxygen atom, sulfur atom and nitrogen atom, wherein said heteroaryl is optionally substituted by 1, 2 or 3 groups selected from the group consisting of alkyl, alkoxy, and a halogen atom; or (i) a 4- to 7-membered monocyclic nonaromatic heterocyclic group containing, besides carbon atom, 1 or 2 hetero atoms selected from the group consisting of oxygen atom, and nitrogen atom, wherein said nonaromatic heterocyclic group is optionally substituted by 1, 2 or 3 groups selected from the group consisting of alkyl, halogenoalkyl, and alkoxy, and the part represented by the following formula:

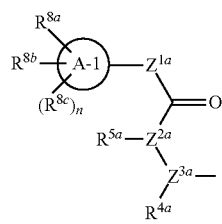

is a group represented by the following formula:

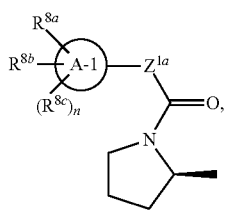

or a pharmacologically acceptable salt thereof.

19. The compound according to claim 18, wherein
ring A-1 is phenyl,
$Z^{1a}$ is an oxygen atom,
$R^{1b}$ is (a) a hydrogen atom; (b) alkyl optionally substituted by phenyl, wherein said phenyl is optionally substituted by 1, 2 or 3 alkoxys; or (c) tetrahydropyranyl,
$R^{2b}$ is (a) alkyl optionally substituted by 1, 2 or 3 groups selected from the group consisting of cyano, a halogen atom, and morpholinyl; (b) cycloalkyl optionally substituted by 1, 2 or 3 groups selected from the group consisting of alkyl, alkoxyalkyl, halogenoalkyl, cyano, alkoxy, and a halogen atom; (c) amino optionally substituted by 1 or 2 alkyls; (d) alkoxy optionally substituted by 1, 2 or 3 halogen atoms; (e) cycloalkoxy optionally substituted by alkyl; (f) phenyl optionally substituted by 1, 2 or 3 groups selected from the group consisting of alkyl, alkoxy optionally substituted by 1, 2 or 3 halogen atoms, and a halogen atom; (g) oxadiazolyl optionally substituted by alkyl; or (i) a nonaromatic heterocyclic group selected from the group consisting of piperidyl, oxetanyl, and tetrahydropyranyl, wherein said nonaromatic heterocyclic group is optionally substituted by 1, 2 or 3 alkyls,
$R^{8a}$, $R^{8b}$ and $R^{8c}$ are each independently a hydrogen atom, alkyl optionally substituted by 1, 2 or 3 halogen atoms, alkoxy optionally substituted by 1, 2 or 3 halogen atoms, or a halogen atom, and
n is 1,
or a pharmacologically acceptable salt thereof.

20. A compound selected from the group consisting of
(R)-2-[6-methyl-5-(3-methyl-[1,2,4]oxadiazol-5-yl)-7-oxo-6,7-dihydro[1,3]thiazolo[5,4-d]pyrimidin-2-yl] pyrrolidine-1-carboxylic acid phenyl ester;
(R)-2-(5-ethyl-6-methyl-7-oxo-6,7-dihydro[1,3]thiazolo [5,4-d]pyrimidin-2-yl)pyrrolidine-1-carboxylic acid phenyl ester;
(R)-2-[7-oxo-5-(propan-2-yl)-6,7-dihydro[1,3]thiazolo[5, 4-d]pyrimidin-2-yl]pyrrolidine-1-carboxylic acid phenyl ester;
(R)-2-(5-ethyl-7-oxo-6,7-dihydro[1,3]thiazolo[5,4-d]pyrimidin-2-yl)pyrrolidine-1-carboxylic acid phenyl ester;
(R)-2-[5-(3-methyl-[1,2,4]oxadiazol-5-yl)-7-oxo-6,7-dihydro[1,3]thiazolo[5,4-d]pyrimidin-2-yl]pyrrolidine-1-carboxylic acid phenyl ester; and
(R)-2-(6-methyl-7-oxo-5-(propan-2-yl)-6,7-dihydro[1,3] thiazolo[5,4-d]pyrimidin-2-yl)pyrrolidine-1-carboxylic acid phenyl ester, or a pharmacologically acceptable salt thereof.

21. A compound selected from the group consisting of
(R)-N-benzyl-1-(6-methyl-7-oxo-5-phenyl-6,7-dihydro [1,3]thiazolo[5,4-d]pyrimidin-2-yl)pyrrolidine-2-carboxamide;
(R)-N-benzyl-1-(6-methyl-7-oxo-5-trifluoromethyl-6,7-dihydro-[1,3]thiazolo[5,4-d]pyrimidin-2-yl)pyrrolidine-2-carboxamide;
(R)-N-benzyl-1-[5-(2,6-difluorophenyl)-6-methyl-7-oxo-6,7-dihydro[1,3]thiazolo[5,4-d]pyrimidin-2-yl]pyrrolidine-2-carboxamide;
(R)-N-benzyl-1-[6-methyl-5-(3-methyl-1,2,4-oxadiazol-5-yl)-7-oxo-6,7-dihydro[1,3]thiazolo[5,4-d]pyrimidin-2-yl]pyrrolidine-2-carboxamide;
(R)-N-benzyl-1-[7-oxo-6-(tetrahydro-2H-pyran-4-yl)-5-trifluoromethyl-6,7-dihydro-[1,3]thiazolo[5,4-d]pyrimidin-2-yl]pyrrolidine-2-carboxamide;

(R)-N-benzyl-1-[5-(1-fluorocyclopropyl)-6-methyl-7-oxo-6,7-dihydro[1,3]thiazolo[5,4-d]pyrimidin-2-yl]pyrrolidine-2-carboxamide;

(R)-N-benzyl-1-(5-difluoromethyl-6-methyl-7-oxo-6,7-dihydro-[1,3]thiazolo[5,4-d]pyrimidin-2-yl)pyrrolidine-2-carboxamide;

(R)-N-benzyl-1-[6-methyl-7-oxo-5-(piperidin-1-yl)-6,7-dihydro[1,3]thiazolo[5,4-d]pyrimidin-2-yl]pyrrolidine-2-carboxamide;

(R)-N-benzyl-1-[5-(2-fluorophenyl)-6-methyl-7-oxo-6,7-dihydro[1,3]thiazolo[5,4-d]pyrimidin-2-yl]pyrrolidine-2-carboxamide;

(R)-N-benzyl-1-[5-(2-fluoropropan-2-yl)-7-oxo-6,7-dihydro[1,3]thiazolo[5,4-d]pyrimidin-2-yl]pyrrolidine-2-carboxamide;

(R)-N-benzyl-1-[5-(2-fluorophenyl)-7-oxo-6,7-dihydro[1,3]thiazolo[5,4-d]pyrimidin-2-yl]pyrrolidine-2-carboxamide;

(R)-N-benzyl-1-(7-oxo-5-trifluoromethyl-6,7-dihydro[1,3]thiazolo[5,4-d]pyrimidin-2-yl)pyrrolidine-2-carboxamide;

(R)-N-benzyl-1-(5-difluoromethyl-7-oxo-6,7-dihydro[1,3]thiazolo[5,4-d]pyrimidin-2-yl)pyrrolidine-2-carboxamide;

(R)-N-benzyl-1-[5-(2,6-difluorophenyl)-7-oxo-6,7-dihydro[1,3]thiazolo[5,4-d]pyrimidin-2-yl]pyrrolidine-2-carboxamide;

(R)-N-benzyl-1-[5-(3-methyl-[1,2,4]oxadiazol-5-yl)-7-oxo-6,7-dihydro[1,3]thiazolo[5,4-d]pyrimidin-2-yl]pyrrolidine-2-carboxamide;

(R)-N-benzyl-1-[5-(2-hydroxypropan-2-yl)-7-oxo-6,7-dihydro[1,3]thiazolo[5,4-d]pyrimidin-2-yl]pyrrolidine-2-carboxamide; and (R)-N-benzyl-1-[7-oxo-5-(piperidin-1-yl)-6,7-dihydro[1,3]thiazolo[5,4-d]pyrimidin-2-yl]pyrrolidine-2-carboxamide, or a pharmacologically acceptable salt thereof.

22. A pharmaceutical composition comprising a compound represented by the formula (I):

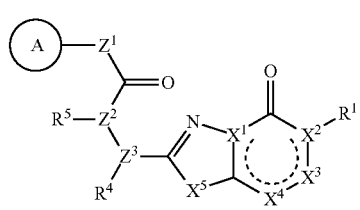

(I)

wherein ring A is an optionally substituted aromatic group,
one of $X^1$ and $X^2$ is a carbon atom, and the other is a nitrogen atom,
$X^3$ is a nitrogen atom, or $CR^2$,
$X^4$ is a nitrogen atom, or $CR^3$,
$X^5$ is a sulfur atom, or —CH=CH—,
$Z^1$ is an oxygen atom, —C($R^6$)($R^7$)—, —NH—, —C($R^6$)($R^7$)—NH—, —NH—C($R^6$)($R^7$)—, —C($R^6$)($R^7$)—O—, or —O—C($R^6$)($R^7$)—, or is a single bond directly linking the adjacent carbonyl group to ring A,
one of $Z^2$ and $Z^3$ is CH and the other is a nitrogen atom, or both are nitrogen atoms,
$R^1$ is a hydrogen atom, optionally substituted alkyl, optionally substituted cycloalkyl, optionally substituted aryl, an optionally substituted nonaromatic heterocyclic group, or a halogen atom, $R^2$ is a hydrogen atom, optionally substituted alkyl, optionally substituted cycloalkyl, optionally substituted amino, optionally substituted aryl, an optionally substituted nonaromatic heterocyclic group, optionally substituted heteroaryl, optionally substituted alkoxy, or optionally substituted cycloalkoxy, or, $R^1$ and $R^2$ are bonded to each other to form, together with the adjacent $X^2$ and carbon atom, an optionally substituted ring, $R^3$ is a hydrogen atom, optionally substituted alkyl, optionally substituted cycloalkyl, or a halogen atom, $R^4$ and $R^5$ are each independently a hydrogen atom, or optionally substituted alkyl, or, $R^4$ and $R^5$ are bonded to each other to form, together with the adjacent $Z^2$ and $Z^3$, an optionally substituted nitrogen-containing non-aromatic heterocycle, $R^6$ and $R^7$ are each independently a hydrogen atom, optionally substituted alkyl, or optionally substituted cycloalkyl, or, $R^6$ and $R^7$ are bonded to each other to form, together with the adjacent carbon atom, an optionally substituted cycloalkane, a part represented by the following formula in the aforementioned formula (I):

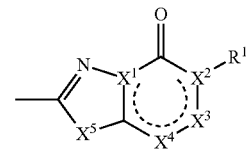

is (A) when $X^1$ is a carbon atom and $X^2$ is a nitrogen atom, a group represented by the following formula (i-a):

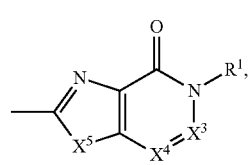

(i-a)

and (B) when $X^1$ is a nitrogen atom and $X^2$ is a carbon atom, a group represented by the following formula (i-b):

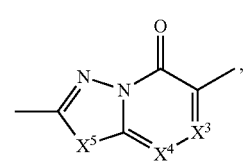

(i-b)

or a pharmacologically acceptable salt thereof.

23. A method for treating a disease in which inhibition of KAT-II activity is expected to improve the pathology, the method comprising administering to a subject an effective amount of a compound represented by the formula (I):

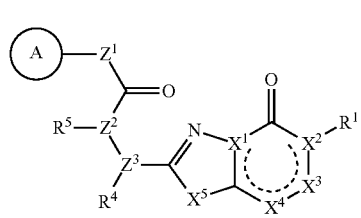
(I)

wherein
ring A is an optionally substituted aromatic group,
one of $X^1$ and $X^2$ is a carbon atom, and the other is a nitrogen atom,
$X^3$ is a nitrogen atom, or $CR^2$,
$X^4$ is a nitrogen atom, or $CR^3$,
$X^5$ is a sulfur atom, or —CH=CH—,
$Z^1$ is an oxygen atom, —C($R^6$)($R^7$)—, —NH—, —C($R^6$)($R^7$)—NH—, —NH—C($R^6$)($R^7$)—, —C($R^6$)($R^7$)—O—, or —O—C($R^6$)($R^7$)—, or is a single bond directly linking the adjacent carbonyl group to ring A,
one of $Z^2$ and $Z^3$ is CH and the other is a nitrogen atom, or both are nitrogen atoms,
$R^1$ is a hydrogen atom, optionally substituted alkyl, optionally substituted cycloalkyl, optionally substituted aryl, an optionally substituted nonaromatic heterocyclic group, or a halogen atom,
$R^2$ is a hydrogen atom, optionally substituted alkyl, optionally substituted cycloalkyl, optionally substituted amino, optionally substituted aryl, an optionally substituted nonaromatic heterocyclic group, optionally substituted heteroaryl, optionally substituted alkoxy, or optionally substituted cycloalkoxy,
or, $R^1$ and $R^2$ are bonded to each other to form, together with the adjacent $X^2$ and carbon atom, an optionally substituted ring,
$R^3$ is a hydrogen atom, optionally substituted alkyl, optionally substituted cycloalkyl, or a halogen atom,
$R^4$ and $R^5$ are each independently a hydrogen atom, or optionally substituted alkyl,
or, $R^4$ and $R^5$ are bonded to each other to form, together with the adjacent $Z^2$ and $Z^3$, an optionally substituted nitrogen-containing non-aromatic heterocycle,
$R^6$ and $R^7$ are each independently a hydrogen atom, optionally substituted alkyl, or optionally substituted cycloalkyl,
or, $R^6$ and $R^7$ are bonded to each other to form, together with the adjacent carbon atom, an optionally substituted cycloalkane,
a part represented by the following formula in the aforementioned formula (I):

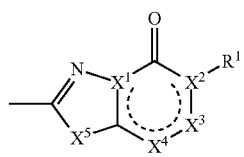

is (A) when $X^1$ is a carbon atom and $X^2$ is a nitrogen atom, a group represented by the following formula (i-a):

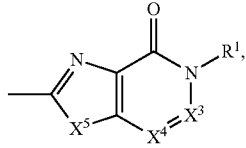
(i-a)

and (B) when $X^1$ is a nitrogen atom and $X^2$ is a carbon atom, a group represented by the following formula (i-b):

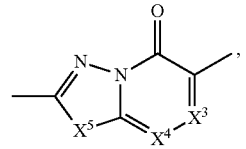
(i-b)

or a pharmacologically acceptable salt thereof.

24. A pharmaceutical composition comprising the compound according to claim 3, or a pharmacologically acceptable salt thereof, and a pharmaceutically acceptable carrier.

25. The pharmaceutical composition according to claim 24, which is suitable for use for the treatment of a disease in which inhibition of KAT-II activity is expected to improve the pathology.

26. The compound according to claim 7, wherein, in the formula (I), the part represented by the following formula:

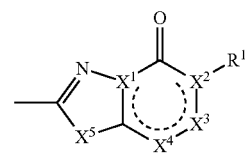

is a group represented by the following formula (iv-a), (iv-b), (iv-c), (iv-d), or (iv-e):

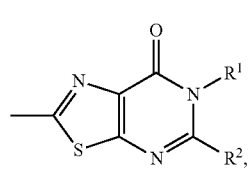
(iv-a)

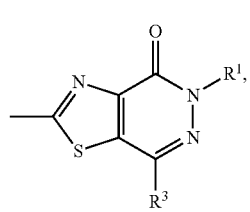
(iv-b)

-continued

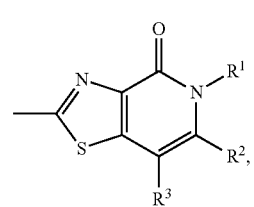
(iv-c)

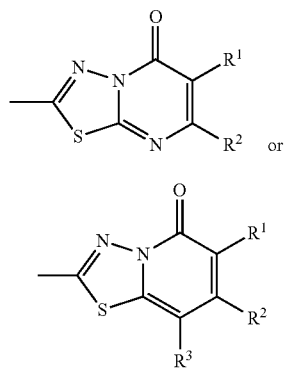
(iv-d)

or (iv-e)

or a pharmacologically acceptable salt thereof.

27. The compound according to claim 26, wherein the part represented by the following formula:

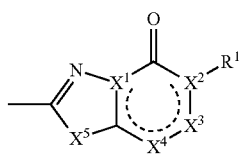

is a group represented by the formula (iv-a), (iv-c), or (iv-d), or a pharmacologically acceptable salt thereof.

28. The compound according to claim 26, wherein the part represented by the following formula:

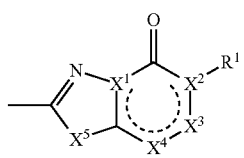

is a group represented by the formula (iv-a), or a pharmacologically acceptable salt thereof.

29. The compound according to claim 13, wherein
ring A-1 is phenyl, indanyl, tetrahydronaphthyl, furyl, thienyl, pyrazolyl, isoxazolyl, thiazolyl, dihydrobenzofuranyl, benzodioxolanyl, or tetrahydroquinolyl,
$Z^{1a}$ is an oxygen atom, —$C(R^{6a})(R^{7a})$—, —NH—, —$C(R^{6a})(R^{7a})$—NH—, —NH—$C(R^{6a})(R^{7a})$—, —$C(R^{6a})(R^{7a})$—O—, or —O—$C(R^{6a})(R^{7a})$—,
$R^{1a}$ is (a) a hydrogen atom; (b) alkyl optionally substituted by 1-7 groups selected from the group consisting of amino (wherein said amino is optionally substituted by 1 or 2 groups selected from the group consisting of alkyl, halogenoalkyl, and alkoxycarbonyl), hydroxy, alkoxy, a halogen atom, phenyl, alkoxyphenyl, and a nonaromatic heterocyclic group selected from the group consisting of pyrrolidyl, piperidyl, oxetanyl, and tetrahydropyranyl, wherein said nonaromatic heterocyclic group is optionally substituted by 1, 2 or 3 groups selected from the group consisting of alkyl, and alkoxycarbonyl; (c) cycloalkyl; (d) phenyl; or (e) a nonaromatic heterocyclic group selected from the group consisting of pyrrolidyl, piperidyl, morpholinyl, oxetanyl, tetrahydrofuranyl, and tetrahydropyranyl, wherein said nonaromatic heterocyclic group is optionally substituted by 1, 2 or 3 groups selected from the group consisting of alkyl, and alkoxycarbonyl,
$R^{2a}$ is (a) a hydrogen atom; (b) alkyl optionally substituted by 1-7 groups selected from the group consisting of cyano, amino (wherein said amino is optionally substituted by 1 or 2 groups selected from the group consisting of alkyl, alkoxyalkyl, halogenoalkyl, and alkoxycarbonyl), hydroxy, alkoxy, alkylsulfonyloxy, oxo, phenylsulfonyl, a halogen atom, phenyl, pyridyl, isoindolyl optionally substituted by 1 or 2 oxos, and a monocyclic nonaromatic heterocyclic group selected from the group consisting of azetidinyl, pyrrolidyl, piperidyl, and morpholinyl, wherein said nonaromatic heterocyclic group is optionally substituted by alkoxy; (c) cycloalkyl optionally substituted by 1, 2 or 3 groups selected from the group consisting of alkyl, alkoxyalkyl, halogenoalkyl, cyano, hydroxy, alkoxy, and a halogen atom; (d) amino optionally substituted by 1 or 2 groups selected from the group consisting of alkyl and alkoxyphenyl; (e) alkoxy optionally substituted by 1, 2 or 3 groups selected from the group consisting of amino (wherein said amino is optionally substituted by 1 or 2 groups selected from the group consisting of alkyl, and alkoxycarbonyl), and a halogen atom; (f) cycloalkoxy optionally substituted by alkyl; (g) phenyl optionally substituted by 1, 2 or 3 groups selected from the group consisting of alkyl, wherein said alkyl is optionally substituted by 1, 2 or 3 groups selected from the group consisting of alkylamino, dialkylamino, hydroxy, and a halogen atom, alkoxy optionally substituted by 1, 2 or 3 halogen atoms, alkylsulfonyl, and a halogen atom; (h) heteroaryl selected from the group consisting of thienyl, pyrazolyl, oxadiazolyl, pyridyl, and pyrimidinyl, wherein said heteroaryl is optionally substituted by 1, 2 or 3 groups selected from the group consisting of alkyl, alkoxy, and a halogen atom; or (i) a nonaromatic heterocyclic group selected from the group consisting of azetidinyl, pyrrolidyl, piperidyl, tetrahydrofuryl, tetrahydropyranyl, piperazinyl, and morpholinyl, wherein said nonaromatic heterocyclic group is optionally substituted by 1, 2 or 3 groups selected from the group consisting of alkyl, halogenoalkyl, and alkoxy,
or $R^{1a}$ and $R^{2a}$ are bonded to each other to form, together with the adjacent nitrogen atom and carbon atom, a nitrogen-containing non-aromatic heterocycle selected from the group consisting of pyrrolidine, piperidine, dihydroimidazole, imidazolidine, and piperazine, wherein said nitrogen-containing non-aromatic heterocycle is optionally substituted by 1, 1, 2 or 3 groups selected from the group consisting of alkyl, halogenoalkyl, alkoxycarbonyl, and a halogen atom,
$R^{4a}$ and $R^{5a}$ are each alkyl, or $R^{4a}$ and $R^{5a}$ are bonded to each other to form, together with the adjacent $Z^{2a}$ and $Z^{3a}$, a nitrogen-containing non-aromatic heterocycle selected from the group consisting of azetidine, pyrrolidine, and piperidine, wherein said nitrogen-containing non-aromatic heterocycle is optionally substituted by 1, 2 or 3 groups selected from the group consisting of amino optionally substituted by one group selected from the group consisting of alkoxycarbonyl and phenylalkoxycarbonyl, and a halogen atom, $R^{6a}$ and $R^{7a}$ are each independently a hydrogen atom, or alkyl, $R^{8a}$, $R^{8b}$ and $R^{8c}$ are each independently (a) a hydrogen atom; (b) alkyl optionally substituted by one group selected from the group consisting of dialkylamino, and alkoxy; (c) cyano; (d) amino optionally substituted by 1 or 2 alkyls; (e) alkoxy; or (f) a halogen atom, and n is 1, or a pharmacologically acceptable salt thereof.

30. The compound according to claim 12, wherein $R^{4a}$ and $R^{5a}$ are bonded to each other to form, together with the adjacent nitrogen atom and carbon atom, pyrrolidine, and $R^{6a}$ and $R^{7a}$ are each a hydrogen atom, or a pharmacologically acceptable salt thereof.

31. The method according to claim 23, wherein the disease is selected from the group consisting of schizophrenia, bipolar disorder, attention deficit/hyperactivity disorder, Alzheimer's disease, major depression, autism, cerebrovascular dementia, HIV encephalopathy, and age-related cognitive dysfunction.

\* \* \* \* \*